US011730712B2

(12) United States Patent
Oniciu

(10) Patent No.: US 11,730,712 B2
(45) Date of Patent: Aug. 22, 2023

(54) FUNCTIONALIZED LONG-CHAIN HYDROCARBON MONO- AND DI-CARBOXYLIC ACIDS AND DERIVATIVES THEREOF, AND THEIR USE FOR THE PREVENTION OR TREATMENT OF DISEASE

(71) Applicant: ESPERVITA THERAPEUTICS, INC., Saline, MI (US)

(72) Inventor: Daniela Carmen Oniciu, Gainesville, FL (US)

(73) Assignee: Espervita Therapeutics, Inc., Saline, MI (US)

( * ) Notice: Subject to any disclaimer, the term of this patent is extended or adjusted under 35 U.S.C. 154(b) by 0 days.

(21) Appl. No.: 17/582,774

(22) Filed: Jan. 24, 2022

(65) Prior Publication Data

US 2023/0111520 A1 Apr. 13, 2023

Related U.S. Application Data

(60) Provisional application No. 63/285,876, filed on Dec. 3, 2021, provisional application No. 63/141,273, filed on Jan. 25, 2021.

(51) Int. Cl.

| | |
|---|---|
| ***A61K 31/7076*** | (2006.01) |
| ***C07H 19/207*** | (2006.01) |
| ***A61K 31/20*** | (2006.01) |
| ***A61P 1/16*** | (2006.01) |
| ***A61P 35/00*** | (2006.01) |
| ***A61K 45/06*** | (2006.01) |

(52) U.S. Cl.
CPC .............. *A61K 31/20* (2013.01); *A61K 45/06* (2013.01); *A61P 1/16* (2018.01); *A61P 35/00* (2018.01)

(58) Field of Classification Search
CPC .......................... C07H 19/207; A61K 31/7076
See application file for complete search history.

(56) References Cited

U.S. PATENT DOCUMENTS

| | | | |
|---|---|---|---|
| 4,689,344 | A | 8/1987 | Bar-Tana |
| 4,711,896 | A | 12/1987 | Bar-Tana et al. |
| 5,387,672 | A | 2/1995 | Bucci et al. |
| 5,648,387 | A | 7/1997 | Bisgaier et al. |
| 6,459,003 | B1 | 10/2002 | Dasseux et al. |
| 6,699,910 | B2 | 3/2004 | Dasseux et al. |
| 6,790,953 | B2 | 9/2004 | Dasseux et al. |
| 7,405,226 | B2 | 7/2008 | Dasseux et al. |
| 9,452,964 | B2 | 9/2016 | Dasseux et al. |
| 11,084,773 | B1 | 8/2021 | Oniciu |
| 11,098,002 | B2 | 8/2021 | Oniciu |
| 11,267,778 | B2 | 3/2022 | Oniciu |
| 2003/0236212 | A1 | 12/2003 | Dasseux et al. |
| 2004/0171688 | A1 | 9/2004 | Bar-Tana |
| 2012/0172337 | A1 | 7/2012 | Dasseux et al. |
| 2014/0378922 | A1 | 12/2014 | Fuchs et al. |
| 2017/0174718 | A1 | 6/2017 | Lewis et al. |
| 2017/0360822 | A1 | 12/2017 | Levy et al. |
| 2019/0291404 | A1 | 9/2019 | Rossignol |
| 2020/0048181 | A1 | 2/2020 | Oniciu et al. |
| 2021/0024447 | A1 | 1/2021 | Oniciu |

FOREIGN PATENT DOCUMENTS

| | | | |
|---|---|---|---|
| CN | 105801405 | A | 7/2016 |
| WO | WO 2016/077832 | A2 | 5/2016 |
| WO | WO 2021/021563 | A1 | 2/2021 |

OTHER PUBLICATIONS

Al-Salama et al. "Lenvatinib: A Review in Hepatocellular Carcinoma", Drugs 2019; 79:665-674.
Barbaras et al. "Abstract 493: Antiatherosclerotic Activity of a New P2y13 Receptor Agonist (ct1007900) in Animal Models", Arteriosclerosis, Thrombosis, and Vascular Biology, 2012; 32:A493, 5 pages.
Bar-Tana et al. "Inhibition of Lipid Synthesis by ββ'-Tetramethyl-substituted, C14-C22, α,ω-Dicarboxylic Acids in the Rat in Vivo*", The Journal of Biological Chemistry, 1985, vol. 260, No. 14, p. 8404-8410.
Bilen et al. "Bempedoic Acid (ETC-1002): An Investigational Inhibitor of ATP Citrate Lyase", Current Atherosclerosis Reports 2016; 18:61.
Broadfield et al. "Salicylate enhances the response of prostate cancer to radiotherapy", Prostate 2019; 79:489-497.
Bruix J. et al. "Focus on hepatocellular carcinoma", Cancer Cell 2004; 5:215-9.
Calvisi et al. Increased lipogenesis, induced by AKT-mTORC1-RPS6 signaling, promotes development of human hepatocellular carcinoma. Gastroenterology 2011; 140:1071-83.
CAS Registry STN Substance Record for 137334-84-0, Nov. 15, 1991, 7 pages.

(Continued)

*Primary Examiner* — Bruck Kifle
(74) *Attorney, Agent, or Firm* — Cooley LLP

(57) ABSTRACT

This invention provides compounds of Formulae (I), (IA), (IB), (IC), (ID), (IE), (IF), (IG), (IH), (IJ), (II), (III), (IIIA), and (IIIB); pharmaceutically acceptable salts and solvates thereof; and compositions thereof. This invention further provides methods for treating a disease, including but not limited to, liver disease or an abnormal liver condition; cancer (such as hepatocellular carcinoma or cholangiocarcinoma); a malignant or benign tumor of the lung, liver, gall bladder, bile duct or digestive tract; an intra- or extra-hepatic bile duct disease; a disorder of lipoprotein; a lipid-and-metabolic disorder; cirrhosis, fibrosis; a disorder of glucose metabolism; a cardiovascular or related vascular disorder; a disease resulting from steatosis, fibrosis, or cirrhosis; a disease associated with increased inflammation (such as hepatic inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

21 Claims, 66 Drawing Sheets

(56) References Cited

OTHER PUBLICATIONS

Chou TC. "Drug combination studies and their synergy quantification using the Chou-Talalay method", Cancer Res 2010; 70:440-446.
Chou T.C. "Theoretical Basis, Experimental Design, and Computerized Simulation of Synergism and Antagonism in Drug Combination Studies", Pharmacological Reviews 2006;58:621-681.
El-Serag et al. "Current Status of Sorafenib Use for Treatment of Hepatocellular Carcinoma", Gastroenterol Hepatol (NY) 2017; 13:623-625.
Franken et al. "Clonogenic assay of cells in vitro", Nat Protoc 2006; 1:2315-9.
Gao et al. "Inactivation of ATP citrate lyase by Cucurbitacin B: A bioactive compound from cucumber, inhibits prostate cancer growth", Cancer Letters 2014; 349:15-25.
Gleiter et al. "Synthesis and Properties of 4,4,9,9-Tetramethyl[12]paracyclophane-5,6,7,8-tetrone", J. Org. Chem., 1992, vol. 57, p. 252-258.
Granchi C. "ATP citrate lyase (ACLY) inhibitors: An anti-cancer strategy at the crossroads of glucose and lipid metabolism", Eur J Med Chem 2018; 157:1276-1291.
Hatzivassiliou et al. "ATP citrate lyase inhibition can suppress tumor cell growth", Cancer Cell 2005;8:311-21.
Huang et al. "Isobologram Analysis: A Comprehensive Review of Methodology and Current Research", Frontiers in Pharmacology, 2019, 10, 12 pages.
Icard et al. "ATP citrate lyase: A central metabolic enzyme in cancer", Cancer Lett 2020 ;471 :125-134.
Khwairakpam et al. "ATP Citrate Lyase (ACLY): A Promising Target for Cancer Prevention and Treatment", Current Drug Targets, 2015; 16:156-63.
Kimura et al. "Immunomodulatory activity of lenvatinib contributes to antitumor activity in the Hepa1-6 hepatocellular carcinoma model", Cancer Science 2018; 109:3993-4002.
Kudo et al. "Lenvatinib versus sorafenib in first-line treatment of patients with unresectable hepatocellular carcinoma: a randomised phase 3 non-inferiority trial", Lancet 2018; 391:1163-1173.
Kuhajda "Fatty-acid synthase and human cancer: new perspectives on its role in tumor biology", Nutrition 2000; 16:202-8.
Leathers et al. "PIB: A Score to Select Sorafenib Treatment Candidates for Hepatocellular Carcinoma in Resource-Limited Settings", Hepat Mon 2018; 18.
Li et al. "2-hydroxy-N-arylbenzenesulfonamides as ATP-citrate lyase inhibitors", Bioorg Med Chem Lett 2007; 17:3208-11.
Llovet et al. "Sorafenib in advanced hepatocellular carcinoma", N Engl J Med 2008; 359:378-90.
Luong et al. "Molecular characterization of human acetyl-CoA synthetase, an enzyme regulated by sterol regulatory element-binding proteins", J Biol Chem 2000; 275:26458-66.
Meynard et al. "Inflammation regulates TMPRSS6 expression via STAT5", PLoS One 2013;8: e82127.
Migita et al. "ATP citrate lyase: activation and therapeutic implications in non-small cell lung cancer", Cancer Research 2008; 68:8547-54.
Oniciu, D.C. et al. "Long hydrocarbon chain diols and diacids with central ether or ketone moieties that favorably alter lipid disorders", Pharmazie, 2006, vol. 61, p. 157-165.
Oniciu, D.C. et al. "In vitro Models Concur with Clinical Results to Confirm Pleiatropic Mechanisms of Action for Gemcabene", Thrombosis, and Vascular Biology 2017, Abstract No. 579, poster, 1 page.
Pawlik et al. Phase II trial of sorafenib combined with concurrent transarterial chemoembolization with drug-eluting beads for hepatocellular carcinoma. Journal of clinical oncology: official journal of the American Society of Clinical Oncology 2011; 29:3960-7.
Pinkosky et al. "AMP-activated protein kinase and ATP-citrate lyase are two distinct molecular targets for ETC-1002, a novel small molecule regulator of lipid and carbohydrate metabolism", J Lipid Res 2013 ;54 :134-51.
Portolani et al. "Early and late recurrence after liver resection for hepatocellular carcinoma: prognostic and therapeutic implications", Annals of Surgery 2006 ; 243 :229-35.
Pubchem-CID: 7734 Create Date: Mar. 27, 2005, pp. 1-46.
Pubchem, SID 228534127, Substance Record for SCHEMBL2421674, Available Date: Feb. 12, 2015 [retrieved on Mar. 18, 2022], Retrieved from the Internet: https://pubchem.ncbi.nlm.nih.gov/substance/228534127. 8 pages.
Pubchem SID 319409634, Substance Record for 124924-91-0; Available Date: Nov. 29, 2016 [retrieved on May 12, 2022], Retrieved from the Internet: https://pubchem.ncbi.nlm.nih.gov/substance/319409634. 6 pages.
Pubchem SID 275387334, Substance Record for 102239157; Available Date: Dec. 25, 2015, 5 pages. [retrieved on Mar. 31, 2022], Retrieved from the Internet: https://pubchem.ncbi.nlm.nih.gov/substance/275387334.
Rose-Kahn et al. "Inhibition of Lipid Synthesis by ββ'-Tetramethyl-substituted, $C_{14}$-$C_{22}$, α,ω-Dicarboxylic Acids in Cultured Rat Hepatocytes*", The Journal of Biological Chemistry, 1985, vol. 260, No. 14, p. 8411-8415.
Spallanzani et al. "Lenvatinib as a therapy for unresectable hepatocellular carcinoma", Expert Review of Anticancer Therapy 2018; 18:1069-1076.
Sur et al. "Inhibition of the key metabolic pathways, glycolysis and lipogenesis, of oral cancer by bitter melon extract", Cell Commun Signal 2019; 17:131.
Venook et al. "The incidence and epidemiology of hepatocellular carcinoma: a global and regional perspective", The Oncologist, 2010;15 Suppl 4:5-13.
Yahagi et al. "Co-ordinate activation of lipogenic enzymes in hepatocellular carcinoma", European Journal of Cancer 2005; 41:1316-22.
Yamamoto et al. "Recurrence of hepatocellular carcinoma after surgery", The British Journal of Surgery 1996; 83:1219-22.
Zaidi et al. "ATP citrate lyase knockdown induces growth arrest and apoptosis through different cell- and environment-dependent mechanisms", Molecular Cancer Therapeutics 2012; 11:1925-35.
Zhao et al. "ATP-Citrate Lyase Controls a Glucose-to-Acetate Metabolic Switch", Cell Reports 2016; 17:1037-1052.
International Search Report and Written Opinion for International Application No. PCT/US2022/013514, dated Jun. 8, 2022, 14 pages.
International Preliminary Report on Patentability for International Application No. PCT/US2020/043274, dated Feb. 1, 2022, 7 pages.
International Search Report and Written Opinion for International Application No. PCT/US2022/013504 dated Jun. 30, 2022, 24 pages.
Invitation to Pay for International Application No. PCT/US2022/013504 dated Apr. 6, 2022, 3 pages.
Non-Final Office Action issued for U.S. Appl. No. 17/240,513, dated Sep. 3, 2021, 13 pages.

| | I-32 | I-32 | I-32 |
|---|---|---|---|
| HILLSLOPE | -1.127 | -2.003 | -1.238 |
| EC50 | 0.0002636 | 0.0002716 | 0.0002200 |

| | I-32-CoA | I-32-CoA | I-32-CoA |
|---|---|---|---|
| HILLSLOPE | -1.275 | -0.7631 | -1.323 |
| EC50 | 5.068e-006 | 4.999e-006 | 6.032e-006 |

| | I-32-CoA | I-32-CoA | I-32-CoA |
|---|---|---|---|
| HILLSLOPE | -1.343 | -0.7925 | -0.9766 |
| EC50 | 5.020e-006 | 4.222e-006 | 3.325e-006 |

| | I-1-CoA | I-1-CoA | I-1-CoA |
|---|---|---|---|
| HILLSLOPE | -1.095 | -1.041 | -1.305 |
| EC50 | 9.409e-006 | 7.719e-006 | 9.061e-006 |

| | CP 640186 |
|---|---|
| HILLSLOPE | -0.6394 |
| EC50 | 7.811e-008 |

| | I-32-CoA | I-32-CoA | I-32-CoA |
|---|---|---|---|
| HILLSLOPE | -0.5629 | -0.5770 | -0.5943 |
| EC50 | 9.883e-007 | 1.224e-006 | 1.442e-006 |

| | I-1-CoA | I-1-CoA | I-1-CoA |
|---|---|---|---|
| HILLSLOPE | -0.5779 | -0.5856 | -0.5783 |
| EC50 | 3.335e-006 | 2.282e-006 | 2.502e-006 |

| | BMS-303141 |
|---|---|
| HILLSLOPE | -1.361 |
| EC50 | 4.451e-007 |

FUNCTIONALIZED LONG-CHAIN HYDROCARBON MONO- AND DI-CARBOXYLIC ACIDS AND DERIVATIVES THEREOF, AND THEIR USE FOR THE PREVENTION OR TREATMENT OF DISEASE

CROSS-REFERENCE TO RELATED APPLICATIONS

This application claims the benefit of U.S. Provisional Application No. 63/141,273, filed Jan. 25, 2021, and U.S. Provisional Application No. 63/285,876, filed Dec. 3, 2021, the disclosure of each of which is incorporated by reference herein in its entirety.

FIELD OF THE INVENTION

This invention provides mono- and di-Coenzyme A (CoA) esters of compounds of Formulae (I), (IA), (IB), (IC), (ID), (IE), (IF), (IG), (IH), (IJ), (II), (III), (IIIA), and (IIIB), pharmaceutically acceptable salts and solvates thereof, and compositions thereof. This invention further provides methods for preventing or treating a disease, including but not limited to, liver disease or an abnormal liver condition; cancer (such as hepatocellular carcinoma, cholangiocarcinoma or cancers of the digestive tract); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation, kidney inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease. This invention further provides methods for slowing the onset of cancer or slowing the progression of cancer, treating viral conditions and inhibiting viral replication.

BACKGROUND OF THE INVENTION

Hepatocellular carcinoma (HCC) is one of the most common primary liver malignancies. Patients with chronic liver disease, such as liver cirrhosis, fibrosis, hepatitis B and hepatitis C, are at increased risk for development of HCC. Thus, patients with chronic liver diseases should be closely monitored for development of HCC. Risk factors for HCC include cirrhosis, non-alcoholic fatty liver disease (NAFLD), nonalcoholic steatohepatitis (NASH), alcoholic steatohepatitis (ASH), chronic alcohol consumption, hepatitis B, and hepatitis C, type IIb hyperlipidemia, mixed dyslipidemia, obesity, and type 2 diabetes.

Type IIb hyperlipidemia patients have a high risk of developing NAFLD and NASH and ultimately HCC, which can develop due to hepatic triglyceride and cholesterol overproduction and accumulation. Elevated levels of low-density lipoprotein cholesterol (LDL-C) and triglycerides are associated with mixed dyslipidemia, including type IIb hyperlipidemia, which is characterized by elevation of apolipoprotein B, very low-density lipoprotein cholesterol (VLDL-C), intermediate density lipoprotein cholesterol (IDL), and small dense low-density lipoprotein (LDL) levels, in addition to elevation in LDL-C and triglyceride levels.

Current treatment options for treatment of type IIb hyperlipidemia are limited. While statins can be effective for lowering LDL-C and reducing inflammation, they are generally not very effective for lowering triglyceride concentrations. Further, high dose statin therapy is often not well tolerated because it can cause muscle pain (myalgia) and increase a patient's risk of serious muscle toxicity, such as rhabdomyolysis. Also, commonly used triglyceride-lowering agents that are administered in combination with statins are often not well-tolerated. When administered with certain statins, fibrates are known to have drug-drug interactions, resulting in increased statin blood drug levels, myalgia, an increased risk of muscle toxicity and an increased safety risk. Indeed, the interaction of the statin Baycol (cerivastatin) with the fibrate gemfibrozil resulted in severe muscle toxicity and deaths and raised safety concerns that resulted in the removal of Baycol from the U.S. market. Fish oil, which has been used to lower triglyceride levels, needs to be taken multiple times daily and can cause a fish oil aftertaste, burping or regurgitation. Niacin causes flushing, particularly when administered in combination with statins.

Gastrointestinal (digestive) cancers can affect the gastrointestinal tract and other organs that are contained within the digestive system, such as the liver. The origins of the digestive cancers are linked strongly to chronic inflammation of the organs that develop through a series of histopathologic stages dependent of the organ affected. For cancers of the gastrointestinal tract or for gastrointestinal stromal tumor (GIST), surgery will likely be recommended to remove the tumor and/or to help maintain normal function. Other treatment options are radiotherapy, chemotherapy, hormone therapy, or targeted therapies.

Fibrosis can be induced by the pathological accumulation of extracellular matrix (ECM) proteins and it results in scarring and thickening of the affected tissue as if it was an exaggerated wound healing response which interferes with normal organ function. Fibrosis can occur in many tissues within the body, typically as a result of inflammation or damage, such as fibrosis of the lungs, liver, brain, heart, kidney, uterus, etc.

There is a need for a safe and effective therapy for treatment or prevention of cancer (such as gastrointestinal cancer, hepatocellular carcinoma, cholangiocarcinoma, pvarian cancer, or prostate cancer); a malignant or benign tumor of the lung, liver, gall bladder, bile duct or digestive tract; liver disease or an abnormal liver condition, an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation (such as hepatic inflammation, kidney inflammation or pulmonary inflammation); hepatocyte ballooning; a peroxisome proliferator activated receptor-associated disorder; an ATP citrate lyase disorder; an acetyl-coenzyme A carboxylase disorder; obesity; pancreatitis; or renal disease.

SUMMARY OF THE INVENTION

The present invention provides (a) mono- and di-CoA ester compounds of Formulae (I), (IA), (IB), (IC), (II), (III), (QIIA), and (IHB), and compounds of Formulae (ID), (IE), (IF), (IG), (IH), (IJ), Table A-18, Table A-19 and Table B5, and pharmaceutically acceptable salts and solvates thereof, (b) pharmaceutically acceptable amino acid, meglumine, eglumine, D-glucamine, glucosamine, or choline salts of compounds of Formulae (I), (IA), (IB), (IC), (II), (III), (QIIA), (IIIB), Table A-7, Table A-8, Table A-9, Table A-10, Table A-11, Table A-12, Table B1, Table B2, Table B3, Table B4, and Table B5, and (c) compounds useful in the methods of the invention (each compound, pharmaceutically acceptable salt and solvate being a "compound of the invention").

The present invention also provides compositions comprising i) an effective amount of a compound of the invention and ii) a pharmaceutically acceptable carrier or vehicle (each composition being a "composition of the invention").

The present invention further provides methods for treating or preventing a disease, comprising administering to a subject in need thereof an effective amount of a compound of the invention, wherein the disease is liver disease or an abnormal liver condition; cancer; a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis; a disorder of glucose metabolism; a cardiovascular or related vascular disorder; a disease resulting from steatosis, fibrosis, or cirrhosis; a disease associated with increased inflammation; hepatocyte ballooning; a peroxisome proliferator activated receptor-associated disorder; an ATP citrate lyase disorder; an acetyl-coenzyme A carboxylase disorder; obesity; pancreatitis; or renal disease.

The present invention further provides methods for reducing in a subject's blood plasma or blood serum, the subject's C-reactive protein (CRP) concentration, serum amyloid A (SAA) concentration, alanine aminotransferase (ALT) concentration, aspartate aminotransferase (AST) concentration, alkaline phosphatase (ALP) concentration, gamma-glutamyl transferase (GGT) concentration, serum creatinine concentration, 7$\alpha$-hydroxy-4-cholesten-3-one (C4) concentration, protein:creatinine ratio, creatine kinase concentration, angiopoietin-like protein 3 concentration, angiopoietin-like protein 4 concentration, angiopoietin-like protein 8 concentration, fibrinogen concentration, total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, apolipoprotein C concentration, lipoprotein(a) concentration, or serum triglyceride concentration, comprising administering to a subject in need thereof an effective amount of a compound of the invention.

The present invention further provides methods for reducing triglyceride concentration in a subject's liver, comprising administering to a subject in need thereof an effective amount of a compound of the invention.

The present invention further provides methods for elevating in a subject's blood plasma or blood serum a concentration of high-density lipoprotein cholesterol, high-density lipoprotein, or lipoprotein lipase, comprising administering to a subject in need thereof an effective amount of a compound of the invention.

The present invention further provides methods for treating a disease, comprising administering to a subject in need thereof an effective amount of a compound of the invention, wherein the disease is inflammatory disease, gastrointestinal disease, irritable bowel syndrome (IBS), inflammatory bowel disease (IBD), or autoimmune disease.

The present invention further provides methods for regressing, reducing the rate of progression, or inhibiting progression, of fibrosis, hepatocyte ballooning or hepatic inflammation, comprising administering to a subject in need thereof an effective amount of a compound of the invention.

The present invention further provides methods for inhibiting, reducing, or delaying advancement of a subject's lipid synthesis, liver steatosis, hepatocyte ballooning, hepatocyte inflammation, liver fibrosis, lung fibrosis, kidney fibrosis, uterine fibrosis, or cirrhosis, comprising administering to a subject in need thereof an effective amount of a compound of the invention.

The present invention further provides methods for elevating HDL concentration in a subject's blood serum or plasma, comprising administering to a subject in need thereof an effective amount of a compound of the invention.

The present invention further provides methods for inhibiting NF-kB or stellate cell activation, comprising administering to a subject in need thereof an effective amount of a compound of the invention.

The present invention further provides methods for activating PPAR (peroxisome proliferator-activated receptor), comprising administering to a subject in need thereof an effective amount of a compound of the invention.

The present invention further provides methods for modulating, directly inhibiting or allosterically inhibiting ATP citrate lyase in a subject, comprising administering to a subject in need thereof an effective amount of a compound of the invention.

The present invention further provides methods for modulating, directly inhibiting or allosterically inhibiting acetyl-CoA carboxylase 1 or acetyl-CoA carboxylase 2 in a subject, comprising administering to a subject in need thereof an effective amount of a compound of the invention.

The present invention further provides methods for reducing fat or cholesterol content of livestock meat or poultry eggs, comprising administering to the livestock or poultry an effective amount of a compound of the invention.

The present invention further provides methods for treating or preventing a disease, comprising administering to a subject in need thereof an effective amount of a compound of the invention, wherein the disease is cancer, a lipid-and-metabolic disorder, a liver disorder, cirrhosis, fibrosis, a disorder of glucose metabolism, a peroxisome proliferator activated receptor-associated disorder, a malignant or benign tumor of the lung, liver, bile and digestive tract, an ATP citrate lyase disorder, an acetyl-coenzyme A carboxylase disorder, obesity, pancreatitis, renal disease, hepatic inflammation, or pulmonary inflammation.

The present invention further provides methods for reducing risk of cancer, slowing the onset of cancer or slowing progression of cancer, comprising administering to a subject in need thereof an effective amount of a compound of the invention, or a composition of the invention.

The present invention further provides methods for treating or preventing a viral infection, comprising administering to the subject an effective amount of a compound of the invention, or a composition of the invention.

The present invention further provides methods for inhibiting replication of a virus, comprising contacting the virus with an effective amount of a compound of the invention, or a composition of the invention.

Each of the above methods is a "method of the invention".

The compounds of the invention and compositions of the invention are useful in the methods of the invention.

BRIEF DESCRIPTION OF THE DRAWINGS

In FIG. 41A, "1+0.015 (μM)" means 1 μM Compound I-32+0.015 μM regorafenib, etc. In FIG. 41B, "1+0.015 (μM)" means 1 μM Compound I-1+0.015 μM regorafenib, etc.

In FIG. 42A, "1+0.05 (μM)" means 1 μM Compound I-32+0.05 μM regorafenib, etc. In FIG. 42B, "1+0.05 (μM)" means 1 μM Compound I-1+0.05 μM regorafenib, etc.

FIG. 44A shows synergism of Compound I-1 in combination with sorafenib at various concentrations in Hep3B cells. In FIG. 44A, "1+0.03 (μM)" means 1 μM Compound I-1+0.03 μM sorafenib, etc. FIG. 44B shows synergism of Compound I-1 in combination with lenvatinib at various concentrations in Hep3B cells. In FIG. 44B, "1+0.005 (μM)" means 1 μM Compound I-1+0.005 μM lenvatinib, etc. FIG. 44C shows synergism of Compound I-32 in combination with sorafenib at all tested concentrations of Compound I-32 and sorafenib in Hep3B cells. In FIG. 44C, "1+0.03 (μM)" means 1 μM Compound I-32+0.03 μM sorafenib, etc. FIG. 44D shows synergism of Compound I-32 in combination with lenvatinib at various concentrations in Hep3B cells. In FIG. 44D, "1+0.005 (μM)" means 1 μM Compound I-32+0.005 μM lenvatinib, etc.

In FIG. 46A, "1+0.05 (μM)" means 1 μM Compound I-1+0.05 μM sorafenib, etc. In FIG. 46B, "1+0.3 (μM)" means 1 μM Compound I-1+0.3 μM lenvatinib, etc. In FIG. 46C, "1+0.05 (μM)" means 1 μM Compound I-32+0.05 μM sorafenib, etc. In FIG. 46D, "1+0.3 (μM)" means 1 μM Compound I-32+0.3 μM lenvatinib, etc.

FIG. 47A shows results as % change in RER compared to the 0 hr vehicle control. FIG. 47B shows % change in RER in each group compared to their respective 0 hr timepoint. * indicates significant difference from vehicle control, $p<0.05$.

FIG. 48A shows total values (day and night) of heat production and FIG. 48B shows heat production values during the day compared to the night.

FIG. 49A shows total values, and FIG. 49B values during the day compared to the night up to 24 hr (day+night). * indicates significant difference from vehicle control, $p<0.05$.

FIG. 50A shows total food intake values (day and night) and FIG. 50B shows food intake values during the day compared to the night.

DETAILED DESCRIPTION OF THE INVENTION

Definitions

Figure 1:
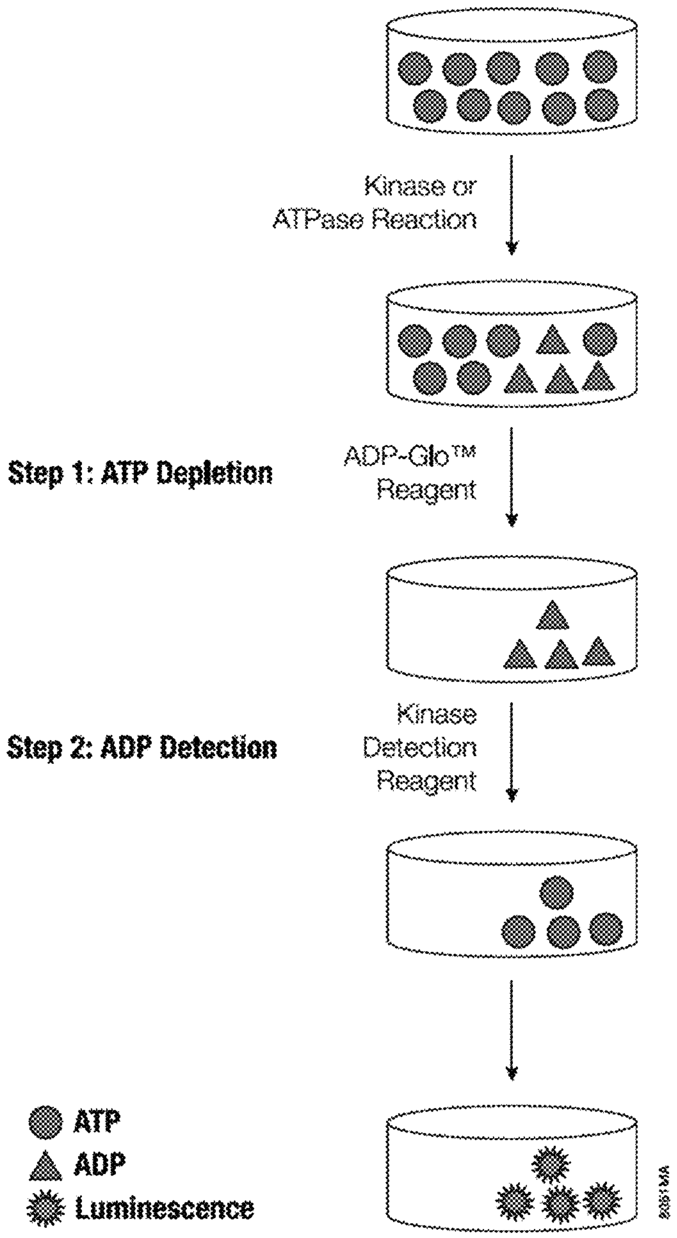
FIG. 1 shows the schematics of ADP-Glo assay.

The term "about" when immediately preceding a numerical value means±up to 20% of the numerical value. For example, "about" a numerical value means±up to 20% of the numerical value, in some embodiments, ±up to 19%, ±up to 18%, ±up to 17%, ±up to 16%, ±up to 15%, ±up to 14%, ±up to 13%, ±up to 12%, ±up to 11%, ±up to 10%, ±up to 9%, ±up to 8%, ±up to 7%, ±up to 6%, ±up to 5%, ±up to 4%, ±up to 3%, ±up to 2%, ±up to 1%, ±up to less than 1%, or any other value or range of values therein.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.). The term "pharmaceutically acceptable salt" includes both an acid and a base addition salt.

Pharmaceutically acceptable salts can be obtained by reacting the compound of the invention having a basic, e.g., an amino group, with an inorganic or organic acid to form a salt, for example, a salt of hydrochloric acid, sulfuric acid, phosphoric acid, methanesulfonic acid, benzenesulfonic acid, p-toluenesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Pharmaceutically acceptable salts can also be obtained by reacting a compound of the invention having an acidic, e.g., a carboxyl, group with an inorganic or organic base to form a salt, for example, a salt of sodium, potassium, lithium, ammonium, calcium, magnesium, iron, zinc, copper, manganese, aluminum, ammonia, isopropylamine, trimethylamine, etc. In some embodiments, the pharmaceutically acceptable salt is a sodium salt, potassium salt, a calcium salt, an ammonium salt, or magnesium salt. In some embodiments, the pharmaceutically acceptable salt is a zinc salt. Pharmaceutically acceptable salts can also be obtained by reacting a compound of the invention having an acidic, e.g., a carboxyl, group with a basic amino acid, including but not limited to a D,L-amino acid, an L-amino acid, and a D-amino acids. Basic amino acids useful for preparing pharmaceutically acceptable salts can be natural amino acids, or synthetic amino acids. In some embodiments, the basic amino acids include, but are not limited to, histidine (H), arginine (R), lysine (K), glutamine (Q), 2,3-diaminopropionic acid (Dpr), ornithine (Orn), homoarginine (hArg), 2,4-diaminobutyric acid (Dbu), 2,3-diaminobutyric acid (Dab), or p-aminophenylalanine (Phe(p-$NH_2$)). In some embodiments, the pharmaceutically acceptable salt is a meglumine (N-methyl-D-glucamine) salt, an eglumine (N-ethyl-D-glucamine) salt, D-glucamine salt, glucosamine salt, a choline salt, a lysine salt, an arginine salt, a histidine salt, or a glutamine salt. In some embodiments, the pharmaceutically acceptable salt is an L-lysine salt, an L-arginine salt, an L-histidine salt, or an L-glutamine salt. Those skilled in the art will further recognize that pharmaceutically acceptable salts can be prepared by reaction of the compounds of the invention with an appropriate inorganic or organic acid or base via any of a number of known methods.

The term "solvate" refers to a solvation complex. Solvates can be formed by solvation (the combination of solvent molecules with molecules or ions of the compounds of the invention), or a solvate can be an aggregate that comprises a solute ion or molecule or a solvent molecules. The solvent can be water, in which case the solvate is a hydrate. Examples of hydrates include, but are not limited to, a hemihydrate, monohydrate, dihydrate, trihydrate, hexahydrate, etc. The solvate can be formed via hydration, including via absorption of moisture. A pharmaceutically acceptable salt can also be a solvate. Where a solvate is obtained via crystallization from a solvent, the solvent can be an alcohol, such as methanol or ethanol; an aldehyde; a ketone, such as acetone; or an ester, such as ethyl acetate.

The compounds of the invention can have one or more asymmetric centers and can thus be enantiomers, racemates, diastereomers, other stereoisomers and mixtures thereof. The compounds of the invention include all such possible isomers (including geometric isomers), as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation or isolation of individual enantiomers include chiral synthesis from a suitable optically pure precursor or resolution of the racemate using, for example, chiral high pressure liquid chromatography (HPLC). When the compounds of the invention comprise an olefinic double bond or another center of geometric asymmetry, and unless specified otherwise, the compounds of the invention include both E and Z geometric isomers. Likewise, the compounds of the invention include all tautomeric forms.

An "effective amount" when used in connection with a compound of the invention means an amount of the compound of the invention that, when administered to a subject is effective in a method of the invention, alone or with another pharmaceutically active agent.

An "effective amount" when used in connection with another pharmaceutically active agent means an amount of the other pharmaceutically active agent that is effective in a composition of the invention or method of the invention, alone or in combination with a compound of the invention.

A "subject" is a human or non-human mammal, e.g., a bovine, horse, feline, canine, rodent, or non-human primate. The human can be a male or female, child, adolescent or adult. The female can be premenarcheal or postmenarcheal.

"Mammal" includes a human, domestic animal such as a laboratory animal (e.g., mouse, rat, rabbit, monkey, dog, etc.) and household pet (e.g., cat, dog, swine, cattle, sheep, goat, horse, rabbit), and a non-domestic, wild animal.

All weight percentages (i.e., "% by weight" and "wt. %" and w/w) referenced herein, unless otherwise indicated, are relative to the total weight of the mixture or composition, as the case may be.

The terms below, as used herein, have the following meanings, unless indicated otherwise:

"Halo", "Hal", or "halogen" refers to Br, Cl, F, or I.

"Alkyl" refers to a fully saturated, straight or branched hydrocarbon chain having from one to twelve carbon atoms, and which is attached to an atom by a single bond. Alkyls with a number of carbon atoms ranging from 1 to 12 are included. An alkyl group with 1 to 12 carbon atoms is a $C_1$-$C_{12}$ alkyl, an alkyl group with 1 to 10 carbon atoms is a $C_1$-$C_{10}$ alkyl, an alkyl group with 1 to 6 carbon atoms is a $C_1$-$C_6$ alkyl and an alkyl group with 1 to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise, an alkyl group can be unsubstituted or substituted with a substituent disclosed herein.

"Alkylene" refers to a fully saturated, straight or branched divalent hydrocarbon, and having from one to twelve carbon atoms. Non-limiting examples of $C_1$-$C_{12}$ alkylene include methylene, ethylene, propylene, n-butylene, and the like. Each alkylene terminus is attached to an atom by a single bond. The points of attachment of the alkylene chain can be one or two atoms. Unless stated otherwise, an alkylene chain can be unsubstituted or substituted with a substituent disclosed herein.

"Alkenyl" refers to a straight or branched hydrocarbon chain having from two to twelve carbon atoms and having one or more carbon-carbon double bonds. Each alkenyl group is attached to an atom by a single bond. Alkenyl groups with a number of carbon atoms ranging from 2 to 12 are included. An alkenyl group with 2 to 12 carbon atoms is a $C_2$-$C_{12}$ alkenyl, an alkenyl group with 2 to 10 carbon atoms is a $C_2$-$C_{10}$ alkenyl, an alkenyl group with 2 to 6 carbon atoms is a $C_2$-$C_6$ alkenyl and an alkenyl group with 2 to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise, an alkyl group can be unsubstituted or substituted with a substituent disclosed herein.

"Alkenylene" refers to a straight or branched divalent hydrocarbon chain radical, having from two to twelve carbon atoms, and having one or more carbon-carbon double bonds. Non-limiting examples of $C_2$-$C_{12}$ alkenylene include ethenylene, propenylene, butenylene, and the like. Each terminus of the alkenylene chain is attached to an atom by a single bond. The points of attachment of the alkenylene chain can be through one two atoms. Unless stated otherwise, an alkenylene chain can be unsubstituted or substituted with a substituent disclosed herein.

"Alkynyl" refers to a straight or branched hydrocarbon chain radical having from two to twelve carbon atoms and having one or more carbon-carbon triple bonds. Each alkynyl group is attached to an atom by a single bond. Alkynyl groups with a number of carbon atoms ranging from 2 to 12 are included. An alkynyl group having 2 to 12 carbon atoms is a $C_2$-$C_{12}$ alkynyl, an alkynyl group with 2 to 10 carbon atoms is a $C_2$-$C_{10}$ alkynyl, an alkynyl group with 2 to 6 carbon atoms is a $C_2$-$C_6$ alkynyl and an alkynyl group with 2 to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise, an alkyl group can be unsubstituted or substituted with a substituent disclosed herein.

“Alkynylene” refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propynylene, butynylene, and the like. Each terminus of the alkynylene chain is attached to an atom through a single bond. The points of attachment of the alkynylene chain can be through one or two atoms. Unless stated otherwise, an alkynylene chain can be unsubstituted or substituted with a substituent disclosed herein.

“Alkoxy” refers to a radical of the formula —$OR_a$ where $R_a$ is an alkyl, alkenyl or alkynl radical as defined herein. Unless stated otherwise, an alkoxy group can be unsubstituted or substituted with a substituent disclosed herein.

“Aryl” refers to a hydrocarbon ring system radical comprising hydrogen, 6 to 18 carbon atoms and at least one aromatic ring. The aryl radical can be a monocyclic, bicyclic, tricyclic or tetracyclic ring system, which can include fused or bridged ring systems. Aryl radicals include, but are not limited to, aceanthrylenyl, acenaphthylenyl, acephenanthrylenyl, anthracenyl, azulenyl, chrysenyl, fluoranthenyl, fluorenyl, as-indacenyl, s-indacenyl, indanyl, indenyl, naphthalenyl, phenalenyl, phenanthrenyl, phenyl, pleiadenyl, pyrenyl, and triphenylenyl. Unless stated otherwise, the aryl can be unsubstituted or substituted with a substituent disclosed herein.

“Arylene” refers to a divalent aryl group, wherein the aryl is as defined herein. Unless stated otherwise, an arylene group can be unsubstituted or substituted with a substituent disclosed herein.

“Arylalkyl” refers to a radical of the formula —$R_b$—$R_c$ where $R_b$ is an alkylene group as defined herein and $R_c$ is an aryl radical as defined herein, for example, benzyl, diphenylmethyl and the like. Unless stated otherwise, an arylalkyl group can be unsubstituted or substituted with a substituent disclosed herein. “Arylalkenyl” refers to a radical of the formula —$R_b$—$R_c$ where $R_b$ is an alkenylene group as defined herein and $R_c$ is an aryl radical as defined herein. Unless stated otherwise, an arylalkenyl group can be unsubstituted or substituted with a substituent disclosed herein.

“Arylalkynyl” refers to a radical of the formula —$R_b$—$R_c$ where $R_b$ is an alkynylene group as defined herein and $R_c$ is an aryl radical as defined herein. Unless stated otherwise, an arylalkynyl group can be unsubstituted or substituted with a substituent disclosed herein.

“Cycloalkyl” refers to a non-aromatic monocyclic or polycyclic fully saturated hydrocarbon radical consisting of carbon and hydrogen atoms, which can include fused or bridged ring systems, having from three to twenty carbon atoms, preferably having from three to ten carbon atoms, and which is attached to an atom by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless stated otherwise, a cycloalkyl group can be unsubstituted or substituted with a substituent disclosed herein.

“Aryloxy” refers to a radical of the formula —O(aryl), wherein the aryl radical is as defined herein. Aryloxy includes, but are is not limited to, phenoxy (—O(phenyl)). Unless stated otherwise, an aryloxy group can be unsubstituted or substituted with a substituent disclosed herein.

“Cycloalkenyl” refers to a non-aromatic monocyclic or polycyclic hydrocarbon radical consisting of carbon and hydrogen atoms and having one or more carbon-carbon double bonds. Cycloalkenyl can include fused or bridged ring systems, having from three to twenty carbon atoms, in some embodiments having from three to ten carbon atoms. A cycloalkenyl group is attached to an atom by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless stated otherwise, a cycloalkenyl group can be unsubstituted or substituted with a substituent disclosed herein.

“Cycloalkynyl” refers to a non-aromatic monocyclic or polycyclic hydrocarbon radical consisting solely of carbon and hydrogen atoms, having one or more carbon-carbon triple bonds, which can include fused or bridged ring systems, having from five to twenty carbon atoms, in some embodiments having from five to ten carbon atoms, and which is attached to the rest of the molecule by a single bond. Monocyclic cycloalkynyl radicals include, for example, cycloheptynyl, cyclooctynyl, and the like. Unless stated otherwise, a cycloalkynyl group can be unsubstituted or substituted with a substituent disclosed herein.

“Cycloalkylalkyl” refers to a radical of the formula —$R_b$—$R_c$ where $R_b$ is an alkylene group as defined herein and $R_d$ is a cycloalkyl radical as defined herein. Unless stated otherwise, a cycloalkylalkyl group can be unsubstituted or substituted with a substituent disclosed herein. “Cycloalkylalkenyl” refers to a radical of the formula —$R_b$—$R_c$ where $R_b$ is an alkenylene group as defined herein and $R_d$ is a cycloalkyl radical as defined herein. Unless stated otherwise, a cycloalkylalkenyl group can be unsubstituted or substituted with a substituent disclosed herein. “Cycloalkylalkynyl” refers to a radical of the formula —$R_b$-$R_d$ where $R_b$ is an alkynylene group as defined herein and $R_c$ is a cycloalkyl radical as defined herein. Unless stated otherwise, a cycloalkylalkynyl group can be unsubstituted or substituted with a substituent disclosed herein.

“Cycloalkenylalkyl” refers to a radical of the formula —$R_b$—$R_c$ where $R_b$ is an alkylene group as defined herein and $R_d$ is a cycloalkenyl radical as defined herein. Unless stated otherwise, a cycloalkenylalkyl group can be unsubstituted or substituted with a substituent disclosed herein. “Cycloalkenylalkenyl” refers to a radical of the formula —$R_b$—$R_d$ where $R_b$ is an alkenylene group as defined herein and $R_c$ is a cycloalkyl radical as defined herein. Unless stated otherwise, a cycloalkenylalkenyl group can be unsubstituted or substituted with a substituent disclosed herein. “Cycloalkenylalkynyl” refers to a radical of the formula —$R_b$-$R_d$ where $R_b$ is an alkynylene group as defined herein and $R_d$ is a cycloalkyl radical as defined herein. Unless stated otherwise, a cycloalkenylalkynyl group can be unsubstituted or substituted with a substituent disclosed herein.

“Cycloalkynylalkyl” refers to a radical of the formula —$R_b$—$R_d$ where $R_b$ is an alkylene group as defined herein and $R_d$ is a cycloalkynyl radical as defined herein. Unless stated otherwise, a cycloalkynylalkyl group can be unsubstituted or substituted with a substituent disclosed herein. “Cycloalkynylalkenyl” refers to a radical of the formula —$R_b$—$R_d$ where $R_b$ is an alkenylene group as defined herein and $R_d$ is a cycloalkyl radical as defined herein. Unless stated otherwise, a cycloalkynylalkenyl group can be unsubstituted or substituted with a substituent disclosed herein. "Cycloalkynylalkynyl" refers to a radical of the formula —$R_b$—$R_d$ where $R_b$ is an alkynylene group as defined herein and $R_d$ is a cycloalkyl radical as defined herein. Unless stated otherwise, a cycloalkynylalkynyl group can be unsubstituted or substituted with a substituent disclosed herein.

"Carbocyclyl," "carbocyclic ring" or "carbocycle" refers to a ring structure, wherein the atoms which form the ring are each carbon. The carbocyclyl, carbocyclic ring or carbocycle can comprise from 3 to 20 carbon atoms in the ring. The carbocyclyl, carbocyclic ring or carbocycle includes aryl, cycloalkyl, cycloalkenyl and cycloalkynyl as defined herein. The carbocyclyl, carbocyclic ring or carbocycle can be a monocyclic, bicyclic, tricyclic or tetracyclic ring system, which can include fused, bridged, and spiral ring systems. Unless stated otherwise, a carbocyclyl group, carbocyclic ring or carbocycle can be unsubstituted or substituted with a substituent disclosed herein.

"Haloalkyl" refers to an alkyl radical, as defined herein, that is substituted by one or more halo radicals, as defined herein, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise, a haloalkyl group can be unsubstituted or substituted with a substituent disclosed herein.

"Haloalkenyl" refers to an alkenyl radical, as defined herein, that is substituted by one or more halo radicals, as defined herein, e.g., 1-fluoropropenyl, 1,1-difluorobutenyl, and the like. Unless stated otherwise, a haloalkenyl group can be unsubstituted or substituted with a substituent disclosed herein.

"Haloalkynyl" refers to an alkynyl radical, as defined herein, that is substituted by one or more halo radicals, as defined herein, e.g., 1-fluoropropynyl, 1-fluorobutynyl, and the like. Unless stated otherwise, a haloalkenyl group can be unsubstituted or substituted with a substituent disclosed herein.

"Heterocyclyl" refers to a 3- to 20-membered non-aromatic, partially unsaturated, or aromatic ring radical which includes two to twelve carbon atoms and from one to six nitrogen, oxygen or sulfur heteroatoms. Heterocycly include heteroaryls as defined herein. Unless stated otherwise, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise, a heterocyclyl group can be unsubstituted or substituted with a substituent disclosed herein.

"Heterocyclylalkyl" refers to a radical of the formula —$R_b$—$R_e$ where $R_b$ is an alkylene group as defined herein and $R_e$ is a heterocyclyl radical as defined herein. Unless stated otherwise, a heterocyclylalkyl group can be unsubstituted or substituted with a substituent disclosed herein.

"Heterocyclylalkenyl" refers to a radical of the formula —$R_b$—$R_e$ where R is an alkenylene group as defined herein and $R_e$ is a heterocyclyl radical as defined herein. Unless stated otherwise, a heterocyclylalkenyl group can be unsubstituted or substituted with a substituent disclosed herein.

"Heterocyclylalkynyl" refers to a radical of the formula —$R_b$—$R_e$ where $R_b$ is an alkynylene group as defined herein and $R_e$ is a heterocyclyl radical as defined herein. Unless stated otherwise, a heterocyclylalkynyl group can be unsubstituted or substituted with a substituent disclosed herein.

"N-heterocyclyl" refers to a heterocyclyl radical as defined herein including at least one nitrogen and where the point of attachment of the heterocyclyl radical of an atom of a compound of the invention is through a nitrogen atom in the heterocyclyl radical. Unless stated otherwise, an N-heterocyclyl group can be unsubstituted or substituted with a substituent disclosed herein.

"Heteroaryl" refers to a 5- to 20-membered ring system radical including hydrogen atoms, one to thirteen carbon atoms, one to six nitrogen, oxygen or sulfur heteroatoms, and at least one aromatic ring. The heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples of heteroaryl include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thienyl). Unless stated otherwise, a heteroaryl group can be unsubstituted or substituted.

"N-heteroaryl" refers to a heteroaryl radical as defined herein having at least one nitrogen atom and where the point of attachment of the heteroaryl radical to an atom of the compound of the invention is through a nitrogen atom in the heteroaryl radical. Unless stated otherwise, an N-heteroaryl group can be unsubstituted or substituted with a substituent disclosed herein.

"Heteroarylalkyl" refers to a radical of the formula —$R_b$-$R_f$ where $R_b$ is an alkylene chain as defined herein and $R_f$ is a heteroaryl radical as defined herein. Unless stated otherwise, a heteroarylalkyl group can be unsubstituted or substituted with a substituent disclosed herein.

"Heteroarylalkenyl" refers to a radical of the formula —$R_b$—$R_f$ where $R_b$ is an alkenylene chain as defined herein and $R_f$ is a heteroaryl radical as defined herein. Unless stated otherwise, a heteroarylalkenyl group can be unsubstituted or substituted with a substituent disclosed herein.

"Heteroarylalkynyl" refers to a radical of the formula $—R_b\text{-}R_f$ where $R_b$ is an alkynylene chain as defined herein and $R_f$ is a heteroaryl radical as defined herein. Unless stated otherwise, a heteroarylalkynyl group can be unsubstituted or substituted with a substituent disclosed herein.

"Ring" refers to a cyclic group which can be saturated or include one or more double or triple bonds. A ring can be monocyclic, bicyclic, tricyclic, or tetracyclic. Unless stated otherwise, a ring can be unsubstituted or substituted with a substituent disclosed herein.

"Thioalkyl" refers to a radical of the formula $—SR_a$ where $R_a$ is an alkyl, alkenyl, or alkynyl radical as defined herein. Unless stated otherwise, a thioalkyl group can be unsubstituted or substituted with a substituent disclosed herein.

"Ms" refers to a mesyl (methanesulfonyl) group.

"Ts" refers to a tosyl (4-toluenesulfonyl) group.

A group or radical disclosed herein can be substituted with one or more of the following substitutents: a halogen atom such as F, Cl, Br, and I; a hydroxyl, alkoxy, or ester; thiol, thioalkyl, sulfone, sulfonyl, or sulfoxide; amine, amide, alkylamine, dialkylamine, arylamine, alkylarylamine, diarylamine, N-oxide, imide, and enamine; trialkylsilyl, dialkylarylsilyl, alkyldiarylsilyl, and triarylsilyl; and other groups, optionally including one or more heteroatoms.

In some embodiments, a group or radical disclosed herein is alternatively or additionally substituted with one or more of the following substituents: oxo, carbonyl, carboxyl, or an ester group; or an imine, oxime, hydrazone, and nitrile.

In some embodiments, a group or radical disclosed herein is alternatively or additionally substituted with one or more of the following substituents: an amino, cyano, hydroxyl, imino, nitro, oxo, thioxo, halo, alkyl, alkenyl, alkynyl, alkoxy, alkylamino, thioalkyl, aryl, arylalkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and heteroarylalkyl group, $—NR_gR_h$, $—NR_gC({=}O)R_h$, $—NR_gC({=}O)NR_gR_h$, $—NR_gC({=}O)OR_h$, $—NR_gSO_2R_h$, $—OC({=}O)NR_gR_h$, $—OR_g$, $—SR_g$, $—SOR_g$, $—SO_2R_g$, $—OSO_2R_g$, $—SO_2OR_g$, $=NSO_2R_g$, $—SO_2NR_gR_h$, $—C({=}O)R_g$, $—C({=}O)OR_g$, $—C({=}O)NR_gR_h$, $—CH_2SO_2R_g$ and $—CH_2SO_2NR_gR_h$, wherein $R_g$ and $R_h$ are the same or different and independently hydrogen, alkyl, alkenyl, alkynyl, alkoxy, alkylamino, thioalkyl, aryl, arylalkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl or heteroarylalkyl, wherein each of the foregoing substituents is unsubstituted or substituted with one or more substituents disclosed herein.

As used herein, "isolated and purified" means isolated and purified from a chemical synthesis reaction mixture, from an organism that is or was living or from cells (e.g., biosynthesis) in vivo or in vitro. In some embodiments, an isolated and purified compound of the invention is at least 90% pure. By "is at least x % pure" means that the compound of the invention includes no more than (100−x) % of one or more other compounds. In some embodiments, an isolated and purified compound, salt or solvate thereof, is at least 95% pure. In some embodiments, an isolated and purified compound, salt or solvate thereof, is at least 96%, at least 97%, at least 98%, or at least 99% pure.

As used herein, the symbol  (a "point of attachment bond") denotes a bond that is a point of attachment between two chemical entities, one of which is depicted as being attached to the point of attachment bond and the other of which is not depicted as being  attached to the point of attachment bond. For example,  indicates that the chemical entity "XY" is bonded to another chemical entity via the point of attachment bond.

A Coenzyme A (CoA) has the structure:

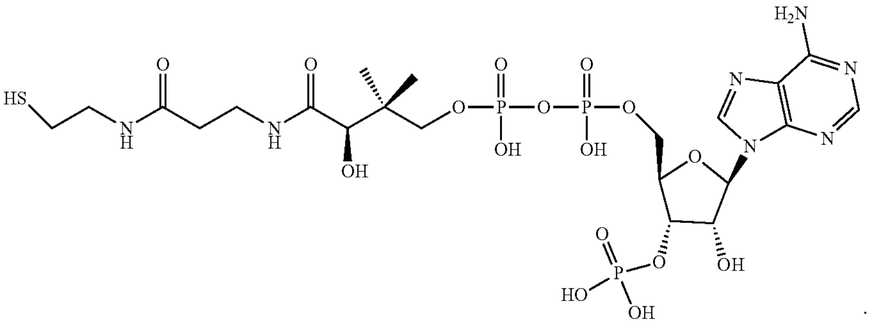

A CoA radical, which is denoted as "—CoA" herein has the following structure:

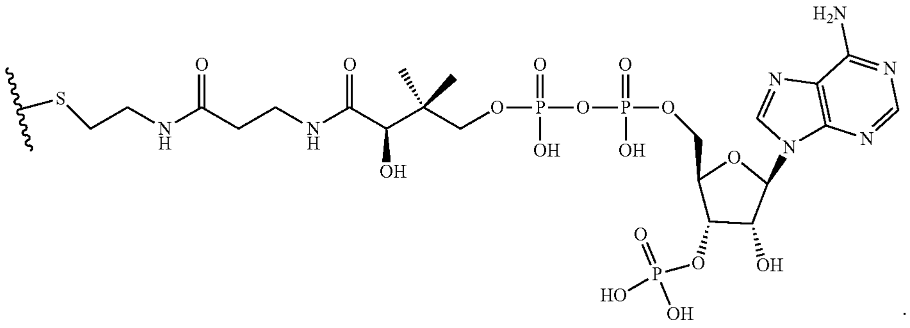

.

The Compounds of the Invention

CoA Ester Compounds of Formula (I)

In some embodiments, the compound of the invention is a compound of Formula (I):

(I)

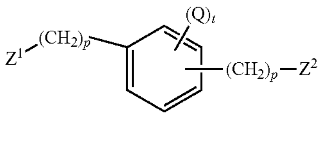

or a pharmaceutically acceptable salt or solvate thereof, wherein:

each p is independently 1, 2, 3, 4, 5, 6, or 7;

each $Z^1$ and $Z^2$ is independently $—C(R^1)(R^2)—(CH_2)_c—X$ or $—W—(CH_2)_c—C(R^3)(R^4)—Y$;

each c is independently 0, 1, 2, or 3;

each $R^1$ and $R^2$ is independently $—C_1$-$C_6$ alkyl, $—C_2$-$C_6$ alkenyl, $—C_2$-$C_6$ alkynyl, phenyl or benzyl, or each carbon atom together with the $R^1$ and $R^2$ attached to the carbon atom independently form a $—C_3$-$C_7$ cycloalkyl group;

each $R^3$ and $R^4$ is independently H, $—C_1$-$C_6$ alkyl, $—C_2$-$C_6$ alkenyl, $—C_2$-$C_6$ alkynyl, $—O(C_1$-$C_6$ alkyl), phenyl, benzyl, Cl, Br, CN, $NO_2$, or $CF_3$, or each carbon atom together with the $R^3$ and $R^4$ attached to the carbon atom independently form a $—C_3$-$C_7$ cycloalkyl group;

Q is independently —OH, $—C_1$-$C_6$ alkyl, $—O(C_1$-$C_6$ alkyl), phenoxy, aryloxy, benzyl, —S-aryl, $—SR^{1A}$, $—NR^{1A}R^{2A}$, F, Cl, Br, I, $—CF_3$, $—COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, $—C_1$-$C_6$ alkyl, $—C_2$-$C_6$ alkenyl, $—C_2$-$C_6$ alkynyl, phenyl or benzyl;

t is 0, 1, 2, 3, or 4;

each X and Y is independently —OH, —COOH, $—COOR^5$, $—CONH_2$, $—CONHR^5$, —CONHMs, —CONHTs, $—SO_3H$,

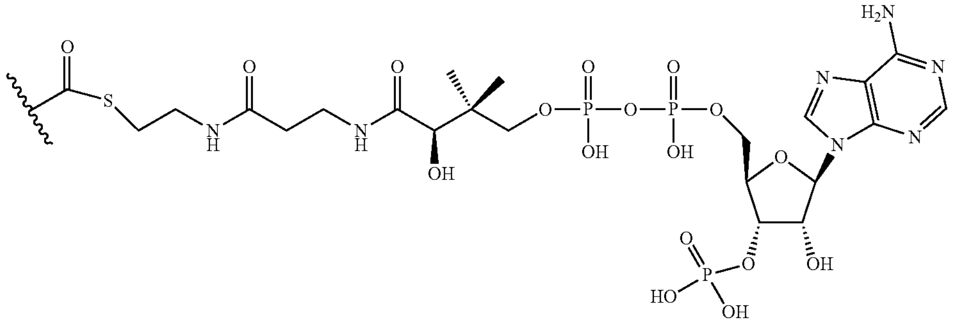

(—CO—CoA),

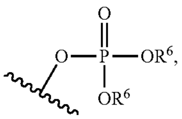

,

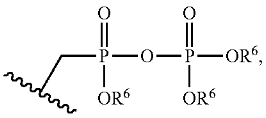

,

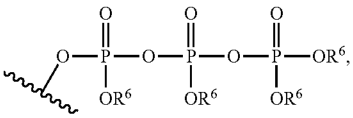

,

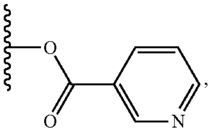

,

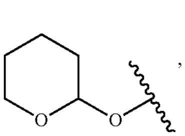

,

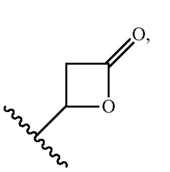

,

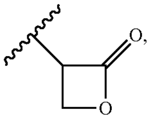

,

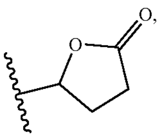

,

-continued

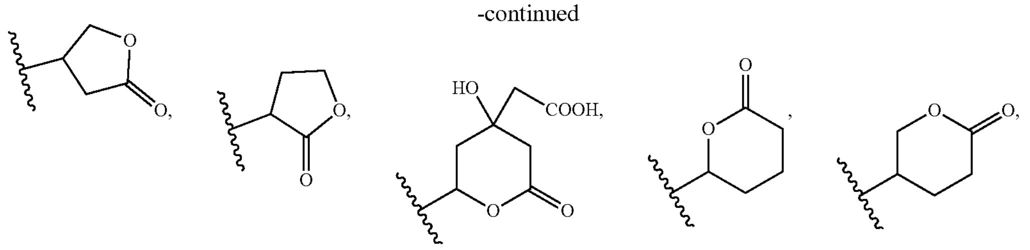

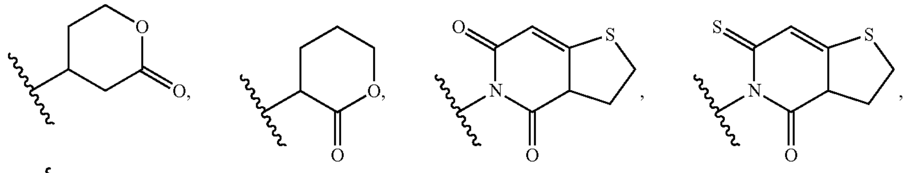

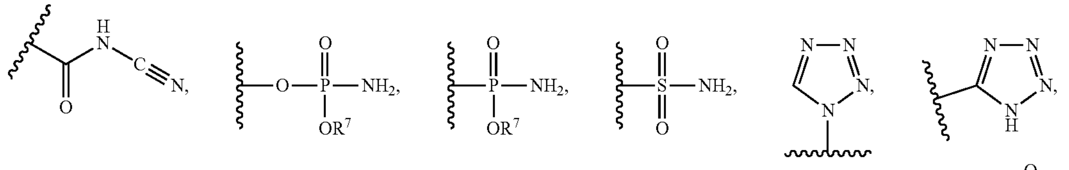

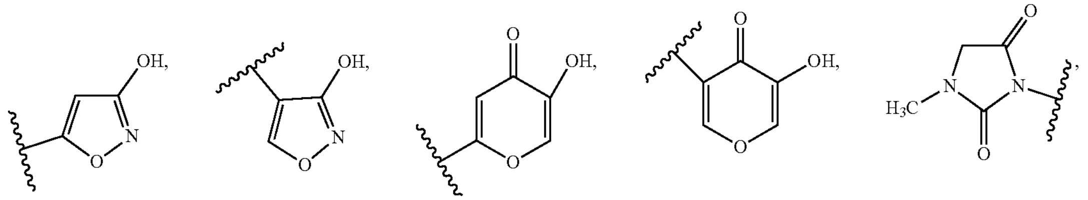

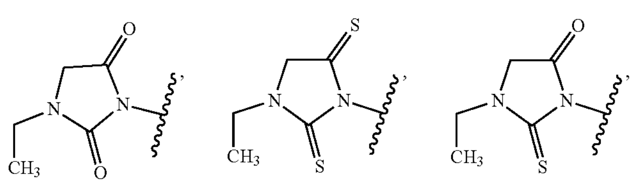

or

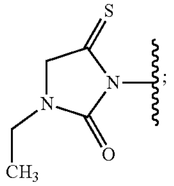

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups;

each $R^7$ is independently H, $-C_1$-$C_6$ alkyl, $-C_2$-$C_6$ alkenyl, or $-C_2$-$C_6$ alkynyl;

each W is independently —O—, —NH—, —N(OH)—, —N(→O)—, —S—, —S(═O)—, $-S(O)_2-$, or —Se—;

each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups; and wherein one or both of $Z^1$ and $Z^2$ are $-C(R^1)(R^2)-(CH_2)_c-CO-CoA$, or one or both of $Z^1$ and $Z^2$ are $-W-(CH_2)_c-C(R^3)(R^4)-CO-CoA$.

In some embodiments, the compound of formula (I) has the structure of Formula (IA), Formula (IB), or Formula (IC), or a pharmaceutically acceptable salt or solvate thereof:

(IA)

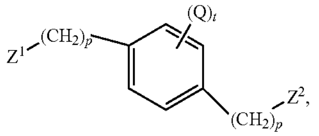

(IB)

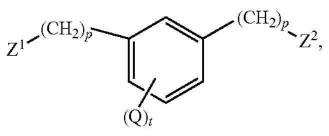

or (IC)

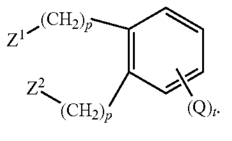

In some embodiments of the compounds of Formula (I), (IA), (IB), or (IC), one or both of $Z^1$ and $Z^2$ are $-C(R^1)(R^2)-(CH_2)_c-CO-CoA$. In some embodiments, one or both of $Z^1$ and $Z^2$ are $-W-(CH_2)_c-C(R^3)(R^4)-Co-CoA$.

In some embodiments, of the compounds of Formula (I), (IA), (IB), or (IC), $Z^1$ is $-C(R)(R^2)(R^2)-(CH_2)_c-CO-CoA$ and $Z^2$ is $-C(R^1)(R^2)-(CH_2)_c-COOH$ or $-C(R^1)(R^2)-(CH_2)_c-COOR^5$.

In some embodiments of the compounds of Formula (I), (IA), (IB), or (IC), each $R^1$ and $R^2$ is independently —$C_1$-$C_6$ alkyl, —$C_2$-$C_6$ alkenyl, or —$C_2$-$C_6$ alkynyl. In some embodiments, each $R^1$ and $R^2$ is independently —$C_1$-$C_3$ alkyl, —$C_2$-$C_3$ alkenyl, or —$C_2$-$C_3$ alkynyl. In some embodiments, $R^1$ and $R^2$ are methyl.

In some embodiments of the compounds of Formula (I), (IA), (IB), or (IC), $Z^1$ is —$C(R^1)(R^2)$—$(CH_2)_c$—CO—CoA and $Z^2$ is —$C(R^1)(R^2)$—$(CH_2)_c$—X, where X is —CO—CoA, —COOH or —$COOR^5$, and $R^1$ and $R^2$ are methyl.

In some embodiments of the compounds of Formula (I), (IA), (IB), or (IC), c is 0 or 1. In some embodiments, c is 0. In some embodiments, c is 1. In some embodiments, c is 2. In some embodiments, c is 3.

In some embodiments of the compounds of Formula (I), (IA), (IB), or (IC), each carbon atom together with the $R^1$ and $R^2$ attached to the carbon atom independently form a —$C_3$-$C_7$ cycloalkyl group. In some embodiments, each carbon atom together with the $R^1$ and $R^2$ attached to the carbon atom independently form a cyclopropyl ring.

In some embodiments of the compounds of Formula (I), (IA), (IB), or (IC), at least one $R^1$ and one $R^2$ together with the carbon atom to which they are attached form a —$C_3$-$C_7$ cycloalkyl group. In some embodiments, at least one $R^1$ and one $R^2$ together with the carbon atom to which they are attached form a cyclopropyl ring.

In some embodiments of the compounds of Formula (I), (IA), (IB), or (IC), $R^3$ and $R^4$ is independently H, —$C_1$-$C_6$ alkyl, —$C_2$-$C_6$ alkenyl, or —$C_2$-$C_6$ alkynyl.

In some embodiments of the compounds of Formula (I), (IA), (IB), or (IC), Y is —COOH or —$COOR^5$.

In some embodiments of the compounds of Formula (I), (IA), (IB), or (IC), $R^5$ is —$C_1$-$C_6$ alkyl, —$C_2$-$C_6$ alkenyl, or —$C_2$-$C_6$ alkynyl. In some embodiments, $R^5$ is —$C_1$-$C_3$ alkyl, —$C_2$-$C_3$ alkenyl, or —$C_2$-$C_3$ alkynyl.

In some embodiments of the compounds of Formula (I), (IA), (IB), or (IC), p is 3, 4, 5, 6, or 7. In some embodiments, p is 4, 5, 6, or 7.

In some embodiments of the compounds of Formula (I), (IA), (IB), or (IC), $Z^1$ is —W—$(CH_2)_c$—$C(R^3)(R^4)$—CO—CoA, $Z^2$ is —W—$(CH_2)_c$—$C(R^3)(R^4)$—Y, and $R^3$ and R is independently H, —$C_1$-$C_6$ alkyl, —$C_2$-$C_6$ alkenyl, or —$C_2$-$C_6$ alkynyl. In some embodiments, $Z^1$ is —W—$(CH_2)_c$—$C(R^3)(R^4)$—CO—CoA, $Z^2$ is —W—$(CH_2)_c$—$C(R^3)(R^4)$—Y, and Y is —CO—CoA, —COOH or —$COOR^5$. In some embodiments, $Z^1$ is —W—$(CH_2)_c$—$(R^3(R^4)$—CO—CoA, $Z^2$ is —W—$(CH_2)_c$—$C(R^3)(R^4)$—Y, Y is —CO—CoA, —COOH or —$COOR^5$, and $R^5$ is —$C_1$-$C_6$ alkyl, —$C_2$-$C_6$ alkenyl, or —$C_2$-$C_6$ alkynyl. In some embodiments, $Z^1$ is —W—$(CH_2)_c$—$(R^3)(R^4)$—CO—CoA, $Z^2$ is —W—$(CH_2)_c$—$C(R^3)(R^4)$—Y, Y is —CO—CoA, —COOH or —$COOR^5$, and $R^5$ is —$C_1$-$C_3$ alkyl, —$C_2$-$C_3$ alkenyl, or —$C_2$-$C_3$ alkynyl.

In some embodiments of the compound of Formula (I), (IA), (IB), or (IC), Q is independently methyl, methoxy, or —OH. In some embodiments, Q is methyl or —OH.

In some embodiments of the compound of Formula (I), (IA), (IB), or (IC), t is 0. In some embodiments, t is 1. In some embodiments, t is 2. In some embodiments, t is 3.

In some embodiments, the compound of Formula (I) or (IA) has any one of the structures shown in Table A-1, or a pharmaceutically acceptable salt or solvate thereof.

TABLE A-1

| Compound No. | Structure and Name |
|---|---|
| III-1-CoA | 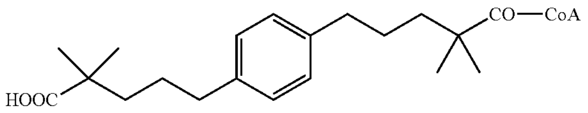<br>5-[4-(4-Carboxy-4-methylpentyl)-phenyl]-2,2-dimethylpentanoic acid Coenzyme A ester |
| III-1-$(CoA)_2$ | 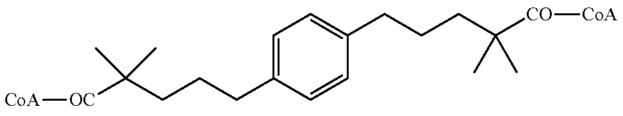<br>5-[4-(4-Carboxy-4-methylpentyl)-phenyl]-2,2-dimethylpentanoic acid di-Coenzyme A ester |
| I-1-CoA | 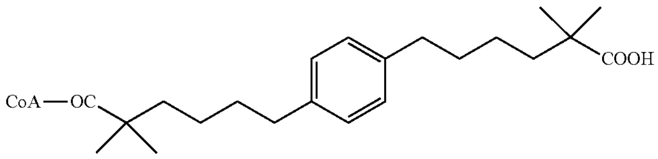<br>6-[4-(5-Carboxy-5-methyl-hexyl)-phenyl]-2,2,-dimethylhexanoic acid Coenzyme A ester |

TABLE A-1-continued

| Compound No. | Structure and Name |
|---|---|
| I-1-(CoA)$_2$ | 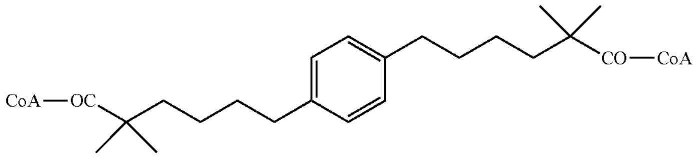<br>6-[4-(5-Carboxy-5-methyl-hexyl)-phenyl]-2,2,-dimethylhexanoic acid di-Coenzyme A ester |
| I-2A-CoA | 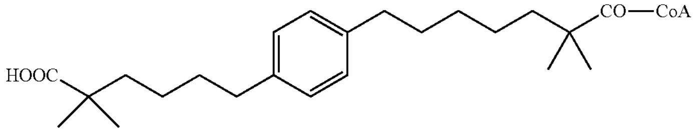<br>7-(4-(5-Carboxy-5-methylhexyl)phenyl)-2,2-dimethylheptanoic acid Coenzyme A ester |
| I-2B-CoA | 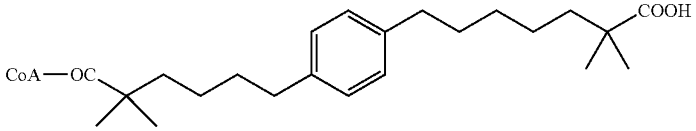<br>7-(4-(5-Carboxy-5-methylhexyl)phenyl)-2,2-dimethylheptanoic acid Coenzyme A ester |
| I-2-(CoA)$_2$ | 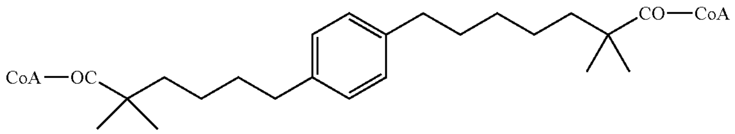<br>7-(4-(5-Carboxy-5-methylhexyl)phenyl)-2,2-dimethylheptanoic acid di-Coenzyme A ester |
| I-3-CoA | 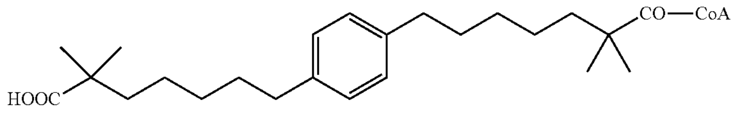<br>7,7'-(1,4-Phenylene)bis(2,2-dimethylheptanoic acid) Coenzyme A ester |
| I-3-(CoA)$_2$ | 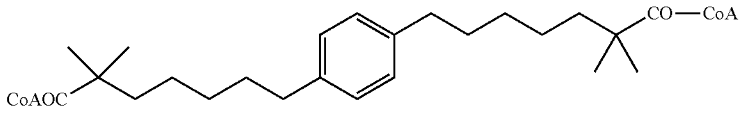<br>7,7'-(1,4-Phenylene)bis(2,2-dimethylheptanoic acid) di-Coenzyme A ester |
| I-4A-CoA | 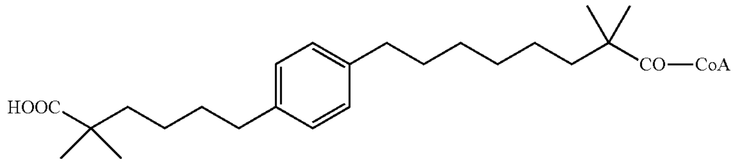<br>8-(4-(5-Carboxy-5-methylhexyl)phenyl)-2,2-dimethyloctanoic acid Coenzyme A ester |

TABLE A-1-continued

| Compound No. | Structure and Name |
|---|---|
| I-4B-CoA | 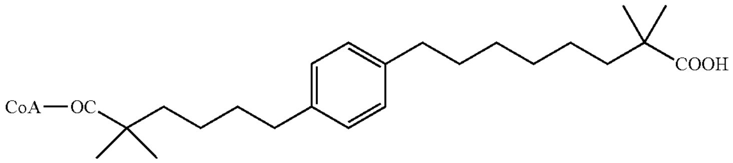<br>8-(4-(5-Carboxy-5-methylhexyl)phenyl)-2,2-dimethyloctanoic acid Coenzyme A ester |
| I-4-$(CoA)_2$ | 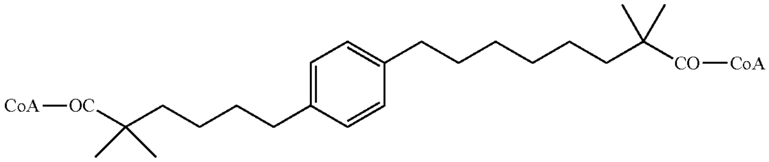<br>8-(4-(5-Carboxy-5-methylhexyl)phenyl)-2,2-dimethyloctanoic acid di-Coenzyme A ester |
| I-5A-CoA | 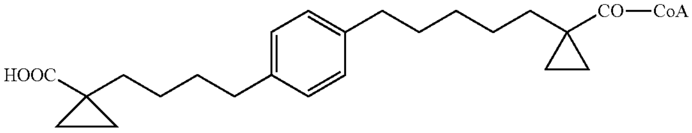<br>1-(5-(4-(4-(1-carboxycyclopropyl)butyl)phenyl)pentyl)cyclopropane-1-carboxylic acid Coenzyme A ester |
| I-5B-CoA | 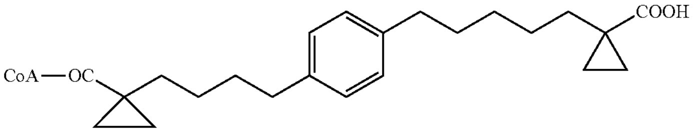<br>1-(5-(4-(4-(1-carboxycyclopropyl)butyl)phenyl)pentyl)cyclopropane-1-carboxylic acid Coenzyme A ester |
| I-5-$(CoA)_2$ | 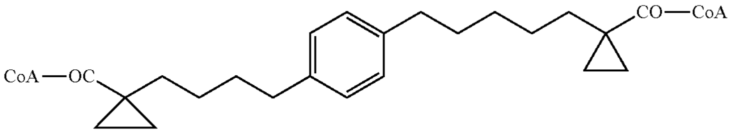<br>1-(5-(4-(4-(1-carboxycyclopropyl)butyl)phenyl)pentyl)cyclopropane-1-carboxylic acid di-Coenzyme A ester |
| I-6A-CoA | 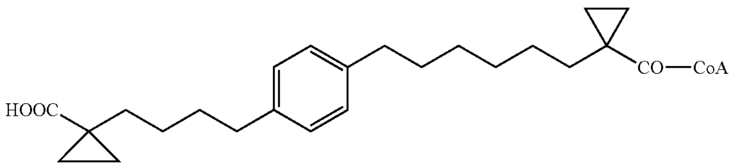<br>1-(6-(4-(4-(1-carboxycyclopropyl)butyl)phenyl)hexyl)cyclopropane-1-carboxylic acid Coenzyme A ester |
| I-6B-CoA | 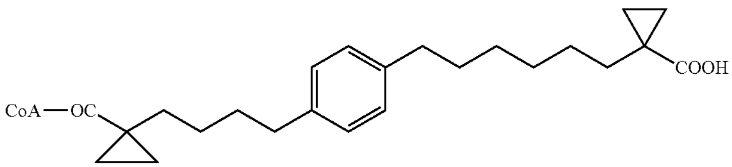<br>1-(6-(4-(4-(1-carboxycyclopropyl)butyl)phenyl)hexyl)cyclopropane-1-carboxylic acid Coenzyme A ester |

TABLE A-1-continued

| Compound No. | Structure and Name |
| --- | --- |
| I-6-(CoA)$_2$ | 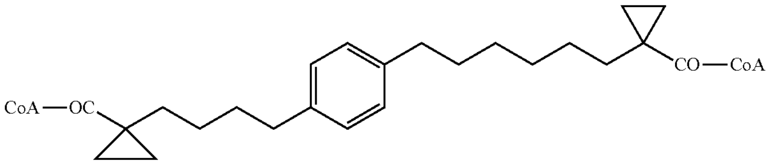 1-(6-(4-(4-(1-carboxycyclopropyl)butyl)phenyl)hexyl)cyclopropane-1-carboxylic acid di-Coenzyme A ester |
| I-7-CoA | 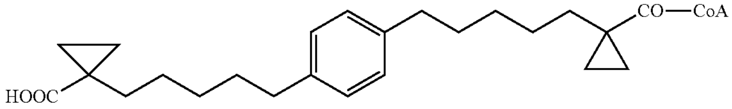 1,1'-(1,4-phenylenebis(pentane-5,1-diyl))bis(cyclopropane-1-carboxylic acid) Coenzyme A ester |
| I-7-(CoA)$_2$ | 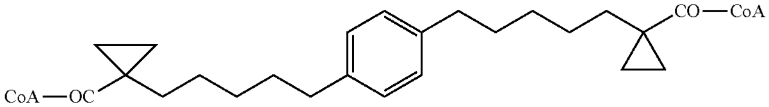 1,1'-(1,4-phenylenebis(pentane-5,1-diyl))bis(cyclopropane-1-carboxylic acid) di-Coenzyme A ester |
| I-8A-CoA | 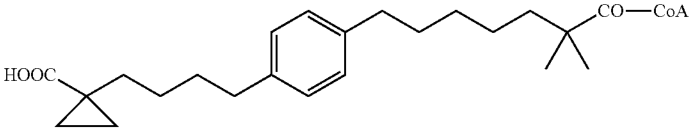 1-(4-(4-(6-carboxy-6-methylheptyl)phenyl)butyl)cyclopropane-1-carboxylic acid Coenzyme A ester |
| I-8B-CoA | 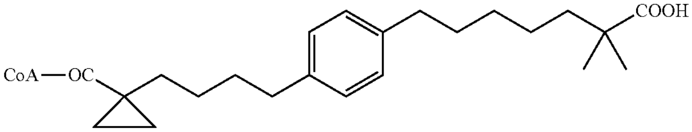 1-(4-(4-(6-carboxy-6-methylheptyl)phenyl)butyl)cyclopropane-1-carboxylic acid Coenzyme A ester |
| I-8-(CoA)$_2$ | 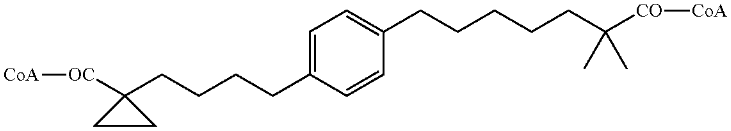 1-(4-(4-(6-carboxy-6-methylheptyl)phenyl)butyl)cyclopropane-1-carboxylic acid di-Coenzyme A ester |
| I-9A-CoA | 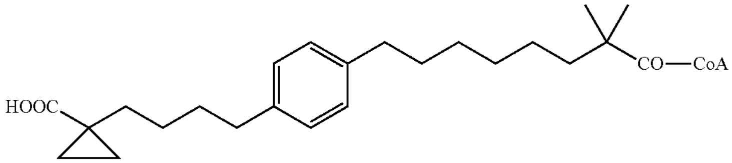 1-(4-(4-(7-carboxy-7-methyloctyl)phenyl)butyl)cyclopropane-1-carboxylic acid Coenzyme A ester |

TABLE A-1-continued

| Compound No. | Structure and Name |
|---|---|
| I-9B-CoA | 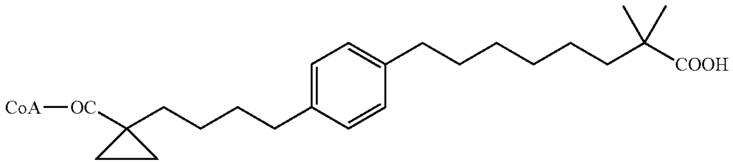 1-(4-(4-(7-carboxy-7-methyloctyl)phenyl)butyl)cyclopropane-1-carboxylic acid Coenzyme A ester |
| I-9-$(CoA)_2$ | 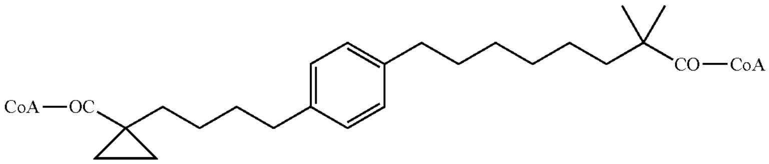 1-(4-(4-(7-carboxy-7-methyloctyl)phenyl)butyl)cyclopropane-1-carboxylic acid di-Coenzyme A ester |
| I-10A-CoA | 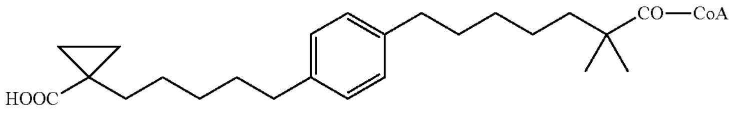 1-(5-(4-(6-carboxy-6-methylheptyl)phenyl)pentyl)cyclopropane-1-carboxylic acid Coenzyme A ester |
| I-10B-CoA | 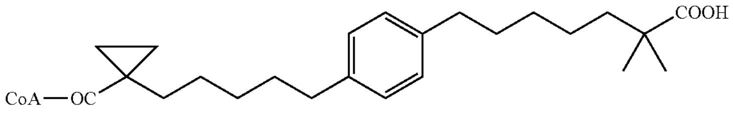 1-(5-(4-(6-carboxy-6-methylheptyl)phenyl)pentyl)cyclopropane-1-carboxylic acid Coenzyme A ester |
| I-10-$(CoA)_2$ | 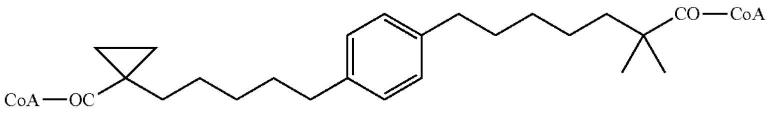 1-(5-(4-(6-carboxy-6-methylheptyl)phenyl)pentyl)cyclopropane-1-carboxylic acid di-Coenzyme A ester |
| I-78-CoA | 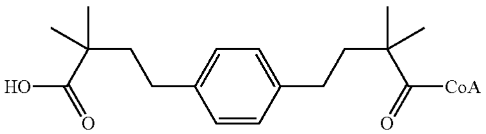 4,4'-(1,4-Phenylene)bis(2,2-dimethylbutanoic acid) Coenzyme A ester |
| I-78-$(CoA)_2$ | 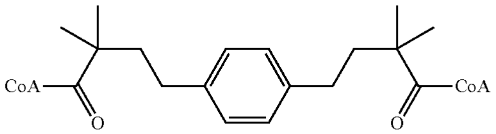 4,4'-(1,4-Phenylene)bis(2,2-dimethylbutanoic acid) di-Coenzyme A ester |
| I-79A-CoA | 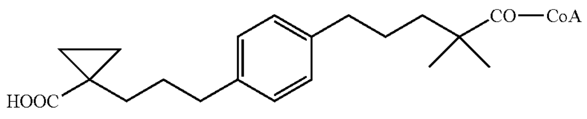 1-(3-(4-(4-carboxy-4-methylpentyl)phenyl)propyl)cyclopropane-1-carboxylic acid Coenzyme A ester |

TABLE A-1-continued

| Compound No. | Structure and Name |
|---|---|
| I-79B-CoA | 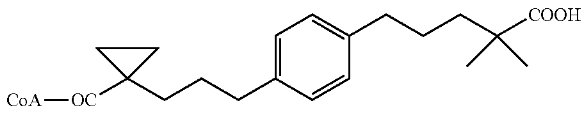 1-(3-(4-(4-carboxy-4-methylpentyl)phenyl)propyl)cyclopropane-1-carboxylic acidCoenzyme A ester |
| I-79-(CoA)$_2$ | 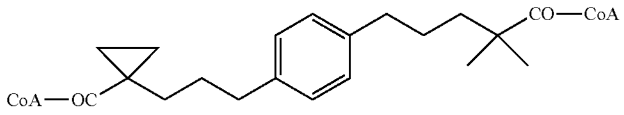 1-(3-(4-(4-carboxy-4-methylpentyl)phenyl)propyl)cyclopropane-1-carboxylic acid di-Coenzyme A ester |
| I-80A-CoA | 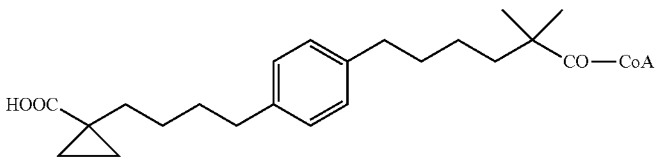 1-(4-(4-(5-carboxy-5-methylhexyl)phenyl)butyl)cyclopropane-1-carboxylic acid Coenzyme A ester |
| I-80B-CoA | 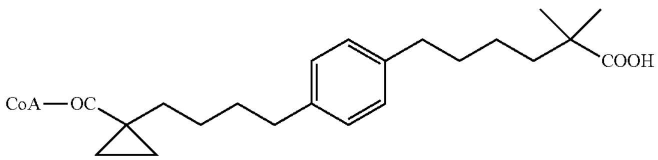 1-(4-(4-(5-carboxy-5-methylhexyl)phenyl)butyl)cyclopropane-1-carboxylic acid Coenzyme A ester |
| I-80-(CoA)$_2$ | 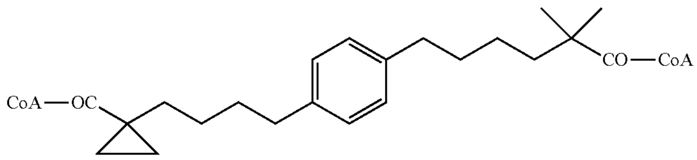 1-(4-(4-(5-carboxy-5-methylhexyl)phenyl)butyl)cyclopropane-1-carboxylic acid di-Coenzyme A ester |
| I-81-CoA | 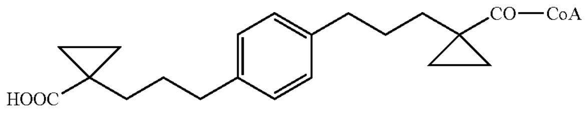 1,1'-(1,4-phenylenebis(propane-3,1-diyl))bis(cyclopropane-1-carboxylic acid) Coenzyme A ester |
| I-81-(CoA)$_2$ | 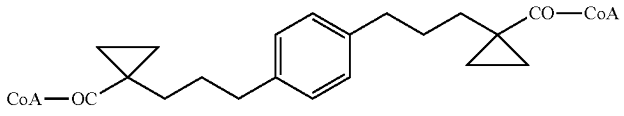 1,1'-(1,4-phenylenebis(propane-3,1-diyl))bis(cyclopropane-1-carboxylic acid) di-Coenzyme A ester |

TABLE A-1-continued

| Compound No. | Structure and Name |
|---|---|
| I-82-CoA | 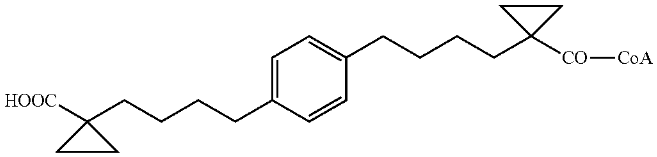 1,1'-(1,4-phenylenebis(butane-4,1-diyl))bis(cyclopropane-1-carboxylic acid) Coenzyme A ester |
| I-82-(CoA)2 | 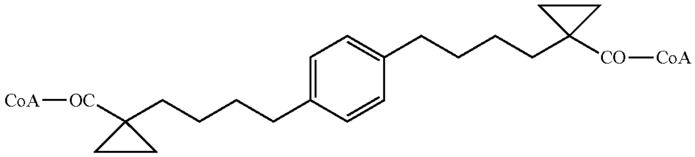 1,1'-(1,4-phenylenebis(butane-4,1-diyl))bis(cyclopropane-1-carboxylic acid) di-Coenzyme A ester |
| I-84-CoA | 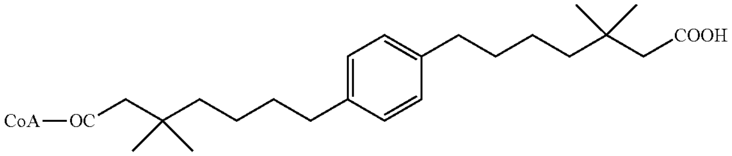 7,7'-(1,4-phenylene)bis(3,3-dimethylheptanoic acid) Coenzyme A ester |
| I-84-$(CoA)_2$ | 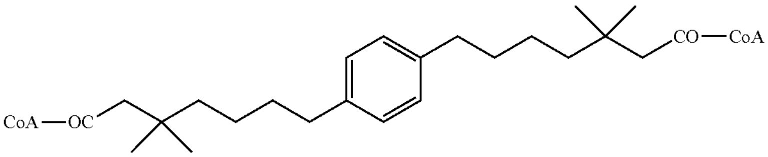 7,7'-(1,4-phenylene)bis(3,3-dimethylheptanoic acid) di-Coenzyme A ester |
| I-87A-CoA | 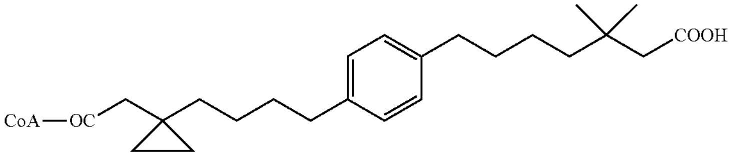 7-(4-(4-(1-(carboxymethyl)cyclopropyl)butyl)phenyl)-3,3-dimethylheptanoic acid Coenzyme A ester |
| I-87B-CoA | 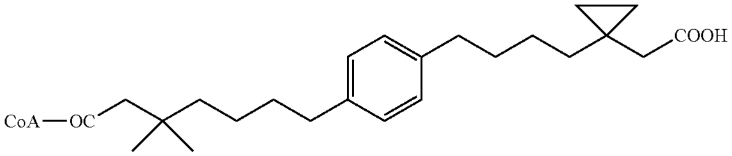 7-(4-(4-(1-(carboxymethyl Coenzyme A ester)cyclopropyl)butyl)-phenyl)-3,3-dimethylheptanoic acid |
| I-87-$(CoA)_2$ | 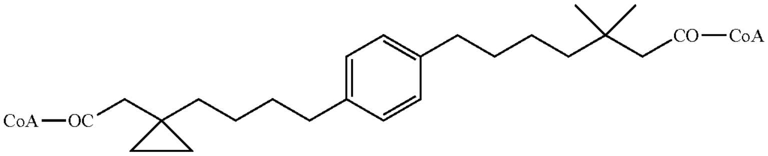 7-(4-(4-(1-(carboxymethyl)cyclopropyl)butyl)phenyl)-3,3-dimethylheptanoic acid di-Coenzyme A ester |

TABLE A-1-continued

| Compound No. | Structure and Name |
|---|---|
| I-88-CoA | 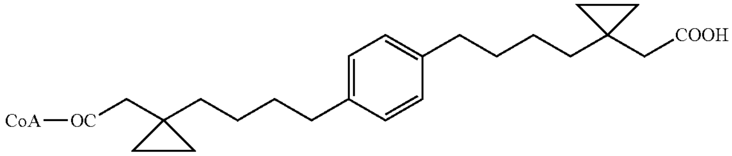<br>2,2'-((1,4-phenylenebis(butane-4,1-diyl))bis(cyclopropane-1,1-diyl))diacetic acid Coenzyme A ester |
| I-88-$(CoA)_2$ | 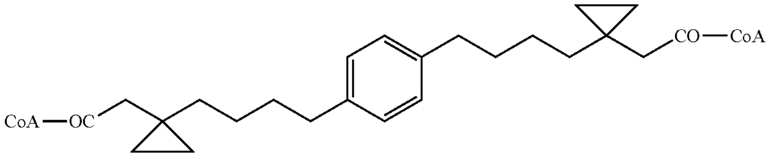<br>2,2'-((1,4-phenylenebis(butane-4,1-diyl))bis(cyclopropane-1,1-diyl))diacetic acid di-Coenzyme A ester |

In some embodiments, the compound of Formula (I) or (IB) has any one of the structures shown in Table A-2, or a pharmaceutically acceptable salt or solvate thereof.

TABLE A-2

| Compound No. | Structure and Name |
|---|---|
| I-31-CoA | 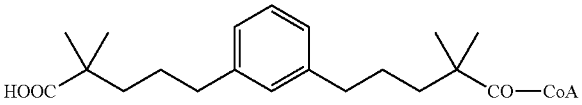<br>5-[3-(4-Carboxy-4-methylpentyl)phenyl]-2,2-dimethylpentanoic acid Coenzyme A ester |
| I-31-$(CoA)_2$ | 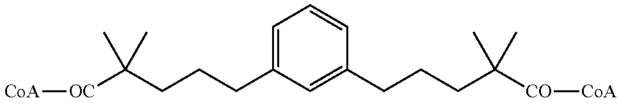<br>5-[3-(4-Carboxy-4-methylpentyl)phenyl]-2,2-dimethylpentanoic acid di-Coenzyme A ester |
| I-32-CoA | 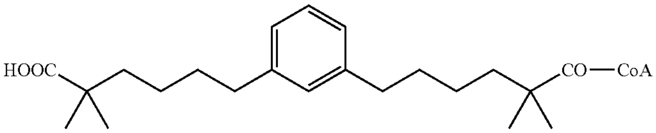<br>6-[3-(5-Carboxy-5-methylhexyl)-phenyl]-2,2-dimethylhexanoic acid Coenzyme A ester |
| I-32-$(CoA)_2$ | 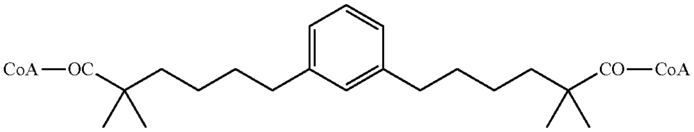<br>6-[3-(5-Carboxy-5-methylhexyl)-phenyl]-2,2-dimethylhexanoic acid di-Coenzyme A ester |
| I-33A-CoA | 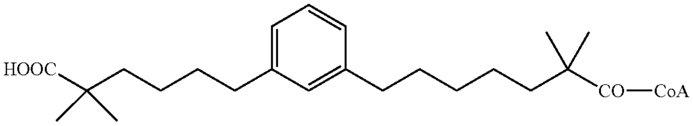 |

TABLE A-2-continued

| Compound No. | Structure and Name |
| --- | --- |
| | 7-(3-(5-Carboxy-5-methylhexyl)phenyl)-2,2-dimethylheptanoic acid Coenzyme A ester |
| I-33B-CoA | 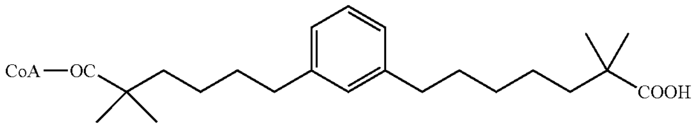 7-(3-(5-Carboxy-5-methylhexyl)phenyl)-2,2-dimethylheptanoic acid Coenzyme A ester |
| I-33-(CoA)$_2$ | 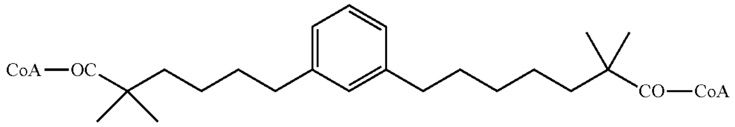 7-(3-(5-Carboxy-5-methylhexyl)phenyl)-2,2-dimethylheptanoic acid di-Coenzyme A ester |
| I-34-CoA | 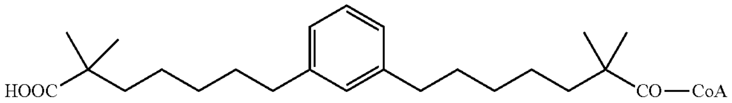 7,7'-(1,3-Phenylene)bis(2,2-dimethylheptanoic acid)Coenzyme A ester |
| I-34-(CoA)$_2$ | 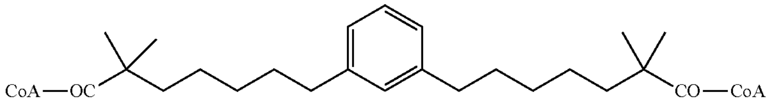 7,7'-(1,3-Phenylene)bis(2,2-dimethylheptanoic acid)di-Coenzyme A ester |
| I-35A-CoA | 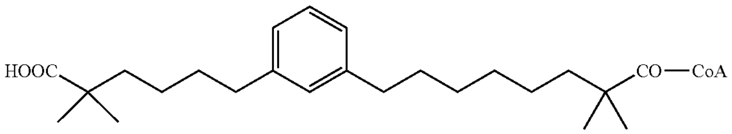 8-(3-(5-Carboxy-5-methylhexyl)phenyl)-2,2-dimethyloctanoic acid Coenzyme A ester |
| I-35B-CoA | 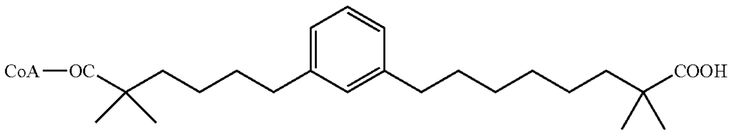 8-(3-(5-Carboxy-5-methylhexyl)phenyl)-2,2-dimethyloctanoic acid Coenzyme A ester |
| I-35-(CoA)$_2$ | 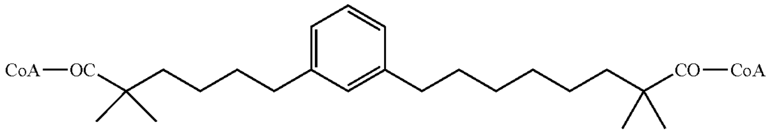 8-(3-(5-Carboxy-5-methylhexyl)phenyl)-2,2-dimethyloctanoic acid di-Coenzyme A ester |
| I-36-CoA | 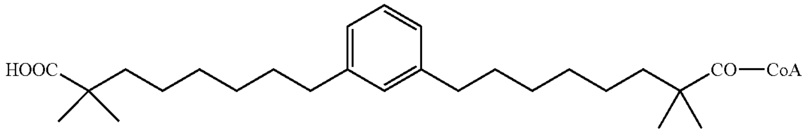 8,8'-(1,3-Phenylene)bis(2,2-dimethyloctanoic acid)Coenzyme A ester |

TABLE A-2-continued

| Compound No. | Structure and Name |
|---|---|
| I-36-(CoA)$_2$ | 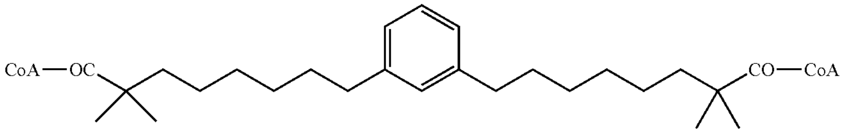 8,8'-(1,3-Phenylene)bis(2,2-dimethyloctanoic acid)di-Coenzyme A ester |
| I-37A-CoA | 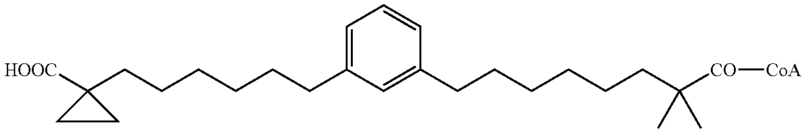 1-(6-(3-(7-carboxy-7-methyloctyl)phenyl)hexyl)cyclopropane-1-carboxylic acid Coenzyme A ester |
| I-37B-CoA | 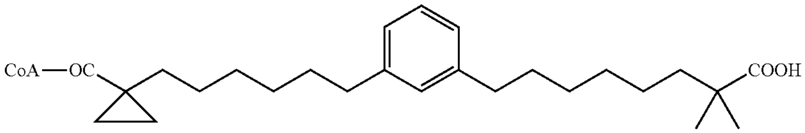 1-(6-(3-(7-carboxy-7-methyloctyl)phenyl)hexyl)cyclopropane-1-carboxylic acid Coenzyme A ester |
| I-37-(CoA)$_2$ | 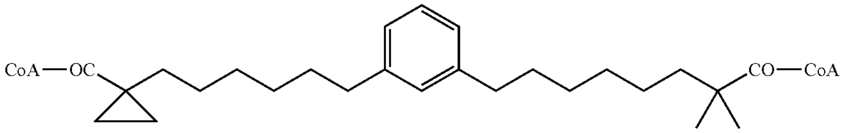 1-(6-(3-(7-carboxy-7-methyloctyl)phenyl)hexyl)cyclopropane-1-carboxylic acid di-Coenzyme A ester |
| I-38-CoA | 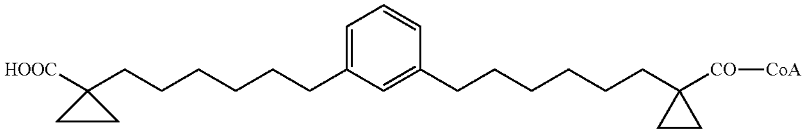 1,1'-(1,3-phenylenebis(hexane-6,1-diyl))bis(cyclopropane-1-carboxylic acid)Coenzyme A ester |
| I-38-(CoA)$_2$ | 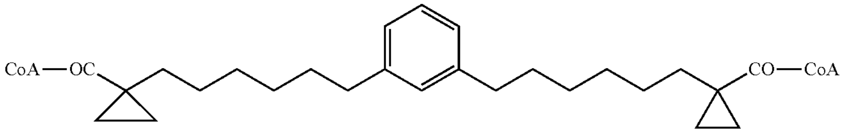 1,1'-(1,3-phenylenebis(hexane-6,1-diyl))bis(cyclopropane-1-carboxylic acid)di-Coenzyme A ester |
| I-39A-CoA | 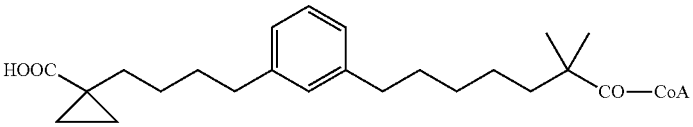 1-(4-(3-(6-carboxy-6-methylheptyl)phenyl)butyl)cyclopropane-1-carboxylic acid Coenzyme A ester |
| I-39B-CoA | 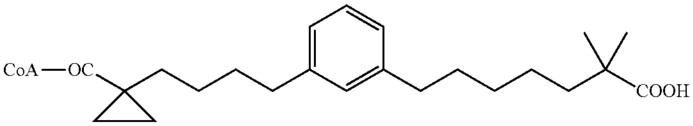 |

TABLE A-2-continued

| Compound No. | Structure and Name |
|---|---|
| | 1-(4-(3-(6-carboxy-6-methylheptyl)phenyl)butyl)cyclopropane-1-carboxylic acid Coenzyme A ester |
| I-39-(CoA)$_2$ | 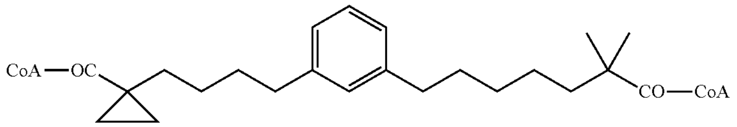 1-(4-(3-(6-carboxy-6-methylheptyl)phenyl)butyl)cyclopropane-1-carboxylic acid di-Coenzyme A ester |
| I-40A-CoA | 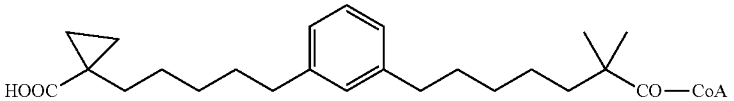 1-(5-(3-(6-carboxy-6-methylheptyl)phenyl)pentyl)cyclopropane-1-carboxylic acid Coenzyme A ester |
| I-40B-CoA | 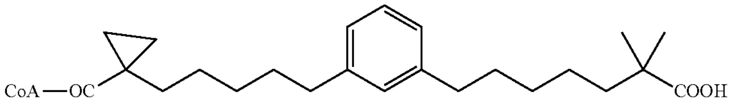 1-(5-(3-(6-carboxy-6-methylheptyl)phenyl)pentyl)cyclopropane-1-carboxylic acid Coenzyme A ester |
| I-40-(CoA)$_2$ | 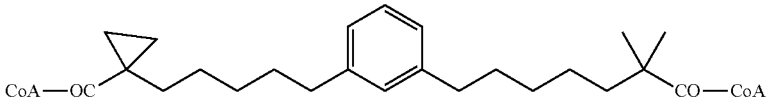 1-(5-(3-(6-carboxy-6-methylheptyl)phenyl)pentyl)cyclopropane-1-carboxylic acid di-Coenzyme A ester |
| I-41A-CoA | 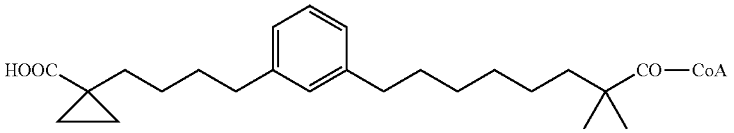 1-(4-(3-(7-carboxy-7-methyloctyl)phenyl)butyl)cyclopropane-1-carboxylic acid Coenzyme A ester |
| I-41B-CoA | 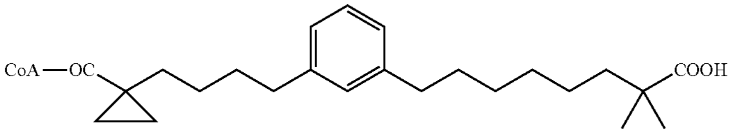 1-(4-(3-(7-carboxy-7-methyloctyl)phenyl)butyl)cyclopropane-1-carboxylic acid Coenzyme A ester |
| I-41-(CoA)$_2$ | 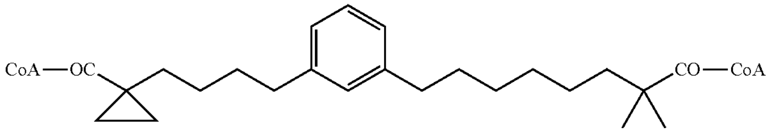 1-(4-(3-(7-carboxy-7-methyloctyl)phenyl)butyl)cyclopropane-1-carboxylic acid di-Coenzyme A ester |
| I-42A-CoA | 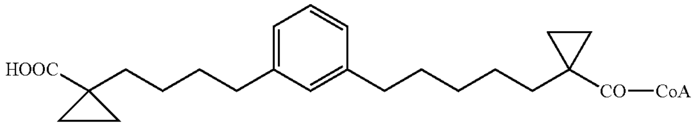 |

TABLE A-2-continued

| Compound No. | Structure and Name |
|---|---|
| | 1-(5-(3-(4-(1-carboxycyclopropyl)butyl)phenyl)pentyl)cyclopropane-1-carboxylic acid Coenzyme A ester |
| I-42B-CoA | 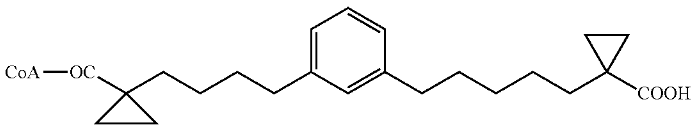 1-(5-(3-(4-(1-carboxycyclopropyl)butyl)phenyl)pentyl)cyclopropane-1-carboxylic acid Coenzyme A ester |
| I-42-(CoA)$_2$ | 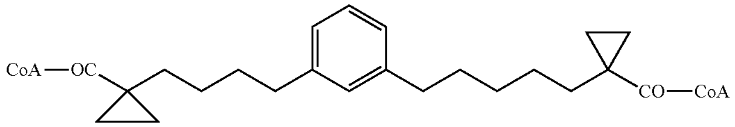 1-(5-(3-(4-(1-carboxycyclopropyl)butyl)phenyl)pentyl)cyclopropane-1-carboxylic acid di-Coenzyme A ester |
| I-43-CoA | 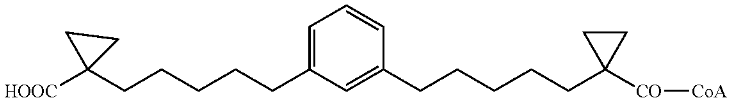 1,1'-(1,3-phenylenebis(pentane-5,1-diyl))bis(cyclopropane-1-carboxylic acid)Coenzyme A ester |
| I-43-(CoA)$_2$ | 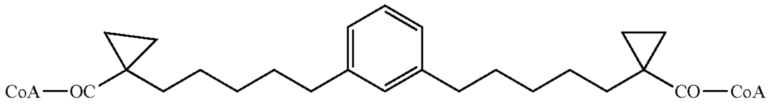 1,1'-(1,3-phenylenebis(pentane-5,1-diyl))bis(cyclopropane-1-carboxylic acid)di-Coenzyme A ester |
| I-44A-CoA | 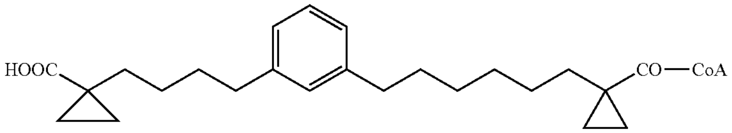 1-(6-(3-(4-(1-carboxycyclopropyl)butyl)phenyl)hexyl)cyclopropane-1-carboxylic acid Coenzyme A ester |
| I-44B-CoA | 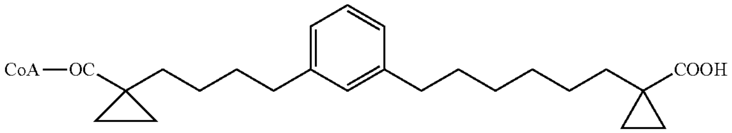 1-(6-(3-(4-(1-carboxycyclopropyl)butyl)phenyl)hexyl)cyclopropane-1-carboxylic acid Coenzyme A ester |
| I-44-(CoA)$_2$ | 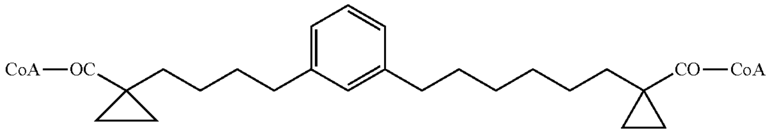 1-(6-(3-(4-(1-carboxycyclopropyl)butyl)phenyl)hexyl)cyclopropane-1-carboxylic acid di-Coenzyme A ester |
| I-45-CoA | 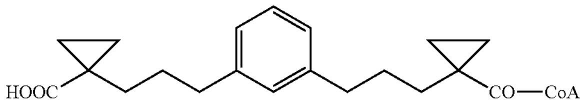 |

TABLE A-2-continued

| Compound No. | Structure and Name |
| --- | --- |
| | 1,1'-(1,3-phenylenebis(propane-3,1-diyl))bis(cyclopropane-1-carboxylic acid)Coenzyme A ester |
| I-45-(CoA)$_2$ | 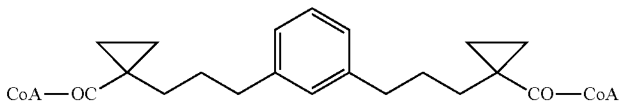 1,1'-(1,3-phenylenebis(propane-3,1-diyl))bis(cyclopropane-1-carboxylic acid)di-Coenzyme A ester |
| I-46A-CoA | 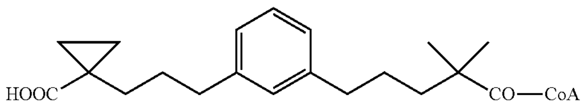 1-(3-(3-(4-carboxy-4-methylpentyl)phenyl)propyl)cyclopropane-1-carboxylic acid Coenzyme A ester |
| I-46B-CoA | 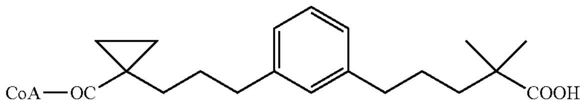 1-(3-(3-(4-carboxy-4-methylpentyl)phenyl)propyl)cyclopropane-1-carboxylic acid Coenzyme A ester |
| I-46-(CoA)$_2$ | 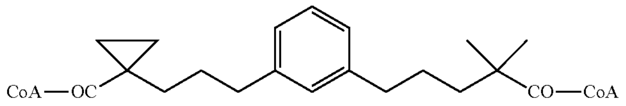 1-(3-(3-(4-carboxy-4-methylpentyl)phenyl)propyl)cyclopropane-1-carboxylic acid di-Coenzyme A ester |
| I-47A-CoA | 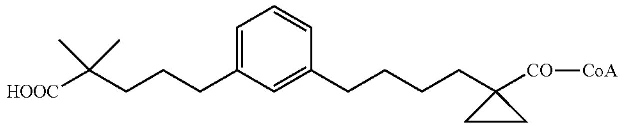 1-(4-(3-(4-carboxy-4-methylpentyl)phenyl)butyl)cyclopropane-1-carboxylic acid Coenzyme A ester |
| I-47B-CoA | 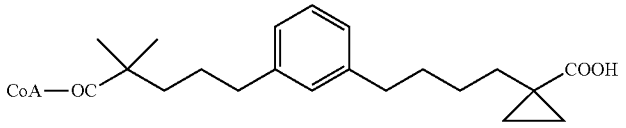 1-(4-(3-(4-carboxy-4-methylpentyl)phenyl)butyl)cyclopropane-1-carboxylic acid Coenzyme A ester |
| I-47-(CoA)$_2$ | 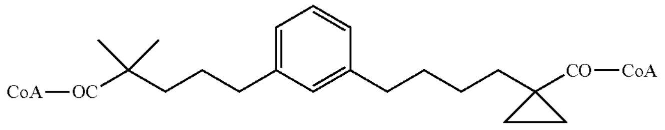 1-(4-(3-(4-carboxy-4-methylpentyl)phenyl)butyl)cyclopropane-1-carboxylic acid di-Coenzyme A ester |
| I-48A-CoA | 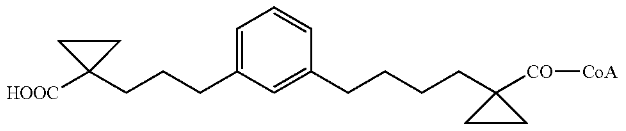 1-(3-(3-(4-(1-carboxycyclopropyl)butyl)phenyl)propyl)cyclopropane-1-carboxylic acid Coenzyme A ester |

TABLE A-2-continued

| Compound No. | Structure and Name |
|---|---|
| I-48B-CoA | 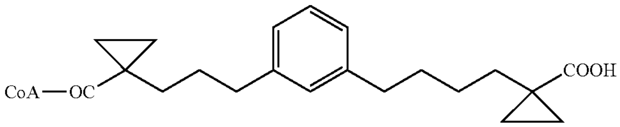 1-(3-(3-(4-(1-carboxycyclopropyl)butyl)phenyl)propyl)cyclopropane-1-carboxylic acid Coenzyme A ester |
| I-48-(CoA)$_2$ | 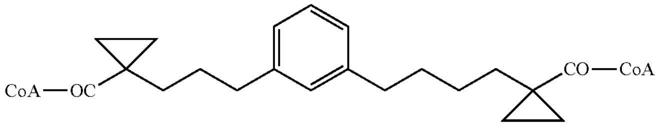 1-(3-(3-(4-(1-carboxycyclopropyl)butyl)phenyl)propyl)cyclopropane-1-carboxylic acid di-Coenzyme A ester |
| I-49A-CoA | 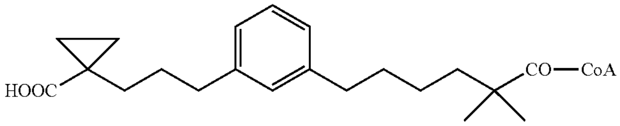 1-(3-(3-(5-carboxy-5-methylhexyl)phenyl)propyl)cyclopropane-1-carboxylic acid Coenzyme A ester |
| I-49B-CoA | 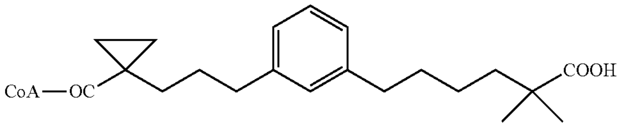 1-(3-(3-(5-carboxy-5-methylhexyl)phenyl)propyl)cyclopropane-1-carboxylic acid Coenzyme A ester |
| I-49-(CoA)$_2$ | 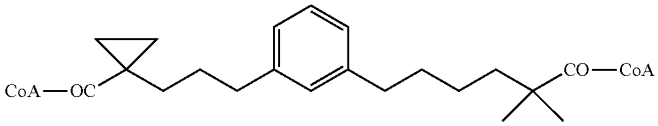 1-(3-(3-(5-carboxy-5-methylhexyl)phenyl)propyl)cyclopropane-1-carboxylic acid di-Coenzyme A ester |
| I-50A-CoA | 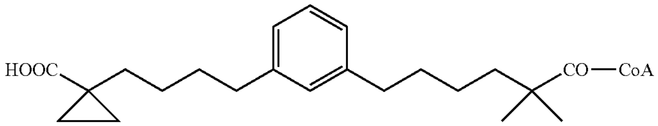 1-(4-(3-(5-carboxy-5-methylhexyl)phenyl)butyl)cyclopropane-1-carboxylic acid Coenzyme A ester |
| I-50B-CoA | 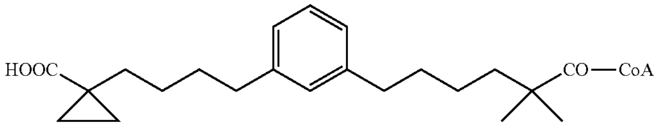 1-(4-(3-(5-carboxy-5-methylhexyl)phenyl)butyl)cyclopropane-1-carboxylic acid Coenzyme A ester |
| I-50-(CoA)$_2$ | 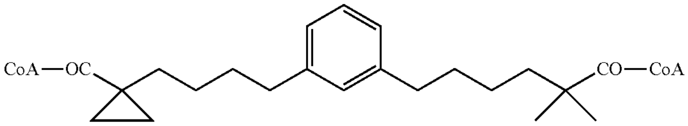 1-(4-(3-(5-carboxy-5-methylhexyl)phenyl)butyl)cyclopropane-1-carboxylic acid di-Coenzyme A ester |

TABLE A-2-continued

| Compound No. | Structure and Name |
| --- | --- |
| I-51-CoA | 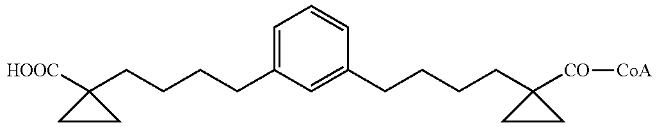 1,1'-(1,3-phenylenebis(butane-4,1-diyl))bis(cyclopropane-1-carboxylic acid)Coenzyme A ester |
| I-51-$(CoA)_2$ | 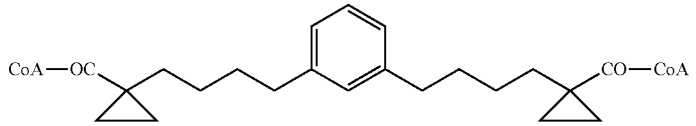 1,1'-(1,3-phenylenebis(butane-4,1-diyl))bis(cyclopropane-1-carboxylic acid)di-Coenzyme A ester |
| I-85-CoA | 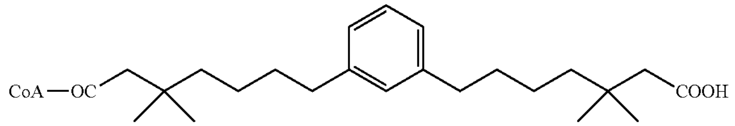 7,7'-(1,3-phenylene)bis(3,3-dimethylheptanoic acid)Coenzyme A ester |
| I-85-$(CoA)_2$ | 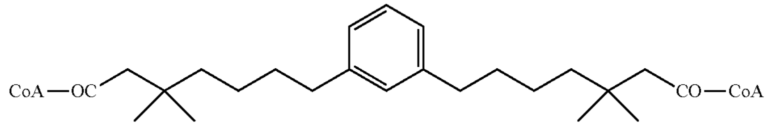 7,7'-(1,3-phenylene)bis(3,3-dimethylheptanoic acid)di-Coenzyme A ester |
| I-89A-CoA | 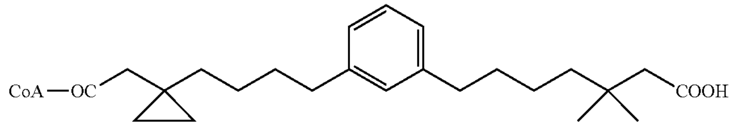 7-(3-(4-(1-(carboxymethyl)cyclopropyl Coenzyme A ester)-butyl)phenyl)-3,3-dimethylheptanoic acid |
| I-89B-CoA | 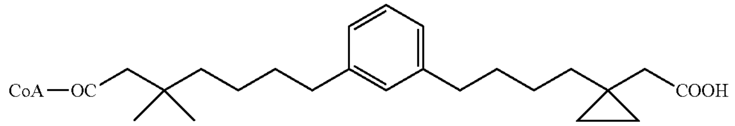 7-(3-(4-(1-(carboxymethyl)cyclopropyl)butyl)phenyl)-3,3-dimethylheptanoic acid Coenzyme A ester |
| I-89-$(CoA)_2$ | 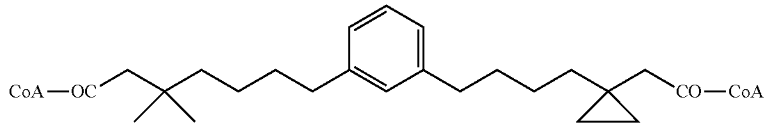 2,2'-((1,3-phenylenebis(butane-4,1-diyl))bis(cyclopropane-1,1-diyl))diacetic acid di-Coenzyme A ester |
| I-90-CoA | 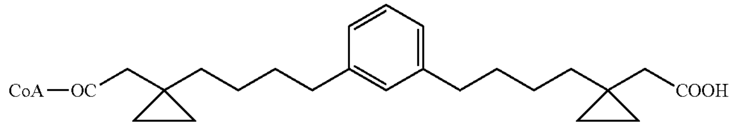 2,2'-((1,3-phenylenebis(butane-4,1-diyl))bis(cyclopropane-1,1-diyl))diacetic acid Coenzyme A ester |

TABLE A-2-continued

| Compound No. | Structure and Name |
|---|---|
| I-90-$(CoA)_2$ | 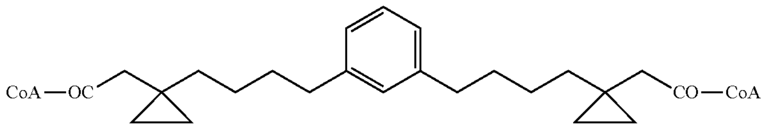<br>7,7'-(1,3-phenylene)bis(3,3-dimethylheptanoic acid)di-Coenzyme A ester |
| I-94-CoA | 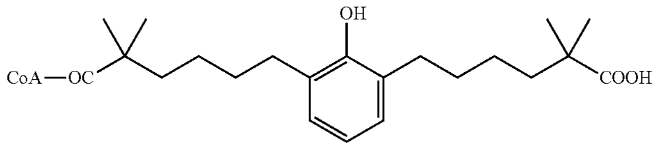<br>6,6'-(2-hydroxy-1,3-phenylene)bis(2,2-dimethylhexanoic acid) Coenzyme A |
| I-94-$(CoA)_2$ | 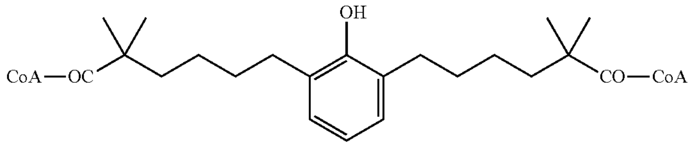<br>6,6'-(2-hydroxy-1,3-phenylene)bis(2,2-dimethylhexanoic acid)di-Coenzyme A |
| I-95-CoA | 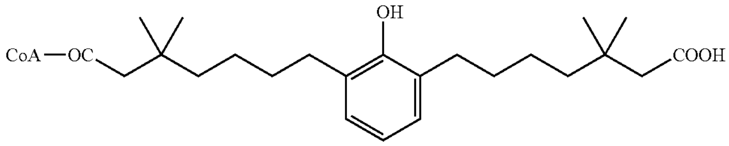<br>7,7'-(2-hydroxy-1,3-phenylene)bis(3,3-dimethylheptanoic acid) Coenzyme A |
| I-95-$(CoA)_2$ | 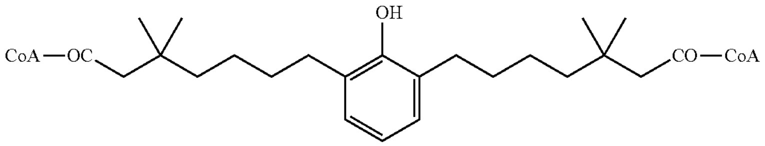<br>7,7'-(2-hydroxy-1,3-phenylene)bis(3,3-dimethylheptanoic acid)di-Coenzyme A |
| I-96-CoA | 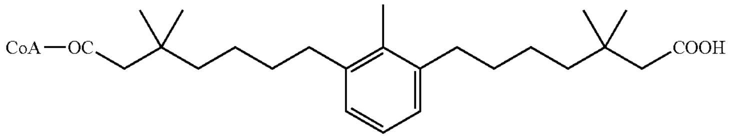<br>7,7'-(2-methyl-1,3-phenylene)bis(3,3-dimethylheptanoic acid) Coenzyme A |
| I-96-$(CoA)_2$ | 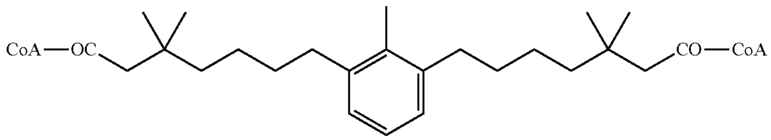<br>7,7'-(2-methyl-1,3-phenylene)bis(3,3-dimethylheptanoic acid)di-Coenzyme A |

TABLE A-2-continued

| Compound No. | Structure and Name |
| --- | --- |
| I-97-CoA | 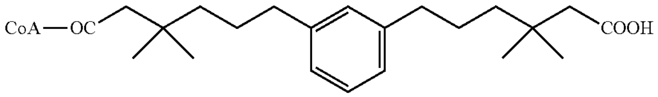 6,6'-(1,3-phenylene)bis(3,3-dimethylhexanoic acid)Coenzyme A |
| I-97-$(CoA)_2$ | 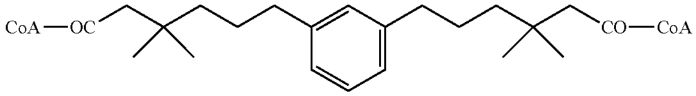 6,6'-(1,3-phenylene)bis(3,3-dimethylhexanoic acid)di-Coenzyme A |
| I-98A-CoA | 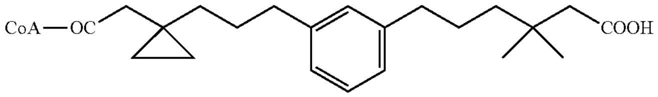 6-(3-(3-(1-(carboxymethyl Coenzyme A)cyclopropyl)propyl)phenyl)-3,3-dimethylhexanoic acid |
| I-98B-CoA | 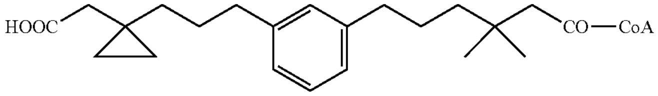 6-(3-(3-(1-(carboxymethyl)cyclopropyl)propyl)phenyl)-3,3-dimethylhexanoic acid Coenzyme A |
| I-98-$(CoA)_2$ | 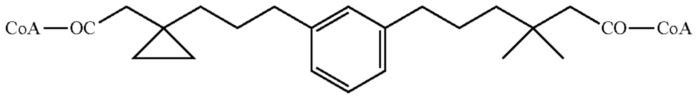 6-(3-(3-(1-(carboxymethyl)cyclopropyl)propyl)phenyl)-3,3-dimethylhexanoic acid di-Coenzyme A |
| I-99-CoA | 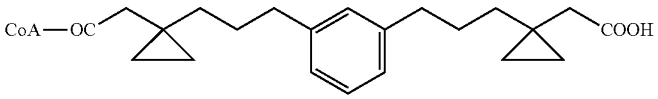 2,2'-((1,3-phenylenebis(propane-3,1-diyl))bis(cyclopropane-1,1-diyl))diacetic acid Coenzyme A |
| I-99-$(CoA)_2$ | 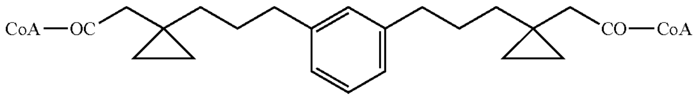 2,2'-((1,3-phenylenebis(propane-3,1-diyl))bis(cyclopropane-1,1-diyl))diacetic acid di-Coenzyme A |

In some embodiments, the compound of Formula (I) or (IQ) has any one of the structures shown in Table A-3, or a pharmaceutically acceptable salt or solvate thereof.

TABLE A-3
| Compound No. | Structure and Name |
| --- | --- |
| I-61-CoA | 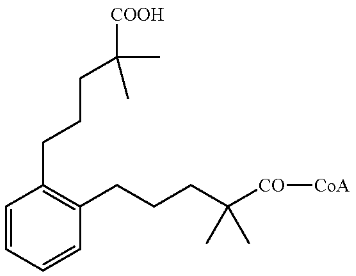<br>5-[2-(4-Carboxy-4-methylpentyl)-phenyl]-2,2-dimethylpentanoic acid Coenzyme A ester |
| I-61-(CoA)$_2$ | 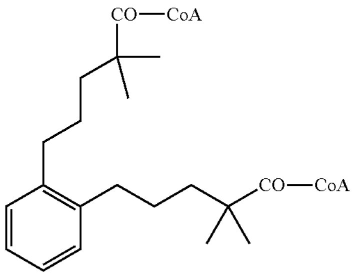<br>5-[2-(4-Carboxy-4-methylpentyl)-phenyl]-2,2-dimethylpentanoic acid di-Coenzyme A ester |
| I-62-CoA | 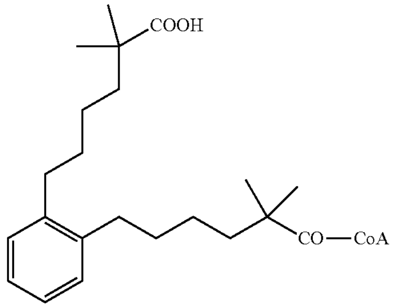<br>6,6'-(1,2-Phenylene)bis(2,2-dimethylhexanoic acid)Coenzyme A ester |
| I-62-(CoA)$_2$ | 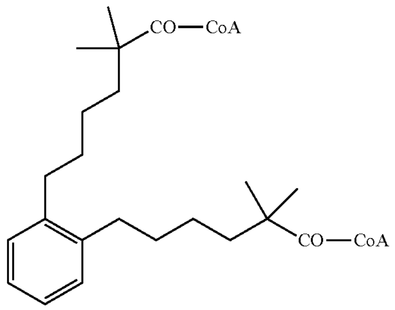<br>6,6'-(1,2-Phenylene)bis(2,2-dimethylhexanoic acid)di-Coenzyme A ester |

TABLE A-3-continued

| Compound No. | Structure and Name |
| --- | --- |
| I-63A-CoA | 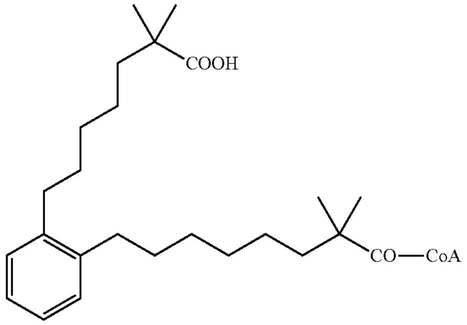 8-(2-(6-Carboxy-6-methylheptyl)phenyl)-2,2-dimethyloctanoic acid Coenzyme A ester |
| I-63B-CoA | 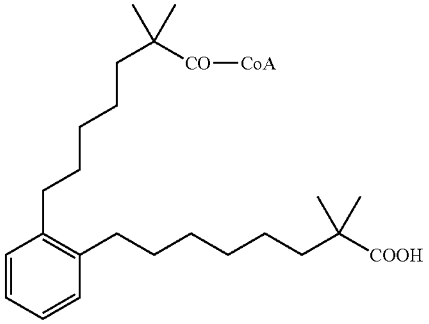 8-(2-(6-Carboxy-6-methylheptyl)phenyl)-2,2-dimethyloctanoic acid Coenzyme A ester |
| I-63-$(CoA)_2$ | 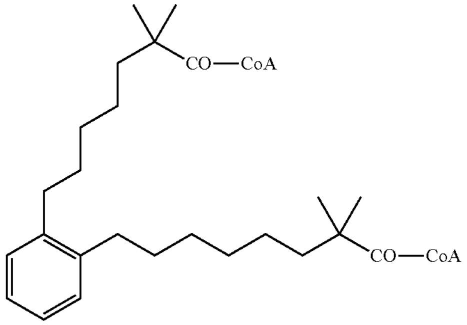 8-(2-(6-Carboxy-6-methylheptyl)phenyl)-2,2-dimethyloctanoic acid di-Coenzyme A ester |
| I-64A-CoA | 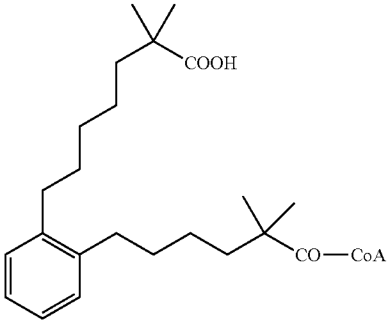 7-(2-(5-Carboxy-5-methylhexyl)phenyl)-2,2-dimethylheptanoic acid Coenzyme A ester |

TABLE A-3-continued
| Compound No. | Structure and Name |
|---|---|
| I-64B-CoA | 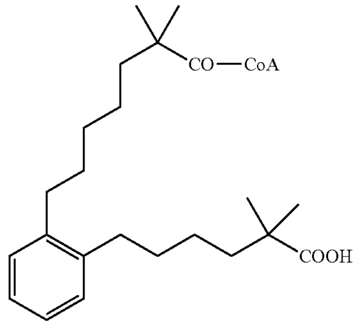<br>7-(2-(5-Carboxy-5-methylhexyl)phenyl)-2,2-dimethylheptanoic acid Coenzyme A ester |
| I-64-(CoA)$_2$ | 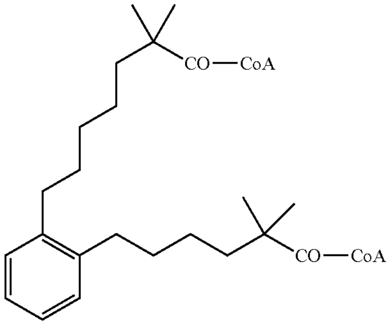<br>7-(2-(5-Carboxy-5-methylhexyl)phenyl)-2,2-dimethylheptanoic acid di-Coenzyme A ester |
| I-65-CoA | 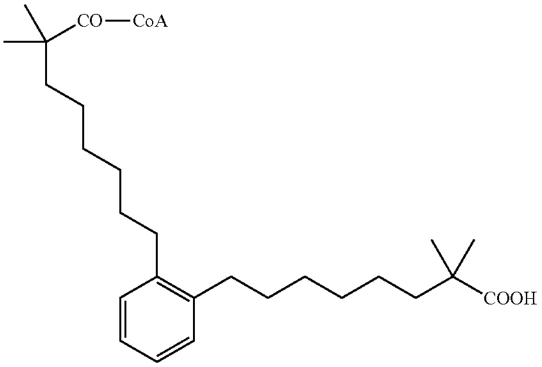<br>8,8'-(1,2-Phenylene)bis(2,2-dimethyloctanoic acid)Coenzyme A ester |
| I-65-(CoA)$_2$ | 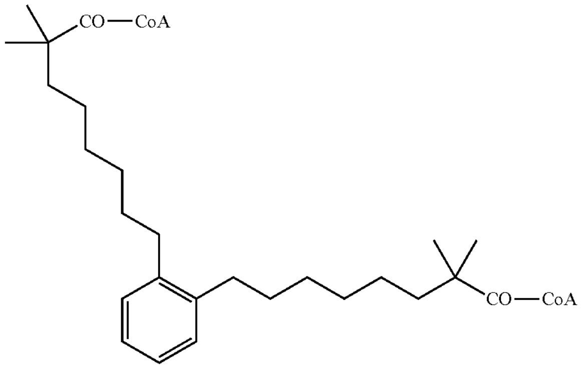<br>8,8'-(1,2-Phenylene)bis(2,2-dimethyloctanoic acid)di-Coenzyme A ester |

TABLE A-3-continued

| Compound No. | Structure and Name |
| --- | --- |
| I-66A-CoA | 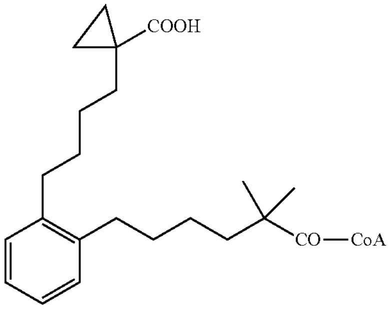 1-(4-(2-(5-carboxy-5-methylhexyl)phenyl)butyl)cyclopropane-1-carboxylic acid Coenzyme A ester |
| I-66A-CoA | 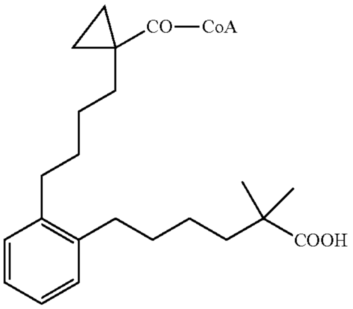 1-(4-(2-(5-carboxy-5-methylhexyl)phenyl)butyl)cyclopropane-1-carboxylic acid Coenzyme A ester |
| I-66-(CoA)$_2$ | 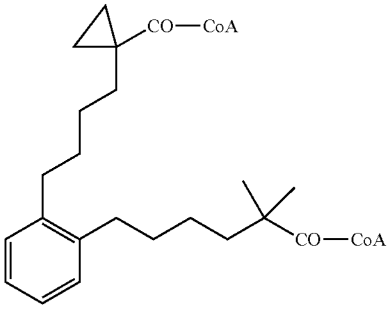 1-(4-(2-(5-carboxy-5-methylhexyl)phenyl)butyl)cyclopropane-1-carboxylic acid di-Coenzyme A ester |
| I-67A-CoA | 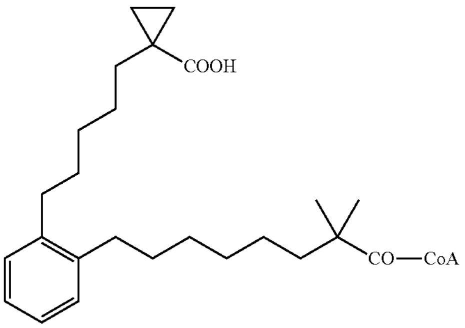 1-(5-(2-(7-carboxy-7-methyloctyl)phenyl)pentyl)cyclopropane-1-carboxylic acid Coenzyme A ester |

TABLE A-3-continued

| Compound No. | Structure and Name |
|---|---|
| I-67B-CoA | 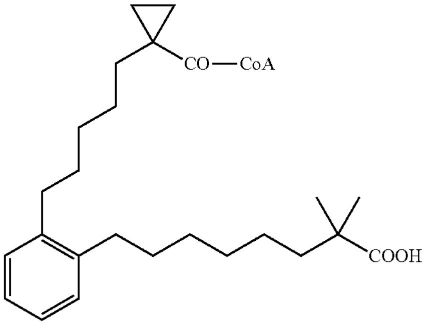<br>1-(5-(2-(7-carboxy-7-methyloctyl)phenyl)pentyl)cyclopropane-1-carboxylic acid Coenzyme A ester |
| I-67-$(CoA)_2$ | 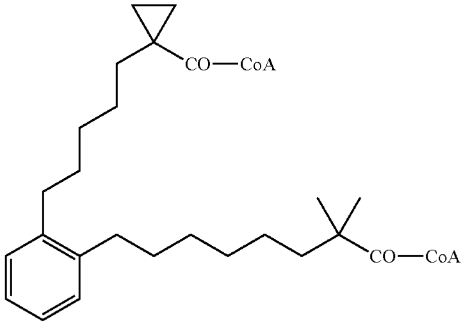<br>1-(5-(2-(7-carboxy-7-methyloctyl)phenyl)pentyl)cyclopropane-1-carboxylic acid di-Coenzyme A ester |
| I-68A-CoA | 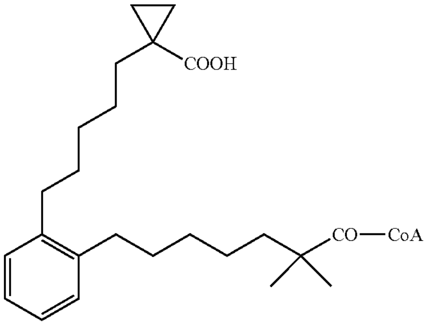<br>1-(5-(2-(6-carboxy-6-methylheptyl)phenyl)pentyl)cyclopropane-1-carboxylic acid Coenzyme A ester |
| I-68B-CoA | 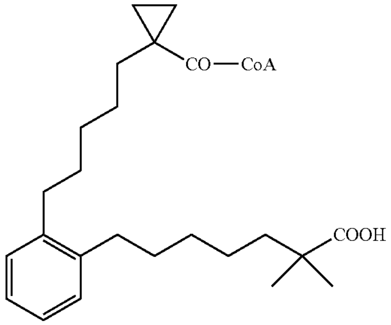<br>1-(5-(2-(6-carboxy-6-methylheptyl)phenyl)pentyl)cyclopropane-1-carboxylic acid Coenzyme A ester |

TABLE A-3-continued

| Compound No. | Structure and Name |
|---|---|
| I-68-(CoA)₂ | 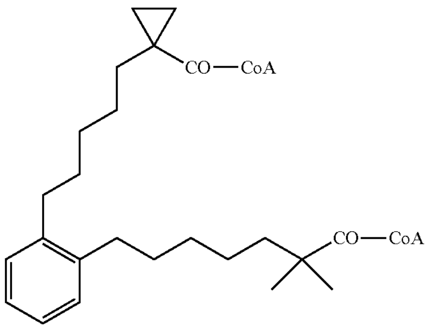<br>1-(5-(2-(6-carboxy-6-methylheptyl)phenyl)pentyl)cyclopropane-1-carboxylic acid di-Coenzyme A ester |
| I-69A-CoA | 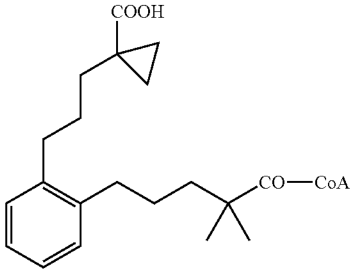<br>1-(3-(2-(4-carboxy-4-methylpentyl)phenyl)propyl)cyclopropane-1-carboxylic acid Coenzyme A ester |
| I-69B-CoA | 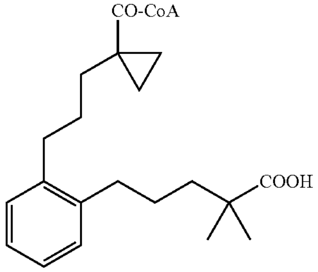<br>1-(3-(2-(4-carboxy-4-methylpentyl)phenyl)propyl)cyclopropane-1-carboxylic acid Coenzyme A ester |
| I-69-(CoA)₂ | 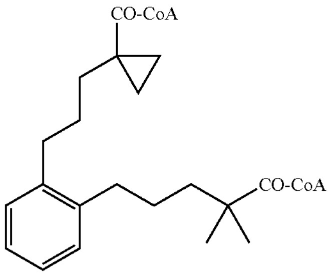<br>1-(3-(2-(4-carboxy-4-methylpentyl)phenyl)propyl)cyclopropane-1-carboxylic acid di-Coenzyme A ester |

TABLE A-3-continued

| Compound No. | Structure and Name |
|---|---|
| I-70A-CoA | 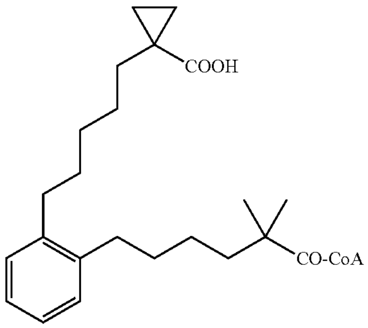 1-(5-(2-(5-carboxy-5-methylhexyl)phenyl)pentyl)cyclopropane-1-carboxylic acid Coenzyme A ester |
| I-70B-CoA | 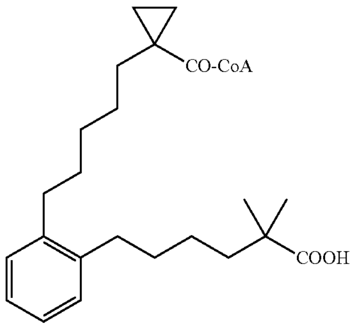 1-(5-(2-(5-carboxy-5-methylhexyl)phenyl)pentyl)cyclopropane-1-carboxylic acid Coenzyme A ester |
| I-70-(CoA)$_2$ | 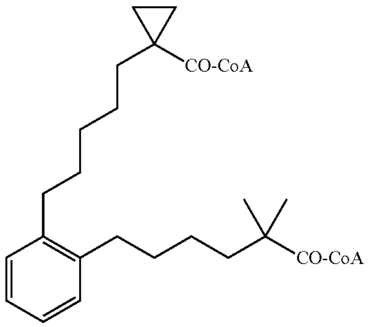 1-(5-(2-(5-carboxy-5-methylhexyl)phenyl)pentyl)cyclopropane-1-carboxylic acid di-Coenzyme A ester |
| I-71A-CoA | 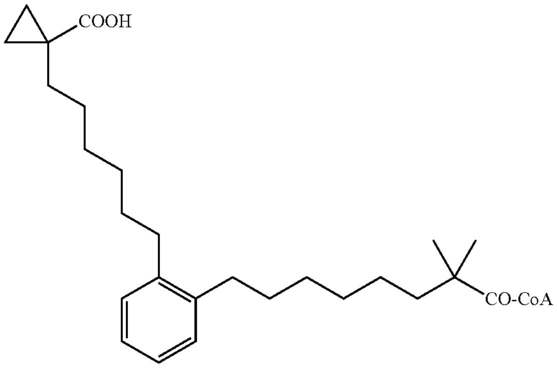 1-(6-(2-(7-carboxy-7-methyloctyl)phenyl)hexyl)cyclopropane-1-carboxylic acid Coenzyme A ester |

TABLE A-3-continued

| Compound No. | Structure and Name |
|---|---|
| I-71B-CoA | 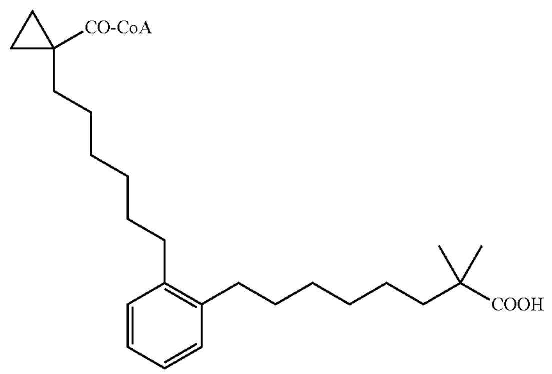 1-(6-(2-(7-carboxy-7-methyloctyl)phenyl)hexyl)cyclopropane-1-carboxylic acid Coenzyme A ester |
| I-71-(CoA)$_2$ | 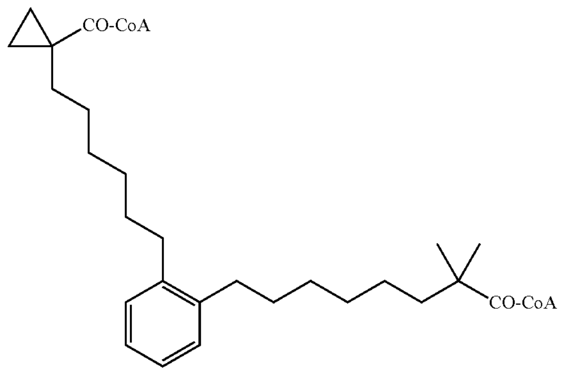 1-(6-(2-(7-carboxy-7-methyloctyl)phenyl)hexyl)cyclopropane-1-carboxylic acid di-Coenzyme A ester |
| I-72-CoA | 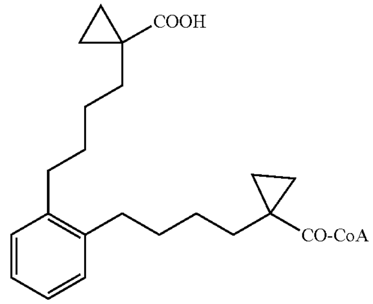 1,1'-(1,2-phenylenebis(butane-4,1-diyl))bis(cyclopropane-1-carboxylic acid)Coenzyme A ester |
| I-72-(CoA)$_2$ | 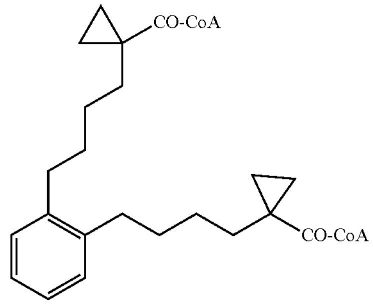 1,1'-(1,2-phenylenebis(butane-4,1-diyl))bis(cyclopropane-1-carboxylic acid)di-Coenzyme A ester |

TABLE A-3-continued

| Compound No. | Structure and Name |
|---|---|
| I-73A-CoA | 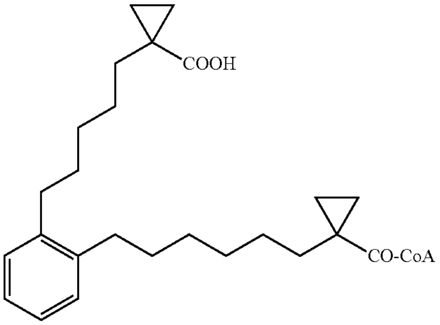 1-(5-(2-(6-(1-carboxycyclopropyl)hexyl)phenyl)pentyl)cyclopropane-1-carboxylic acid Coenzyme A ester |
| I-73B-CoA | 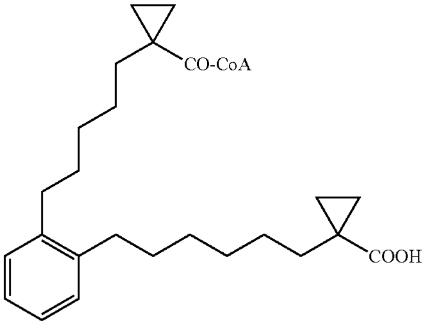 1-(5-(2-(6-(1-carboxycyclopropyl)hexyl)phenyl)pentyl)cyclopropane-1-carboxylic acid Coenzyme A ester |
| I-73-(CoA)$_2$ | 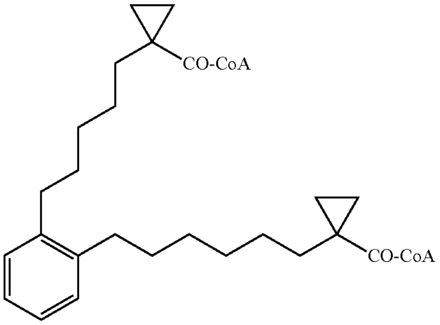 1-(5-(2-(6-(1-carboxycyclopropyl)hexyl)phenyl)pentyl)cyclopropane-1-carboxylic acid di-Coenzyme A ester |
| I-74-CoA | 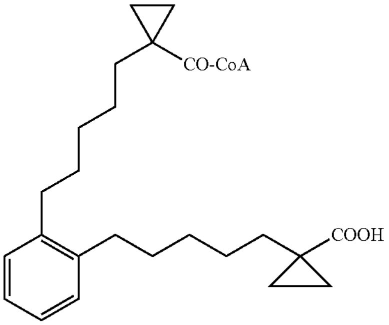 1,1'-(1,2-phenylenebis(pentane-5,1-diyl))bis(cyclopropane-1-carboxylic acid)Coenzyme A ester |

TABLE A-3-continued

| Compound No. | Structure and Name |
|---|---|
| I-74-(CoA)$_2$ | 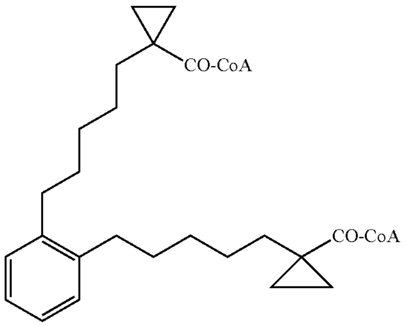 1,1'-(1,2-phenylenebis(pentane-5,1-diyl))bis(cyclopropane-1-carboxylic acid)di-Coenzyme A ester |
| I-75-CoA | 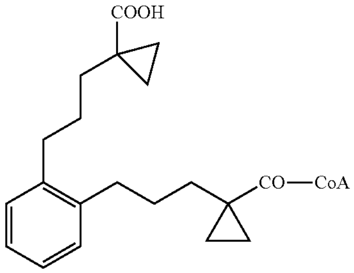 1,1'-(1,2-phenylenebis(propane-3,1-diyl))bis(cyclopropane-1-carboxylic acid)Coenzyme A ester |
| I-75-(CoA)$_2$ | 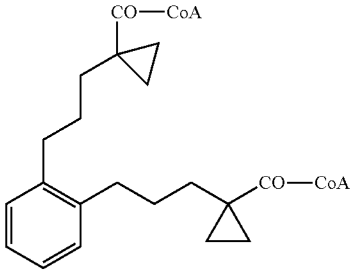 1,1'-(1,2-phenylenebis(propane-3,1-diyl))bis(cyclopropane-1-carboxylic acid)di-Coenzyme A ester |
| I-76A-CoA | 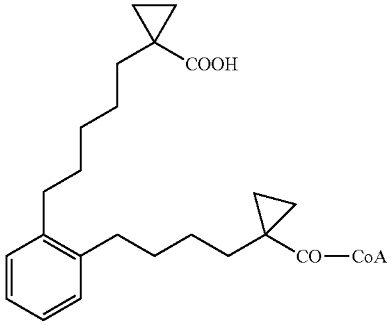 1-(5-(2-(4-(1-carboxycyclopropyl)butyl)phenyl)pentyl)cyclopropane-1-carboxylic acid Coenzyme A ester |

TABLE A-3-continued
| Compound No. | Structure and Name |
|---|---|
| I-76B-CoA | 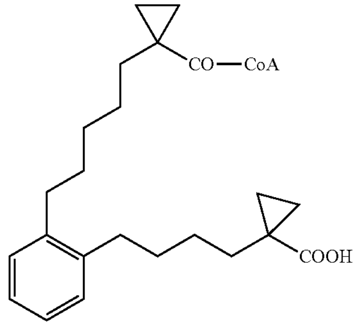<br>1-(5-(2-(4-(1-carboxycyclopropyl)butyl)phenyl)pentyl)cyclopropane-1-carboxylic acid Coenzyme A ester |
| I-76-(CoA)$_2$ | 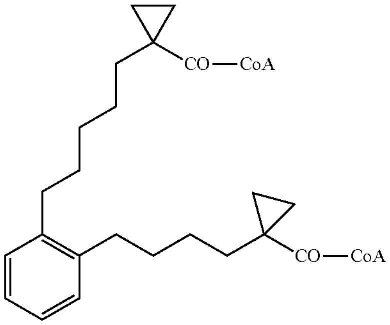<br>1-(5-(2-(4-(1-carboxycyclopropyl)butyl)phenyl)pentyl)cyclopropane-1-carboxylic acid di-Coenzyme A ester |
| I-77-CoA | 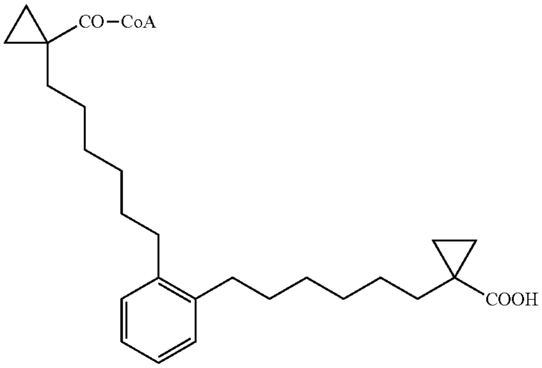<br>1,1'-(1,2-phenylenebis(hexane-6,1-diyl))bis(cyclopropane-1-carboxylic acid)Coenzyme A ester |
| I-77-(CoA)$_2$ | 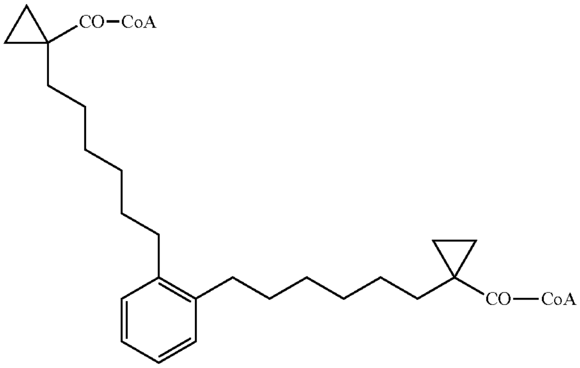 |

TABLE A-3-continued

| Compound No. | Structure and Name |
|---|---|
| | 1,1'-(1,2-phenylenebis(hexane-6,1-diyl))bis(cyclopropane-1-carboxylic acid)di-Coenzyme A ester |
| I-86-CoA | 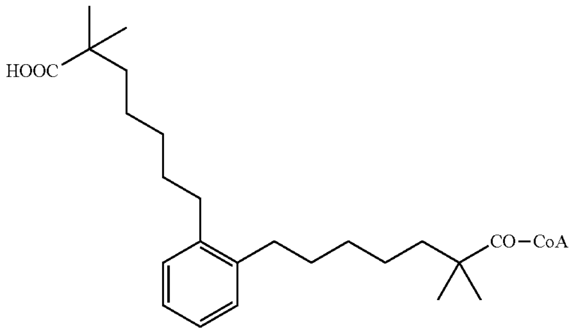 7,7'-(1,2-phenylene)bis(2,2-dimethylheptanoic acid)Coenzyme A ester |
| I-86-(CoA)$_2$ | 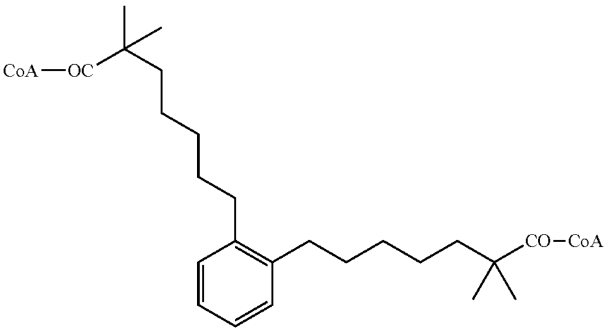 7,7'-(1,2-phenylene)bis(2,2-dimethylheptanoic acid)di-Coenzyme A ester |
| I-91-CoA | 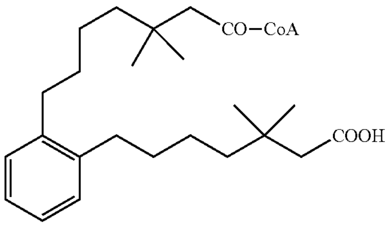 7,7'-(1,2-phenylene)bis(3,3-dimethylheptanoic acid)Coenzyme A ester |
| I-91-(CoA)$_2$ | 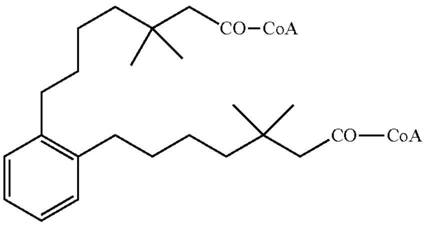 7,7'-(1,2-phenylene)bis(3,3-dimethylheptanoic acid)di-Coenzyme A ester |

TABLE A-3-continued

| Compound No. | Structure and Name |
|---|---|
| I-92A-CoA | 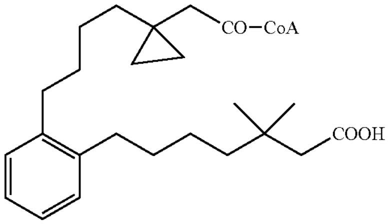 7-(2-(4-(1-(carboxymethyl-Coenzyme A ester)cyclopropyl)butyl)phenyl)-3,3-dimethylheptanoic acid |
| I-92B-CoA | 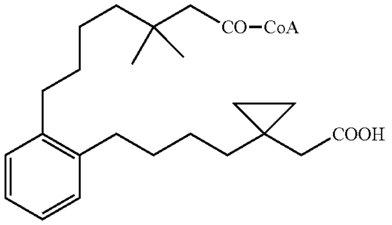 7-(2-(4-(1-(carboxymethyl)cyclopropyl)butyl)phenyl)-3,3-dimethylheptanoic acid Coenzyme A ester |
| I-92-(CoA)$_2$ | 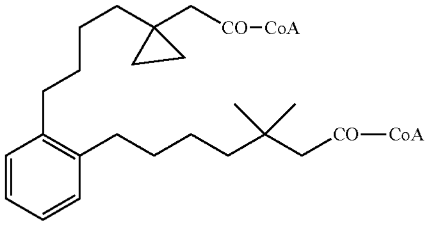 7-(2-(4-(1-(carboxymethyl)cyclopropyl)butyl)phenyl)-3,3-dimethylheptanoic acid di-Coenzyme A ester |
| I-93-CoA | 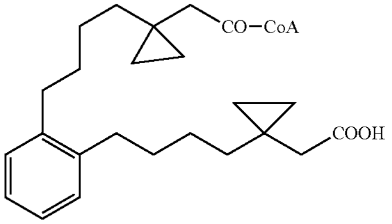 2,2'-((1,2-phenylenebis(butane-4,1-diyl))bis(cyclopropane-1,1-diyl))diacetic acid Coenzyme A ester |
| I-93-(CoA)$_2$ | 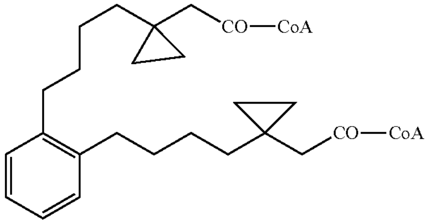 2,2'-((1,2-phenylenebis(butane-4,1-diyl))bis(cyclopropane-1,1-diyl))diacetic acid di-Coenzyme A ester |

In some embodiments, the compound of Formula (I) or (IA) has any one of the structures shown in Table A-4 and defined by $C^1$ and $C^2$, or a pharmaceutically acceptable salt or solvate thereof.

TABLE A-4

| Structure |
|---|
| 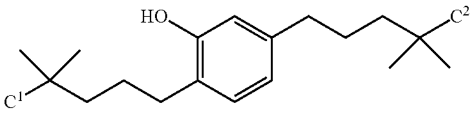<br>wherein $C^1$ = COOH and $C^2$ = CO-CoA; $C^1$ = CO-CoA and $C^2$ = COOH; or $C^1$ and $C^2$ = CO-CoA |
| 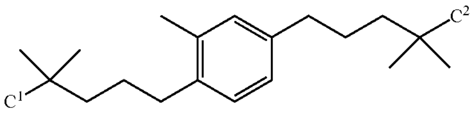<br>wherein $C^1$ = COOH and $C^2$ = CO-CoA; $C^1$ = CO-CoA and $C^2$ = COOH; or $C^1$ and $C^2$ = CO-CoA |
| 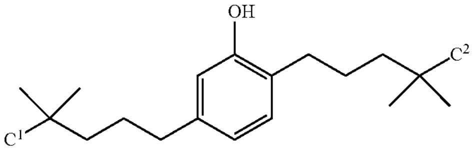<br>wherein $C^1$ = COOH and $C^2$ = CO-CoA; $C^1$ = CO-CoA and $C^2$ = COOH; or $C^1$ and $C^2$ = CO-CoA |
| 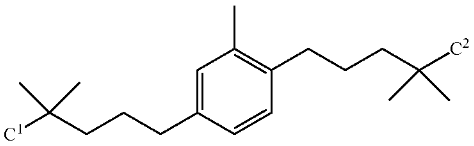<br>wherein $C^1$ = COOH and $C^2$ = CO-CoA; $C^1$ = CO-CoA and $C^2$ = COOH; or $C^1$ and $C^2$ = CO-CoA |
| 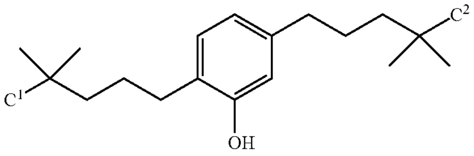<br>wherein $C^1$ = COOH and $C^2$ = CO-CoA; $C^1$ = CO-CoA and $C^2$ = COOH; or $C^1$ and $C^2$ = CO-CoA |
| 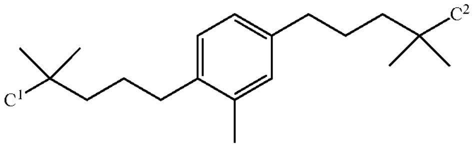<br>wherein $C^1$ = COOH and $C^2$ = CO-CoA; $C^1$ = CO-CoA and $C^2$ = COOH; or $C^1$ and $C^2$ = CO-CoA |
| 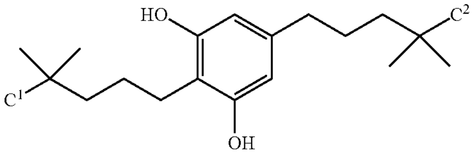 |

TABLE A-4-continued

| Structure |
|---|
| wherein $C^1$ = COOH and $C^2$ = CO-CoA; $C^1$ = CO-CoA and $C^2$ = COOH; or $C^1$ and $C^2$ = CO-CoA |
| 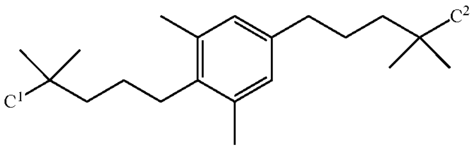 |
| wherein $C^1$ = COOH and $C^2$ = CO-CoA; $C^1$ = CO-CoA and $C^2$ = COOH; or $C^1$ and $C^2$ = CO-CoA |
| 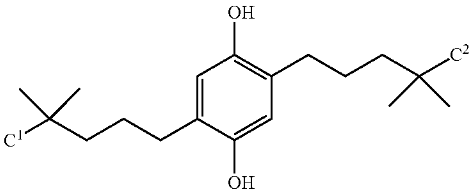 |
| wherein $C^1$ = COOH and $C^2$ = CO-CoA; $C^1$ = CO-CoA and $C^2$ = COOH; or $C^1$ and $C^2$ = CO-CoA |
| 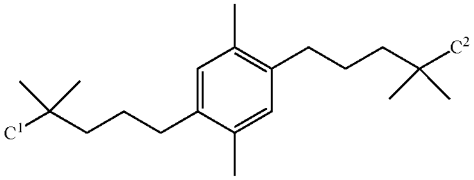 |
| wherein $C^1$ = COOH and $C^2$ = CO-CoA; $C^1$ = CO-CoA and $C^2$ = COOH; or $C^1$ and $C^2$ = CO-CoA |
| 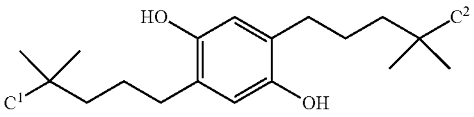 |
| wherein $C^1$ = COOH and $C^2$ = CO-CoA; $C^1$ = CO-CoA and $C^2$ = COOH; or $C^1$ and $C^2$ = CO-CoA |
| 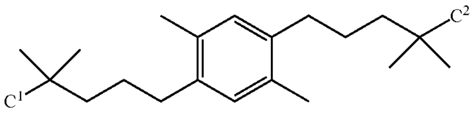 |
| wherein $C^1$ = COOH and $C^2$ = CO-CoA; $C^1$ = CO-CoA and $C^2$ = COOH; or $C^1$ and $C^2$ = CO-CoA |
| 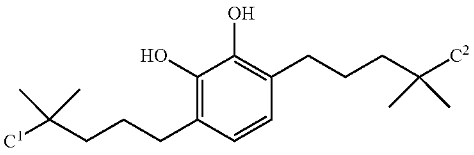 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 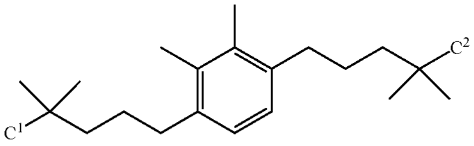 wherein $C^1$ = COOH and $C^2$ = CO-CoA; $C^1$ = CO-CoA and $C^2$ = COOH; or $C^1$ and $C^2$ = CO-CoA |
| 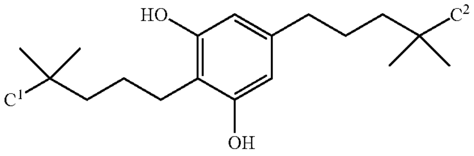 wherein $C^1$ = COOH and $C^2$ = CO-CoA; $C^1$ = CO-CoA and $C^2$ = COOH; or $C^1$ and $C^2$ = CO-CoA |
| 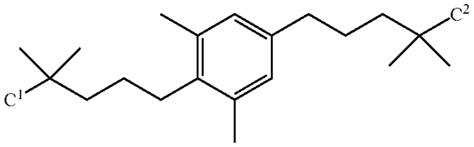 wherein $C^1$ = COOH and $C^2$ = CO-CoA; $C^1$ = CO-CoA and $C^2$ = COOH; or $C^1$ and $C^2$ = CO-CoA |
| 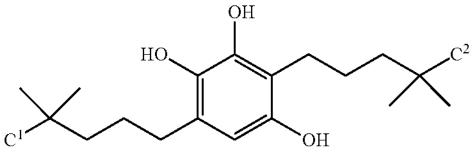 wherein $C^1$ = COOH and $C^2$ = CO-CoA; $C^1$ = CO-CoA and $C^2$ = COOH; or $C^1$ and $C^2$ = CO-CoA |
| 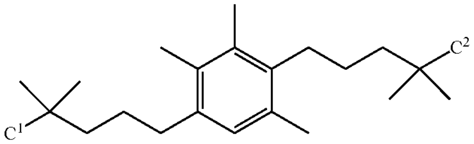 wherein $C^1$ = COOH and $C^2$ = CO-CoA; $C^1$ = CO-CoA and $C^2$ = COOH; or $C^1$ and $C^2$ = CO-CoA |
| 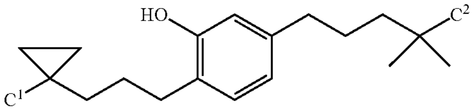 wherein $C^1$ = COOH and $C^2$ = CO-CoA; $C^1$ = CO-CoA and $C^2$ = COOH; or $C^1$ and $C^2$ = CO-CoA |
| 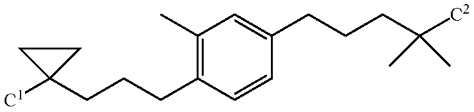 wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 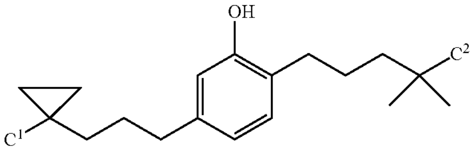 |
| wherein $C^1$ = COOH and $C^2$ = CO-CoA; $C^1$ = CO-CoA and $C^2$ = COOH; or $C^1$ and $C^2$ = CO-CoA |
| 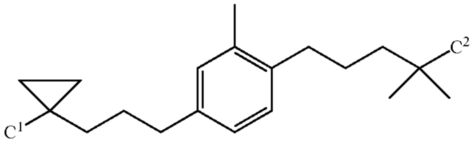 |
| wherein $C^1$ = COOH and $C^2$ = CO-CoA; $C^1$ = CO-CoA and $C^2$ = COOH; or $C^1$ and $C^2$ = CO-CoA |
| 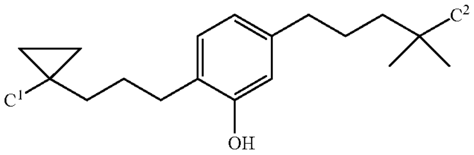 |
| wherein $C^1$ = COOH and $C^2$ = CO-CoA; $C^1$ = CO-CoA and $C^2$ = COOH; or $C^1$ and $C^2$ = CO-CoA |
| 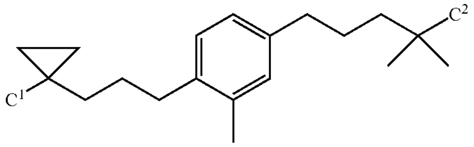 |
| wherein $C^1$ = COOH and $C^2$ = CO-CoA; $C^1$ = CO-CoA and $C^2$ = COOH; or $C^1$ and $C^2$ = CO-CoA |
| 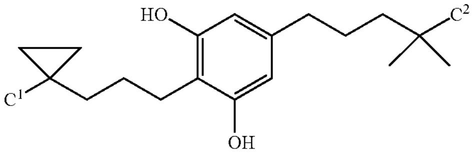 |
| wherein $C^1$ = COOH and $C^2$ = CO-CoA; $C^1$ = CO-CoA and $C^2$ = COOH; or $C^1$ and $C^2$ = CO-CoA |
| 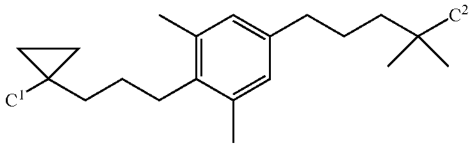 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 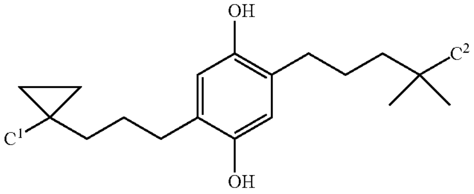<br>wherein $C^1$ = COOH and $C^2$ = CO-CoA; $C^1$ = CO-CoA and $C^2$ = COOH; or $C^1$ and $C^2$ = CO-CoA |
| 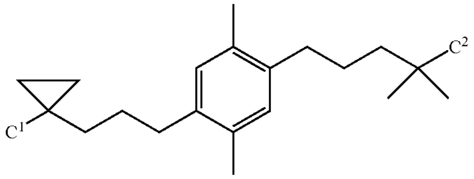<br>wherein $C^1$ = COOH and $C^2$ = CO-CoA; $C^1$ = CO-CoA and $C^2$ = COOH; or $C^1$ and $C^2$ = CO-CoA |
| 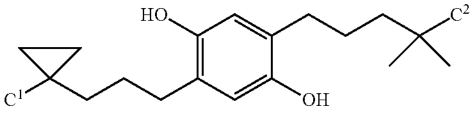<br>wherein $C^1$ = COOH and $C^2$ = CO-CoA; $C^1$ = CO-CoA and $C^2$ = COOH; or $C^1$ and $C^2$ = CO-CoA |
| 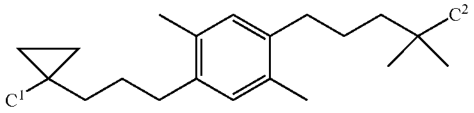<br>wherein $C^1$ = COOH and $C^2$ = CO-CoA; $C^1$ = CO-CoA and $C^2$ = COOH; or $C^1$ and $C^2$ = CO-CoA |
| 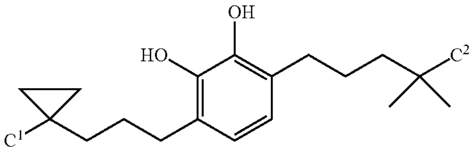<br>wherein $C^1$ = COOH and $C^2$ = CO-CoA; $C^1$ = CO-CoA and $C^2$ = COOH; or $C^1$ and $C^2$ = CO-CoA |
| 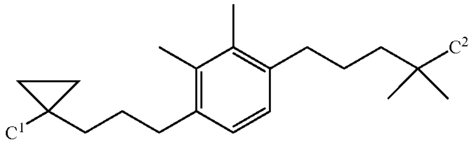<br>wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 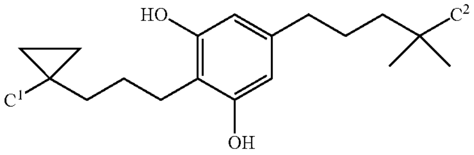 |
| wherein $C^1$ = COOH and $C^2$ = CO-CoA; $C^1$ = CO-CoA and $C^2$ = COOH; or $C^1$ and $C^2$ = CO-CoA |
| 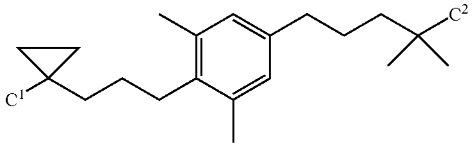 |
| wherein $C^1$ = COOH and $C^2$ = CO-CoA; $C^1$ = CO-CoA and $C^2$ = COOH; or $C^1$ and $C^2$ = CO-CoA |
| 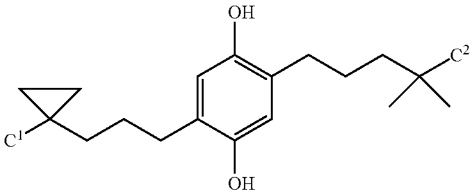 |
| wherein $C^1$ = COOH and $C^2$ = CO-CoA; $C^1$ = CO-CoA and $C^2$ = COOH; or $C^1$ and $C^2$ = CO-CoA |
| 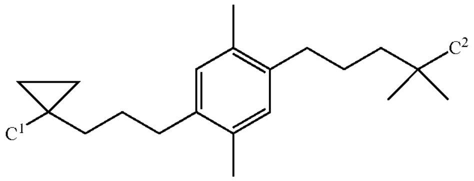 |
| wherein $C^1$ = COOH and $C^2$ = CO-CoA; $C^1$ = CO-CoA and $C^2$ = COOH; or $C^1$ and $C^2$ = CO-CoA |
| 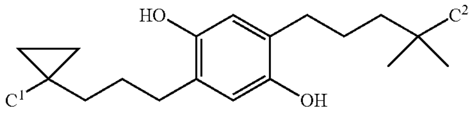 |
| wherein $C^1$ = COOH and $C^2$ = CO-CoA; $C^1$ = CO-CoA and $C^2$ = COOH; or $C^1$ and $C^2$ = CO-CoA |
| 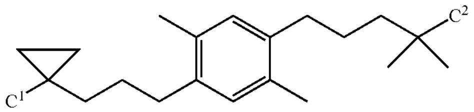 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 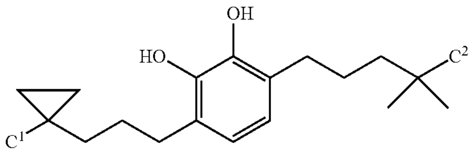 |
| wherein $C^1$ = COOH and $C^2$ = CO-CoA; $C^1$ = CO-CoA and $C^2$ = COOH; or $C^1$ and $C^2$ = CO-CoA |
| 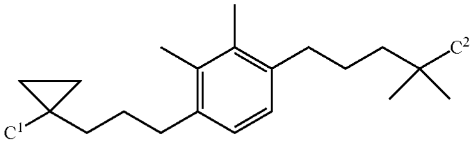 |
| wherein $C^1$ = COOH and $C^2$ = CO-CoA; $C^1$ = CO-CoA and $C^2$ = COOH; or $C^1$ and $C^2$ = CO-CoA |
| 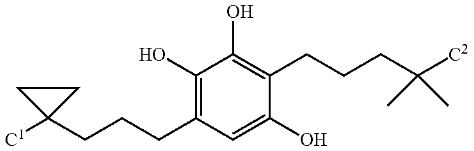 |
| wherein $C^1$ = COOH and $C^2$ = CO-CoA; $C^1$ = CO-CoA and $C^2$ = COOH; or $C^1$ and $C^2$ = CO-CoA |
| 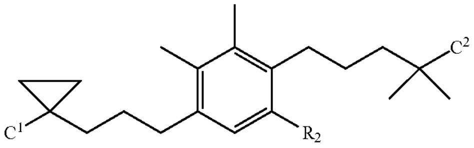 |
| wherein $C^1$ = COOH and $C^2$ = CO-CoA; $C^1$ = CO-CoA and $C^2$ = COOH; or $C^1$ and $C^2$ = CO-CoA |
| 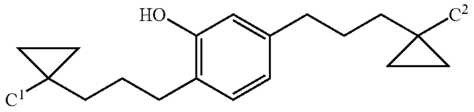 |
| wherein $C^1$ = COOH and $C^2$ = CO-CoA; $C^1$ = CO-CoA and $C^2$ = COOH; or $C^1$ and $C^2$ = CO-CoA |
| 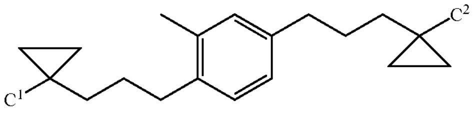 |
| wherein $C^1$ = COOH and $C^2$ = CO-CoA; $C^1$ = CO-CoA and $C^2$ = COOH; or $C^1$ and $C^2$ = CO-CoA |
| 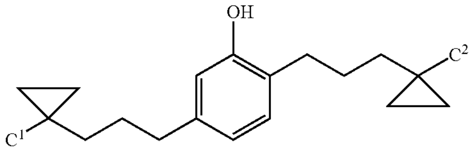 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 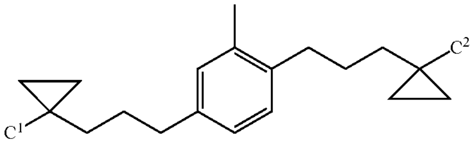 |
| wherein $C^1$ = COOH and $C^2$ = CO-CoA; $C^1$ = CO-CoA and $C^2$ = COOH; or $C^1$ and $C^2$ = CO-CoA |
| 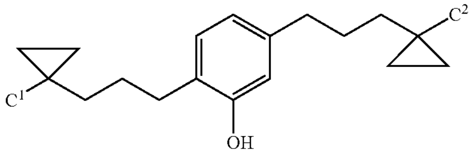 |
| wherein $C^1$ = COOH and $C^2$ = CO-CoA; $C^1$ = CO-CoA and $C^2$ = COOH; or $C^1$ and $C^2$ = CO-CoA |
| 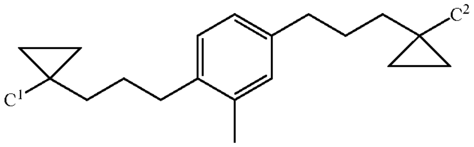 |
| wherein $C^1$ = COOH and $C^2$ = CO-CoA; $C^1$ = CO-CoA and $C^2$ = COOH; or $C^1$ and $C^2$ = CO-CoA |
| 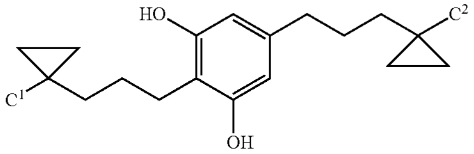 |
| wherein $C^1$ = COOH and $C^2$ = CO-CoA; $C^1$ = CO-CoA and $C^2$ = COOH; or $C^1$ and $C^2$ = CO-CoA |
| 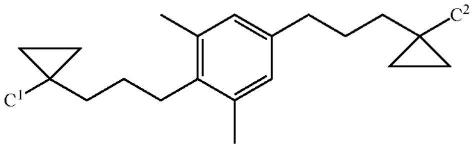 |
| wherein $C^1$ = COOH and $C^2$ = CO-CoA; $C^1$ = CO-CoA and $C^2$ = COOH; or $C^1$ and $C^2$ = CO-CoA |
| 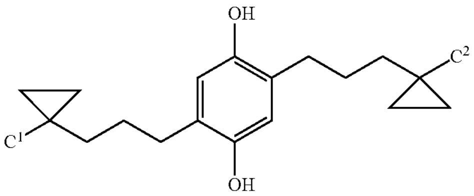 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 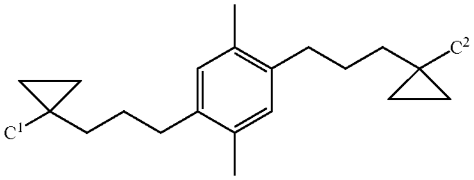 |
| wherein $C^1$ = COOH and $C^2$ = CO-CoA; $C^1$ = CO-CoA and $C^2$ = COOH; or $C^1$ and $C^2$ = CO-CoA |
| 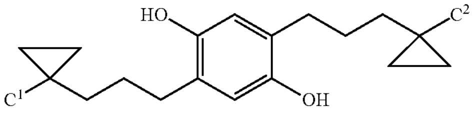 |
| wherein $C^1$ = COOH and $C^2$ = CO-CoA; $C^1$ = CO-CoA and $C^2$ = COOH; or $C^1$ and $C^2$ = CO-CoA |
| 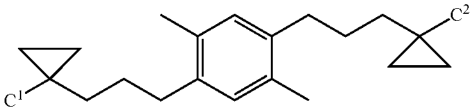 |
| wherein $C^1$ = COOH and $C^2$ = CO-CoA; $C^1$ = CO-CoA and $C^2$ = COOH; or $C^1$ and $C^2$ = CO-CoA |
| 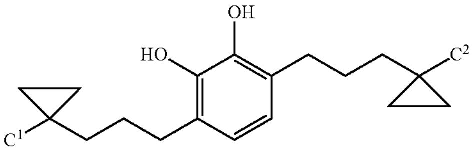 |
| wherein $C^1$ = COOH and $C^2$ = CO-CoA; $C^1$ = CO-CoA and $C^2$ = COOH; or $C^1$ and $C^2$ = CO-CoA |
| 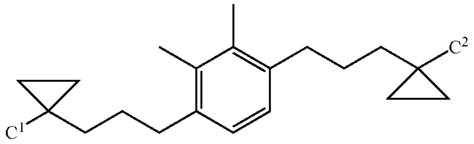 |
| wherein $C^1$ = COOH and $C^2$ = CO-CoA; $C^1$ = CO-CoA and $C^2$ = COOH; or $C^1$ and $C^2$ = CO-CoA |
| 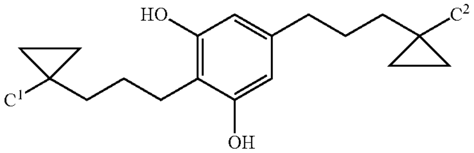 |
| wherein $C^1$ = COOH and $C^2$ = CO-CoA; $C^1$ = CO-CoA and $C^2$ = COOH; or $C^1$ and $C^2$ = CO-CoA |
| 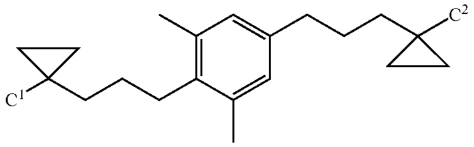 |

TABLE A-4-continued

| Structure |
|---|
| wherein $C^1$ = COOH and $C^2$ = CO-CoA; $C^1$ = CO-CoA and $C^2$ = COOH; or $C^1$ and $C^2$ = CO-CoA |
| 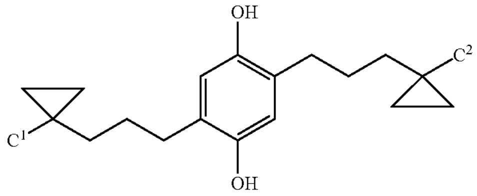 |
| wherein $C^1$ = COOH and $C^2$ = CO-CoA; $C^1$ = CO-CoA and $C^2$ = COOH; or $C^1$ and $C^2$ = CO-CoA |
| 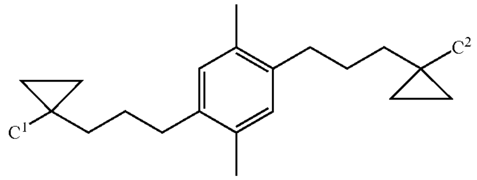 |
| wherein $C^1$ = COOH and $C^2$ = CO-CoA; $C^1$ = CO-CoA and $C^2$ = COOH; or $C^1$ and $C^2$ = CO-CoA |
| 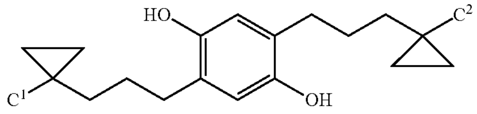 |
| wherein $C^1$ = COOH and $C^2$ = CO-CoA; $C^1$ = CO-CoA and $C^2$ = COOH; or $C^1$ and $C^2$ = CO-CoA |
| 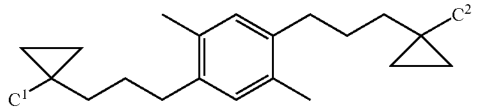 |
| wherein $C^1$ = COOH and $C^2$ = CO-CoA; $C^1$ = CO-CoA and $C^2$ = COOH; or $C^1$ and $C^2$ = CO-CoA |
| 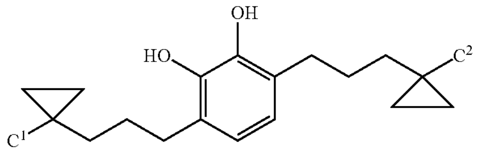 |
| wherein $C^1$ = COOH and $C^2$ = CO-CoA; $C^1$ = CO-CoA and $C^2$ = COOH; or $C^1$ and $C^2$ = CO-CoA |
| 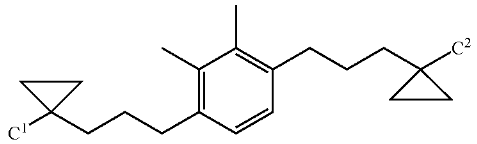 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 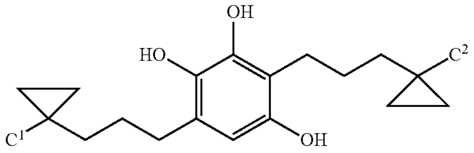 |
| wherein $C^1$ = COOH and $C^2$ = CO-CoA; $C^1$ = CO-CoA and $C^2$ = COOH; or $C^1$ and $C^2$ = CO-CoA |
| 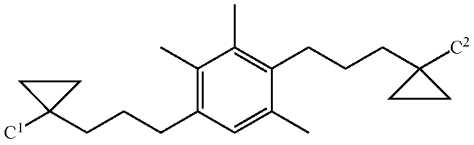 |
| wherein $C^1$ = COOH and $C^2$ = CO-CoA; $C^1$ = CO-CoA and $C^2$ = COOH; or $C^1$ and $C^2$ = CO-CoA |
| 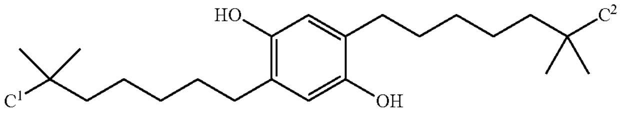 |
| wherein $C^1$ = COOH and $C^2$ = CO-CoA; $C^1$ = CO-CoA and $C^2$ = COOH; or $C^1$ and $C^2$ = CO-CoA |
| 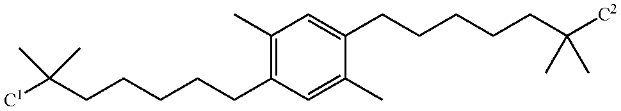 |
| wherein $C^1$ = COOH and $C^2$ = CO-CoA; $C^1$ = CO-CoA and $C^2$ = COOH; or $C^1$ and $C^2$ = CO-CoA |
| 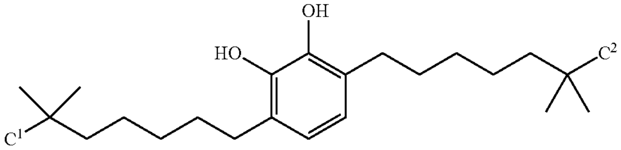 |
| wherein $C^1$ = COOH and $C^2$ = CO-CoA; $C^1$ = CO-CoA and $C^2$ = COOH; or $C^1$ and $C^2$ = CO-CoA |
| 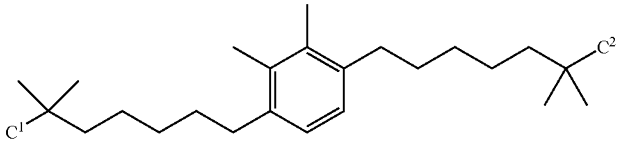 |
| wherein $C^1$ = COOH and $C^2$ = CO-CoA; $C^1$ = CO-CoA and $C^2$ = COOH; or $C^1$ and $C^2$ = CO-CoA |
| 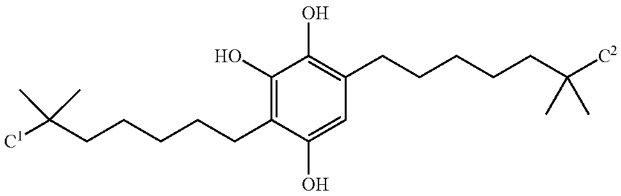 |

TABLE A-4-continued

| Structure |
| --- |
| wherein $C^1$ = COOH and $C^2$ = CO-CoA; $C^1$ = CO-CoA and $C^2$ = COOH; or $C^1$ and $C^2$ = CO-CoA |
| 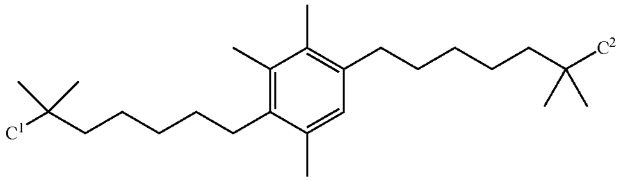 |
| wherein $C^1$ = COOH and $C^2$ = CO-CoA; $C^1$ = CO-CoA and $C^2$ = COOH; or $C^1$ and $C^2$ = CO-CoA |
| 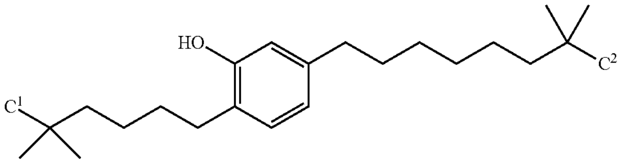 |
| wherein $C^1$ = COOH and $C^2$ = CO-CoA; $C^1$ = CO-CoA and $C^2$ = COOH; or $C^1$ and $C^2$ = CO-CoA |
| 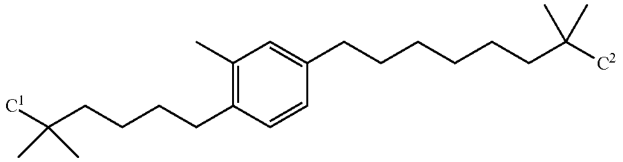 |
| wherein $C^1$ = COOH and $C^2$ = CO-CoA; $C^1$ = CO-CoA and $C^2$ = COOH; or $C^1$ and $C^2$ = CO-CoA |
| 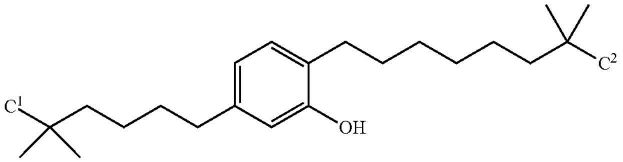 |
| wherein $C^1$ = COOH and $C^2$ = CO-CoA; $C^1$ = CO-CoA and $C^2$ = COOH; or $C^1$ and $C^2$ = CO-CoA |
| 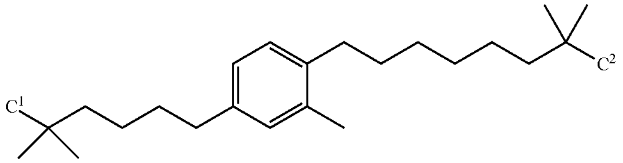 |
| wherein $C^1$ = COOH and $C^2$ = CO-CoA; $C^1$ = CO-CoA and $C^2$ = COOH; or $C^1$ and $C^2$ = CO-CoA |
| 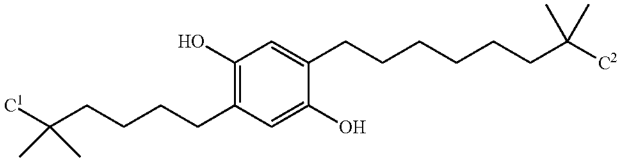 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 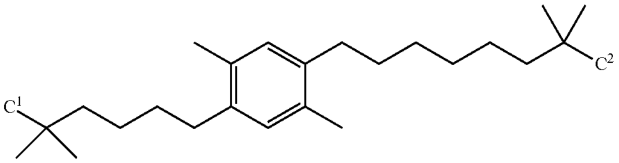 wherein $C^1$ = COOH and $C^2$ = CO-CoA; $C^1$ = CO-CoA and $C^2$ = COOH; or $C^1$ and $C^2$ = CO-CoA |
| 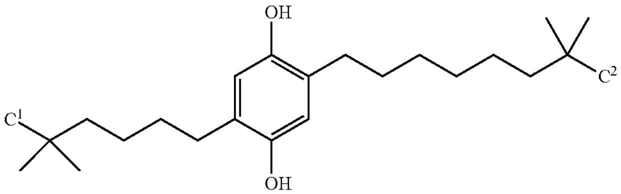 wherein $C^1$ = COOH and $C^2$ = CO-CoA; $C^1$ = CO-CoA and $C^2$ = COOH; or $C^1$ and $C^2$ = CO-CoA |
| 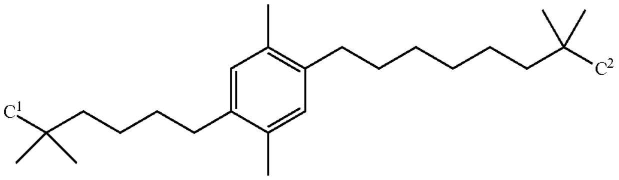 wherein $C^1$ = COOH and $C^2$ = CO-CoA; $C^1$ = CO-CoA and $C^2$ = COOH; or $C^1$ and $C^2$ = CO-CoA |
| 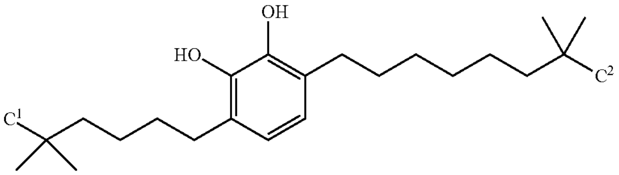 wherein $C^1$ = COOH and $C^2$ = CO-CoA; $C^1$ = CO-CoA and $C^2$ = COOH; or $C^1$ and $C^2$ = CO-CoA |
| 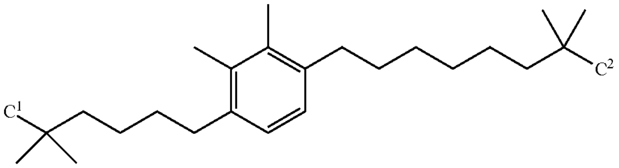 wherein $C^1$ = COOH and $C^2$ = CO-CoA; $C^1$ = CO-CoA and $C^2$ = COOH; or $C^1$ and $C^2$ = CO-CoA |
| 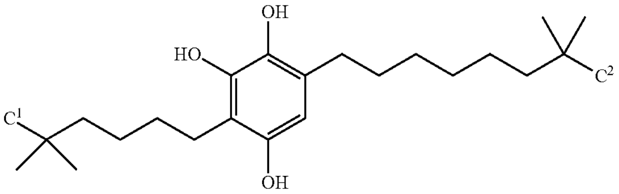 |

TABLE A-4-continued

| Structure |
| --- |
| wherein $C^1$ = COOH and $C^2$ = CO-CoA; $C^1$ = CO-CoA and $C^2$ = COOH; or $C^1$ and $C^2$ = CO-CoA |
| 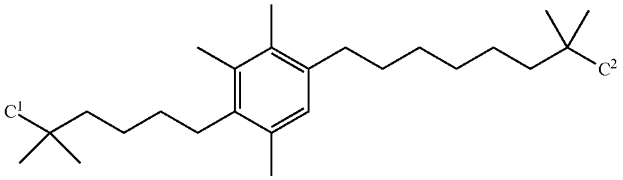 |
| wherein $C^1$ = COOH and $C^2$ = CO-CoA; $C^1$ = CO-CoA and $C^2$ = COOH; or $C^1$ and $C^2$ = CO-CoA |
| 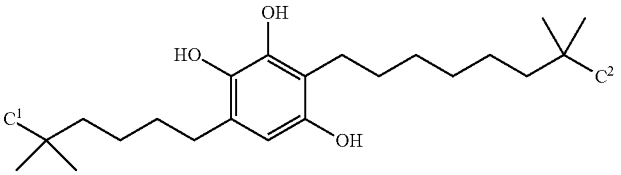 |
| wherein $C^1$ = COOH and $C^2$ = CO-CoA; $C^1$ = CO-CoA and $C^2$ = COOH; or $C^1$ and $C^2$ = CO-CoA |
| 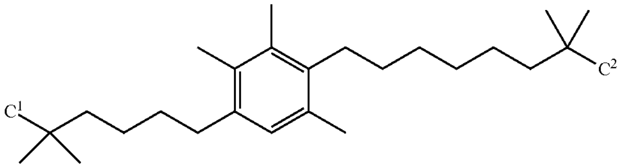 |
| wherein $C^1$ = COOH and $C^2$ = CO-CoA; $C^1$ = CO-CoA and $C^2$ = COOH; or $C^1$ and $C^2$ = CO-CoA |
| 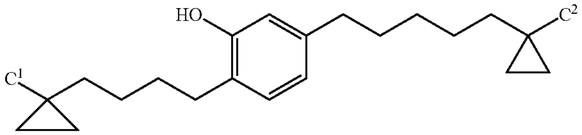 |
| wherein $C^1$ = COOH and $C^2$ = CO-CoA; $C^1$ = CO-CoA and $C^2$ = COOH; or $C^1$ and $C^2$ = CO-CoA |
| 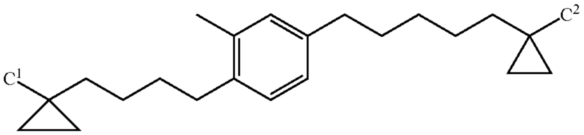 |
| wherein $C^1$ = COOH and $C^2$ = CO-CoA; $C^1$ = CO-CoA and $C^2$ = COOH; or $C^1$ and $C^2$ = CO-CoA |
| 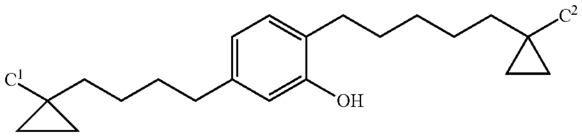 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 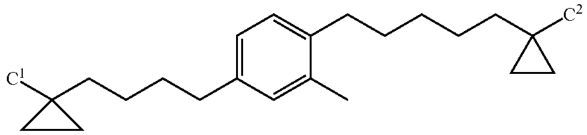<br>wherein $C^1$ = COOH and $C^2$ = CO-CoA; $C^1$ = CO-CoA and $C^2$ = COOH; or $C^1$ and $C^2$ = CO-CoA |
| 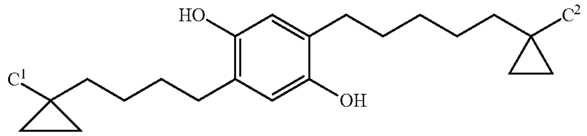<br>wherein $C^1$ = COOH and $C^2$ = CO-CoA; $C^1$ = CO-CoA and $C^2$ = COOH; or $C^1$ and $C^2$ = CO-CoA |
| 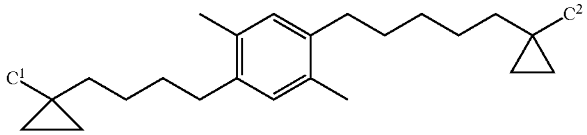<br>wherein $C^1$ = COOH and $C^2$ = CO-CoA; $C^1$ = CO-CoA and $C^2$ = COOH; or $C^1$ and $C^2$ = CO-CoA |
| 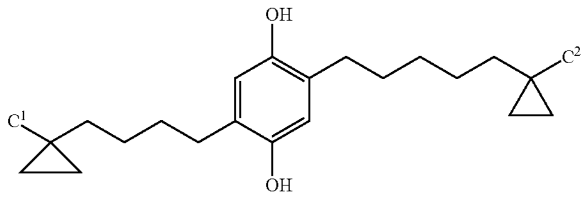<br>wherein $C^1$ = COOH and $C^2$ = CO-CoA; $C^1$ = CO-CoA and $C^2$ = COOH; or $C^1$ and $C^2$ = CO-CoA |
| 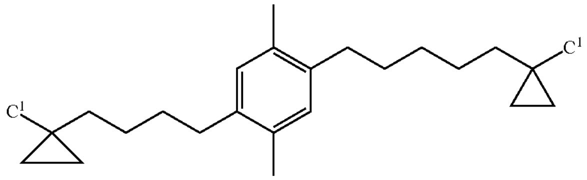<br>wherein $C^1$ = COOH and $C^2$ = CO-CoA; $C^1$ = CO-CoA and $C^2$ = COOH; or $C^1$ and $C^2$ = CO-CoA |
| 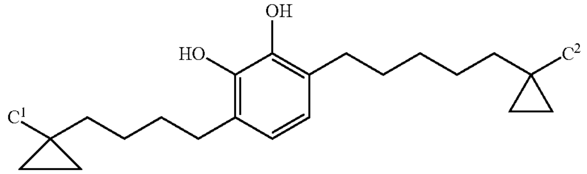<br>wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 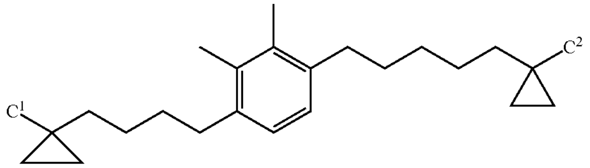 |
| wherein $C^1$ = COOH and $C^2$ = CO-CoA; $C^1$ = CO-CoA and $C^2$ = COOH; or $C^1$ and $C^2$ = CO-CoA |
| 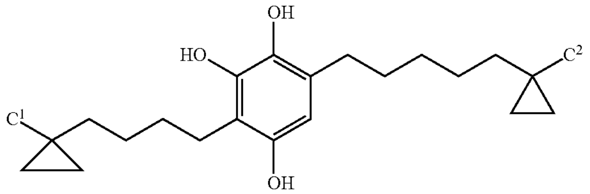 |
| wherein $C^1$ = COOH and $C^2$ = CO-CoA; $C^1$ = CO-CoA and $C^2$ = COOH; or $C^1$ and $C^2$ = CO-CoA |
| 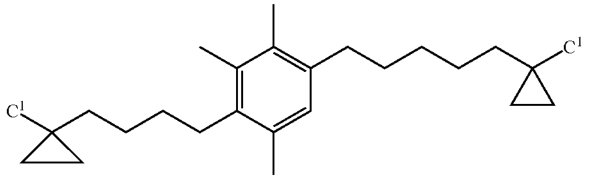 |
| wherein $C^1$ = COOH and $C^2$ = CO-CoA; $C^1$ = CO-CoA and $C^2$ = COOH; or $C^1$ and $C^2$ = CO-CoA |
| 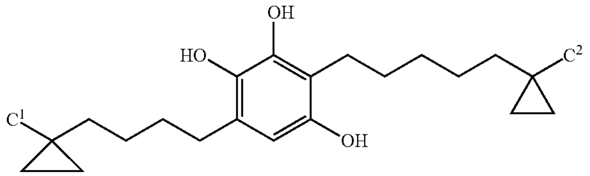 |
| wherein $C^1$ = COOH and $C^2$ = CO-CoA; $C^1$ = CO-CoA and $C^2$ = COOH; or $C^1$ and $C^2$ = CO-CoA |
| 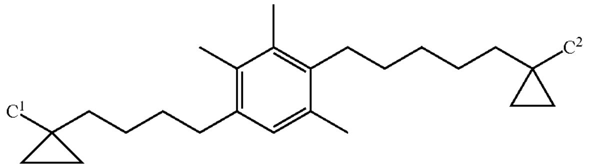 |
| wherein $C^1$ = COOH and $C^2$ = CO-CoA; $C^1$ = CO-CoA and $C^2$ = COOH; or $C^1$ and $C^2$ = CO-CoA |
| 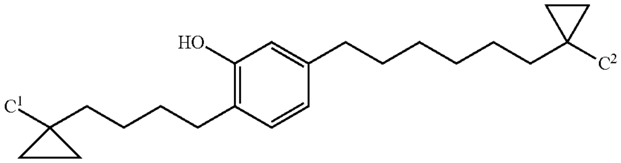 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 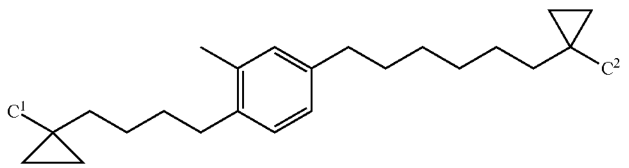 |
| wherein $C^1$ = COOH and $C^2$ = CO-CoA; $C^1$ = CO-CoA and $C^2$ = COOH; or $C^1$ and $C^2$ = CO-CoA |
| 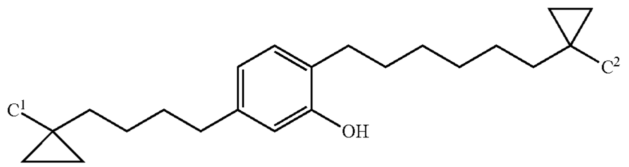 |
| wherein $C^1$ = COOH and $C^2$ = CO-CoA; $C^1$ = CO-CoA and $C^2$ = COOH; or $C^1$ and $C^2$ = CO-CoA |
| 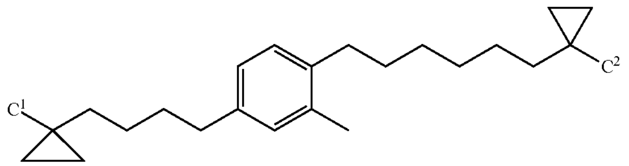 |
| wherein $C^1$ = COOH and $C^2$ = CO-CoA; $C^1$ = CO-CoA and $C^2$ = COOH; or $C^1$ and $C^2$ = CO-CoA |
| 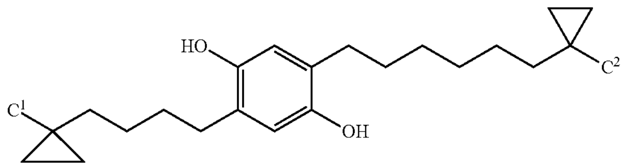 |
| wherein $C^1$ = COOH and $C^2$ = CO-CoA; $C^1$ = CO-CoA and $C^2$ = COOH; or $C^1$ and $C^2$ = CO-CoA |
| 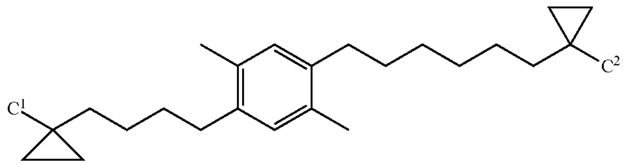 |
| wherein $C^1$ = COOH and $C^2$ = CO-CoA; $C^1$ = CO-CoA and $C^2$ = COOH; or $C^1$ and $C^2$ = CO-CoA |
| 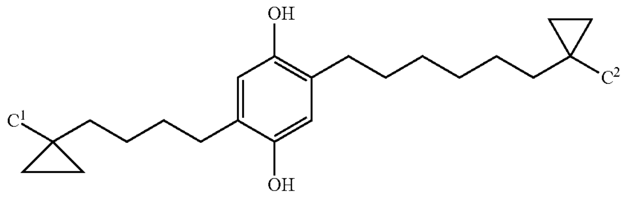 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 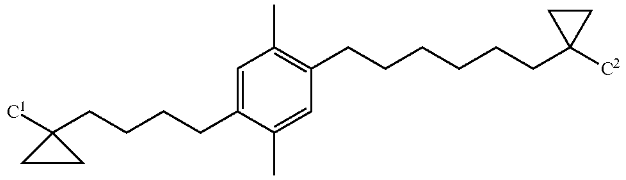 |
| wherein $C^1$ = COOH and $C^2$ = CO-CoA; $C^1$ = CO-CoA and $C^2$ = COOH; or $C^1$ and $C^2$ = CO-CoA |
| 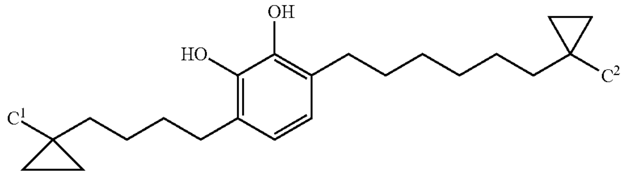 |
| wherein $C^1$ = COOH and $C^2$ = CO-CoA; $C^1$ = CO-CoA and $C^2$ = COOH; or $C^1$ and $C^2$ = CO-CoA |
| 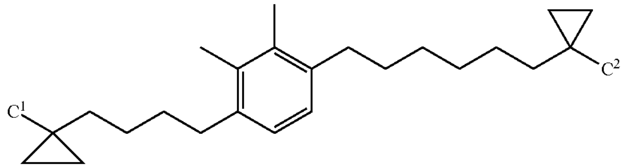 |
| wherein $C^1$ = COOH and $C^2$ = CO-CoA; $C^1$ = CO-CoA and $C^2$ = COOH; or $C^1$ and $C^2$ = CO-CoA |
| 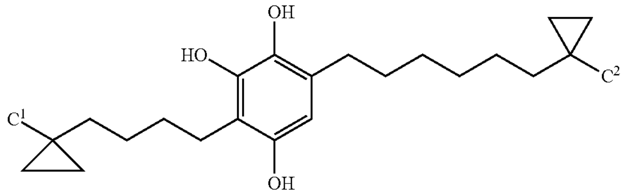 |
| wherein $C^1$ = COOH and $C^2$ = CO-CoA; $C^1$ = CO-CoA and $C^2$ = COOH; or $C^1$ and $C^2$ = CO-CoA |
| 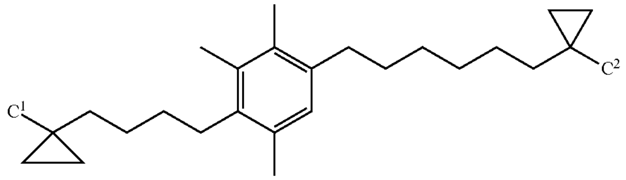 |
| wherein $C^1$ = COOH and $C^2$ = CO-CoA; $C^1$ = CO-CoA and $C^2$ = COOH; or $C^1$ and $C^2$ = CO-CoA |
| 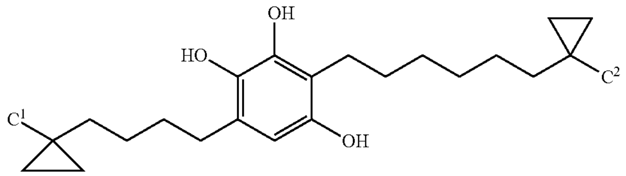 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 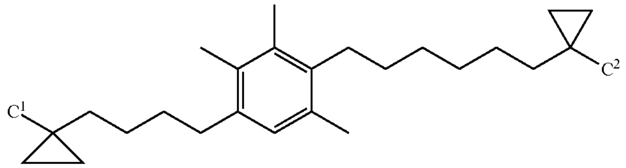 |
| wherein $C^1$ = COOH and $C^2$ = CO-CoA; $C^1$ = CO-CoA and $C^2$ = COOH; or $C^1$ and $C^2$ = CO-CoA |
| 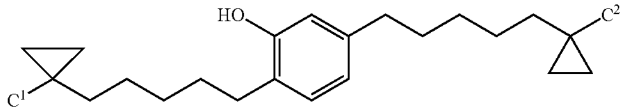 |
| wherein $C^1$ = COOH and $C^2$ = CO-CoA; $C^1$ = CO-CoA and $C^2$ = COOH; or $C^1$ and $C^2$ = CO-CoA |
| 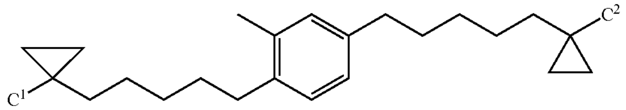 |
| wherein $C^1$ = COOH and $C^2$ = CO-CoA; $C^1$ = CO-CoA and $C^2$ = COOH; or $C^1$ and $C^2$ = CO-CoA |
| 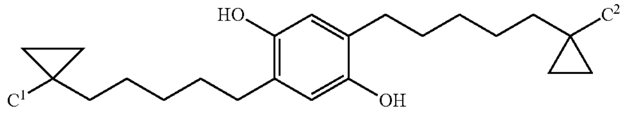 |
| wherein $C^1$ = COOH and $C^2$ = CO-CoA; $C^1$ = CO-CoA and $C^2$ = COOH; or $C^1$ and $C^2$ = CO-CoA |
| 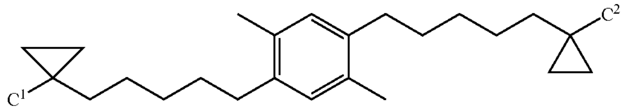 |
| wherein $C^1$ = COOH and $C^2$ = CO-CoA; $C^1$ = CO-CoA and $C^2$ = COOH; or $C^1$ and $C^2$ = CO-CoA |
| 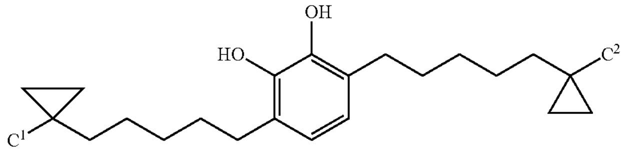 |
| wherein $C^1$ = COOH and $C^2$ = CO-CoA; $C^1$ = CO-CoA and $C^2$ = COOH; or $C^1$ and $C^2$ = CO-CoA |
| 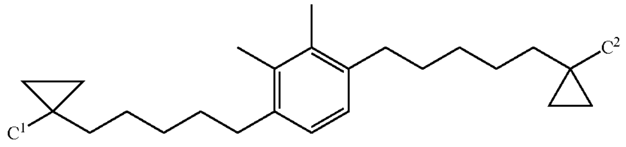 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
|---|
| 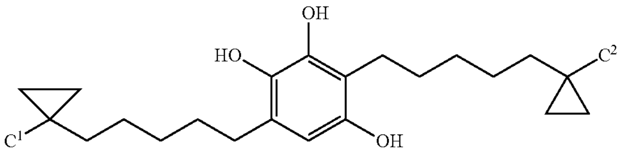 |
| wherein $C^1$ = COOH and $C^2$ = CO-CoA; $C^1$ = CO-CoA and $C^2$ = COOH; or $C^1$ and $C^2$ = CO-CoA |
| 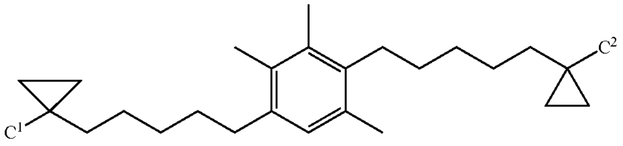 |
| wherein $C^1$ = COOH and $C^2$ = CO-CoA; $C^1$ = CO-CoA and $C^2$ = COOH; or $C^1$ and $C^2$ = CO-CoA |
| 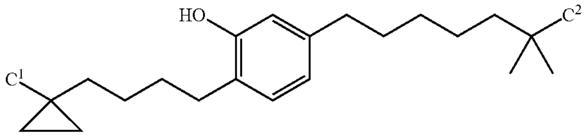 |
| wherein $C^1$ = COOH and $C^2$ = CO-CoA; $C^1$ = CO-CoA and $C^2$ = COOH; or $C^1$ and $C^2$ = CO-CoA |
| 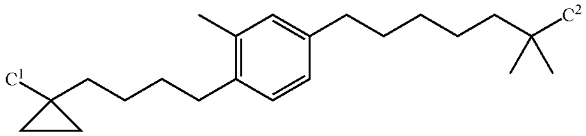 |
| wherein $C^1$ = COOH and $C^2$ = CO-CoA; $C^1$ = CO-CoA and $C^2$ = COOH; or $C^1$ and $C^2$ = CO-CoA |
| 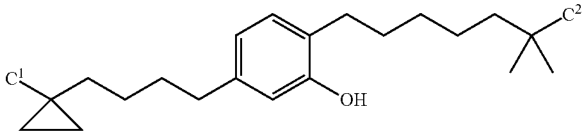 |
| wherein $C^1$ = COOH and $C^2$ = CO-CoA; $C^1$ = CO-CoA and $C^2$ = COOH; or $C^1$ and $C^2$ = CO-CoA |
| 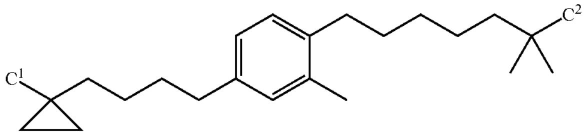 |
| wherein $C^1$ = COOH and $C^2$ = CO-CoA; $C^1$ = CO-CoA and $C^2$ = COOH; or $C^1$ and $C^2$ = CO-CoA |
| 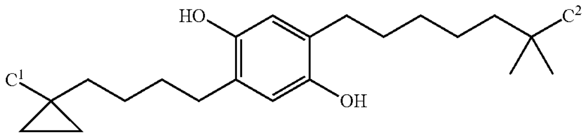 |

TABLE A-4-continued

| Structure |
|---|
| wherein $C^1$ = COOH and $C^2$ = CO-CoA; $C^1$ = CO-CoA and $C^2$ = COOH; or $C^1$ and $C^2$ = CO-CoA |
| 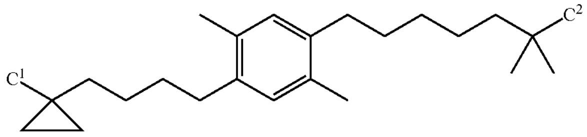 |
| wherein $C^1$ = COOH and $C^2$ = CO-CoA; $C^1$ = CO-CoA and $C^2$ = COOH; or $C^1$ and $C^2$ = CO-CoA |
| 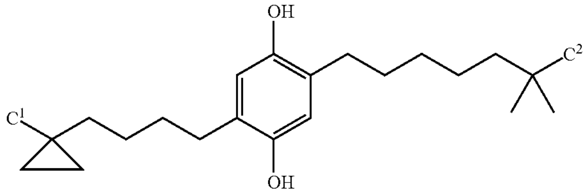 |
| wherein $C^1$ = COOH and $C^2$ = CO-CoA; $C^1$ = CO-CoA and $C^2$ = COOH; or $C^1$ and $C^2$ = CO-CoA |
| 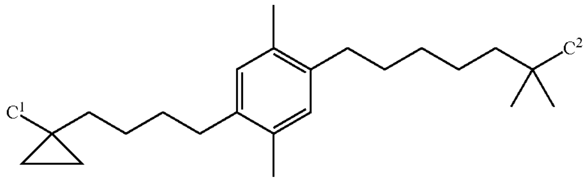 |
| wherein $C^1$ = COOH and $C^2$ = CO-CoA; $C^1$ = CO-CoA and $C^2$ = COOH; or $C^1$ and $C^2$ = CO-CoA |
| 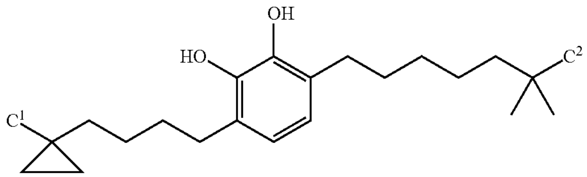 |
| wherein $C^1$ = COOH and $C^2$ = CO-CoA; $C^1$ = CO-CoA and $C^2$ = COOH; or $C^1$ and $C^2$ = CO-CoA |
| 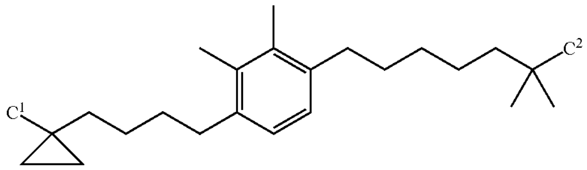 |
| wherein $C^1$ = COOH and $C^2$ = CO-CoA; $C^1$ = CO-CoA and $C^2$ = COOH; or $C^1$ and $C^2$ = CO-CoA |
| 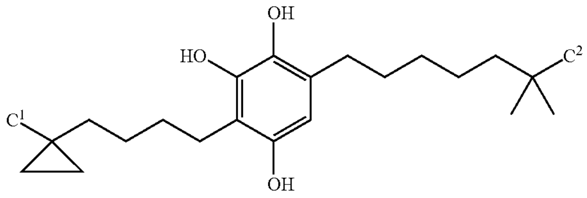 |

TABLE A-4-continued

| Structure |
| --- |
| wherein $C^1$ = COOH and $C^2$ = CO-CoA; $C^1$ = CO-CoA and $C^2$ = COOH; or $C^1$ and $C^2$ = CO-CoA |
| 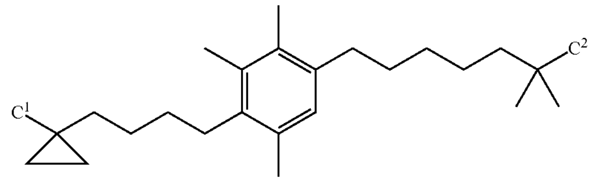 |
| wherein $C^1$ = COOH and $C^2$ = CO-CoA; $C^1$ = CO-CoA and $C^2$ = COOH; or $C^1$ and $C^2$ = CO-CoA |
| 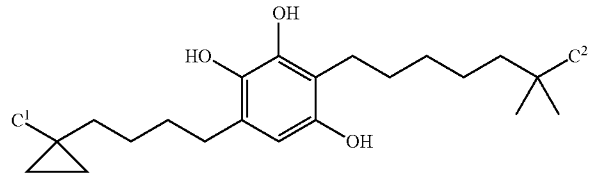 |
| wherein $C^1$ = COOH and $C^2$ = CO-CoA; $C^1$ = CO-CoA and $C^2$ = COOH; or $C^1$ and $C^2$ = CO-CoA |
| 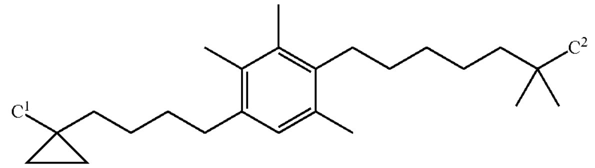 |
| wherein $C^1$ = COOH and $C^2$ = CO-CoA; $C^1$ = CO-CoA and $C^2$ = COOH; or $C^1$ and $C^2$ = CO-CoA |
| 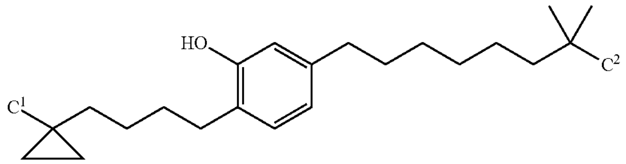 |
| wherein $C^1$ = COOH and $C^2$ = CO-CoA; $C^1$ = CO-CoA and $C^2$ = COOH; or $C^1$ and $C^2$ = CO-CoA |
| 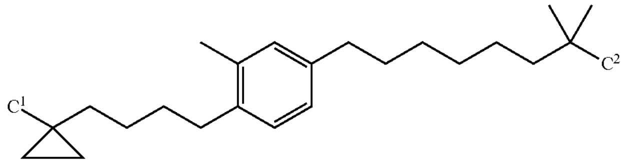 |
| wherein $C^1$ = COOH and $C^2$ = CO-CoA; $C^1$ = CO-CoA and $C^2$ = COOH; or $C^1$ and $C^2$ = CO-CoA |
| 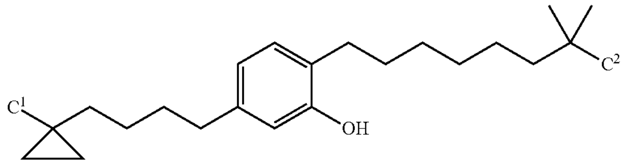 |

TABLE A-4-continued

| Structure |
| --- |
| wherein $C^1$ = COOH and $C^2$ = CO-CoA; $C^1$ = CO-CoA and $C^2$ = COOH; or $C^1$ and $C^2$ = CO-CoA |
| 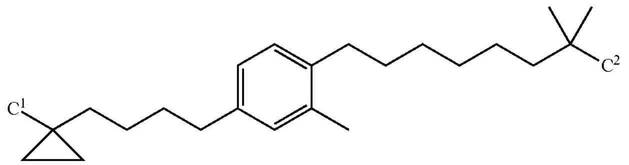 |
| wherein $C^1$ = COOH and $C^2$ = CO-CoA; $C^1$ = CO-CoA and $C^2$ = COOH; or $C^1$ and $C^2$ = CO-CoA |
| 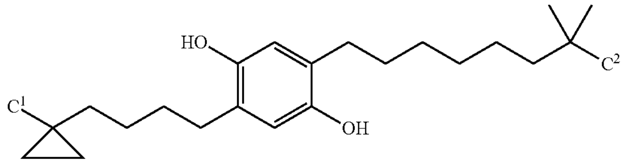 |
| wherein $C^1$ = COOH and $C^2$ = CO-CoA; $C^1$ = CO-CoA and $C^2$ = COOH; or $C^1$ and $C^2$ = CO-CoA |
| 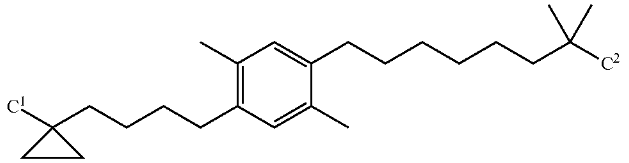 |
| wherein $C^1$ = COOH and $C^2$ = CO-CoA; $C^1$ = CO-CoA and $C^2$ = COOH; or $C^1$ and $C^2$ = CO-CoA |
| 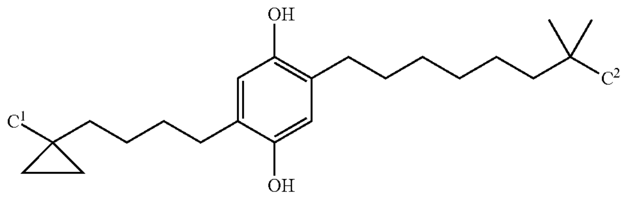 |
| wherein $C^1$ = COOH and $C^2$ = CO-CoA; $C^1$ = CO-CoA and $C^2$ = COOH; or $C^1$ and $C^2$ = CO-CoA |
| 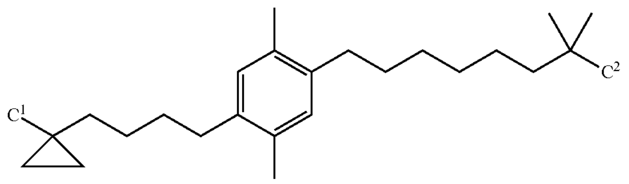 |
| wherein $C^1$ = COOH and $C^2$ = CO-CoA; $C^1$ = CO-CoA and $C^2$ = COOH; or $C^1$ and $C^2$ = CO-CoA |
| 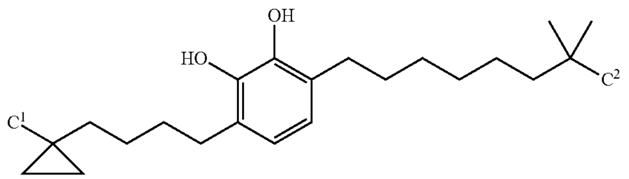 |

TABLE A-4-continued

| Structure |
|---|
| wherein $C^1$ = COOH and $C^2$ = CO-CoA; $C^1$ = CO-CoA and $C^2$ = COOH; or $C^1$ and $C^2$ = CO-CoA |
| 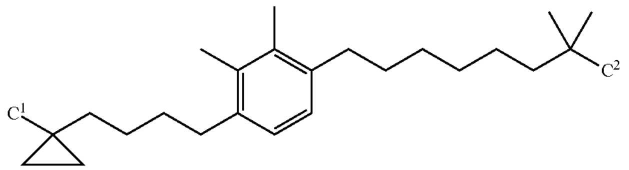 |
| wherein $C^1$ = COOH and $C^2$ = CO-CoA; $C^1$ = CO-CoA and $C^2$ = COOH; or $C^1$ and $C^2$ = CO-CoA |
| 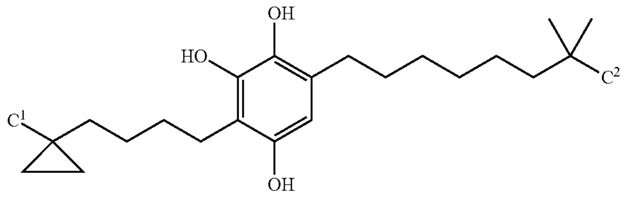 |
| wherein $C^1$ = COOH and $C^2$ = CO-CoA; $C^1$ = CO-CoA and $C^2$ = COOH; or $C^1$ and $C^2$ = CO-CoA |
| 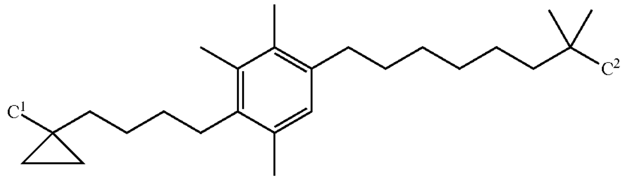 |
| wherein $C^1$ = COOH and $C^2$ = CO-CoA; $C^1$ = CO-CoA and $C^2$ = COOH; or $C^1$ and $C^2$ = CO-CoA |
| 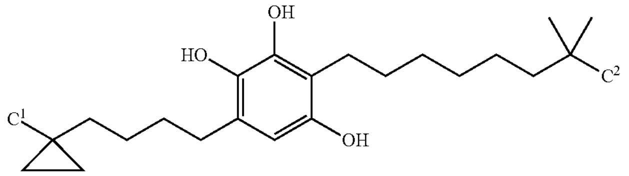 |
| wherein $C^1$ = COOH and $C^2$ = CO-CoA; $C^1$ = CO-CoA and $C^2$ = COOH; or $C^1$ and $C^2$ = CO-CoA |
| 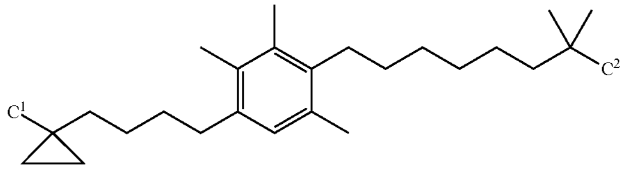 |
| wherein $C^1$ = COOH and $C^2$ = CO-CoA; $C^1$ = CO-CoA and $C^2$ = COOH; or $C^1$ and $C^2$ = CO-CoA |
| 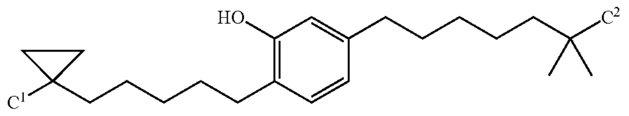 |

TABLE A-4-continued

| Structure |
| --- |
| wherein $C^1$ = COOH and $C^2$ = CO-CoA; $C^1$ = CO-CoA and $C^2$ = COOH; or $C^1$ and $C^2$ = CO-CoA |
| 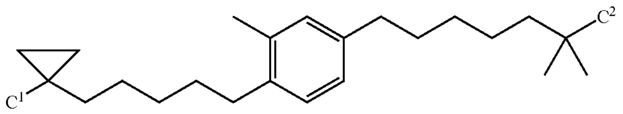 |
| wherein $C^1$ = COOH and $C^2$ = CO-CoA; $C^1$ = CO-CoA and $C^2$ = COOH; or $C^1$ and $C^2$ = CO-CoA |
| 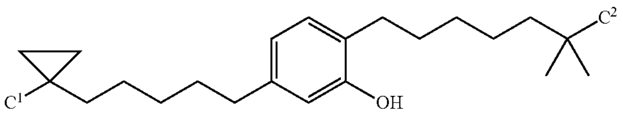 |
| wherein $C^1$ = COOH and $C^2$ = CO-CoA; $C^1$ = CO-CoA and $C^2$ = COOH; or $C^1$ and $C^2$ = CO-CoA |
| 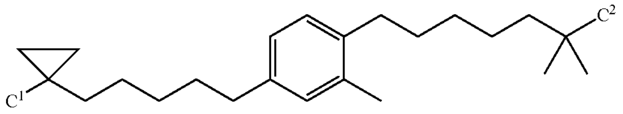 |
| wherein $C^1$ = COOH and $C^2$ = CO-CoA; $C^1$ = CO-CoA and $C^2$ = COOH; or $C^1$ and $C^2$ = CO-CoA |
| 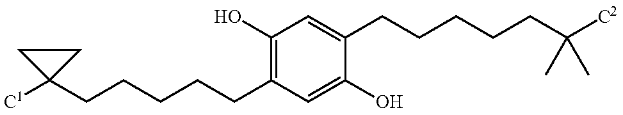 |
| wherein $C^1$ = COOH and $C^2$ = CO-CoA; $C^1$ = CO-CoA and $C^2$ = COOH; or $C^1$ and $C^2$ = CO-CoA |
| 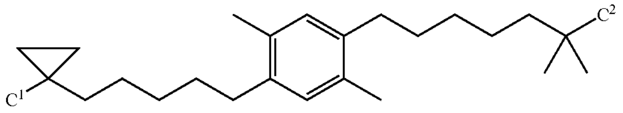 |
| wherein $C^1$ = COOH and $C^2$ = CO-CoA; $C^1$ = CO-CoA and $C^2$ = COOH; or $C^1$ and $C^2$ = CO-CoA |
| 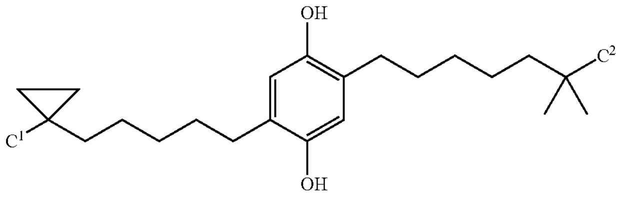 |
| wherein $C^1$ = COOH and $C^2$ = CO-CoA; $C^1$ = CO-CoA and $C^2$ = COOH; or $C^1$ and $C^2$ = CO-CoA |
| 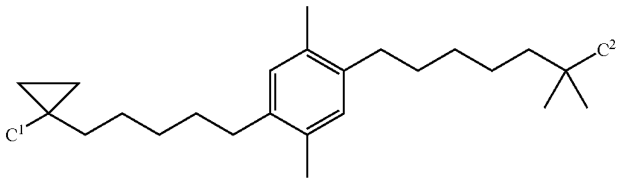 |

TABLE A-4-continued

| Structure |
|---|
| wherein $C^1$ = COOH and $C^2$ = CO-CoA; $C^1$ = CO-CoA and $C^2$ = COOH; or $C^1$ and $C^2$ = CO-CoA |
| 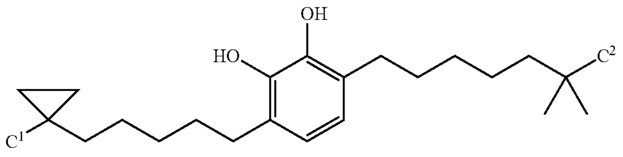 |
| wherein $C^1$ = COOH and $C^2$ = CO-CoA; $C^1$ = CO-CoA and $C^2$ = COOH; or $C^1$ and $C^2$ = CO-CoA |
| 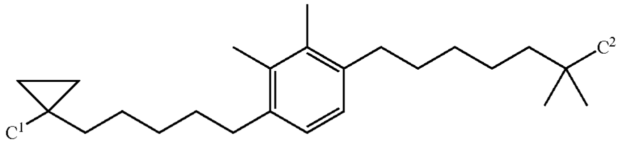 |
| wherein $C^1$ = COOH and $C^2$ = CO-CoA; $C^1$ = CO-CoA and $C^2$ = COOH; or $C^1$ and $C^2$ = CO-CoA |
| 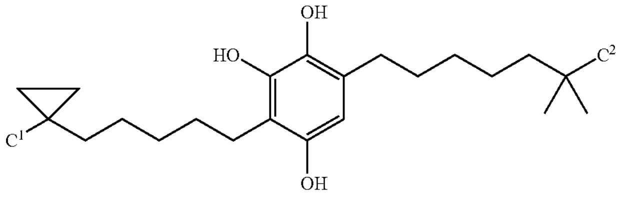 |
| wherein $C^1$ = COOH and $C^2$ = CO-CoA; $C^1$ = CO-CoA and $C^2$ = COOH; or $C^1$ and $C^2$ = CO-CoA |
| 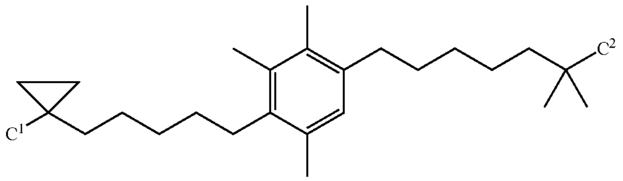 |
| wherein $C^1$ = COOH and $C^2$ = CO-CoA; $C^1$ = CO-CoA and $C^2$ = COOH; or $C^1$ and $C^2$ = CO-CoA |
| 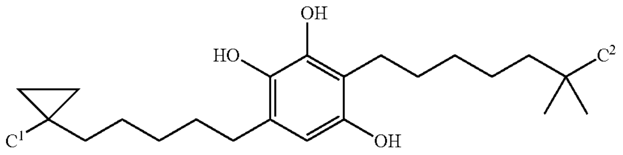 |
| wherein $C^1$ = COOH and $C^2$ = CO-CoA; $C^1$ = CO-CoA and $C^2$ = COOH; or $C^1$ and $C^2$ = CO-CoA |

TABLE A-4-continued

| Structure |
| --- |
| 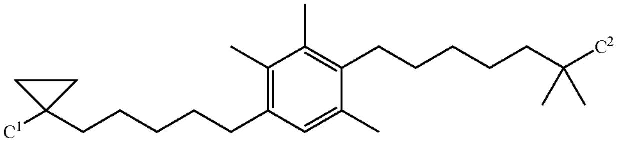 |
| wherein $C^1$ = COOH and $C^2$ = CO-CoA; $C^1$ = CO-CoA and $C^2$ = COOH; or $C^1$ and $C^2$ = CO-CoA |

In some embodiments, the compound of Formula (I) or (IB) has any one of the structures shown in Table A-5 and defined by $C^1$ and $C^2$, or a pharmaceutically acceptable salt or solvate thereof.

TABLE A-5

| Structure |
| --- |
| 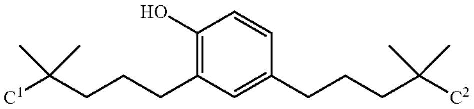 |
| wherein $C^1$ = COOH and $C^2$ = CO—CoA; $C^1$ = CO—CoA and $C^2$ = COOH; or $C^1$ and $C^2$ = CO—CoA |
| 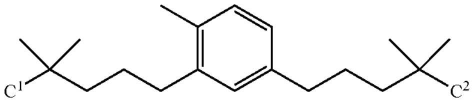 |
| wherein $C^1$ = COOH and $C^2$ = CO—CoA; $C^1$ = CO—CoA and $C^2$ = COOH; or $C^1$ and $C^2$ = CO—CoA |
| 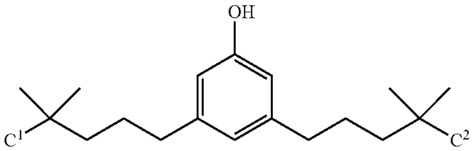 |
| wherein $C^1$ = COOH and $C^2$ = CO—CoA; $C^1$ = CO—CoA and $C^2$ = COOH; or $C^1$ and $C^2$ = CO—CoA |
| 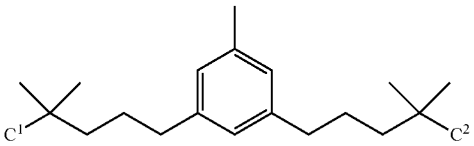 |
| wherein $C^1$ = COOH and $C^2$ = CO—CoA; $C^1$ = CO—CoA and $C^2$ = COOH; or $C^1$ and $C^2$ = CO—CoA |
| 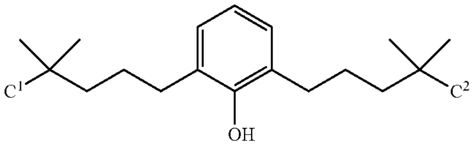 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 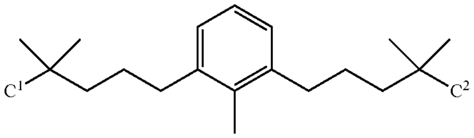 wherein $C^1$ = COOH and $C^2$ = CO—CoA; $C^1$ = CO—CoA and $C^2$ = COOH; or $C^1$ and $C^2$ = CO—CoA |
| 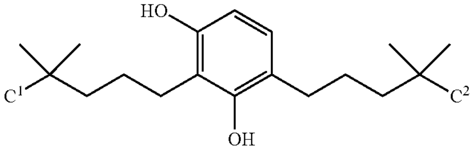 wherein $C^1$ = COOH and $C^2$ = CO—CoA; $C^1$ = CO—CoA and $C^2$ = COOH; or $C^1$ and $C^2$ = CO—CoA |
| 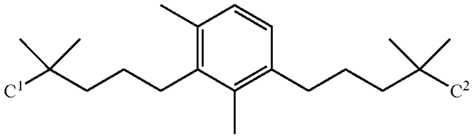 wherein $C^1$ = COOH and $C^2$ = CO—CoA; $C^1$ = CO—CoA and $C^2$ = COOH; or $C^1$ and $C^2$ = CO—CoA |
| 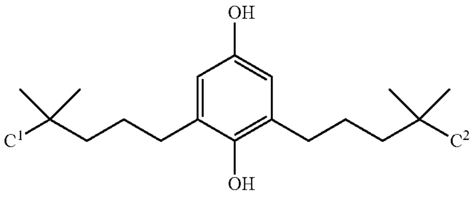 wherein $C^1$ = COOH and $C^2$ = CO—CoA; $C^1$ = CO—CoA and $C^2$ = COOH; or $C^1$ and $C^2$ = CO—CoA |
| 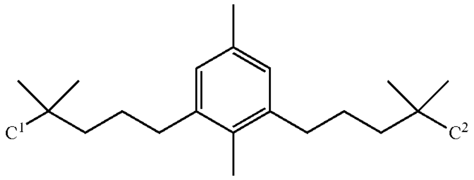 wherein $C^1$ = COOH and $C^2$ = CO—CoA; $C^1$ = CO—CoA and $C^2$ = COOH; or $C^1$ and $C^2$ = CO—CoA |
| 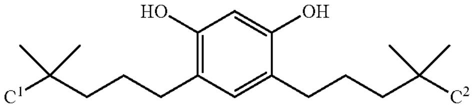 wherein $C^1$ = COOH and $C^2$= CO—CoA; $C^1$ = CO—CoA and $C^2$ = COOH; or $C^1$ and $C^2$ = CO—CoA |
| 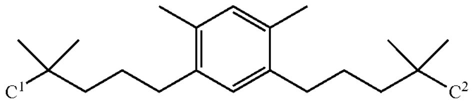 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 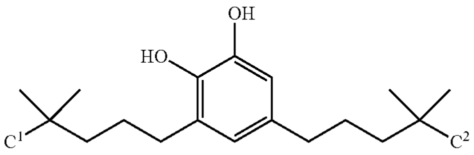 |
| wherein $C^1$ = COOH and $C^2$ = CO—CoA; $C^1$ = CO—CoA and $C^2$ = COOH; or $C^1$ and $C^2$ = CO—CoA |
| 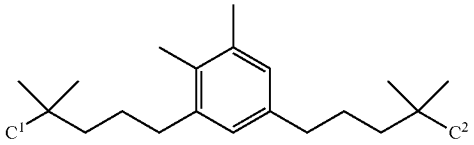 |
| wherein $C^1$ = COOH and $C^2$ = CO—CoA; $C^1$ = CO—CoA and $C^2$ = COOH; or $C^1$ and $C^2$ = CO—CoA |
| 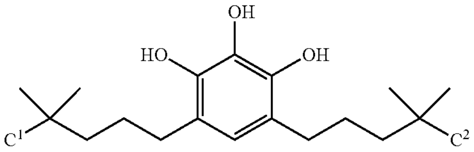 |
| wherein $C^1$ = COOH and $C^2$ = CO—CoA; $C^1$ = CO—CoA and $C^2$ = COOH; or $C^1$ and $C^2$ = CO—CoA |
| 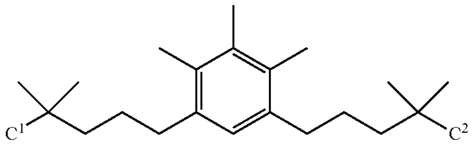 |
| wherein $C^1$ = COOH and $C^2$ = CO—CoA; $C^1$ = CO—CoA and $C^2$ = COOH; or $C^1$ and $C^2$ = CO—CoA |
| 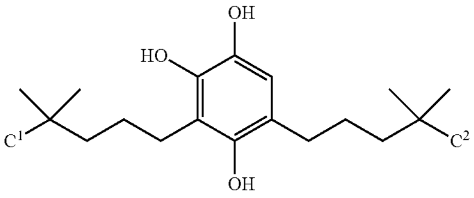 |
| wherein $C^1$ = COOH and $C^2$ = CO—CoA; $C^1$ = CO—CoA and $C^2$ = COOH; or $C^1$ and $C^2$ = CO—CoA |
| 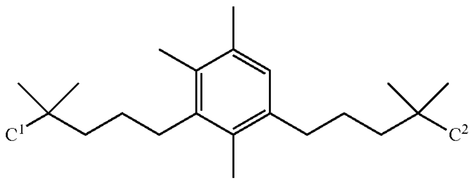 |
| wherein $C^1$ = COOH and $C^2$ = CO—CoA; $C^1$ = CO—CoA and $C^2$ = COOH; or $C^1$ and $C^2$ = CO—CoA |
| 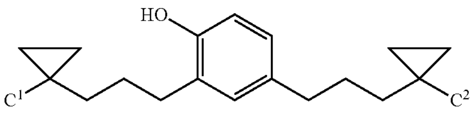 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 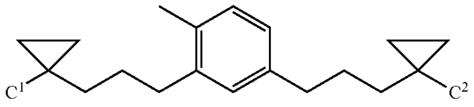 |
| wherein $C^1$ = COOH and $C^2$ = CO—CoA; $C^1$ = CO—CoA and $C^2$ = COOH; or $C^1$ and $C^2$ = CO—CoA |
| 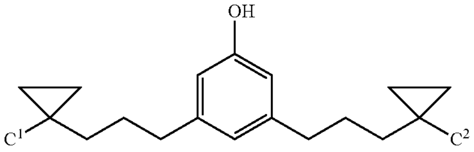 |
| wherein $C^1$ = COOH and $C^2$ = CO—CoA; $C^1$ = CO—CoA and $C^2$ = COOH; or $C^1$ and $C^2$ = CO—CoA |
| 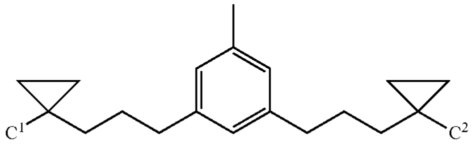 |
| wherein $C^1$ = COOH and $C^2$ = CO—CoA; $C^1$ = CO—CoA and $C^2$ = COOH; or $C^1$ and $C^2$ = CO—CoA |
| 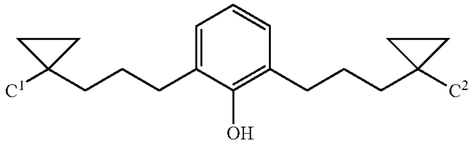 |
| wherein $C^1$ = COOH and $C^2$ = CO—CoA; $C^1$ = CO—CoA and $C^2$ = COOH; or $C^1$ and $C^2$ = CO—CoA |
| 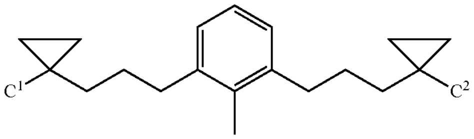 |
| wherein $C^1$ = COOH and $C^2$ = CO—CoA; $C^1$ = CO—CoA and $C^2$ = COOH; or $C^1$ and $C^2$ = CO—CoA |
| 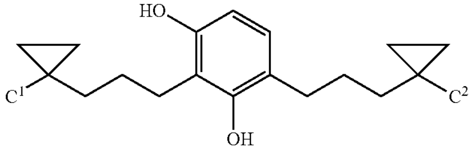 |
| wherein $C^1$ = COOH and $C^2$ = CO—CoA; $C^1$ = CO—CoA and $C^2$ = COOH; or $C^1$ and $C^2$ = CO—CoA |
| 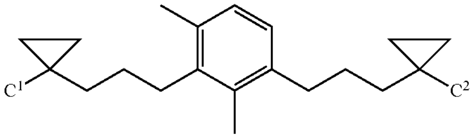 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 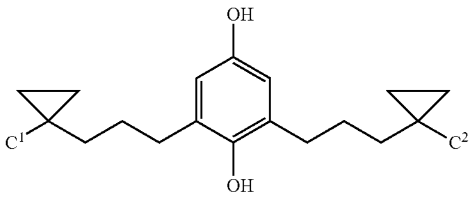 |
| wherein $C^1$ = COOH and $C^2$ = CO—CoA; $C^1$ = CO—CoA and $C^2$ = COOH; or $C^1$ and $C^2$ = CO—CoA |
| 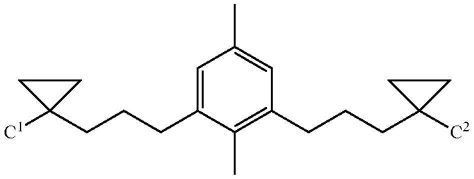 |
| wherein $C^1$ = COOH and $C^2$ = CO—CoA; $C^1$ = CO—CoA and $C^2$ = COOH; or $C^1$ and $C^2$ = CO—CoA |
| 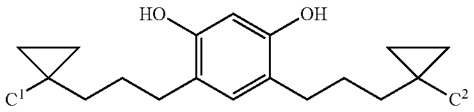 |
| wherein $C^1$ = COOH and $C^2$ = CO—CoA; $C^1$ = CO—CoA and $C^2$ = COOH; or $C^1$ and $C^2$ = CO—CoA |
| 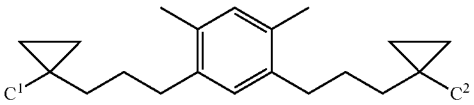 |
| wherein $C^1$ = COOH and $C^2$ = CO—CoA; $C^1$ = CO—CoA and $C^2$ = COOH; or $C^1$ and $C^2$ = CO—CoA |
| 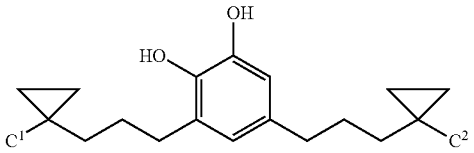 |
| wherein $C^1$ = COOH and $C^2$ = CO—CoA; $C^1$ = CO—CoA and $C^2$ = COOH; or $C^1$ and $C^2$ = CO—CoA |
| 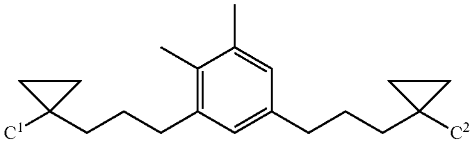 |
| wherein $C^1$ = COOH and $C^2$ = CO—CoA; $C^1$ = CO—CoA and $C^2$ = COOH; or $C^1$ and $C^2$ = CO—CoA |
| 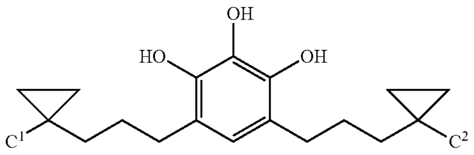 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 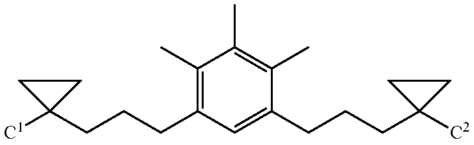 wherein $C^1$ = COOH and $C^2$ = CO—CoA; $C^1$ = CO—CoA and $C^2$ = COOH; or $C^1$ and $C^2$ = CO—CoA |
| 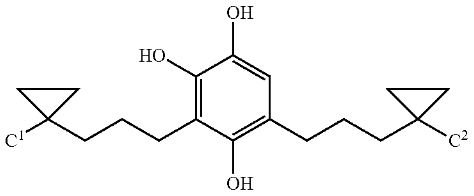 wherein $C^1$ = COOH and $C^2$ = CO—CoA; $C^1$ = CO—CoA and $C^2$ = COOH; or $C^1$ and $C^2$ = CO—CoA |
| 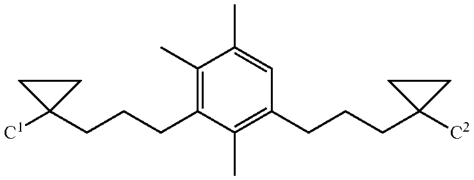 wherein $C^1$ = COOH and $C^2$ = CO—CoA; $C^1$ = CO—CoA and $C^2$ = COOH; or $C^1$ and $C^2$ = CO—CoA |
| 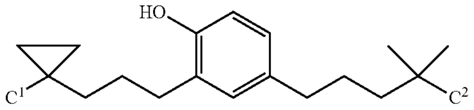 wherein $C^1$ = COOH and $C^2$ = CO—CoA; $C^1$ = CO—CoA and $C^2$ = COOH; or $C^1$ and $C^2$ = CO—CoA |
| 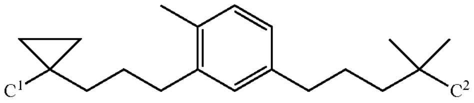 wherein $C^1$ = COOH and $C^2$ = CO—CoA; $C^1$ = CO—CoA and $C^2$ = COOH; or $C^1$ and $C^2$ = CO—CoA |
| 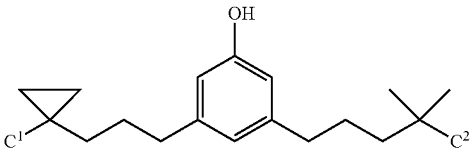 wherein $C^1$ = COOH and $C^2$ = CO—CoA; $C^1$ = CO—CoA and $C^2$ = COOH; or $C^1$ and $C^2$ = CO—CoA |
| 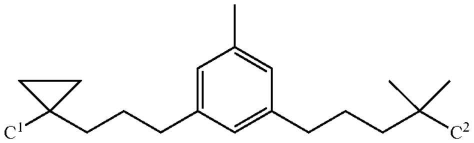 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 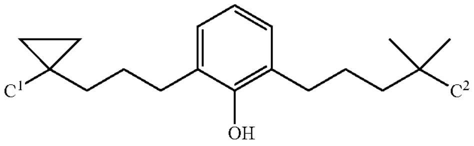 |
| wherein $C^1$ = COOH and $C^2$ = CO—CoA; $C^1$ = CO—CoA and $C^2$ = COOH; or $C^1$ and $C^2$ = CO—CoA |
| 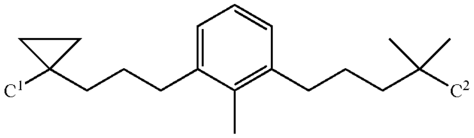 |
| wherein $C^1$ = COOH and $C^2$ = CO—CoA; $C^1$ = CO—CoA and $C^2$ = COOH; or $C^1$ and $C^2$ = CO—CoA |
| 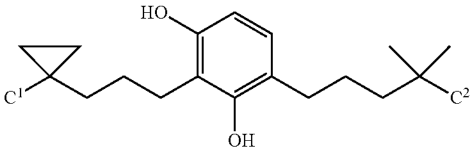 |
| wherein $C^1$ = COOH and $C^2$ = CO—CoA; $C^1$ = CO—CoA and $C^2$ = COOH; or $C^1$ and $C^2$ = CO—CoA |
| 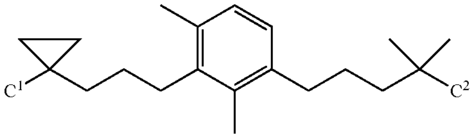 |
| wherein $C^1$ = COOH and $C^2$ = CO—CoA; $C^1$ = CO—CoA and $C^2$ = COOH; or $C^1$ and $C^2$ = CO—CoA |
| 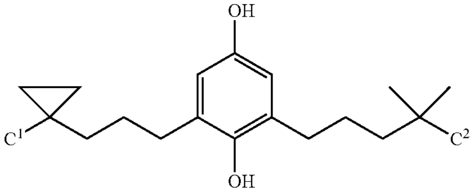 |
| wherein $C^1$ = COOH and $C^2$ = CO—CoA; $C^1$ = CO—CoA and $C^2$ = COOH; or $C^1$ and $C^2$ = CO—CoA |
| 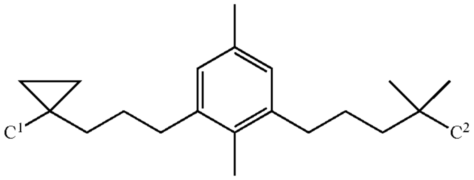 |
| wherein $C^1$ = COOH and $C^2$ = CO—CoA; $C^1$ = CO—CoA and $C^2$ = COOH; or $C^1$ and $C^2$ = CO—CoA |
| 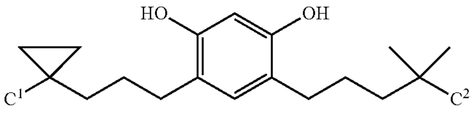 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 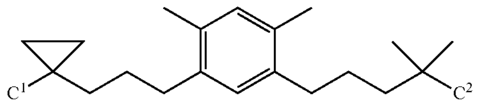 |
| wherein $C^1$ = COOH and $C^2$ = CO—CoA; $C^1$ = CO—CoA and $C^2$ = COOH; or $C^1$ and $C^2$ = CO—CoA |
| 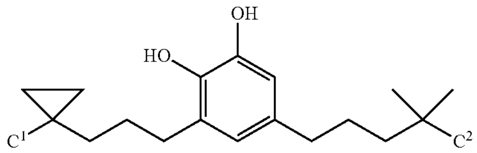 |
| wherein $C^1$ = COOH and $C^2$ = CO—CoA; $C^1$ = CO—CoA and $C^2$ = COOH; or $C^1$ and $C^2$ = CO—CoA |
| 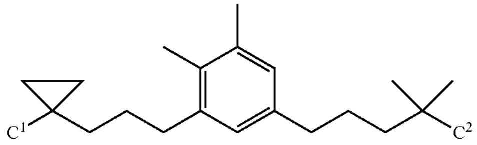 |
| wherein $C^1$ = COOH and $C^2$ = CO—CoA; $C^1$ = CO—CoA and $C^2$ = COOH; or $C^1$ and $C^2$ = CO—CoA |
| 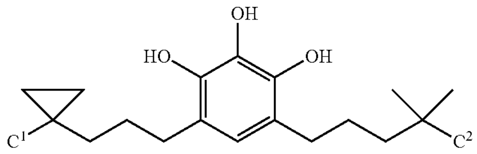 |
| wherein $C^1$ = COOH and $C^2$ = CO—CoA; $C^1$ = CO—CoA and $C^2$ = COOH; or $C^1$ and $C^2$ = CO—CoA |
| 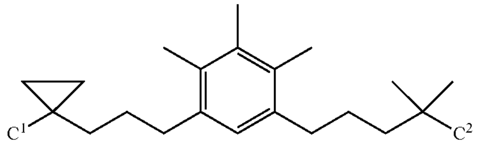 |
| wherein $C^1$ = COOH and $C^2$ = CO—CoA; $C^1$ = CO—CoA and $C^2$ = COOH; or $C^1$ and $C^2$ = CO—CoA |
| 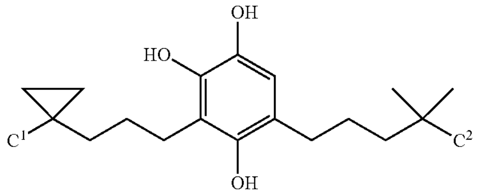 |
| wherein $C^1$ = COOH and $C^2$ = CO—CoA; $C^1$ = CO—CoA and $C^2$ = COOH; or $C^1$ and $C^2$ = CO—CoA |
| 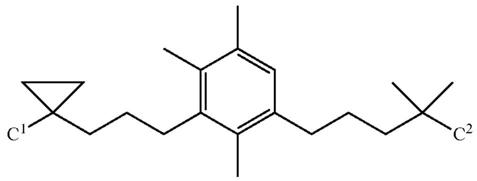 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 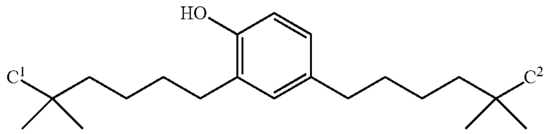 |
| wherein $C^1$ = COOH and $C^2$ = CO—CoA; $C^1$ = CO—CoA and $C^2$ = COOH; or $C^1$ and $C^2$ = CO—CoA |
| 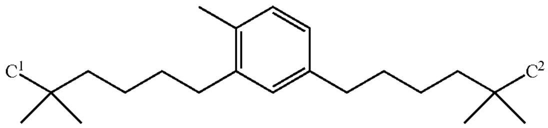 |
| wherein $C^1$ = COOH and $C^2$ = CO—CoA; $C^1$ = CO—CoA and $C^2$ = COOH; or $C^1$ and $C^2$ = CO—CoA |
| 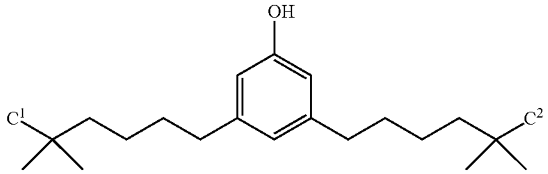 |
| wherein $C^1$ = COOH and $C^2$ = CO—CoA; $C^1$ = CO—CoA and $C^2$ = COOH; or $C^1$ and $C^2$ = CO—CoA |
| 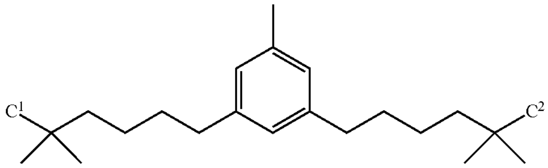 |
| wherein $C^1$ = COOH and $C^2$ = CO—CoA; $C^1$ = CO—CoA and $C^2$ = COOH; or $C^1$ and $C^2$ = CO—CoA |
| 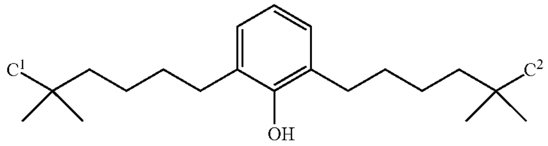 |
| wherein $C^1$ = COOH and $C^2$= CO—CoA; $C^1$ = CO—CoA and $C^2$ = COOH; or $C^1$ and $C^2$ = CO—CoA |
| 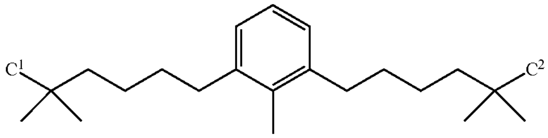 |
| wherein $C^1$ = COOH and $C^2$ = CO—CoA; $C^1$ = CO—CoA and $C^2$ = COOH; or $C^1$ and $C^2$ = CO—CoA |
| 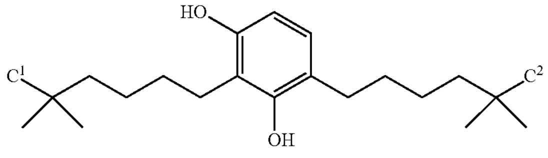 |
| wherein $C^1$ = COOH and $C^2$= CO—CoA; $C^1$ = CO—CoA and $C^2$ = COOH; or $C^1$ and $C^2$ = CO—CoA |

TABLE A-5-continued

| Structure |
| --- |
| 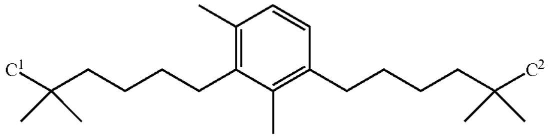<br>wherein $C^1$ = COOH and $C^2$ = CO—CoA; $C^1$ = CO—CoA and $C^2$ = COOH; or $C^1$ and $C^2$ = CO—CoA |
| 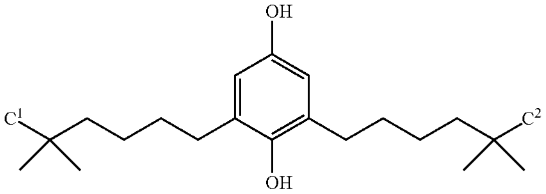<br>wherein $C^1$ = COOH and $C^2$ = CO—CoA; $C^1$ = CO—CoA and $C^2$ = COOH; or $C^1$ and $C^2$ = CO—CoA |
| 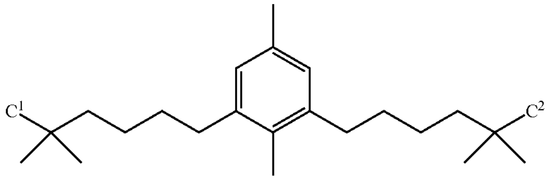<br>wherein $C^1$ = COOH and $C^2$ = CO—CoA; $C^1$ = CO—CoA and $C^2$ = COOH; or $C^1$ and $C^2$ = CO—CoA |
| 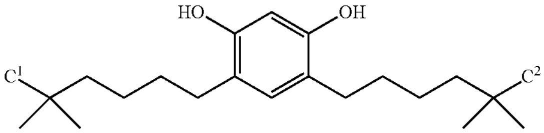<br>wherein $C^1$ = COOH and $C^2$ = CO—CoA; $C^1$ = CO—CoA and $C^2$ = COOH; or $C^1$ and $C^2$ = CO—CoA |
| 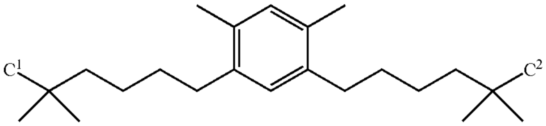<br>wherein $C^1$ = COOH and $C^2$ = CO—CoA; $C^1$ = CO—CoA and $C^2$ = COOH; or $C^1$ and $C^2$ = CO—CoA |
| 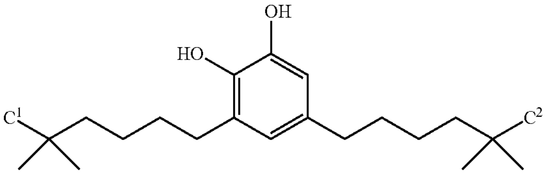<br>wherein $C^1$ = COOH and $C^2$ = CO—CoA; $C^1$ = CO—CoA and $C^2$ = COOH; or $C^1$ and $C^2$ = CO—CoA |
| 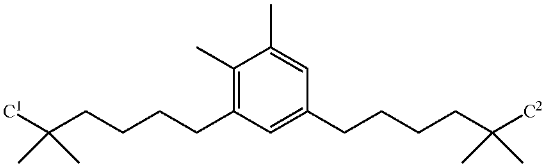<br>wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 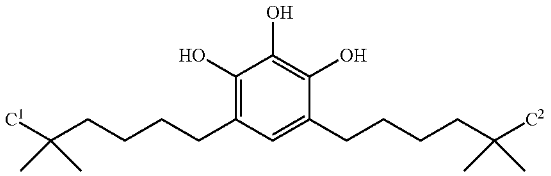 |
| wherein $C^1$ = COOH and $C^2$ = CO—CoA; $C^1$ = CO—CoA and $C^2$ = COOH; or $C^1$ and $C^2$ = CO—CoA |
| 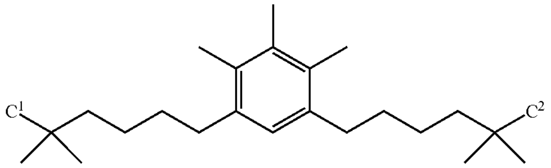 |
| wherein $C^1$ = COOH and $C^2$ = CO—CoA; $C^1$ = CO—CoA and $C^2$ = COOH; or $C^1$ and $C^2$ = CO—CoA |
| 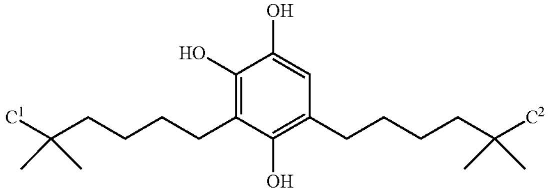 |
| wherein $C^1$ = COOH and $C^2$ = CO—CoA; $C^1$ = CO—CoA and $C^2$ = COOH; or $C^1$ and $C^2$ = CO—CoA |
| 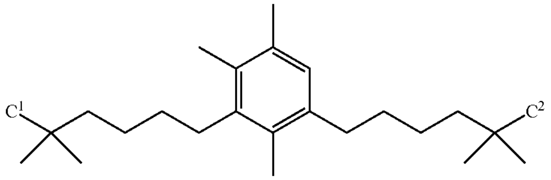 |
| wherein $C^1$ = COOH and $C^2$ = CO—CoA; $C^1$ = CO—CoA and $C^2$ = COOH; or $C^1$ and $C^2$ = CO—CoA |
| 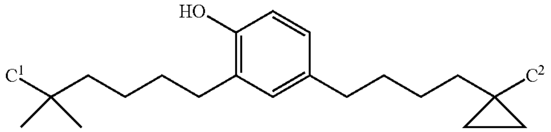 |
| wherein $C^1$ = COOH and $C^2$ = CO—CoA; $C^1$ = CO—CoA and $C^2$ = COOH; or $C^1$ and $C^2$ = CO—CoA |
| 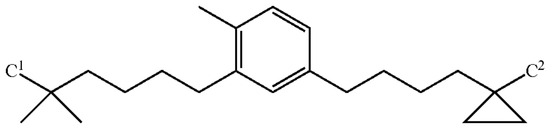 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 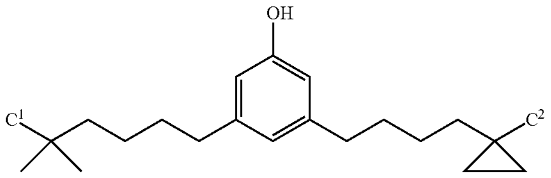 |
| wherein $C^1$ = COOH and $C^2$ = CO—CoA; $C^1$ = CO—CoA and $C^2$ = COOH; or $C^1$ and $C^2$ = CO—CoA |
| 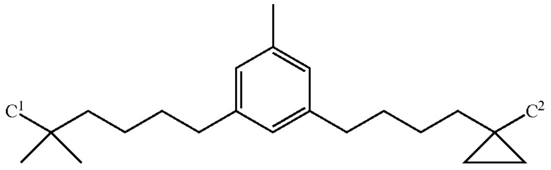 |
| wherein $C^1$ = COOH and $C^2$ = CO—CoA; $C^1$ = CO—CoA and $C^2$ = COOH; or $C^1$ and $C^2$ = CO—CoA |
| 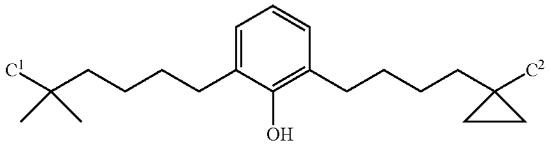 |
| wherein $C^1$ = COOH and $C^2$= CO—CoA; $C^1$ = CO—CoA and $C^2$ = COOH; or $C^1$ and $C^2$ = CO—CoA |
| 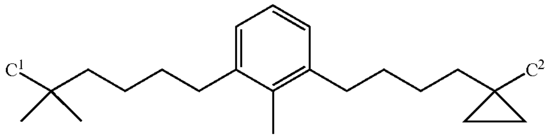 |
| wherein $C^1$ = COOH and $C^2$ = CO—CoA; $C^1$ = CO—CoA and $C^2$ = COOH; or $C^1$ and $C^2$ = CO—CoA |
| 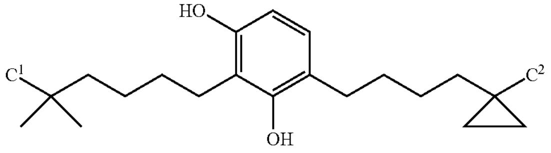 |
| wherein $C^1$ = COOH and $C^2$ = CO—CoA; $C^1$ = CO—CoA and $C^2$ = COOH; or $C^1$ and $C^2$ = CO—CoA |
| 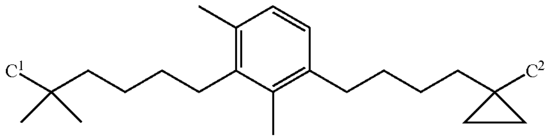 |
| wherein $C^1$ = COOH and $C^2$= CO—CoA; $C^1$ = CO—CoA and $C^2$ = COOH; or $C^1$ and $C^2$ = CO—CoA |
| 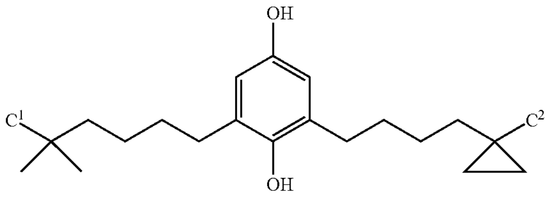 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 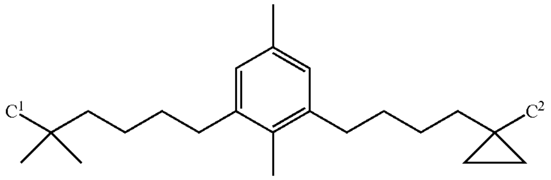 |
| wherein $C^1$ = COOH and $C^2$ = CO—CoA; $C^1$ = CO—CoA and $C^2$ = COOH; or $C^1$ and $C^2$ = CO—CoA |
| 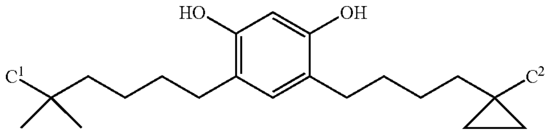 |
| wherein $C^1$ = COOH and $C^2$ = CO—CoA; $C^1$ = CO—CoA and $C^2$ = COOH; or $C^1$ and $C^2$ = CO—CoA |
| 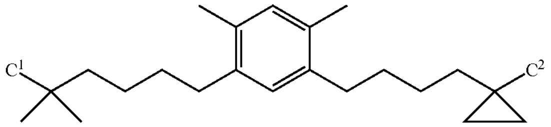 |
| wherein $C^1$ = COOH and $C^2$ = CO—CoA; $C^1$ = CO—CoA and $C^2$ = COOH; or $C^1$ and $C^2$ = CO—CoA |
| 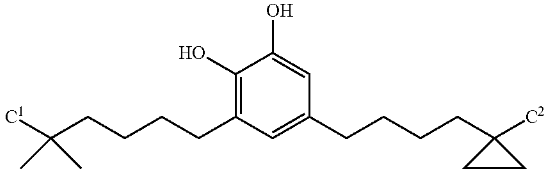 |
| wherein $C^1$ = COOH and $C^2$ = CO—CoA; $C^1$ = CO—CoA and $C^2$ = COOH; or $C^1$ and $C^2$ = CO—CoA |
| 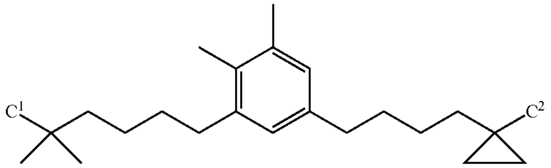 |
| wherein $C^1$ = COOH and $C^2$ = CO—CoA; $C^1$ = CO—CoA and $C^2$ = COOH; or $C^1$ and $C^2$ = CO—CoA |
| 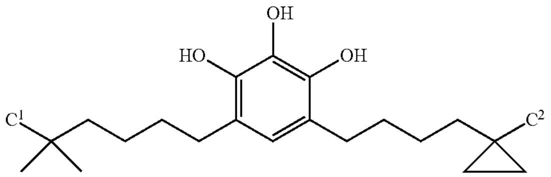 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 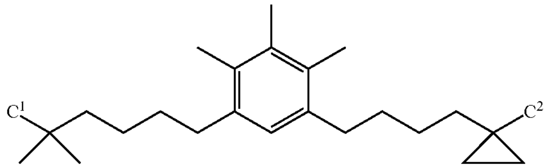 |
| wherein $C^1$ = COOH and $C^2$ = CO—CoA; $C^1$ = CO—CoA and $C^2$ = COOH; or $C^1$ and $C^2$ = CO—CoA |
| 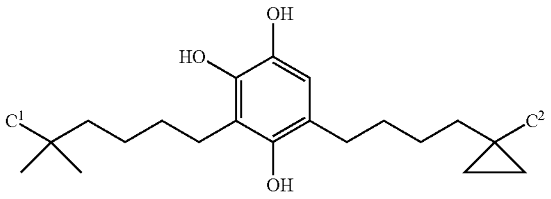 |
| wherein $C^1$ = COOH and $C^2$= CO—CoA; $C^1$ = CO—CoA and $C^2$ = COOH; or $C^1$ and $C^2$ = CO—CoA |
| 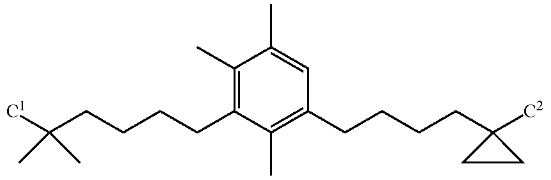 |
| wherein $C^1$ = COOH and $C^2$ = CO—CoA; $C^1$ = CO—CoA and $C^2$ = COOH; or $C^1$ and $C^2$ = CO—CoA |
| 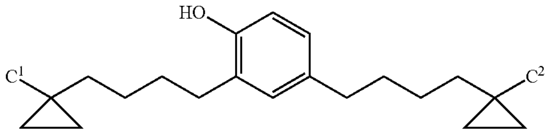 |
| wherein $C^1$ = COOH and $C^2$ = CO—CoA; $C^1$ = CO—CoA and $C^2$ = COOH; or $C^1$ and $C^2$ = CO—CoA |
| 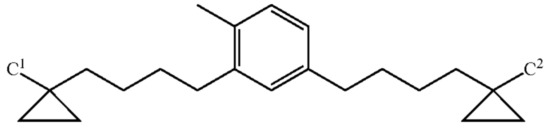 |
| wherein $C^1$ = COOH and $C^2$ = CO—CoA; $C^1$ = CO—CoA and $C^2$ = COOH; or $C^1$ and $C^2$ = CO—CoA |
| 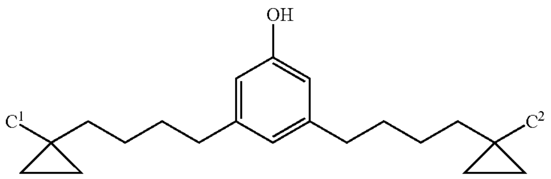 |
| wherein $C^1$ = COOH and $C^2$ = CO—CoA; $C^1$ = CO—CoA and $C^2$ = COOH; or $C^1$ and $C^2$ = CO—CoA |
| 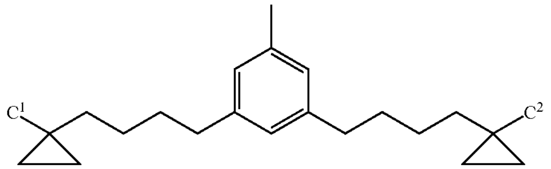 |

TABLE A-5-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 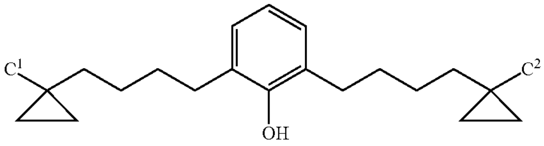 |
| wherein $C^1$ = COOH and $C^2$ = CO—CoA; $C^1$ = CO—CoA and $C^2$ = COOH; or $C^1$ and $C^2$ = CO—CoA |
| 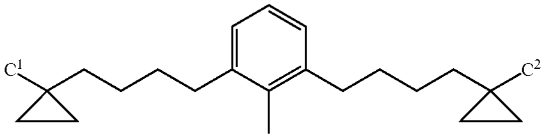 |
| wherein $C^1$ = COOH and $C^2$ = CO—CoA; $C^1$ = CO—CoA and $C^2$ = COOH; or $C^1$ and $C^2$ = CO—CoA |
| 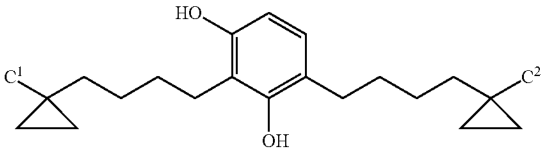 |
| wherein $C^1$ = COOH and $C^2$ = CO—CoA; $C^1$ = CO—CoA and $C^2$ = COOH; or $C^1$ and $C^2$ = CO—CoA |
| 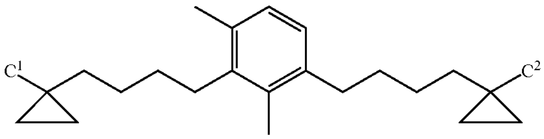 |
| wherein $C^1$ = COOH and $C^2$= CO—CoA; $C^1$ = CO—CoA and $C^2$ = COOH; or $C^1$ and $C^2$ = CO—CoA |
| 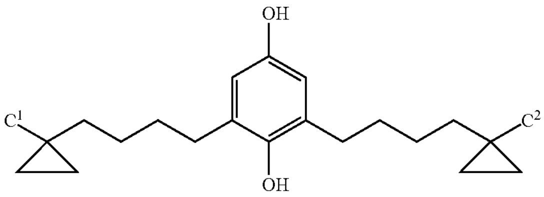 |
| wherein $C^1$ = COOH and $C^2$ = CO—CoA; $C^1$ = CO—CoA and $C^2$ = COOH; or $C^1$ and $C^2$ = CO—CoA |
| 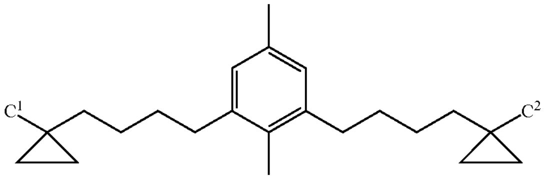 |
| wherein $C^1$ = COOH and $C^2$ = CO—CoA; $C^1$ = CO—CoA and $C^2$ = COOH; or $C^1$ and $C^2$ = CO—CoA |
| 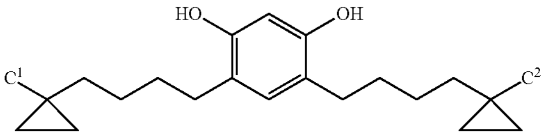 |

TABLE A-5-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 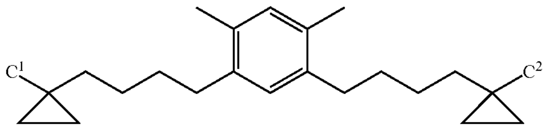 |
| wherein $C^1$ = COOH and $C^2$ = CO—CoA; $C^1$ = CO—CoA and $C^2$ = COOH; or $C^1$ and $C^2$ = CO—CoA |
| 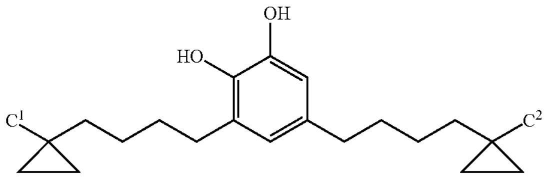 |
| wherein $C^1$ = COOH and $C^2$ = CO—CoA; $C^1$ = CO—CoA and $C^2$ = COOH; or $C^1$ and $C^2$ = CO—CoA |
| 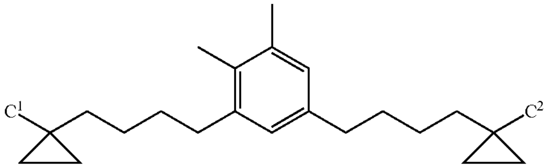 |
| wherein $C^1$ = COOH and $C^2$ = CO—CoA; $C^1$ = CO—CoA and $C^2$ = COOH; or $C^1$ and $C^2$ = CO—CoA |
| 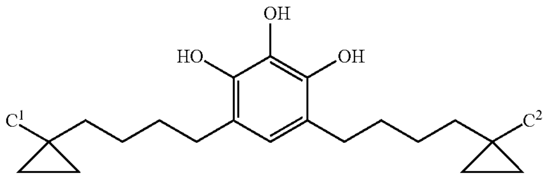 |
| wherein $C^1$ = COOH and $C^2$ = CO—CoA; $C^1$ = CO—CoA and $C^2$ = COOH; or $C^1$ and $C^2$ = CO—CoA |
| 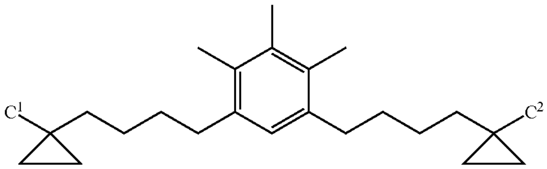 |
| wherein $C^1$ = COOH and $C^2$ = CO—CoA; $C^1$ = CO—CoA and $C^2$ = COOH; or $C^1$ and $C^2$ = CO—CoA |
| 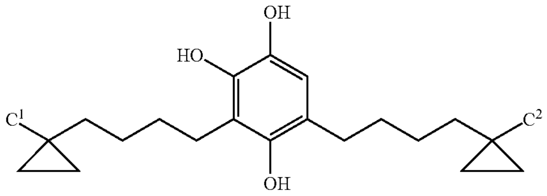 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 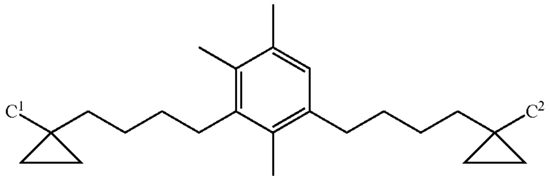 |
| wherein $C^1$ = COOH and $C^2$ = CO—CoA; $C^1$ = CO—CoA and $C^2$ = COOH; or $C^1$ and $C^2$ = CO—CoA |
| 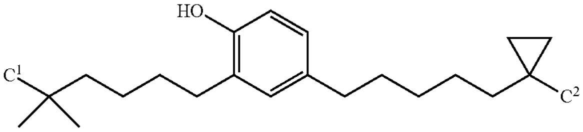 |
| wherein $C^1$ = COOH and $C^2$ = CO—CoA; $C^1$ = CO—CoA and $C^2$ = COOH; or $C^1$ and $C^2$ = CO—CoA |
| 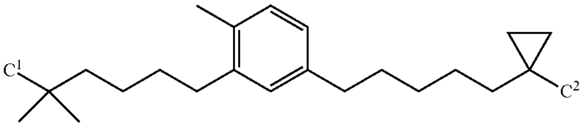 |
| wherein $C^1$ = COOH and $C^2$ = CO—CoA; $C^1$ = CO—CoA and $C^2$ = COOH; or $C^1$ and $C^2$ = CO—CoA |
| 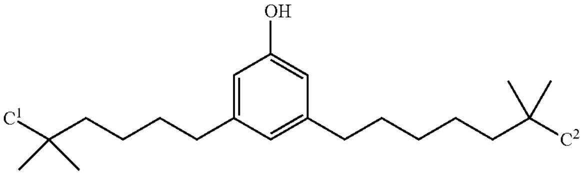 |
| wherein $C^1$ = COOH and $C^2$= CO—CoA; $C^1$ = CO—CoA and $C^2$ = COOH; or $C^1$ and $C^2$ = CO—CoA |
| 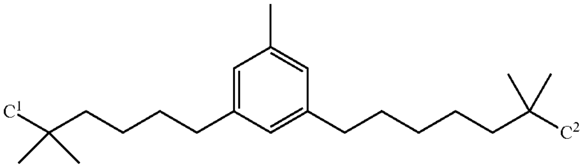 |
| wherein $C^1$ = COOH and $C^2$ = CO—CoA; $C^1$ = CO—CoA and $C^2$ = COOH; or $C^1$ and $C^2$ = CO—CoA |
| 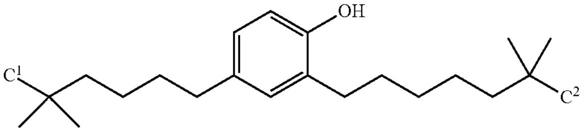 |
| wherein $C^1$ = COOH and $C^2$ = CO—CoA; $C^1$ = CO—CoA and $C^2$ = COOH; or $C^1$ and $C^2$ = CO—CoA |
| 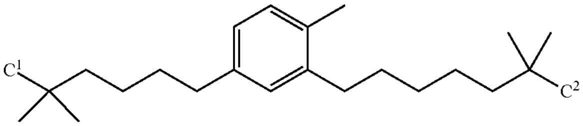 |
| wherein $C^1$ = COOH and $C^2$= CO—CoA; $C^1$ = CO—CoA and $C^2$ = COOH; or $C^1$ and $C^2$ = CO—CoA |

TABLE A-5-continued

| Structure |
|---|
| 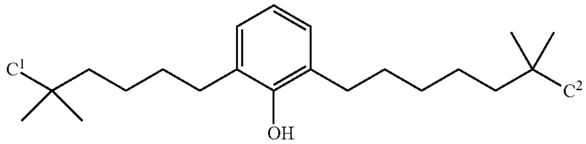 wherein $C^1$ = COOH and $C^2$ = CO—CoA; $C^1$ = CO—CoA and $C^2$ = COOH; or $C^1$ and $C^2$ = CO—CoA |
| 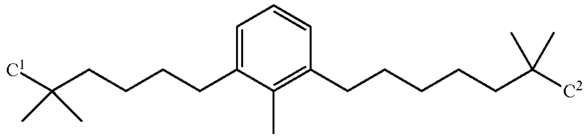 wherein $C^1$ = COOH and $C^2$ = CO—CoA; $C^1$ = CO—CoA and $C^2$ = COOH; or $C^1$ and $C^2$ = CO—CoA |
| 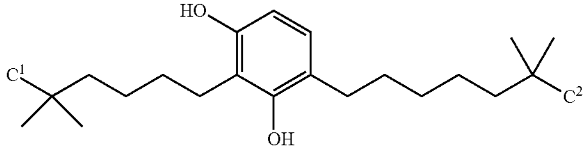 wherein $C^1$ = COOH and $C^2$ = CO—CoA; $C^1$ = CO—CoA and $C^2$ = COOH; or $C^1$ and $C^2$ = CO—CoA |
| 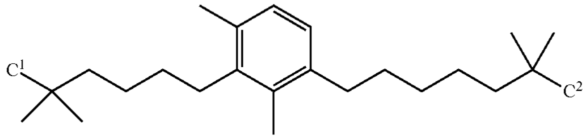 wherein $C^1$ = COOH and $C^2$ = CO—CoA; $C^1$ = CO—CoA and $C^2$ = COOH; or $C^1$ and $C^2$ = CO—CoA |
| 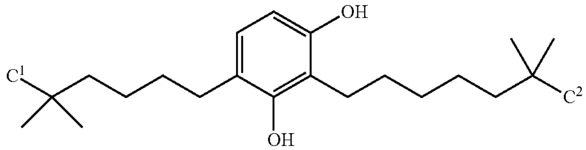 wherein $C^1$ = COOH and $C^2$ = CO—CoA; $C^1$ = CO—CoA and $C^2$ = COOH; or $C^1$ and $C^2$ = CO—CoA |
| 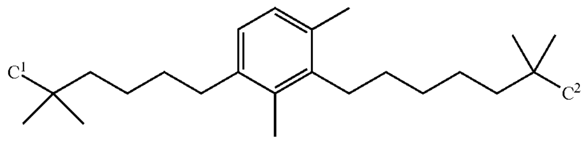 wherein $C^1$ = COOH and $C^2$ = CO—CoA; $C^1$ = CO—CoA and $C^2$ = COOH; or $C^1$ and $C^2$ = CO—CoA |
| 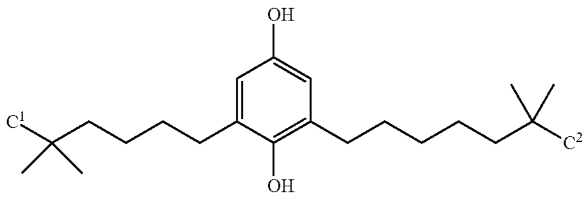 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 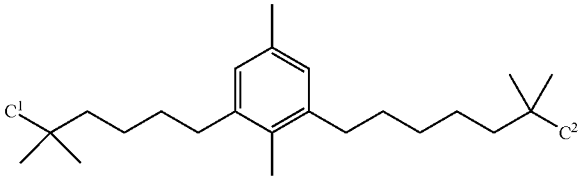 |
| wherein $C^1$ = COOH and $C^2$ = CO—CoA; $C^1$ = CO—CoA and $C^2$ = COOH; or $C^1$ and $C^2$ = CO—CoA |
| 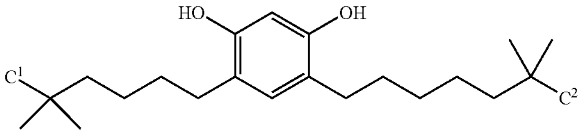 |
| wherein $C^1$ = COOH and $C^2$ = CO—CoA; $C^1$ = CO—CoA and $C^2$ = COOH; or $C^1$ and $C^2$ = CO—CoA |
| 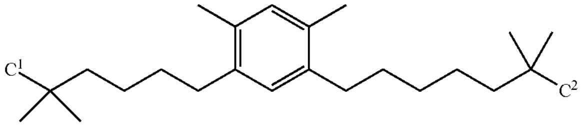 |
| wherein $C^1$ = COOH and $C^2$ = CO—CoA; $C^1$ = CO—CoA and $C^2$ = COOH; or $C^1$ and $C^2$ = CO—CoA |
| 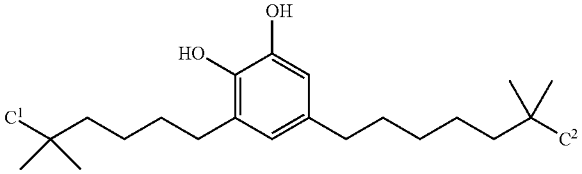 |
| wherein $C^1$ = COOH and $C^2$ = CO—CoA; $C^1$ = CO—CoA and $C^2$ = COOH; or $C^1$ and $C^2$ = CO—CoA |
| 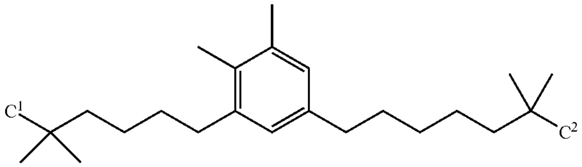 |
| wherein $C^1$ = COOH and $C^2$ = CO—CoA; $C^1$ = CO—CoA and $C^2$ = COOH; or $C^1$ and $C^2$ = CO—CoA |
| 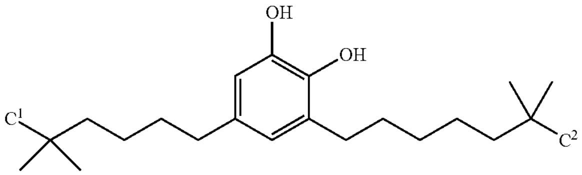 |
| wherein $C^1$ = COOH and $C^2$ = CO—CoA; $C^1$ = CO—CoA and $C^2$ = COOH; or $C^1$ and $C^2$ = CO—CoA |
| 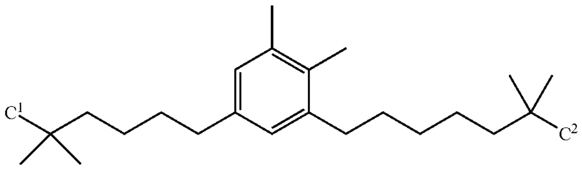 |

TABLE A-5-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 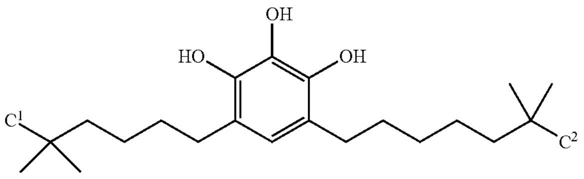 |
| wherein $C^1$ = COOH and $C^2$ = CO—CoA; $C^1$ = CO—CoA and $C^2$ = COOH; or $C^1$ and $C^2$ = CO—CoA |
| 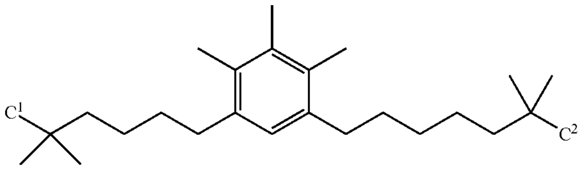 |
| wherein $C^1$ = COOH and $C^2$ = CO—CoA; $C^1$ = CO—CoA and $C^2$ = COOH; or $C^1$ and $C^2$ = CO—CoA |
| 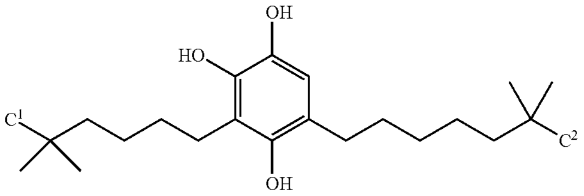 |
| wherein $C^1$ = COOH and $C^2$ = CO—CoA; $C^1$ = CO—CoA and $C^2$ = COOH; or $C^1$ and $C^2$ = CO—CoA |
| 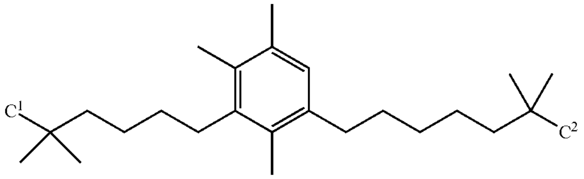 |
| wherein $C^1$ = COOH and $C^2$ = CO—CoA; $C^1$ = CO—CoA and $C^2$ = COOH; or $C^1$ and $C^2$ = CO—CoA |
| 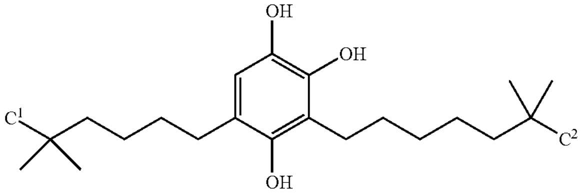 |
| wherein $C^1$ = COOH and $C^2$ = CO—CoA; $C^1$ = CO—CoA and $C^2$ = COOH; or $C^1$ and $C^2$ = CO—CoA |
| 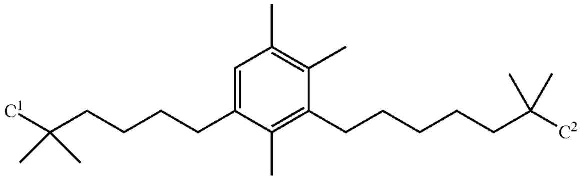 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 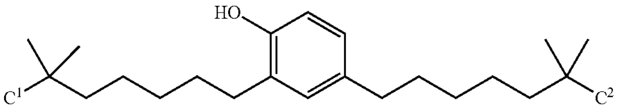 |
| wherein $C^1$ = COOH and $C^2$ = CO—CoA; $C^1$ = CO—CoA and $C^2$ = COOH; or $C^1$ and $C^2$ = CO—CoA |
| 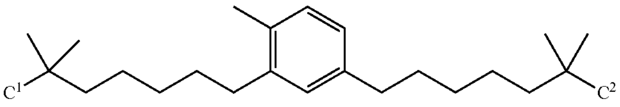 |
| wherein $C^1$ = COOH and $C^2$ = CO—CoA; $C^1$ = CO—CoA and $C^2$ = COOH; or $C^1$ and $C^2$ = CO—CoA |
| 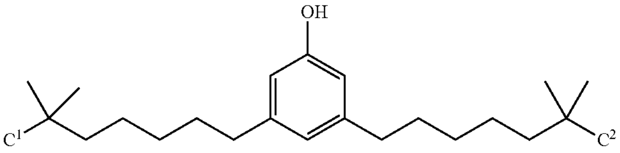 |
| wherein $C^1$ = COOH and $C^2$ = CO—CoA; $C^1$ = CO—CoA and $C^2$ = COOH; or $C^1$ and $C^2$ = CO—CoA |
| 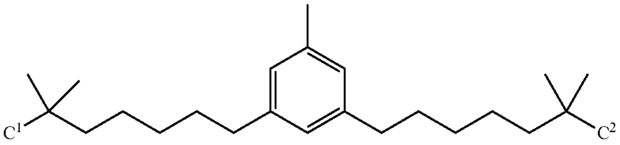 |
| wherein $C^1$ = COOH and $C^2$ = CO—CoA; $C^1$ = CO—CoA and $C^2$ = COOH; or $C^1$ and $C^2$ = CO—CoA |
| 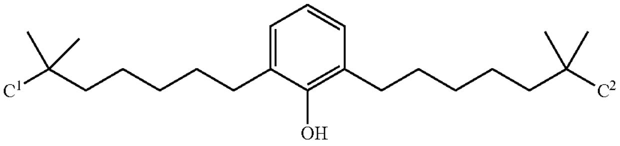 |
| wherein $C^1$ = COOH and $C^2$ = CO—CoA; $C^1$ = CO—CoA and $C^2$ = COOH; or $C^1$ and $C^2$ = CO—CoA |
| 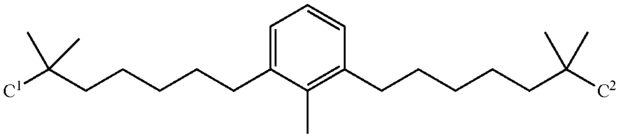 |
| wherein $C^1$ = COOH and $C^2$ = CO—CoA; $C^1$ = CO—CoA and $C^2$ = COOH; or $C^1$ and $C^2$ = CO—CoA |
| 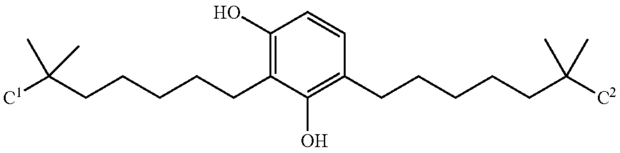 |
| wherein $C^1$ = COOH and $C^2$ = CO—CoA; $C^1$ = CO—CoA and $C^2$ = COOH; or $C^1$ and $C^2$ = CO—CoA |
| 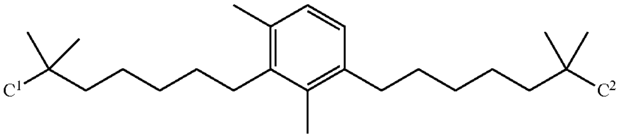 |

TABLE A-5-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 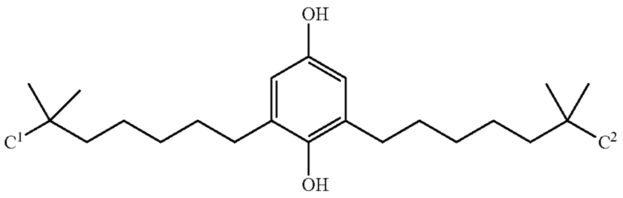 |
| wherein $C^1$ = COOH and $C^2$ = CO—CoA; $C^1$ = CO—CoA and $C^2$ = COOH; or $C^1$ and $C^2$ = CO—CoA |
| 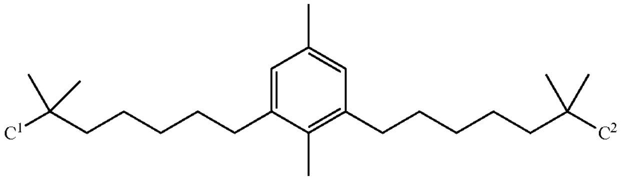 |
| wherein $C^1$ = COOH and $C^2$ = CO—CoA; $C^1$ = CO—CoA and $C^2$ = COOH; or $C^1$ and $C^2$ = CO—CoA |
| 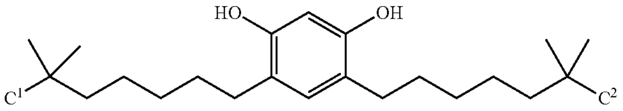 |
| wherein $C^1$ = COOH and $C^2$ = CO—CoA; $C^1$ = CO—CoA and $C^2$ = COOH; or $C^1$ and $C^2$ = CO—CoA |
| 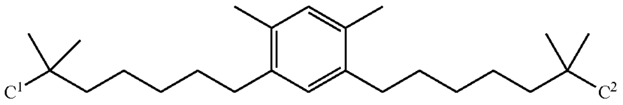 |
| wherein $C^1$ = COOH and $C^2$ = CO—CoA; $C^1$ = CO—CoA and $C^2$ = COOH; or $C^1$ and $C^2$ = CO—CoA |
| 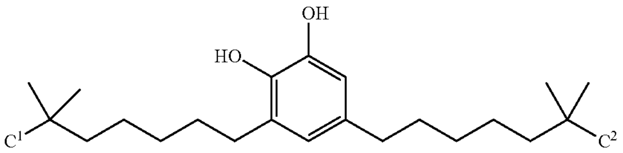 |
| wherein $C^1$ = COOH and $C^2$ = CO—CoA; $C^1$ = CO—CoA and $C^2$ = COOH; or $C^1$ and $C^2$ = CO—CoA |
| 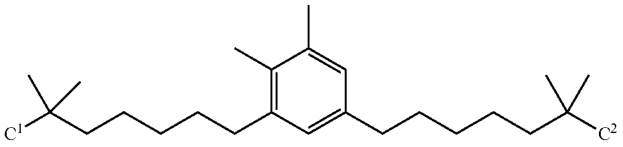 |
| wherein $C^1$ = COOH and $C^2$ = CO—CoA; $C^1$ = CO—CoA and $C^2$ = COOH; or $C^1$ and $C^2$ = CO—CoA |
| 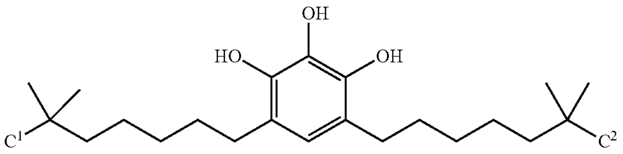 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 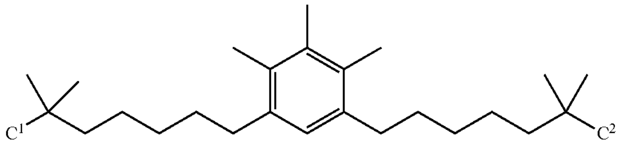 wherein $C^1$ = COOH and $C^2$ = CO—CoA; $C^1$ = CO—CoA and $C^2$ = COOH; or $C^1$ and $C^2$ = CO—CoA |
| 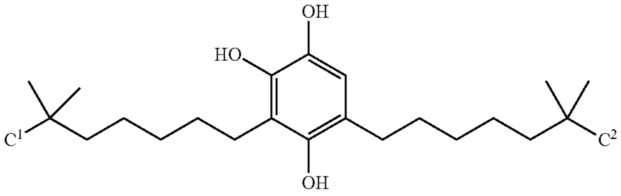 wherein $C^1$ = COOH and $C^2$= CO—CoA; $C^1$ = CO—CoA and $C^2$ = COOH; or $C^1$ and $C^2$ = CO—CoA |
| 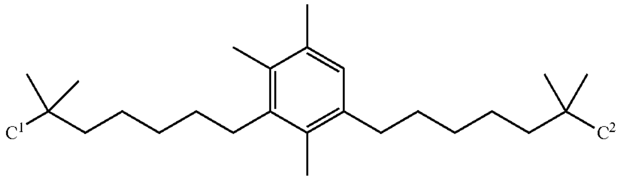 wherein $C^1$ = COOH and $C^2$ = CO—CoA; $C^1$ = CO—CoA and $C^2$ = COOH; or $C^1$ and $C^2$ = CO—CoA |
| 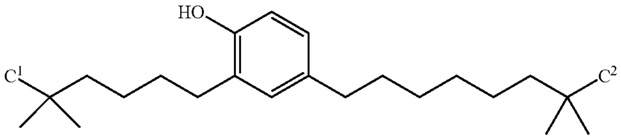 wherein $C^1$ = COOH and $C^2$ = CO—CoA; $C^1$ = CO—CoA and $C^2$ = COOH; or $C^1$ and $C^2$ = CO—CoA |
| 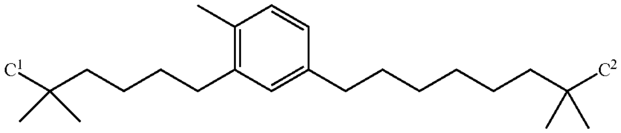 wherein $C^1$ = COOH and $C^2$ = CO—CoA; $C^1$ = CO—CoA and $C^2$ = COOH; or $C^1$ and $C^2$ = CO—CoA |
| 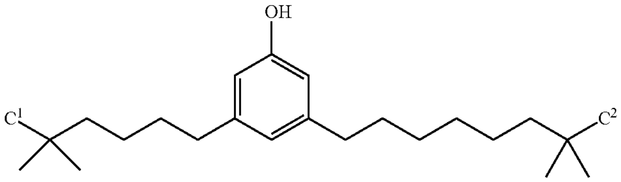 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 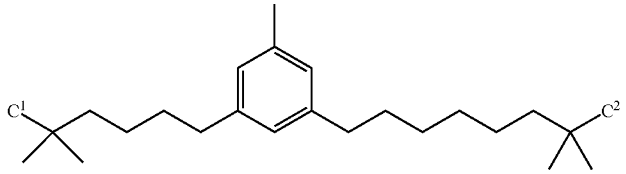 wherein $C^1$ = COOH and $C^2$ = CO—CoA; $C^1$ = CO—CoA and $C^2$ = COOH; or $C^1$ and $C^2$ = CO—CoA |
| 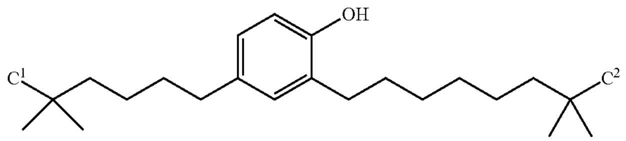 wherein $C^1$ = COOH and $C^2$ = CO—CoA; $C^1$ = CO—CoA and $C^2$ = COOH; or $C^1$ and $C^2$ = CO—CoA |
| 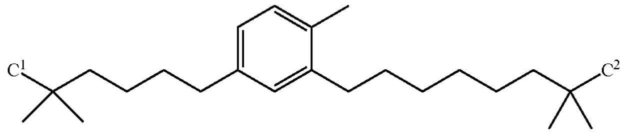 wherein $C^1$ = COOH and $C^2$ = CO—CoA; $C^1$ = CO—CoA and $C^2$ = COOH; or $C^1$ and $C^2$ = CO—CoA |
| 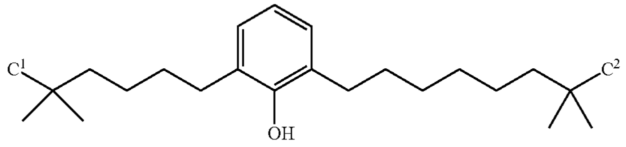 wherein $C^1$ = COOH and $C^2$ = CO—CoA; $C^1$ = CO—CoA and $C^2$ = COOH; or $C^1$ and $C^2$ = CO—CoA |
| 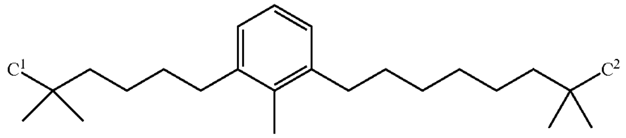 wherein $C^1$ = COOH and $C^2$ = CO—CoA; $C^1$ = CO—CoA and $C^2$ = COOH; or $C^1$ and $C^2$ = CO—CoA |
| 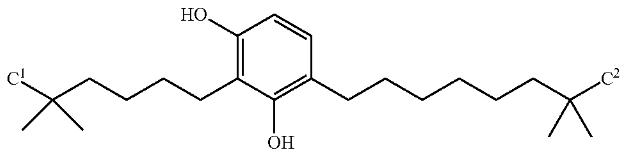 wherein $C^1$ = COOH and $C^2$ = CO—CoA; $C^1$ = CO—CoA and $C^2$ = COOH; or $C^1$ and $C^2$ = CO—CoA |
| 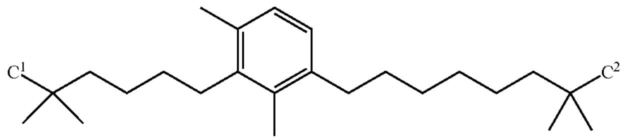 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 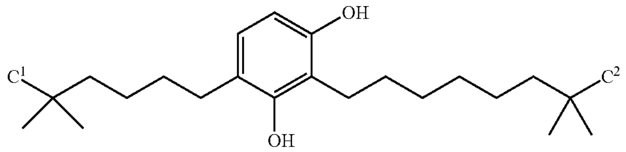<br>wherein $C^1$ = COOH and $C^2$ = CO—CoA; $C^1$ = CO—CoA and $C^2$ = COOH; or $C^1$ and $C^2$ = CO—CoA |
| 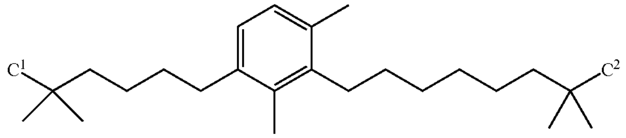<br>wherein $C^1$ = COOH and $C^2$ = CO—CoA; $C^1$ = CO—CoA and $C^2$ = COOH; or $C^1$ and $C^2$ = CO—CoA |
| 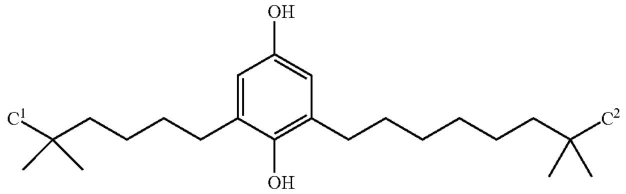<br>wherein $C^1$ = COOH and $C^2$ = CO—CoA; $C^1$ = CO—CoA and $C^2$ = COOH; or $C^1$ and $C^2$ = CO—CoA |
| 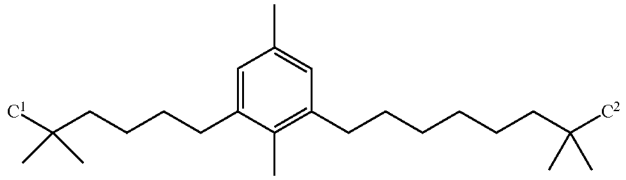<br>wherein $C^1$ = COOH and $C^2$ = CO—CoA; $C^1$ = CO—CoA and $C^2$ = COOH; or $C^1$ and $C^2$ = CO—CoA |
| 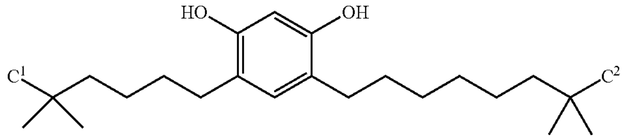<br>wherein $C^1$ = COOH and $C^2$ = CO—CoA; $C^1$ = CO—CoA and $C^2$ = COOH; or $C^1$ and $C^2$ = CO—CoA |
| 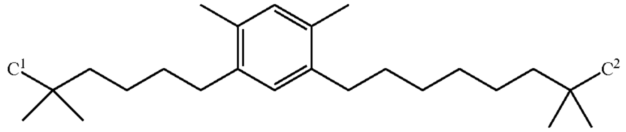<br>wherein $C^1$ = COOH and $C^2$ = CO—CoA; $C^1$ = CO—CoA and $C^2$ = COOH; or $C^1$ and $C^2$ = CO—CoA |
| 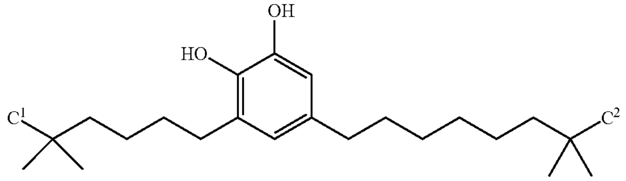<br>wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 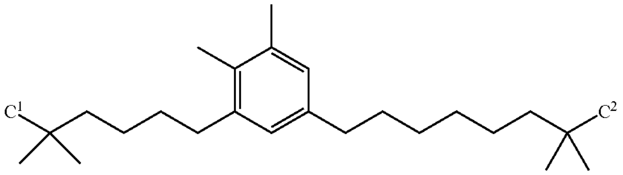 |
| wherein $C^1$ = COOH and $C^2$ = CO—CoA; $C^1$ = CO—CoA and $C^2$ = COOH; or $C^1$ and $C^2$ = CO—CoA |
| 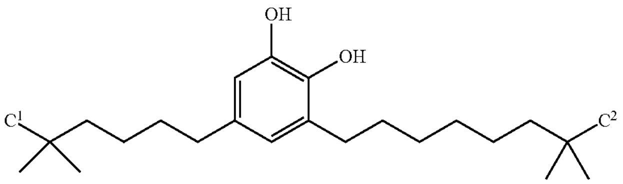 |
| wherein $C^1$ = COOH and $C^2$ = CO—CoA; $C^1$ = CO—CoA and $C^2$ = COOH; or $C^1$ and $C^2$ = CO—CoA |
| 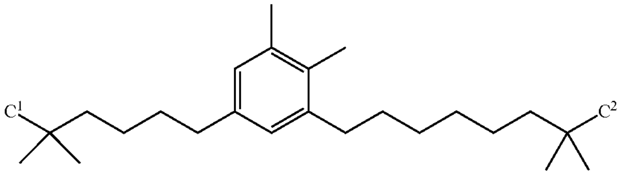 |
| wherein $C^1$ = COOH and $C^2$ = CO—CoA; $C^1$ = CO—CoA and $C^2$ = COOH; or $C^1$ and $C^2$ = CO—CoA |
| 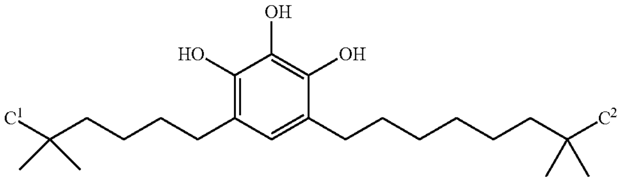 |
| wherein $C^1$ = COOH and $C^2$ = CO—CoA; $C^1$ = CO—CoA and $C^2$ = COOH; or $C^1$ and $C^2$ = CO—CoA |
| 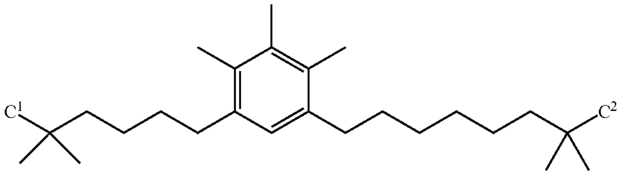 |
| wherein $C^1$ = COOH and $C^2$ = CO—CoA; $C^1$ = CO—CoA and $C^2$ = COOH; or $C^1$ and $C^2$ = CO—CoA |
| 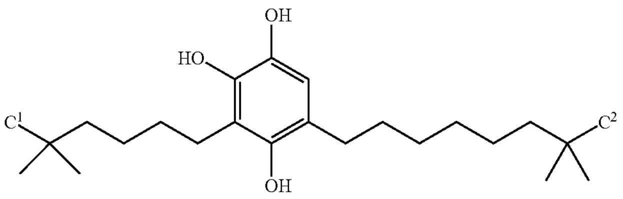 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 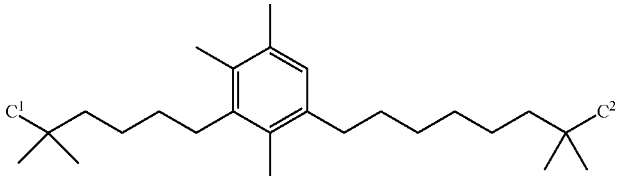 |
| wherein $C^1$ = COOH and $C^2$ = CO—CoA; $C^1$ = CO—CoA and $C^2$ = COOH; or $C^1$ and $C^2$ = CO—CoA |
| 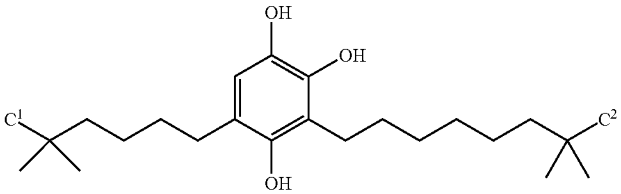 |
| wherein $C^1$ = COOH and $C^2$ = CO—CoA; $C^1$ = CO—CoA and $C^2$ = COOH; or $C^1$ and $C^2$ = CO—CoA |
| 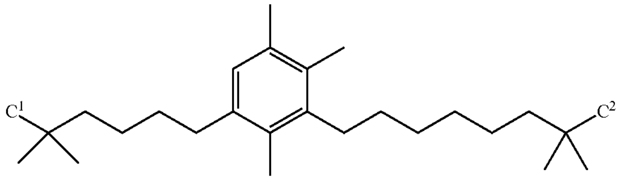 |
| wherein $C^1$ = COOH and $C^2$ = CO—CoA; $C^1$ = CO—CoA and $C^2$ = COOH; or $C^1$ and $C^2$ = CO—CoA |
| 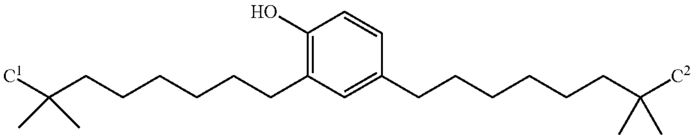 |
| wherein $C^1$ = COOH and $C^2$= CO—CoA; $C^1$ = CO—CoA and $C^2$ = COOH; or $C^1$ and $C^2$ = CO—CoA |
| 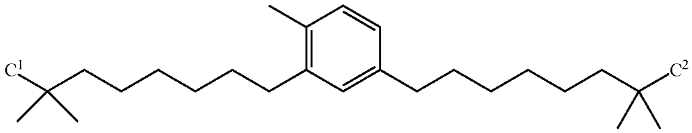 |
| wherein $C^1$ = COOH and $C^2$ = CO—CoA; $C^1$ = CO—CoA and $C^2$ = COOH; or $C^1$ and $C^2$ = CO—CoA |
| 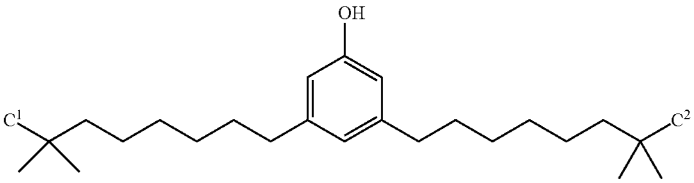 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 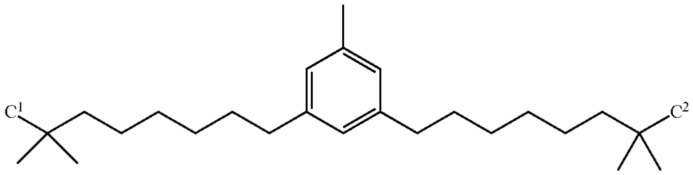 wherein $C^1$ = COOH and $C^2$ = CO—CoA; $C^1$ = CO—CoA and $C^2$ = COOH; or $C^1$ and $C^2$ = CO—CoA |
| 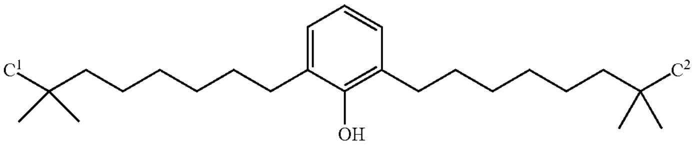 wherein $C^1$ = COOH and $C^2$= CO—CoA; $C^1$ = CO—CoA and $C^2$ = COOH; or $C^1$ and $C^2$ = CO—CoA |
| 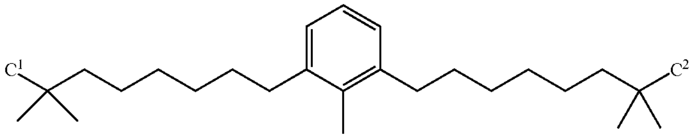 wherein $C^1$ = COOH and $C^2$ = CO—CoA; $C^1$ = CO—CoA and $C^2$ = COOH; or $C^1$ and $C^2$ = CO—CoA |
| 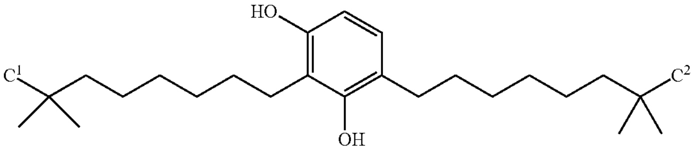 wherein $C^1$ = COOH and $C^2$ = CO—CoA; $C^1$ = CO—CoA and $C^2$ = COOH; or $C^1$ and $C^2$ = CO—CoA |
| 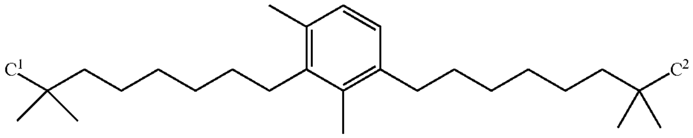 wherein $C^1$ = COOH and $C^2$ = CO—CoA; $C^1$ = CO—CoA and $C^2$ = COOH; or $C^1$ and $C^2$ = CO—CoA |
| 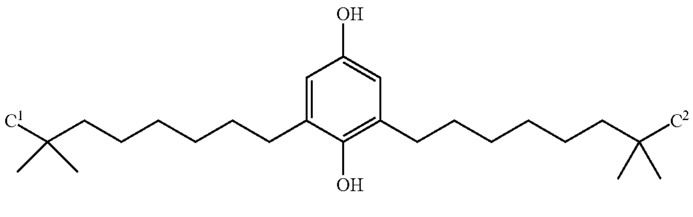 wherein $C^1$ = COOH and $C^2$ = CO—CoA; $C^1$ = CO—CoA and $C^2$ = COOH; or $C^1$ and $C^2$ = CO—CoA |
| 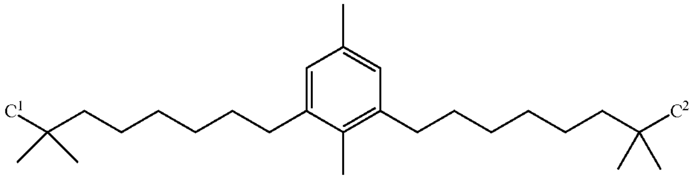 |

TABLE A-5-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 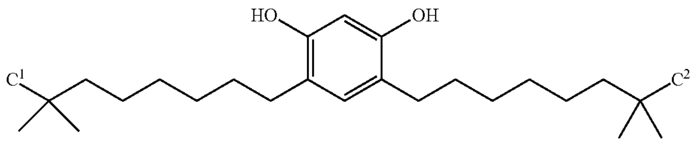 |
| wherein $C^1$ = COOH and $C^2$ = CO—CoA; $C^1$ = CO—CoA and $C^2$ = COOH; or $C^1$ and $C^2$ = CO—CoA |
| 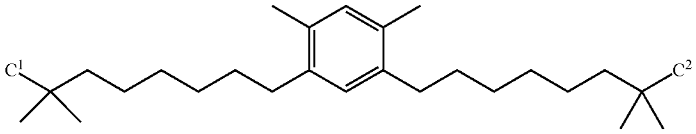 |
| wherein $C^1$ = COOH and $C^2$ = CO—CoA; $C^1$ = CO—CoA and $C^2$ = COOH; or $C^1$ and $C^2$ = CO—CoA |
| 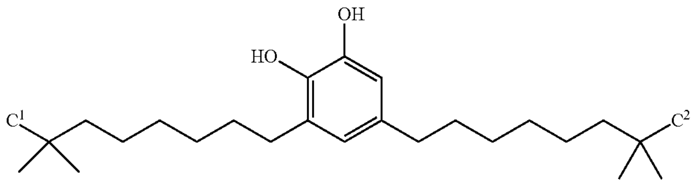 |
| wherein $C^1$ = COOH and $C^2$ = CO—CoA; $C^1$ = CO—CoA and $C^2$ = COOH; or $C^1$ and $C^2$ = CO—CoA |
| 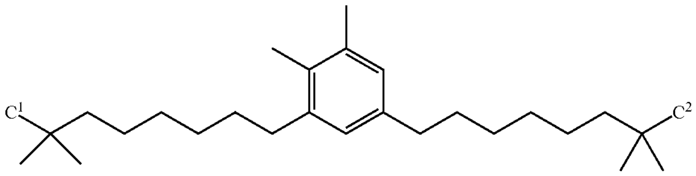 |
| wherein $C^1$ = COOH and $C^2$ = CO—CoA; $C^1$ = CO—CoA and $C^2$ = COOH; or $C^1$ and $C^2$ = CO—CoA |
| 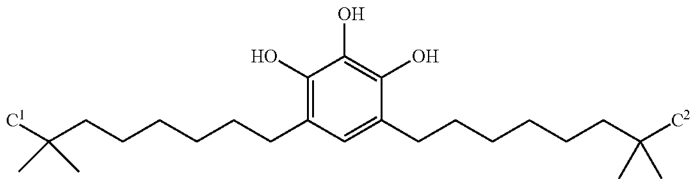 |
| wherein $C^1$ = COOH and $C^2$ = CO—CoA; $C^1$ = CO—CoA and $C^2$ = COOH; or $C^1$ and $C^2$ = CO—CoA |
| 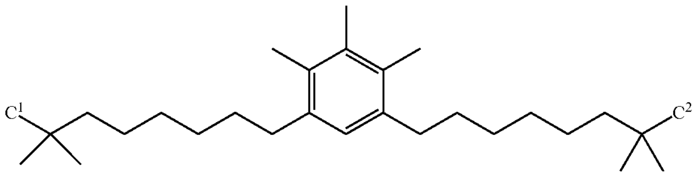 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 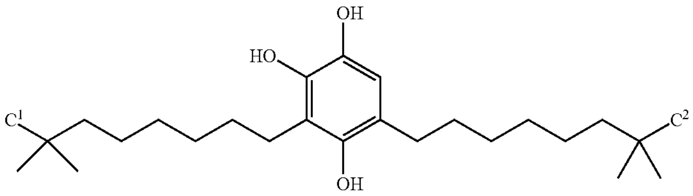 |
| wherein $C^1$ = COOH and $C^2$ = CO—CoA; $C^1$ = CO—CoA and $C^2$ = COOH; or $C^1$ and $C^2$ = CO—CoA |
| 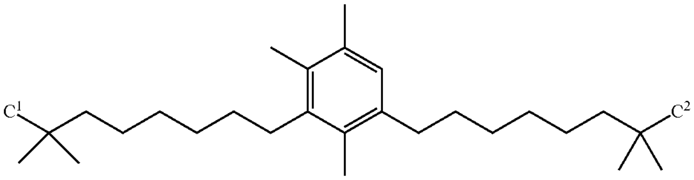 |
| wherein $C^1$ = COOH and $C^2$ = CO—CoA; $C^1$ = CO—CoA and $C^2$ = COOH; or $C^1$ and $C^2$ = CO—CoA |
| 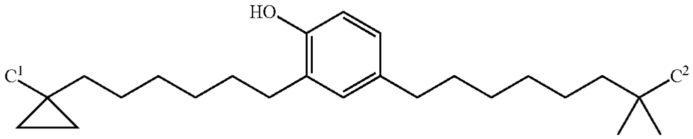 |
| wherein $C^1$ = COOH and $C^2$ = CO—CoA; $C^1$ = CO—CoA and $C^2$ = COOH; or $C^1$ and $C^2$ = CO—CoA |
| 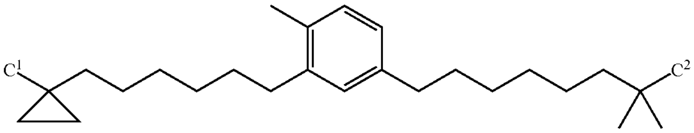 |
| wherein $C^1$ = COOH and $C^2$ = CO—CoA; $C^1$ = CO—CoA and $C^2$ = COOH; or $C^1$ and $C^2$ = CO—CoA |
| 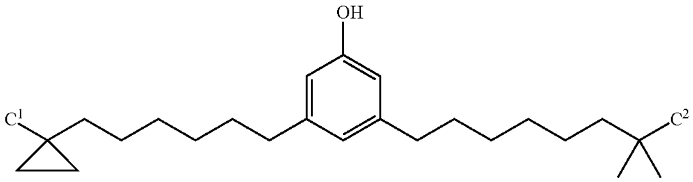 |
| wherein $C^1$ = COOH and $C^2$ = CO—CoA; $C^1$ = CO—CoA and $C^2$ = COOH; or $C^1$ and $C^2$ = CO—CoA |
| 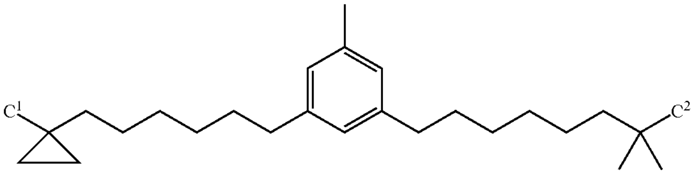 |
| wherein $C^1$ = COOH and $C^2$ = CO—CoA; $C^1$ = CO—CoA and $C^2$ = COOH; or $C^1$ and $C^2$ = CO—CoA |
| 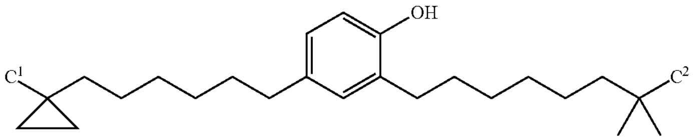 |

TABLE A-5-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 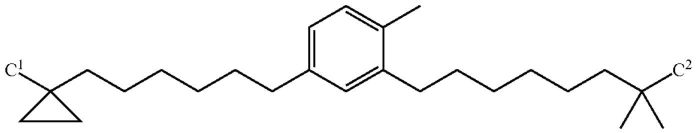 |
| wherein $C^1$ = COOH and $C^2$ = CO—CoA; $C^1$ = CO—CoA and $C^2$ = COOH; or $C^1$ and $C^2$ = CO—CoA |
| 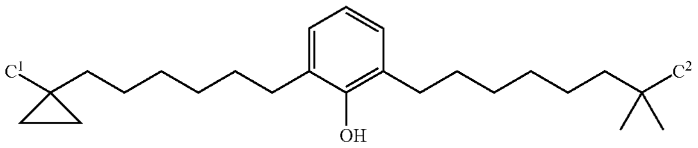 |
| wherein $C^1$ = COOH and $C^2$ = CO—CoA; $C^1$ = CO—CoA and $C^2$ = COOH; or $C^1$ and $C^2$ = CO—CoA |
| 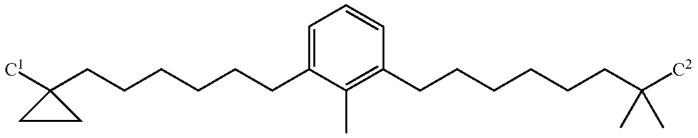 |
| wherein $C^1$ = COOH and $C^2$ = CO—CoA; $C^1$ = CO—CoA and $C^2$ = COOH; or $C^1$ and $C^2$ = CO—CoA |
| 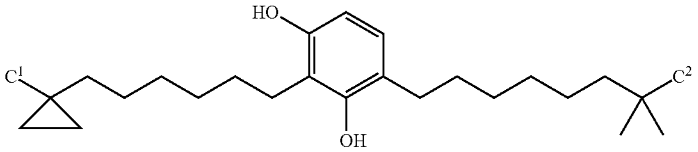 |
| wherein $C^1$ = COOH and $C^2$ = CO—CoA; $C^1$ = CO—CoA and $C^2$ = COOH; or $C^1$ and $C^2$ = CO—CoA |
| 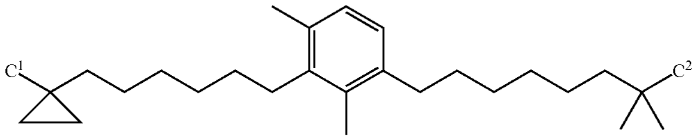 |
| wherein $C^1$ = COOH and $C^2$ = CO—CoA; $C^1$ = CO—CoA and $C^2$ = COOH; or $C^1$ and $C^2$ = CO—CoA |
| 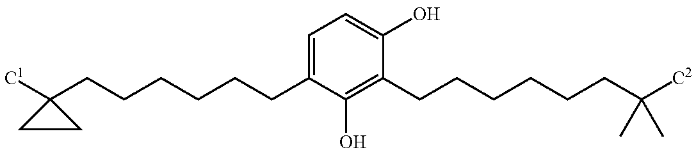 |
| wherein $C^1$ = COOH and $C^2$ = CO—CoA; $C^1$ = CO—CoA and $C^2$ = COOH; or $C^1$ and $C^2$ = CO—CoA |
| 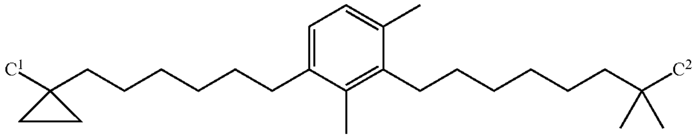 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 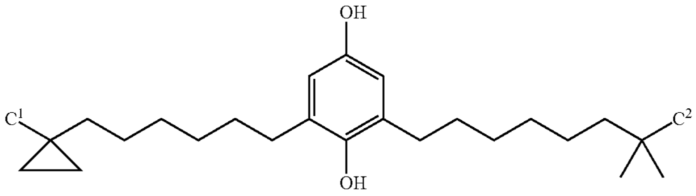 |
| wherein $C^1$ = COOH and $C^2$ = CO—CoA; $C^1$ = CO—CoA and $C^2$ = COOH; or $C^1$ and $C^2$ = CO—CoA |
| 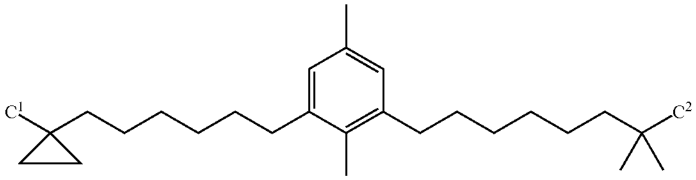 |
| wherein $C^1$ = COOH and $C^2$ = CO—CoA; $C^1$ = CO—CoA and $C^2$ = COOH; or $C^1$ and $C^2$ = CO—CoA |
| 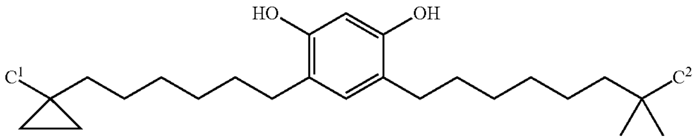 |
| wherein $C^1$ = COOH and $C^2$ = CO—CoA; $C^1$ = CO—CoA and $C^2$ = COOH; or $C^1$ and $C^2$ = CO—CoA |
| 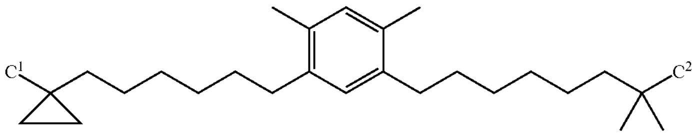 |
| wherein $C^1$ = COOH and $C^2$ = CO—CoA; $C^1$ = CO—CoA and $C^2$ = COOH; or $C^1$ and $C^2$ = CO—CoA |
| 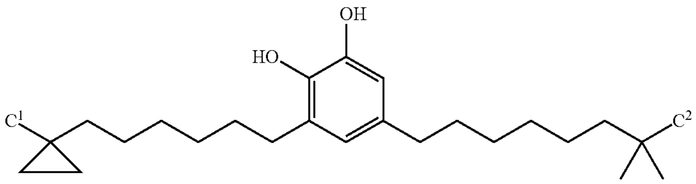 |
| wherein $C^1$ = COOH and $C^2$ = CO—CoA; $C^1$ = CO—CoA and $C^2$ = COOH; or $C^1$ and $C^2$ = CO—CoA |
| 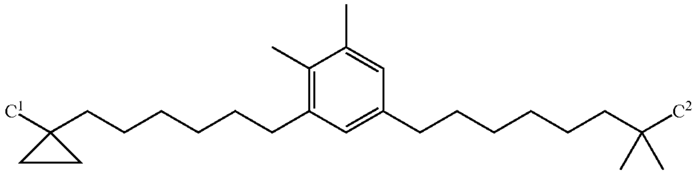 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 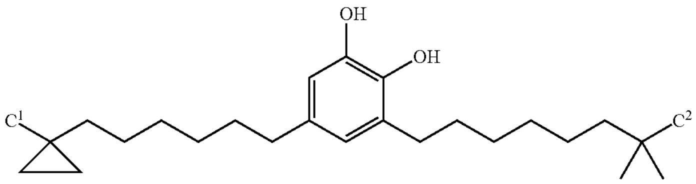 |
| wherein $C^1$ = COOH and $C^2$ = CO—CoA; $C^1$ = CO—CoA and $C^2$ = COOH; or $C^1$ and $C^2$ = CO—CoA |
| 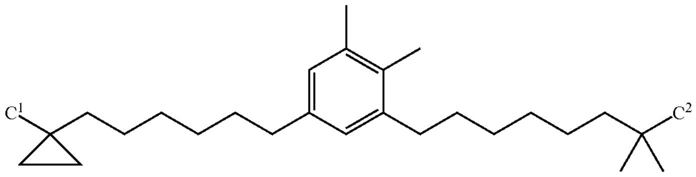 |
| wherein $C^1$ = COOH and $C^2$ = CO—CoA; $C^1$ = CO—CoA and $C^2$ = COOH; or $C^1$ and $C^2$ = CO—CoA |
| 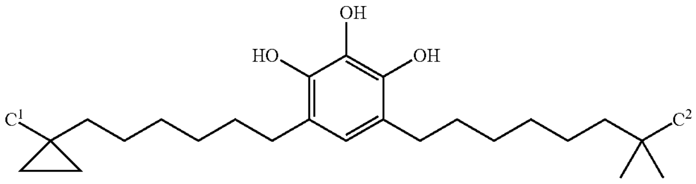 |
| wherein $C^1$ = COOH and $C^2$ = CO—CoA; $C^1$ = CO—CoA and $C^2$ = COOH; or $C^1$ and $C^2$ = CO—CoA |
| 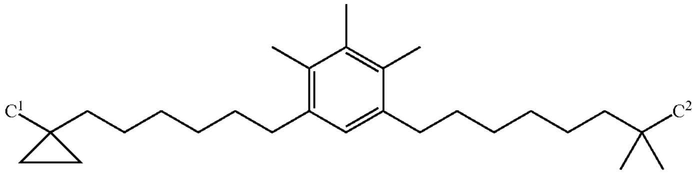 |
| wherein $C^1$ = COOH and $C^2$ = CO—CoA; $C^1$ = CO—CoA and $C^2$ = COOH; or $C^1$ and $C^2$ = CO—CoA |
| 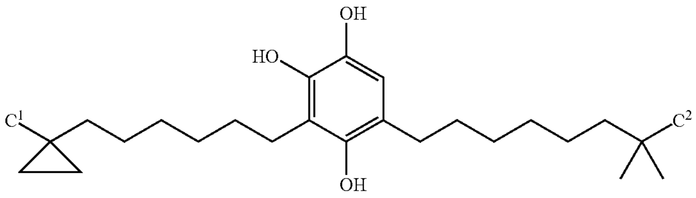 |
| wherein $C^1$ = COOH and $C^2$ = CO—CoA; $C^1$ = CO—CoA and $C^2$ = COOH; or $C^1$ and $C^2$ = CO—CoA |
| 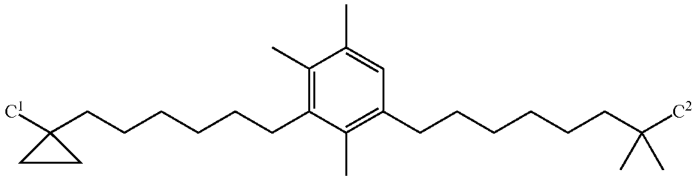 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 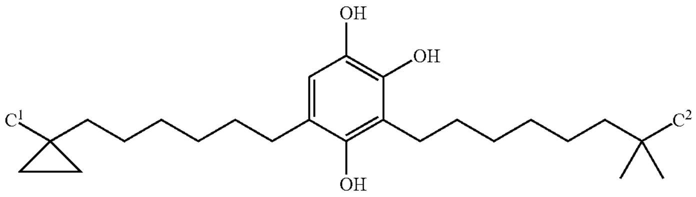 |
| wherein $C^1$ = COOH and $C^2$ = CO—CoA; $C^1$ = CO—CoA and $C^2$ = COOH; or $C^1$ and $C^2$ = CO—CoA |
| 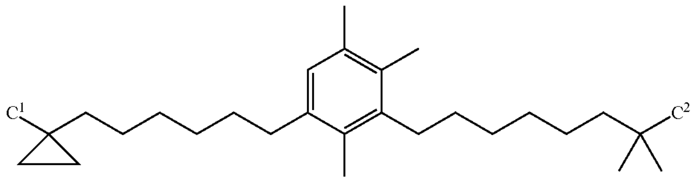 |
| wherein $C^1$ = COOH and $C^2$ = CO—CoA; $C^1$ = CO—CoA and $C^2$ = COOH; or $C^1$ and $C^2$ = CO—CoA |
| 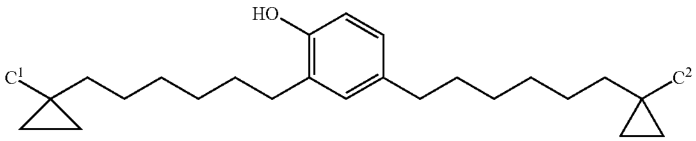 |
| wherein $C^1$ = COOH and $C^2$ = CO—CoA; $C^1$ = CO—CoA and $C^2$ = COOH; or $C^1$ and $C^2$ = CO—CoA |
| 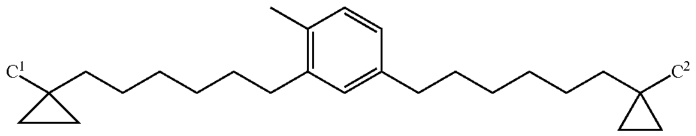 |
| wherein $C^1$ = COOH and $C^2$ = CO—CoA; $C^1$ = CO—CoA and $C^2$ = COOH; or $C^1$ and $C^2$ = CO—CoA |
| 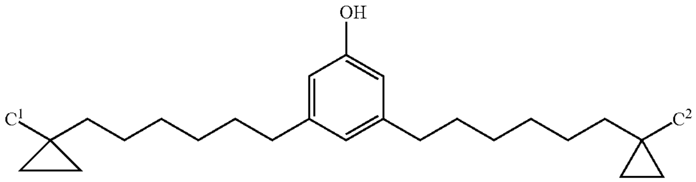 |
| wherein $C^1$ = COOH and $C^2$ = CO—CoA; $C^1$ = CO—CoA and $C^2$ = COOH; or $C^1$ and $C^2$ = CO—CoA |
| 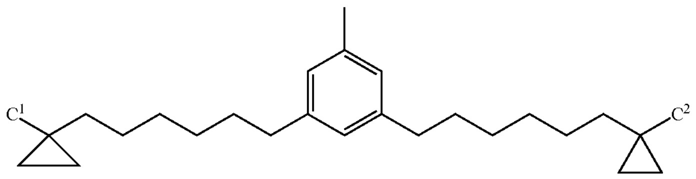 |
| wherein $C^1$ = COOH and $C^2$ = CO—CoA; $C^1$ = CO—CoA and $C^2$ = COOH; or $C^1$ and $C^2$ = CO—CoA |
| 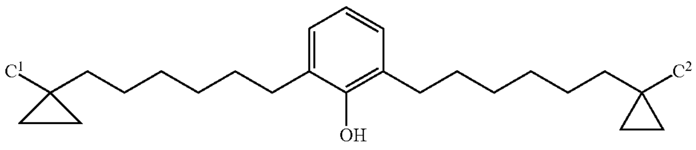 |

TABLE A-5-continued

Structure wherein $C^1$ = COOH and $C^2$ = CO—CoA; $C^1$ = CO—CoA and $C^2$ = COOH; or $C^1$ and $C^2$ = CO—CoA

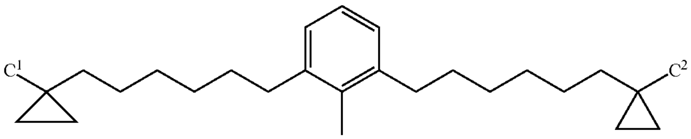

wherein $C^1$ = COOH and $C^2$ = CO—CoA; $C^1$ = CO—CoA and $C^2$ = COOH; or $C^1$ and $C^2$ = CO—CoA

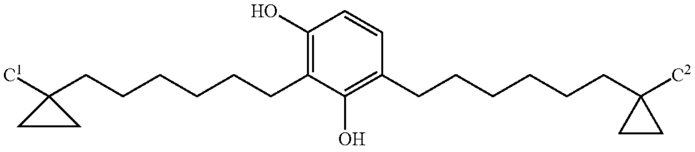

wherein $C^1$ = COOH and $C^2$ = CO—CoA; $C^1$ = CO—CoA and $C^2$ = COOH; or $C^1$ and $C^2$ = CO—CoA

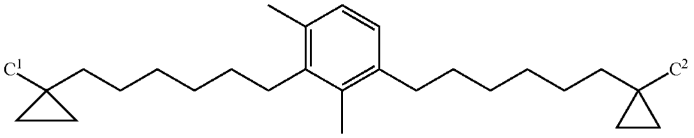

wherein $C^1$ = COOH and $C^2$ = CO—CoA; $C^1$ = CO—CoA and $C^2$ = COOH; or $C^1$ and $C^2$ = CO—CoA

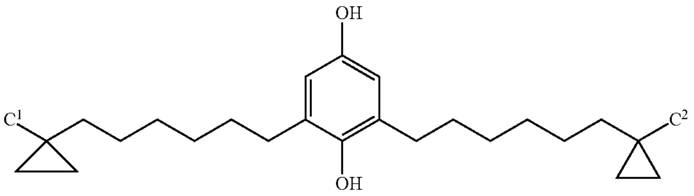

wherein $C^1$ = COOH and $C^2$ = CO—CoA; $C^1$ = CO—CoA and $C^2$ = COOH; or $C^1$ and $C^2$ = CO—CoA

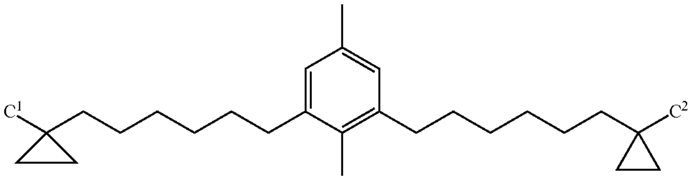

wherein $C^1$ = COOH and $C^2$ = CO—CoA; $C^1$ = CO—CoA and $C^2$ = COOH; or $C^1$ and $C^2$ = CO—CoA

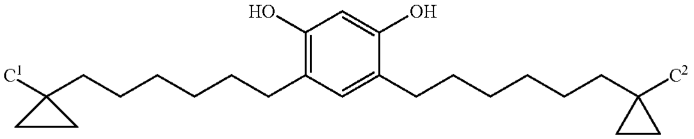

wherein $C^1$ = COOH and $C^2$ = CO—CoA; $C^1$ = CO—CoA and $C^2$ = COOH; or $C^1$ and $C^2$ = CO—CoA

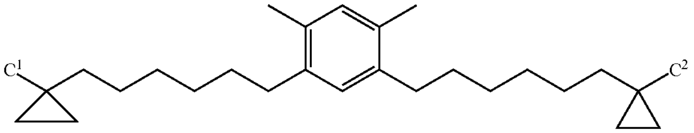

TABLE A-5-continued

| Structure |
|---|

wherein $C^1$ = COOH and $C^2$ = CO—CoA; $C^1$ = CO—CoA and $C^2$ = COOH; or $C^1$ and $C^2$ = CO—CoA

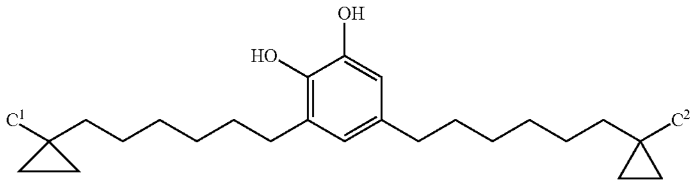

wherein $C^1$ = COOH and $C^2$ = CO—CoA; $C^1$ = CO—CoA and $C^2$ = COOH; or $C^1$ and $C^2$ = CO—CoA

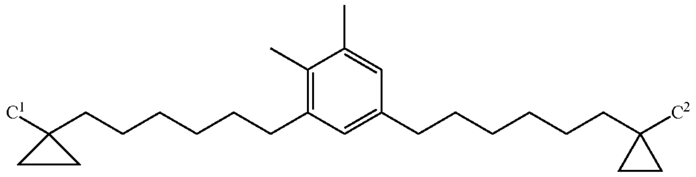

wherein $C^1$ = COOH and $C^2$ = CO—CoA; $C^1$ = CO—CoA and $C^2$ = COOH; or $C^1$ and $C^2$ = CO—CoA

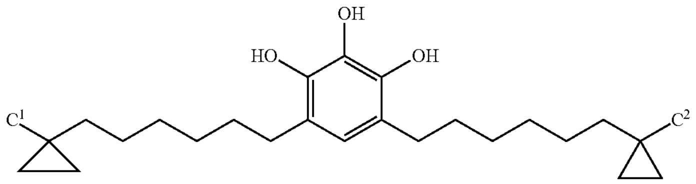

wherein $C^1$ = COOH and $C^2$ = CO—CoA; $C^1$ = CO—CoA and $C^2$ = COOH; or $C^1$ and $C^2$ = CO—CoA

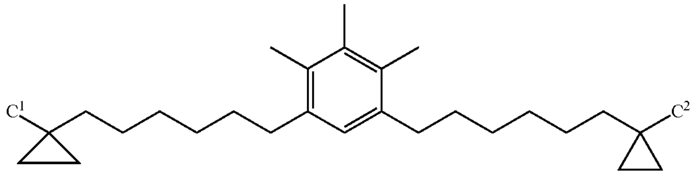

wherein $C^1$ = COOH and $C^2$ = CO—CoA; $C^1$ = CO—CoA and $C^2$ = COOH; or $C^1$ and $C^2$ = CO—CoA

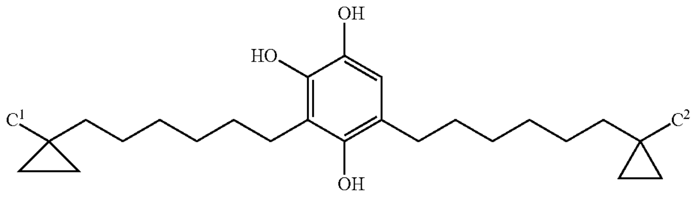

wherein $C^1$ = COOH and $C^2$ = CO—CoA; $C^1$ = CO—CoA and $C^2$ = COOH; or $C^1$ and $C^2$ = CO—CoA

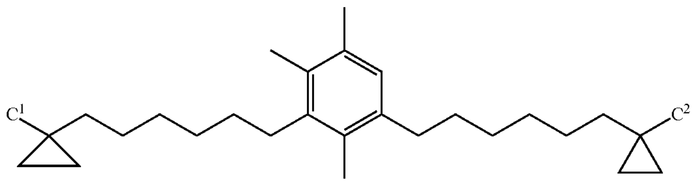

wherein $C^1$ = COOH and $C^2$ = CO—CoA; $C^1$ = CO—CoA and $C^2$ = COOH; or $C^1$ and $C^2$ = CO—CoA TABLE A-5-continued

| Structure |
| --- |

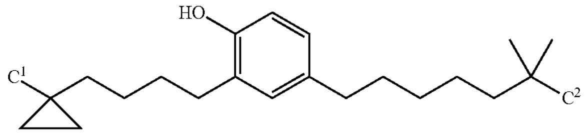

wherein $C^1$ = COOH and $C^2$ = CO—CoA; $C^1$ = CO—CoA and $C^2$ = COOH; or $C^1$ and $C^2$ = CO—CoA

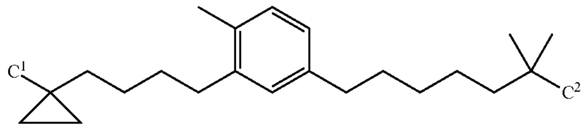

wherein $C^1$ = COOH and $C^2$ = CO—CoA; $C^1$ = CO—CoA and $C^2$ = COOH; or $C^1$ and $C^2$ = CO—CoA

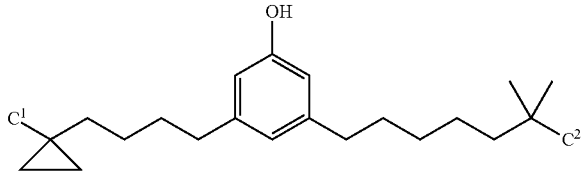

wherein $C^1$ = COOH and $C^2$= CO—CoA; $C^1$ = CO—CoA and $C^2$ = COOH; or $C^1$ and $C^2$ = CO—CoA

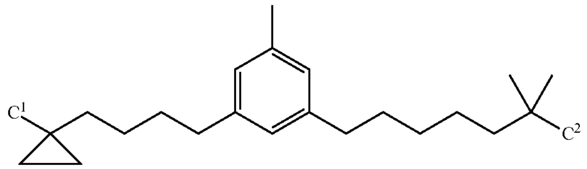

wherein $C^1$ = COOH and $C^2$ = CO—CoA; $C^1$ = CO—CoA and $C^2$ = COOH; or $C^1$ and $C^2$ = CO—CoA

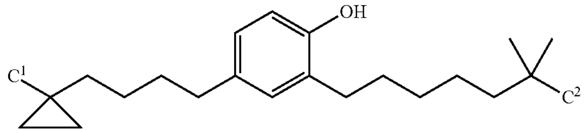

wherein $C^1$ = COOH and $C^2$ = CO—CoA; $C^1$ = CO—CoA and $C^2$ = COOH; or $C^1$ and $C^2$ = CO—CoA

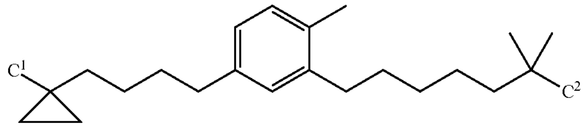

wherein $C^1$ = COOH and $C^2$ = CO—CoA; $C^1$ = CO—CoA and $C^2$ = COOH; or $C^1$ and $C^2$ = CO—CoA

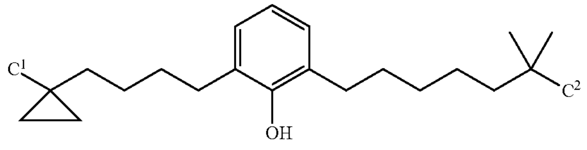

wherein $C^1$ = COOH and $C^2$ = CO—CoA; $C^1$ = CO—CoA and $C^2$ = COOH; or $C^1$ and $C^2$ = CO—CoA TABLE A-5-continued

| Structure |
|---|
| 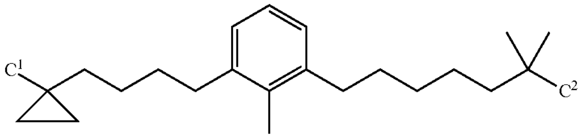 |
| wherein $C^1$ = COOH and $C^2$ = CO—CoA; $C^1$ = CO—CoA and $C^2$ = COOH; or $C^1$ and $C^2$ = CO—CoA |
| 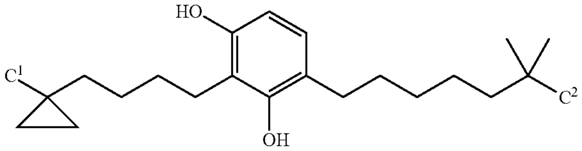 |
| wherein $C^1$ = COOH and $C^2$ = CO—CoA; $C^1$ = CO—CoA and $C^2$ = COOH; or $C^1$ and $C^2$ = CO—CoA |
| 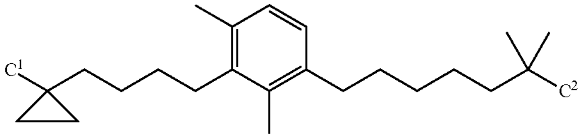 |
| wherein $C^1$ = COOH and $C^2$ = CO—CoA; $C^1$ = CO—CoA and $C^2$ = COOH; or $C^1$ and $C^2$ = CO—CoA |
| 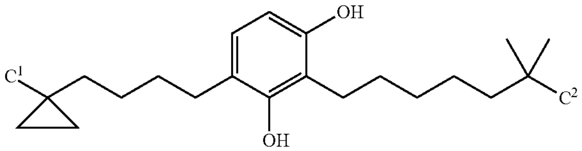 |
| wherein $C^1$ = COOH and $C^2$ = CO—CoA; $C^1$ = CO—CoA and $C^2$ = COOH; or $C^1$ and $C^2$ = CO—CoA |
| 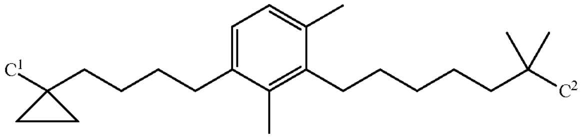 |
| wherein $C^1$ = COOH and $C^2$ = CO—CoA; $C^1$ = CO—CoA and $C^2$ = COOH; or $C^1$ and $C^2$ = CO—CoA |
| 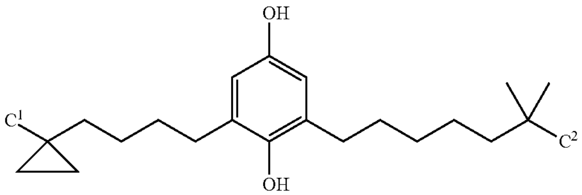 |
| wherein $C^1$ = COOH and $C^2$ = CO—CoA; $C^1$ = CO—CoA and $C^2$ = COOH; or $C^1$ and $C^2$ = CO—CoA |
| 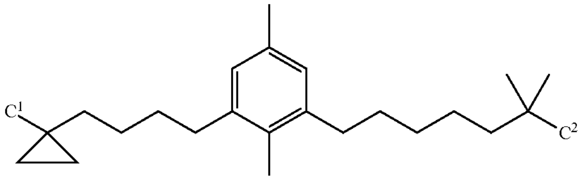 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 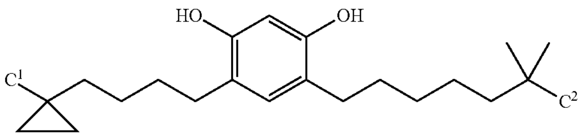 |
| wherein $C^1$ = COOH and $C^2$ = CO—CoA; $C^1$ = CO—CoA and $C^2$ = COOH; or $C^1$ and $C^2$ = CO—CoA |
| 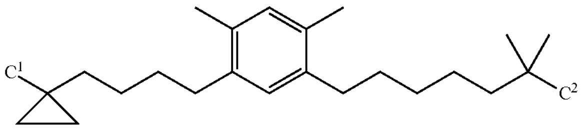 |
| wherein $C^1$ = COOH and $C^2$ = CO—CoA; $C^1$ = CO—CoA and $C^2$ = COOH; or $C^1$ and $C^2$ = CO—CoA |
| 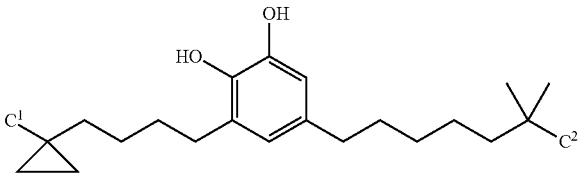 |
| wherein $C^1$ = COOH and $C^2$ = CO—CoA; $C^1$ = CO—CoA and $C^2$ = COOH; or $C^1$ and $C^2$ = CO—CoA |
| 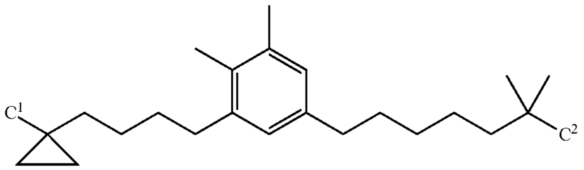 |
| wherein $C^1$ = COOH and $C^2$ = CO—CoA; $C^1$ = CO—CoA and $C^2$ = COOH; or $C^1$ and $C^2$ = CO—CoA |
| 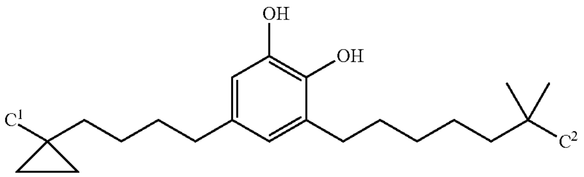 |
| wherein $C^1$ = COOH and $C^2$ = CO—CoA; $C^1$ = CO—CoA and $C^2$ = COOH; or $C^1$ and $C^2$ = CO—CoA |
| 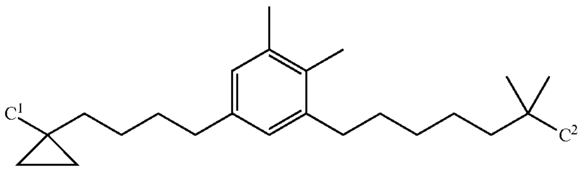 |
| wherein $C^1$ = COOH and $C^2$ = CO—CoA; $C^1$ = CO—CoA and $C^2$ = COOH; or $C^1$ and $C^2$ = CO—CoA |
| 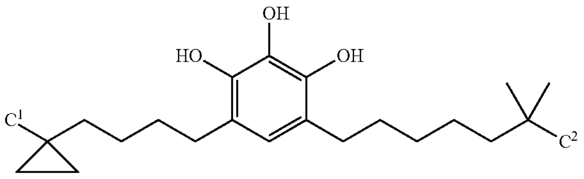 |

TABLE A-5-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 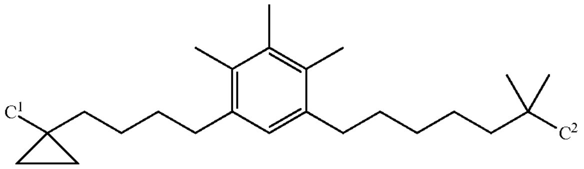 |
| wherein $C^1$ = COOH and $C^2$ = CO—CoA; $C^1$ = CO—CoA and $C^2$ = COOH; or $C^1$ and $C^2$ = CO—CoA |
| 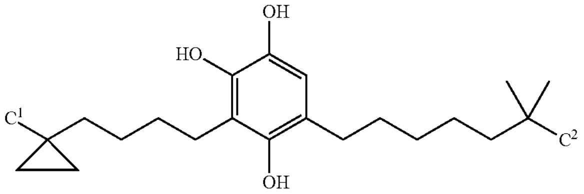 |
| wherein $C^1$ = COOH and $C^2$ = CO—CoA; $C^1$ = CO—CoA and $C^2$ = COOH; or $C^1$ and $C^2$ = CO—CoA |
| 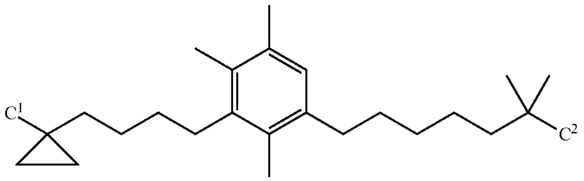 |
| wherein $C^1$ = COOH and $C^2$ = CO—CoA; $C^1$ = CO—CoA and $C^2$ = COOH; or $C^1$ and $C^2$ = CO—CoA |
| 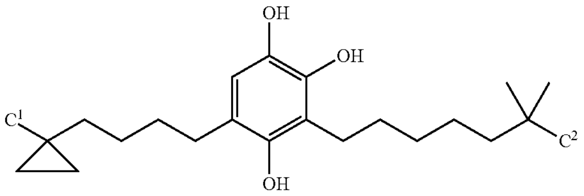 |
| wherein $C^1$ = COOH and $C^2$ = CO—CoA; $C^1$ = CO—CoA and $C^2$ = COOH; or $C^1$ and $C^2$ = CO—CoA |
| 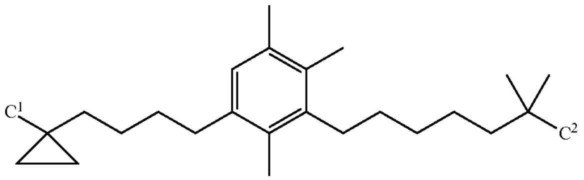 |
| wherein $C^1$ = COOH and $C^2$ = CO—CoA; $C^1$ = CO—CoA and $C^2$ = COOH; or $C^1$ and $C^2$ = CO—CoA |
| 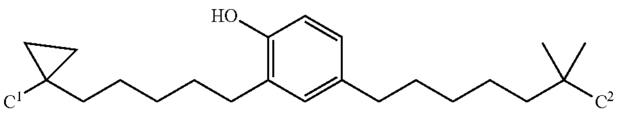 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 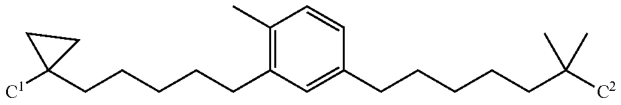 |
| wherein $C^1$ = COOH and $C^2$ = CO—CoA; $C^1$ = CO—CoA and $C^2$ = COOH; or $C^1$ and $C^2$ = CO—CoA |
| 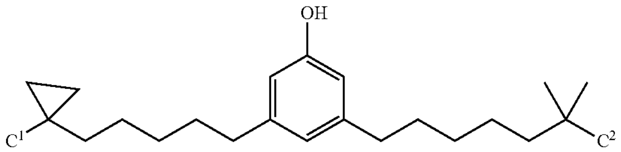 |
| wherein $C^1$ = COOH and $C^2$ = CO—CoA; $C^1$ = CO—CoA and $C^2$ = COOH; or $C^1$ and $C^2$ = CO—CoA |
| 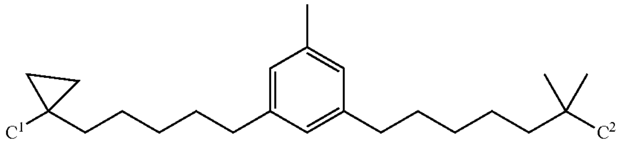 |
| wherein $C^1$ = COOH and $C^2$ = CO—CoA; $C^1$ = CO—CoA and $C^2$ = COOH; or $C^1$ and $C^2$ = CO—CoA |
| 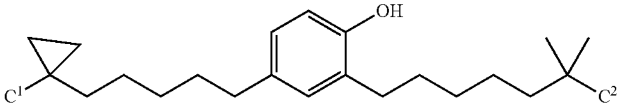 |
| wherein $C^1$ = COOH and $C^2$ = CO—CoA; $C^1$ = CO—CoA and $C^2$ = COOH; or $C^1$ and $C^2$ = CO—CoA |
| 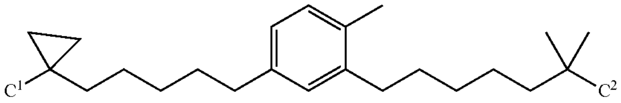 |
| wherein $C^1$ = COOH and $C^2$ = CO—CoA; $C^1$ = CO—CoA and $C^2$ = COOH; or $C^1$ and $C^2$ = CO—CoA |
| 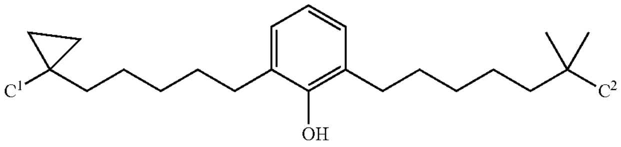 |
| wherein $C^1$ = COOH and $C^2$ = CO—CoA; $C^1$ = CO—CoA and $C^2$ = COOH; or $C^1$ and $C^2$ = CO—CoA |
| 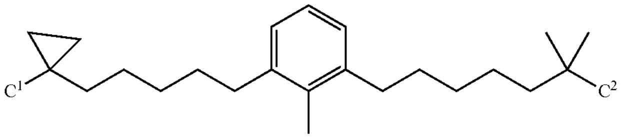 |
| wherein $C^1$ = COOH and $C^2$ = CO—CoA; $C^1$ = CO—CoA and $C^2$ = COOH; or $C^1$ and $C^2$ = CO—CoA |
| 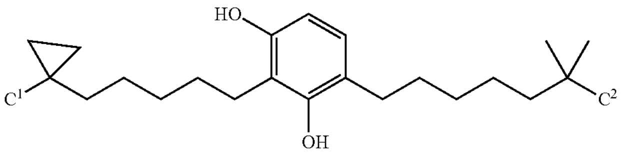 |

TABLE A-5-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 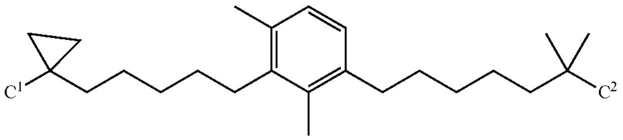 |
| wherein $C^1$ = COOH and $C^2$ = CO—CoA; $C^1$ = CO—CoA and $C^2$ = COOH; or $C^1$ and $C^2$ = CO—CoA |
| 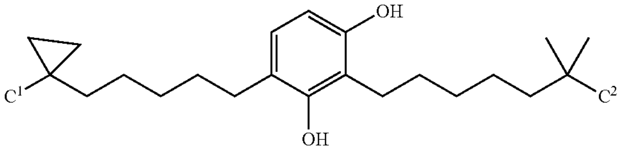 |
| wherein $C^1$ = COOH and $C^2$ = CO—CoA; $C^1$ = CO—CoA and $C^2$ = COOH; or $C^1$ and $C^2$ = CO—CoA |
| 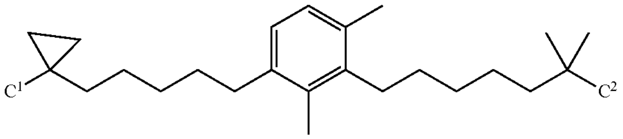 |
| wherein $C^1$ = COOH and $C^2$ = CO—CoA; $C^1$ = CO—CoA and $C^2$ = COOH; or $C^1$ and $C^2$ = CO—CoA |
| 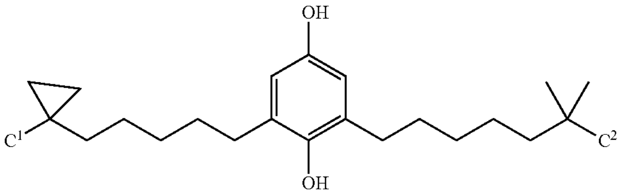 |
| wherein $C^1$ = COOH and $C^2$ = CO—CoA; $C^1$ = CO—CoA and $C^2$ = COOH; or $C^1$ and $C^2$ = CO—CoA |
| 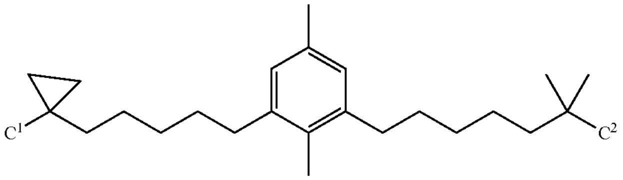 |
| wherein $C^1$ = COOH and $C^2$ = CO—CoA; $C^1$ = CO—CoA and $C^2$ = COOH; or $C^1$ and $C^2$ = CO—CoA |
| 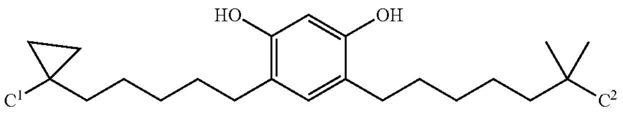 |
| wherein $C^1$ = COOH and $C^2$ = CO—CoA; $C^1$ = CO—CoA and $C^2$ = COOH; or $C^1$ and $C^2$ = CO—CoA |
| 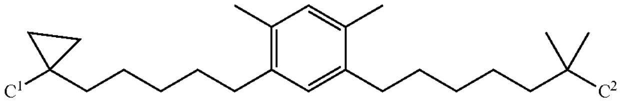 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

Structure

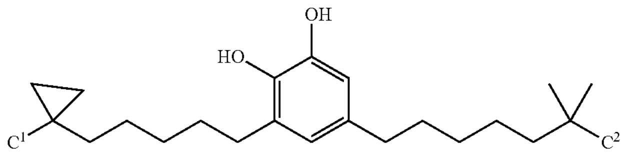

wherein $C^1$ = COOH and $C^2$ = CO—CoA; $C^1$ = CO—CoA and $C^2$ = COOH; or $C^1$ and $C^2$ = CO—CoA

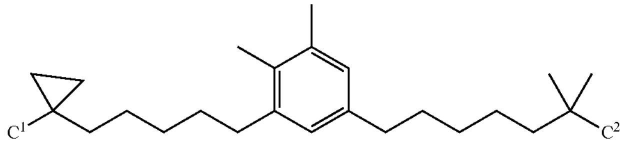

wherein $C^1$ = COOH and $C^2$ = CO—CoA; $C^1$ = CO—CoA and $C^2$ = COOH; or $C^1$ and $C^2$ = CO—CoA

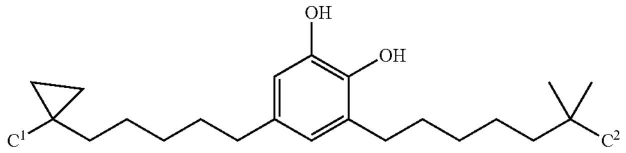

wherein $C^1$ = COOH and $C^2$ = CO—CoA; $C^1$ = CO—CoA and $C^2$ = COOH; or $C^1$ and $C^2$ = CO—CoA

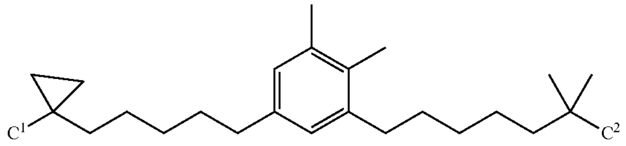

wherein $C^1$ = COOH and $C^2$ = CO—CoA; $C^1$ = CO—CoA and $C^2$ = COOH; or $C^1$ and $C^2$ = CO—CoA

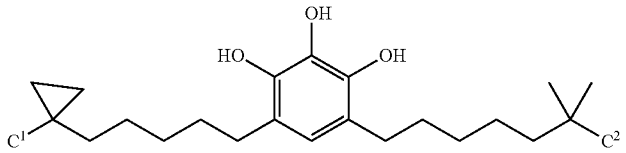

wherein $C^1$ = COOH and $C^2$ = CO—CoA; $C^1$ = CO—CoA and $C^2$ = COOH; or $C^1$ and $C^2$ = CO—CoA

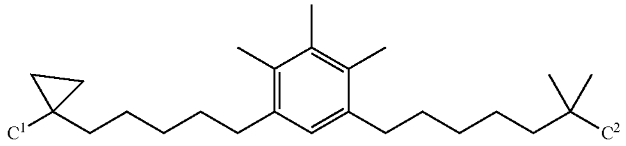

wherein $C^1$ = COOH and $C^2$ = CO—CoA; $C^1$ = CO—CoA and $C^2$ = COOH; or $C^1$ and $C^2$ = CO—CoA

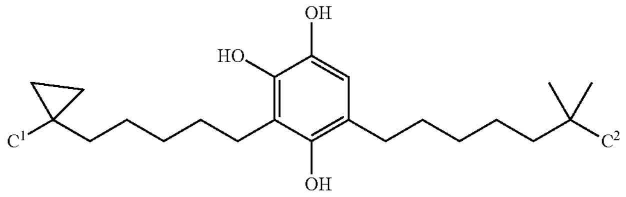

wherein $C^1$ = COOH and $C^2$ = CO—CoA; $C^1$ = CO—CoA and $C^2$ = COOH; or $C^1$ and $C^2$ = CO—CoA TABLE A-5-continued

| Structure |
| --- |
| 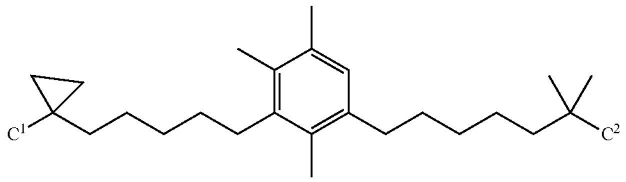 |
| wherein $C^1$ = COOH and $C^2$ = CO—CoA; $C^1$ = CO—CoA and $C^2$ = COOH; or $C^1$ and $C^2$ = CO—CoA |
| 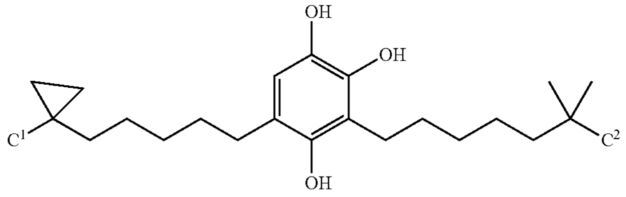 |
| wherein $C^1$ = COOH and $C^2$ = CO—CoA; $C^1$ = CO—CoA and $C^2$ = COOH; or $C^1$ and $C^2$ = CO—CoA |
| 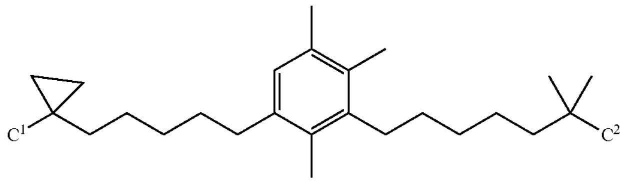 |
| wherein $C^1$ = COOH and $C^2$ = CO—CoA; $C^1$ = CO—CoA and $C^2$ = COOH; or $C^1$ and $C^2$ = CO—CoA |
| 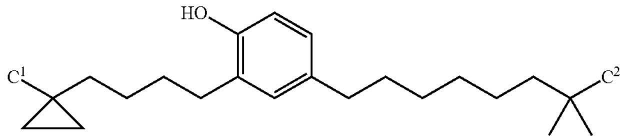 |
| wherein $C^1$ = COOH and $C^2$ = CO—CoA; $C^1$ = CO—CoA and $C^2$ = COOH; or $C^1$ and $C^2$ = CO—CoA |
| 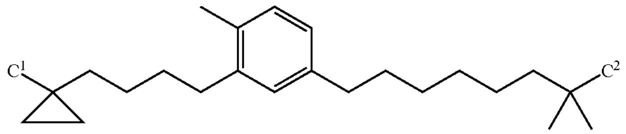 |
| wherein $C^1$ = COOH and $C^2$ = CO—CoA; $C^1$ = CO—CoA and $C^2$ = COOH; or $C^1$ and $C^2$ = CO—CoA |
| 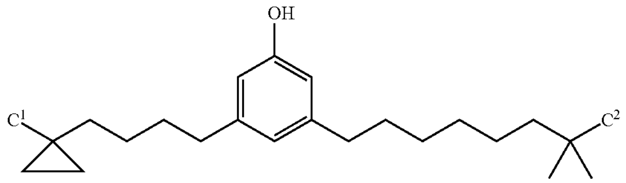 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 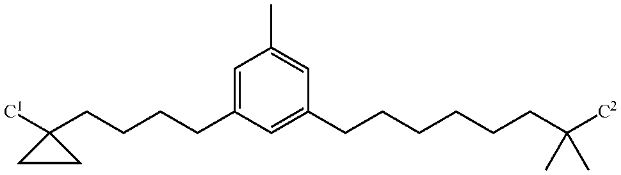 |
| wherein $C^1$ = COOH and $C^2$ = CO—CoA; $C^1$ = CO—CoA and $C^2$ = COOH; or $C^1$ and $C^2$ = CO—CoA |
| 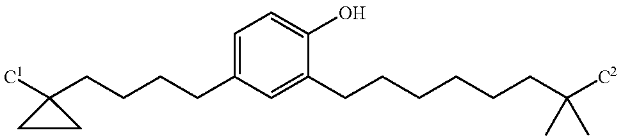 |
| wherein $C^1$ = COOH and $C^2$ = CO—CoA; $C^1$ = CO—CoA and $C^2$ = COOH; or $C^1$ and $C^2$ = CO—CoA |
| 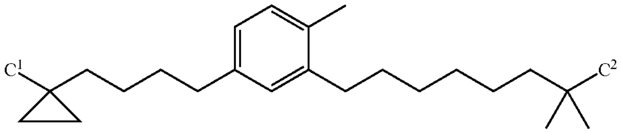 |
| wherein $C^1$ = COOH and $C^2$ = CO—CoA; $C^1$ = CO—CoA and $C^2$ = COOH; or $C^1$ and $C^2$ = CO—CoA |
| 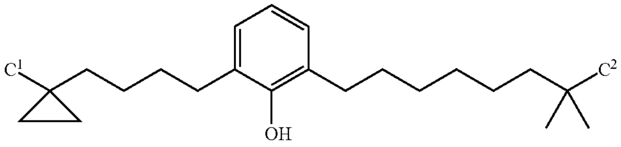 |
| wherein $C^1$ = COOH and $C^2$ = CO—CoA; $C^1$ = CO—CoA and $C^2$ = COOH; or $C^1$ and $C^2$ = CO—CoA |
| 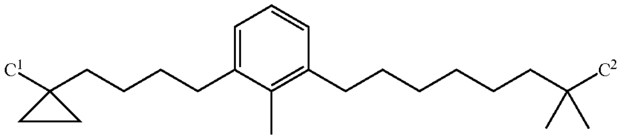 |
| wherein $C^1$ = COOH and $C^2$ = CO—CoA; $C^1$ = CO—CoA and $C^2$ = COOH; or $C^1$ and $C^2$ = CO—CoA |
| 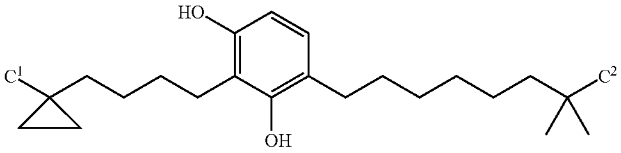 |
| wherein $C^1$ = COOH and $C^2$ = CO—CoA; $C^1$ = CO—CoA and $C^2$ = COOH; or $C^1$ and $C^2$ = CO—CoA |
| 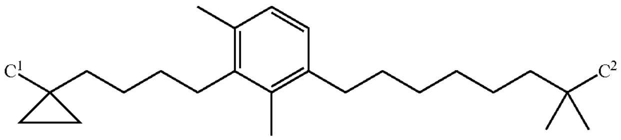 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 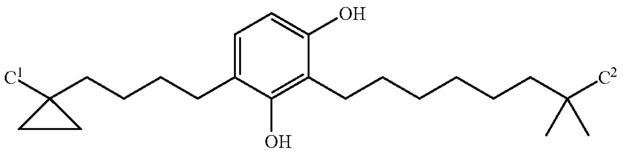 |
| wherein $C^1$ = COOH and $C^2$ = CO—CoA; $C^1$ = CO—CoA and $C^2$ = COOH; or $C^1$ and $C^2$ = CO—CoA |
| 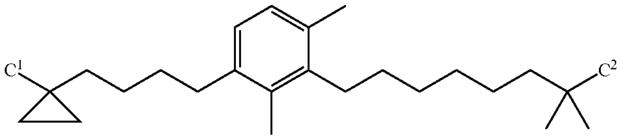 |
| wherein $C^1$ = COOH and $C^2$ = CO—CoA; $C^1$ = CO—CoA and $C^2$ = COOH; or $C^1$ and $C^2$ = CO—CoA |
| 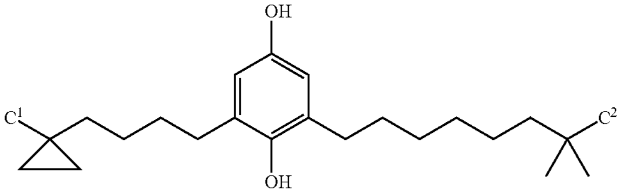 |
| wherein $C^1$ = COOH and $C^2$ = CO—CoA; $C^1$ = CO—CoA and $C^2$ = COOH; or $C^1$ and $C^2$ = CO—CoA |
| 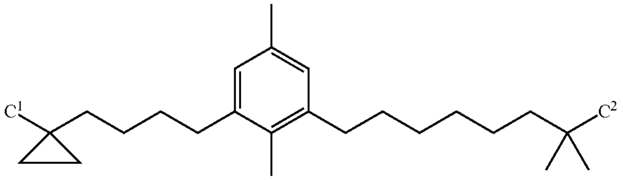 |
| wherein $C^1$ = COOH and $C^2$ = CO—CoA; $C^1$ = CO—CoA and $C^2$ = COOH; or $C^1$ and $C^2$ = CO—CoA |
| 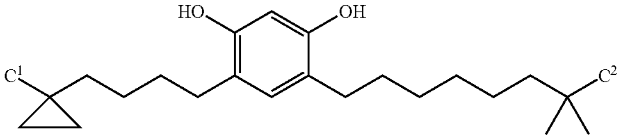 |
| wherein $C^1$ = COOH and $C^2$ = CO—CoA; $C^1$ = CO—CoA and $C^2$ = COOH; or $C^1$ and $C^2$ = CO—CoA |
| 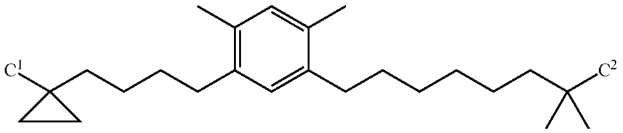 |
| wherein $C^1$ = COOH and $C^2$ = CO—CoA; $C^1$ = CO—CoA and $C^2$ = COOH; or $C^1$ and $C^2$ = CO—CoA |
| 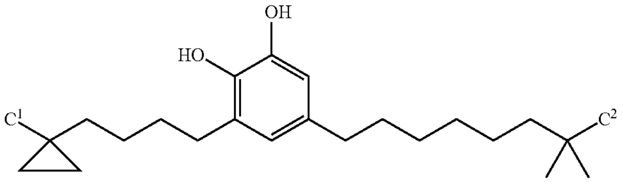 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 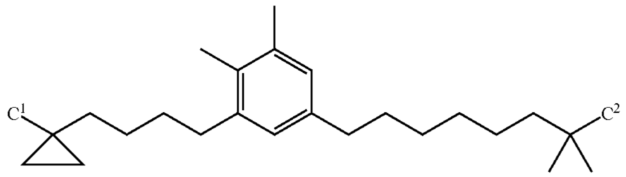 |
| wherein $C^1$ = COOH and $C^2$ = CO—CoA; $C^1$ = CO—CoA and $C^2$ = COOH; or $C^1$ and $C^2$ = CO—CoA |
| 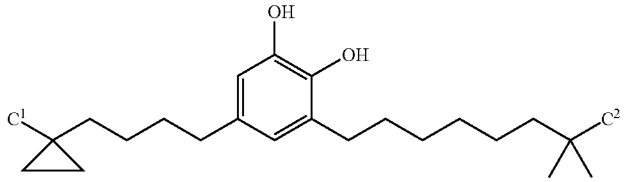 |
| wherein $C^1$ = COOH and $C^2$ = CO—CoA; $C^1$ = CO—CoA and $C^2$ = COOH; or $C^1$ and $C^2$ = CO—CoA |
| 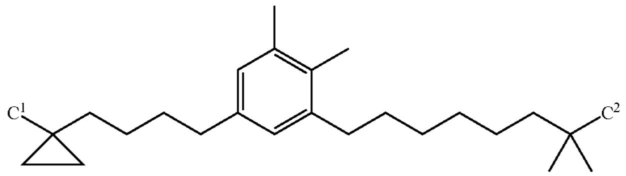 |
| wherein $C^1$ = COOH and $C^2$ = CO—CoA; $C^1$ = CO—CoA and $C^2$ = COOH; or $C^1$ and $C^2$ = CO—CoA |
| 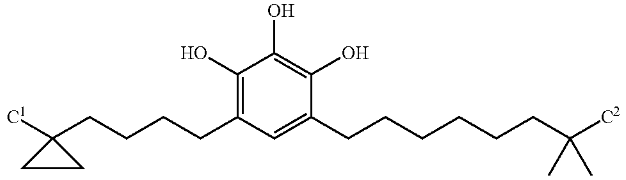 |
| wherein $C^1$ = COOH and $C^2$ = CO—CoA; $C^1$ = CO—CoA and $C^2$ = COOH; or $C^1$ and $C^2$ = CO—CoA |
| 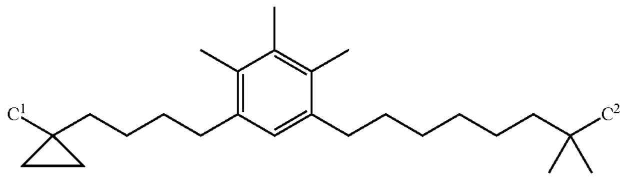 |
| wherein $C^1$ = COOH and $C^2$ = CO—CoA; $C^1$ = CO—CoA and $C^2$ = COOH; or $C^1$ and $C^2$ = CO—CoA |
| 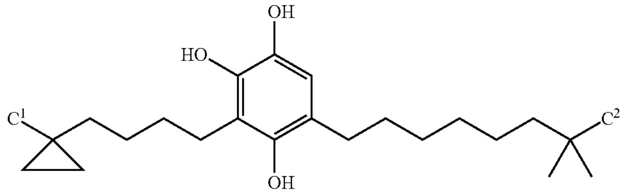 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 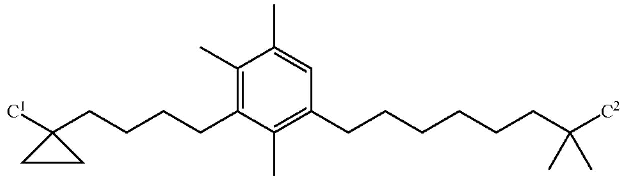 |
| wherein $C^1$ = COOH and $C^2$ = CO—CoA; $C^1$ = CO—CoA and $C^2$ = COOH; or $C^1$ and $C^2$ = CO—CoA |
| 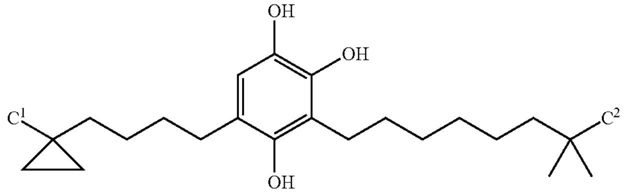 |
| wherein $C^1$ = COOH and $C^2$ = CO—CoA; $C^1$ = CO—CoA and $C^2$ = COOH; or $C^1$ and $C^2$ = CO—CoA |
| 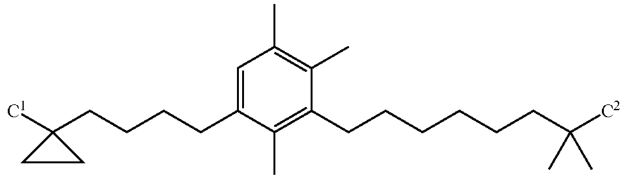 |
| wherein $C^1$ = COOH and $C^2$ = CO—CoA; $C^1$ = CO—CoA and $C^2$ = COOH; or $C^1$ and $C^2$ = CO—CoA |
| 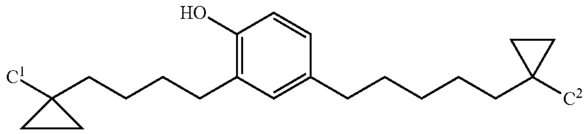 |
| wherein $C^1$ = COOH and $C^2$ = CO—CoA; $C^1$ = CO—CoA and $C^2$ = COOH; or $C^1$ and $C^2$ = CO—CoA |
| 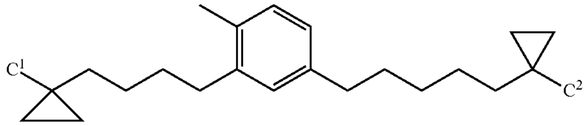 |
| wherein $C^1$ = COOH and $C^2$ = CO—CoA; $C^1$ = CO—CoA and $C^2$ = COOH; or $C^1$ and $C^2$ = CO—CoA |
| 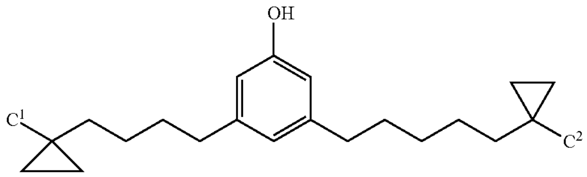 |
| wherein $C^1$ = COOH and $C^2$ = CO—CoA; $C^1$ = CO—CoA and $C^2$ = COOH; or $C^1$ and $C^2$ = CO—CoA |
| 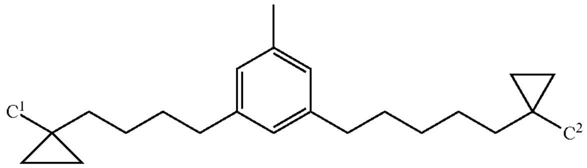 |

TABLE A-5-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 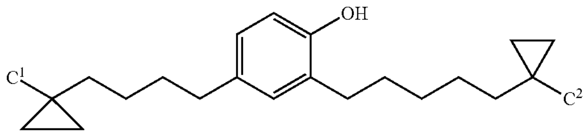 |
| wherein $C^1$ = COOH and $C^2$ = CO—CoA; $C^1$ = CO—CoA and $C^2$ = COOH; or $C^1$ and $C^2$ = CO—CoA |
| 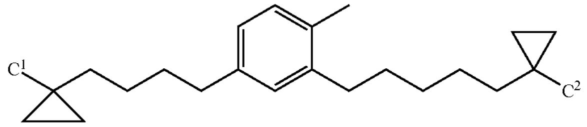 |
| wherein $C^1$ = COOH and $C^2$ = CO—CoA; $C^1$ = CO—CoA and $C^2$ = COOH; or $C^1$ and $C^2$ = CO—CoA |
| 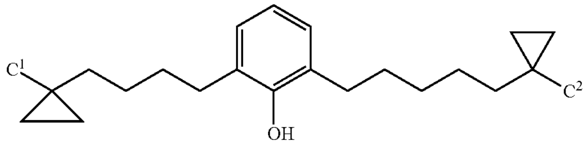 |
| wherein $C^1$ = COOH and $C^2$ = CO—CoA; $C^1$ = CO—CoA and $C^2$ = COOH; or $C^1$ and $C^2$ = CO—CoA |
| 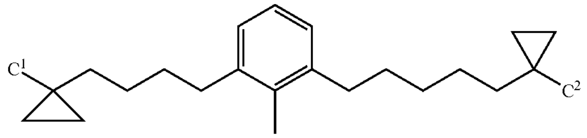 |
| wherein $C^1$ = COOH and $C^2$ = CO—CoA; $C^1$ = CO—CoA and $C^2$ = COOH; or $C^1$ and $C^2$ = CO—CoA |
| 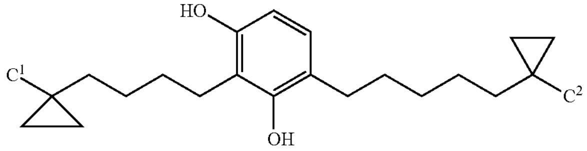 |
| wherein $C^1$ = COOH and $C^2$ = CO—CoA; $C^1$ = CO—CoA and $C^2$ = COOH; or $C^1$ and $C^2$ = CO—CoA |
| 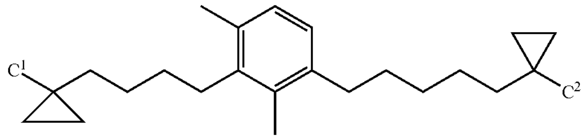 |
| wherein $C^1$ = COOH and $C^2$ = CO—CoA; $C^1$ = CO—CoA and $C^2$ = COOH; or $C^1$ and $C^2$ = CO—CoA |
| 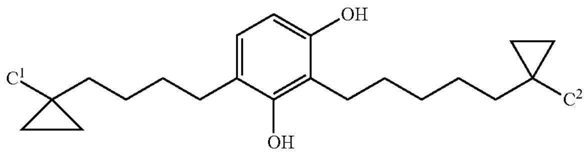 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 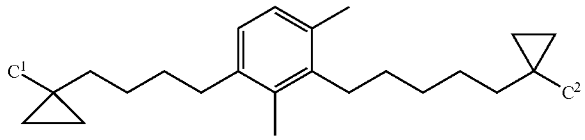 |
| wherein $C^1$ = COOH and $C^2$ = CO—CoA; $C^1$ = CO—CoA and $C^2$ = COOH; or $C^1$ and $C^2$ = CO—CoA |
| 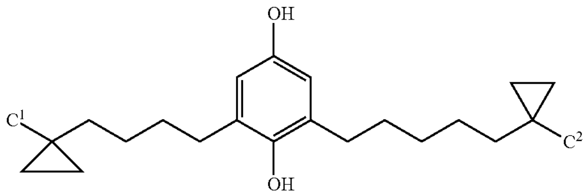 |
| wherein $C^1$ = COOH and $C^2$ = CO—CoA; $C^1$ = CO—CoA and $C^2$ = COOH; or $C^1$ and $C^2$ = CO—CoA |
| 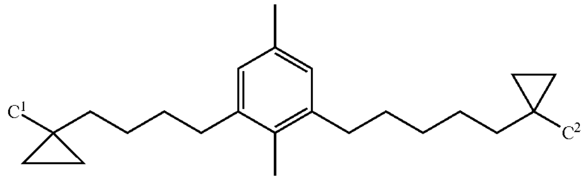 |
| wherein $C^1$ = COOH and $C^2$ = CO—CoA; $C^1$ = CO—CoA and $C^2$ = COOH; or $C^1$ and $C^2$ = CO—CoA |
| 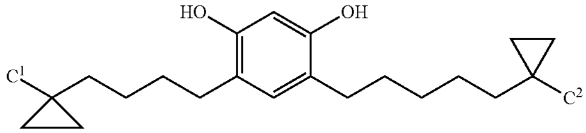 |
| wherein $C^1$ = COOH and $C^2$ = CO—CoA; $C^1$ = CO—CoA and $C^2$ = COOH; or $C^1$ and $C^2$ = CO—CoA |
| 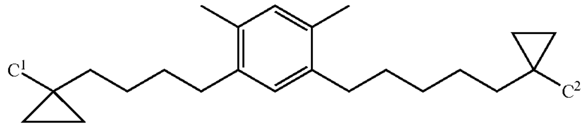 |
| wherein $C^1$ = COOH and $C^2$ = CO—CoA; $C^1$ = CO—CoA and $C^2$ = COOH; or $C^1$ and $C^2$ = CO—CoA |
| 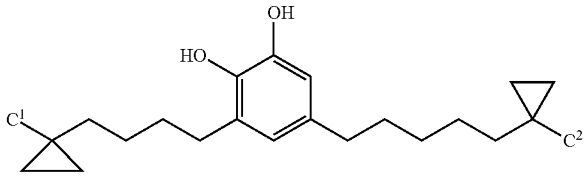 |
| wherein $C^1$ = COOH and $C^2$ = CO—CoA; $C^1$ = CO—CoA and $C^2$ = COOH; or $C^1$ and $C^2$ = CO—CoA |
| 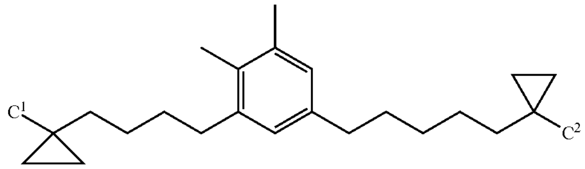 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 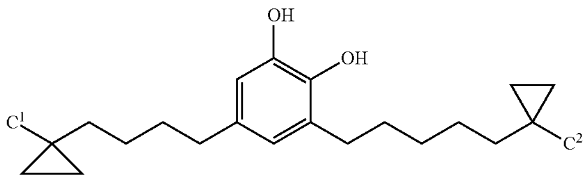 |
| wherein $C^1$ = COOH and $C^2$ = CO—CoA; $C^1$ = CO—CoA and $C^2$ = COOH; or $C^1$ and $C^2$ = CO—CoA |
| 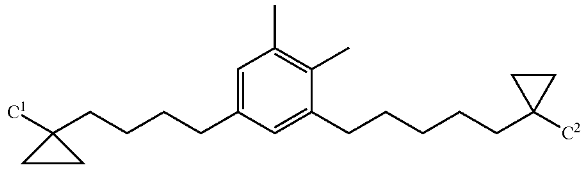 |
| wherein $C^1$ = COOH and $C^2$ = CO—CoA; $C^1$ = CO—CoA and $C^2$ = COOH; or $C^1$ and $C^2$ = CO—CoA |
| 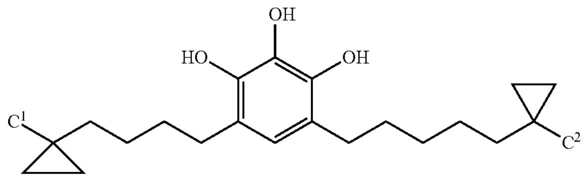 |
| wherein $C^1$ = COOH and $C^2$ = CO—CoA; $C^1$ = CO—CoA and $C^2$ = COOH; or $C^1$ and $C^2$ = CO—CoA |
| 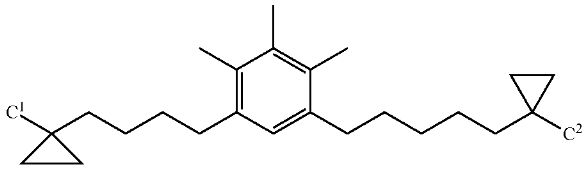 |
| wherein $C^1$ = COOH and $C^2$ = CO—CoA; $C^1$ = CO—CoA and $C^2$ = COOH; or $C^1$ and $C^2$ = CO—CoA |
| 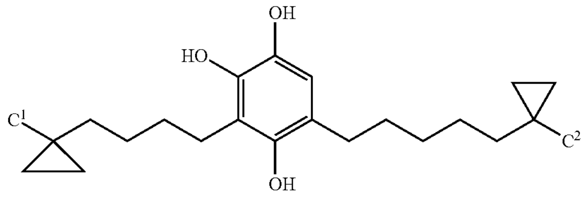 |
| wherein $C^1$ = COOH and $C^2$ = CO—CoA; $C^1$ = CO—CoA and $C^2$ = COOH; or $C^1$ and $C^2$ = CO—CoA |
| 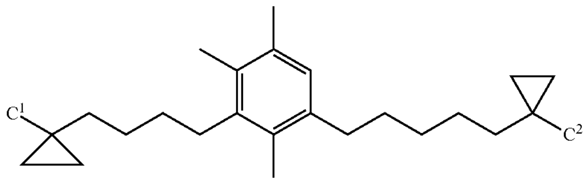 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 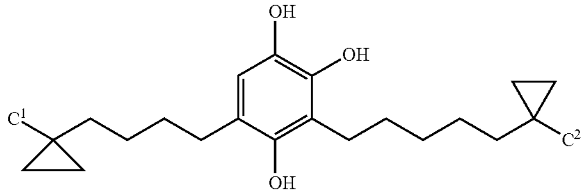 |
| wherein $C^1$ = COOH and $C^2$ = CO—CoA; $C^1$ = CO—CoA and $C^2$ = COOH; or $C^1$ and $C^2$ = CO—CoA |
| 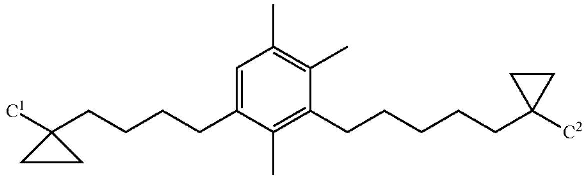 |
| wherein $C^1$ = COOH and $C^2$ = CO—CoA; $C^1$ = CO—CoA and $C^2$ = COOH; or $C^1$ and $C^2$ = CO—CoA |
| 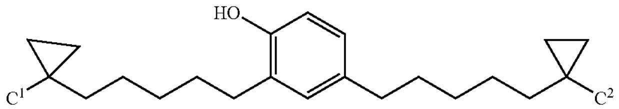 |
| wherein $C^1$ = COOH and $C^2$ = CO—CoA; $C^1$ = CO—CoA and $C^2$ = COOH; or $C^1$ and $C^2$ = CO—CoA |
| 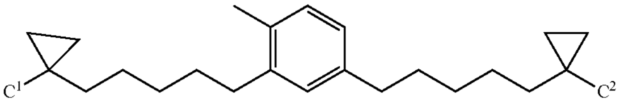 |
| wherein $C^1$ = COOH and $C^2$ = CO—CoA; $C^1$ = CO—CoA and $C^2$ = COOH; or $C^1$ and $C^2$ = CO—CoA |
| 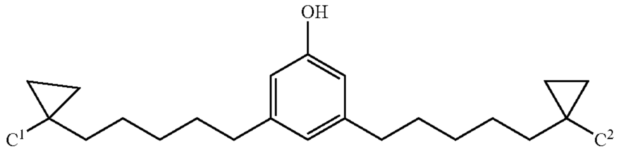 |
| wherein $C^1$ = COOH and $C^2$ = CO—CoA; $C^1$ = CO—CoA and $C^2$ = COOH; or $C^1$ and $C^2$ = CO—CoA |
| 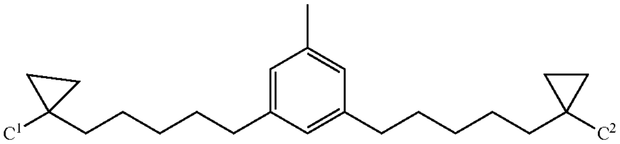 |
| wherein $C^1$ = COOH and $C^2$ = CO—CoA; $C^1$ = CO—CoA and $C^2$ = COOH; or $C^1$ and $C^2$ = CO—CoA |
| 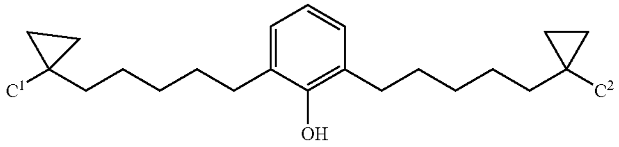 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 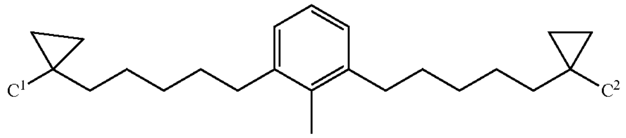 |
| wherein $C^1$ = COOH and $C^2$ = CO—CoA; $C^1$ = CO—CoA and $C^2$ = COOH; or $C^1$ and $C^2$ = CO—CoA |
| 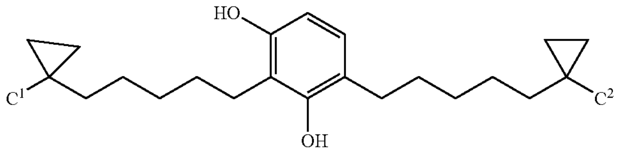 |
| wherein $C^1$ = COOH and $C^2$ = CO—CoA; $C^1$ = CO—CoA and $C^2$ = COOH; or $C^1$ and $C^2$ = CO—CoA |
| 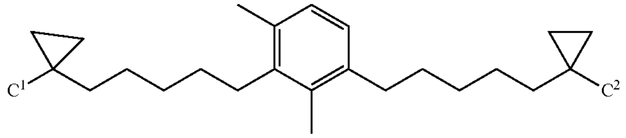 |
| wherein $C^1$ = COOH and $C^2$ = CO—CoA; $C^1$ = CO—CoA and $C^2$ = COOH; or $C^1$ and $C^2$ = CO—CoA |
| 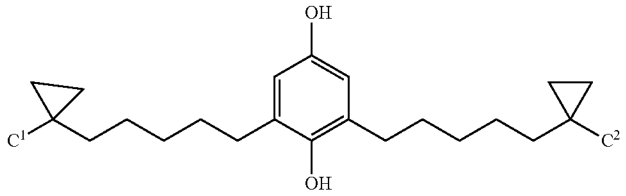 |
| wherein $C^1$ = COOH and $C^2$ = CO—CoA; $C^1$ = CO—CoA and $C^2$ = COOH; or $C^1$ and $C^2$ = CO—CoA |
| 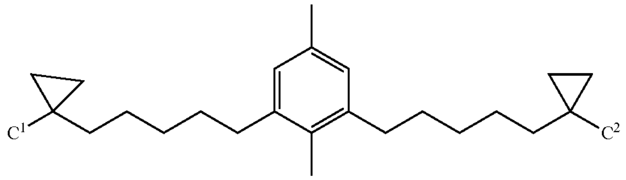 |
| wherein $C^1$ = COOH and $C^2$= CO—CoA; $C^1$ = CO—CoA and $C^2$ = COOH; or $C^1$ and $C^2$ = CO—CoA |
| 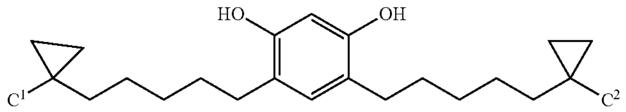 |
| wherein $C^1$ = COOH and $C^2$ = CO—CoA; $C^1$ = CO—CoA and $C^2$ = COOH; or $C^1$ and $C^2$ = CO—CoA |
| 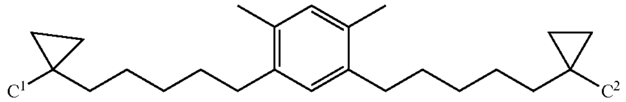 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
| --- |
| 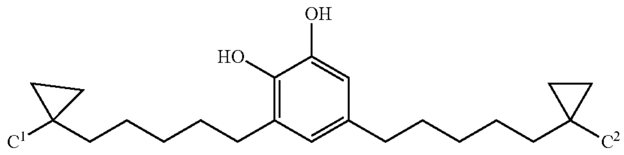<br>wherein $C^1$ = COOH and $C^2$ = CO—CoA; $C^1$ = CO—CoA and $C^2$ = COOH; or $C^1$ and $C^2$ = CO—CoA |
| 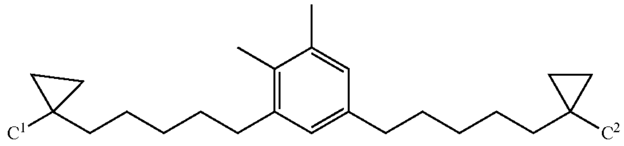<br>wherein $C^1$ = COOH and $C^2$ = CO—CoA; $C^1$ = CO—CoA and $C^2$ = COOH; or $C^1$ and $C^2$ = CO—CoA |
| 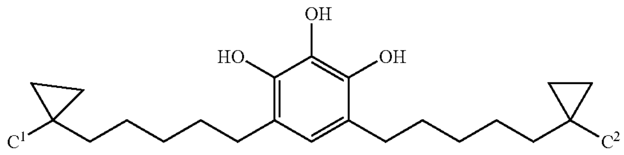<br>wherein $C^1$ = COOH and $C^2$ = CO—CoA; $C^1$ = CO—CoA and $C^2$ = COOH; or $C^1$ and $C^2$ = CO—CoA |
| 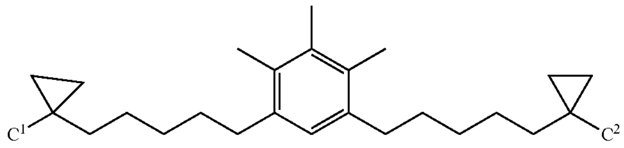<br>wherein $C^1$ = COOH and $C^2$ = CO—CoA; $C^1$ = CO—CoA and $C^2$ = COOH; or $C^1$ and $C^2$ = CO—CoA |
| 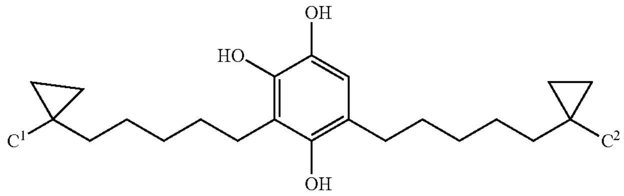<br>wherein $C^1$ = COOH and $C^2$ = CO—CoA; $C^1$ = CO—CoA and $C^2$ = COOH; or $C^1$ and $C^2$ = CO—CoA |
| 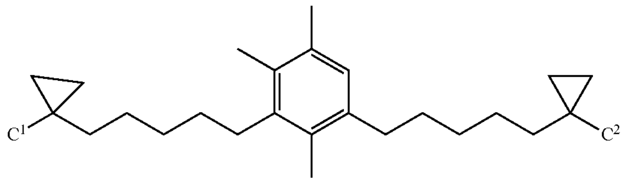<br>wherein $C^1$ = COOH and $C^2$ = CO—CoA; $C^1$ = CO—CoA and $C^2$ = COOH; or $C^1$ and $C^2$ = CO—CoA |
| 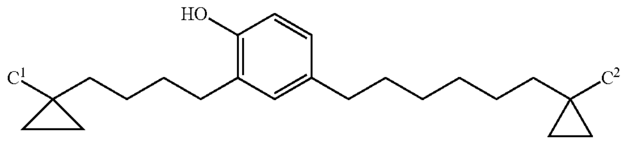<br>wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 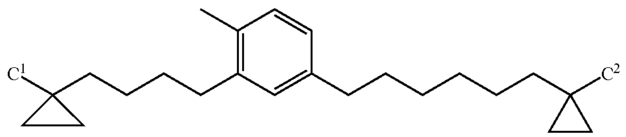 |
| wherein $C^1$ = COOH and $C^2$ = CO—CoA; $C^1$ = CO—CoA and $C^2$ = COOH; or $C^1$ and $C^2$ = CO—CoA |
| 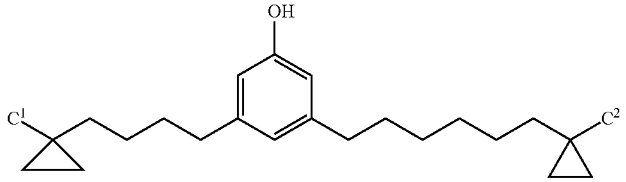 |
| wherein $C^1$ = COOH and $C^2$ = CO—CoA; $C^1$ = CO—CoA and $C^2$ = COOH; or $C^1$ and $C^2$ = CO—CoA |
| 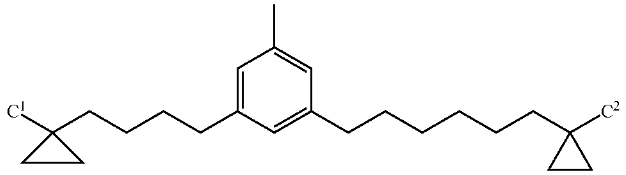 |
| wherein $C^1$ = COOH and $C^2$ = CO—CoA; $C^1$ = CO—CoA and $C^2$ = COOH; or $C^1$ and $C^2$ = CO—CoA |
| 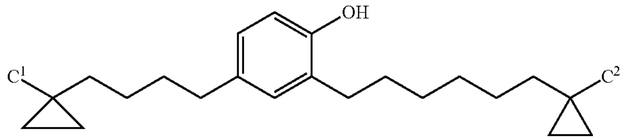 |
| wherein $C^1$ = COOH and $C^2$ = CO—CoA; $C^1$ = CO—CoA and $C^2$ = COOH; or $C^1$ and $C^2$ = CO—CoA |
| 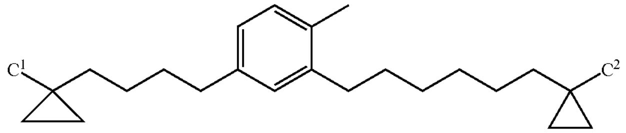 |
| wherein $C^1$ = COOH and $C^2$ = CO—CoA; $C^1$ = CO—CoA and $C^2$ = COOH; or $C^1$ and $C^2$ = CO—CoA |
| 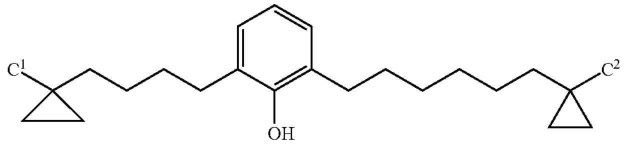 |
| wherein $C^1$ = COOH and $C^2$ = CO—CoA; $C^1$ = CO—CoA and $C^2$ = COOH; or $C^1$ and $C^2$ = CO—CoA |
| 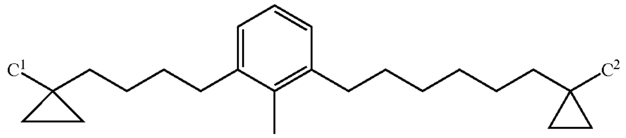 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 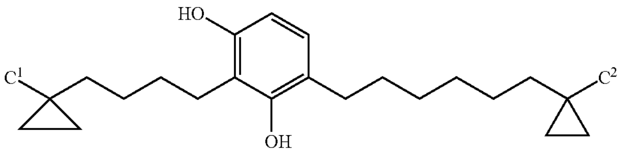 wherein $C^1$ = COOH and $C^2$ = CO—CoA; $C^1$ = CO—CoA and $C^2$ = COOH; or $C^1$ and $C^2$ = CO—CoA |
| 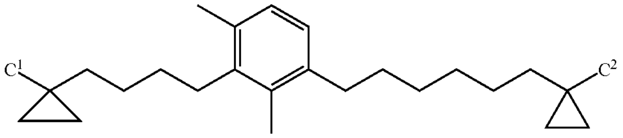 wherein $C^1$ = COOH and $C^2$ = CO—CoA; $C^1$ = CO—CoA and $C^2$ = COOH; or $C^1$ and $C^2$ = CO—CoA |
| 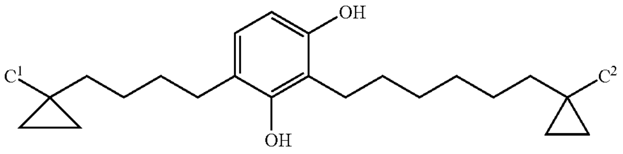 wherein $C^1$ = COOH and $C^2$ = CO—CoA; $C^1$ = CO—CoA and $C^2$ = COOH; or $C^1$ and $C^2$ = CO—CoA |
| 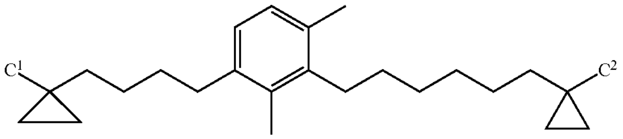 wherein $C^1$ = COOH and $C^2$ = CO—CoA; $C^1$ = CO—CoA and $C^2$ = COOH; or $C^1$ and $C^2$ = CO—CoA |
| 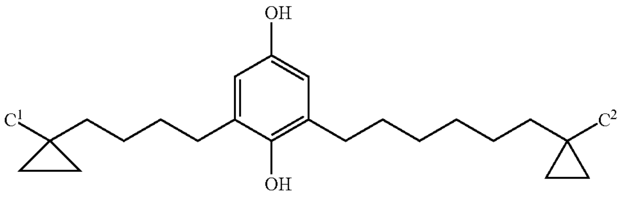 wherein $C^1$ = COOH and $C^2$ = CO—CoA; $C^1$ = CO—CoA and $C^2$ = COOH; or $C^1$ and $C^2$ = CO—CoA |
| 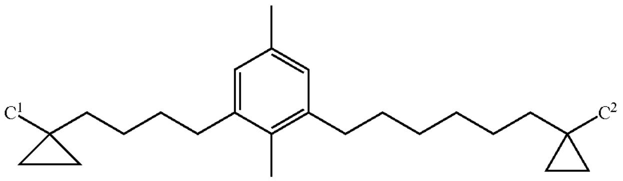 wherein $C^1$ = COOH and $C^2$ = CO—CoA; $C^1$ = CO—CoA and $C^2$ = COOH; or $C^1$ and $C^2$ = CO—CoA |
| 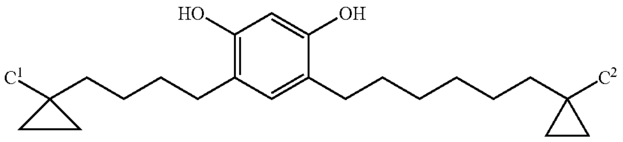 wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 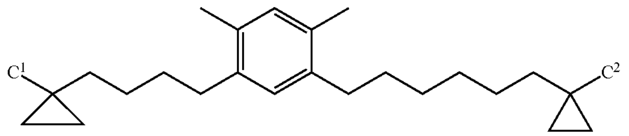 |
| wherein $C^1$ = COOH and $C^2$ = CO—CoA; $C^1$ = CO—CoA and $C^2$ = COOH; or $C^1$ and $C^2$ = CO—CoA |
| 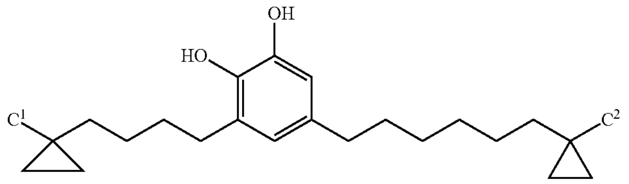 |
| wherein $C^1$ = COOH and $C^2$ = CO—CoA; $C^1$ = CO—CoA and $C^2$ = COOH; or $C^1$ and $C^2$ = CO—CoA |
| 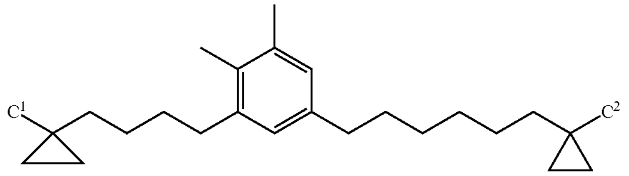 |
| wherein $C^1$ = COOH and $C^2$ = CO—CoA; $C^1$ = CO—CoA and $C^2$ = COOH; or $C^1$ and $C^2$ = CO—CoA |
| 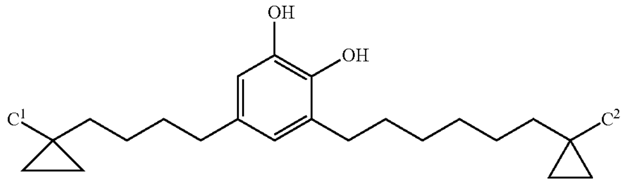 |
| wherein $C^1$ = COOH and $C^2$ = CO—CoA; $C^1$ = CO—CoA and $C^2$ = COOH; or $C^1$ and $C^2$ = CO—CoA |
| 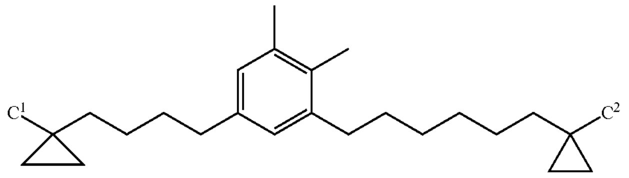 |
| wherein $C^1$ = COOH and $C^2$ = CO—CoA; $C^1$ = CO—CoA and $C^2$ = COOH; or $C^1$ and $C^2$ = CO—CoA |
| 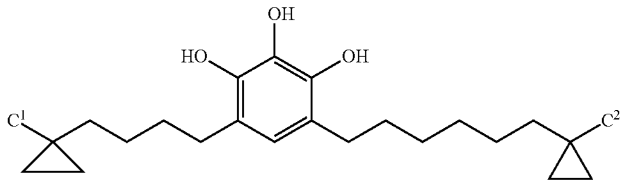 |
| wherein $C^1$ = COOH and $C^2$ = CO—CoA; $C^1$ = CO—CoA and $C^2$ = COOH; or $C^1$ and $C^2$ = CO—CoA |

TABLE A-5-continued

| Structure |
|---|
| 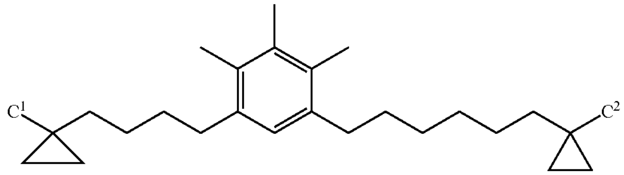 |
| wherein $C^1$ = COOH and $C^2$ = CO—CoA; $C^1$ = CO—CoA and $C^2$ = COOH; or $C^1$ and $C^2$ = CO—CoA |
| 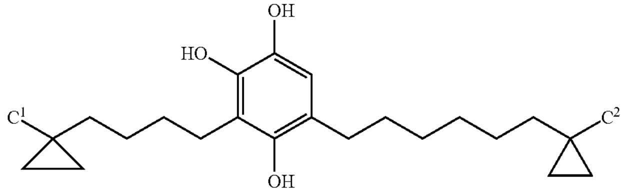 |
| wherein $C^1$ = COOH and $C^2$ = CO—CoA; $C^1$ = CO—CoA and $C^2$ = COOH; or $C^1$ and $C^2$ = CO—CoA |
| 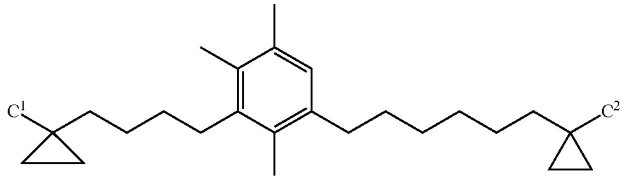 |
| wherein $C^1$ = COOH and $C^2$ = CO—CoA; $C^1$ = CO—CoA and $C^2$ = COOH; or $C^1$ and $C^2$ = CO—CoA |
| 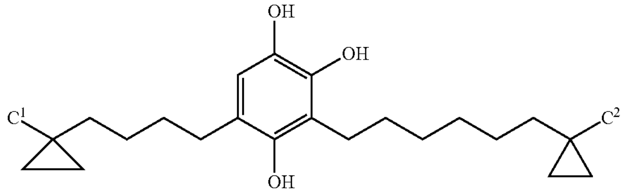 |
| wherein $C^1$ = COOH and $C^2$ = CO—CoA; $C^1$ = CO—CoA and $C^2$ = COOH; or $C^1$ and $C^2$ = CO—CoA |
| 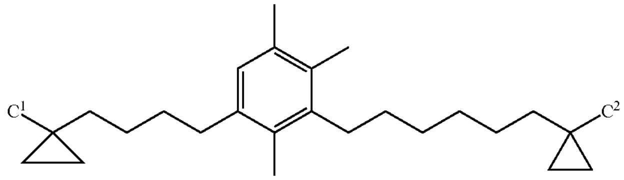 |
| wherein $C^1$ = COOH and $C^2$ = CO—CoA; $C^1$ = CO—CoA and $C^2$ = COOH; or $C^1$ and $C^2$ = CO—CoA |

In some embodiments, the compound of Formula (I) or (IC) has any one of the structures shown in Table A-6 and defined by $C^1$ and $C^2$, or a pharmaceutically acceptable salt or solvate thereof.

TABLE A-6

| Structure |
|---|
| 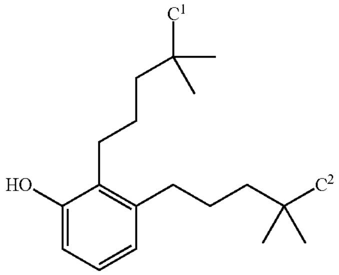 |
| wherein $C^1$ = COOH and $C^2$ = CO—CoA; $C^1$ = CO—CoA and $C^2$ = COOH; or $C^1$ and $C^2$ = CO—CoA |
| 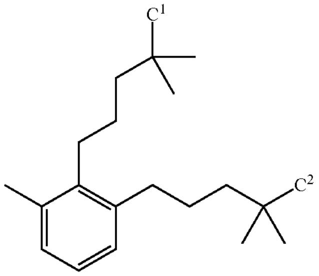 |
| wherein $C^1$ = COOH and $C^2$ = CO—CoA; $C^1$ = CO—CoA and $C^2$ = COOH; or $C^1$ and $C^2$ = CO—CoA |
| 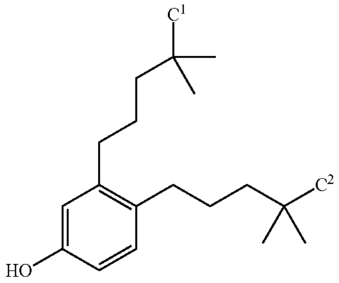 |
| wherein $C^1$ = COOH and $C^2$ = CO—CoA; $C^1$ = CO—CoA and $C^2$ = COOH; or $C^1$ and $C^2$ = CO—CoA |
| 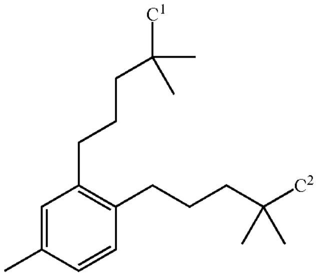 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 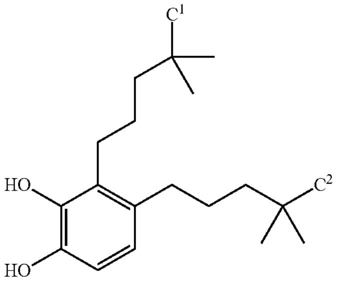 |
| wherein $C^1$ = COOH and $C^2$ = CO—CoA; $C^1$ = CO—CoA and $C^2$ = COOH; or $C^1$ and $C^2$ = CO—CoA |
| 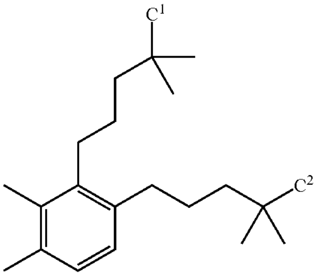 |
| wherein $C^1$ = COOH and $C^2$ = CO—CoA; $C^1$ = CO—CoA and $C^2$ = COOH; or $C^1$ and $C^2$ = CO—CoA |
| 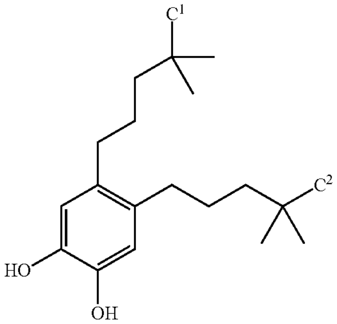 |
| wherein $C^1$ = COOH and $C^2$ = CO—CoA; $C^1$ = CO—CoA and $C^2$ = COOH; or $C^1$ and $C^2$ = CO—CoA |
| 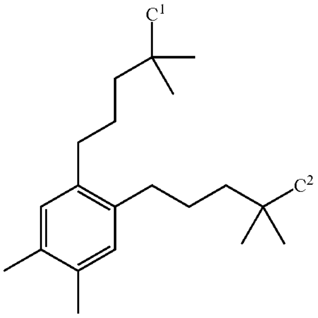 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

Structure

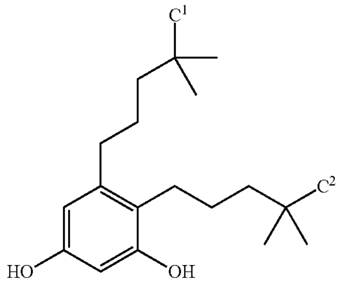

wherein $C^1$ = COOH and $C^2$ = CO—CoA; $C^1$ = CO—CoA and $C^2$ = COOH; or $C^1$ and $C^2$ = CO—CoA

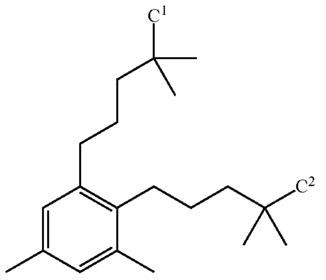

wherein $C^1$ = COOH and $C^2$ = CO—CoA; $C^1$ = CO—CoA and $C^2$ = COOH; or $C^1$ and $C^2$ = CO—CoA

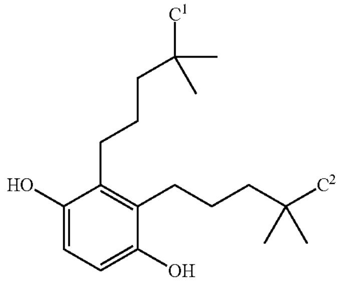

wherein $C^1$ = COOH and $C^2$ = CO—CoA; $C^1$ = CO—CoA and $C^2$ = COOH; or $C^1$ and $C^2$ = CO—CoA

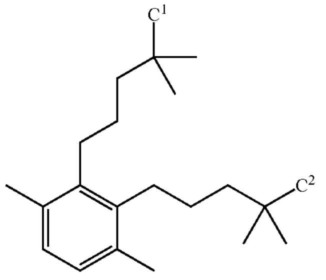

wherein $C^1$ = COOH and $C^2$ = CO—CoA; $C^1$ = CO—CoA and $C^2$ = COOH; or $C^1$ and $C^2$ = CO—CoA TABLE A-6-continued Structure

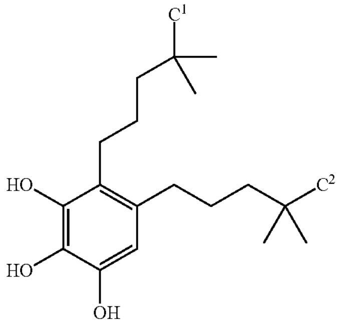

wherein $C^1$ = COOH and $C^2$ = CO—CoA; $C^1$ = CO—CoA and $C^2$ = COOH; or $C^1$ and $C^2$ = CO—CoA

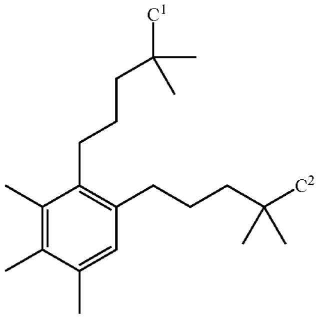

wherein $C^1$ = COOH and $C^2$ = CO—CoA; $C^1$ = CO—CoA and $C^2$ = COOH; or $C^1$ and $C^2$ = CO—CoA

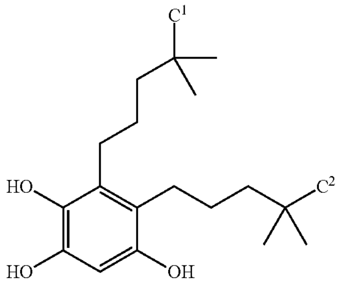

wherein $C^1$ = COOH and $C^2$ = CO—CoA; $C^1$ = CO—CoA and $C^2$ = COOH; or $C^1$ and $C^2$ = CO—CoA

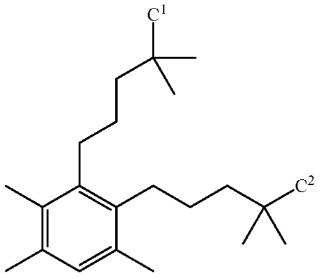

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 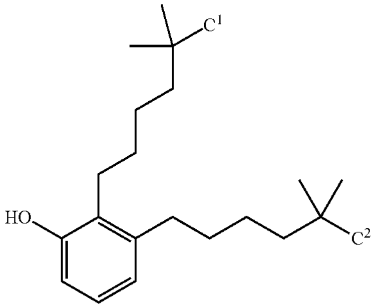 wherein $C^1$ = COOH and $C^2$ = CO—CoA; $C^1$ = CO—CoA and $C^2$ = COOH; or $C^1$ and $C^2$ = CO—CoA |
| 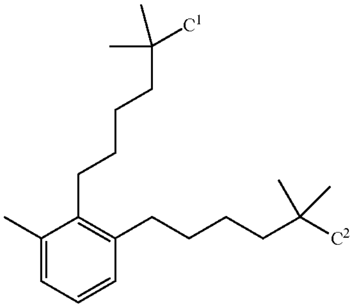 wherein $C^1$ = COOH and $C^2$ = CO—CoA; $C^1$ = CO—CoA and $C^2$ = COOH; or $C^1$ and $C^2$ = CO—CoA |
| 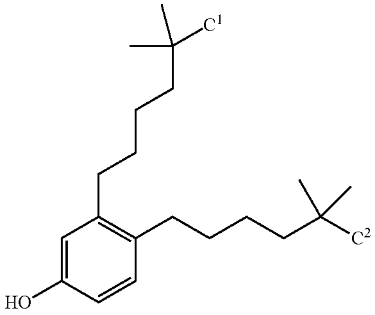 wherein $C^1$ = COOH and $C^2$ = CO—CoA; $C^1$ = CO—CoA and $C^2$ = COOH; or $C^1$ and $C^2$ = CO—CoA |
| 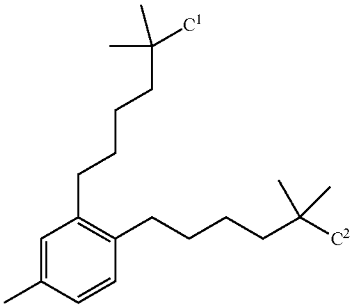 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 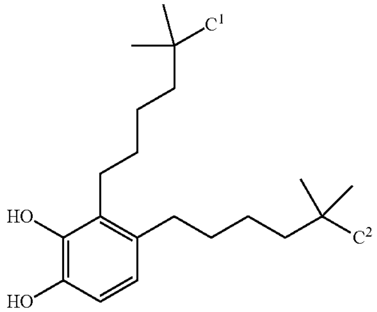 wherein $C^1$ = COOH and $C^2$ = CO—CoA; $C^1$ = CO—CoA and $C^2$ = COOH; or $C^1$ and $C^2$ = CO—CoA |
| 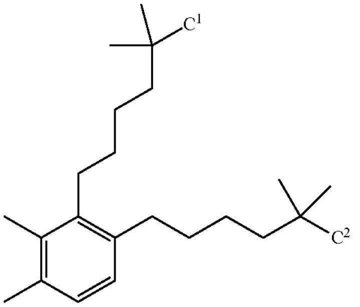 wherein $C^1$ = COOH and $C^2$ = CO—CoA; $C^1$ = CO—CoA and $C^2$ = COOH; or $C^1$ and $C^2$ = CO—CoA |
| 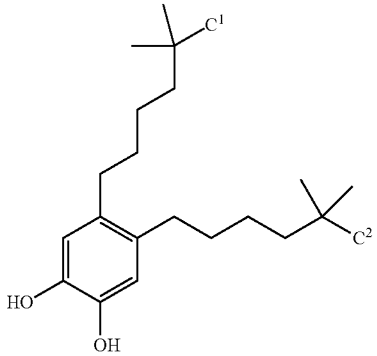 wherein $C^1$ = COOH and $C^2$ = CO—CoA; $C^1$ = CO—CoA and $C^2$ = COOH; or $C^1$ and $C^2$ = CO—CoA |
| 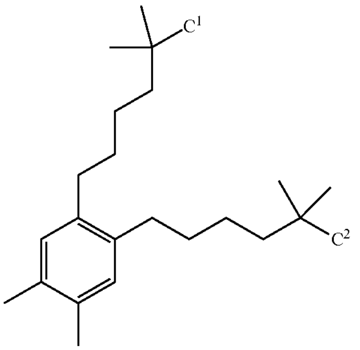 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 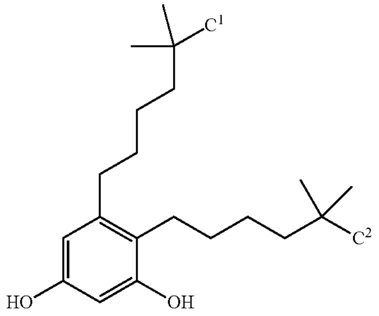 |
| wherein $C^1$ = COOH and $C^2$ = CO—CoA; $C^1$ = CO—CoA and $C^2$ = COOH; or $C^1$ and $C^2$ = CO—CoA |
| 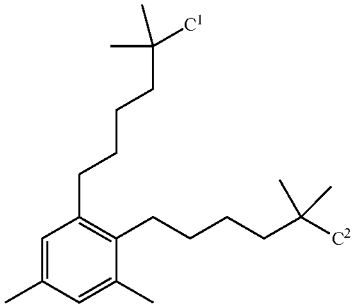 |
| wherein $C^1$ = COOH and $C^2$ = CO—CoA; $C^1$ = CO—CoA and $C^2$ = COOH; or $C^1$ and $C^2$ = CO—CoA |
| 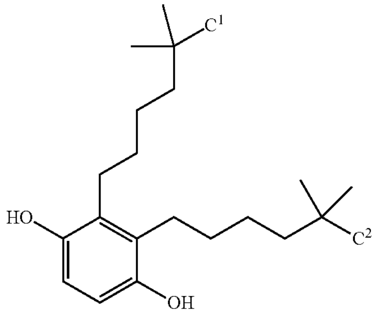 |
| wherein $C^1$ = COOH and $C^2$ = CO—CoA; $C^1$ = CO—CoA and $C^2$ = COOH; or $C^1$ and $C^2$ = CO—CoA |
| 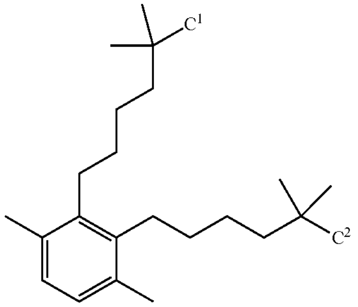 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 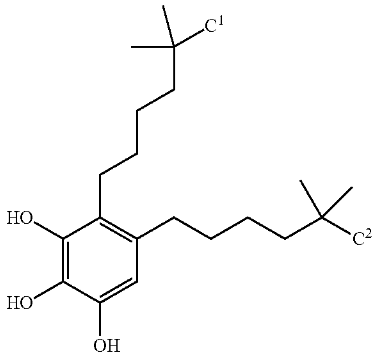 |
| wherein $C^1$ = COOH and $C^2$ = CO—CoA; $C^1$ = CO—CoA and $C^2$ = COOH; or $C^1$ and $C^2$ = CO—CoA |
| 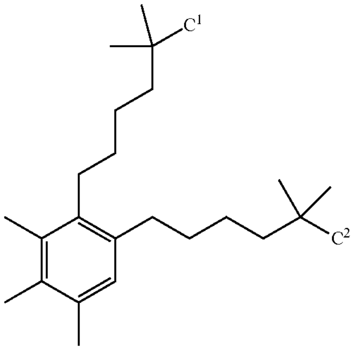 |
| wherein $C^1$ = COOH and $C^2$ = CO—CoA; $C^1$ = CO—CoA and $C^2$ = COOH; or $C^1$ and $C^2$ = CO—CoA |
| 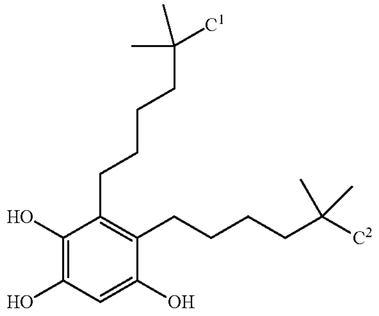 |
| wherein $C^1$ = COOH and $C^2$ = CO—CoA; $C^1$ = CO—CoA and $C^2$ = COOH; or $C^1$ and $C^2$ = CO—CoA |
| 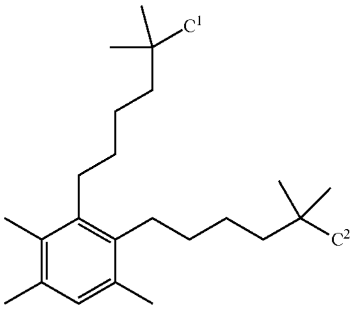 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 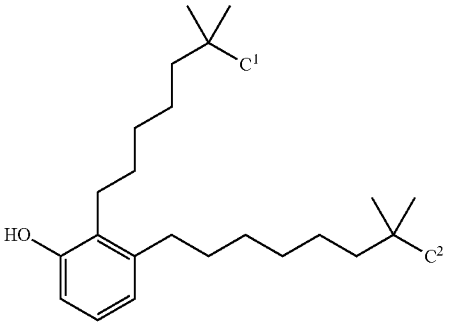 wherein $C^1$ = COOH and $C^2$ = CO—CoA; $C^1$ = CO—CoA and $C^2$ = COOH; or $C^1$ and $C^2$ = CO—CoA |
| 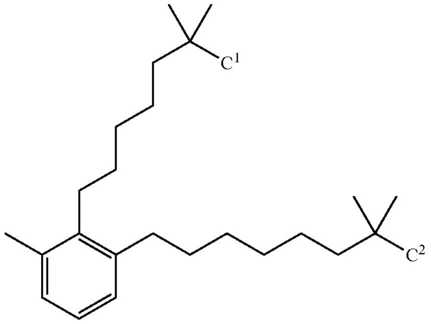 wherein $C^1$ = COOH and $C^2$ = CO—CoA; $C^1$ = CO—CoA and $C^2$ = COOH; or $C^1$ and $C^2$ = CO—CoA |
| 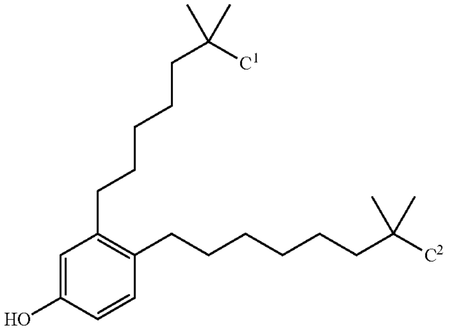 wherein $C^1$ = COOH and $C^2$ = CO—CoA; $C^1$ = CO—CoA and $C^2$ = COOH; or $C^1$ and $C^2$ = CO—CoA |
| 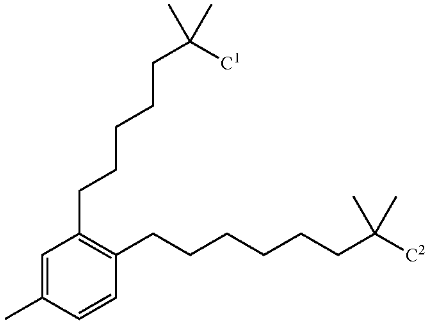 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 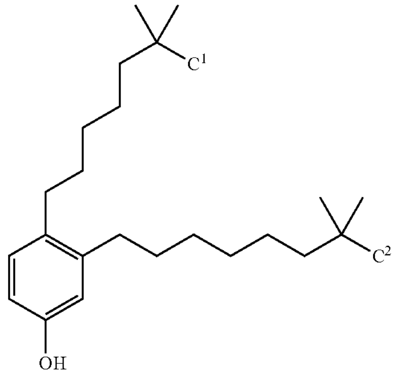 wherein $C^1$ = COOH and $C^2$ = CO—CoA; $C^1$ = CO—CoA and $C^2$ = COOH; or $C^1$ and $C^2$ = CO—CoA |
| 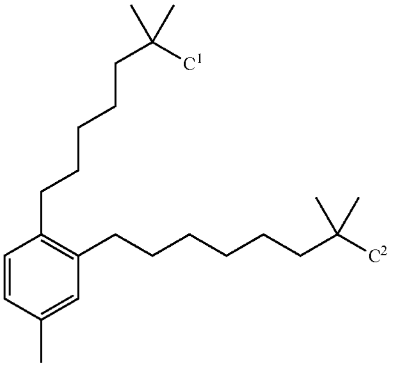 wherein $C^1$ = COOH and $C^2$ = CO—CoA; $C^1$ = CO—CoA and $C^2$ = COOH; or $C^1$ and $C^2$ = CO—CoA |
| 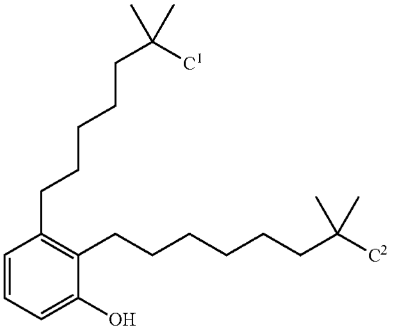 wherein $C^1$ = COOH and $C^2$ = CO—CoA; $C^1$ = CO—CoA and $C^2$ = COOH; or $C^1$ and $C^2$ = CO—CoA |
| 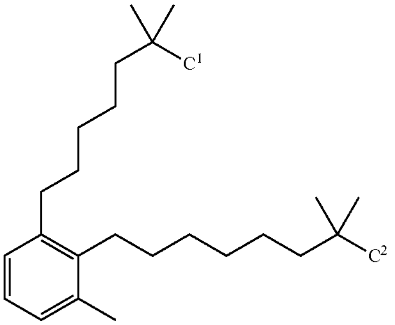 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 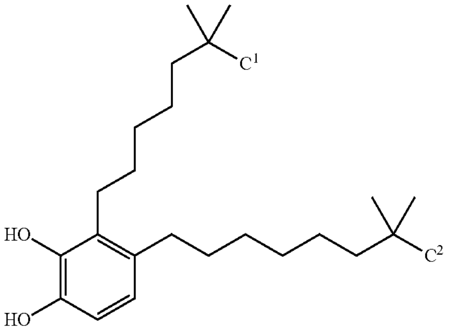 |
| wherein $C^1$ = COOH and $C^2$ = CO—CoA; $C^1$ = CO—CoA and $C^2$ = COOH; or $C^1$ and $C^2$ = CO—CoA |
| 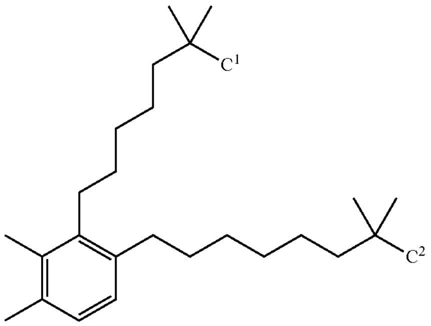 |
| wherein $C^1$ = COOH and $C^2$ = CO—CoA; $C^1$ = CO—CoA and $C^2$ = COOH; or $C^1$ and $C^2$ = CO—CoA |
| 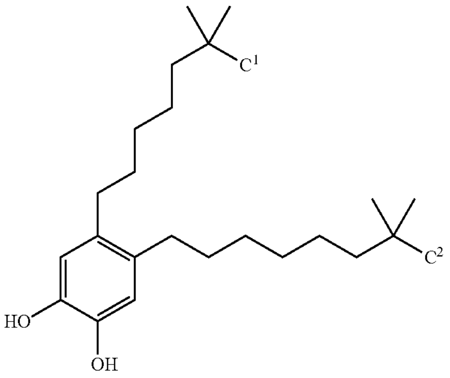 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 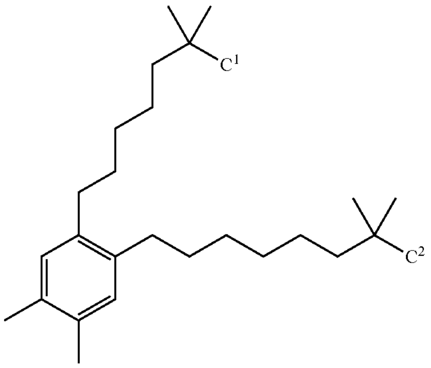 |
| wherein $C^1$ = COOH and $C^2$ = CO—CoA; $C^1$ = CO—CoA and $C^2$ = COOH; or $C^1$ and $C^2$ = CO—CoA |
| 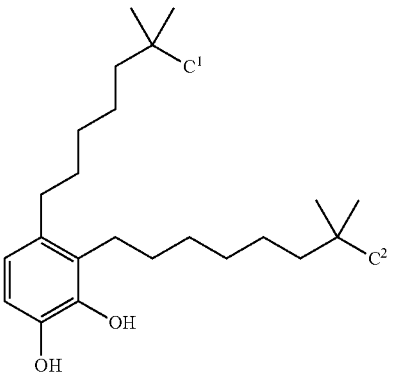 |
| wherein $C^1$ = COOH and $C^2$ = CO—CoA; $C^1$ = CO—CoA and $C^2$ = COOH; or $C^1$ and $C^2$ = CO—CoA |
| 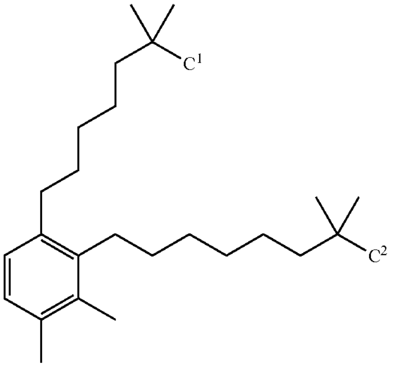 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 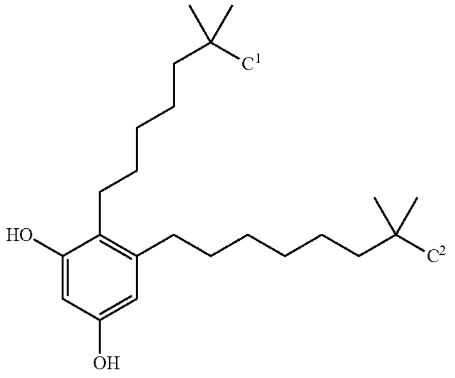 |
| wherein $C^1$ = COOH and $C^2$ = CO—CoA; $C^1$ = CO—CoA and $C^2$ = COOH; or $C^1$ and $C^2$ = CO—CoA |
| 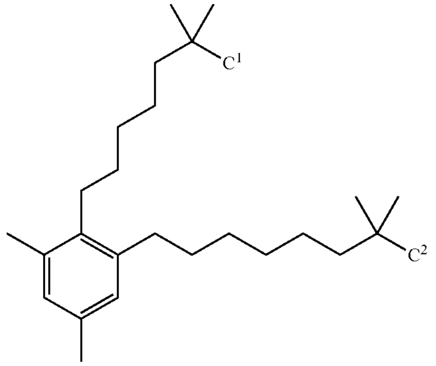 |
| wherein $C^1$ = COOH and $C^2$ = CO—CoA; $C^1$ = CO—CoA and $C^2$ = COOH; or $C^1$ and $C^2$ = CO—CoA |
| 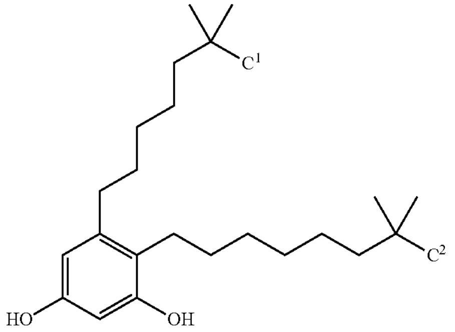 |
| wherein $C^1$ = COOH and $C^2$ = CO—CoA; $C^1$ = CO—CoA and $C^2$ = COOH; or $C^1$ and $C^2$ = CO—CoA |
| 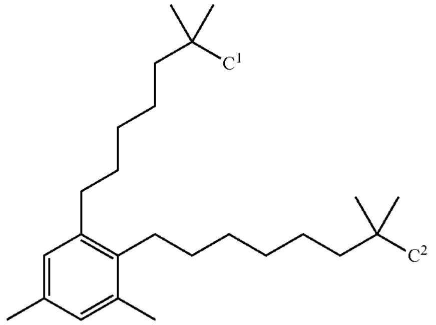 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 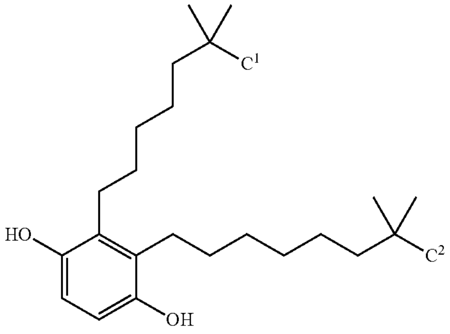 |
| wherein $C^1$ = COOH and $C^2$ = CO—CoA; $C^1$ = CO—CoA and $C^2$ = COOH; or $C^1$ and $C^2$ = CO—CoA |
| 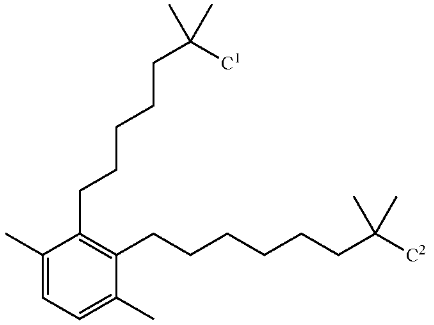 |
| wherein $C^1$ = COOH and $C^2$ = CO—CoA; $C^1$ = CO—CoA and $C^2$ = COOH; or $C^1$ and $C^2$ = CO—CoA |
| 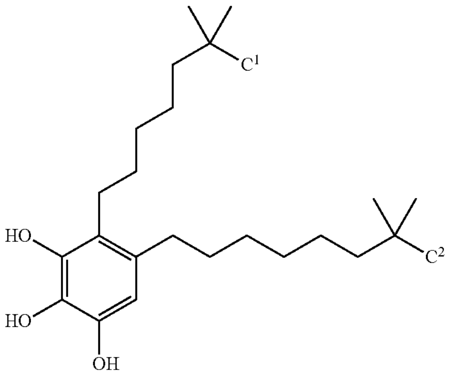 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 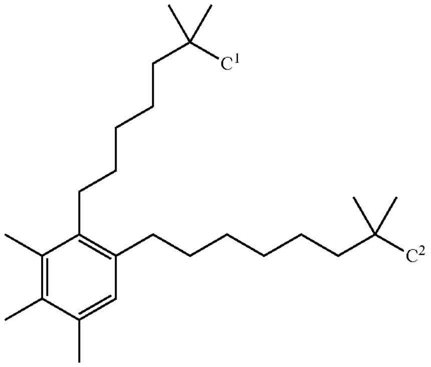 |
| wherein $C^1$ = COOH and $C^2$ = CO—CoA; $C^1$ = CO—CoA and $C^2$ = COOH; or $C^1$ and $C^2$ = CO—CoA |
| 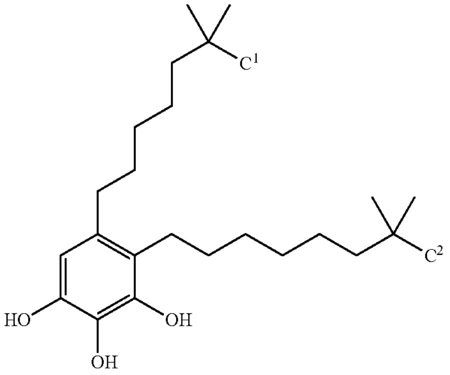 |
| wherein $C^1$ = COOH and $C^2$ = CO—CoA; $C^1$ = CO—CoA and $C^2$ = COOH; or $C^1$ and $C^2$ = CO—CoA |
| 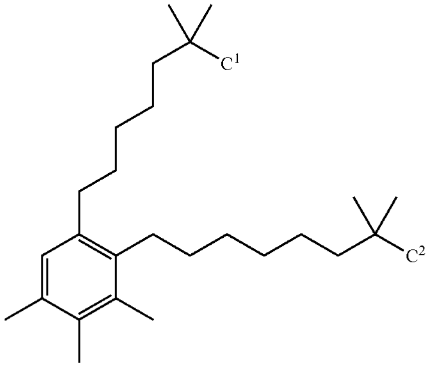 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 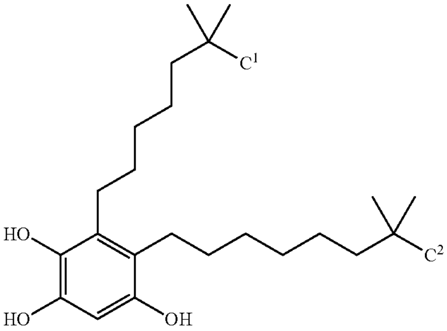 |
| wherein $C^1$ = COOH and $C^2$ = CO—CoA; $C^1$ = CO—CoA and $C^2$ = COOH; or $C^1$ and $C^2$ = CO—CoA |
| 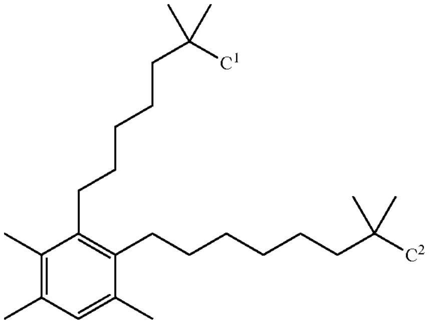 |
| wherein $C^1$ = COOH and $C^2$ = CO—CoA; $C^1$ = CO—CoA and $C^2$ = COOH; or $C^1$ and $C^2$ = CO—CoA |
| 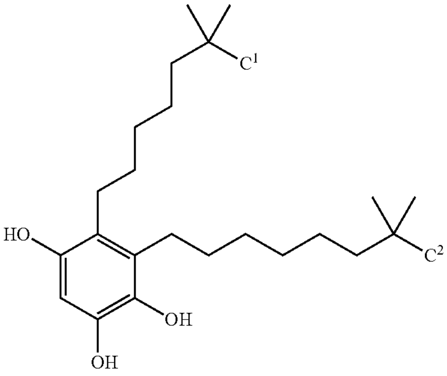 |
| wherein $C^1$ = COOH and $C^2$ = CO—CoA; $C^1$ = CO—CoA and $C^2$ = COOH; or $C^1$ and $C^2$ = CO—CoA |
| 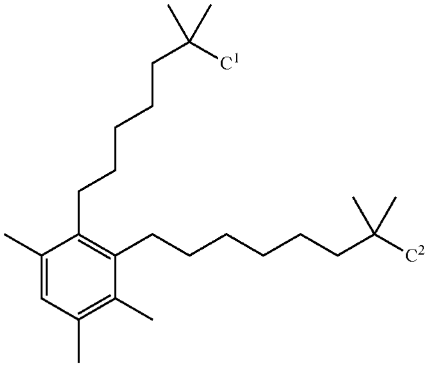 |

TABLE A-6-continued

| Structure |
|---|
| wherein $C^1$ = COOH and $C^2$= CO—CoA; $C^1$ = CO—CoA and $C^2$ = COOH; or $C^1$ and $C^2$ = CO—CoA |
| 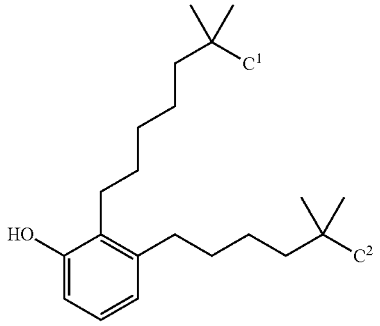 |
| wherein $C^1$ = COOH and $C^2$ = CO—CoA; $C^1$ = CO—CoA and $C^2$ = COOH; or $C^1$ and $C^2$ = CO—CoA |
| 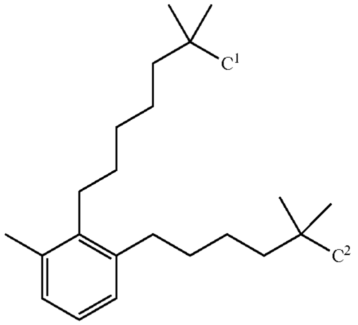 |
| wherein $C^1$ = COOH and $C^2$ = CO—CoA; $C^1$ = CO—CoA and $C^2$ = COOH; or $C^1$ and $C^2$ = CO—CoA |
| 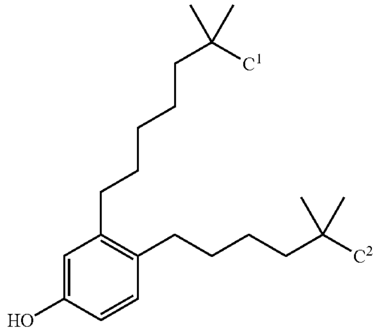 |
| wherein $C^1$ = COOH and $C^2$ = CO—CoA; $C^1$ = CO—CoA and $C^2$ = COOH; or $C^1$ and $C^2$ = CO—CoA |
| 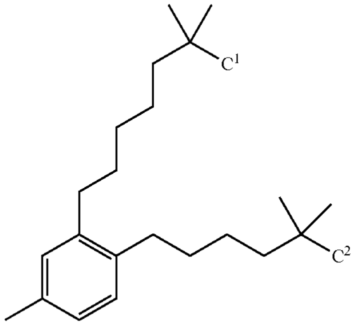 |

TABLE A-6-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 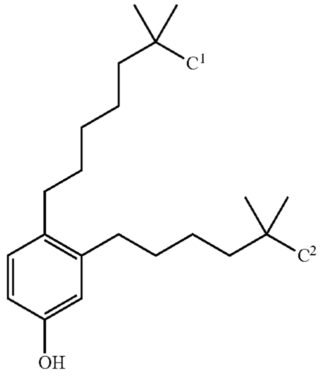 |
| wherein $C^1$ = COOH and $C^2$ = CO—CoA; $C^1$ = CO—CoA and $C^2$ = COOH; or $C^1$ and $C^2$ = CO—CoA |
| 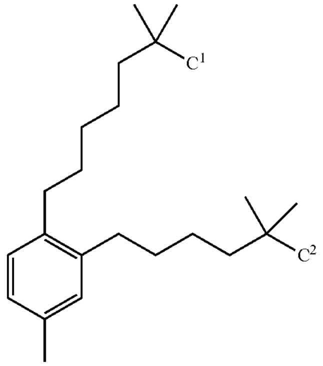 |
| wherein $C^1$ = COOH and $C^2$ = CO—CoA; $C^1$ = CO—CoA and $C^2$ = COOH; or $C^1$ and $C^2$ = CO—CoA |
| 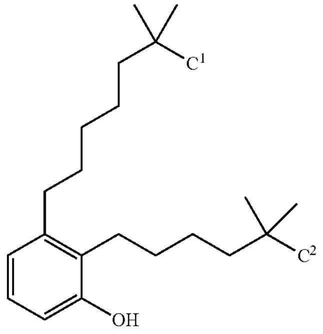 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 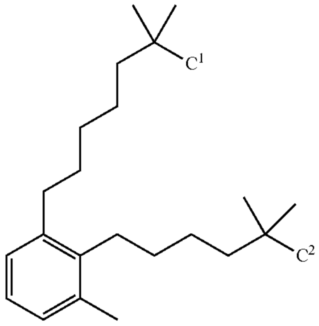 wherein $C^1$ = COOH and $C^2$ = CO—CoA; $C^1$ = CO—CoA and $C^2$ = COOH; or $C^1$ and $C^2$ = CO—CoA |
| 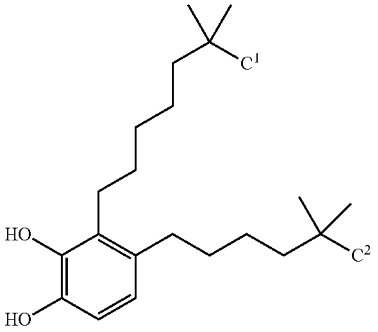 wherein $C^1$ = COOH and $C^2$ = CO—CoA; $C^1$ = CO—CoA and $C^2$ = COOH; or $C^1$ and $C^2$ = CO—CoA |
| 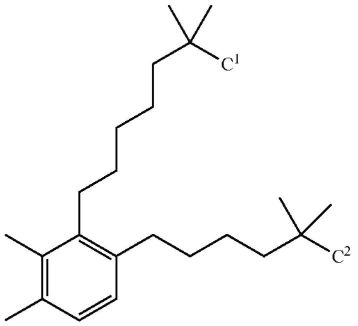 wherein $C^1$ = COOH and $C^2$ = CO—CoA; $C^1$ = CO—CoA and $C^2$ = COOH; or $C^1$ and $C^2$ = CO—CoA |
| 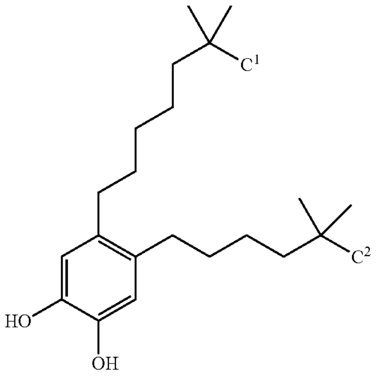 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 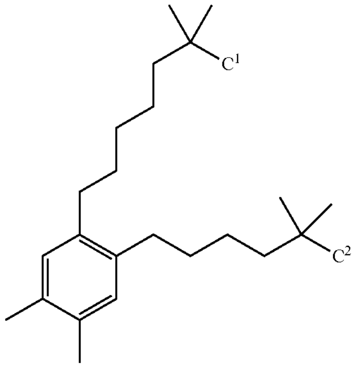 wherein $C^1$ = COOH and $C^2$ = CO—CoA; $C^1$ = CO—CoA and $C^2$ = COOH; or $C^1$ and $C^2$ = CO—CoA |
| 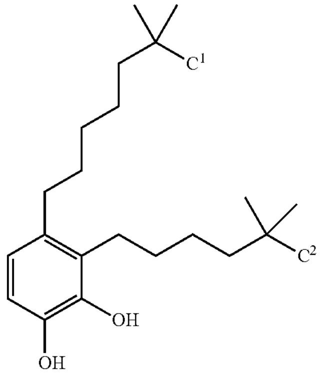 wherein $C^1$ = COOH and $C^2$ = CO—CoA; $C^1$ = CO—CoA and $C^2$ = COOH; or $C^1$ and $C^2$ = CO—CoA |
| 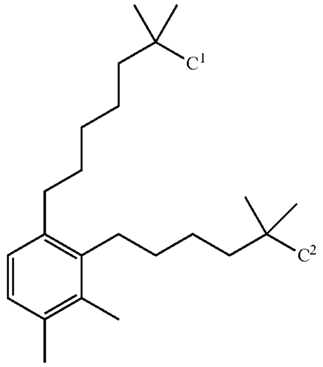 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

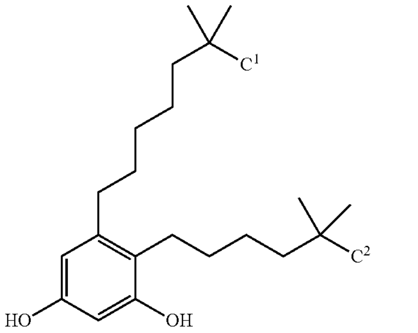

wherein $C^1$ = COOH and $C^2$ = CO—CoA; $C^1$ = CO—CoA and $C^2$ = COOH; or $C^1$ and $C^2$ = CO—CoA

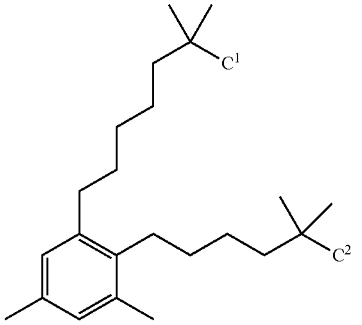

wherein $C^1$ = COOH and $C^2$ = CO—CoA; $C^1$ = CO—CoA and $C^2$ = COOH; or $C^1$ and $C^2$ = CO—CoA

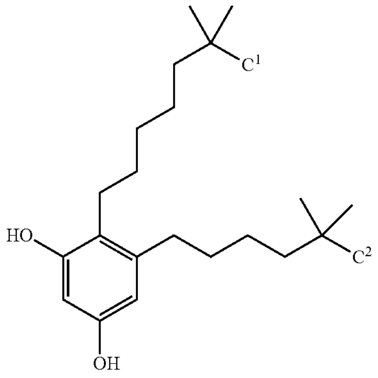

wherein $C^1$ = COOH and $C^2$ = CO—CoA; $C^1$ = CO—CoA and $C^2$ = COOH; or $C^1$ and $C^2$ = CO—CoA

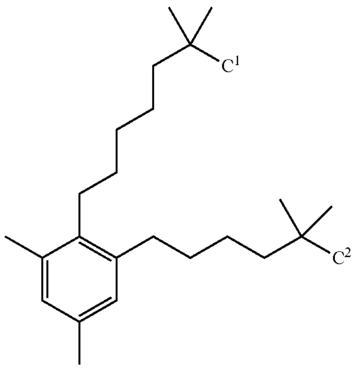

TABLE A-6-continued

| Structure |
| --- |

wherein $C^1$ = COOH and $C^2$ = CO—CoA; $C^1$ = CO—CoA and $C^2$ = COOH; or $C^1$ and $C^2$ = CO—CoA

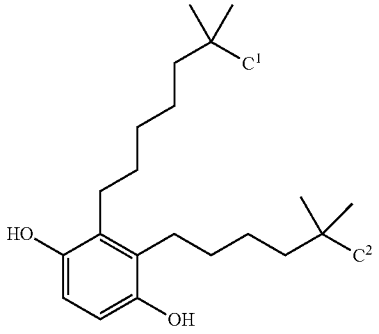

wherein $C^1$ = COOH and $C^2$ = CO—CoA; $C^1$ = CO—CoA and $C^2$ = COOH; or $C^1$ and $C^2$ = CO—CoA

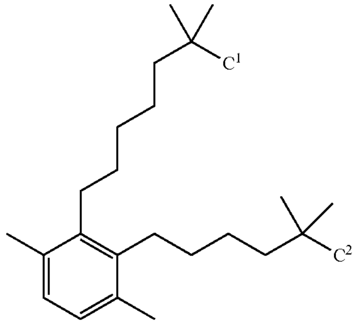

wherein $C^1$ = COOH and $C^2$ = CO—CoA; $C^1$ = CO—CoA and $C^2$ = COOH; or $C^1$ and $C^2$ = CO—CoA

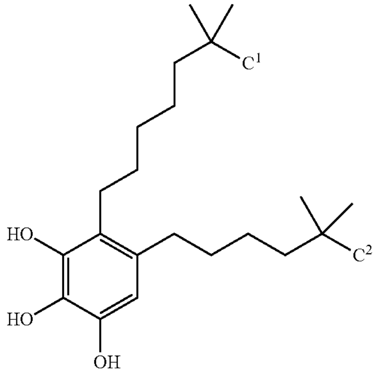

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|
| 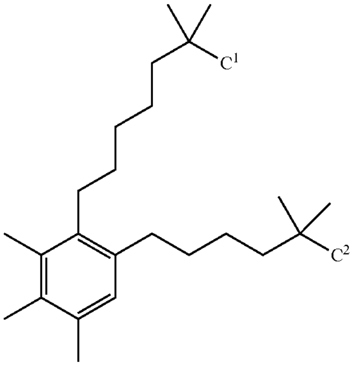 wherein $C^1$ = COOH and $C^2$= CO—CoA; $C^1$ = CO—CoA and $C^2$ = COOH; or $C^1$ and $C^2$ = CO—CoA |
| 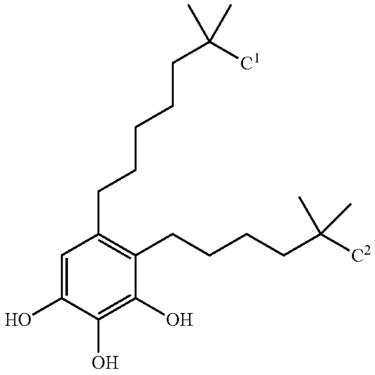 wherein $C^1$ = COOH and $C^2$ = CO—CoA; $C^1$ = CO—CoA and $C^2$ = COOH; or $C^1$ and $C^2$ = CO—CoA |
| 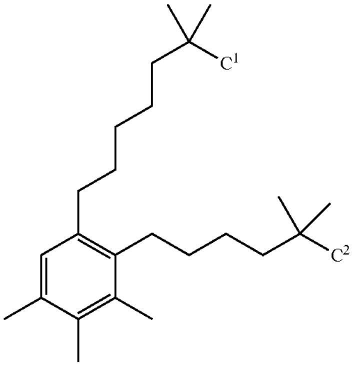 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 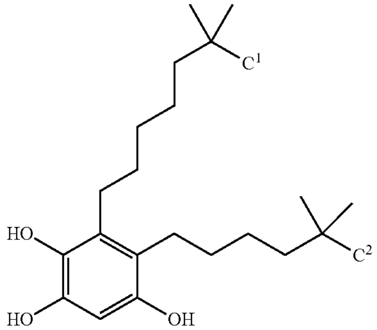 wherein $C^1$ = COOH and $C^2$ = CO—CoA; $C^1$ = CO—CoA and $C^2$ = COOH; or $C^1$ and $C^2$ = CO—CoA |
| 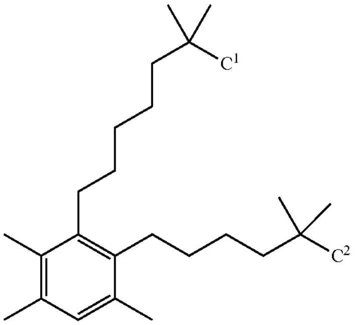 wherein $C^1$ = COOH and $C^2$ = CO—CoA; $C^1$ = CO—CoA and $C^2$ = COOH; or $C^1$ and $C^2$ = CO—CoA |
| 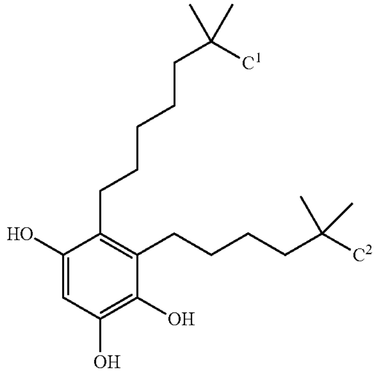 wherein $C^1$ = COOH and $C^2$= CO—CoA; $C^1$ = CO—CoA and $C^2$ = COOH; or $C^1$ and $C^2$ = CO—CoA |
| 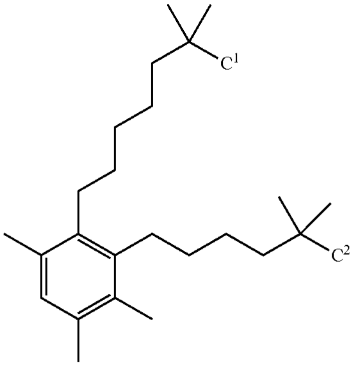 |

TABLE A-6-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 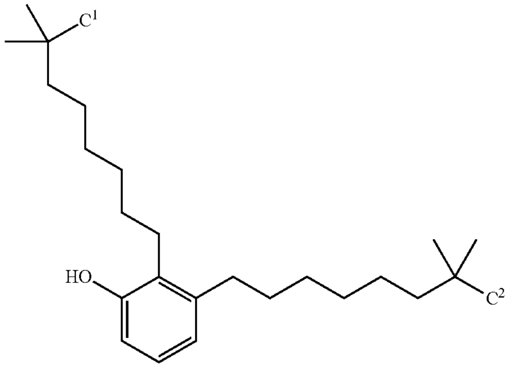 |
| wherein $C^1$ = COOH and $C^2$= CO—CoA; $C^1$ = CO—CoA and $C^2$ = COOH; or $C^1$ and $C^2$ = CO—CoA |
| 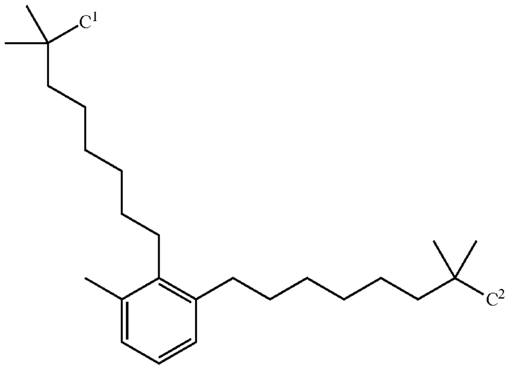 |
| wherein $C^1$ = COOH and $C^2$ = CO—CoA; $C^1$ = CO—CoA and $C^2$ = COOH; or $C^1$ and $C^2$ = CO—CoA |
| 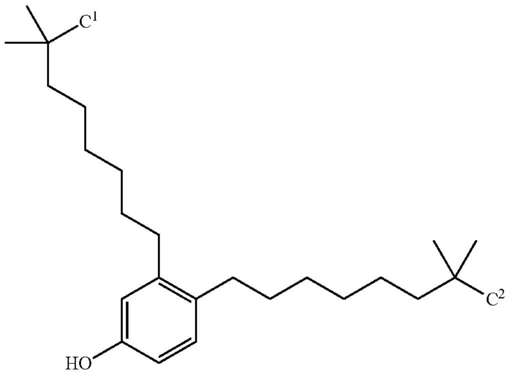 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 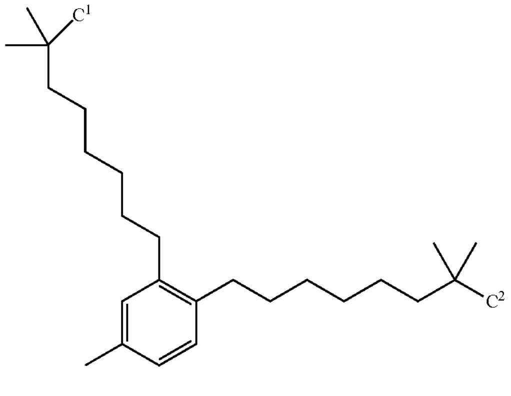 |
| wherein $C^1$ = COOH and $C^2$ = CO—CoA; $C^1$ = CO—CoA and $C^2$ = COOH; or $C^1$ and $C^2$ = CO—CoA |
| 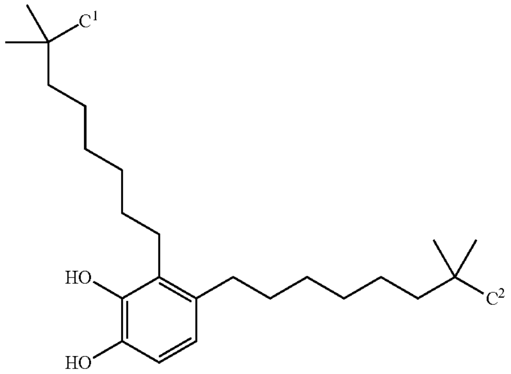 |
| wherein $C^1$ = COOH and $C^2$ = CO—CoA; $C^1$ = CO—CoA and $C^2$ = COOH; or $C^1$ and $C^2$ = CO—CoA |
| 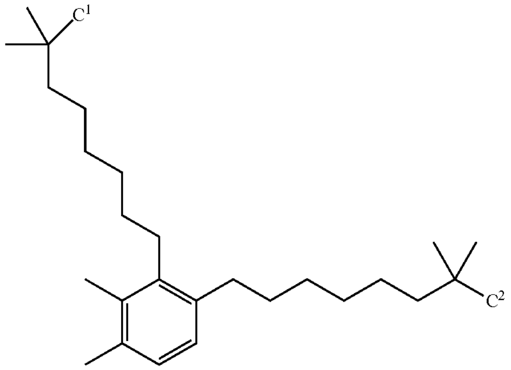 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 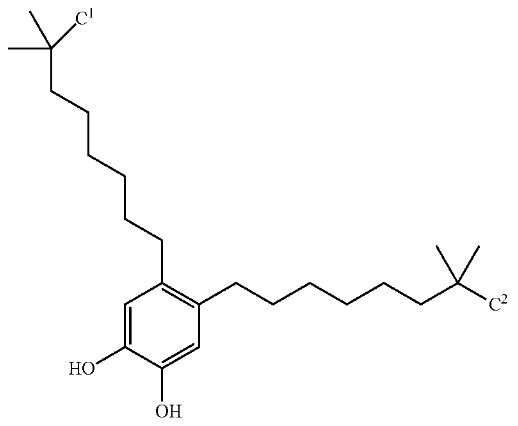 |
| wherein $C^1$ = COOH and $C^2$ = CO—CoA; $C^1$ = CO—CoA and $C^2$ = COOH; or $C^1$ and $C^2$ = CO—CoA |
| 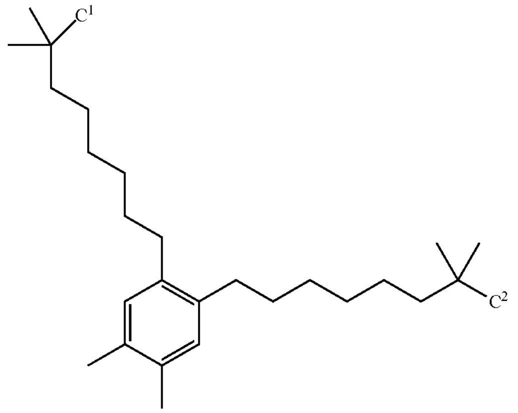 |
| wherein $C^1$ = COOH and $C^2$ = CO—CoA; $C^1$ = CO—CoA and $C^2$ = COOH; or $C^1$ and $C^2$ = CO—CoA |
| 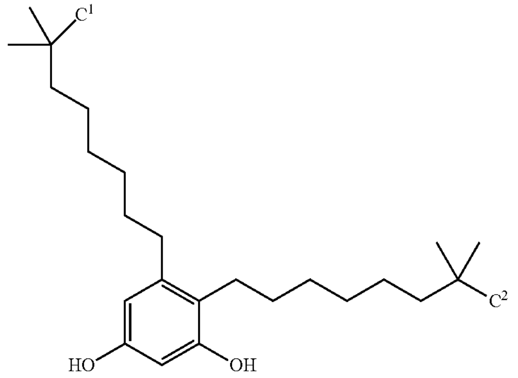 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 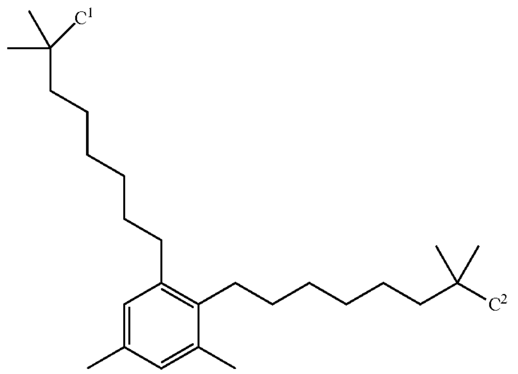 |
| wherein $C^1$ = COOH and $C^2$ = CO—CoA; $C^1$ = CO—CoA and $C^2$ = COOH; or $C^1$ and $C^2$ = CO—CoA |
| 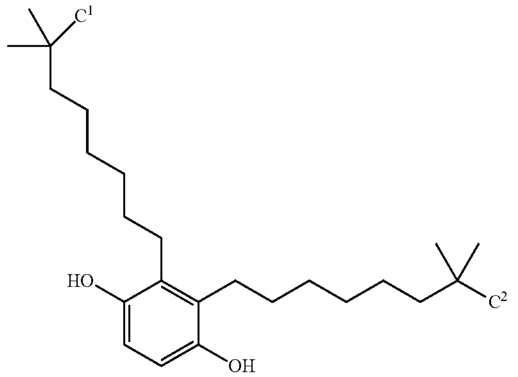 |
| wherein $C^1$ = COOH and $C^2$ = CO—CoA; $C^1$ = CO—CoA and $C^2$ = COOH; or $C^1$ and $C^2$ = CO—CoA |
| 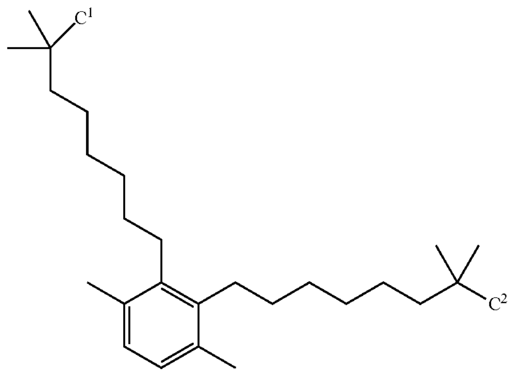 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 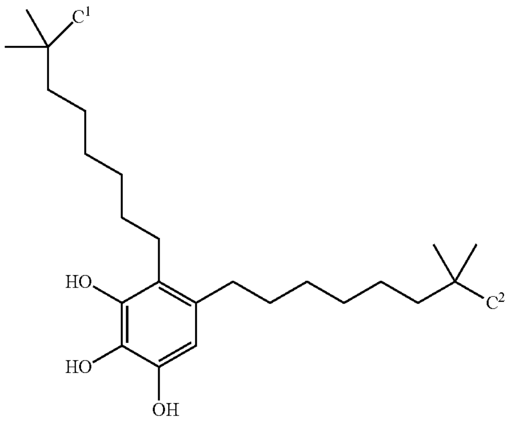 |
| wherein $C^1$ = COOH and $C^2$ = CO—CoA; $C^1$ = CO—CoA and $C^2$ = COOH; or $C^1$ and $C^2$ = CO—CoA |
| 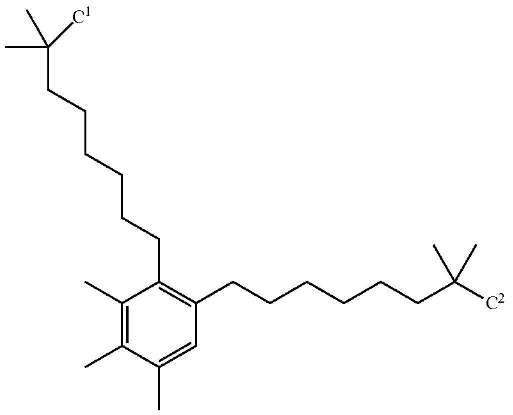 |
| wherein $C^1$ = COOH and $C^2$ = CO—CoA; $C^1$ = CO—CoA and $C^2$ = COOH; or $C^1$ and $C^2$ = CO—CoA |
| 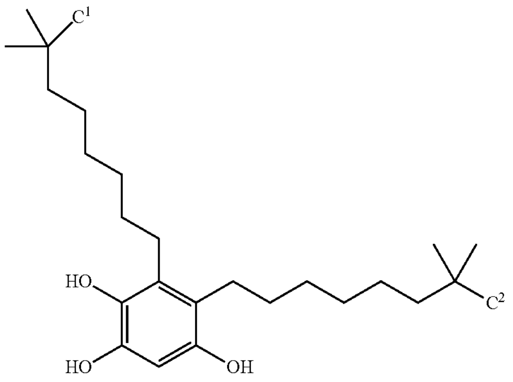 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 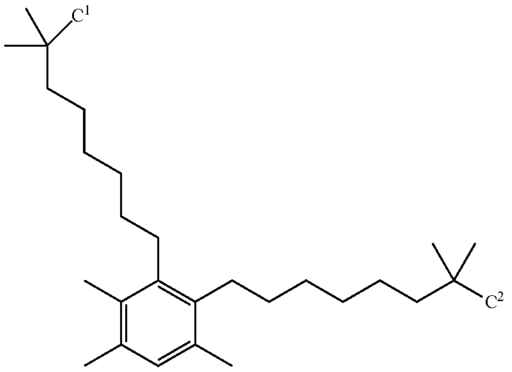 |
| wherein $C^1$ = COOH and $C^2$ = CO—CoA; $C^1$ = CO—CoA and $C^2$ = COOH; or $C^1$ and $C^2$ = CO—CoA |
| 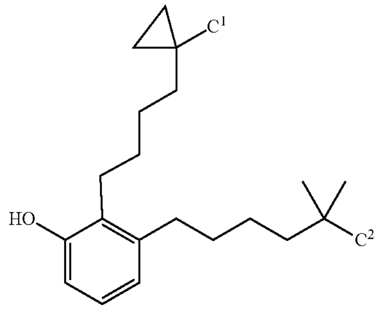 |
| wherein $C^1$ = COOH and $C^2$ = CO—CoA; $C^1$ = CO—CoA and $C^2$ = COOH; or $C^1$ and $C^2$ = CO—CoA |
| 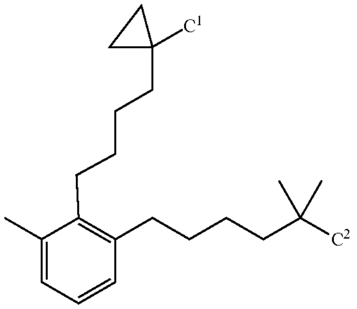 |
| wherein $C^1$ = COOH and $C^2$ = CO—CoA; $C^1$ = CO—CoA and $C^2$ = COOH; or $C^1$ and $C^2$ = CO—CoA |
| 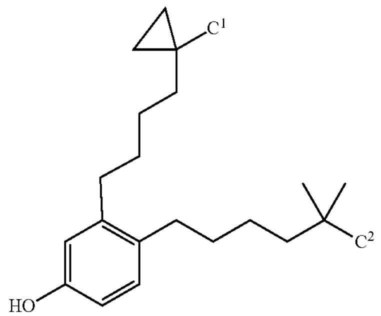 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 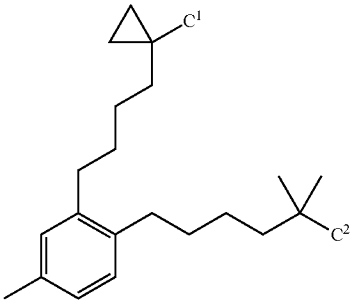 |
| wherein $C^1$ = COOH and $C^2$ = CO—CoA; $C^1$ = CO—CoA and $C^2$ = COOH; or $C^1$ and $C^2$ = CO—CoA |
| 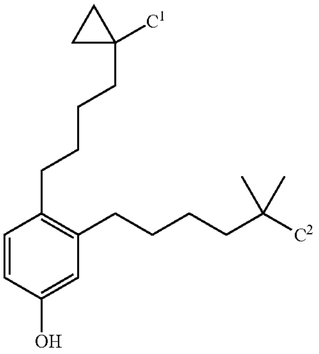 |
| wherein $C^1$ = COOH and $C^2$ = CO—CoA; $C^1$ = CO—CoA and $C^2$ = COOH; or $C^1$ and $C^2$ = CO—CoA |
| 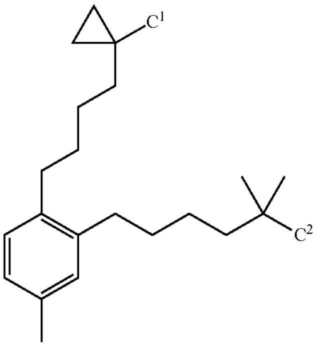 |
| wherein $C^1$ = COOH and $C^2$ = CO—CoA; $C^1$ = CO—CoA and $C^2$ = COOH; or $C^1$ and $C^2$ = CO—CoA |
| 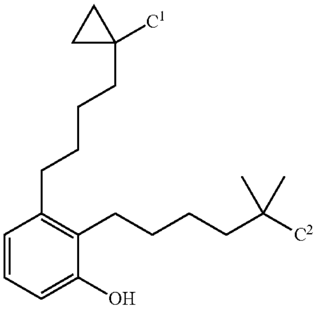 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 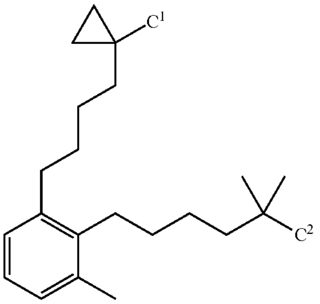 |
| wherein $C^1$ = COOH and $C^2$ = CO—CoA; $C^1$ = CO—CoA and $C^2$ = COOH; or $C^1$ and $C^2$ = CO—CoA |
| 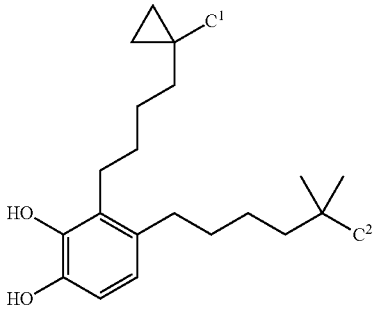 |
| wherein $C^1$ = COOH and $C^2$ = CO—CoA; $C^1$ = CO—CoA and $C^2$ = COOH; or $C^1$ and $C^2$ = CO—CoA |
| 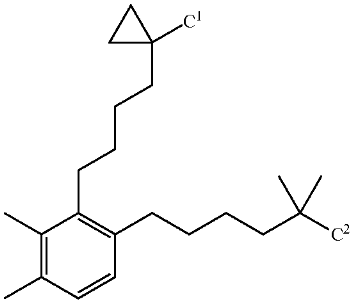 |
| wherein $C^1$ = COOH and $C^2$ = CO—CoA; $C^1$ = CO—CoA and $C^2$ = COOH; or $C^1$ and $C^2$ = CO—CoA |
| 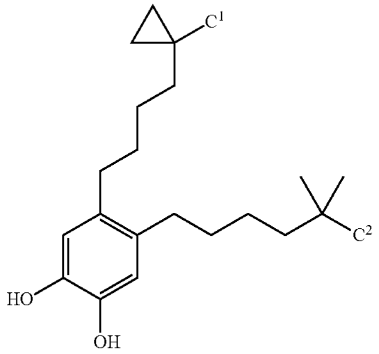 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

Structure

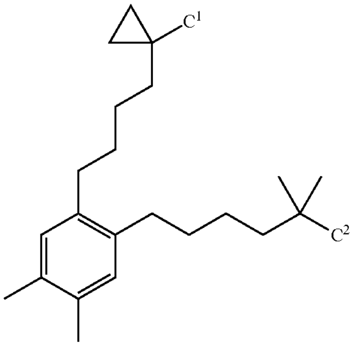

wherein $C^1$ = COOH and $C^2$ = CO—CoA; $C^1$ = CO—CoA and $C^2$ = COOH; or $C^1$ and $C^2$ = CO—CoA

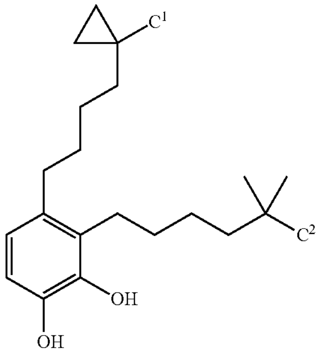

wherein $C^1$ = COOH and $C^2$ = CO—CoA; $C^1$ = CO—CoA and $C^2$ = COOH; or $C^1$ and $C^2$ = CO—CoA

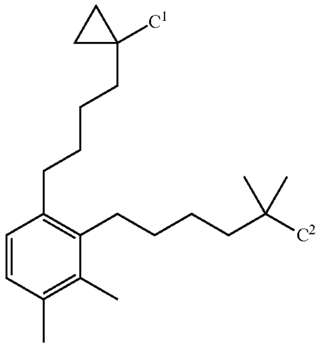

wherein $C^1$ = COOH and $C^2$ = CO—CoA; $C^1$ = CO—CoA and $C^2$ = COOH; or $C^1$ and $C^2$ = CO—CoA

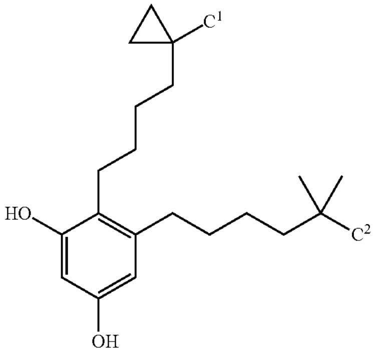

TABLE A-6-continued

Structure wherein $C^1$ = COOH and $C^2$ = CO—CoA; $C^1$ = CO—CoA and $C^2$ = COOH; or $C^1$ and $C^2$ = CO—CoA

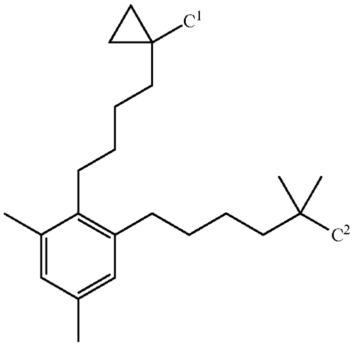

wherein $C^1$ = COOH and $C^2$ = CO—CoA; $C^1$ = CO—CoA and $C^2$ = COOH; or $C^1$ and $C^2$ = CO—CoA

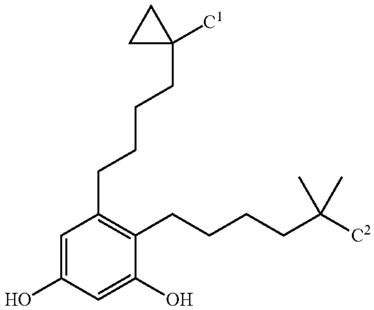

wherein $C^1$ = COOH and $C^2$ = CO—CoA; $C^1$ = CO—CoA and $C^2$ = COOH; or $C^1$ and $C^2$ = CO—CoA

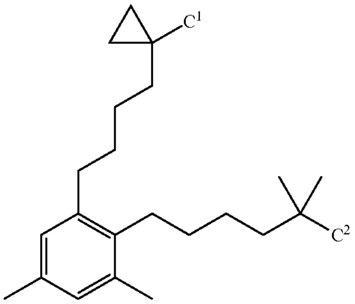

wherein $C^1$ = COOH and $C^2$ = CO—CoA; $C^1$ = CO—CoA and $C^2$ = COOH; or $C^1$ and $C^2$ = CO—CoA

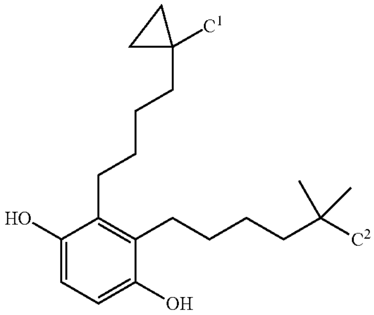

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|
| 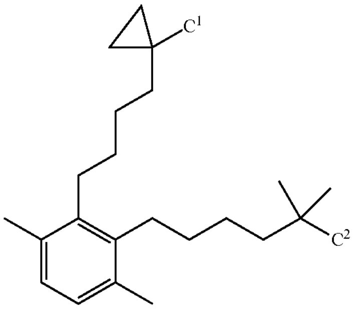 |
| wherein $C^1$ = COOH and $C^2$ = CO—CoA; $C^1$ = CO—CoA and $C^2$ = COOH; or $C^1$ and $C^2$ = CO—CoA |
| 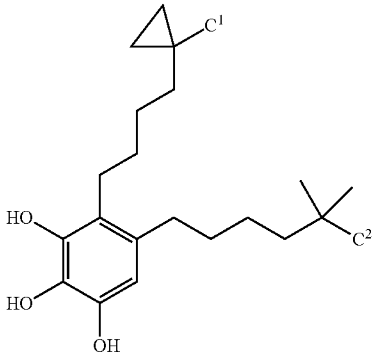 |
| wherein $C^1$ = COOH and $C^2$ = CO—CoA; $C^1$ = CO—CoA and $C^2$ = COOH; or $C^1$ and $C^2$ = CO—CoA |
| 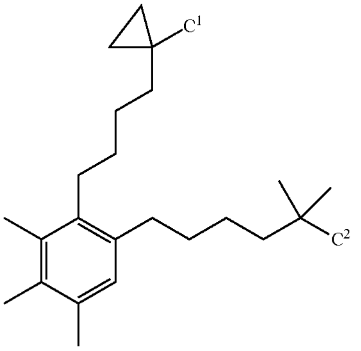 |
| wherein $C^1$ = COOH and $C^2$ = CO—CoA; $C^1$ = CO—CoA and $C^2$ = COOH; or $C^1$ and $C^2$ = CO—CoA |
| 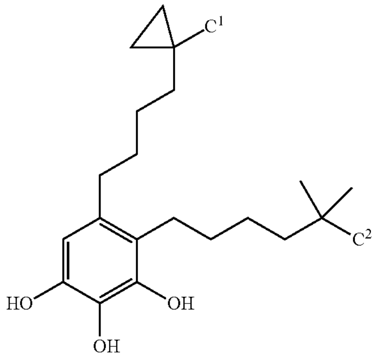 |

TABLE A-6-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 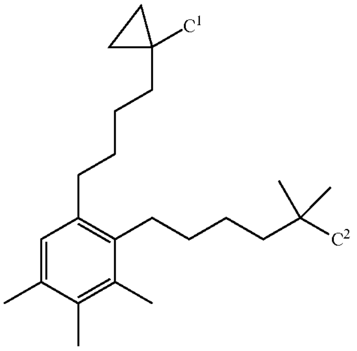 |
| wherein $C^1$ = COOH and $C^2$= CO—CoA; $C^1$ = CO—CoA and $C^2$ = COOH; or $C^1$ and $C^2$ = CO—CoA |
| 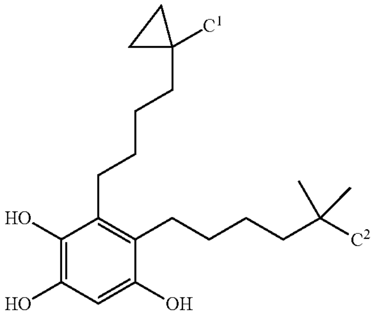 |
| wherein $C^1$ = COOH and $C^2$ = CO—CoA; $C^1$ = CO—CoA and $C^2$ = COOH; or $C^1$ and $C^2$ = CO—CoA |
| 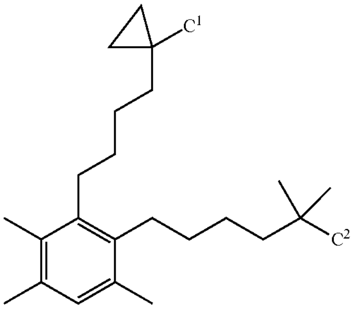 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

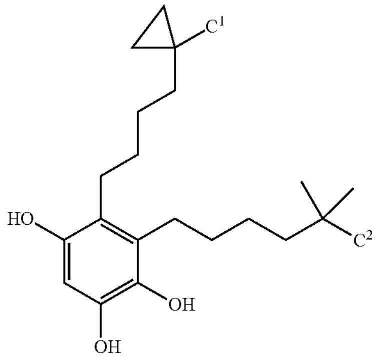

wherein $C^1$ = COOH and $C^2$ = CO—CoA; $C^1$ = CO—CoA and $C^2$ = COOH; or $C^1$ and $C^2$ = CO—CoA

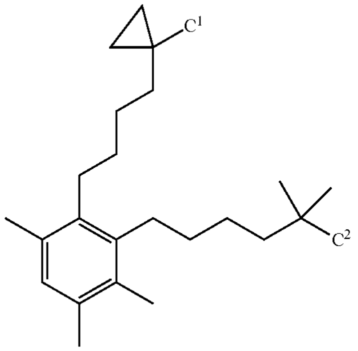

wherein $C^1$ = COOH and $C^2$ = CO—CoA; $C^1$ = CO—CoA and $C^2$ = COOH; or $C^1$ and $C^2$ = CO—CoA

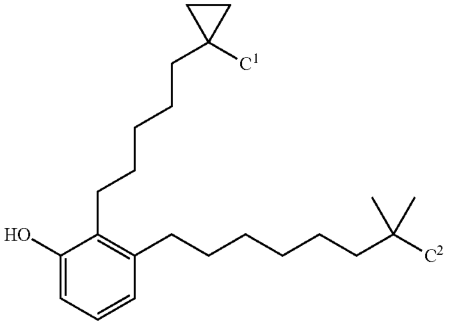

wherein $C^1$ = COOH and $C^2$ = CO—CoA; $C^1$ = CO—CoA and $C^2$ = COOH; or $C^1$ and $C^2$ = CO—CoA

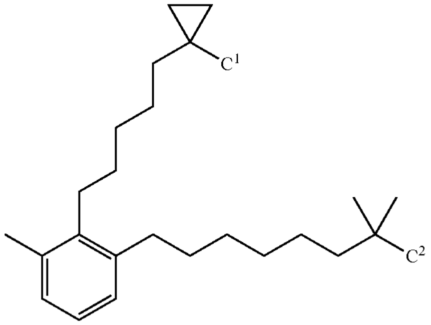

TABLE A-6-continued

| Structure |
| --- |

wherein $C^1$ = COOH and $C^2$ = CO—CoA; $C^1$ = CO—CoA and $C^2$ = COOH; or $C^1$ and $C^2$ = CO—CoA

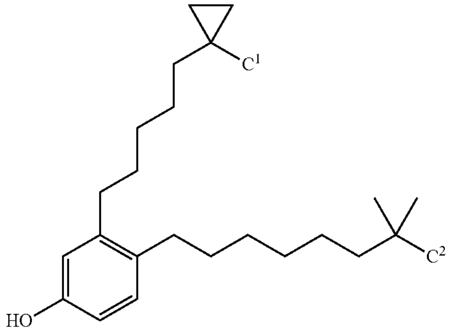

wherein $C^1$ = COOH and $C^2$ = CO—CoA; $C^1$ = CO—CoA and $C^2$ = COOH; or $C^1$ and $C^2$ = CO—CoA

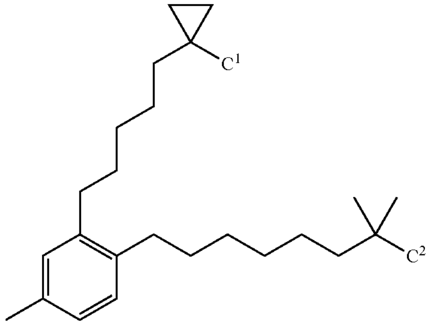

wherein $C^1$ = COOH and $C^2$ = CO—CoA; $C^1$ = CO—CoA and $C^2$ = COOH; or $C^1$ and $C^2$ = CO—CoA

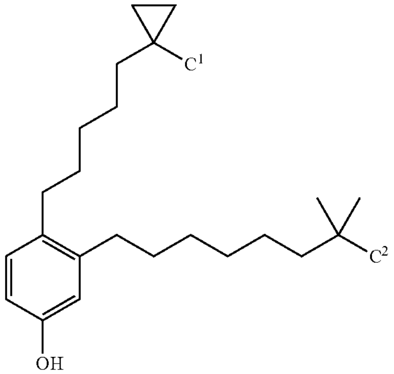

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 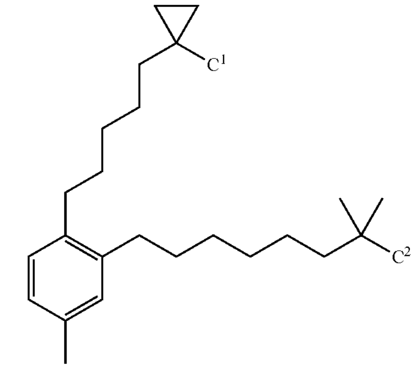 |
| wherein $C^1$ = COOH and $C^2$ = CO—CoA; $C^1$ = CO—CoA and $C^2$ = COOH; or $C^1$ and $C^2$ = CO—CoA |
| 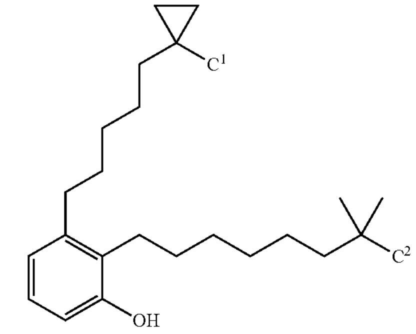 |
| wherein $C^1$ = COOH and $C^2$ = CO—CoA; $C^1$ = CO—CoA and $C^2$ = COOH; or $C^1$ and $C^2$ = CO—CoA |
| 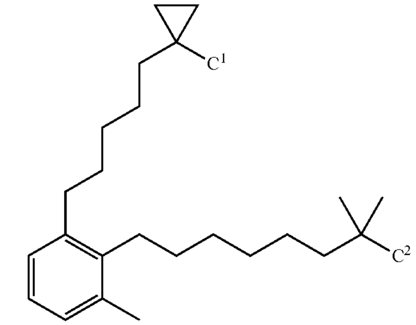 |
| wherein $C^1$ = COOH and $C^2$ = CO—CoA; $C^1$ = CO—CoA and $C^2$ = COOH; or $C^1$ and $C^2$ = CO—CoA |
| 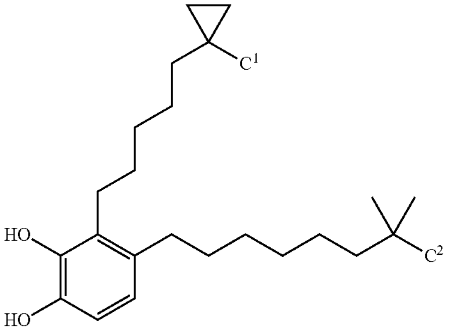 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 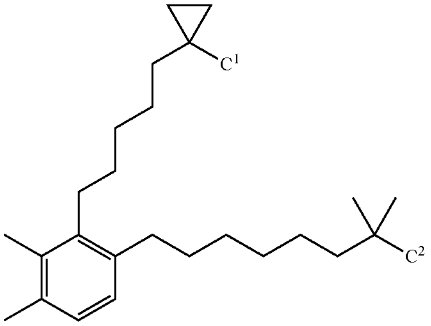 |
| wherein $C^1$ = COOH and $C^2$ = CO—CoA; $C^1$ = CO—CoA and $C^2$ = COOH; or $C^1$ and $C^2$ = CO—CoA |
| 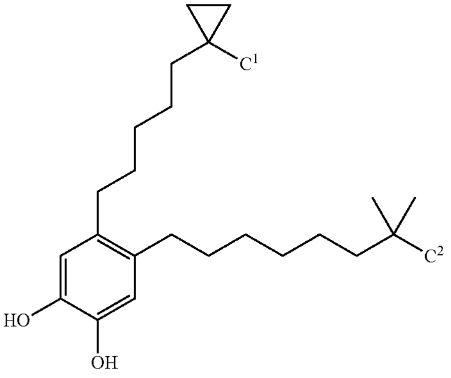 |
| wherein $C^1$ = COOH and $C^2$ = CO—CoA; $C^1$ = CO—CoA and $C^2$ = COOH; or $C^1$ and $C^2$ = CO—CoA |
| 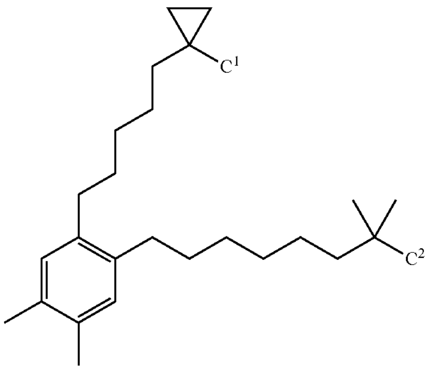 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 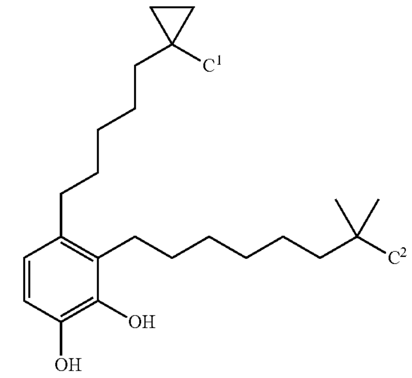 |
| wherein $C^1$ = COOH and $C^2$ = CO—CoA; $C^1$ = CO—CoA and $C^2$ = COOH; or $C^1$ and $C^2$ = CO—CoA |
| 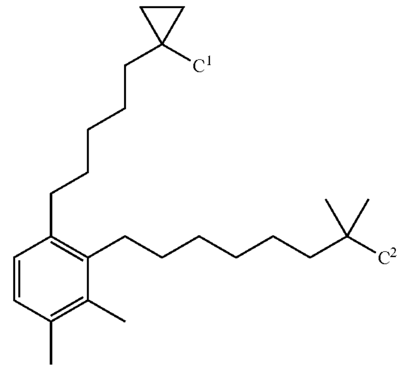 |
| wherein $C^1$ = COOH and $C^2$ = CO—CoA; $C^1$ = CO—CoA and $C^2$ = COOH; or $C^1$ and $C^2$ = CO—CoA |
| 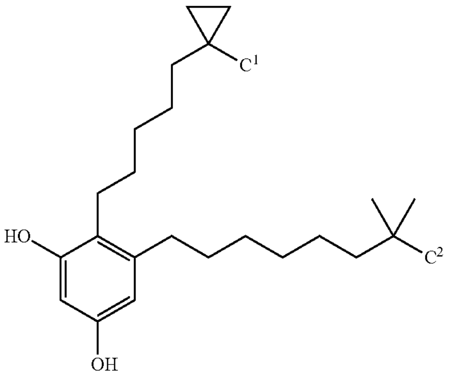 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 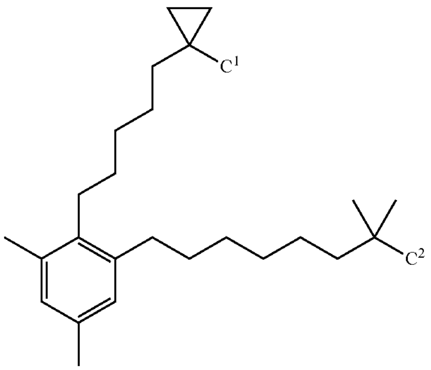 |
| wherein $C^1$ = COOH and $C^2$ = CO—CoA; $C^1$ = CO—CoA and $C^2$ = COOH; or $C^1$ and $C^2$ = CO—CoA |
| 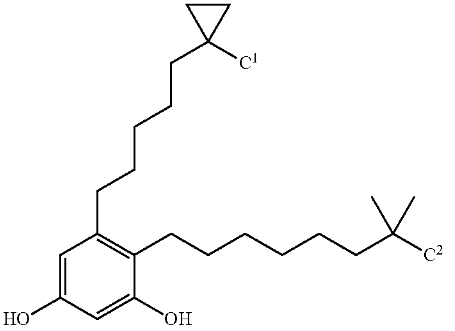 |
| wherein $C^1$ = COOH and $C^2$ = CO—CoA; $C^1$ = CO—CoA and $C^2$ = COOH; or $C^1$ and $C^2$ = CO—CoAc |
| 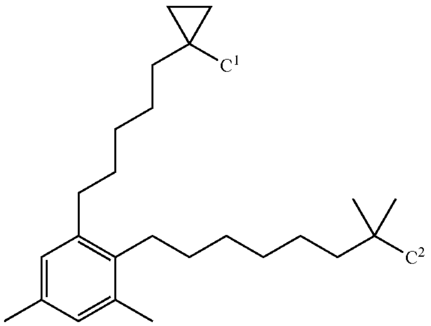 |
| wherein $C^1$ = COOH and $C^2$ = CO—CoA; $C^1$ = CO—CoA and $C^2$ = COOH; or $C^1$ and $C^2$ = CO—CoA |
| 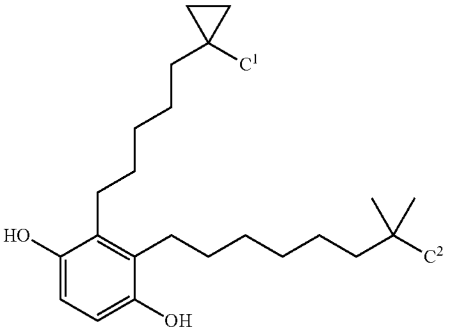 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 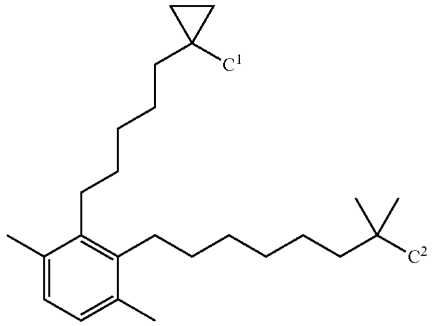 wherein $C^1$ = COOH and $C^2$ = CO—CoA; $C^1$ = CO—CoA and $C^2$ = COOH; or $C^1$ and $C^2$ = CO—CoA |
| 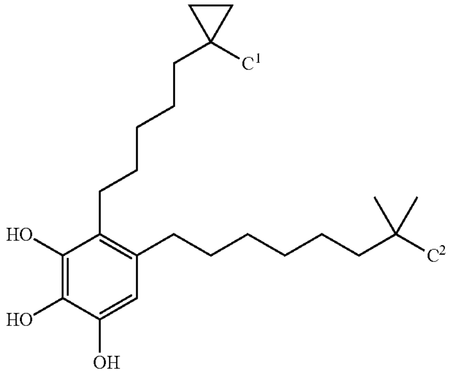 wherein $C^1$ = COOH and $C^2$ = CO—CoA; $C^1$ = CO—CoA and $C^2$ = COOH; or $C^1$ and $C^2$ = CO—CoA |
| 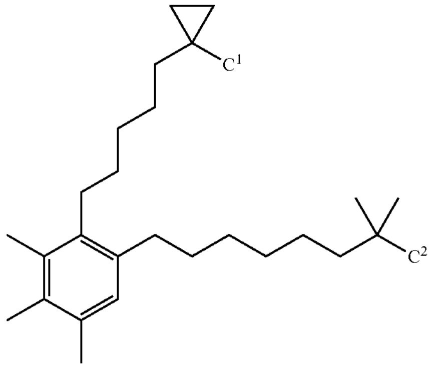 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 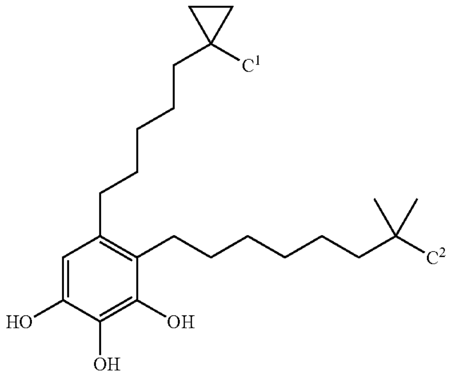 wherein $C^1$ = COOH and $C^2$ = CO—CoA; $C^1$ = CO—CoA and $C^2$ = COOH; or $C^1$ and $C^2$ = CO—CoA |
| 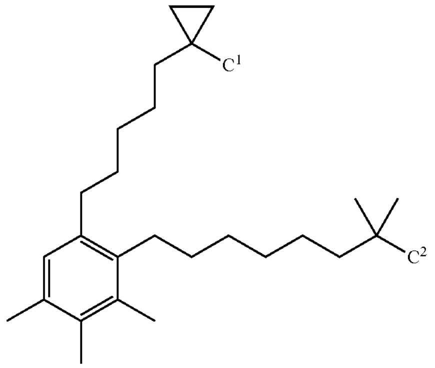 wherein $C^1$ = COOH and $C^2$ = CO—CoA; $C^1$ = CO—CoA and $C^2$ = COOH; or $C^1$ and $C^2$ = CO—CoA |
| 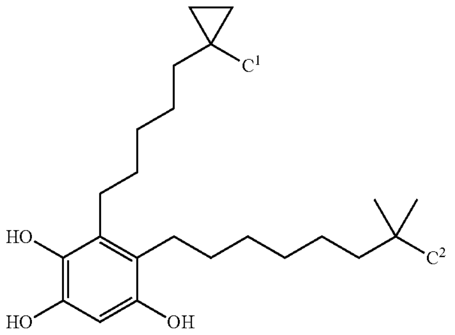 wherein $C^1$ = COOH and $C^2$ = CO—CoA; $C^1$ = CO—CoA and $C^2$ = COOH; or $C^1$ and $C^2$ = CO—CoA |
| 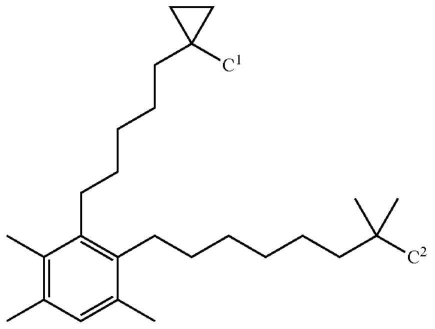 |

TABLE A-6-continued

| Structure |
|---|

wherein $C^1$ = COOH and $C^2$ = CO—CoA; $C^1$ = CO—CoA and $C^2$ = COOH; or $C^1$ and $C^2$ = CO—CoA

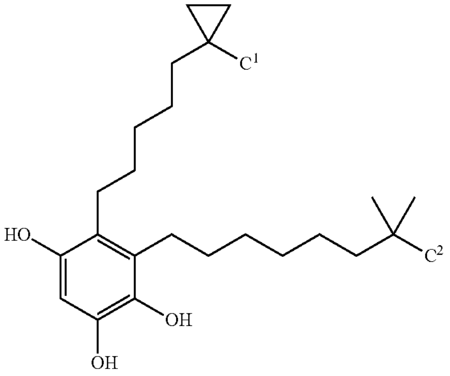

wherein $C^1$ = COOH and $C^2$ = CO—CoA; $C^1$ = CO—CoA and $C^2$ = COOH; or $C^1$ and $C^2$ = CO—CoA

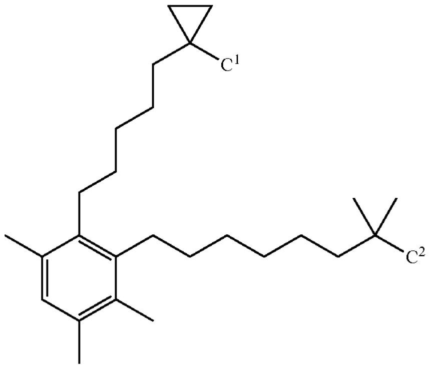

wherein $C^1$ = COOH and $C^2$ = CO—CoA; $C^1$ = CO—CoA and $C^2$ = COOH; or $C^1$ and $C^2$ = CO—CoA

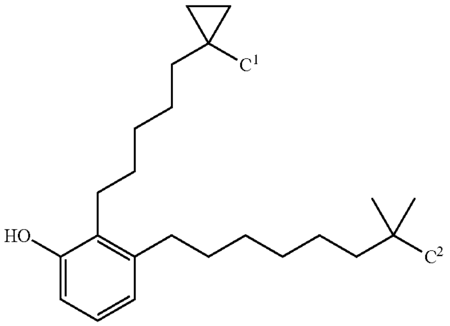

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|

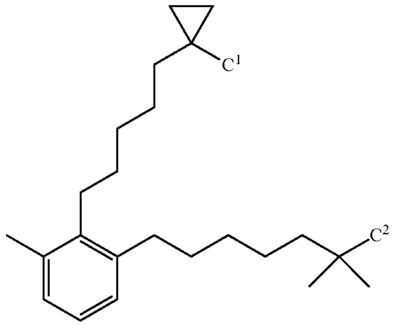

wherein $C^1$ = COOH and $C^2$ = CO—CoA; $C^1$ = CO—CoA and $C^2$ = COOH; or $C^1$ and $C^2$ = CO—CoA

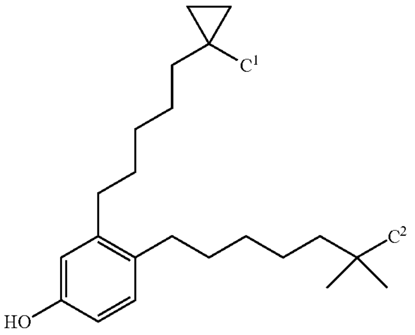

wherein $C^1$ = COOH and $C^2$ = CO—CoA; $C^1$ = CO—CoA and $C^2$ = COOH; or $C^1$ and $C^2$ = CO—CoA

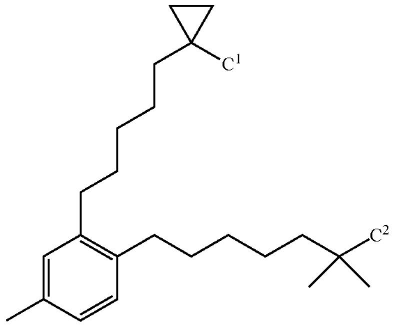

wherein $C^1$ = COOH and $C^2$ = CO—CoA; $C^1$ = CO—CoA and $C^2$ = COOH; or $C^1$ and $C^2$ = CO—CoA

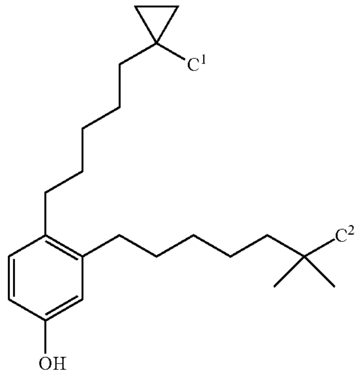

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|

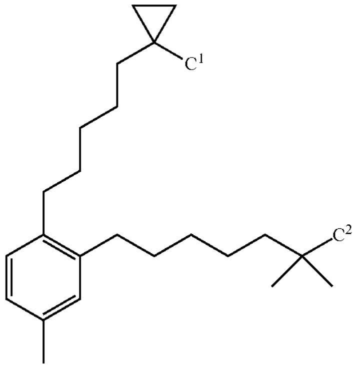

wherein $C^1$ = COOH and $C^2$ = CO—CoA; $C^1$ = CO—CoA and $C^2$ = COOH; or $C^1$ and $C^2$ = CO—CoA

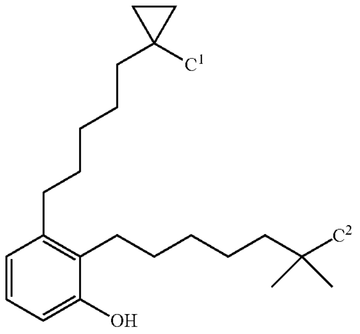

wherein $C^1$ = COOH and $C^2$ = CO—CoA; $C^1$ = CO—CoA and $C^2$ = COOH; or $C^1$ and $C^2$ = CO—CoA

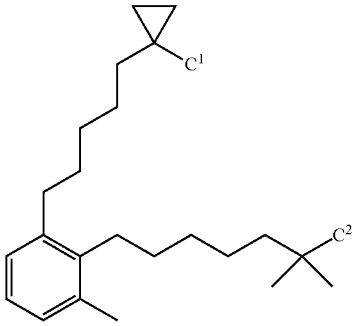

wherein $C^1$ = COOH and $C^2$ = CO—CoA; $C^1$ = CO—CoA and $C^2$ = COOH; or $C^1$ and $C^2$ = CO—CoA

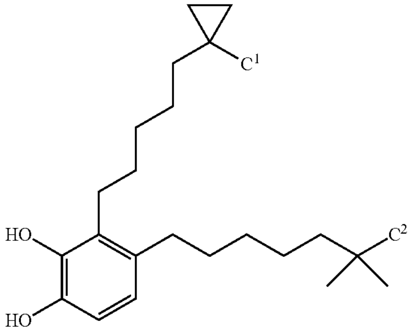

TABLE A-6-continued

| Structure |
|---|

wherein $C^1$ = COOH and $C^2$ = CO—CoA; $C^1$ = CO—CoA and $C^2$ = COOH; or $C^1$ and $C^2$ = CO—CoA

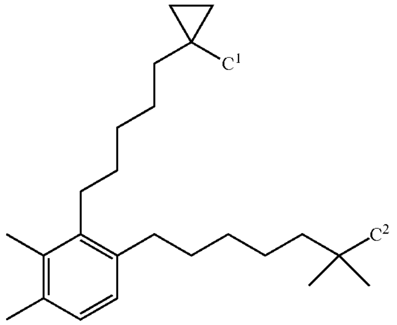

wherein $C^1$ = COOH and $C^2$ = CO—CoA; $C^1$ = CO—CoA and $C^2$ = COOH; or $C^1$ and $C^2$ = CO—CoA

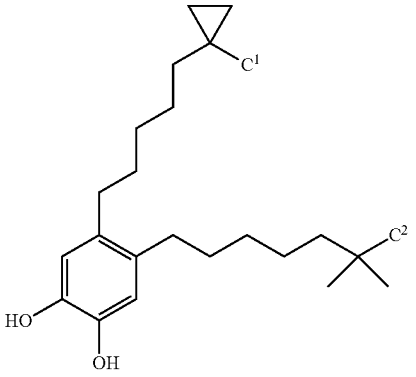

wherein $C^1$ = COOH and $C^2$ = CO—CoA; $C^1$ = CO—CoA and $C^2$ = COOH; or $C^1$ and $C^2$ = CO—CoA

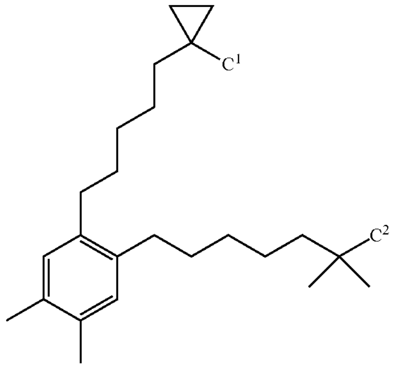

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 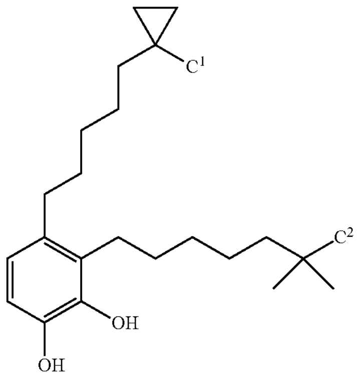 |
| wherein $C^1$ = COOH and $C^2$ = CO—CoA; $C^1$ = CO—CoA and $C^2$ = COOH; or $C^1$ and $C^2$ = CO—CoA |
| 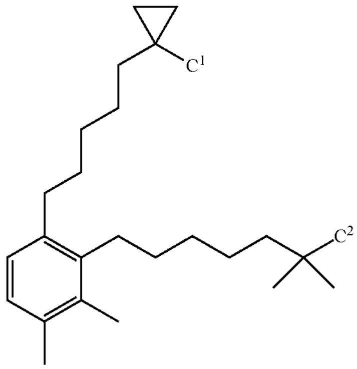 |
| wherein $C^1$ = COOH and $C^2$ = CO—CoA; $C^1$ = CO—CoA and $C^2$ = COOH; or $C^1$ and $C^2$ = CO—CoA |
| 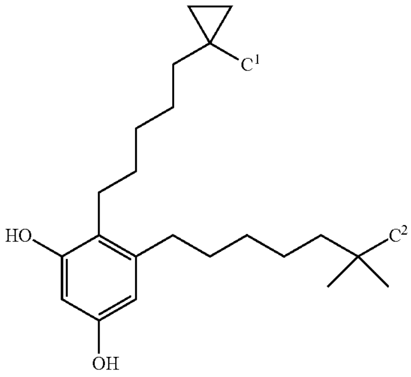 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 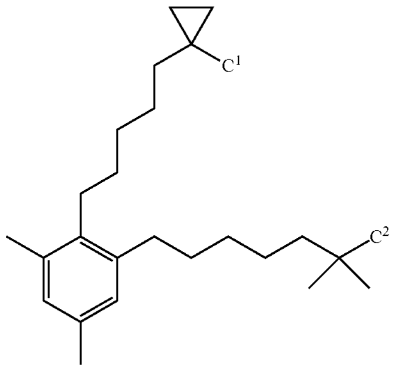 |
| wherein $C^1$ = COOH and $C^2$ = CO—CoA; $C^1$ = CO—CoA and $C^2$ = COOH; or $C^1$ and $C^2$ = CO—CoA |
| 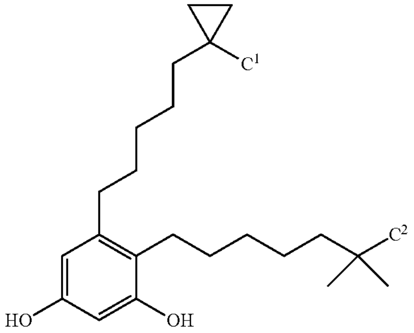 |
| wherein $C^1$ = COOH and $C^2$ = CO—CoA; $C^1$ = CO—CoA and $C^2$ = COOH; or $C^1$ and $C^2$ = CO—CoA |
| 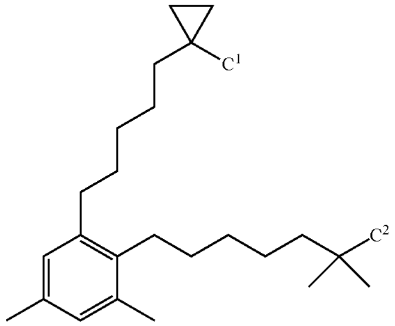 |
| wherein $C^1$ = COOH and $C^2$ = CO—CoA; $C^1$ = CO—CoA and $C^2$ = COOH; or $C^1$ and $C^2$ = CO—CoA |
| 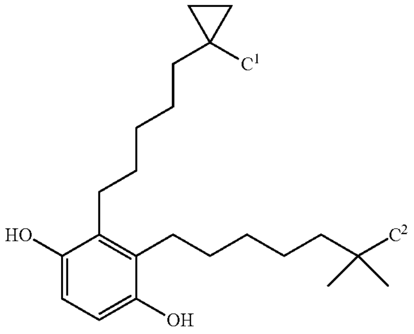 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 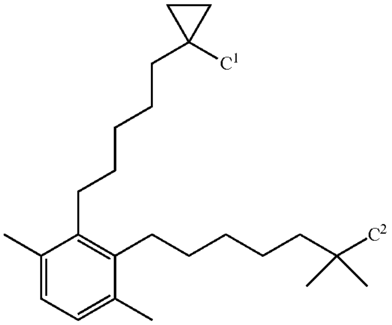 |
| wherein $C^1$ = COOH and $C^2$ = CO—CoA; $C^1$ = CO—CoA and $C^2$ = COOH; or $C^1$ and $C^2$ = CO—CoA |
| 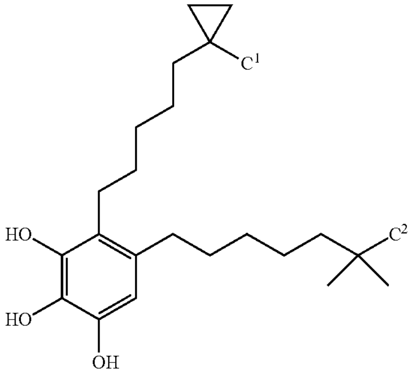 |
| wherein $C^1$ = COOH and $C^2$ = CO—CoA; $C^1$ = CO—CoA and $C^2$ = COOH; or $C^1$ and $C^2$ = CO—CoA |
| 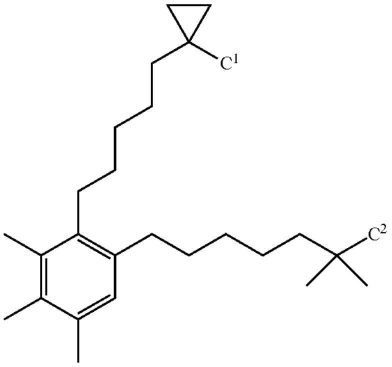 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 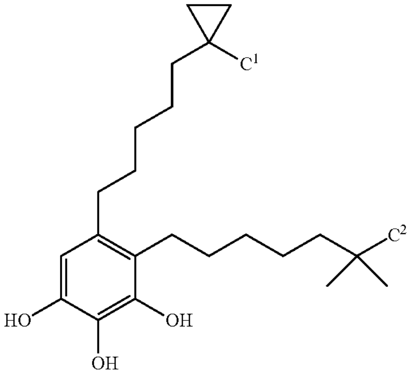 |
| wherein $C^1$ = COOH and $C^2$ = CO—CoA; $C^1$ = CO—CoA and $C^2$ = COOH; or $C^1$ and $C^2$ = CO—CoA |
| 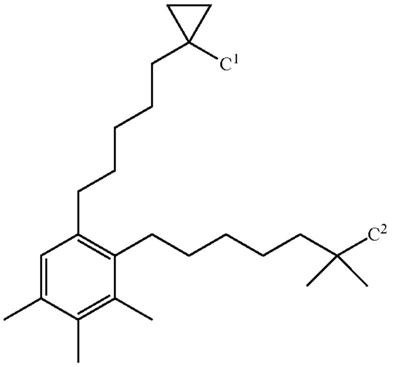 |
| wherein $C^1$ = COOH and $C^2$= CO—CoA; $C^1$ = CO—CoA and $C^2$ = COOH; or $C^1$ and $C^2$ = CO—CoA |
| 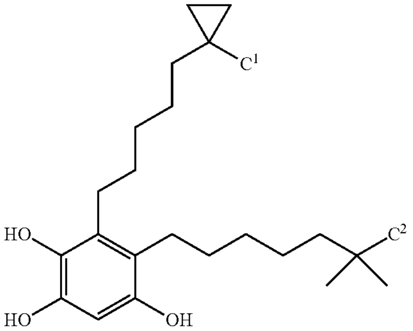 |
| wherein $C^1$ = COOH and $C^2$ = CO—CoA; $C^1$ = CO—CoA and $C^2$ = COOH; or $C^1$ and $C^2$ = CO—CoA |
| 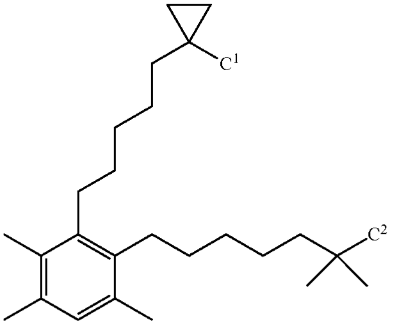 |

TABLE A-6-continued

Structure wherein $C^1$ = COOH and $C^2$ = CO—CoA; $C^1$ = CO—CoA and $C^2$ = COOH; or $C^1$ and $C^2$ = CO—CoA

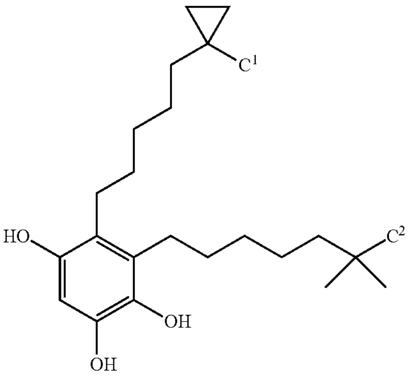

wherein $C^1$ = COOH and $C^2$ = CO—CoA; $C^1$ = CO—CoA and $C^2$ = COOH; or $C^1$ and $C^2$ = CO—CoA

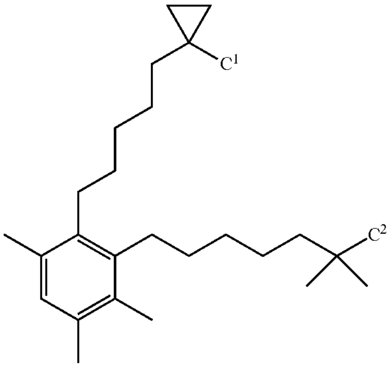

wherein $C^1$ = COOH and $C^2$ = CO—CoA; $C^1$ = CO—CoA and $C^2$ = COOH; or $C^1$ and $C^2$ = CO—CoA

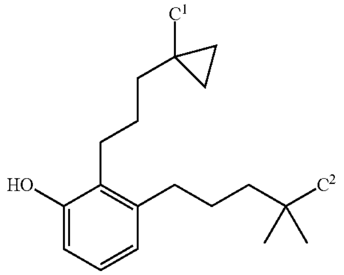

wherein $C^1$ = COOH and $C^2$ = CO—CoA; $C^1$ = CO—CoA and $C^2$ = COOH; or $C^1$ and $C^2$ = CO—CoA

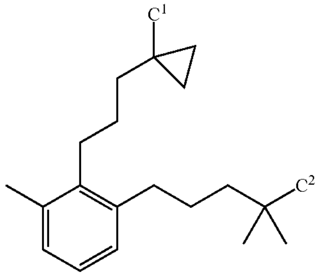

TABLE A-6-continued

Structure wherein $C^1$ = COOH and $C^2$ = CO—CoA; $C^1$ = CO—CoA and $C^2$ = COOH; or $C^1$ and $C^2$ = CO—CoA

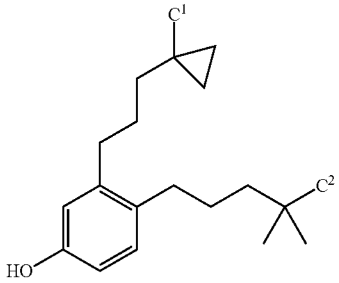

wherein $C^1$ = COOH and $C^2$ = CO—CoA; $C^1$ = CO—CoA and $C^2$ = COOH; or $C^1$ and $C^2$ = CO—CoA

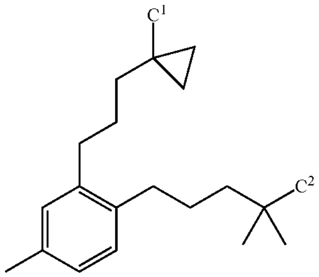

wherein $C^1$ = COOH and $C^2$= CO—CoA; $C^1$ = CO—CoA and $C^2$ = COOH; or $C^1$ and $C^2$ = CO—CoA

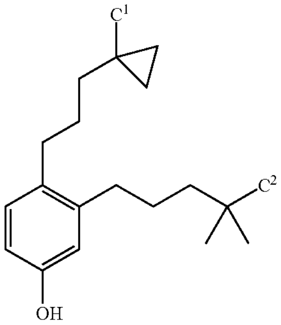

wherein $C^1$ = COOH and $C^2$ = CO—CoA; $C^1$ = CO—CoA and $C^2$ = COOH; or $C^1$ and $C^2$ = CO—CoA

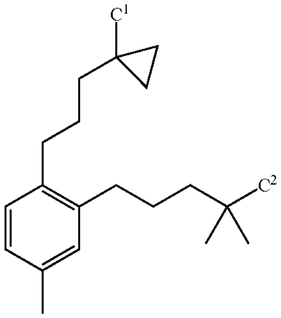

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 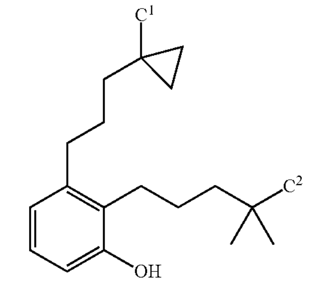<br>wherein $C^1$ = COOH and $C^2$ = CO—CoA; $C^1$ = CO—CoA and $C^2$ = COOH; or $C^1$ and $C^2$ = CO—CoA |
| 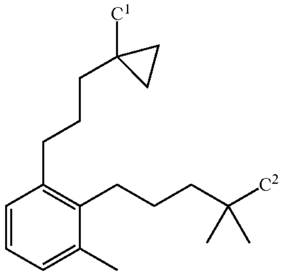<br>wherein $C^1$ = COOH and $C^2$ = CO—CoA; $C^1$ = CO—CoA and $C^2$ = COOH; or $C^1$ and $C^2$ = CO—CoA |
| 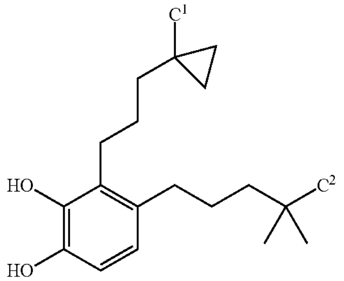<br>wherein $C^1$ = COOH and $C^2$ = CO—CoA; $C^1$ = CO—CoA and $C^2$ = COOH; or $C^1$ and $C^2$ = CO—CoA |
| 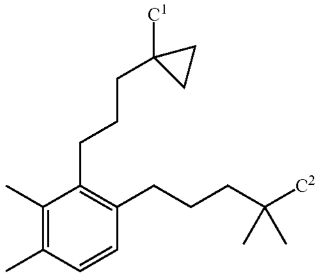<br>wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 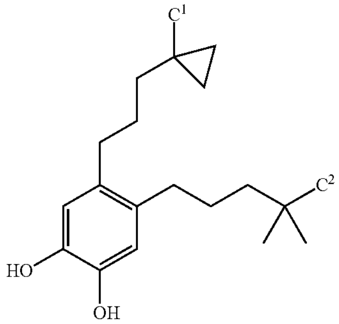<br>wherein $C^1$ = COOH and $C^2$ = CO—CoA; $C^1$ = CO—CoA and $C^2$ = COOH; or $C^1$ and $C^2$ = CO—CoA |
| 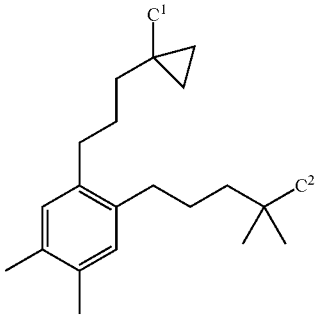<br>wherein $C^1$ = COOH and $C^2$ = CO—CoA; $C^1$ = CO—CoA and $C^2$ = COOH; or $C^1$ and $C^2$ = CO—CoA |
| 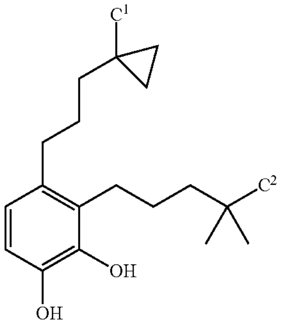<br>wherein $C^1$ = COOH and $C^2$ = CO—CoA; $C^1$ = CO—CoA and $C^2$ = COOH; or $C^1$ and $C^2$ = CO—CoA |
| 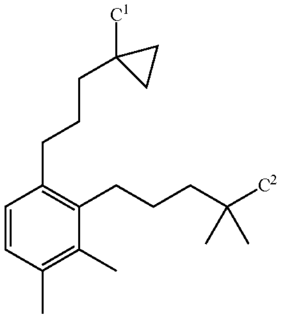<br>wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|

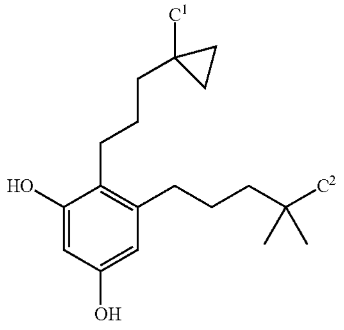

wherein $C^1$ = COOH and $C^2$ = CO—CoA; $C^1$ = CO—CoA and $C^2$ = COOH; or $C^1$ and $C^2$ = CO—CoA

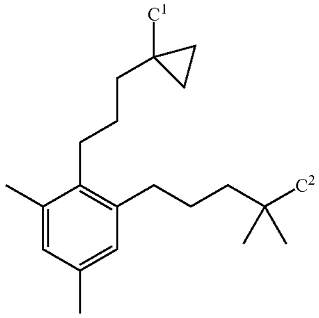

wherein $C^1$ = COOH and $C^2$ = CO—CoA; $C^1$ = CO—CoA and $C^2$ = COOH; or $C^1$ and $C^2$ = CO—CoA

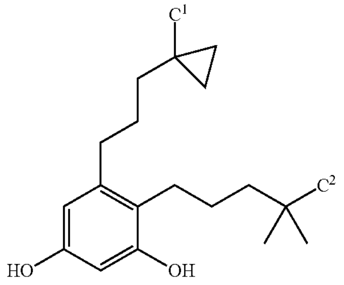

wherein $C^1$ = COOH and $C^2$ = CO—CoA; $C^1$ = CO—Co Aand $C^2$ = COOH; or $C^1$ and $C^2$ = CO—CoA

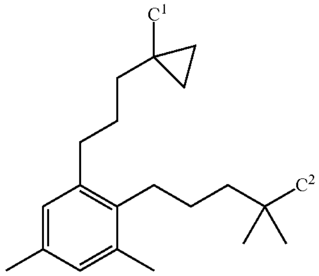

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|

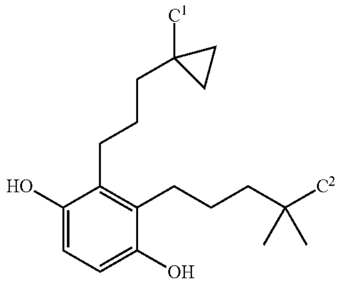

wherein $C^1$ = COOH and $C^2$ = CO—CoA; $C^1$ = CO—CoA and $C^2$ = COOH; or $C^1$ and $C^2$ = CO—CoA

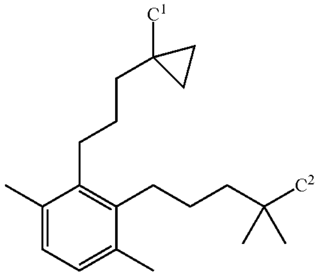

wherein $C^1$ = COOH and $C^2$ = CO—CoA; $C^1$ = CO—CoA and $C^2$ = COOH; or $C^1$ and $C^2$ = CO—CoA

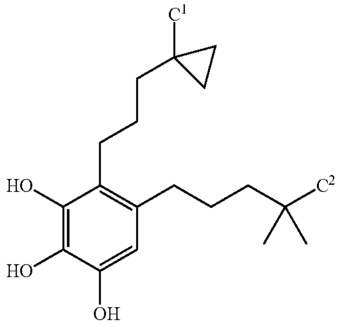

wherein $C^1$ = COOH and $C^2$ = CO—CoA; $C^1$ = CO—CoA and $C^2$ = COOH; or $C^1$ and $C^2$ = CO—CoA

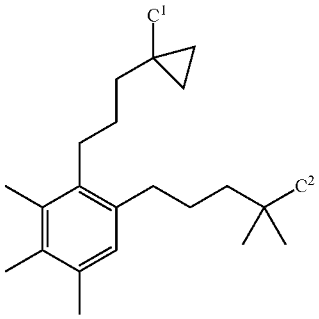

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 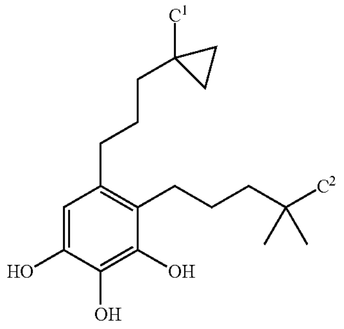 |
| wherein $C^1$ = COOH and $C^2$ = CO—CoA; $C^1$ = CO—CoA and $C^2$ = COOH; or $C^1$ and $C^2$ = CO—CoA |
| 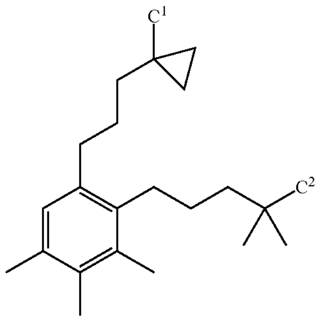 |
| wherein $C^1$ = COOH and $C^2$ = CO—CoA; $C^1$ = CO—CoA and $C^2$ = COOH; or $C^1$ and $C^2$ = CO—CoA |
| 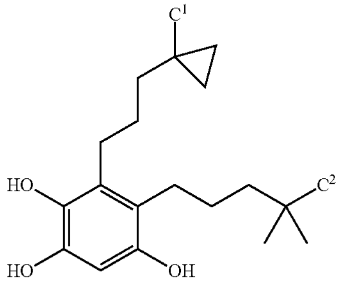 |
| wherein $C^1$ = COOH and $C^2$ = CO—CoA; $C^1$ = CO—CoA and $C^2$ = COOH; or $C^1$ and $C^2$ = CO—CoA |
| 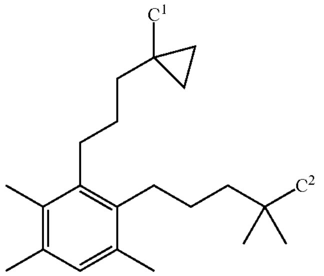 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 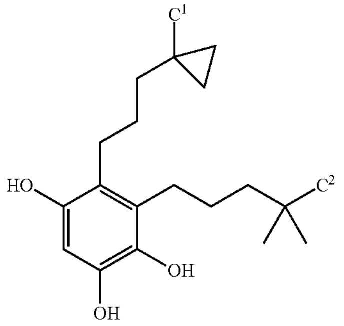 |
| wherein $C^1$ = COOH and $C^2$ = CO—CoA; $C^1$ = CO—CoA and $C^2$ = COOH; or $C^1$ and $C^2$ = CO—CoA |
| 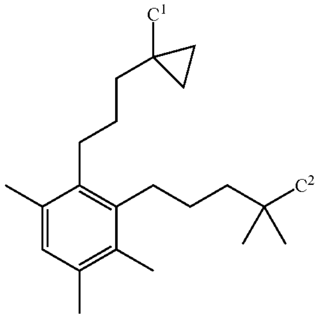 |
| wherein $C^1$ = COOH and $C^2$ = CO—CoA; $C^1$ = CO—CoA and $C^2$ = COOH; or $C^1$ and $C^2$ = CO—CoA |
| 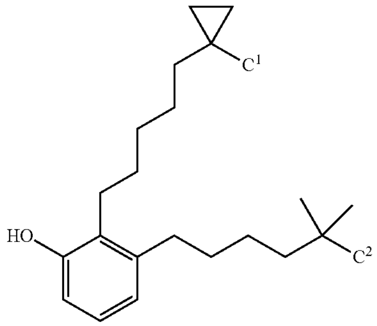 |
| wherein $C^1$ = COOH and $C^2$ = CO—CoA; $C^1$ = CO—CoA and $C^2$ = COOH; or $C^1$ and $C^2$ = CO—CoA |
| 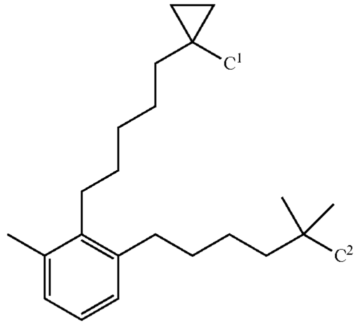 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 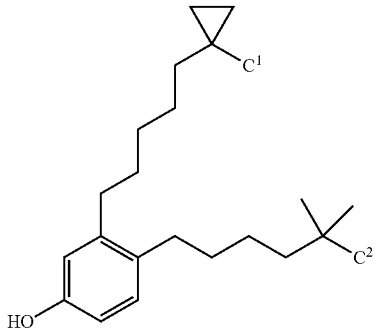 |
| wherein $C^1$ = COOH and $C^2$ = CO—CoA; $C^1$ = CO—CoA and $C^2$ = COOH; or $C^1$ and $C^2$ = CO—CoA |
| 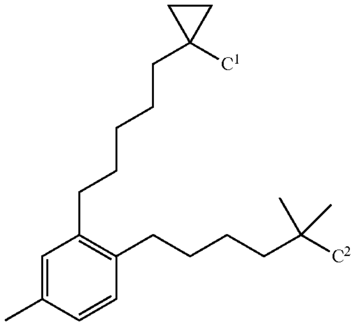 |
| wherein $C^1$ = COOH and $C^2$ = CO—CoA; $C^1$ = CO—CoA and $C^2$ = COOH; or $C^1$ and $C^2$ = CO—CoA |
| 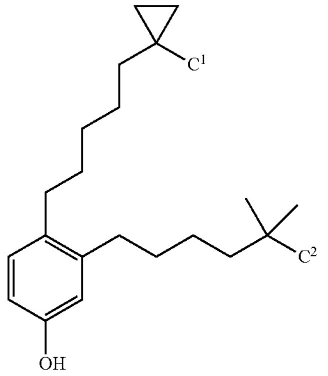 |
| wherein $C^1$ = COOH and $C^2$ = CO—CoA; $C^1$ = CO—CoA and $C^2$ = COOH; or $C^1$ and $C^2$ = CO—CoA |
| 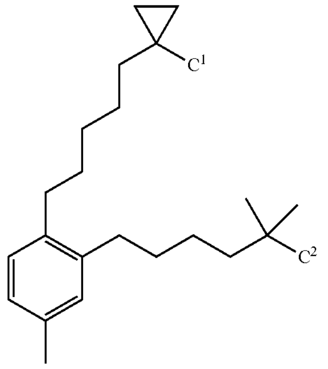 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 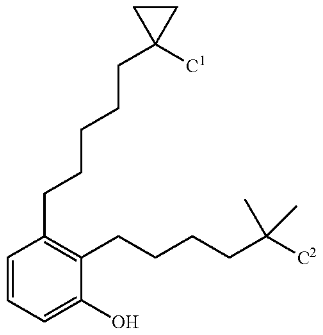 |
| wherein $C^1$ = COOH and $C^2$ = CO—CoA; $C^1$ = CO—CoA and $C^2$ = COOH; or $C^1$ and $C^2$ = CO—CoA |
| 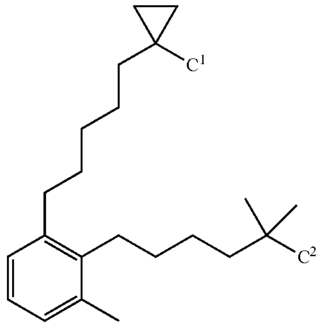 |
| wherein $C^1$ = COOH and $C^2$ = CO—CoA; $C^1$ = CO—CoA and $C^2$ = COOH; or $C^1$ and $C^2$ = CO—CoA |
| 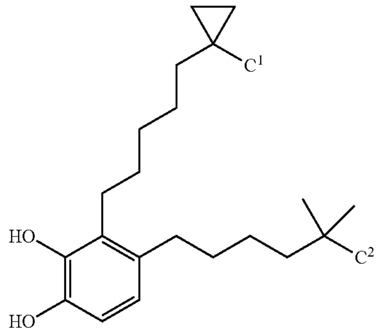 |
| wherein $C^1$ = COOH and $C^2$ = CO—CoA; $C^1$ = CO—CoA and $C^2$ = COOH; or $C^1$ and $C^2$ = CO—CoA |
| 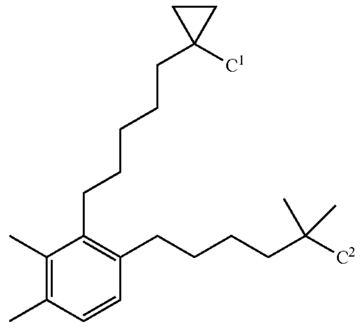 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 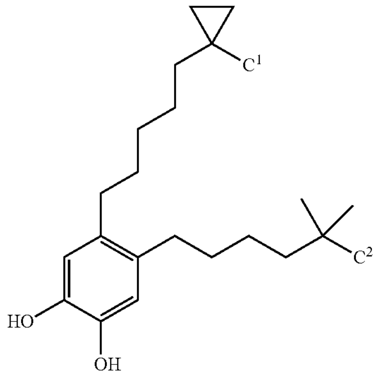 |
| wherein $C^1$ = COOH and $C^2$ = CO—CoA; $C^1$ = CO—CoA and $C^2$ = COOH; or $C^1$ and $C^2$ = CO—CoA |
| 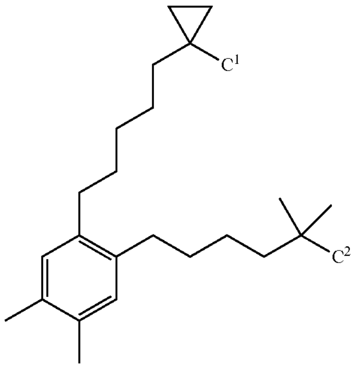 |
| wherein $C^1$ = COOH and $C^2$ = CO—CoA; $C^1$ = CO—CoA and $C^2$ = COOH; or $C^1$ and $C^2$ = CO—CoA |
| 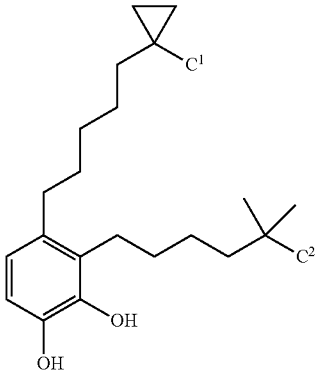 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 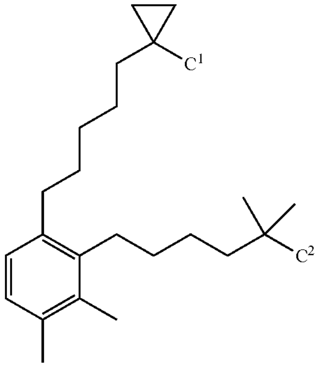 |
| wherein $C^1$ = COOH and $C^2$ = CO—CoA; $C^1$ = CO—CoA and $C^2$ = COOH; or $C^1$ and $C^2$ = CO—CoA |
| 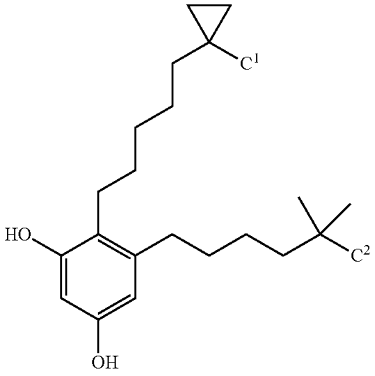 |
| wherein $C^1$ = COOH and $C^2$ = CO—CoA; $C^1$ = CO—CoA and $C^2$ = COOH; or $C^1$ and $C^2$ = CO—CoA |
| 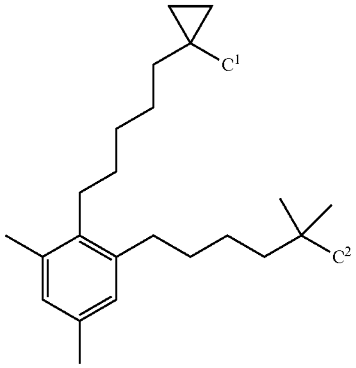 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 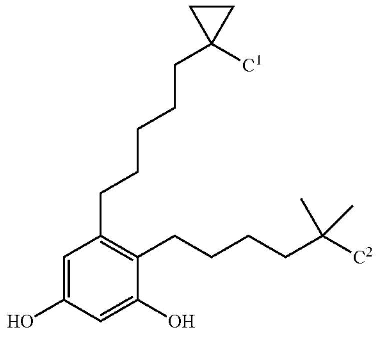 |
| wherein $C^1$ = COOH and $C^2$ = CO—CoA; $C^1$ = CO—CoA and $C^2$ = COOH; or $C^1$ and $C^2$ = CO—CoA |
| 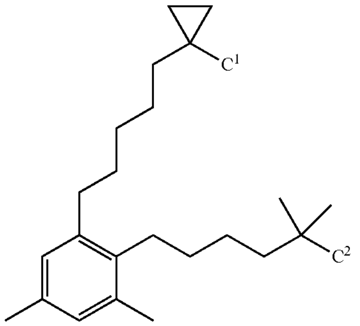 |
| wherein $C^1$ = COOH and $C^2$ = CO—CoA; $C^1$ = CO—CoA and $C^2$ = COOH; or $C^1$ and $C^2$ = CO—CoA |
| 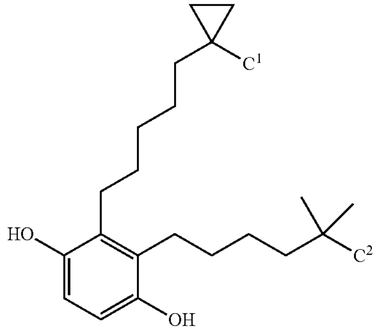 |
| wherein $C^1$ = COOH and $C^2$ = CO—CoA; $C^1$ = CO—CoA and $C^2$ = COOH; or $C^1$ and $C^2$ = CO—CoA |
| 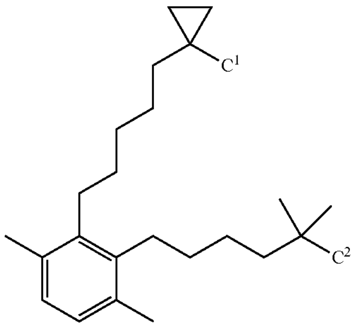 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 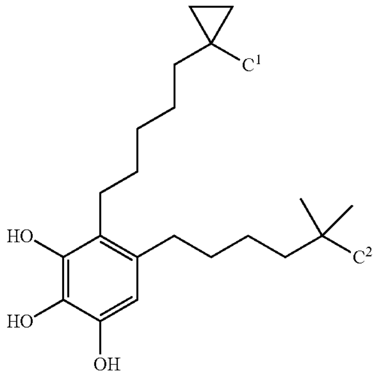 |
| wherein $C^1$ = COOH and $C^2$ = CO—CoA; $C^1$ = CO—CoA and $C^2$ = COOH; or $C^1$ and $C^2$ = CO—CoA |
| 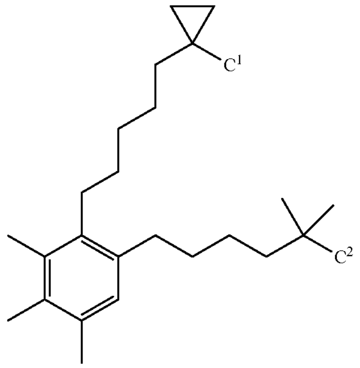 |
| wherein $C^1$ = COOH and $C^2$ = CO—CoA; $C^1$ = CO—CoA and $C^2$ = COOH; or $C^1$ and $C^2$ = CO—CoA |
| 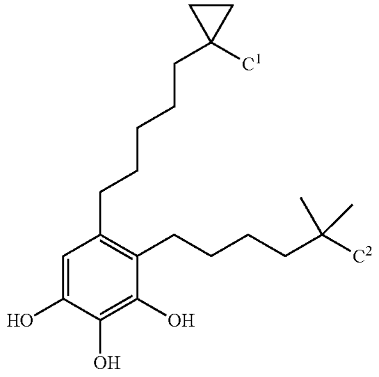 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

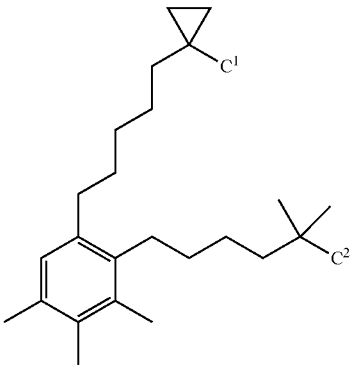

wherein $C^1$ = COOH and $C^2$ = CO—CoA; $C^1$ = CO—CoA and $C^2$ = COOH; or $C^1$ and $C^2$ = CO—CoA

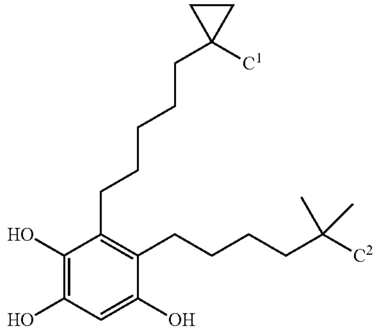

wherein $C^1$ = COOH and $C^2$ = CO—CoA; $C^1$ = CO—CoA and $C^2$ = COOH; or $C^1$ and $C^2$ = CO—CoA

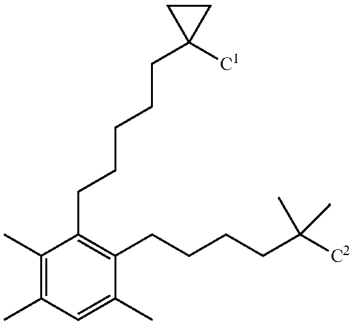

wherein $C^1$ = COOH and $C^2$ = CO—CoA; $C^1$ = CO—CoA and $C^2$ = COOH; or $C^1$ and $C^2$ = CO—CoA

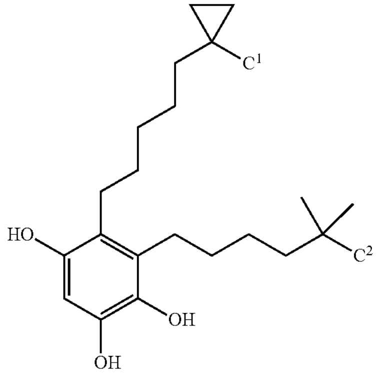

TABLE A-6-continued

| Structure |
| --- |

wherein $C^1$ = COOH and $C^2$ = CO—CoA; $C^1$ = CO—CoA and $C^2$ = COOH; or $C^1$ and $C^2$ = CO—CoA

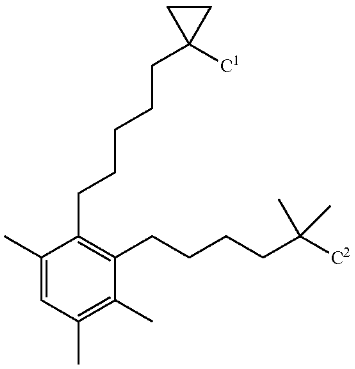

wherein $C^1$ = COOH and $C^2$ = CO—CoA; $C^1$ = CO—CoA and $C^2$ = COOH; or $C^1$ and $C^2$ = CO—CoA

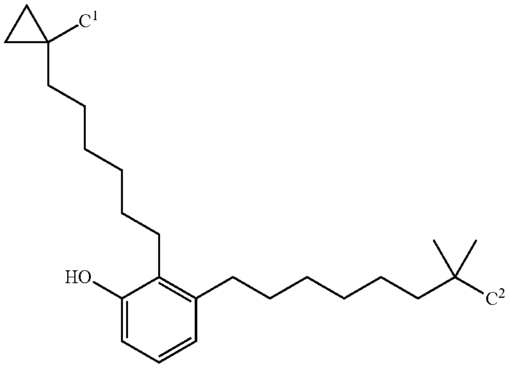

wherein $C^1$ = COOH and $C^2$ = CO—CoA; $C^1$ = CO—CoA and $C^2$ = COOH; or $C^1$ and $C^2$ = CO—CoA

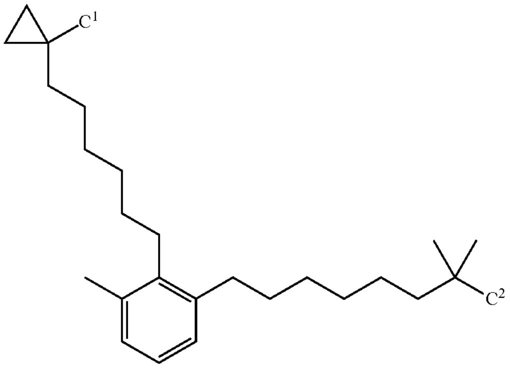

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|
| 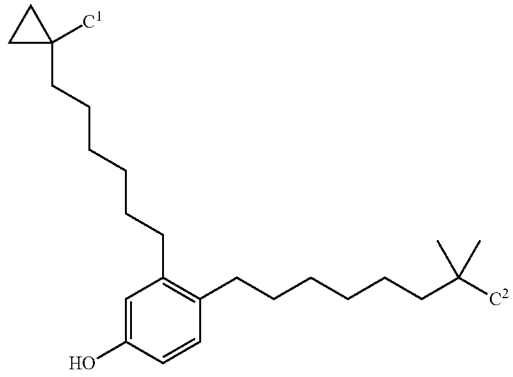 |
| wherein $C^1$ = COOH and $C^2$ = CO—CoA; $C^1$ = CO—CoA and $C^2$ = COOH; or $C^1$ and $C^2$ = CO—CoA |
| 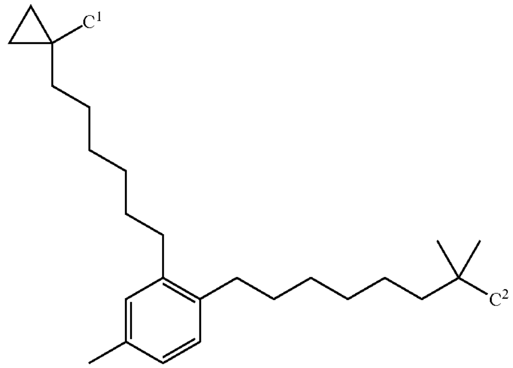 |
| wherein $C^1$ = COOH and $C^2$ = CO—CoA; $C^1$ = CO—CoA and $C^2$ = COOH; or $C^1$ and $C^2$ = CO—CoA |
| 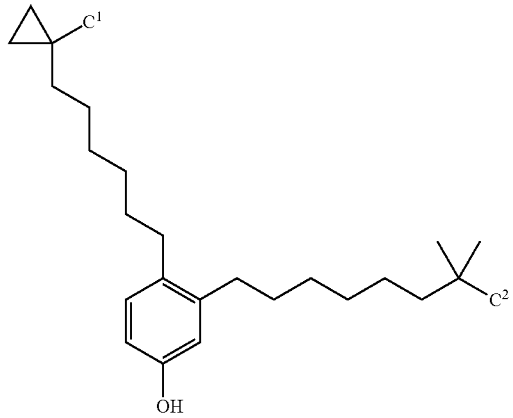 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 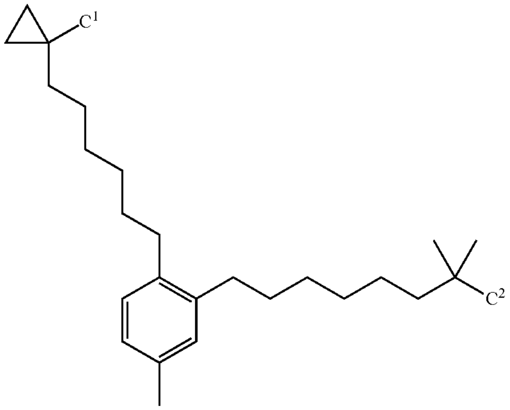 |
| wherein $C^1$ = COOH and $C^2$ = CO—CoA; $C^1$ = CO—CoA and $C^2$ = COOH; or $C^1$ and $C^2$ = CO—CoA |
| 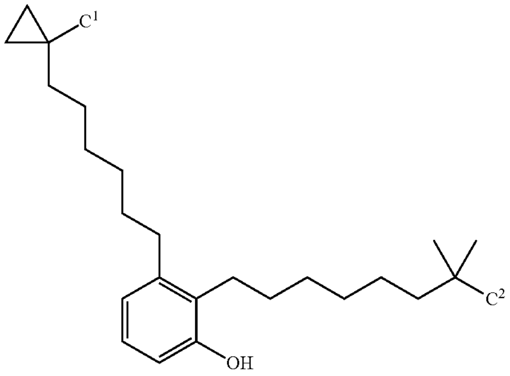 |
| wherein $C^1$ = COOH and $C^2$ = CO—CoA; $C^1$ = CO—CoA and $C^2$ = COOH; or $C^1$ and $C^2$ = CO—CoA |
| 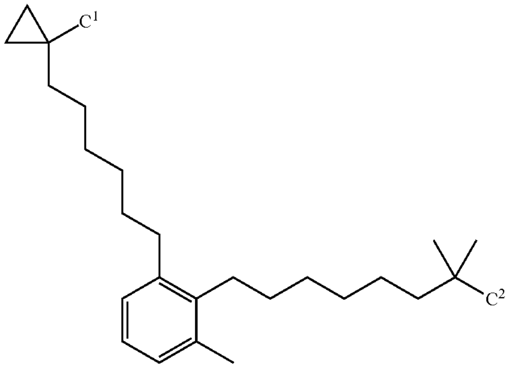 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 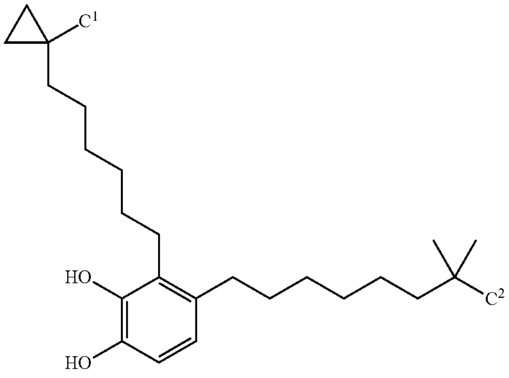 wherein $C^1$ = COOH and $C^2$ = CO—CoA; $C^1$ = CO—CoA and $C^2$ = COOH; or $C^1$ and $C^2$ = CO—CoA |
| 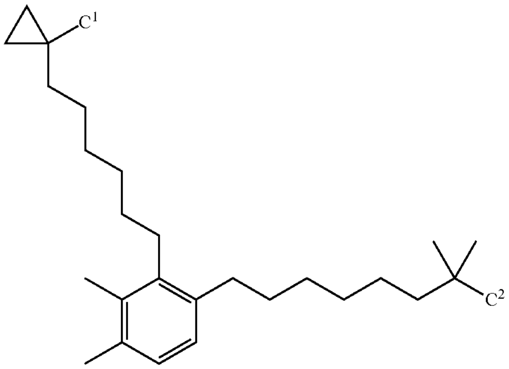 wherein $C^1$ = COOH and $C^2$ = CO—CoA; $C^1$ = CO—CoA and $C^2$ = COOH; or $C^1$ and $C^2$ = CO—CoA |
| 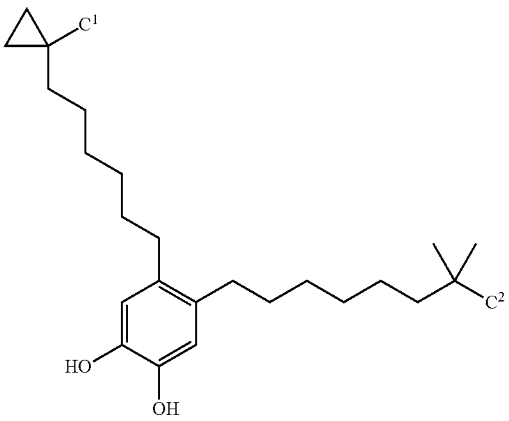 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 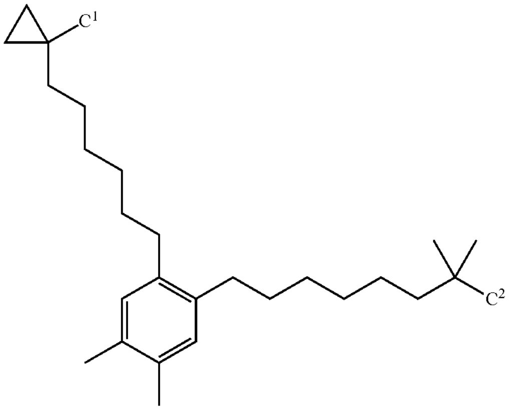 wherein $C^1$ = COOH and $C^2$ = CO—CoA; $C^1$ = CO—CoA and $C^2$ = COOH; or $C^1$ and $C^2$ = CO—CoA |
| 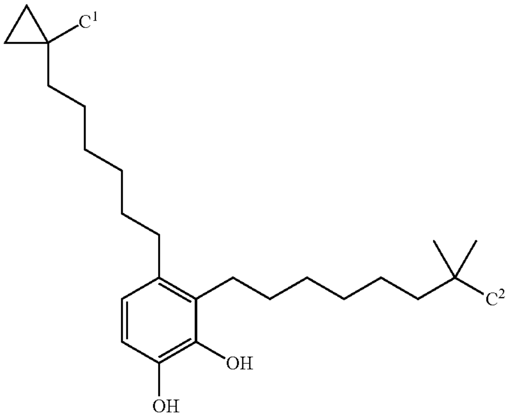 wherein $C^1$ = COOH and $C^2$ = CO—CoA; $C^1$ = CO—CoA and $C^2$ = COOH; or $C^1$ and $C^2$ = CO—CoA |
| 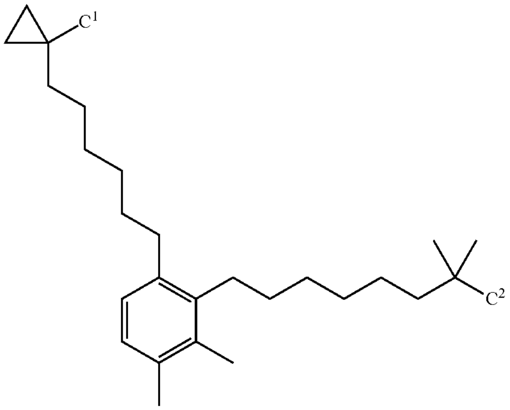 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

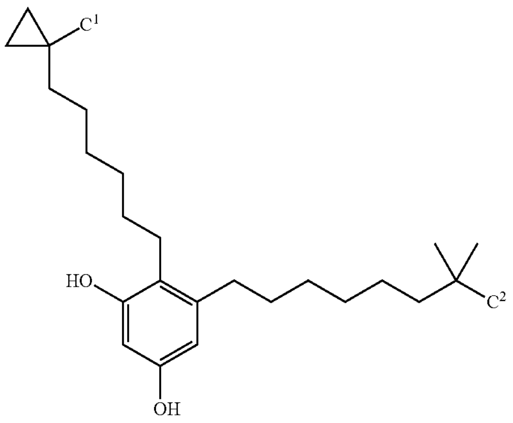

wherein $C^1$ = COOH and $C^2$ = CO—CoA; $C^1$ = CO—CoA and $C^2$ = COOH; or $C^1$ and $C^2$ = CO—CoA

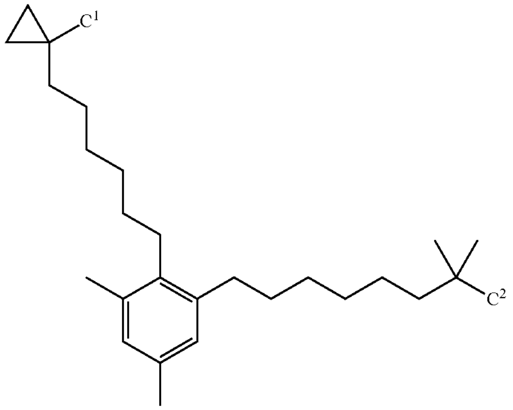

wherein $C^1$ = COOH and $C^2$ = CO—CoA; $C^1$ = CO—CoA and $C^2$ = COOH; or $C^1$ and $C^2$ = CO—CoA

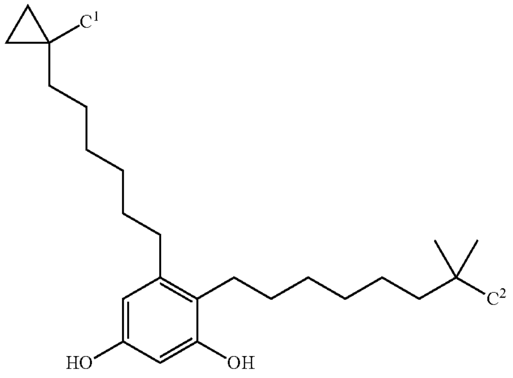

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |

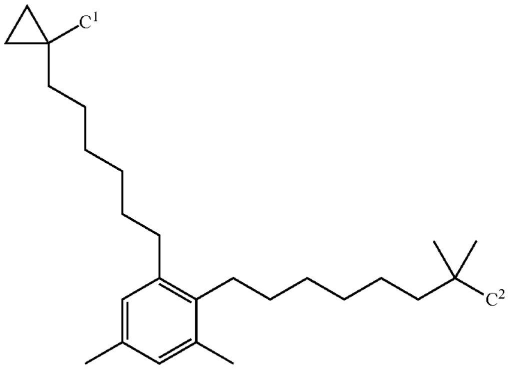

wherein $C^1$ = COOH and $C^2$ = CO—CoA; $C^1$ = CO—CoA and $C^2$ = COOH; or $C^1$ and $C^2$ = CO—CoA

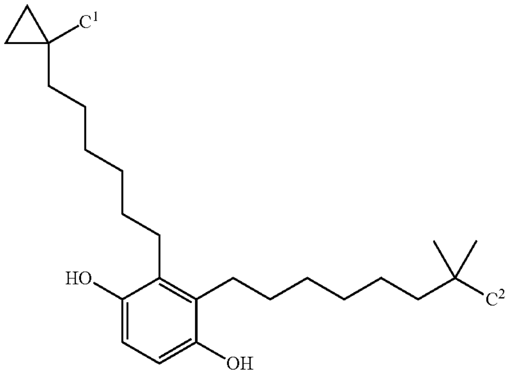

wherein $C^1$ = COOH and $C^2$ = CO—CoA; $C^1$ = CO—CoA and $C^2$ = COOH; or $C^1$ and $C^2$ = CO—CoA

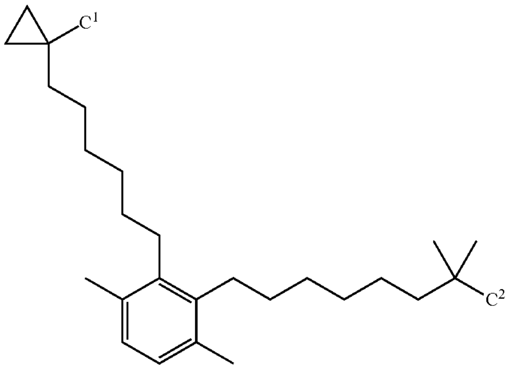

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|
| 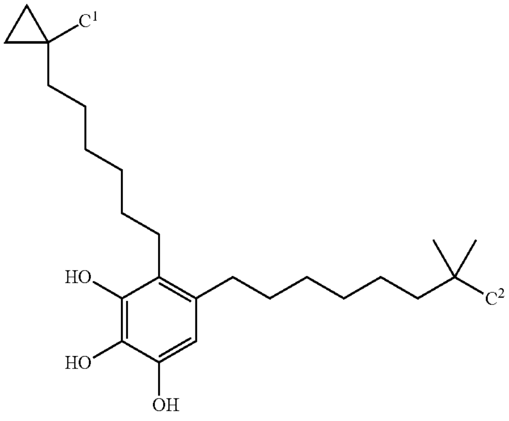 |
| wherein $C^1$ = COOH and $C^2$ = CO—CoA; $C^1$ = CO—CoA and $C^2$ = COOH; or $C^1$ and $C^2$ = CO—CoA |
| 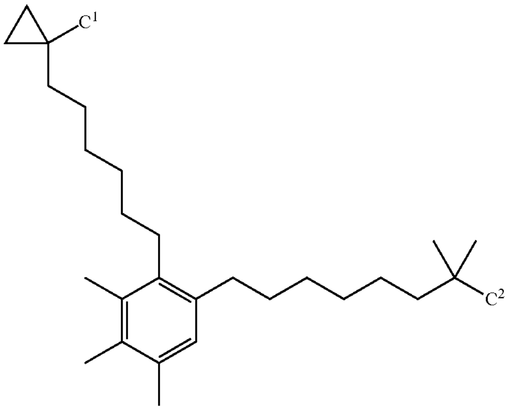 |
| wherein $C^1$ = COOH and $C^2$ = CO—CoA; $C^1$ = CO—CoA and $C^2$ = COOH; or $C^1$ and $C^2$ = CO—CoA |
| 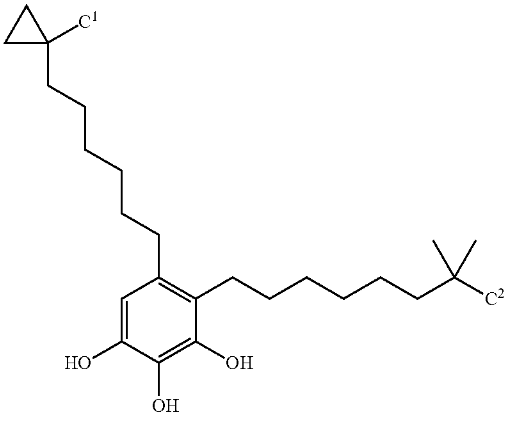 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 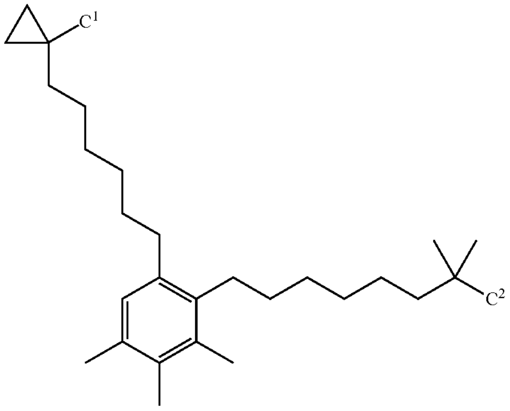 |
| wherein $C^1$ = COOH and $C^2$ = CO—CoA; $C^1$ = CO—CoA and $C^2$ = COOH; or $C^1$ and $C^2$ = CO—CoA |
| 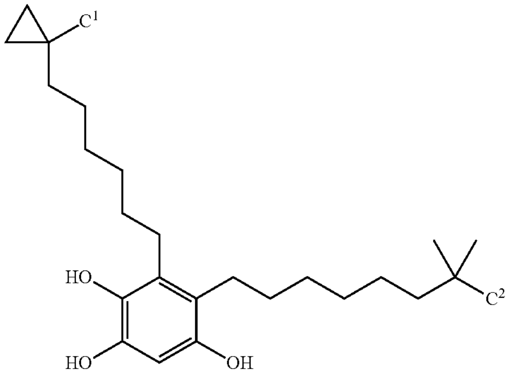 |
| wherein $C^1$ = COOH and $C^2$ = CO—CoA; $C^1$ = CO—CoA and $C^2$ = COOH; or $C^1$ and $C^2$ = CO—CoA |
| 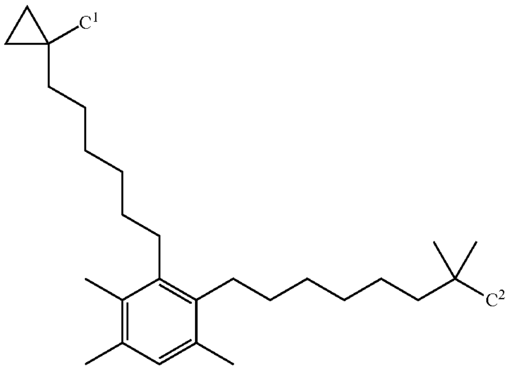 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 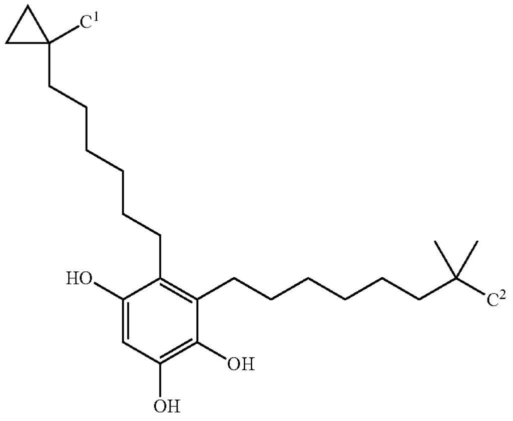 wherein $C^1$ = COOH and $C^2$ = CO—CoA; $C^1$ = CO—CoA and $C^2$ = COOH; or $C^1$ and $C^2$ = CO—CoA |
| 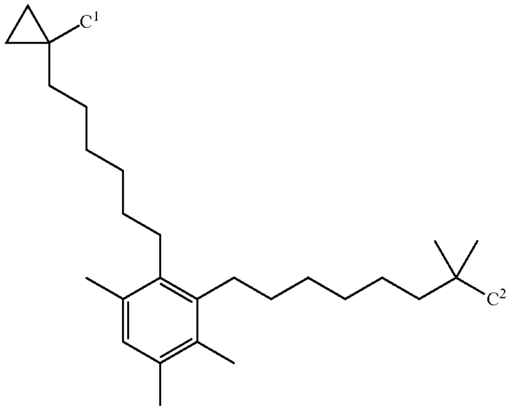 wherein $C^1$ = COOH and $C^2$ = CO—CoA; $C^1$ = CO—CoA and $C^2$ = COOH; or $C^1$ and $C^2$ = CO—CoA |
| 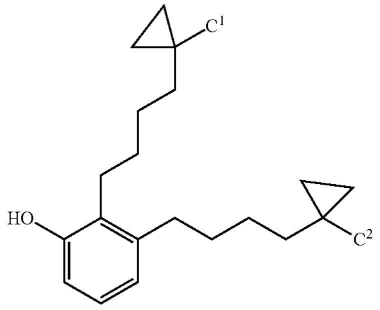 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 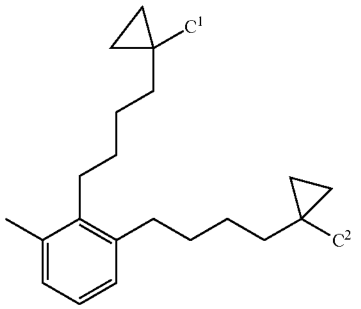 wherein $C^1$ = COOH and $C^2$ = CO—CoA; $C^1$ = CO—CoA and $C^2$ = COOH; or $C^1$ and $C^2$ = CO—CoA |
| 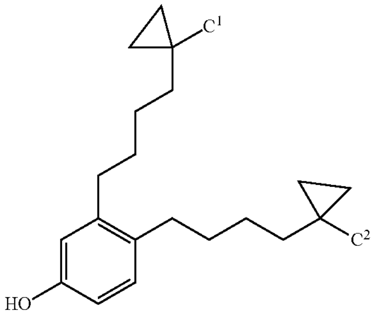 wherein $C^1$ = COOH and $C^2$ = CO—CoA; $C^1$ = CO—CoA and $C^2$ = COOH; or $C^1$ and $C^2$ = CO—CoA |
| 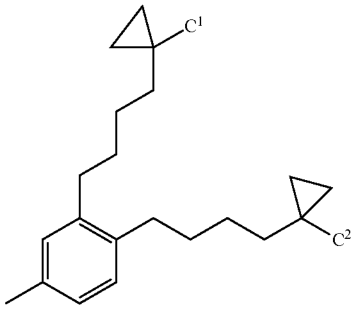 wherein $C^1$ = COOH and $C^2$ = CO—CoA; $C^1$ = CO—CoA and $C^2$ = COOH; or $C^1$ and $C^2$ = CO—CoA |
| 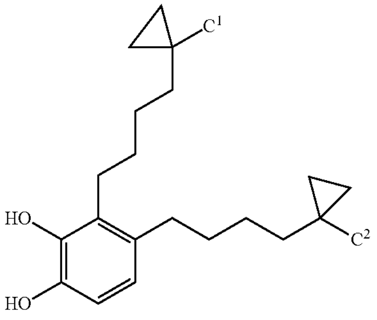 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 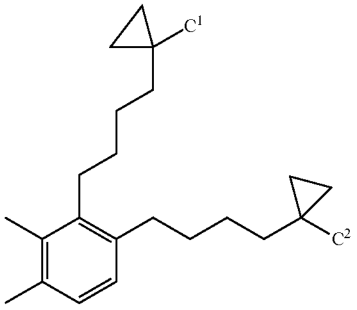 |
| wherein $C^1$ = COOH and $C^2$ = CO—CoA; $C^1$ = CO—CoA and $C^2$ = COOH; or $C^1$ and $C^2$ = CO—CoA |
| 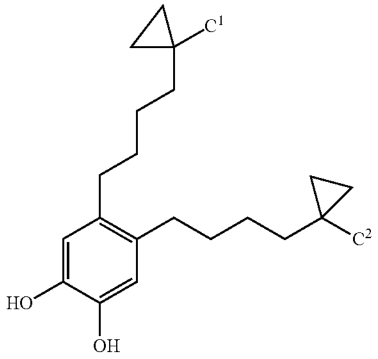 |
| wherein $C^1$ = COOH and $C^2$ = CO—CoA; $C^1$ = CO—CoA and $C^2$ = COOH; or $C^1$ and $C^2$ = CO—CoA |
| 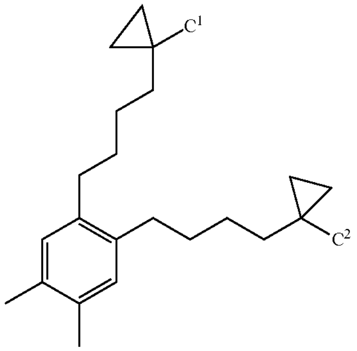 |
| wherein $C^1$ = COOH and $C^2$ = CO—CoA; $C^1$ = CO—CoA and $C^2$ = COOH; or $C^1$ and $C^2$ = CO—CoA |
| 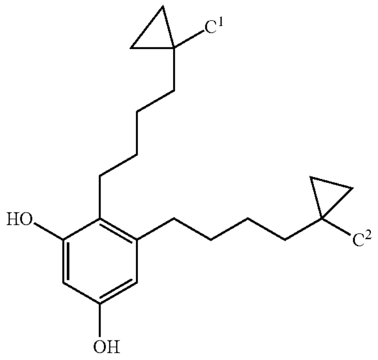 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 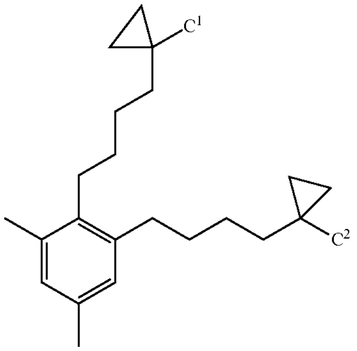 |
| wherein $C^1$ = COOH and $C^2$ = CO—CoA; $C^1$ = CO—CoA and $C^2$ = COOH; or $C^1$ and $C^2$ = CO—CoA |
| 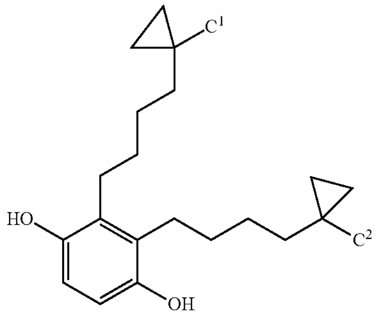 |
| wherein $C^1$ = COOH and $C^2$ = CO—CoA; $C^1$ = CO—CoA and $C^2$ = COOH; or $C^1$ and $C^2$ = CO—CoA |
| 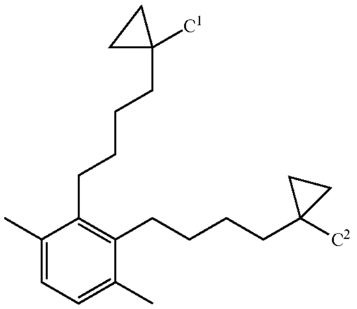 |
| wherein $C^1$ = COOH and $C^2$ = CO—CoA; $C^1$ = CO—CoA and $C^2$ = COOH; or $C^1$ and $C^2$ = CO—CoA |
| 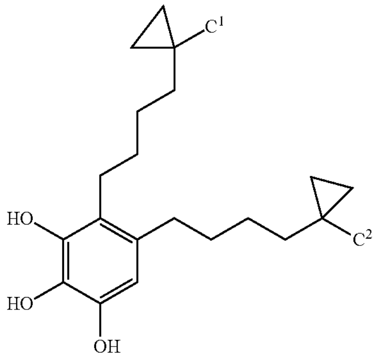 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 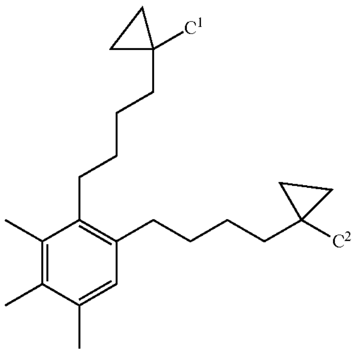 |
| wherein $C^1$ = COOH and $C^2$ = CO—CoA; $C^1$ = CO—CoA and $C^2$ = COOH; or $C^1$ and $C^2$ = CO—CoA |
| 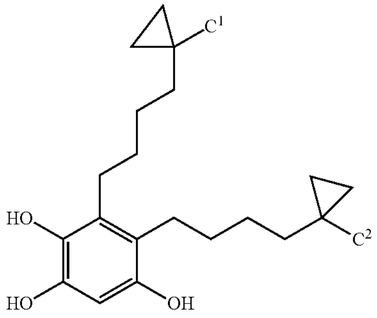 |
| wherein $C^1$ = COOH and $C^2$ = CO—CoA; $C^1$ = CO—CoA and $C^2$ = COOH; or $C^1$ and $C^2$ = CO—CoA |
| 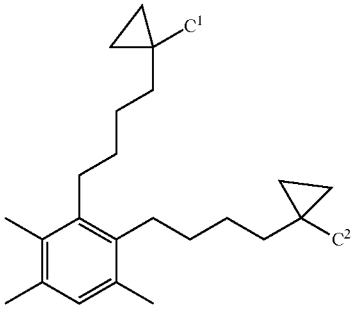 |
| wherein $C^1$ = COOH and $C^2$ = CO—CoA; $C^1$ = CO—CoA and $C^2$ = COOH; or $C^1$ and $C^2$ = CO—CoA |
| 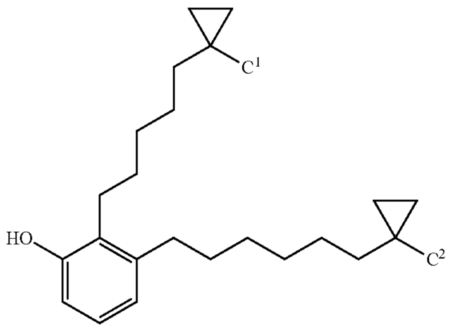 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 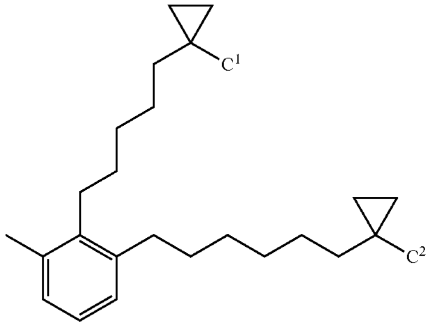 |
| wherein $C^1$ = COOH and $C^2$ = CO—CoA; $C^1$ = CO—CoA and $C^2$ = COOH; or $C^1$ and $C^2$ = CO—CoA |
| 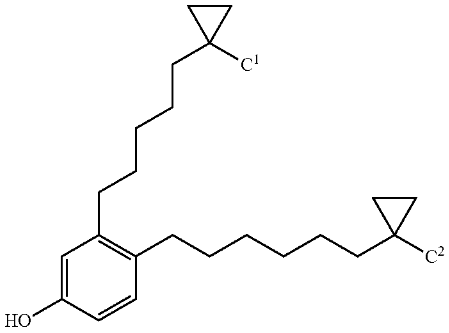 |
| wherein $C^1$ = COOH and $C^2$ = CO—CoA; $C^1$ = CO—CoA and $C^2$ = COOH; or $C^1$ and $C^2$ = CO—CoA |
| 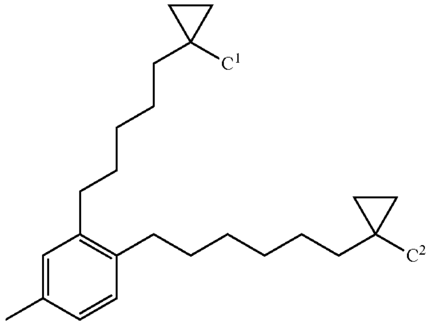 |
| wherein $C^1$ = COOH and $C^2$ = CO—CoA; $C^1$ = CO—CoA and $C^2$ = COOH; or $C^1$ and $C^2$ = CO—CoA |
| 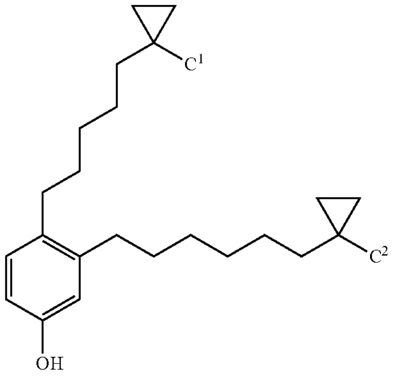 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

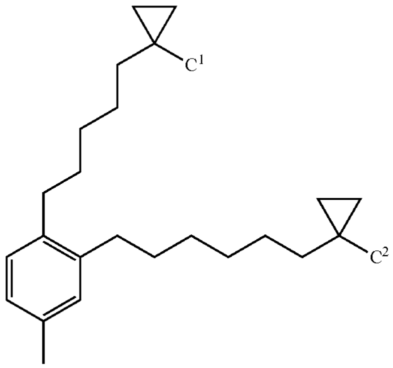

wherein $C^1$ = COOH and $C^2$ = CO—CoA; $C^1$ = CO—CoA and $C^2$ = COOH; or $C^1$ and $C^2$ = CO—CoA

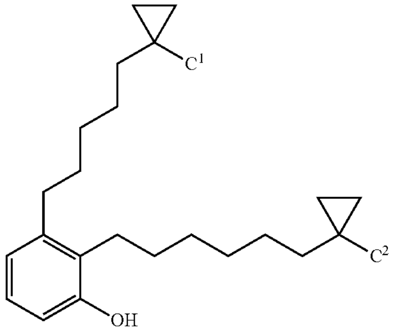

wherein $C^1$ = COOH and $C^2$ = CO—CoA; $C^1$ = CO—CoA and $C^2$ = COOH; or $C^1$ and $C^2$ = CO—CoA

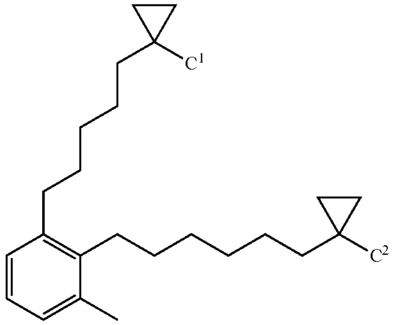

wherein $C^1$ = COOH and $C^2$ = CO—CoA; $C^1$ = CO—CoA and $C^2$ = COOH; or $C^1$ and $C^2$ = CO—CoA

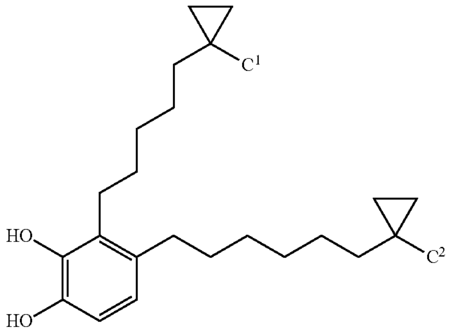

TABLE A-6-continued

| Structure |
| --- |

wherein $C^1$ = COOH and $C^2$ = CO—CoA; $C^1$ = CO—CoA and $C^2$ = COOH; or $C^1$ and $C^2$ = CO—CoA

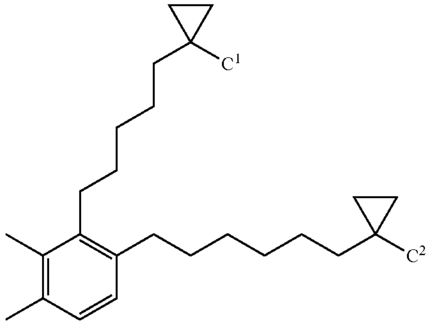

wherein $C^1$ = COOH and $C^2$ = CO—CoA; $C^1$ = CO—CoA and $C^2$ = COOH; or $C^1$ and $C^2$ = CO—CoA

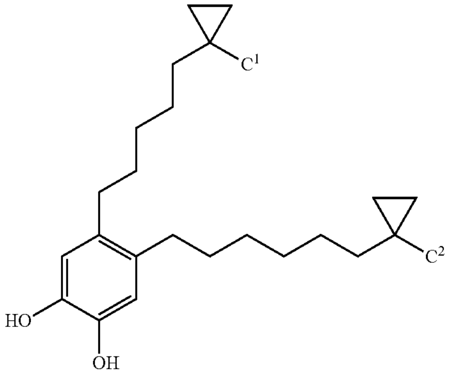

wherein $C^1$ = COOH and $C^2$ = CO—CoA; $C^1$ = CO—CoA and $C^2$ = COOH; or $C^1$ and $C^2$ = CO—CoA

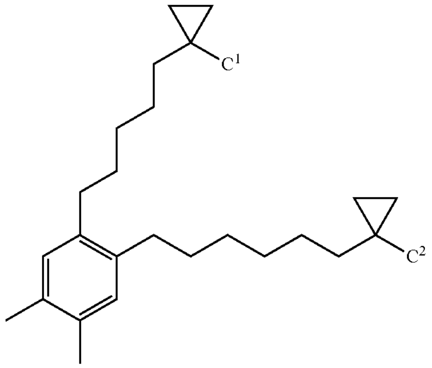

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 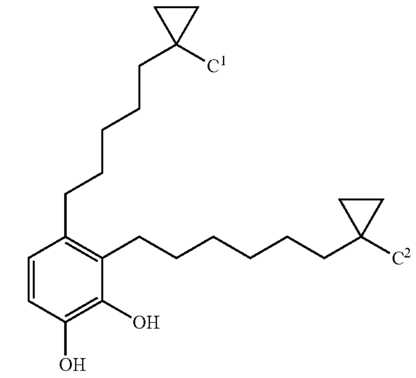 |
| wherein $C^1$ = COOH and $C^2$ = CO—CoA; $C^1$ = CO—CoA and $C^2$ = COOH; or $C^1$ and $C^2$ = CO—CoA |
| 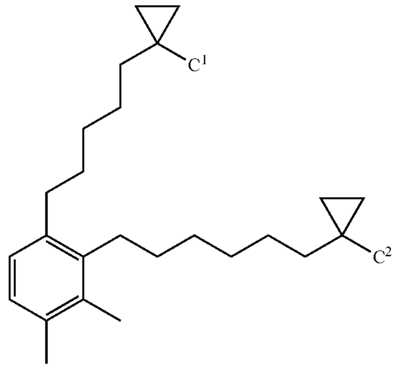 |
| wherein $C^1$ = COOH and $C^2$ = CO—CoA; $C^1$ = CO—CoA and $C^2$ = COOH; or $C^1$ and $C^2$ = CO—CoA |
| 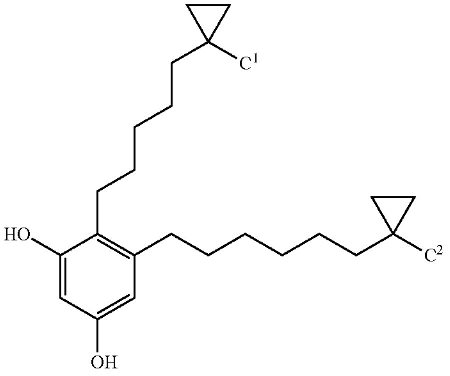 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 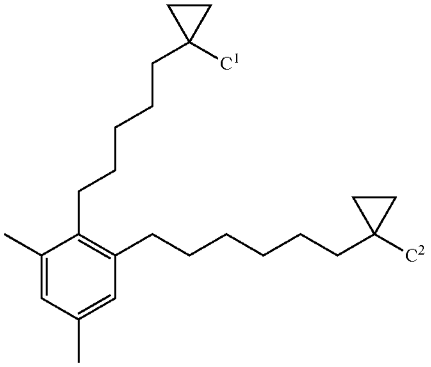 |
| wherein $C^1$ = COOH and $C^2$ = CO—CoA; $C^1$ = CO—CoA and $C^2$ = COOH; or $C^1$ and $C^2$ = CO—CoA |
| 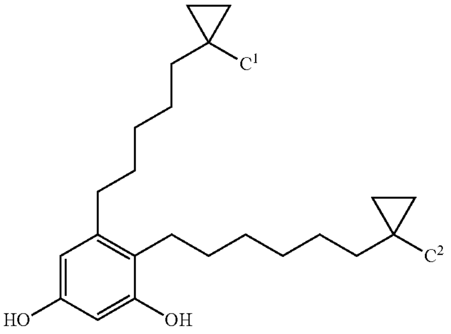 |
| wherein $C^1$ = COOH and $C^2$ = CO—CoA; $C^1$ = CO—CoA and $C^2$ = COOH; or $C^1$ and $C^2$ = CO—CoA |
| 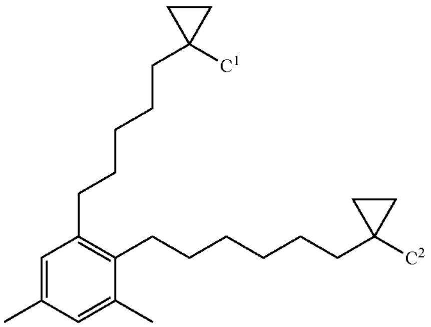 |
| wherein $C^1$ = COOH and $C^2$ = CO—CoA; $C^1$ = CO—CoA and $C^2$ = COOH; or $C^1$ and $C^2$ = CO—CoA |
| 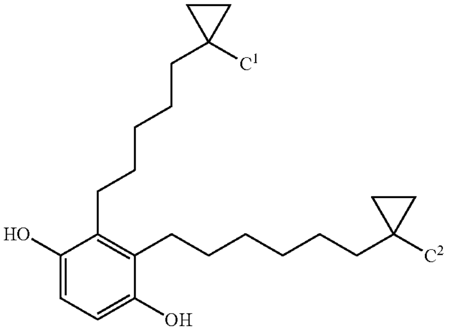 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 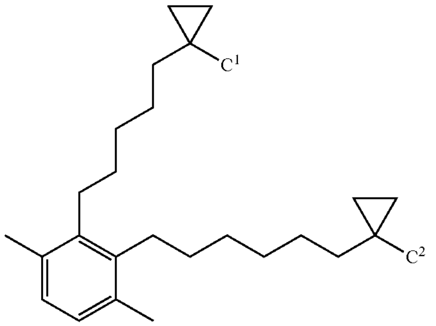 |
| wherein $C^1$ = COOH and $C^2$ = CO—CoA; $C^1$ = CO—CoA and $C^2$ = COOH; or $C^1$ and $C^2$ = CO—CoA |
| 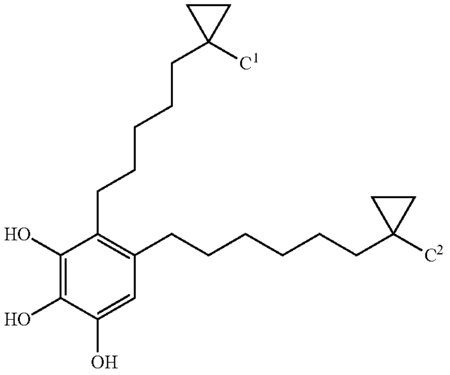 |
| wherein $C^1$ = COOH and $C^2$ = CO—CoA; $C^1$ = CO—CoA and $C^2$ = COOH; or $C^1$ and $C^2$ = CO—CoA |
| 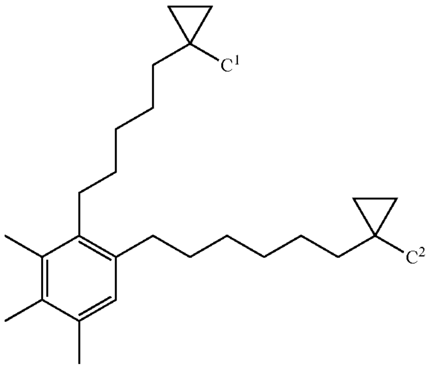 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 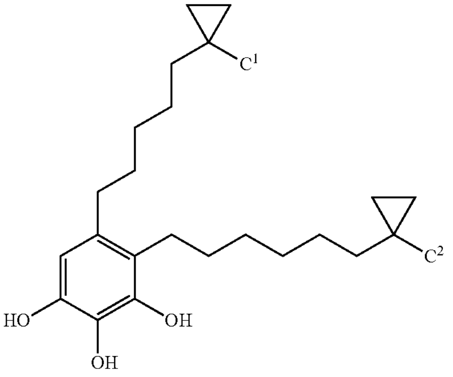 |
| wherein $C^1$ = COOH and $C^2$ = CO—CoA; $C^1$ = CO—CoA and $C^2$ = COOH; or $C^1$ and $C^2$ = CO—CoA |
| 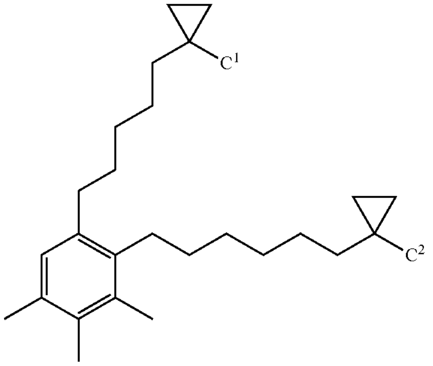 |
| wherein $C^1$ = COOH and $C^2$ = CO—CoA; $C^1$ = CO—CoA and $C^2$ = COOH; or $C^1$ and $C^2$ = CO—CoA |
| 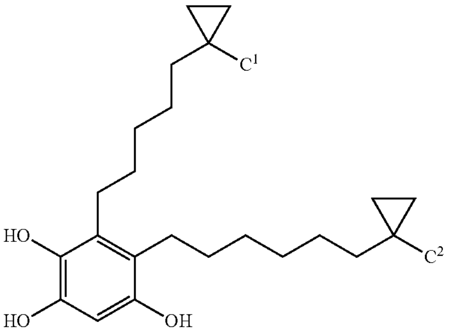 |
| wherein $C^1$ = COOH and $C^2$ = CO—CoA; $C^1$ = CO—CoA and $C^2$ = COOH; or $C^1$ and $C^2$ = CO—CoA |
| 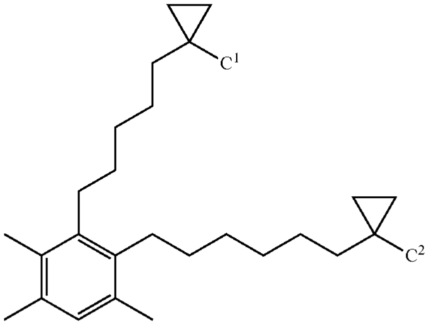 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 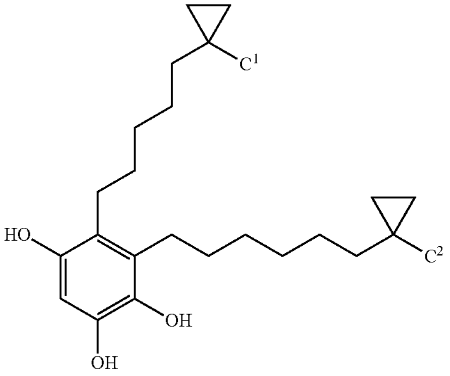 |
| wherein $C^1$ = COOH and $C^2$ = CO—CoA; $C^1$ = CO—CoA and $C^2$ = COOH; or $C^1$ and $C^2$ = CO—CoA |
| 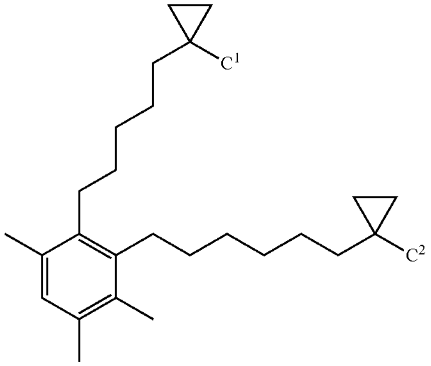 |
| wherein $C^1$ = COOH and $C^2$ = CO—CoA; $C^1$ = CO—CoA and $C^2$ = COOH; or $C^1$ and $C^2$ = CO—CoA |
| 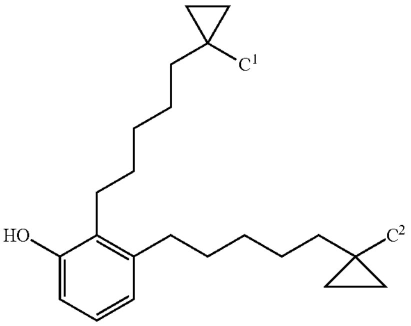 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 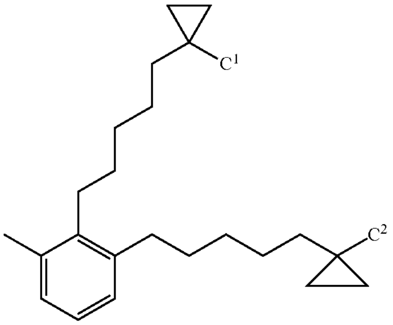 |
| wherein $C^1$ = COOH and $C^2$ = CO—CoA; $C^1$ = CO—CoA and $C^2$ = COOH; or $C^1$ and $C^2$ = CO—CoA |
| 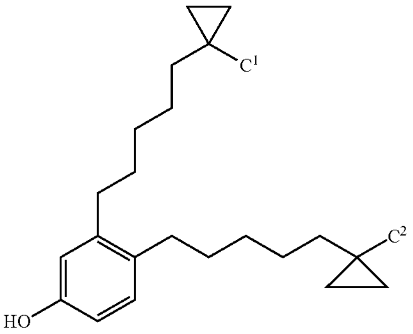 |
| wherein $C^1$ = COOH and $C^2$ = CO—CoA; $C^1$ = CO—CoA and $C^2$ = COOH; or $C^1$ and $C^2$ = CO—CoA |
| 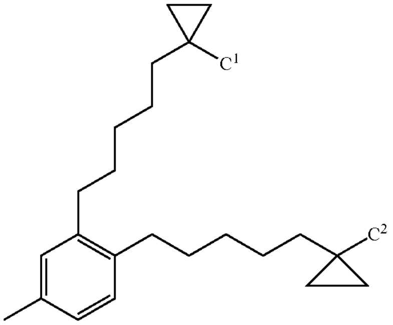 |
| wherein $C^1$ = COOH and $C^2$ = CO—CoA; $C^1$ = CO—CoA and $C^2$ = COOH; or $C^1$ and $C^2$ = CO—CoA |
| 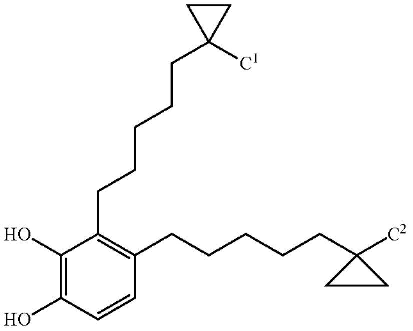 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|

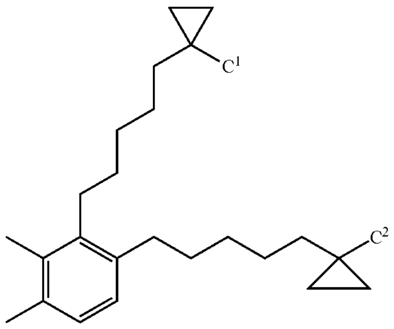

wherein $C^1$ = COOH and $C^2$ = CO—CoA; $C^1$ = CO—CoA and $C^2$ = COOH; or $C^1$ and $C^2$ = CO—CoA

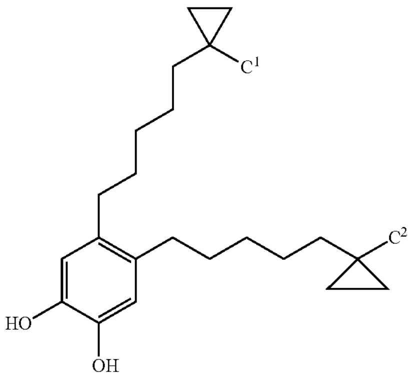

wherein $C^1$ = COOH and $C^2$ = CO—CoA; $C^1$ = CO—CoA and $C^2$ = COOH; or $C^1$ and $C^2$ = CO—CoA

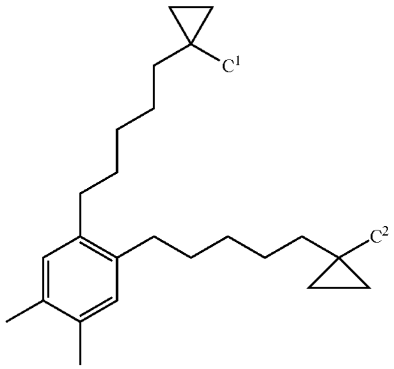

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|

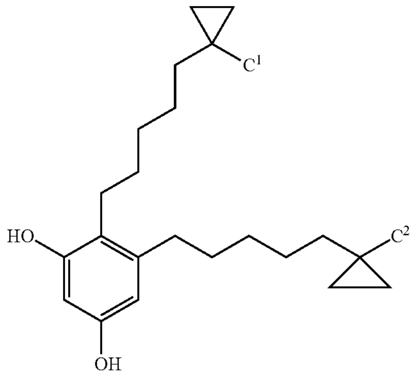

wherein $C^1$ = COOH and $C^2$ = CO—CoA; $C^1$ = CO—CoA and $C^2$ = COOH; or $C^1$ and $C^2$ = CO—CoA

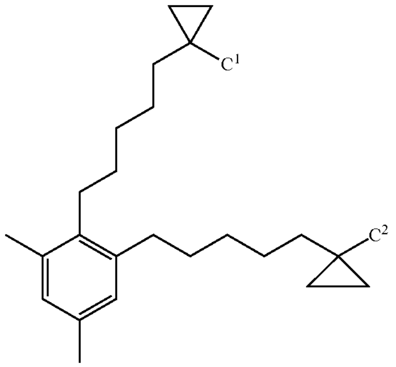

wherein $C^1$ = COOH and $C^2$ = CO—CoA; $C^1$ = CO—CoA and $C^2$ = COOH; or $C^1$ and $C^2$ = CO—CoA

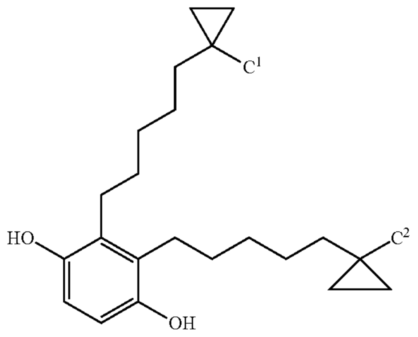

wherein $C^1$ = COOH and $C^2$ = CO—CoA; $C^1$ = CO—CoA and $C^2$ = COOH; or $C^1$ and $C^2$ = CO—CoA

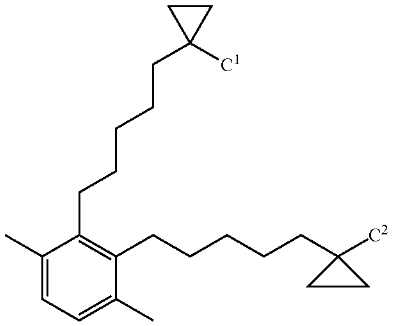

TABLE A-6-continued

| Structure |
| --- |

wherein $C^1$ = COOH and $C^2$ = CO—CoA; $C^1$ = CO—CoA and $C^2$ = COOH; or $C^1$ and $C^2$ = CO—CoA

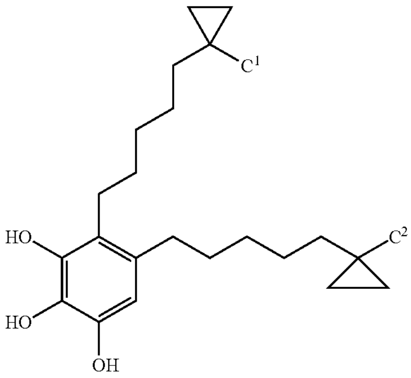

wherein $C^1$ = COOH and $C^2$ = CO—CoA; $C^1$ = CO—CoA and $C^2$ = COOH; or $C^1$ and $C^2$ = CO—CoA

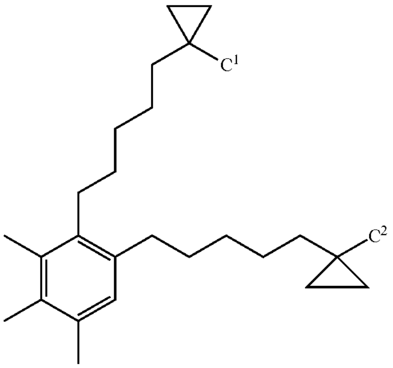

wherein $C^1$ = COOH and $C^2$ = CO—CoA; $C^1$ = CO—CoA and $C^2$ = COOH; or $C^1$ and $C^2$ = CO—CoA

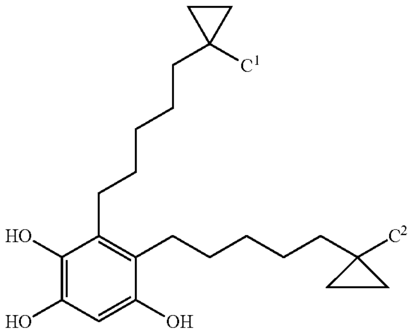

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |

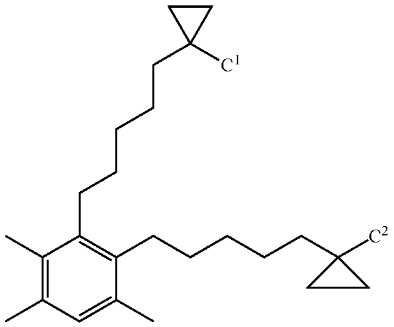

wherein $C^1$ = COOH and $C^2$ = CO—CoA; $C^1$ = CO—CoA and $C^2$ = COOH; or $C^1$ and $C^2$ = CO—CoA

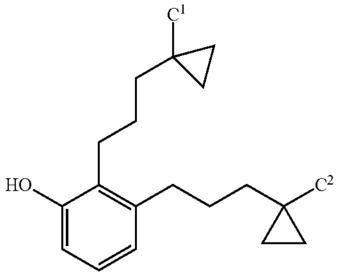

wherein $C^1$ = COOH and $C^2$ = CO—CoA; $C^1$ = CO—CoA and $C^2$ = COOH; or $C^1$ and $C^2$ = CO—CoA

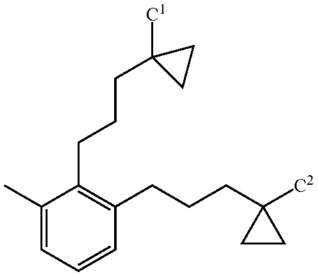

wherein $C^1$ = COOH and $C^2$ = CO—CoA; $C^1$ = CO—CoA and $C^2$ = COOH; or $C^1$ and $C^2$ = CO—CoA

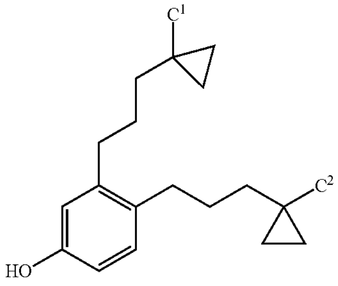

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |
| 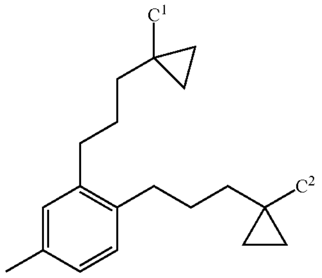<br>wherein $C^1$ = COOH and $C^2$ = CO—CoA; $C^1$ = CO—CoA and $C^2$ = COOH; or $C^1$ and $C^2$ = CO—CoA |
| 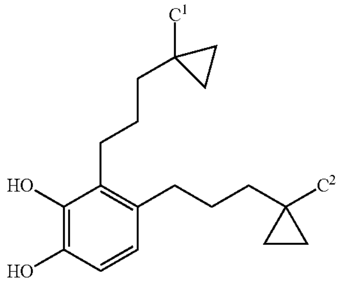<br>wherein $C^1$ = COOH and $C^2$ = CO—CoA; $C^1$ = CO—CoA and $C^2$ = COOH; or $C^1$ and $C^2$ = CO—CoA |
| 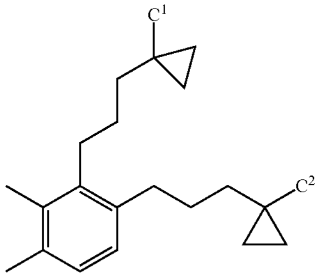<br>wherein $C^1$ = COOH and $C^2$ = CO—CoA; $C^1$ = CO—CoA and $C^2$ = COOH; or $C^1$ and $C^2$ = CO—CoA |
| 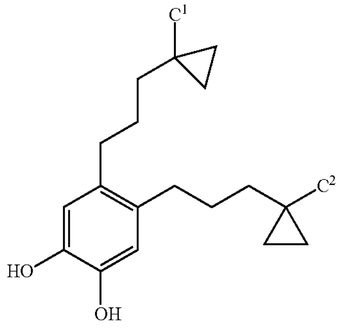<br>wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 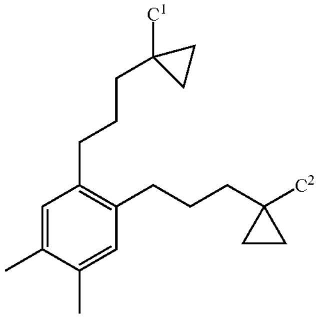<br>wherein $C^1$ = COOH and $C^2$ = CO—CoA; $C^1$ = CO—CoA and $C^2$ = COOH; or $C^1$ and $C^2$ = CO—CoA |
| 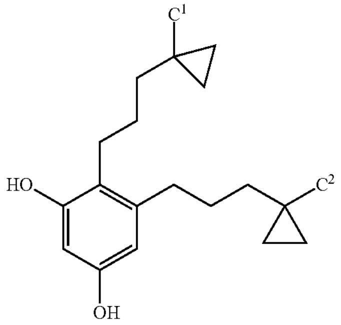<br>wherein $C^1$ = COOH and $C^2$ = CO—CoA; $C^1$ = CO—CoA and $C^2$ = COOH; or $C^1$ and $C^2$ = CO—CoA |
| 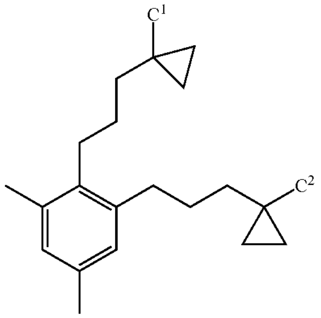<br>wherein $C^1$ = COOH and $C^2$ = CO—CoA; $C^1$ = CO—CoA and $C^2$ = COOH; or $C^1$ and $C^2$ = CO—CoA |
| 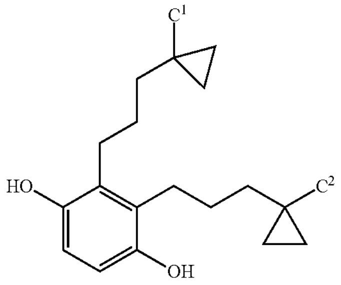<br>wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 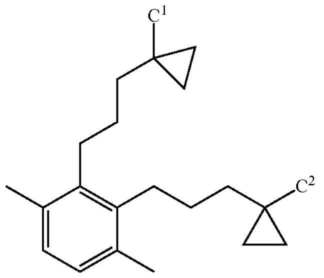 |
| wherein $C^1$ = COOH and $C^2$ = CO—CoA; $C^1$ = CO—CoA and $C^2$ = COOH; or $C^1$ and $C^2$ = CO—CoA |
| 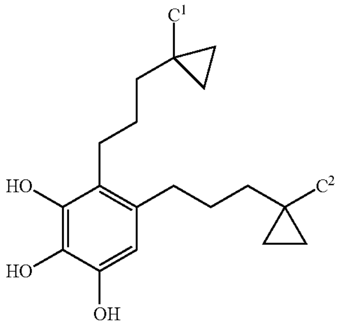 |
| wherein $C^1$ = COOH and $C^2$ = CO—CoA; $C^1$ = CO—CoA and $C^2$ = COOH; or $C^1$ and $C^2$ = CO—CoA |
| 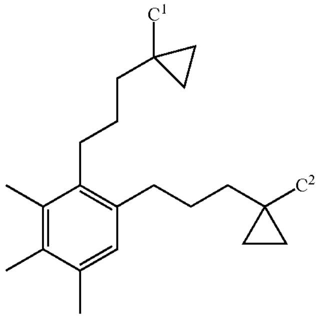 |
| wherein $C^1$ = COOH and $C^2$ = CO—CoA; $C^1$ = CO—CoA and $C^2$ = COOH; or $C^1$ and $C^2$ = CO—CoA |
| 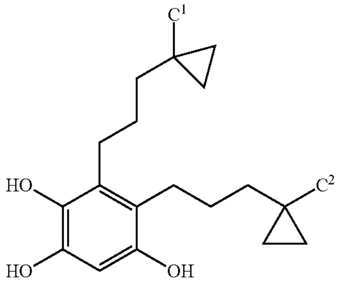 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 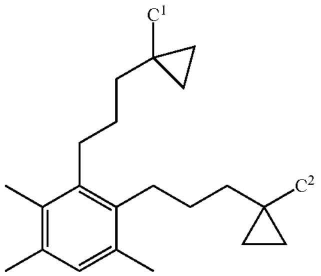 |
| wherein $C^1$ = COOH and $C^2$ = CO—CoA; $C^1$ = CO—CoA and $C^2$ = COOH; or $C^1$ and $C^2$ = CO—CoA |
| 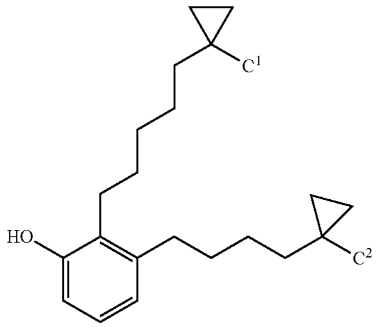 |
| wherein $C^1$ = COOH and $C^2$ = CO—CoA; $C^1$ = CO—CoA and $C^2$ = COOH; or $C^1$ and $C^2$ = CO—CoA |
| 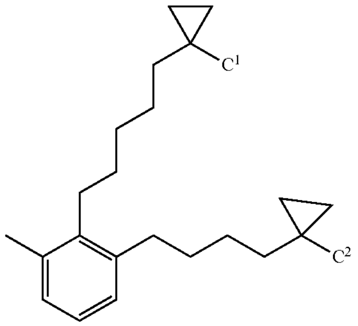 |
| wherein $C^1$ = COOH and $C^2$ = CO—CoA; $C^1$ = CO—CoA and $C^2$ = COOH; or $C^1$ and $C^2$ = CO—CoA |
| 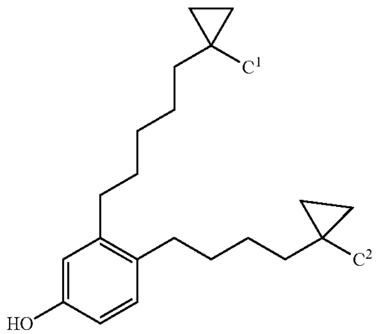 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 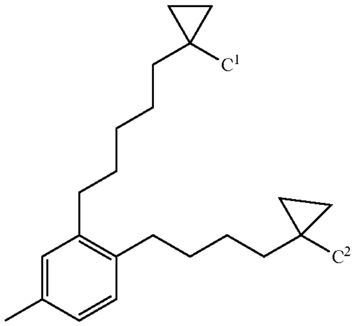 |
| wherein $C^1$ = COOH and $C^2$ = CO—CoA; $C^1$ = CO—CoA and $C^2$ = COOH; or $C^1$ and $C^2$ = CO—CoA |
| 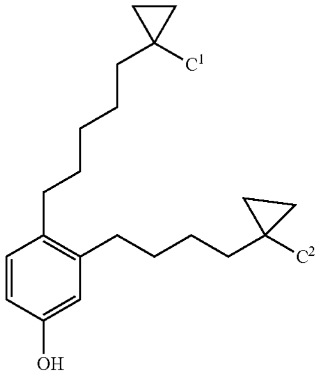 |
| wherein $C^1$ = COOH and $C^2$ = CO—CoA; $C^1$ = CO—CoA and $C^2$ = COOH; or $C^1$ and $C^2$ = CO—CoA |
| 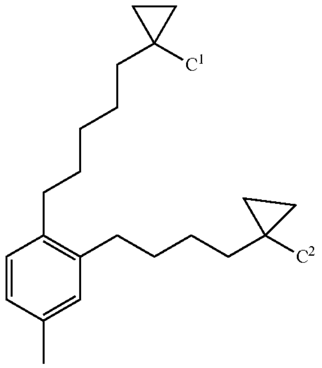 |
| wherein $C^1$ = COOH and $C^2$ = CO—CoA; $C^1$ = CO—CoA and $C^2$ = COOH; or $C^1$ and $C^2$ = CO—CoA |
| 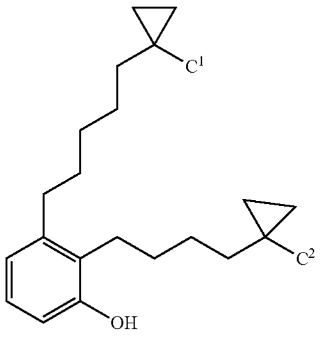 |

TABLE A-6-continued

| Structure |
| --- |
| wherein $C^1$ = COOH and $C^2$ = CO—CoA; $C^1$ = CO—CoA and $C^2$ = COOH; or $C^1$ and $C^2$ = CO—CoA |
| 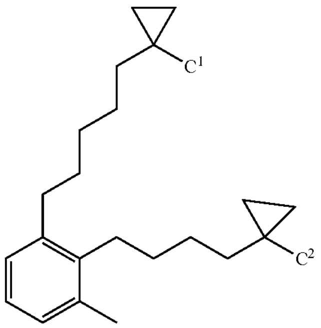 |
| wherein $C^1$ = COOH and $C^2$ = CO—CoA; $C^1$ = CO—CoA and $C^2$ = COOH; or $C^1$ and $C^2$ = CO—CoA |
| 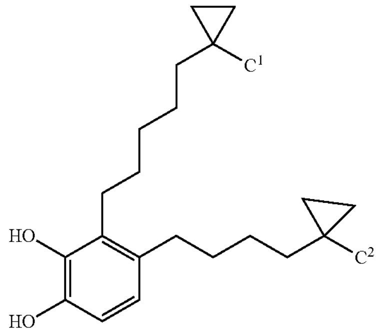 |
| wherein $C^1$ = COOH and $C^2$ = CO—CoA; $C^1$ = CO—CoA and $C^2$ = COOH; or $C^1$ and $C^2$ = CO—CoA |
| 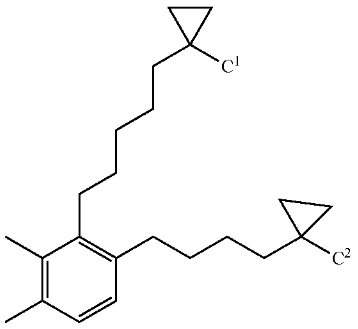 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 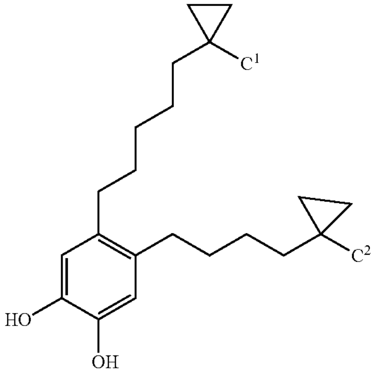 wherein $C^1$ = COOH and $C^2$ = CO—CoA; $C^1$ = CO—CoA and $C^2$ = COOH; or $C^1$ and $C^2$ = CO—CoA |
| 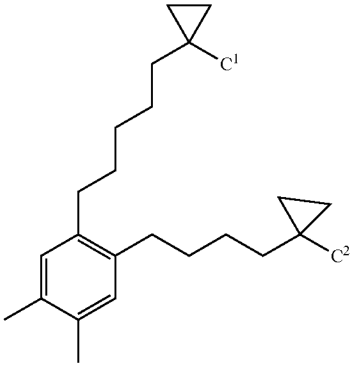 wherein $C^1$ = COOH and $C^2$ = CO—CoA; $C^1$ = CO—CoA and $C^2$ = COOH; or $C^1$ and $C^2$ = CO—CoA |
| 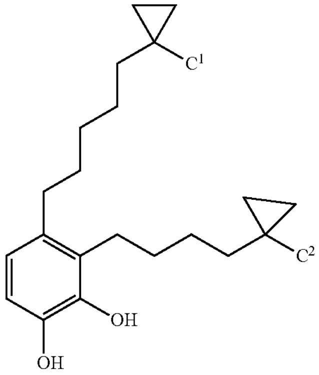 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 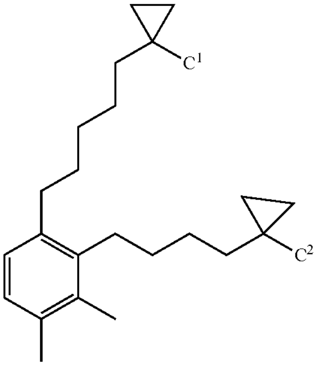 wherein $C^1$ = COOH and $C^2$ = CO—CoA; $C^1$ = CO—CoA and $C^2$ = COOH; or $C^1$ and $C^2$ = CO—CoA |
| 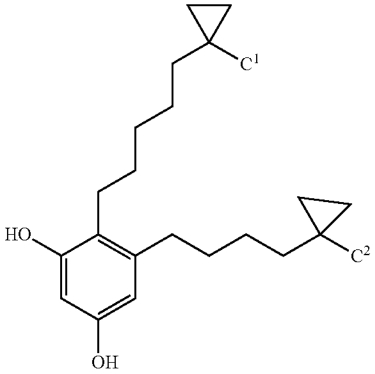 wherein $C^1$ = COOH and $C^2$ = CO—CoA; $C^1$ = CO—CoA and $C^2$ = COOH; or $C^1$ and $C^2$ = CO—CoA |
| 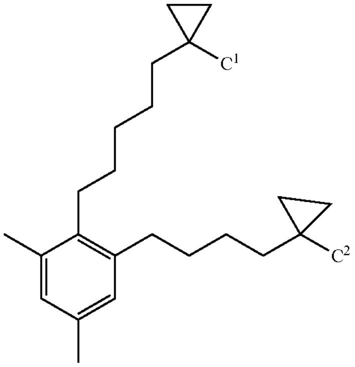 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 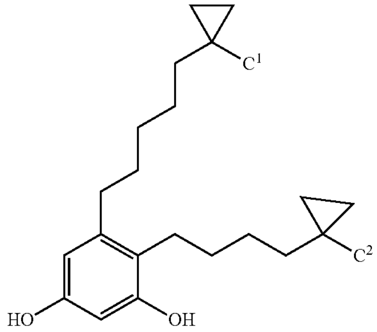 |
| wherein $C^1$ = COOH and $C^2$ = CO—CoA; $C^1$ = CO—CoA and $C^2$ = COOH; or $C^1$ and $C^2$ = CO—CoA |
| 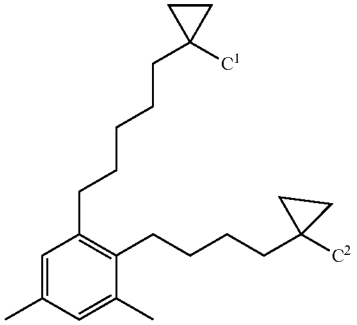 |
| wherein $C^1$ = COOH and $C^2$ = CO—CoA; $C^1$ = CO—CoA and $C^2$ = COOH; or $C^1$ and $C^2$ = CO—CoA |
| 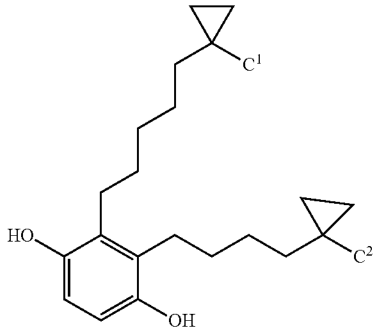 |
| wherein $C^1$ = COOH and $C^2$ = CO—CoA; $C^1$ = CO—CoA and $C^2$ = COOH; or $C^1$ and $C^2$ = CO—CoA |
| 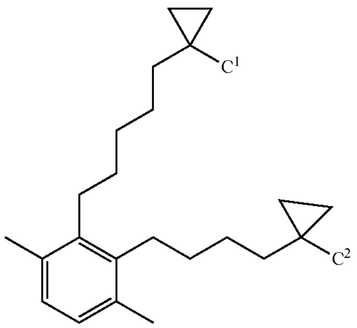 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 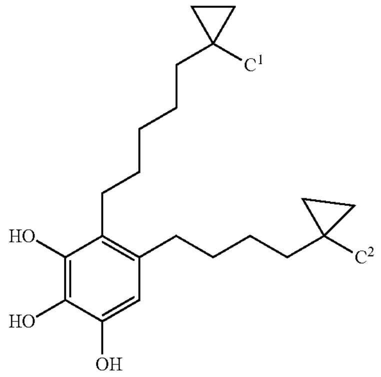 |
| wherein $C^1$ = COOH and $C^2$ = CO—CoA; $C^1$ = CO—CoA and $C^2$ = COOH; or $C^1$ and $C^2$ = CO—CoA |
| 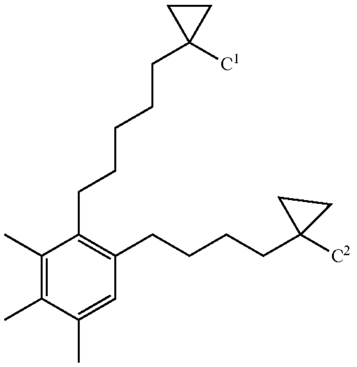 |
| wherein $C^1$ = COOH and $C^2$ = CO—CoA; $C^1$ = CO—CoA and $C^2$ = COOH; or $C^1$ and $C^2$ = CO—CoA |
| 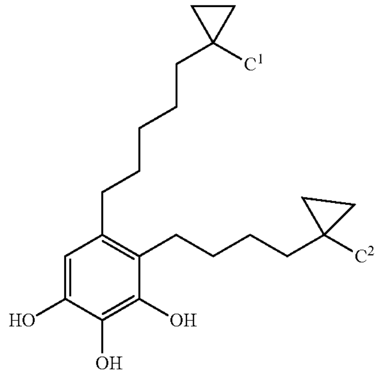 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
|---|
| 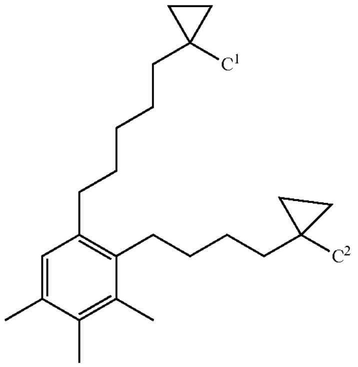 |
| wherein $C^1$ = COOH and $C^2$ = CO—CoA; $C^1$ = CO—CoA and $C^2$ = COOH; or $C^1$ and $C^2$ = CO—CoA |
| 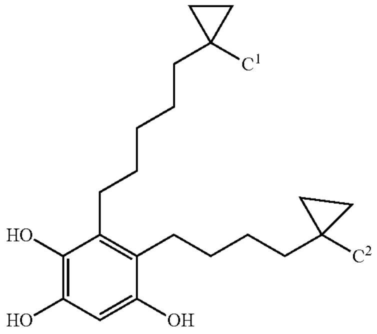 |
| wherein $C^1$ = COOH and $C^2$ = CO—CoA; $C^1$ = CO—CoA and $C^2$ = COOH; or $C^1$ and $C^2$ = CO—CoA |
| 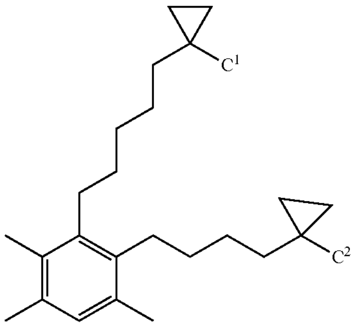 |
| wherein $C^1$ = COOH and $C^2$ = CO—CoA; $C^1$ = CO—CoA and $C^2$ = COOH; or $C^1$ and $C^2$ = CO—CoA |
| 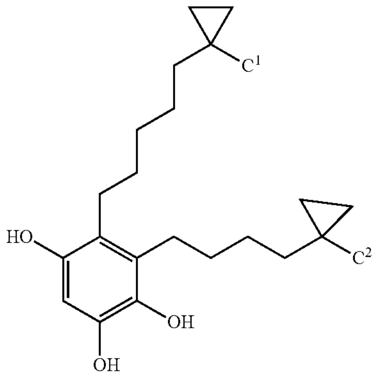 |

TABLE A-6-continued

| Structure |
|---|
| wherein $C^1$ = COOH and $C^2$ = CO—CoA; $C^1$ = CO—CoA and $C^2$ = COOH; or $C^1$ and $C^2$ = CO—CoA |
| 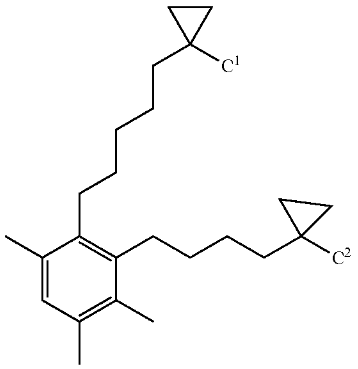 |
| wherein $C^1$ = COOH and $C^2$ = CO—CoA; $C^1$ = CO—CoA and $C^2$ = COOH; or $C^1$ and $C^2$ = CO—CoA |
| 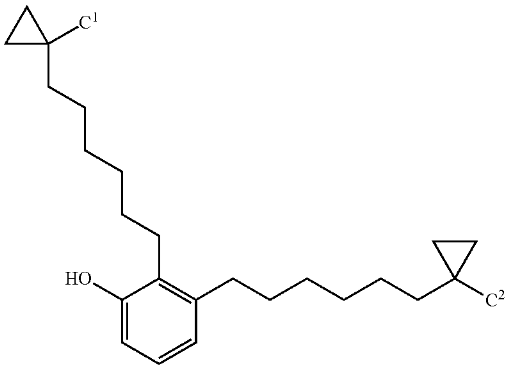 |
| wherein $C^1$ = COOH and $C^2$ = CO—CoA; $C^1$ = CO—CoA and $C^2$ = COOH; or $C^1$ and $C^2$ = CO—CoA |
| 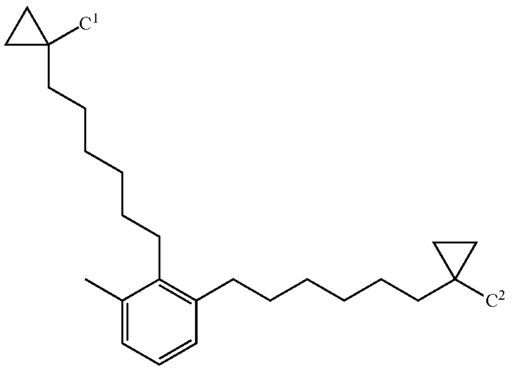 |
| wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 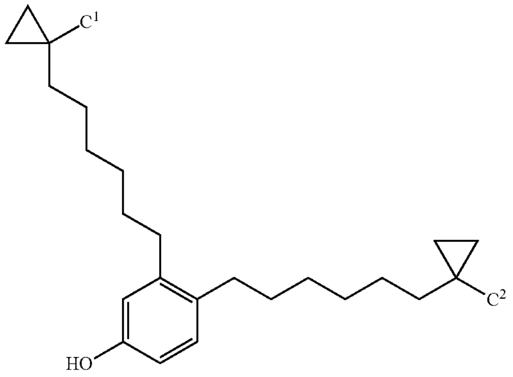 wherein $C^1$ = COOH and $C^2$ = CO—CoA; $C^1$ = CO—CoA and $C^2$ = COOH; or $C^1$ and $C^2$ = CO—CoA |
| 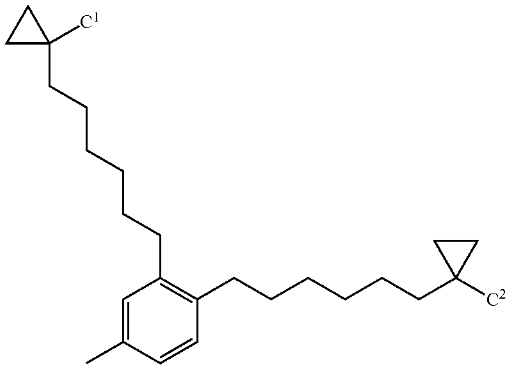 wherein $C^1$ = COOH and $C^2$ = CO—CoA; $C^1$ = CO—CoA and $C^2$ = COOH; or $C^1$ and $C^2$ = CO—CoA |
| 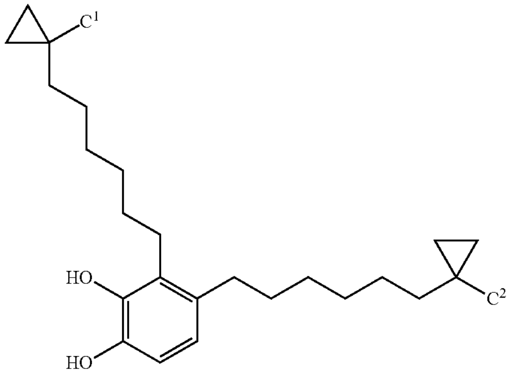 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |
| 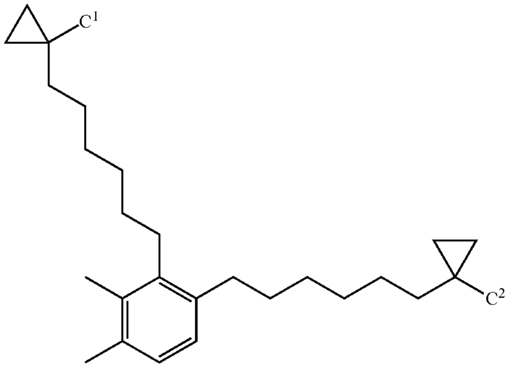 wherein $C^1$ = COOH and $C^2$ = CO—CoA; $C^1$ = CO—CoA and $C^2$ = COOH; or $C^1$ and $C^2$ = CO—CoA |
| 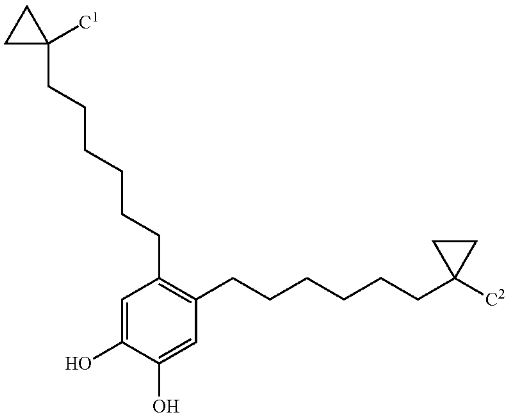 wherein $C^1$ = COOH and $C^2$ = CO—CoA; $C^1$ = CO—CoA and $C^2$ = COOH; or $C^1$ and $C^2$ = CO—CoA |
| 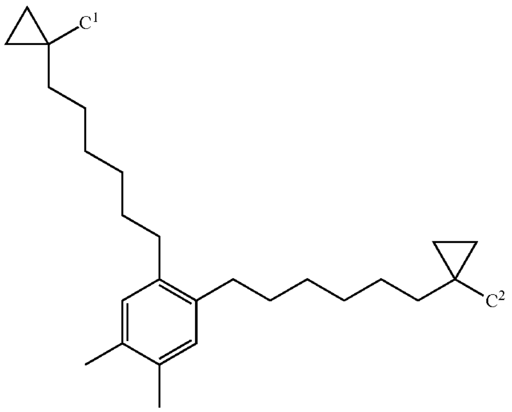 wherein $C^1$ = COOH and $C^2$ = CO—CoA; $C^1$ = CO—CoA and $C^2$ = COOH; or $C^1$ and $C^2$ = CO—CoA |

TABLE A-6-continued

| Structure |
| --- |

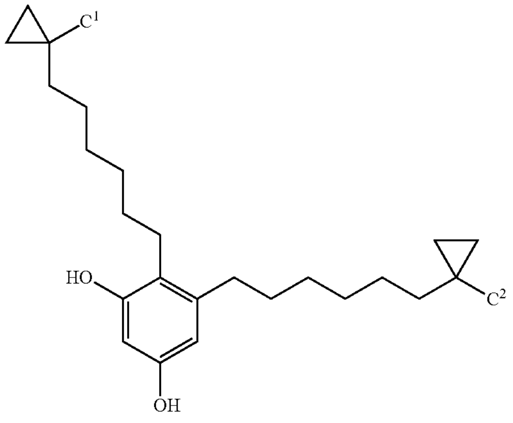

wherein $C^1$ = COOH and $C^2$ = CO—CoA; $C^1$ = CO—CoA and $C^2$ = COOH; or $C^1$ and $C^2$ = CO—CoA

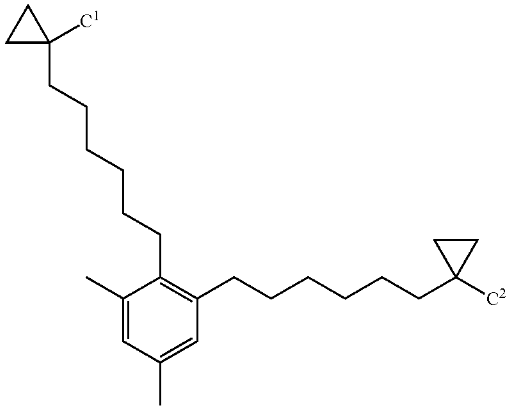

wherein $C^1$ = COOH and $C^2$ = CO—CoA; $C^1$ = CO—CoA and $C^2$ = COOH; or $C^1$ and $C^2$ = CO—CoA

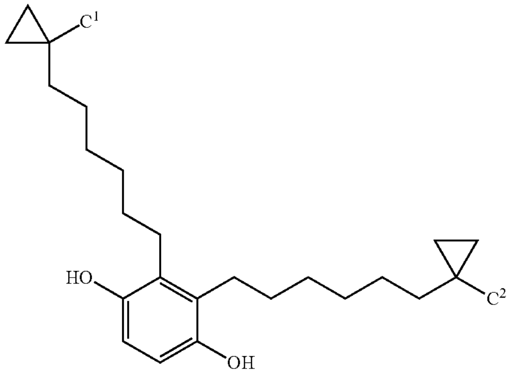

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
| --- |

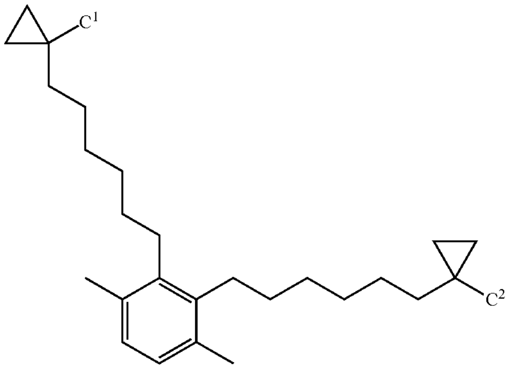

wherein $C^1$ = COOH and $C^2$ = CO—CoA; $C^1$ = CO—CoA and $C^2$ = COOH; or $C^1$ and $C^2$ = CO—CoA

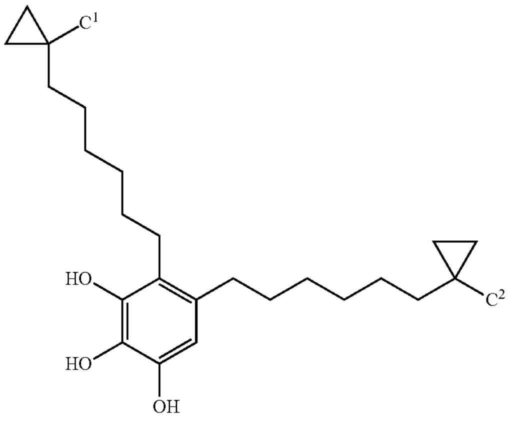

wherein $C^1$ = COOH and $C^2$ = CO—CoA; $C^1$ = CO—CoA and $C^2$ = COOH; or $C^1$ and $C^2$ = CO—CoA

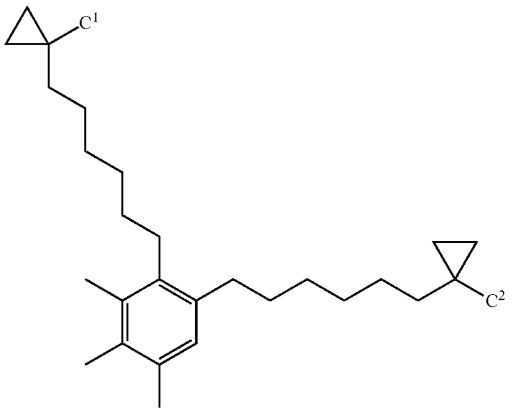

wherein $C^1$ = COOH and $C^2$ = CO—CoA; $C^1$ = CO—CoA and $C^2$ = COOH; or $C^1$ and $C^2$ = CO—CoA TABLE A-6-continued

| Structure |
|---|
| 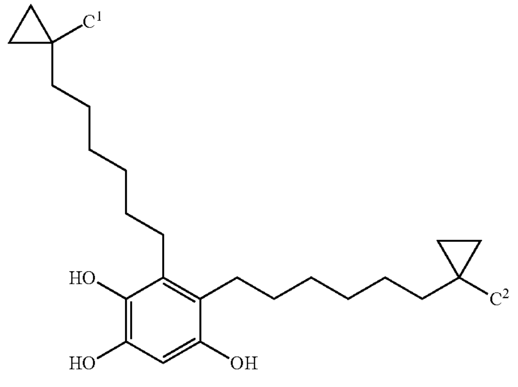 wherein $C^1$ = COOH and $C^2$ = CO—CoA; $C^1$ = CO—CoA and $C^2$ = COOH; or $C^1$ and $C^2$ = CO—CoA |
| 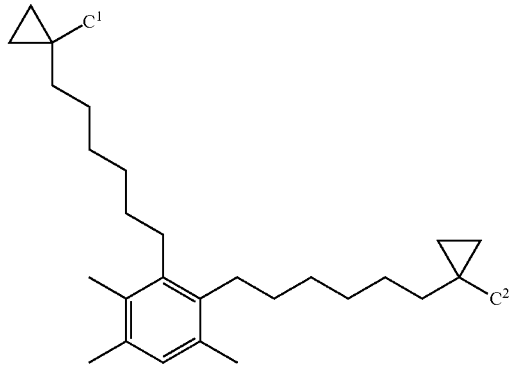 wherein $C^1$ = COOH and $C^2$ = CO—CoA; $C^1$ = CO—CoA and $C^2$ = COOH; or $C^1$ and $C^2$ = CO—CoA |

In some embodiments, the compound of Formula (I) has any one of the structures shown in Table A-1, A-2, A-3, A-4 and defined by $C^1$ and $C^2$, A-5 and defined by $C^1$ and $C^2$, or A-6 and defined by $C^1$ and $C^2$, wherein the compound's phenyl ring is mono- or di-substituted with —OH or —$CH_3$, or a pharmaceutically acceptable salt or solvate thereof. In some embodiments, the pharmaceutically acceptable salt of a compound having any one of the structures shown in Table A-1, A-2, A-3, A-4 and defined by $C^1$ and $C^2$, A-5 and defined by $C^1$ and $C^2$, or A-6 and defined by $C^1$ and $C^2$ is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the compound of Formula (I), (IA), (IB), or (IC) is a Coenzyme A mono(thioester) or di(thioester) of a compound having any one of the structures shown in Table A-7, Table A-8, Table A-9, Table A-10, Table A-11, or Table A-12, or a pharmaceutically acceptable salt or solvate thereof. In some embodiments, the pharmaceutically acceptable salt of a compound having any one of the structures shown in Table A-7, Table A-8, Table A-9, Table A-10, Table A-11, or Table A-12 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the pharmaceutically acceptable salt of a compound having any one of the structures shown in Table A-7, Table A-8, Table A-9, Table A-10, Table A-11, or Table A-12 is a zinc salt. In some embodiments, the pharmaceutically acceptable salt of a compound having any one of the structures shown in Table A-8, Table A-9, or Table A-12 is a zinc salt. For example, a zinc salt of Compound 1-61 in Table A-9 has the structure depicted immediately below:

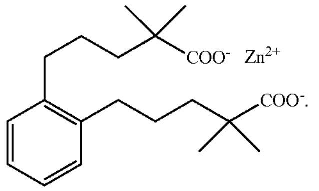

TABLE A-7

| Compound No. | Structure and Name |
|---|---|
| III-1 | 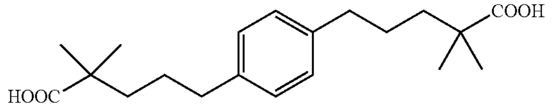 [SMILES: CC(C)(CCCc1ccc(CCCC(C)(C)C(=O)O)cc1)C(=O)O] 5,5'-(1,4-phenylene)bis(2,2-dimethylpentanoic acid) |
| I-1 | 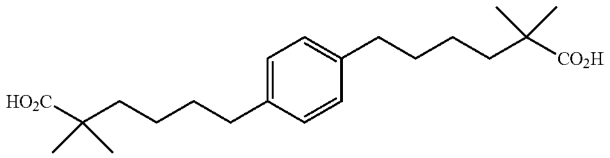 [SMILES: CC(C)(CCCCc1ccc(CCCCC(C)(C)C(=O)O)cc1)C(=O)O] 6-[4-(5-Carboxy-5-methyl-hexyl)-phenyl]-2,2,-dimethylhexanoic acid |

TABLE A-7-continued

| Compound No. | Structure and Name |
| --- | --- |
| I-2 | 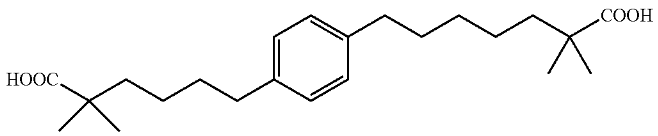 [SMILES: CC(C)(CCCCCc1ccc(CCCCC(C)(C)C(=O)O)cc1)C(=O)O]<br>7-(4-(5-Carboxy-5-methylhexyl)phenyl)-2,2-dimethylheptanoic acid |
| I-3 | 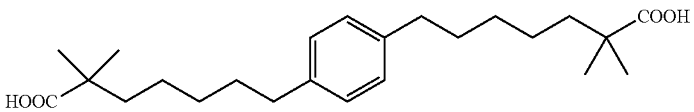 [SMILES: CC(C)(CCCCCc1ccc(CCCCCC(C)(C)C(=O)O)cc1)C(=O)O]<br>7,7'-(1,4-Phenylene)bis(2,2-dimethylheptanoic acid) |
| I-4 | 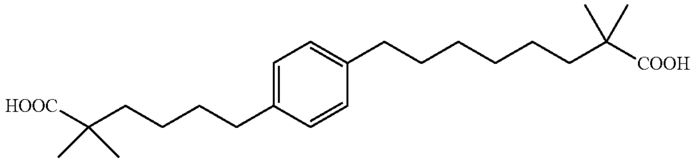 [SMILES: CC(C)(CCCCCCc1ccc(CCCCC(C)(C)C(=O)O)cc1)C(=O)O]<br>8-(4-(5-Carboxy-5-methylhexyl)phenyl)-2,2-dimethyloctanoic acid |
| I-5 | 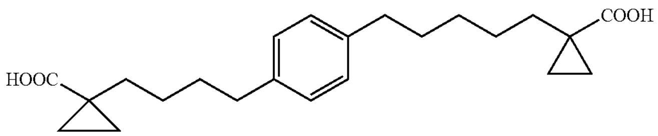 [SMILES: O=C(O)C1(CCCCCc2ccc(CCCCC3(C(=O)O)CC3)cc2)CC1]<br>1-(5-(4-(4-(1-carboxycyclopropyl)butyl)phenyl)pentyl)cyclopropane-1-carboxylic acid |
| I-6 | 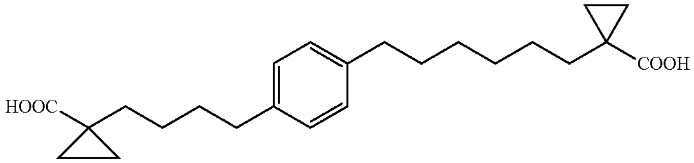 [SMILES: O=C(O)C1(CCCCCCc2ccc(CCCCC3(C(=O)O)CC3)cc2)CC1]<br>1-(6-(4-(4-(1-carboxycyclopropyl)butyl)phenyl)hexyl)cyclopropane-1-carboxylic acid |
| I-7 | 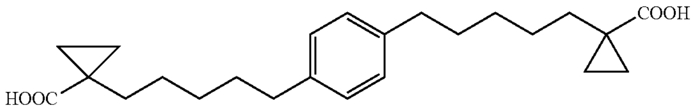 [SMILES: O=C(O)C1(CCCCCc2ccc(CCCCCC3(C(=O)O)CC3)cc2)CC1]<br>1,1'-(1,4-phenylenebis(pentane-5,1-diyl))bis(cyclopropane-1-carboxylic acid) |
| I-8 | 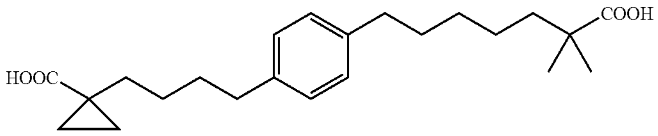 [SMILES: CC(C)(CCCCCc1ccc(CCCCC2(C(=O)O)CC2)cc1)C(=O)O]<br>1-(4-(4-(6-carboxy-6-methylheptyl)phenyl)butyl)cyclopropane-1-carboxylic acid |

TABLE A-7-continued

| Compound No. | Structure and Name |
| --- | --- |
| I-9 | 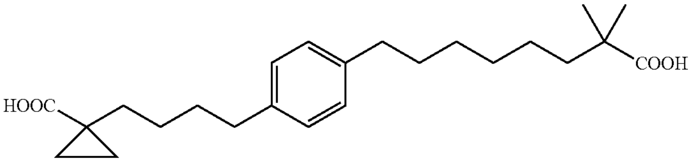 [SMILES: CC(C)(CCCCCCc1ccc(CCCCC2(C(=O)O)CC2)cc1)C(=O)O] 1-(4-(4-(7-carboxy-7-methyloctyl)phenyl)butyl)cyclopropane-1-carboxylic acid |
| I-10 | 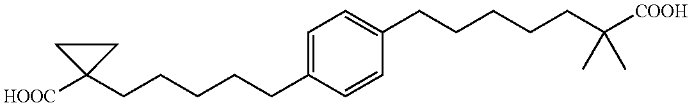 [SMILES: CC(C)(CCCCCc1ccc(CCCCCC2(C(=O)O)CC2)cc1)C(=O)O] 1-(5-(4-(6-carboxy-6-methylheptyl)phenyl)pentyl)cyclopropane-1-carboxylic acid |
| I-78 | 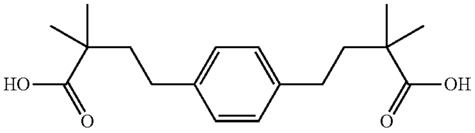 [SMILES: CC(C)(CCc1ccc(CCC(C)(C)C(=O)O)cc1)C(=O)O] 4,4'-(1,4-phenylene)bis(2,2-dimethylbutanoic acid) |
| I-84 | 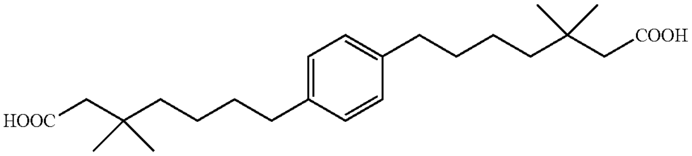 [SMILES: CC(C)(CCCCc1ccc(CCCCC(C)(C)CC(=O)O)cc1)CC(=O)O] 7,7'-(1,4-phenylene)bis(3,3-dimethylheptanoic acid) |
| I-87 | 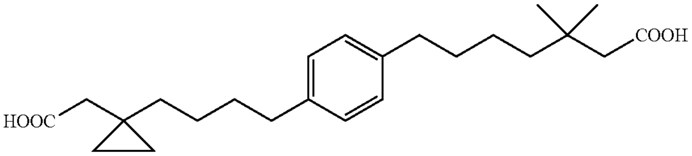 [SMILES: CC(C)(CCCCc1ccc(CCCCC2(CC(=O)O)CC2)cc1)CC(=O)O] 7-(4-(4-(1-(carboxymethyl)cyclopropyl)butyl)phenyl)-3,3-dimethylheptanoic acid |
| I-88 | 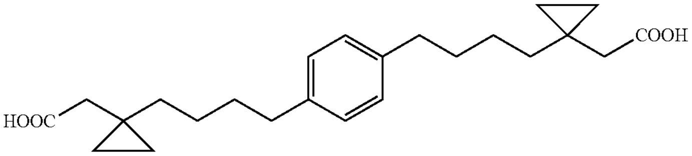 [SMILES: O=C(O)CC1(CCCCc2ccc(CCCCC3(CC(=O)O)CC3)cc2)CC1] 2,2'-((1,4-phenylenebis(butane-4,1-diyl))bis(cyclopropane-1,1-diyl))diacetic acid |

TABLE A-8

| Compound No. | Structure and Name |
| --- | --- |
| I-31 | 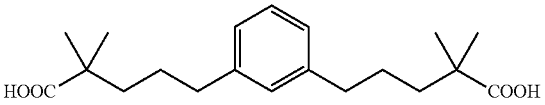 [SMILES: CC(C)(CCCc1cccc(CCCC(C)(C)C(=O)O)c1)C(=O)O] 5-[3-(4-Carboxy-4-methylpentyl)phenyl]-2,2-dimethylpentanoic acid |

TABLE A-8-continued

| Compound No. | Structure and Name |
|---|---|
| I-32 | 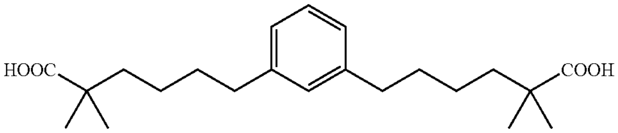 [SMILES: CC(C)(CCCCc1cccc(CCCCC(C)(C)C(=O)O)c1)C(=O)O] 6-[3-(5-Carboxy-5-methylhexyl)-phenyl]-2,2-dimethylhexanoic acid |
| I-33 | 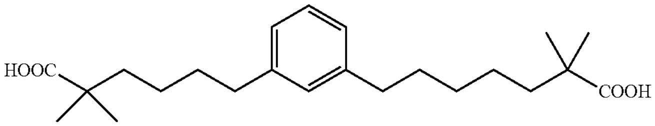 [SMILES: CC(C)(CCCCCc1cccc(CCCCC(C)(C)C(=O)O)c1)C(=O)O] 7-(3-(5-Carboxy-5-methylhexyl)phenyl)-2,2-dimethylheptanoic acid |
| I-34 | 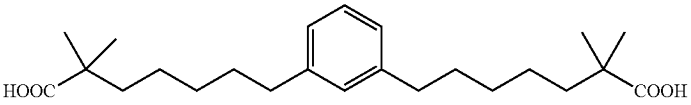 [SMILES: CC(C)(CCCCCc1cccc(CCCCCC(C)(C)C(=O)O)c1)C(=O)O] 7,7'-(1,3-Phenylene)bis(2,2-dimethylheptanoic acid) |
| I-35 | 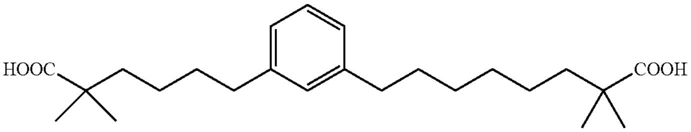 [SMILES: CC(C)(CCCCCCc1cccc(CCCCC(C)(C)C(=O)O)c1)C(=O)O] 8-(3-(5-Carboxy-5-methylhexyl)phenyl)-2,2-dimethyloctanoic acid |
| I-36 | 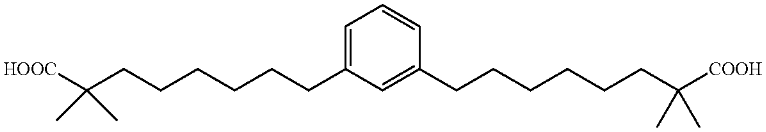 [SMILES: CC(C)(CCCCCCc1cccc(CCCCCCC(C)(C)C(=O)O)c1)C(=O)O] 8,8'-(1,3-Phenylene)bis(2,2-dimethyloctanoic acid) |
| I-37 | 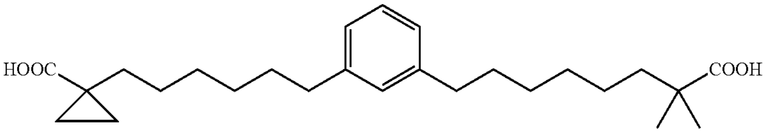 [SMILES: CC(C)(CCCCCCc1cccc(CCCCCCC2(C(=O)O)CC2)c1)C(=O)O] 1-(6-(3-(7-carboxy-7-methyloctyl)phenyl)hexyl)cyclopropane-1-carboxylic acid |
| I-38 | 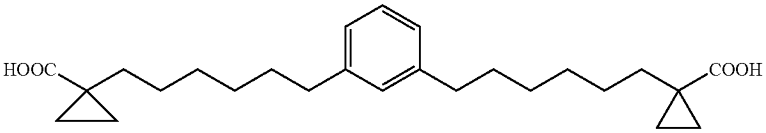 [SMILES: O=C(O)C1(CCCCCCc2cccc(CCCCCCC3(C(=O)O)CC3)c2)CC1] 1,1'-(1,3-phenylenebis(hexane-6,1-diyl))bis(cyclopropane-1-carboxylic acid) |
| I-39 | 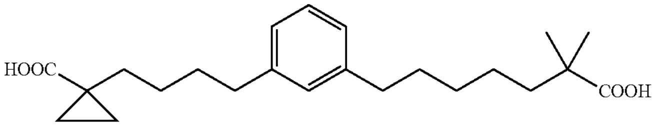 [SMILES: CC(C)(CCCCCc1cccc(CCCCC2(C(=O)O)CC2)c1)C(=O)O] 1-(4-(3-(6-carboxy-6-methylheptyl)phenyl)butyl)cyclopropane-1-carboxylic acid |

TABLE A-8-continued

| Compound No. | Structure and Name |
|---|---|
| I-40 | 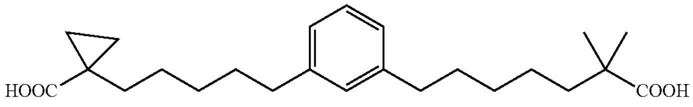 [SMILES: CC(C)(CCCCCc1cccc(CCCCCC2(C(=O)O)CC2)c1)C(=O)O] 1-(5-(3-(6-carboxy-6-methylheptyl)phenyl)pentyl)cyclopropane-1-carboxylic acid |
| I-41 | 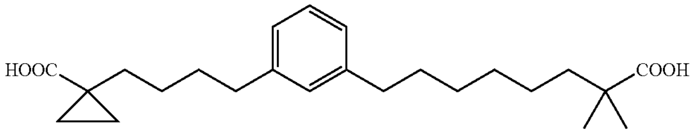 [SMILES: CC(C)(CCCCCCc1cccc(CCCCC2(C(=O)O)CC2)c1)C(=O)O] 1-(4-(3-(7-carboxy-7-methyloctyl)phenyl)butyl)cyclopropane-1-carboxylic acid |
| I-42 | 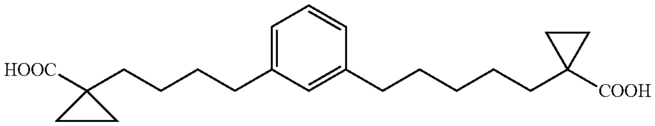 [SMILES: O=C(O)C1(CCCCCc2cccc(CCCCC3(C(=O)O)CC3)c2)CC1] 1-(5-(3-(4-(1-carboxycyclopropyl)butyl)phenyl)pentyl)cyclopropane-1-carboxylic acid |
| I-43 | 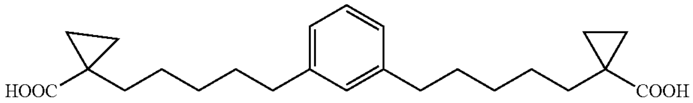 [SMILES: O=C(O)C1(CCCCCc2cccc(CCCCCC3(C(=O)O)CC3)c2)CC1] 1,1'-(1,3-phenylenebis(pentane-5,1-diyl))bis(cyclopropane-1-carboxylic acid) |
| I-44 | 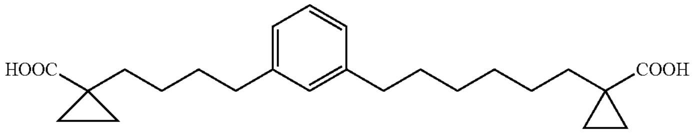 1-(6-(3-(4-(1-carboxycyclopropyl)butyl)phenyl)hexyl)cyclopropane-1-carboxylic acid |
| I-85 | 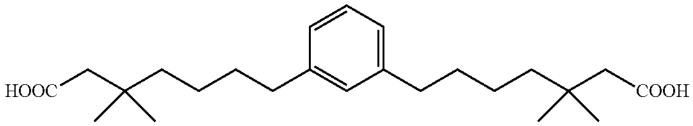 [SMILES: CC(C)(CCCCc1cccc(CCCCC(C)(C)CC(=O)O)c1)CC(=O)O] 7,7'-(1,3-phenylene)bis(3,3-dimethylheptanoic acid) |
| I-89 | 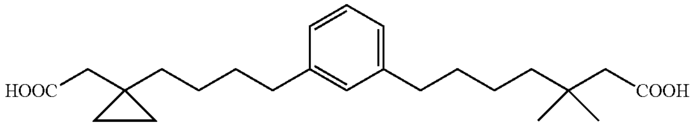 [SMILES: CC(C)(CCCCc1cccc(CCCCC2(CC(=O)O)CC2)c1)CC(=O)O] 7-(3-(4-(1-(carboxymethyl)cyclopropyl)butyl)phenyl)-3,3-dimethylheptanoic acid |
| I-90 | 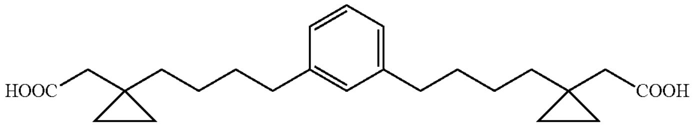 [SMILES: O=C(O)CC1(CCCCc2cccc(CCCCC3(CC(=O)O)CC3)c2)CC1] 2,2'-((1,3-phenylenebis(butane-4,1-diyl))bis(cyclopropane-1,1-diyl))diacetic acid |

TABLE A-8-continued

| Compound No. | Structure and Name |
| --- | --- |
| I-97 | 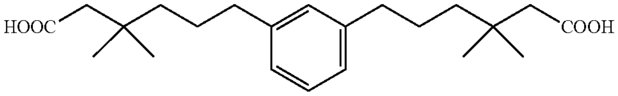 [SMILES: CC(C)(CCCc1cccc(CCCC(C)(C)CC(=O)O)c1)CC(=O)O]<br>6,6'-(1,3-phenylene)bis(3,3-dimethylhexanoic acid) |
| I-98 | 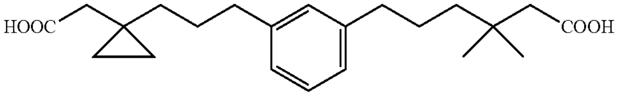 [SMILES: CC(C)(CCCc1cccc(CCCC2(CC(=O)O)CC2)c1)CC(=O)O]<br>6-(3-(3-(1-(carboxymethyl)cyclopropyl)propyl)phenyl)-3,3-dimethylhexanoic acid |
| I-99 | 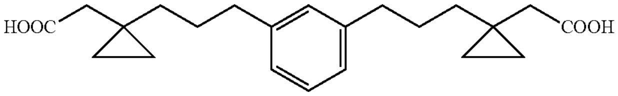 [SMILES: O=C(O)CC1(CCCc2cccc(CCCC3(CC(=O)O)CC3)c2)CC1]<br>2,2'-((1,3-phenylenebis(propane-3,1-diyl))bis(cyclopropane-1,1-diyl))diacetic acid |

TABLE A-9

| Compound No. | Structure and Name |
| --- | --- |
| I-61 | 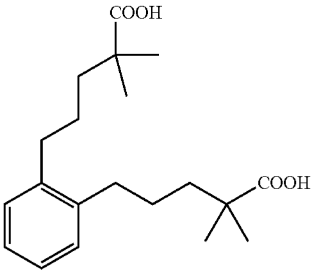 [SMILES: CC(C)(CCCc1ccccc1CCCC(C)(C)C(=O)O)C(=O)O]<br>5-[2-(4-Carboxy-4-methylpentyl)-phenyl]-2,2-dimethylpentanoic acid |
| I-62 | 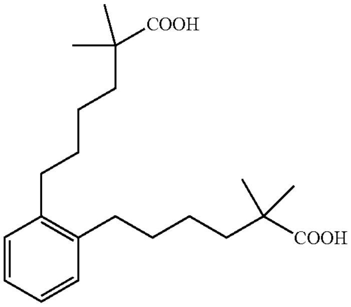 [SMILES: CC(C)(CCCCc1ccccc1CCCCC(C)(C)C(=O)O)C(=O)O]<br>6,6'-(1,2-Phenylene)bis(2,2-dimethylhexanoic acid) |

TABLE A-9-continued
| Compound No. | Structure and Name |
|---|---|
| I-63 | 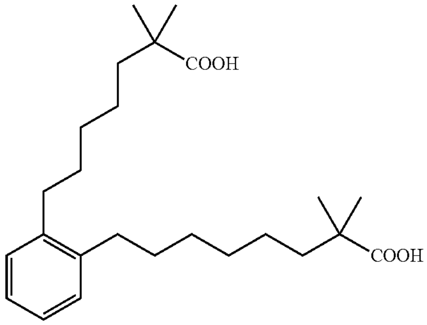 [SMILES: CC(C)(CCCCCCc1ccccc1CCCCCC(C)(C)C(=O)O)C(=O)O] 8-(2-(6-Carboxy-6-methylheptyl)phenyl)-2,2-dimethyloctanoic acid |
| I-64 | 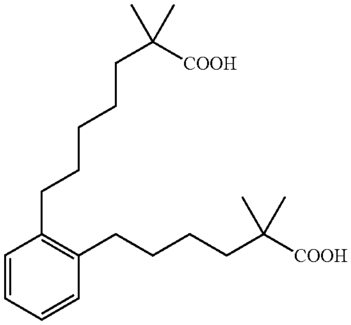 [SMILES: CC(C)(CCCCCc1ccccc1CCCCC(C)(C)C(=O)O)C(=O)O] 7-(2-(5-Carboxy-5-methylhexyl)phenyl)-2,2-dimethylheptanoic acid |
| I-65 | 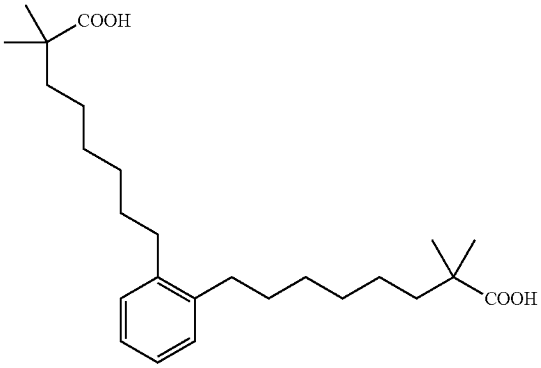 [SMILES: CC(C)(CCCCCCc1ccccc1CCCCCCC(C)(C)C(=O)O)C(=O)O] 8,8'-(1,2-Phenylene)bis(2,2-dimethyloctanoic acid) |
| I-66 | 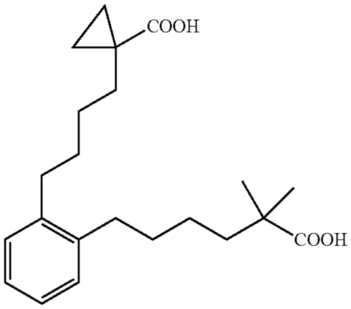 [SMILES: CC(C)(CCCCc1ccccc1CCCCC1(C(=O)O)CC1)C(=O)O] 1-(4-(2-(5-carboxy-5-methylhexyl)phenyl)butyl)cyclopropane-1-carboxylic acid |

TABLE A-9-continued
| Compound No. | Structure and Name |
|---|---|
| I-67 | 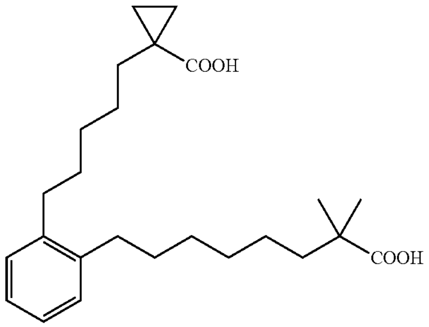 [SMILES: CC(C)(CCCCCCc1ccccc1CCCCCC1(C(=O)O)CC1)C(=O)O] 1-(5-(2-(7-carboxy-7-methyloctyl)phenyl)pentyl)cyclopropane-1-carboxylic acid |
| I-68 | 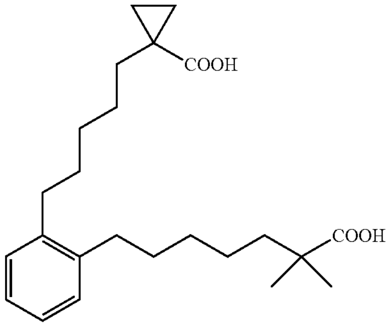 [SMILES: CC(C)(CCCCCc1ccccc1CCCCCC1(C(=O)O)CC1)C(=O)O] 1-(5-(2-(6-carboxy-6-methylheptyl)phenyl)pentyl)cyclopropane-1-carboxylic acid |
| I-69 | 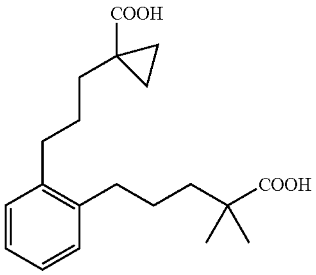 [SMILES: CC(C)(CCCc1ccccc1CCCC1(C(=O)O)CC1)C(=O)O] 1-(3-(2-(4-carboxy-4-methylpentyl)phenyl)propyl)cyclopropane-1-carboxylic acid |
| I-70 | 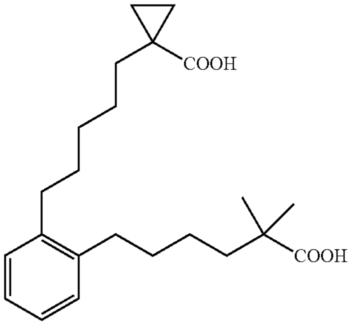 [SMILES: CC(C)(CCCCc1ccccc1CCCCCC1(C(=O)O)CC1)C(=O)O] 1-(5-(2-(5-carboxy-5-methylhexyl)phenyl)pentyl)cyclopropane-1-carboxylic acid |

TABLE A-9-continued
| Compound No. | Structure and Name |
| --- | --- |
| I-71 | 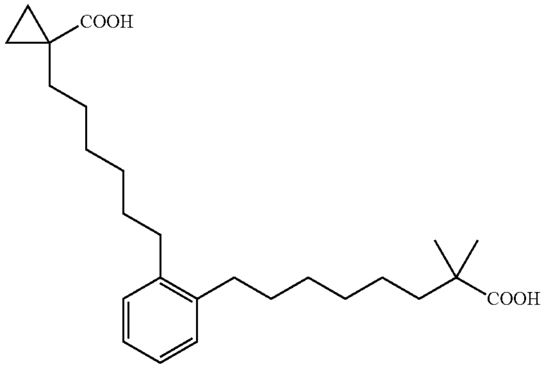 1-(6-(2-(7-carboxy-7-methyloctyl)phenyl)hexyl)cyclopropane-1-carboxylic acid |
| I-72 | 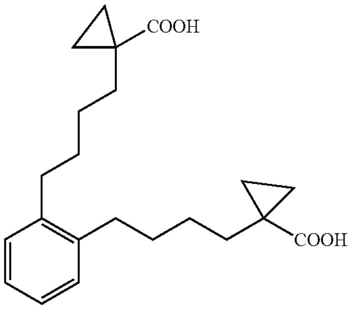 [SMILES: O=C(O)C1(CCCCc2ccccc2CCCCC2(C(=O)O)CC2)CC1] 1,1'-(1,2-phenylenebis(butane-4,1-diyl))bis(cyclopropane-1-carboxylic acid) |
| I-73 | 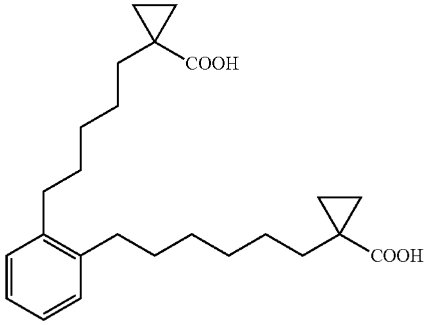 [SMILES: O=C(O)C1(CCCCCCc2ccccc2CCCCCC2(C(=O)O)CC2)CC1] 1-(5-(2-(6-(1-carboxycyclopropyl)hexyl)phenyl)pentyl)cyclopropane-1-carboxylic acid |
| I-74 | 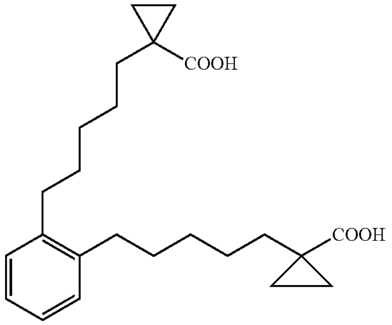 [SMILES: O=C(O)C1(CCCCCc2ccccc2CCCCCC2(C(=O)O)CC2)CC1] 1,1'-(1,2-phenylenebis(pentane-5,1-diyl))bis(cyclopropane-1-carboxylic acid) |

TABLE A-9-continued
| Compound No. | Structure and Name |
| --- | --- |
| I-75 | 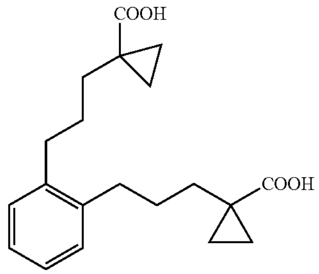 [SMILES: O=C(O)C1(CCCc2ccccc2CCCC2(C(=O)O)CC2)CC1] 1,1'-(1,2-phenylenebis(propane-3,1-diyl))bis(cyclopropane-1-carboxylic acid) |
| I-76 | 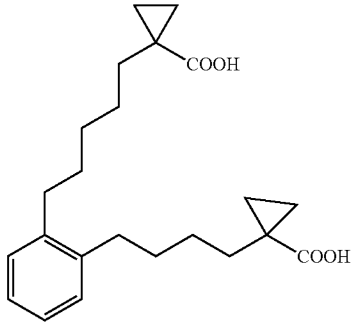 [SMILES: O=C(O)C1(CCCCCc2ccccc2CCCCC2(C(=O)O)CC2)CC1] 1-(5-(2-(4-(1-carboxycyclopropyl)butyl)phenyl)pentyl)cyclopropane-1-carboxylic acid |
| I-77 | 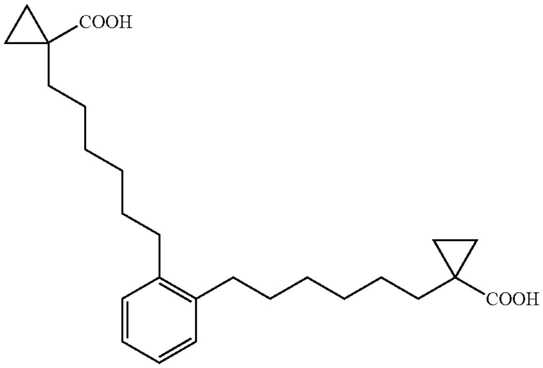 [SMILES: O=C(O)C1(CCCCCCc2ccccc2CCCCCCC2(C(=O)O)CC2)CC1] 1,1'-(1,2-phenylenebis(hexane-6,1-diyl))bis(cyclopropane-1-carboxylic acid) |
| I-91 | 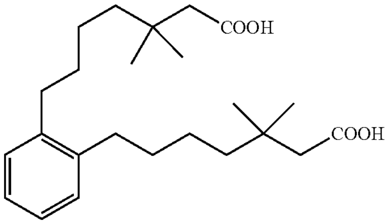 [SMILES: CC(C)(CCCCc1ccccc1CCCCC(C)(C)CC(=O)O)CC(=O)O] |

TABLE A-9-continued
| Compound No. | Structure and Name |
|---|---|
| I-92 | 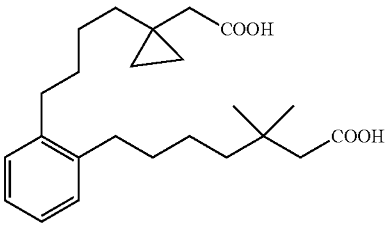 [SMILES: CC(C)(CCCCc1ccccc1CCCCC1(CC(=O)O)CC1)CC(=O)O] |
| I-93 | 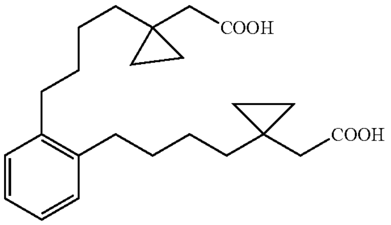 [SMILES: O=C(O)CC1(CCCCc2ccccc2CCCCC2(CC(=O)O)CC2)CC1] |
TABLE A-10
| Structure |
|---|
| 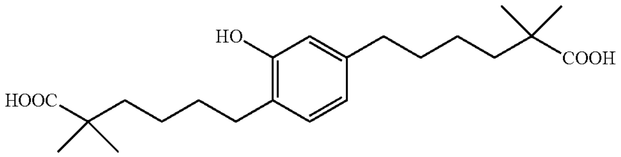 [SMILES: CC(C)(CCCCc1ccc(CCCCC(C)(C)C(=O)O)c(O)c1)C(=O)O] |
| 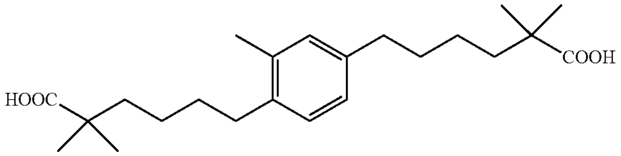 [SMILES: Cc1cc(CCCCC(C)(C)C(=O)O)ccc1CCCCC(C)(C)C(=O)O] |
| 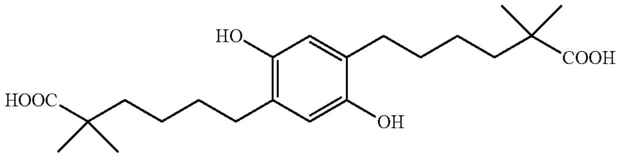 [SMILES: CC(C)(CCCCc1cc(O)c(CCCCC(C)(C)C(=O)O)cc1O)C(=O)O] |
| 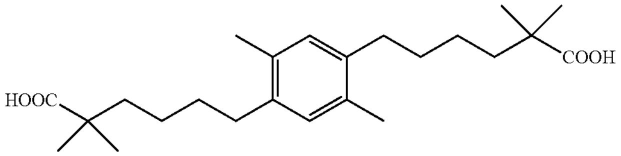 [SMILES: Cc1cc(CCCCC(C)(C)C(=O)O)c(C)cc1CCCCC(C)(C)C(=O)O] |
| 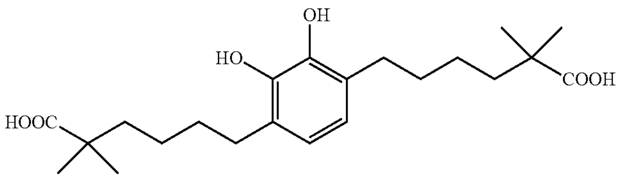 [SMILES: CC(C)(CCCCc1ccc(CCCCC(C)(C)C(=O)O)c(O)c1O)C(=O)O] |

TABLE A-10-continued
| Structure |
| --- |
| 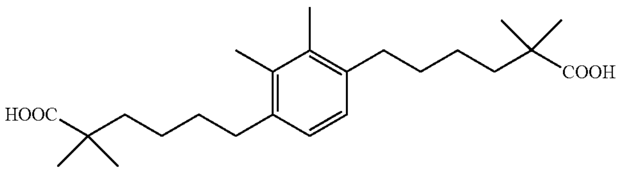 [SMILES: Cc1c(CCCCC(C)(C)C(=O)O)ccc(CCCCC(C)(C)C(=O)O)c1C] |
| 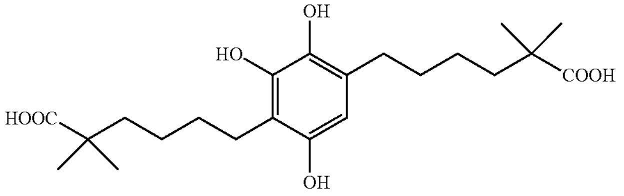 [SMILES: CC(C)(CCCCc1cc(O)c(CCCCC(C)(C)C(=O)O)c(O)c1O)C(=O)O] |
| 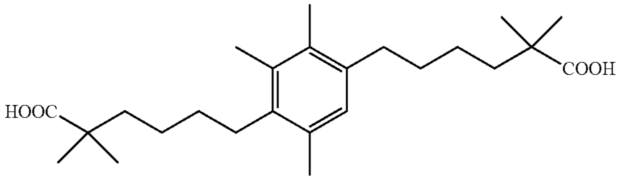 [SMILES: Cc1cc(CCCCC(C)(C)C(=O)O)c(C)c(C)c1CCCCC(C)(C)C(=O)O] |
| 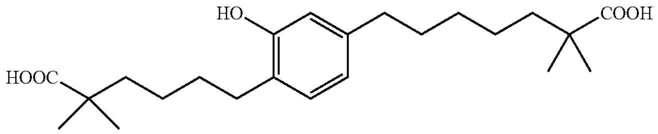 [SMILES: CC(C)(CCCCCc1ccc(CCCCC(C)(C)C(=O)O)c(O)c1)C(=O)O] |
| 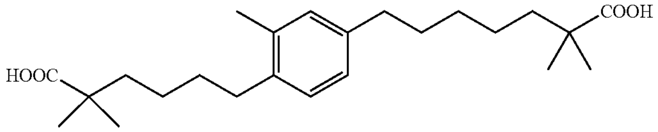 [SMILES: Cc1cc(CCCCCC(C)(C)C(=O)O)ccc1CCCCC(C)(C)C(=O)O] |
| 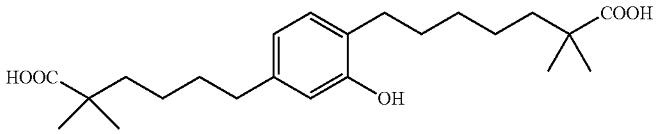 [SMILES: CC(C)(CCCCCc1ccc(CCCCC(C)(C)C(=O)O)cc1O)C(=O)O] |
| 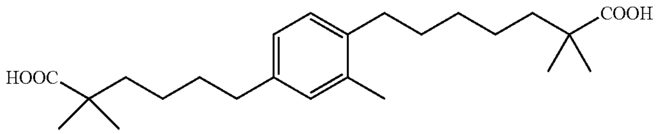 [SMILES: Cc1cc(CCCCC(C)(C)C(=O)O)ccc1CCCCCC(C)(C)C(=O)O] |
| 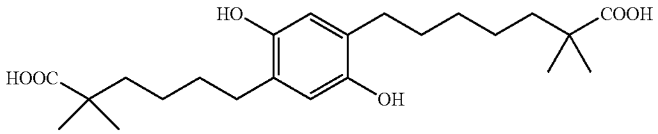 [SMILES: CC(C)(CCCCCc1cc(O)c(CCCCC(C)(C)C(=O)O)cc1O)C(=O)O] |
| 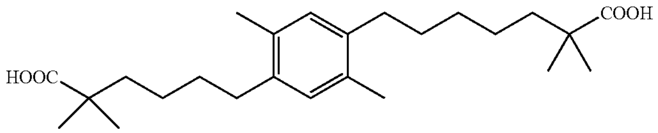 [SMILES: Cc1cc(CCCCC(C)(C)C(=O)O)c(C)cc1CCCCCC(C)(C)C(=O)O] |

TABLE A-10-continued
| Structure |
| --- |
| 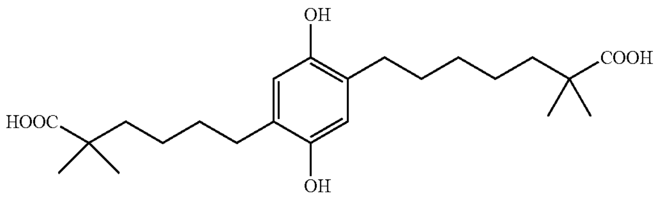 [SMILES: CC(C)(CCCCCc1cc(O)c(CCCCC(C)(C)C(=O)O)cc1O)C(=O)O] |
| 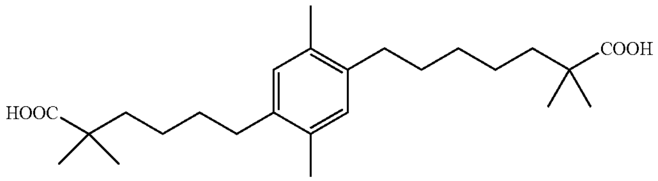 [SMILES: Cc1cc(CCCCC(C)(C)C(=O)O)c(C)cc1CCCCCC(C)(C)C(=O)O] |
| 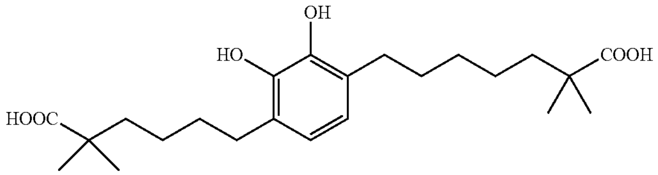 [SMILES: CC(C)(CCCCCc1ccc(CCCCC(C)(C)C(=O)O)c(O)c1O)C(=O)O] |
| 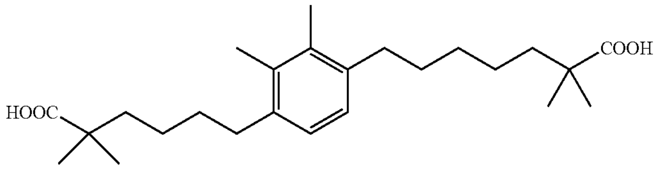 [SMILES: Cc1c(CCCCCC(C)(C)C(=O)O)ccc(CCCCC(C)(C)C(=O)O)c1C] |
| 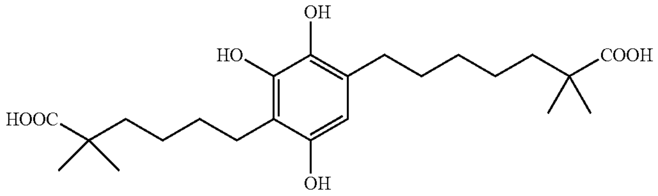 [SMILES: CC(C)(CCCCCc1cc(O)c(CCCCC(C)(C)C(=O)O)c(O)c1O)C(=O)O] |
| 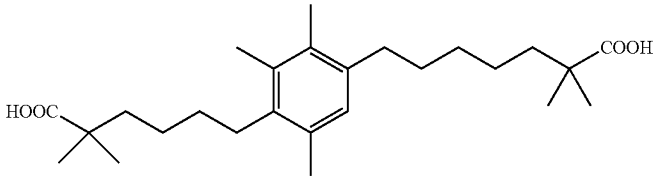 [SMILES: Cc1cc(CCCCCC(C)(C)C(=O)O)c(C)c(C)c1CCCCC(C)(C)C(=O)O] |
| 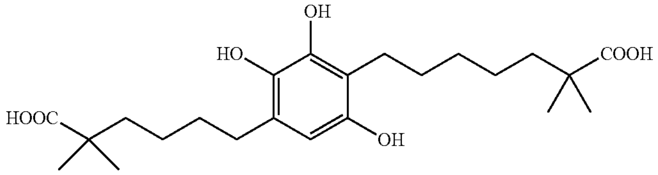 [SMILES: CC(C)(CCCCCc1c(O)cc(CCCCC(C)(C)C(=O)O)c(O)c1O)C(=O)O] |
| 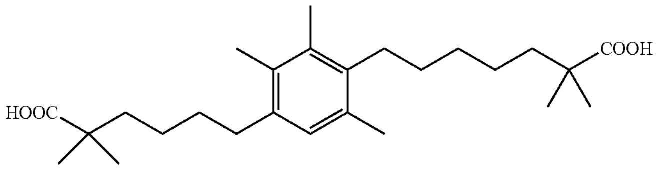 [SMILES: Cc1cc(CCCCC(C)(C)C(=O)O)c(C)c(C)c1CCCCCC(C)(C)C(=O)O] |

TABLE A-10-continued
| Structure |
| --- |
| 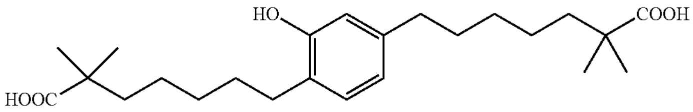 [SMILES: CC(C)(CCCCCc1ccc(CCCCCC(C)(C)C(=O)O)c(O)c1)C(=O)O] |
| 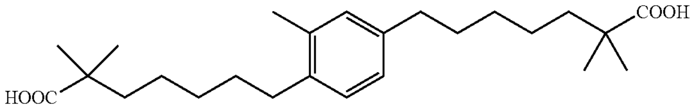 [SMILES: Cc1cc(CCCCCC(C)(C)C(=O)O)ccc1CCCCCC(C)(C)C(=O)O] |
| 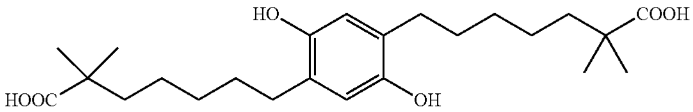 [SMILES: CC(C)(CCCCCc1cc(O)c(CCCCCC(C)(C)C(=O)O)cc1O)C(=O)O] |
| 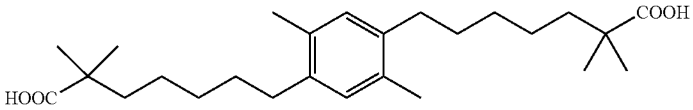 [SMILES: Cc1cc(CCCCCC(C)(C)C(=O)O)c(C)cc1CCCCCC(C)(C)C(=O)O] |
| 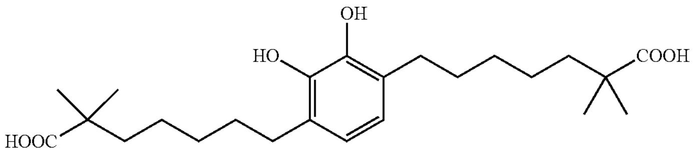 [SMILES: CC(C)(CCCCCc1ccc(CCCCCC(C)(C)C(=O)O)c(O)c1O)C(=O)O] |
| 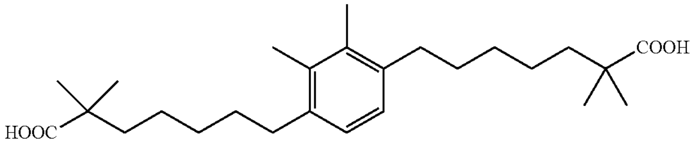 [SMILES: Cc1c(CCCCCC(C)(C)C(=O)O)ccc(CCCCCC(C)(C)C(=O)O)c1C] |
| 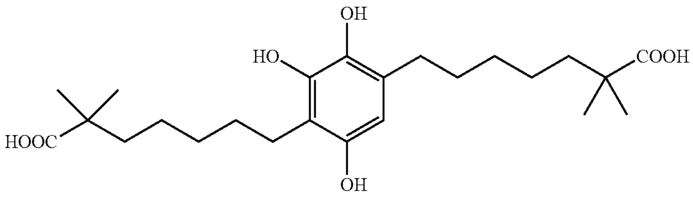 [SMILES: CC(C)(CCCCCc1cc(O)c(CCCCCC(C)(C)C(=O)O)c(O)c1O)C(=O)O] |
| 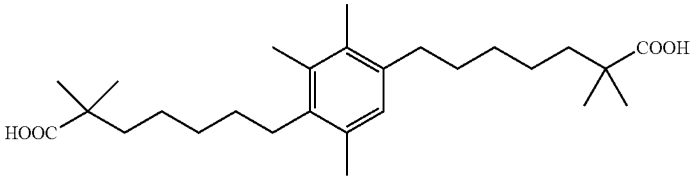 [SMILES: Cc1cc(CCCCCC(C)(C)C(=O)O)c(C)c(C)c1CCCCCC(C)(C)C(=O)O] |
| 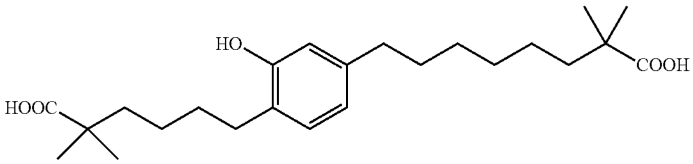 [SMILES: CC(C)(CCCCCCc1ccc(CCCCC(C)(C)C(=O)O)c(O)c1)C(=O)O] |
| 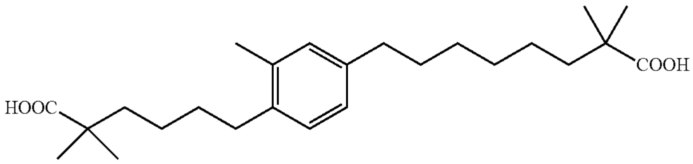 [SMILES: Cc1cc(CCCCCCC(C)(C)C(=O)O)ccc1CCCCC(C)(C)C(=O)O] |

TABLE A-10-continued
| Structure |
| --- |
| 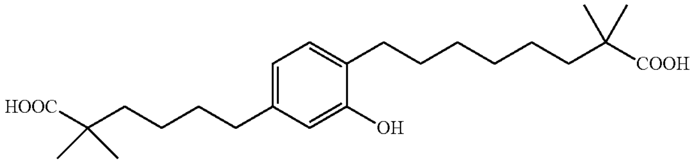 [SMILES: CC(C)(CCCCCCc1ccc(CCCCC(C)(C)C(=O)O)cc1O)C(=O)O] |
| 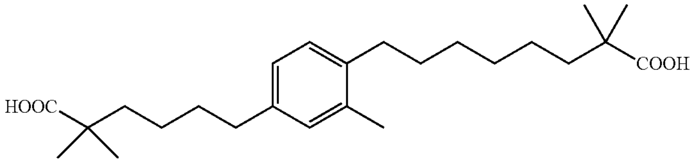 [SMILES: Cc1cc(CCCCC(C)(C)C(=O)O)ccc1CCCCCCC(C)(C)C(=O)O] |
| 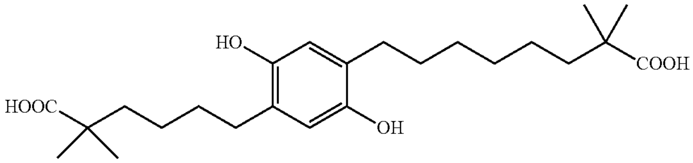 [SMILES: CC(C)(CCCCCCc1cc(O)c(CCCCC(C)(C)C(=O)O)cc1O)C(=O)O] |
| 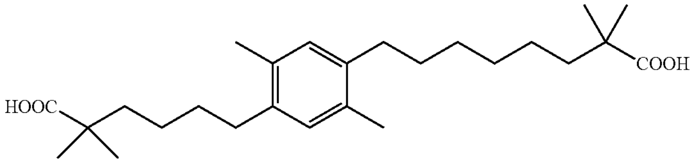 [SMILES: Cc1cc(CCCCC(C)(C)C(=O)O)c(C)cc1CCCCCCC(C)(C)C(=O)O] |
| 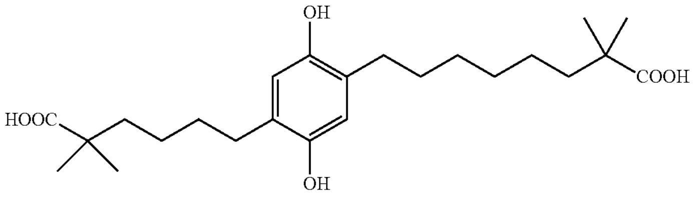 [SMILES: CC(C)(CCCCCCc1cc(O)c(CCCCC(C)(C)C(=O)O)cc1O)C(=O)O] |
| 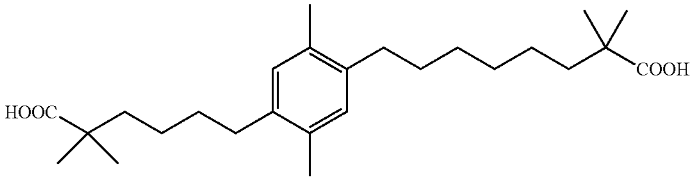 [SMILES: Cc1cc(CCCCC(C)(C)C(=O)O)c(C)cc1CCCCCCC(C)(C)C(=O)O] |
| 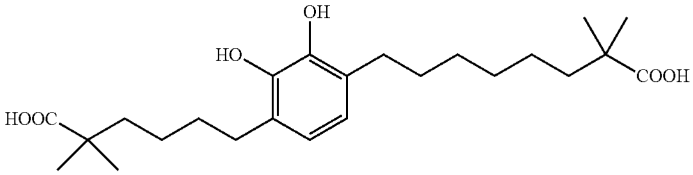 [SMILES: CC(C)(CCCCCCc1ccc(CCCCC(C)(C)C(=O)O)c(O)c1O)C(=O)O] |
| 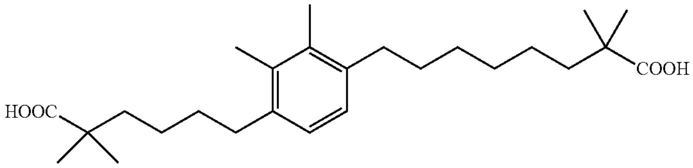 [SMILES: Cc1c(CCCCCCC(C)(C)C(=O)O)ccc(CCCCC(C)(C)C(=O)O)c1C] |

TABLE A-10-continued
| Structure |
| --- |
| 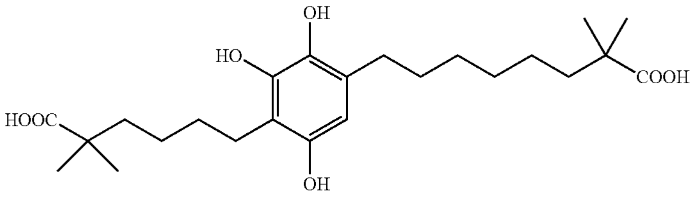 [SMILES: CC(C)(CCCCCCc1cc(O)c(CCCCC(C)(C)C(=O)O)c(O)c1O)C(=O)O] |
| 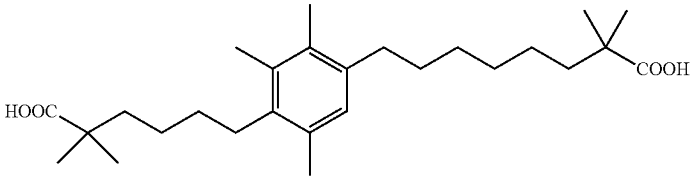 [SMILES: Cc1cc(CCCCCCC(C)(C)C(=O)O)c(C)c(C)c1CCCCC(C)(C)C(=O)O] |
| 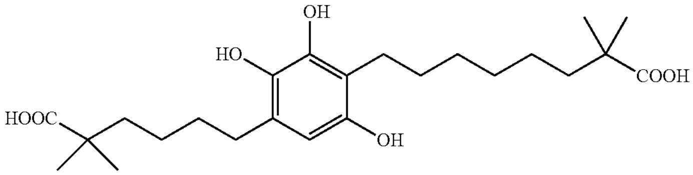 [SMILES: CC(C)(CCCCCCc1c(O)cc(CCCCC(C)(C)C(=O)O)c(O)c1O)C(=O)O] |
| 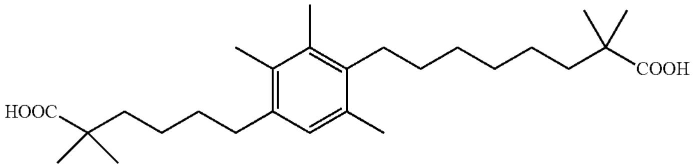 [SMILES: Cc1cc(CCCCC(C)(C)C(=O)O)c(C)c(C)c1CCCCCCC(C)(C)C(=O)O] |
| 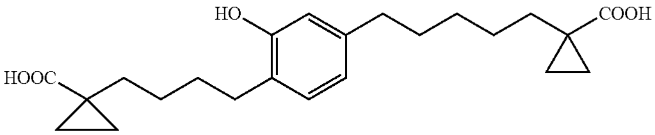 [SMILES: O=C(O)C1(CCCCCc2ccc(CCCCC3(C(=O)O)CC3)c(O)c2)CC1] |
| 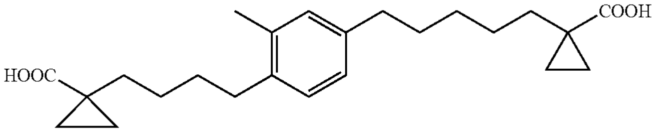 [SMILES: Cc1cc(CCCCCC2(C(=O)O)CC2)ccc1CCCCC1(C(=O)O)CC1] |
| 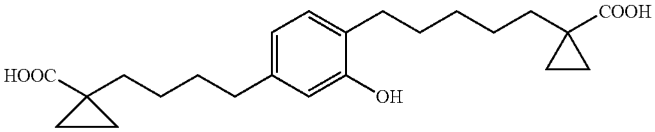 [SMILES: O=C(O)C1(CCCCCc2ccc(CCCCC3(C(=O)O)CC3)cc2O)CC1] |
| 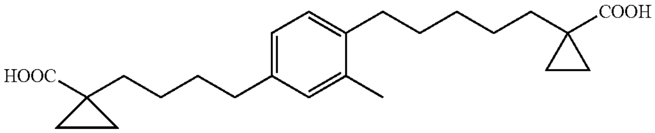 [SMILES: Cc1cc(CCCCC2(C(=O)O)CC2)ccc1CCCCCC1(C(=O)O)CC1] |
| 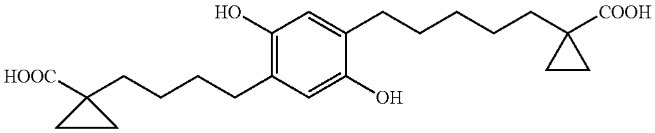 [SMILES: O=C(O)C1(CCCCCc2cc(O)c(CCCCC3(C(=O)O)CC3)cc2O)CC1] |

TABLE A-10-continued
| Structure |
| --- |
| 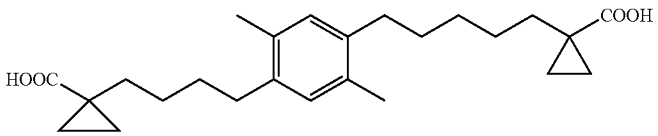 [SMILES: Cc1cc(CCCCC2(C(=O)O)CC2)c(C)cc1CCCCCC1(C(=O)O)CC1] |
| 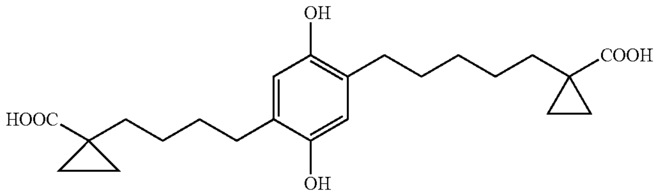 [SMILES: O=C(O)C1(CCCCCc2cc(O)c(CCCCC3(C(=O)O)CC3)cc2O)CC1] |
| 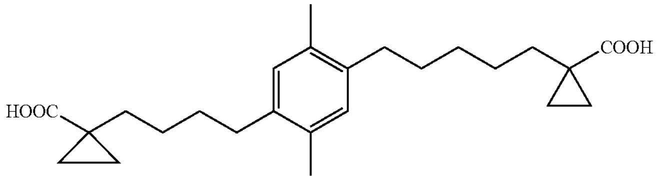 [SMILES: Cc1cc(CCCCC2(C(=O)O)CC2)c(C)cc1CCCCCC1(C(=O)O)CC1] |
| 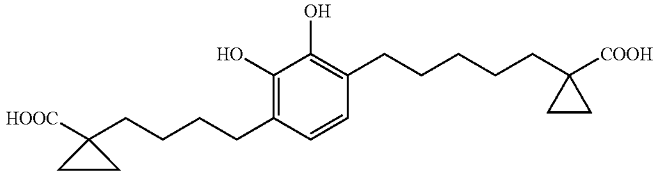 [SMILES: O=C(O)C1(CCCCCc2ccc(CCCCC3(C(=O)O)CC3)c(O)c2O)CC1] |
| 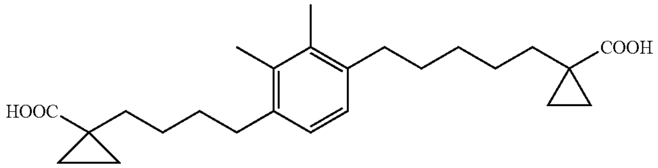 [SMILES: Cc1c(CCCCCC2(C(=O)O)CC2)ccc(CCCCC2(C(=O)O)CC2)c1C] |
| 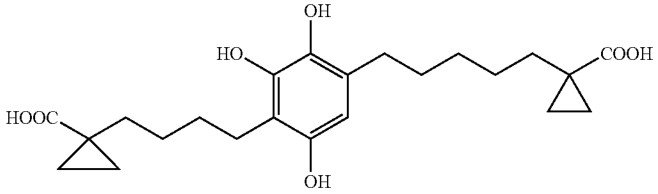 [SMILES: O=C(O)C1(CCCCCc2cc(O)c(CCCCC3(C(=O)O)CC3)c(O)c2O)CC1] |
| 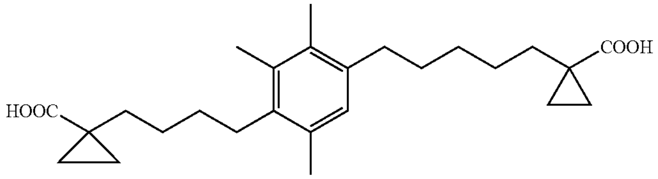 [SMILES: Cc1cc(CCCCCC2(C(=O)O)CC2)c(C)c(C)c1CCCCC1(C(=O)O)CC1] |
| 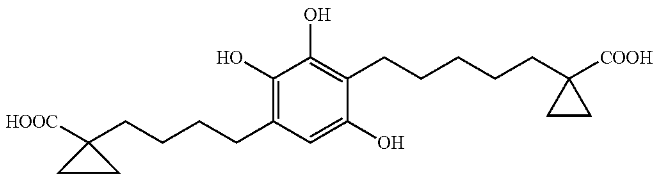 [SMILES: O=C(O)C1(CCCCCc2c(O)cc(CCCCC3(C(=O)O)CC3)c(O)c2O)CC1] |

TABLE A-10-continued
| Structure |
| --- |
| 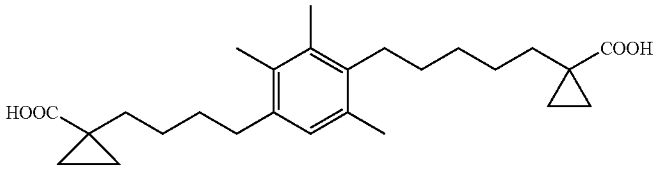 [SMILES: Cc1cc(CCCCC2(C(=O)O)CC2)c(C)c(C)c1CCCCCC1(C(=O)O)CC1] |
| 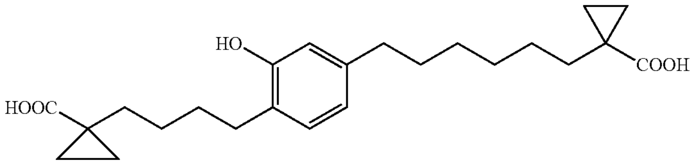 [SMILES: O=C(O)C1(CCCCCCc2ccc(CCCCC3(C(=O)O)CC3)c(O)c2)CC1] |
| 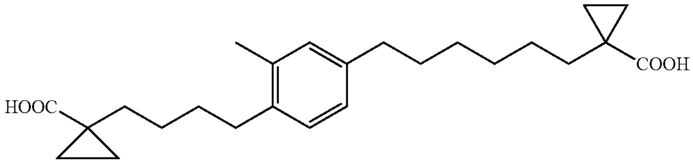 [SMILES: Cc1cc(CCCCCCC2(C(=O)O)CC2)ccc1CCCCC1(C(=O)O)CC1] |
| 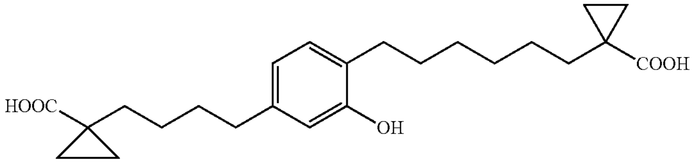 [SMILES: O=C(O)C1(CCCCCCc2ccc(CCCCC3(C(=O)O)CC3)cc2O)CC1] |
| 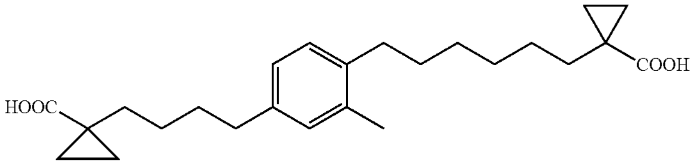 [SMILES: Cc1cc(CCCCC2(C(=O)O)CC2)ccc1CCCCCCC1(C(=O)O)CC1] |
| 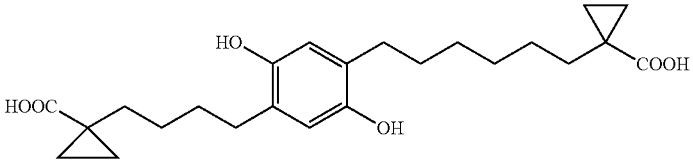 [SMILES: O=C(O)C1(CCCCCCc2cc(O)c(CCCCC3(C(=O)O)CC3)cc2O)CC1] |
| 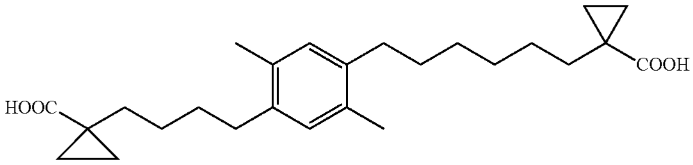 [SMILES: Cc1cc(CCCCC2(C(=O)O)CC2)c(C)cc1CCCCCCC1(C(=O)O)CC1] |
| 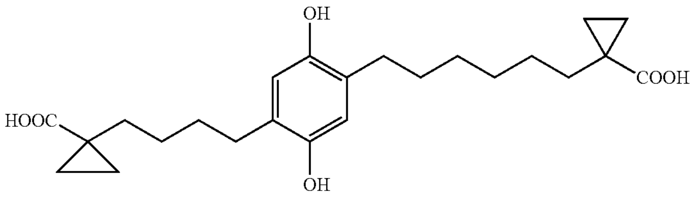 [SMILES: O=C(O)C1(CCCCCCc2cc(O)c(CCCCC3(C(=O)O)CC3)cc2O)CC1] |

TABLE A-10-continued
| Structure |
| --- |
| 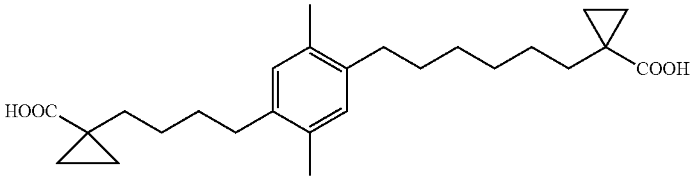 [SMILES: Cc1cc(CCCCC2(C(=O)O)CC2)c(C)cc1CCCCCCC1(C(=O)O)CC1] |
| 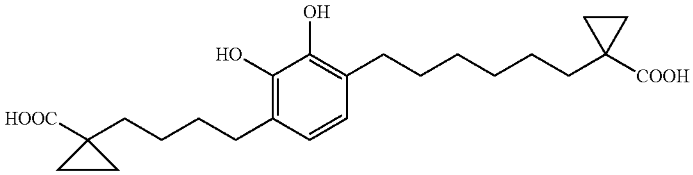 [SMILES: O=C(O)C1(CCCCCCc2ccc(CCCCC3(C(=O)O)CC3)c(O)c2O)CC1] |
| 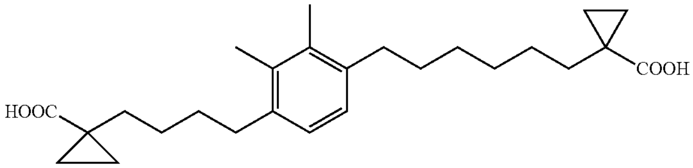 [SMILES: Cc1c(CCCCCCC2(C(=O)O)CC2)ccc(CCCCC2(C(=O)O)CC2)c1C] |
| 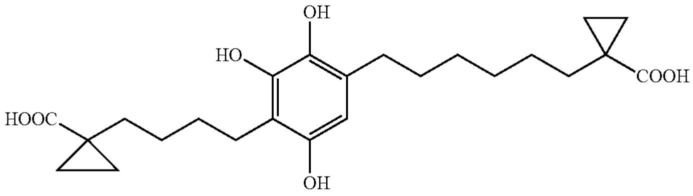 [SMILES: O=C(O)C1(CCCCCCc2cc(O)c(CCCCC3(C(=O)O)CC3)c(O)c2O)CC1] |
| 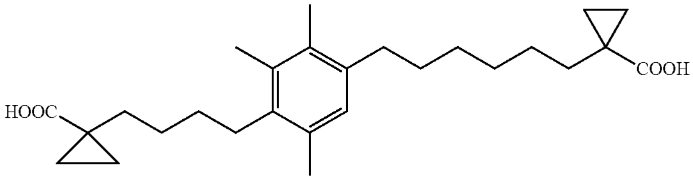 [SMILES: Cc1cc(CCCCCCC2(C(=O)O)CC2)c(C)c(C)c1CCCCC1(C(=O)O)CC1] |
| 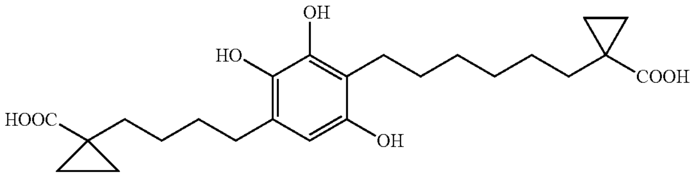 [SMILES: O=C(O)C1(CCCCCCc2c(O)cc(CCCCC3(C(=O)O)CC3)c(O)c2O)CC1] |
| 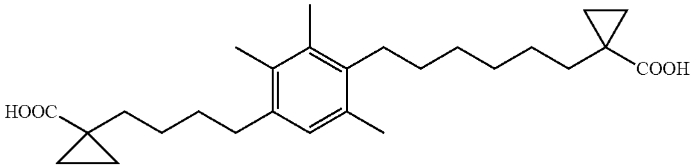 [SMILES: Cc1cc(CCCCC2(C(=O)O)CC2)c(C)c(C)c1CCCCCCC1(C(=O)O)CC1] |
| 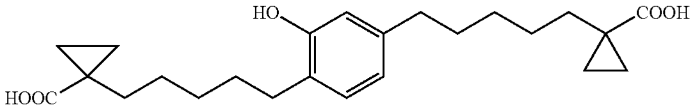 [SMILES: O=C(O)C1(CCCCCc2ccc(CCCCCC3(C(=O)O)CC3)c(O)c2)CC1] |
| 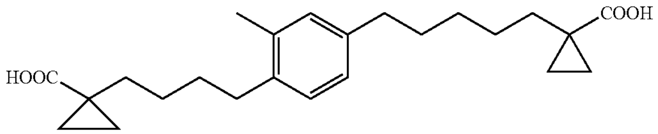 [SMILES: Cc1cc(CCCCCC2(C(=O)O)CC2)ccc1CCCCC1(C(=O)O)CC1] |

TABLE A-10-continued
| Structure |
|---|
| 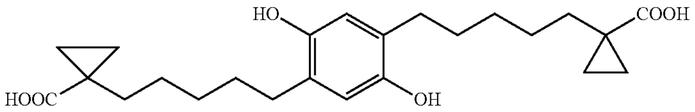 [SMILES: O=C(O)C1(CCCCCc2cc(O)c(CCCCCC3(C(=O)O)CC3)cc2O)CC1] |
| 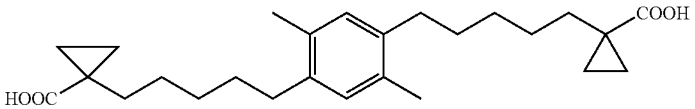 |
| 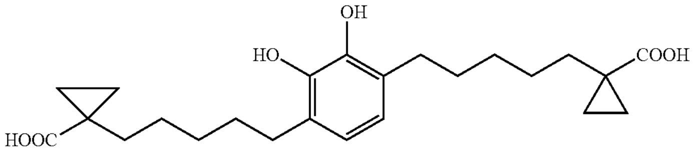 [SMILES: O=C(O)C1(CCCCCc2ccc(CCCCCC3(C(=O)O)CC3)c(O)c2O)CC1] |
| 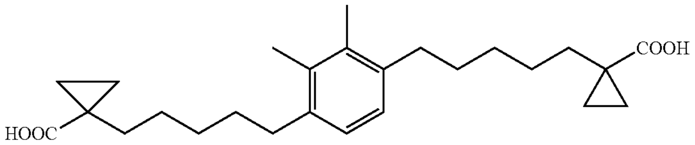 [SMILES: Cc1c(CCCCCC2(C(=O)O)CC2)ccc(CCCCCC2(C(=O)O)CC2)c1C] |
| 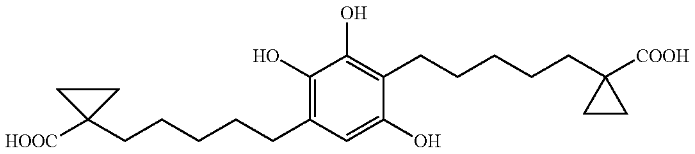 [SMILES: O=C(O)C1(CCCCCc2cc(O)c(CCCCCC3(C(=O)O)CC3)c(O)c2O)CC1] |
| 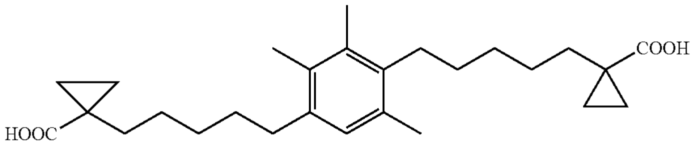 [SMILES: Cc1cc(CCCCCC2(C(=O)O)CC2)c(C)c(C)c1CCCCCC1(C(=O)O)CC1] |
| 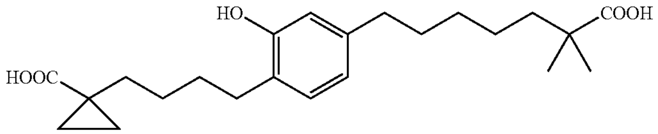 [SMILES: CC(C)(CCCCCc1ccc(CCCCC2(C(=O)O)CC2)c(O)c1)C(=O)O] |
| 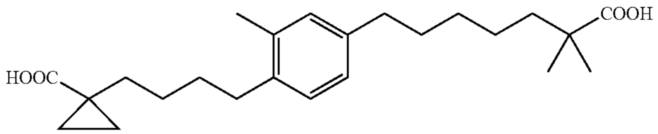 [SMILES: Cc1cc(CCCCCC(C)(C)C(=O)O)ccc1CCCCC1(C(=O)O)CC1] |
| 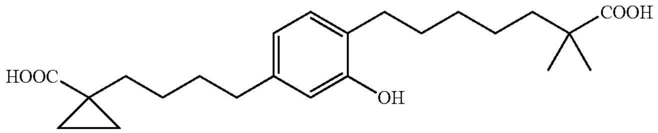 [SMILES: CC(C)(CCCCCc1ccc(CCCCC2(C(=O)O)CC2)cc1O)C(=O)O] |
| 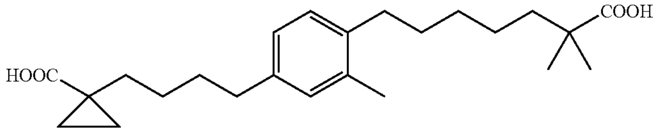 [SMILES: Cc1cc(CCCCC2(C(=O)O)CC2)ccc1CCCCCC(C)(C)C(=O)O] |
| 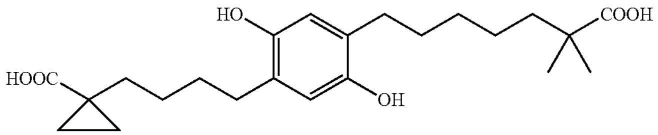 [SMILES: CC(C)(CCCCCc1cc(O)c(CCCCC2(C(=O)O)CC2)cc1O)C(=O)O] |

TABLE A-10-continued
| Structure |
| --- |
| 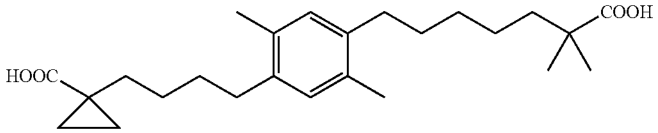 [SMILES: Cc1cc(CCCCC2(C(=O)O)CC2)c(C)cc1CCCCCC(C)(C)C(=O)O] |
| 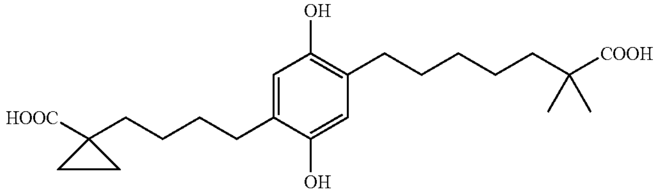 [SMILES: CC(C)(CCCCCc1cc(O)c(CCCCC2(C(=O)O)CC2)cc1O)C(=O)O] |
| 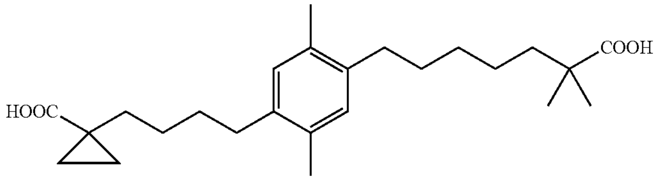 [SMILES: Cc1cc(CCCCC2(C(=O)O)CC2)c(C)cc1CCCCCC(C)(C)C(=O)O] |
| 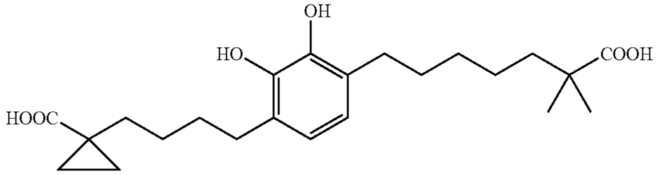 [SMILES: CC(C)(CCCCCc1ccc(CCCCC2(C(=O)O)CC2)c(O)c1O)C(=O)O] |
| 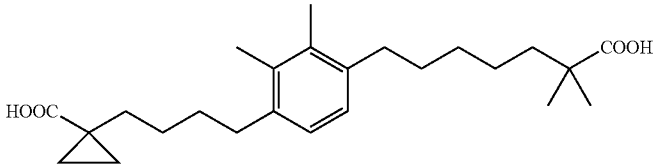 [SMILES: Cc1c(CCCCCC(C)(C)C(=O)O)ccc(CCCCC2(C(=O)O)CC2)c1C] |
| 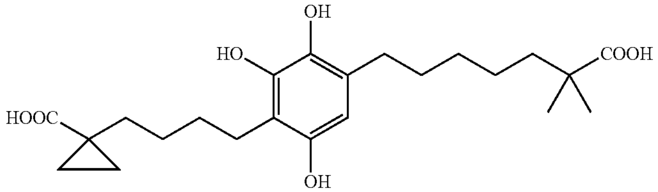 [SMILES: CC(C)(CCCCCc1cc(O)c(CCCCC2(C(=O)O)CC2)c(O)c1O)C(=O)O] |
| 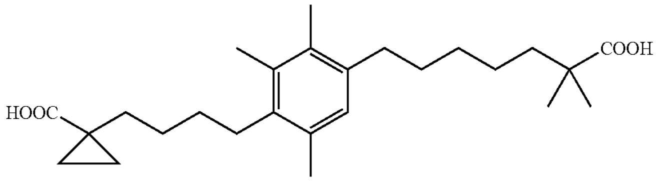 [SMILES: Cc1cc(CCCCCC(C)(C)C(=O)O)c(C)c(C)c1CCCCC1(C(=O)O)CC1] |
| 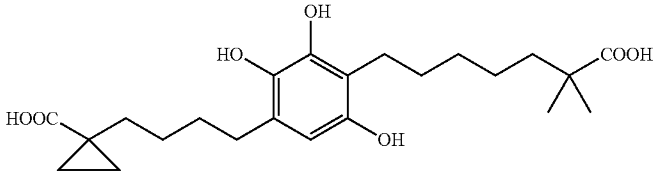 [SMILES: CC(C)(CCCCCc1c(O)cc(CCCCC2(C(=O)O)CC2)c(O)c1O)C(=O)O] |

TABLE A-10-continued
| Structure |
|---|
| 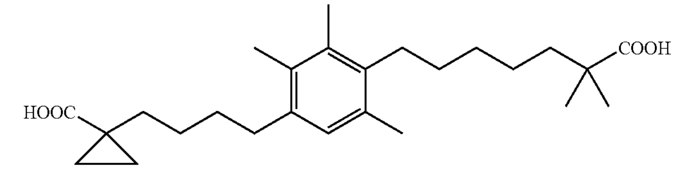 [SMILES: Cc1cc(CCCCC2(C(=O)O)CC2)c(C)c(C)c1CCCCCC(C)(C)C(=O)O] |
| 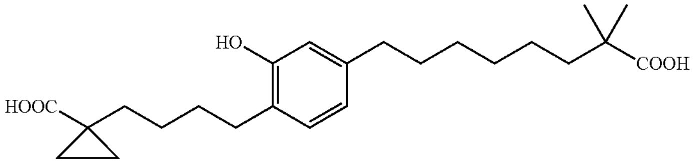 [SMILES: CC(C)(CCCCCCc1ccc(CCCCC2(C(=O)O)CC2)c(O)c1)C(=O)O] |
| 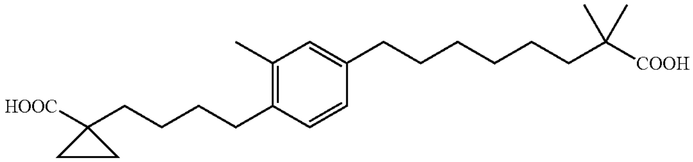 [SMILES: Cc1cc(CCCCCCC(C)(C)C(=O)O)ccc1CCCCC1(C(=O)O)CC1] |
| 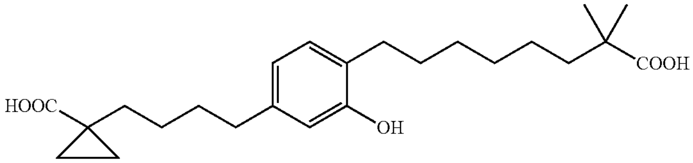 [SMILES: CC(C)(CCCCCCc1ccc(CCCCC2(C(=O)O)CC2)cc1O)C(=O)O] |
| 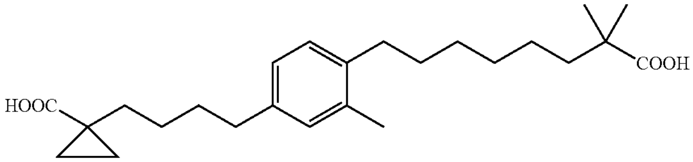 [SMILES: Cc1cc(CCCCC2(C(=O)O)CC2)ccc1CCCCCCC(C)(C)C(=O)O] |
| 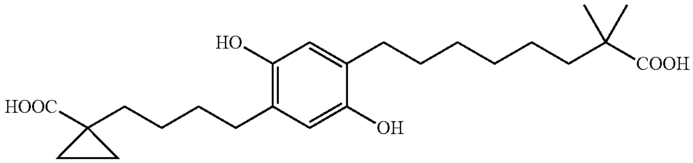 [SMILES: CC(C)(CCCCCCc1cc(O)c(CCCCC2(C(=O)O)CC2)cc1O)C(=O)O] |
| 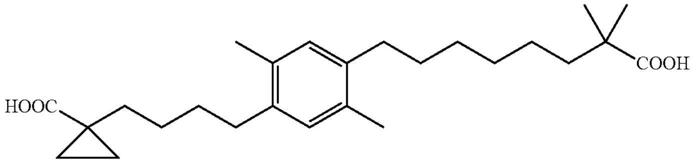 [SMILES: Cc1cc(CCCCC2(C(=O)O)CC2)c(C)cc1CCCCCCC(C)(C)C(=O)O] |
| 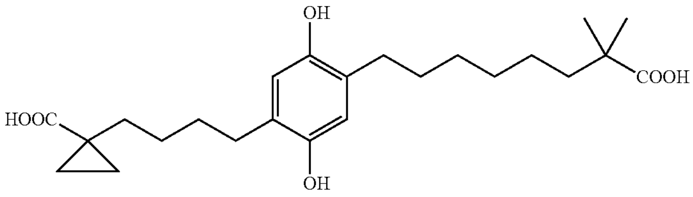 [SMILES: CC(C)(CCCCCCc1cc(O)c(CCCCC2(C(=O)O)CC2)cc1O)C(=O)O] |

TABLE A-10-continued
| Structure |
| --- |
| 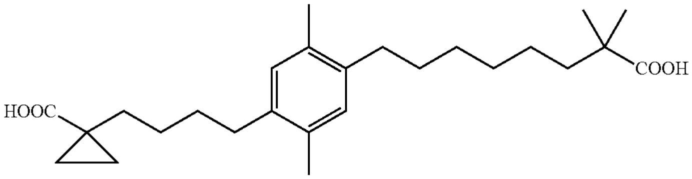 [SMILES: Cc1cc(CCCCC2(C(=O)O)CC2)c(C)cc1CCCCCCC(C)(C)C(=O)O] |
| 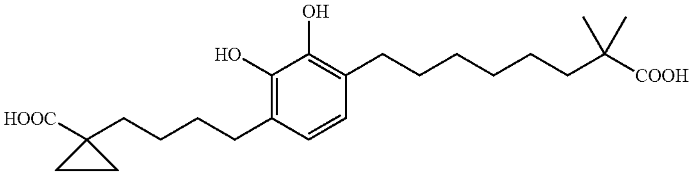 [SMILES: CC(C)(CCCCCCc1ccc(CCCCC2(C(=O)O)CC2)c(O)c1O)C(=O)O] |
| 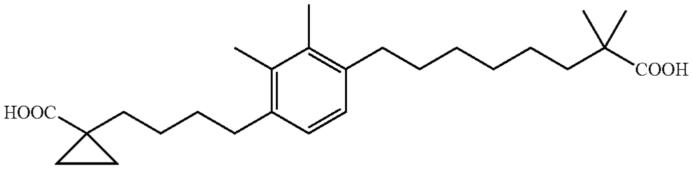 [SMILES: Cc1c(CCCCCCC(C)(C)C(=O)O)ccc(CCCCC2(C(=O)O)CC2)c1C] |
| 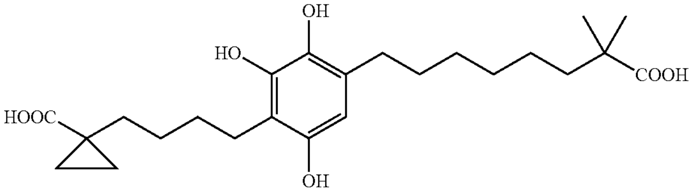 |
| 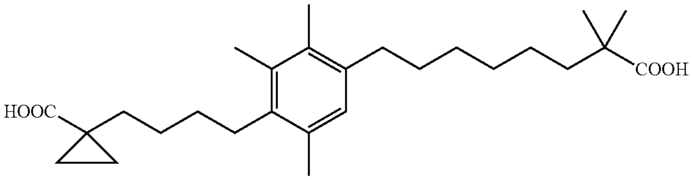 [SMILES: Cc1cc(CCCCCCC(C)(C)C(=O)O)c(C)c(C)c1CCCCC1(C(=O)O)CC1] |
| 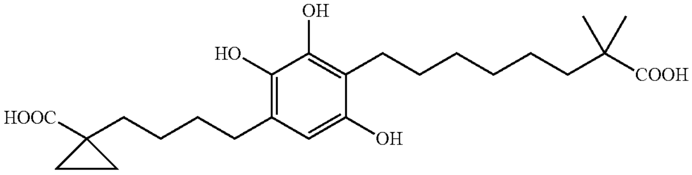 [SMILES: CC(C)(CCCCCCc1c(O)cc(CCCCC2(C(=O)O)CC2)c(O)c1O)C(=O)O] |
| 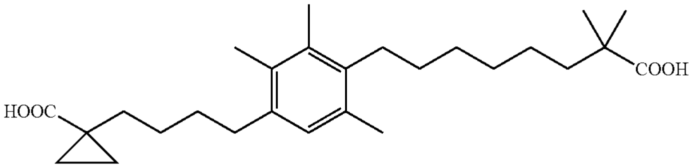 [SMILES: Cc1cc(CCCCC2(C(=O)O)CC2)c(C)c(C)c1CCCCCCC(C)(C)C(=O)O] |
| 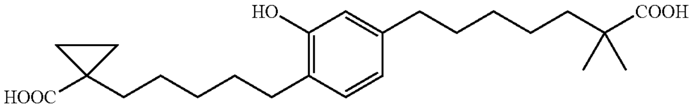 |
| 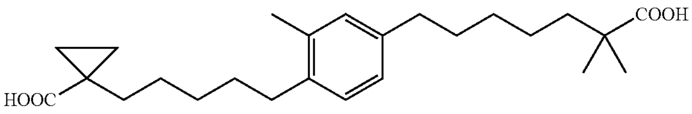 [SMILES: Cc1cc(CCCCCC(C)(C)C(=O)O)ccc1CCCCCC1(C(=O)O)CC1] |

TABLE A-10-continued
| Structure |
| --- |
| 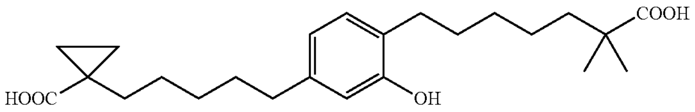 |
| 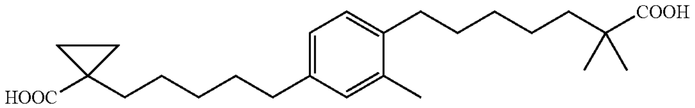 [SMILES: Cc1cc(CCCCCC2(C(=O)O)CC2)ccc1CCCCCC(C)(C)C(=O)O] |
| 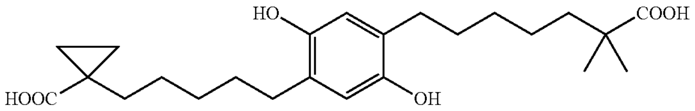 [SMILES: CC(C)(CCCCCc1cc(O)c(CCCCCC2(C(=O)O)CC2)cc1O)C(=O)O] |
| 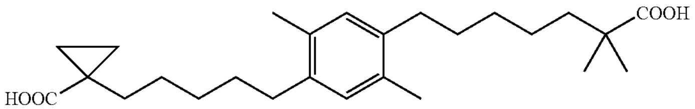 [SMILES: Cc1cc(CCCCCC2(C(=O)O)CC2)c(C)cc1CCCCCC(C)(C)C(=O)O] |
| 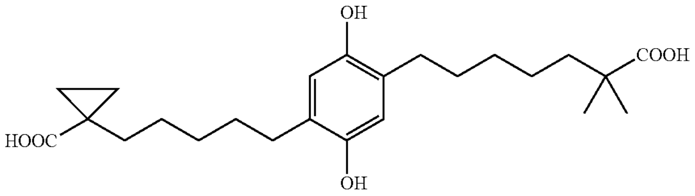 [SMILES: CC(C)(CCCCCc1cc(O)c(CCCCCC2(C(=O)O)CC2)cc1O)C(=O)O] |
| 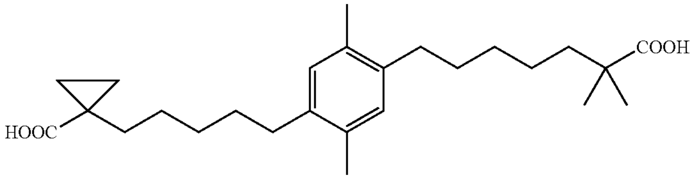 [SMILES: Cc1cc(CCCCCC2(C(=O)O)CC2)c(C)cc1CCCCCC(C)(C)C(=O)O] |
| 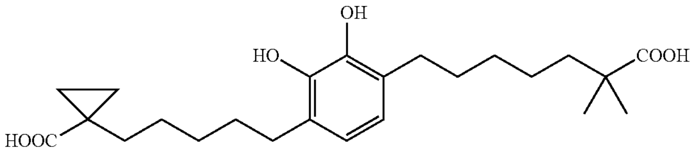 [SMILES: CC(C)(CCCCCc1ccc(CCCCCC2(C(=O)O)CC2)c(O)c1O)C(=O)O] |
| 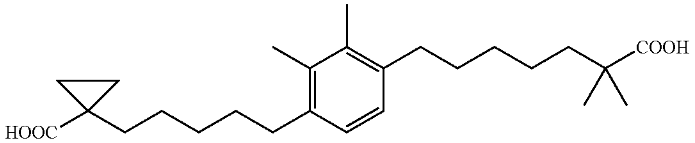 [SMILES: Cc1c(CCCCCC(C)(C)C(=O)O)ccc(CCCCCC2(C(=O)O)CC2)c1C] |
| 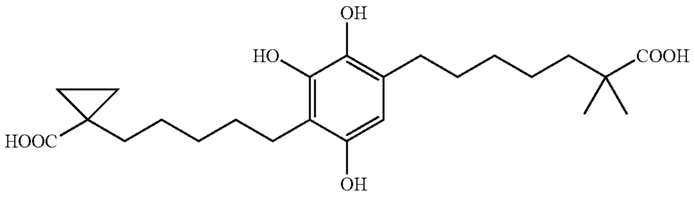 [SMILES: CC(C)(CCCCCc1cc(O)c(CCCCCC2(C(=O)O)CC2)c(O)c1O)C(=O)O] |
| 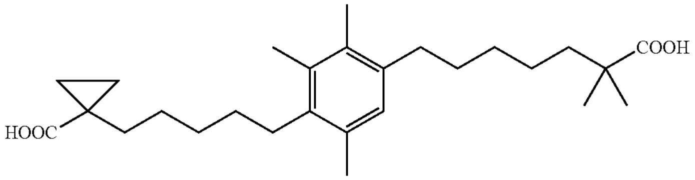 [SMILES: Cc1cc(CCCCCC(C)(C)C(=O)O)c(C)c(C)c1CCCCCC1(C(=O)O)CC1] |

TABLE A-10-continued
| Structure |
|---|
| 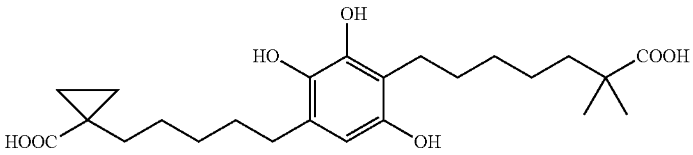 [SMILES: CC(C)(CCCCCc1c(O)cc(CCCCCC2(C(=O)O)CC2)c(O)c1O)C(=O)O] |
| 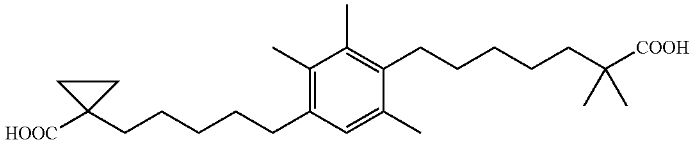 [SMILES: Cc1cc(CCCCCC2(C(=O)O)CC2)c(C)c(C)c1CCCCCC(C)(C)C(=O)O] |
TABLE A-11
| Structure |
|---|
| 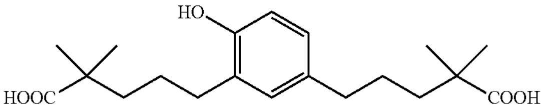 [SMILES: CC(C)(CCCc1ccc(O)c(CCCC(C)(C)C(=O)O)c1)C(=O)O] |
| 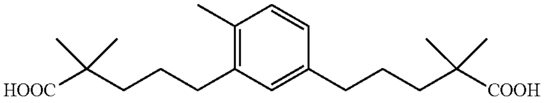 [SMILES: Cc1ccc(CCCC(C)(C)C(=O)O)cc1CCCC(C)(C)C(=O)O] |
| 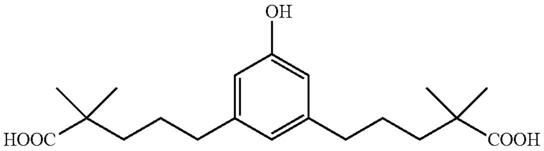 [SMILES: CC(C)(CCCc1cc(O)cc(CCCC(C)(C)C(=O)O)c1)C(=O)O] |
| 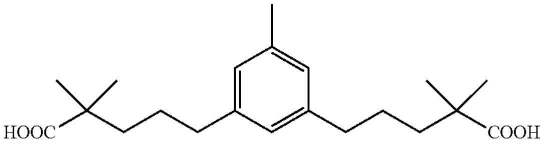 [SMILES: Cc1cc(CCCC(C)(C)C(=O)O)cc(CCCC(C)(C)C(=O)O)c1] |
| 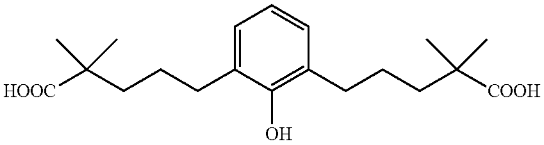 [SMILES: CC(C)(CCCc1cccc(CCCC(C)(C)C(=O)O)c1O)C(=O)O] |
| 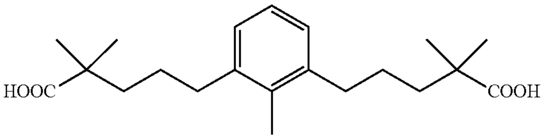 [SMILES: Cc1c(CCCC(C)(C)C(=O)O)cccc1CCCC(C)(C)C(=O)O] |
| 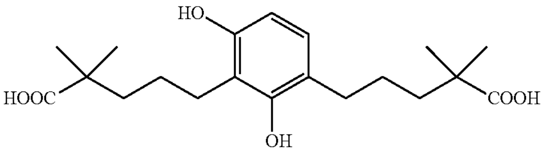 [SMILES: CC(C)(CCCc1ccc(O)c(CCCC(C)(C)C(=O)O)c1O)C(=O)O] |

TABLE A-11-continued
| Structure |
| --- |
| 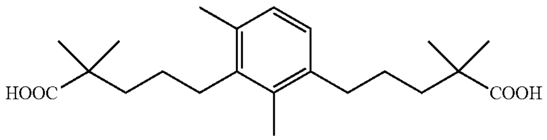 [SMILES: Cc1ccc(CCCC(C)(C)C(=O)O)c(C)c1CCCC(C)(C)C(=O)O] |
| 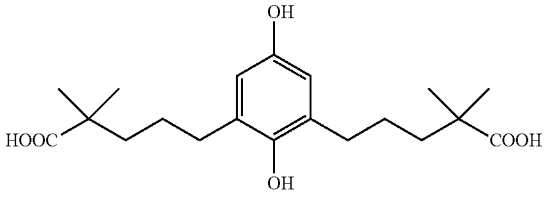 [SMILES: CC(C)(CCCc1cc(O)cc(CCCC(C)(C)C(=O)O)c1O)C(=O)O] |
| 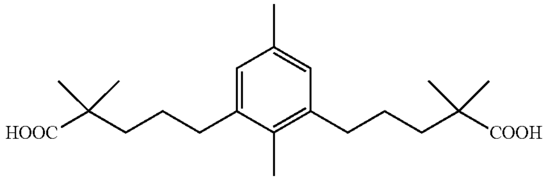 [SMILES: Cc1cc(CCCC(C)(C)C(=O)O)c(C)c(CCCC(C)(C)C(=O)O)c1] |
| 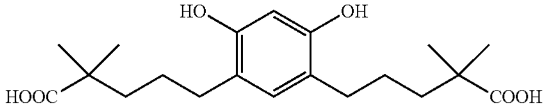 [SMILES: CC(C)(CCCc1cc(CCCC(C)(C)C(=O)O)c(O)cc1O)C(=O)O] |
| 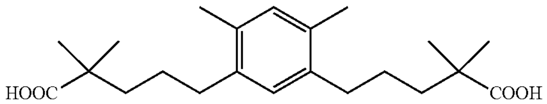 [SMILES: Cc1cc(C)c(CCCC(C)(C)C(=O)O)cc1CCCC(C)(C)C(=O)O] |
| 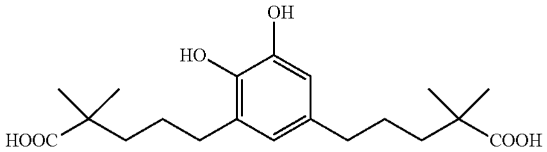 [SMILES: CC(C)(CCCc1cc(O)c(O)c(CCCC(C)(C)C(=O)O)c1)C(=O)O] |
| 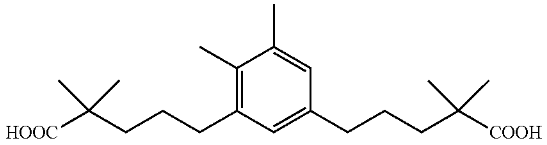 [SMILES: Cc1cc(CCCC(C)(C)C(=O)O)cc(CCCC(C)(C)C(=O)O)c1C] |
| 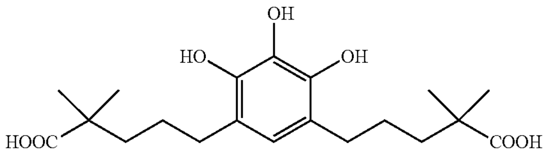 [SMILES: CC(C)(CCCc1cc(CCCC(C)(C)C(=O)O)c(O)c(O)c1O)C(=O)O] |
| 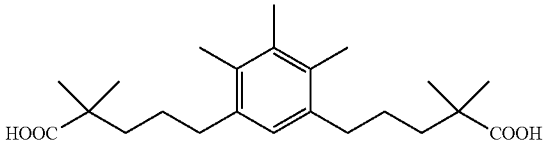 [SMILES: Cc1c(CCCC(C)(C)C(=O)O)cc(CCCC(C)(C)C(=O)O)c(C)c1C] |

TABLE A-11-continued
| Structure |
| --- |
| 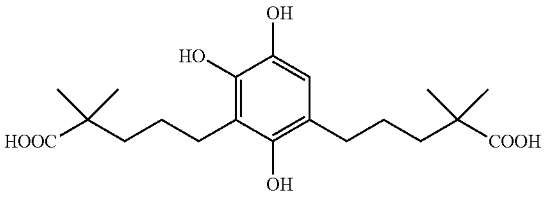 [SMILES: CC(C)(CCCc1cc(O)c(O)c(CCCC(C)(C)C(=O)O)c1O)C(=O)O] |
| 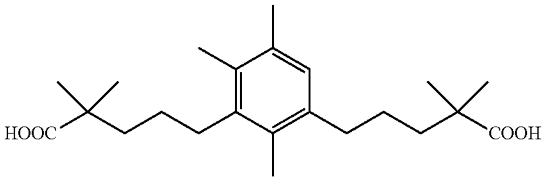 [SMILES: Cc1cc(CCCC(C)(C)C(=O)O)c(C)c(CCCC(C)(C)C(=O)O)c1C] |
| 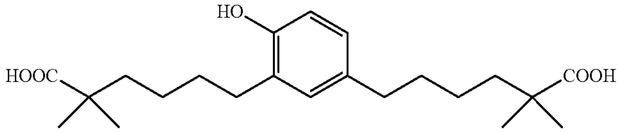 [SMILES: CC(C)(CCCCc1ccc(O)c(CCCCC(C)(C)C(=O)O)c1)C(=O)O] |
| 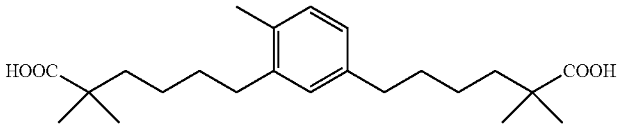 [SMILES: Cc1ccc(CCCCC(C)(C)C(=O)O)cc1CCCCC(C)(C)C(=O)O] |
| 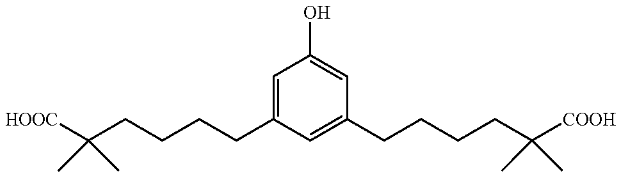 [SMILES: CC(C)(CCCCc1cc(O)cc(CCCCC(C)(C)C(=O)O)c1)C(=O)O] |
| 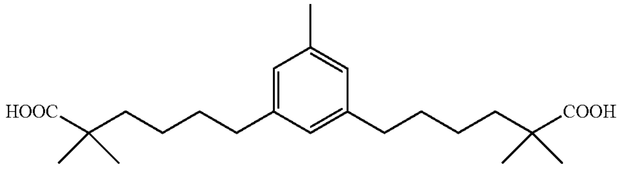 [SMILES: Cc1cc(CCCCC(C)(C)C(=O)O)cc(CCCCC(C)(C)C(=O)O)c1] |
| 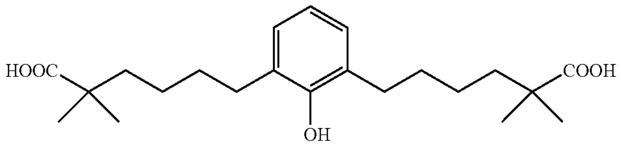 [SMILES: CC(C)(CCCCc1cccc(CCCCC(C)(C)C(=O)O)c1O)C(=O)O] |
| I-94 |
| 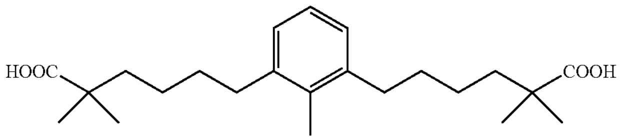 [SMILES: Cc1c(CCCCC(C)(C)C(=O)O)cccc1CCCCC(C)(C)C(=O)O] |
| 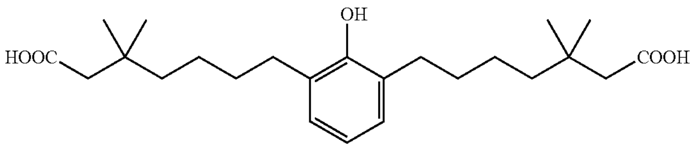 [SMILES: CC(C)(CCCCc1cccc(CCCCC(C)(C)CC(=O)O)c1O)CC(=O)O] |
| I-95 |

TABLE A-11-continued
| Structure |
| --- |
| 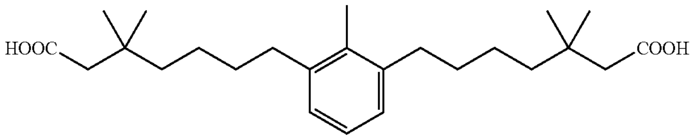 [SMILES: Cc1c(CCCCC(C)(C)CC(=O)O)cccc1CCCCC(C)(C)CC(=O)O] |
| I-96 |
| 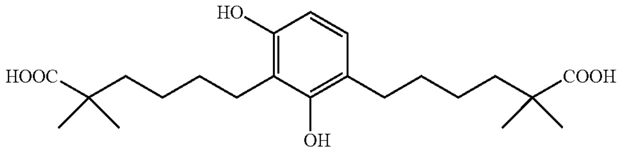 [SMILES: CC(C)(CCCCc1ccc(O)c(CCCCC(C)(C)C(=O)O)c1O)C(=O)O] |
| 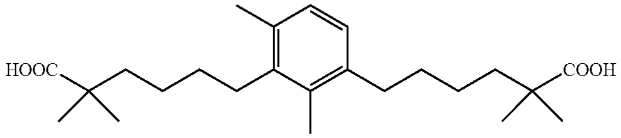 [SMILES: Cc1ccc(CCCCC(C)(C)C(=O)O)c(C)c1CCCCC(C)(C)C(=O)O] |
| 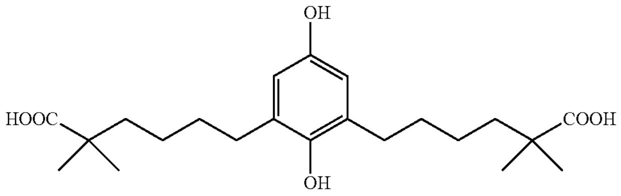 [SMILES: CC(C)(CCCCc1cc(O)cc(CCCCC(C)(C)C(=O)O)c1O)C(=O)O] |
| 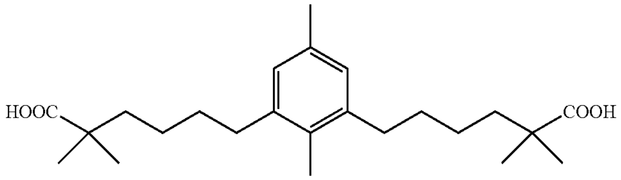 [SMILES: Cc1cc(CCCCC(C)(C)C(=O)O)c(C)c(CCCCC(C)(C)C(=O)O)c1] |
| 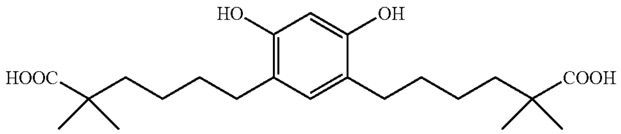 [SMILES: CC(C)(CCCCc1cc(CCCCC(C)(C)C(=O)O)c(O)cc1O)C(=O)O] |
| 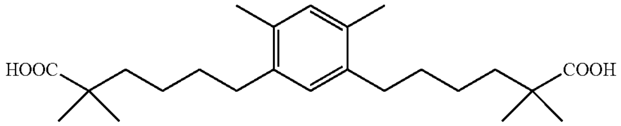 [SMILES: Cc1cc(C)c(CCCCC(C)(C)C(=O)O)cc1CCCCC(C)(C)C(=O)O] |
| 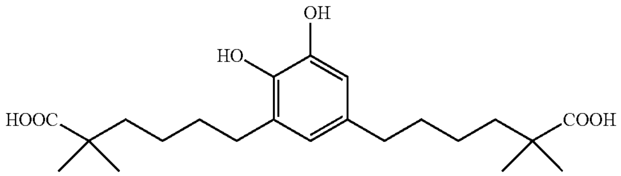 [SMILES: CC(C)(CCCCc1cc(O)c(O)c(CCCCC(C)(C)C(=O)O)c1)C(=O)O] |
| 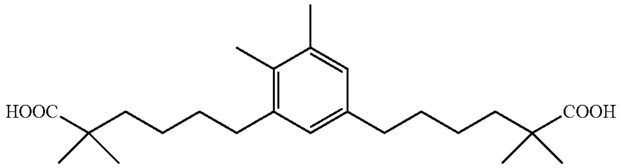 [SMILES: Cc1cc(CCCCC(C)(C)C(=O)O)cc(CCCCC(C)(C)C(=O)O)c1C] |

TABLE A-11-continued
| Structure |
| --- |
| 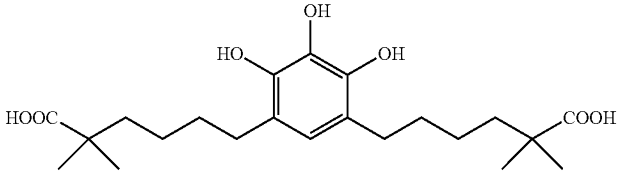 [SMILES: CC(C)(CCCCc1cc(CCCCC(C)(C)C(=O)O)c(O)c(O)c1O)C(=O)O] |
| 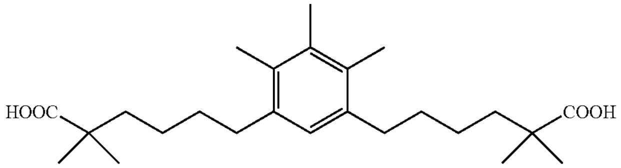 [SMILES: Cc1c(CCCCC(C)(C)C(=O)O)cc(CCCCC(C)(C)C(=O)O)c(C)c1C] |
| 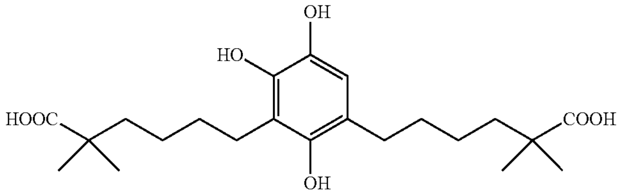 [SMILES: CC(C)(CCCCc1cc(O)c(O)c(CCCCC(C)(C)C(=O)O)c1O)C(=O)O] |
| 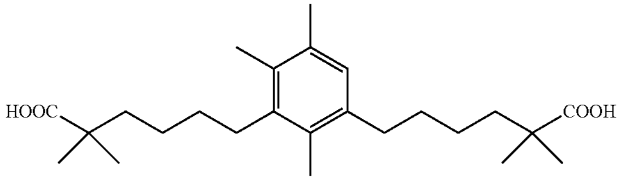 [SMILES: Cc1cc(CCCCC(C)(C)C(=O)O)c(C)c(CCCCC(C)(C)C(=O)O)c1C] |
| 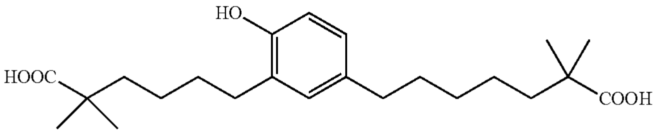 [SMILES: CC(C)(CCCCCc1ccc(O)c(CCCCC(C)(C)C(=O)O)c1)C(=O)O] |
| 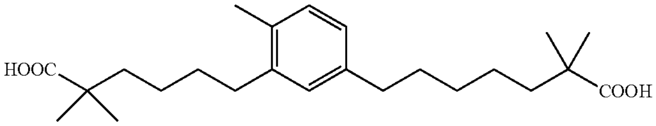 [SMILES: Cc1ccc(CCCCCC(C)(C)C(=O)O)cc1CCCCC(C)(C)C(=O)O] |
| 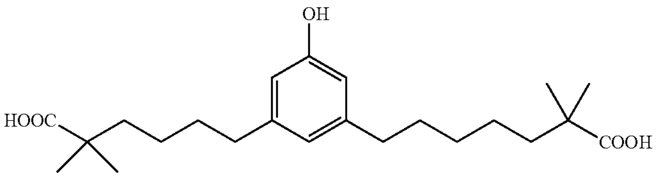 [SMILES: CC(C)(CCCCCc1cc(O)cc(CCCCC(C)(C)C(=O)O)c1)C(=O)O] |
| 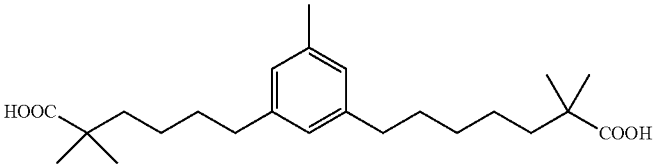 [SMILES: Cc1cc(CCCCCC(C)(C)C(=O)O)cc(CCCCC(C)(C)C(=O)O)c1] |
| 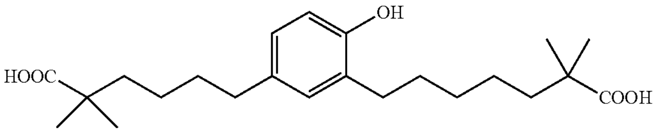 [SMILES: CC(C)(CCCCCc1cc(CCCCC(C)(C)C(=O)O)ccc1O)C(=O)O] |

TABLE A-11-continued
| Structure |
| --- |
| 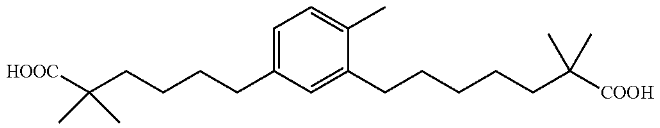 [SMILES: Cc1ccc(CCCCC(C)(C)C(=O)O)cc1CCCCCC(C)(C)C(=O)O] |
| 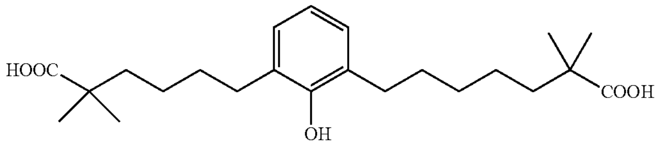 [SMILES: CC(C)(CCCCCc1cccc(CCCCC(C)(C)C(=O)O)c1O)C(=O)O] |
| 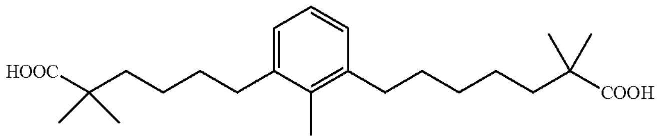 [SMILES: Cc1c(CCCCCC(C)(C)C(=O)O)cccc1CCCCC(C)(C)C(=O)O] |
| 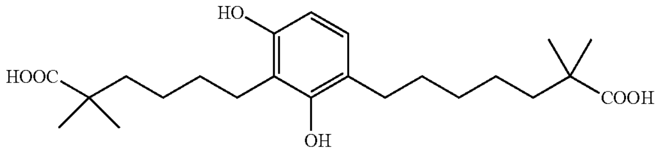 [SMILES: CC(C)(CCCCCc1ccc(O)c(CCCCC(C)(C)C(=O)O)c1O)C(=O)O] |
| 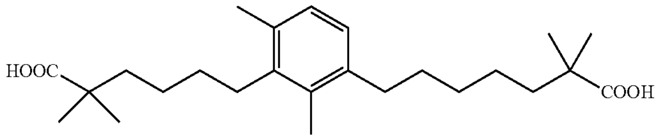 [SMILES: Cc1ccc(CCCCCC(C)(C)C(=O)O)c(C)c1CCCCC(C)(C)C(=O)O] |
| 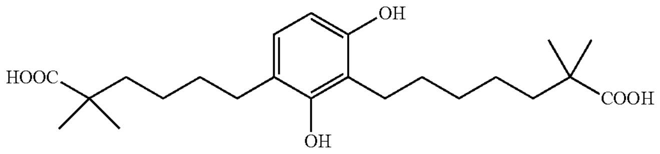 [SMILES: CC(C)(CCCCCc1c(O)ccc(CCCCC(C)(C)C(=O)O)c1O)C(=O)O] |
| 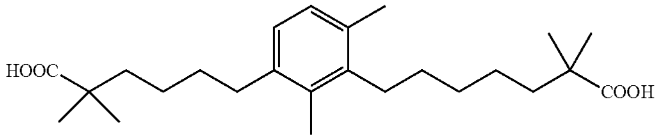 [SMILES: Cc1ccc(CCCCC(C)(C)C(=O)O)c(C)c1CCCCCC(C)(C)C(=O)O] |
| 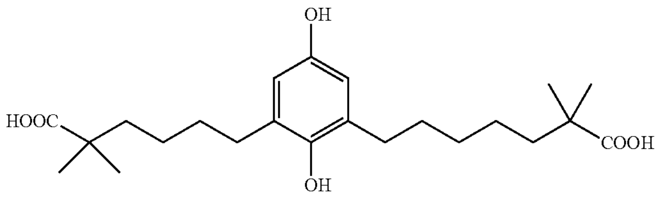 [SMILES: CC(C)(CCCCCc1cc(O)cc(CCCCC(C)(C)C(=O)O)c1O)C(=O)O] |
| 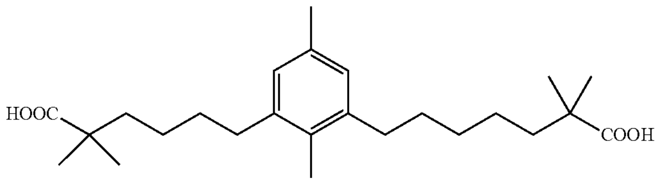 [SMILES: Cc1cc(CCCCCC(C)(C)C(=O)O)c(C)c(CCCCC(C)(C)C(=O)O)c1] |
| 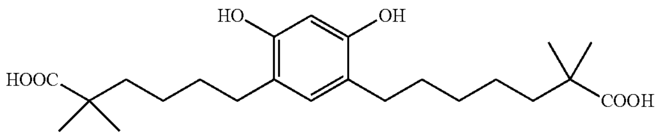 [SMILES: CC(C)(CCCCCc1cc(CCCCC(C)(C)C(=O)O)c(O)cc1O)C(=O)O]

TABLE A-11-continued
| Structure |
| --- |
| 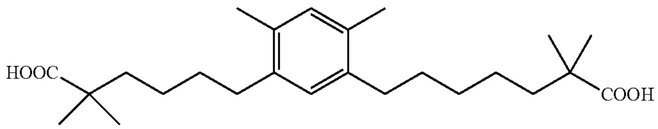 [SMILES: Cc1cc(C)c(CCCCC(C)(C)C(=O)O)cc1CCCCCC(C)(C)C(=O)O] |
| 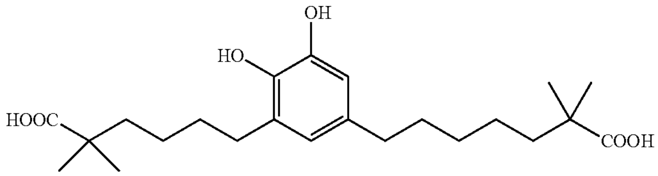 [SMILES: CC(C)(CCCCCc1cc(O)c(O)c(CCCCC(C)(C)C(=O)O)c1)C(=O)O] |
| 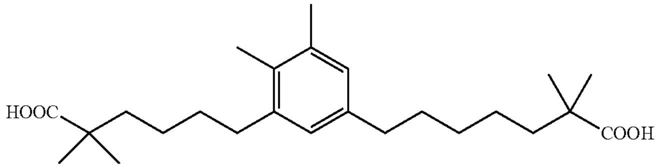 [SMILES: Cc1cc(CCCCCC(C)(C)C(=O)O)cc(CCCCC(C)(C)C(=O)O)c1C] |
| 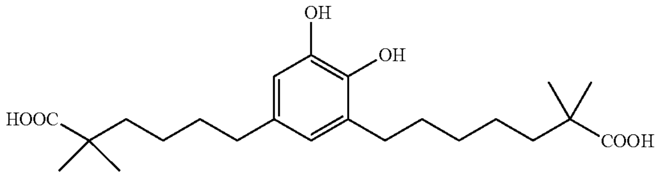 [SMILES: CC(C)(CCCCCc1cc(CCCCC(C)(C)C(=O)O)cc(O)c1O)C(=O)O] |
| 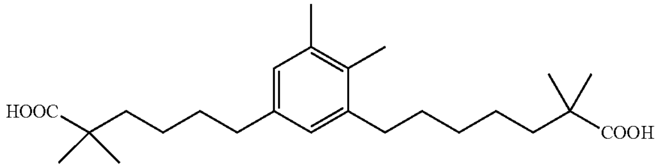 [SMILES: Cc1cc(CCCCC(C)(C)C(=O)O)cc(CCCCCC(C)(C)C(=O)O)c1C] |
| 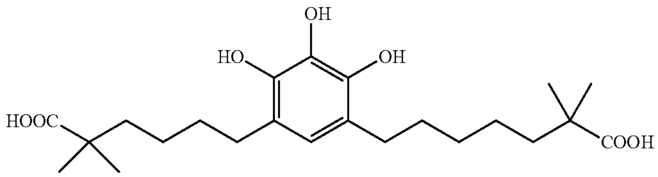 [SMILES: CC(C)(CCCCCc1cc(CCCCC(C)(C)C(=O)O)c(O)c(O)c1O)C(=O)O] |
| 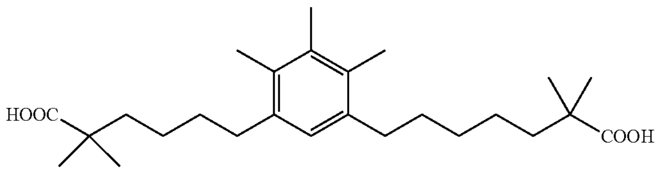 [SMILES: Cc1c(CCCCCC(C)(C)C(=O)O)cc(CCCCC(C)(C)C(=O)O)c(C)c1C] |
| 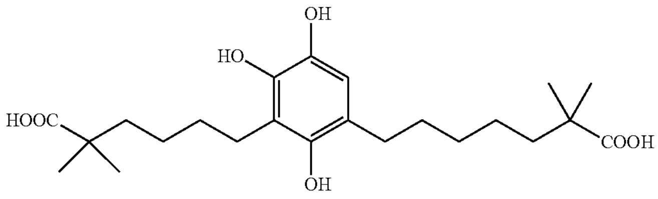 [SMILES: CC(C)(CCCCCc1cc(O)c(O)c(CCCCC(C)(C)C(=O)O)c1O)C(=O)O] |

TABLE A-11-continued
| Structure |
| --- |
| 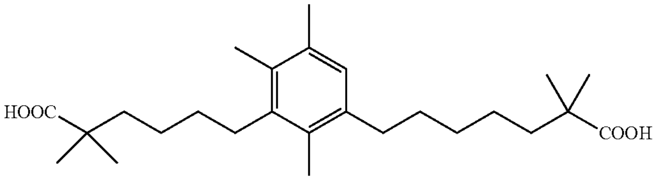 [SMILES: Cc1cc(CCCCCC(C)(C)C(=O)O)c(C)c(CCCCC(C)(C)C(=O)O)c1C] |
| 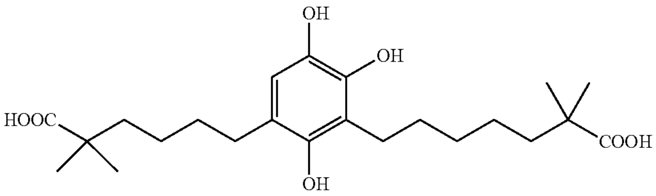 [SMILES: CC(C)(CCCCCc1c(O)c(O)cc(CCCCC(C)(C)C(=O)O)c1O)C(=O)O] |
| 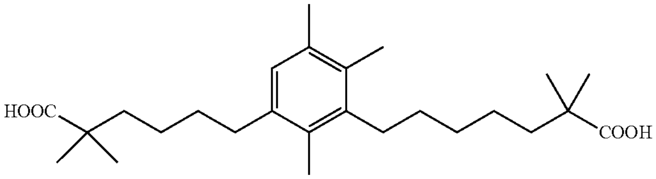 [SMILES: Cc1cc(CCCCC(C)(C)C(=O)O)c(C)c(CCCCCC(C)(C)C(=O)O)c1C] |
| 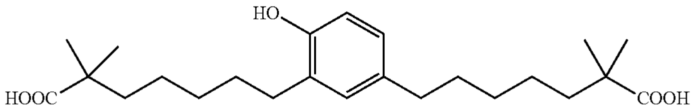 [SMILES: CC(C)(CCCCCc1ccc(O)c(CCCCCC(C)(C)C(=O)O)c1)C(=O)O] |
| 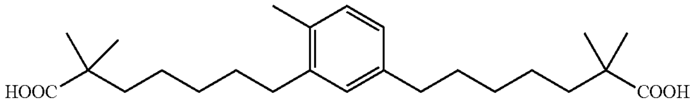 [SMILES: Cc1ccc(CCCCCC(C)(C)C(=O)O)cc1CCCCCC(C)(C)C(=O)O] |
| 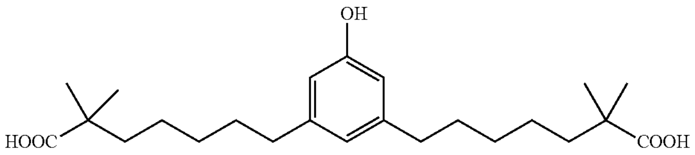 [SMILES: CC(C)(CCCCCc1cc(O)cc(CCCCCC(C)(C)C(=O)O)c1)C(=O)O] |
| 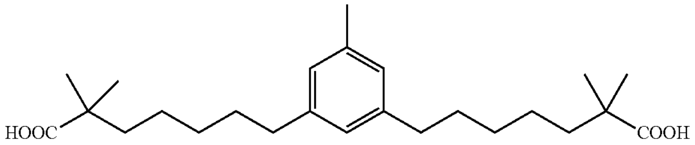 [SMILES: Cc1cc(CCCCCC(C)(C)C(=O)O)cc(CCCCCC(C)(C)C(=O)O)c1] |
| 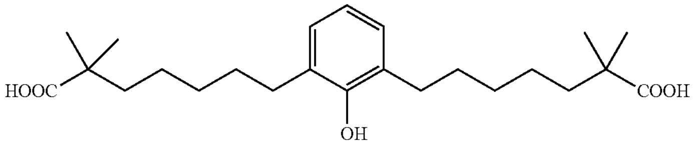 [SMILES: CC(C)(CCCCCc1cccc(CCCCCC(C)(C)C(=O)O)c1O)C(=O)O] |
| 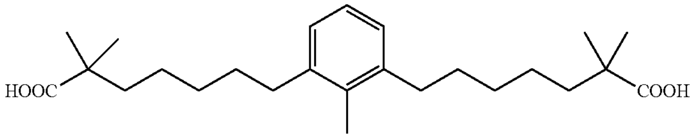 [SMILES: Cc1c(CCCCCC(C)(C)C(=O)O)cccc1CCCCCC(C)(C)C(=O)O] |
| 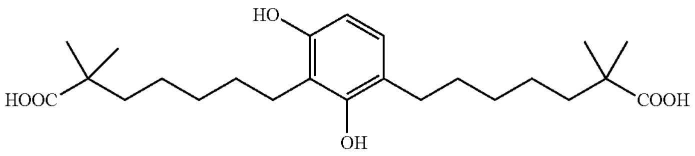 [SMILES: CC(C)(CCCCCc1ccc(O)c(CCCCCC(C)(C)C(=O)O)c1O)C(=O)O] |

TABLE A-11-continued
| Structure |
| --- |
| 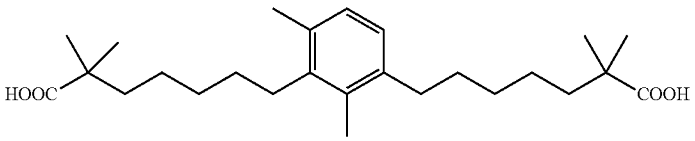 [SMILES: Cc1ccc(CCCCCC(C)(C)C(=O)O)c(C)c1CCCCCC(C)(C)C(=O)O] |
| 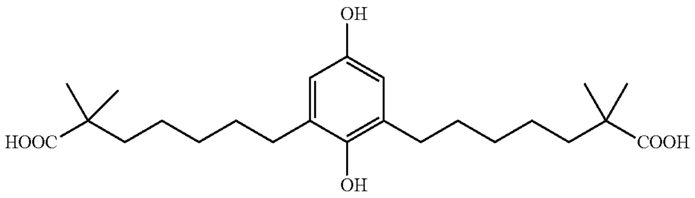 [SMILES: CC(C)(CCCCCc1cc(O)cc(CCCCCC(C)(C)C(=O)O)c1O)C(=O)O] |
| 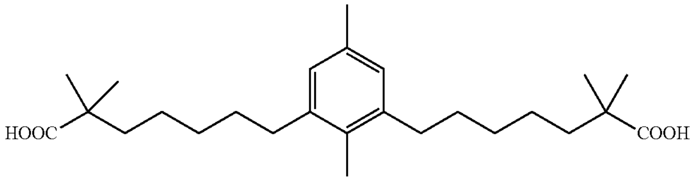 [SMILES: Cc1cc(CCCCCC(C)(C)C(=O)O)c(C)c(CCCCCC(C)(C)C(=O)O)c1] |
| 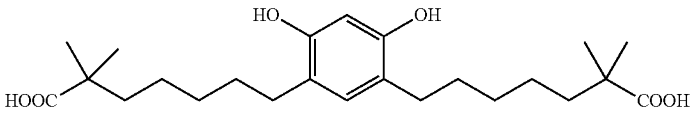 [SMILES: CC(C)(CCCCCc1cc(CCCCCC(C)(C)C(=O)O)c(O)cc1O)C(=O)O] |
| 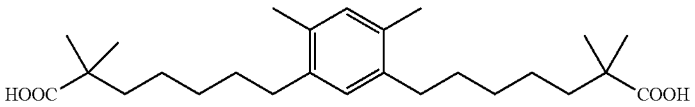 [SMILES: Cc1cc(C)c(CCCCCC(C)(C)C(=O)O)cc1CCCCCC(C)(C)C(=O)O] |
| 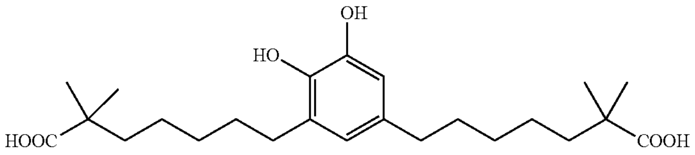 [SMILES: CC(C)(CCCCCc1cc(O)c(O)c(CCCCCC(C)(C)C(=O)O)c1)C(=O)O] |
| 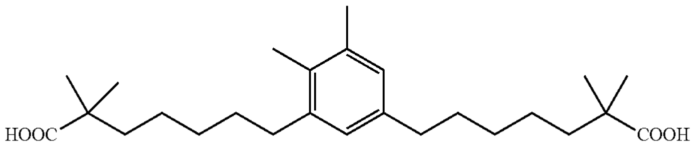 [SMILES: Cc1cc(CCCCCC(C)(C)C(=O)O)cc(CCCCCC(C)(C)C(=O)O)c1C] |
| 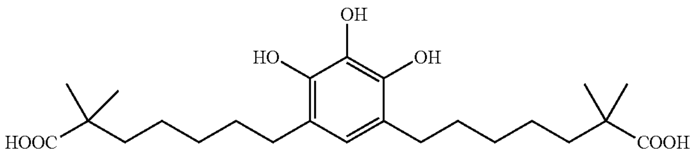 [SMILES: CC(C)(CCCCCc1cc(CCCCCC(C)(C)C(=O)O)c(O)c(O)c1O)C(=O)O] |
| 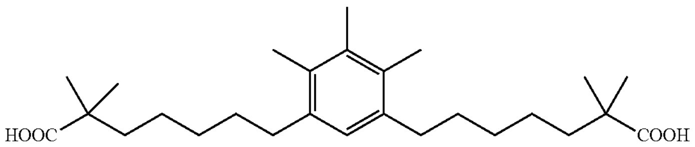 [SMILES: Cc1c(CCCCCC(C)(C)C(=O)O)cc(CCCCCC(C)(C)C(=O)O)c(C)c1C] |

TABLE A-11-continued
| Structure |
| --- |
| 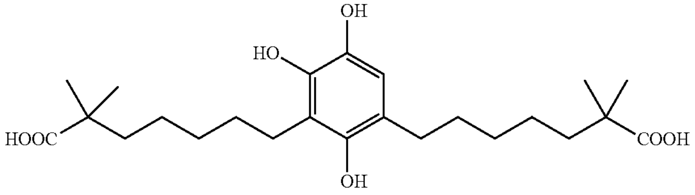 [SMILES: CC(C)(CCCCCc1cc(O)c(O)c(CCCCCC(C)(C)C(=O)O)c1O)C(=O)O] |
| 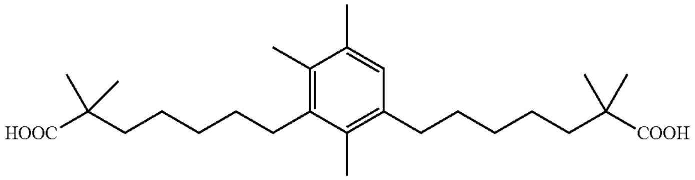 [SMILES: Cc1cc(CCCCCC(C)(C)C(=O)O)c(C)c(CCCCCC(C)(C)C(=O)O)c1C] |
| 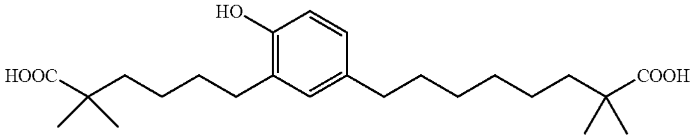 [SMILES: CC(C)(CCCCCCc1ccc(O)c(CCCCC(C)(C)C(=O)O)c1)C(=O)O] |
| 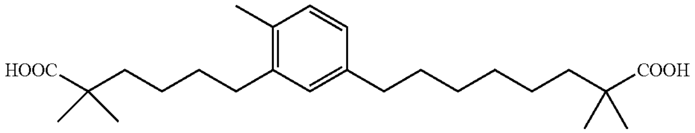 [SMILES: Cc1ccc(CCCCCCC(C)(C)C(=O)O)cc1CCCCC(C)(C)C(=O)O] |
| 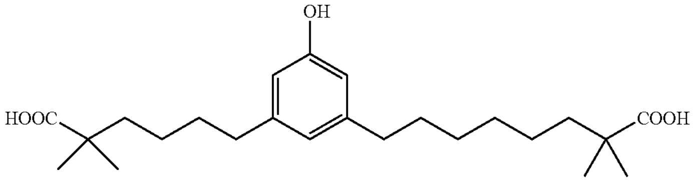 [SMILES: CC(C)(CCCCCCc1cc(O)cc(CCCCC(C)(C)C(=O)O)c1)C(=O)O] |
| 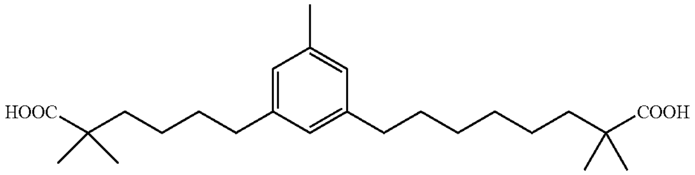 [SMILES: Cc1cc(CCCCCCC(C)(C)C(=O)O)cc(CCCCC(C)(C)C(=O)O)c1] |
| 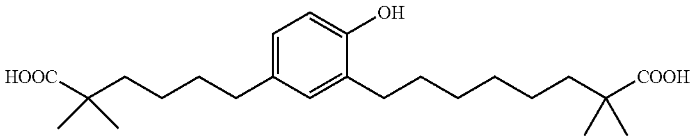 [SMILES: CC(C)(CCCCCCc1cc(CCCCC(C)(C)C(=O)O)ccc1O)C(=O)O] |
| 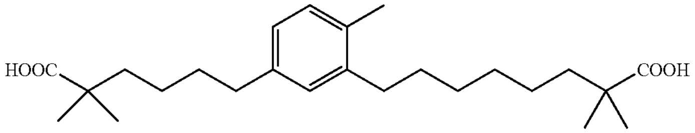 [SMILES: Cc1ccc(CCCCC(C)(C)C(=O)O)cc1CCCCCCC(C)(C)C(=O)O] |
| 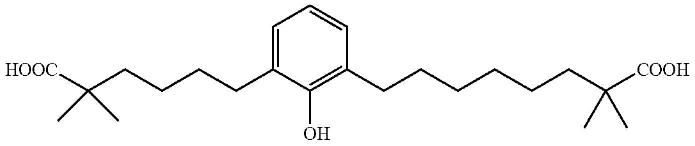 [SMILES: CC(C)(CCCCCCc1cccc(CCCCC(C)(C)C(=O)O)c1O)C(=O)O] |

TABLE A-11-continued
| Structure |
| --- |
| 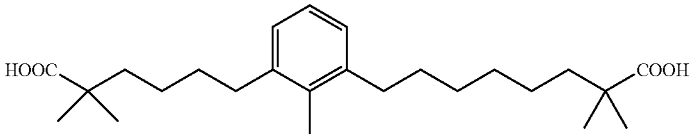 [SMILES: Cc1c(CCCCCCC(C)(C)C(=O)O)cccc1CCCCC(C)(C)C(=O)O] |
| 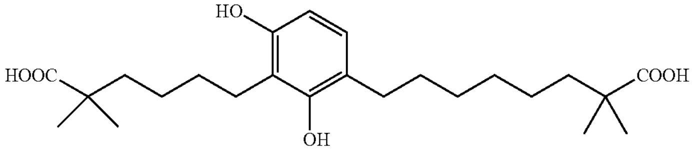 [SMILES: CC(C)(CCCCCCc1ccc(O)c(CCCCC(C)(C)C(=O)O)c1O)C(=O)O] |
| 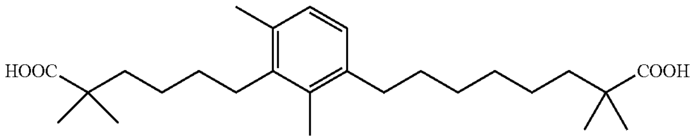 [SMILES: Cc1ccc(CCCCCCC(C)(C)C(=O)O)c(C)c1CCCCC(C)(C)C(=O)O] |
| 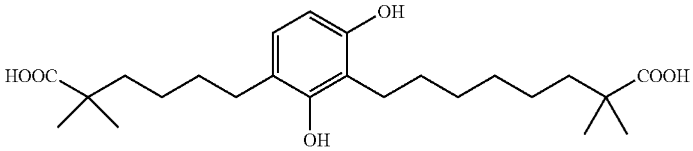 [SMILES: CC(C)(CCCCCCc1c(O)ccc(CCCCC(C)(C)C(=O)O)c1O)C(=O)O] |
| 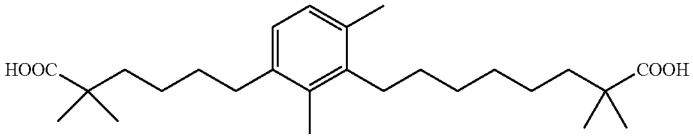 [SMILES: Cc1ccc(CCCCC(C)(C)C(=O)O)c(C)c1CCCCCCC(C)(C)C(=O)O] |
| 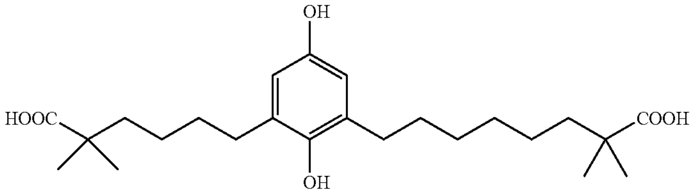 [SMILES: CC(C)(CCCCCCc1cc(O)cc(CCCCC(C)(C)C(=O)O)c1O)C(=O)O] |
| 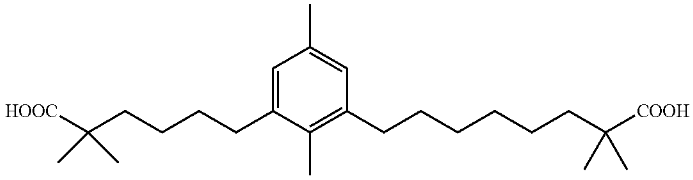 [SMILES: Cc1cc(CCCCCCC(C)(C)C(=O)O)c(C)c(CCCCC(C)(C)C(=O)O)c1] |
| 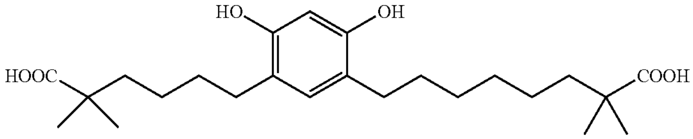 [SMILES: CC(C)(CCCCCCc1cc(CCCCC(C)(C)C(=O)O)c(O)cc1O)C(=O)O] |
| 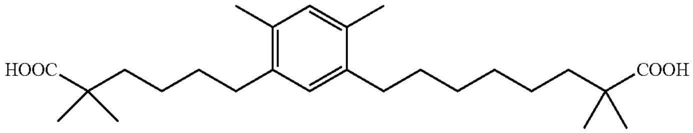 [SMILES: Cc1cc(C)c(CCCCC(C)(C)C(=O)O)cc1CCCCCCC(C)(C)C(=O)O] |

TABLE A-11-continued
| Structure |
| --- |
| 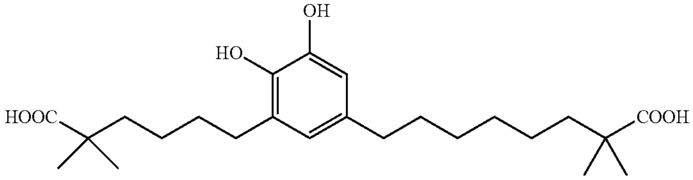 [SMILES: CC(C)(CCCCCCc1cc(O)c(O)c(CCCCC(C)(C)C(=O)O)c1)C(=O)O] |
| 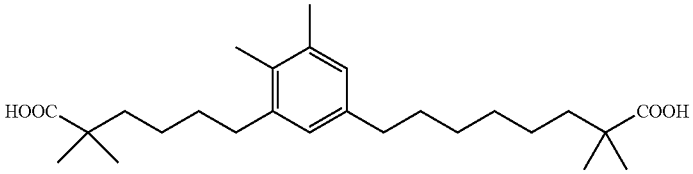 [SMILES: Cc1cc(CCCCCCC(C)(C)C(=O)O)cc(CCCCC(C)(C)C(=O)O)c1C] |
| 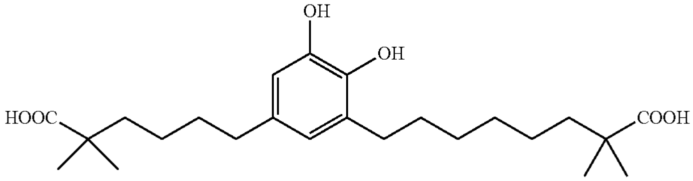 [SMILES: CC(C)(CCCCCCc1cc(CCCCC(C)(C)C(=O)O)cc(O)c1O)C(=O)O] |
| 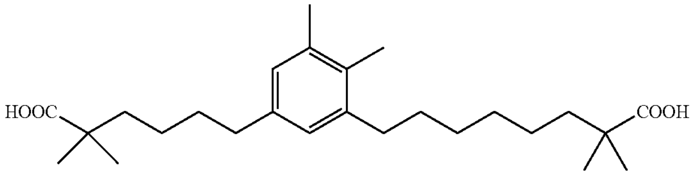 [SMILES: Cc1cc(CCCCC(C)(C)C(=O)O)cc(CCCCCCC(C)(C)C(=O)O)c1C] |
| 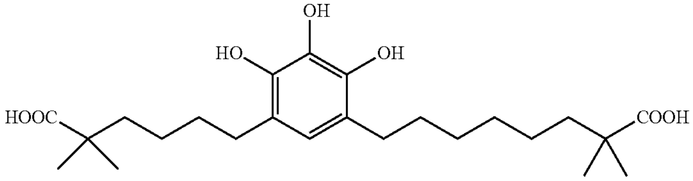 [SMILES: CC(C)(CCCCCCc1cc(CCCCC(C)(C)C(=O)O)c(O)c(O)c1O)C(=O)O] |
| 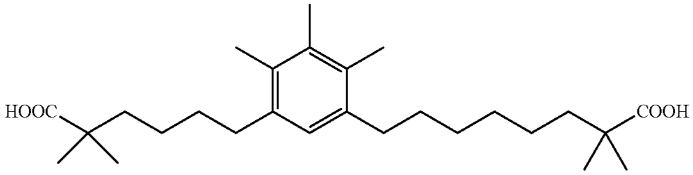 [SMILES: Cc1c(CCCCCCC(C)(C)C(=O)O)cc(CCCCC(C)(C)C(=O)O)c(C)c1C] |
| 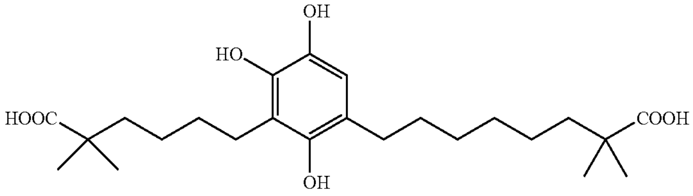 [SMILES: CC(C)(CCCCCCc1cc(O)c(O)c(CCCCC(C)(C)C(=O)O)c1O)C(=O)O] |
| 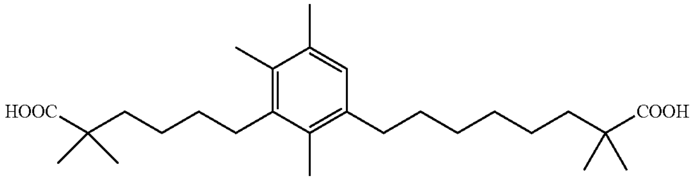 [SMILES: Cc1cc(CCCCCCC(C)(C)C(=O)O)c(C)c(CCCCC(C)(C)C(=O)O)c1C]

TABLE A-11-continued
| Structure |
| --- |
| 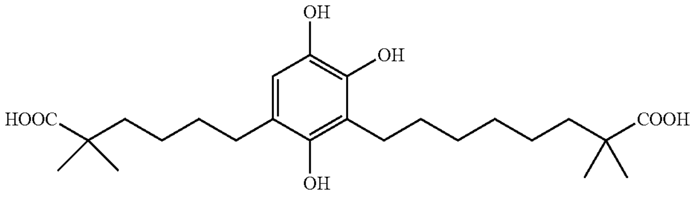 [SMILES: CC(C)(CCCCCCc1c(O)c(O)cc(CCCCC(C)(C)C(=O)O)c1O)C(=O)O] |
| 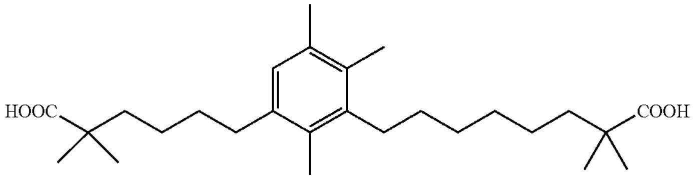 [SMILES: Cc1cc(CCCCC(C)(C)C(=O)O)c(C)c(CCCCCCC(C)(C)C(=O)O)c1C] |
| 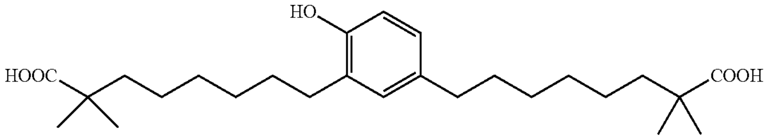 [SMILES: CC(C)(CCCCCCc1ccc(O)c(CCCCCCC(C)(C)C(=O)O)c1)C(=O)O] |
| 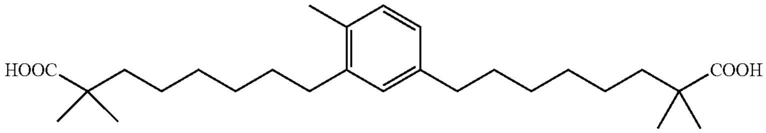 [SMILES: Cc1ccc(CCCCCCC(C)(C)C(=O)O)cc1CCCCCCC(C)(C)C(=O)O] |
| 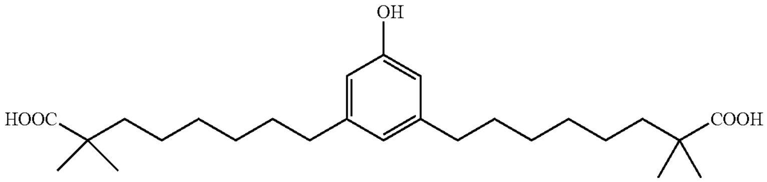 [SMILES: CC(C)(CCCCCCc1cc(O)cc(CCCCCCC(C)(C)C(=O)O)c1)C(=O)O] |
| 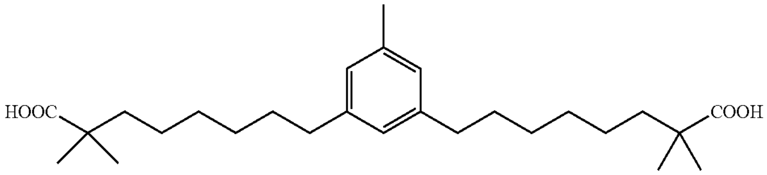 [SMILES: Cc1cc(CCCCCCC(C)(C)C(=O)O)cc(CCCCCCC(C)(C)C(=O)O)c1] |
| 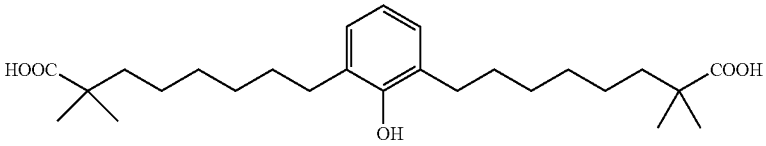 [SMILES: CC(C)(CCCCCCc1cccc(CCCCCCC(C)(C)C(=O)O)c1O)C(=O)O] |
| 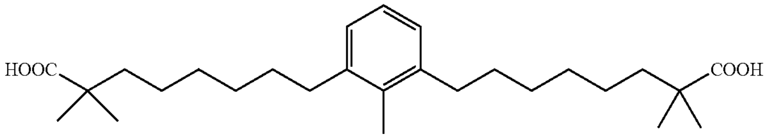 [SMILES: Cc1c(CCCCCCC(C)(C)C(=O)O)cccc1CCCCCCC(C)(C)C(=O)O] |
| 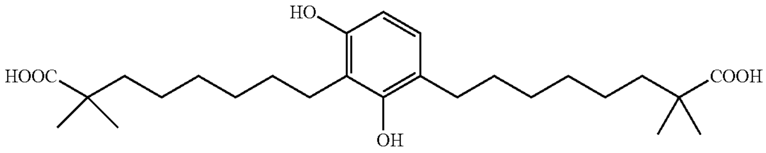 [SMILES: CC(C)(CCCCCCc1ccc(O)c(CCCCCCC(C)(C)C(=O)O)c1O)C(=O)O] |

TABLE A-11-continued
| Structure |
| --- |
| 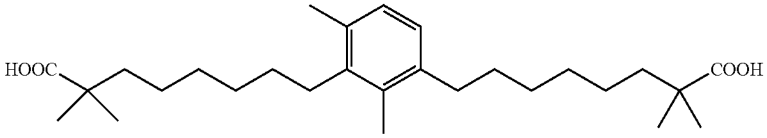 [SMILES: Cc1ccc(CCCCCCC(C)(C)C(=O)O)c(C)c1CCCCCCC(C)(C)C(=O)O] |
| 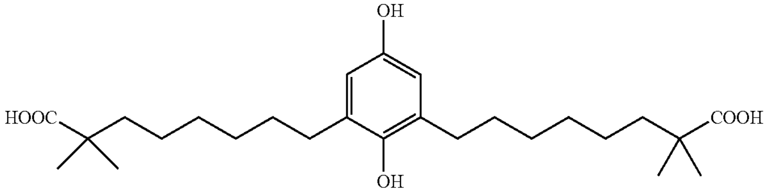 [SMILES: CC(C)(CCCCCCc1cc(O)cc(CCCCCCC(C)(C)C(=O)O)c1O)C(=O)O] |
| 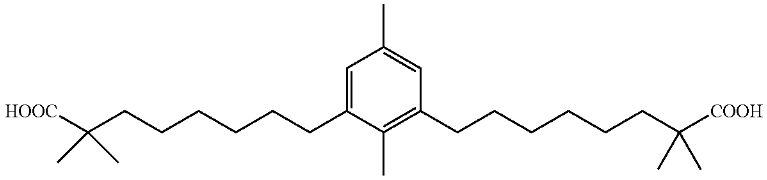 [SMILES: Cc1cc(CCCCCCC(C)(C)C(=O)O)c(C)c(CCCCCCC(C)(C)C(=O)O)c1] |
| 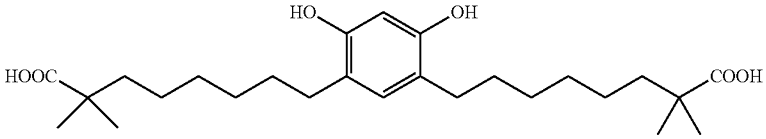 [SMILES: CC(C)(CCCCCCc1cc(CCCCCCC(C)(C)C(=O)O)c(O)cc1O)C(=O)O] |
| 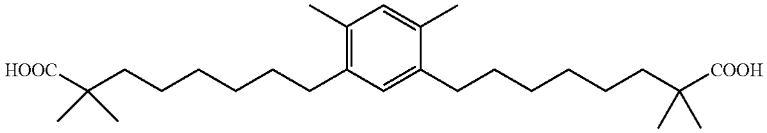 [SMILES: Cc1cc(C)c(CCCCCCC(C)(C)C(=O)O)cc1CCCCCCC(C)(C)C(=O)O] |
| 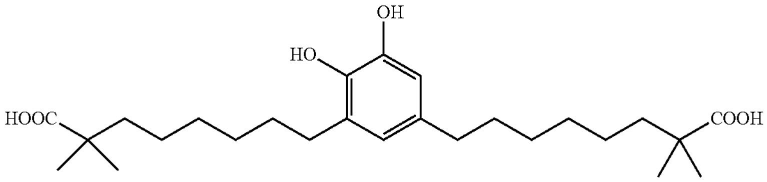 [SMILES: CC(C)(CCCCCCc1cc(O)c(O)c(CCCCCCC(C)(C)C(=O)O)c1)C(=O)O] |
| 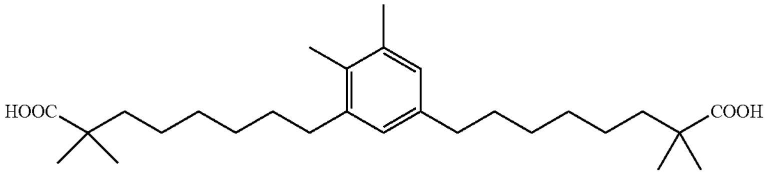 [SMILES: Cc1cc(CCCCCCC(C)(C)C(=O)O)cc(CCCCCCC(C)(C)C(=O)O)c1C] |
| 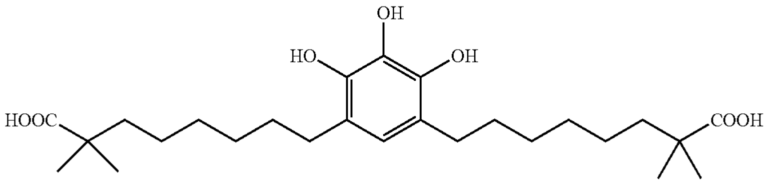 [SMILES: CC(C)(CCCCCCc1cc(CCCCCCC(C)(C)C(=O)O)c(O)c(O)c1O)C(=O)O] |
| 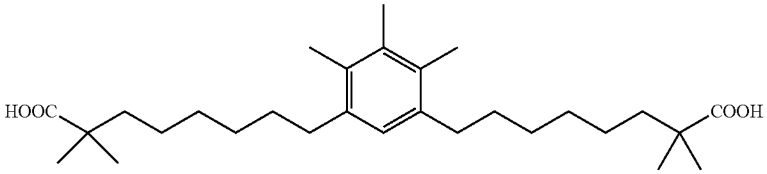 [SMILES: Cc1c(CCCCCCC(C)(C)C(=O)O)cc(CCCCCCC(C)(C)C(=O)O)c(C)c1C] |

TABLE A-11-continued
| Structure |
| --- |
| 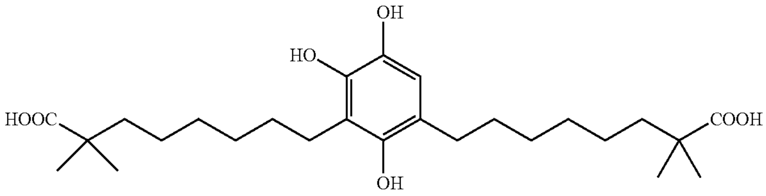 [SMILES: CC(C)(CCCCCCc1cc(O)c(O)c(CCCCCCC(C)(C)C(=O)O)c1O)C(=O)O] |
| 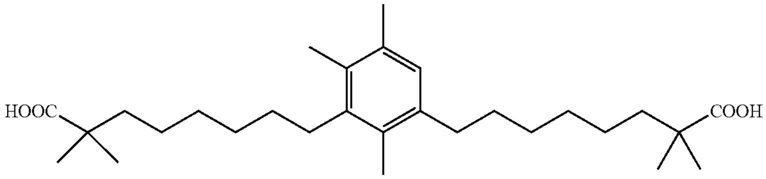 [SMILES: Cc1cc(CCCCCCC(C)(C)C(=O)O)c(C)c(CCCCCCC(C)(C)C(=O)O)c1C] |
| 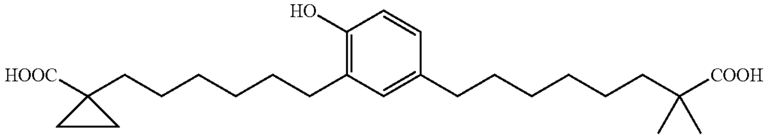 [SMILES: CC(C)(CCCCCCc1ccc(O)c(CCCCCCC2(C(=O)O)CC2)c1)C(=O)O] |
| 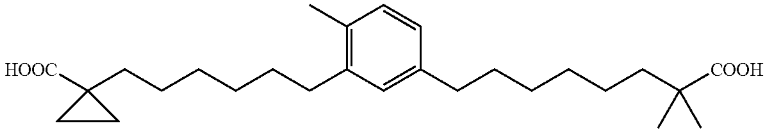 [SMILES: Cc1ccc(CCCCCCC(C)(C)C(=O)O)cc1CCCCCCC1(C(=O)O)CC1] |
| 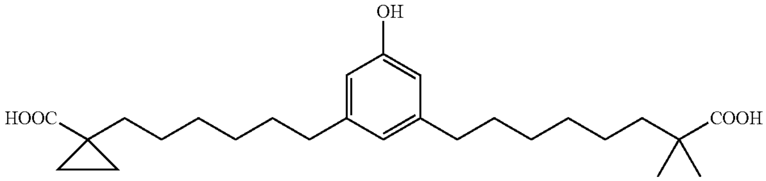 [SMILES: CC(C)(CCCCCCc1cc(O)cc(CCCCCCC2(C(=O)O)CC2)c1)C(=O)O] |
| 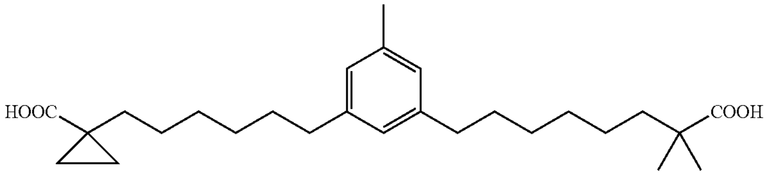 [SMILES: Cc1cc(CCCCCCC(C)(C)C(=O)O)cc(CCCCCCC2(C(=O)O)CC2)c1] |
| 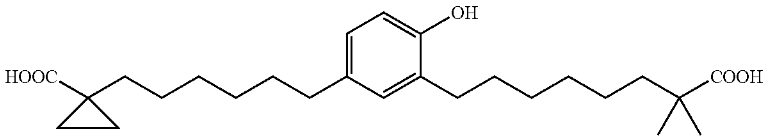 [SMILES: CC(C)(CCCCCCc1cc(CCCCCCC2(C(=O)O)CC2)ccc1O)C(=O)O] |
| 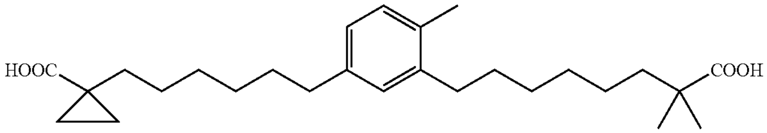 [SMILES: Cc1ccc(CCCCCCC2(C(=O)O)CC2)cc1CCCCCCC(C)(C)C(=O)O] |
| 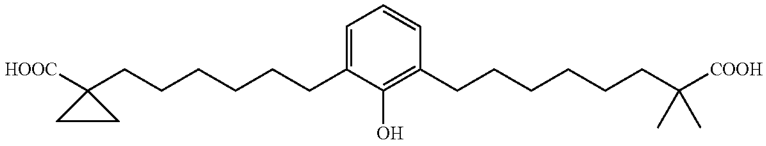 [SMILES: CC(C)(CCCCCCc1cccc(CCCCCCC2(C(=O)O)CC2)c1O)C(=O)O] |

TABLE A-11-continued
| Structure |
|---|
| 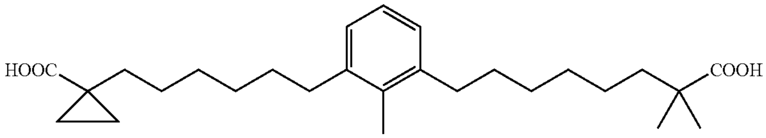 [SMILES: Cc1c(CCCCCCC(C)(C)C(=O)O)cccc1CCCCCCC1(C(=O)O)CC1] |
| 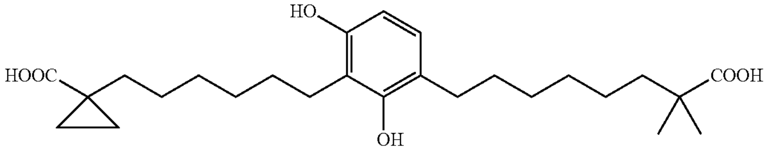 [SMILES: CC(C)(CCCCCCc1ccc(O)c(CCCCCCC2(C(=O)O)CC2)c1O)C(=O)O] |
| 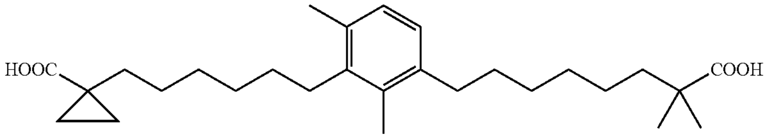 [SMILES: Cc1ccc(CCCCCCC(C)(C)C(=O)O)c(C)c1CCCCCCC1(C(=O)O)CC1] |
| 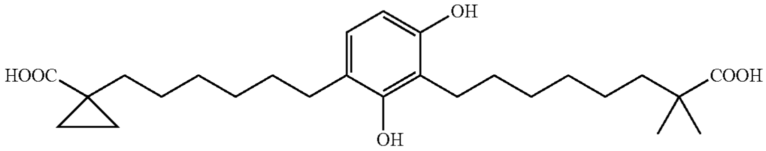 [SMILES: CC(C)(CCCCCCc1c(O)ccc(CCCCCCC2(C(=O)O)CC2)c1O)C(=O)O] |
| 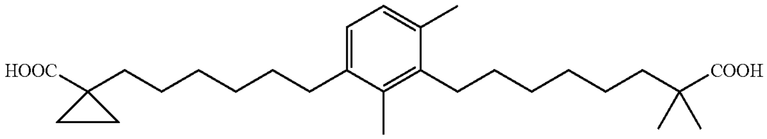 [SMILES: Cc1ccc(CCCCCCC2(C(=O)O)CC2)c(C)c1CCCCCCC(C)(C)C(=O)O] |
| 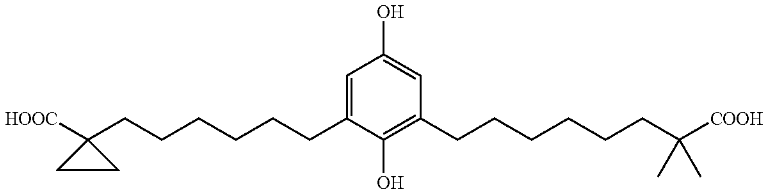 [SMILES: CC(C)(CCCCCCc1cc(O)cc(CCCCCCC2(C(=O)O)CC2)c1O)C(=O)O] |
| 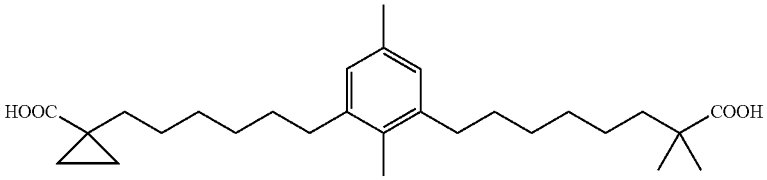 [SMILES: Cc1cc(CCCCCCC(C)(C)C(=O)O)c(C)c(CCCCCCC2(C(=O)O)CC2)c1] |
| 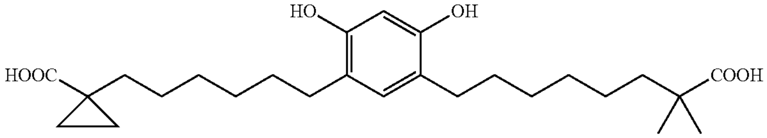 [SMILES: CC(C)(CCCCCCc1cc(CCCCCCC2(C(=O)O)CC2)c(O)cc1O)C(=O)O] |
| 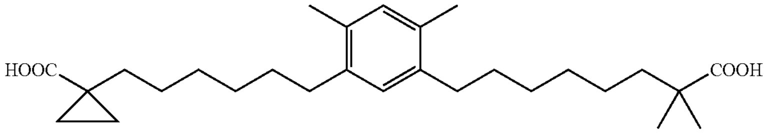 [SMILES: Cc1cc(C)c(CCCCCCC2(C(=O)O)CC2)cc1CCCCCCC(C)(C)C(=O)O] |

TABLE A-11-continued
| Structure |
| --- |
| 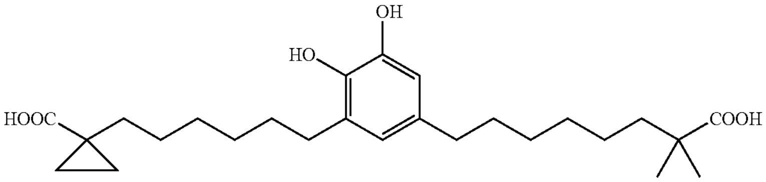 [SMILES: CC(C)(CCCCCCc1cc(O)c(O)c(CCCCCCC2(C(=O)O)CC2)c1)C(=O)O] |
| 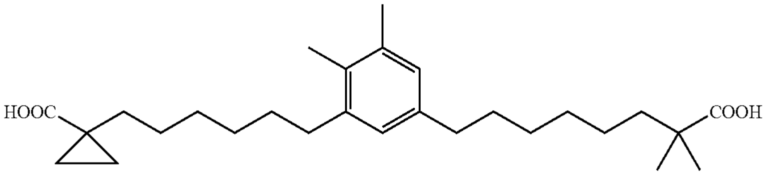 |
| 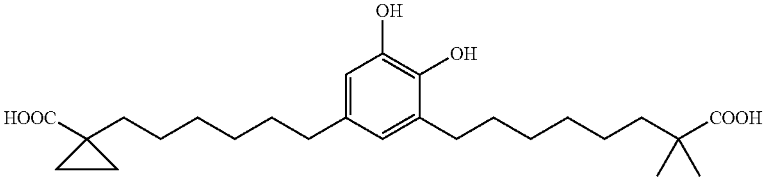 [SMILES: CC(C)(CCCCCCc1cc(CCCCCCC2(C(=O)O)CC2)cc(O)c1O)C(=O)O] |
| 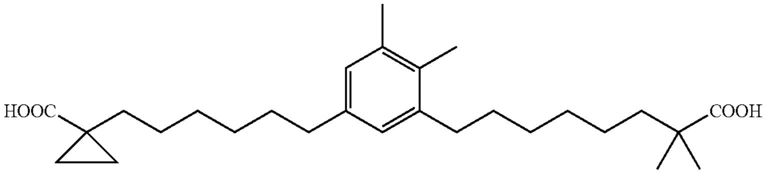 |
| 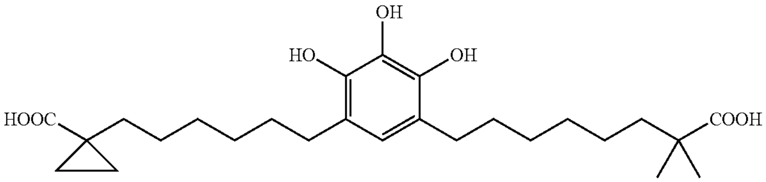 [SMILES: CC(C)(CCCCCCc1cc(CCCCCCC2(C(=O)O)CC2)c(O)c(O)c1O)C(=O)O] |
| 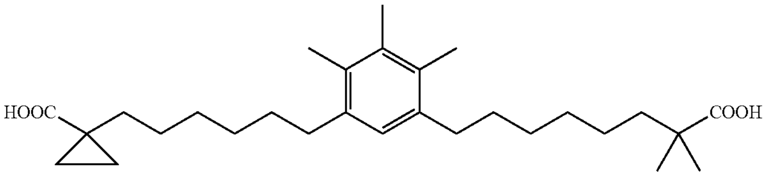 [SMILES: Cc1c(CCCCCCC(C)(C)C(=O)O)cc(CCCCCCC2(C(=O)O)CC2)c(C)c1C] |
| 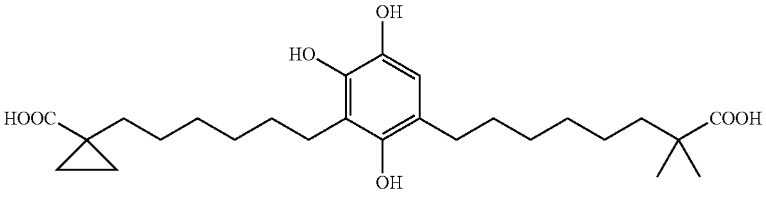 [SMILES: CC(C)(CCCCCCc1cc(O)c(O)c(CCCCCCC2(C(=O)O)CC2)c1O)C(=O)O] |
| 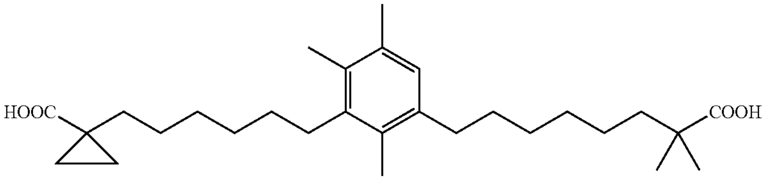 [SMILES: Cc1cc(CCCCCCC(C)(C)C(=O)O)c(C)c(CCCCCCC2(C(=O)O)CC2)c1C] |

TABLE A-11-continued
| Structure |
| --- |
| 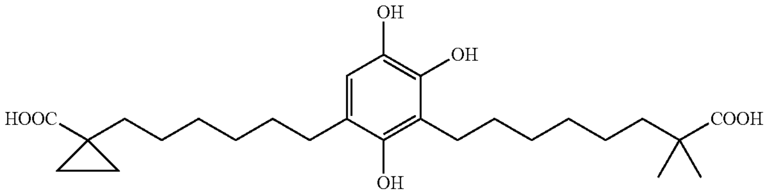 [SMILES: CC(C)(CCCCCCc1c(O)c(O)cc(CCCCCCC2(C(=O)O)CC2)c1O)C(=O)O] |
| 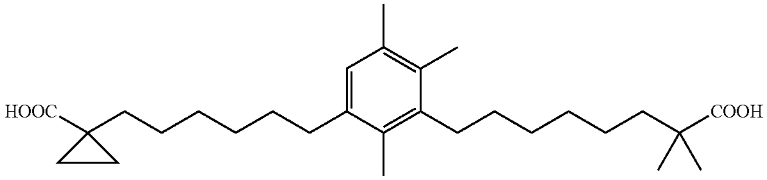 [SMILES: Cc1cc(CCCCCCC2(C(=O)O)CC2)c(C)c(CCCCCCC(C)(C)C(=O)O)c1C] |
| 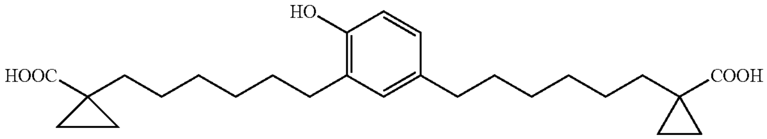 [SMILES: O=C(O)C1(CCCCCCc2ccc(O)c(CCCCCCC3(C(=O)O)CC3)c2)CC1] |
| 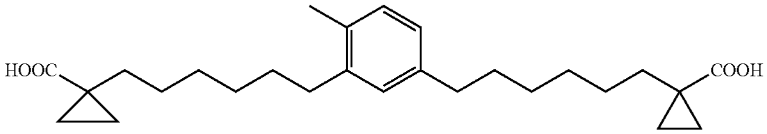 |
| 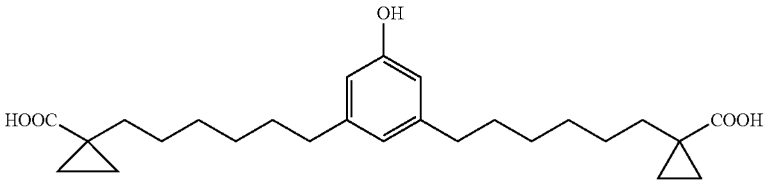 [SMILES: O=C(O)C1(CCCCCCc2cc(O)cc(CCCCCCC3(C(=O)O)CC3)c2)CC1] |
| 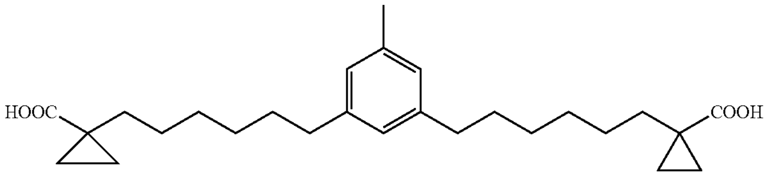 [SMILES: Cc1cc(CCCCCCC2(C(=O)O)CC2)cc(CCCCCCC2(C(=O)O)CC2)c1] |
| 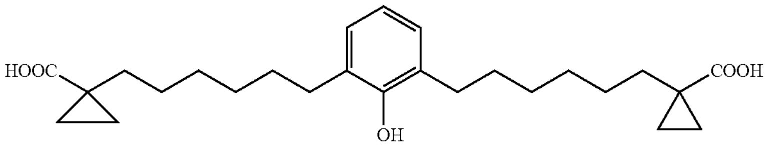 [SMILES: O=C(O)C1(CCCCCCc2cccc(CCCCCCC3(C(=O)O)CC3)c2O)CC1] |
| 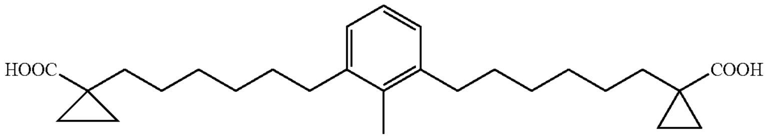 [SMILES: Cc1c(CCCCCCC2(C(=O)O)CC2)cccc1CCCCCCC1(C(=O)O)CC1] |
| 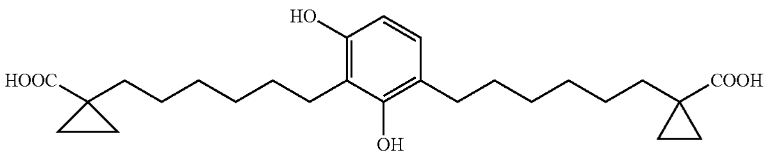 [SMILES: O=C(O)C1(CCCCCCc2ccc(O)c(CCCCCCC3(C(=O)O)CC3)c2O)CC1] |

TABLE A-11-continued
| Structure |
|---|
| 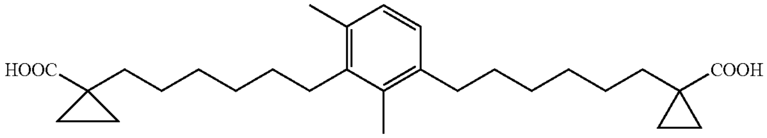 [SMILES: Cc1ccc(CCCCCCC2(C(=O)O)CC2)c(C)c1CCCCCCC1(C(=O)O)CC1] |
| 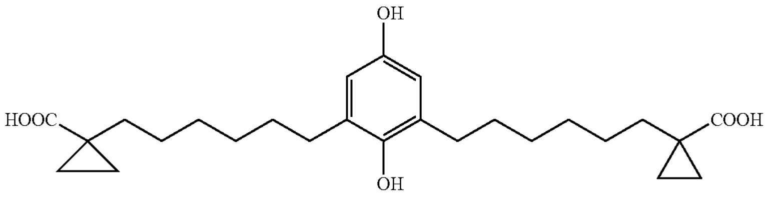 [SMILES: O=C(O)C1(CCCCCCc2cc(O)cc(CCCCCCC3(C(=O)O)CC3)c2O)CC1] |
| 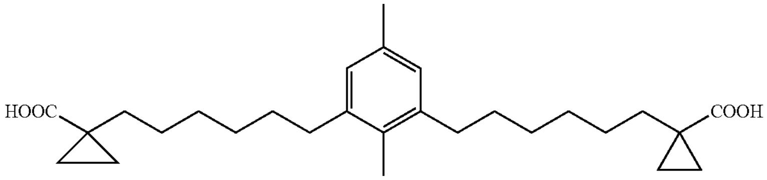 [SMILES: Cc1cc(CCCCCCC2(C(=O)O)CC2)c(C)c(CCCCCCC2(C(=O)O)CC2)c1] |
| 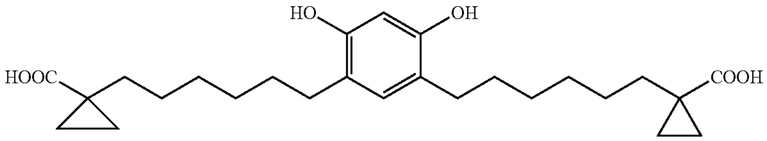 [SMILES: O=C(O)C1(CCCCCCc2cc(CCCCCCC3(C(=O)O)CC3)c(O)cc2O)CC1] |
| 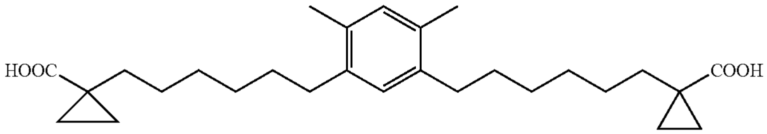 [SMILES: Cc1cc(C)c(CCCCCCC2(C(=O)O)CC2)cc1CCCCCCC1(C(=O)O)CC1] |
| 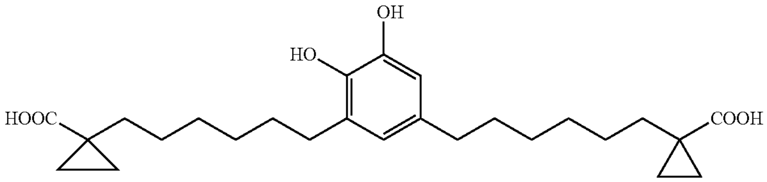 [SMILES: O=C(O)C1(CCCCCCc2cc(O)c(O)c(CCCCCCC3(C(=O)O)CC3)c2)CC1] |
| 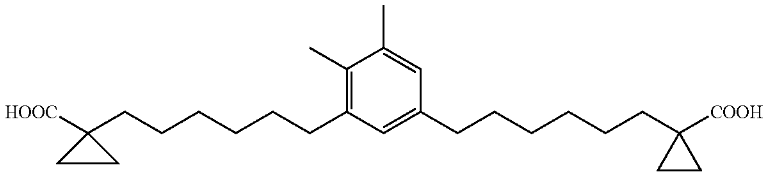 [SMILES: Cc1cc(CCCCCCC2(C(=O)O)CC2)cc(CCCCCCC2(C(=O)O)CC2)c1C] |
| 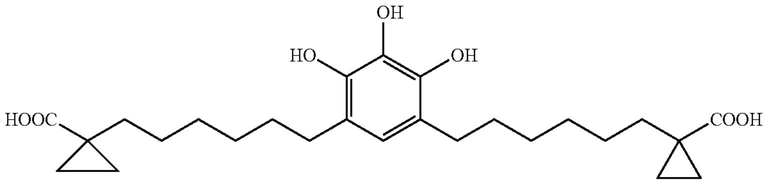 [SMILES: O=C(O)C1(CCCCCCc2cc(CCCCCCC3(C(=O)O)CC3)c(O)c(O)c2O)CC1] |
| 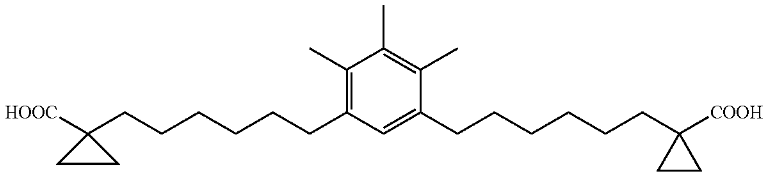 [SMILES: Cc1c(CCCCCCC2(C(=O)O)CC2)cc(CCCCCCC2(C(=O)O)CC2)c(C)c1C] |

TABLE A-11-continued
| Structure |
| --- |
| 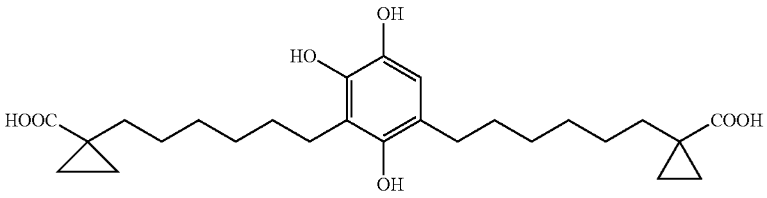 [SMILES: O=C(O)C1(CCCCCCc2cc(O)c(O)c(CCCCCCC3(C(=O)O)CC3)c2O)CC1] |
| 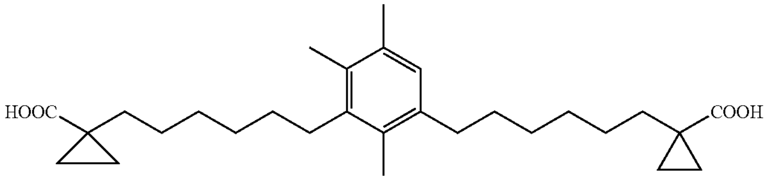 [SMILES: Cc1cc(CCCCCCC2(C(=O)O)CC2)c(C)c(CCCCCCC2(C(=O)O)CC2)c1C] |
| 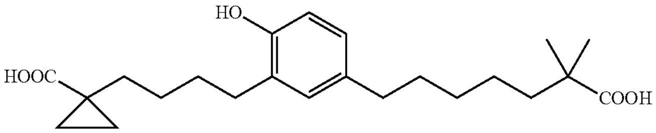 [SMILES: CC(C)(CCCCCc1ccc(O)c(CCCCC2(C(=O)O)CC2)c1)C(=O)O] |
| 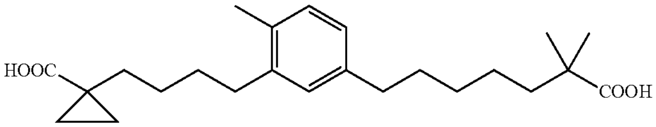 [SMILES: Cc1ccc(CCCCCC(C)(C)C(=O)O)cc1CCCCC1(C(=O)O)CC1] |
| 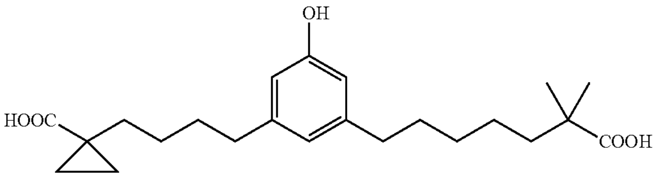 [SMILES: CC(C)(CCCCCc1cc(O)cc(CCCCC2(C(=O)O)CC2)c1)C(=O)O] |
| 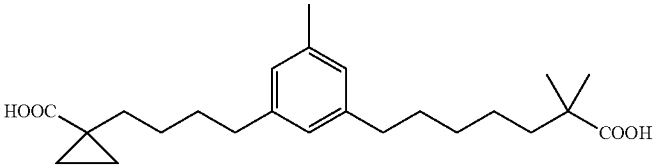 [SMILES: Cc1cc(CCCCCC(C)(C)C(=O)O)cc(CCCCC2(C(=O)O)CC2)c1] |
| 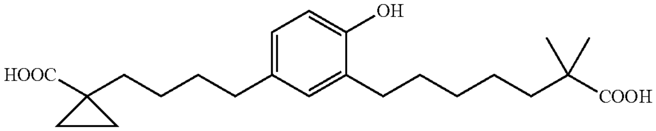 [SMILES: CC(C)(CCCCCc1cc(CCCCC2(C(=O)O)CC2)ccc1O)C(=O)O] |
| 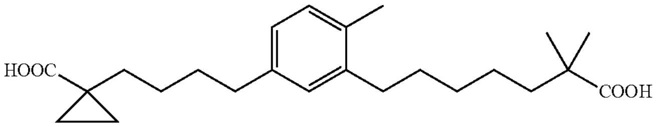 [SMILES: Cc1ccc(CCCCC2(C(=O)O)CC2)cc1CCCCCC(C)(C)C(=O)O] |
| 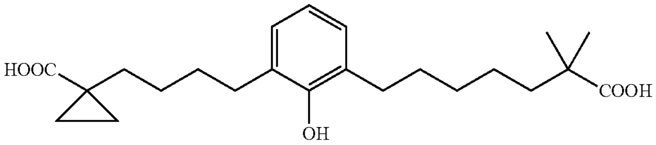 [SMILES: CC(C)(CCCCCc1cccc(CCCCC2(C(=O)O)CC2)c1O)C(=O)O] |

TABLE A-11-continued
| Structure |
|---|
| 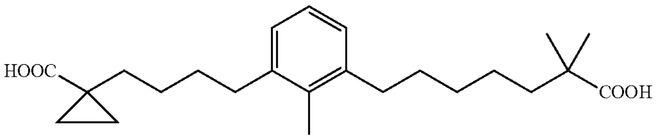 [SMILES: Cc1c(CCCCCC(C)(C)C(=O)O)cccc1CCCCC1(C(=O)O)CC1] |
| 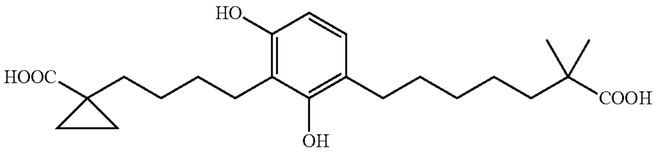 [SMILES: CC(C)(CCCCCc1ccc(O)c(CCCCC2(C(=O)O)CC2)c1O)C(=O)O] |
| 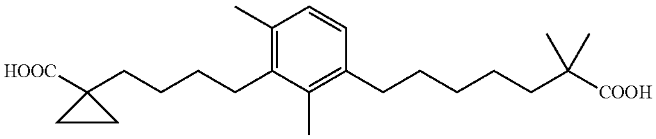 [SMILES: Cc1ccc(CCCCCC(C)(C)C(=O)O)c(C)c1CCCCC1(C(=O)O)CC1] |
| 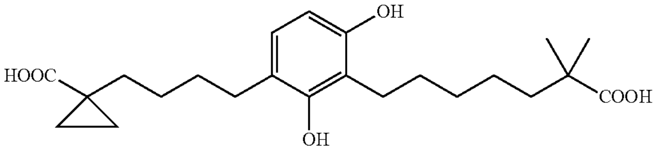 [SMILES: CC(C)(CCCCCc1c(O)ccc(CCCCC2(C(=O)O)CC2)c1O)C(=O)O] |
| 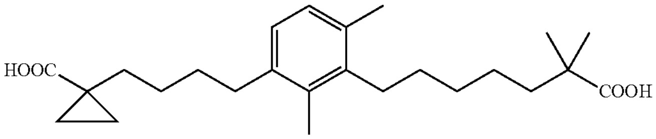 [SMILES: Cc1ccc(CCCCC2(C(=O)O)CC2)c(C)c1CCCCCC(C)(C)C(=O)O] |
| 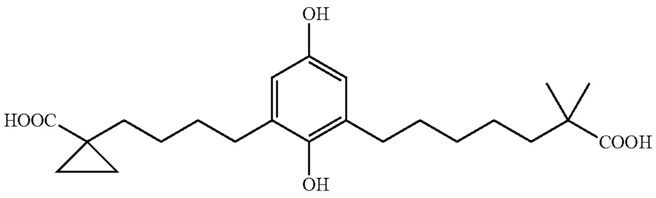 [SMILES: CC(C)(CCCCCc1cc(O)cc(CCCCC2(C(=O)O)CC2)c1O)C(=O)O] |
| 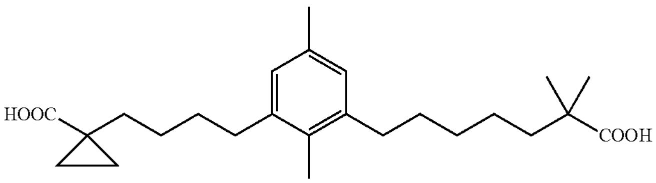 [SMILES: Cc1cc(CCCCCC(C)(C)C(=O)O)c(C)c(CCCCC2(C(=O)O)CC2)c1] |
| 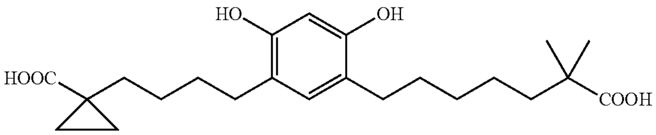 [SMILES: CC(C)(CCCCCc1cc(CCCCC2(C(=O)O)CC2)c(O)cc1O)C(=O)O] |
| 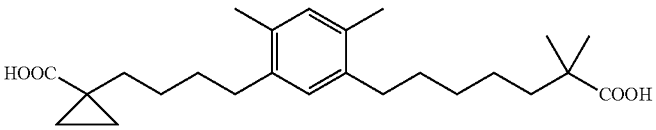 [SMILES: Cc1cc(C)c(CCCCC2(C(=O)O)CC2)cc1CCCCCC(C)(C)C(=O)O] |

TABLE A-11-continued
| Structure |
|---|
| 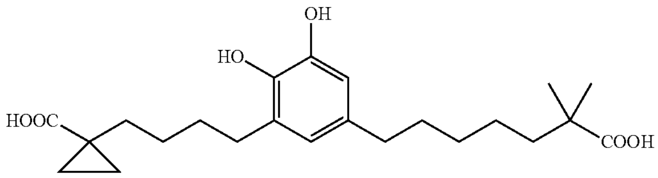 [SMILES: CC(C)(CCCCCc1cc(O)c(O)c(CCCCC2(C(=O)O)CC2)c1)C(=O)O] |
| 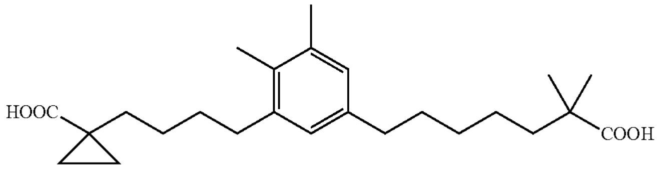 [SMILES: Cc1cc(CCCCCC(C)(C)C(=O)O)cc(CCCCC2(C(=O)O)CC2)c1C] |
| 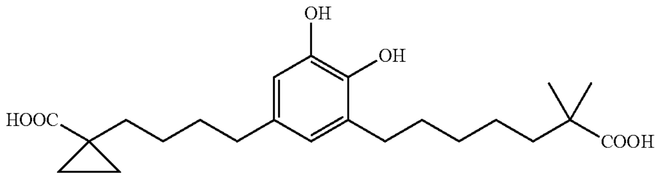 [SMILES: CC(C)(CCCCCc1cc(CCCCC2(C(=O)O)CC2)cc(O)c1O)C(=O)O] |
| 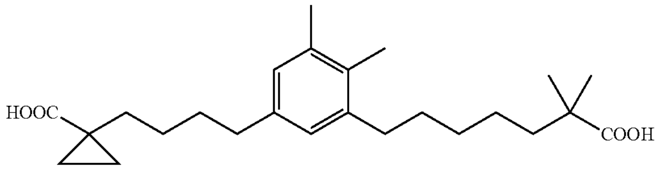 [SMILES: Cc1cc(CCCCC2(C(=O)O)CC2)cc(CCCCCC(C)(C)C(=O)O)c1C] |
| 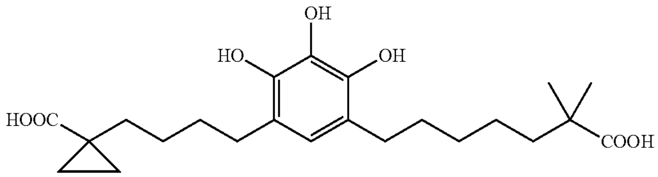 [SMILES: CC(C)(CCCCCc1cc(CCCCC2(C(=O)O)CC2)c(O)c(O)c1O)C(=O)O] |
| 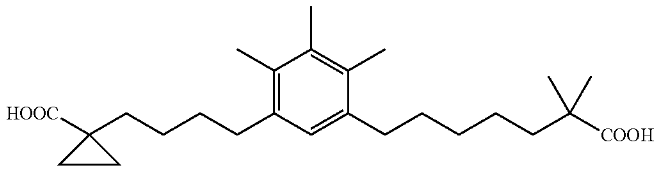 [SMILES: Cc1c(CCCCCC(C)(C)C(=O)O)cc(CCCCC2(C(=O)O)CC2)c(C)c1C] |
| 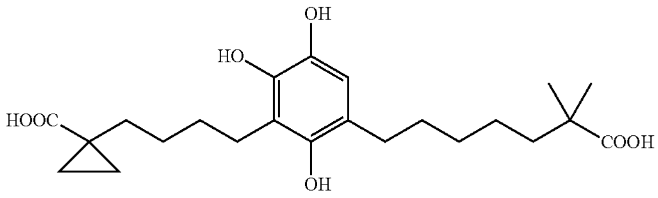 [SMILES: CC(C)(CCCCCc1cc(O)c(O)c(CCCCC2(C(=O)O)CC2)c1O)C(=O)O] |
| 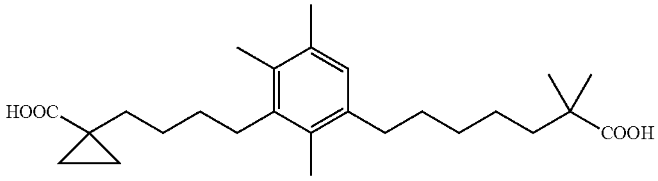 [SMILES: Cc1cc(CCCCCC(C)(C)C(=O)O)c(C)c(CCCCC2(C(=O)O)CC2)c1C] |

TABLE A-11-continued
| Structure |
| --- |
| 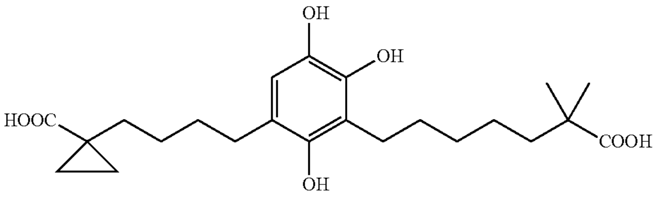 [SMILES: CC(C)(CCCCCc1c(O)c(O)cc(CCCCC2(C(=O)O)CC2)c1O)C(=O)O] |
| 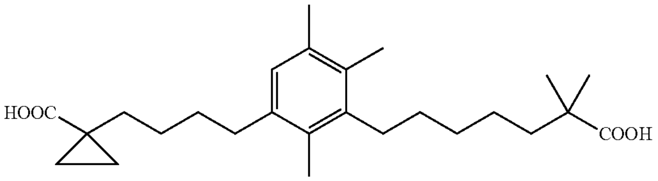 [SMILES: Cc1cc(CCCCC2(C(=O)O)CC2)c(C)c(CCCCCC(C)(C)C(=O)O)c1C] |
| 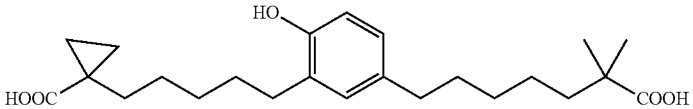 [SMILES: CC(C)(CCCCCc1ccc(O)c(CCCCCC2(C(=O)O)CC2)c1)C(=O)O] |
| 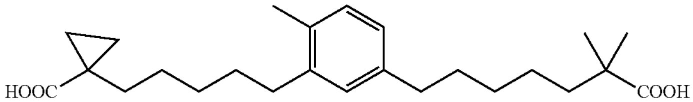 [SMILES: Cc1ccc(CCCCCC(C)(C)C(=O)O)cc1CCCCCC1(C(=O)O)CC1] |
| 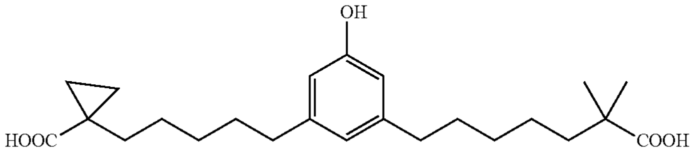 [SMILES: CC(C)(CCCCCc1cc(O)cc(CCCCCC2(C(=O)O)CC2)c1)C(=O)O] |
| 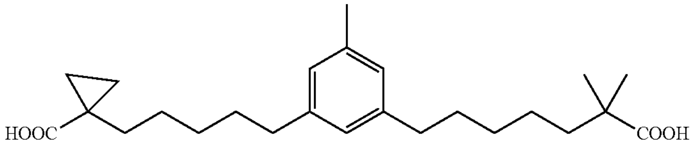 [SMILES: Cc1cc(CCCCCC(C)(C)C(=O)O)cc(CCCCCC2(C(=O)O)CC2)c1] |
| 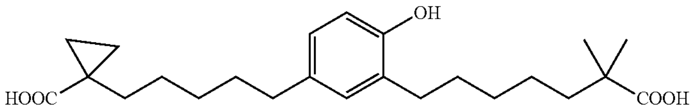 [SMILES: CC(C)(CCCCCc1cc(CCCCCC2(C(=O)O)CC2)ccc1O)C(=O)O] |
| 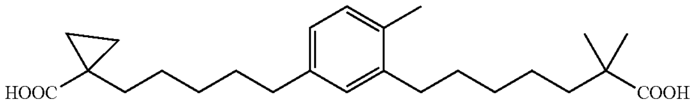 [SMILES: Cc1ccc(CCCCCC2(C(=O)O)CC2)cc1CCCCCC(C)(C)C(=O)O] |
| 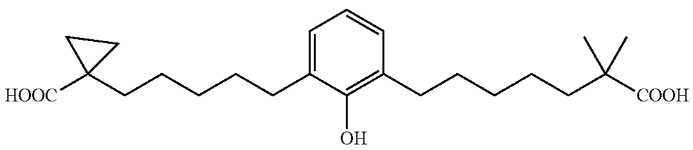 [SMILES: CC(C)(CCCCCc1cccc(CCCCCC2(C(=O)O)CC2)c1O)C(=O)O] |
| 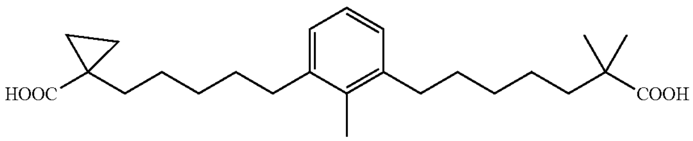 [SMILES: Cc1c(CCCCCC(C)(C)C(=O)O)cccc1CCCCCC1(C(=O)O)CC1] |

TABLE A-11-continued
| Structure |
| --- |
| 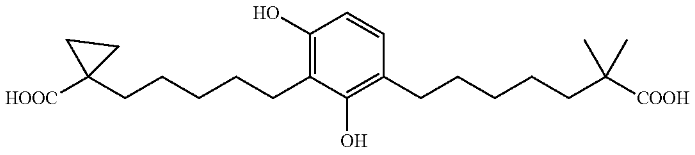 [SMILES: CC(C)(CCCCCc1ccc(O)c(CCCCCC2(C(=O)O)CC2)c1O)C(=O)O] |
| 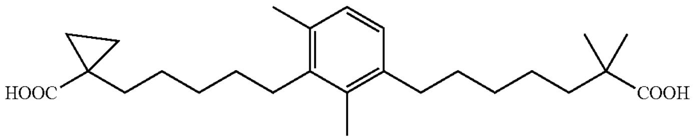 [SMILES: Cc1ccc(CCCCCC(C)(C)C(=O)O)c(C)c1CCCCCC1(C(=O)O)CC1] |
| 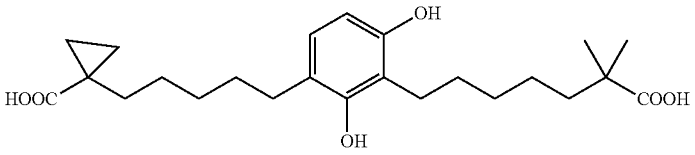 [SMILES: CC(C)(CCCCCc1c(O)ccc(CCCCCC2(C(=O)O)CC2)c1O)C(=O)O] |
| 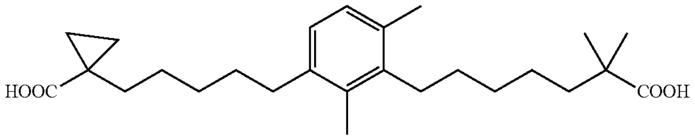 [SMILES: Cc1ccc(CCCCCC2(C(=O)O)CC2)c(C)c1CCCCCC(C)(C)C(=O)O] |
| 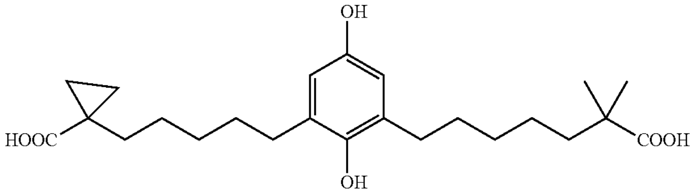 [SMILES: CC(C)(CCCCCc1cc(O)cc(CCCCCC2(C(=O)O)CC2)c1O)C(=O)O] |
| 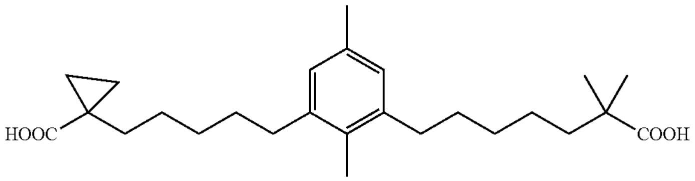 [SMILES: Cc1cc(CCCCCC(C)(C)C(=O)O)c(C)c(CCCCCC2(C(=O)O)CC2)c1] |
| 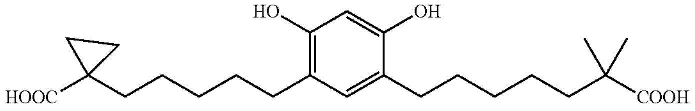 [SMILES: CC(C)(CCCCCc1cc(CCCCCC2(C(=O)O)CC2)c(O)cc1O)C(=O)O] |
| 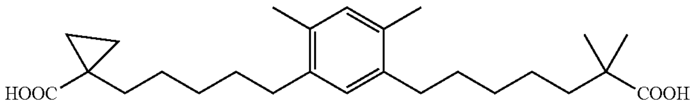 [SMILES: Cc1cc(C)c(CCCCCC2(C(=O)O)CC2)cc1CCCCCC(C)(C)C(=O)O] |
| 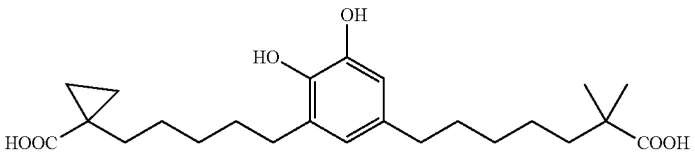 [SMILES: CC(C)(CCCCCc1cc(O)c(O)c(CCCCCC2(C(=O)O)CC2)c1)C(=O)O] |
| 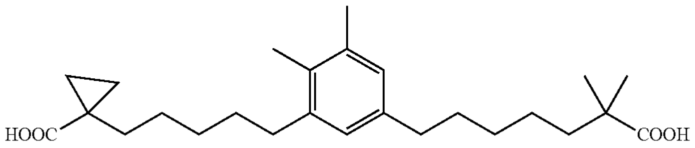 [SMILES: Cc1cc(CCCCCC(C)(C)C(=O)O)cc(CCCCCC2(C(=O)O)CC2)c1C] |

TABLE A-11-continued
| Structure |
| --- |
| 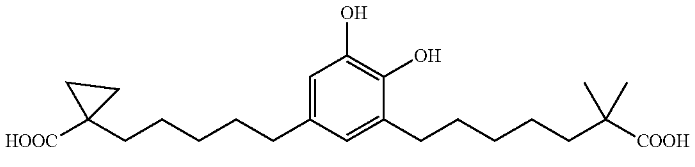 [SMILES: CC(C)(CCCCCc1cc(CCCCCC2(C(=O)O)CC2)cc(O)c1O)C(=O)O] |
| 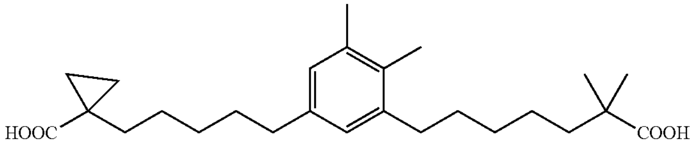 [SMILES: Cc1cc(CCCCCC2(C(=O)O)CC2)cc(CCCCCC(C)(C)C(=O)O)c1C] |
| 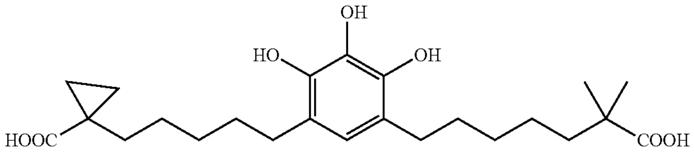 [SMILES: CC(C)(CCCCCc1cc(CCCCCC2(C(=O)O)CC2)c(O)c(O)c1O)C(=O)O] |
| 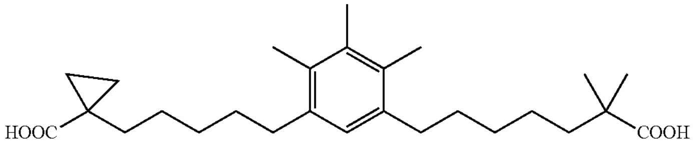 [SMILES: Cc1c(CCCCCC(C)(C)C(=O)O)cc(CCCCCC2(C(=O)O)CC2)c(C)c1C] |
| 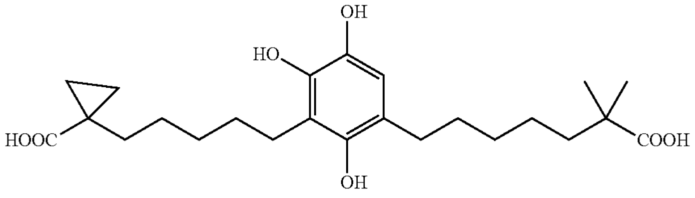 [SMILES: CC(C)(CCCCCc1cc(O)c(O)c(CCCCCC2(C(=O)O)CC2)c1O)C(=O)O] |
| 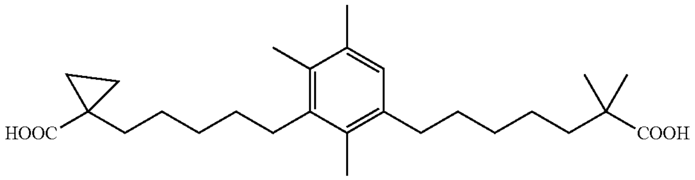 [SMILES: Cc1cc(CCCCCC(C)(C)C(=O)O)c(C)c(CCCCCC2(C(=O)O)CC2)c1C] |
| 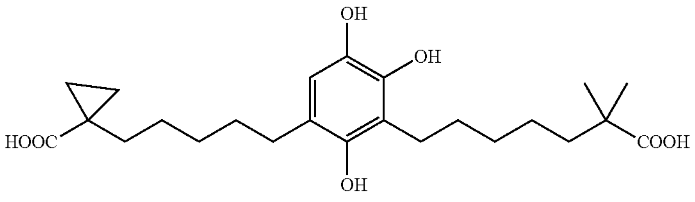 [SMILES: CC(C)(CCCCCc1c(O)c(O)cc(CCCCCC2(C(=O)O)CC2)c1O)C(=O)O] |
| 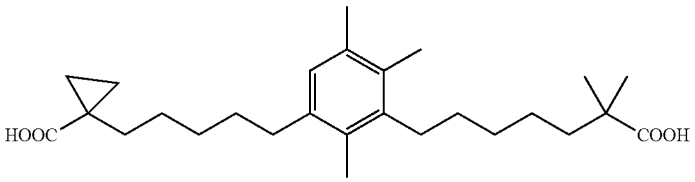 [SMILES: Cc1cc(CCCCCC2(C(=O)O)CC2)c(C)c(CCCCCC(C)(C)C(=O)O)c1C] |
| 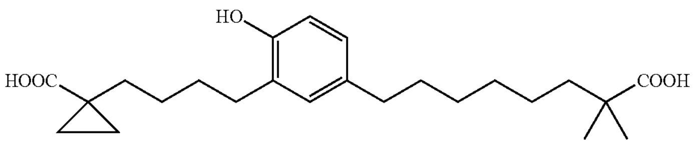 [SMILES: CC(C)(CCCCCCc1ccc(O)c(CCCCC2(C(=O)O)CC2)c1)C(=O)O] |

TABLE A-11-continued
| Structure |
|---|
| 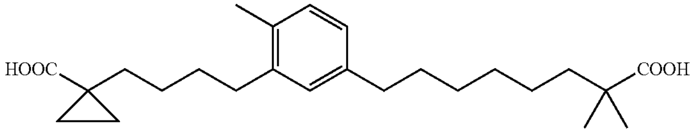 [SMILES: Cc1ccc(CCCCCCC(C)(C)C(=O)O)cc1CCCCC1(C(=O)O)CC1] |
| 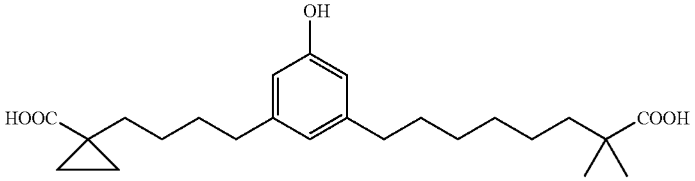 [SMILES: CC(C)(CCCCCCc1cc(O)cc(CCCCC2(C(=O)O)CC2)c1)C(=O)O] |
| 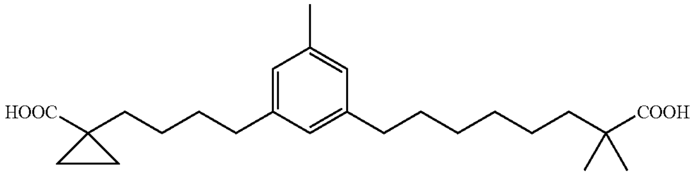 |
| 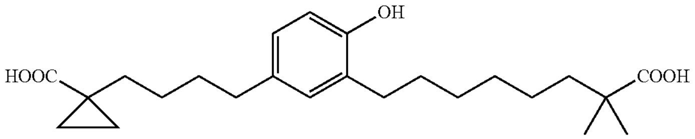 [SMILES: CC(C)(CCCCCCc1cc(CCCCC2(C(=O)O)CC2)ccc1O)C(=O)O] |
| 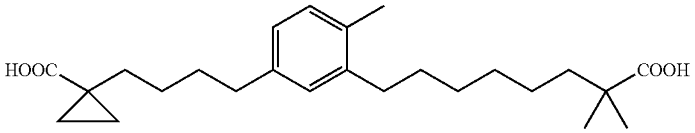 [SMILES: Cc1ccc(CCCCC2(C(=O)O)CC2)cc1CCCCCCC(C)(C)C(=O)O] |
| 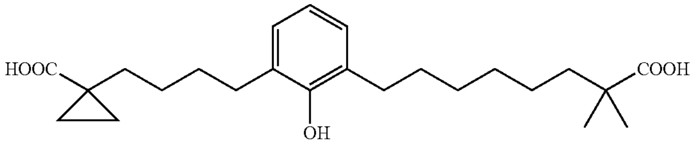 [SMILES: CC(C)(CCCCCCc1cccc(CCCCC2(C(=O)O)CC2)c1O)C(=O)O] |
| 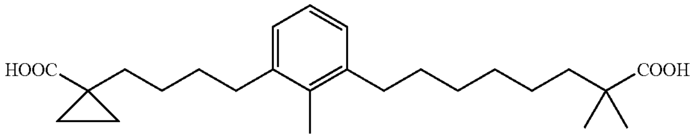 [SMILES: Cc1c(CCCCCCC(C)(C)C(=O)O)cccc1CCCCC1(C(=O)O)CC1] |
| 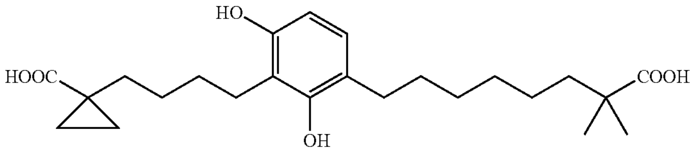 [SMILES: CC(C)(CCCCCCc1ccc(O)c(CCCCC2(C(=O)O)CC2)c1O)C(=O)O] |
| 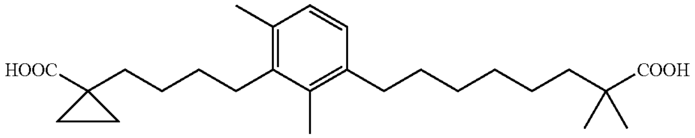 [SMILES: Cc1ccc(CCCCCCC(C)(C)C(=O)O)c(C)c1CCCCC1(C(=O)O)CC1] |
| 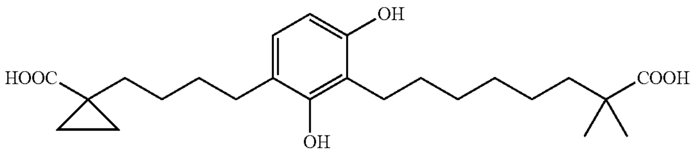 [SMILES: CC(C)(CCCCCCc1c(O)ccc(CCCCC2(C(=O)O)CC2)c1O)C(=O)O] |

TABLE A-11-continued
| Structure |
| --- |
| 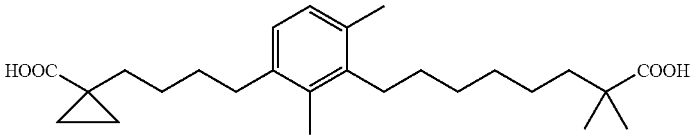 [SMILES: Cc1ccc(CCCCC2(C(=O)O)CC2)c(C)c1CCCCCCC(C)(C)C(=O)O] |
| 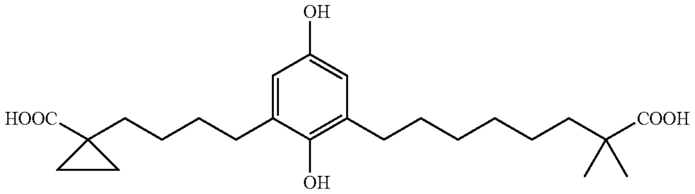 [SMILES: CC(C)(CCCCCCc1cc(O)cc(CCCCC2(C(=O)O)CC2)c1O)C(=O)O] |
| 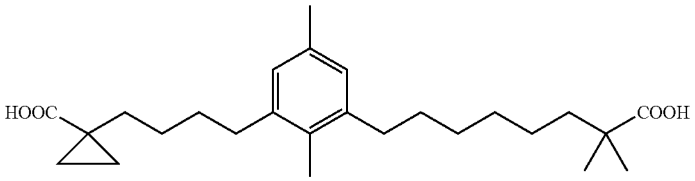 [SMILES: Cc1cc(CCCCCCC(C)(C)C(=O)O)c(C)c(CCCCC2(C(=O)O)CC2)c1] |
| 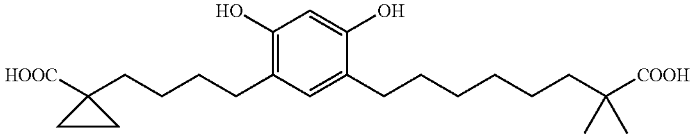 [SMILES: CC(C)(CCCCCCc1cc(CCCCC2(C(=O)O)CC2)c(O)cc1O)C(=O)O] |
| 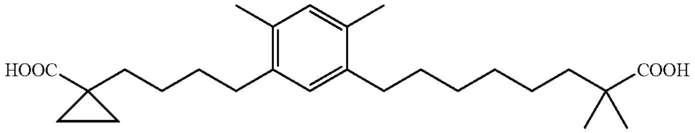 [SMILES: Cc1cc(C)c(CCCCC2(C(=O)O)CC2)cc1CCCCCCC(C)(C)C(=O)O] |
| 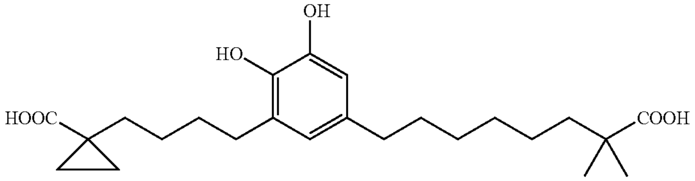 [SMILES: CC(C)(CCCCCCc1cc(O)c(O)c(CCCCC2(C(=O)O)CC2)c1)C(=O)O] |
| 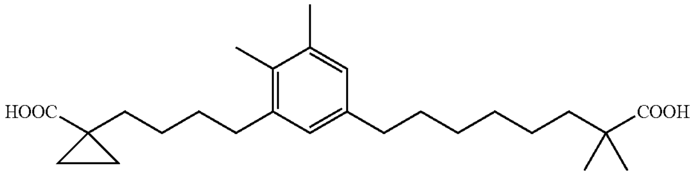 [SMILES: Cc1cc(CCCCCCC(C)(C)C(=O)O)cc(CCCCC2(C(=O)O)CC2)c1C] |
| 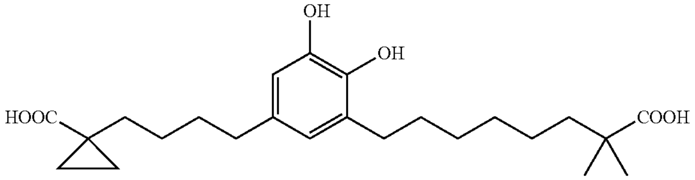 [SMILES: CC(C)(CCCCCCc1cc(CCCCC2(C(=O)O)CC2)cc(O)c1O)C(=O)O] |

TABLE A-11-continued
| Structure |
| --- |
| 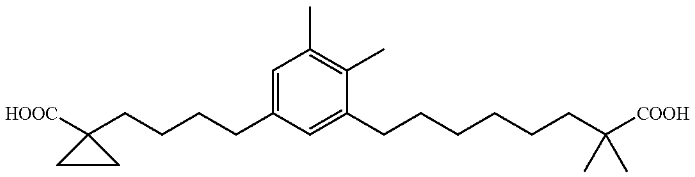 [SMILES: Cc1cc(CCCCC2(C(=O)O)CC2)cc(CCCCCCC(C)(C)C(=O)O)c1C] |
| 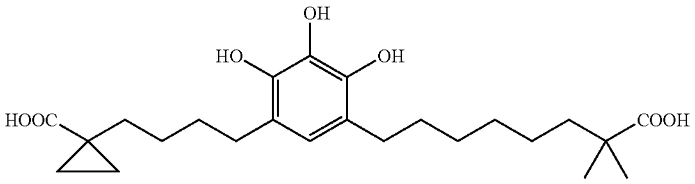 [SMILES: CC(C)(CCCCCCc1cc(CCCCC2(C(=O)O)CC2)c(O)c(O)c1O)C(=O)O] |
| 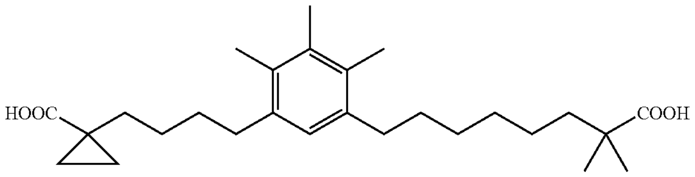 [SMILES: Cc1c(CCCCCCC(C)(C)C(=O)O)cc(CCCCC2(C(=O)O)CC2)c(C)c1C] |
| 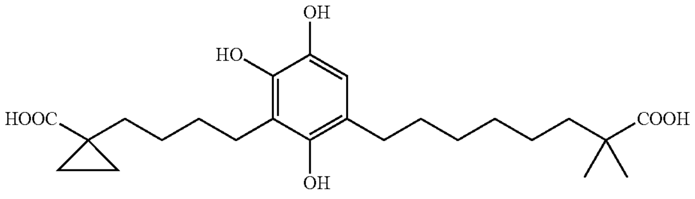 [SMILES: CC(C)(CCCCCCc1cc(O)c(O)c(CCCCC2(C(=O)O)CC2)c1O)C(=O)O] |
| 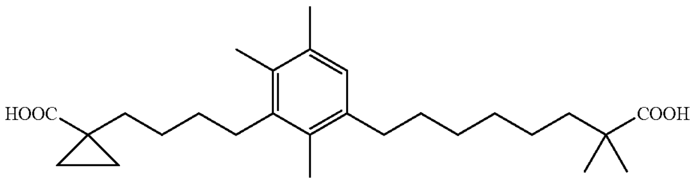 [SMILES: Cc1cc(CCCCCCC(C)(C)C(=O)O)c(C)c(CCCCC2(C(=O)O)CC2)c1C] |
| 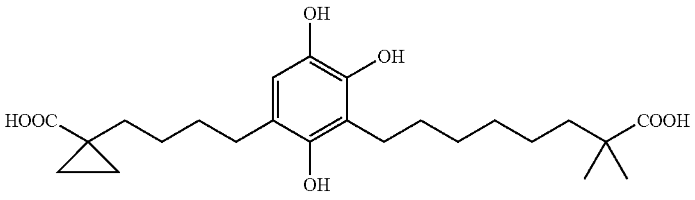 [SMILES: CC(C)(CCCCCCc1c(O)c(O)cc(CCCCC2(C(=O)O)CC2)c1O)C(=O)O] |
| 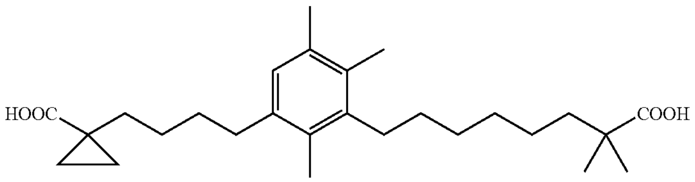 [SMILES: Cc1cc(CCCCC2(C(=O)O)CC2)c(C)c(CCCCCCC(C)(C)C(=O)O)c1C] |
| 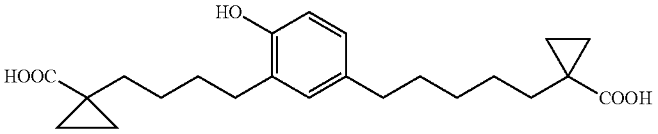 [SMILES: O=C(O)C1(CCCCCc2ccc(O)c(CCCCC3(C(=O)O)CC3)c2)CC1] |

TABLE A-11-continued
| Structure |
| --- |
| 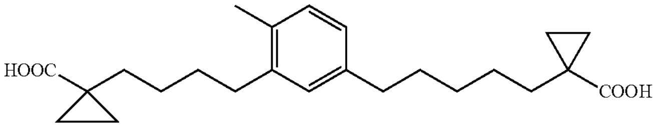 [SMILES: Cc1ccc(CCCCCC2(C(=O)O)CC2)cc1CCCCC1(C(=O)O)CC1] |
| 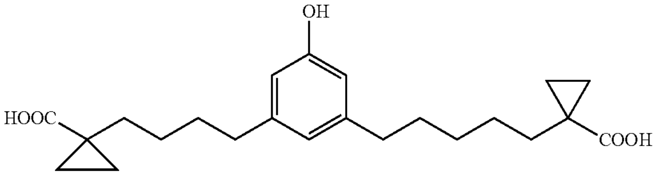 [SMILES: O=C(O)C1(CCCCCc2cc(O)cc(CCCCC3(C(=O)O)CC3)c2)CC1] |
| 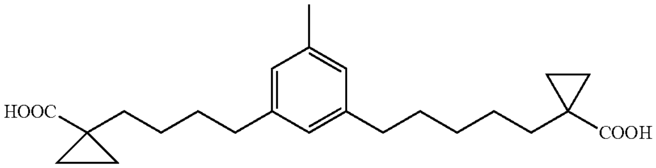 [SMILES: Cc1cc(CCCCCC2(C(=O)O)CC2)cc(CCCCC2(C(=O)O)CC2)c1] |
| 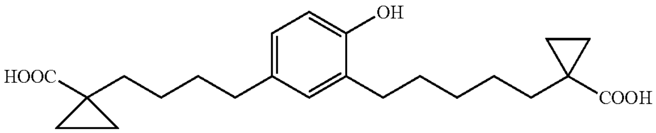 [SMILES: O=C(O)C1(CCCCCc2cc(CCCCC3(C(=O)O)CC3)ccc2O)CC1] |
| 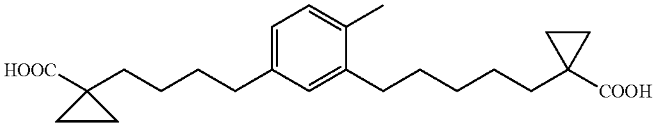 [SMILES: Cc1ccc(CCCCC2(C(=O)O)CC2)cc1CCCCCC1(C(=O)O)CC1] |
| 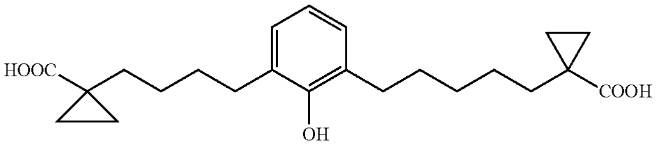 [SMILES: O=C(O)C1(CCCCCc2cccc(CCCCC3(C(=O)O)CC3)c2O)CC1] |
| 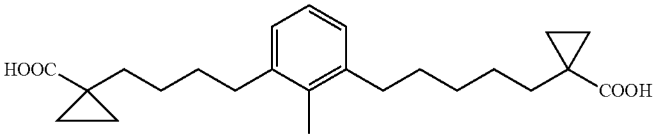 [SMILES: Cc1c(CCCCCC2(C(=O)O)CC2)cccc1CCCCC1(C(=O)O)CC1] |
| 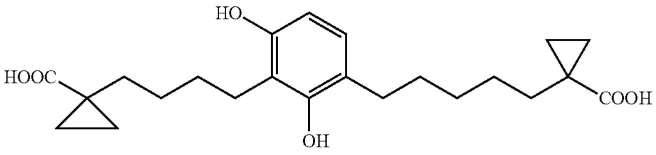 [SMILES: O=C(O)C1(CCCCCc2ccc(O)c(CCCCC3(C(=O)O)CC3)c2O)CC1] |
| 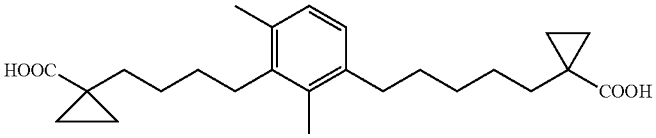 [SMILES: Cc1ccc(CCCCCC2(C(=O)O)CC2)c(C)c1CCCCC1(C(=O)O)CC1] |
| 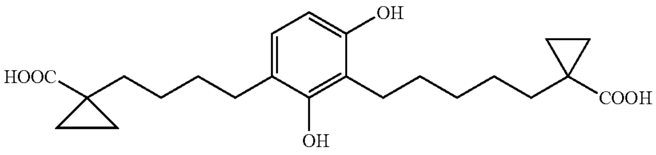 [SMILES: O=C(O)C1(CCCCCc2c(O)ccc(CCCCC3(C(=O)O)CC3)c2O)CC1] |

TABLE A-11-continued
| Structure |
| --- |
| 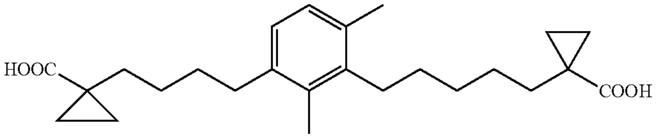 [SMILES: Cc1ccc(CCCCC2(C(=O)O)CC2)c(C)c1CCCCCC1(C(=O)O)CC1] |
| 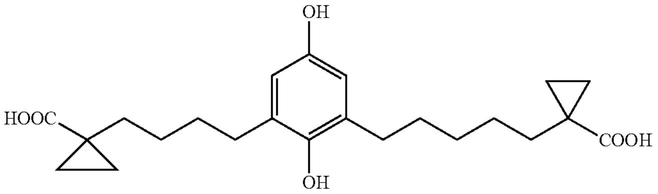 [SMILES: O=C(O)C1(CCCCCc2cc(O)cc(CCCCC3(C(=O)O)CC3)c2O)CC1] |
| 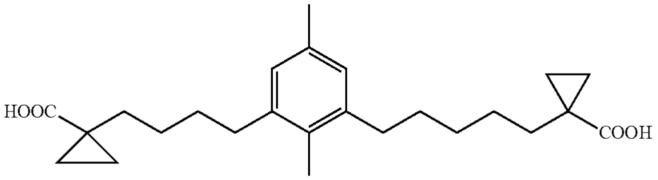 [SMILES: Cc1cc(CCCCCC2(C(=O)O)CC2)c(C)c(CCCCC2(C(=O)O)CC2)c1] |
| 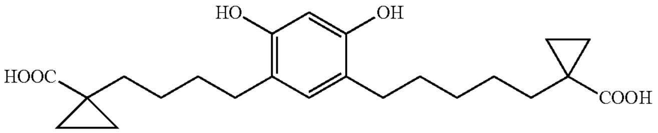 [SMILES: O=C(O)C1(CCCCCc2cc(CCCCC3(C(=O)O)CC3)c(O)cc2O)CC1] |
| 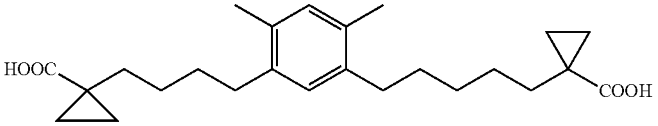 [SMILES: Cc1cc(C)c(CCCCC2(C(=O)O)CC2)cc1CCCCCC1(C(=O)O)CC1] |
| 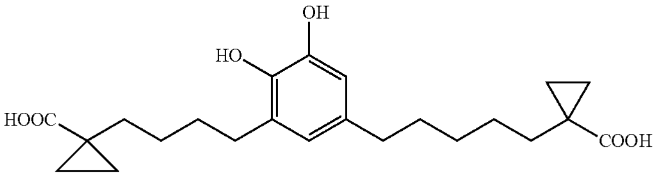 [SMILES: O=C(O)C1(CCCCCc2cc(O)c(O)c(CCCCC3(C(=O)O)CC3)c2)CC1] |
| 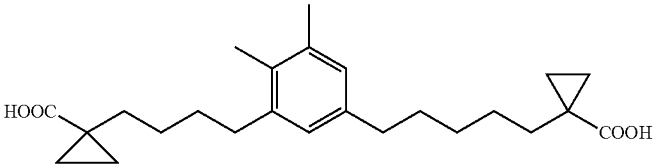 [SMILES: Cc1cc(CCCCCC2(C(=O)O)CC2)cc(CCCCC2(C(=O)O)CC2)c1C] |
| 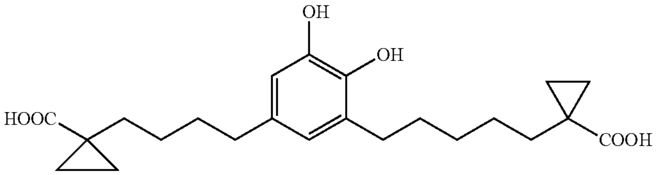 [SMILES: O=C(O)C1(CCCCCc2cc(CCCCC3(C(=O)O)CC3)cc(O)c2O)CC1] |
| 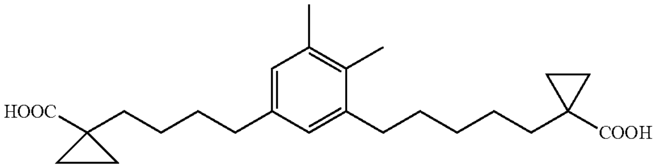 [SMILES: Cc1cc(CCCCC2(C(=O)O)CC2)cc(CCCCCC2(C(=O)O)CC2)c1C] |

TABLE A-11-continued
| Structure |
| --- |
| 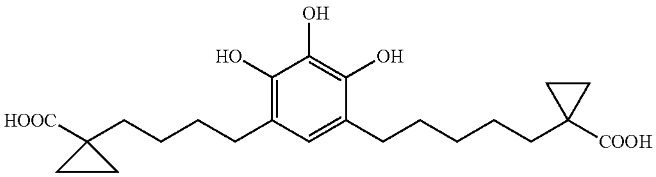 [SMILES: O=C(O)C1(CCCCCc2cc(CCCCC3(C(=O)O)CC3)c(O)c(O)c2O)CC1] |
| 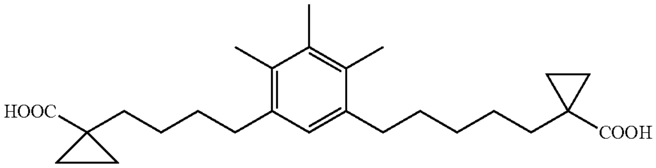 [SMILES: Cc1c(CCCCCC2(C(=O)O)CC2)cc(CCCCC2(C(=O)O)CC2)c(C)c1C] |
| 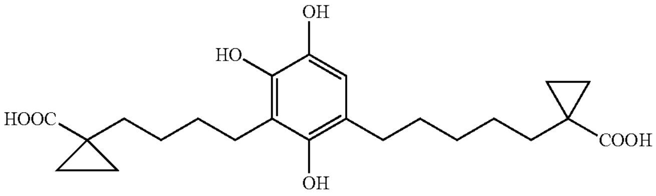 [SMILES: O=C(O)C1(CCCCCc2cc(O)c(O)c(CCCCC3(C(=O)O)CC3)c2O)CC1] |
| 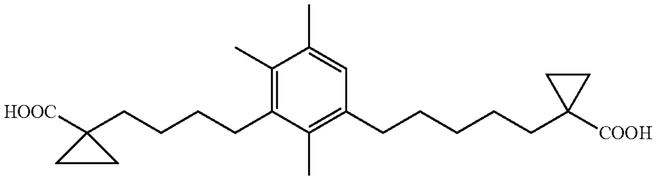 [SMILES: Cc1cc(CCCCCC2(C(=O)O)CC2)c(C)c(CCCCC2(C(=O)O)CC2)c1C] |
| 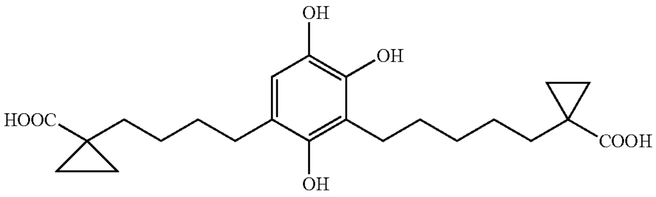 [SMILES: O=C(O)C1(CCCCCc2c(O)c(O)cc(CCCCC3(C(=O)O)CC3)c2O)CC1] |
| 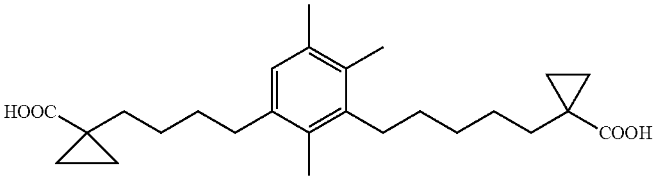 [SMILES: Cc1cc(CCCCC2(C(=O)O)CC2)c(C)c(CCCCCC2(C(=O)O)CC2)c1C] |
| 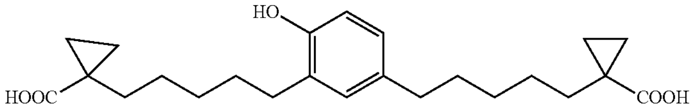 [SMILES: O=C(O)C1(CCCCCc2ccc(O)c(CCCCCC3(C(=O)O)CC3)c2)CC1] |
| 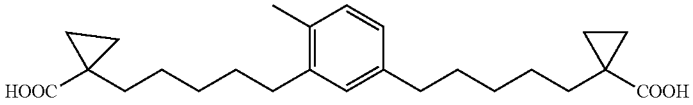 [SMILES: Cc1ccc(CCCCCC2(C(=O)O)CC2)cc1CCCCCC1(C(=O)O)CC1] |
| 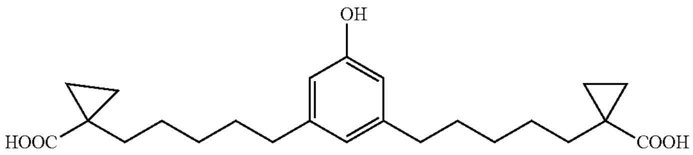 [SMILES: O=C(O)C1(CCCCCc2cc(O)cc(CCCCCC3(C(=O)O)CC3)c2)CC1] |

TABLE A-11-continued
| Structure |
| --- |
| 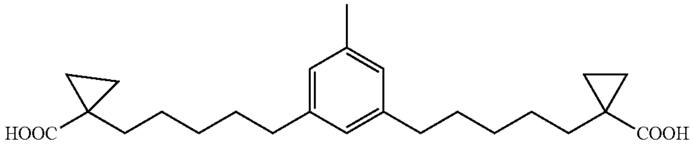 [SMILES: Cc1cc(CCCCCC2(C(=O)O)CC2)cc(CCCCCC2(C(=O)O)CC2)c1] |
| 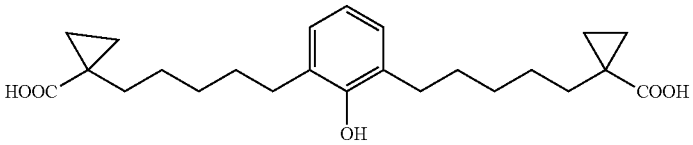 [SMILES: O=C(O)C1(CCCCCc2cccc(CCCCCC3(C(=O)O)CC3)c2O)CC1] |
| 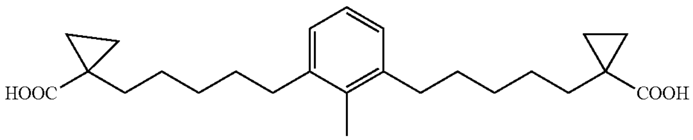 [SMILES: Cc1c(CCCCCC2(C(=O)O)CC2)cccc1CCCCCC1(C(=O)O)CC1] |
| 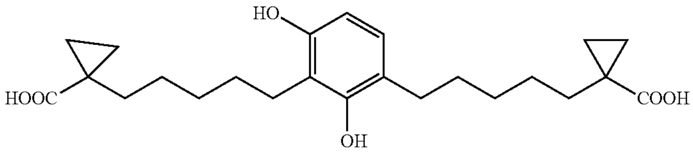 [SMILES: O=C(O)C1(CCCCCc2ccc(O)c(CCCCCC3(C(=O)O)CC3)c2O)CC1] |
| 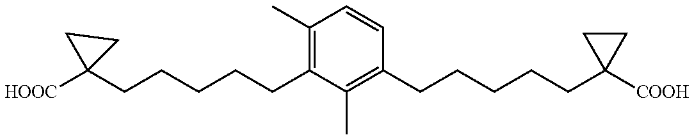 [SMILES: Cc1ccc(CCCCCC2(C(=O)O)CC2)c(C)c1CCCCCC1(C(=O)O)CC1] |
| 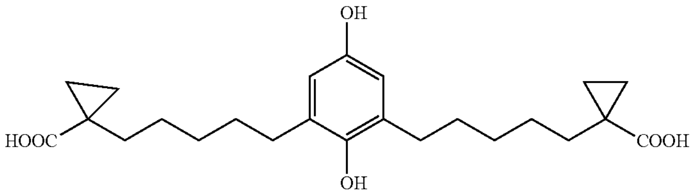 [SMILES: O=C(O)C1(CCCCCc2cc(O)cc(CCCCCC3(C(=O)O)CC3)c2O)CC1] |
| 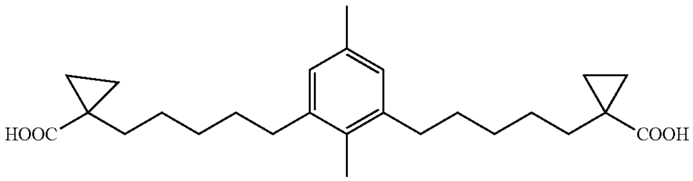 [SMILES: Cc1cc(CCCCCC2(C(=O)O)CC2)c(C)c(CCCCCC2(C(=O)O)CC2)c1] |
| 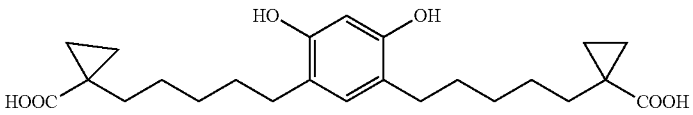 [SMILES: O=C(O)C1(CCCCCc2cc(CCCCCC3(C(=O)O)CC3)c(O)cc2O)CC1] |
| 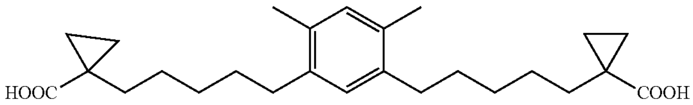 [SMILES: Cc1cc(C)c(CCCCCC2(C(=O)O)CC2)cc1CCCCCC1(C(=O)O)CC1] |
| 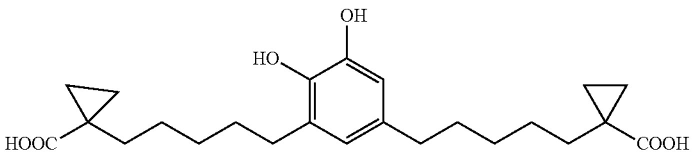 [SMILES: O=C(O)C1(CCCCCc2cc(O)c(O)c(CCCCCC3(C(=O)O)CC3)c2)CC1] |

TABLE A-11-continued
| Structure |
| --- |
| 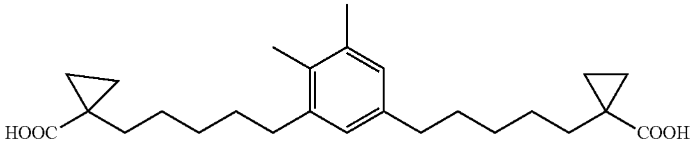 [SMILES: Cc1cc(CCCCCC2(C(=O)O)CC2)cc(CCCCCC2(C(=O)O)CC2)c1C] |
| 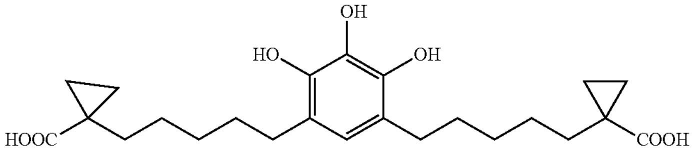 [SMILES: O=C(O)C1(CCCCCc2cc(CCCCCC3(C(=O)O)CC3)c(O)c(O)c2O)CC1] |
| 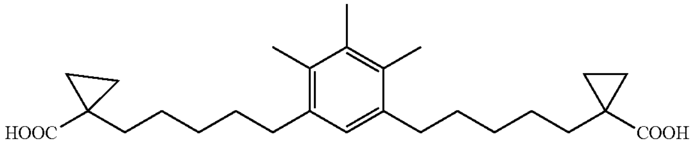 [SMILES: Cc1c(CCCCCC2(C(=O)O)CC2)cc(CCCCCC2(C(=O)O)CC2)c(C)c1C] |
| 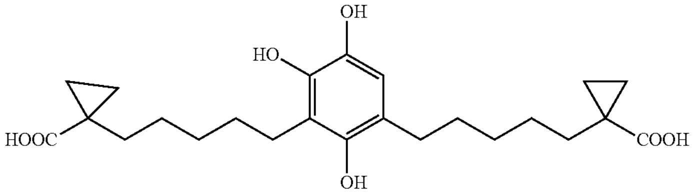 [SMILES: O=C(O)C1(CCCCCc2cc(O)c(O)c(CCCCCC3(C(=O)O)CC3)c2O)CC1] |
| 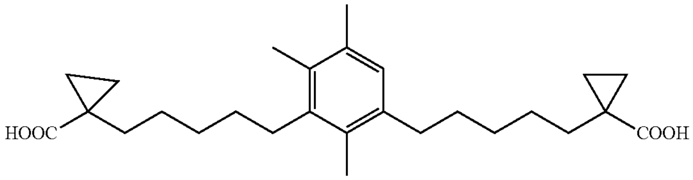 [SMILES: Cc1cc(CCCCCC2(C(=O)O)CC2)c(C)c(CCCCCC2(C(=O)O)CC2)c1C] |
| 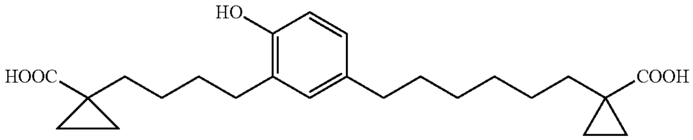 [SMILES: O=C(O)C1(CCCCCCc2ccc(O)c(CCCCC3(C(=O)O)CC3)c2)CC1] |
| 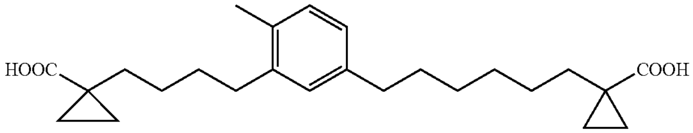 [SMILES: Cc1ccc(CCCCCCC2(C(=O)O)CC2)cc1CCCCC1(C(=O)O)CC1] |
| 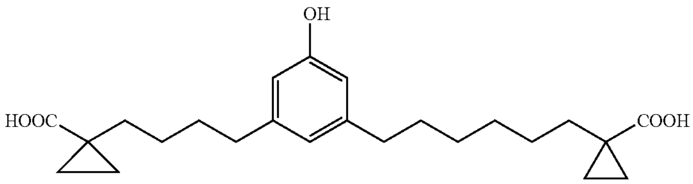 [SMILES: O=C(O)C1(CCCCCCc2cc(O)cc(CCCCC3(C(=O)O)CC3)c2)CC1] |
| 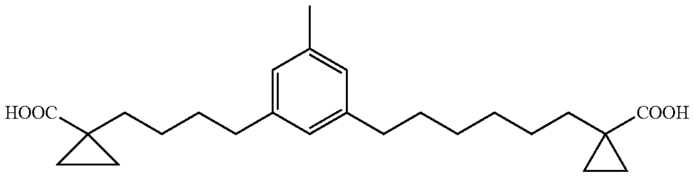 [SMILES: Cc1cc(CCCCCCC2(C(=O)O)CC2)cc(CCCCC2(C(=O)O)CC2)c1] |

TABLE A-11-continued
| Structure |
| --- |
| 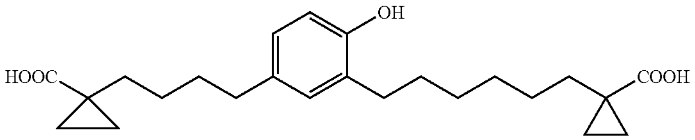 [SMILES: O=C(O)C1(CCCCCCc2cc(CCCCC3(C(=O)O)CC3)ccc2O)CC1] |
| 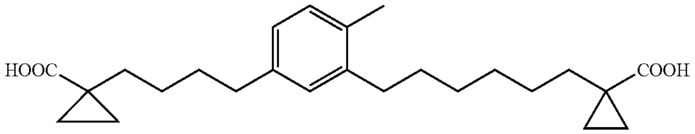 [SMILES: Cc1ccc(CCCCC2(C(=O)O)CC2)cc1CCCCCCC1(C(=O)O)CC1] |
| 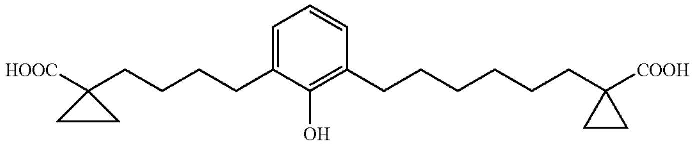 [SMILES: O=C(O)C1(CCCCCCc2cccc(CCCCC3(C(=O)O)CC3)c2O)CC1] |
| 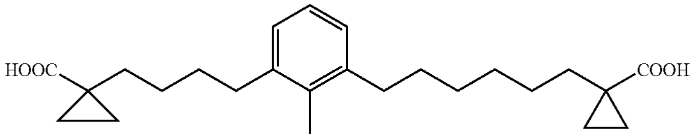 [SMILES: Cc1c(CCCCCCC2(C(=O)O)CC2)cccc1CCCCC1(C(=O)O)CC1] |
| 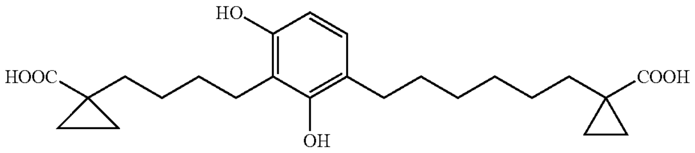 [SMILES: O=C(O)C1(CCCCCCc2ccc(O)c(CCCCC3(C(=O)O)CC3)c2O)CC1] |
| 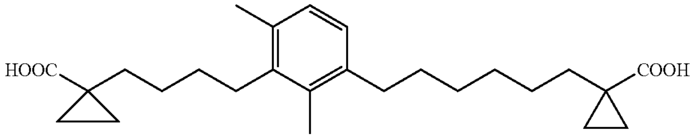 [SMILES: Cc1ccc(CCCCCCC2(C(=O)O)CC2)c(C)c1CCCCC1(C(=O)O)CC1] |
| 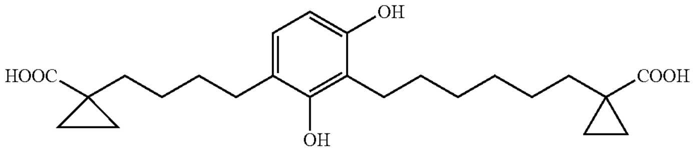 [SMILES: O=C(O)C1(CCCCCCc2c(O)ccc(CCCCC3(C(=O)O)CC3)c2O)CC1] |
| 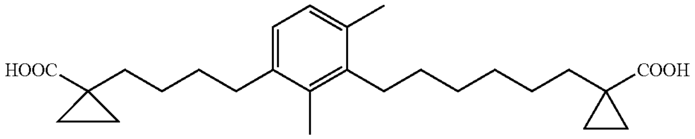 [SMILES: Cc1ccc(CCCCC2(C(=O)O)CC2)c(C)c1CCCCCCC1(C(=O)O)CC1] |
| 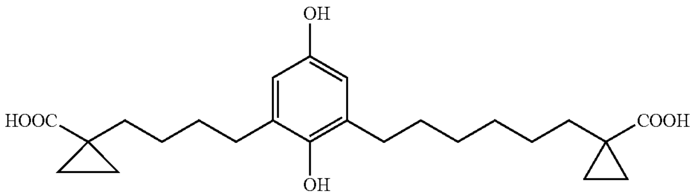 [SMILES: O=C(O)C1(CCCCCCc2cc(O)cc(CCCCC3(C(=O)O)CC3)c2O)CC1] |

TABLE A-11-continued
| Structure |
|---|
| 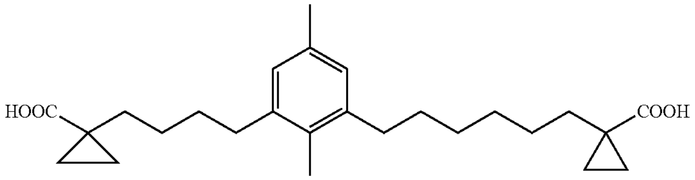 [SMILES: Cc1cc(CCCCCCC2(C(=O)O)CC2)c(C)c(CCCCC2(C(=O)O)CC2)c1] |
| 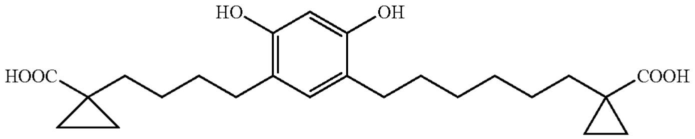 [SMILES: O=C(O)C1(CCCCCCc2cc(CCCCC3(C(=O)O)CC3)c(O)cc2O)CC1] |
| 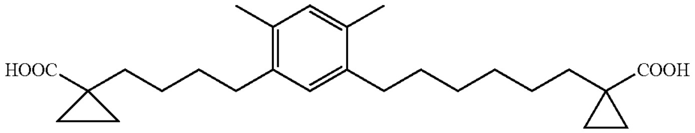 [SMILES: Cc1cc(C)c(CCCCC2(C(=O)O)CC2)cc1CCCCCCC1(C(=O)O)CC1] |
| 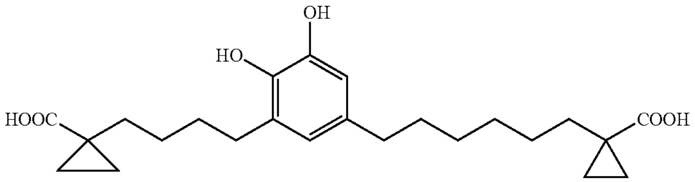 [SMILES: O=C(O)C1(CCCCCCc2cc(O)c(O)c(CCCCC3(C(=O)O)CC3)c2)CC1] |
| 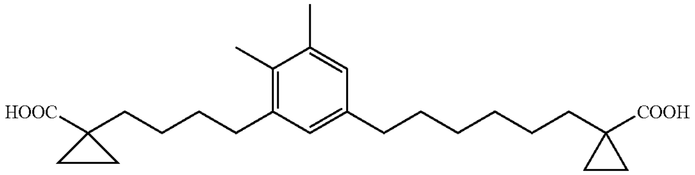 [SMILES: Cc1cc(CCCCCCC2(C(=O)O)CC2)cc(CCCCC2(C(=O)O)CC2)c1C] |
| 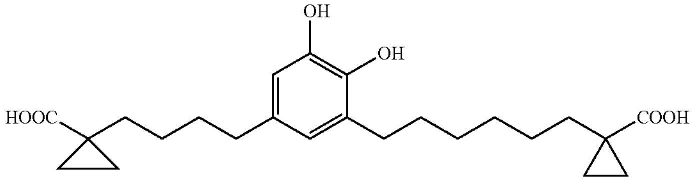 [SMILES: O=C(O)C1(CCCCCCc2cc(CCCCC3(C(=O)O)CC3)cc(O)c2O)CC1] |
| 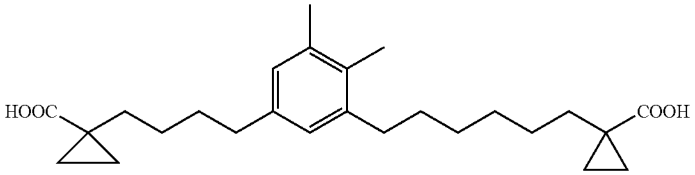 [SMILES: Cc1cc(CCCCC2(C(=O)O)CC2)cc(CCCCCCC2(C(=O)O)CC2)c1C] |
| 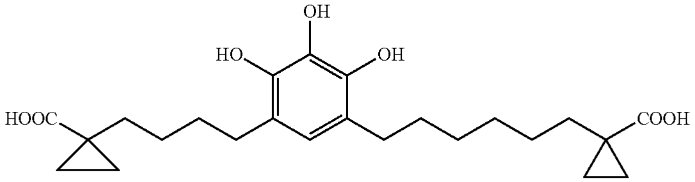 [SMILES: O=C(O)C1(CCCCCCc2cc(CCCCC3(C(=O)O)CC3)c(O)c(O)c2O)CC1] |

TABLE A-11-continued
| Structure |
|---|
| 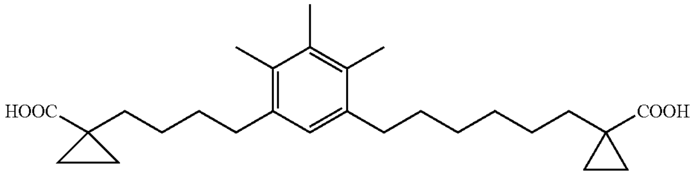 [SMILES: Cc1c(CCCCCCC2(C(=O)O)CC2)cc(CCCCC2(C(=O)O)CC2)c(C)c1C] |
| 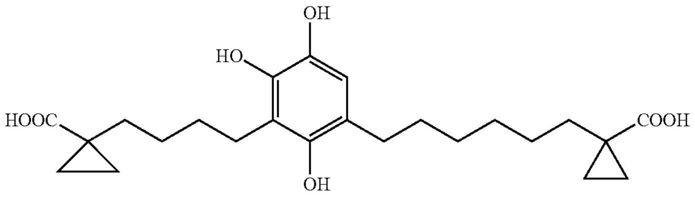 [SMILES: O=C(O)C1(CCCCCCc2cc(O)c(O)c(CCCCC3(C(=O)O)CC3)c2O)CC1] |
| 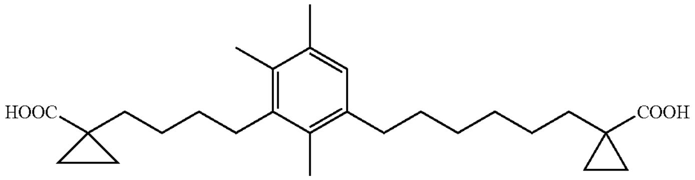 [SMILES: Cc1cc(CCCCCCC2(C(=O)O)CC2)c(C)c(CCCCC2(C(=O)O)CC2)c1C] |
| 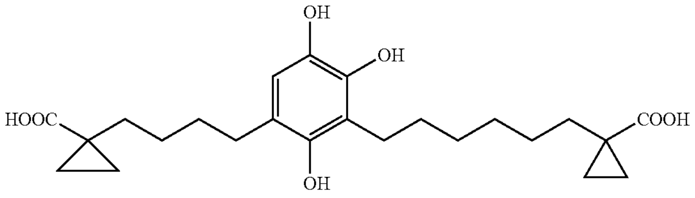 [SMILES: O=C(O)C1(CCCCCCc2c(O)c(O)cc(CCCCC3(C(=O)O)CC3)c2O)CC1] |
| 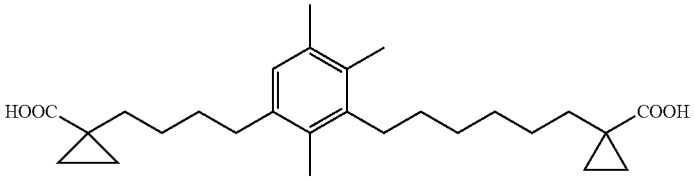 [SMILES: Cc1cc(CCCCC2(C(=O)O)CC2)c(C)c(CCCCCCC2(C(=O)O)CC2)c1C] |
TABLE A-12
| Structure | Structure |
|---|---|
| 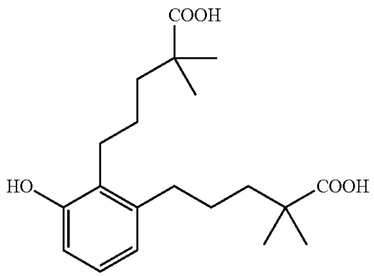 [SMILES: CC(C)(CCCc1cccc(O)c1CCCC(C)(C)C(=O)O)C(=O)O] | 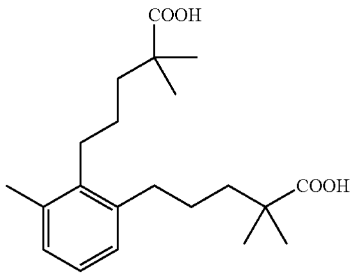 [SMILES: Cc1cccc(CCCC(C)(C)C(=O)O)c1CCCC(C)(C)C(=O)O] |

TABLE A-12-continued
| Structure | Structure |
| --- | --- |
| 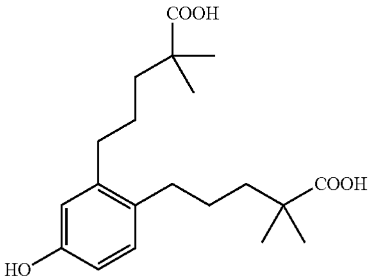 [SMILES: CC(C)(CCCc1ccc(O)cc1CCCC(C)(C)C(=O)O)C(=O)O] | 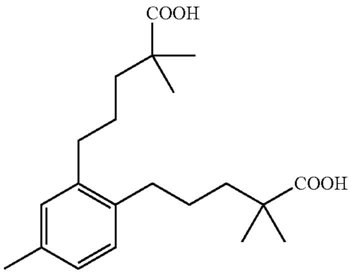 [SMILES: Cc1ccc(CCCC(C)(C)C(=O)O)c(CCCC(C)(C)C(=O)O)c1] |
| 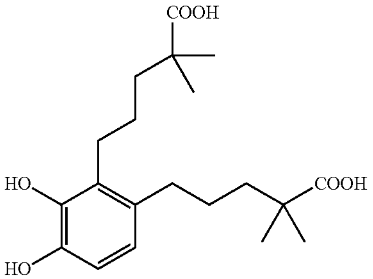 [SMILES: CC(C)(CCCc1ccc(O)c(O)c1CCCC(C)(C)C(=O)O)C(=O)O] | 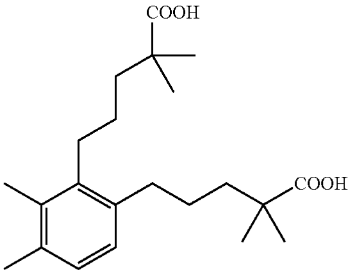 [SMILES: Cc1ccc(CCCC(C)(C)C(=O)O)c(CCCC(C)(C)C(=O)O)c1C] |
| 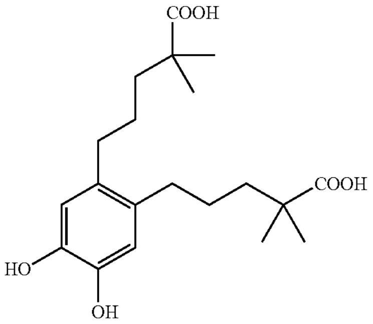 [SMILES: CC(C)(CCCc1cc(O)c(O)cc1CCCC(C)(C)C(=O)O)C(=O)O] | 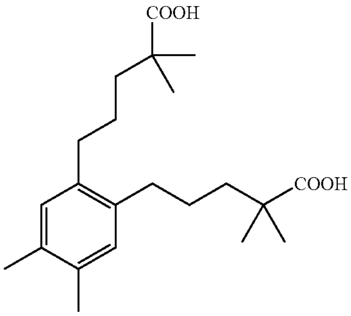 [SMILES: Cc1cc(CCCC(C)(C)C(=O)O)c(CCCC(C)(C)C(=O)O)cc1C] |
| 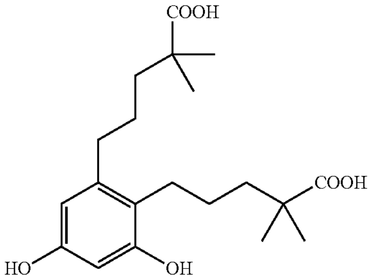 [SMILES: CC(C)(CCCc1cc(O)cc(O)c1CCCC(C)(C)C(=O)O)C(=O)O] | 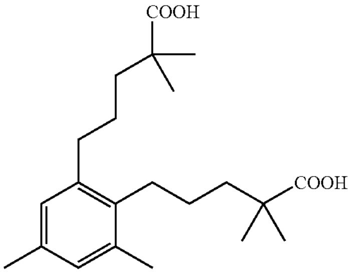 [SMILES: Cc1cc(C)c(CCCC(C)(C)C(=O)O)c(CCCC(C)(C)C(=O)O)c1] |
| 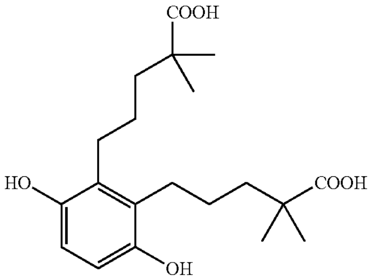 [SMILES: CC(C)(CCCc1c(O)ccc(O)c1CCCC(C)(C)C(=O)O)C(=O)O] | 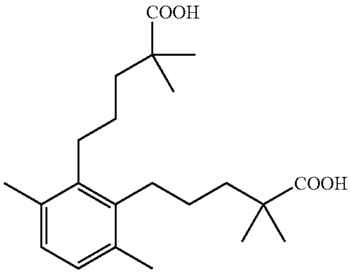 [SMILES: Cc1ccc(C)c(CCCC(C)(C)C(=O)O)c1CCCC(C)(C)C(=O)O] |

TABLE A-12-continued
| Structure | Structure |
| --- | --- |
| 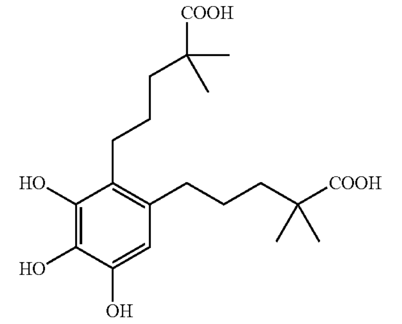 [SMILES: CC(C)(CCCc1cc(O)c(O)c(O)c1CCCC(C)(C)C(=O)O)C(=O)O] | 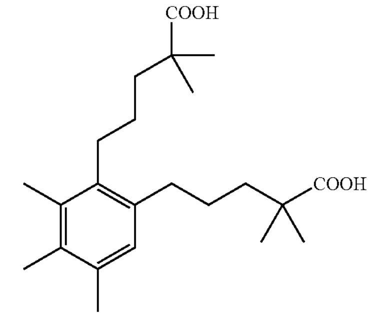 [SMILES: Cc1cc(CCCC(C)(C)C(=O)O)c(CCCC(C)(C)C(=O)O)c(C)c1C] |
| 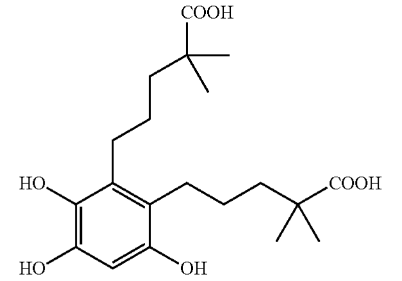 [SMILES: CC(C)(CCCc1c(O)cc(O)c(O)c1CCCC(C)(C)C(=O)O)C(=O)O] | 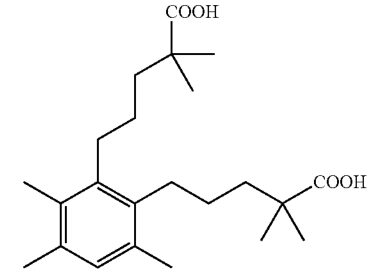 [SMILES: Cc1cc(C)c(CCCC(C)(C)C(=O)O)c(CCCC(C)(C)C(=O)O)c1C] |
| 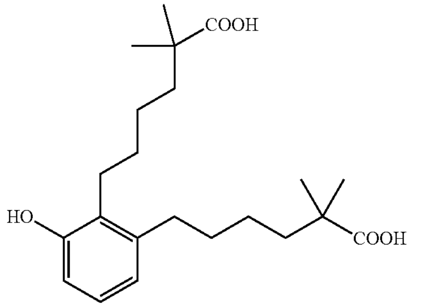 [SMILES: CC(C)(CCCCc1cccc(O)c1CCCCC(C)(C)C(=O)O)C(=O)O] | 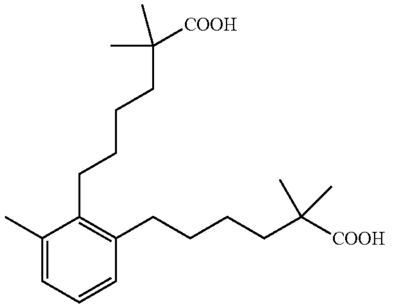 [SMILES: Cc1cccc(CCCCC(C)(C)C(=O)O)c1CCCCC(C)(C)C(=O)O] |
| 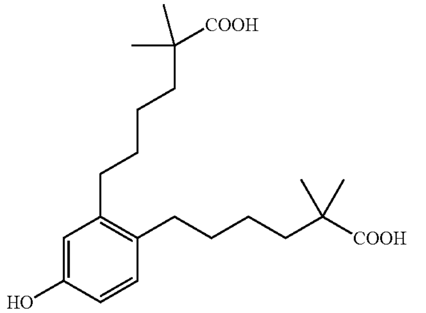 [SMILES: CC(C)(CCCCc1ccc(O)cc1CCCCC(C)(C)C(=O)O)C(=O)O] | 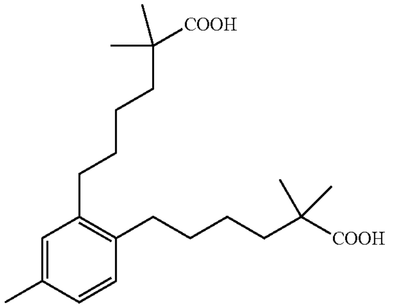 [SMILES: Cc1ccc(CCCCC(C)(C)C(=O)O)c(CCCCC(C)(C)C(=O)O)c1] |
| 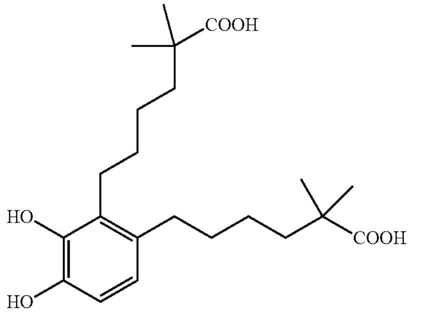 [SMILES: CC(C)(CCCCc1ccc(O)c(O)c1CCCCC(C)(C)C(=O)O)C(=O)O] | 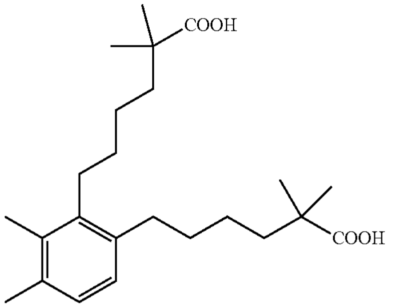 [SMILES: Cc1ccc(CCCCC(C)(C)C(=O)O)c(CCCCC(C)(C)C(=O)O)c1C] |

TABLE A-12-continued
| Structure | Structure |
| --- | --- |
| 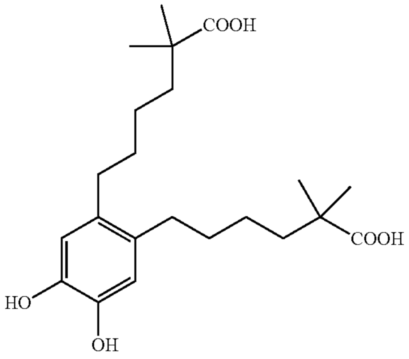 [SMILES: CC(C)(CCCCc1cc(O)c(O)cc1CCCCC(C)(C)C(=O)O)C(=O)O] | 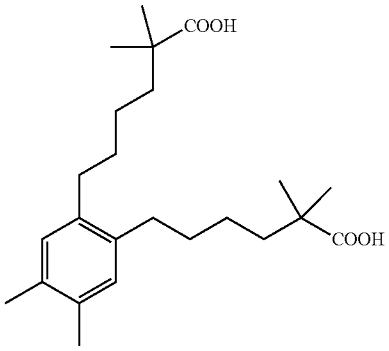 [SMILES: Cc1cc(CCCCC(C)(C)C(=O)O)c(CCCCC(C)(C)C(=O)O)cc1C] |
| 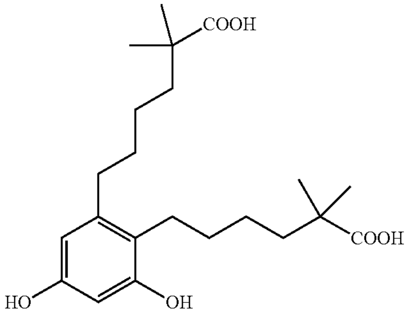 [SMILES: CC(C)(CCCCc1cc(O)cc(O)c1CCCCC(C)(C)C(=O)O)C(=O)O] | 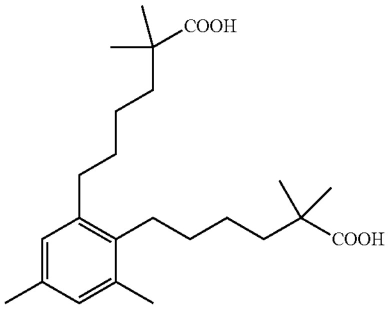 [SMILES: Cc1cc(C)c(CCCCC(C)(C)C(=O)O)c(CCCCC(C)(C)C(=O)O)c1] |
| 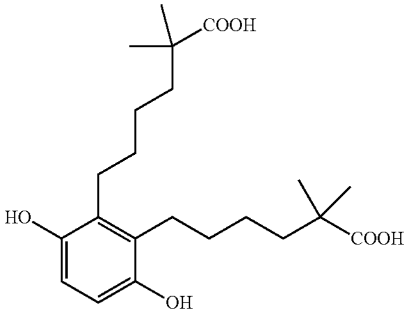 [SMILES: CC(C)(CCCCc1c(O)ccc(O)c1CCCCC(C)(C)C(=O)O)C(=O)O] | 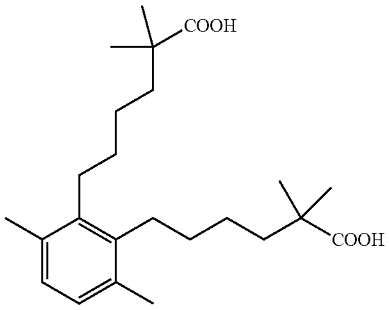 [SMILES: Cc1ccc(C)c(CCCCC(C)(C)C(=O)O)c1CCCCC(C)(C)C(=O)O] |
| 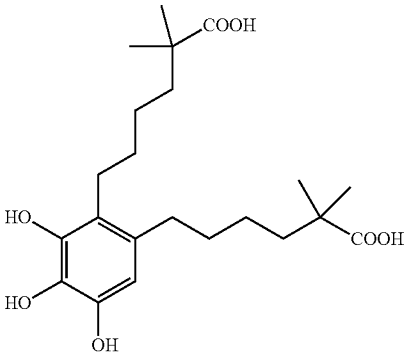 [SMILES: CC(C)(CCCCc1cc(O)c(O)c(O)c1CCCCC(C)(C)C(=O)O)C(=O)O] | 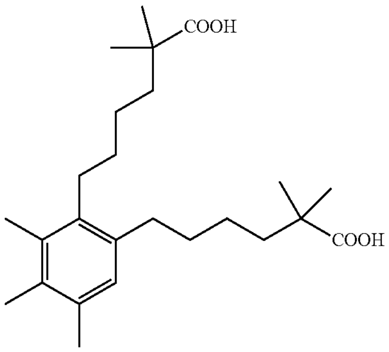 [SMILES: Cc1cc(CCCCC(C)(C)C(=O)O)c(CCCCC(C)(C)C(=O)O)c(C)c1C] |

TABLE A-12-continued
| Structure | Structure |
|---|---|
| 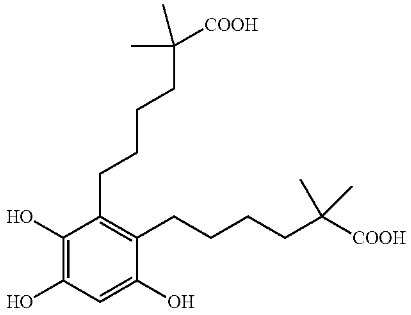 [SMILES: CC(C)(CCCCc1c(O)cc(O)c(O)c1CCCCC(C)(C)C(=O)O)C(=O)O] | 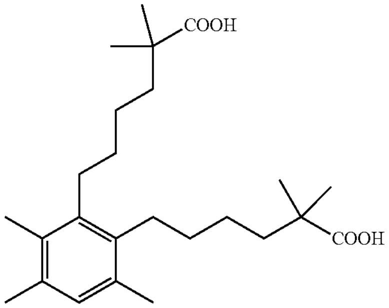 [SMILES: Cc1cc(C)c(CCCCC(C)(C)C(=O)O)c(CCCCC(C)(C)C(=O)O)c1C] |
| 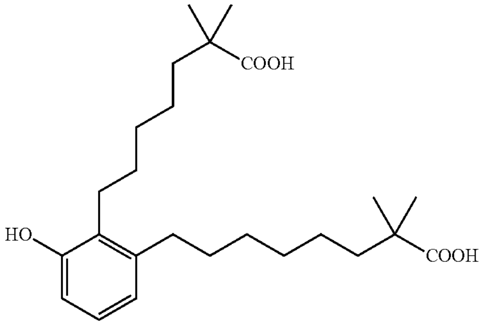 [SMILES: CC(C)(CCCCCCc1cccc(O)c1CCCCCC(C)(C)C(=O)O)C(=O)O] | 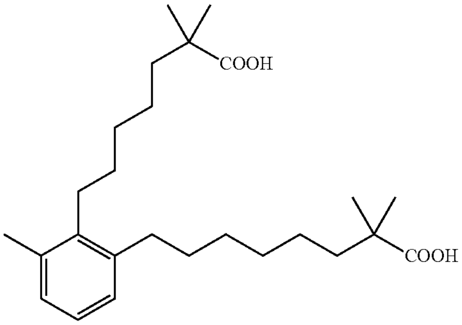 [SMILES: Cc1cccc(CCCCCCC(C)(C)C(=O)O)c1CCCCCC(C)(C)C(=O)O] |
| 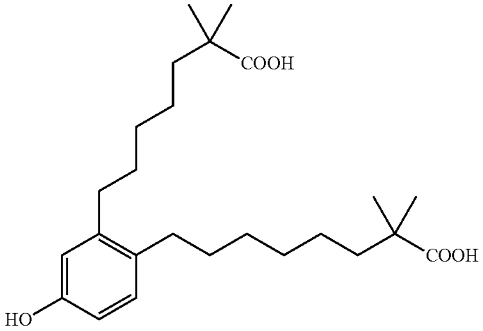 [SMILES: CC(C)(CCCCCCc1ccc(O)cc1CCCCCC(C)(C)C(=O)O)C(=O)O] | 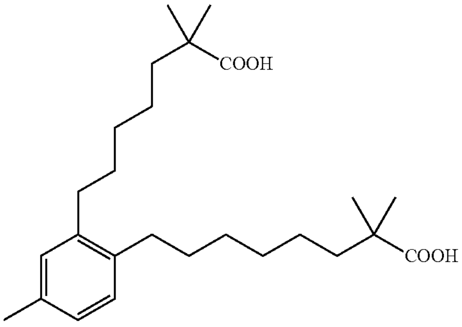 [SMILES: Cc1ccc(CCCCCCC(C)(C)C(=O)O)c(CCCCCC(C)(C)C(=O)O)c1] |
| 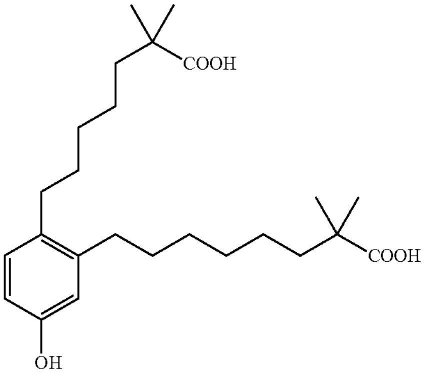 [SMILES: CC(C)(CCCCCCc1cc(O)ccc1CCCCCC(C)(C)C(=O)O)C(=O)O] | 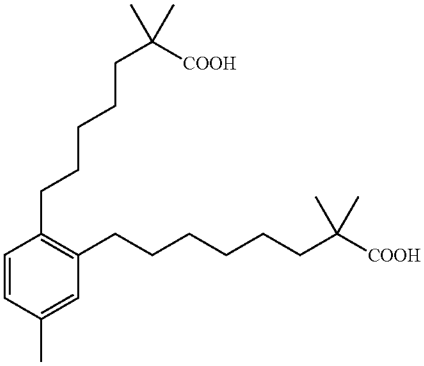 [SMILES: Cc1ccc(CCCCCC(C)(C)C(=O)O)c(CCCCCCC(C)(C)C(=O)O)c1] |

TABLE A-12-continued
| Structure | Structure |
|---|---|
| 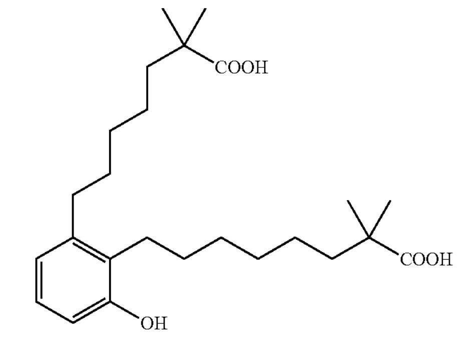 [SMILES: CC(C)(CCCCCCc1c(O)cccc1CCCCCC(C)(C)C(=O)O)C(=O)O] | 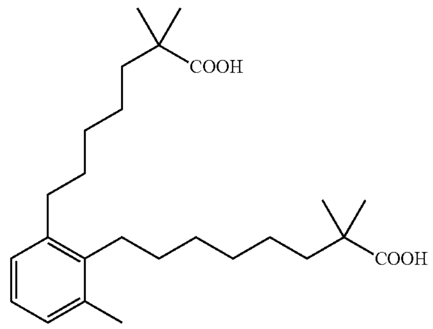 [SMILES: Cc1cccc(CCCCCC(C)(C)C(=O)O)c1CCCCCCC(C)(C)C(=O)O] |
| 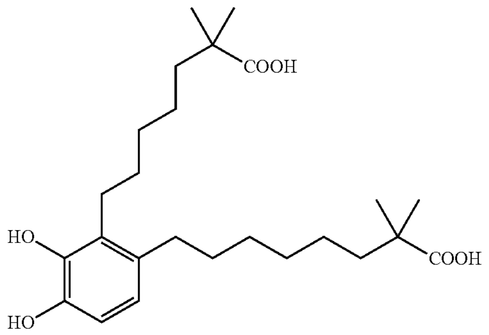 [SMILES: CC(C)(CCCCCCc1ccc(O)c(O)c1CCCCCC(C)(C)C(=O)O)C(=O)O] | 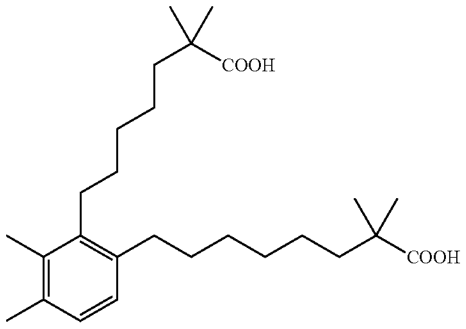 [SMILES: Cc1ccc(CCCCCCC(C)(C)C(=O)O)c(CCCCCC(C)(C)C(=O)O)c1C] |
| 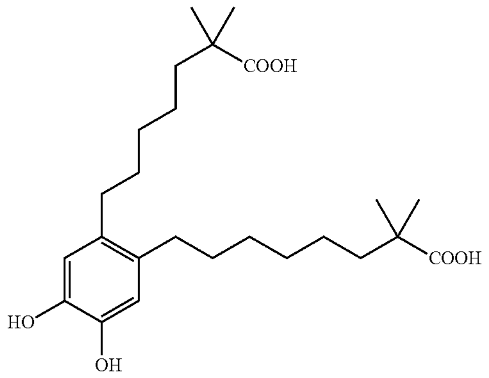 [SMILES: CC(C)(CCCCCCc1cc(O)c(O)cc1CCCCCC(C)(C)C(=O)O)C(=O)O] | 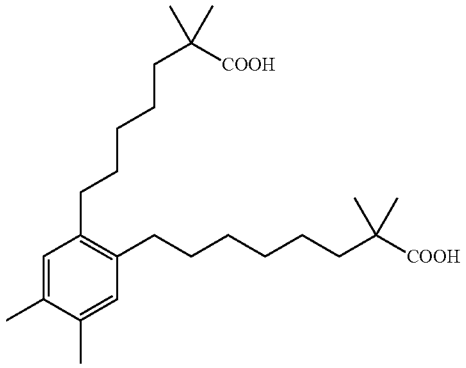 [SMILES: Cc1cc(CCCCCCC(C)(C)C(=O)O)c(CCCCCC(C)(C)C(=O)O)cc1C] |
| 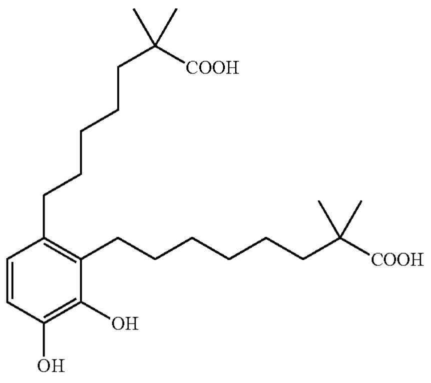 [SMILES: CC(C)(CCCCCCc1c(CCCCCC(C)(C)C(=O)O)ccc(O)c1O)C(=O)O] | 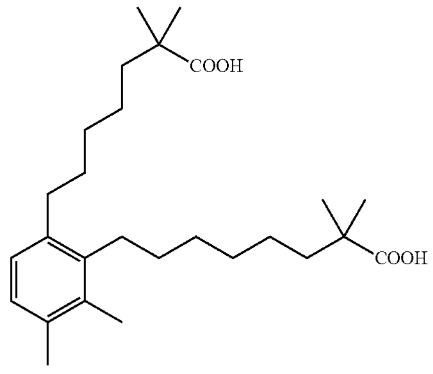 [SMILES: Cc1ccc(CCCCCC(C)(C)C(=O)O)c(CCCCCCC(C)(C)C(=O)O)c1C] |

TABLE A-12-continued
| Structure | Structure |
| --- | --- |
| 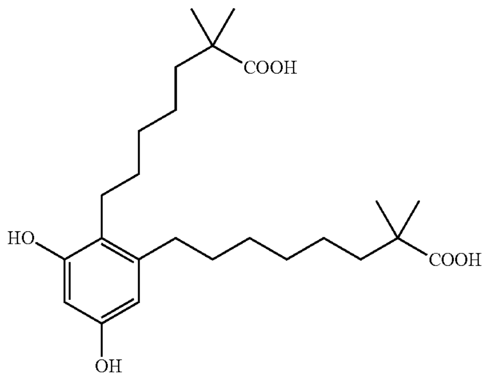 [SMILES: CC(C)(CCCCCCc1cc(O)cc(O)c1CCCCCC(C)(C)C(=O)O)C(=O)O] | 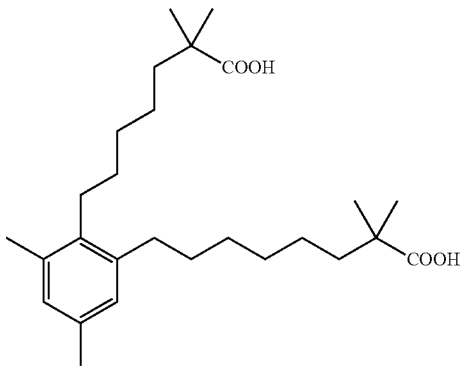 [SMILES: Cc1cc(C)c(CCCCCC(C)(C)C(=O)O)c(CCCCCCC(C)(C)C(=O)O)c1] |
| 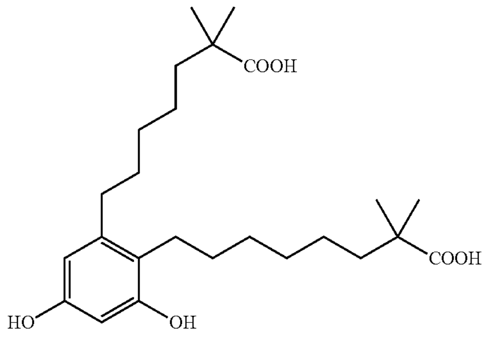 [SMILES: CC(C)(CCCCCCc1c(O)cc(O)cc1CCCCCC(C)(C)C(=O)O)C(=O)O] | 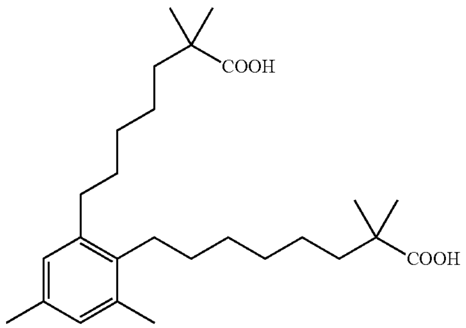 [SMILES: Cc1cc(C)c(CCCCCCC(C)(C)C(=O)O)c(CCCCCC(C)(C)C(=O)O)c1] |
| 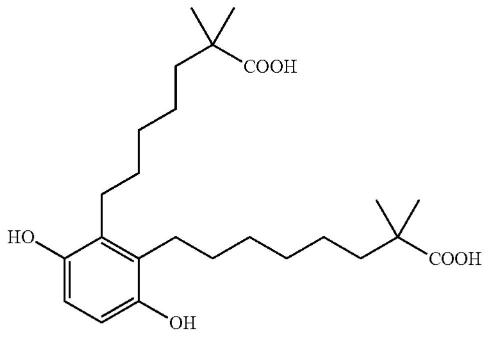 [SMILES: CC(C)(CCCCCCc1c(O)ccc(O)c1CCCCCC(C)(C)C(=O)O)C(=O)O] | 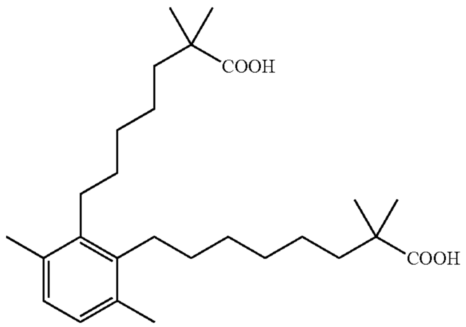 [SMILES: Cc1ccc(C)c(CCCCCC(C)(C)C(=O)O)c1CCCCCCC(C)(C)C(=O)O] |
| 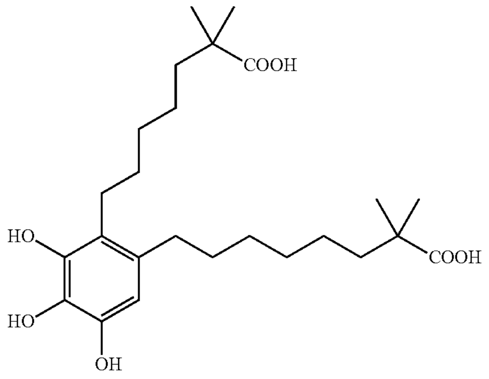 [SMILES: CC(C)(CCCCCCc1cc(O)c(O)c(O)c1CCCCCC(C)(C)C(=O)O)C(=O)O] | 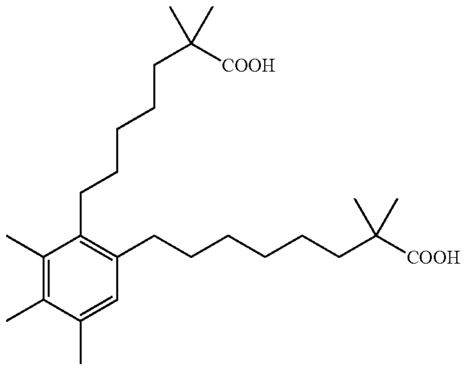 [SMILES: Cc1cc(CCCCCCC(C)(C)C(=O)O)c(CCCCCC(C)(C)C(=O)O)c(C)c1C] |

TABLE A-12-continued
| Structure | Structure |
| --- | --- |
| 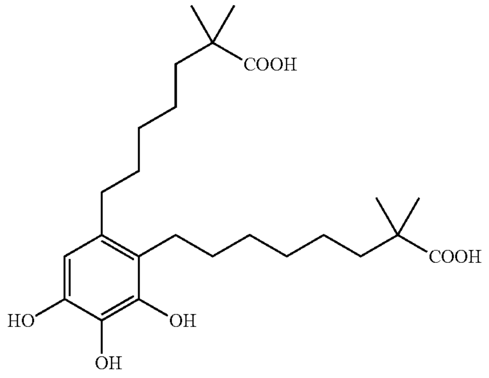 [SMILES: CC(C)(CCCCCCc1c(CCCCCC(C)(C)C(=O)O)cc(O)c(O)c1O)C(=O)O] | 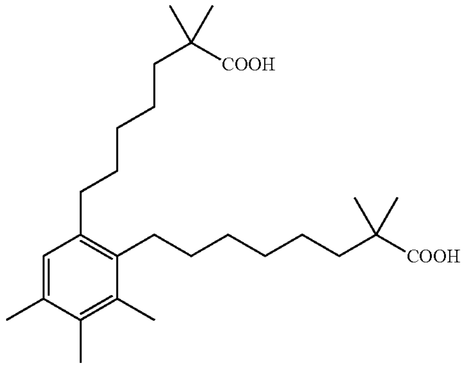 [SMILES: Cc1cc(CCCCCC(C)(C)C(=O)O)c(CCCCCCC(C)(C)C(=O)O)c(C)c1C] |
| 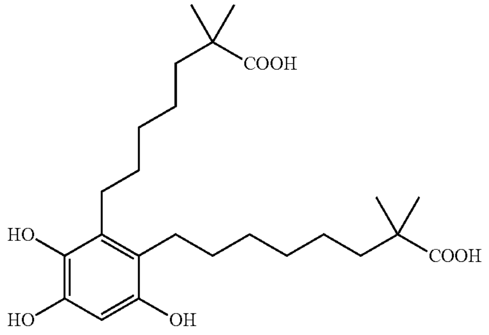 [SMILES: CC(C)(CCCCCCc1c(O)cc(O)c(O)c1CCCCCC(C)(C)C(=O)O)C(=O)O] | 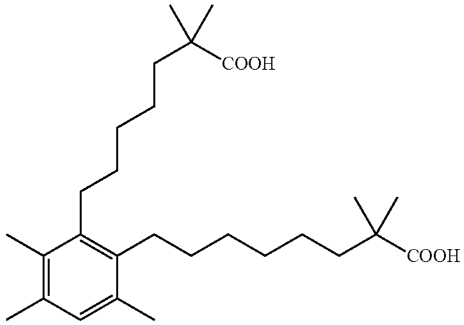 [SMILES: Cc1cc(C)c(CCCCCCC(C)(C)C(=O)O)c(CCCCCC(C)(C)C(=O)O)c1C] |
| 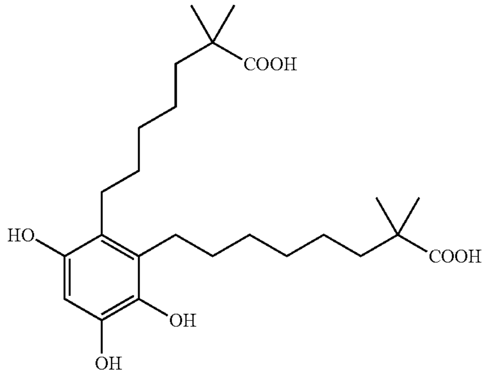 [SMILES: CC(C)(CCCCCCc1c(O)c(O)cc(O)c1CCCCCC(C)(C)C(=O)O)C(=O)O] | 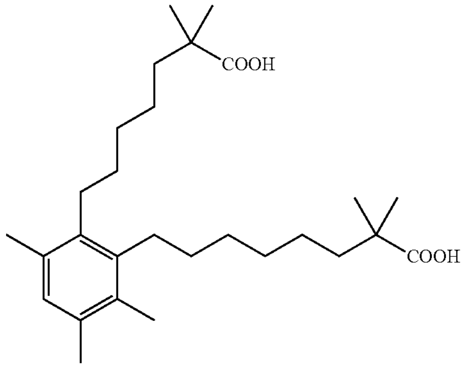 [SMILES: Cc1cc(C)c(CCCCCC(C)(C)C(=O)O)c(CCCCCCC(C)(C)C(=O)O)c1C] |
| 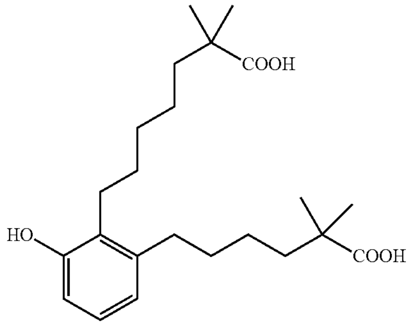 [SMILES: CC(C)(CCCCCc1c(O)cccc1CCCCC(C)(C)C(=O)O)C(=O)O] | 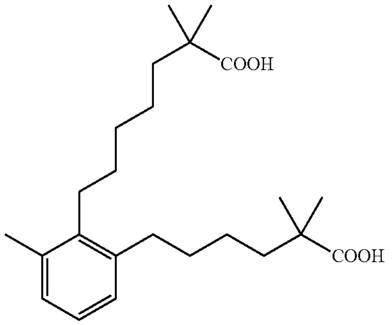 [SMILES: Cc1cccc(CCCCC(C)(C)C(=O)O)c1CCCCCC(C)(C)C(=O)O] |

TABLE A-12-continued
| Structure | Structure |
|---|---|
| 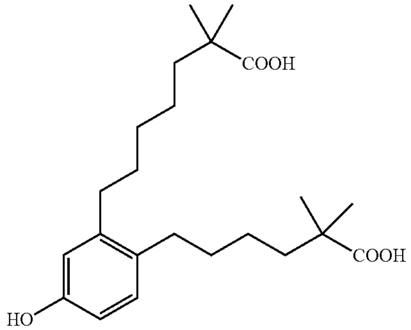 [SMILES: CC(C)(CCCCCc1cc(O)ccc1CCCCC(C)(C)C(=O)O)C(=O)O] | 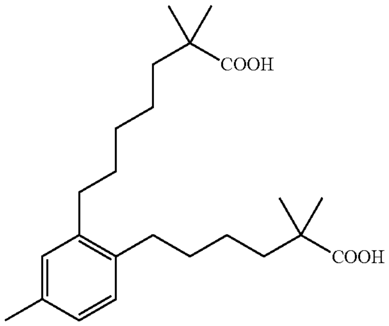 [SMILES: Cc1ccc(CCCCC(C)(C)C(=O)O)c(CCCCCC(C)(C)C(=O)O)c1] |
| 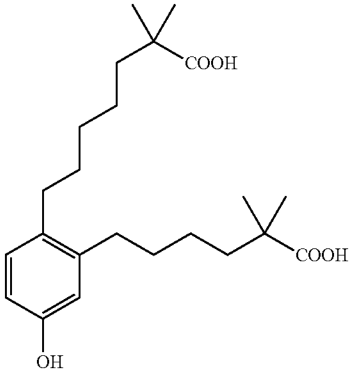 [SMILES: CC(C)(CCCCCc1ccc(O)cc1CCCCC(C)(C)C(=O)O)C(=O)O] | 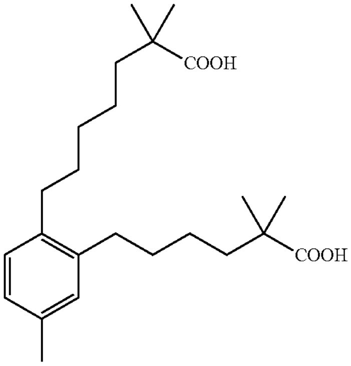 [SMILES: Cc1ccc(CCCCCC(C)(C)C(=O)O)c(CCCCC(C)(C)C(=O)O)c1] |
| 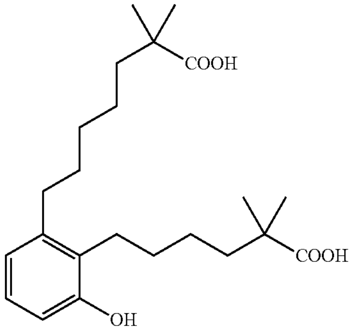 [SMILES: CC(C)(CCCCCc1cccc(O)c1CCCCC(C)(C)C(=O)O)C(=O)O] | 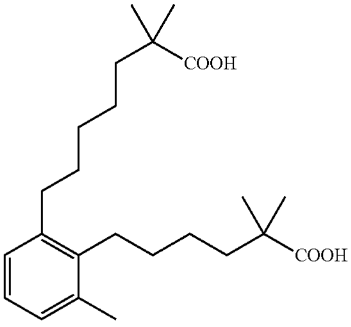 [SMILES: Cc1cccc(CCCCCC(C)(C)C(=O)O)c1CCCCC(C)(C)C(=O)O] |
| 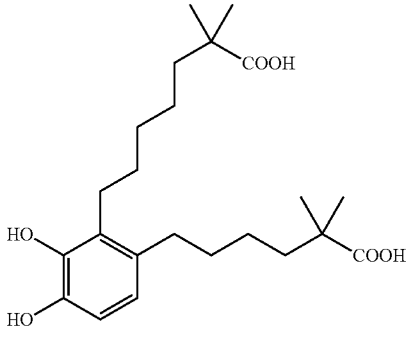 [SMILES: CC(C)(CCCCCc1c(CCCCC(C)(C)C(=O)O)ccc(O)c1O)C(=O)O] | 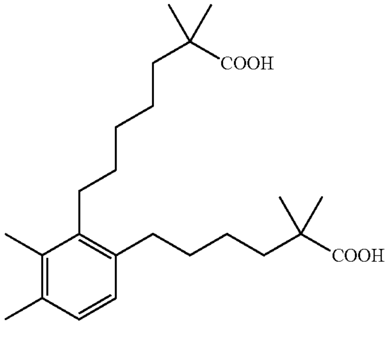 [SMILES: Cc1ccc(CCCCC(C)(C)C(=O)O)c(CCCCCC(C)(C)C(=O)O)c1C] |

TABLE A-12-continued
| Structure | Structure |
| --- | --- |
| 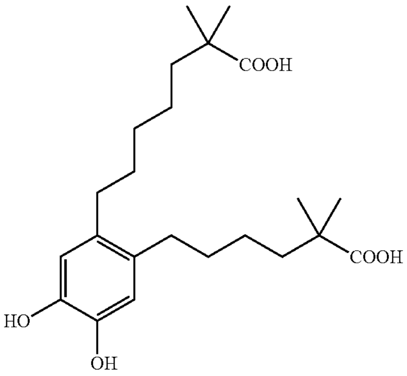 [SMILES: CC(C)(CCCCCc1cc(O)c(O)cc1CCCCC(C)(C)C(=O)O)C(=O)O] | 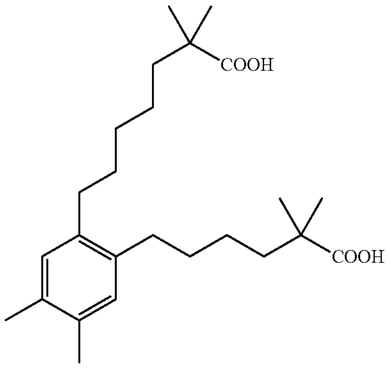 [SMILES: Cc1cc(CCCCCC(C)(C)C(=O)O)c(CCCCC(C)(C)C(=O)O)cc1C] |
| 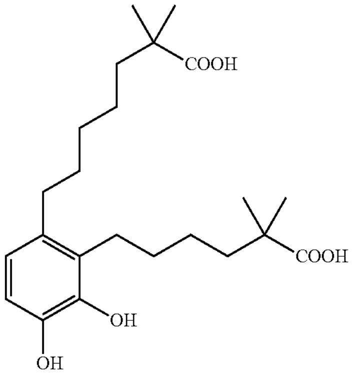 [SMILES: CC(C)(CCCCCc1ccc(O)c(O)c1CCCCC(C)(C)C(=O)O)C(=O)O] | 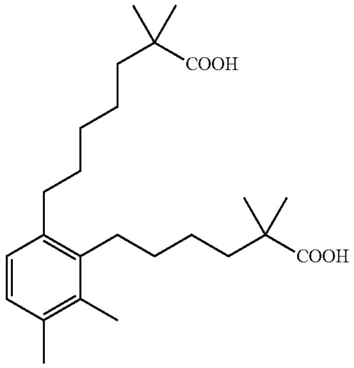 [SMILES: Cc1ccc(CCCCCC(C)(C)C(=O)O)c(CCCCC(C)(C)C(=O)O)c1C] |
| 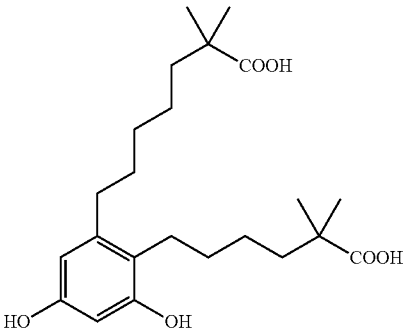 [SMILES: CC(C)(CCCCCc1cc(O)cc(O)c1CCCCC(C)(C)C(=O)O)C(=O)O] | 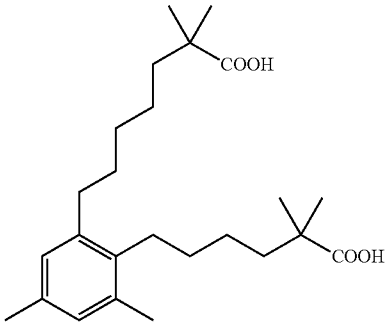 [SMILES: Cc1cc(C)c(CCCCC(C)(C)C(=O)O)c(CCCCCC(C)(C)C(=O)O)c1] |
| 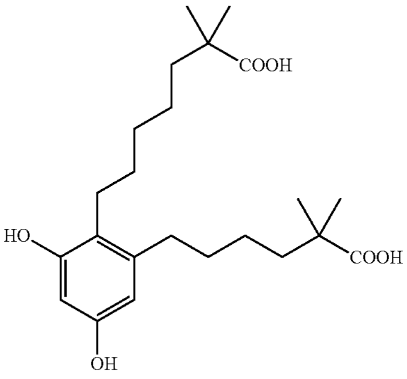 [SMILES: CC(C)(CCCCCc1c(O)cc(O)cc1CCCCC(C)(C)C(=O)O)C(=O)O] | 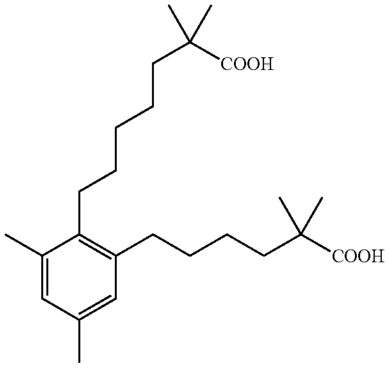 [SMILES: Cc1cc(C)c(CCCCCC(C)(C)C(=O)O)c(CCCCC(C)(C)C(=O)O)c1] |

TABLE A-12-continued
| Structure | Structure |
|---|---|
| 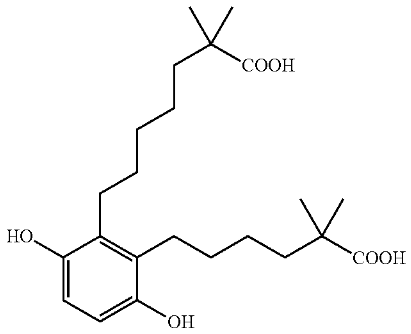 [SMILES: CC(C)(CCCCCc1c(O)ccc(O)c1CCCCC(C)(C)C(=O)O)C(=O)O] | 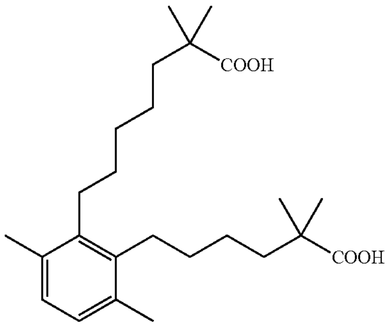 [SMILES: Cc1ccc(C)c(CCCCC(C)(C)C(=O)O)c1CCCCCC(C)(C)C(=O)O] |
| 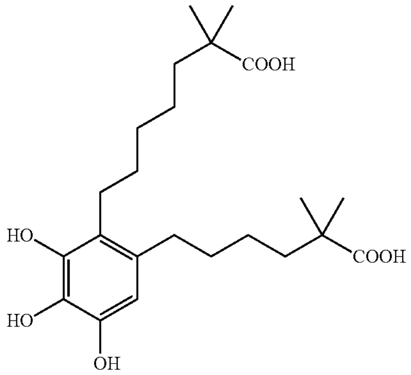 [SMILES: CC(C)(CCCCCc1c(CCCCC(C)(C)C(=O)O)cc(O)c(O)c1O)C(=O)O] | 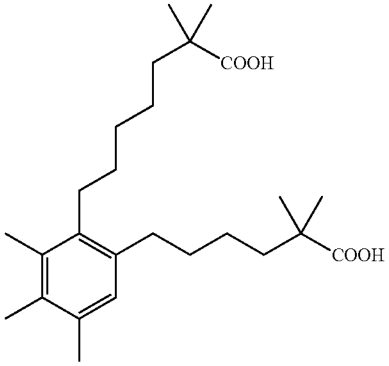 [SMILES: Cc1cc(CCCCC(C)(C)C(=O)O)c(CCCCCC(C)(C)C(=O)O)c(C)c1C] |
| 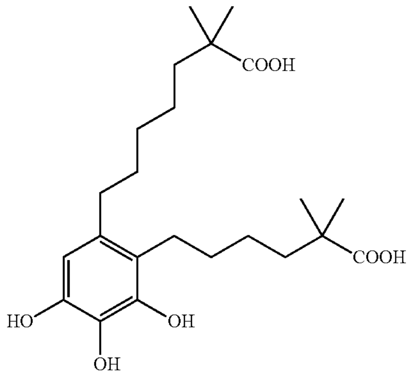 [SMILES: CC(C)(CCCCCc1cc(O)c(O)c(O)c1CCCCC(C)(C)C(=O)O)C(=O)O] | 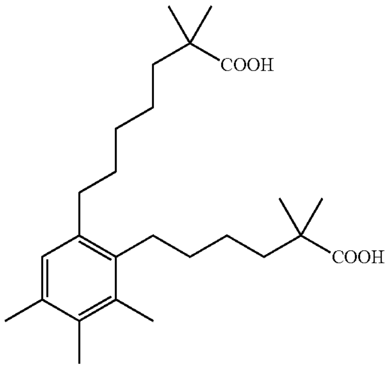 [SMILES: Cc1cc(CCCCCC(C)(C)C(=O)O)c(CCCCC(C)(C)C(=O)O)c(C)c1C] |
| 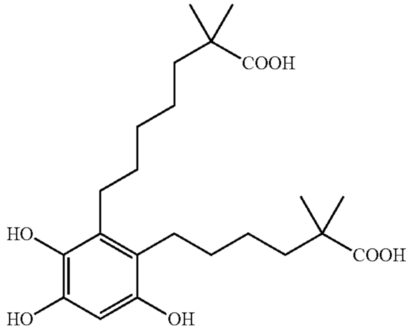 [SMILES: CC(C)(CCCCCc1c(O)c(O)cc(O)c1CCCCC(C)(C)C(=O)O)C(=O)O] | 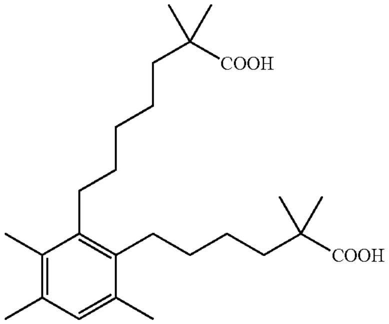 [SMILES: Cc1cc(C)c(CCCCC(C)(C)C(=O)O)c(CCCCCC(C)(C)C(=O)O)c1C] |

TABLE A-12-continued
| Structure | Structure |
| --- | --- |
| 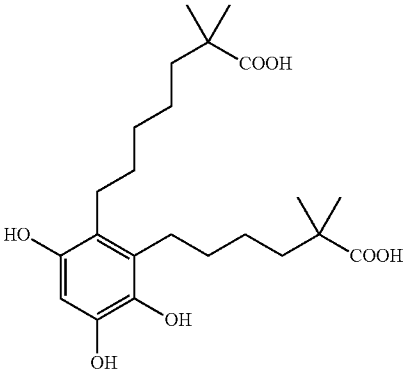 [SMILES: CC(C)(CCCCCc1c(O)cc(O)c(O)c1CCCCC(C)(C)C(=O)O)C(=O)O] | 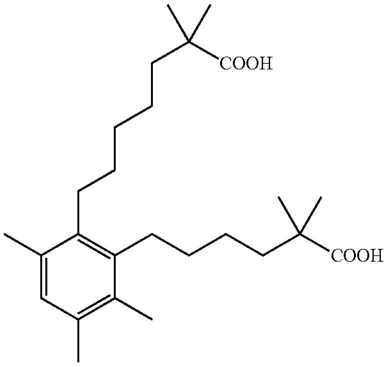 [SMILES: Cc1cc(C)c(CCCCCC(C)(C)C(=O)O)c(CCCCC(C)(C)C(=O)O)c1C] |
| 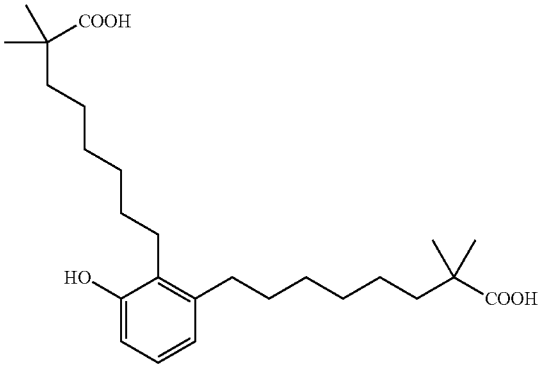 [SMILES: CC(C)(CCCCCCc1cccc(O)c1CCCCCCC(C)(C)C(=O)O)C(=O)O] | 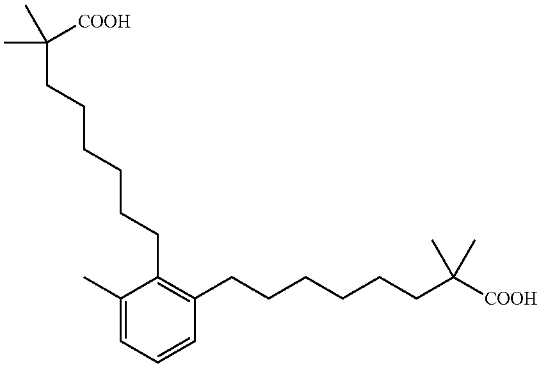 [SMILES: Cc1cccc(CCCCCCC(C)(C)C(=O)O)c1CCCCCCC(C)(C)C(=O)O] |
| 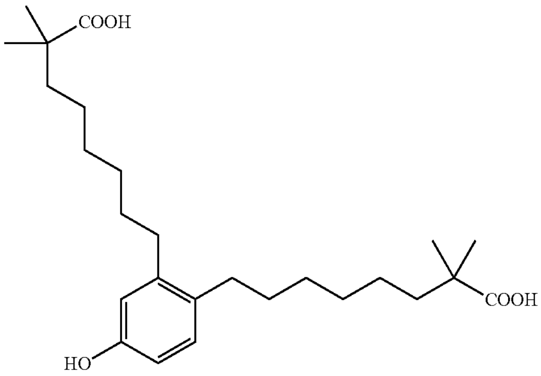 [SMILES: CC(C)(CCCCCCc1ccc(O)cc1CCCCCCC(C)(C)C(=O)O)C(=O)O] | 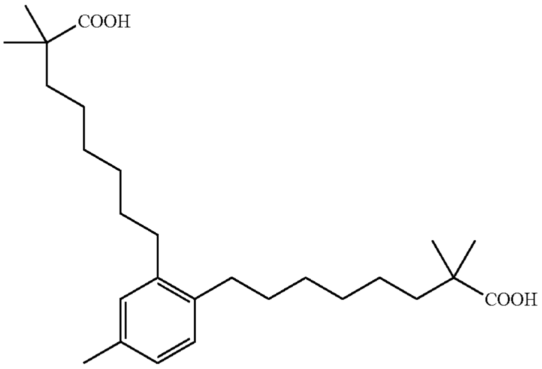 [SMILES: Cc1ccc(CCCCCCC(C)(C)C(=O)O)c(CCCCCCC(C)(C)C(=O)O)c1] |
| 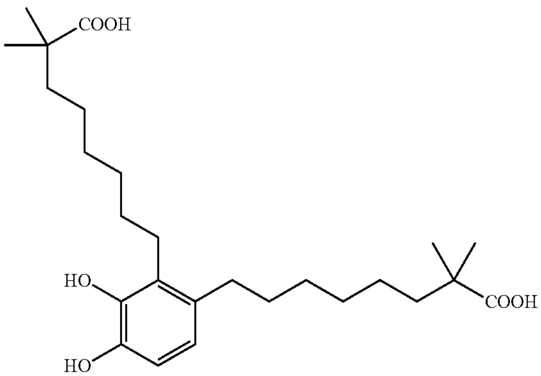 [SMILES: CC(C)(CCCCCCc1ccc(O)c(O)c1CCCCCCC(C)(C)C(=O)O)C(=O)O] | 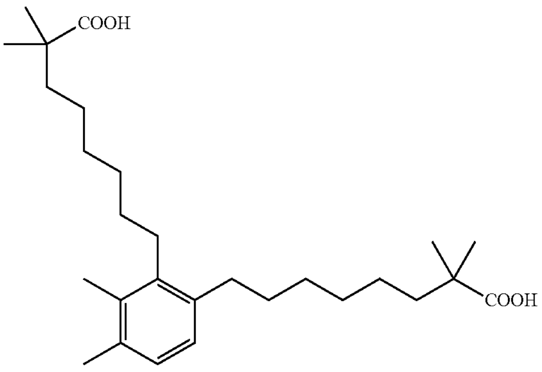 [SMILES: Cc1ccc(CCCCCCC(C)(C)C(=O)O)c(CCCCCCC(C)(C)C(=O)O)c1C] |

TABLE A-12-continued
| Structure | Structure |
| --- | --- |
| 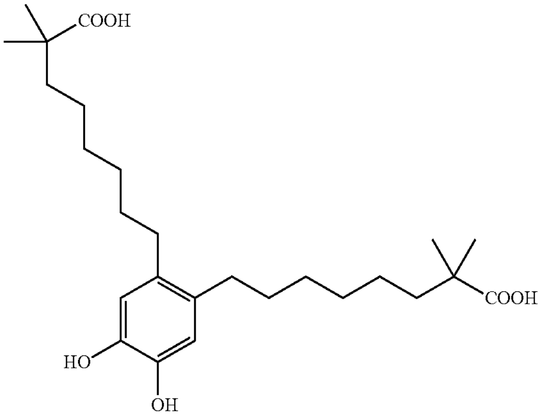 [SMILES: CC(C)(CCCCCCc1cc(O)c(O)cc1CCCCCCC(C)(C)C(=O)O)C(=O)O] | 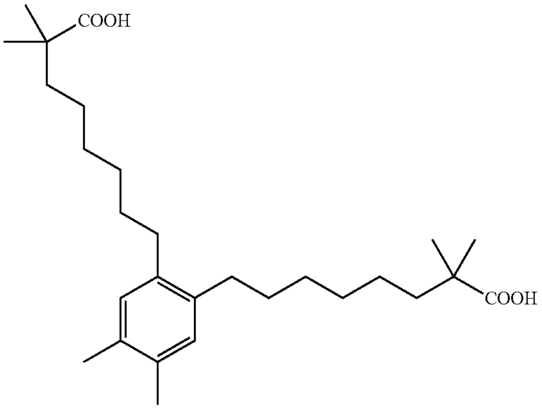 [SMILES: Cc1cc(CCCCCCC(C)(C)C(=O)O)c(CCCCCCC(C)(C)C(=O)O)cc1C] |
| 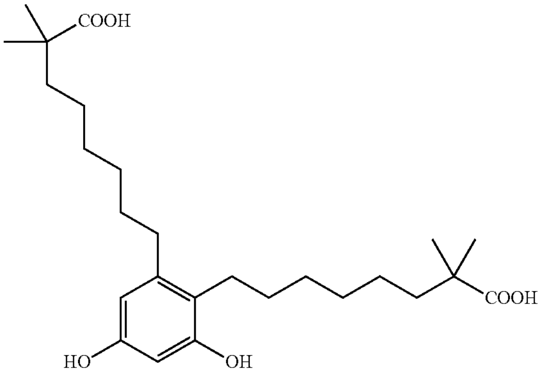 [SMILES: CC(C)(CCCCCCc1cc(O)cc(O)c1CCCCCCC(C)(C)C(=O)O)C(=O)O] | 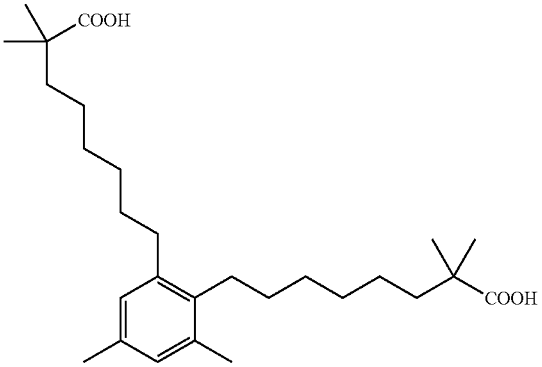 [SMILES: Cc1cc(C)c(CCCCCCC(C)(C)C(=O)O)c(CCCCCCC(C)(C)C(=O)O)c1] |
| 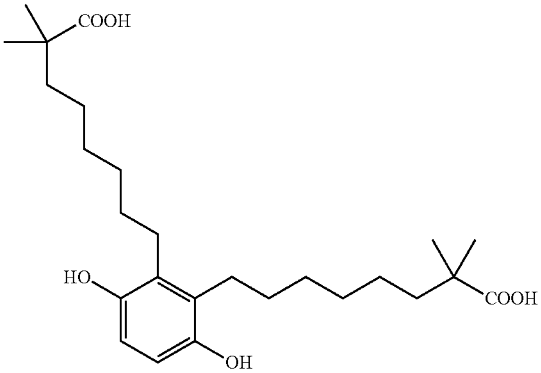 [SMILES: CC(C)(CCCCCCc1c(O)ccc(O)c1CCCCCCC(C)(C)C(=O)O)C(=O)O] | 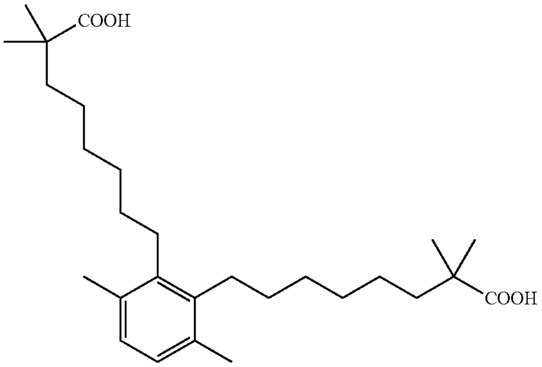 [SMILES: Cc1ccc(C)c(CCCCCCC(C)(C)C(=O)O)c1CCCCCCC(C)(C)C(=O)O] |
| 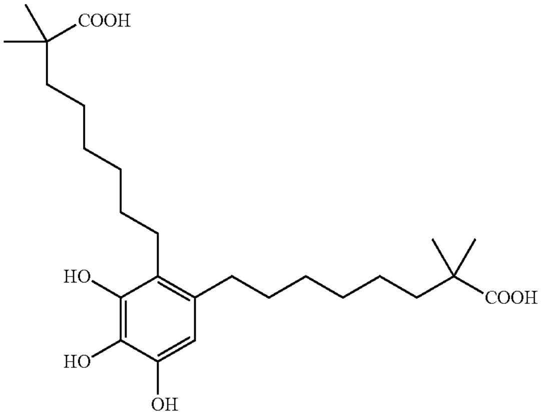 [SMILES: CC(C)(CCCCCCc1cc(O)c(O)c(O)c1CCCCCCC(C)(C)C(=O)O)C(=O)O] | 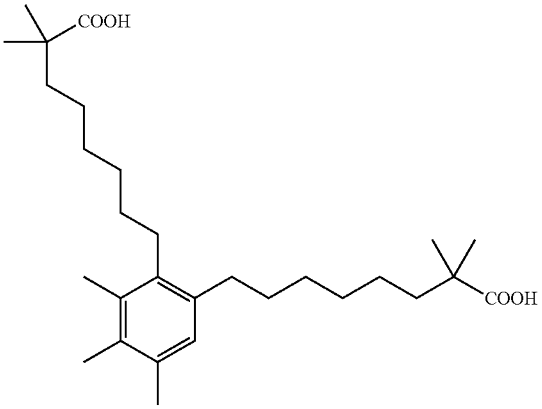 [SMILES: Cc1cc(CCCCCCC(C)(C)C(=O)O)c(CCCCCCC(C)(C)C(=O)O)c(C)c1C] |

TABLE A-12-continued
| Structure | Structure |
|---|---|
| 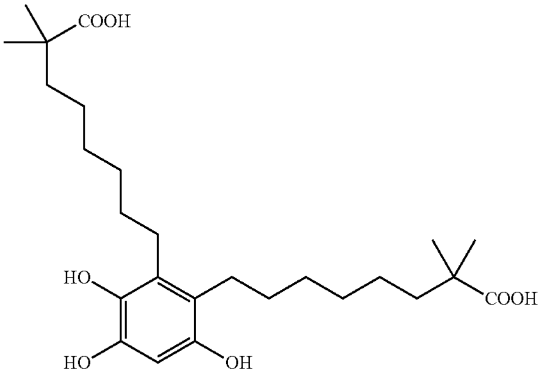 [SMILES: CC(C)(CCCCCCc1c(O)cc(O)c(O)c1CCCCCCC(C)(C)C(=O)O)C(=O)O] | 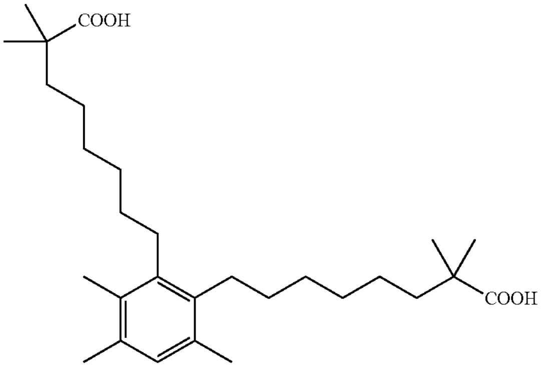 [SMILES: Cc1cc(C)c(CCCCCCC(C)(C)C(=O)O)c(CCCCCCC(C)(C)C(=O)O)c1C] |
| 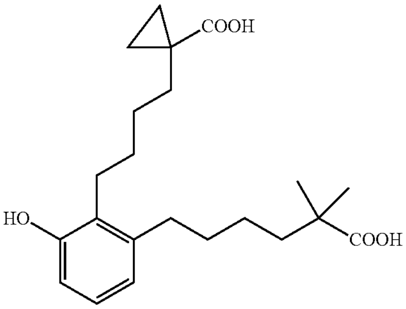 [SMILES: CC(C)(CCCCc1cccc(O)c1CCCCC1(C(=O)O)CC1)C(=O)O] | 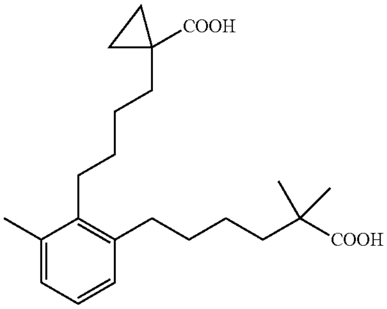 [SMILES: Cc1cccc(CCCCC(C)(C)C(=O)O)c1CCCCC1(C(=O)O)CC1] |
| 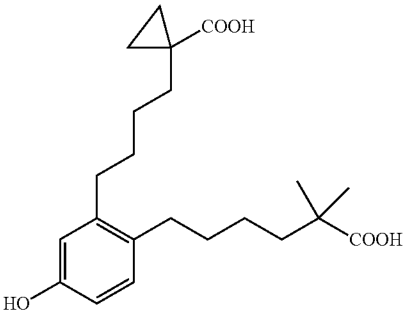 [SMILES: CC(C)(CCCCc1ccc(O)cc1CCCCC1(C(=O)O)CC1)C(=O)O] | 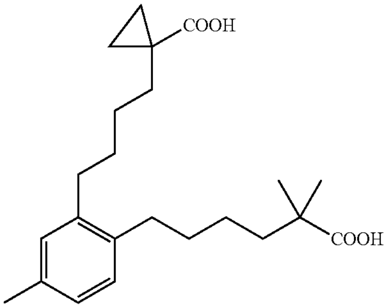 [SMILES: Cc1ccc(CCCCC(C)(C)C(=O)O)c(CCCCC2(C(=O)O)CC2)c1] |
| 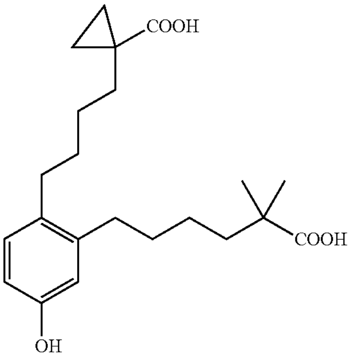 [SMILES: CC(C)(CCCCc1cc(O)ccc1CCCCC1(C(=O)O)CC1)C(=O)O] | 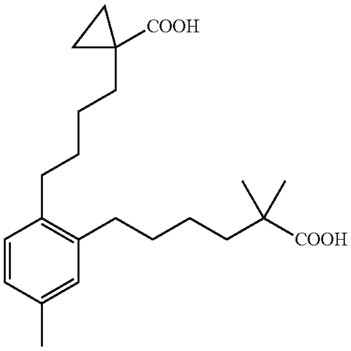 [SMILES: Cc1ccc(CCCCC2(C(=O)O)CC2)c(CCCCC(C)(C)C(=O)O)c1] |

TABLE A-12-continued
| Structure | Structure |
|---|---|
| 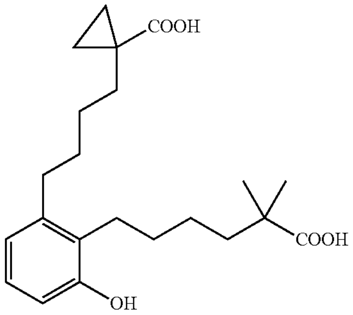 [SMILES: CC(C)(CCCCc1c(O)cccc1CCCCC1(C(=O)O)CC1)C(=O)O] | 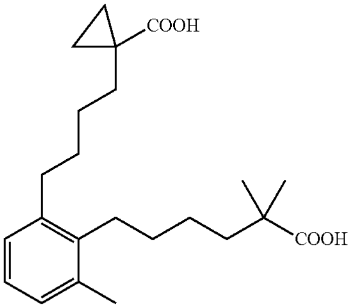 [SMILES: Cc1cccc(CCCCC2(C(=O)O)CC2)c1CCCCC(C)(C)C(=O)O] |
| 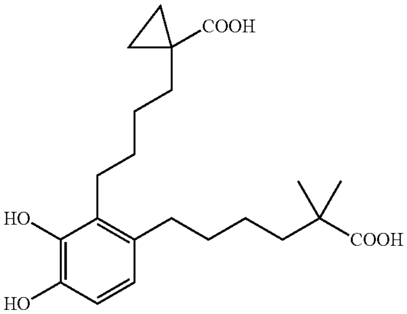 [SMILES: CC(C)(CCCCc1ccc(O)c(O)c1CCCCC1(C(=O)O)CC1)C(=O)O] | 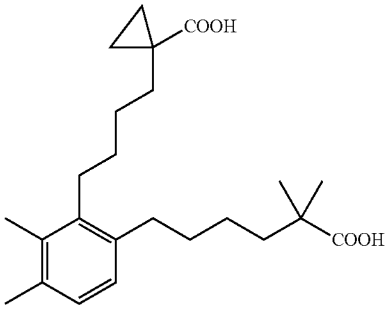 [SMILES: Cc1ccc(CCCCC(C)(C)C(=O)O)c(CCCCC2(C(=O)O)CC2)c1C] |
| 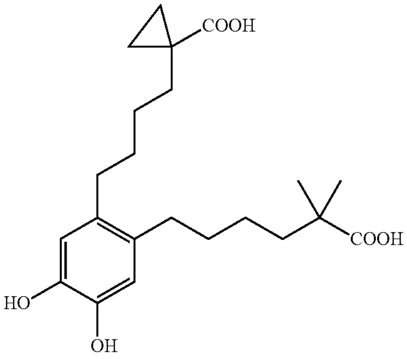 [SMILES: CC(C)(CCCCc1cc(O)c(O)cc1CCCCC1(C(=O)O)CC1)C(=O)O] | 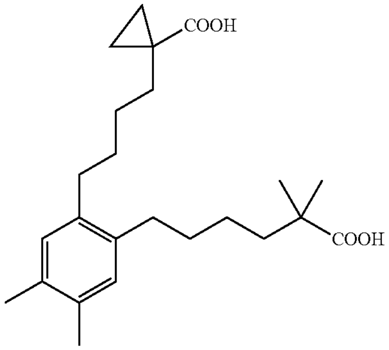 [SMILES: Cc1cc(CCCCC(C)(C)C(=O)O)c(CCCCC2(C(=O)O)CC2)cc1C] |
| 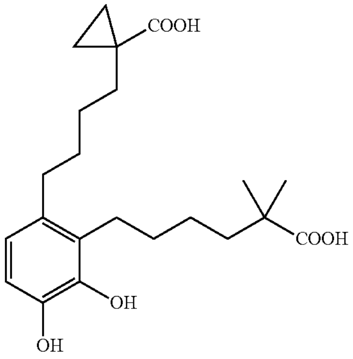 [SMILES: CC(C)(CCCCc1c(CCCCC2(C(=O)O)CC2)ccc(O)c1O)C(=O)O] | 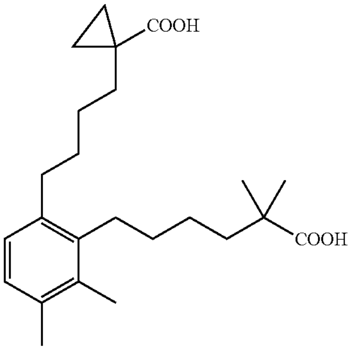 [SMILES: Cc1ccc(CCCCC2(C(=O)O)CC2)c(CCCCC(C)(C)C(=O)O)c1C] |

TABLE A-12-continued
| Structure | Structure |
| --- | --- |
| 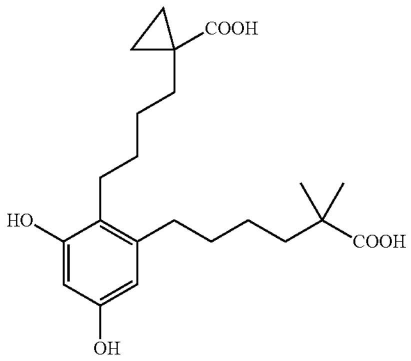 [SMILES: CC(C)(CCCCc1cc(O)cc(O)c1CCCCC1(C(=O)O)CC1)C(=O)O] | 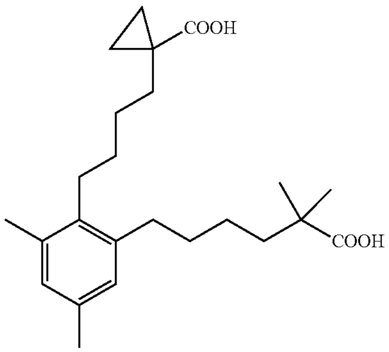 [SMILES: Cc1cc(C)c(CCCCC2(C(=O)O)CC2)c(CCCCC(C)(C)C(=O)O)c1] |
| 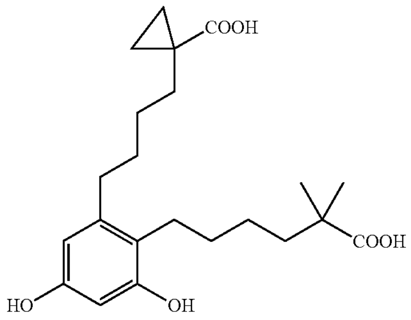 [SMILES: CC(C)(CCCCc1c(O)cc(O)cc1CCCCC1(C(=O)O)CC1)C(=O)O] | 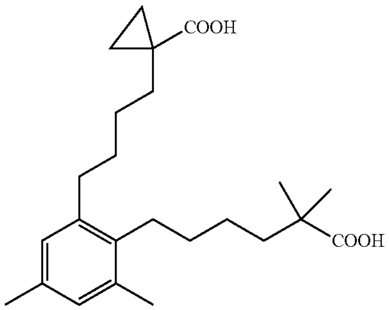 [SMILES: Cc1cc(C)c(CCCCC(C)(C)C(=O)O)c(CCCCC2(C(=O)O)CC2)c1] |
| 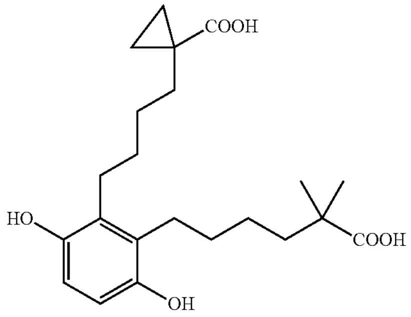 [SMILES: CC(C)(CCCCc1c(O)ccc(O)c1CCCCC1(C(=O)O)CC1)C(=O)O] | 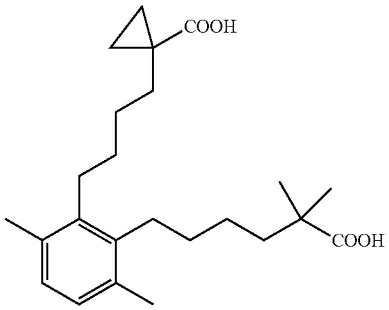 [SMILES: Cc1ccc(C)c(CCCCC2(C(=O)O)CC2)c1CCCCC(C)(C)C(=O)O] |
| 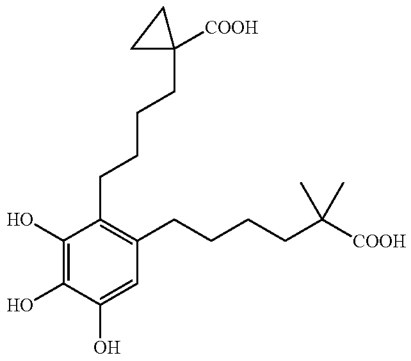 [SMILES: CC(C)(CCCCc1cc(O)c(O)c(O)c1CCCCC1(C(=O)O)CC1)C(=O)O] | 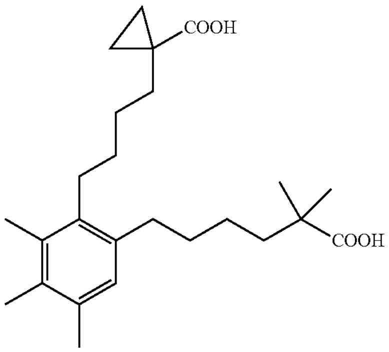 [SMILES: Cc1cc(CCCCC(C)(C)C(=O)O)c(CCCCC2(C(=O)O)CC2)c(C)c1C] |

TABLE A-12-continued
| Structure | Structure |
| --- | --- |
| 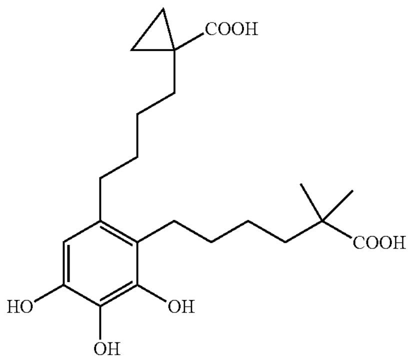 [SMILES: CC(C)(CCCCc1c(CCCCC2(C(=O)O)CC2)cc(O)c(O)c1O)C(=O)O] | 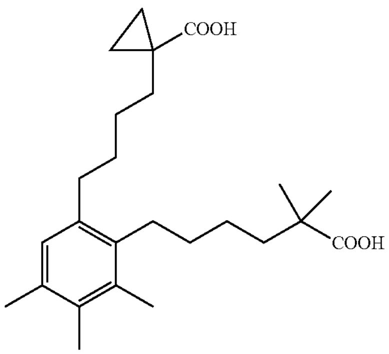 [SMILES: Cc1cc(CCCCC2(C(=O)O)CC2)c(CCCCC(C)(C)C(=O)O)c(C)c1C] |
| 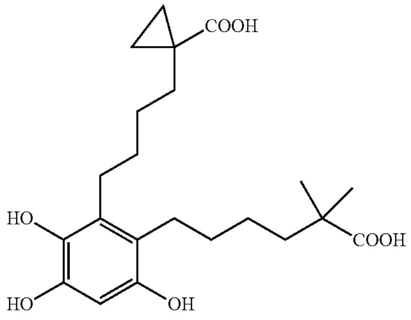 [SMILES: CC(C)(CCCCc1c(O)cc(O)c(O)c1CCCCC1(C(=O)O)CC1)C(=O)O] | 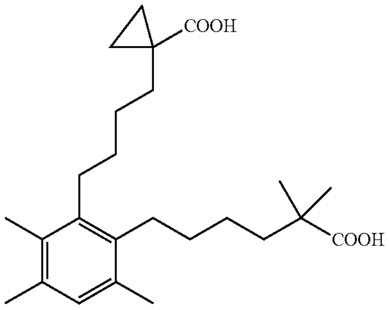 [SMILES: Cc1cc(C)c(CCCCC(C)(C)C(=O)O)c(CCCCC2(C(=O)O)CC2)c1C] |
| 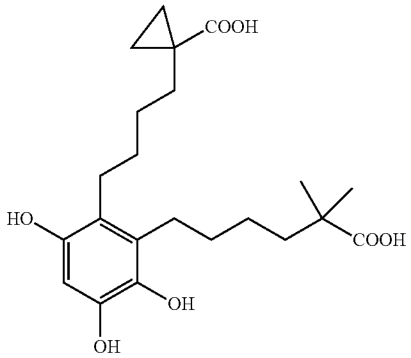 [SMILES: CC(C)(CCCCc1c(O)c(O)cc(O)c1CCCCC1(C(=O)O)CC1)C(=O)O] | 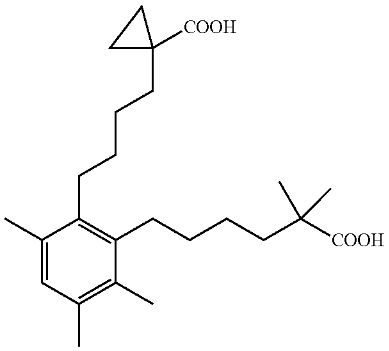 [SMILES: Cc1cc(C)c(CCCCC2(C(=O)O)CC2)c(CCCCC(C)(C)C(=O)O)c1C] |
| 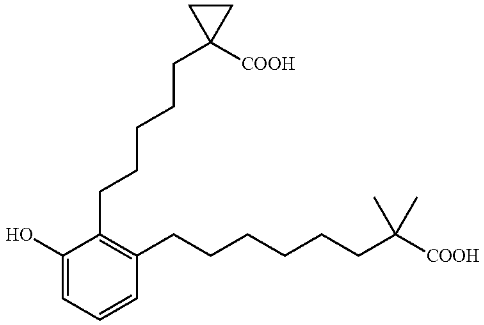 [SMILES: CC(C)(CCCCCCc1cccc(O)c1CCCCCC1(C(=O)O)CC1)C(=O)O] | 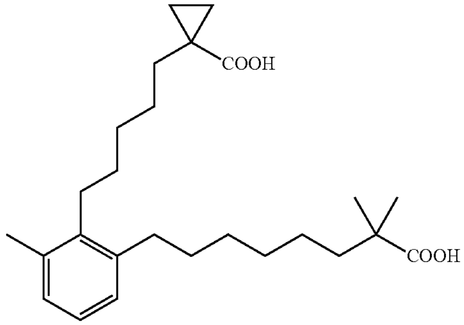 [SMILES: Cc1cccc(CCCCCCC(C)(C)C(=O)O)c1CCCCCC1(C(=O)O)CC1] |

TABLE A-12-continued
| Structure | Structure |
| --- | --- |
| 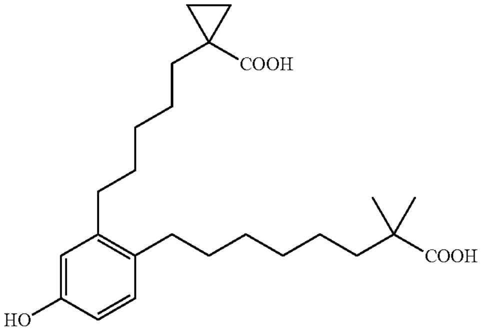 [SMILES: CC(C)(CCCCCCc1ccc(O)cc1CCCCCC1(C(=O)O)CC1)C(=O)O] | 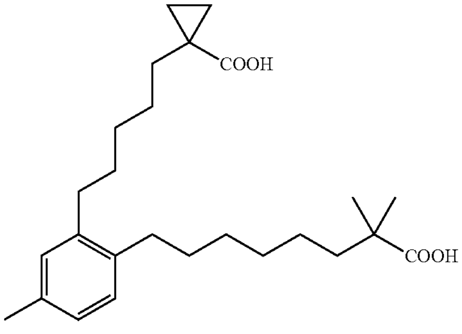 [SMILES: Cc1ccc(CCCCCCC(C)(C)C(=O)O)c(CCCCCC2(C(=O)O)CC2)c1] |
| 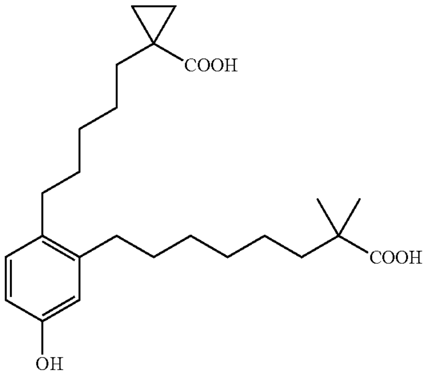 [SMILES: CC(C)(CCCCCCc1cc(O)ccc1CCCCCC1(C(=O)O)CC1)C(=O)O] | 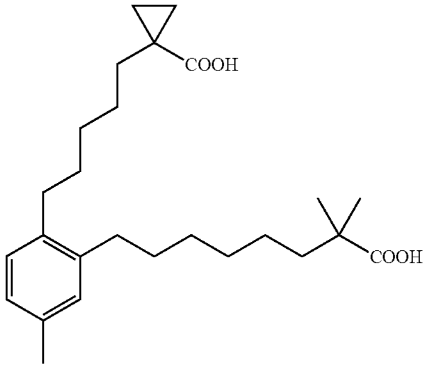 [SMILES: Cc1ccc(CCCCCC2(C(=O)O)CC2)c(CCCCCCC(C)(C)C(=O)O)c1] |
| 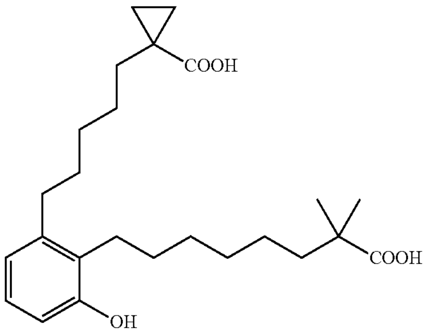 [SMILES: CC(C)(CCCCCCc1c(O)cccc1CCCCCC1(C(=O)O)CC1)C(=O)O] | 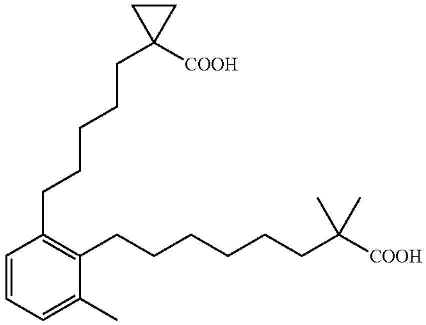 [SMILES: Cc1cccc(CCCCCC2(C(=O)O)CC2)c1CCCCCCC(C)(C)C(=O)O] |
| 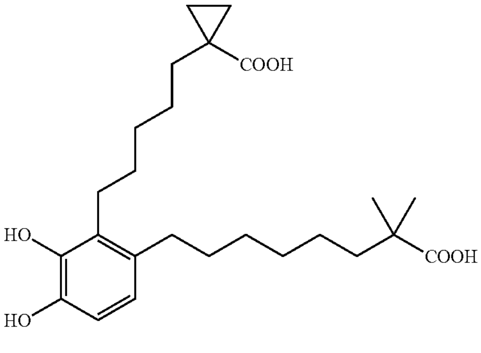 [SMILES: CC(C)(CCCCCCc1ccc(O)c(O)c1CCCCCC1(C(=O)O)CC1)C(=O)O] | 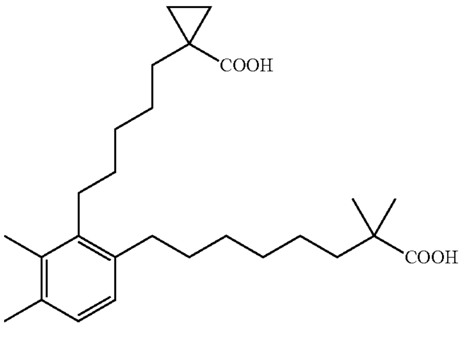 [SMILES: Cc1ccc(CCCCCCC(C)(C)C(=O)O)c(CCCCCC2(C(=O)O)CC2)c1C] |

TABLE A-12-continued
| Structure | Structure |
|---|---|
| 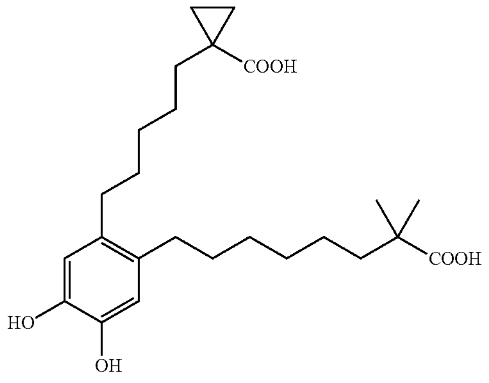 [SMILES: CC(C)(CCCCCCc1cc(O)c(O)cc1CCCCCC1(C(=O)O)CC1)C(=O)O] | 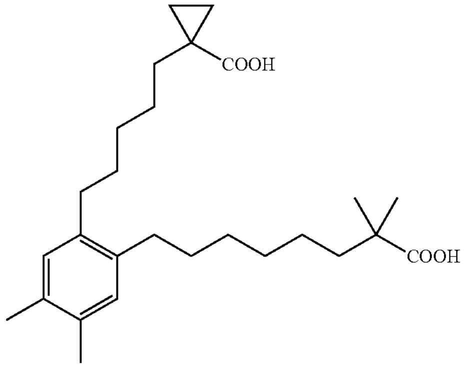 [SMILES: Cc1cc(CCCCCCC(C)(C)C(=O)O)c(CCCCCC2(C(=O)O)CC2)cc1C] |
| 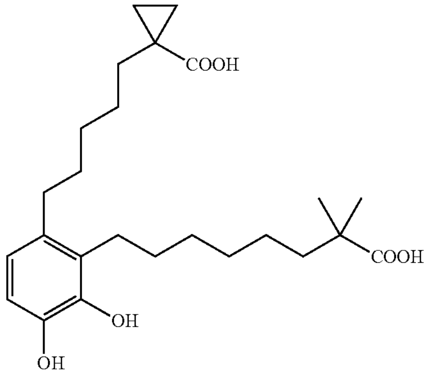 [SMILES: CC(C)(CCCCCCc1c(CCCCCC2(C(=O)O)CC2)ccc(O)c1O)C(=O)O] | 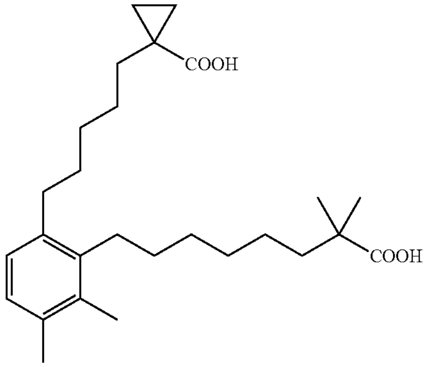 [SMILES: Cc1ccc(CCCCCC2(C(=O)O)CC2)c(CCCCCCC(C)(C)C(=O)O)c1C] |
| 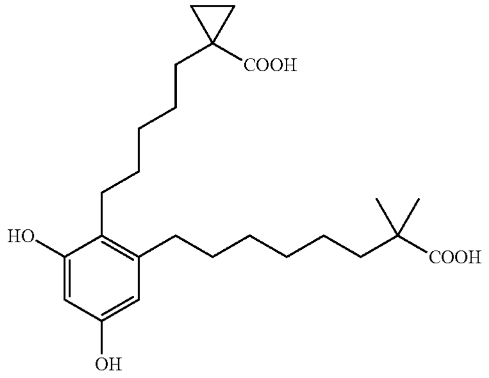 [SMILES: CC(C)(CCCCCCc1cc(O)cc(O)c1CCCCCC1(C(=O)O)CC1)C(=O)O] | 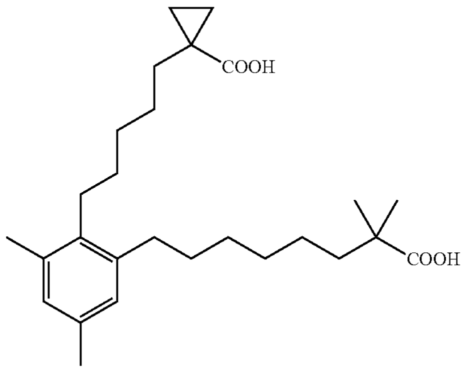 [SMILES: Cc1cc(C)c(CCCCCC2(C(=O)O)CC2)c(CCCCCCC(C)(C)C(=O)O)c1] |
| 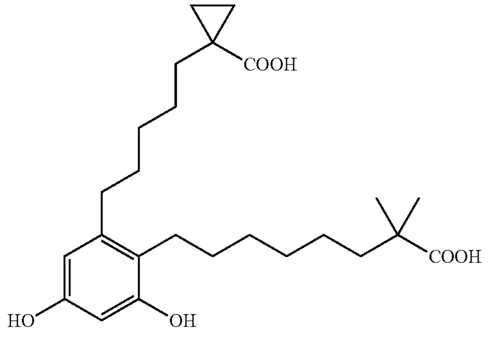 [SMILES: CC(C)(CCCCCCc1c(O)cc(O)cc1CCCCCC1(C(=O)O)CC1)C(=O)O] | 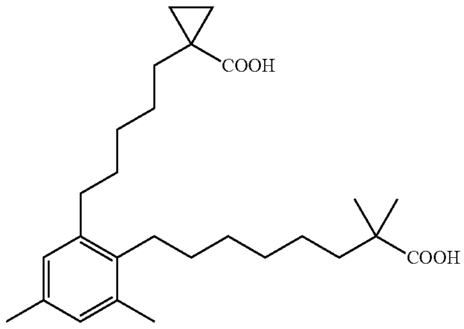 [SMILES: Cc1cc(C)c(CCCCCCC(C)(C)C(=O)O)c(CCCCCC2(C(=O)O)CC2)c1] |

TABLE A-12-continued
| Structure | Structure |
| --- | --- |
| 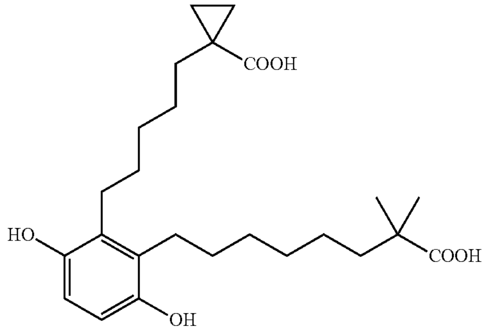 [SMILES: CC(C)(CCCCCCc1c(O)ccc(O)c1CCCCCC1(C(=O)O)CC1)C(=O)O] | 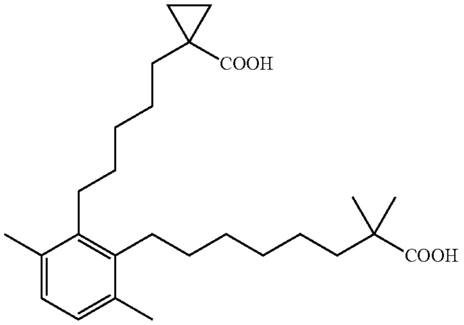 [SMILES: Cc1ccc(C)c(CCCCCC2(C(=O)O)CC2)c1CCCCCCC(C)(C)C(=O)O] |
| 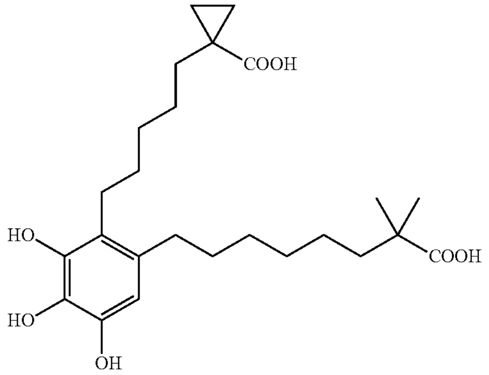 [SMILES: CC(C)(CCCCCCc1cc(O)c(O)c(O)c1CCCCCC1(C(=O)O)CC1)C(=O)O] | 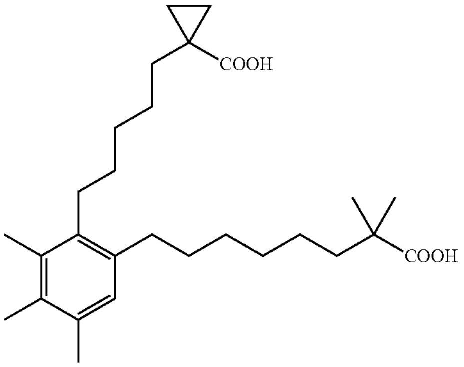 [SMILES: Cc1cc(CCCCCCC(C)(C)C(=O)O)c(CCCCCC2(C(=O)O)CC2)c(C)c1C] |
| 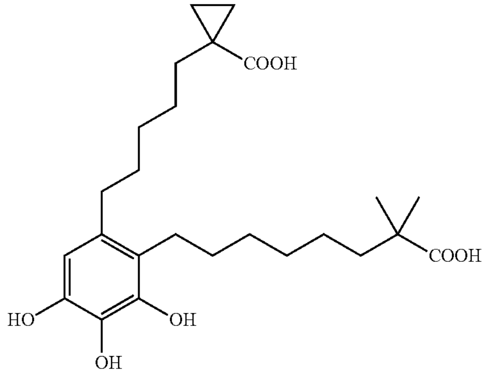 [SMILES: CC(C)(CCCCCCc1c(CCCCCC2(C(=O)O)CC2)cc(O)c(O)c1O)C(=O)O] | 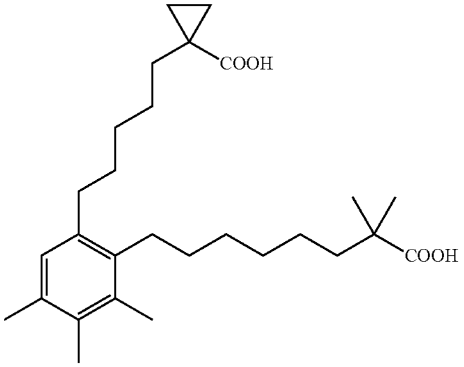 [SMILES: Cc1cc(CCCCCC2(C(=O)O)CC2)c(CCCCCCC(C)(C)C(=O)O)c(C)c1C] |
| 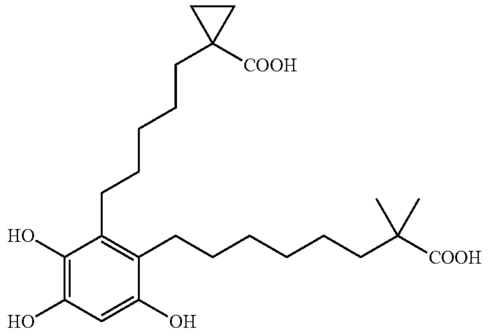 [SMILES: CC(C)(CCCCCCc1c(O)cc(O)c(O)c1CCCCCC1(C(=O)O)CC1)C(=O)O] | 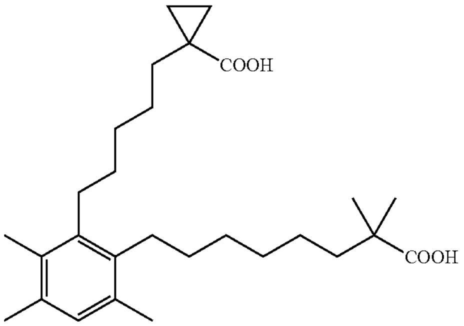 [SMILES: Cc1cc(C)c(CCCCCCC(C)(C)C(=O)O)c(CCCCCC2(C(=O)O)CC2)c1C] |

TABLE A-12-continued
| Structure | Structure |
|---|---|
| 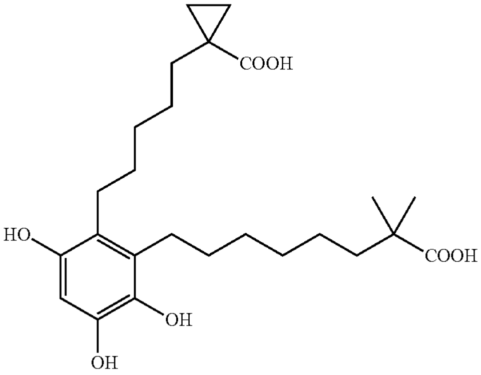 [SMILES: CC(C)(CCCCCCc1c(O)c(O)cc(O)c1CCCCCC1(C(=O)O)CC1)C(=O)O] | 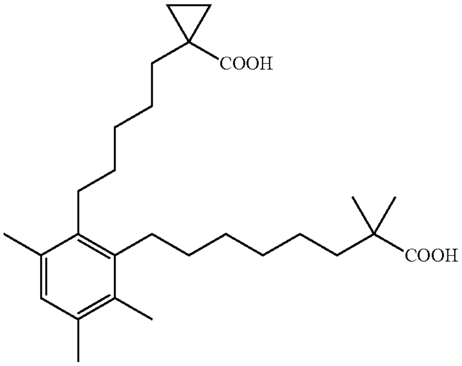 [SMILES: Cc1cc(C)c(CCCCCC2(C(=O)O)CC2)c(CCCCCCC(C)(C)C(=O)O)c1C] |
| 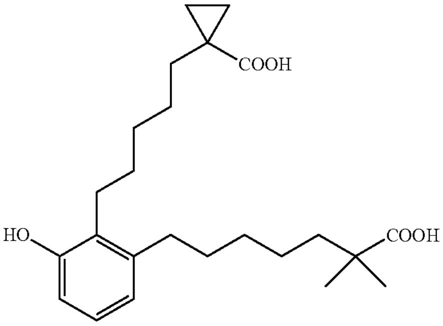 [SMILES: CC(C)(CCCCCc1cccc(O)c1CCCCCC1(C(=O)O)CC1)C(=O)O] | 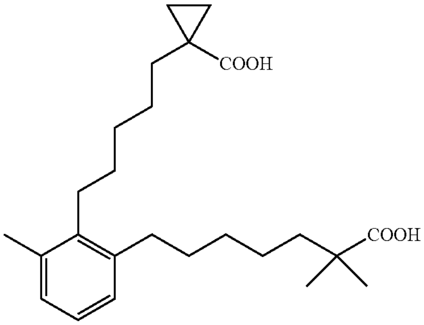 [SMILES: Cc1cccc(CCCCCC(C)(C)C(=O)O)c1CCCCCC1(C(=O)O)CC1] |
| 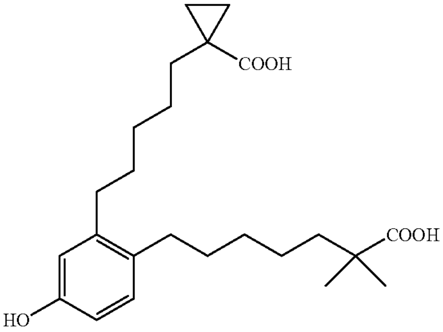 [SMILES: CC(C)(CCCCCc1ccc(O)cc1CCCCCC1(C(=O)O)CC1)C(=O)O] | 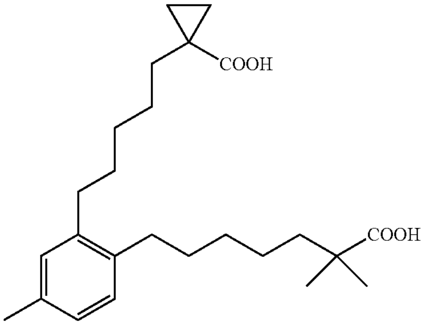 [SMILES: Cc1ccc(CCCCCC(C)(C)C(=O)O)c(CCCCCC2(C(=O)O)CC2)c1] |
| 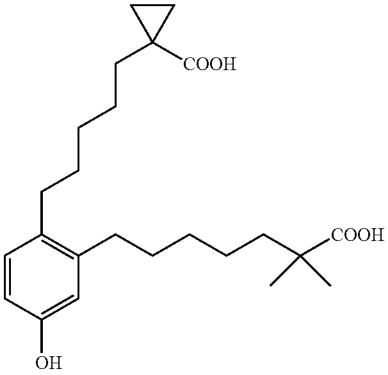 [SMILES: CC(C)(CCCCCc1cc(O)ccc1CCCCCC1(C(=O)O)CC1)C(=O)O] | 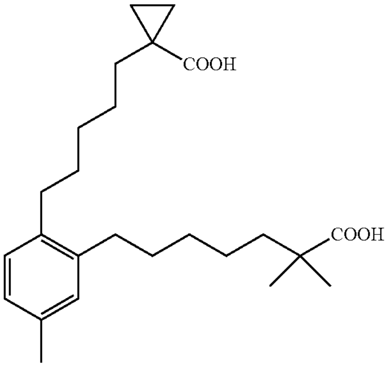 [SMILES: Cc1ccc(CCCCCC2(C(=O)O)CC2)c(CCCCCC(C)(C)C(=O)O)c1] |

TABLE A-12-continued
| Structure | Structure |
|---|---|
| 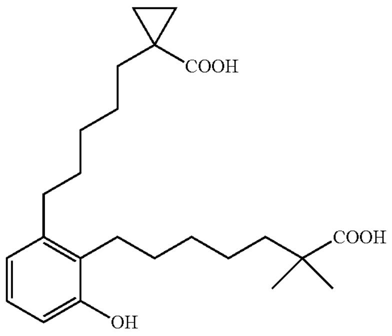 [SMILES: CC(C)(CCCCCc1c(O)cccc1CCCCCC1(C(=O)O)CC1)C(=O)O] | 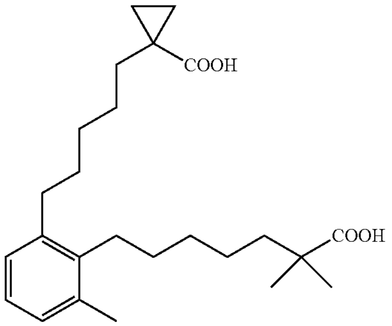 [SMILES: Cc1cccc(CCCCCC2(C(=O)O)CC2)c1CCCCCC(C)(C)C(=O)O] |
| 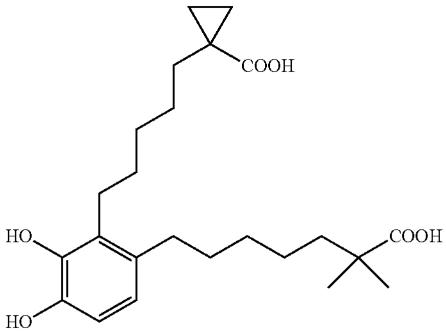 [SMILES: CC(C)(CCCCCc1ccc(O)c(O)c1CCCCCC1(C(=O)O)CC1)C(=O)O] | 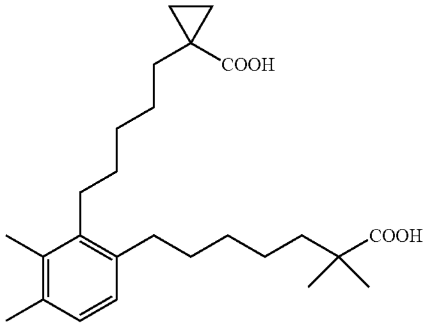 [SMILES: Cc1ccc(CCCCCC(C)(C)C(=O)O)c(CCCCCC2(C(=O)O)CC2)c1C] |
| 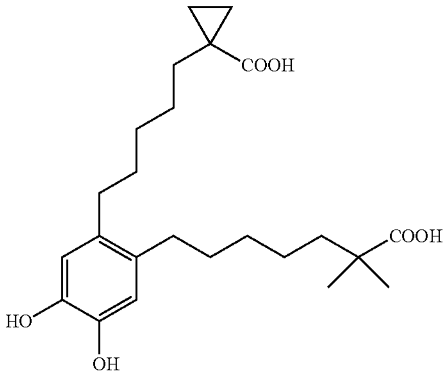 [SMILES: CC(C)(CCCCCc1cc(O)c(O)cc1CCCCCC1(C(=O)O)CC1)C(=O)O] | 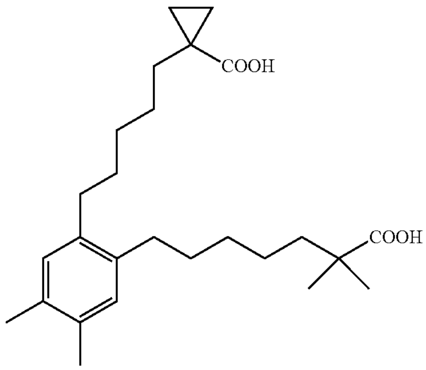 [SMILES: Cc1cc(CCCCCC(C)(C)C(=O)O)c(CCCCCC2(C(=O)O)CC2)cc1C] |
| 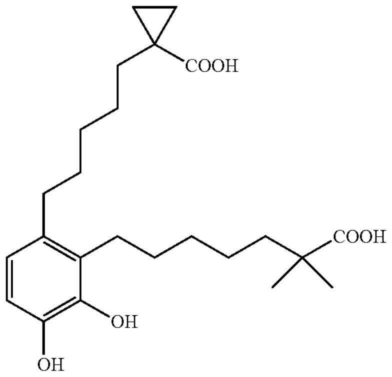 [SMILES: CC(C)(CCCCCc1c(CCCCCC2(C(=O)O)CC2)ccc(O)c1O)C(=O)O] | 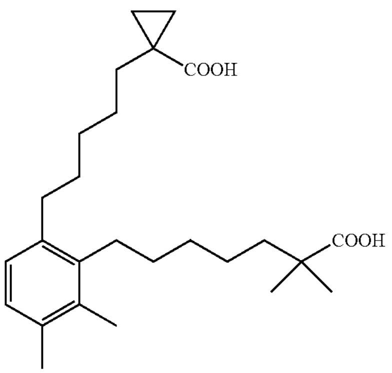 [SMILES: Cc1ccc(CCCCCC2(C(=O)O)CC2)c(CCCCCC(C)(C)C(=O)O)c1C] |

TABLE A-12-continued
| Structure | Structure |
| --- | --- |
| 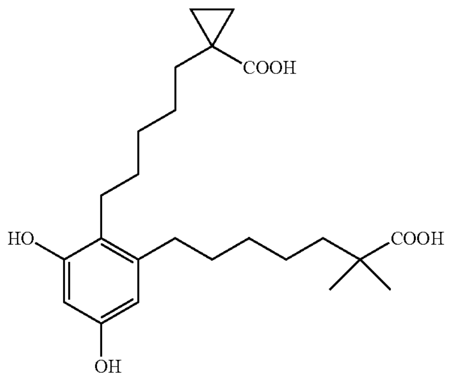 [SMILES: CC(C)(CCCCCc1cc(O)cc(O)c1CCCCCC1(C(=O)O)CC1)C(=O)O] | 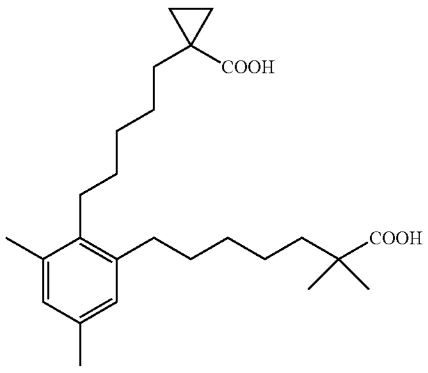 [SMILES: Cc1cc(C)c(CCCCCC2(C(=O)O)CC2)c(CCCCCC(C)(C)C(=O)O)c1] |
| 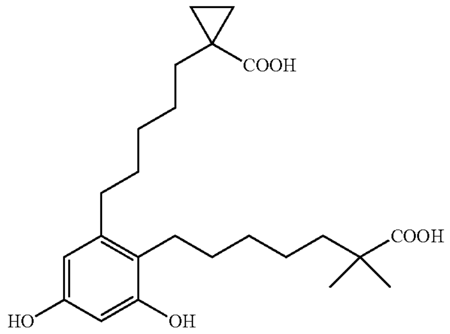 [SMILES: CC(C)(CCCCCc1c(O)cc(O)cc1CCCCCC1(C(=O)O)CC1)C(=O)O] | 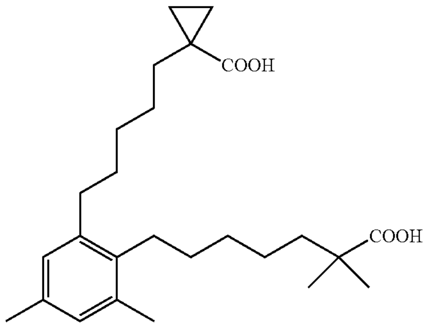 [SMILES: Cc1cc(C)c(CCCCCC(C)(C)C(=O)O)c(CCCCCC2(C(=O)O)CC2)c1] |
| 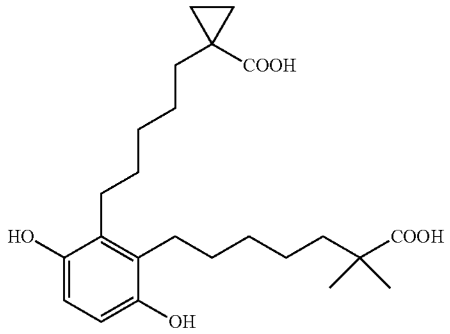 [SMILES: CC(C)(CCCCCc1c(O)ccc(O)c1CCCCCC1(C(=O)O)CC1)C(=O)O] | 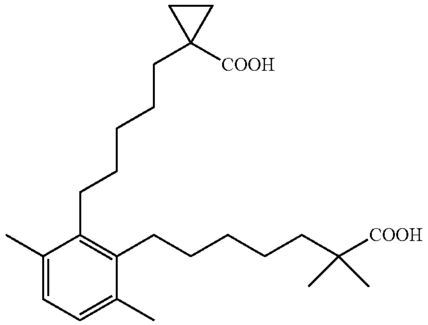 [SMILES: Cc1ccc(C)c(CCCCCC2(C(=O)O)CC2)c1CCCCCC(C)(C)C(=O)O] |
| 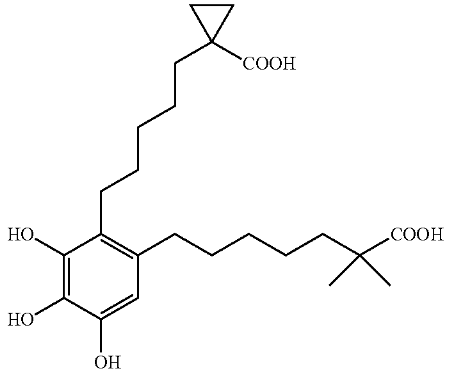 [SMILES: CC(C)(CCCCCc1cc(O)c(O)c(O)c1CCCCCC1(C(=O)O)CC1)C(=O)O] | 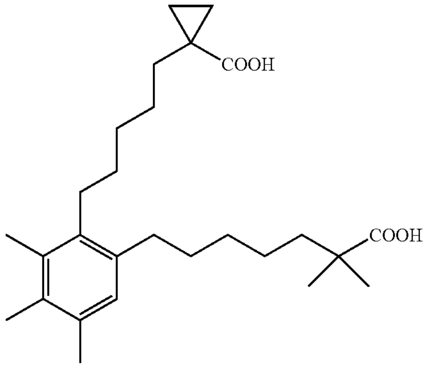 [SMILES: Cc1cc(CCCCCC(C)(C)C(=O)O)c(CCCCCC2(C(=O)O)CC2)c(C)c1C] |

TABLE A-12-continued
| Structure | Structure |
| --- | --- |
| 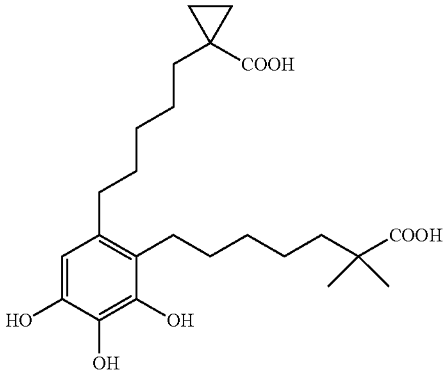 [SMILES: CC(C)(CCCCCc1c(CCCCCC2(C(=O)O)CC2)cc(O)c(O)c1O)C(=O)O] | 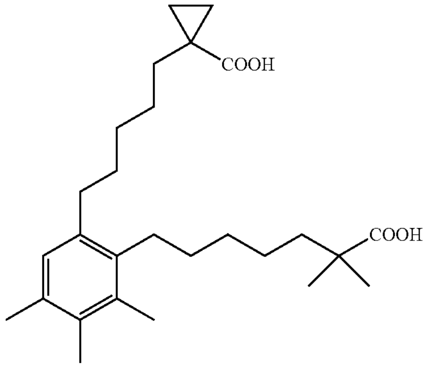 [SMILES: Cc1cc(CCCCCC2(C(=O)O)CC2)c(CCCCCC(C)(C)C(=O)O)c(C)c1C] |
| 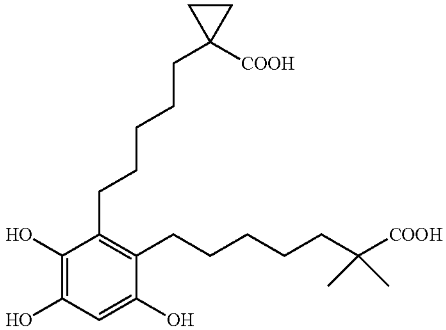 [SMILES: CC(C)(CCCCCc1c(O)cc(O)c(O)c1CCCCCC1(C(=O)O)CC1)C(=O)O] | 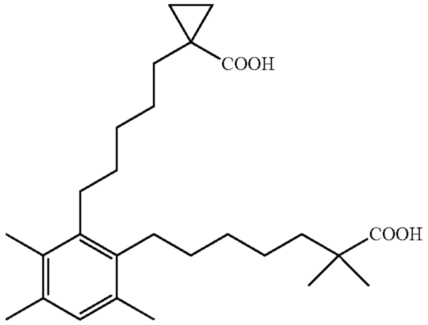 [SMILES: Cc1cc(C)c(CCCCCC(C)(C)C(=O)O)c(CCCCCC2(C(=O)O)CC2)c1C] |
| 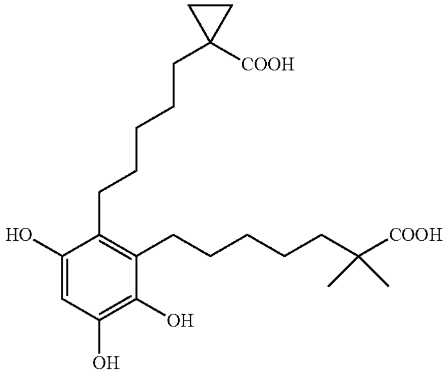 [SMILES: CC(C)(CCCCCc1c(O)c(O)cc(O)c1CCCCCC1(C(=O)O)CC1)C(=O)O] | 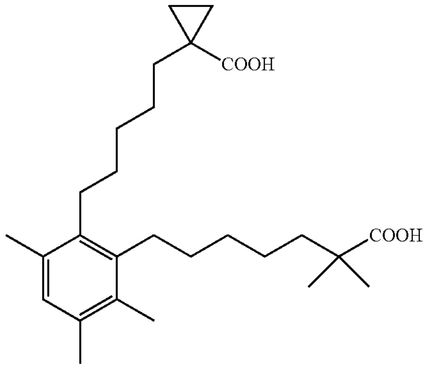 [SMILES: Cc1cc(C)c(CCCCCC2(C(=O)O)CC2)c(CCCCCC(C)(C)C(=O)O)c1C] |
| 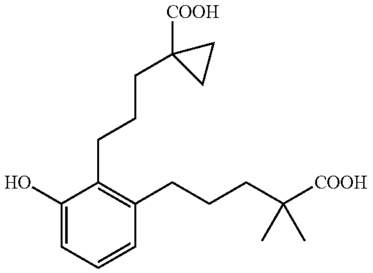 [SMILES: CC(C)(CCCc1cccc(O)c1CCCC1(C(=O)O)CC1)C(=O)O] | 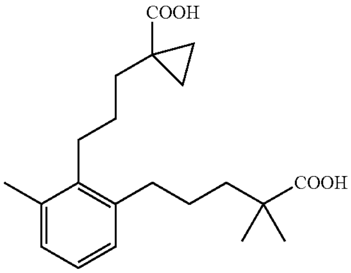 [SMILES: Cc1cccc(CCCC(C)(C)C(=O)O)c1CCCC1(C(=O)O)CC1] |

TABLE A-12-continued
| Structure | Structure |
|---|---|
| 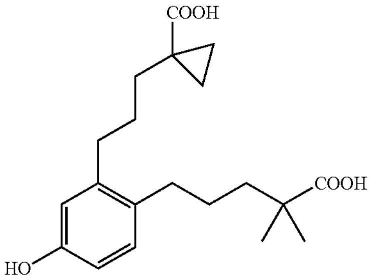 [SMILES: CC(C)(CCCc1ccc(O)cc1CCCC1(C(=O)O)CC1)C(=O)O] | 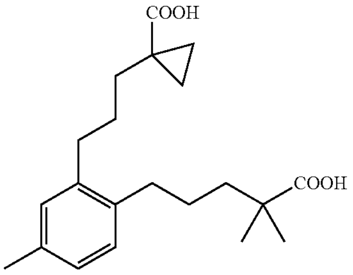 [SMILES: Cc1ccc(CCCC(C)(C)C(=O)O)c(CCCC2(C(=O)O)CC2)c1] |
| 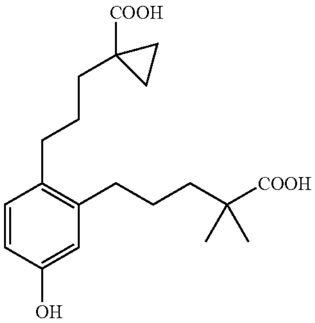 [SMILES: CC(C)(CCCc1cc(O)ccc1CCCC1(C(=O)O)CC1)C(=O)O] | 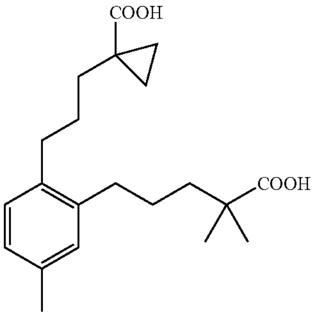 [SMILES: Cc1ccc(CCCC2(C(=O)O)CC2)c(CCCC(C)(C)C(=O)O)c1] |
| 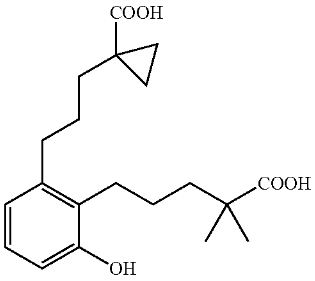 [SMILES: CC(C)(CCCc1c(O)cccc1CCCC1(C(=O)O)CC1)C(=O)O] | 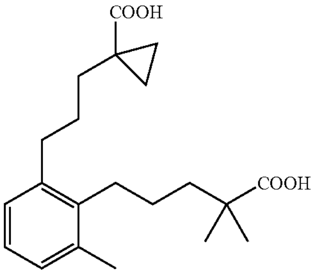 [SMILES: Cc1cccc(CCCC2(C(=O)O)CC2)c1CCCC(C)(C)C(=O)O] |
| 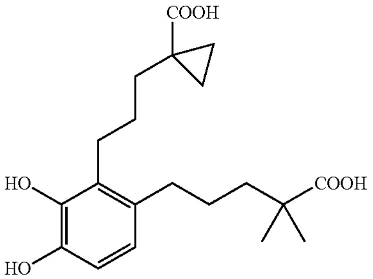 [SMILES: CC(C)(CCCc1ccc(O)c(O)c1CCCC1(C(=O)O)CC1)C(=O)O] | 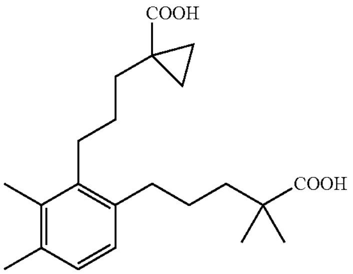 [SMILES: Cc1ccc(CCCC(C)(C)C(=O)O)c(CCCC2(C(=O)O)CC2)c1C] |
| 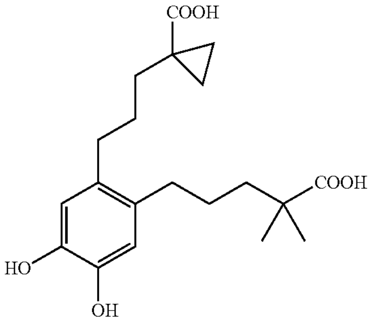 [SMILES: CC(C)(CCCc1cc(O)c(O)cc1CCCC1(C(=O)O)CC1)C(=O)O] | 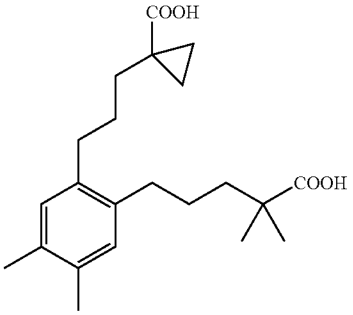 [SMILES: Cc1cc(CCCC(C)(C)C(=O)O)c(CCCC2(C(=O)O)CC2)cc1C] |

TABLE A-12-continued
| Structure | Structure |
|---|---|
| 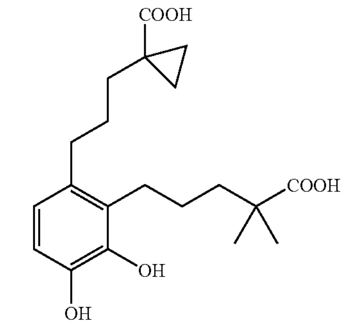 [SMILES: CC(C)(CCCc1c(CCCC2(C(=O)O)CC2)ccc(O)c1O)C(=O)O] | 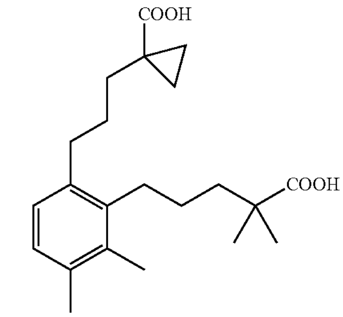 [SMILES: Cc1ccc(CCCC2(C(=O)O)CC2)c(CCCC(C)(C)C(=O)O)c1C] |
| 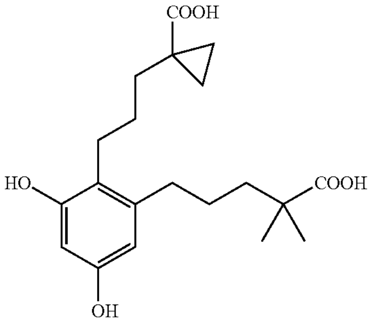 [SMILES: CC(C)(CCCc1cc(O)cc(O)c1CCCC1(C(=O)O)CC1)C(=O)O] | 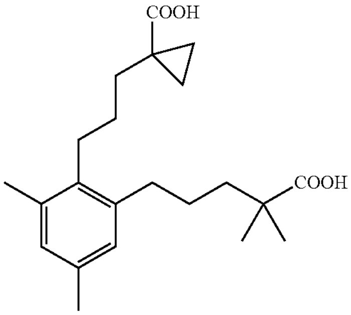 [SMILES: Cc1cc(C)c(CCCC2(C(=O)O)CC2)c(CCCC(C)(C)C(=O)O)c1] |
| 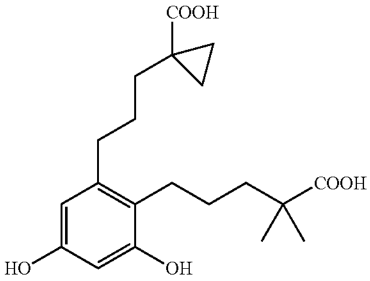 [SMILES: CC(C)(CCCc1c(O)cc(O)cc1CCCC1(C(=O)O)CC1)C(=O)O] | 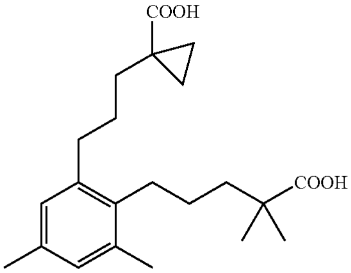 [SMILES: Cc1cc(C)c(CCCC(C)(C)C(=O)O)c(CCCC2(C(=O)O)CC2)c1] |
| 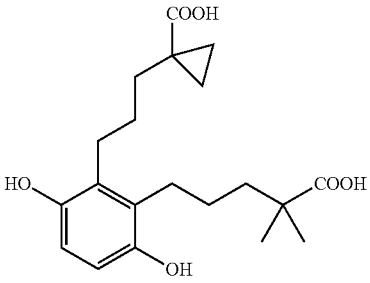 [SMILES: CC(C)(CCCc1c(O)ccc(O)c1CCCC1(C(=O)O)CC1)C(=O)O] | 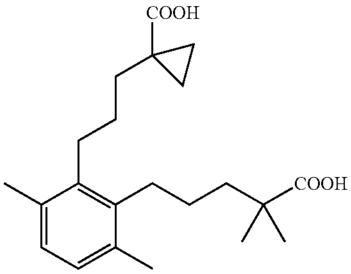 [SMILES: Cc1ccc(C)c(CCCC2(C(=O)O)CC2)c1CCCC(C)(C)C(=O)O] |
| 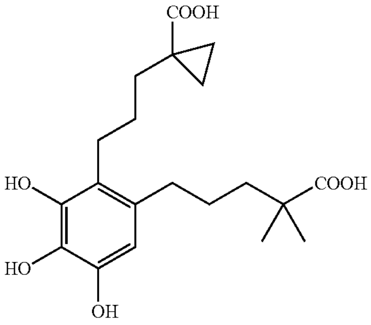 [SMILES: CC(C)(CCCc1cc(O)c(O)c(O)c1CCCC1(C(=O)O)CC1)C(=O)O] | 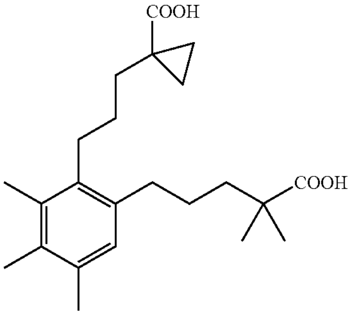 [SMILES: Cc1cc(CCCC(C)(C)C(=O)O)c(CCCC2(C(=O)O)CC2)c(C)c1C] |

TABLE A-12-continued
| Structure | Structure |
|---|---|
| 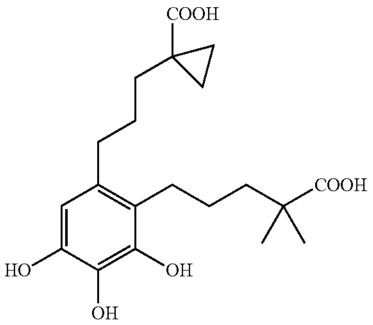 [SMILES: CC(C)(CCCc1c(CCCC2(C(=O)O)CC2)cc(O)c(O)c1O)C(=O)O] | 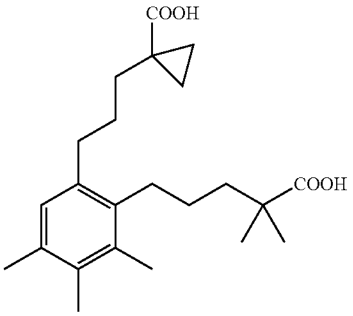 [SMILES: Cc1cc(CCCC2(C(=O)O)CC2)c(CCCC(C)(C)C(=O)O)c(C)c1C] |
| 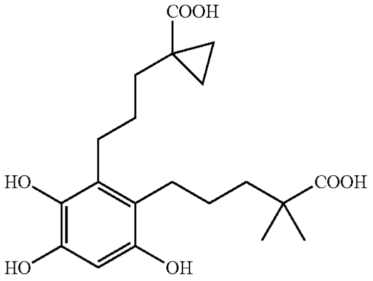 [SMILES: CC(C)(CCCc1c(O)cc(O)c(O)c1CCCC1(C(=O)O)CC1)C(=O)O] | 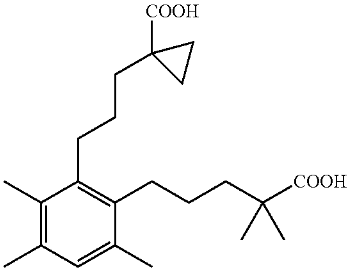 [SMILES: Cc1cc(C)c(CCCC(C)(C)C(=O)O)c(CCCC2(C(=O)O)CC2)c1C] |
| 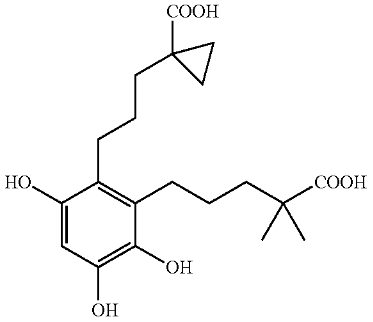 [SMILES: CC(C)(CCCc1c(O)c(O)cc(O)c1CCCC1(C(=O)O)CC1)C(=O)O] | 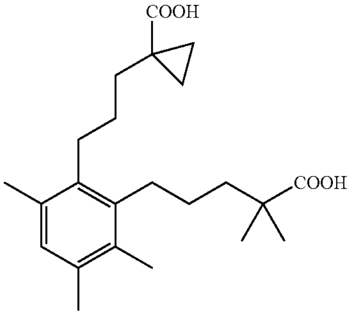 [SMILES: Cc1cc(C)c(CCCC2(C(=O)O)CC2)c(CCCC(C)(C)C(=O)O)c1C] |
| 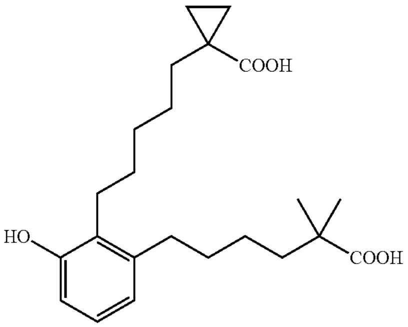 [SMILES: CC(C)(CCCCc1cccc(O)c1CCCCCC1(C(=O)O)CC1)C(=O)O] | 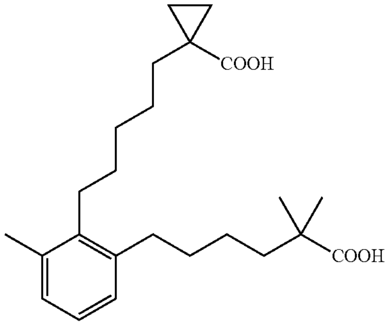 [SMILES: Cc1cccc(CCCCC(C)(C)C(=O)O)c1CCCCCC1(C(=O)O)CC1] |
| 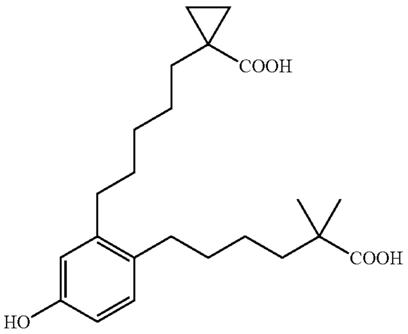 [SMILES: CC(C)(CCCCc1ccc(O)cc1CCCCCC1(C(=O)O)CC1)C(=O)O] | 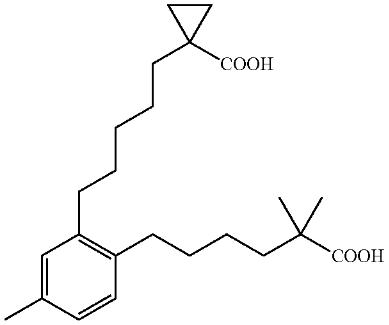 [SMILES: Cc1ccc(CCCCC(C)(C)C(=O)O)c(CCCCCC2(C(=O)O)CC2)c1] |

TABLE A-12-continued
| Structure | Structure |
|---|---|
| 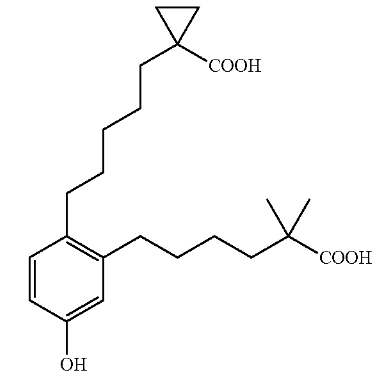 [SMILES: CC(C)(CCCCc1cc(O)ccc1CCCCCC1(C(=O)O)CC1)C(=O)O] | 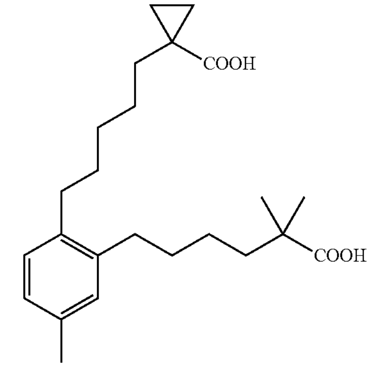 [SMILES: Cc1ccc(CCCCCC2(C(=O)O)CC2)c(CCCCC(C)(C)C(=O)O)c1] |
| 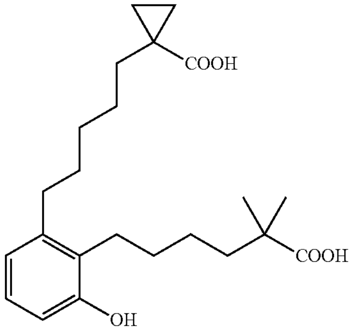 [SMILES: CC(C)(CCCCc1c(O)cccc1CCCCCC1(C(=O)O)CC1)C(=O)O] | 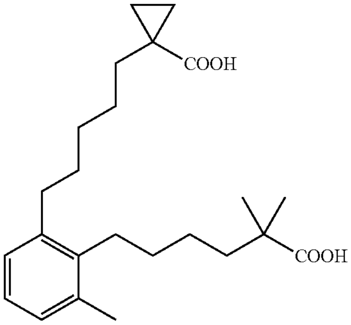 [SMILES: Cc1cccc(CCCCCC2(C(=O)O)CC2)c1CCCCC(C)(C)C(=O)O] |
| 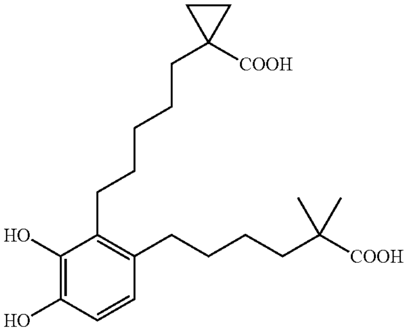 [SMILES: CC(C)(CCCCc1ccc(O)c(O)c1CCCCCC1(C(=O)O)CC1)C(=O)O] | 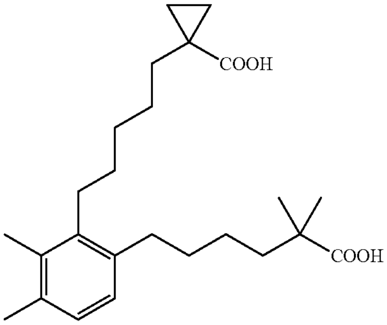 [SMILES: Cc1ccc(CCCCC(C)(C)C(=O)O)c(CCCCCC2(C(=O)O)CC2)c1C] |
| 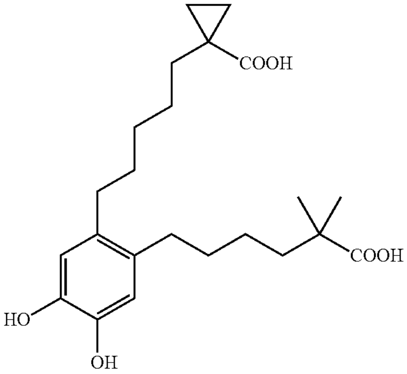 [SMILES: CC(C)(CCCCc1cc(O)c(O)cc1CCCCCC1(C(=O)O)CC1)C(=O)O] | 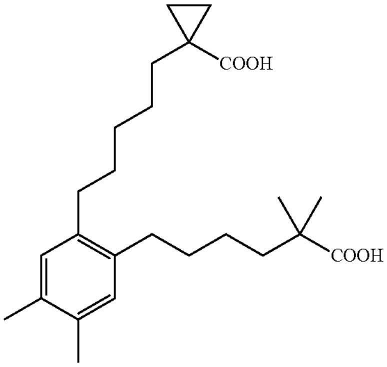 [SMILES: Cc1cc(CCCCCC2(C(=O)O)CC2)c(CCCCC(C)(C)C(=O)O)cc1C] |

TABLE A-12-continued
| Structure | Structure |
| --- | --- |
| 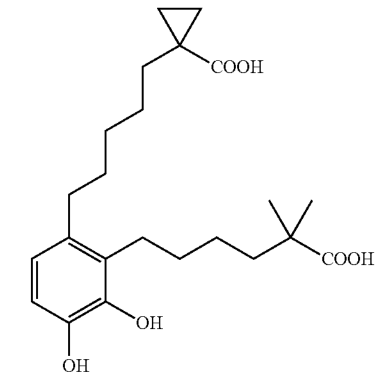 [SMILES: CC(C)(CCCCc1c(CCCCCC2(C(=O)O)CC2)ccc(O)c1O)C(=O)O] | 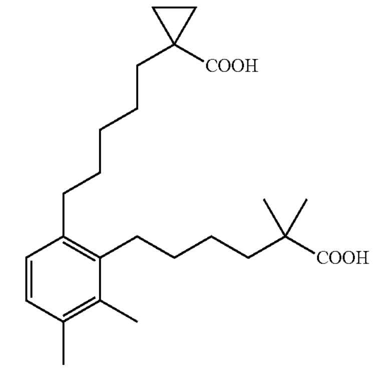 [SMILES: Cc1ccc(CCCCCC2(C(=O)O)CC2)c(CCCCC(C)(C)C(=O)O)c1C] |
| 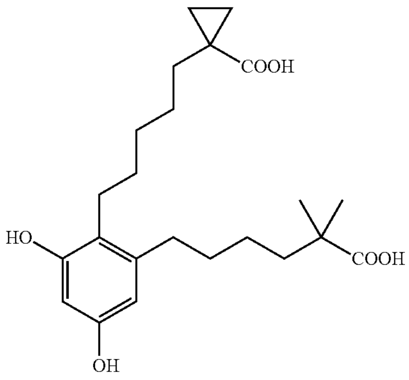 [SMILES: CC(C)(CCCCc1cc(O)cc(O)c1CCCCCC1(C(=O)O)CC1)C(=O)O] | 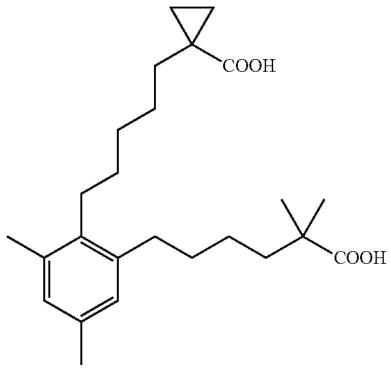 [SMILES: Cc1cc(C)c(CCCCCC2(C(=O)O)CC2)c(CCCCC(C)(C)C(=O)O)c1] |
| 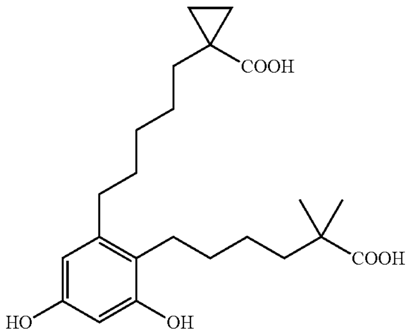 [SMILES: CC(C)(CCCCc1c(O)cc(O)cc1CCCCCC1(C(=O)O)CC1)C(=O)O] | 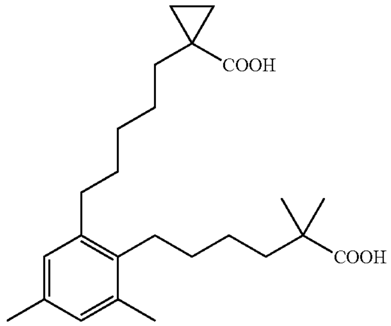 [SMILES: Cc1cc(C)c(CCCCC(C)(C)C(=O)O)c(CCCCCC2(C(=O)O)CC2)c1] |
| 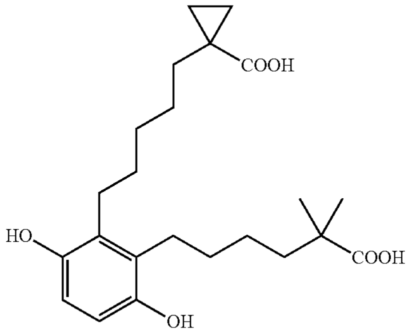 [SMILES: CC(C)(CCCCc1c(O)ccc(O)c1CCCCCC1(C(=O)O)CC1)C(=O)O] | 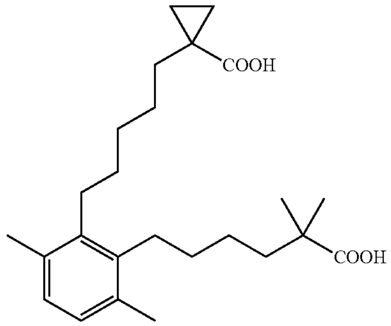 [SMILES: Cc1ccc(C)c(CCCCC(C)(C)C(=O)O)c1CCCCCC1(C(=O)O)CC1] |

TABLE A-12-continued
| Structure | Structure |
| --- | --- |
| 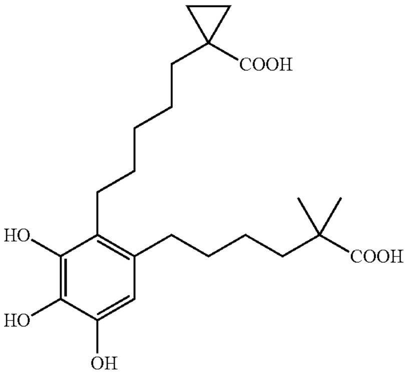 [SMILES: CC(C)(CCCCc1cc(O)c(O)c(O)c1CCCCCC1(C(=O)O)CC1)C(=O)O] | 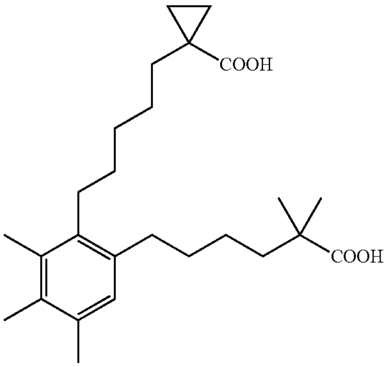 [SMILES: Cc1cc(CCCCC(C)(C)C(=O)O)c(CCCCCC2(C(=O)O)CC2)c(C)c1C] |
| 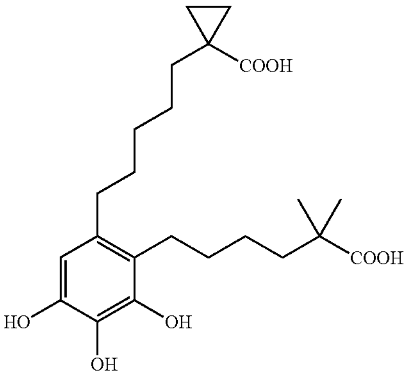 [SMILES: CC(C)(CCCCc1c(CCCCCC2(C(=O)O)CC2)cc(O)c(O)c1O)C(=O)O] | 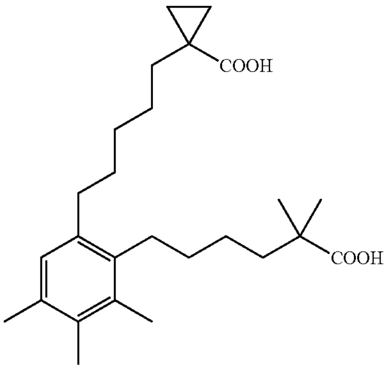 [SMILES: Cc1cc(CCCCCC2(C(=O)O)CC2)c(CCCCC(C)(C)C(=O)O)c(C)c1C] |
| 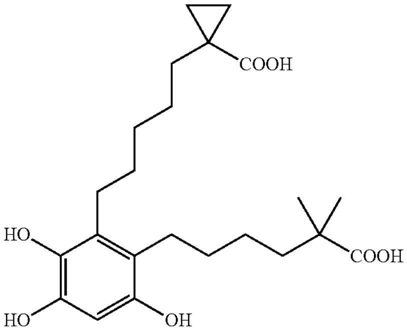 [SMILES: CC(C)(CCCCc1c(O)cc(O)c(O)c1CCCCCC1(C(=O)O)CC1)C(=O)O] | 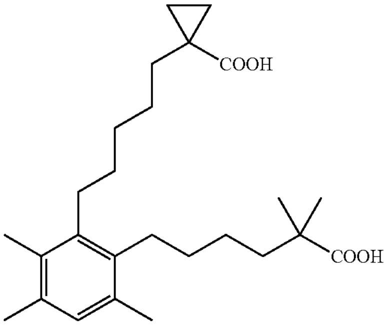 [SMILES: Cc1cc(C)c(CCCCC(C)(C)C(=O)O)c(CCCCCC2(C(=O)O)CC2)c1C] |
| 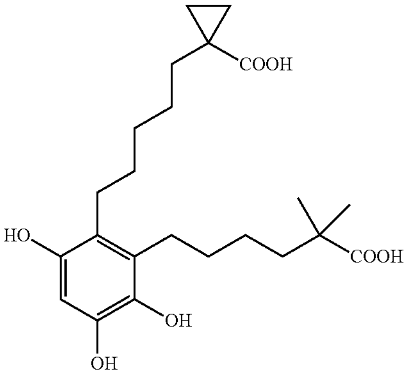 [SMILES: CC(C)(CCCCc1c(O)c(O)cc(O)c1CCCCCC1(C(=O)O)CC1)C(=O)O] | 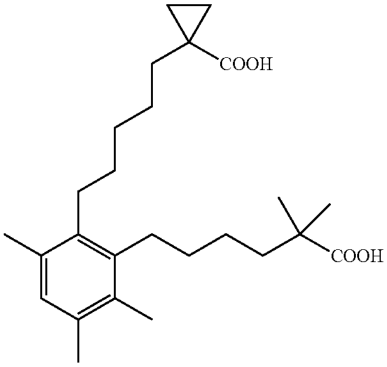 [SMILES: Cc1cc(C)c(CCCCCC2(C(=O)O)CC2)c(CCCCC(C)(C)C(=O)O)c1C] |

TABLE A-12-continued
| Structure | Structure |
|---|---|
| 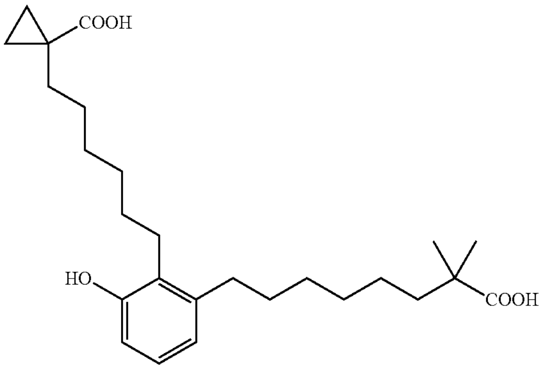 [SMILES: CC(C)(CCCCCCc1cccc(O)c1CCCCCCC1(C(=O)O)CC1)C(=O)O] | 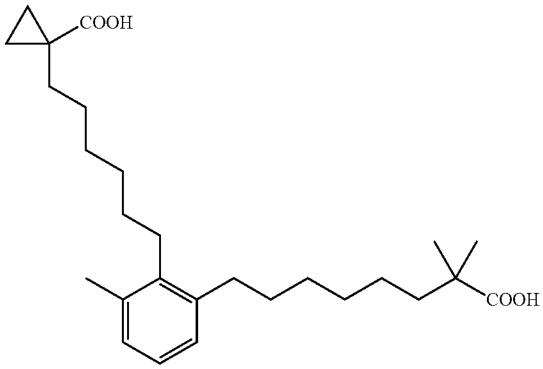 [SMILES: Cc1cccc(CCCCCCC(C)(C)C(=O)O)c1CCCCCCC1(C(=O)O)CC1] |
| 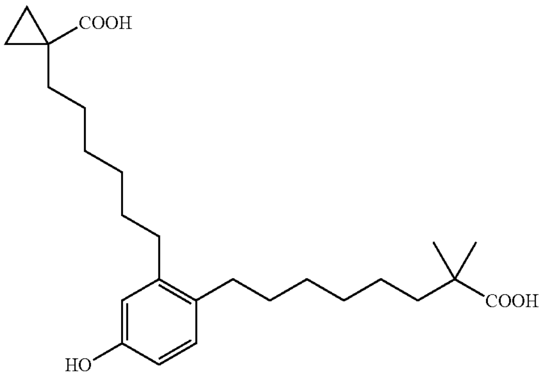 [SMILES: CC(C)(CCCCCCc1ccc(O)cc1CCCCCCC1(C(=O)O)CC1)C(=O)O] | 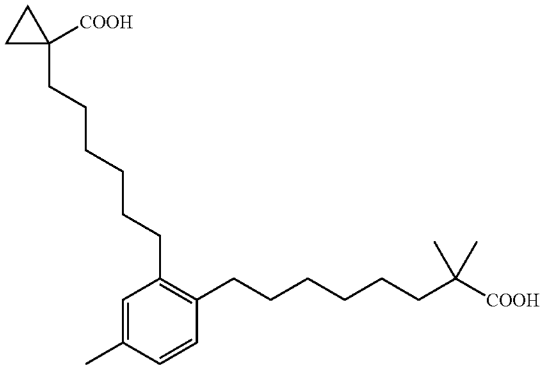 [SMILES: Cc1ccc(CCCCCCC(C)(C)C(=O)O)c(CCCCCCC2(C(=O)O)CC2)c1] |
| 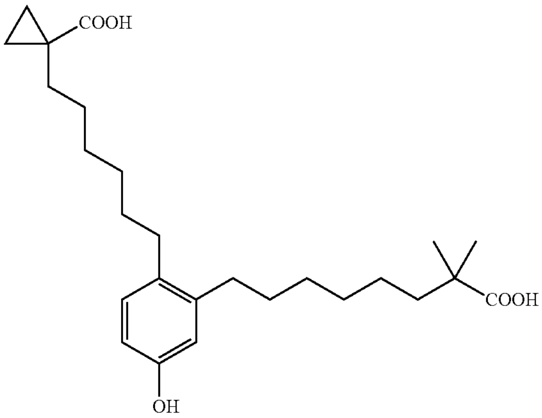 [SMILES: CC(C)(CCCCCCc1cc(O)ccc1CCCCCCC1(C(=O)O)CC1)C(=O)O] | 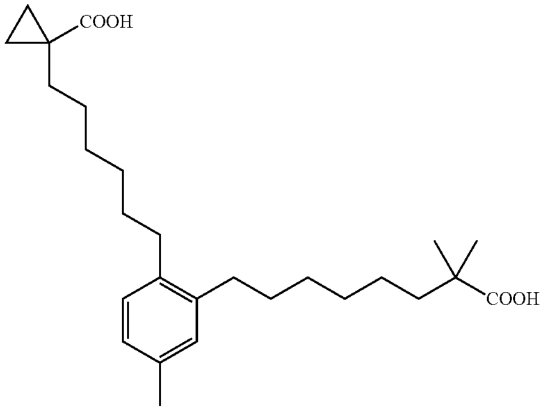 [SMILES: Cc1ccc(CCCCCCC2(C(=O)O)CC2)c(CCCCCCC(C)(C)C(=O)O)c1] |
| 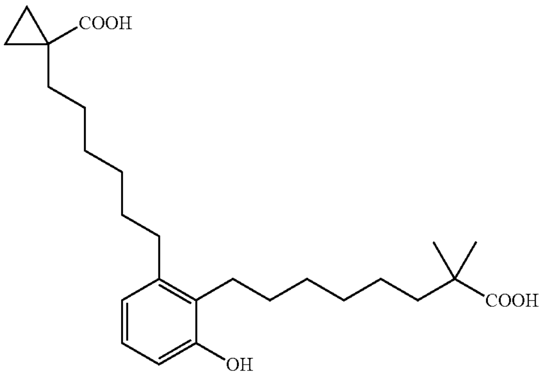 [SMILES: CC(C)(CCCCCCc1c(O)cccc1CCCCCCC1(C(=O)O)CC1)C(=O)O] | 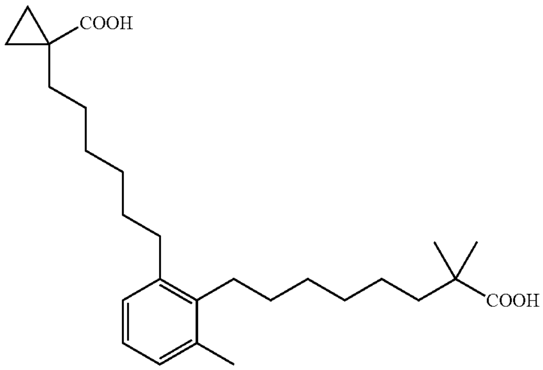 [SMILES: Cc1cccc(CCCCCCC2(C(=O)O)CC2)c1CCCCCCC(C)(C)C(=O)O] |

TABLE A-12-continued
| Structure | Structure |
|---|---|
| 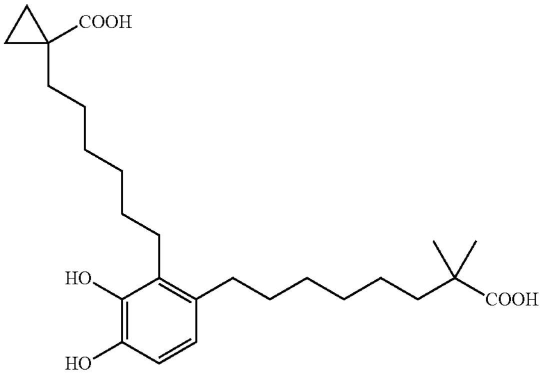 [SMILES: CC(C)(CCCCCCc1ccc(O)c(O)c1CCCCCCC1(C(=O)O)CC1)C(=O)O] | 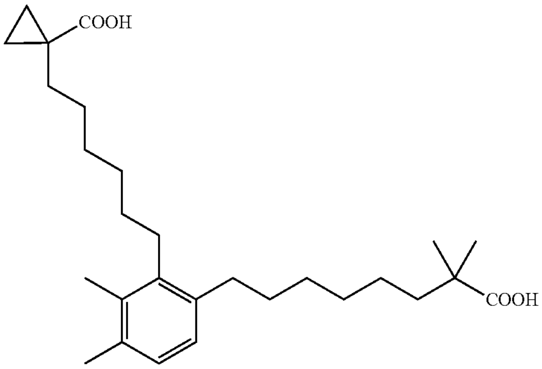 [SMILES: Cc1ccc(CCCCCCC(C)(C)C(=O)O)c(CCCCCCC2(C(=O)O)CC2)c1C] |
| 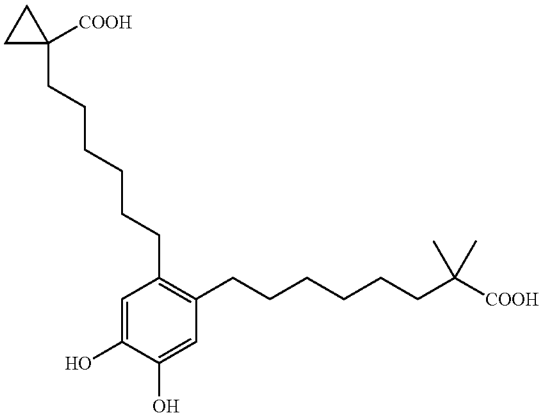 [SMILES: CC(C)(CCCCCCc1cc(O)c(O)cc1CCCCCCC1(C(=O)O)CC1)C(=O)O] | 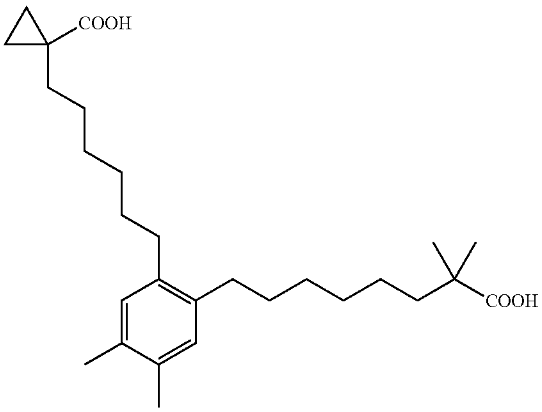 [SMILES: Cc1cc(CCCCCCC(C)(C)C(=O)O)c(CCCCCCC2(C(=O)O)CC2)cc1C] |
| 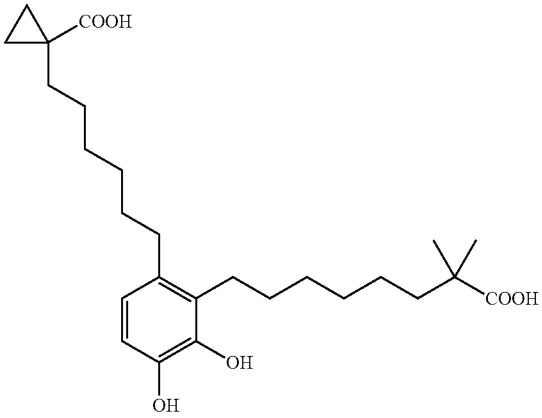 [SMILES: CC(C)(CCCCCCc1c(CCCCCCC2(C(=O)O)CC2)ccc(O)c1O)C(=O)O] | 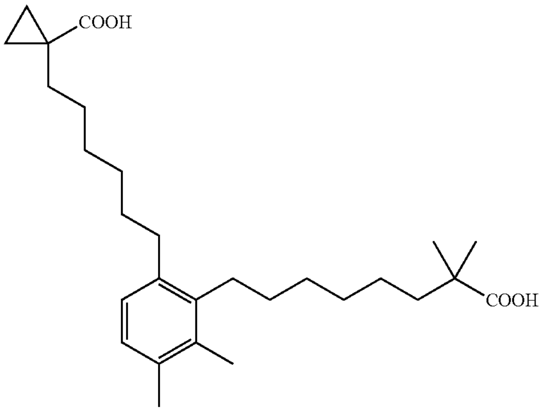 [SMILES: Cc1ccc(CCCCCCC2(C(=O)O)CC2)c(CCCCCCC(C)(C)C(=O)O)c1C] |

TABLE A-12-continued
| Structure | Structure |
|---|---|
| 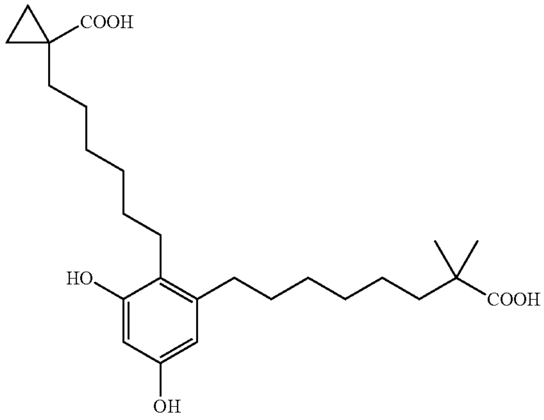 [SMILES: CC(C)(CCCCCCc1cc(O)cc(O)c1CCCCCCC1(C(=O)O)CC1)C(=O)O] | 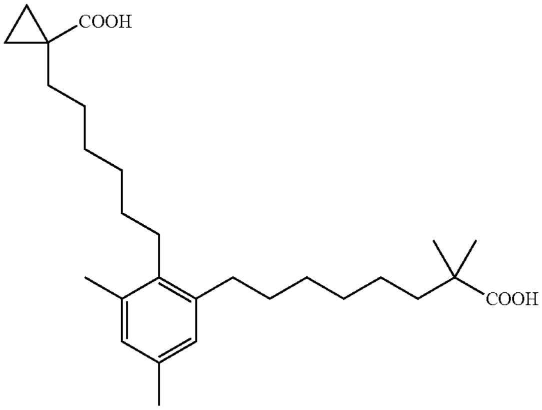 [SMILES: Cc1cc(C)c(CCCCCCC2(C(=O)O)CC2)c(CCCCCCC(C)(C)C(=O)O)c1] |
| 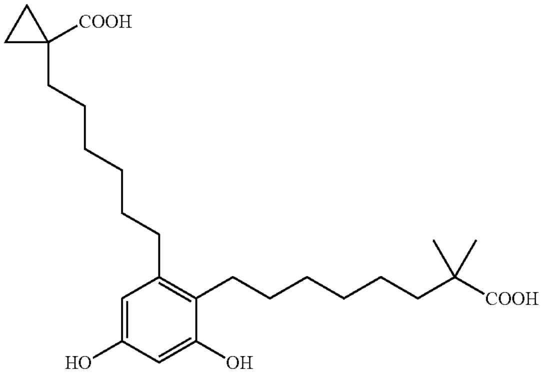 [SMILES: CC(C)(CCCCCCc1c(O)cc(O)cc1CCCCCCC1(C(=O)O)CC1)C(=O)O] | 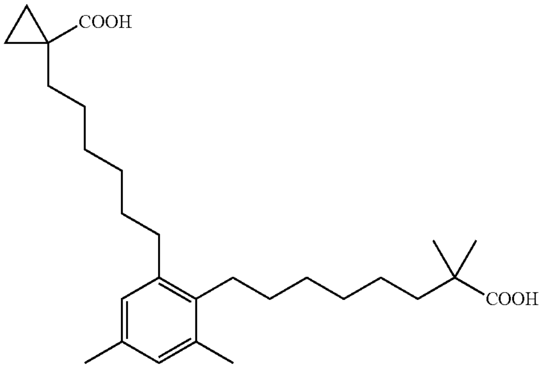 [SMILES: Cc1cc(C)c(CCCCCCC(C)(C)C(=O)O)c(CCCCCCC2(C(=O)O)CC2)c1] |
| 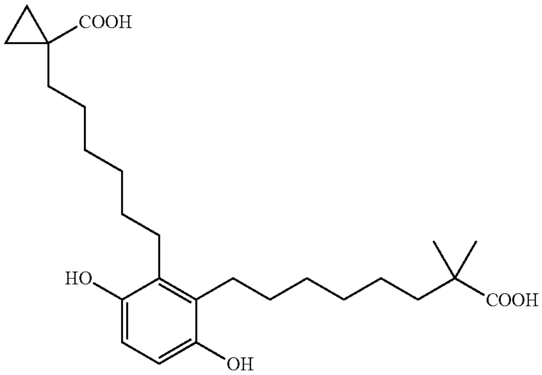 [SMILES: CC(C)(CCCCCCc1c(O)ccc(O)c1CCCCCCC1(C(=O)O)CC1)C(=O)O] | 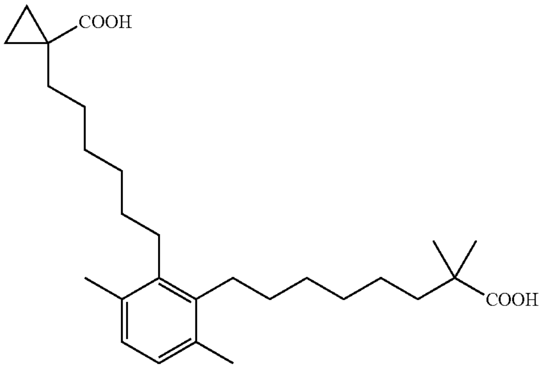 [SMILES: Cc1ccc(C)c(CCCCCCC2(C(=O)O)CC2)c1CCCCCCC(C)(C)C(=O)O] |
| 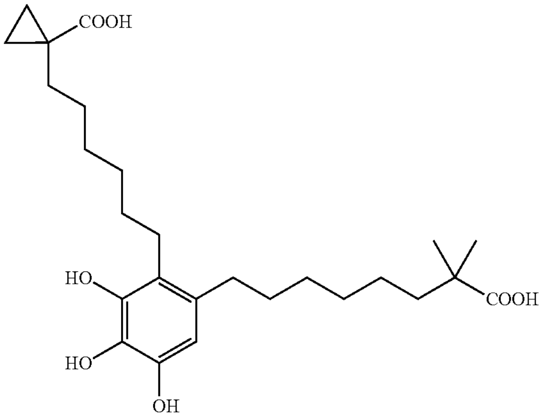 | 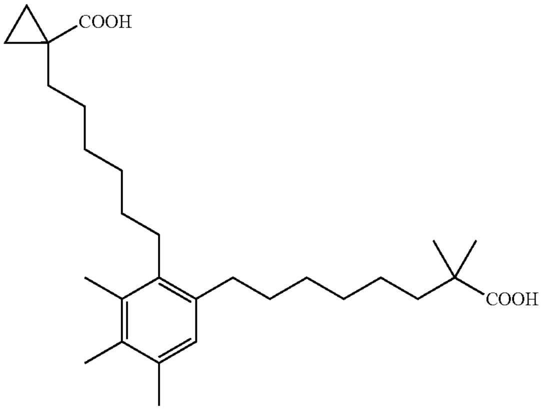 [SMILES: Cc1cc(CCCCCCC(C)(C)C(=O)O)c(CCCCCCC2(C(=O)O)CC2)c(C)c1C] |

TABLE A-12-continued
| Structure | Structure |
|---|---|
| 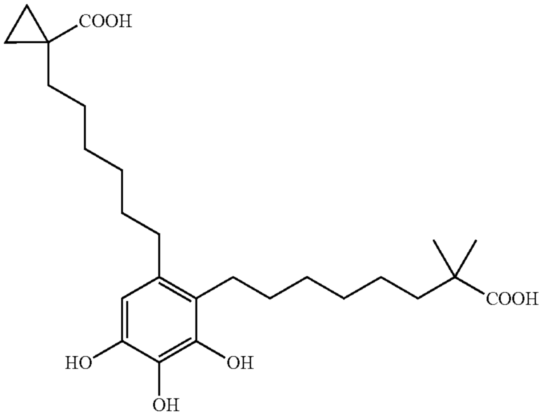 [SMILES: CC(C)(CCCCCCc1c(CCCCCCC2(C(=O)O)CC2)cc(O)c(O)c1O)C(=O)O] | 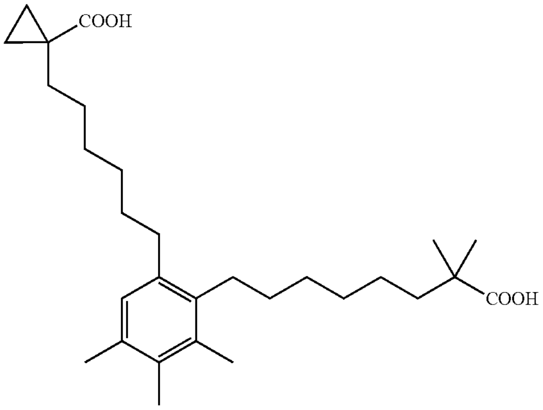 [SMILES: Cc1cc(CCCCCCC2(C(=O)O)CC2)c(CCCCCCC(C)(C)C(=O)O)c(C)c1C] |
| 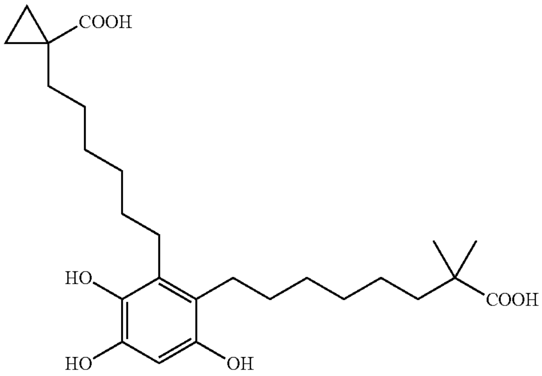 [SMILES: CC(C)(CCCCCCc1c(O)cc(O)c(O)c1CCCCCCC1(C(=O)O)CC1)C(=O)O] | 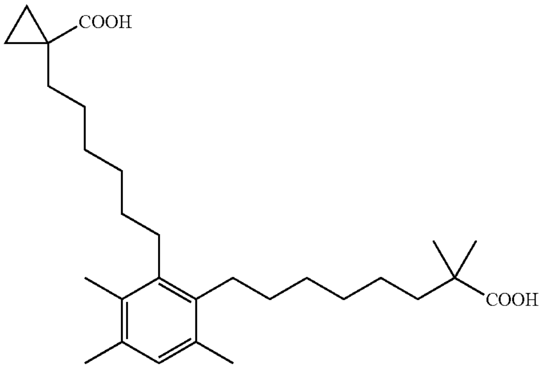 [SMILES: Cc1cc(C)c(CCCCCCC(C)(C)C(=O)O)c(CCCCCCC2(C(=O)O)CC2)c1C] |
| 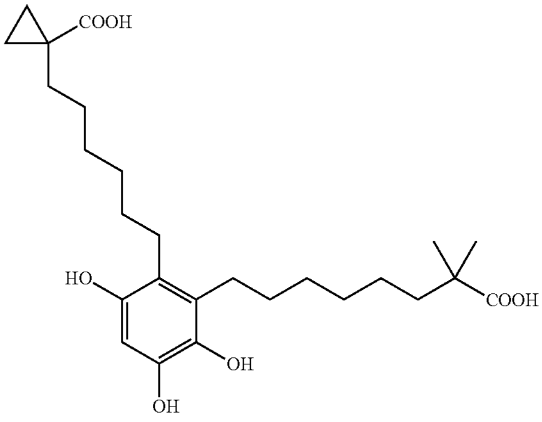 [SMILES: CC(C)(CCCCCCc1c(O)c(O)cc(O)c1CCCCCCC1(C(=O)O)CC1)C(=O)O] | 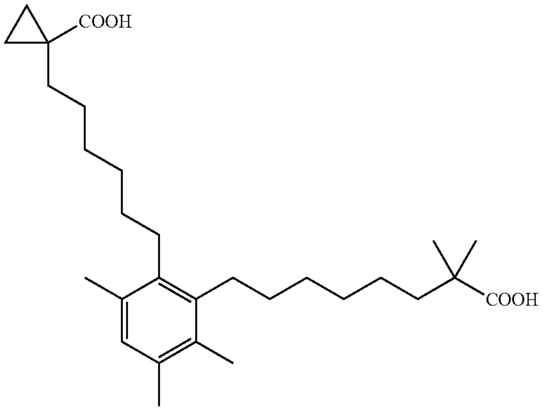 [SMILES: Cc1cc(C)c(CCCCCCC2(C(=O)O)CC2)c(CCCCCCC(C)(C)C(=O)O)c1C] |
| 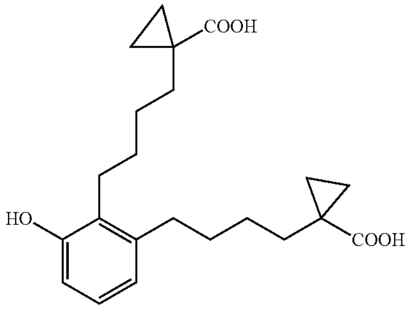 [SMILES: O=C(O)C1(CCCCc2cccc(O)c2CCCCC2(C(=O)O)CC2)CC1] | 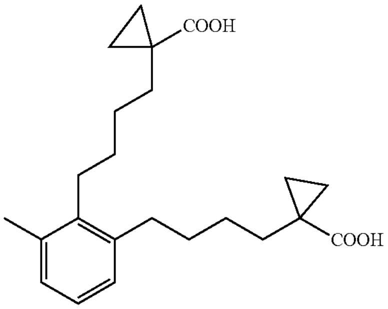 [SMILES: Cc1cccc(CCCCC2(C(=O)O)CC2)c1CCCCC1(C(=O)O)CC1] |

TABLE A-12-continued
| Structure | Structure |
|---|---|
| 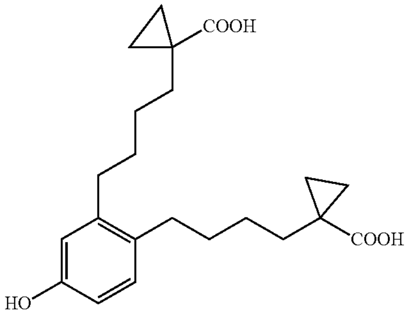 [SMILES: O=C(O)C1(CCCCc2ccc(O)cc2CCCCC2(C(=O)O)CC2)CC1] | 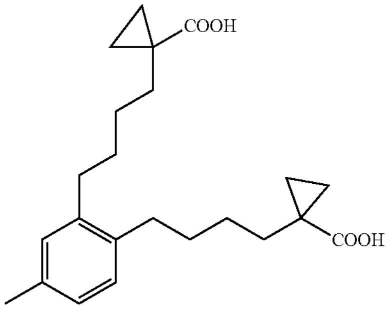 [SMILES: Cc1ccc(CCCCC2(C(=O)O)CC2)c(CCCCC2(C(=O)O)CC2)c1] |
| 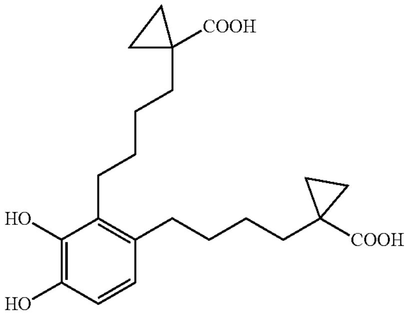 [SMILES: O=C(O)C1(CCCCc2ccc(O)c(O)c2CCCCC2(C(=O)O)CC2)CC1] | 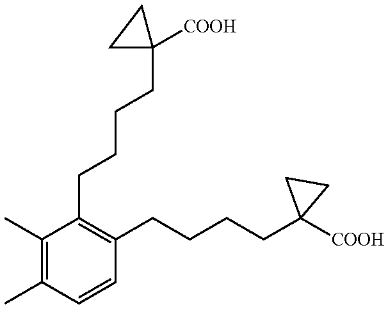 [SMILES: Cc1ccc(CCCCC2(C(=O)O)CC2)c(CCCCC2(C(=O)O)CC2)c1C] |
| 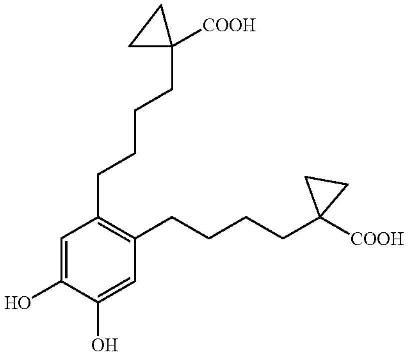 [SMILES: O=C(O)C1(CCCCc2cc(O)c(O)cc2CCCCC2(C(=O)O)CC2)CC1] | 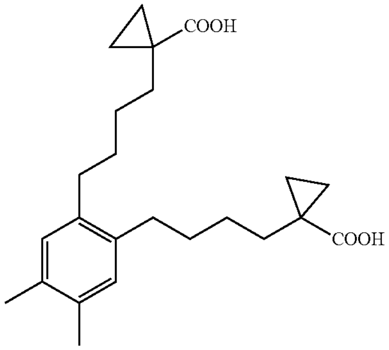 [SMILES: Cc1cc(CCCCC2(C(=O)O)CC2)c(CCCCC2(C(=O)O)CC2)cc1C] |
| 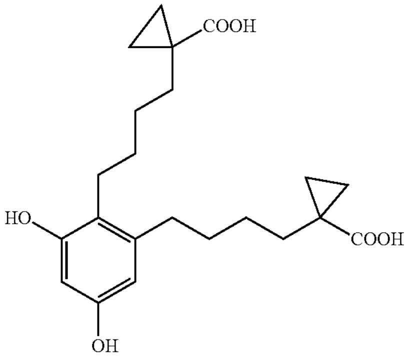 [SMILES: O=C(O)C1(CCCCc2cc(O)cc(O)c2CCCCC2(C(=O)O)CC2)CC1] | 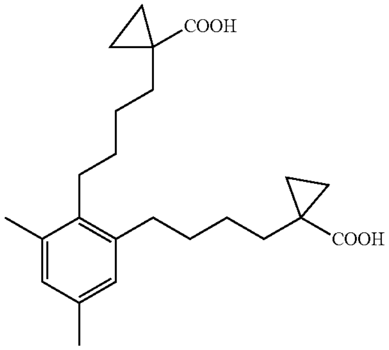 [SMILES: Cc1cc(C)c(CCCCC2(C(=O)O)CC2)c(CCCCC2(C(=O)O)CC2)c1] |

TABLE A-12-continued
| Structure | Structure |
| --- | --- |
| 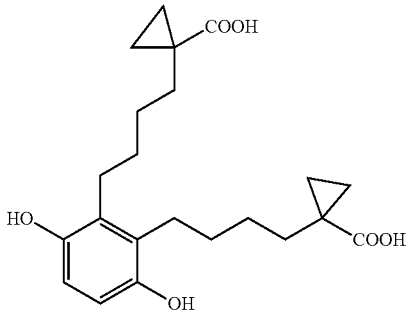 [SMILES: O=C(O)C1(CCCCc2c(O)ccc(O)c2CCCCC2(C(=O)O)CC2)CC1] | 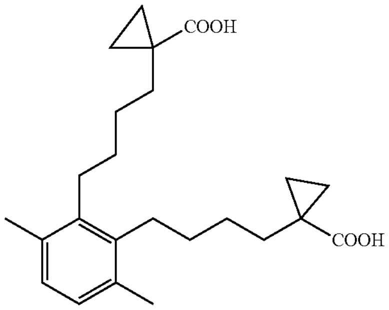 [SMILES: Cc1ccc(C)c(CCCCC2(C(=O)O)CC2)c1CCCCC1(C(=O)O)CC1] |
| 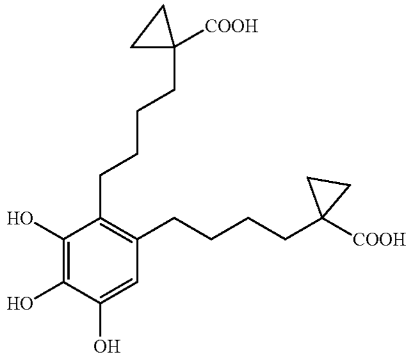 [SMILES: O=C(O)C1(CCCCc2cc(O)c(O)c(O)c2CCCCC2(C(=O)O)CC2)CC1] | 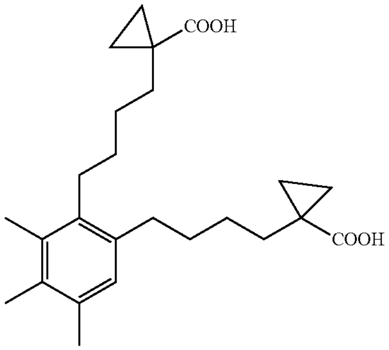 [SMILES: Cc1cc(CCCCC2(C(=O)O)CC2)c(CCCCC2(C(=O)O)CC2)c(C)c1C] |
| 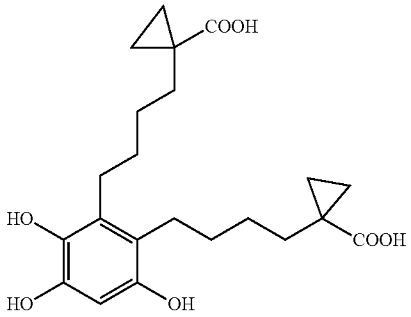 [SMILES: O=C(O)C1(CCCCc2c(O)cc(O)c(O)c2CCCCC2(C(=O)O)CC2)CC1] | 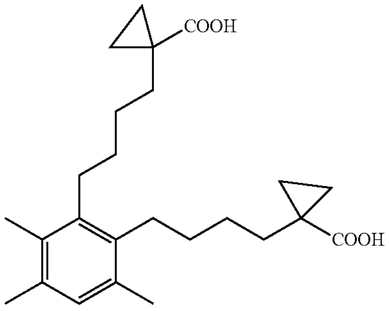 [SMILES: Cc1cc(C)c(CCCCC2(C(=O)O)CC2)c(CCCCC2(C(=O)O)CC2)c1C] |
| 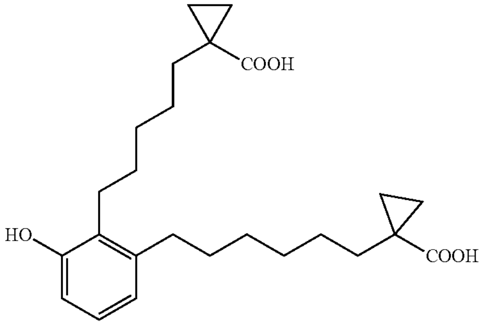 [SMILES: O=C(O)C1(CCCCCCc2cccc(O)c2CCCCCC2(C(=O)O)CC2)CC1] | 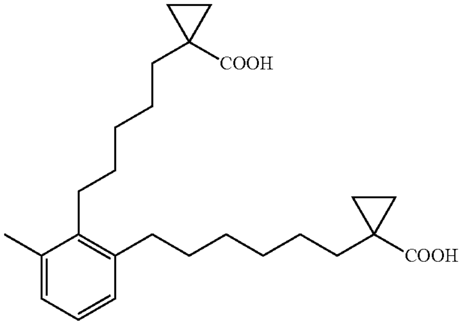 [SMILES: Cc1cccc(CCCCCCC2(C(=O)O)CC2)c1CCCCCC1(C(=O)O)CC1] |

TABLE A-12-continued
| Structure | Structure |
| --- | --- |
| 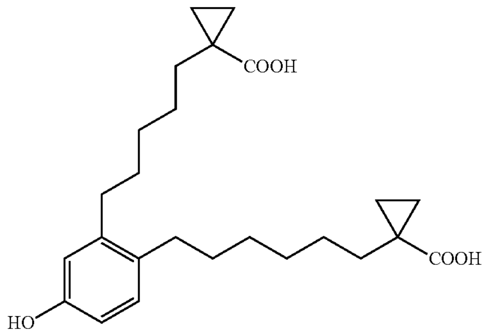 [SMILES: O=C(O)C1(CCCCCCc2ccc(O)cc2CCCCCC2(C(=O)O)CC2)CC1] | 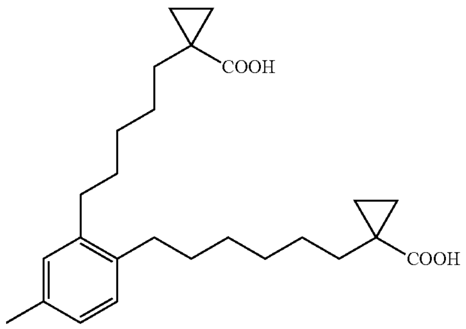 [SMILES: Cc1ccc(CCCCCCC2(C(=O)O)CC2)c(CCCCCC2(C(=O)O)CC2)c1] |
| 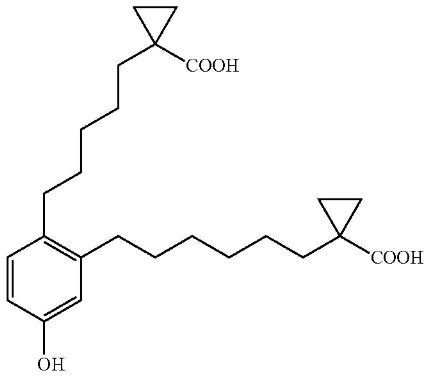 [SMILES: O=C(O)C1(CCCCCCc2cc(O)ccc2CCCCCC2(C(=O)O)CC2)CC1] | 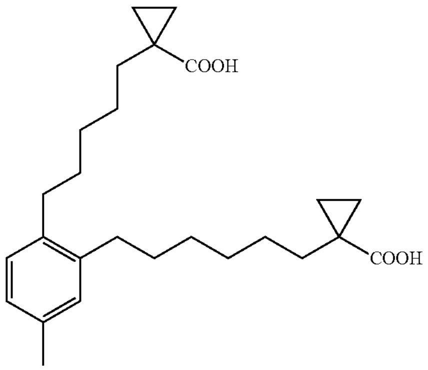 [SMILES: Cc1ccc(CCCCCC2(C(=O)O)CC2)c(CCCCCCC2(C(=O)O)CC2)c1] |
| 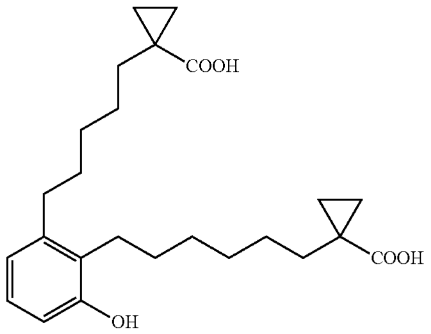 [SMILES: O=C(O)C1(CCCCCCc2c(O)cccc2CCCCCC2(C(=O)O)CC2)CC1] | 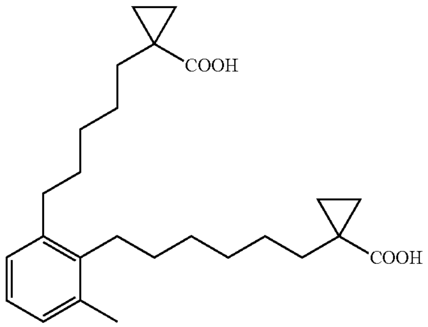 [SMILES: Cc1cccc(CCCCCC2(C(=O)O)CC2)c1CCCCCCC1(C(=O)O)CC1] |
| 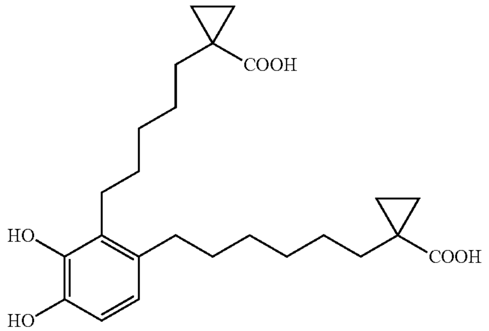 [SMILES: O=C(O)C1(CCCCCCc2ccc(O)c(O)c2CCCCCC2(C(=O)O)CC2)CC1] | 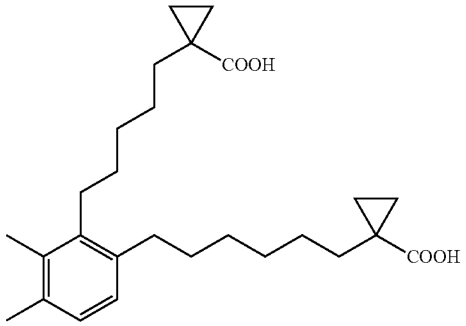 [SMILES: Cc1ccc(CCCCCCC2(C(=O)O)CC2)c(CCCCCC2(C(=O)O)CC2)c1C] |

TABLE A-12-continued
| Structure | Structure |
|---|---|
| 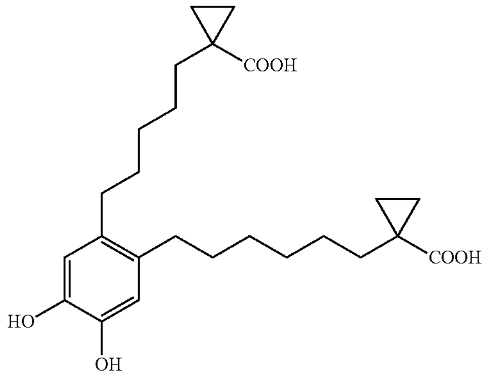 [SMILES: O=C(O)C1(CCCCCCc2cc(O)c(O)cc2CCCCCC2(C(=O)O)CC2)CC1] | 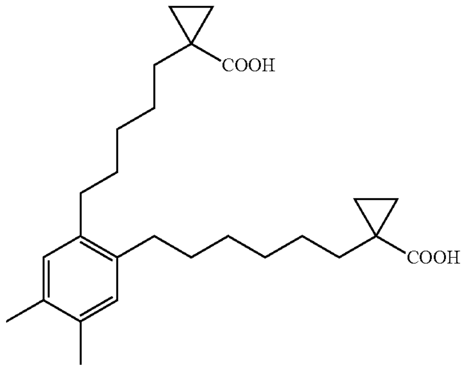 [SMILES: Cc1cc(CCCCCCC2(C(=O)O)CC2)c(CCCCCC2(C(=O)O)CC2)cc1C] |
| 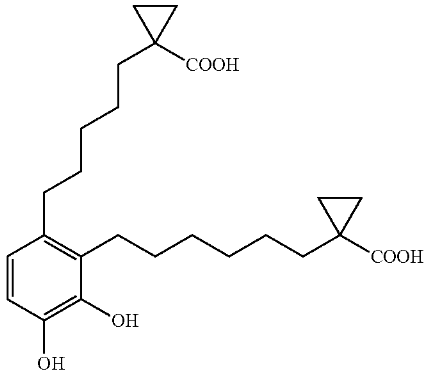 [SMILES: O=C(O)C1(CCCCCCc2c(CCCCCC3(C(=O)O)CC3)ccc(O)c2O)CC1] | 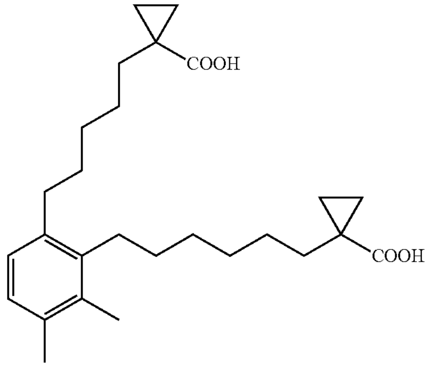 [SMILES: Cc1ccc(CCCCCC2(C(=O)O)CC2)c(CCCCCCC2(C(=O)O)CC2)c1C] |
| 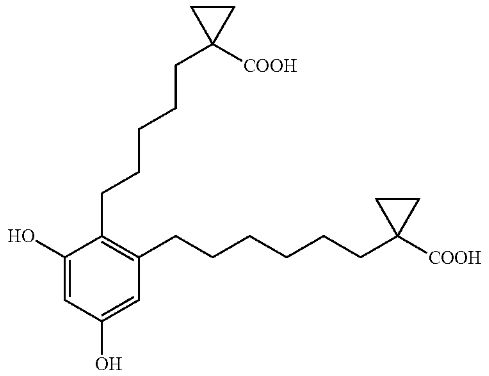 [SMILES: O=C(O)C1(CCCCCCc2cc(O)cc(O)c2CCCCCC2(C(=O)O)CC2)CC1] | 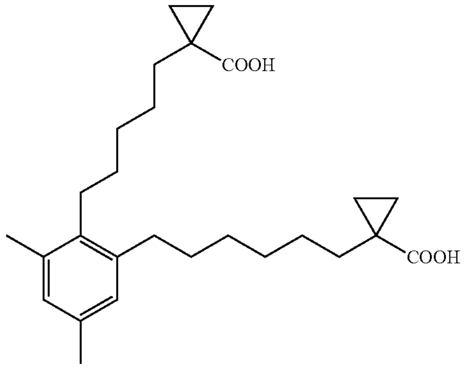 [SMILES: Cc1cc(C)c(CCCCCC2(C(=O)O)CC2)c(CCCCCCC2(C(=O)O)CC2)c1] |
| 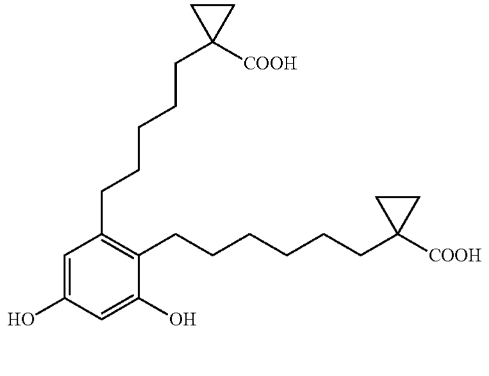 [SMILES: O=C(O)C1(CCCCCCc2c(O)cc(O)cc2CCCCCC2(C(=O)O)CC2)CC1] | 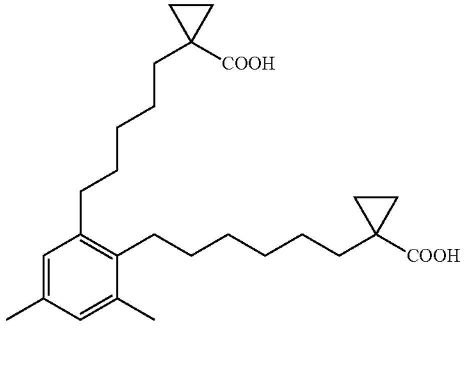 [SMILES: Cc1cc(C)c(CCCCCCC2(C(=O)O)CC2)c(CCCCCC2(C(=O)O)CC2)c1] |

TABLE A-12-continued
| Structure | Structure |
| --- | --- |
| 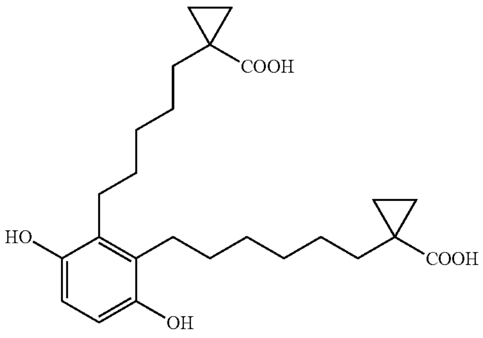 [SMILES: O=C(O)C1(CCCCCCc2c(O)ccc(O)c2CCCCCC2(C(=O)O)CC2)CC1] | 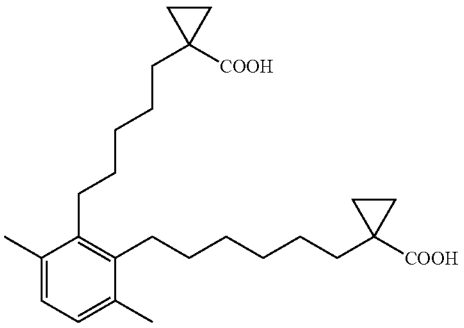 [SMILES: Cc1ccc(C)c(CCCCCC2(C(=O)O)CC2)c1CCCCCCC1(C(=O)O)CC1] |
| 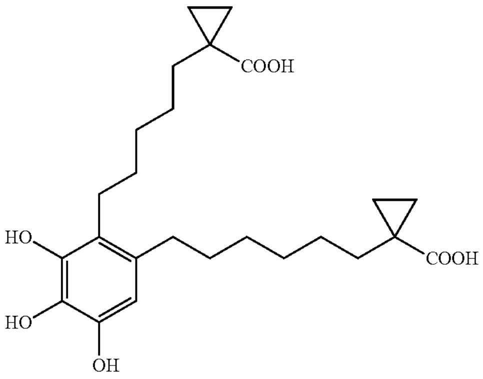 [SMILES: O=C(O)C1(CCCCCCc2cc(O)c(O)c(O)c2CCCCCC2(C(=O)O)CC2)CC1] | 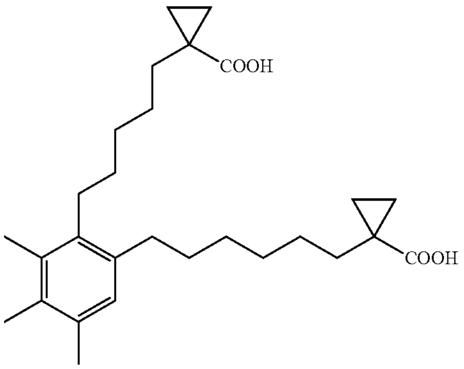 [SMILES: Cc1cc(CCCCCCC2(C(=O)O)CC2)c(CCCCCC2(C(=O)O)CC2)c(C)c1C] |
| 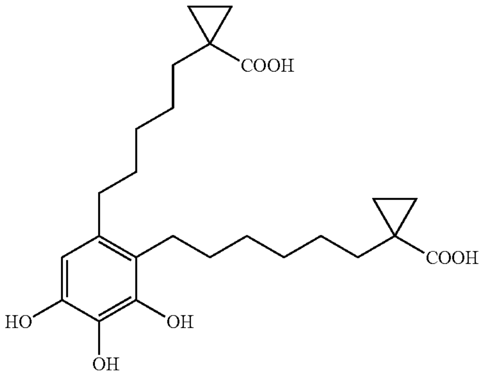 [SMILES: O=C(O)C1(CCCCCCc2c(CCCCCC3(C(=O)O)CC3)cc(O)c(O)c2O)CC1] | 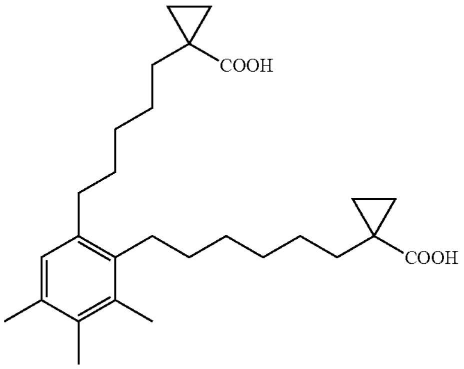 [SMILES: Cc1cc(CCCCCC2(C(=O)O)CC2)c(CCCCCCC2(C(=O)O)CC2)c(C)c1C] |
| 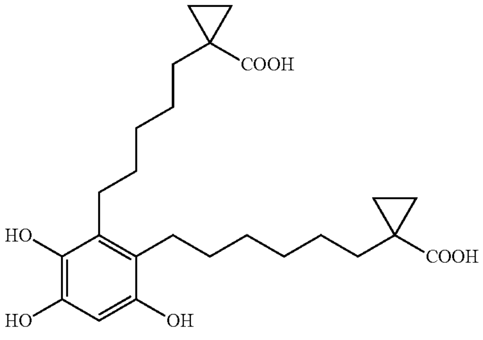 [SMILES: O=C(O)C1(CCCCCCc2c(O)cc(O)c(O)c2CCCCCC2(C(=O)O)CC2)CC1] | 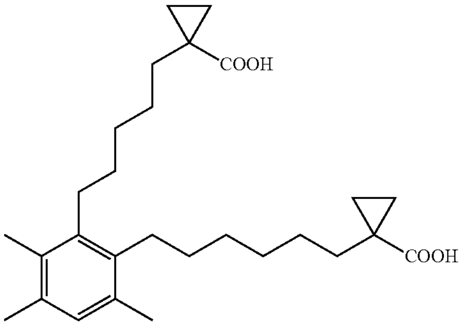 [SMILES: Cc1cc(C)c(CCCCCCC2(C(=O)O)CC2)c(CCCCCC2(C(=O)O)CC2)c1C] |

TABLE A-12-continued
| Structure | Structure |
| --- | --- |
| 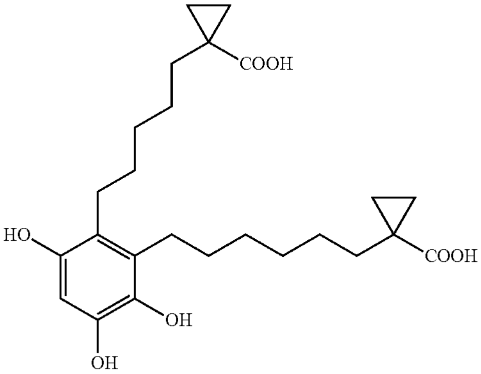 [SMILES: O=C(O)C1(CCCCCCc2c(O)c(O)cc(O)c2CCCCCC2(C(=O)O)CC2)CC1] | 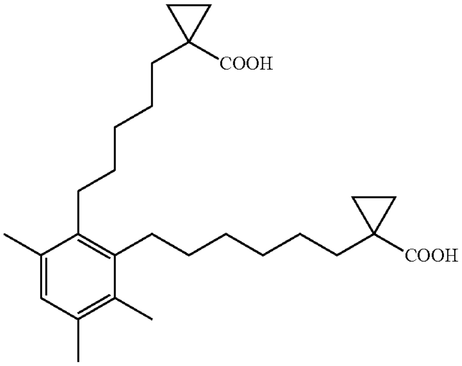 [SMILES: Cc1cc(C)c(CCCCCC2(C(=O)O)CC2)c(CCCCCCC2(C(=O)O)CC2)c1C] |
| 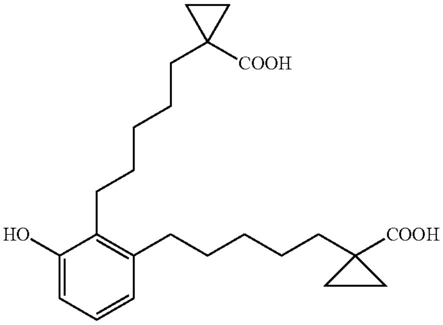 [SMILES: O=C(O)C1(CCCCCc2cccc(O)c2CCCCCC2(C(=O)O)CC2)CC1] | 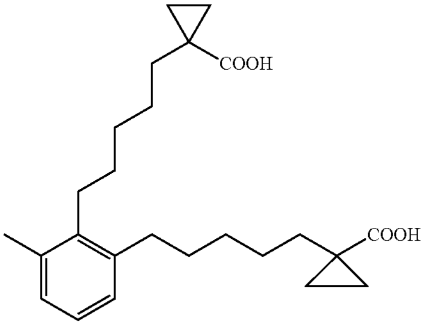 [SMILES: Cc1cccc(CCCCCC2(C(=O)O)CC2)c1CCCCCC1(C(=O)O)CC1] |
| 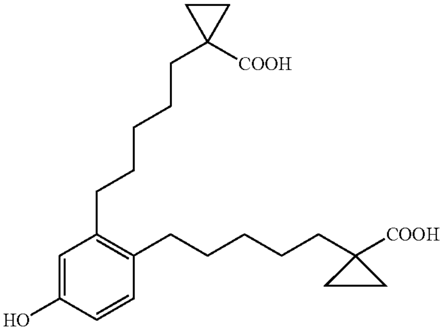 [SMILES: O=C(O)C1(CCCCCc2ccc(O)cc2CCCCCC2(C(=O)O)CC2)CC1] | 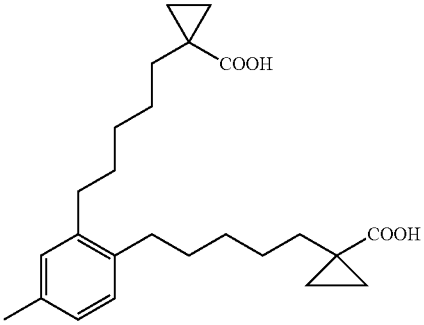 [SMILES: Cc1ccc(CCCCCC2(C(=O)O)CC2)c(CCCCCC2(C(=O)O)CC2)c1] |
| 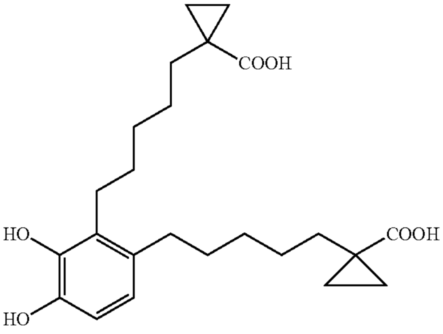 [SMILES: O=C(O)C1(CCCCCc2ccc(O)c(O)c2CCCCCC2(C(=O)O)CC2)CC1] | 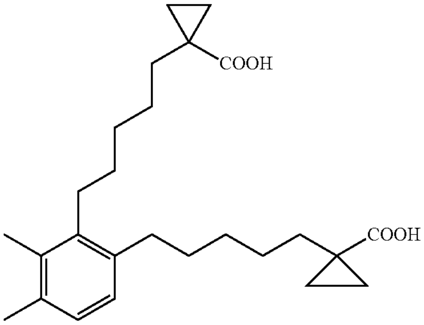 [SMILES: Cc1ccc(CCCCCC2(C(=O)O)CC2)c(CCCCCC2(C(=O)O)CC2)c1C] |

TABLE A-12-continued
| Structure | Structure |
| --- | --- |
| 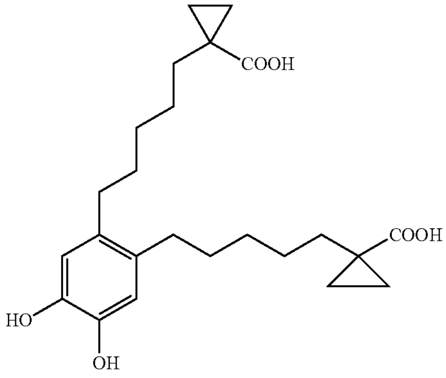 [SMILES: O=C(O)C1(CCCCCc2cc(O)c(O)cc2CCCCCC2(C(=O)O)CC2)CC1] | 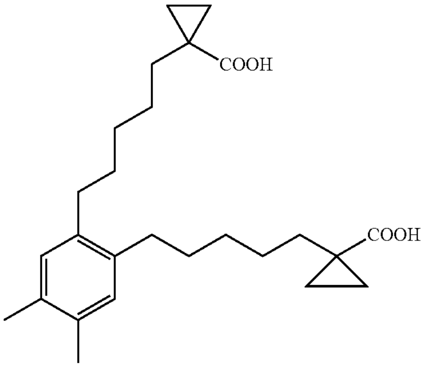 [SMILES: Cc1cc(CCCCCC2(C(=O)O)CC2)c(CCCCCC2(C(=O)O)CC2)cc1C] |
| 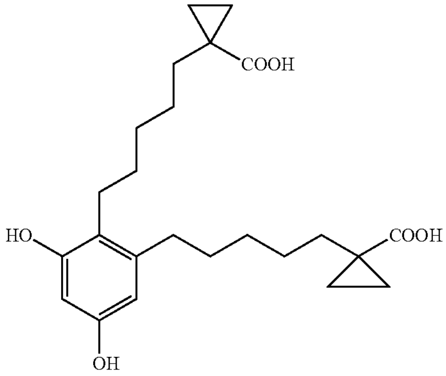 [SMILES: O=C(O)C1(CCCCCc2cc(O)cc(O)c2CCCCCC2(C(=O)O)CC2)CC1] | 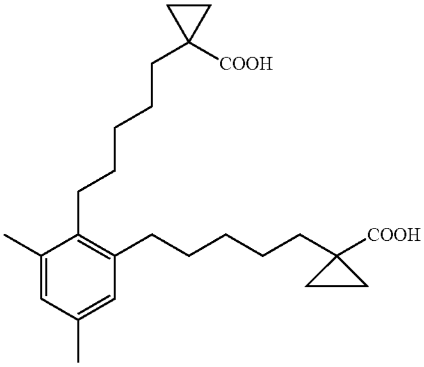 [SMILES: Cc1cc(C)c(CCCCCC2(C(=O)O)CC2)c(CCCCCC2(C(=O)O)CC2)c1] |
| 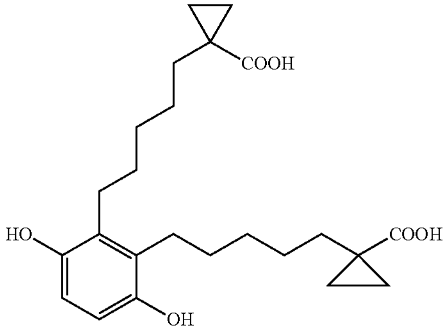 [SMILES: O=C(O)C1(CCCCCc2c(O)ccc(O)c2CCCCCC2(C(=O)O)CC2)CC1] | 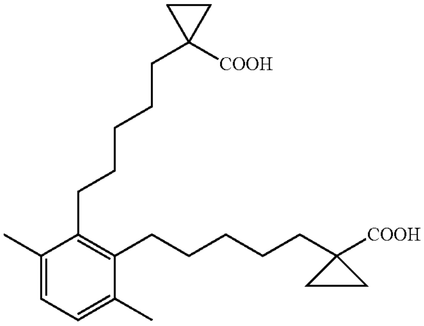 [SMILES: Cc1ccc(C)c(CCCCCC2(C(=O)O)CC2)c1CCCCCC1(C(=O)O)CC1] |
| 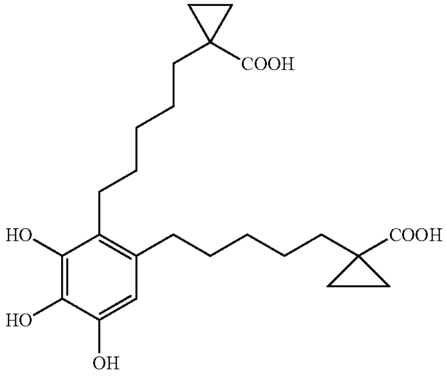 [SMILES: O=C(O)C1(CCCCCc2cc(O)c(O)c(O)c2CCCCCC2(C(=O)O)CC2)CC1] | 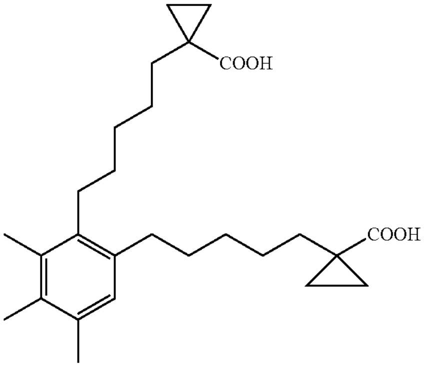 [SMILES: Cc1cc(CCCCCC2(C(=O)O)CC2)c(CCCCCC2(C(=O)O)CC2)c(C)c1C] |

TABLE A-12-continued
| Structure | Structure |
| --- | --- |
| 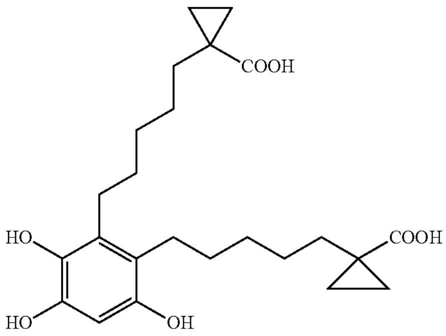 [SMILES: O=C(O)C1(CCCCCc2c(O)cc(O)c(O)c2CCCCCC2(C(=O)O)CC2)CC1] | 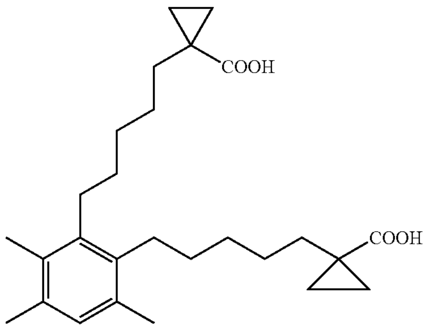 [SMILES: Cc1cc(C)c(CCCCCC2(C(=O)O)CC2)c(CCCCCC2(C(=O)O)CC2)c1C] |
| 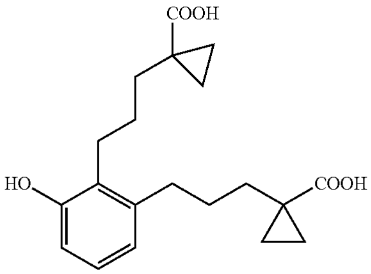 [SMILES: O=C(O)C1(CCCc2cccc(O)c2CCCC2(C(=O)O)CC2)CC1] | 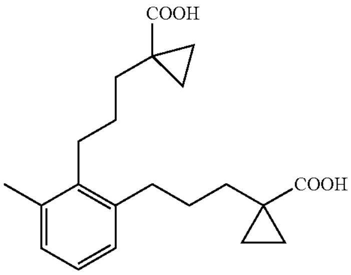 [SMILES: Cc1cccc(CCCC2(C(=O)O)CC2)c1CCCC1(C(=O)O)CC1] |
| 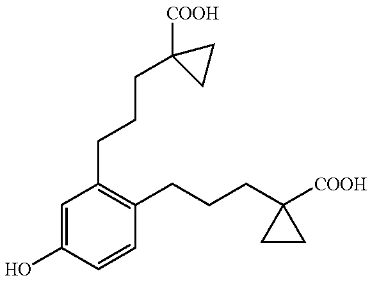 [SMILES: O=C(O)C1(CCCc2ccc(O)cc2CCCC2(C(=O)O)CC2)CC1] | 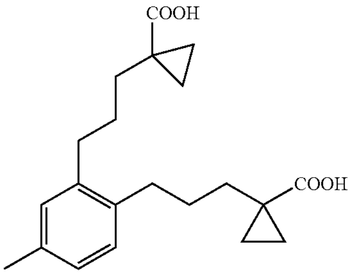 [SMILES: Cc1ccc(CCCC2(C(=O)O)CC2)c(CCCC2(C(=O)O)CC2)c1] |
| 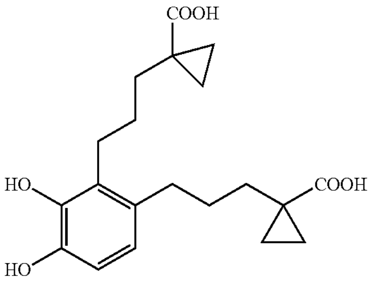 [SMILES: O=C(O)C1(CCCc2ccc(O)c(O)c2CCCC2(C(=O)O)CC2)CC1] | 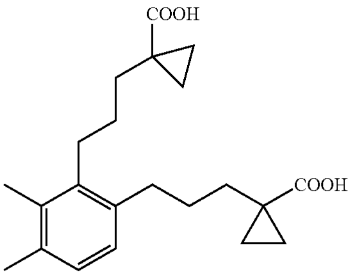 [SMILES: Cc1ccc(CCCC2(C(=O)O)CC2)c(CCCC2(C(=O)O)CC2)c1C] |
| 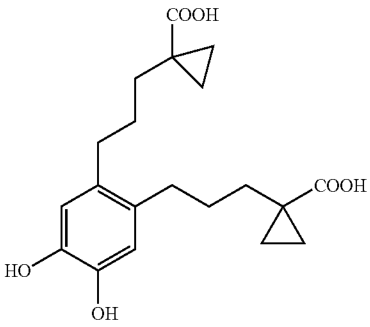 [SMILES: O=C(O)C1(CCCc2cc(O)c(O)cc2CCCC2(C(=O)O)CC2)CC1] | 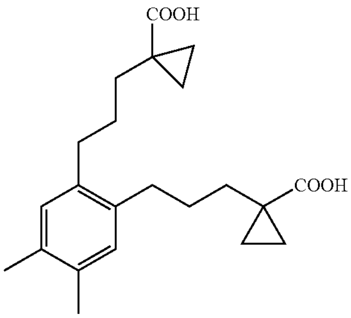 [SMILES: Cc1cc(CCCC2(C(=O)O)CC2)c(CCCC2(C(=O)O)CC2)cc1C] |

TABLE A-12-continued
| Structure | Structure |
|---|---|
| 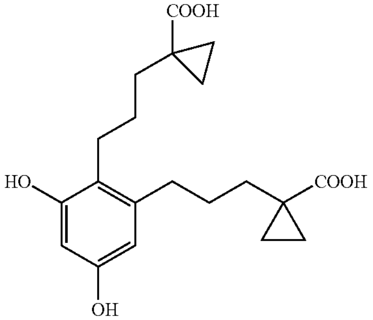 [SMILES: O=C(O)C1(CCCc2cc(O)cc(O)c2CCCC2(C(=O)O)CC2)CC1] | 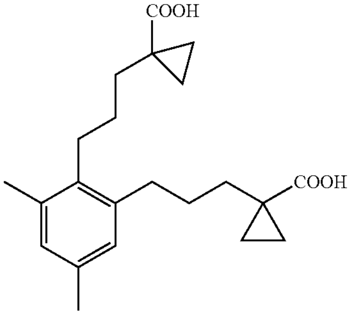 [SMILES: Cc1cc(C)c(CCCC2(C(=O)O)CC2)c(CCCC2(C(=O)O)CC2)c1] |
| 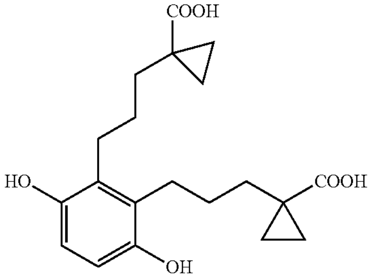 [SMILES: O=C(O)C1(CCCc2c(O)ccc(O)c2CCCC2(C(=O)O)CC2)CC1] | 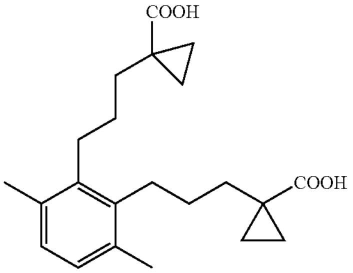 |
| 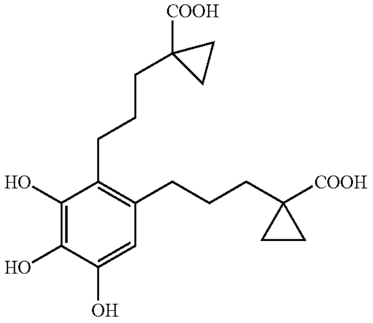 [SMILES: O=C(O)C1(CCCc2cc(O)c(O)c(O)c2CCCC2(C(=O)O)CC2)CC1] | 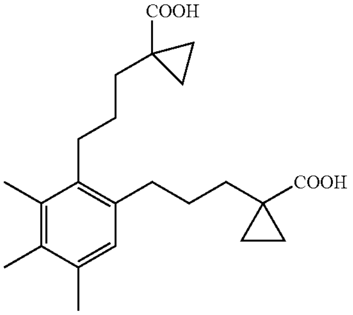 [SMILES: Cc1cc(CCCC2(C(=O)O)CC2)c(CCCC2(C(=O)O)CC2)c(C)c1C] |
| 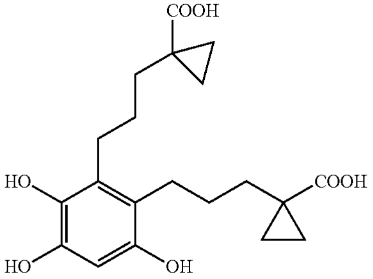 [SMILES: O=C(O)C1(CCCc2c(O)cc(O)c(O)c2CCCC2(C(=O)O)CC2)CC1] | 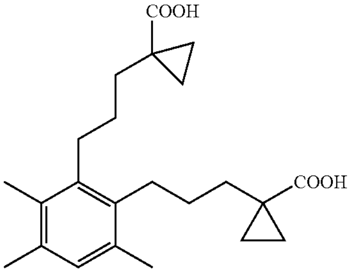 [SMILES: Cc1cc(C)c(CCCC2(C(=O)O)CC2)c(CCCC2(C(=O)O)CC2)c1C] |
| 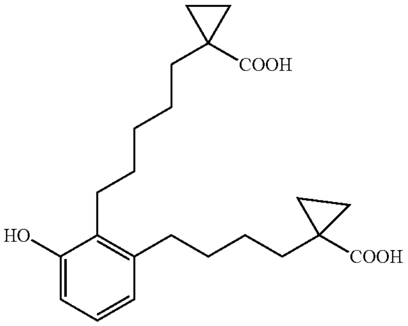 [SMILES: O=C(O)C1(CCCCCc2c(O)cccc2CCCCC2(C(=O)O)CC2)CC1] | 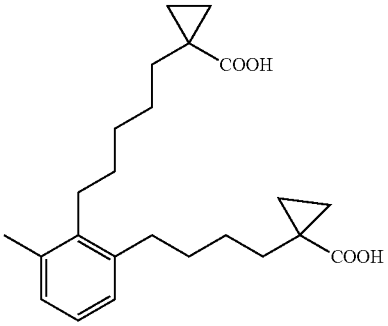 [SMILES: Cc1cccc(CCCCC2(C(=O)O)CC2)c1CCCCCC1(C(=O)O)CC1] |

TABLE A-12-continued
| Structure | Structure |
| --- | --- |
| 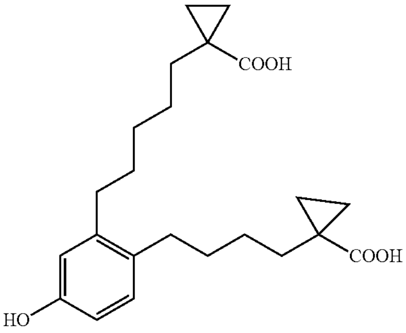 [SMILES: O=C(O)C1(CCCCCc2cc(O)ccc2CCCCC2(C(=O)O)CC2)CC1] | 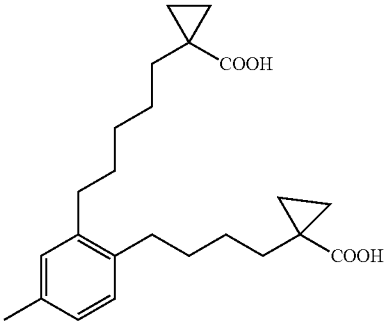 [SMILES: Cc1ccc(CCCCC2(C(=O)O)CC2)c(CCCCCC2(C(=O)O)CC2)c1] |
| 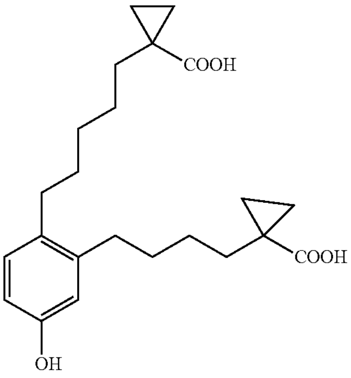 [SMILES: O=C(O)C1(CCCCCc2ccc(O)cc2CCCCC2(C(=O)O)CC2)CC1] | 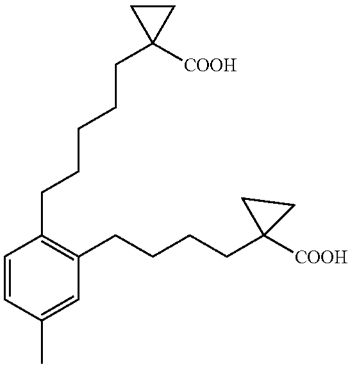 [SMILES: Cc1ccc(CCCCCC2(C(=O)O)CC2)c(CCCCC2(C(=O)O)CC2)c1] |
| 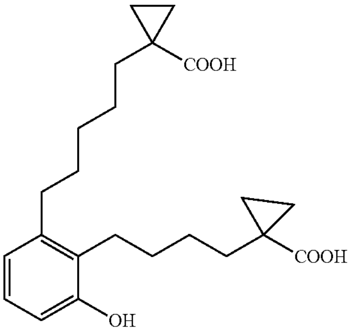 [SMILES: O=C(O)C1(CCCCCc2cccc(O)c2CCCCC2(C(=O)O)CC2)CC1] | 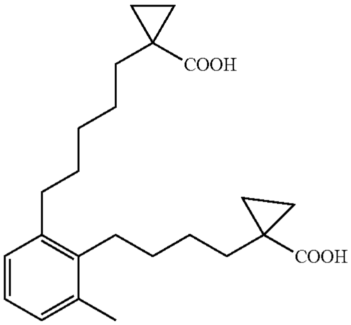 [SMILES: Cc1cccc(CCCCCC2(C(=O)O)CC2)c1CCCCC1(C(=O)O)CC1] |
| 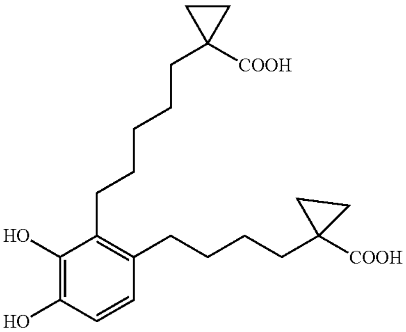 [SMILES: O=C(O)C1(CCCCCc2c(CCCCC3(C(=O)O)CC3)ccc(O)c2O)CC1] | 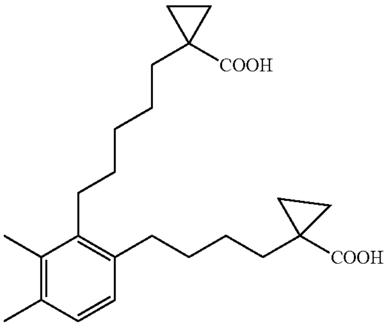 [SMILES: Cc1ccc(CCCCC2(C(=O)O)CC2)c(CCCCCC2(C(=O)O)CC2)c1C] |

TABLE A-12-continued
| Structure | Structure |
|---|---|
| 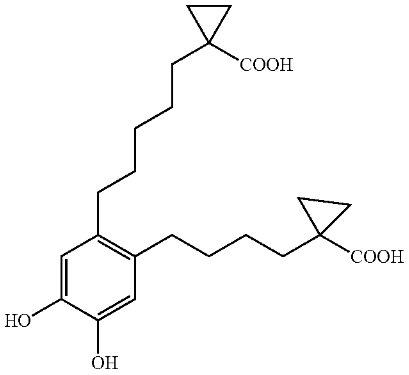 [SMILES: O=C(O)C1(CCCCCc2cc(O)c(O)cc2CCCCC2(C(=O)O)CC2)CC1] | 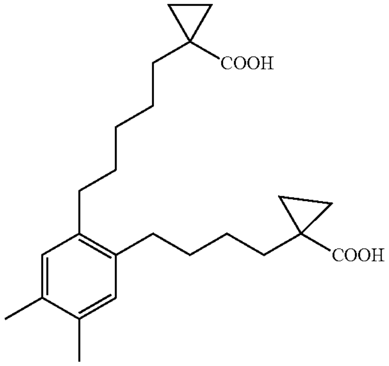 [SMILES: Cc1cc(CCCCCC2(C(=O)O)CC2)c(CCCCC2(C(=O)O)CC2)cc1C] |
| 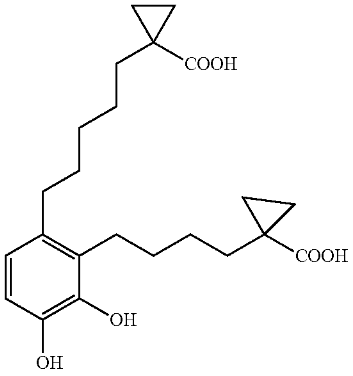 [SMILES: O=C(O)C1(CCCCCc2ccc(O)c(O)c2CCCCC2(C(=O)O)CC2)CC1] | 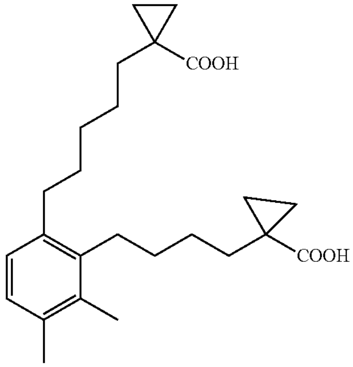 [SMILES: Cc1ccc(CCCCCC2(C(=O)O)CC2)c(CCCCC2(C(=O)O)CC2)c1C] |
| 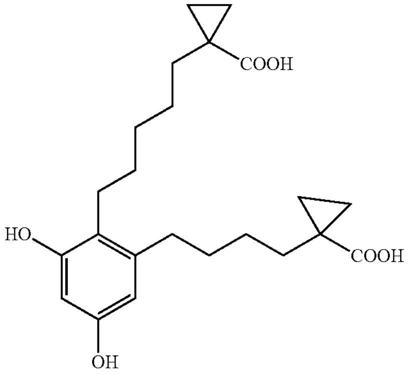 [SMILES: O=C(O)C1(CCCCCc2c(O)cc(O)cc2CCCCC2(C(=O)O)CC2)CC1] | 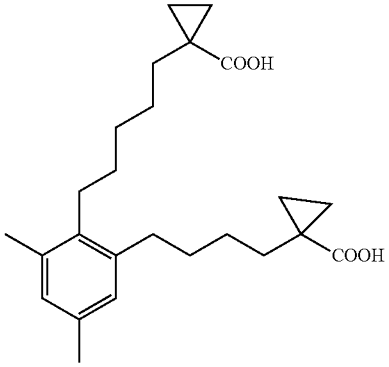 [SMILES: Cc1cc(C)c(CCCCCC2(C(=O)O)CC2)c(CCCCC2(C(=O)O)CC2)c1] |
| 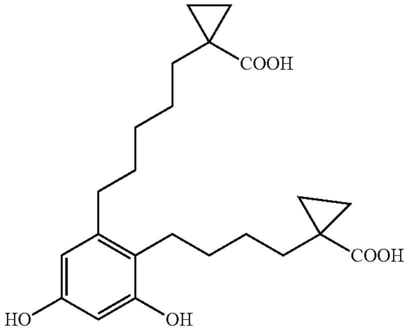 [SMILES: O=C(O)C1(CCCCCc2cc(O)cc(O)c2CCCCC2(C(=O)O)CC2)CC1] | 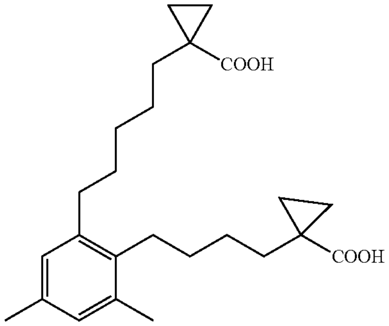 [SMILES: Cc1cc(C)c(CCCCC2(C(=O)O)CC2)c(CCCCCC2(C(=O)O)CC2)c1] |

TABLE A-12-continued
| Structure | Structure |
| --- | --- |
| 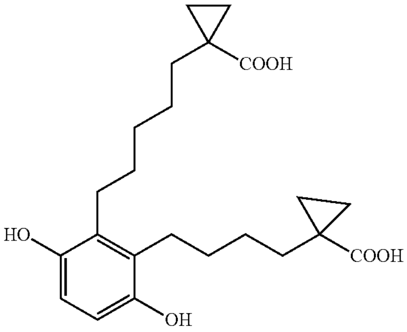 [SMILES: O=C(O)C1(CCCCCc2c(O)ccc(O)c2CCCCC2(C(=O)O)CC2)CC1] | 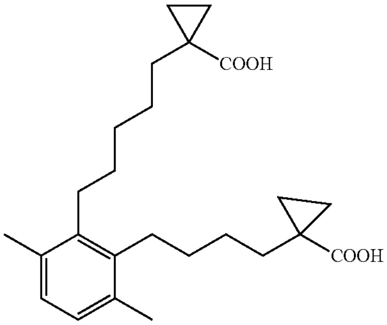 [SMILES: Cc1ccc(C)c(CCCCC2(C(=O)O)CC2)c1CCCCCC1(C(=O)O)CC1] |
| 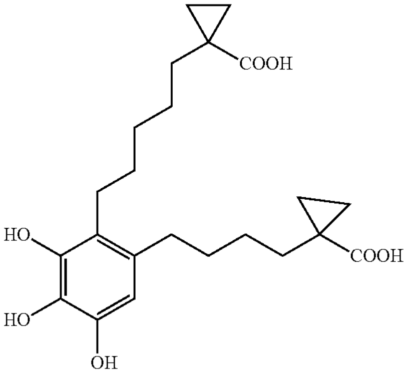 [SMILES: O=C(O)C1(CCCCCc2c(CCCCC3(C(=O)O)CC3)cc(O)c(O)c2O)CC1] | 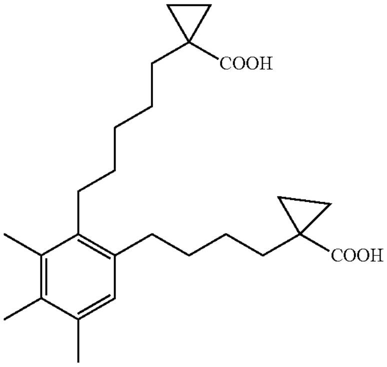 [SMILES: Cc1cc(CCCCC2(C(=O)O)CC2)c(CCCCCC2(C(=O)O)CC2)c(C)c1C] |
| 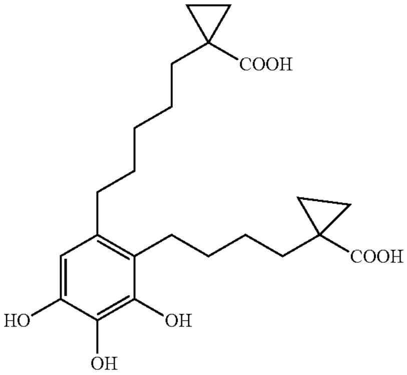 [SMILES: O=C(O)C1(CCCCCc2cc(O)c(O)c(O)c2CCCCC2(C(=O)O)CC2)CC1] | 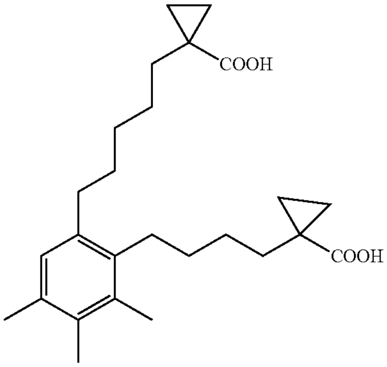 [SMILES: Cc1cc(CCCCCC2(C(=O)O)CC2)c(CCCCC2(C(=O)O)CC2)c(C)c1C] |
| 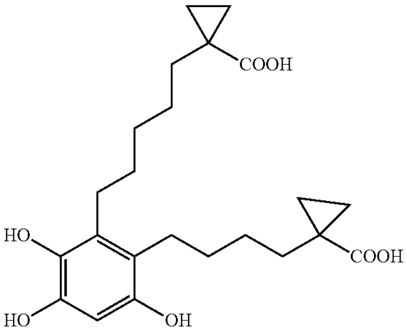 [SMILES: O=C(O)C1(CCCCCc2c(O)c(O)cc(O)c2CCCCC2(C(=O)O)CC2)CC1] | 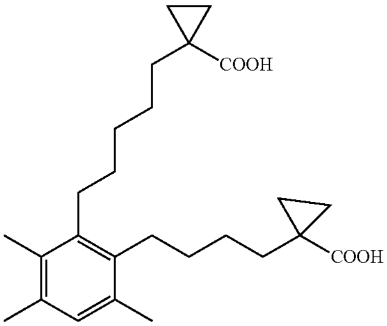 [SMILES: Cc1cc(C)c(CCCCC2(C(=O)O)CC2)c(CCCCCC2(C(=O)O)CC2)c1C] |

TABLE A-12-continued
| Structure | Structure |
|---|---|
| 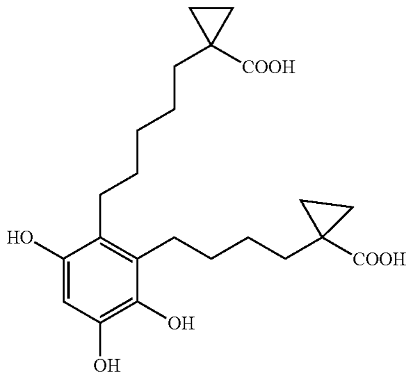 [SMILES: O=C(O)C1(CCCCCc2c(O)cc(O)c(O)c2CCCCC2(C(=O)O)CC2)CC1] | 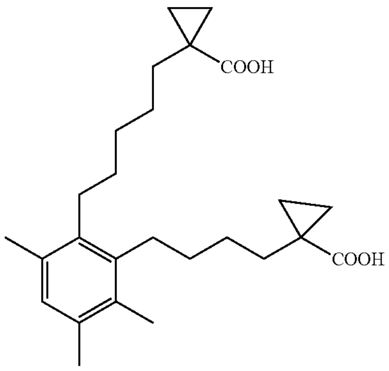 [SMILES: Cc1cc(C)c(CCCCCC2(C(=O)O)CC2)c(CCCCC2(C(=O)O)CC2)c1C] |
| 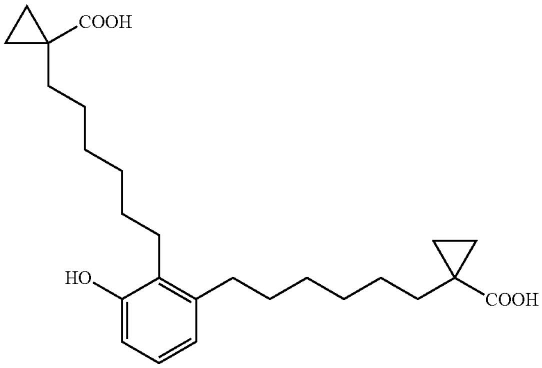 [SMILES: O=C(O)C1(CCCCCCc2cccc(O)c2CCCCCCC2(C(=O)O)CC2)CC1] | 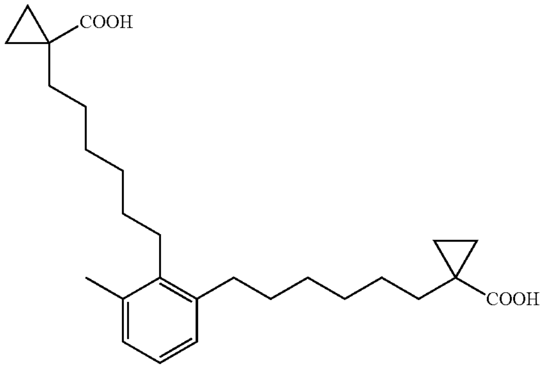 [SMILES: Cc1cccc(CCCCCCC2(C(=O)O)CC2)c1CCCCCCC1(C(=O)O)CC1] |
| 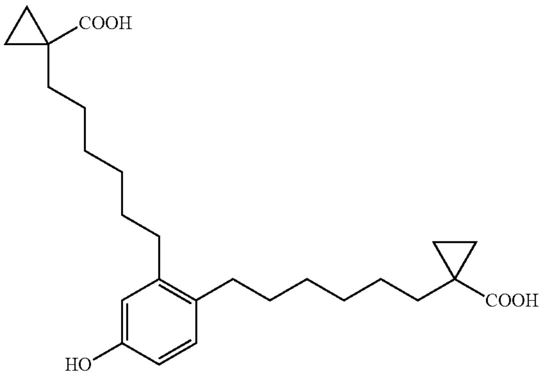 [SMILES: O=C(O)C1(CCCCCCc2ccc(O)cc2CCCCCCC2(C(=O)O)CC2)CC1] | 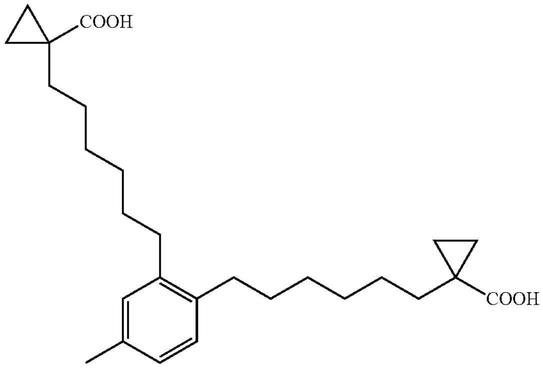 [SMILES: Cc1ccc(CCCCCCC2(C(=O)O)CC2)c(CCCCCCC2(C(=O)O)CC2)c1] |
| 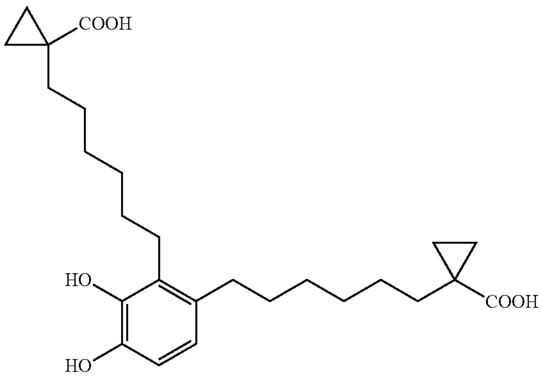 [SMILES: O=C(O)C1(CCCCCCc2ccc(O)c(O)c2CCCCCCC2(C(=O)O)CC2)CC1] | 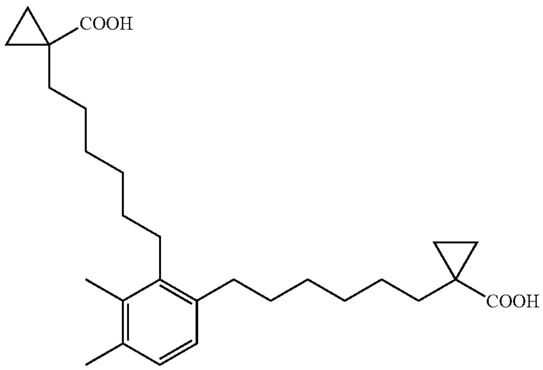 [SMILES: Cc1ccc(CCCCCCC2(C(=O)O)CC2)c(CCCCCCC2(C(=O)O)CC2)c1C] |

TABLE A-12-continued
| Structure | Structure |
| --- | --- |
| 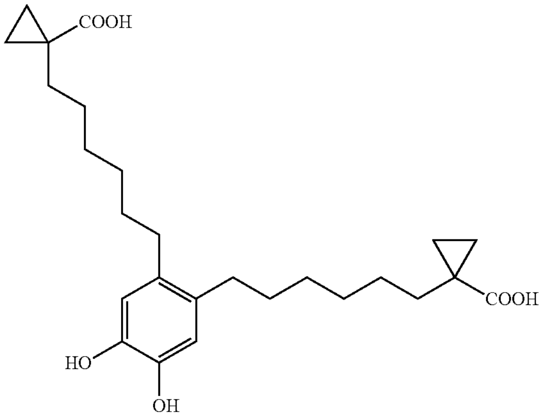 [SMILES: O=C(O)C1(CCCCCCc2cc(O)c(O)cc2CCCCCCC2(C(=O)O)CC2)CC1] | 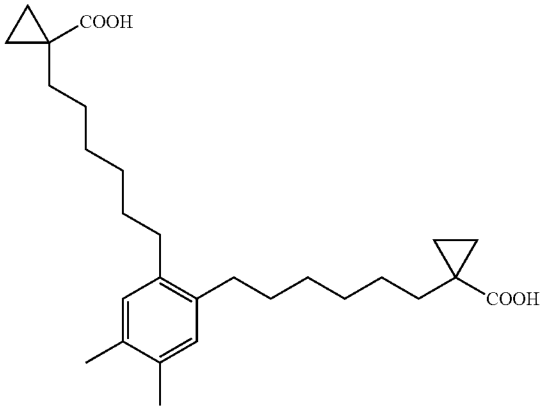 [SMILES: Cc1cc(CCCCCCC2(C(=O)O)CC2)c(CCCCCCC2(C(=O)O)CC2)cc1C] |
| 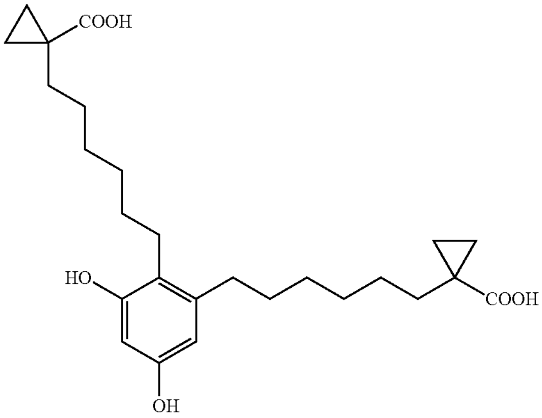 [SMILES: O=C(O)C1(CCCCCCc2cc(O)cc(O)c2CCCCCCC2(C(=O)O)CC2)CC1] | 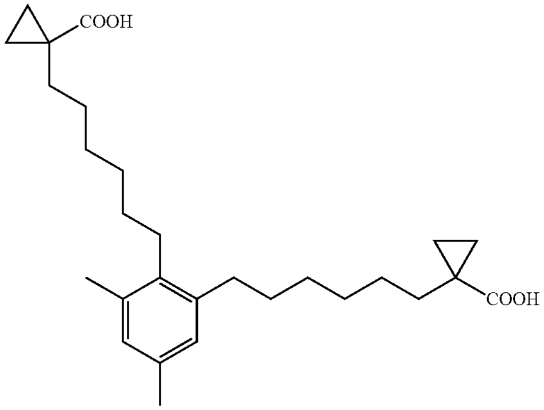 [SMILES: Cc1cc(C)c(CCCCCCC2(C(=O)O)CC2)c(CCCCCCC2(C(=O)O)CC2)c1] |
| 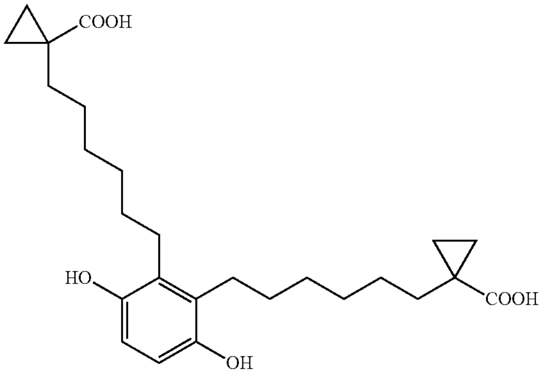 [SMILES: O=C(O)C1(CCCCCCc2c(O)ccc(O)c2CCCCCCC2(C(=O)O)CC2)CC1] | 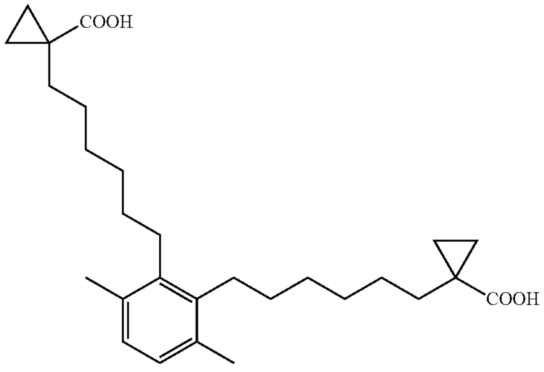 [SMILES: Cc1ccc(C)c(CCCCCCC2(C(=O)O)CC2)c1CCCCCCC1(C(=O)O)CC1] |

TABLE A-12-continued

| Structure | Structure |
| --- | --- |
| 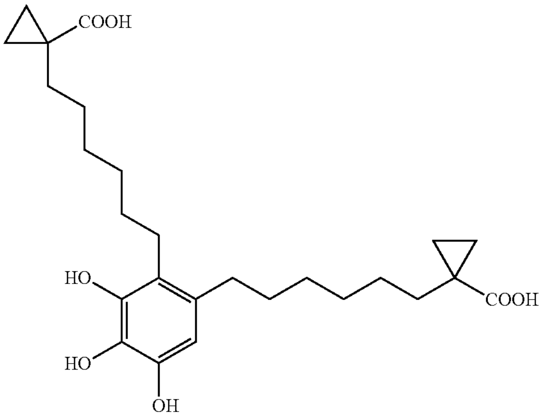 [SMILES: O=C(O)C1(CCCCCCc2cc(O)c(O)c(O)c2CCCCCCC2(C(=O)O)CC2)CC1] | 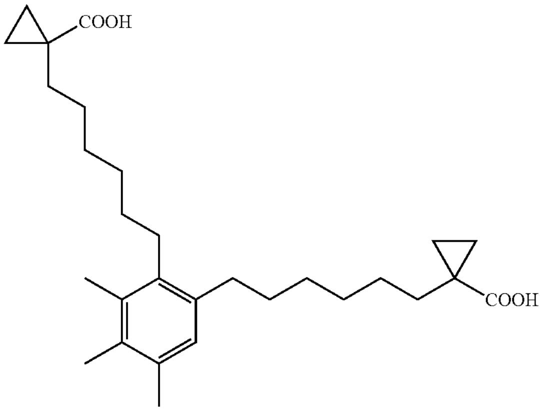 [SMILES: Cc1cc(CCCCCCC2(C(=O)O)CC2)c(CCCCCCC2(C(=O)O)CC2)c(C)c1C] |
| 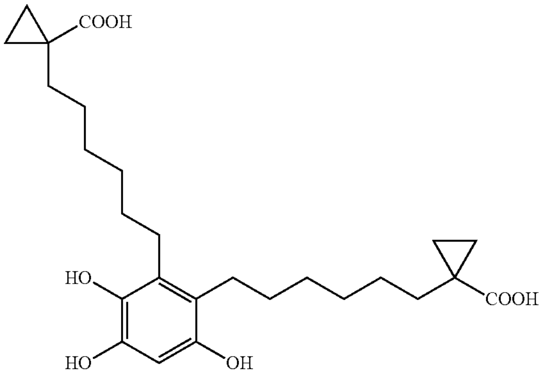 [SMILES: O=C(O)C1(CCCCCCc2c(O)cc(O)c(O)c2CCCCCCC2(C(=O)O)CC2)CC1] | 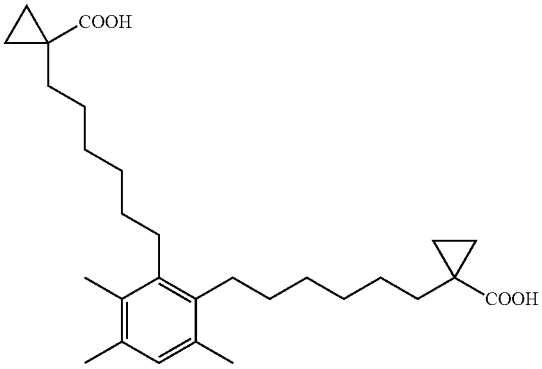 [SMILES: Cc1cc(C)c(CCCCCCC2(C(=O)O)CC2)c(CCCCCCC2(C(=O)O)CC2)c1C] |

In some embodiments, the compound of the invention is isolated and purified. In some embodiments, the compound of Formula (I), (IA), (IB), or (IC), or a pharmaceutically acceptable salt or solvate thereof, is isolated and purified. In some embodiments, the compound of Formula (I), (IA), (IB), or (IC), or a pharmaceutically acceptable salt or solvate thereof, is ex vivo.

Compounds of Formula (ID)

In some embodiments, the compound of the invention is a compound of Formula (ID):

(ID)

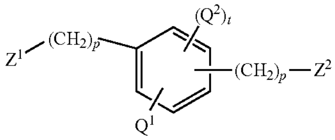

or a pharmaceutically acceptable salt or solvate thereof, wherein:

each p is independently 1, 2, 3, 4, 5, 6, or 7;

each $Z^1$ and $Z^2$ is independently —$C(R^1)(R^2)$—$(CH_2)_c$—X or —W—$(CH_2)_c$—$C(R^3)(R^4)$—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

$Q^1$ is F, Cl, Br, —$CF_3$, or —O($C_1$-$C_4$ alkyl);

each $Q^2$ is independently —OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

t is 0, 1, 2, or 3;

each X and Y is independently —OH, —COOH, —$COOR^5$, —$CONH_2$, —$CONHR^5$, —CONHMs, —CONHTs, —$SO_3H$,

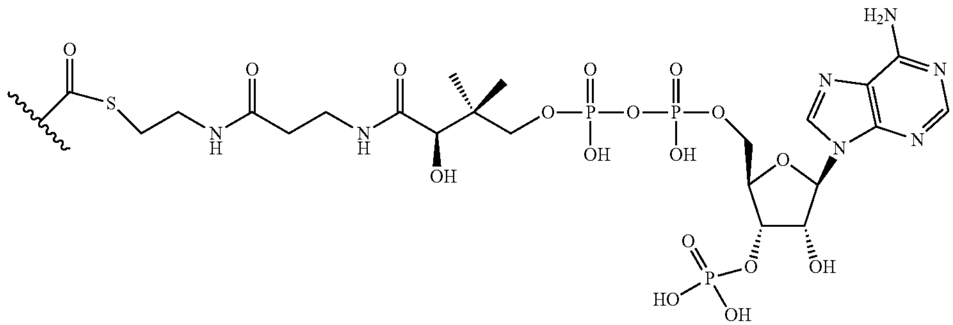
(-CO-CoA),
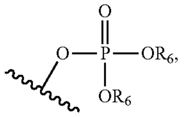
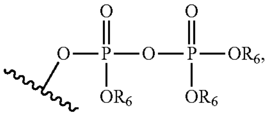
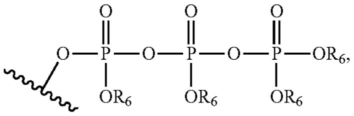
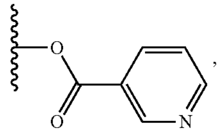
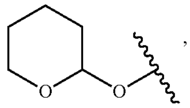
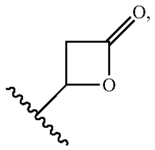
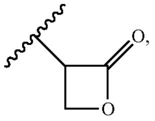
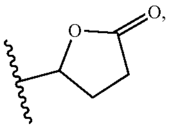
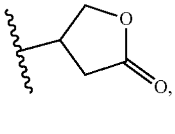
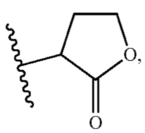
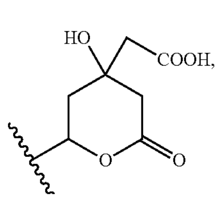
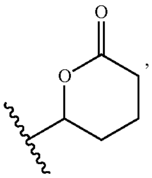
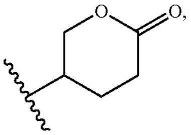
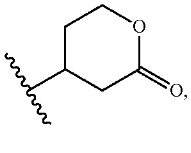
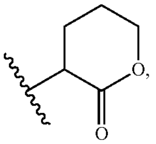
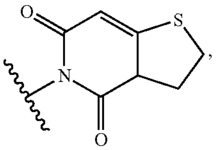
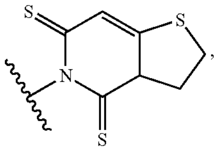
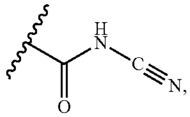
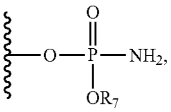
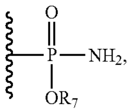
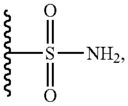
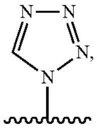
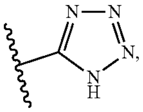
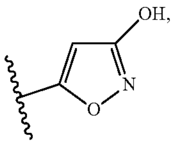
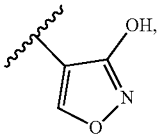
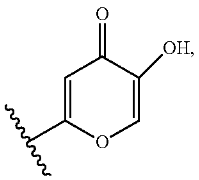
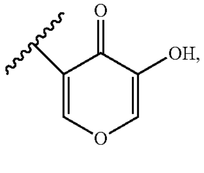
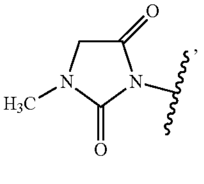
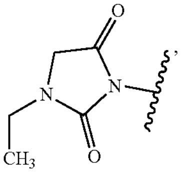
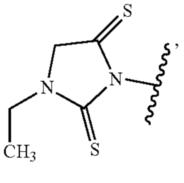
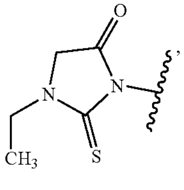
or
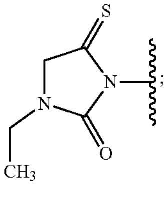

each $R^6$ is independently H, $—C_1-C_6$ alkyl, $—C_2-C_6$ alkenyl, or $—C_2-C_6$ alkynyl, wherein the $—C_1-C_6$ alkyl, $—C_2-C_6$ alkenyl, or $—C_2-C_6$ alkynyl is unsubstituted or substituted with one or two halogen, —OH, $—O(C_1-C_6$ alkyl), or phenyl groups;

each $R^7$ is independently H, $—C_1-C_6$ alkyl, $—C_2-C_6$ alkenyl, or $—C_2-C_6$ alkynyl;

each W is independently —O—, —NH—, —N(OH)—, —N(→O)—, —S—, —S(═O)—, $—S(O)_2—$, or —Se—;

each $R^5$ is independently $—C_1-C_6$ alkyl, $—C_2-C_6$ alkenyl, $—C_2-C_6$ alkynyl, phenyl, or benzyl, each being unsubstituted or substituted with one or more halogen, —OH, $—O(C_1-C_6$ alkyl), or phenyl groups.

In some embodiments, the compound of formula (ID) has the structure of Formula (IE), Formula (IF), or Formula (IG), or a pharmaceutically acceptable salt or solvate thereof:

(IE)

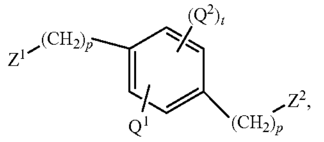

(IF)

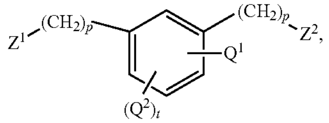

or (IG)

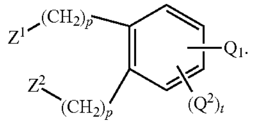

In some embodiments of the compounds of Formula (ID), (IE), (IF), or (IG), $Z^1$ and $Z^2$ are each independently $—C(R^1)(R^2)—(CH_2)_c—X$. In some embodiments, one or both of $Z^1$ and $Z^2$ is $—W—(CH_2)_c—C(R^3)(R^4)—Y$.

In some embodiments of the compounds of Formula (ID), (IE), (IF), or (IG), X is —COOH, —CO—CoA, or $—COOR^5$.

In some embodiments, of the compounds of Formula (ID), (IE), (IF), or (IG), $Z^1$ is $—C(R^1)(R^2)—(CH_2)_c—CO—$CoA and $Z^2$ is $—C(R^1)(R^2)—(CH_2)_c—COOH$ or $—C(R^1)(R^2)—(CH_2)_c—COOR^5$. In some embodiments, of the compounds of Formula (ID), (IE), (IF), or (IG), $Z^2$ is $—C(R^1)(R^2)—(CH_2)_c—CO—$CoA and $Z^1$ is $—C(R^1)(R^2)—(CH_2)_c—COOH$ or $—C(R^1)(R^2)—(CH_2)_c—COOR^5$.

In some embodiments of the compounds of Formula (ID), (IE), (IF), or (IG), one or both of $Z^1$ and $Z^2$ are $—C(R^1)(R^2)—(CH_2)_c—CO—$CoA. In some embodiments, one or both of $Z^1$ and $Z^2$ are $—W—(CH_2)_c—C(R^3)(R^4)—$Co—CoA.

In some embodiments of the compounds of Formula (ID), (IE), (IF), or (IG), each $R^1$ and $R^2$ is independently $—C_1-C_6$ alkyl, $—C_2-C_6$ alkenyl, or $—C_2-C_6$ alkynyl. In some embodiments, each $R^1$ and $R^2$ is independently $—C_1-C_3$ alkyl, $—C_2-C_3$ alkenyl, or $—C_2-C_3$ alkynyl. In some embodiments, $R^1$ and $R^2$ are methyl.

In some embodiments of the compounds of Formula (ID), (IE), (IF), or (IG), $Z^1$ is $—C(R^1)(R^2)—(CH_2)_c—CO—$CoA and $Z^2$ is $—C(R^1)(R^2)—(CH_2)_c—X$, where X is —CO—CoA, —COOH or $—COOR^5$, and $R^1$ and $R^2$ are methyl.

In some embodiments of the compounds of Formula (ID), (IE), (IF), or (IG), c is 0 or 1. In some embodiments, c is 0. In some embodiments, c is 1. In some embodiments, c is 2. In some embodiments, c is 3.

In some embodiments of the compounds of Formula (ID), (IE), (IF), or (IG), each carbon atom together with the $R^1$ and $R^2$ attached to the carbon atom independently form a $—C_3-C_7$ cycloalkyl group. In some embodiments, each carbon atom together with the $R^1$ and $R^2$ attached to the carbon atom independently form a cyclopropyl ring.

In some embodiments of the compounds of Formula (ID), (IE), (IF), or (IG), at least one $R^1$ and one $R^2$ together with the carbon atom to which they are attached form a $—C_3-C_7$ cycloalkyl group. In some embodiments, at least one $R^1$ and one $R^2$ together with the carbon atom to which they are attached form a cyclopropyl ring.

In some embodiments of the compounds of Formula (ID), (IE), (IF), or (IG), $R^3$ and $R^4$ is independently H, $—C_1-C_6$ alkyl, $—C_2-C_6$ alkenyl, or $—C_2-C_6$ alkynyl.

In some embodiments of the compounds of Formula (ID), (IE), (IF), or (IG), Y is —COOH or $—COOR^5$.

In some embodiments of the compounds of Formula (ID), (IE), (IF), or (IG), $R^5$ is $—C_1-C_6$ alkyl, $—C_2-C_6$ alkenyl, or $—C_2-C_6$ alkynyl. In some embodiments, $R^5$ is $—C_1-C_3$ alkyl, $—C_2-C_3$ alkenyl, or $—C_2-C_3$ alkynyl.

In some embodiments of the compounds of Formula (ID), (IE), (IF), or (IG), p is 3, 4, 5, 6, or 7. In some embodiments, p is 4, 5, 6, or 7.

In some embodiments of the compounds of Formula (ID), (IE), (IF), or (IG), $Z^1$ is $—W—(CH_2)_c—C(R^3)(R^4)—CO—$CoA, $Z^2$ is $—W—(CH_2)_c—C(R^3)(R^4)—Y$, and $R^3$ and $R^4$ is independently H, $—C_1-C_6$ alkyl, $—C_2-C_6$ alkenyl, or $—C_2-C_6$ alkynyl. In some embodiments, $Z^1$ is $—W—(CH_2)_c—C(R^3)(R^4)—CO—$CoA, $Z^2$ is $—W—(CH_2)_c—C(R^3)(R^4)—Y$, and Y is —CO—CoA, —COOH or $—COOR^5$. In some embodiments, $Z^1$ is $—W—(CH_2)_c—C(R^3)(R^4)—CO—$CoA, $Z^2$ is $—W—(CH_2)_c—C(R^3)(R^4)—Y$, Y is —CO—CoA, —COOH or $—COOR^5$, and $R^5$ is $—C_1-C_6$ alkyl, $—C_2-C_6$ alkenyl, or $—C_2-C_6$ alkynyl. In some embodiments, $Z^1$ is $—W—(CH_2)_c—C(R^3)(R^4)—CO—$CoA, $Z^2$ is $—W—(CH_2)_c—C(R^3)(R^4)—Y$, Y is —CO—CoA, —COOH or $—COOR^5$, and $R^5$ is $—C_1-C_3$ alkyl, $—C_2-C_3$ alkenyl, or $—C_2-C_3$ alkynyl.

In some embodiments of the compound of Formula (ID), (IE), (IF), or (IG), t is 0. In some embodiments, t is 1. In some embodiments, t is 2. In some embodiments, t is 3.

In some embodiments, the pharmaceutically acceptable salt of a compound of Formula (ID), (IE), (IF), or (IG) is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the pharmaceutically acceptable salt of the compounds of Formula (ID), (IE), (IF), or (IG), is a zinc salt. In some embodiments, the pharmaceutically acceptable salt of the compounds of Formula (IF) or (IG), is a zinc salt.

In some embodiments, the pharmaceutically acceptable salt of the compounds of Formula (IF) or (IG), is a zinc salt, wherein p is 3 or 4 and each X and Y is —COOH.

In some embodiments, the compound of Formula (ID) or (IE), has any one of the structures shown in Table A-13, defined by $C^1$ and $C^2$, and defined by R, $R^1$ and $R^2$, where present, or a pharmaceutically acceptable salt or solvate thereof. In some embodiments, R of the compound of Table A-13 is $CH_3$. In some embodiments, one or more of R, $R_1$ and $R_2$ of the compound of Table A-13 is $CH_3$. In some embodiments, one or more of R, $R_1$ and $R_2$ of the compound of Table A-13 is F. In some embodiments, one or more of R, $R_1$ and $R_2$ of the compound of Table A-13 is Cl. In some embodiments, one or more of R, $R_1$ and $R_2$ of the compound of Table A-13 is Br. In some embodiments, one or more of R, $R_1$ and $R_2$ of the compound of Table A-13 is $CF_3$.

In some embodiments, the pharmaceutically acceptable salt of a compound having any one of the structures shown in Table A-13 and defined by $C^1$ and $C^2$, and defined by R, $R_1$ and $R_2$, where present, is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

TABLE A-13

| Structure |
|---|
| 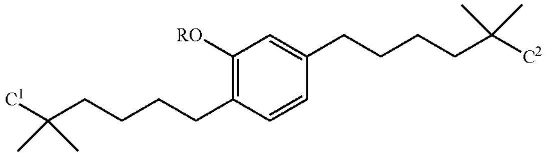 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 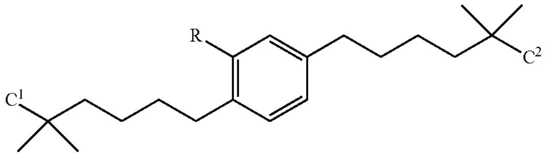 wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 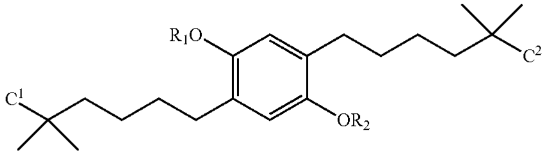 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl, or $R_2$ = H and $R_1$ = (C1-C4)alkyl |
| 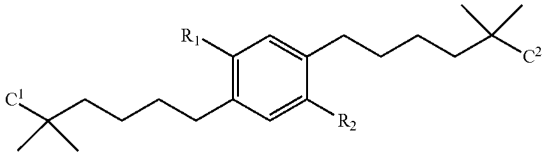 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl, or $R_2$ = F, Cl, Br, or $CF_3$ and $R_1$ = H or (C1-C4)alkyl |

TABLE A-13-continued

| Structure |
|---|
| 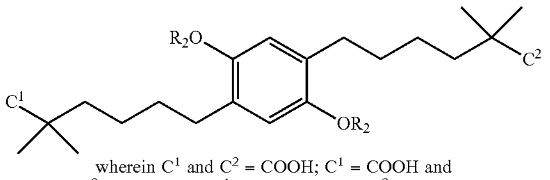 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 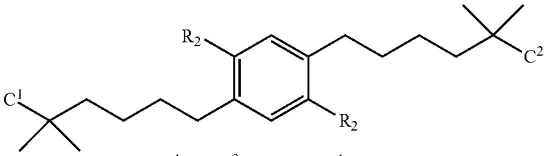 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 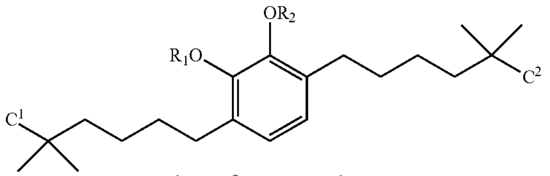 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 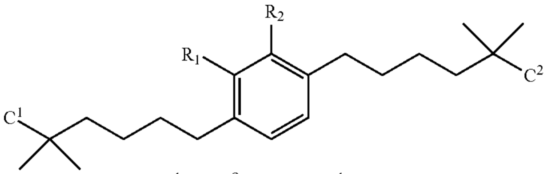 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 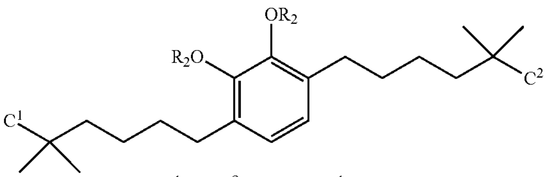 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 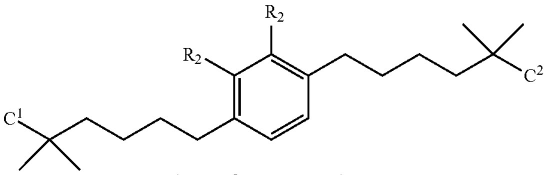 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-13-continued

Structure

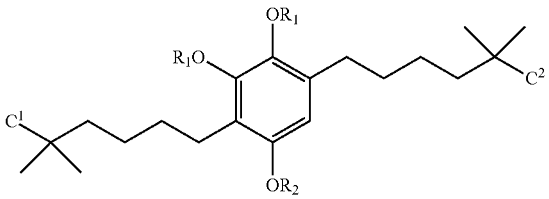

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

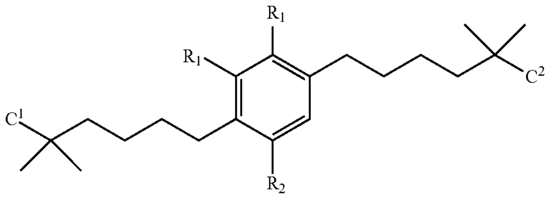

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

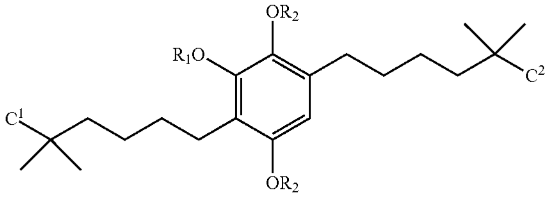

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each R = H and R = (C1-C4)alkyl

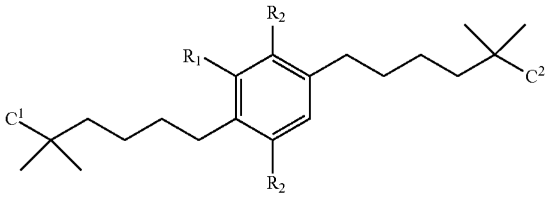

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

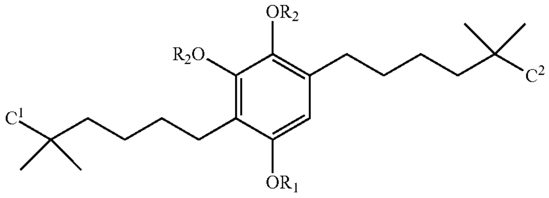

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H TABLE A-13-continued Structure and each $R_2$ is independently a (C1-C4)alky; or each $R_2$ = H and $R_1$ = (C1-C4)alkyl

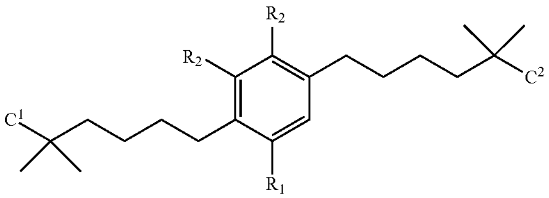

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

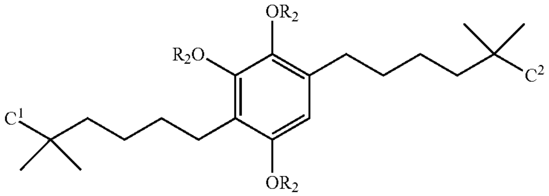

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

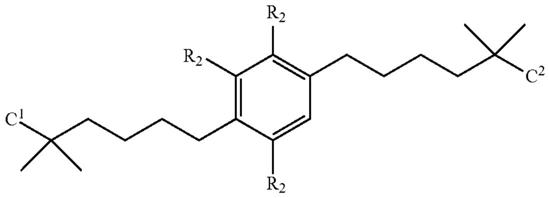

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

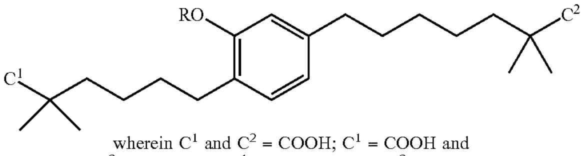

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

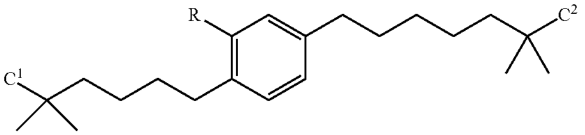

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$

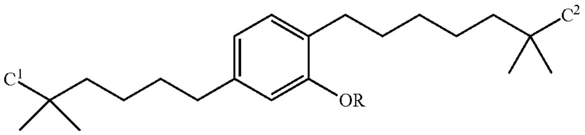

TABLE A-13-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 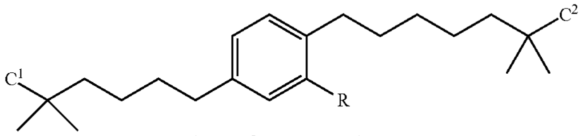 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 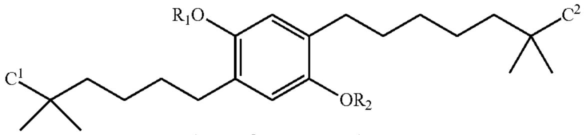 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and R = (C1-C4)alkyl |
| 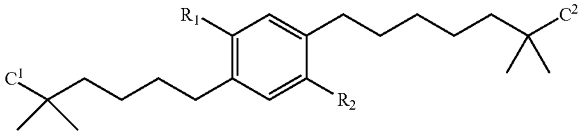 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 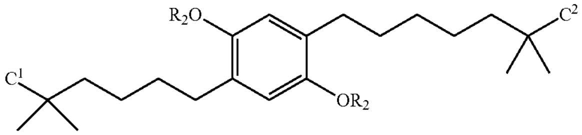 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 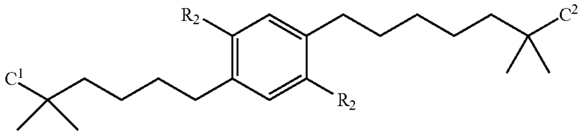 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 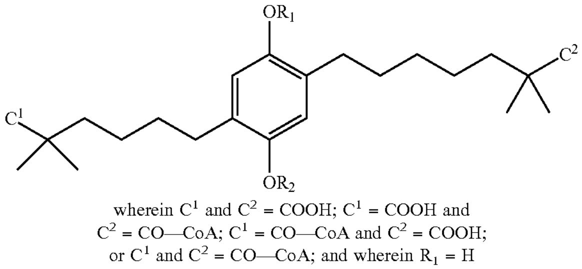 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 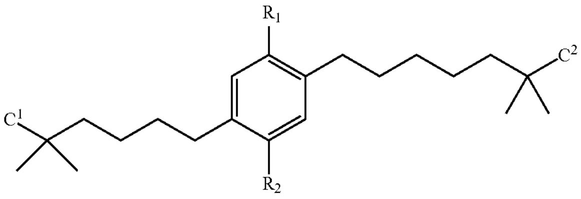 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 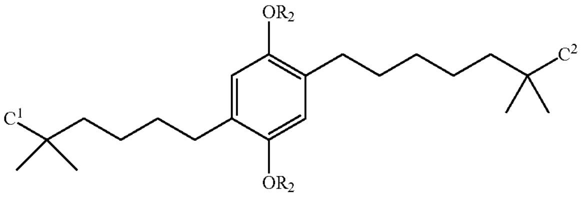 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 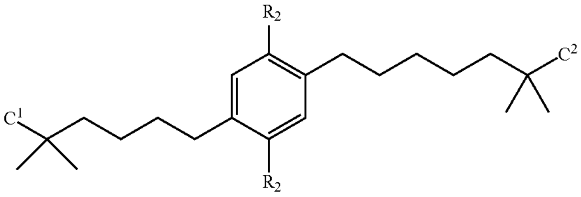 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 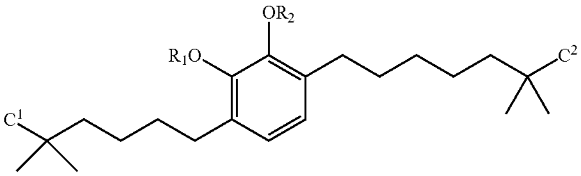 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 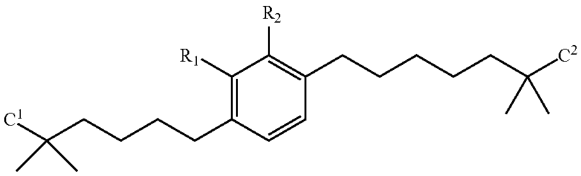 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-13-continued

| Structure |
|---|
| 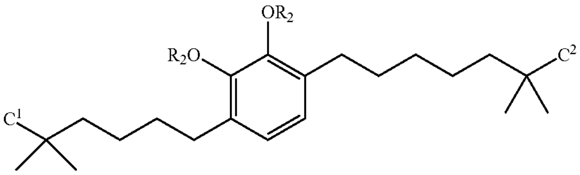 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 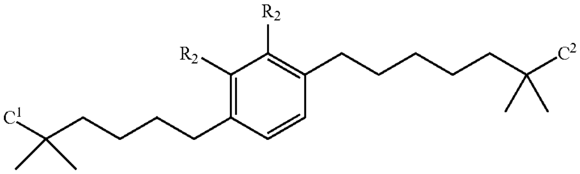 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 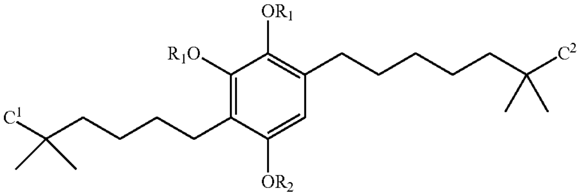 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 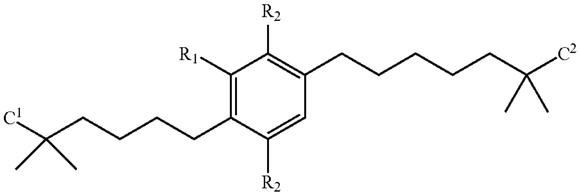 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 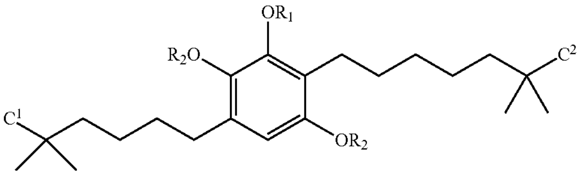 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |

TABLE A-13-continued

| Structure |
|---|
| 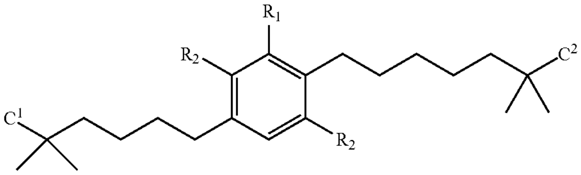 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 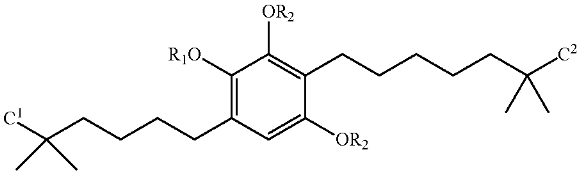 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each R = H and $R_1$ = (C1-C4)alkyl |
| 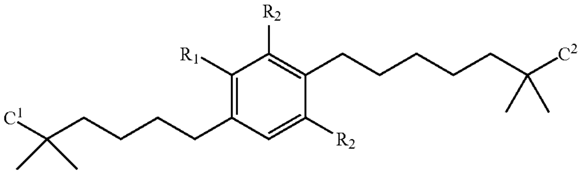 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 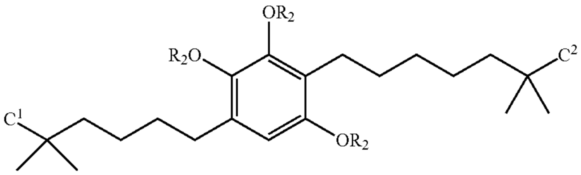 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 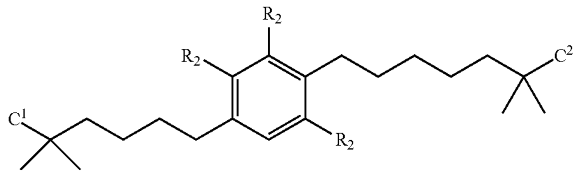 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 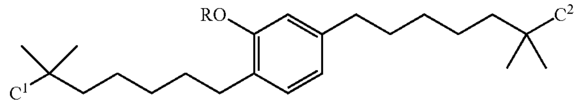 |
| wherein $C^1$ and $C^2$ = COOH; $C^1$ = COOH and $C^2$ = CO—CoA; $C^1$ = CO—CoA and $C^2$ = COOH; |

TABLE A-13-continued

| Structure |
| --- |
| or $C^1$ and $C^2$ = CO—CoA; and wherein R = (C1-C4)alkyl |
| 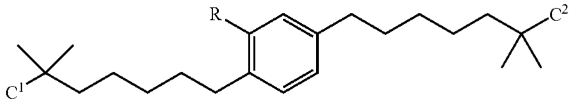 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 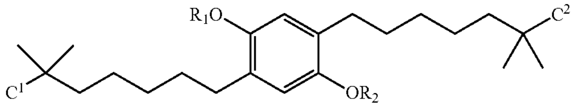 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 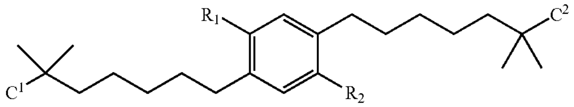 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 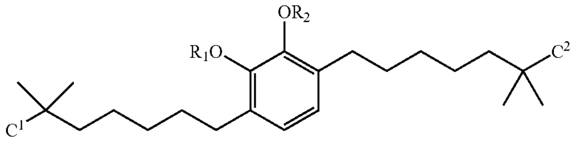 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 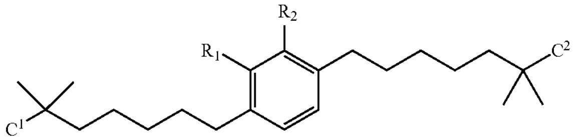 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 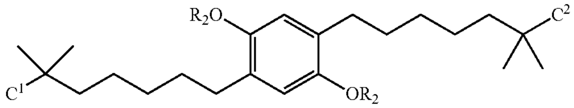 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 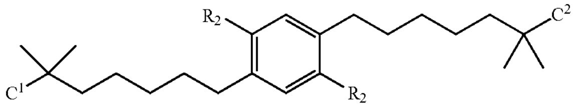 |

TABLE A-13-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 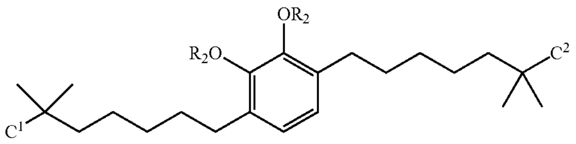 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 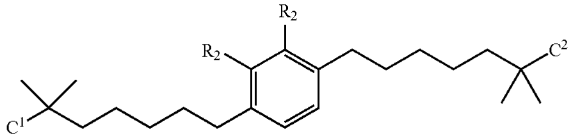 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 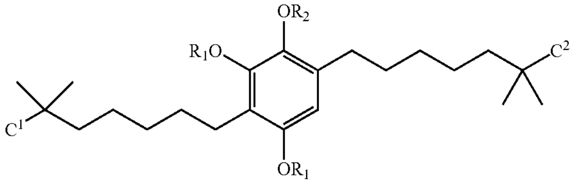 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 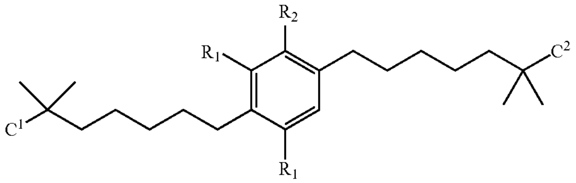 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 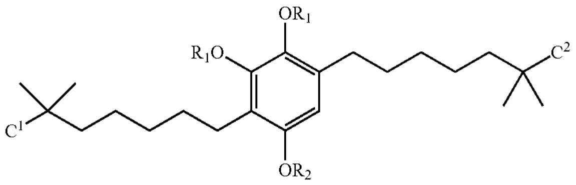 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-13-continued

| Structure |
|---|
| 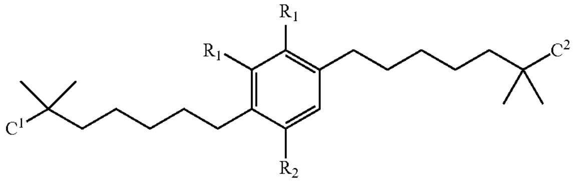 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 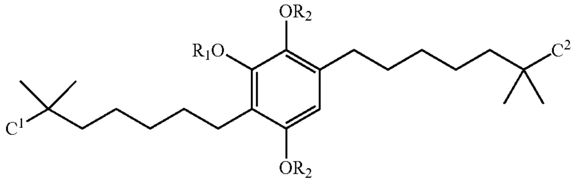 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 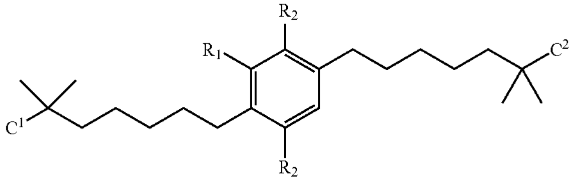 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 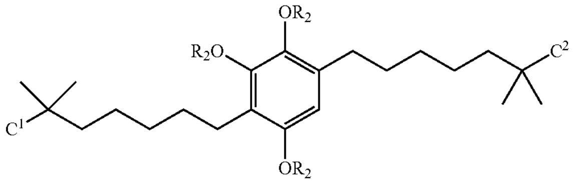 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 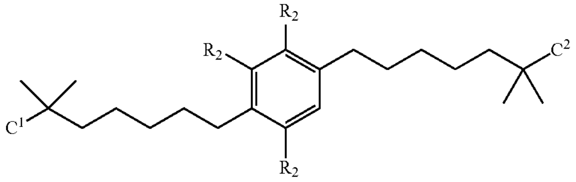 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-13-continued

| Structure |
|---|
| 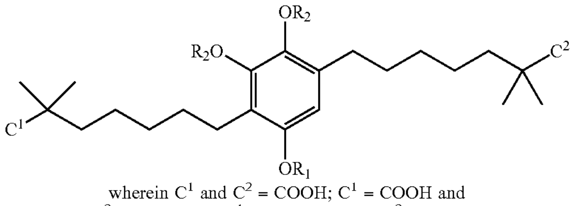 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 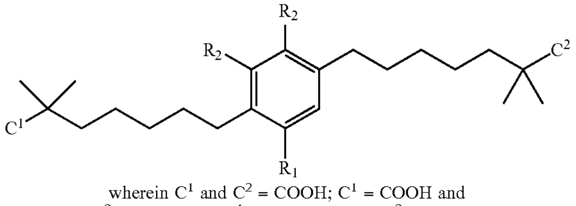 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 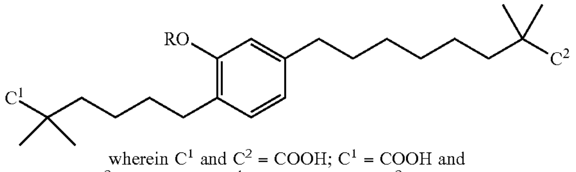 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 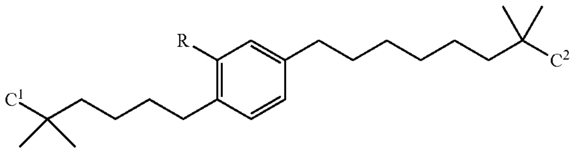 wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 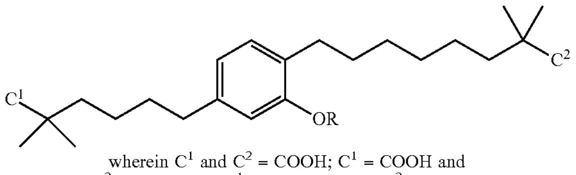 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 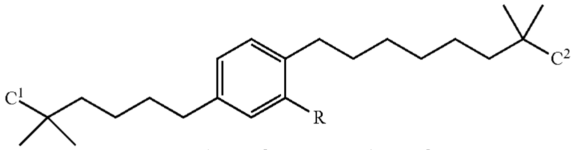 wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |

TABLE A-13-continued

| Structure |
|---|
| 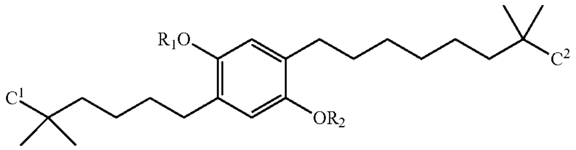 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 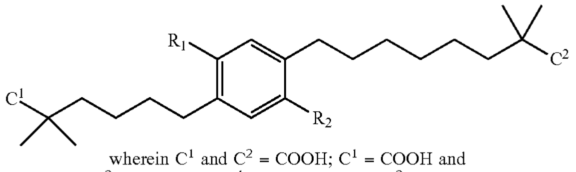 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 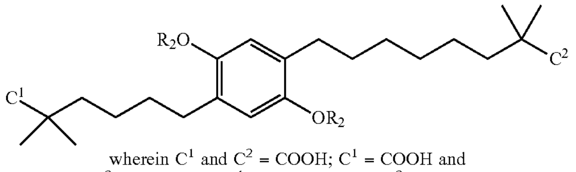 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 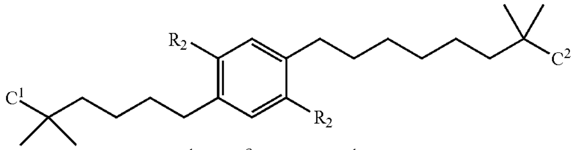 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 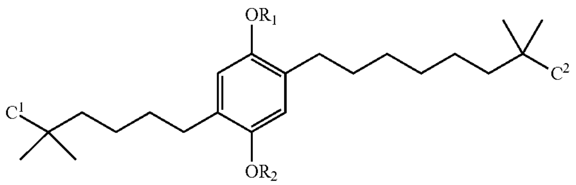 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 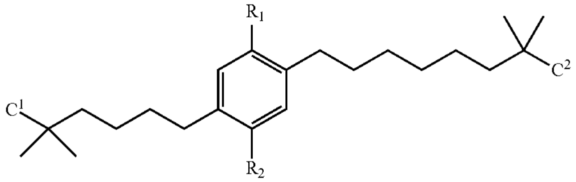 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 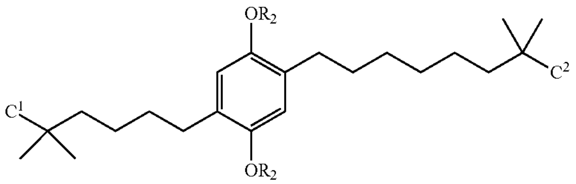 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 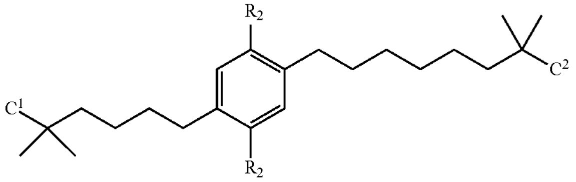 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 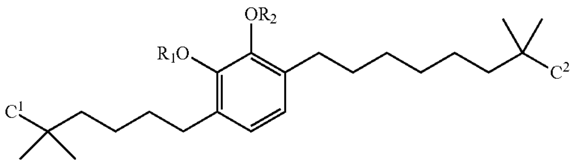 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 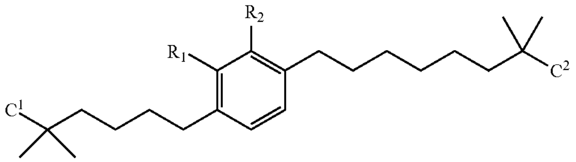 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 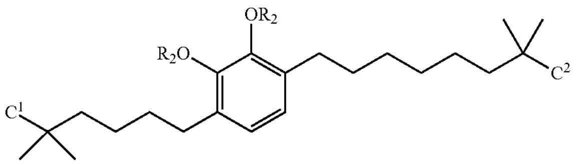 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-13-continued

| Structure |
|---|
| 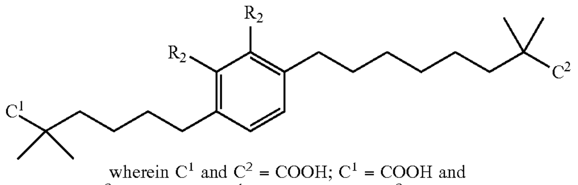 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 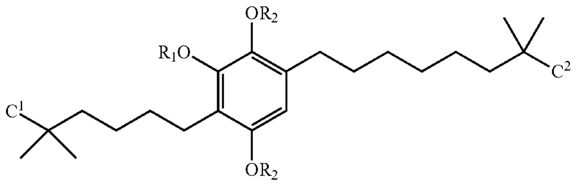 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 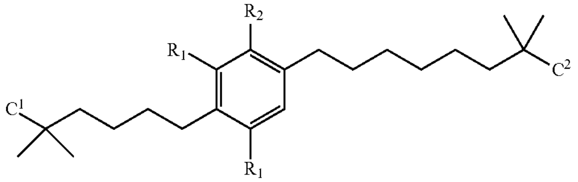 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 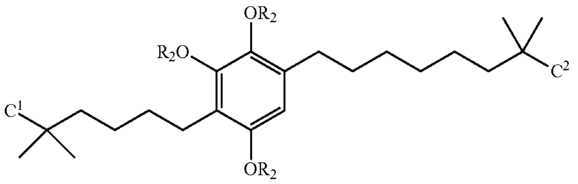 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 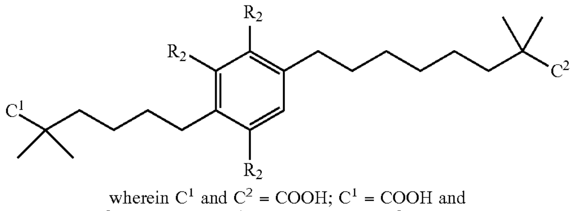 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 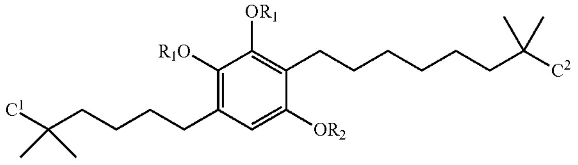 |

TABLE A-13-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 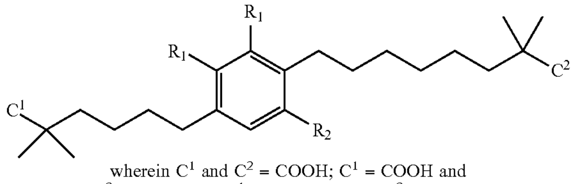 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 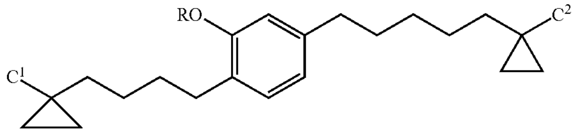 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 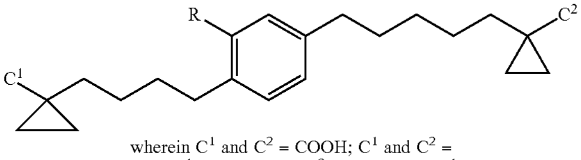 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 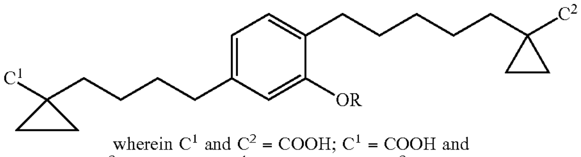 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyll |
| 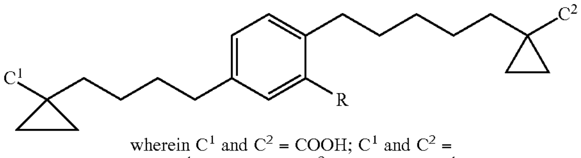 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 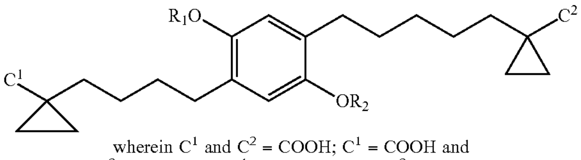 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-13-continued

| Structure |
|---|
| 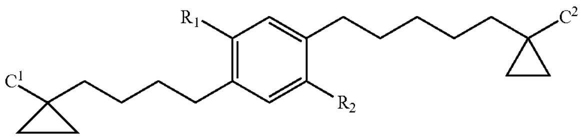 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 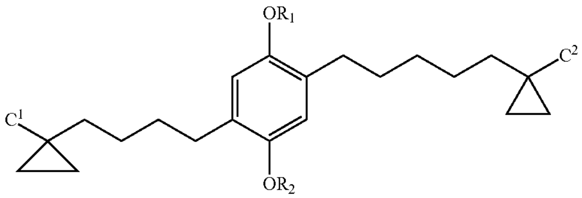 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 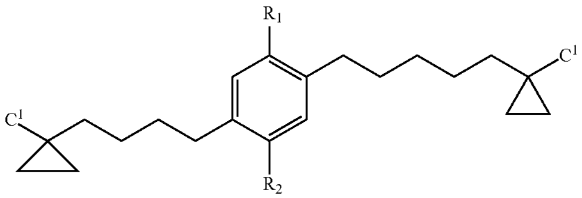 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 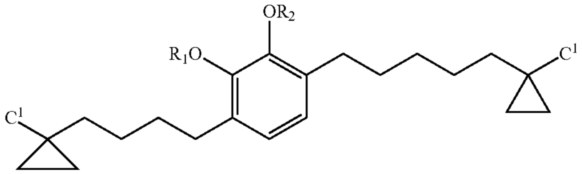 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 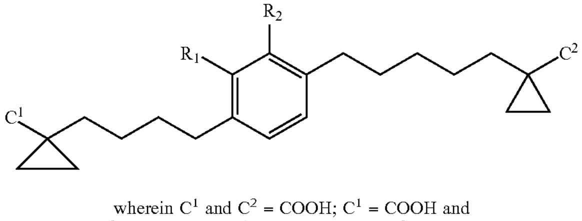 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-13-continued

| Structure |
|---|
| 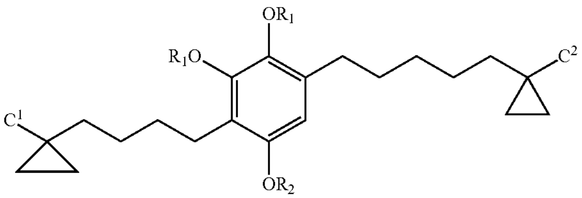 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 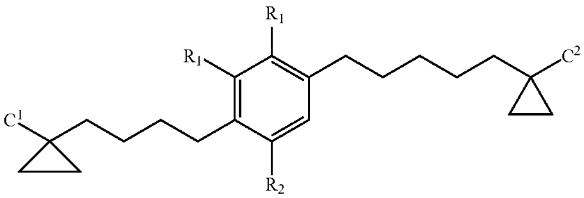 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 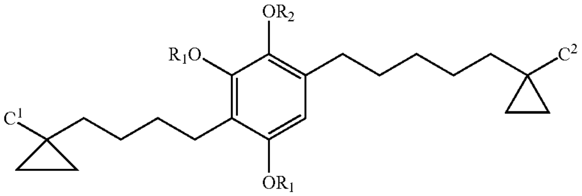 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or R = H and each $R_1$ is independently a (C1-C4)alkyl |
| 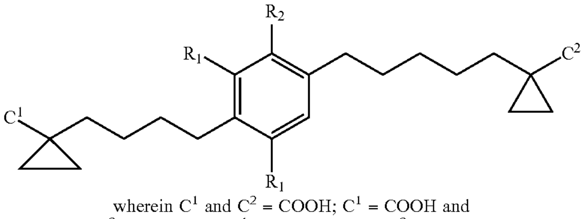 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 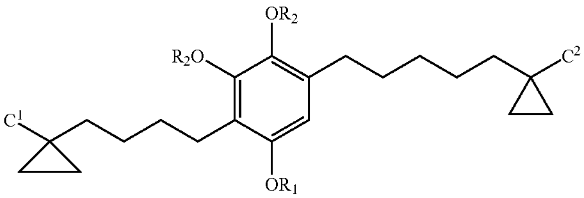 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |

TABLE A-13-continued

Structure

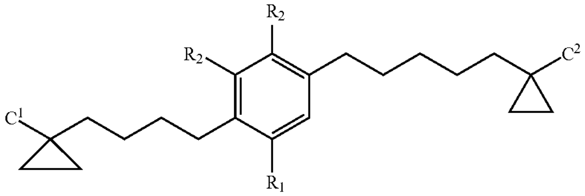

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

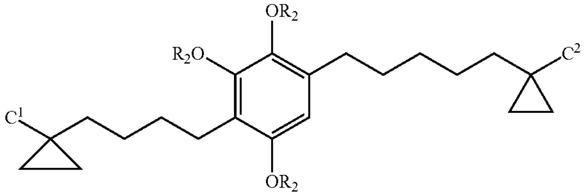

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

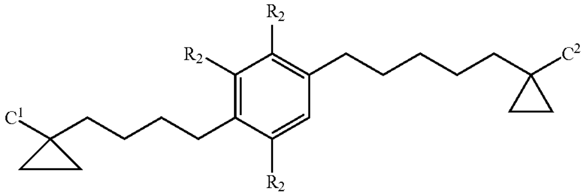

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

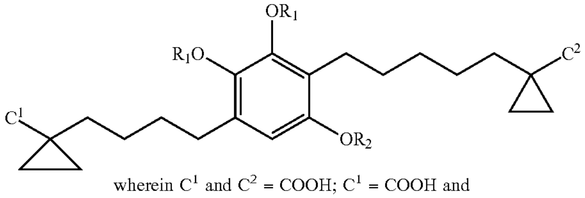

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

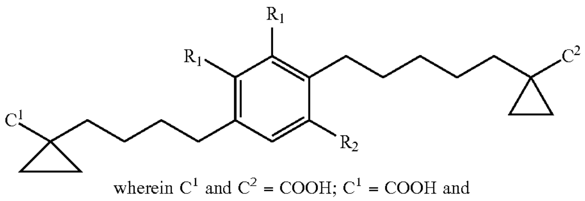

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl TABLE A-13-continued Structure

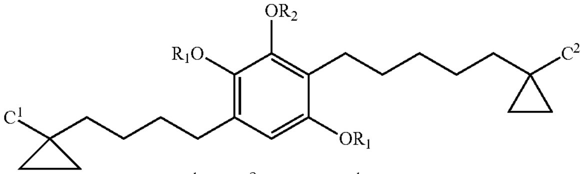

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

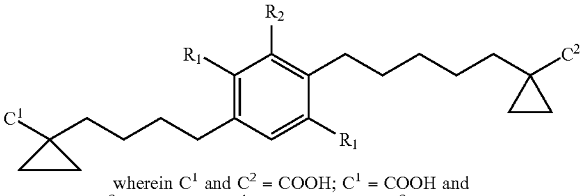

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

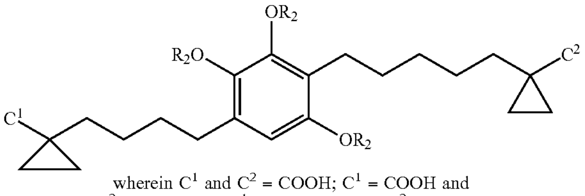

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

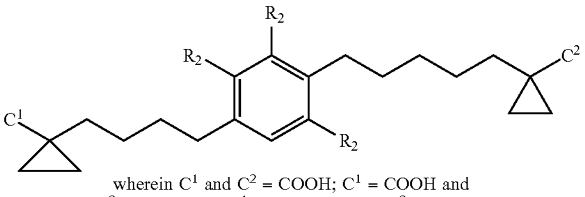

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

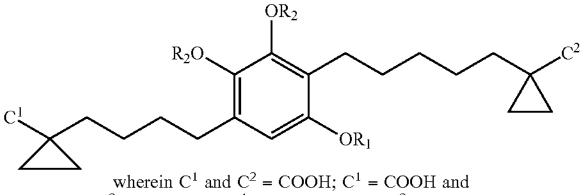

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl

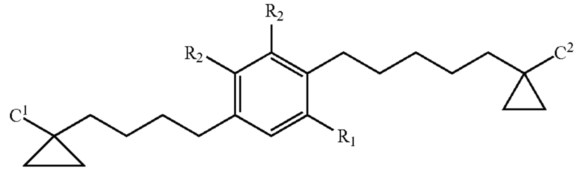

TABLE A-13-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 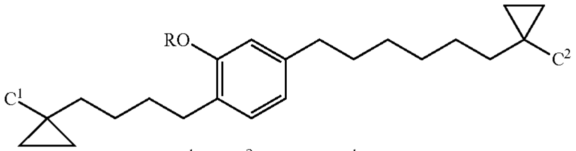 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 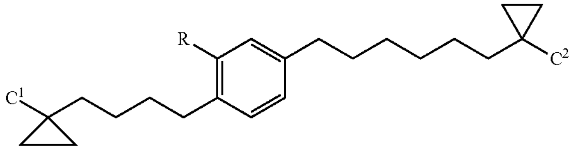 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 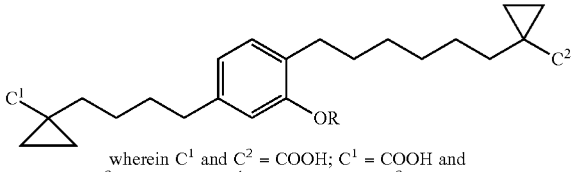 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 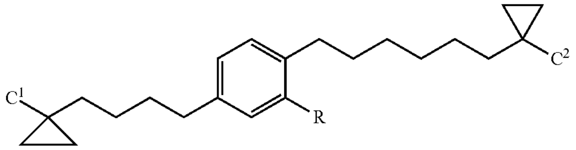 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 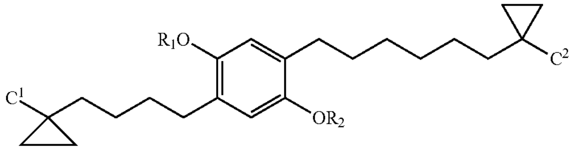 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 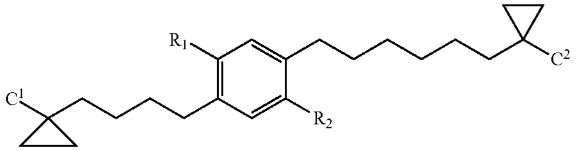 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 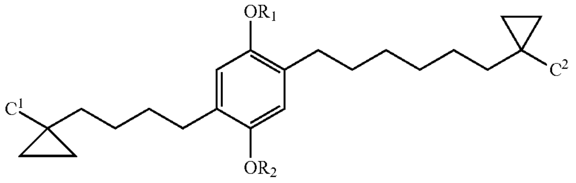 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 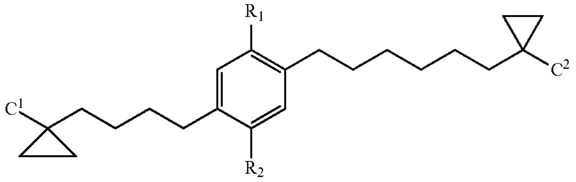 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 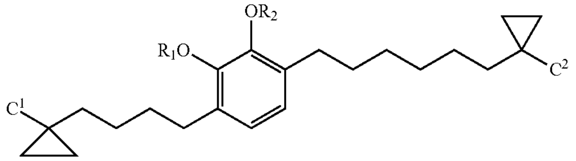 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 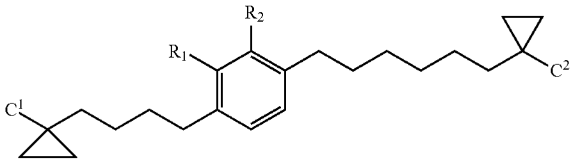 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 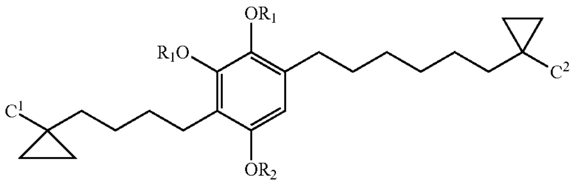 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or R = H and each $R_1$ is independently a (C1-C4)alkyl |

TABLE A-13-continued

| Structure |
| --- |
| 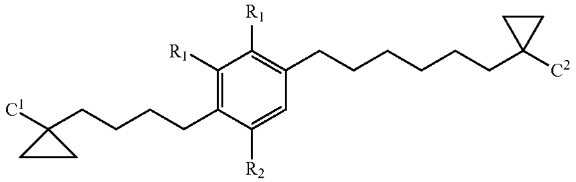 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 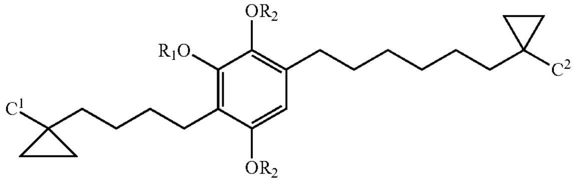 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 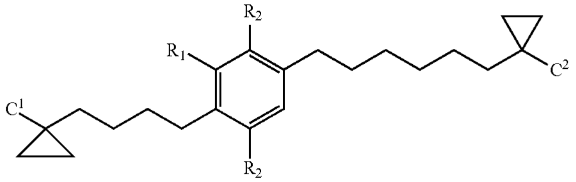 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 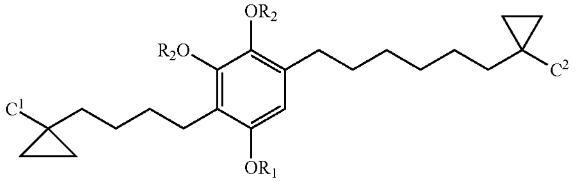 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 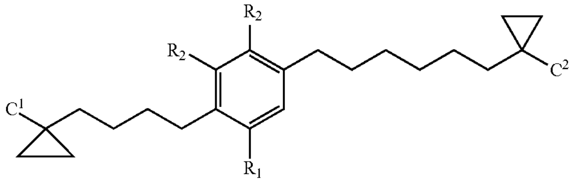 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-13-continued

| Structure |
| --- |
| 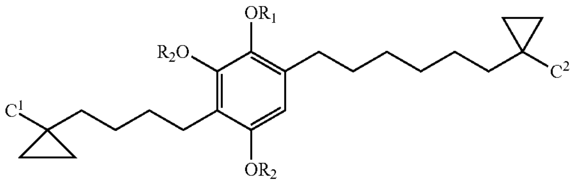 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 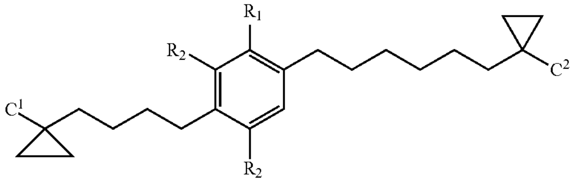 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 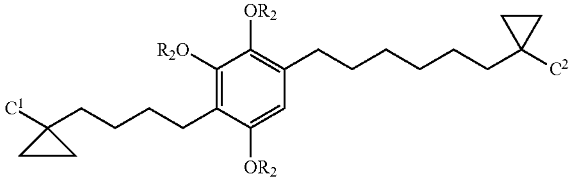 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 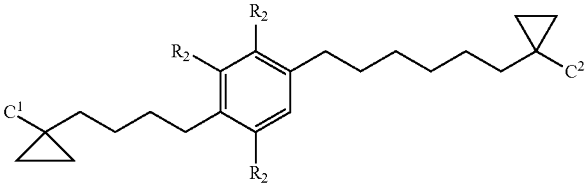 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 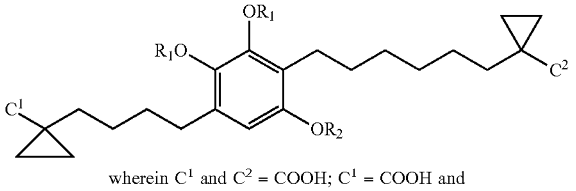 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-13-continued

| Structure |
|---|
| 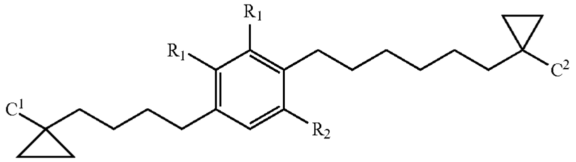 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 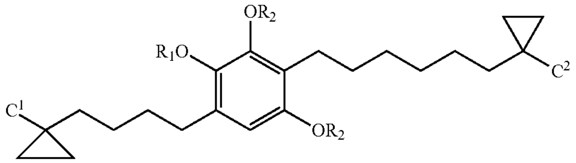 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 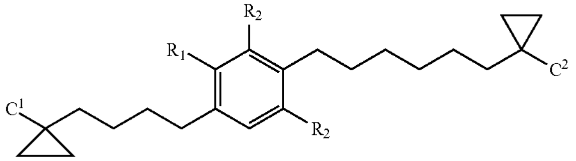 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 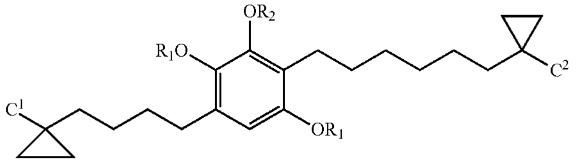 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 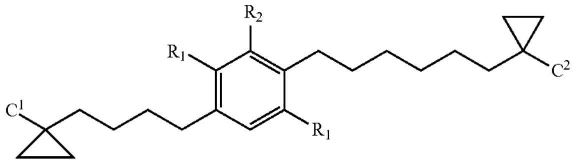 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-13-continued

| Structure |
|---|
| 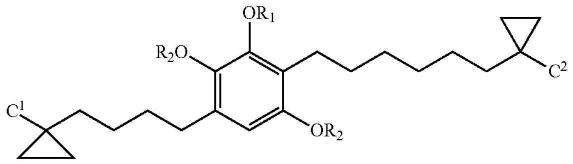 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 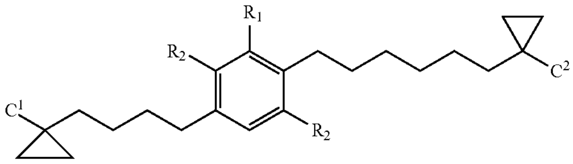 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 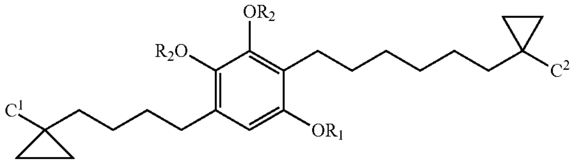 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 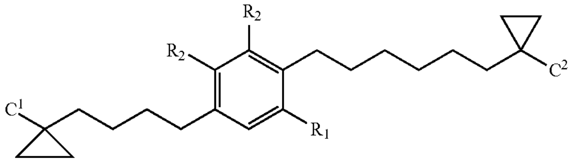 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 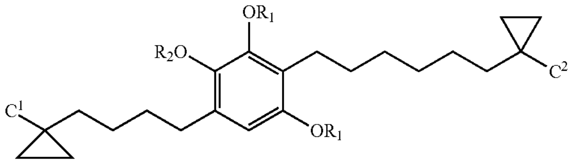 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 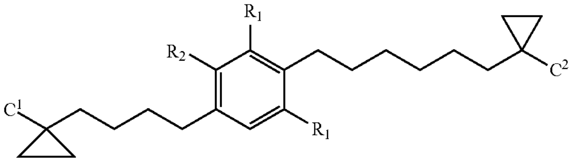 |

TABLE A-13-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 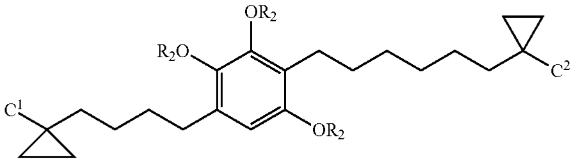 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 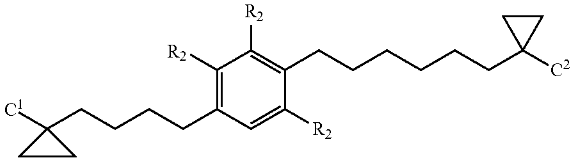 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 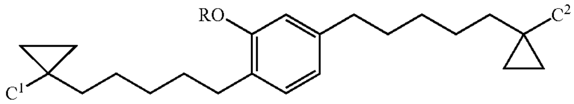 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 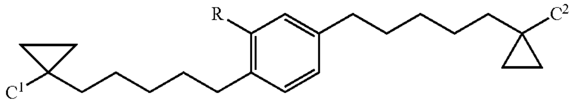 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 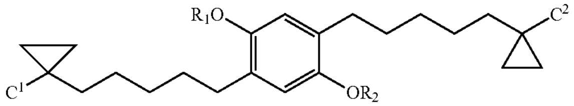 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 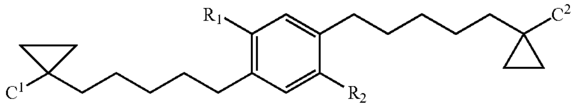 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-13-continued

| Structure |
|---|
| 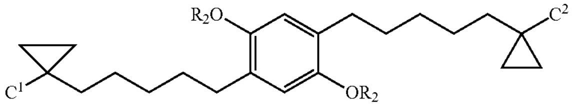 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 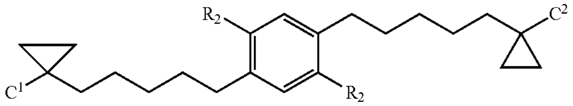 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 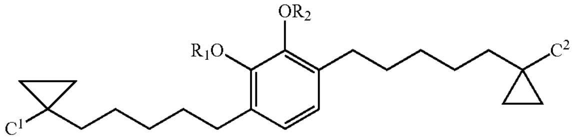 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 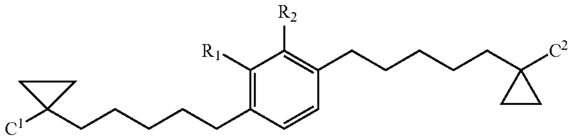 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 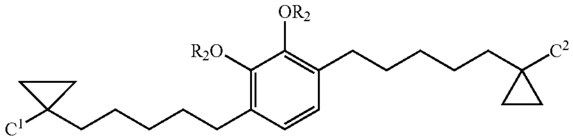 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 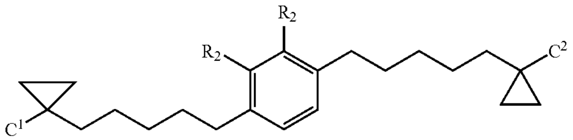 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 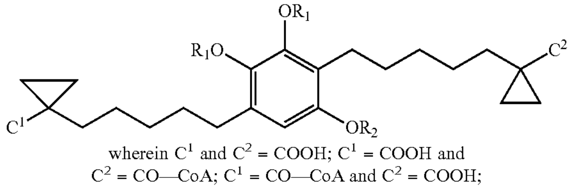 |
| wherein $C^1$ and $C^2$ = COOH; $C^1$ = COOH and $C^2$ = CO—CoA; $C^1$ = CO—CoA and $C^2$ = COOH; |

TABLE A-13-continued

| Structure |
| --- |
| or $C^1$ and $C^2$ = CO—CoA; and wherein each $R_1$ is H and $R_2$ = (C1-C4)alkyl; or R = H and each $R_1$ is independently a (C1-C4)alkyl |
| 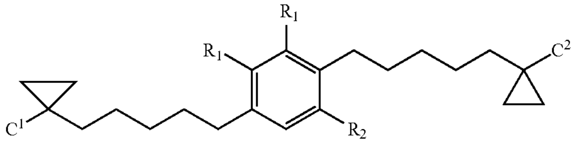 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 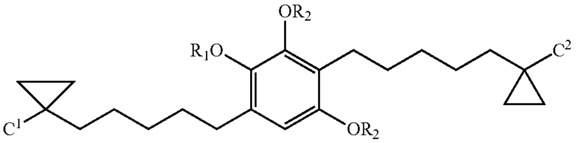 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 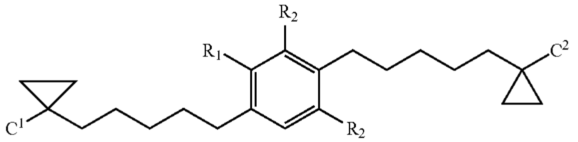 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 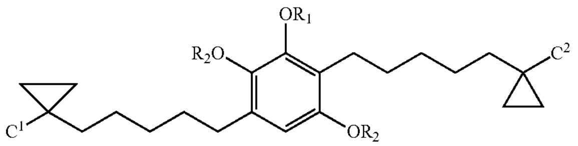 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 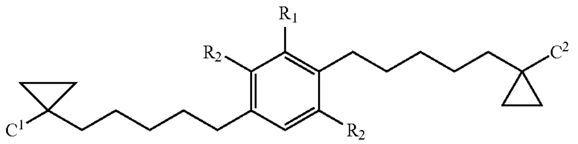 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 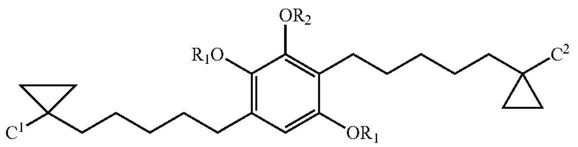 |

TABLE A-13-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 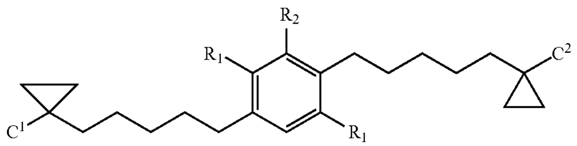 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 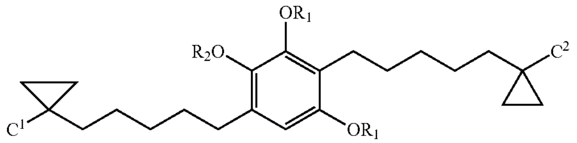 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 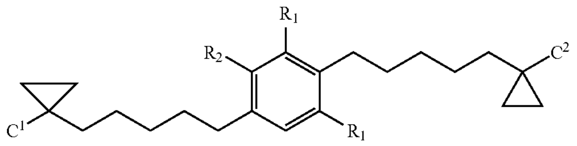 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 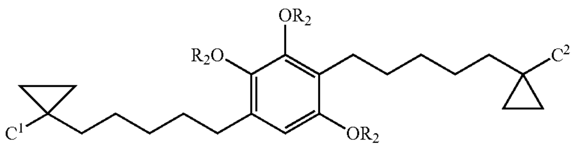 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 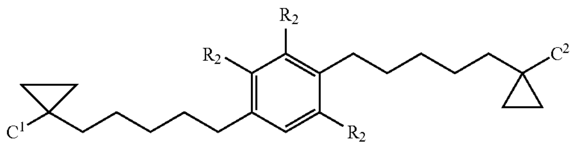 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 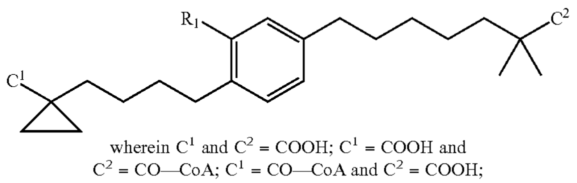 |
| wherein $C^1$ and $C^2$ = COOH; $C^1$ = COOH and $C^2$ = CO—CoA; $C^1$ = CO—CoA and $C^2$ = COOH; |

TABLE A-13-continued

| Structure |
| --- |
| or $C^1$ and $C^2$ = CO—CoA; and wherein R = (C1-C4)alkyl |
| 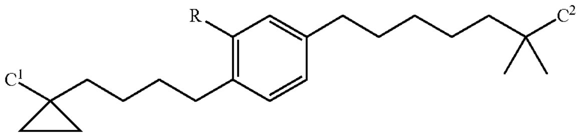 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 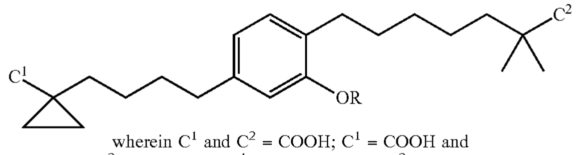 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 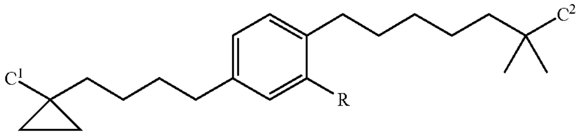 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 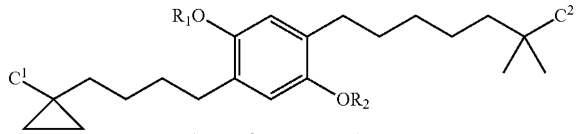 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 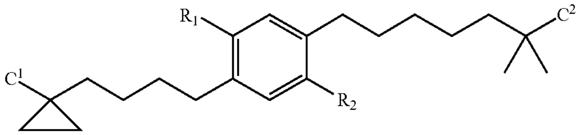 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 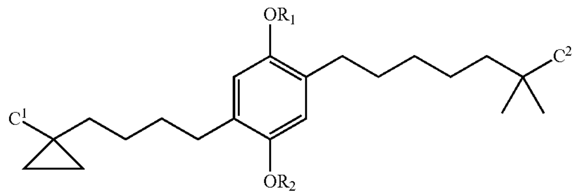 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-13-continued

| Structure |
| --- |
| 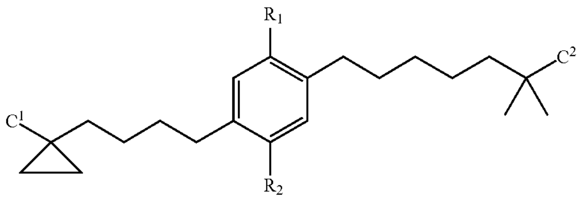 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 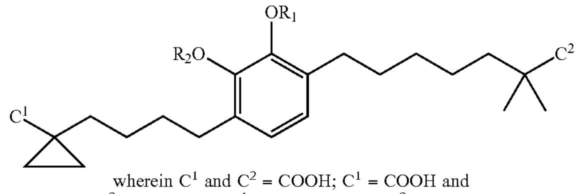 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and R = (C1-C4)alkyl |
| 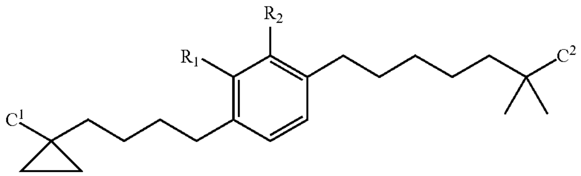 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 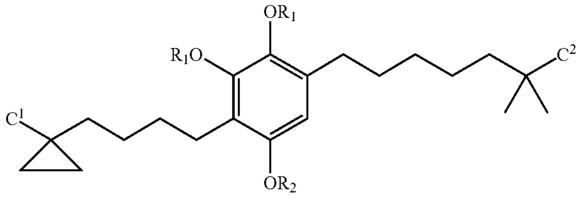 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 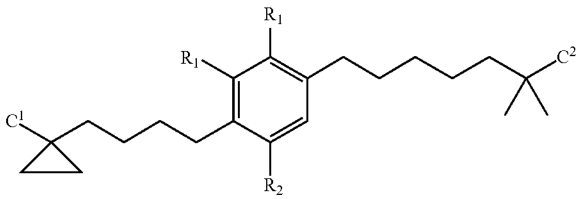 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-13-continued

| Structure |
| --- |
| 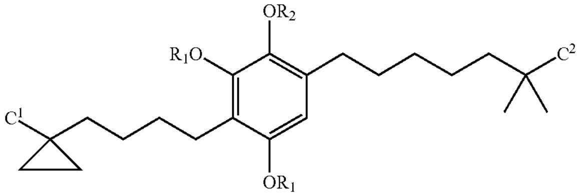 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 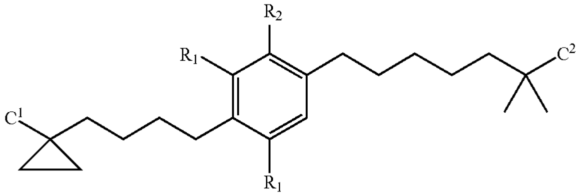 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each R is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 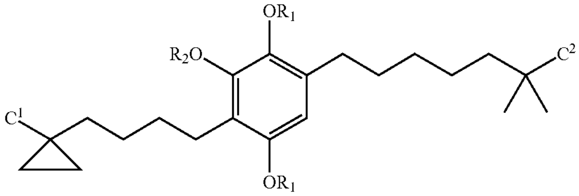 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 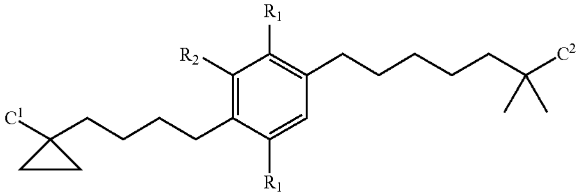 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 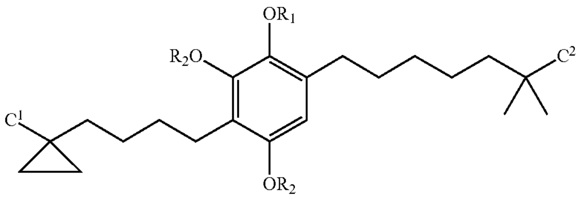 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |

TABLE A-13-continued

| Structure |
| --- |
| 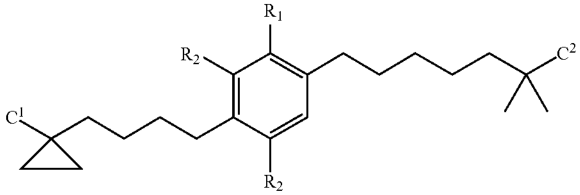 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 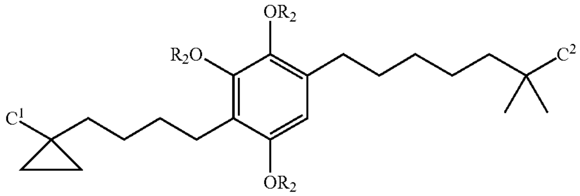 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 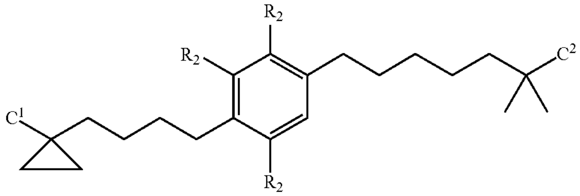 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 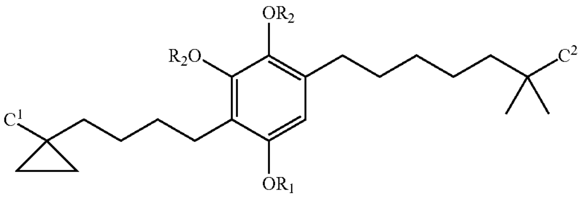 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 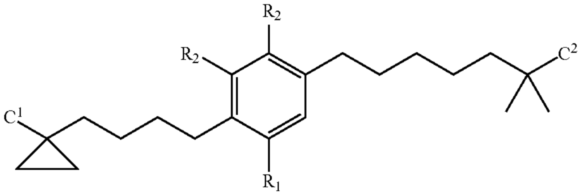 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-13-continued

| Structure |
|---|
| 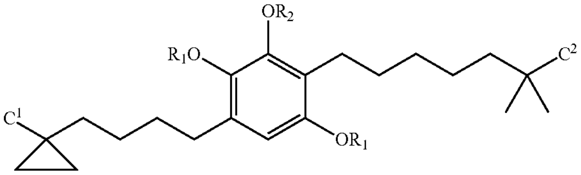 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 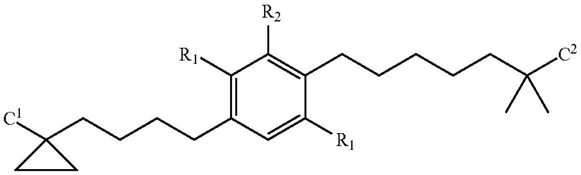 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 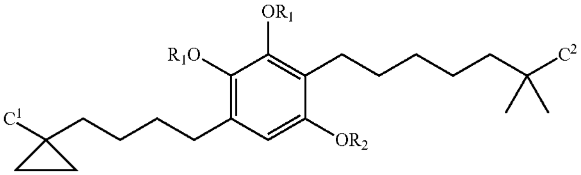 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 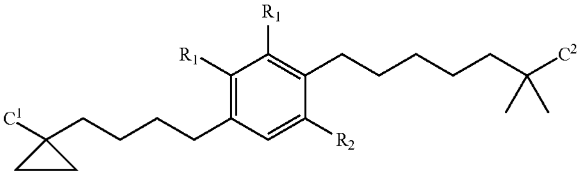 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 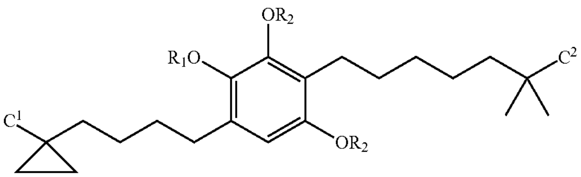 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |

TABLE A-13-continued

| Structure |
|---|
| 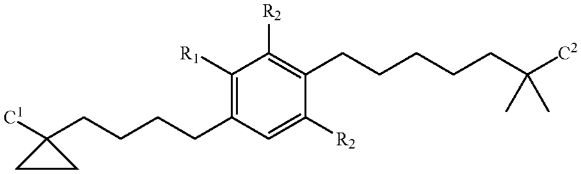 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 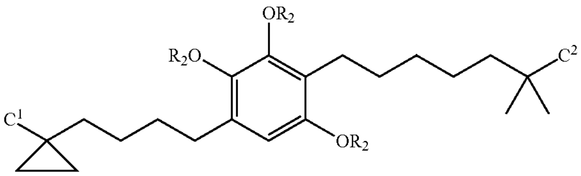 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 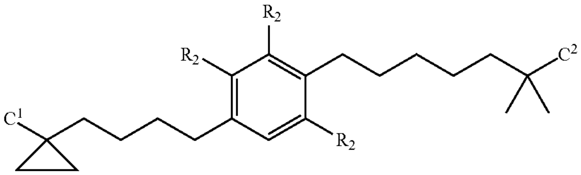 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 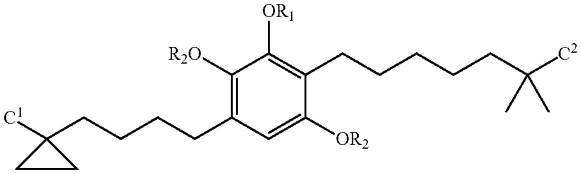 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 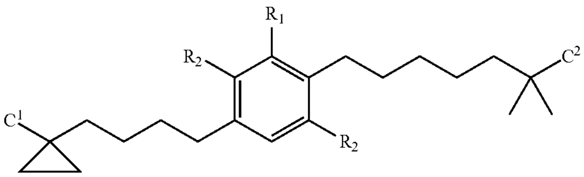 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-13-continued

| Structure |
| --- |
| 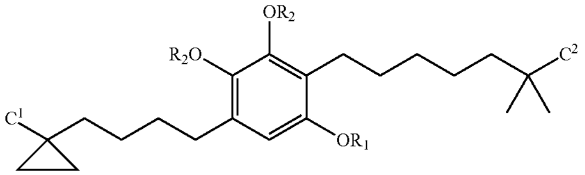 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 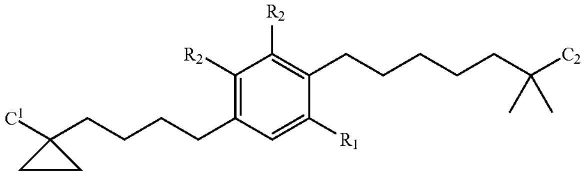 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 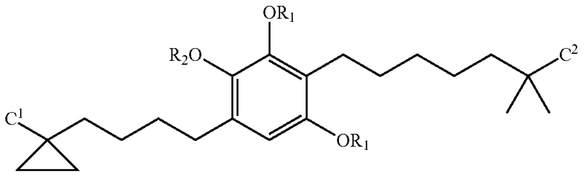 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 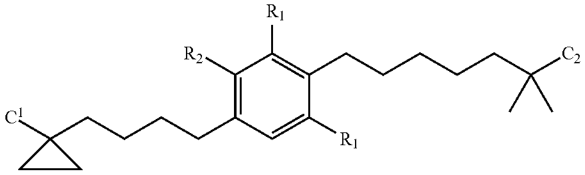 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 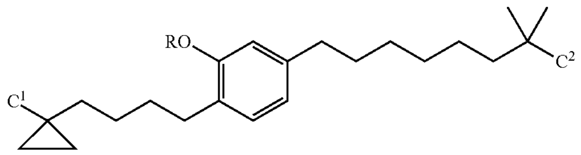 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 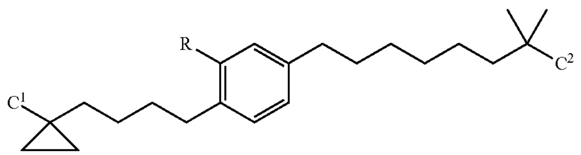 |

TABLE A-13-continued

| Structure |
| --- |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 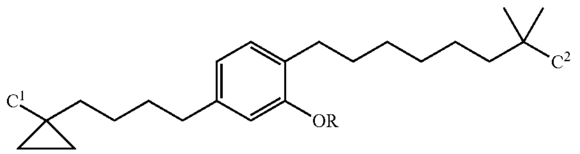 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 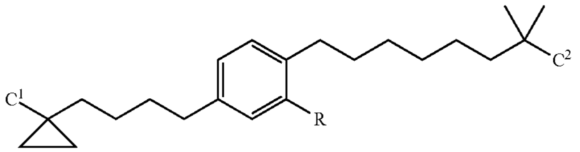 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 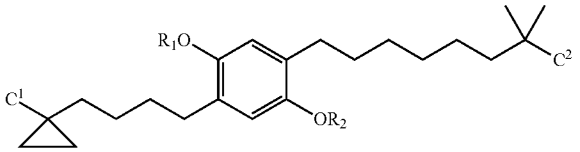 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 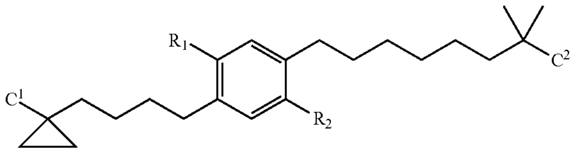 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 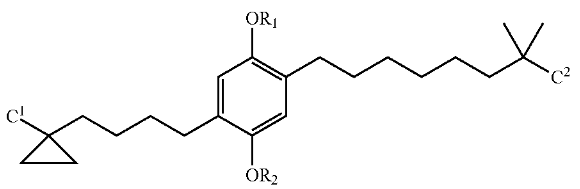 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-13-continued

| Structure |
|---|
| 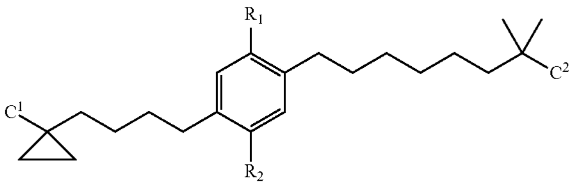 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 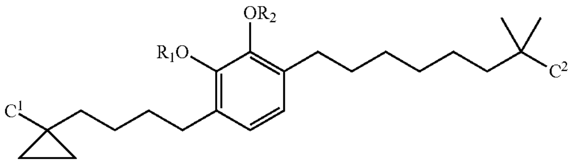 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 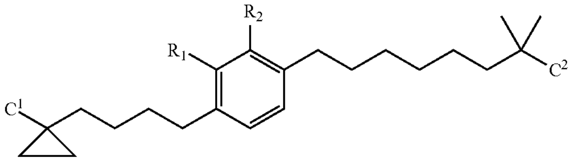 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 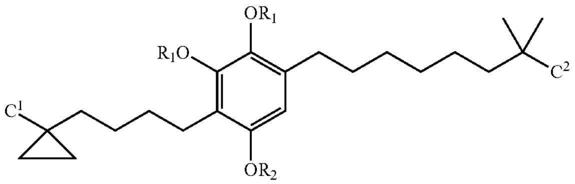 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 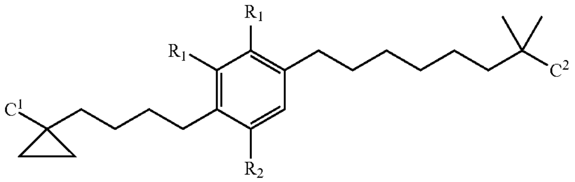 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-13-continued

| Structure |
|---|
| 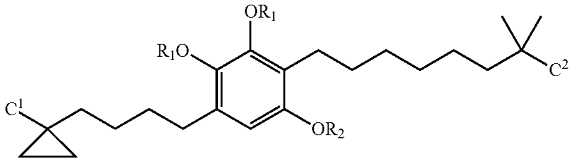 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 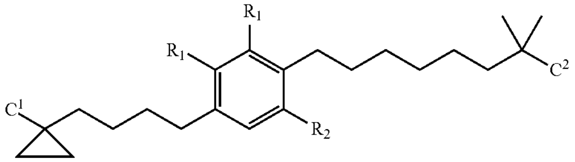 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 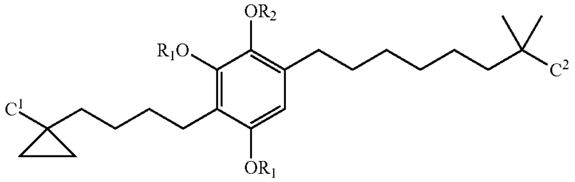 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 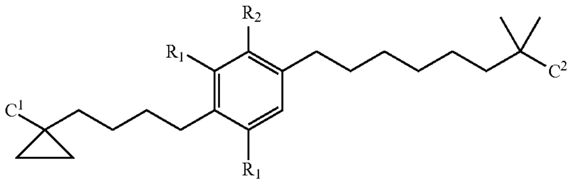 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 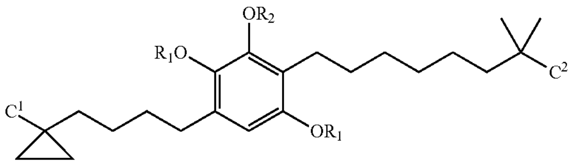 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-13-continued

| Structure |
| --- |
| 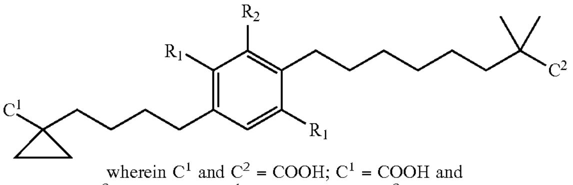 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 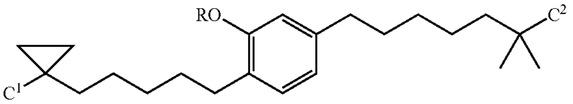 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 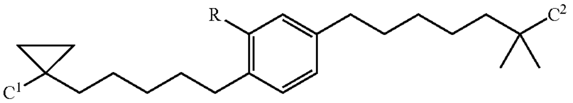 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 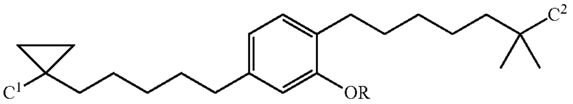 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 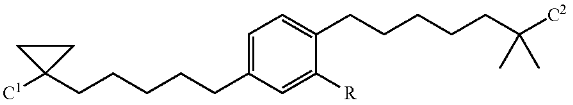 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 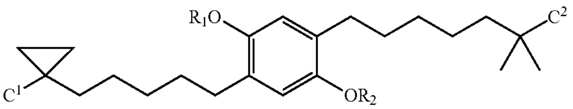 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 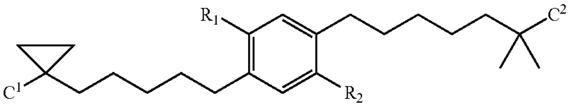 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-13-continued

| Structure |
| --- |
| 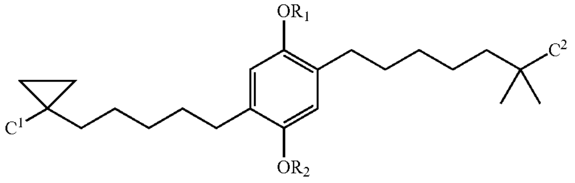 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 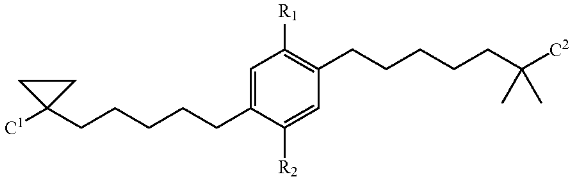 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 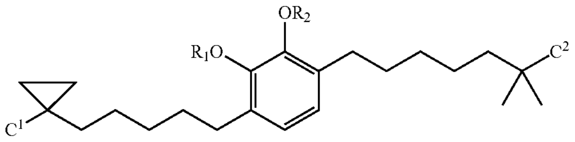 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 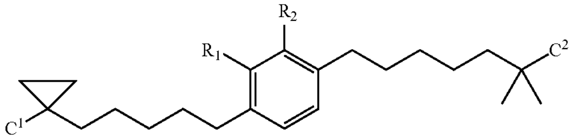 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 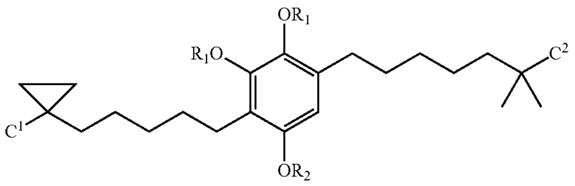 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-13-continued

| Structure |
|---|
| 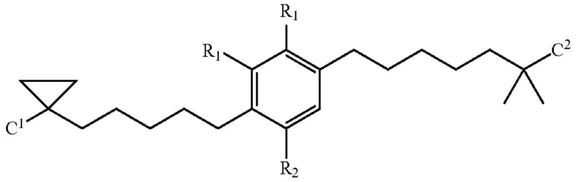 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 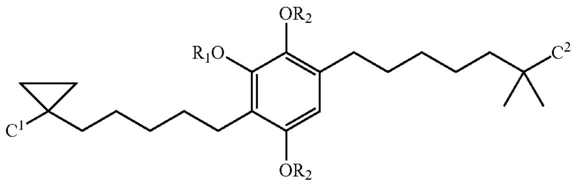 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 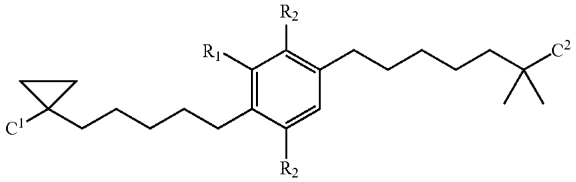 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 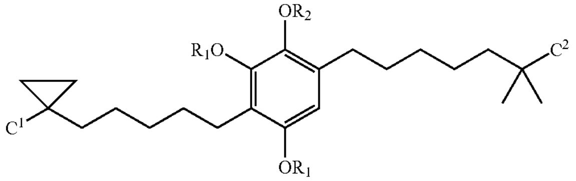 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 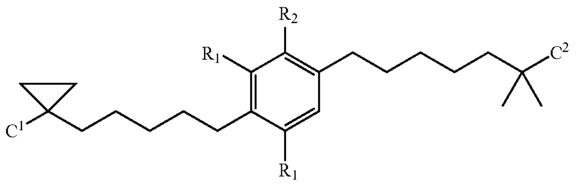 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-13-continued

| Structure |
|---|
| 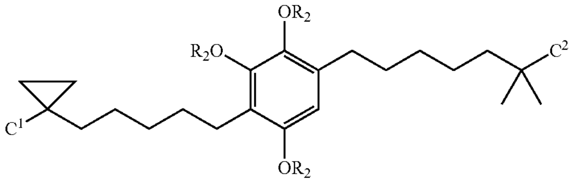 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 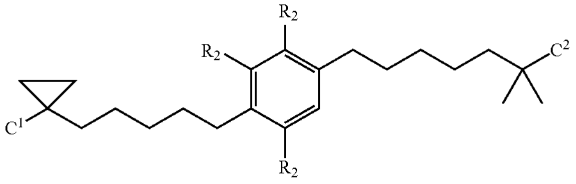 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 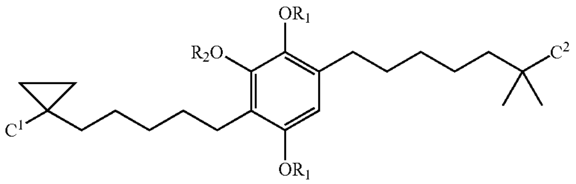 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 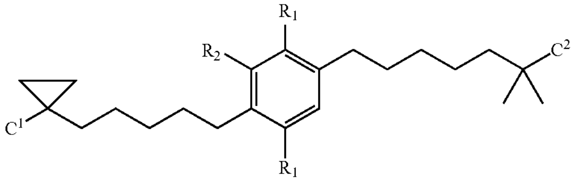 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 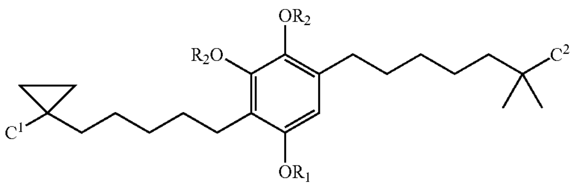 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |

TABLE A-13-continued

| Structure |
|---|
| 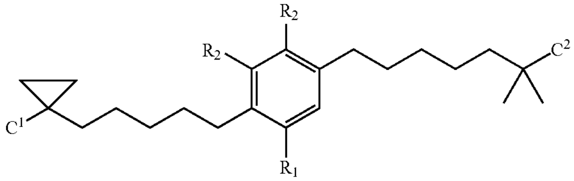 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 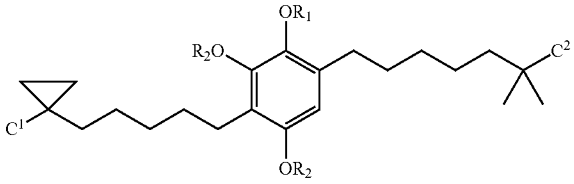 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 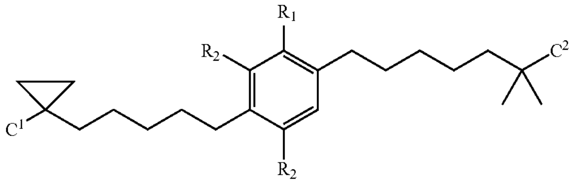 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 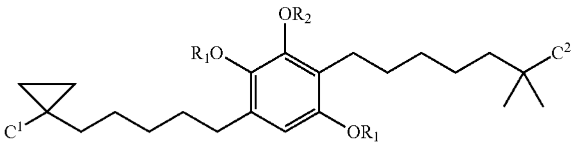 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 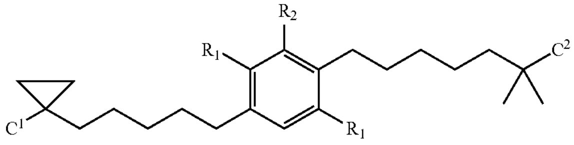 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each R is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-13-continued

| Structure |
|---|
| 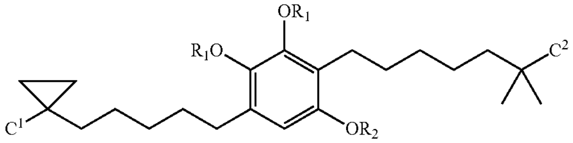 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 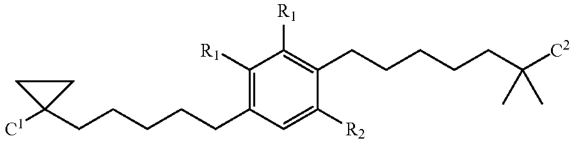 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 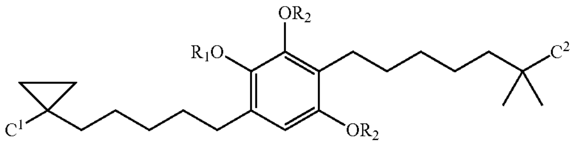 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 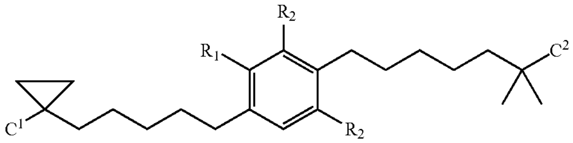 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 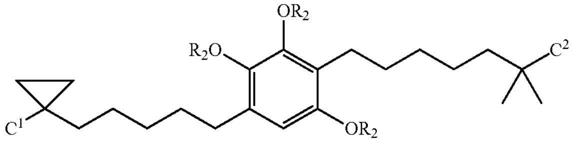 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 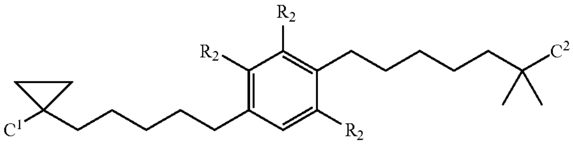 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-13-continued

| Structure |
| --- |
| 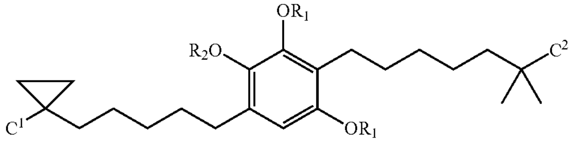 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 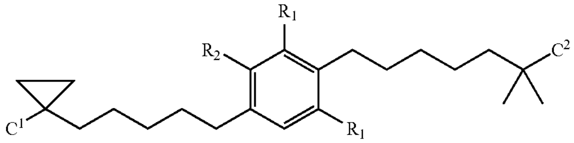 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 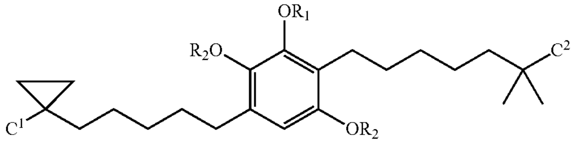 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each R = H and $R_1$ = (C1-C4)alkyl |
| 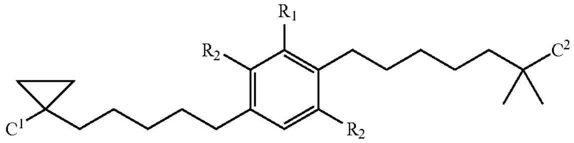 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 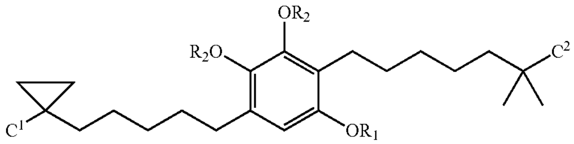 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 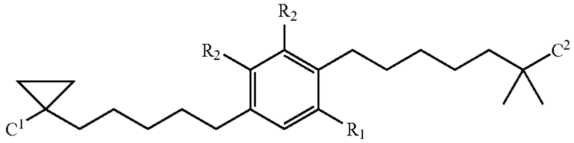 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-13-continued

| Structure |
| --- |
| 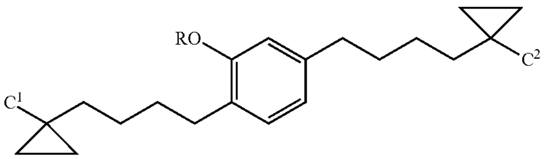 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 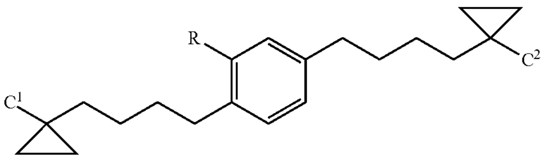 wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO-CoA; and wherein R = F, Cl, Br, or $CF_3$ |
| 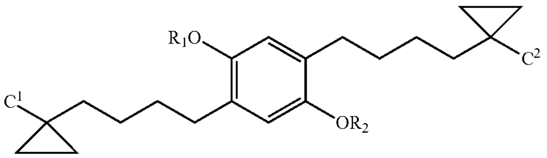 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 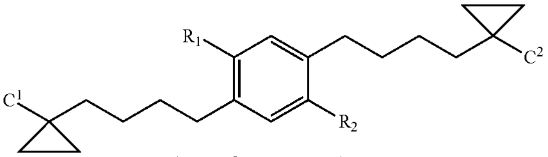 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 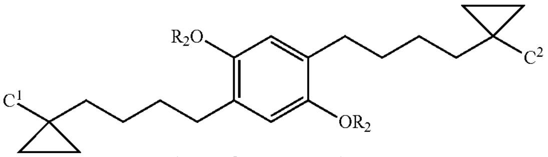 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 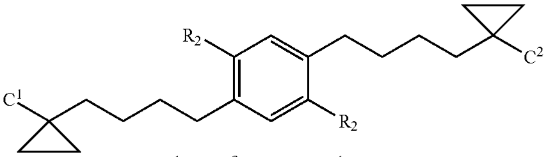 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-13-continued

| Structure |
|---|
| 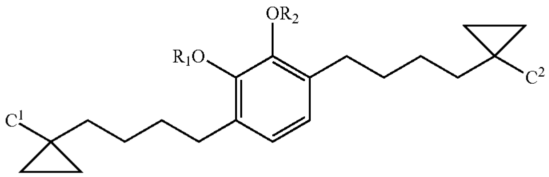 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 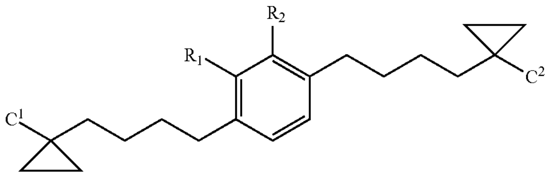 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 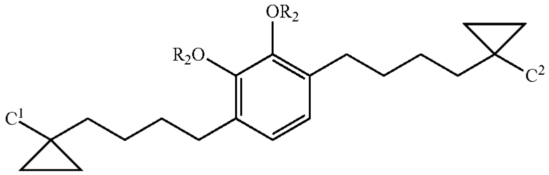 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 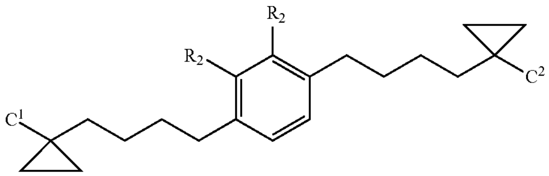 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 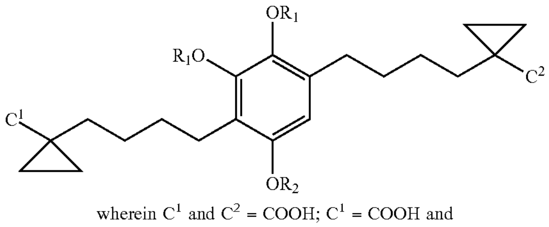 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-13-continued

| Structure |
|---|
| 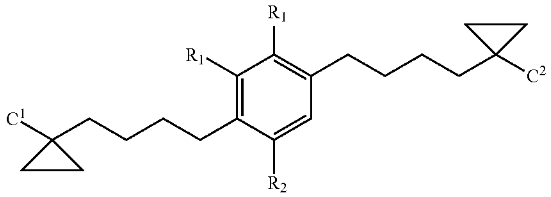 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 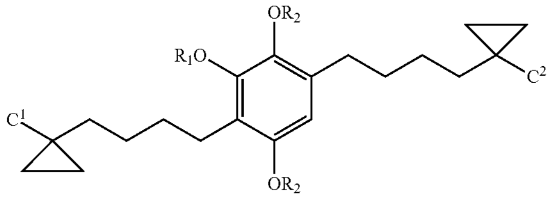 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 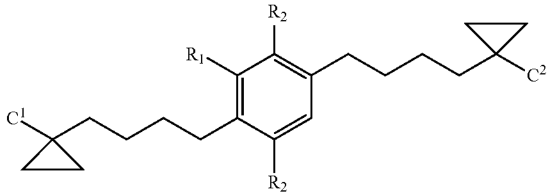 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 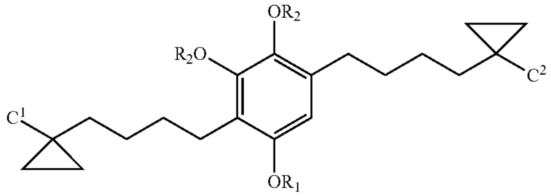 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alky; or each $R_2$ = H and $R_1$ = (C1-C4)alkyl |
| 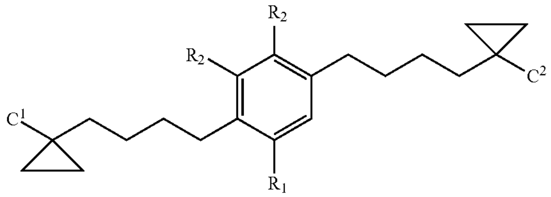 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-13-continued

| Structure |
|---|
| 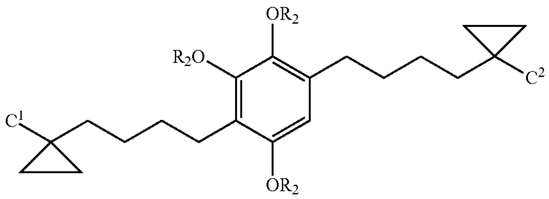 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 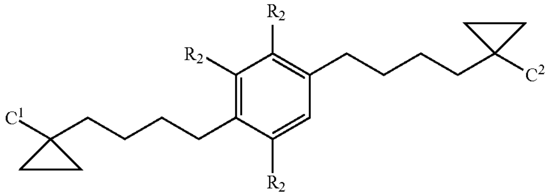 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

In some embodiments, the compound of Formula (ID) or (IF), has any one of the structures shown in Table A-14 and defined by $C^1$ and $C^2$, and defined by R, $R^1$ and $R^2$, where present, or a pharmaceutically acceptable salt or solvate thereof. In some embodiments, R of the compound of Table A-14 is $CH_3$. In some embodiments, one or more of R, $R_1$ and $R_2$ of the compound of Table A-14 is $CH_3$. In some embodiments, one or more of R, $R_1$ and $R_2$ of the compound of Table A-14 is F. In some embodiments, one or more of R, $R_1$ and $R_2$ of the compound of Table A-14 is Cl. In some embodiments, one or more of R, $R_1$ and $R_2$ of the compound of Table A-14 is Br. In some embodiments, one or more of R, $R_1$ and $R_2$ of the compound of Table A-14 is $CF_3$.

In some embodiments, the pharmaceutically acceptable salt of a compound having any one of the structures shown in Table A-14 and defined by $C^1$ and $C^2$, and defined by R, $R_1$ and $R_2$, where present, is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

TABLE A

| Structure |
|---|
| 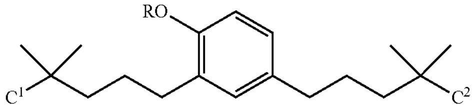 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 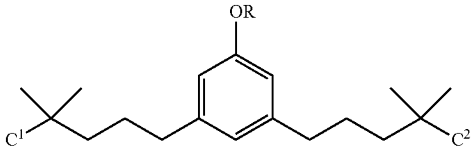 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 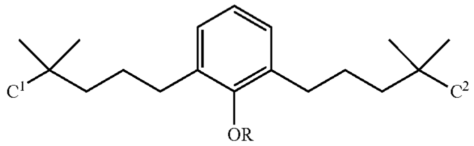 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
| --- |
| 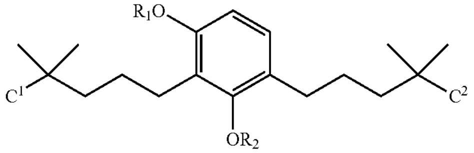 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and R2 = (C1-C4)alkyl; or $R_2$ = H and $R_1$ = (C1-C4)alkyl |
| 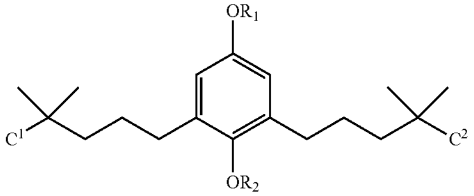 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 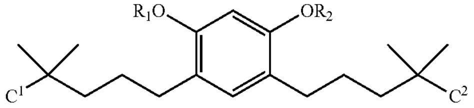 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 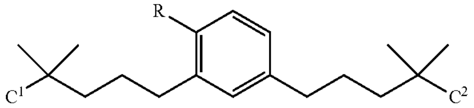 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 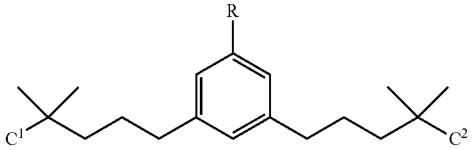 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 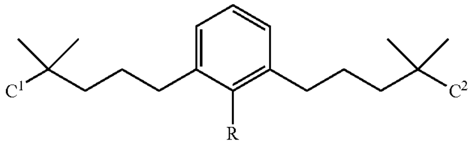 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
| --- |
| 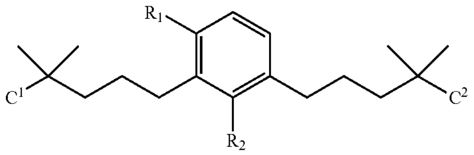 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 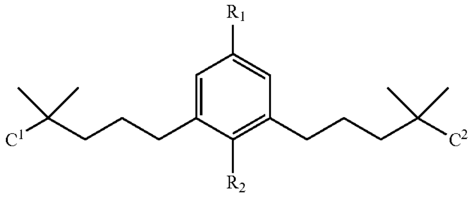 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and R = H or (C1-C4)alkyl |
| 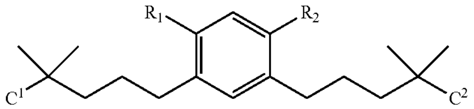 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 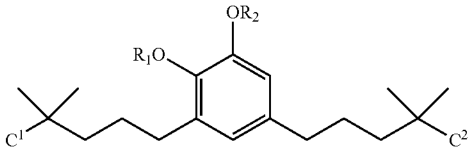 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 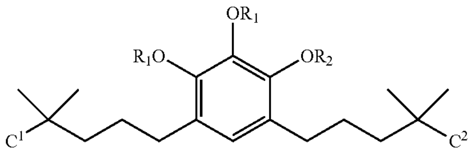 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 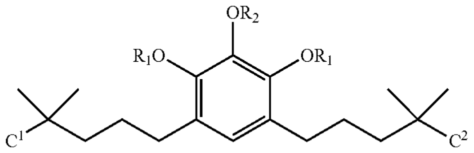 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 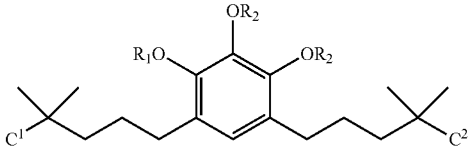 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 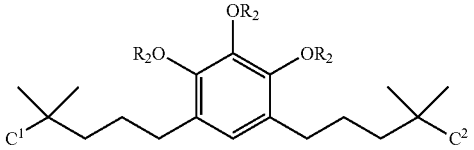 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 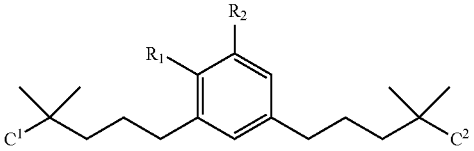 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 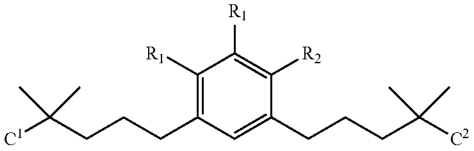 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 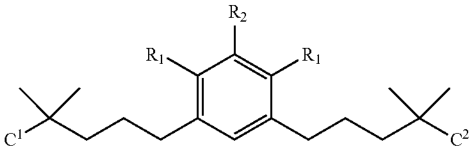 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 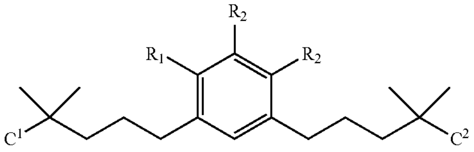 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 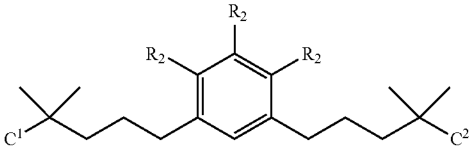 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 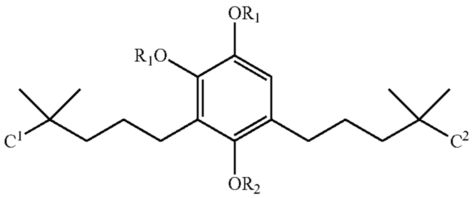 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 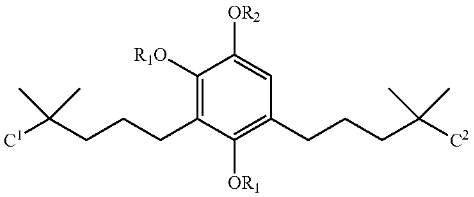 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 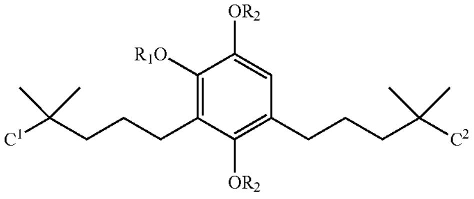 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 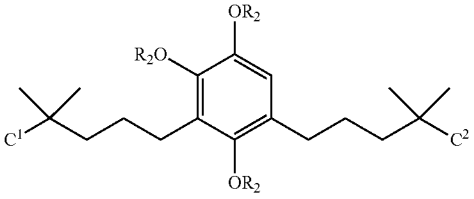 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 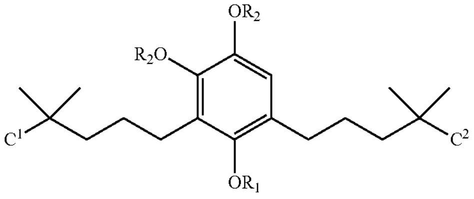 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 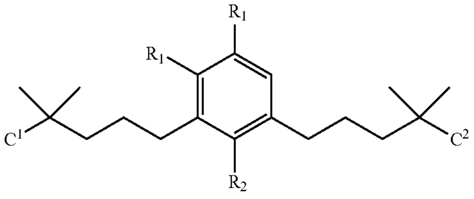 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 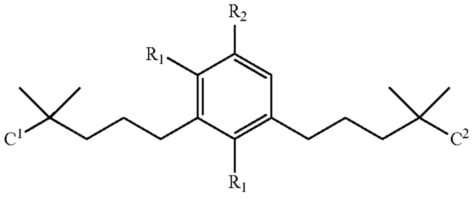 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 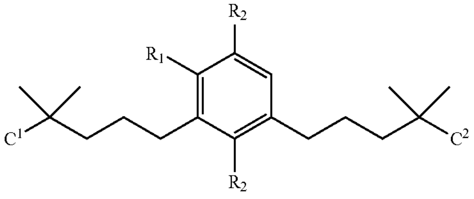 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 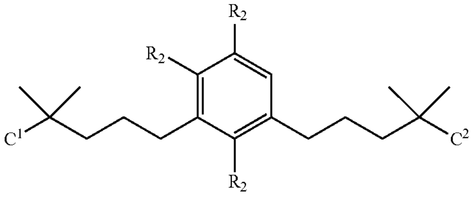 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 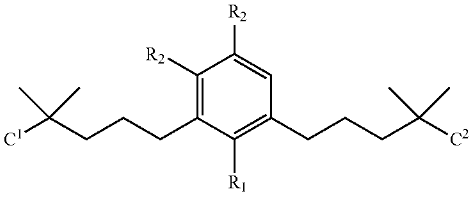 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
|---|
| 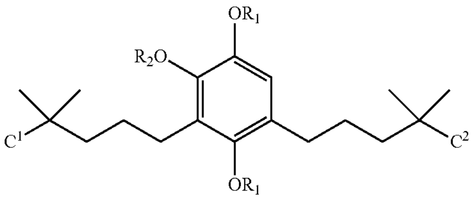 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 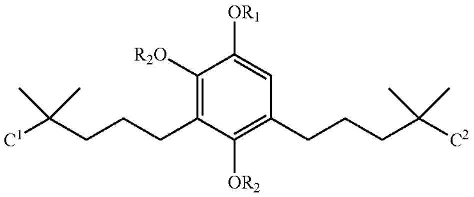 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 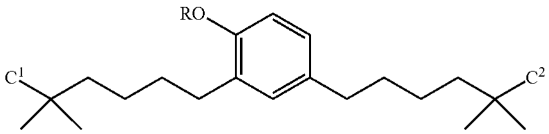 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 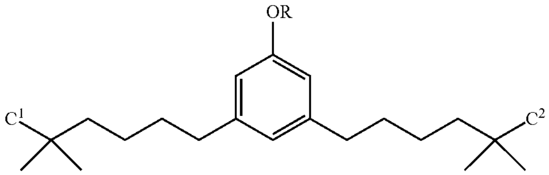 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 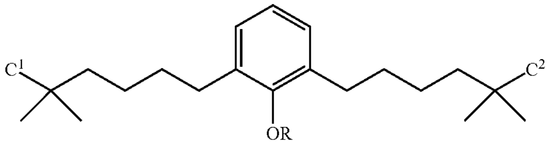 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 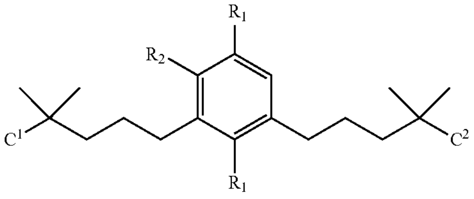 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 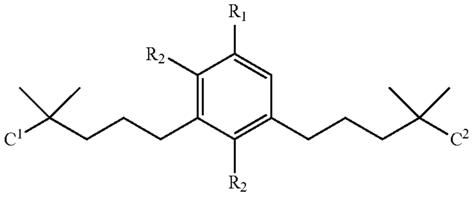 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 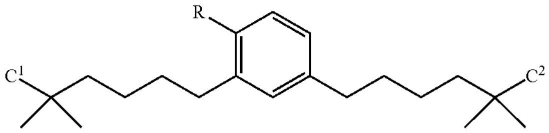 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 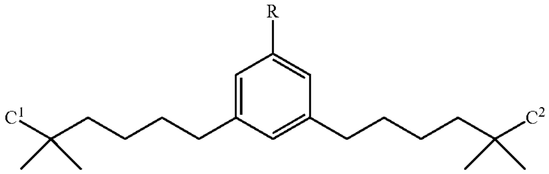 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 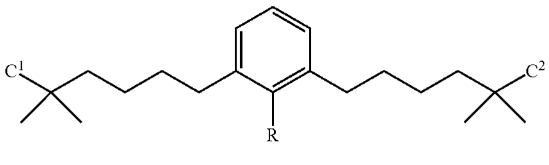 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 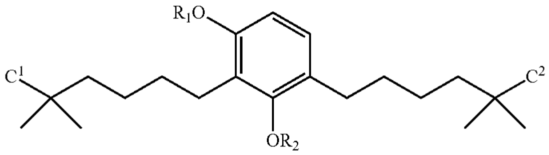 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 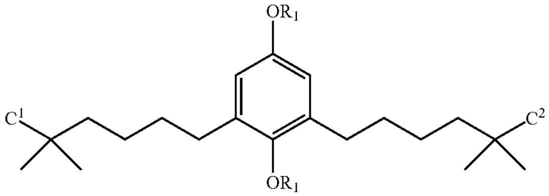 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 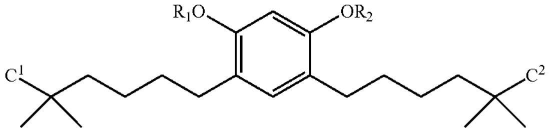 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 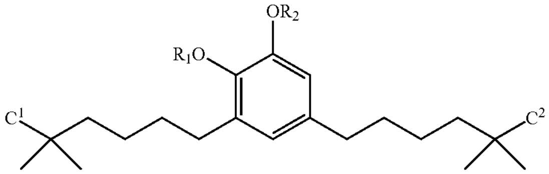 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 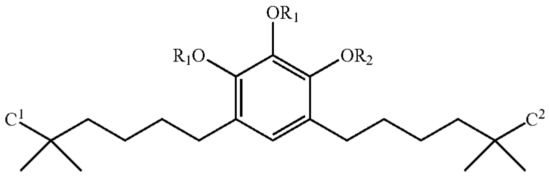 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 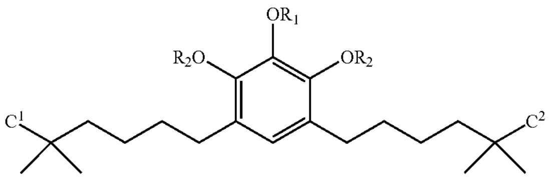 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 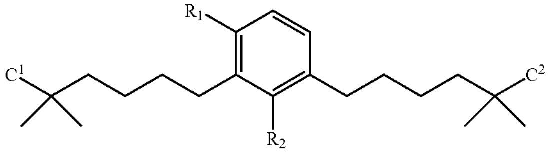 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 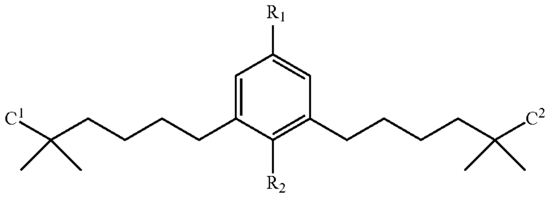 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or CF3 and $R_2$ = H or (C1-C4)alkyl; or $R_2$ = F, Cl, Br, or $CF_3$ and $R_1$ = H or (C1-C4)alkyl |
| 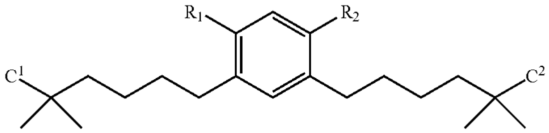 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 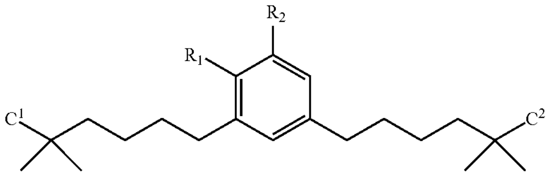 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 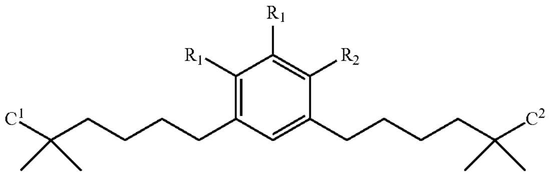 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 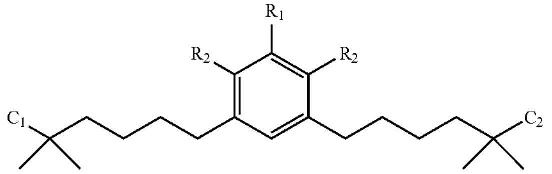 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 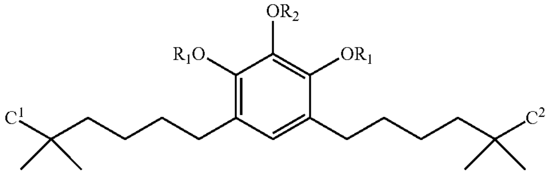 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 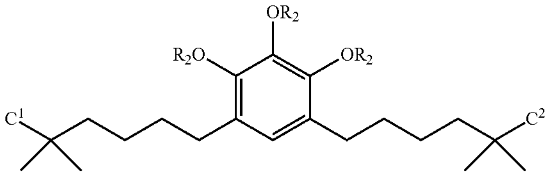 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 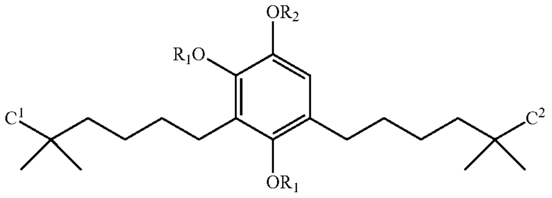 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 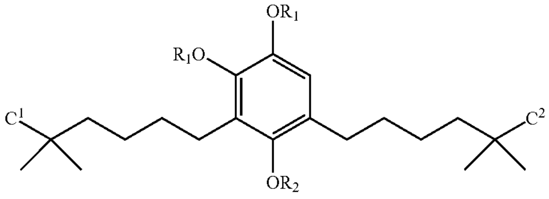 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 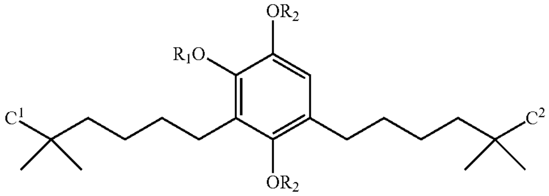 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 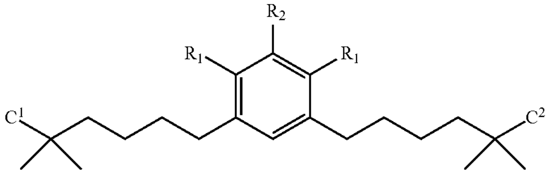 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 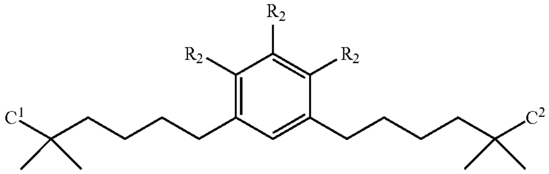 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
| --- |
| 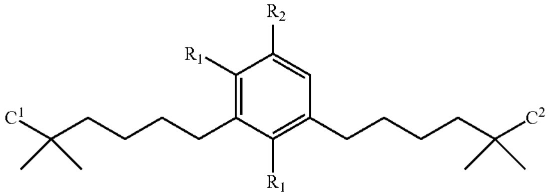 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 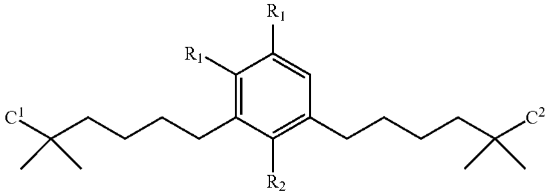 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 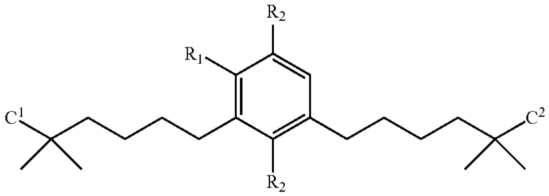 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 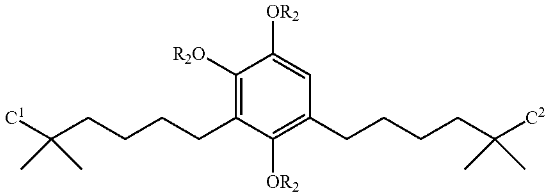 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-continued

| Structure |
| --- |
| 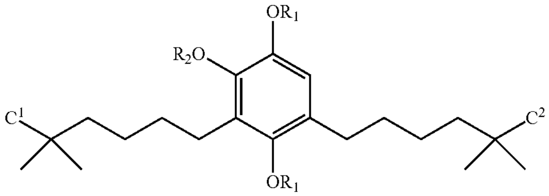 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 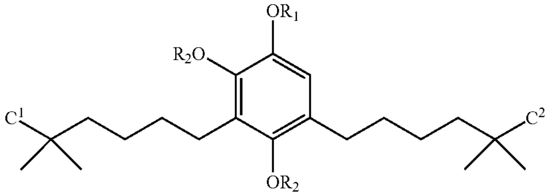 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 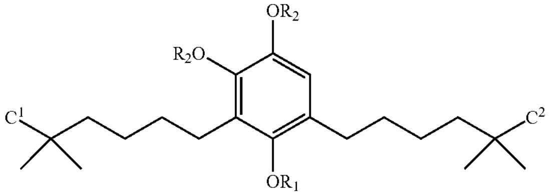 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 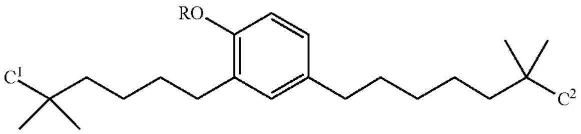 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 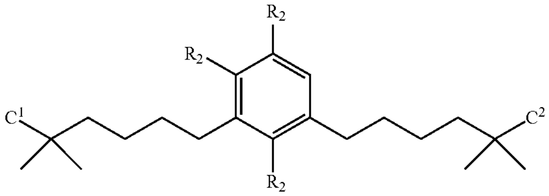 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
|---|
| 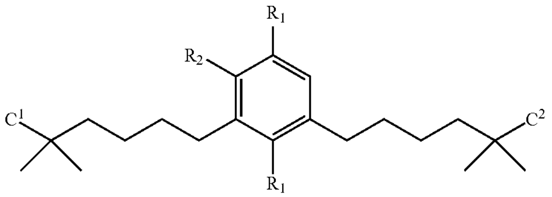 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 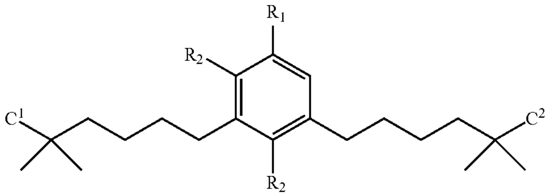 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 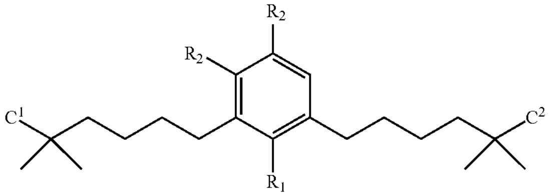 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and$R_1$ = H or (C1-C4)alkyl |
| 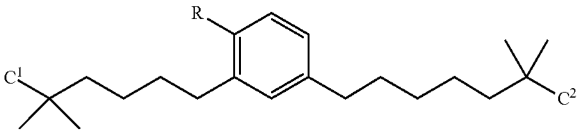 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 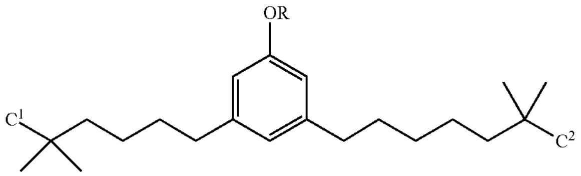 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 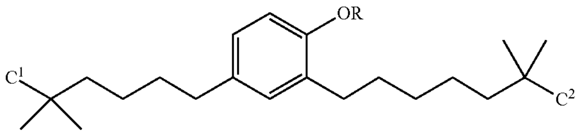 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 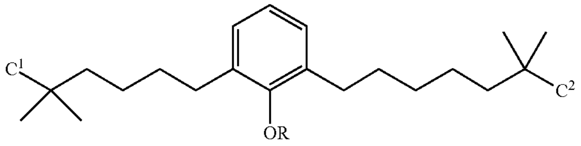 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 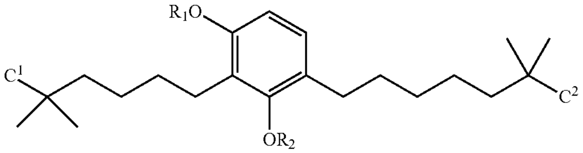 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 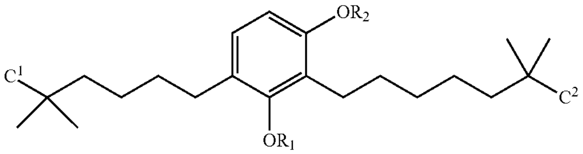 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 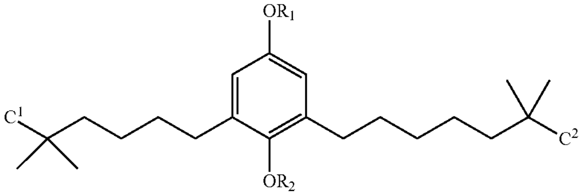 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 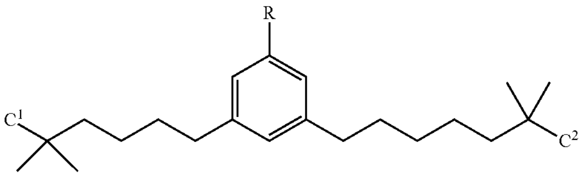<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 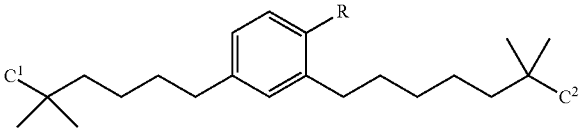<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 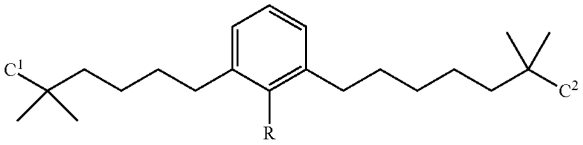<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 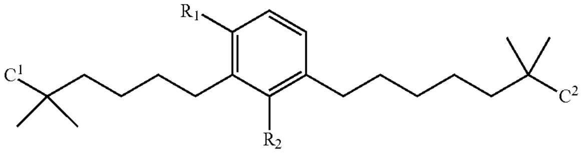<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 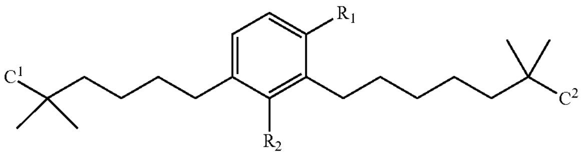<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 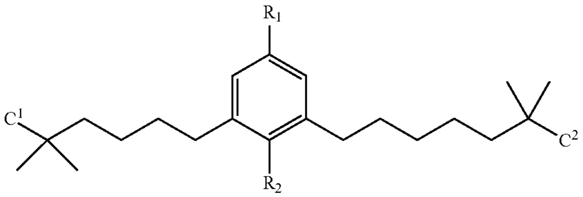 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 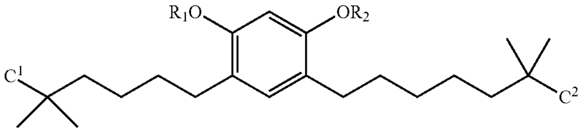 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 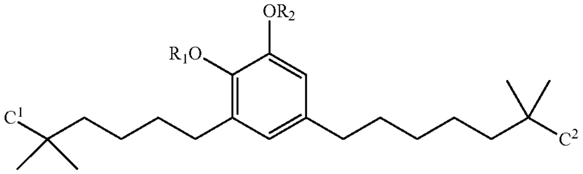 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 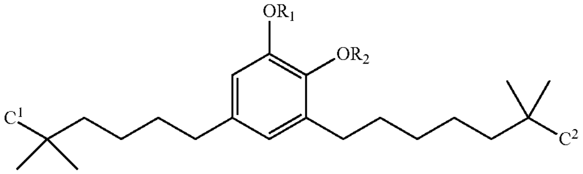 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 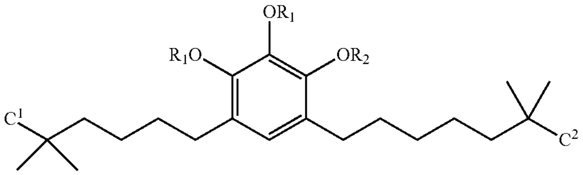 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 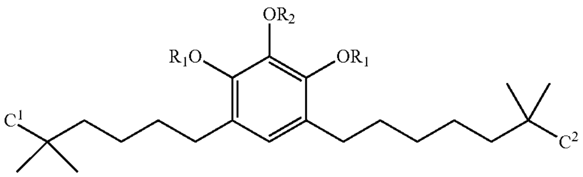 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 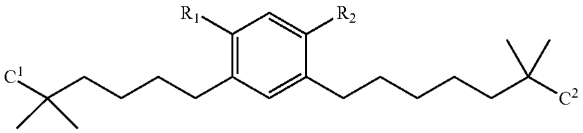 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 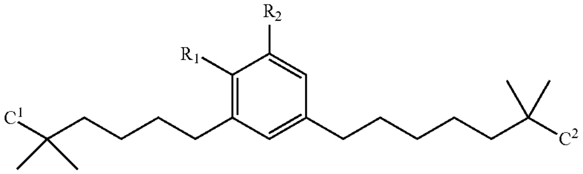 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 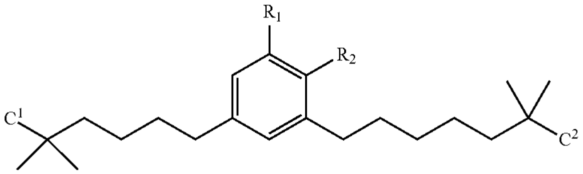 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 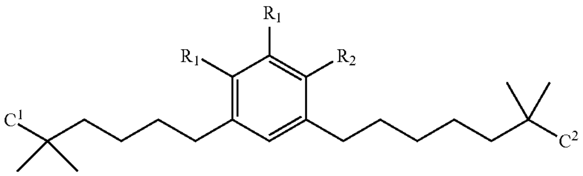 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 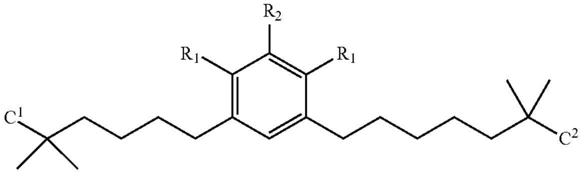 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 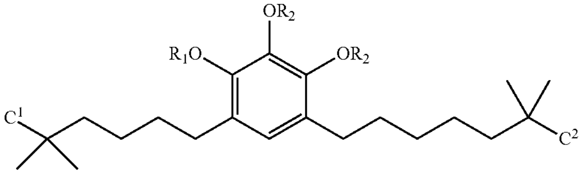 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 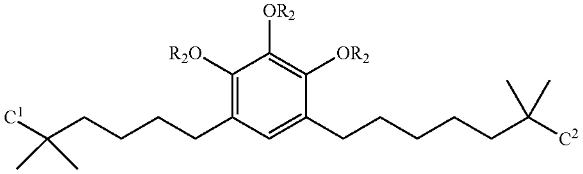 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 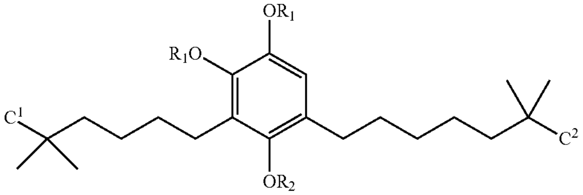 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 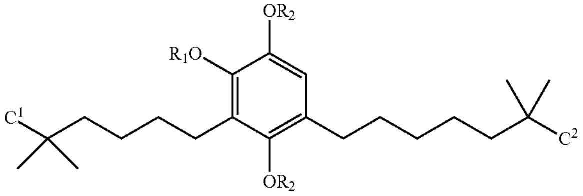 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-continued

| Structure |
| --- |
| 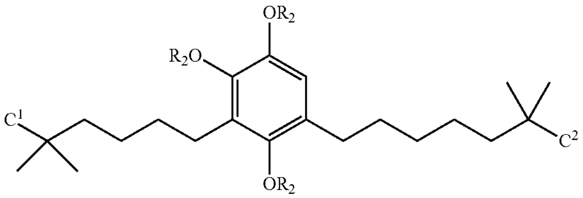 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 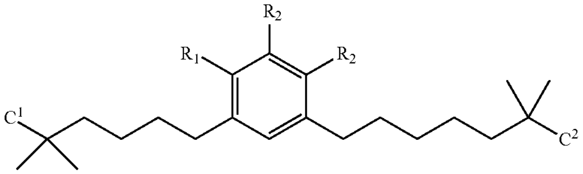 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 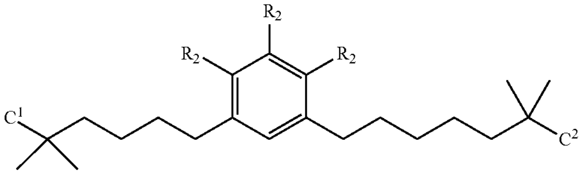 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 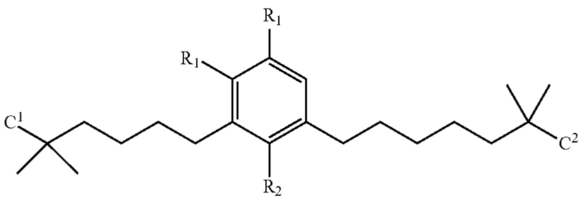 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 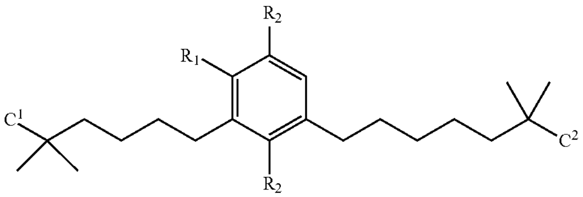 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 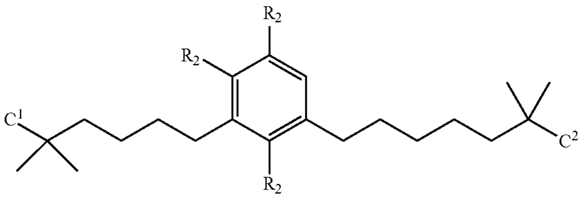 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 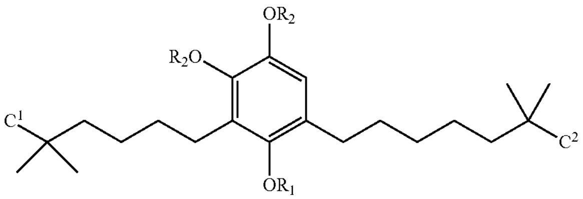 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 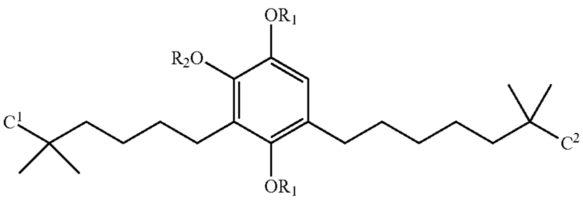 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 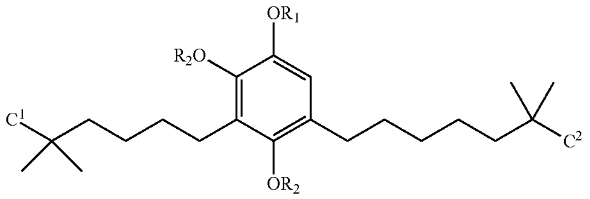 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 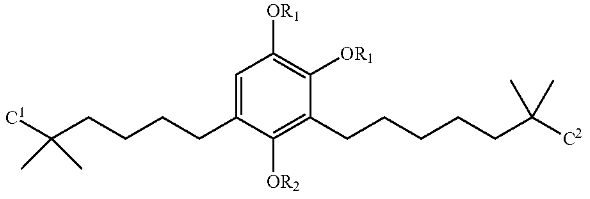 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 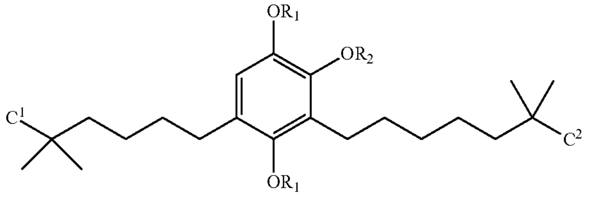 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 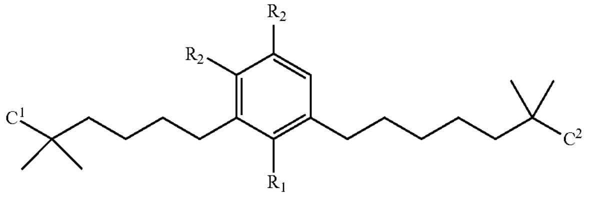 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
| --- |
| 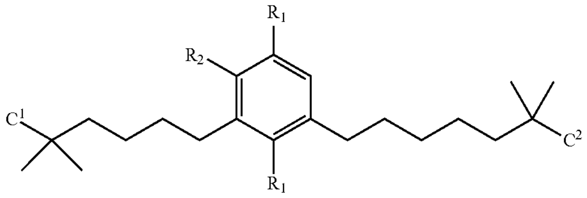 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 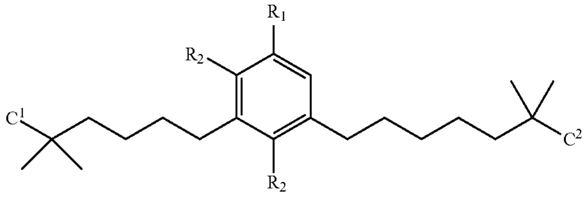 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 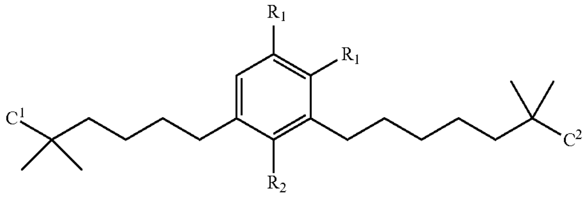 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 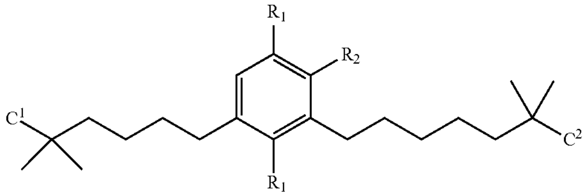 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 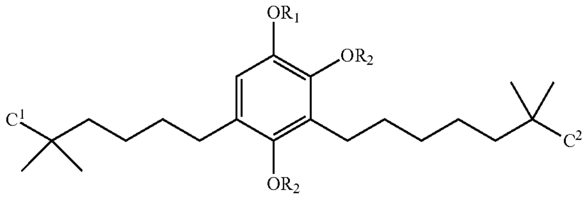 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 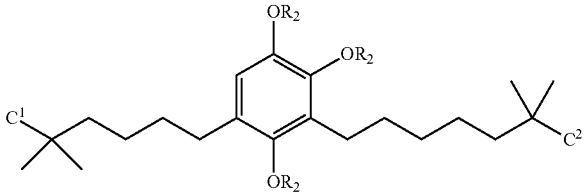 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 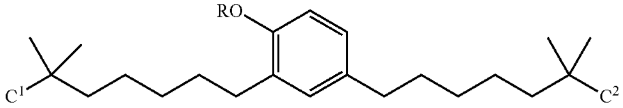 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 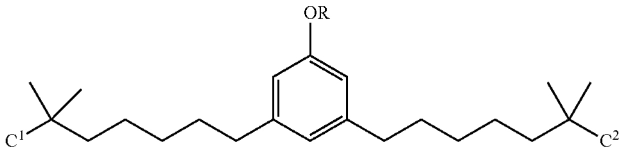 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 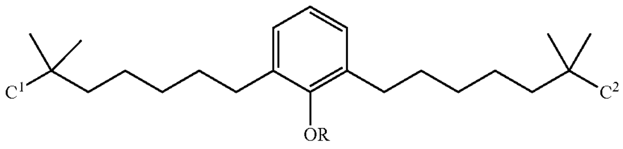 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 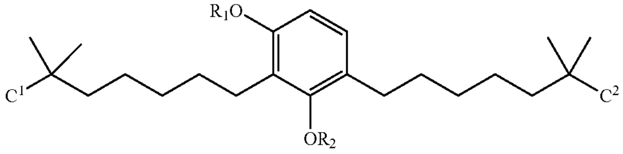 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
|---|
| 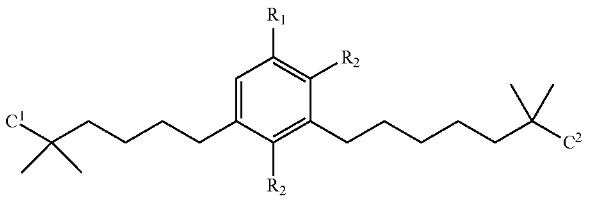 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 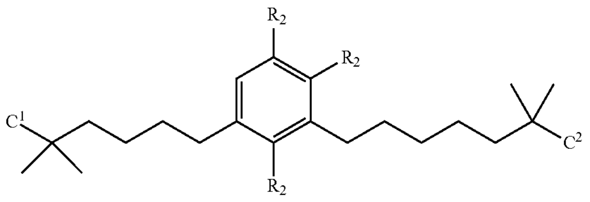 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 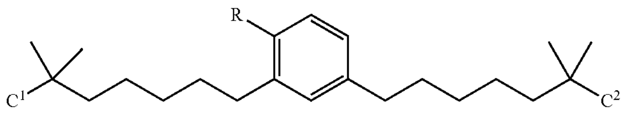 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 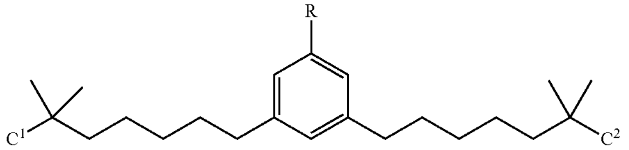 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 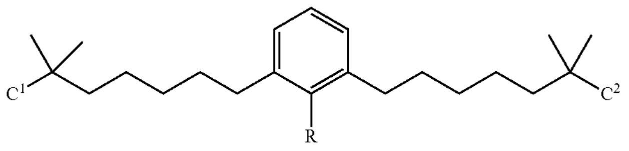 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
| --- |
| 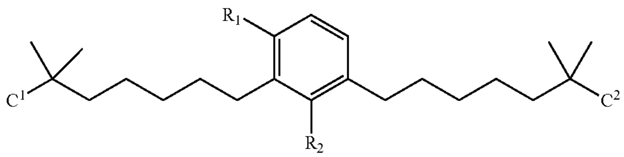 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 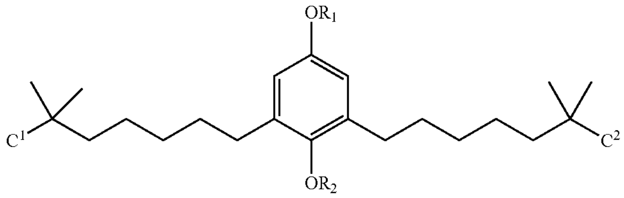 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 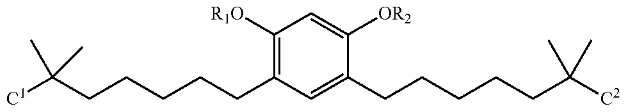 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 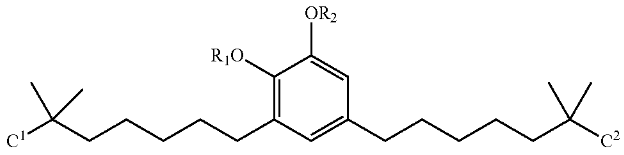 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 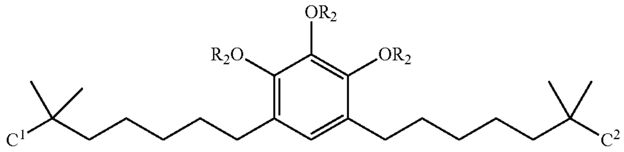 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-continued

| Structure |
| --- |
| 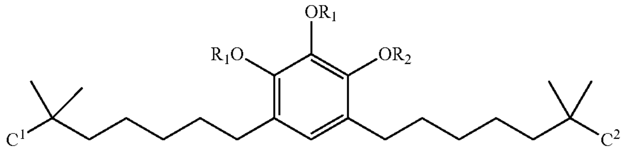 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 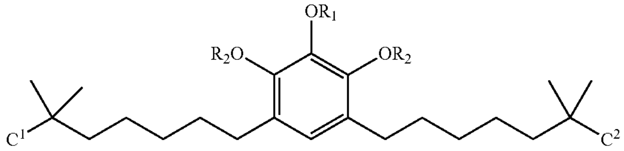 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 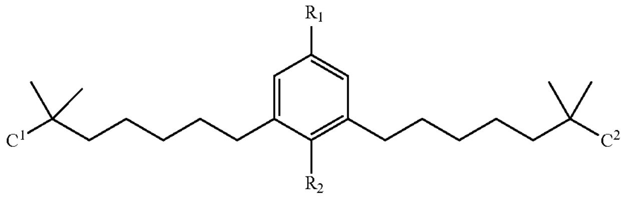 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 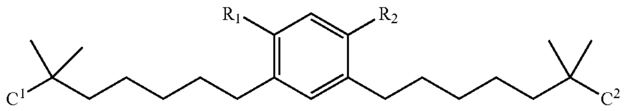 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 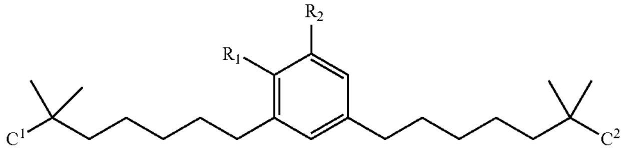 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 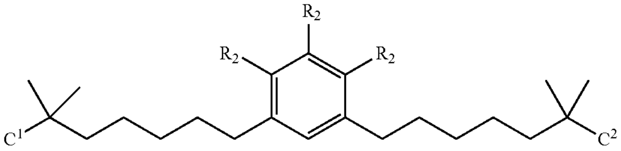 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 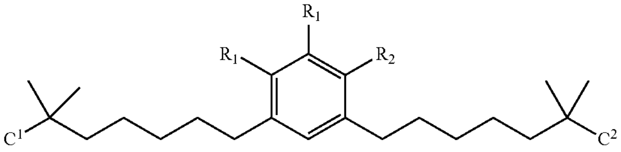 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 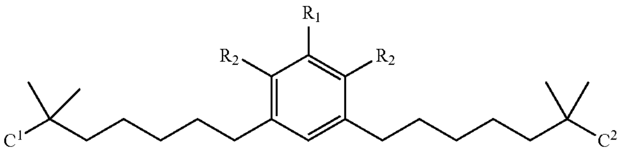 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 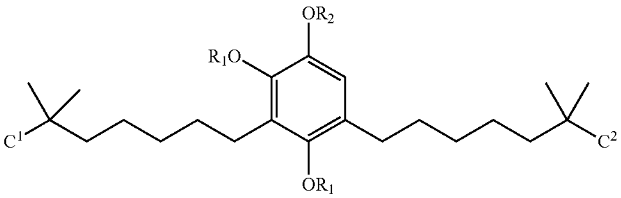 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 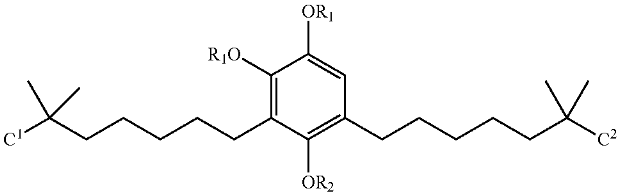 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 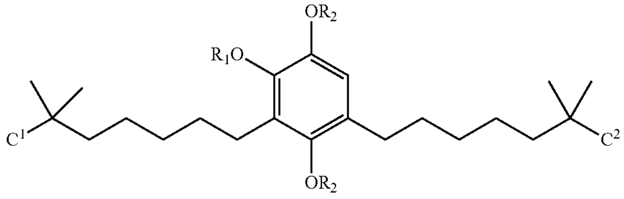 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 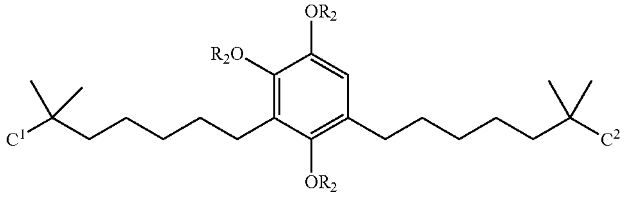 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 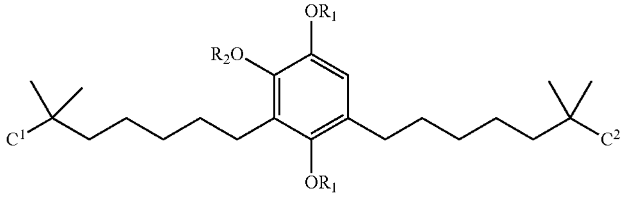 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 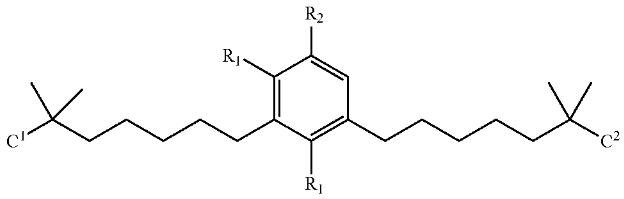 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 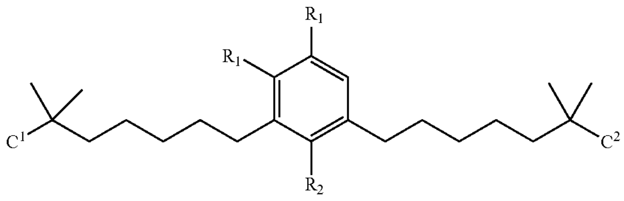 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 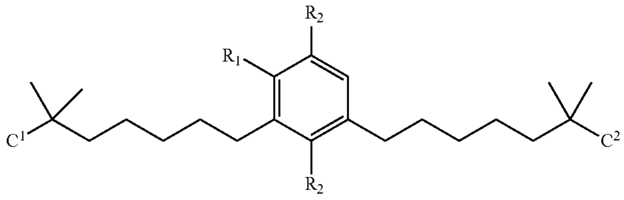 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 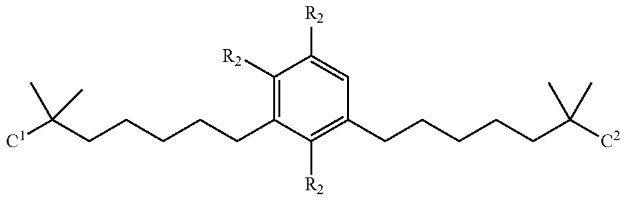 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 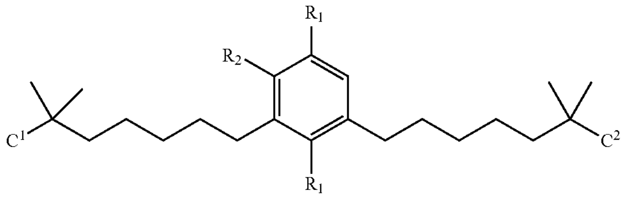 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 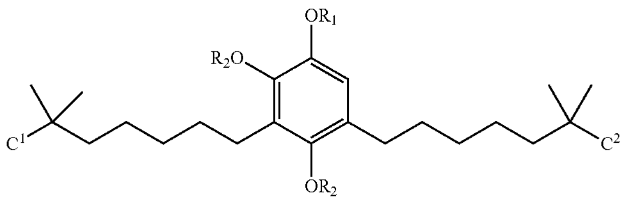 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 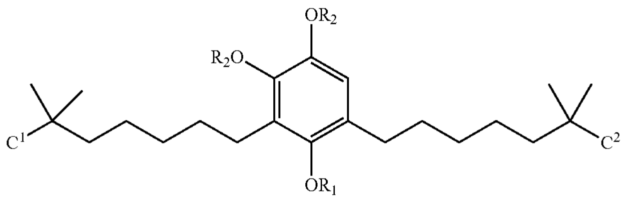 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 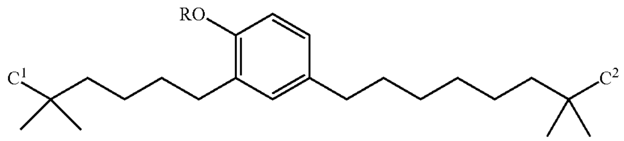 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 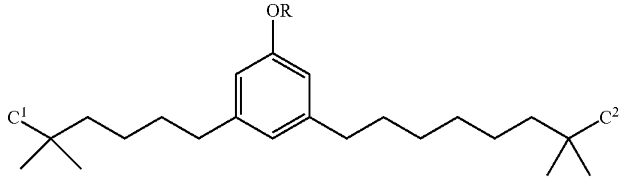 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 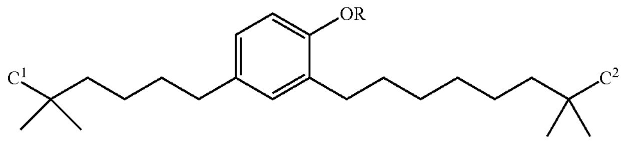 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 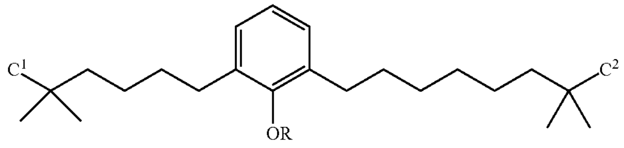 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 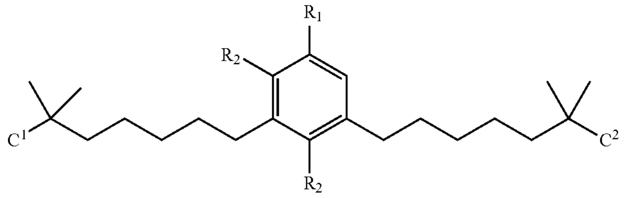 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 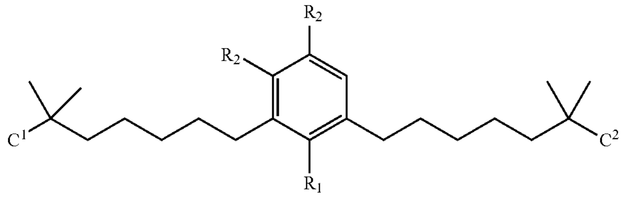 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 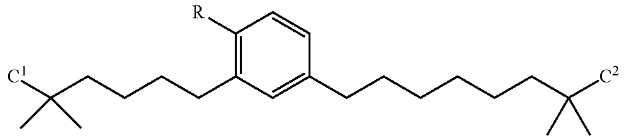 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 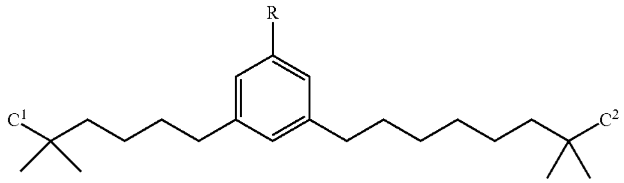 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 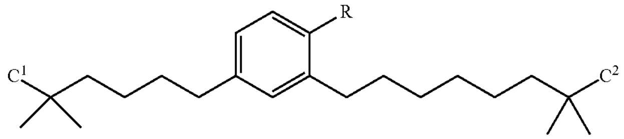 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 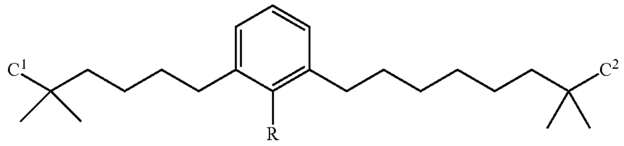 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 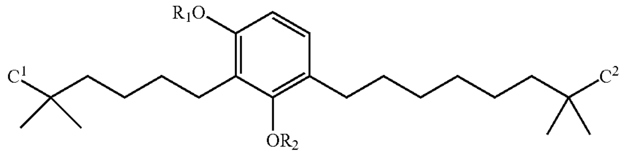 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 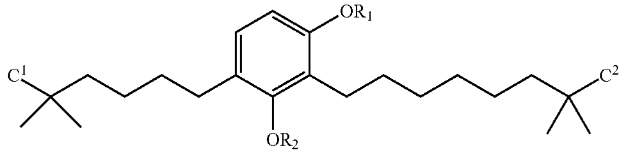 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 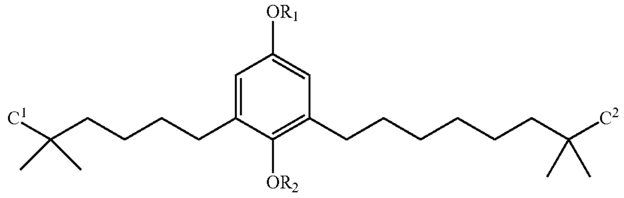 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 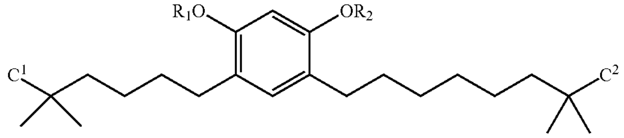 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 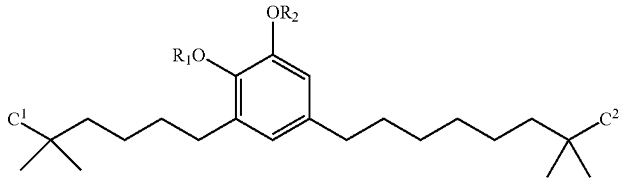 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 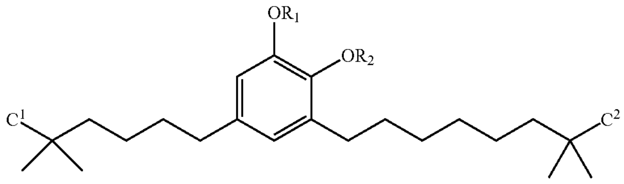 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 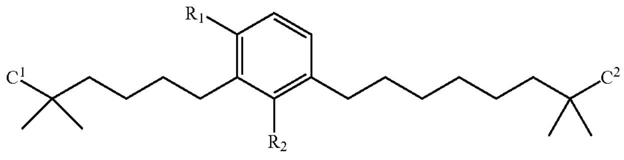 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 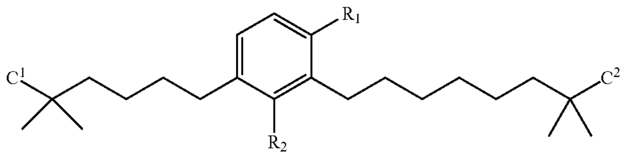 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 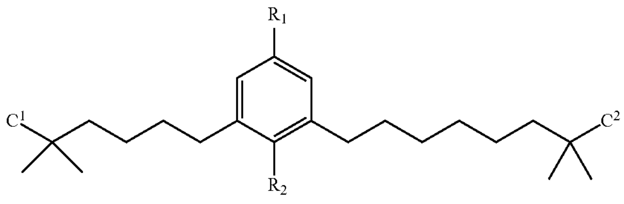 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 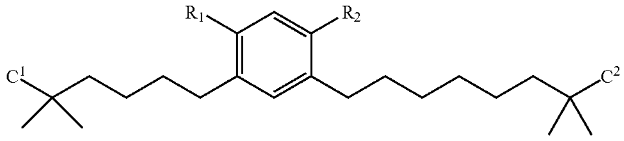 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 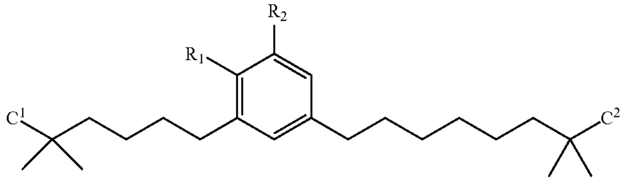 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 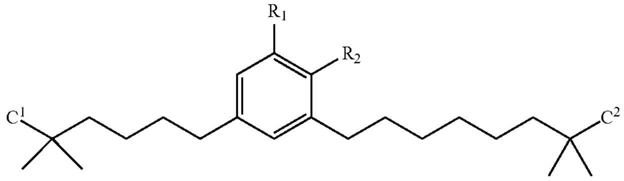 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 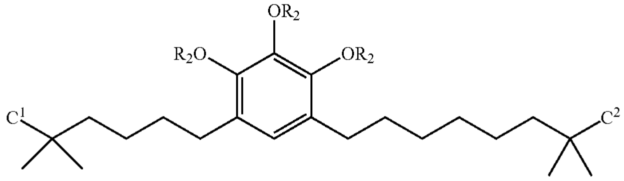 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 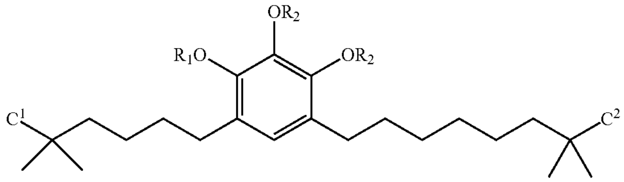 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-continued

Structure

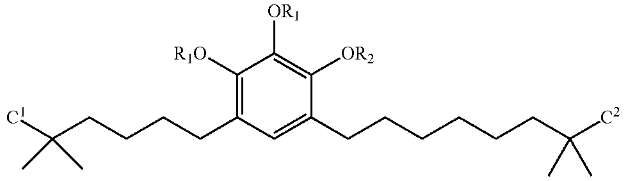

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

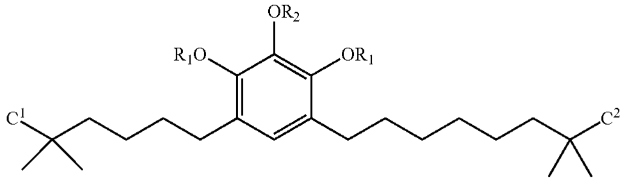

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

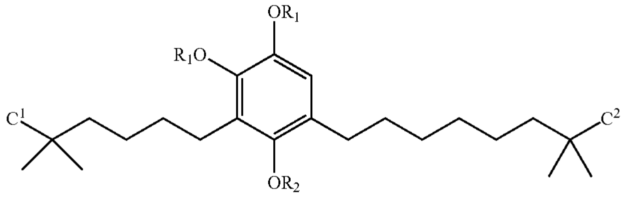

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

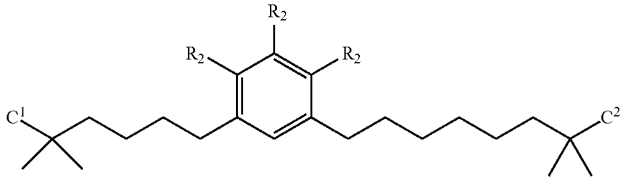

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

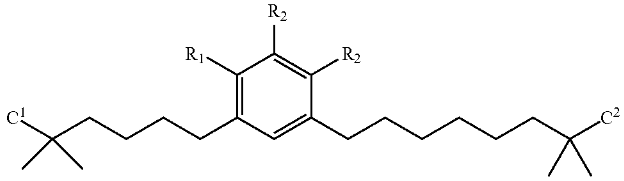

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl TABLE A-continued

| Structure |
| --- |
| 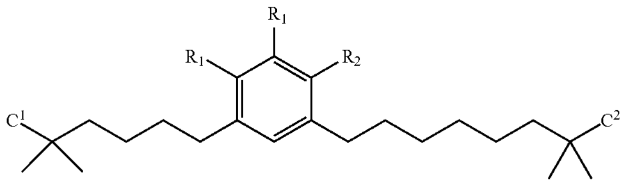 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 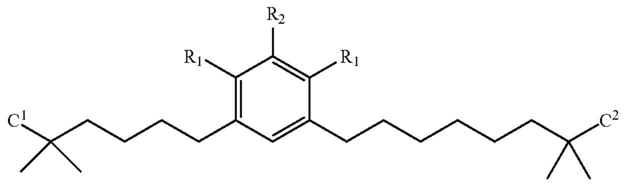 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 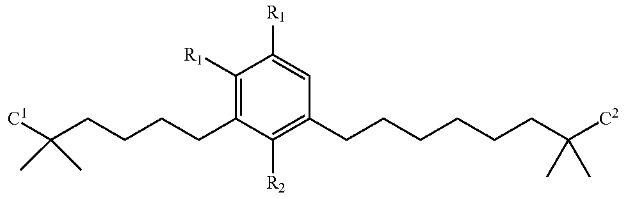 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 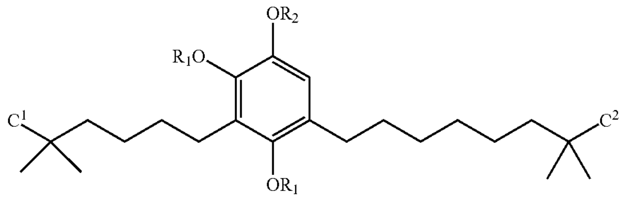 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 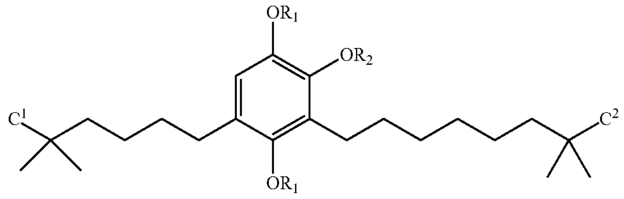 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 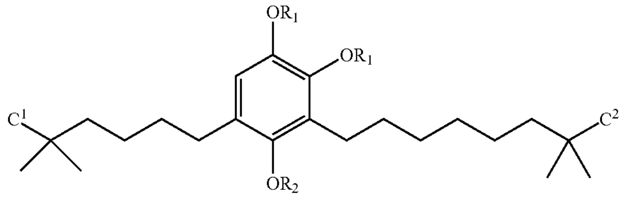 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 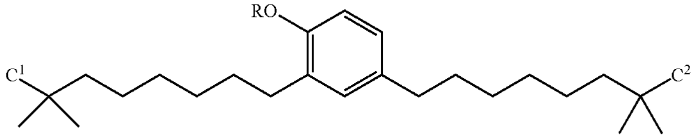 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 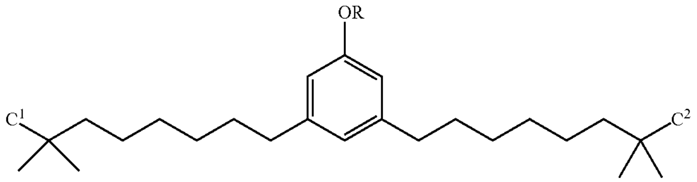 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 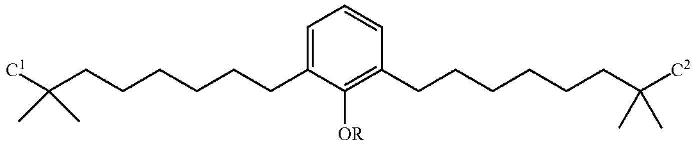 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 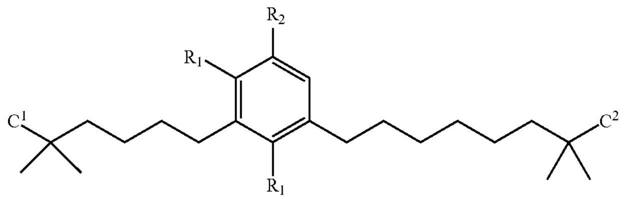 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 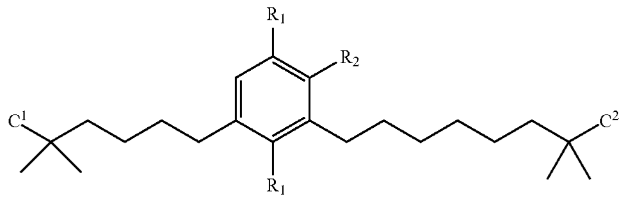 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 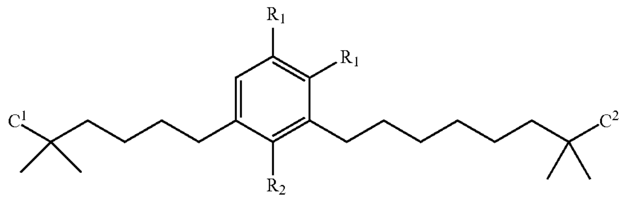 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 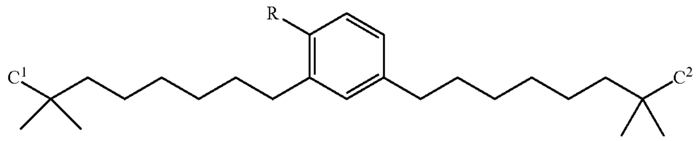 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 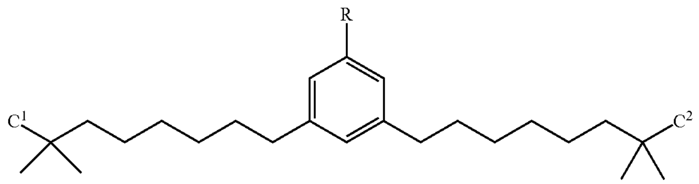 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 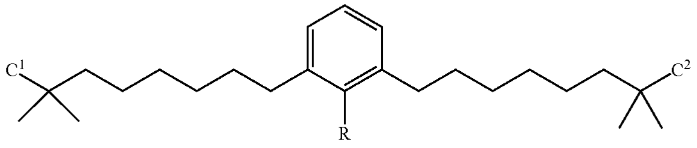 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 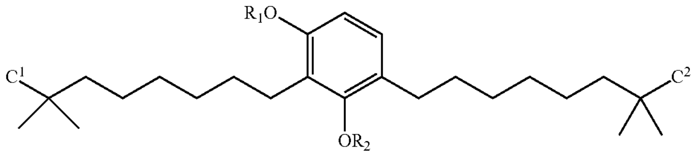 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 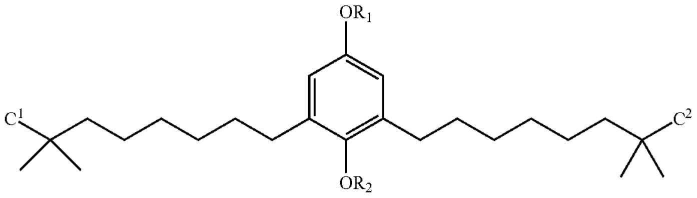 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 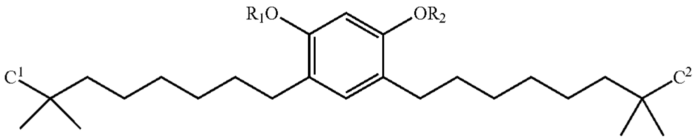 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 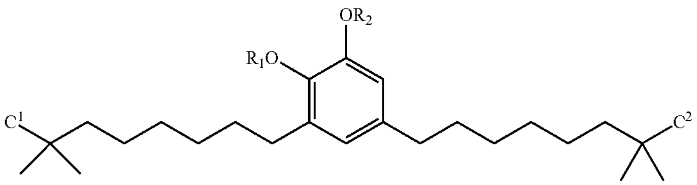 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 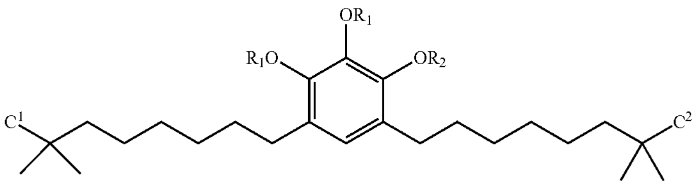 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 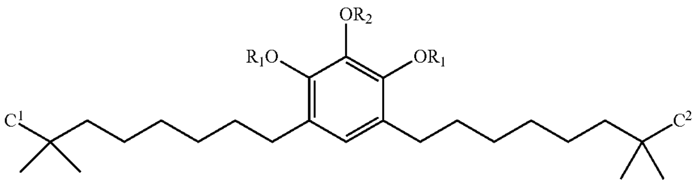 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 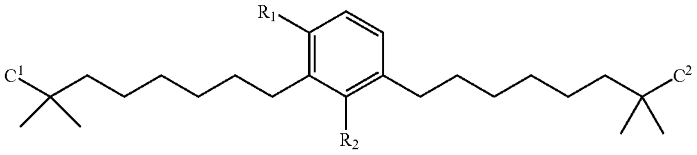 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 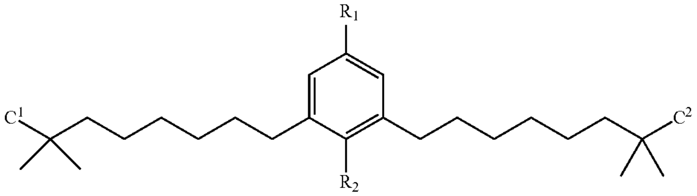 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 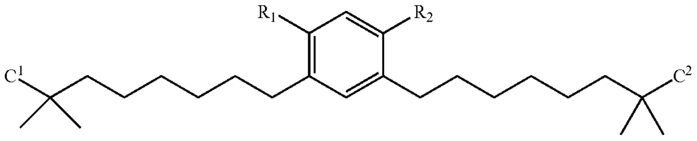 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 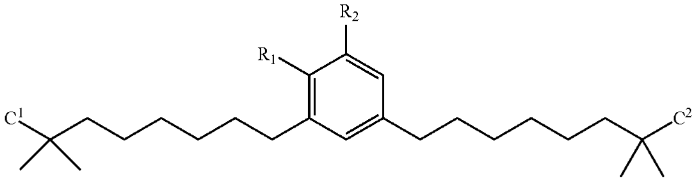 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 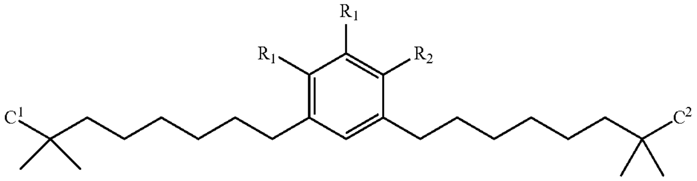 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 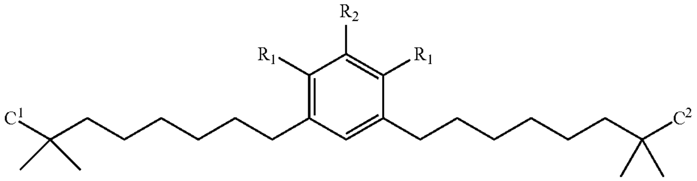 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 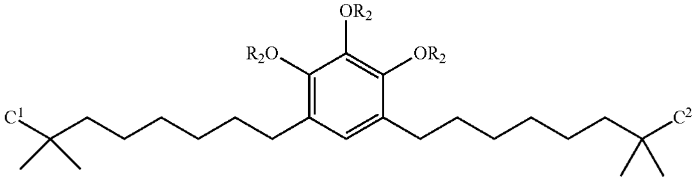 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 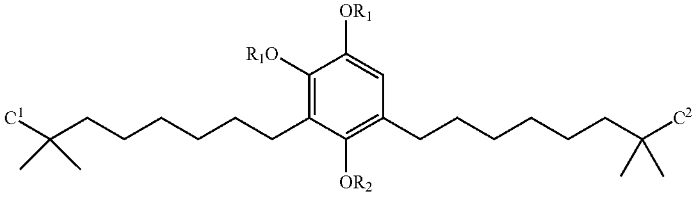 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 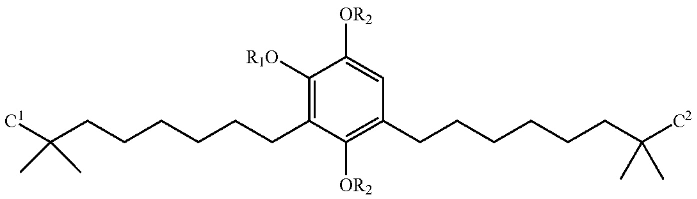 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 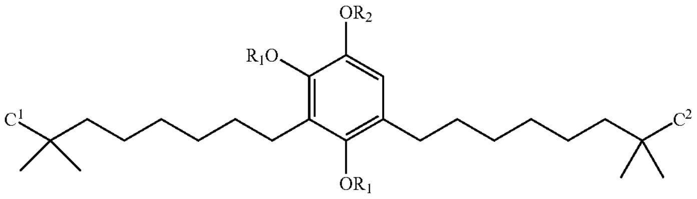 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 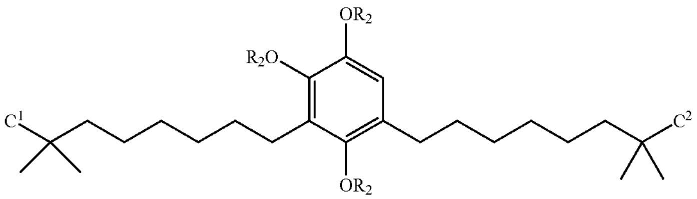 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 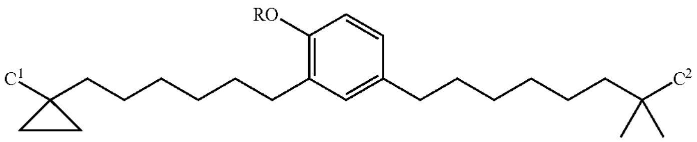 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 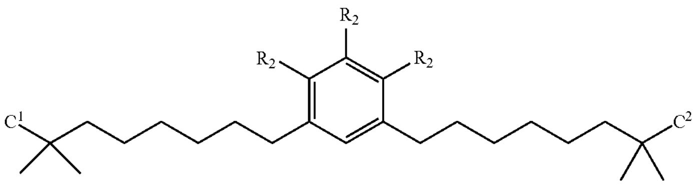 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
| --- |
| 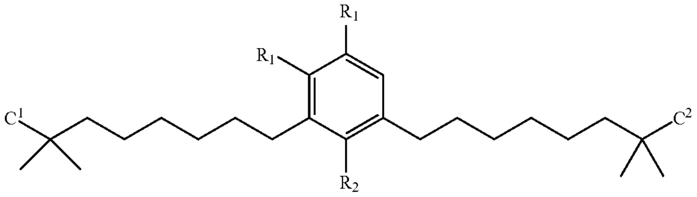 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 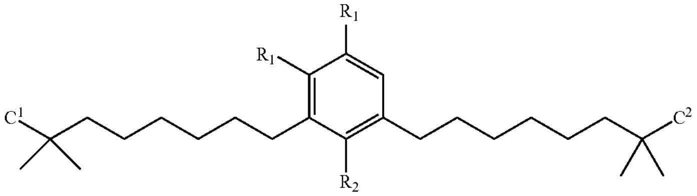 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 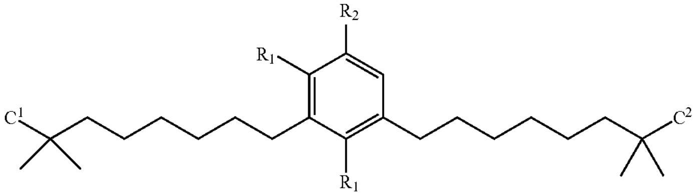 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 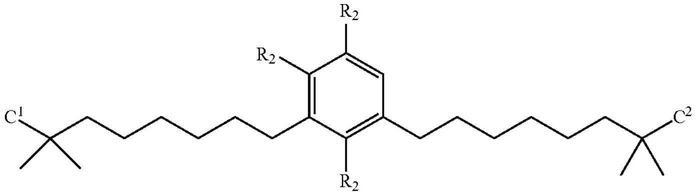 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 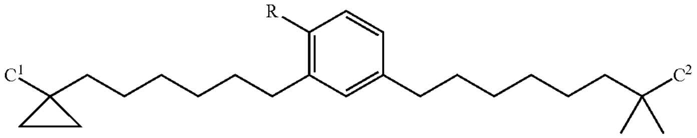 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 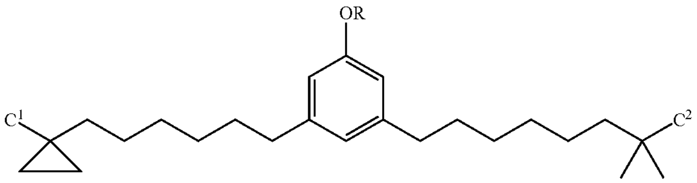 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 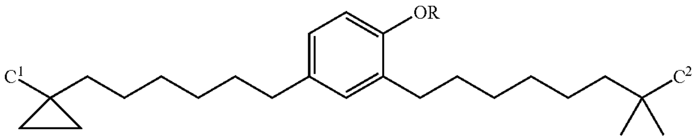 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 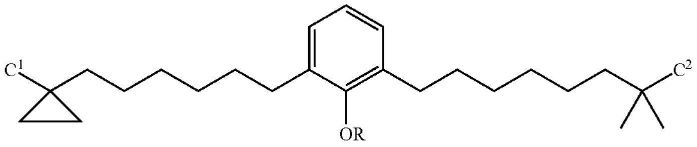 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 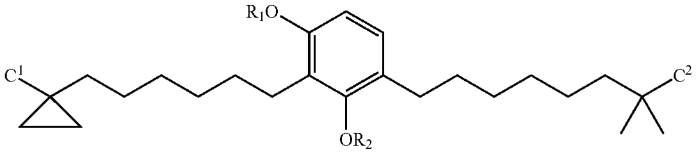 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 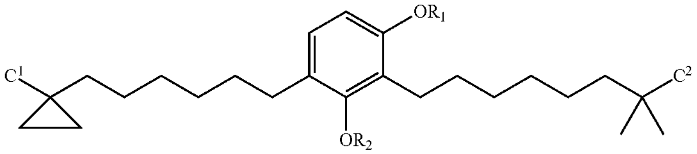 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 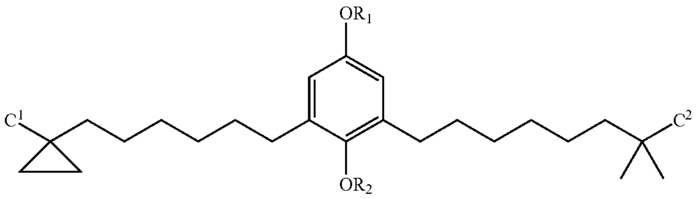 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 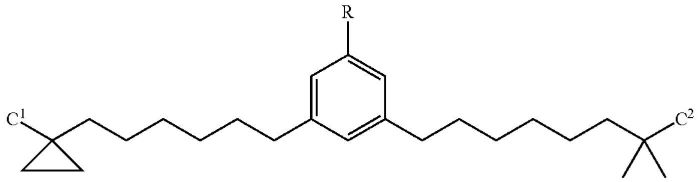 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 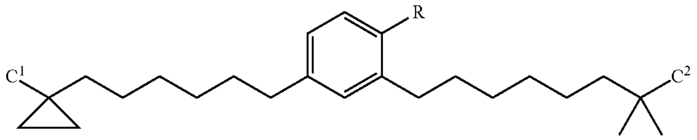 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 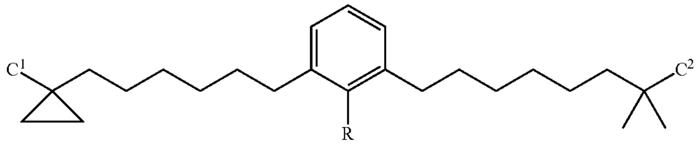 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 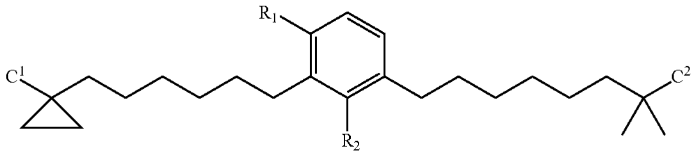 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 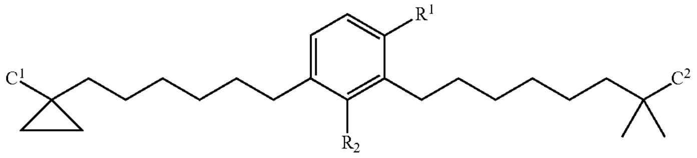 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 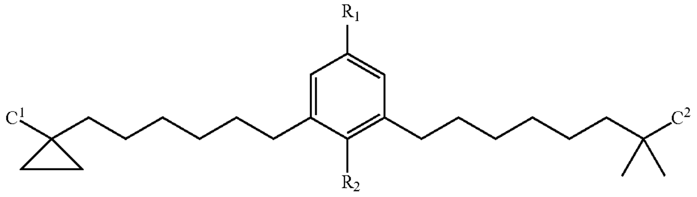 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 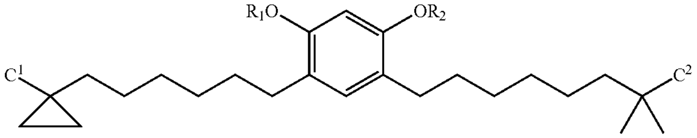 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 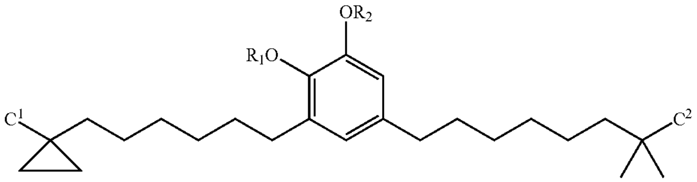 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 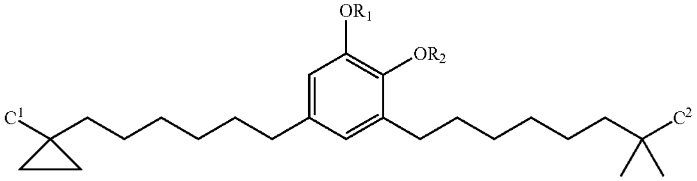 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 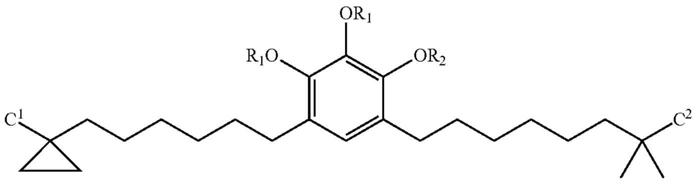 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 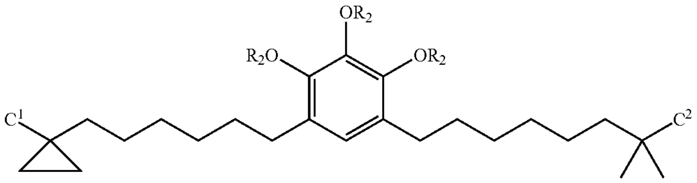 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 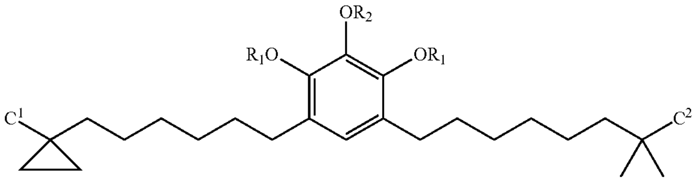 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 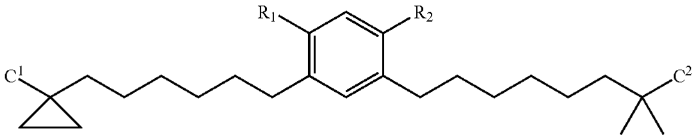 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 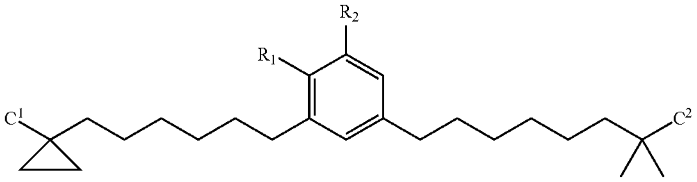 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 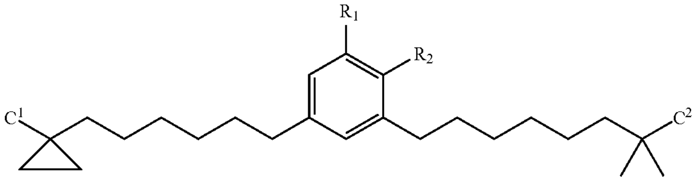 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 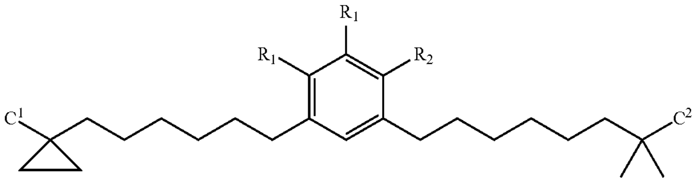 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 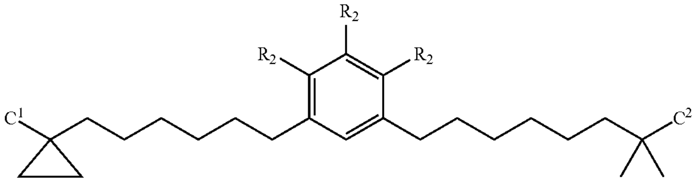 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 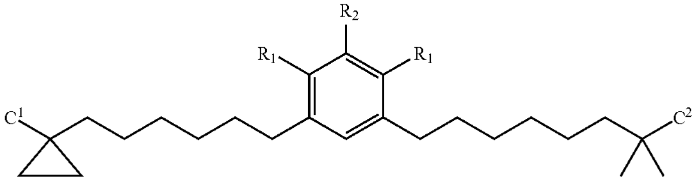 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 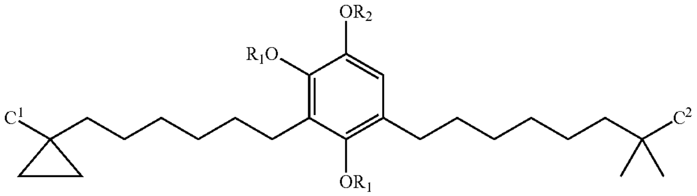 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 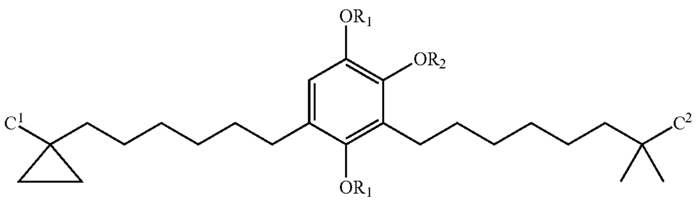 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 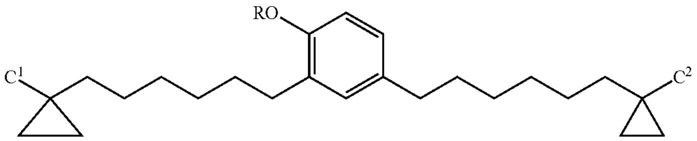 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 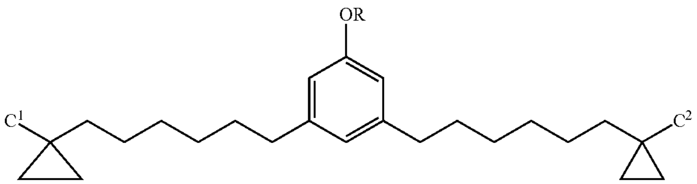 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 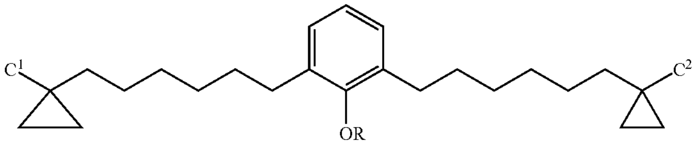 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 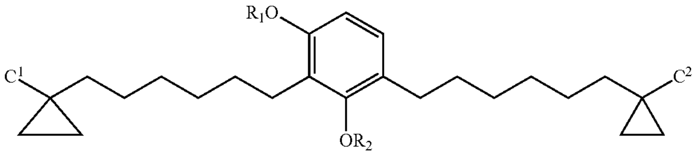 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 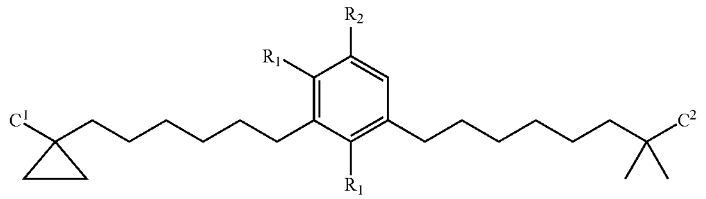 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 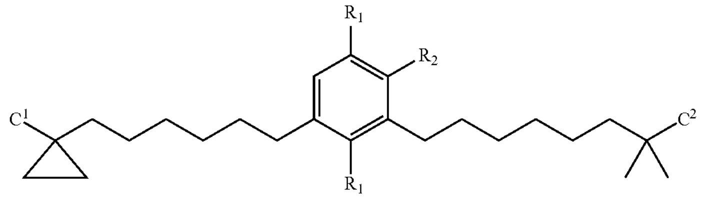 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 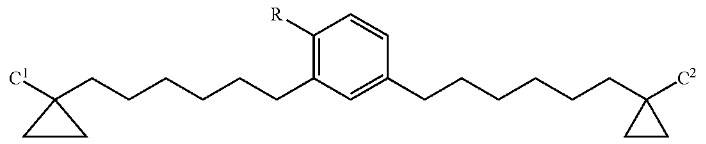 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 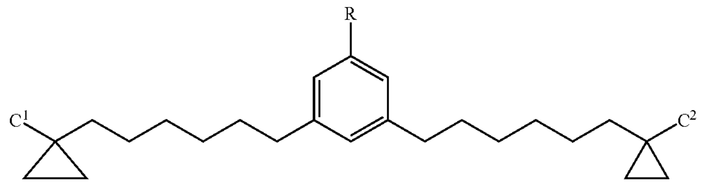 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 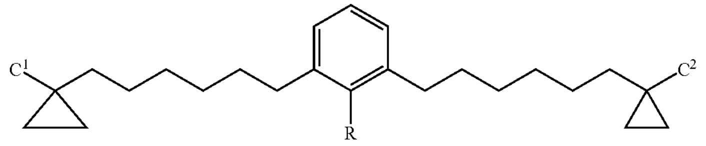 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 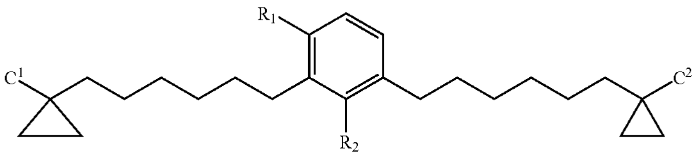 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 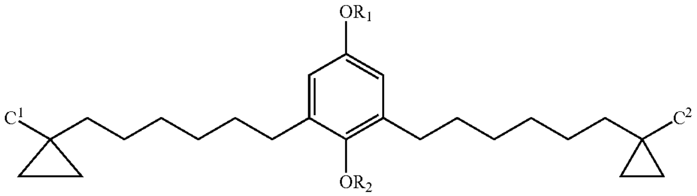 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 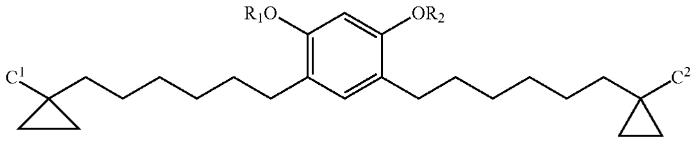 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 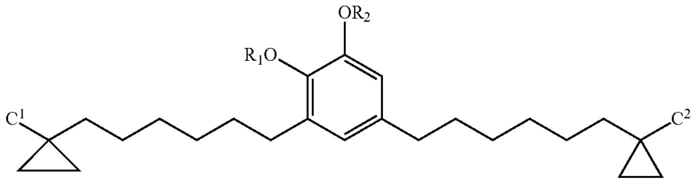 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 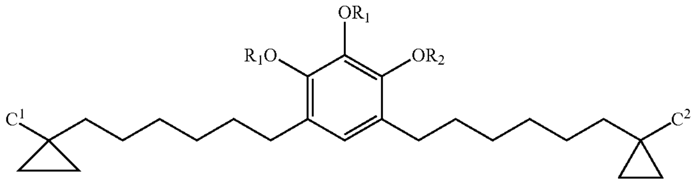 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 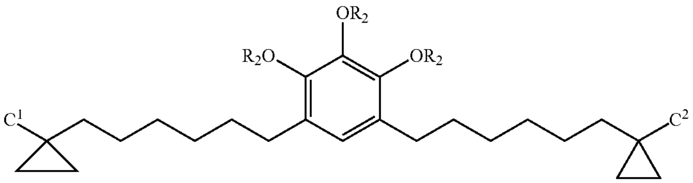 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 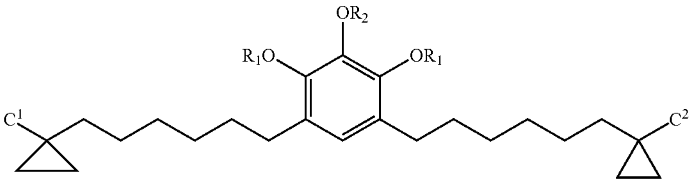 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 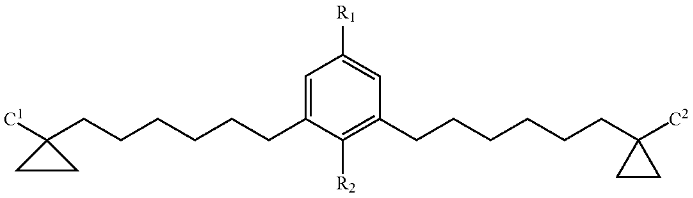 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 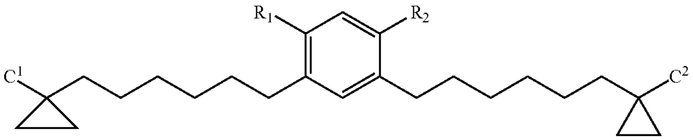 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 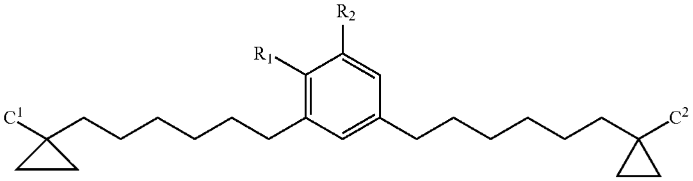 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 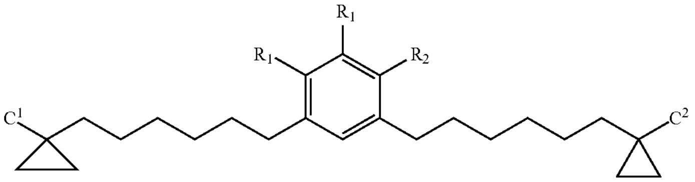 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 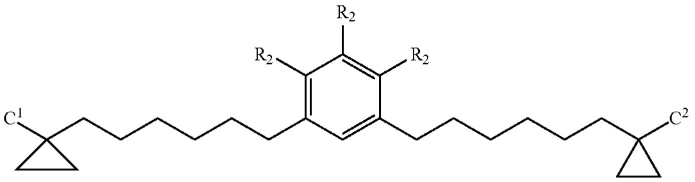 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 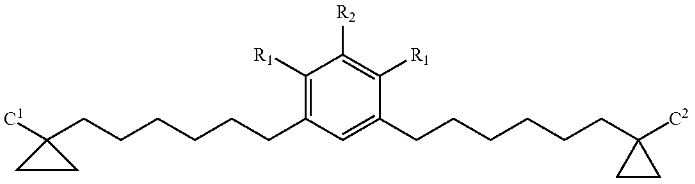 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 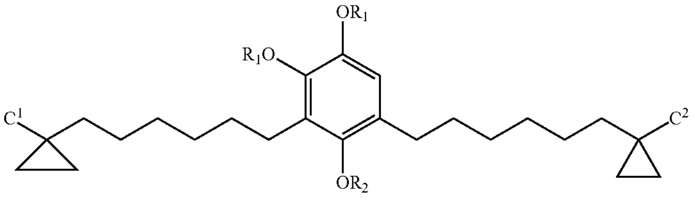 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 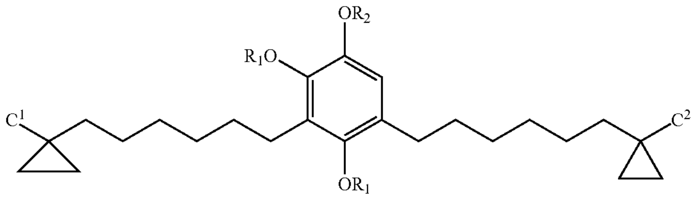 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 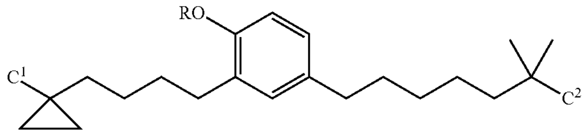 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 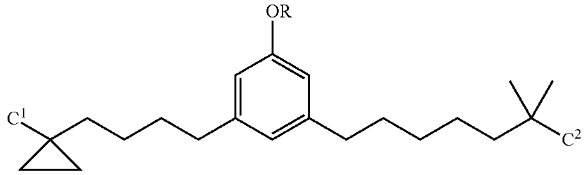 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 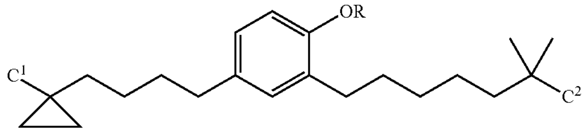 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 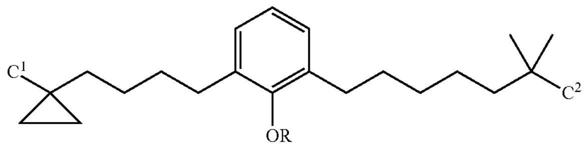 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
| --- |
| 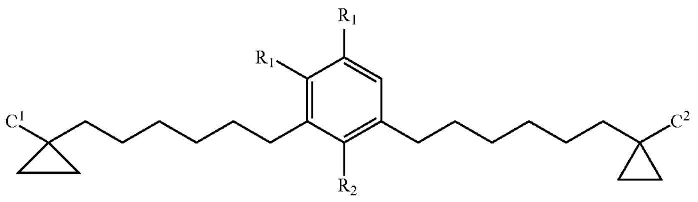 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 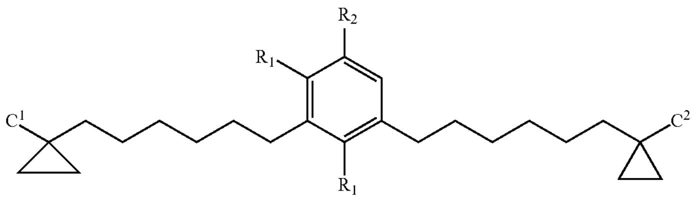 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 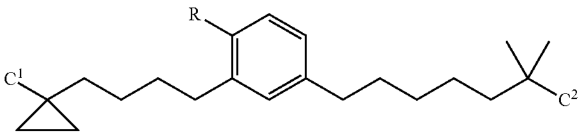 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 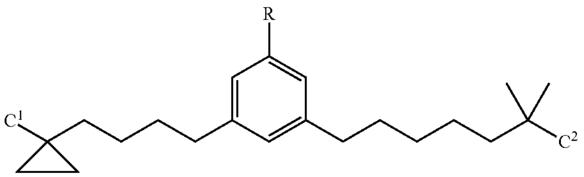 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 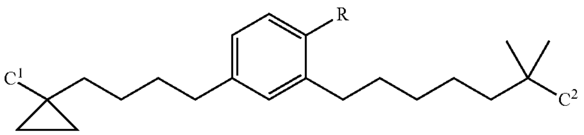 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |

TABLE A-continued

| Structure |
|---|
| 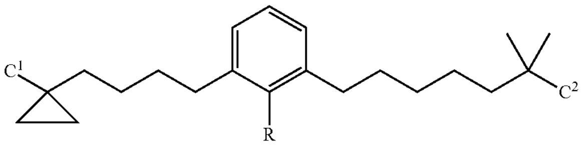 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 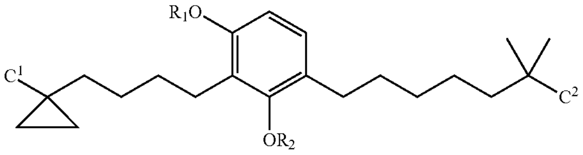 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 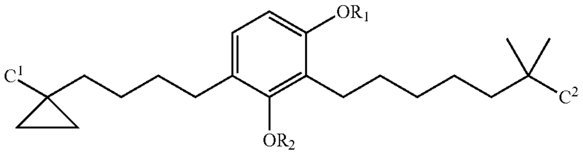 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 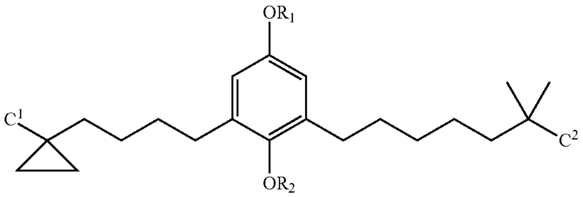 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 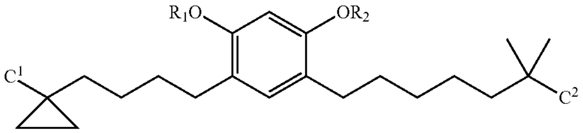 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
|---|
| 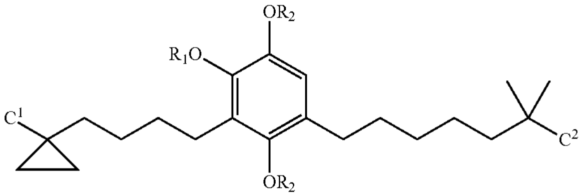 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 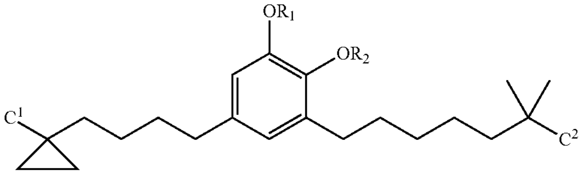 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 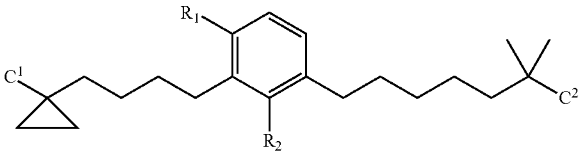 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 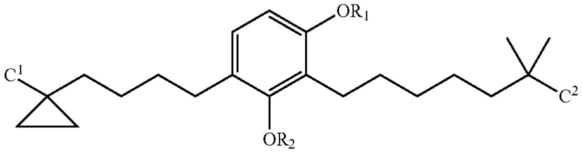 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 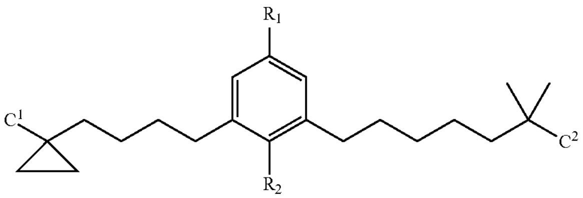 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
| --- |
| 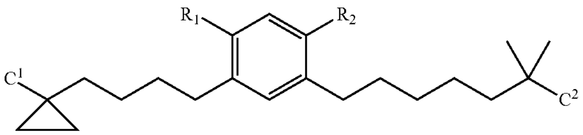 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 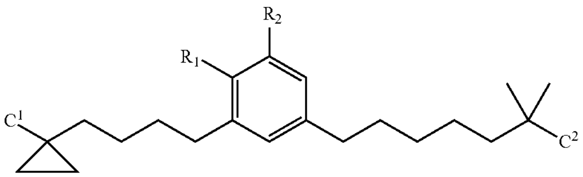 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 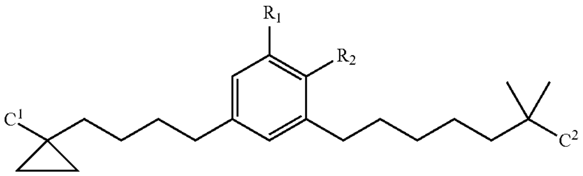 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 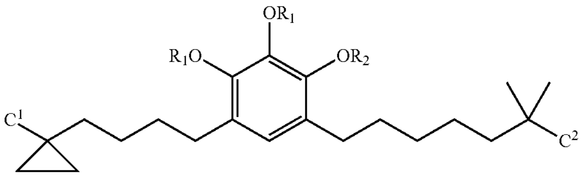 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 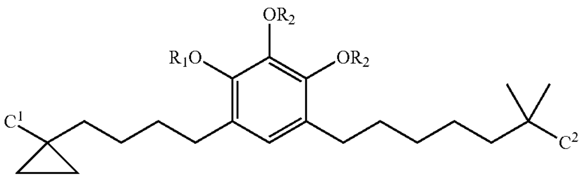 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-continued

| Structure |
| --- |
| 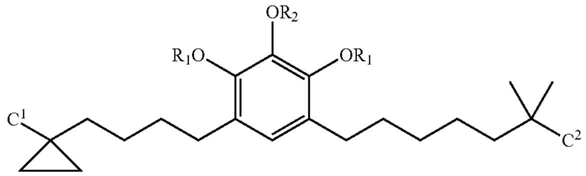 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 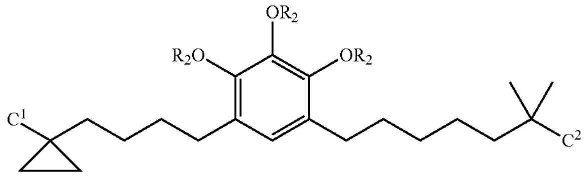 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 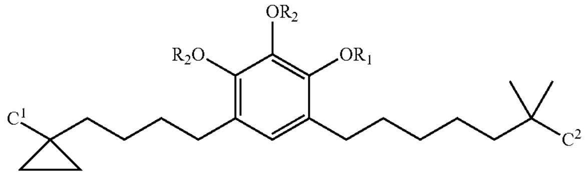 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 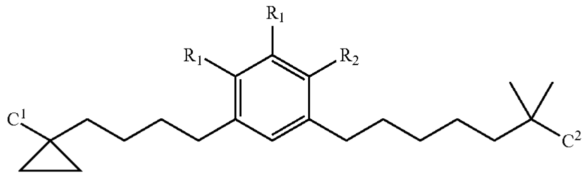 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 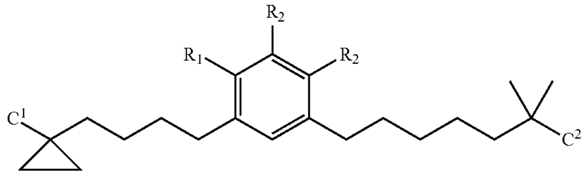 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
|---|
| 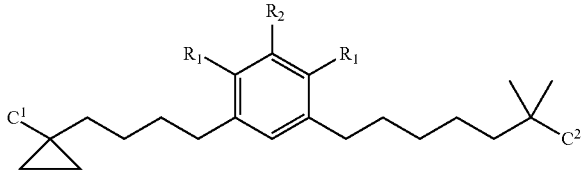 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 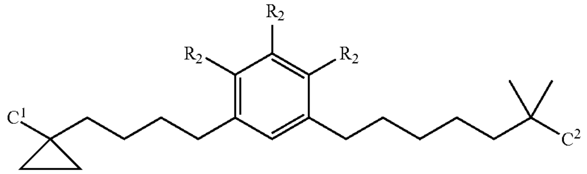 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 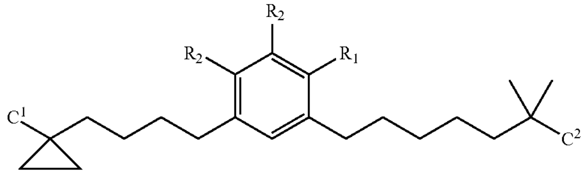 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 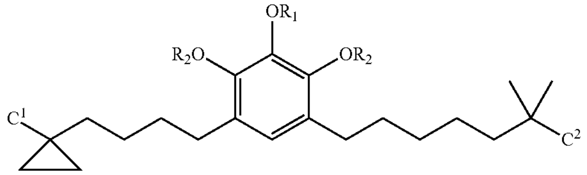 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 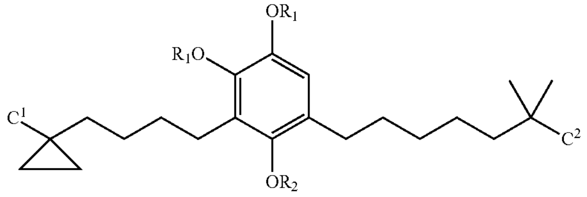 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 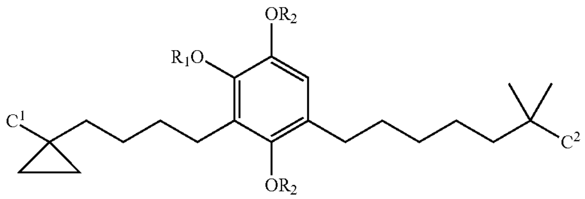 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 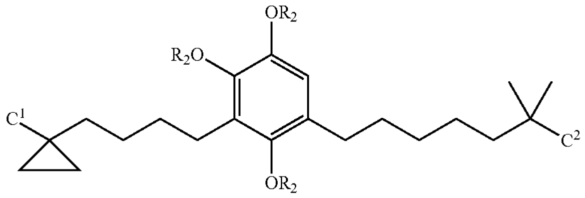 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 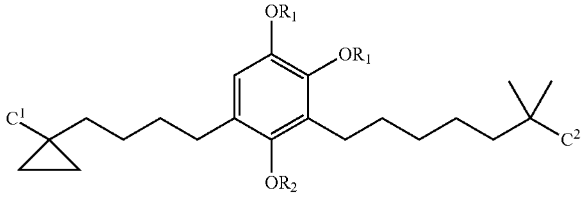 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 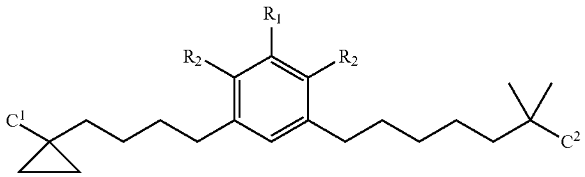 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
|---|
| 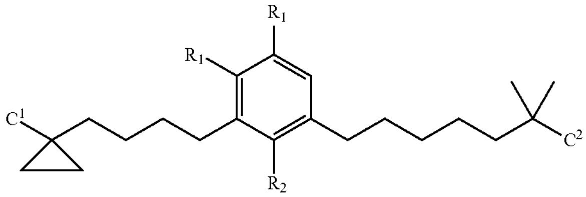 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 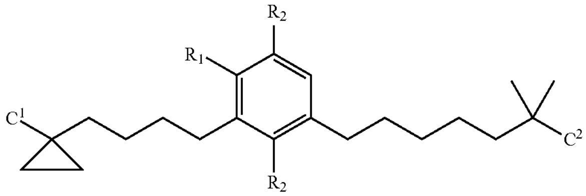 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 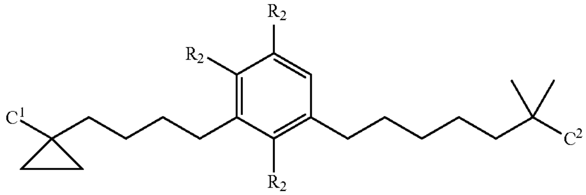 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 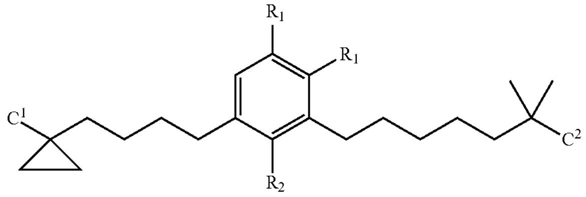 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 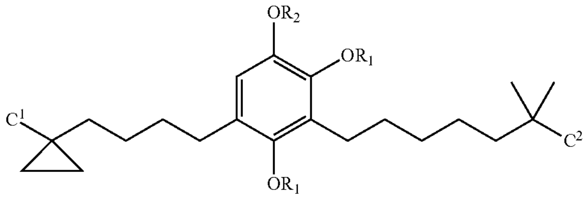 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 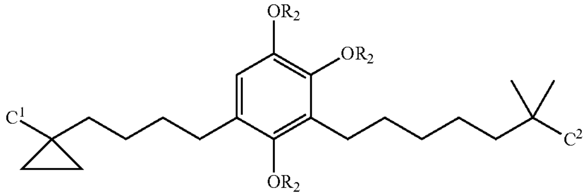 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 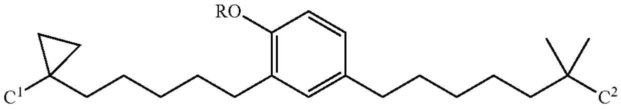 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 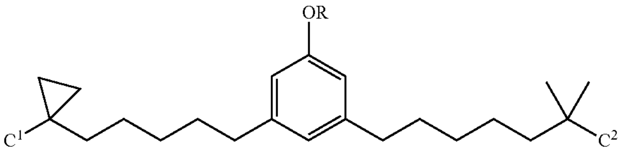 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 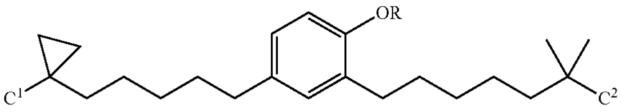 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 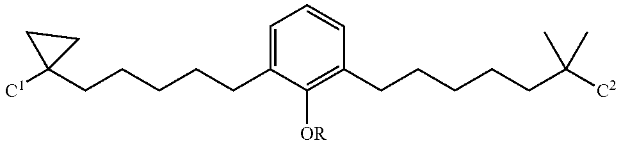 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 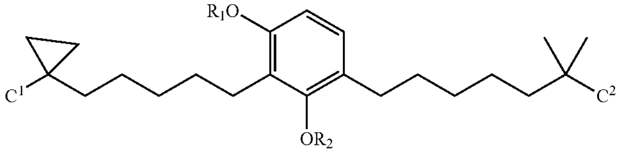 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 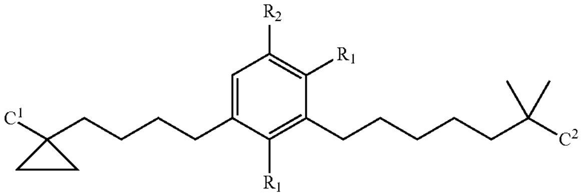 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 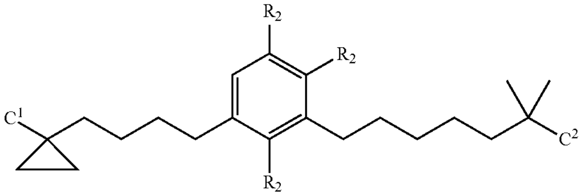 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 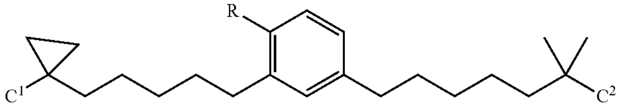 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 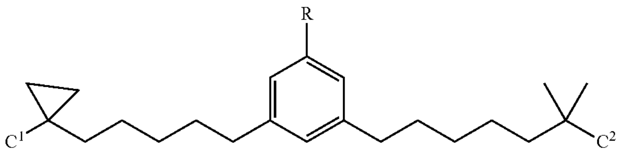 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
|---|
| 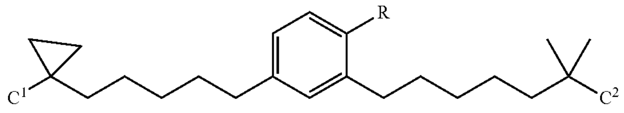 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 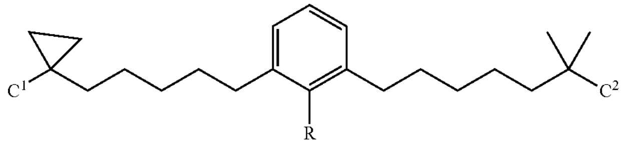 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 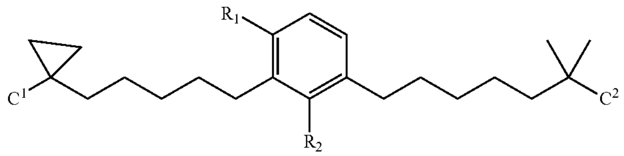 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 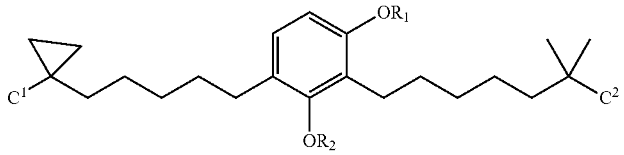 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 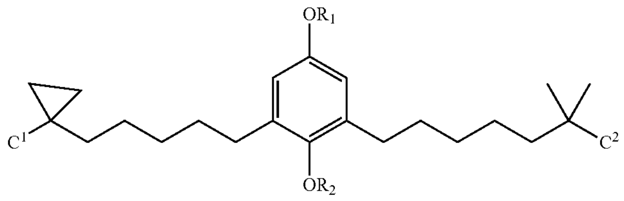 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 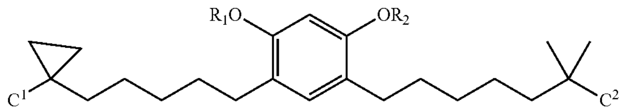 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 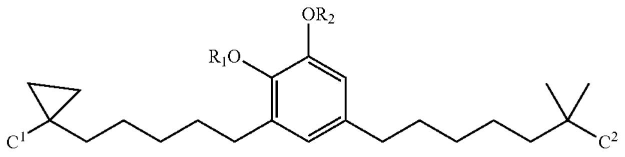 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 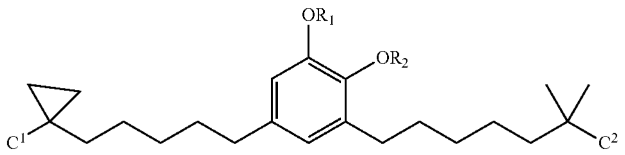 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 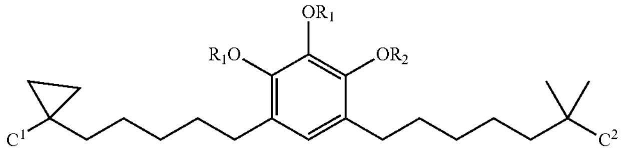 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 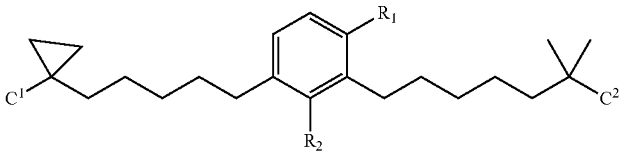 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 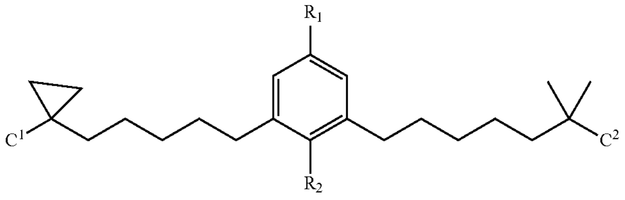 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
| --- |
| 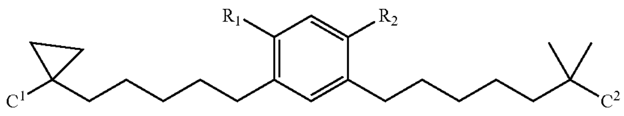 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 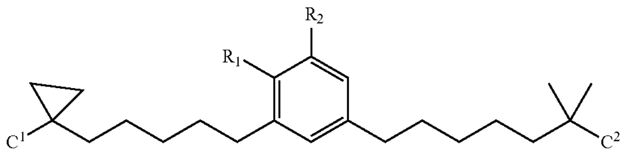 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 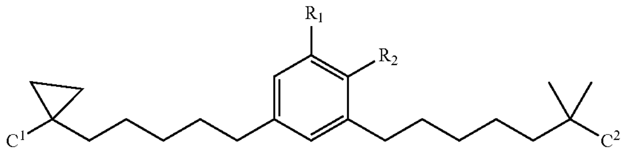 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 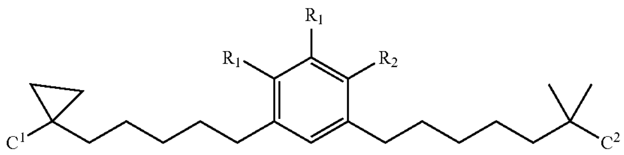 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 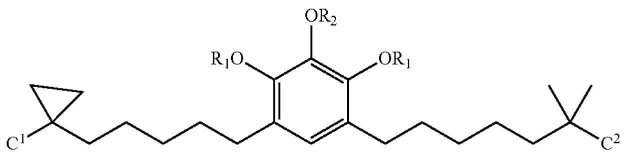 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 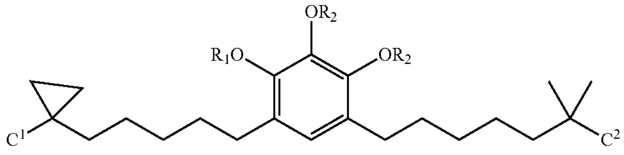 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 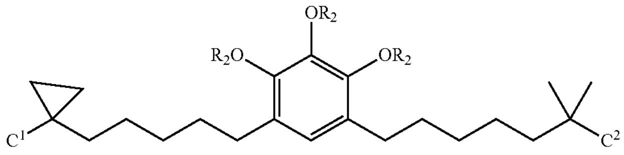 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 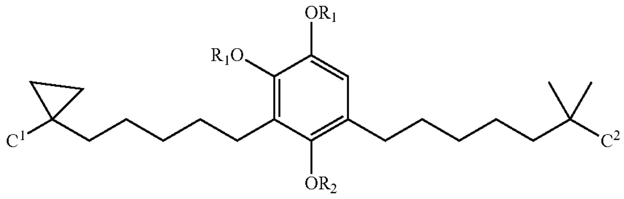 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 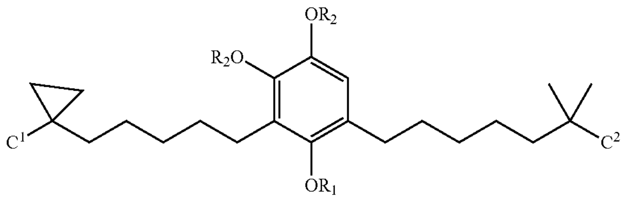 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 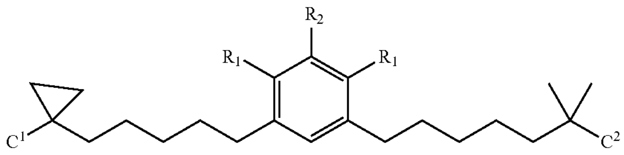 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 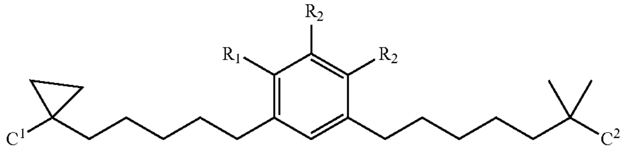 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 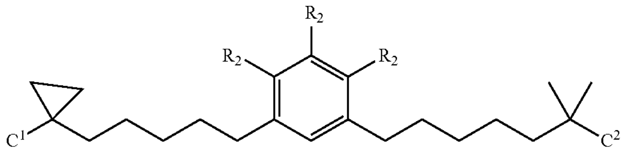 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 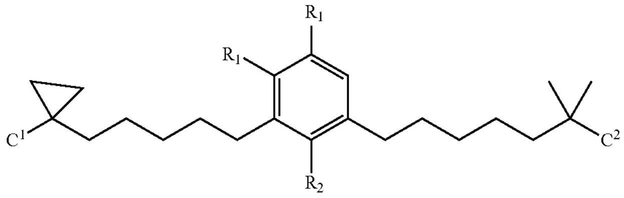 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 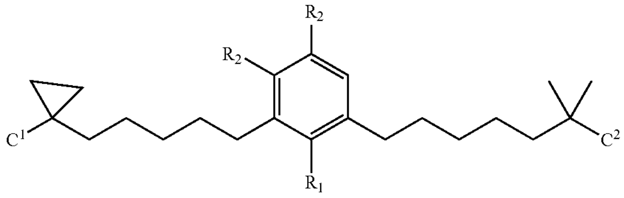 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 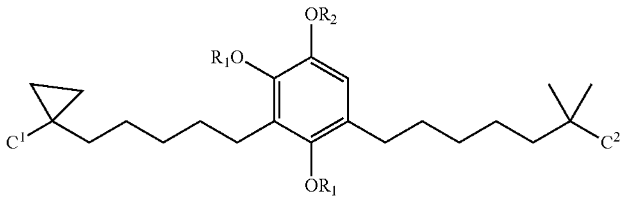 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 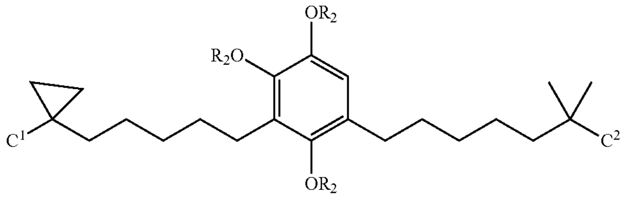 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 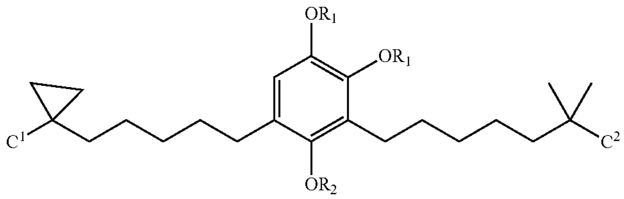 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 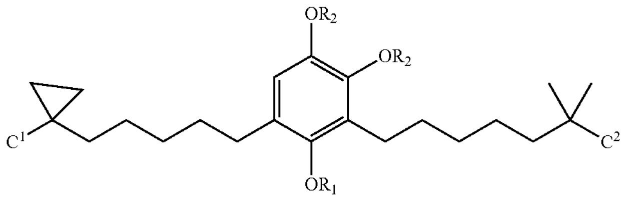 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 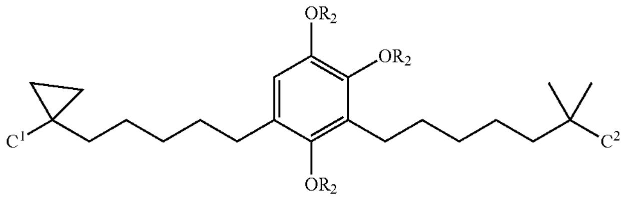 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-continued

| Structure |
|---|
| 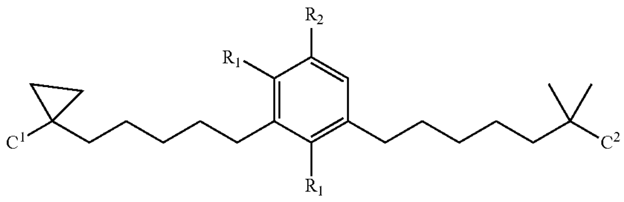 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 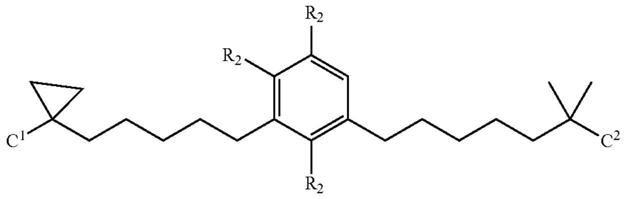 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 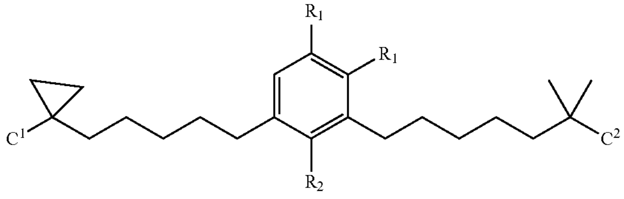 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 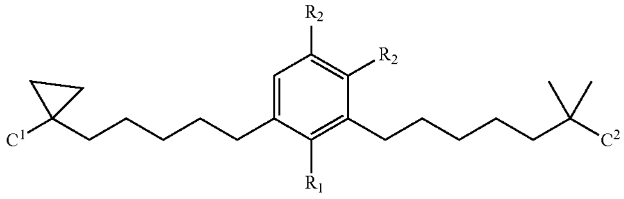 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
| --- |
| 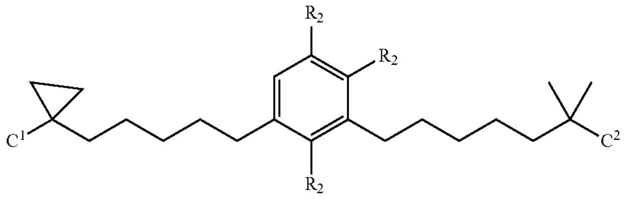 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 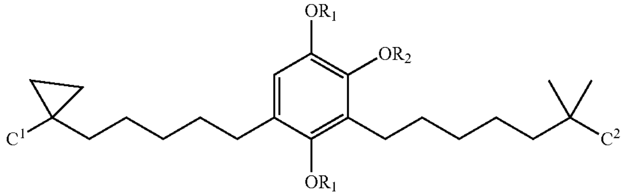 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 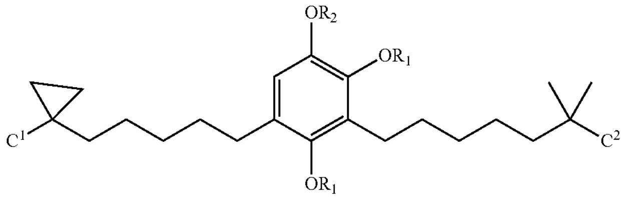 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 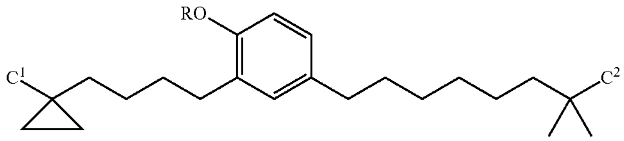 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 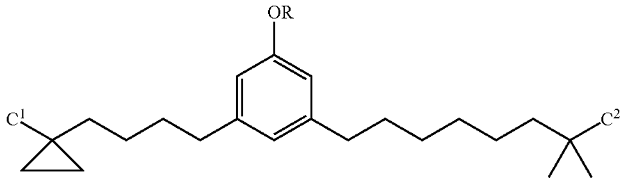 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
| --- |
| 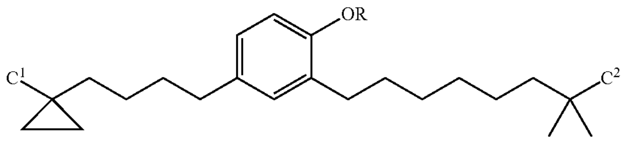 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 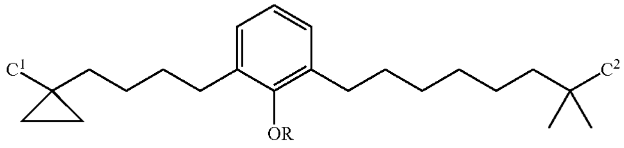 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 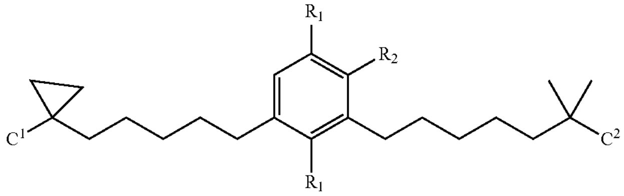 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 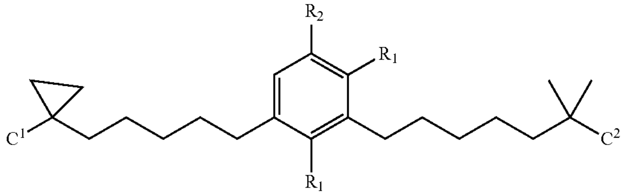 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 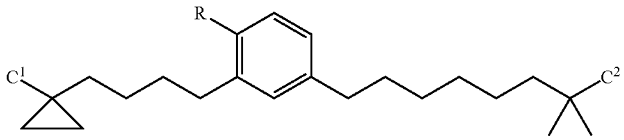 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |

TABLE A-continued

| Structure |
|---|
| 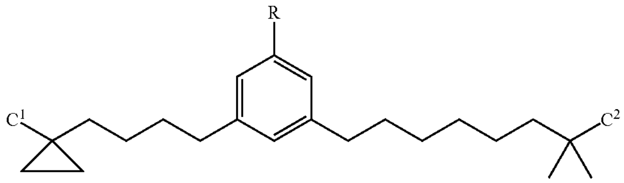 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 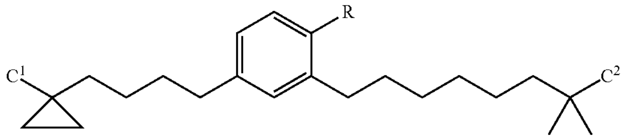 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 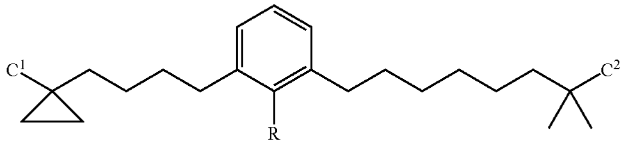 |
| wherein $C^1$ and $C^2$ = COOH; $C^1$ and $C^2$ = COOH; $C^1$ = COOH and $C^2$= CO—CoA; $C^1$ = CO—CoA and $C^2$ = COOH; or $C^1$ and $C^2$ = CO-CoA; and wherein R = F, Cl, Br, or $CF_3$ |
| 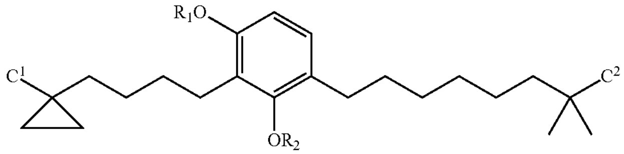 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 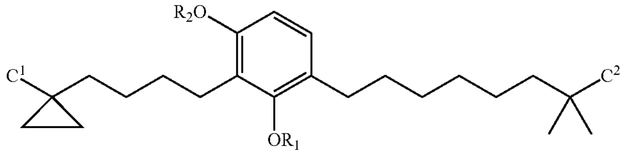 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 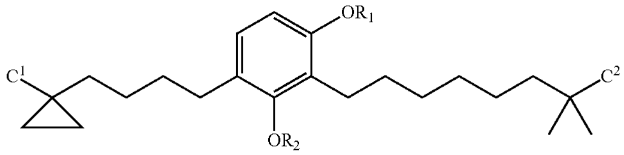 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 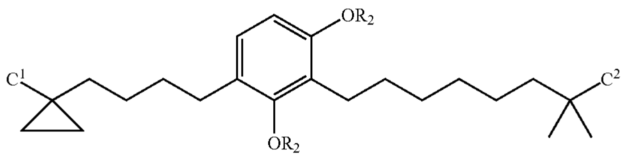 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 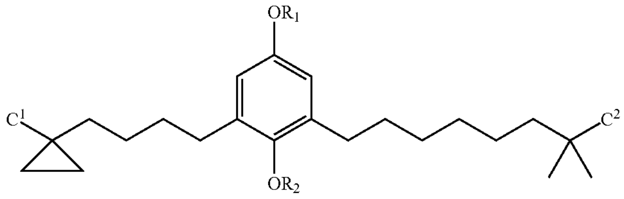 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 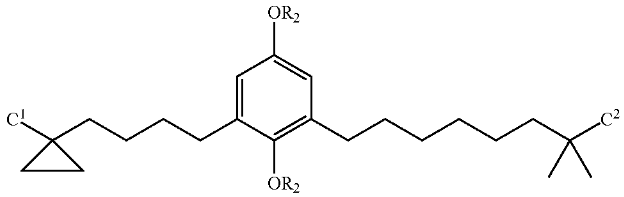 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 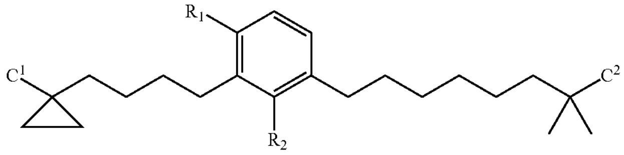 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 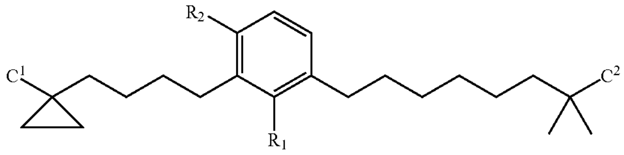 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 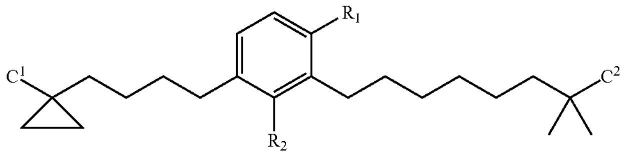 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 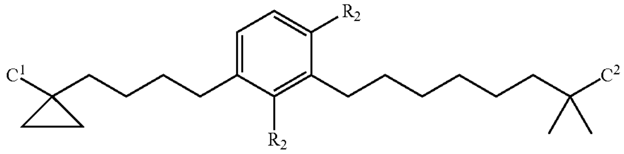 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 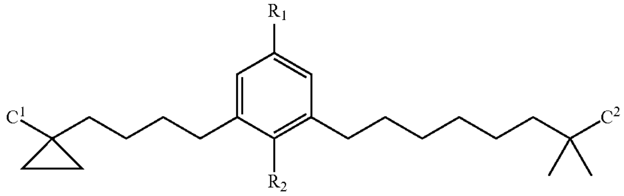 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 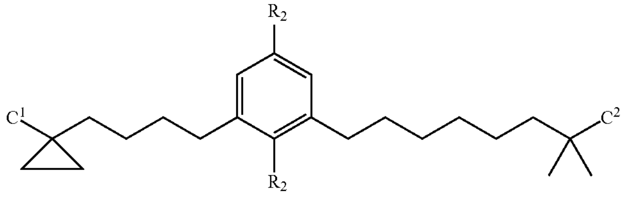 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 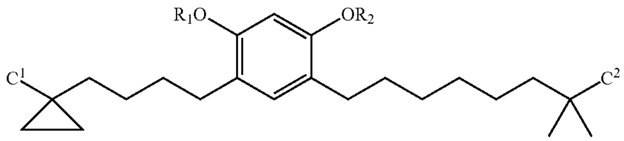 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
|---|
| 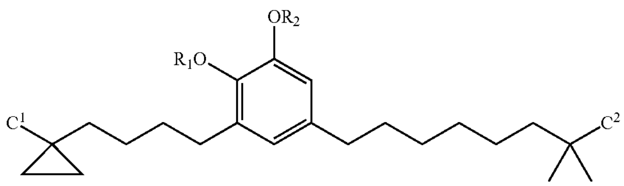 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 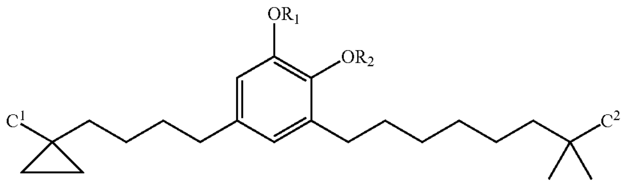 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 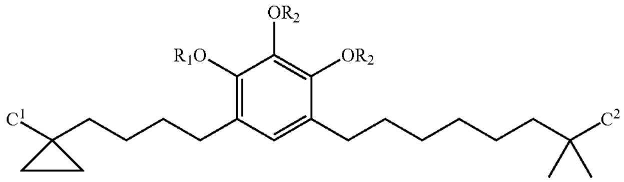 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 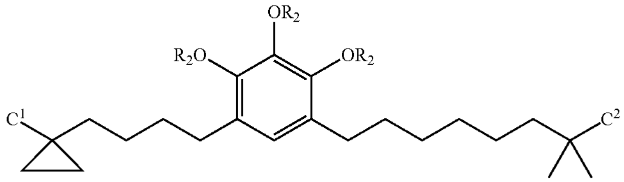 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 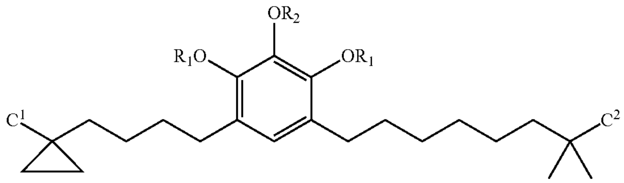 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 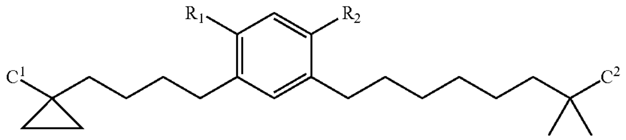 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 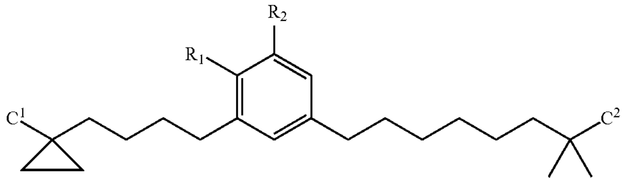 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 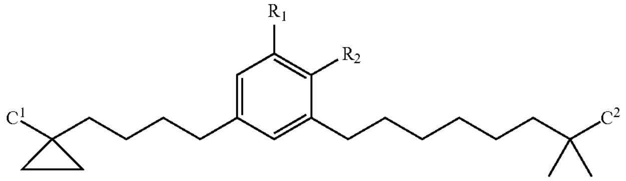 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 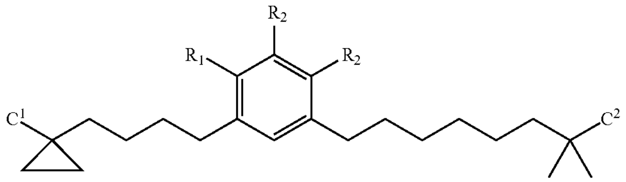 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 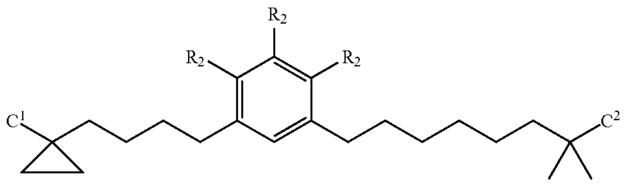 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
| --- |
| 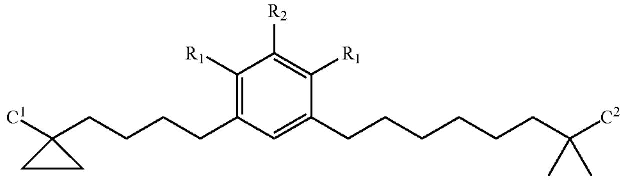 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 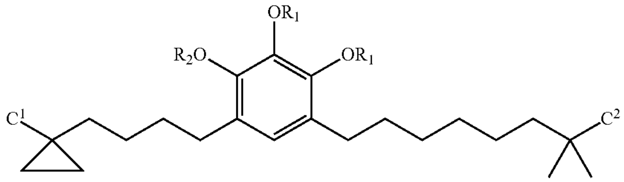 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 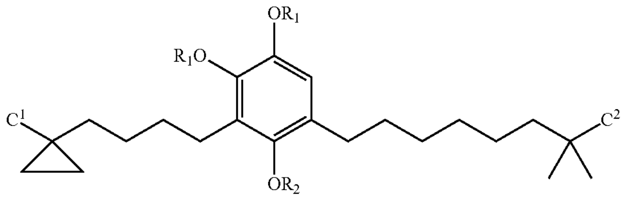 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 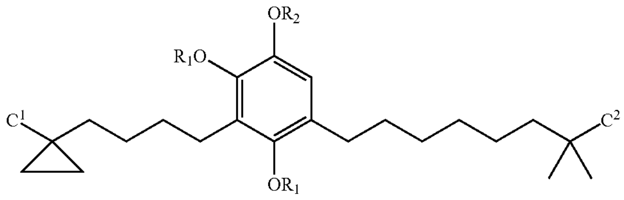 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 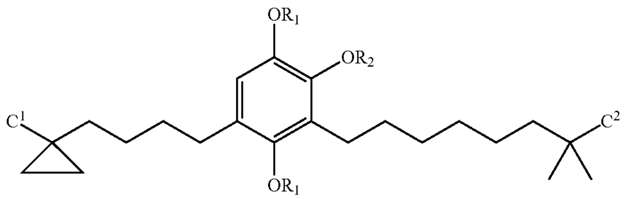 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 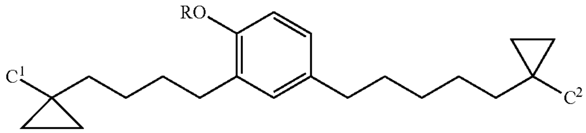 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 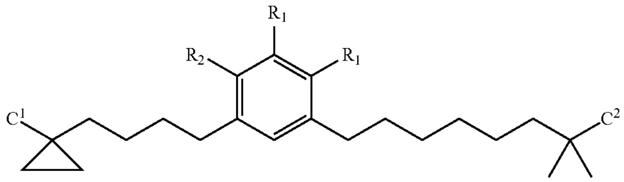 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 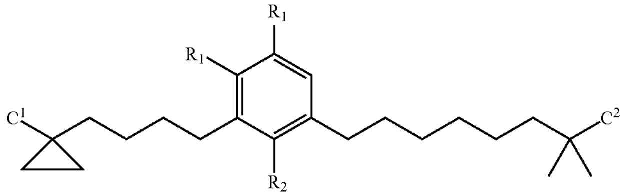 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 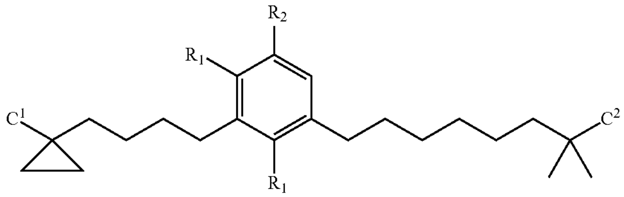 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 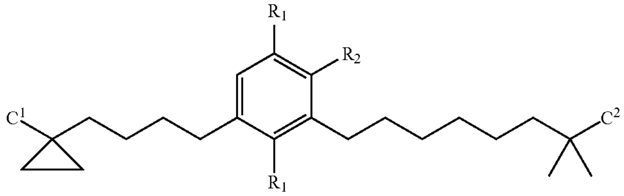 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 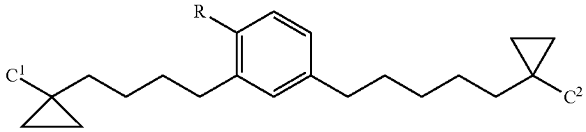 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 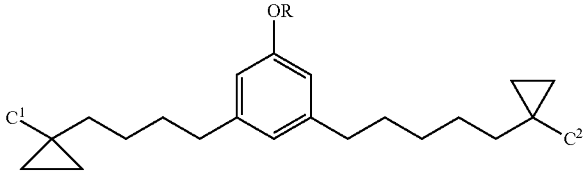 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 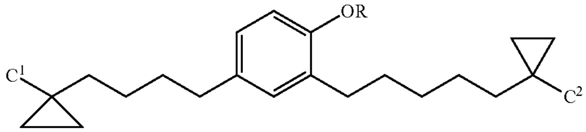 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 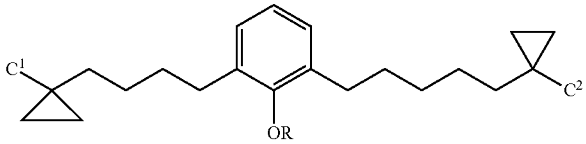 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 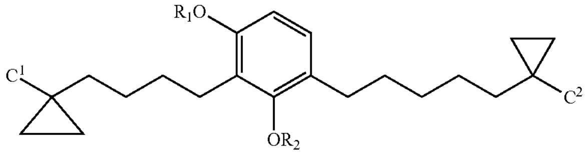 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
|---|
| 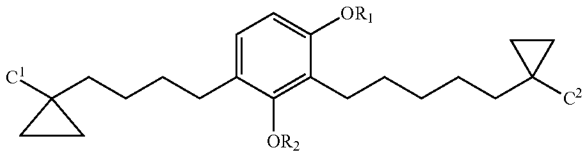<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 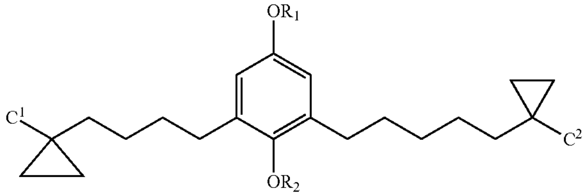<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 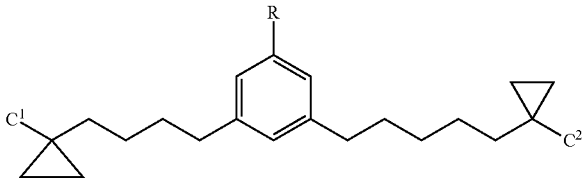<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 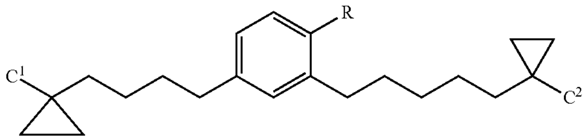<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 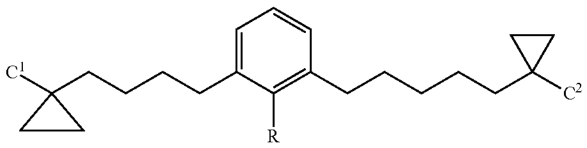<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
| --- |
| 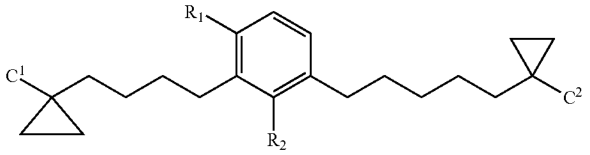 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 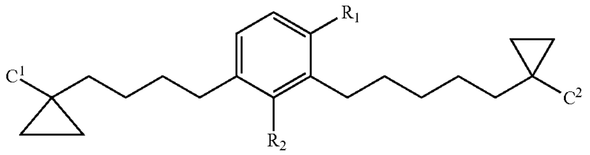 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 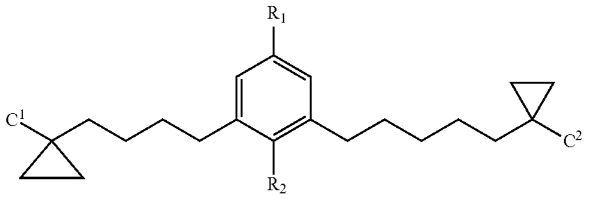 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 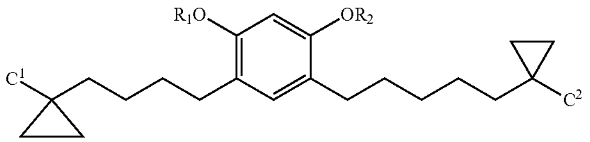 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 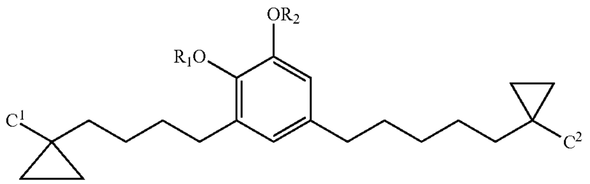 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 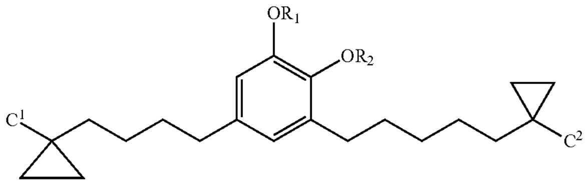 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 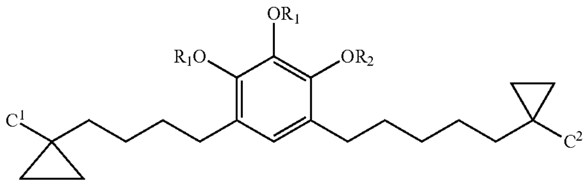 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 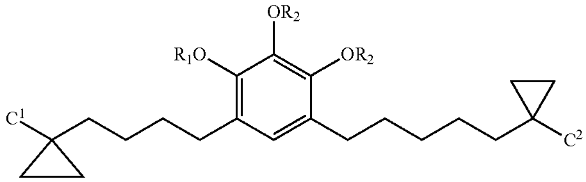 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 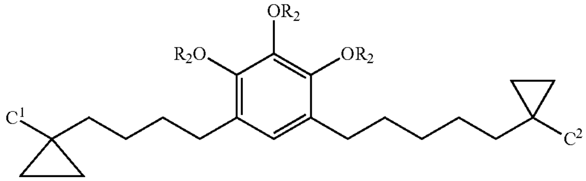 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 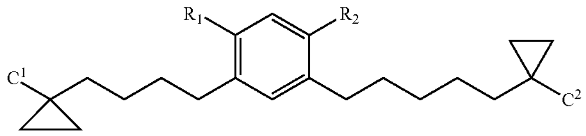 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
|---|
| 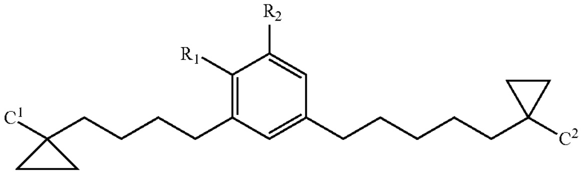 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 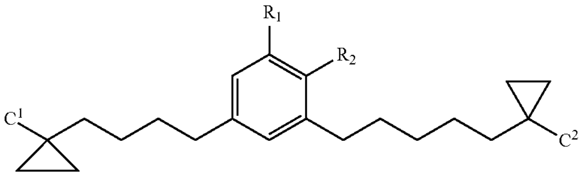 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 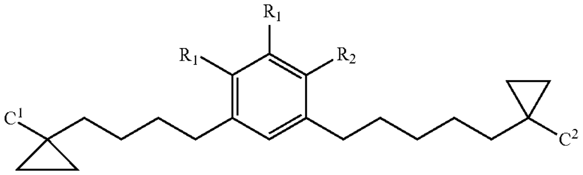 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 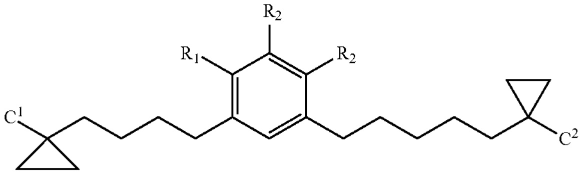 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 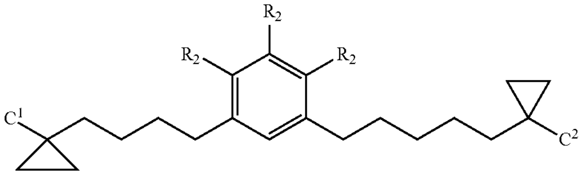 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
|---|
| 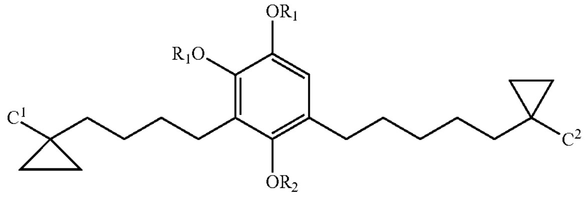 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 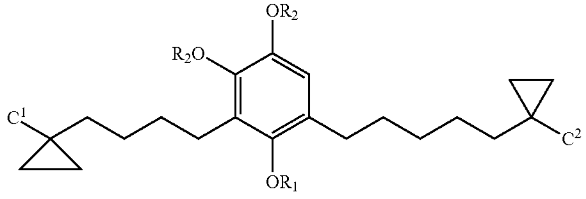 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 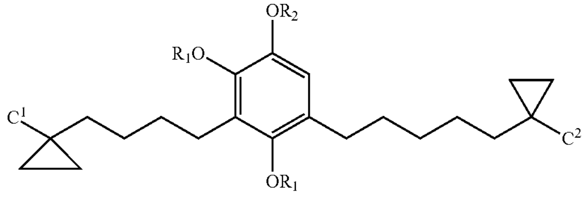 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 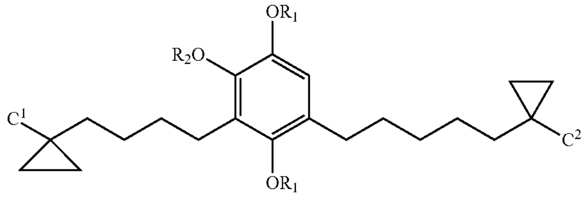 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
|---|
| 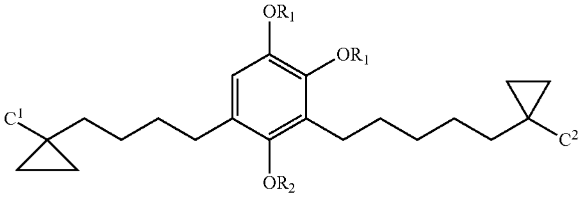 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 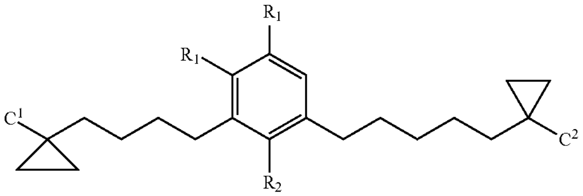 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 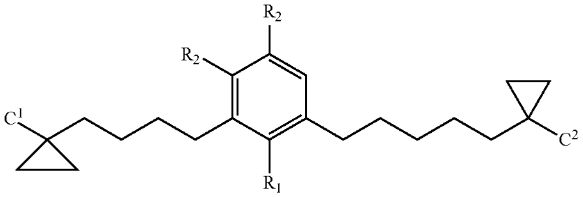 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 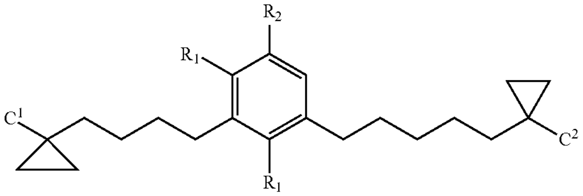 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 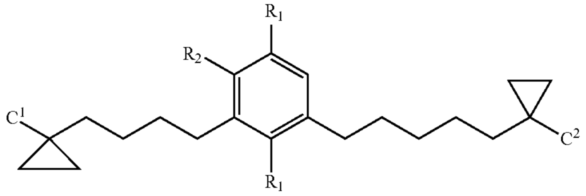 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 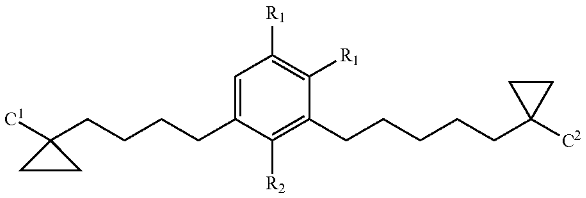 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 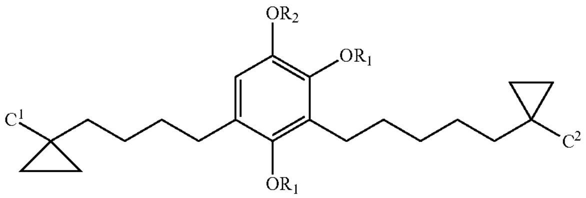 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 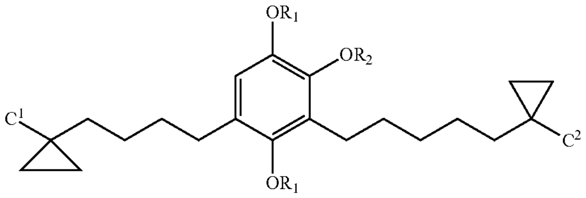 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 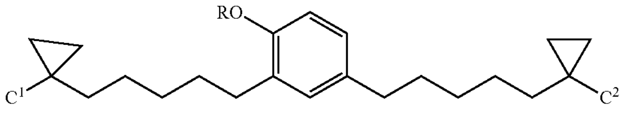 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
|---|
| 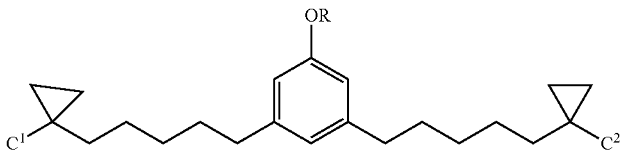<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 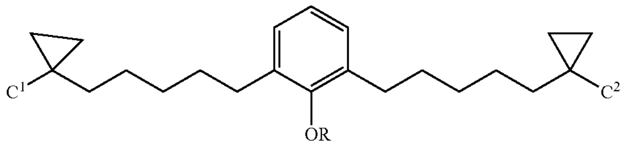<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 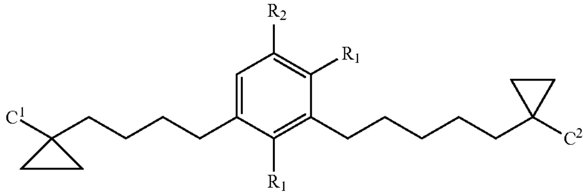<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 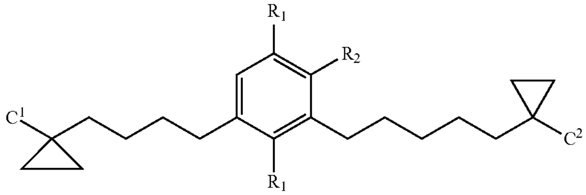<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 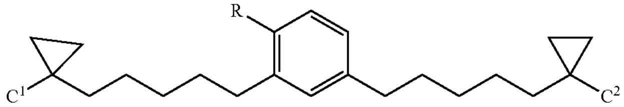<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
| --- |
| 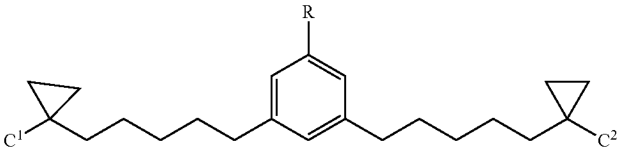 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 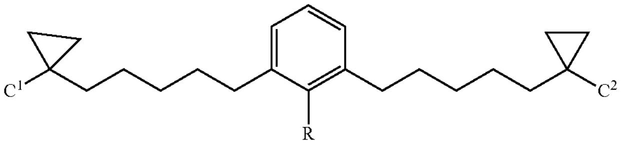 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 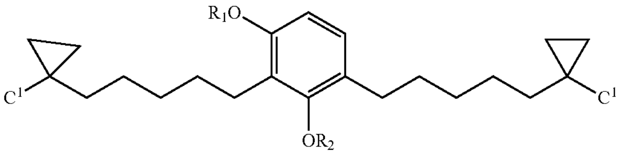 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 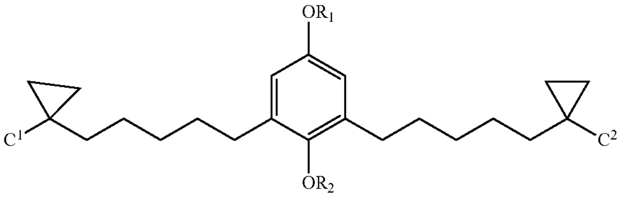 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 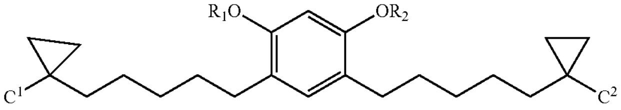 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 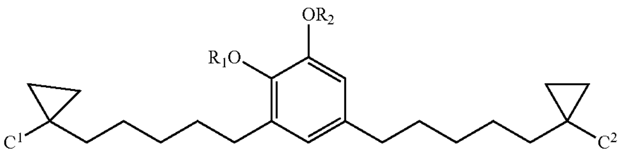 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
| --- |
| 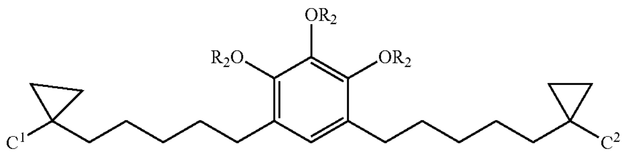 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 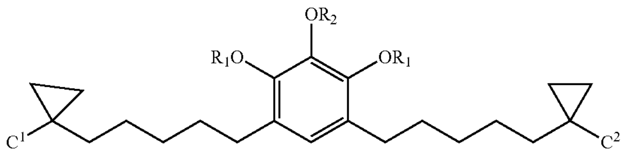 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 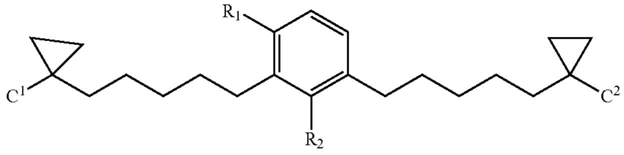 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 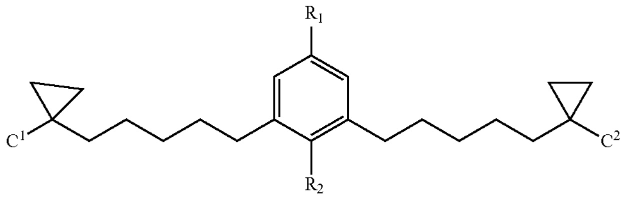 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 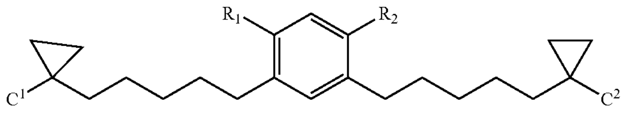 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
| --- |
| 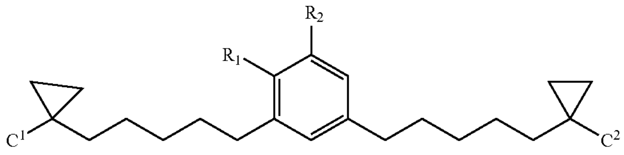 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 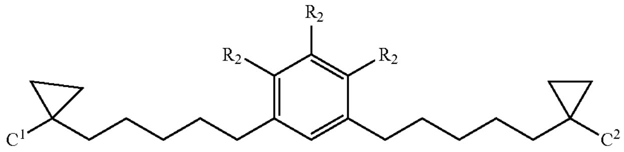 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 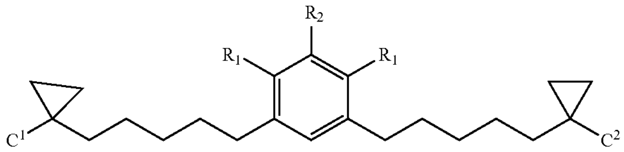 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 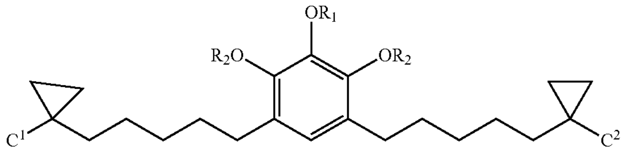 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 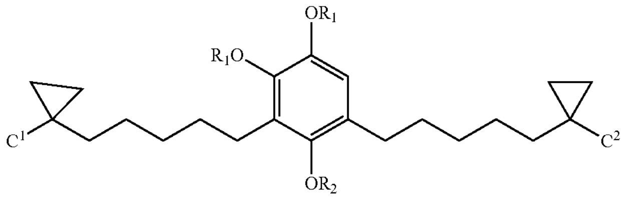 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 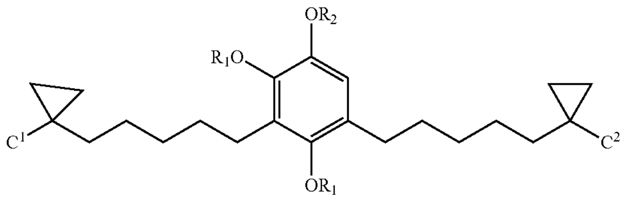 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 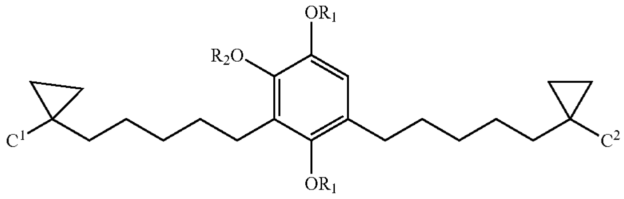 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 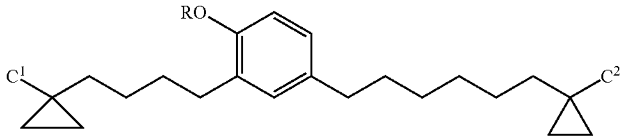 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 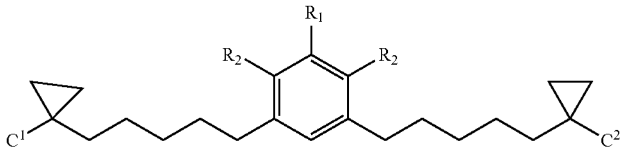 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 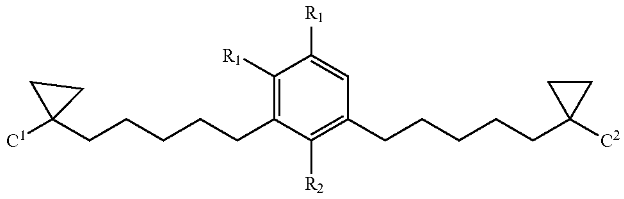 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 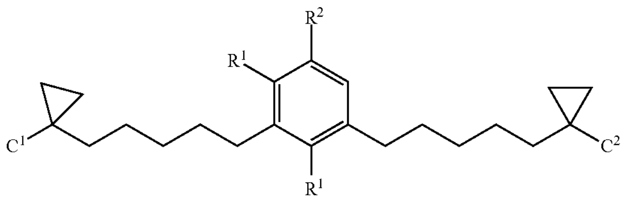 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 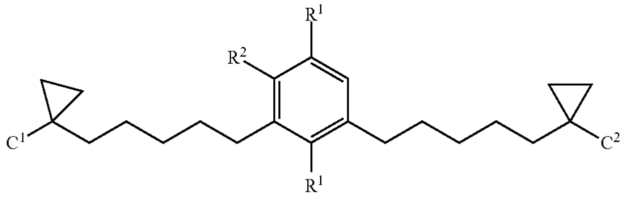 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 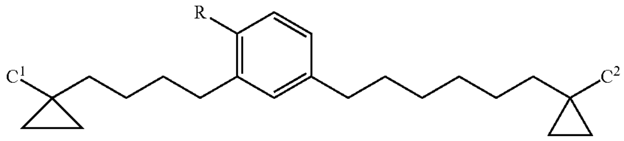 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 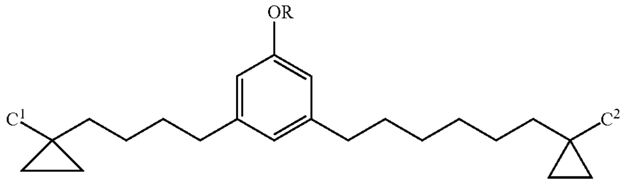 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 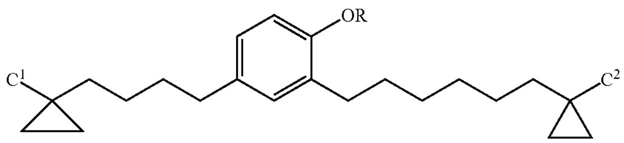 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-continued

| Structure |
| --- |
| 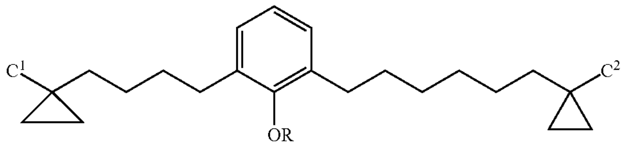 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 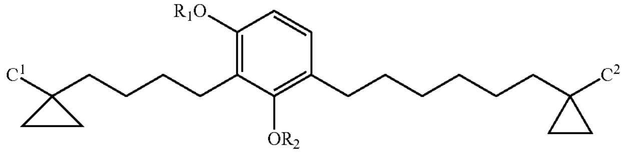 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 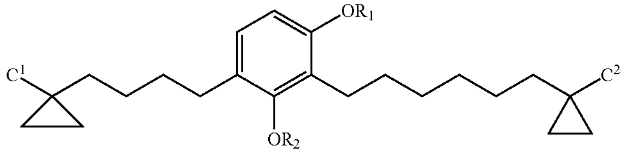 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 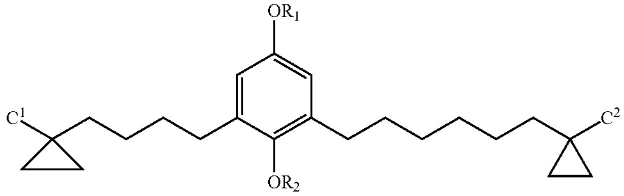 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 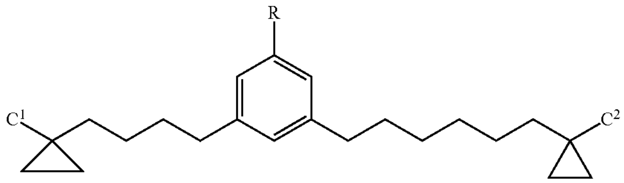 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-continued

| Structure |
| --- |
| 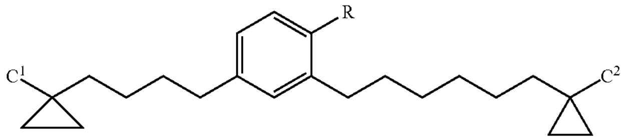 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 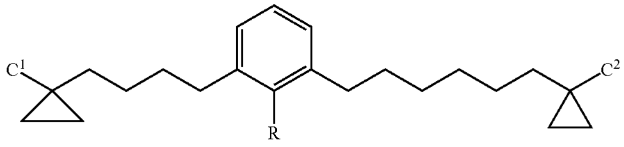 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 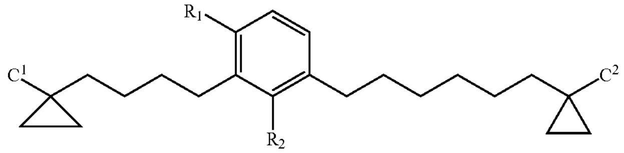 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 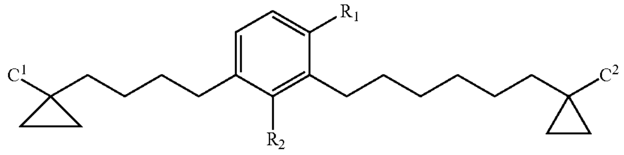 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 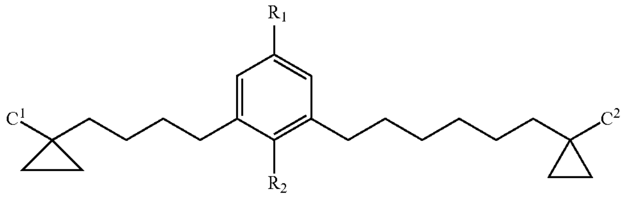 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
| --- |
| 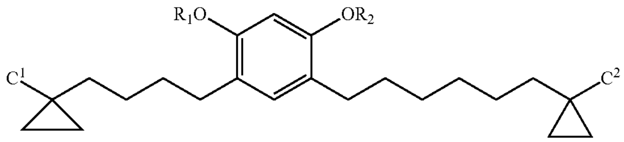 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 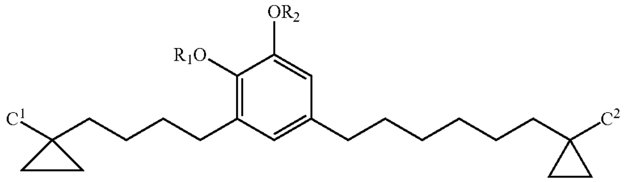 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 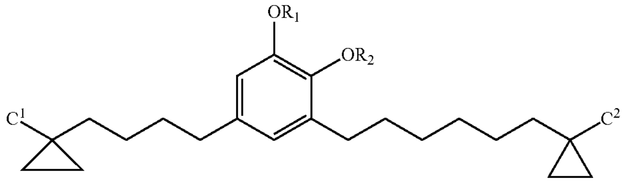 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 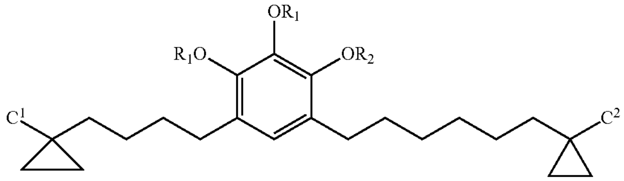 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 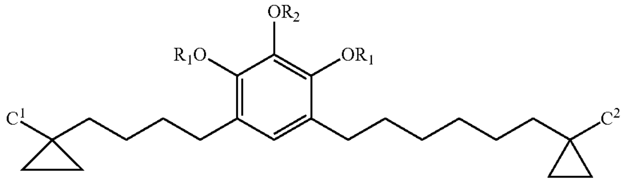 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 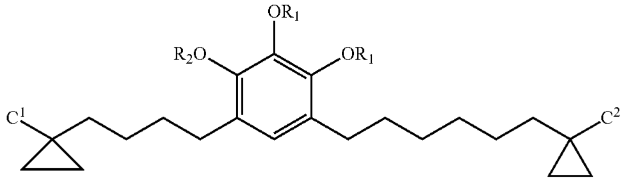 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 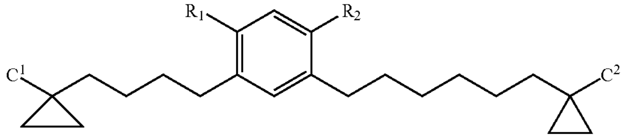 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 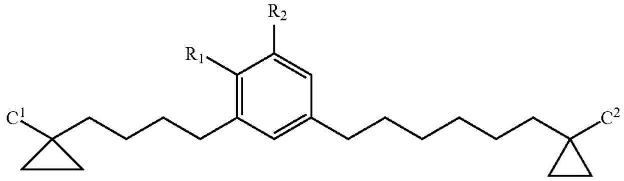 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 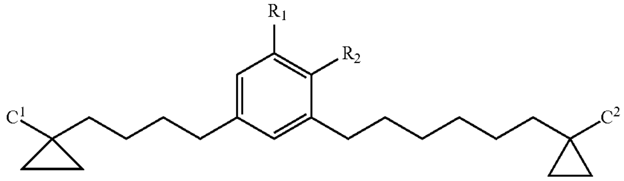 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 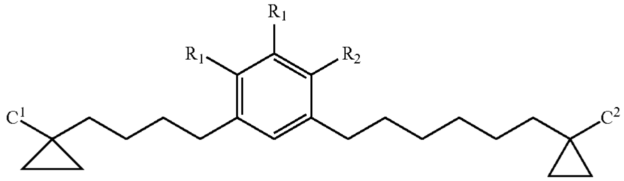 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 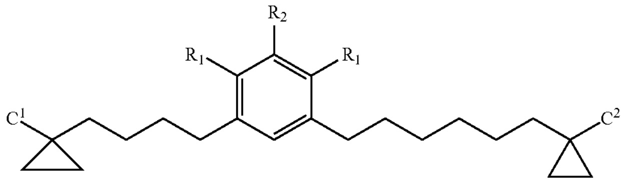<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 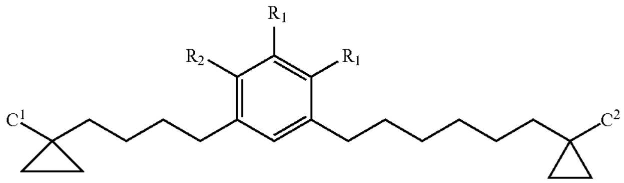<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 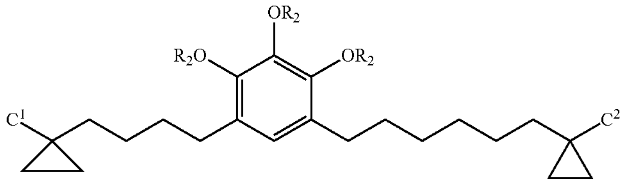<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 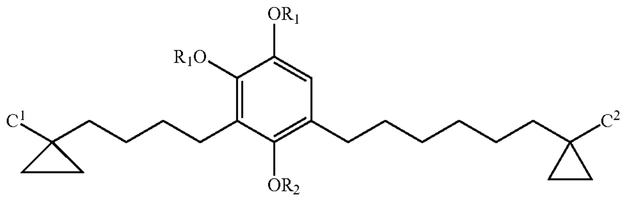<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 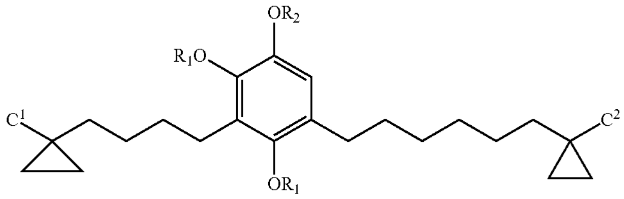 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 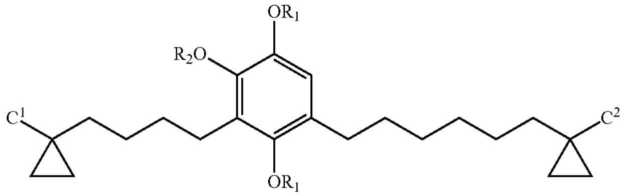 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 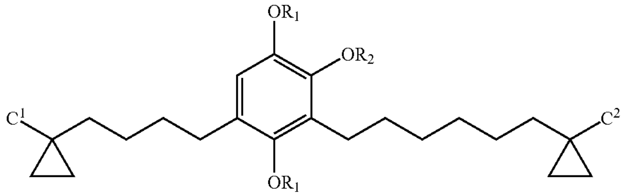 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 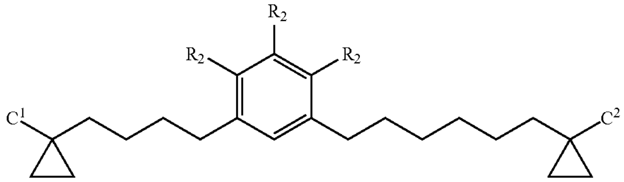 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-continued

| Structure |
| --- |
| 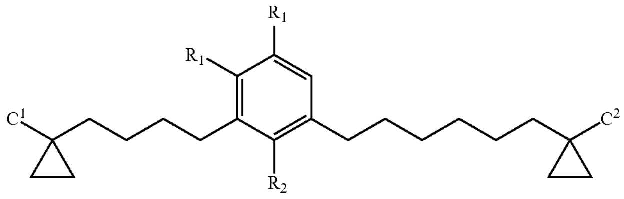 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 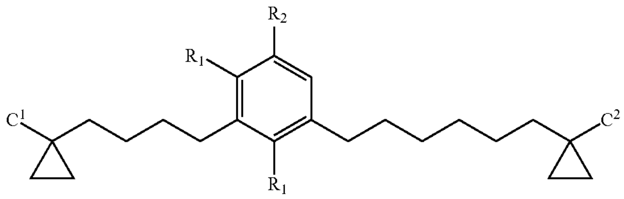 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 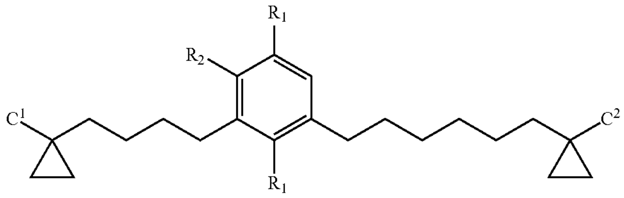 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 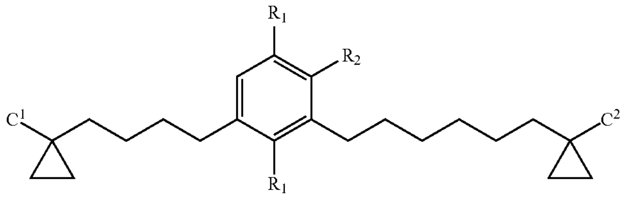 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 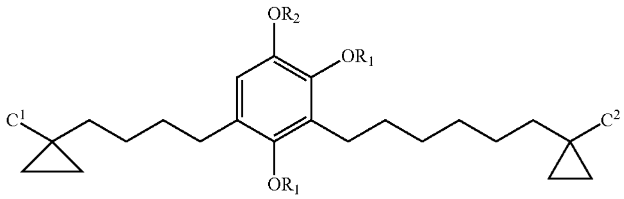 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 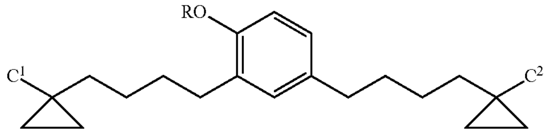 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 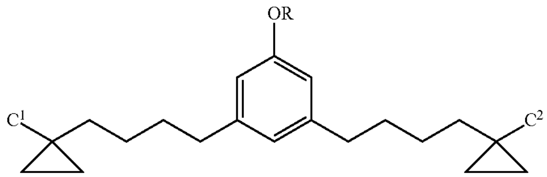 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 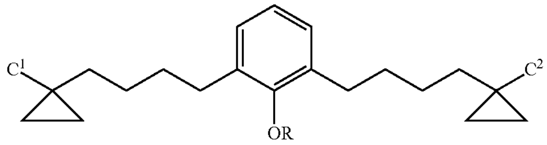 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 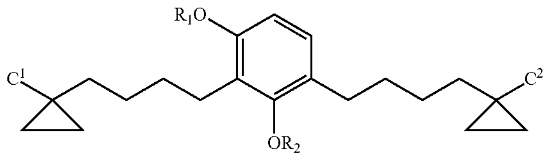 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-continued

| Structure |
|---|
| 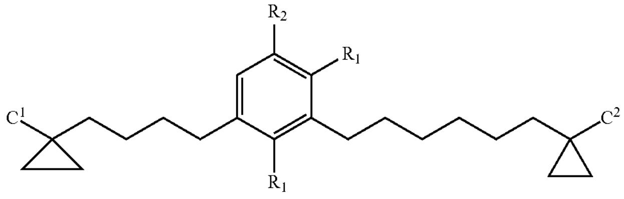 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 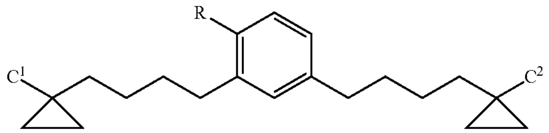 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 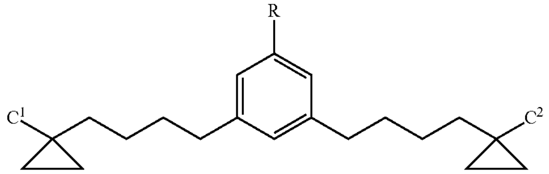 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 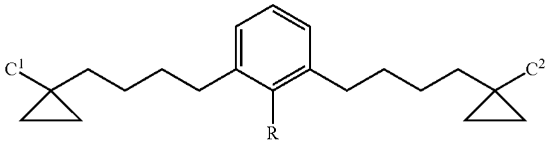 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 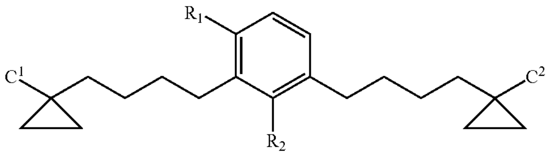 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-continued

| Structure |
| --- |
| 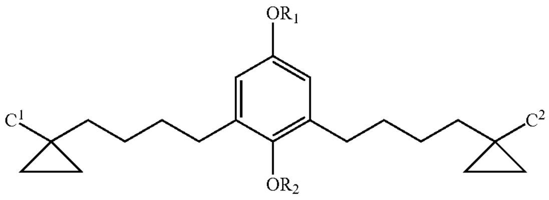 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 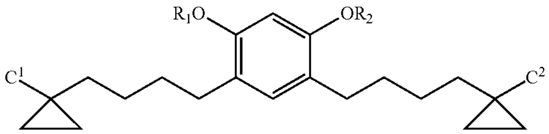 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 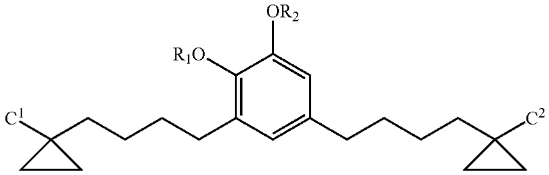 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 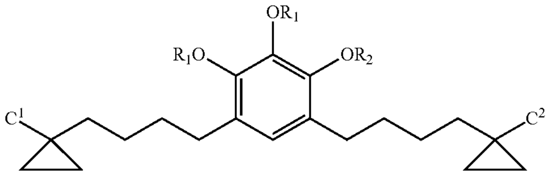 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 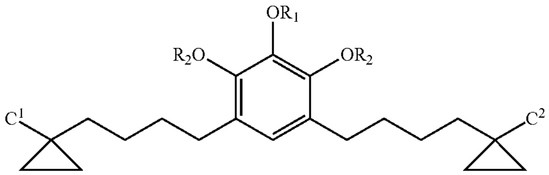 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-continued

| Structure |
| --- |
| 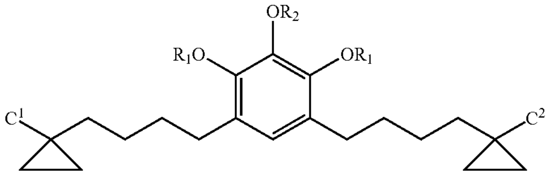 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 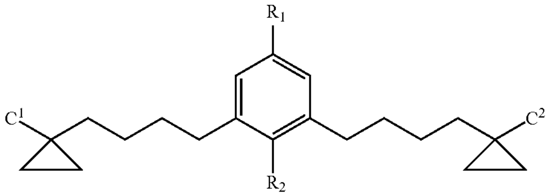 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 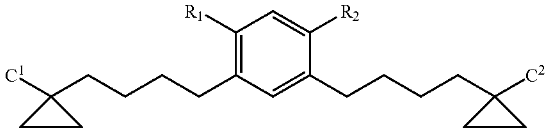 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 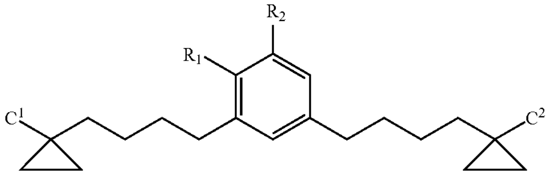 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 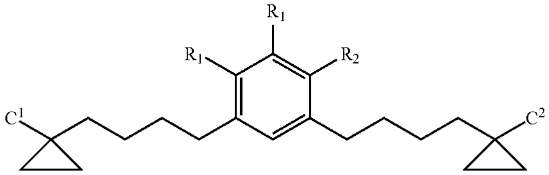 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
| --- |
| 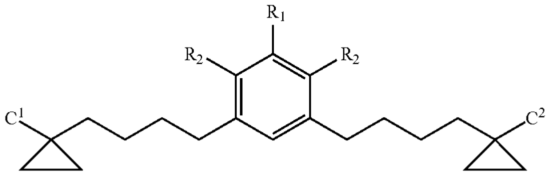 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 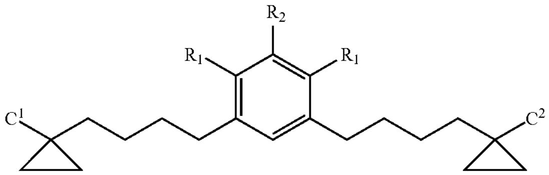 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 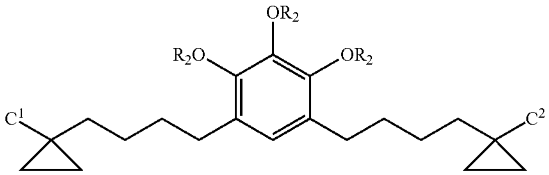 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 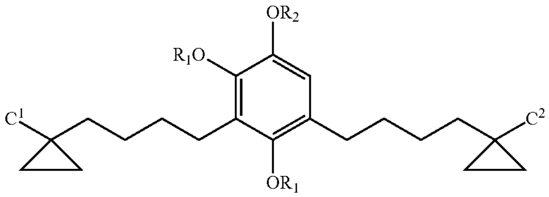 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 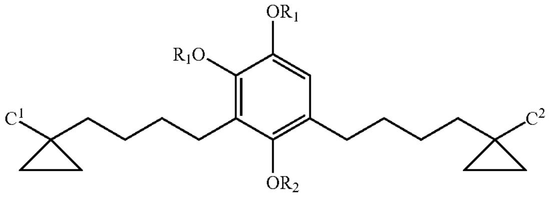 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 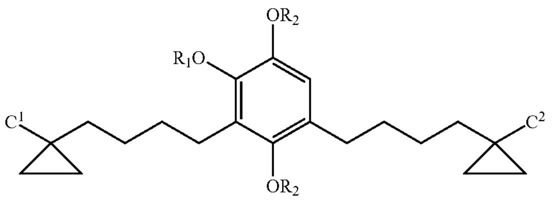 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 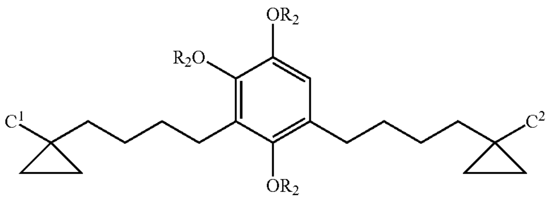 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 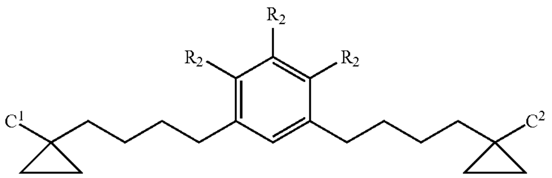 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 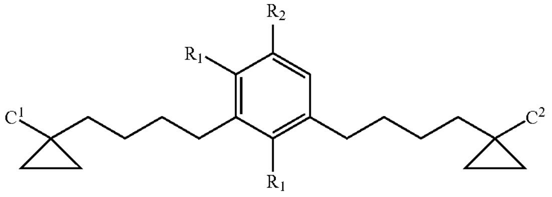 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-continued

| Structure |
|---|
| 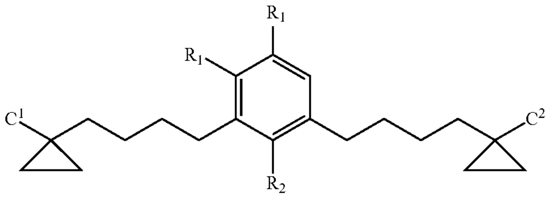 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 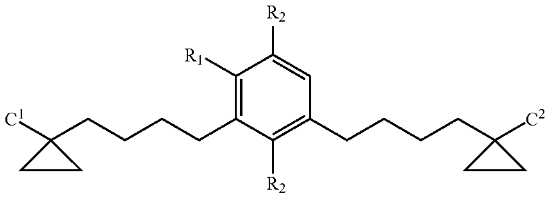 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 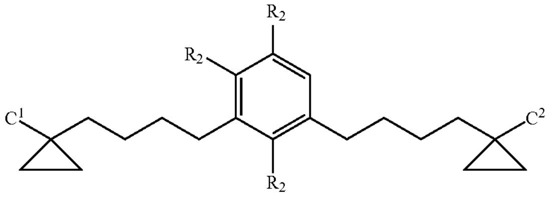 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 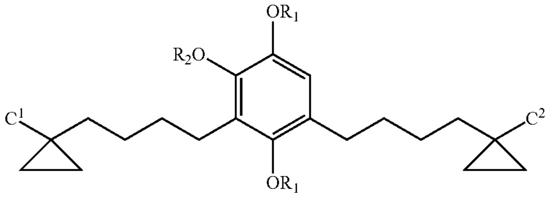 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-continued

| Structure |
| --- |
| 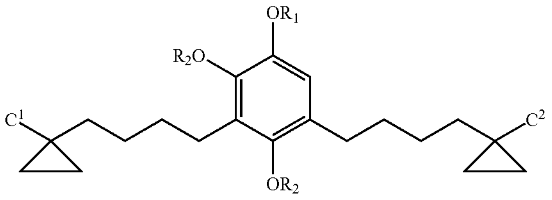 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 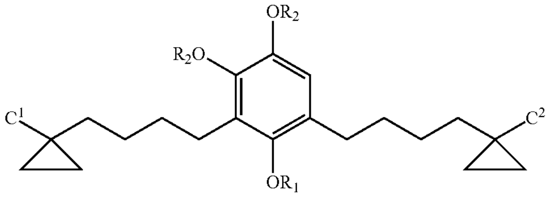 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 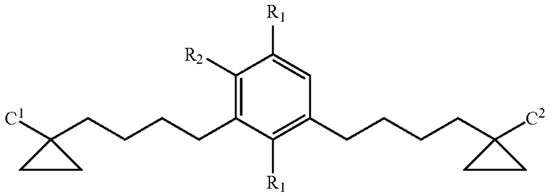 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 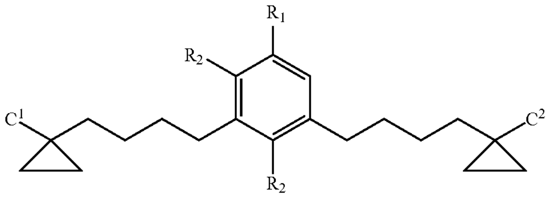 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-continued

| Structure |
| --- |
| 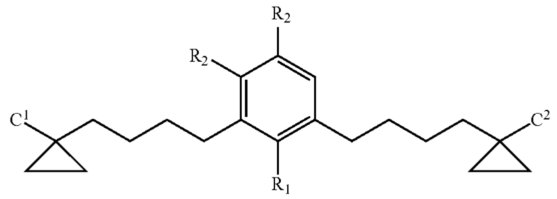 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

In some embodiments, the compound of Formula (ID) or (IG), has any one of the structures shown in Table A-15, defined by $C^1$ and $C^2$, and defined by R, $R_1$ and $R_2$, where present, or a pharmaceutically acceptable salt or solvate thereof. In some embodiments, R of the compound of Table A-15 is $CH_3$. In some embodiments, one or more of R, $R_1$ and $R_2$ of the compound of Table A-15 is $CH_3$. In some embodiments, one or more of R, $R_1$ and $R_2$ of the compound of Table A-15 is F. In some embodiments, one or more of R, $R_1$ and $R_2$ of the compound of Table A-15 is Cl. In some embodiments, one or more of R, $R_1$ and $R_2$ of the compound of Table A-15 is Br. In some embodiments, one or more of R, $R_1$ and $R_2$ of the compound of Table A-15 is $CF_3$.

In some embodiments, the pharmaceutically acceptable salt of a compound having any one of the structures shown in Table A-15 and defined by $C^1$ and $C^2$, and defined by R, $R_1$ and $R_2$, where present, is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

TABLE A-15

| Structure |
| --- |
| 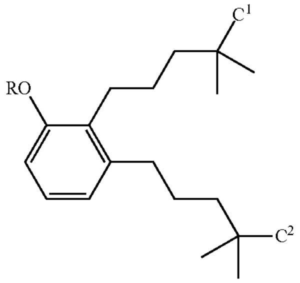 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 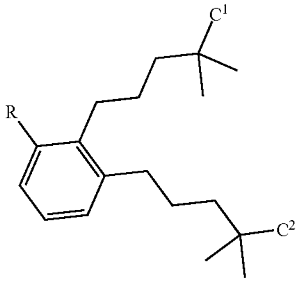 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 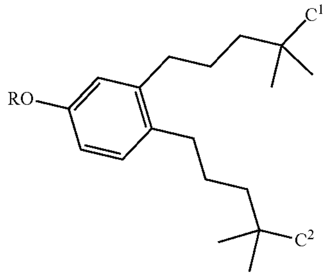 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 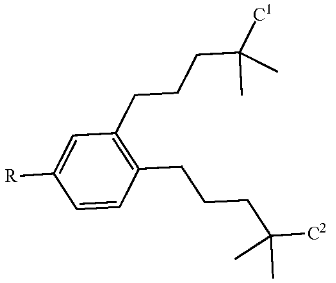 |
| wherein $C^1$ and $C^2$ = COOH; $C^1$ and $C^2$ = COOH; $C^1$ = COOH and $C^2$ = CO—CoA; $C^1$ = |

TABLE A-15-continued

| Structure |
|---|
| CO—CoA and $C^2$ = COOH; or $C^1$ and $C^2$ = CO—CoA; and wherein R = F, Cl, Br, or $CF_3$ |
| 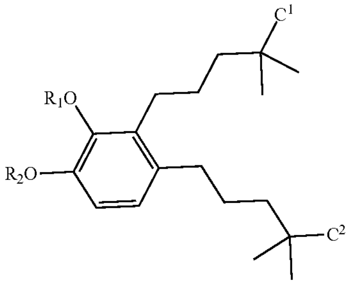 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 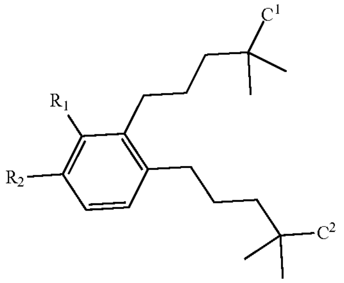 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 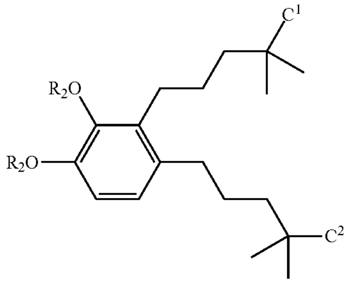 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 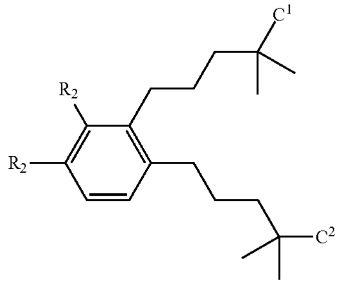 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 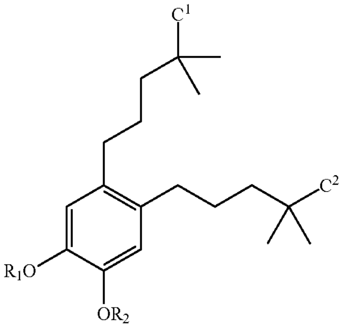 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 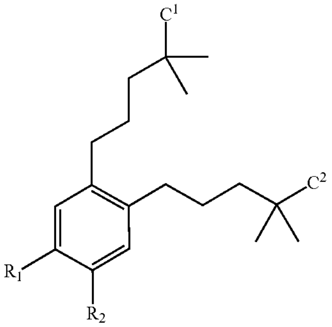 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 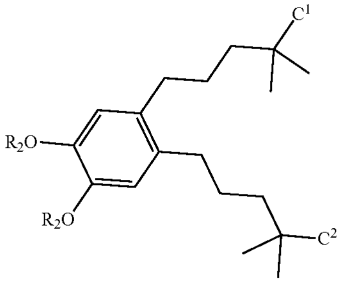 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 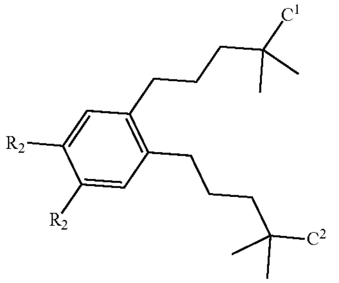 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 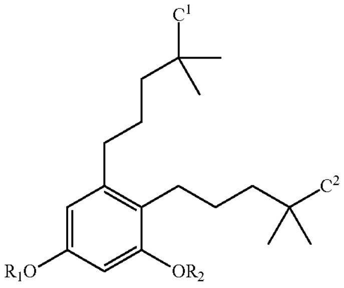 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 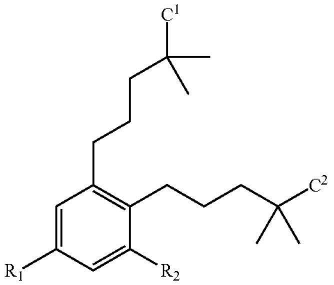 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 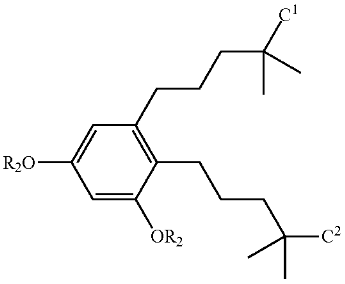 |
| wherein $C^1$ and $C^2$ = COOH; $C^1$ = COOH and $C^2$ = CO—CoA; $C^1$ = CO—CoA and $C^2$ = COOH; or |

TABLE A-15-continued

| Structure |
| --- |
| $C^1$ and $C^2$ = CO—CoA; and wherein each $R_2$ is independently a (C1-C4)alkyl |
| 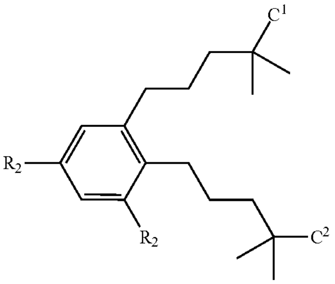 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 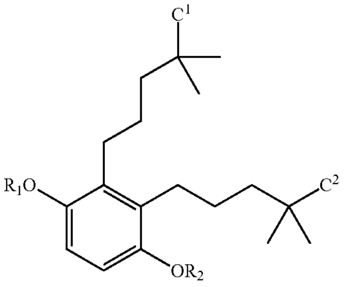 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 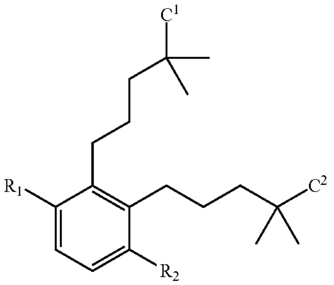 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 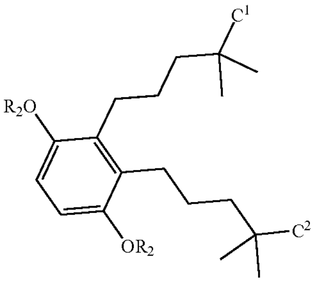 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 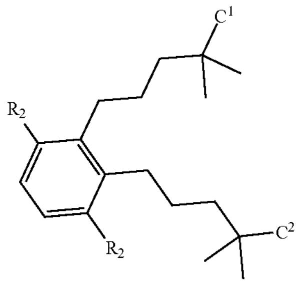 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 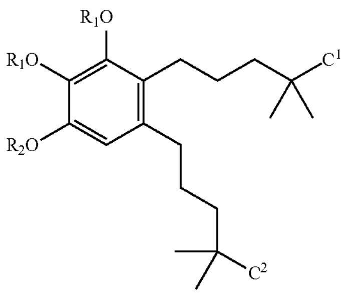 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 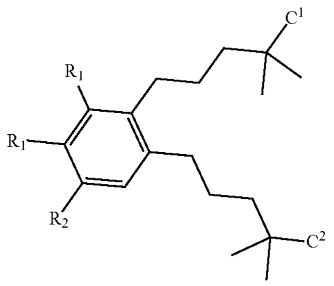 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
|---|
| 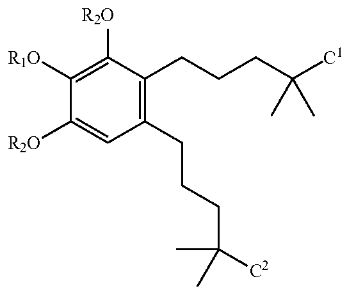 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 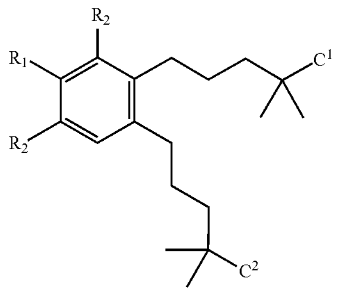 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 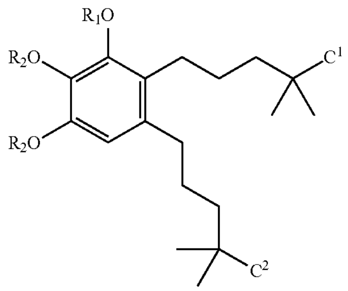 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 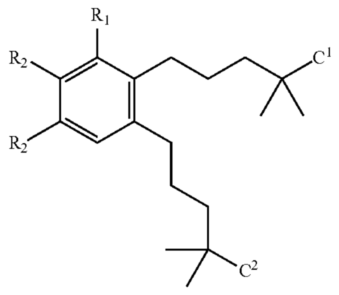 |

TABLE A-15-continued

| Structure |
|---|

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

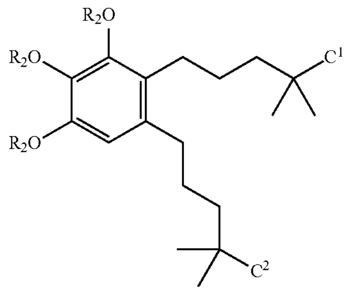

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

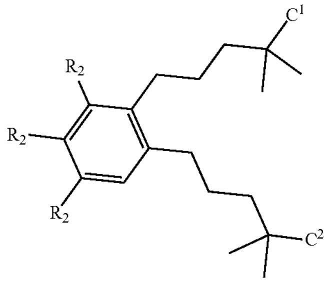

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

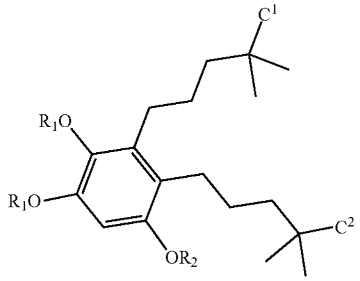

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl TABLE A-15-continued

| Structure |
|---|

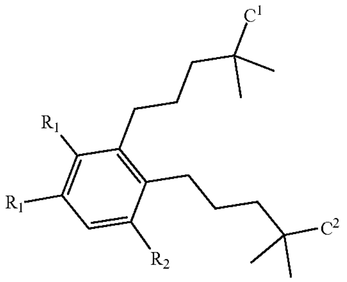

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

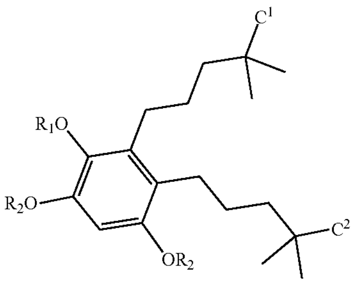

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

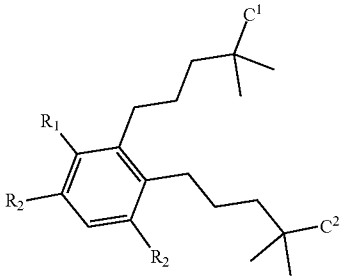

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

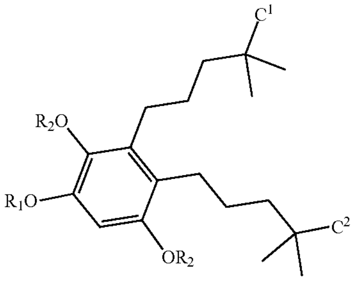

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 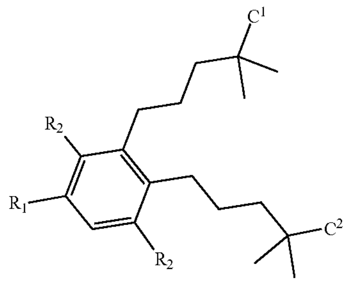 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 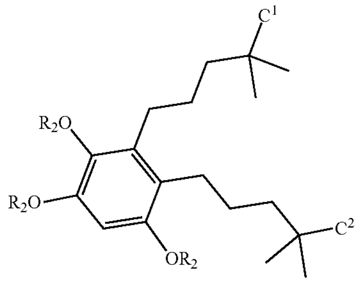 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 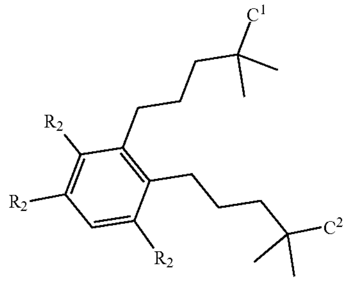 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 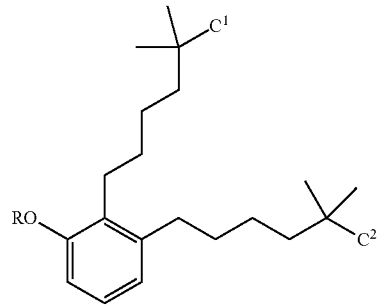 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 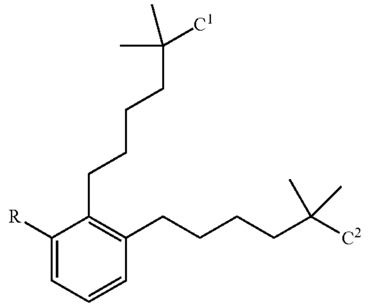 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 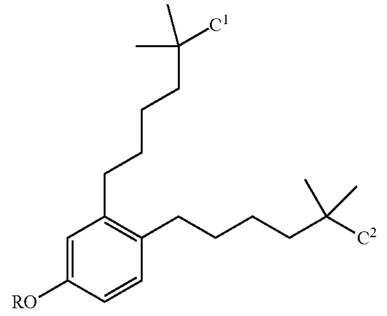 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 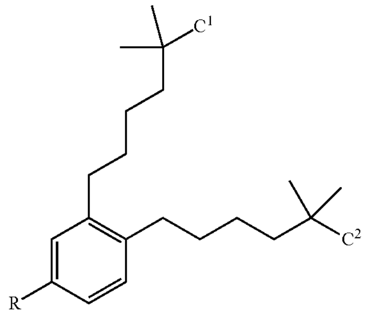 |

TABLE A-15-continued

| Structure |
| --- |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 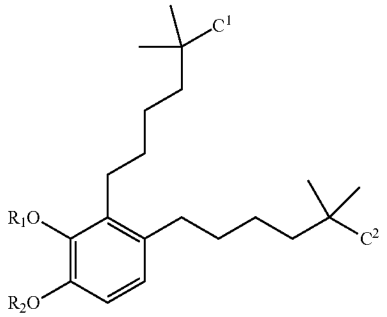 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 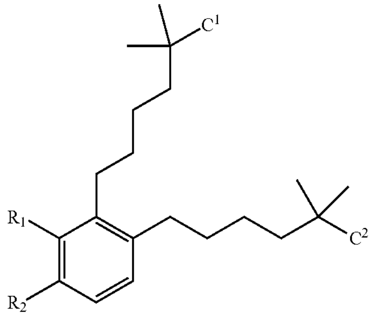 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 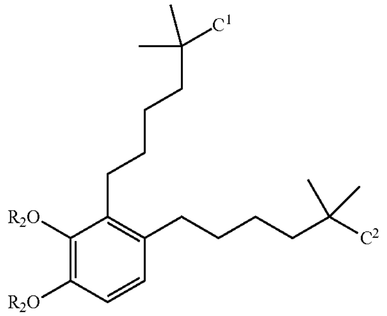 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 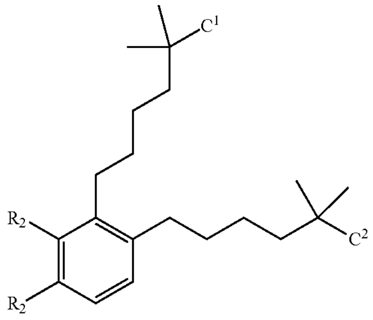 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 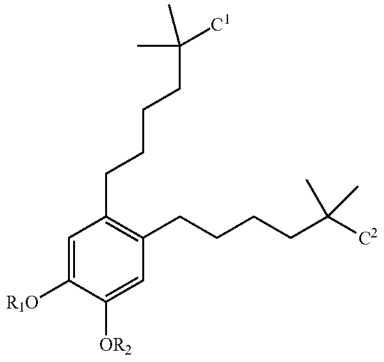 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 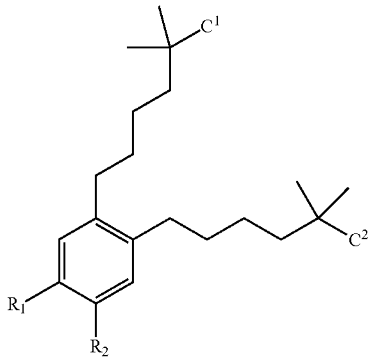 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 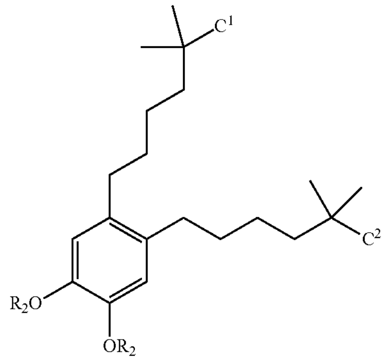 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 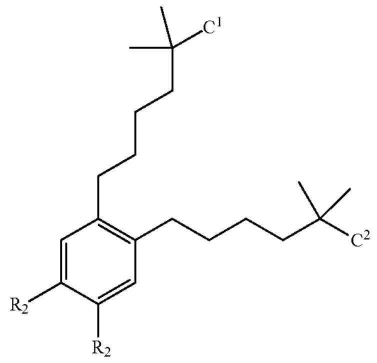 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 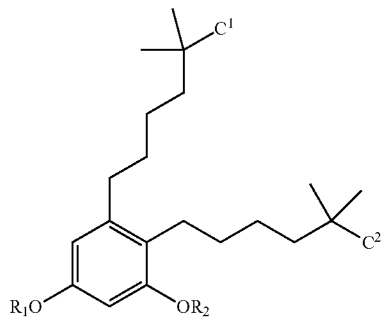 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 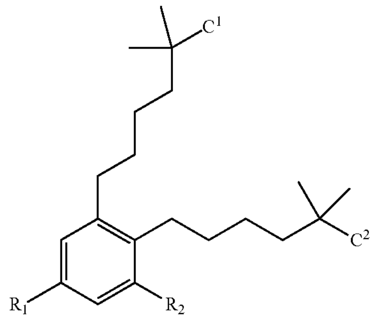 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 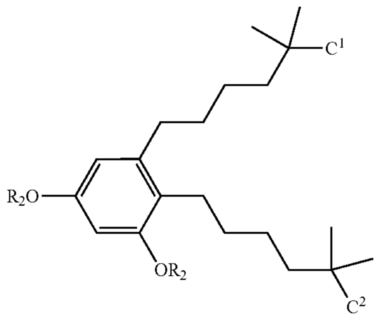 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 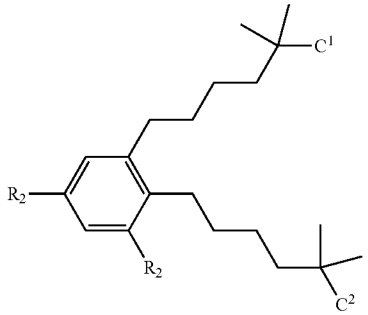 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 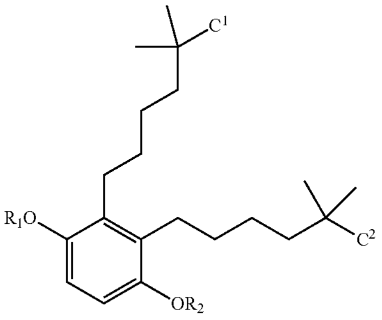 |

TABLE A-15-continued

Structure wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl

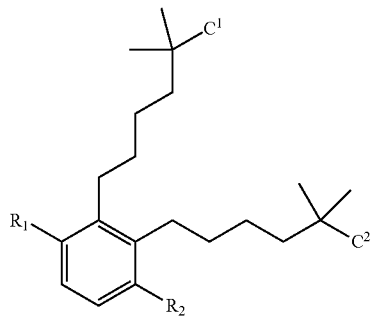

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl

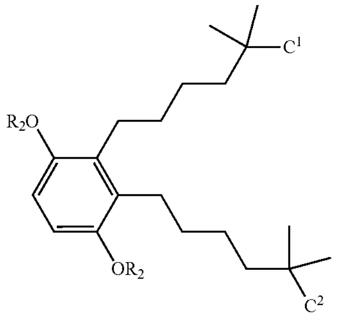

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

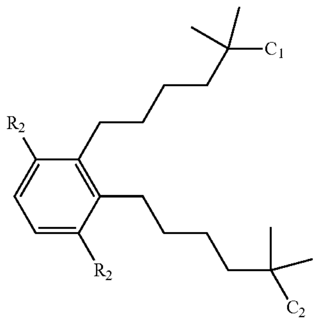

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ TABLE A-15-continued Structure

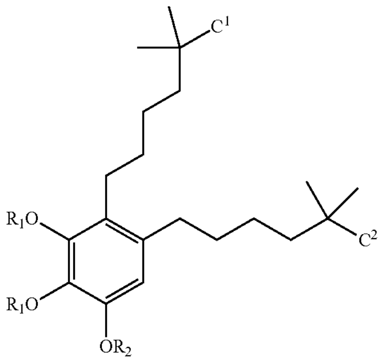

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

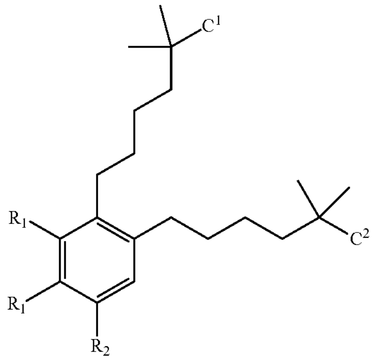

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

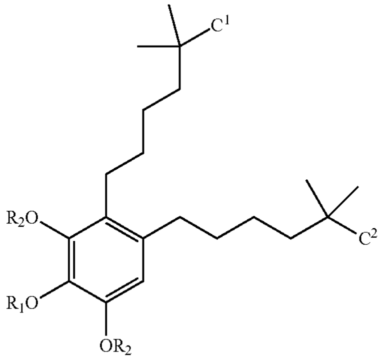

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl TABLE A-15-continued

| Structure |
| --- |
| 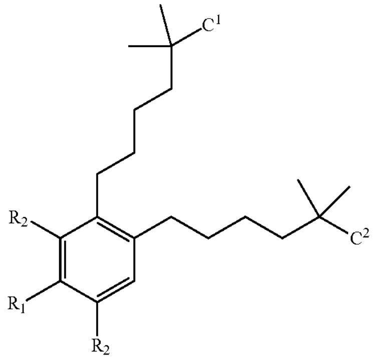 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 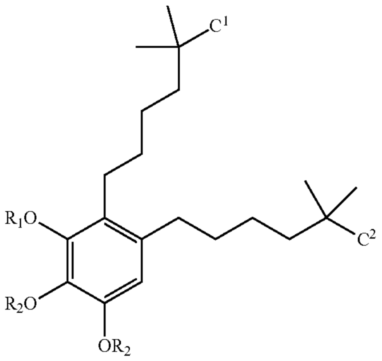 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 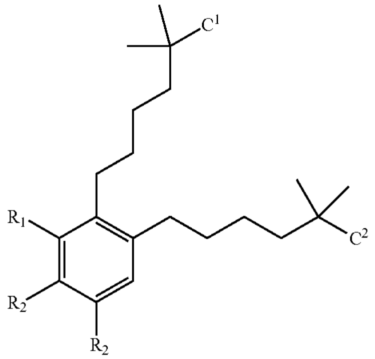 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 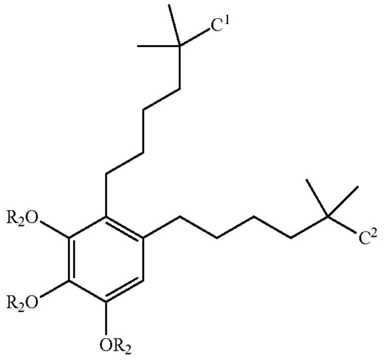 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 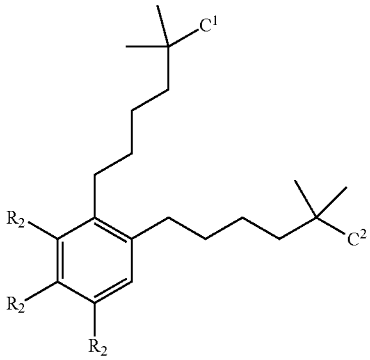 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 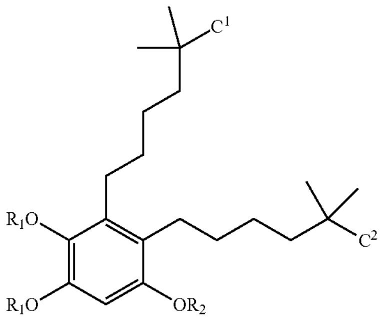 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 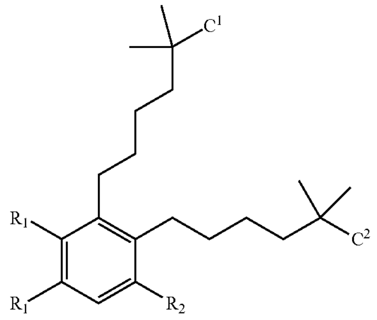 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alky |
| 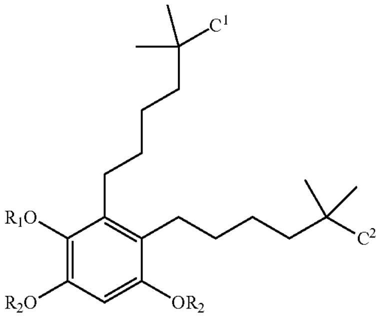 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 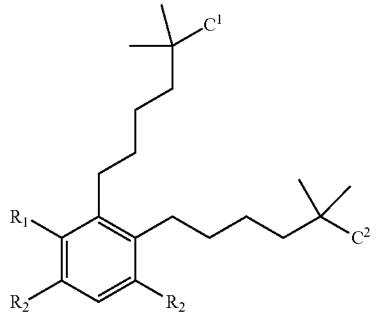 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 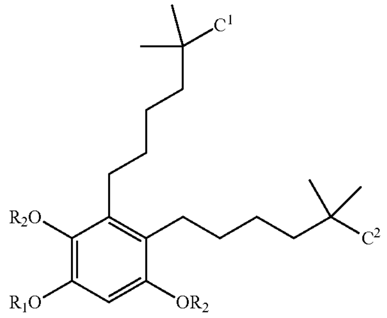 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 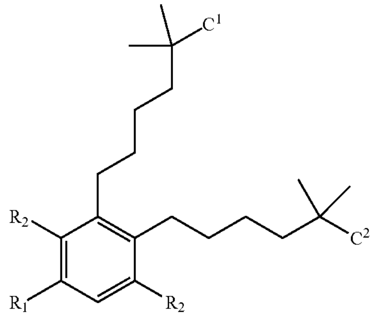 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 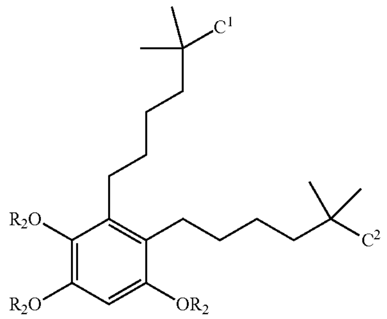 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 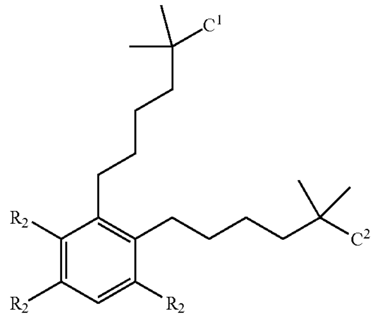 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 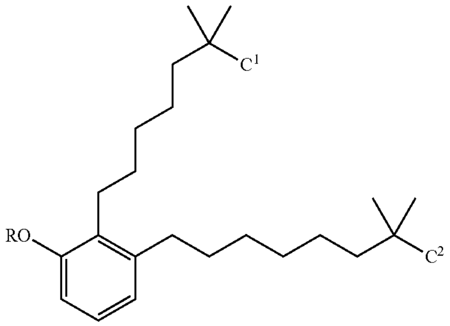 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 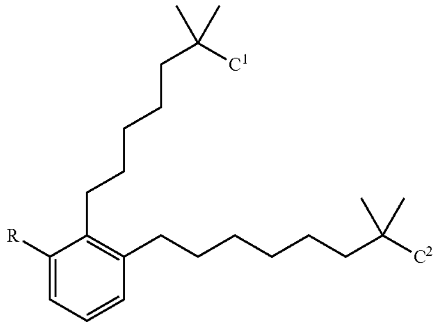 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |
| 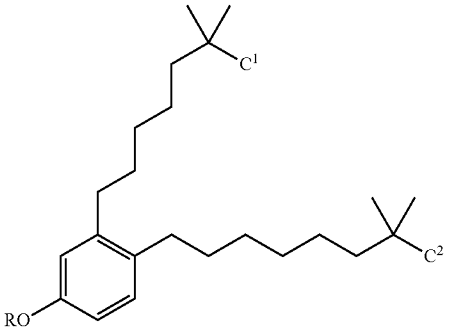 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 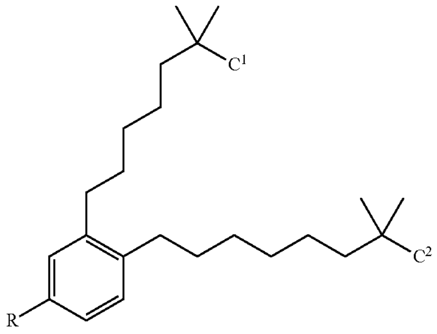 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 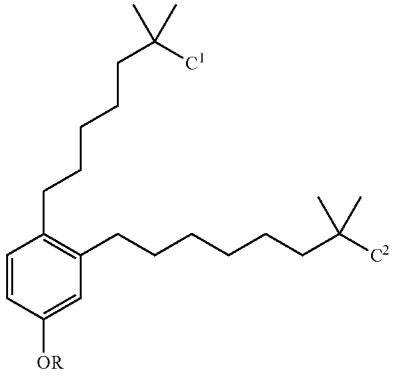 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R= (C1-C4)alkyl |

TABLE A-15-continued

| Structure |
|---|
| 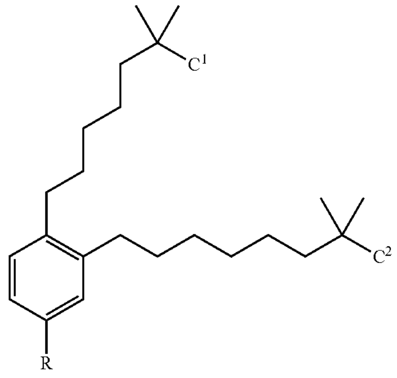 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R= F, Cl, Br, or $CF_3$ |
| 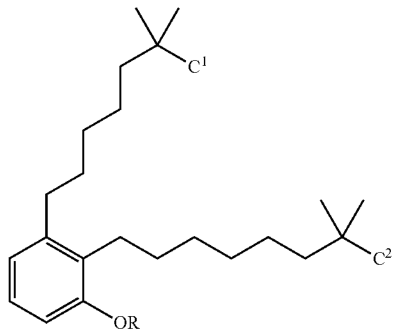 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 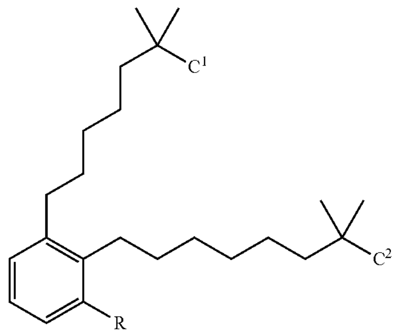 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 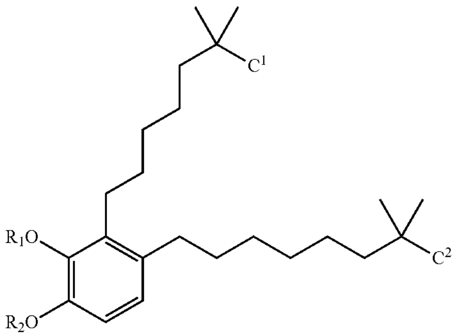 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 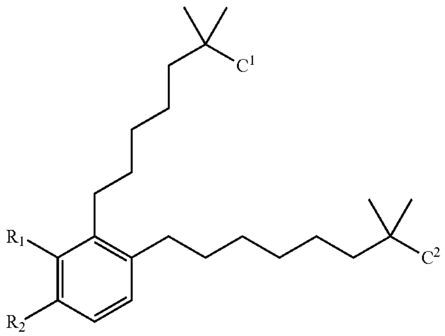 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 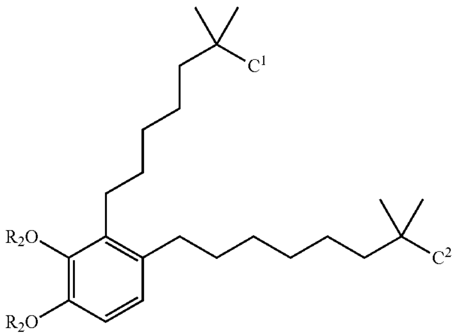 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 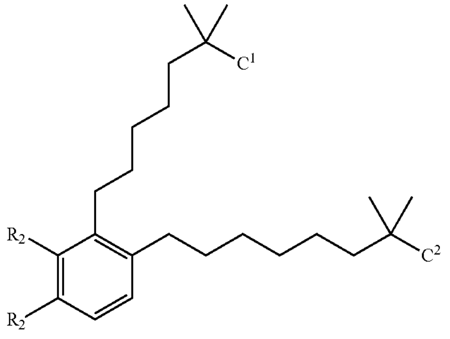 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 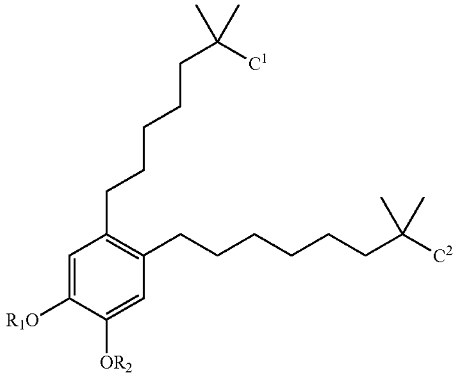 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 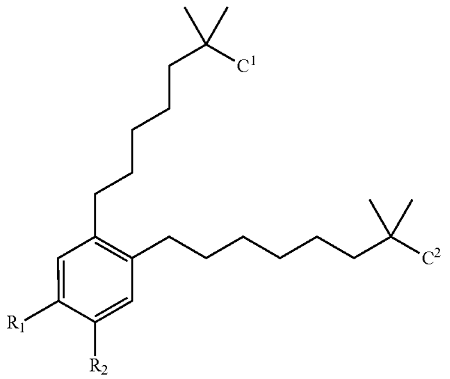 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 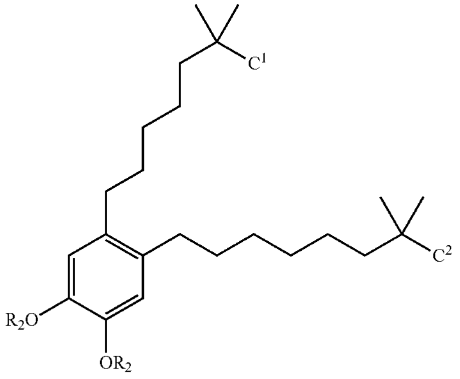 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 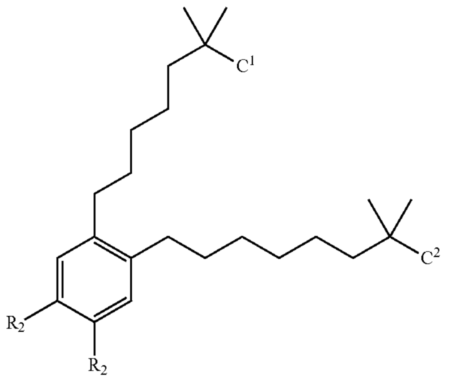 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 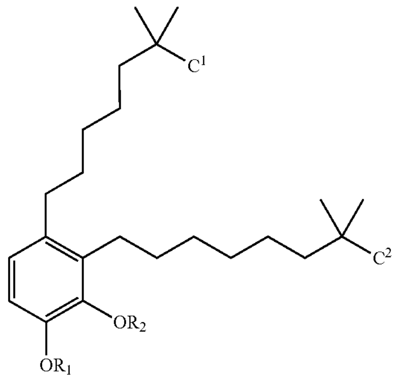 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 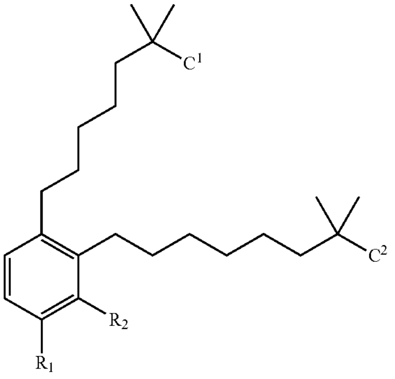 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 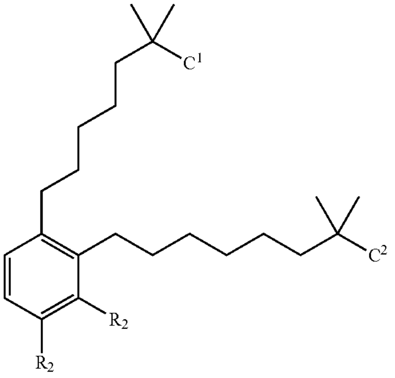 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 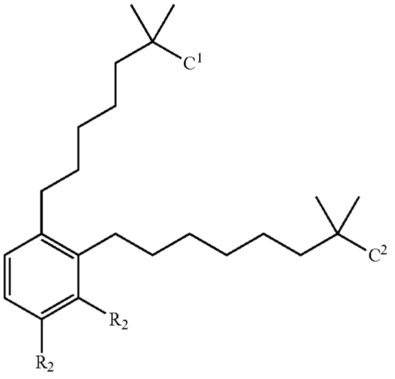 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 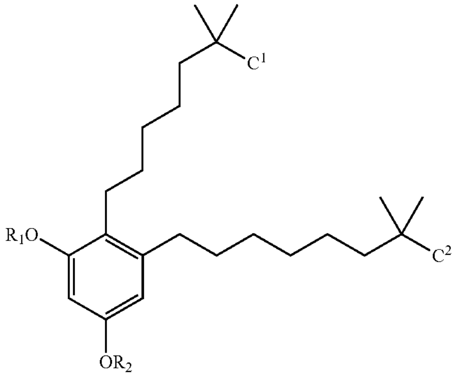 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 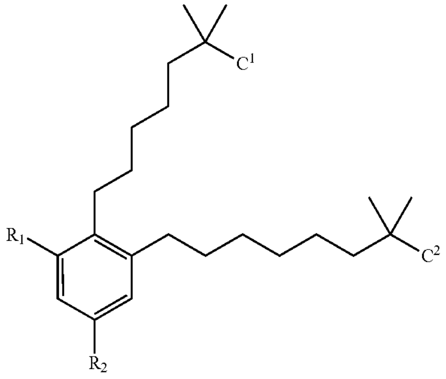 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 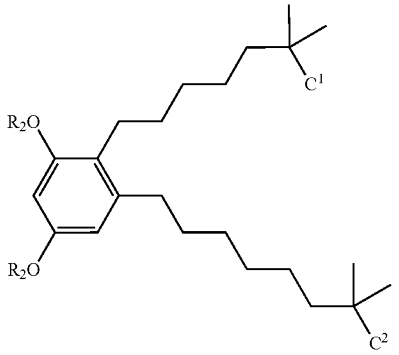 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 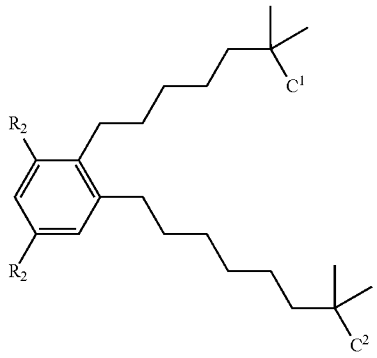 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 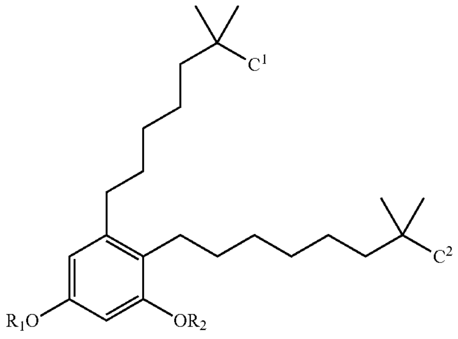 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 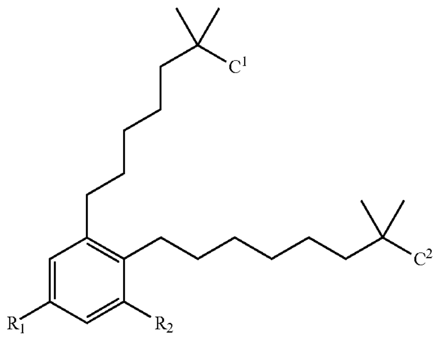 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 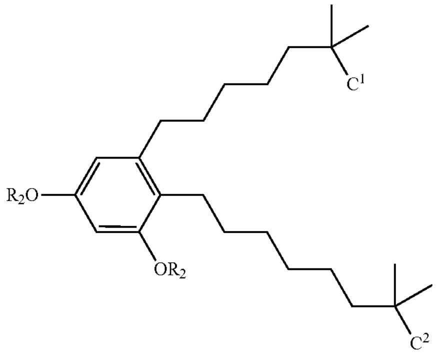 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 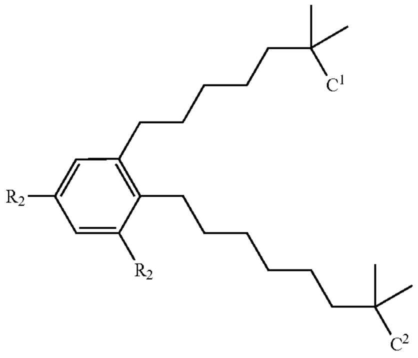 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 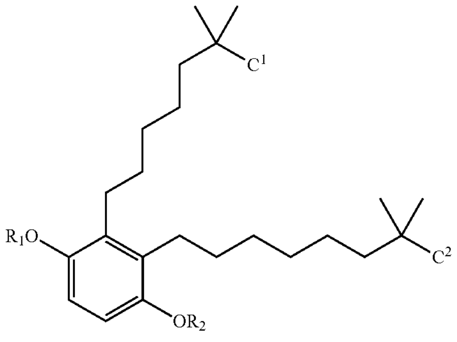 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 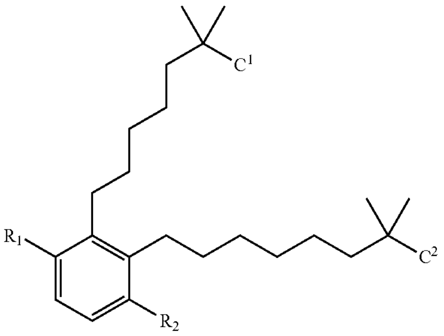 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 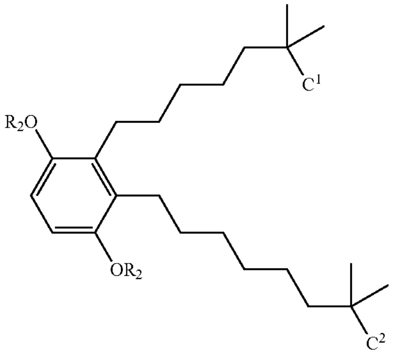 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 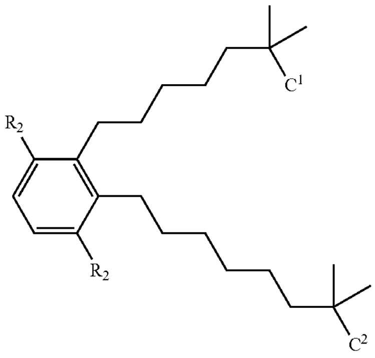 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 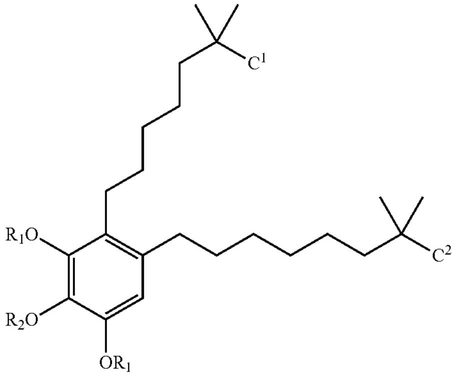 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 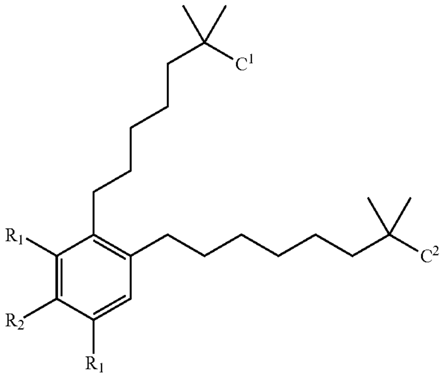 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 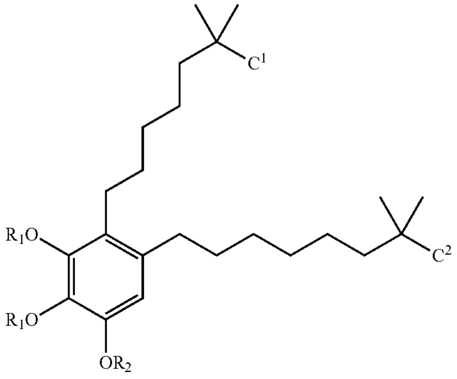 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 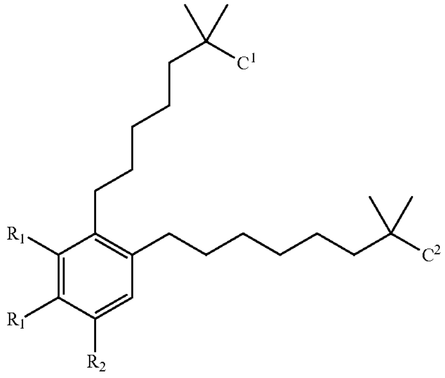 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 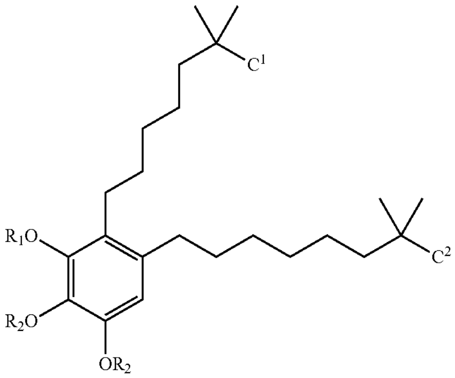 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 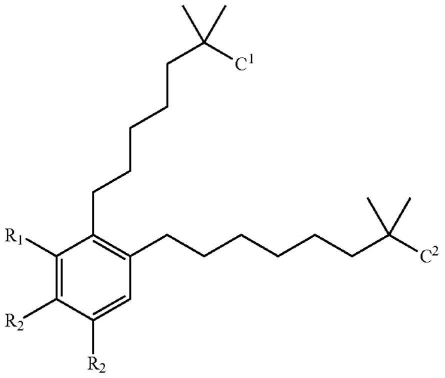 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 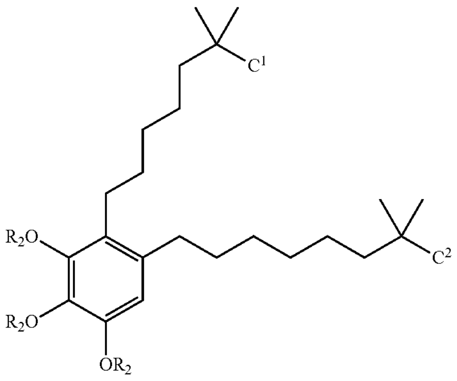 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 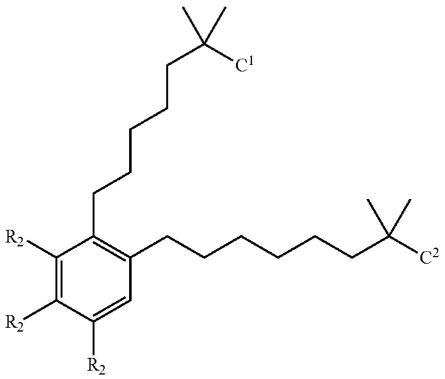 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 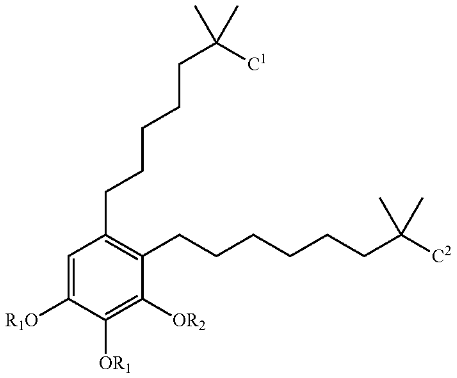 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 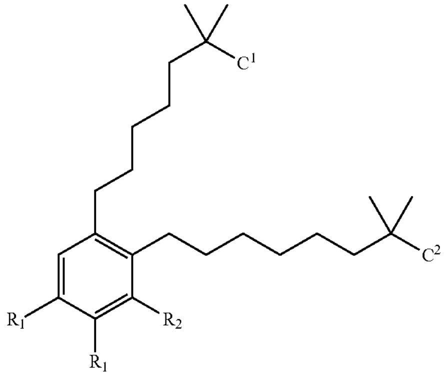 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 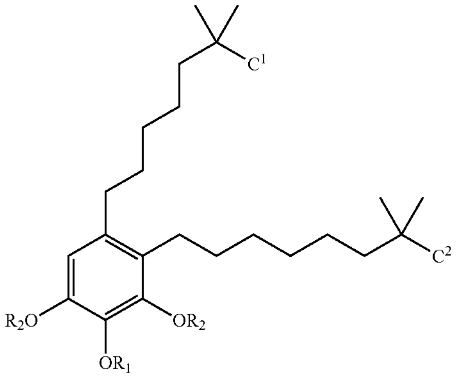 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 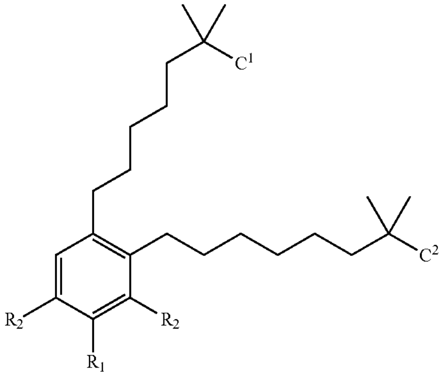 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 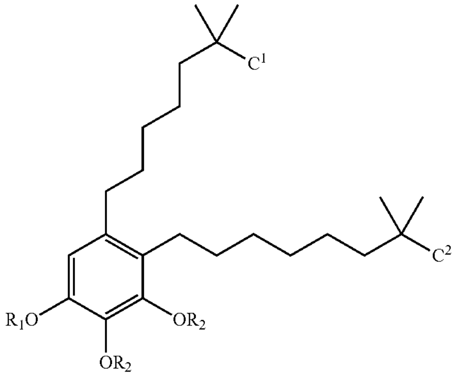 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 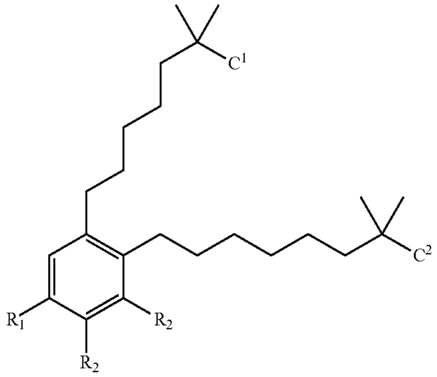 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 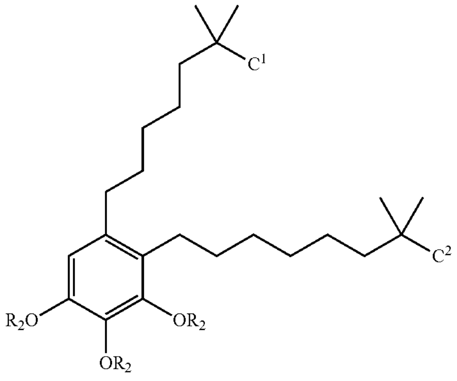 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 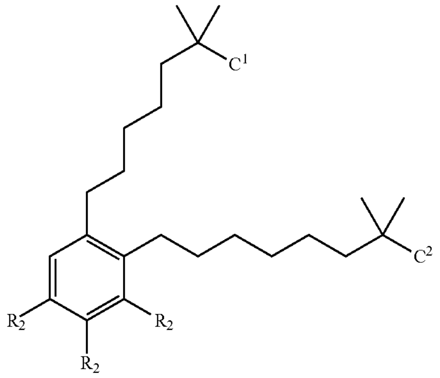 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 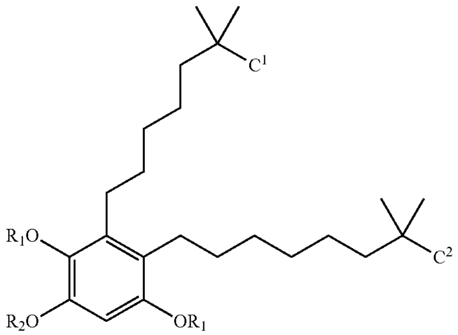 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 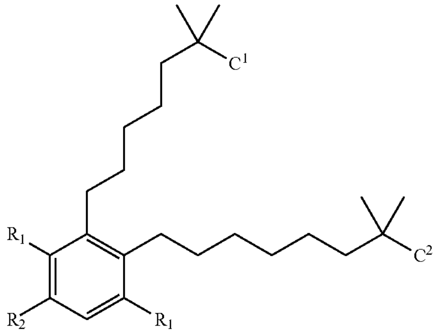 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
|---|
| 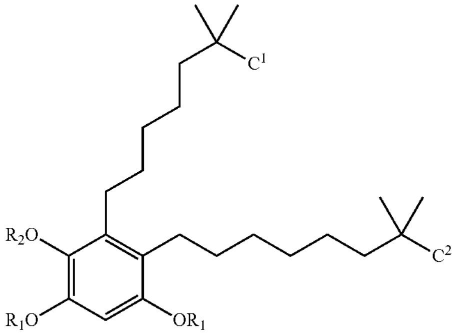 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 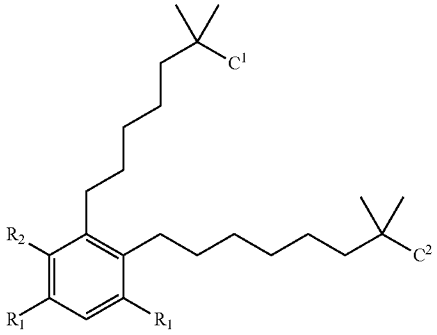 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 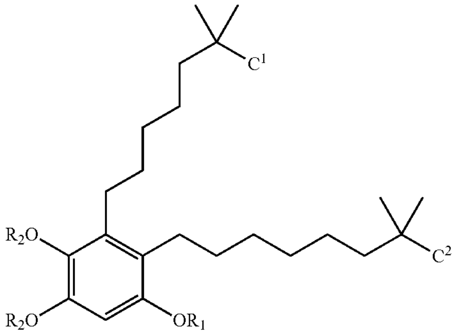 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 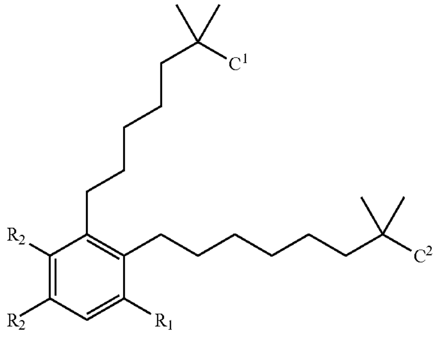 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 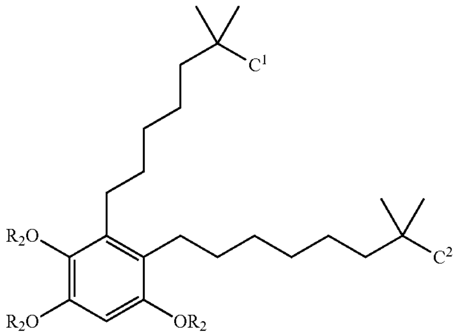 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 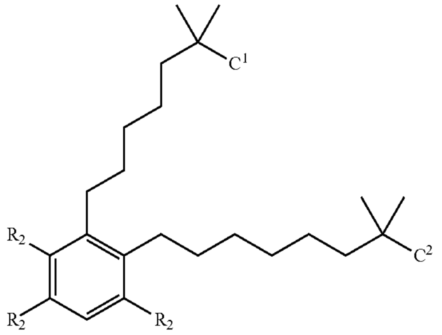 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 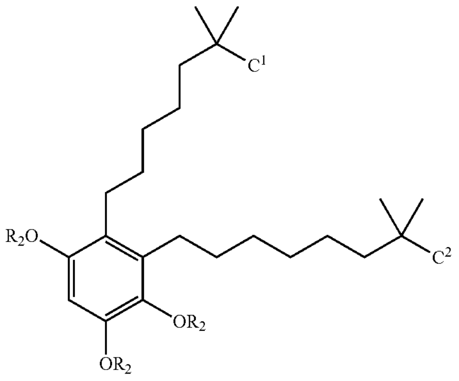 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 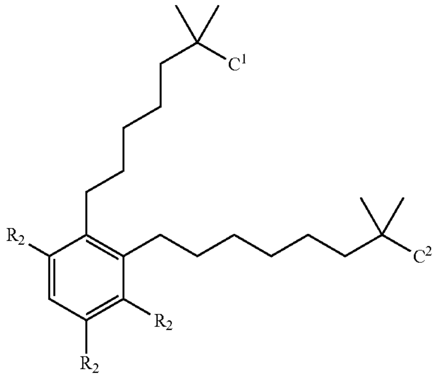 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 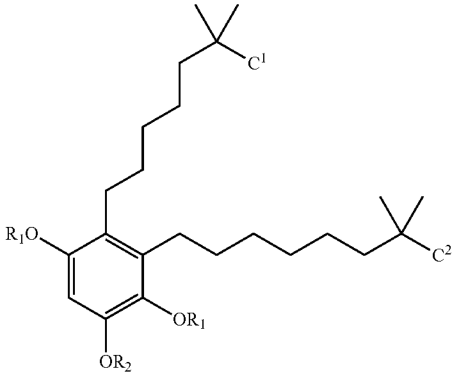 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 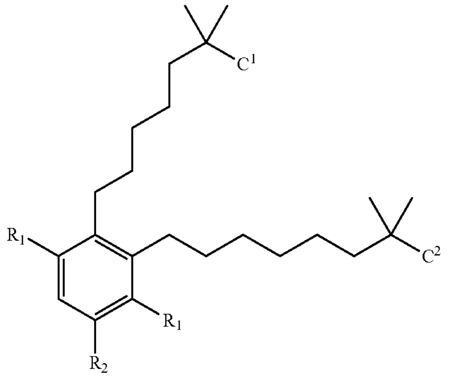 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each |
| 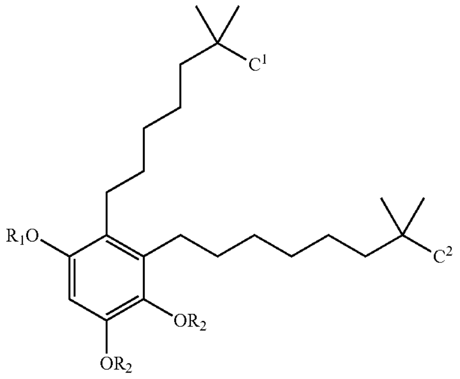 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 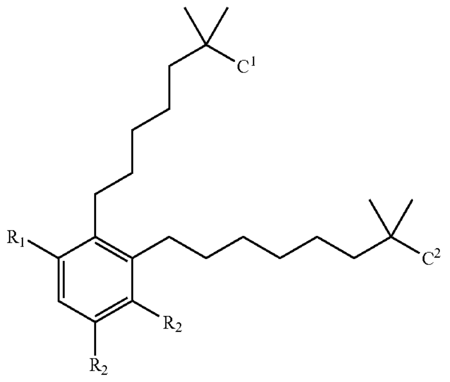 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_2$ = H or (C1-C4)alkyl |

TABLE A-15-continued

| Structure |
| --- |
| 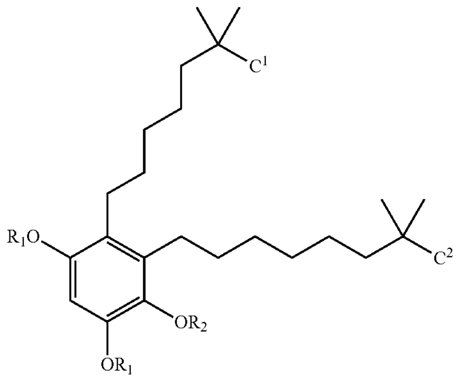 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 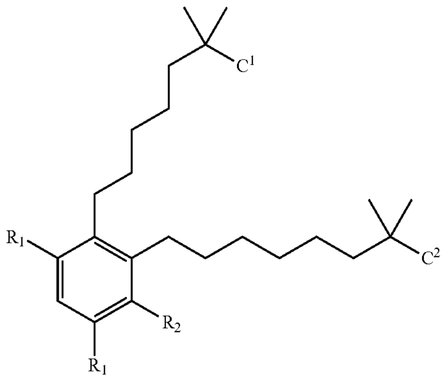 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 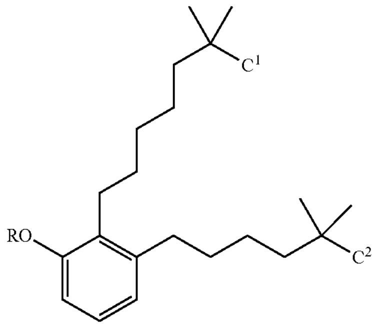 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 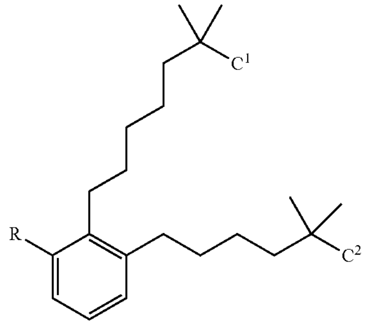 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 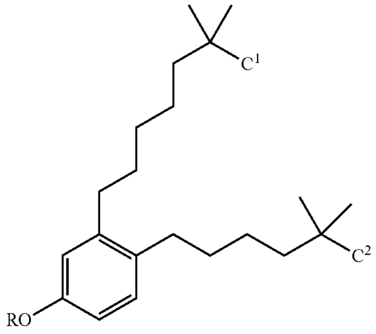 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 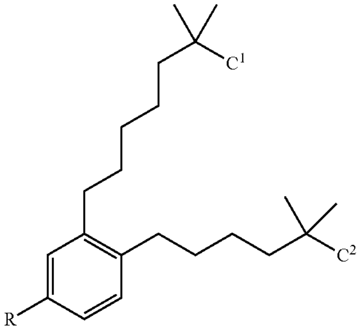 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |
| 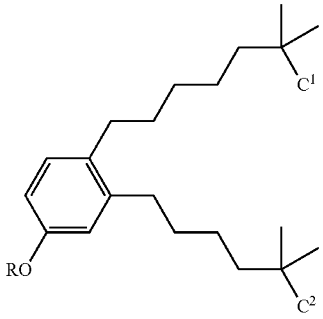 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 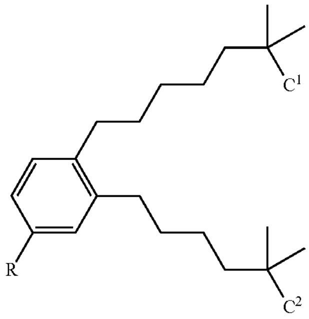 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 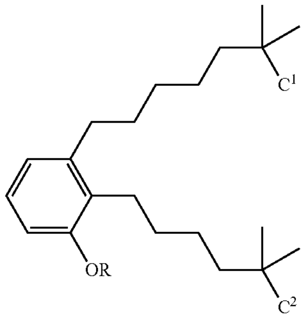 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 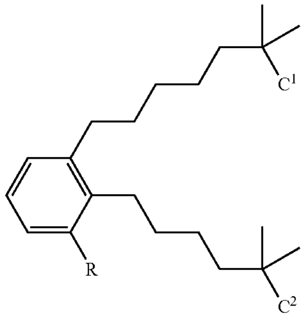 |

TABLE A-15-continued

| Structure |
| --- |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 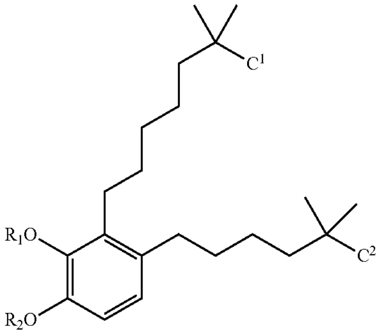 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 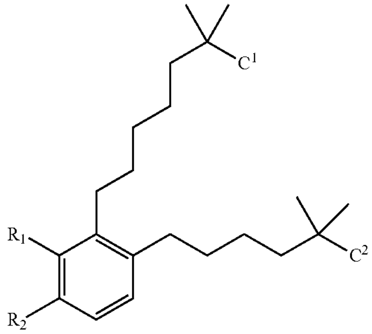 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 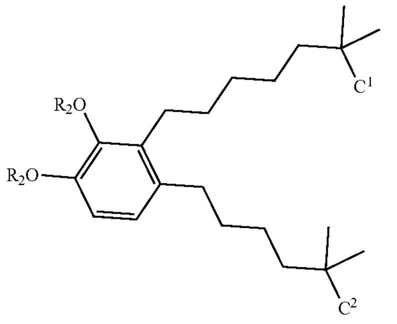 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 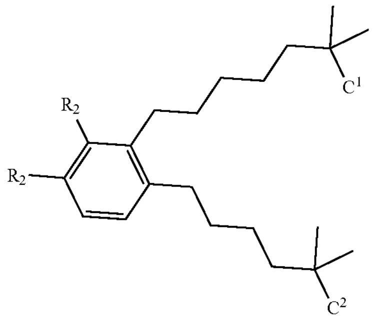 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 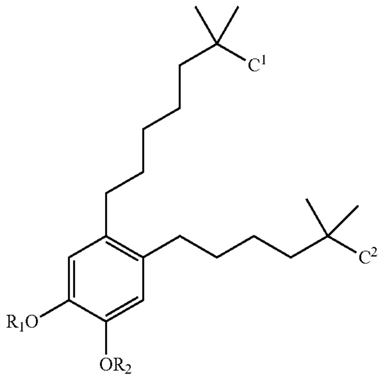 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 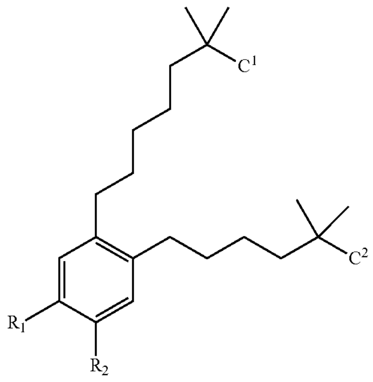 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 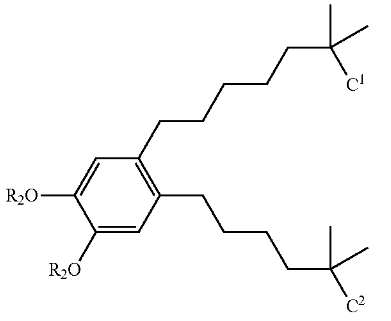 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 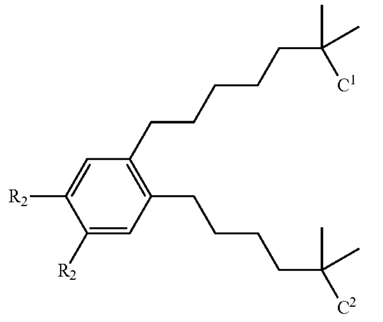 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 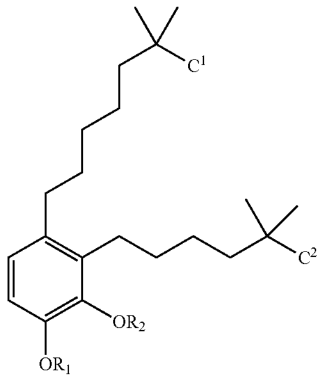 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 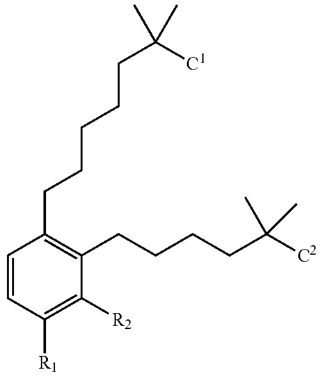 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 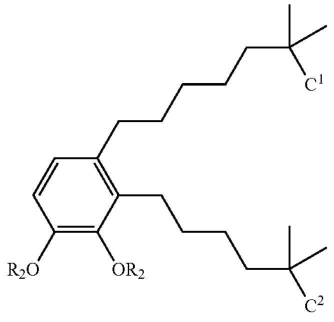 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 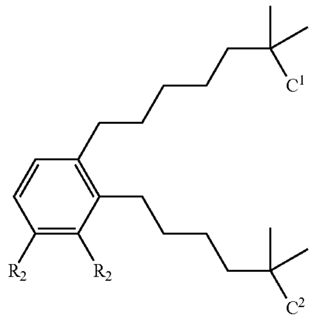 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 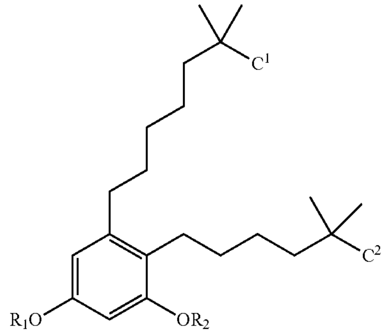 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 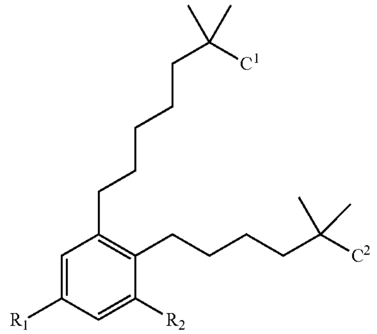 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 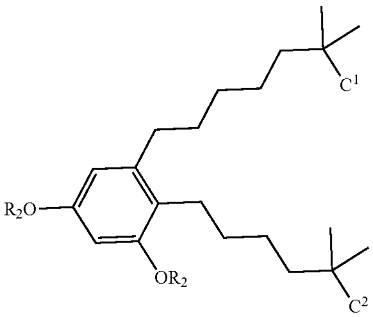 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 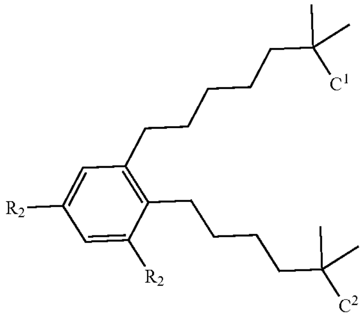 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 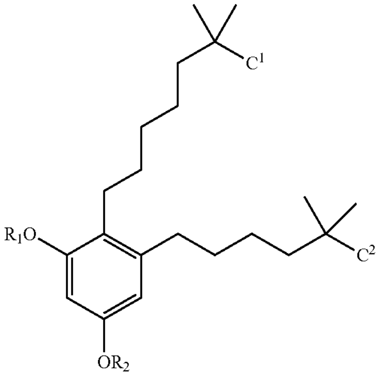 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 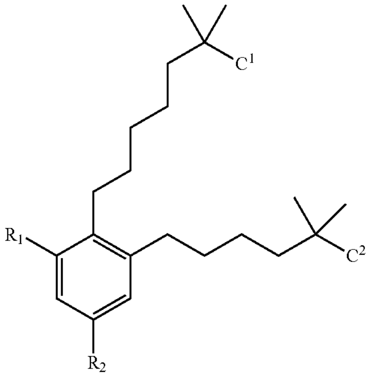 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 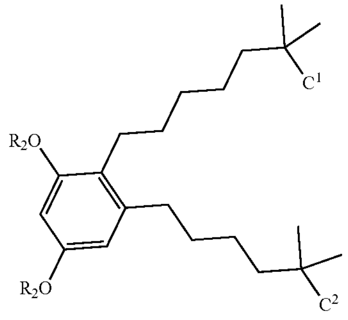 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 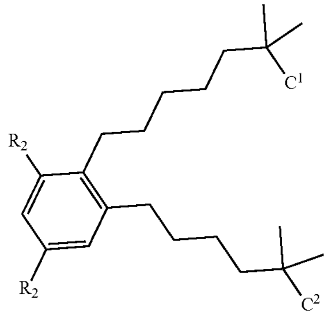 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 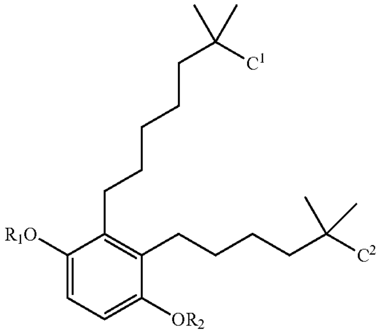 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 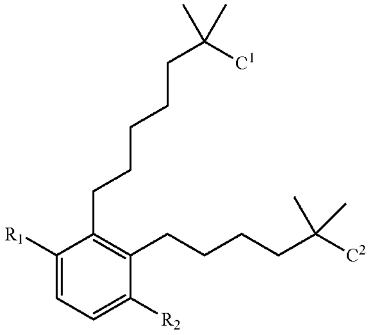 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 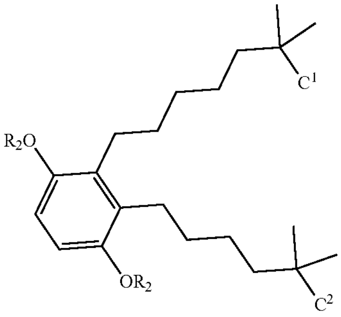 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 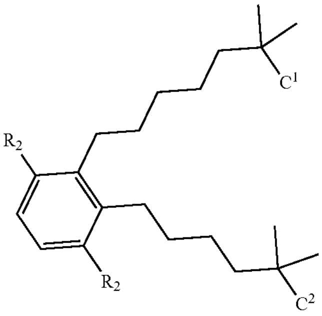 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 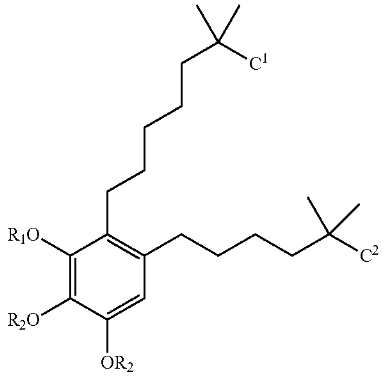 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 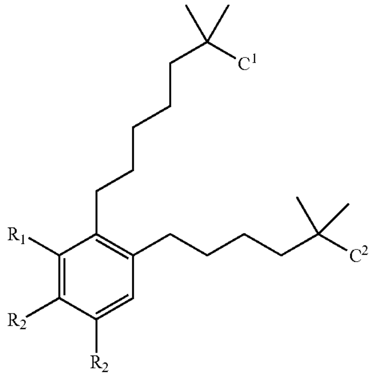 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 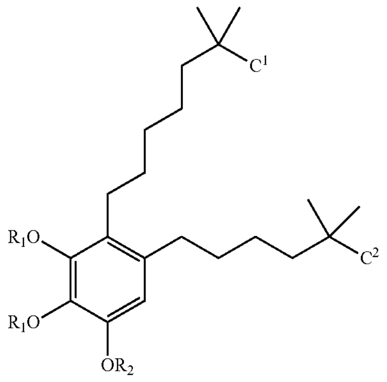 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 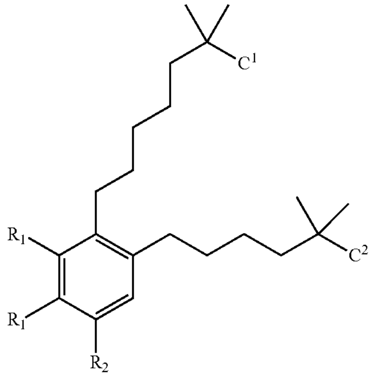 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 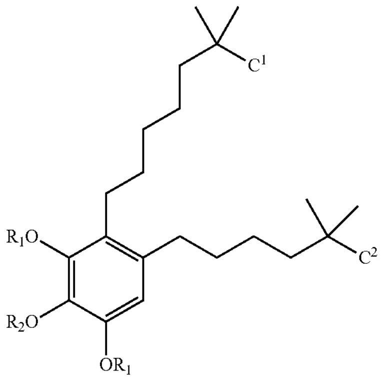 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 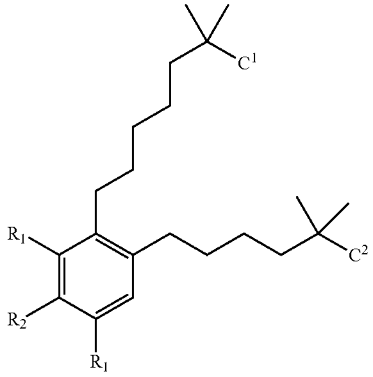 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 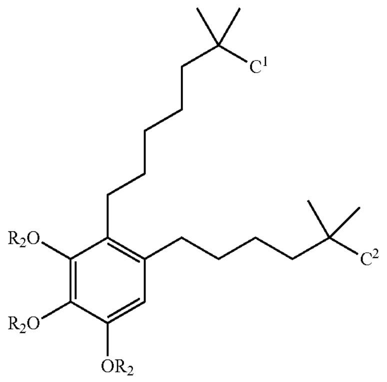 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 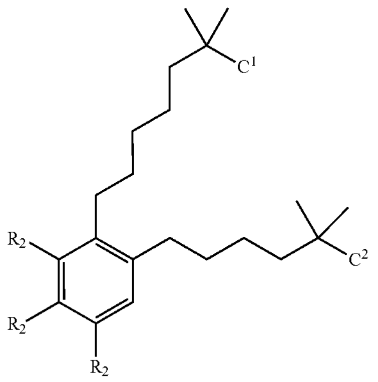 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 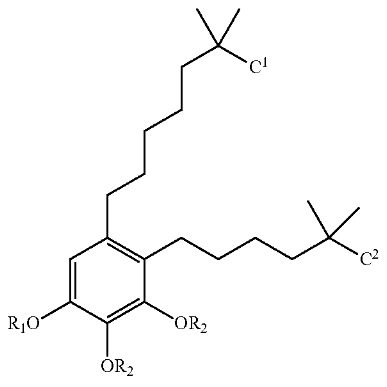 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 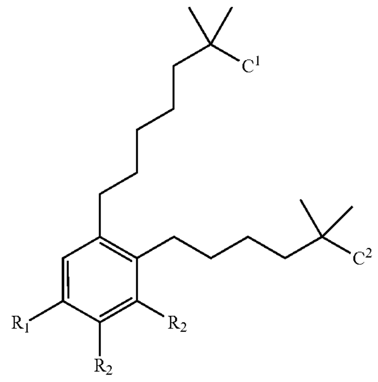 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 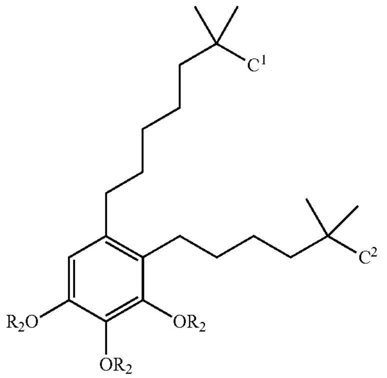 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 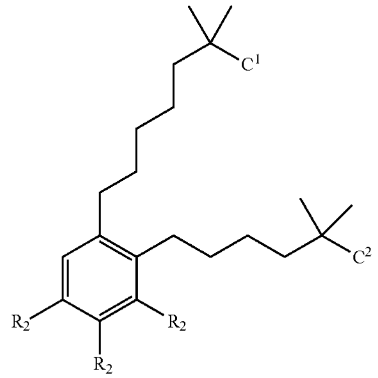 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 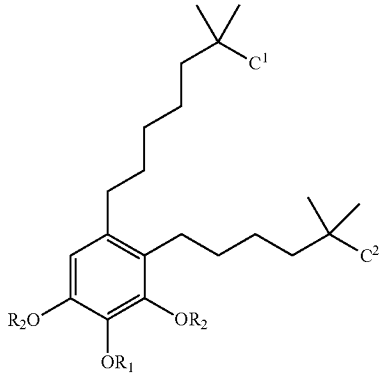 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 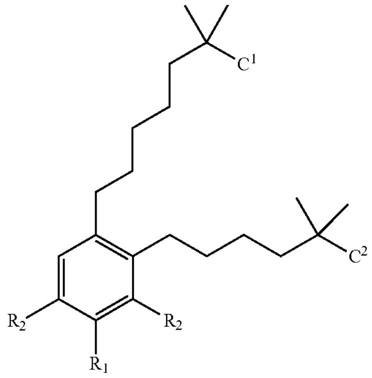 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 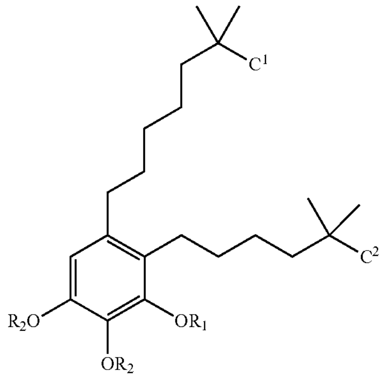 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 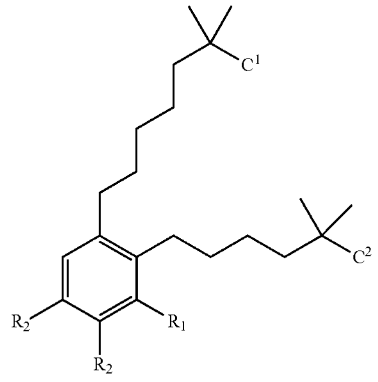 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 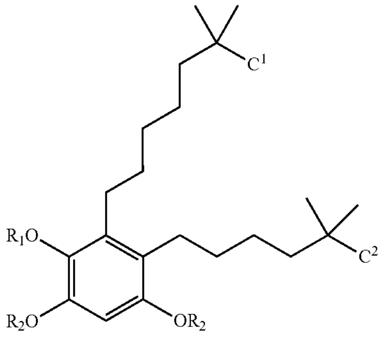 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 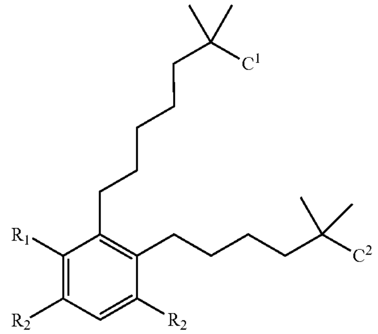 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

Structure

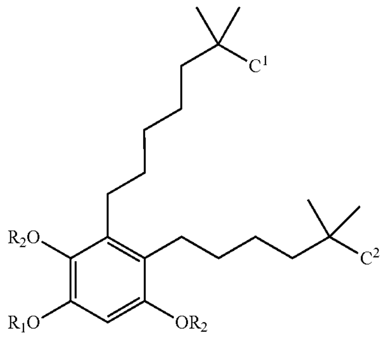

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

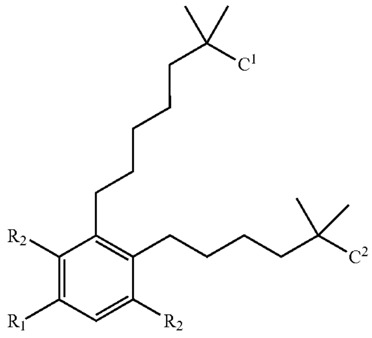

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

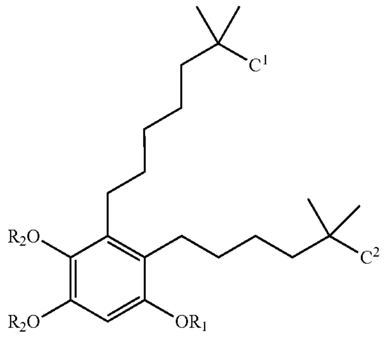

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl TABLE A-15-continued Structure

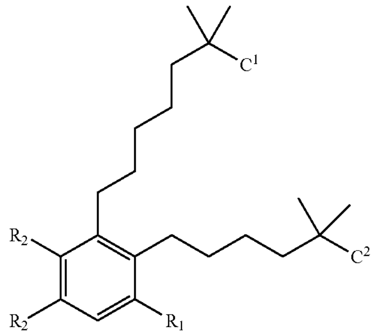

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

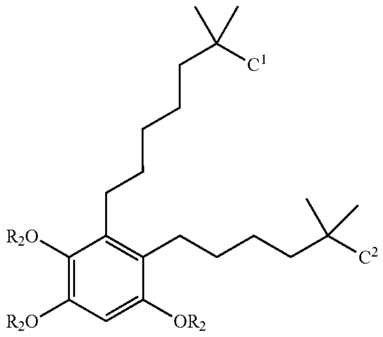

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

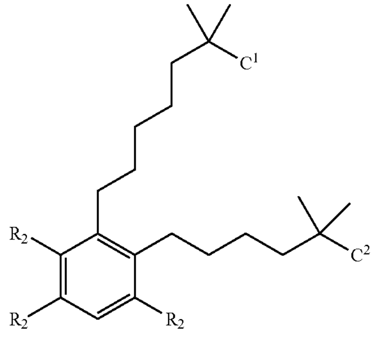

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ TABLE A-15-continued

| Structure |
|---|
| 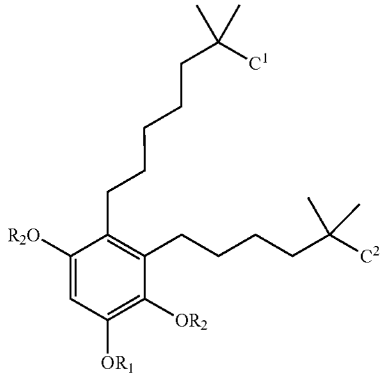 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 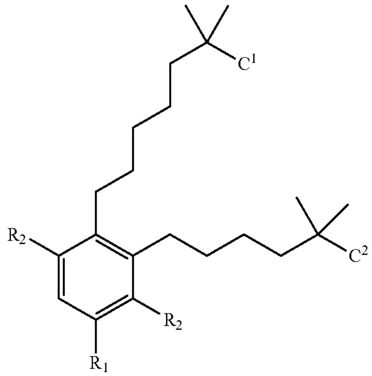 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 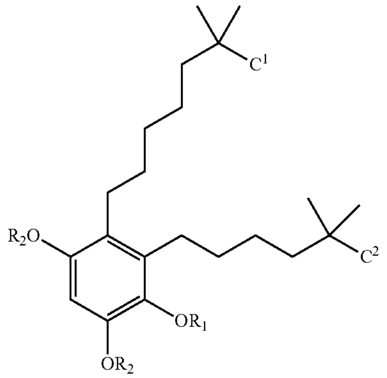 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 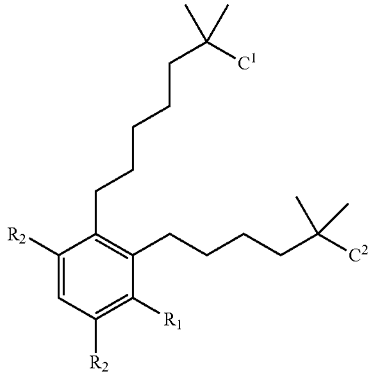 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 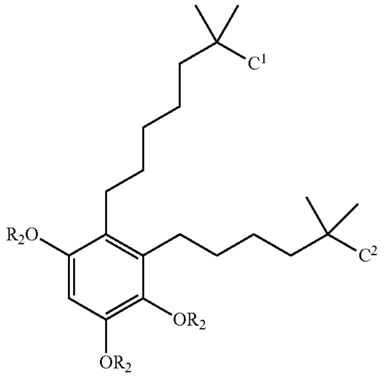 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 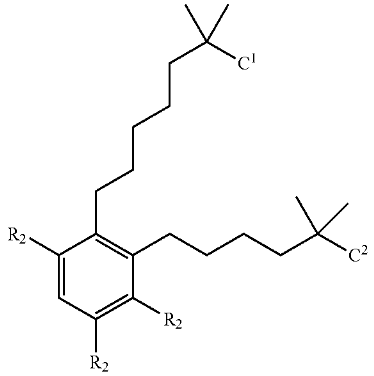 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 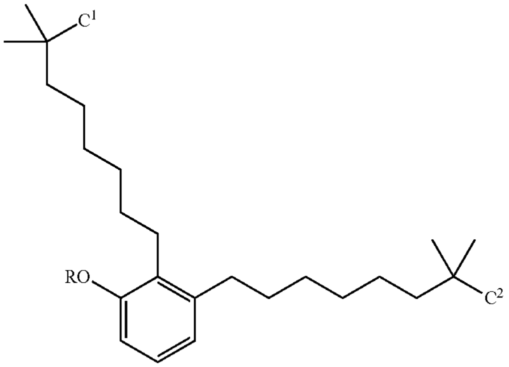 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 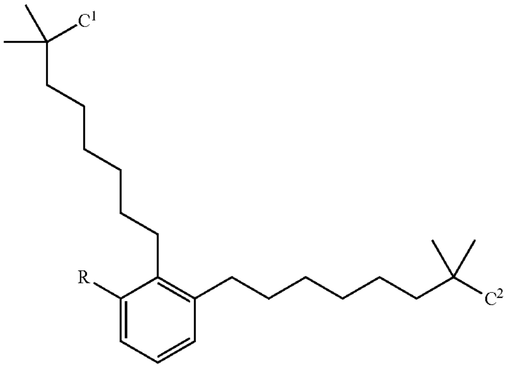 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 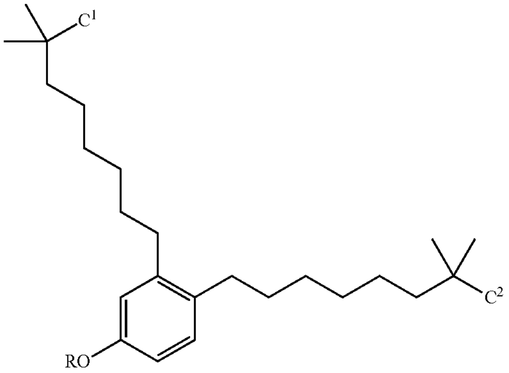 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
|---|
| 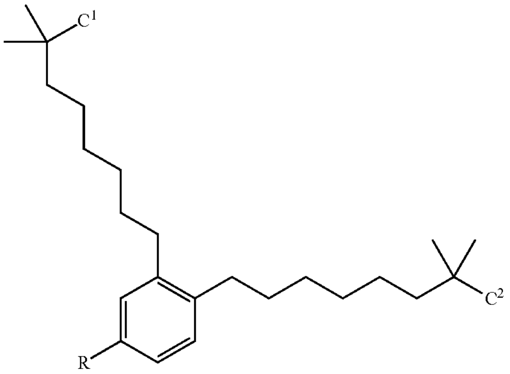 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 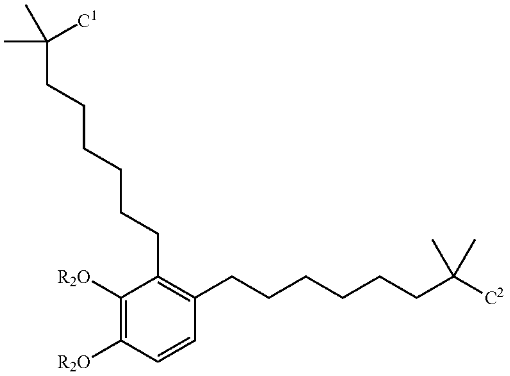 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 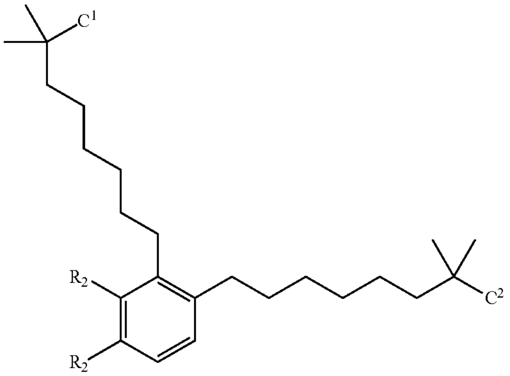 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 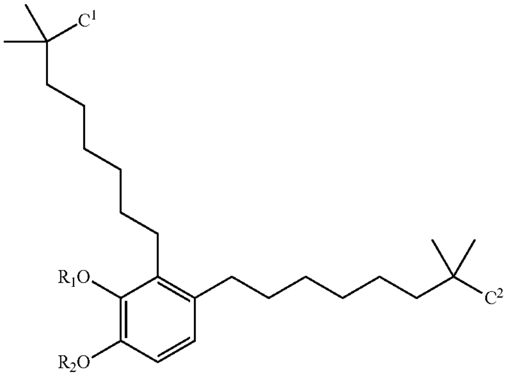 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ is H and $R_1$ = (C1-C4)alkyl |
| 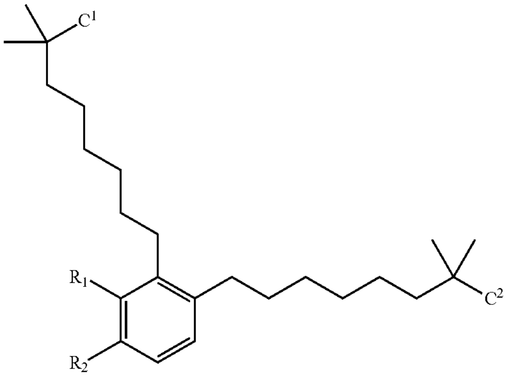 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 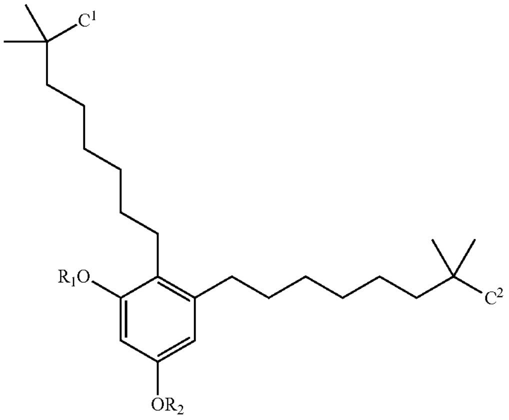 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ is H and $R_1$ = (C1-C4)alkyl |

TABLE A-15-continued

| Structure |
|---|
| 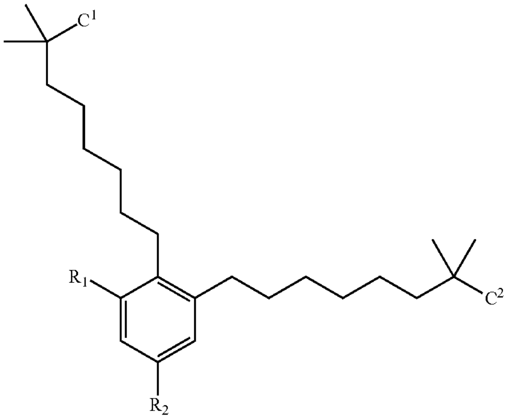 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 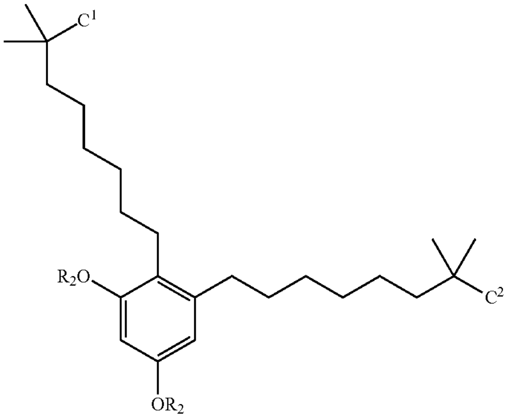 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 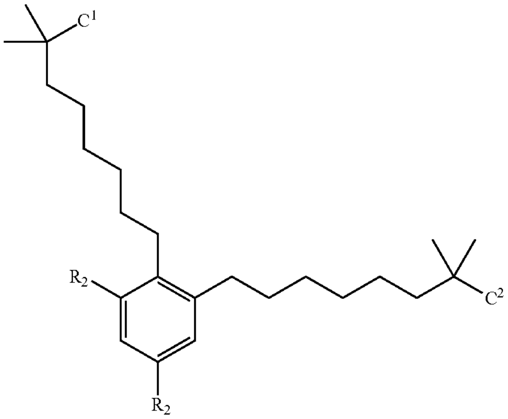 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 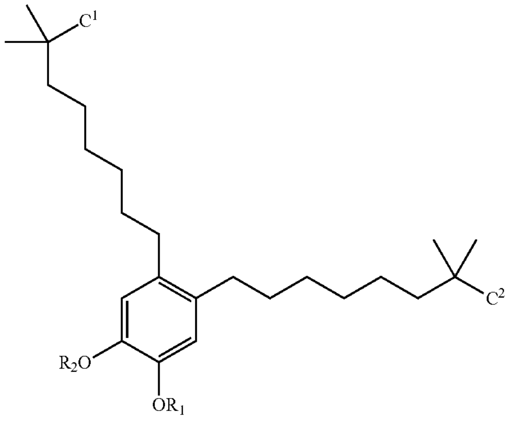 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ is H and $R_1$ = (C1-C4)alkyl |
| 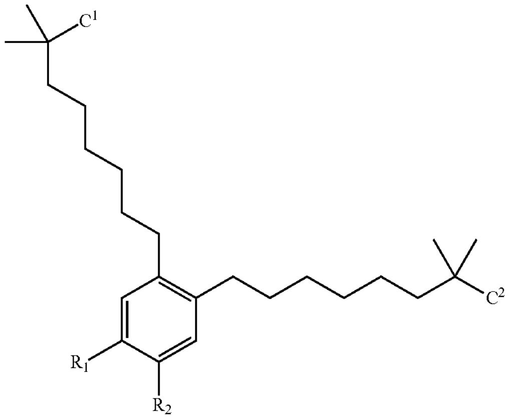 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 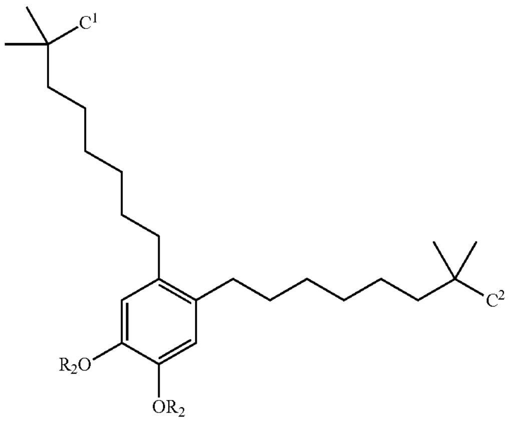 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 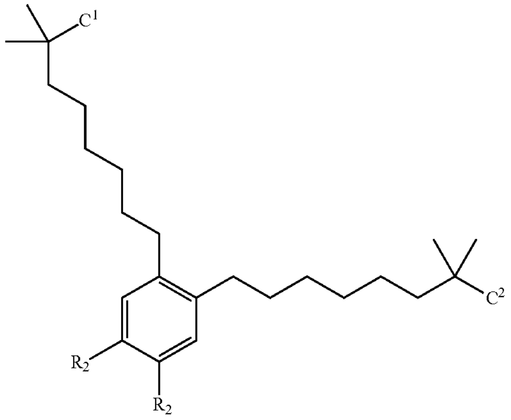 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 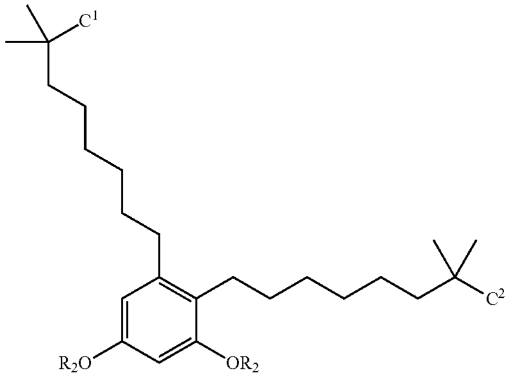 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 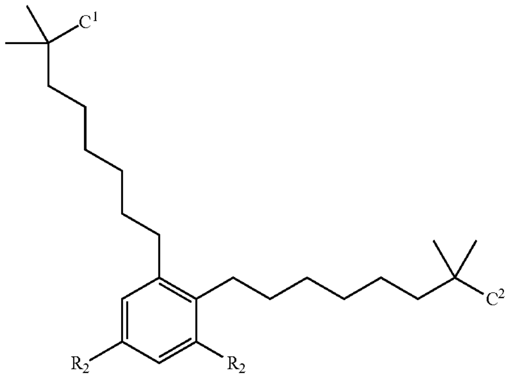 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 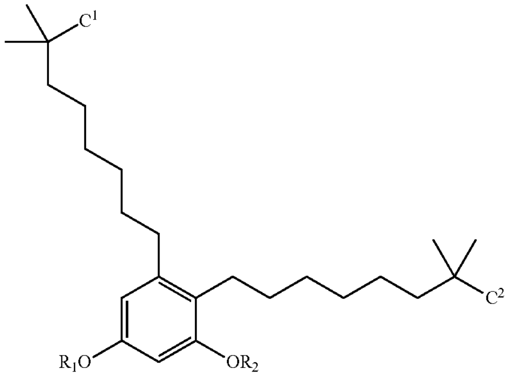 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ is H and $R_1$ = (C1-C4)alkyl |
| 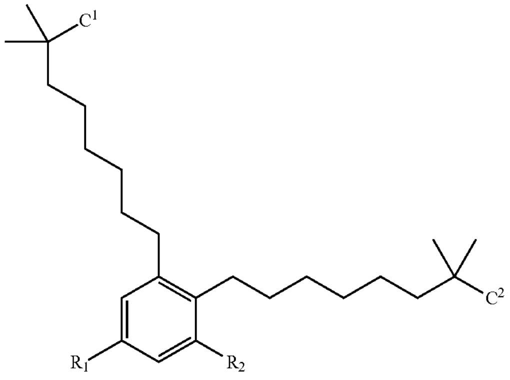 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 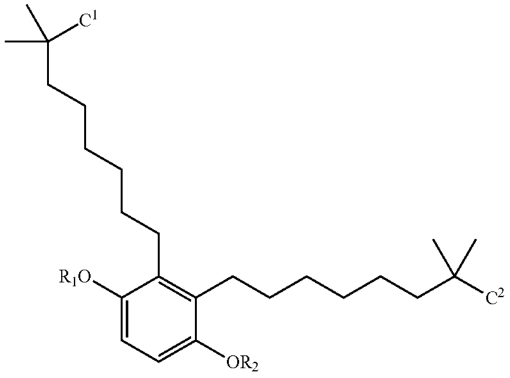 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ is H and $R_1$ = (C1-C4)alkyl |

TABLE A-15-continued

| Structure |
|---|
| 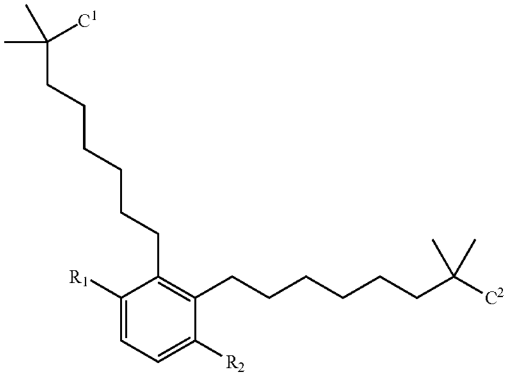 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 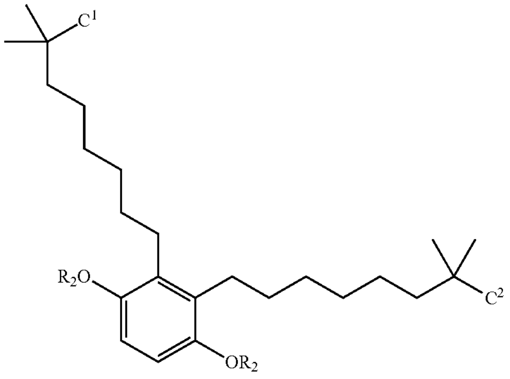 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 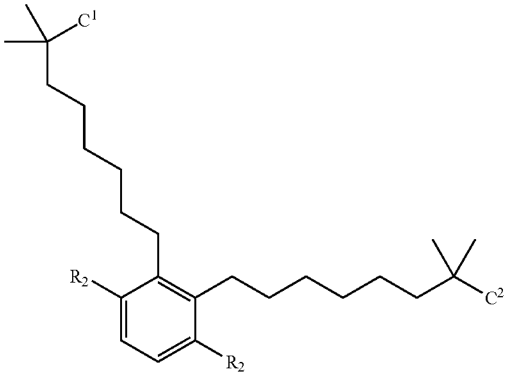 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 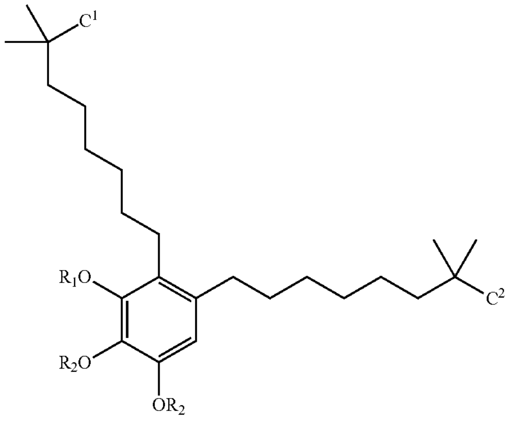 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 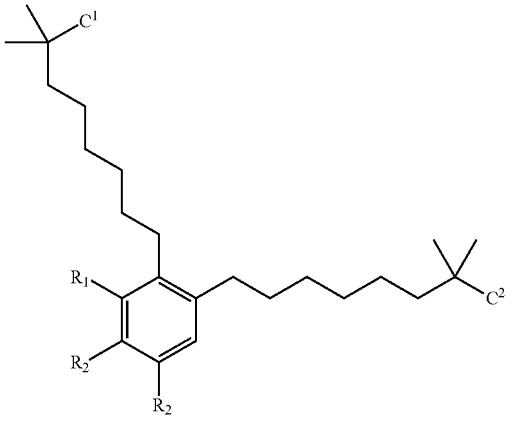 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 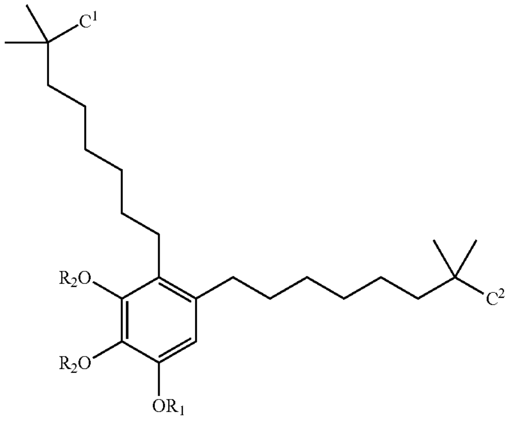 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 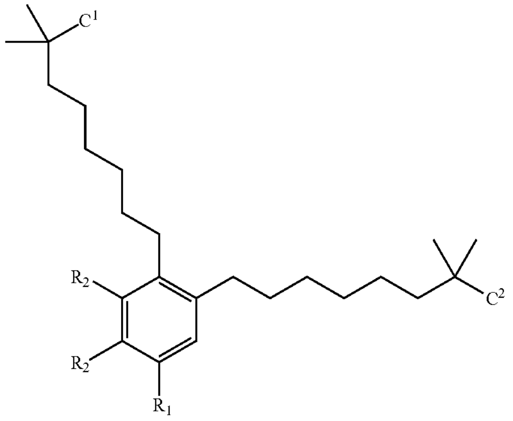 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 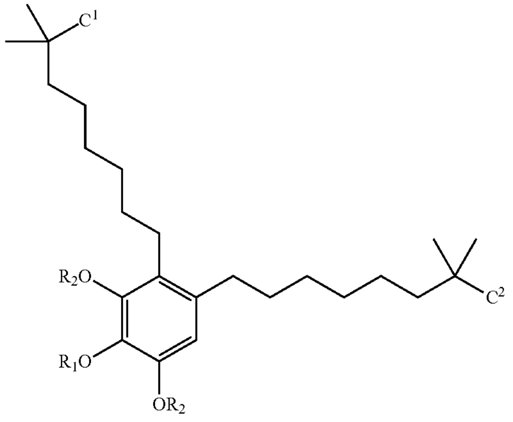 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 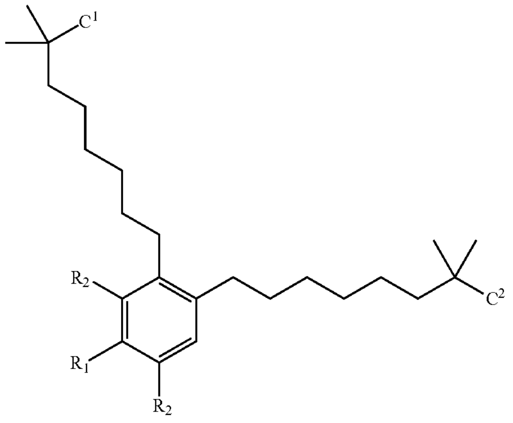 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 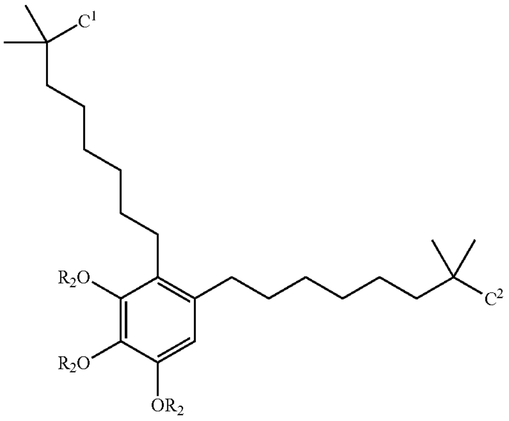 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 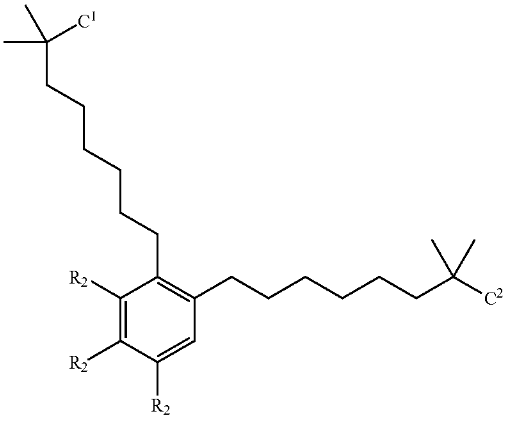 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 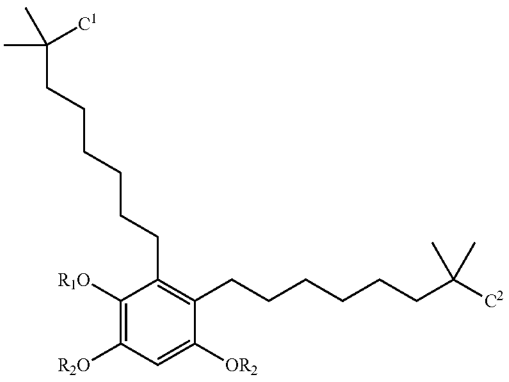 |

TABLE A-15-continued

Structure

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 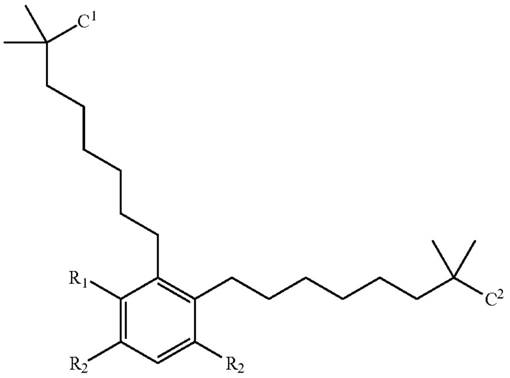 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 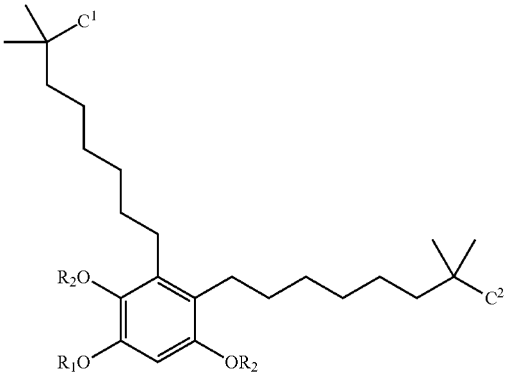 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 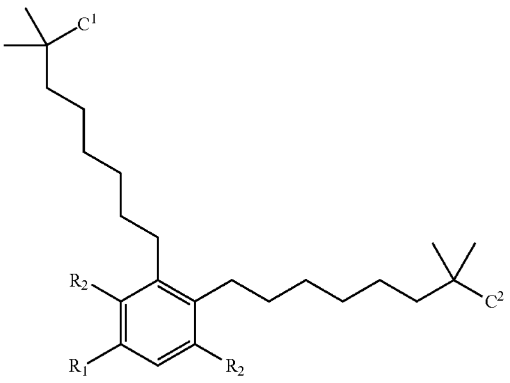 |
| wherein $C^1$ and $C^2$ = COOH; $C^1$ = COOH and $C^2$ = CO—CoA; $C^1$ = CO—CoA and $C^2$ = COOH; or |

TABLE A-15-continued

| Structure |
|---|
| $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 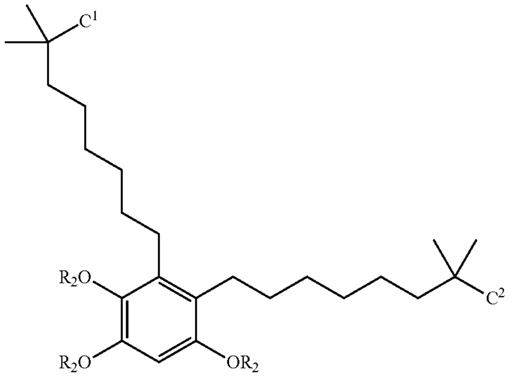 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 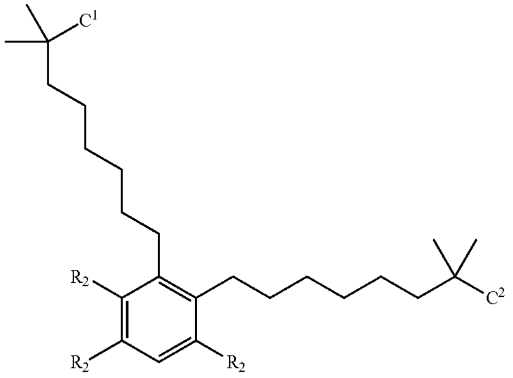 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 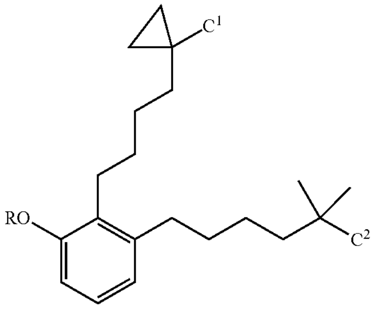 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
|---|
| 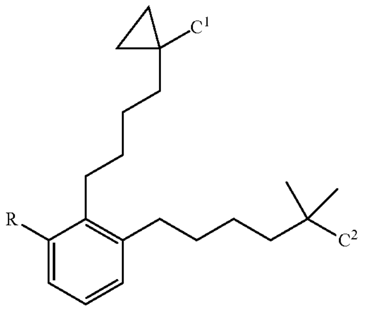 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 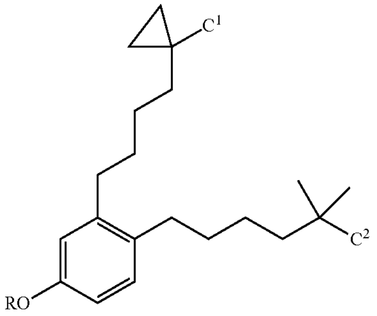 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 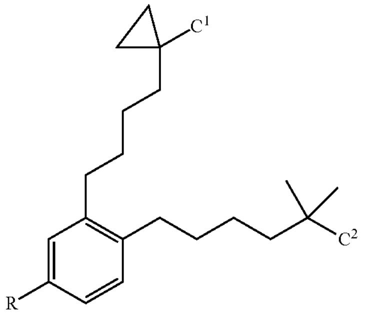 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ |
| 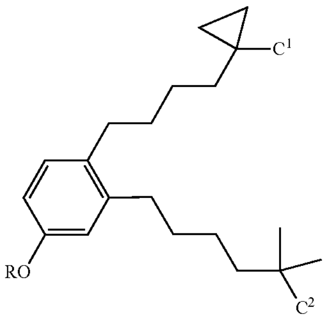 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 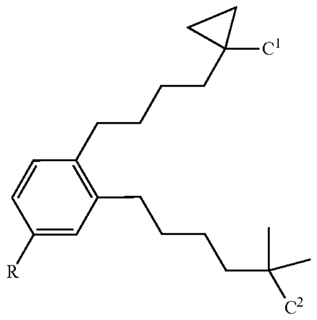 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 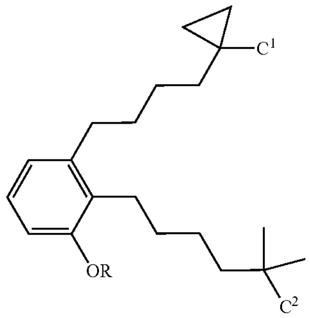 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 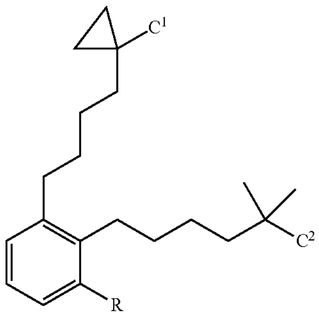 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 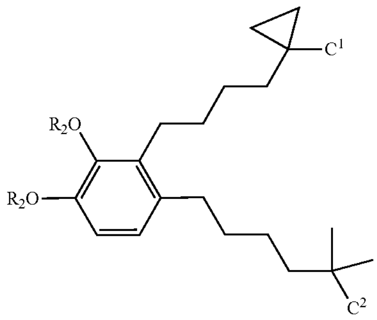 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 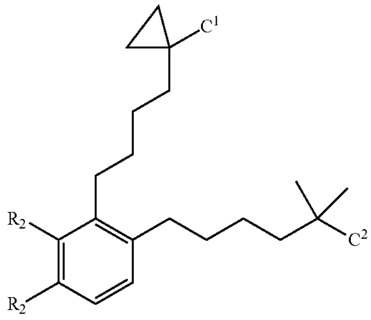 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 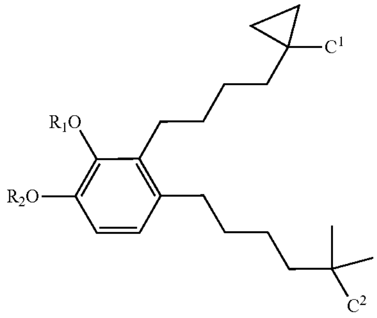 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 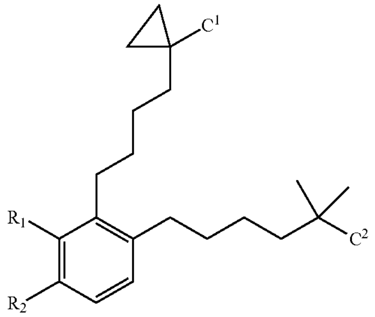 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 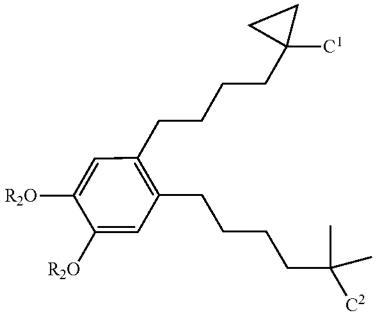 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 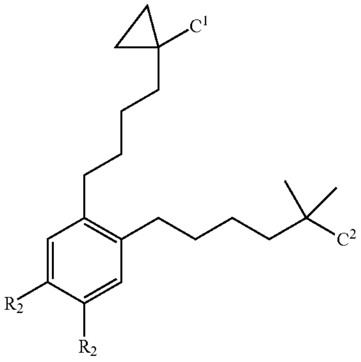 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 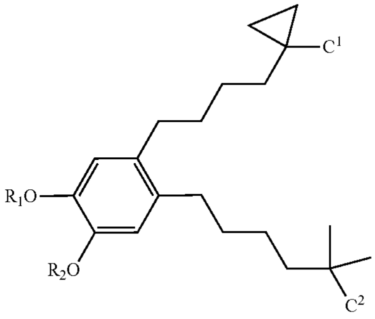 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 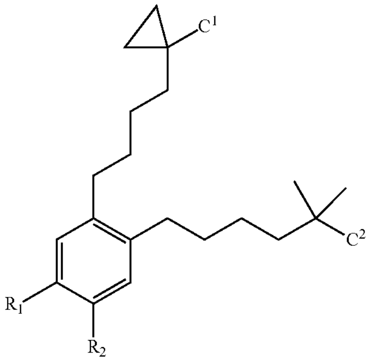 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 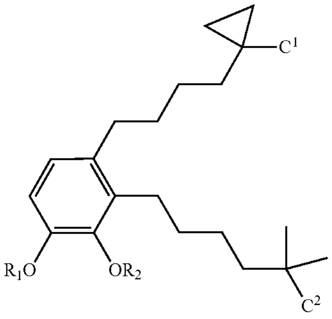 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 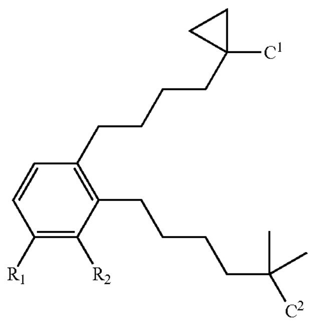 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 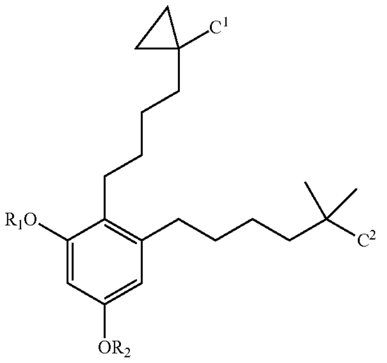 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 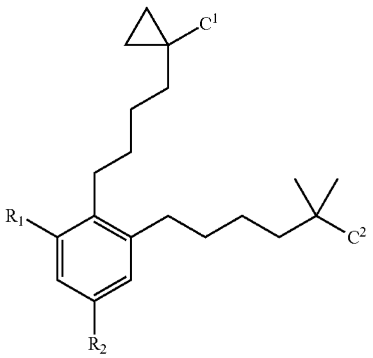 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 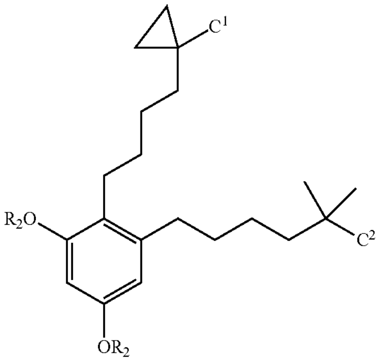 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 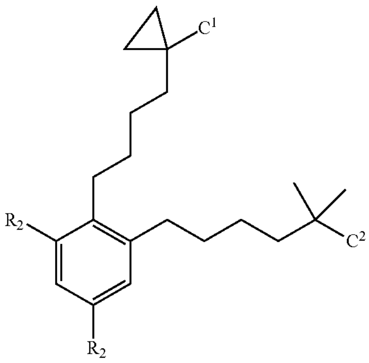 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 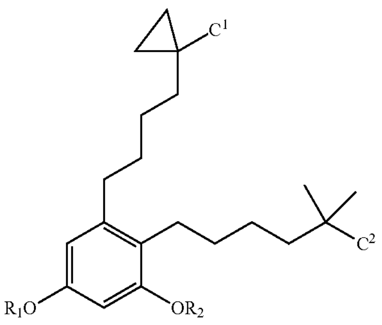 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 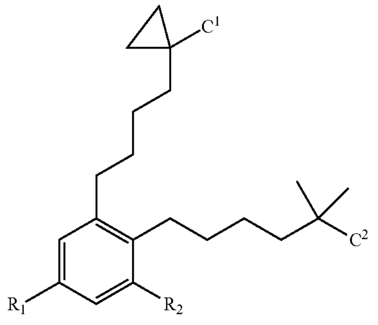 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 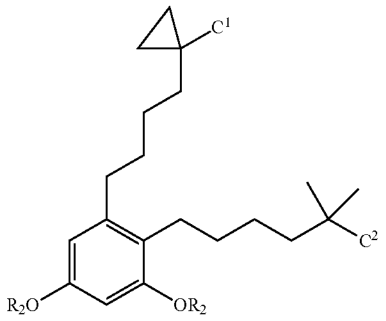 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 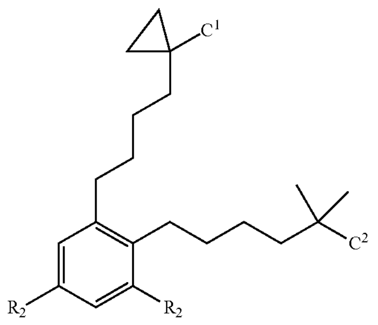 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 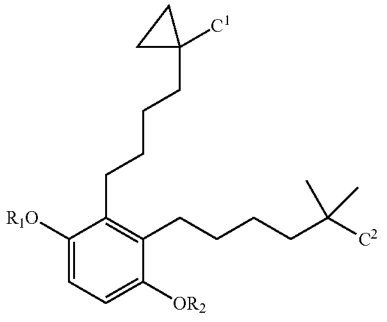 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 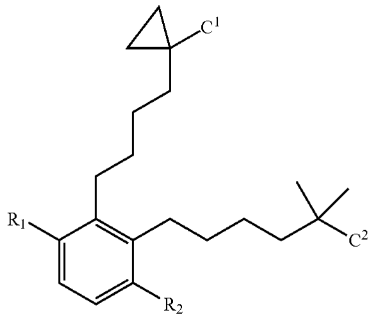 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 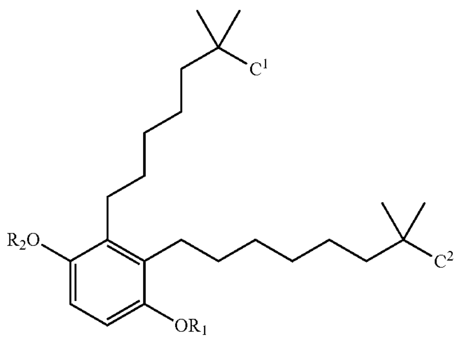 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 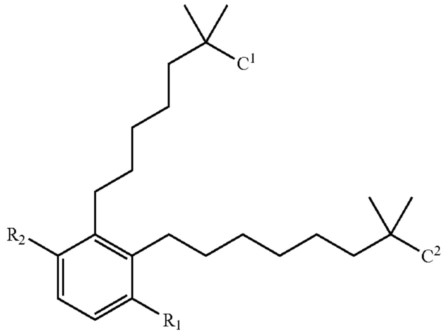 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 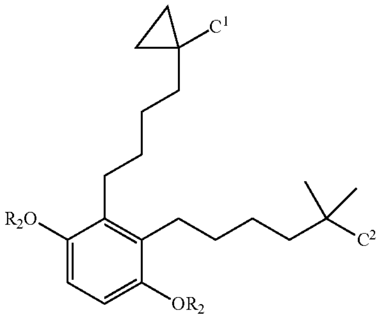 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 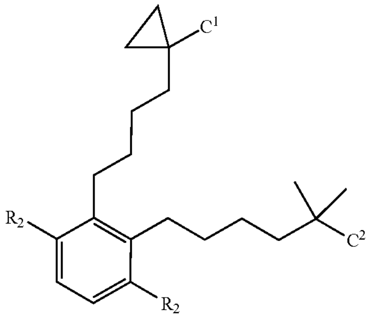 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 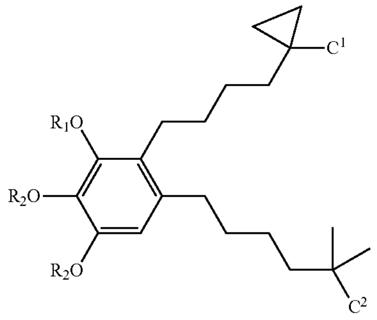 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 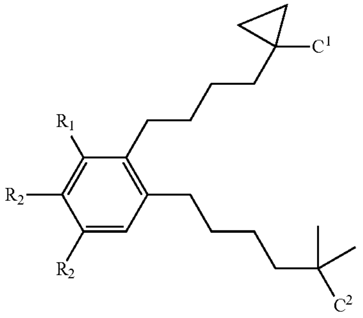 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 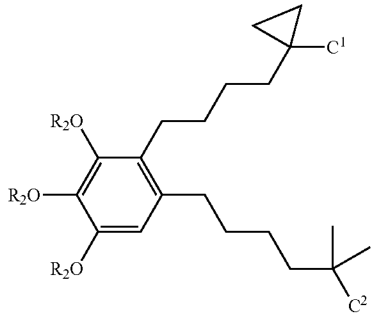 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 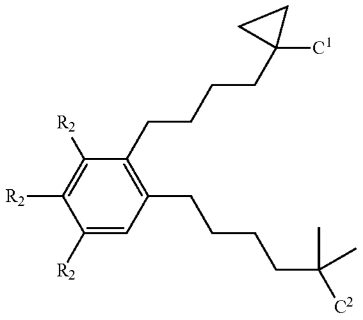 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 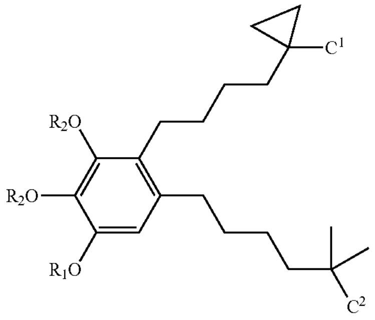 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 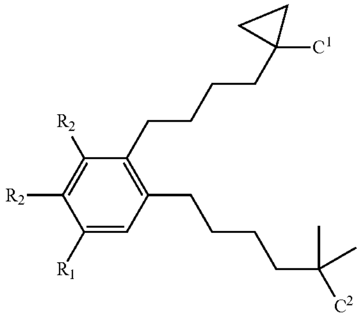 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 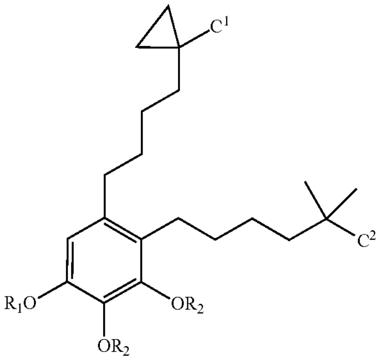 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 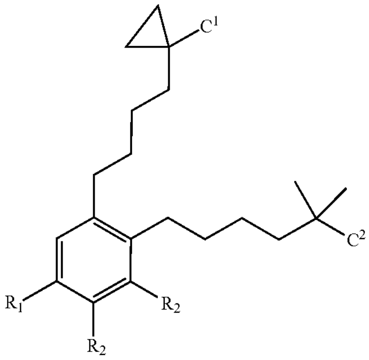 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 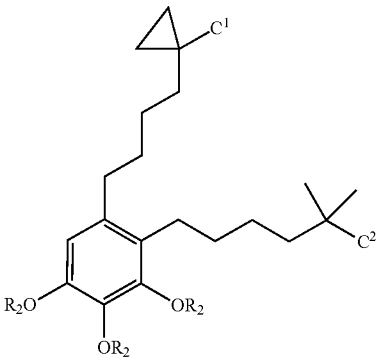 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 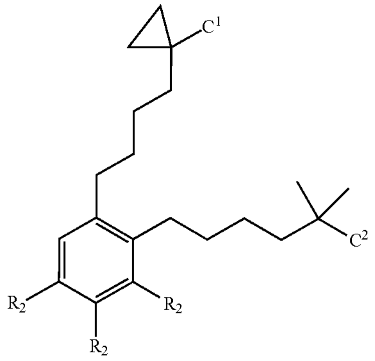 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 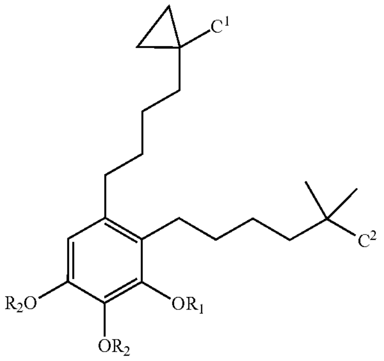 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 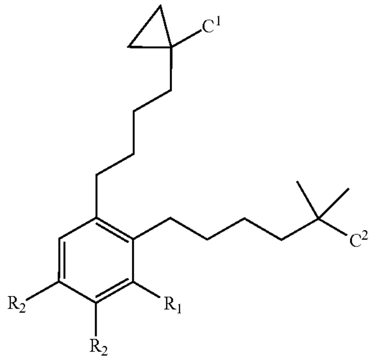 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 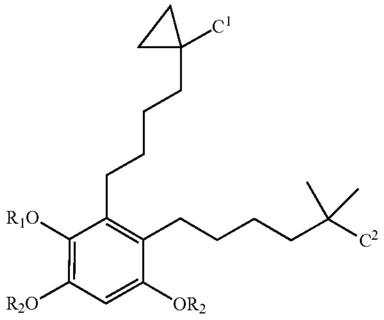 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 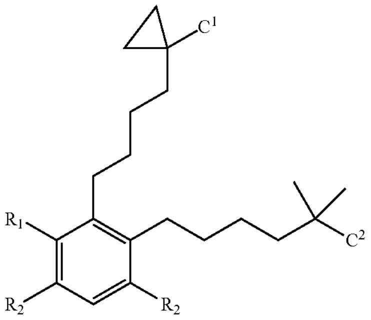 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 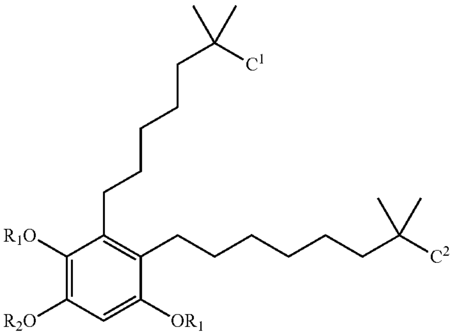 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
|---|
| 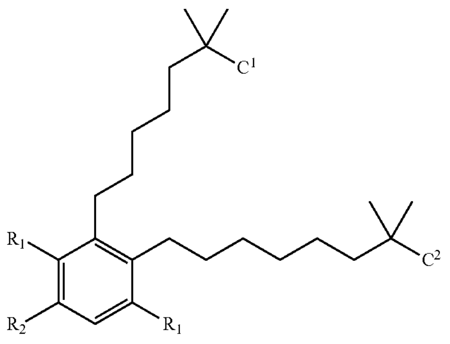 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 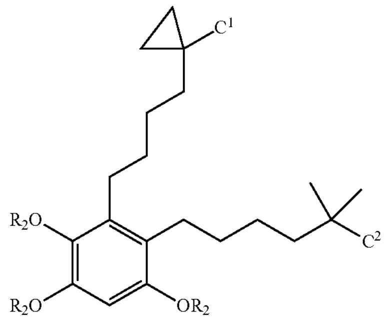 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 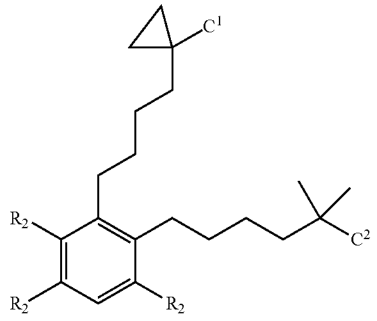 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 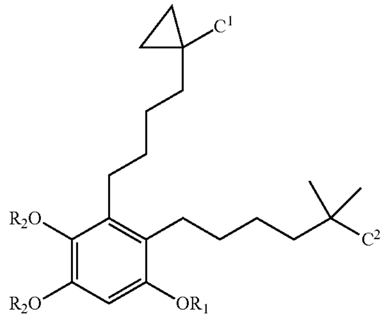 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 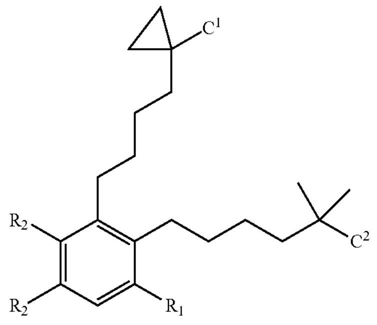 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 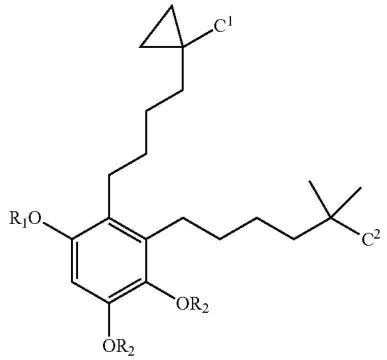 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 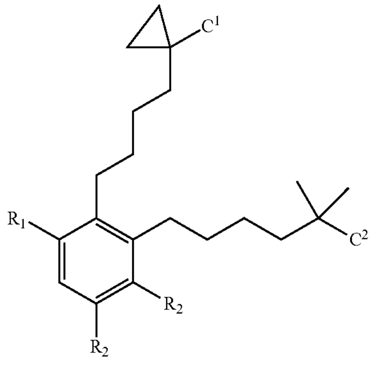 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 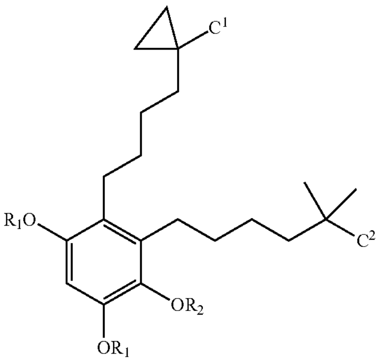 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each R, is independently a (C1-C4)alkyl |
| 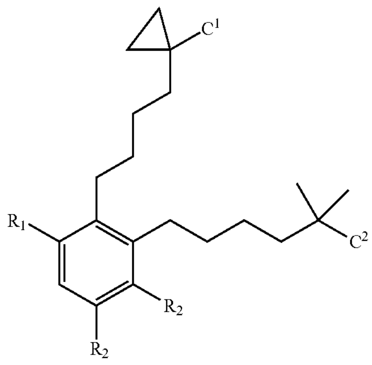 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 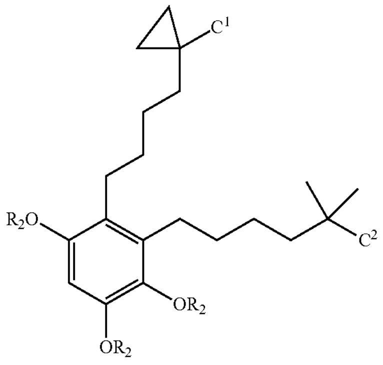 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 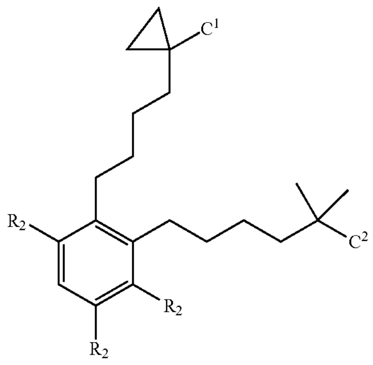 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 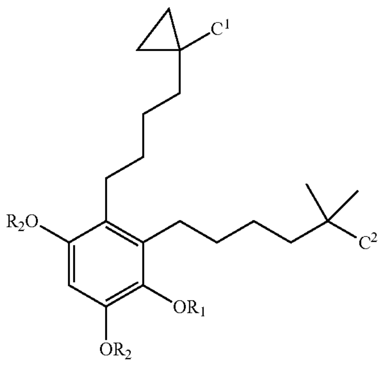 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 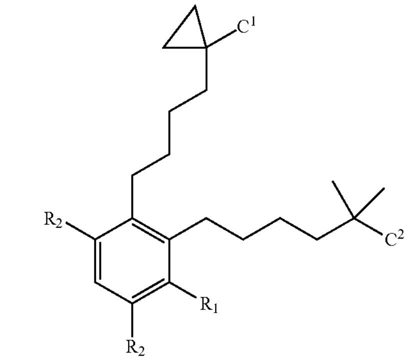 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 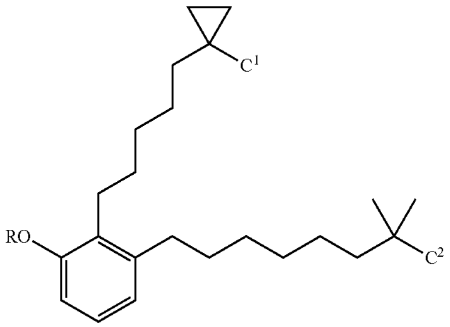 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 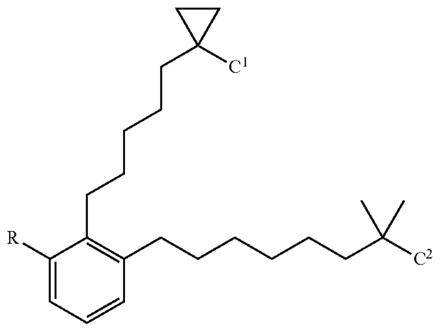 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 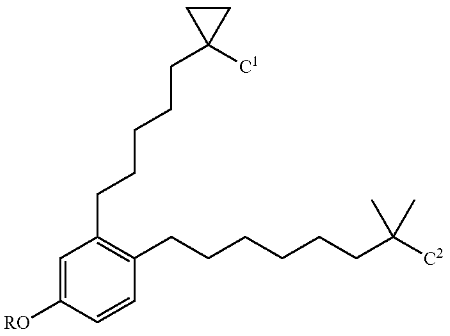 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 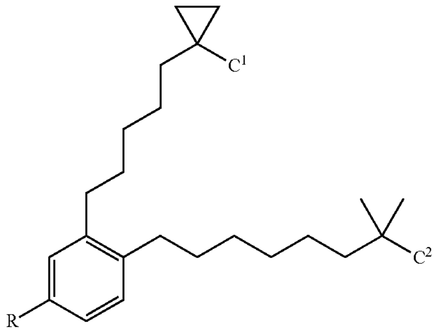 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 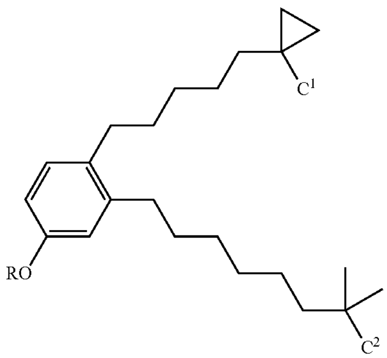 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
|---|
| 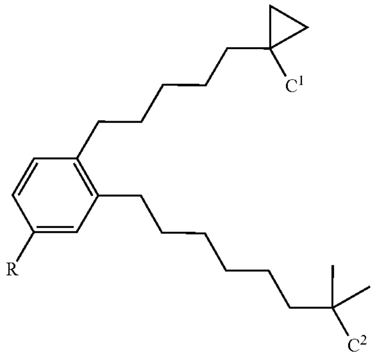 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 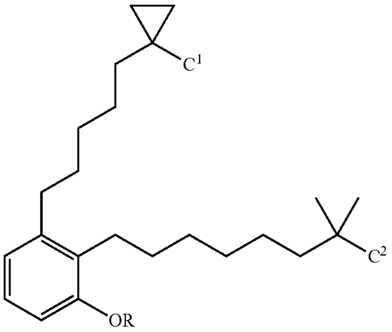 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 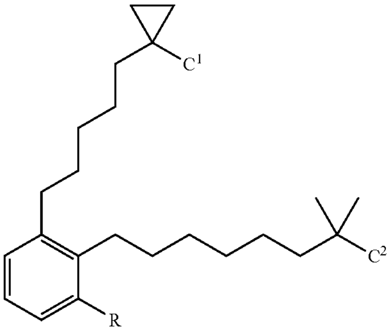 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 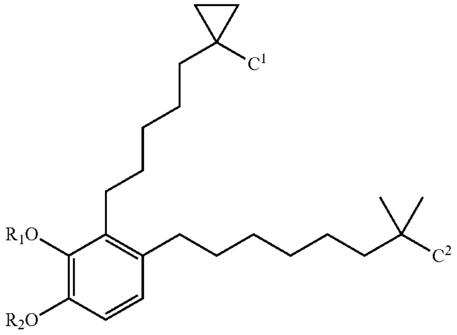 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 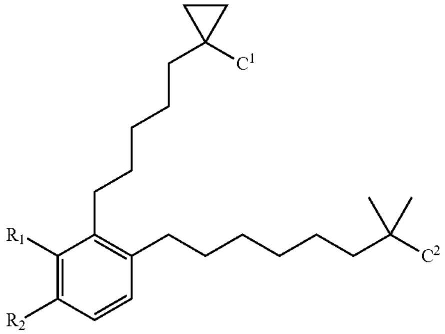 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 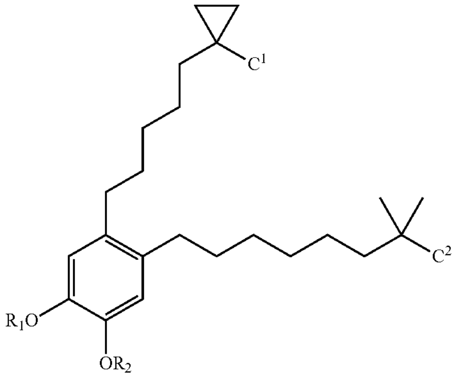 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 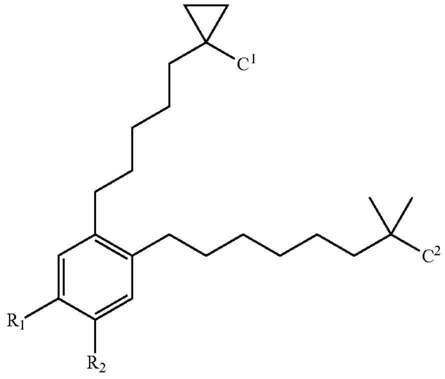 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 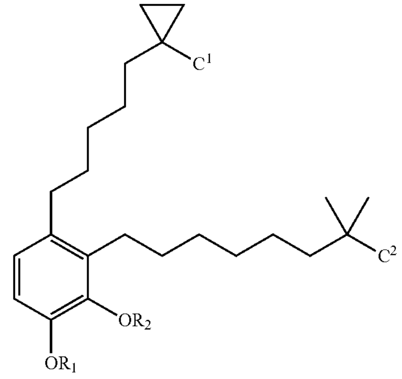 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 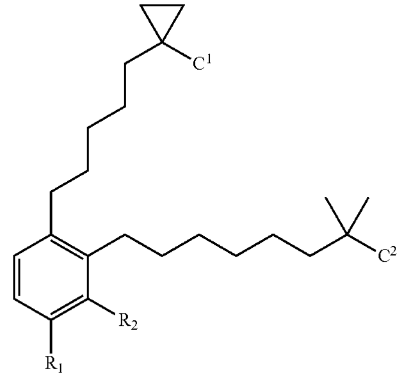 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 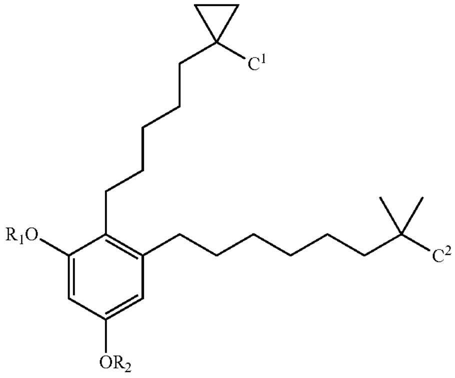 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 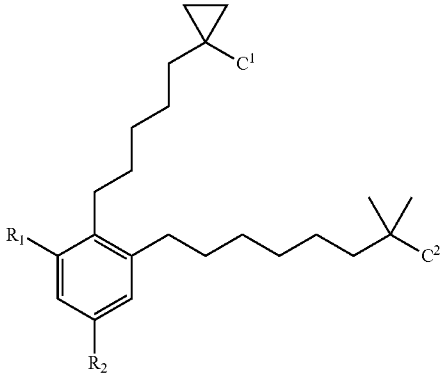 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 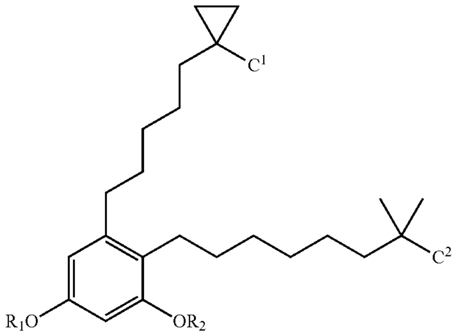 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 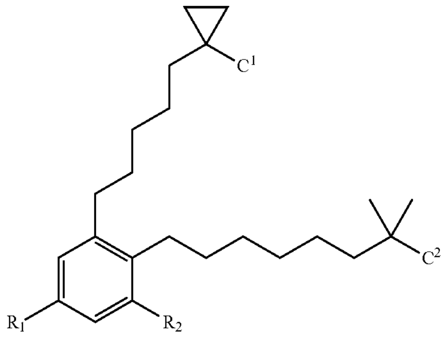 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 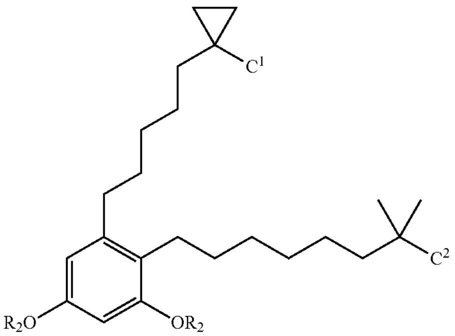 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 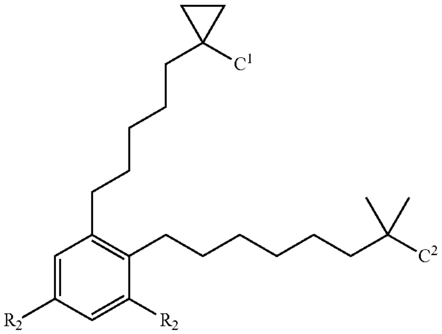 |
| wherein $C^1$ and $C^2$ = COOH; $C^1$ = COOH and $C^2$ = CO—CoA; $C^1$ = CO—CoA and $C^2$ = COOH; or $C^1$ and $C^2$= CO—CoA; and wherein each $R_2$ is independently F, Cl, Br, or $CF_3$ |

TABLE A-15-continued

| Structure |
|---|
| 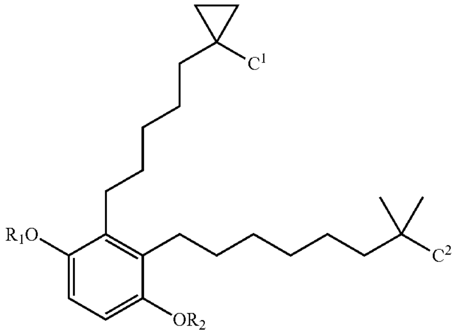 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 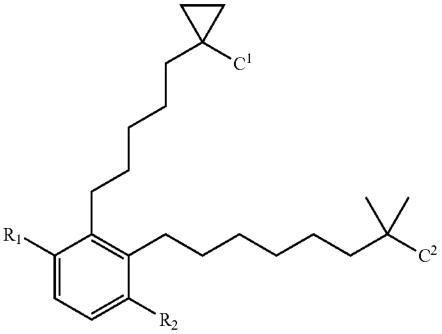 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ is H or (C1-C4)alkyl; or $R_2$ is F, Cl, Br, or $CF_3$ and $R_1$ = H or (C1-C4)alkyl |
| 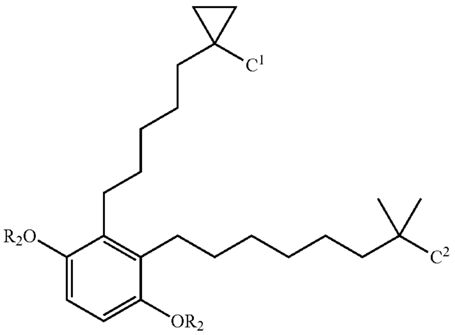 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 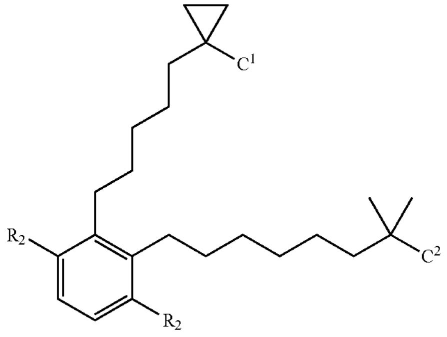 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 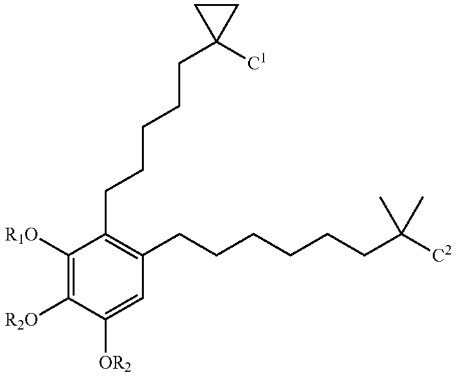 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 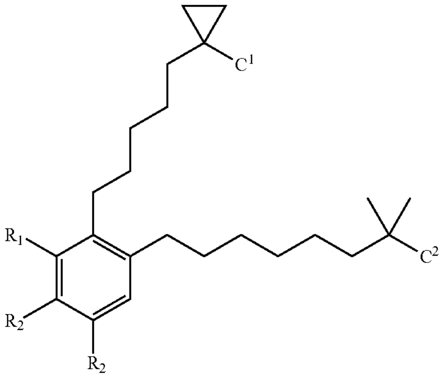 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 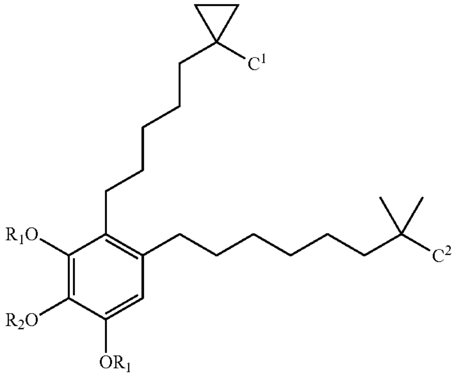 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ = H and $R_2$ is independently a (C1-C4)alkyl; or $R_2$ is H and each $R_1$ = (C1-C4)alkyl |
| 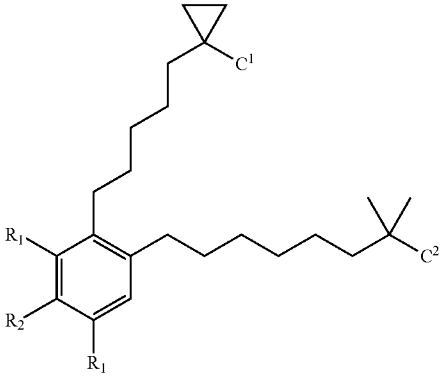 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 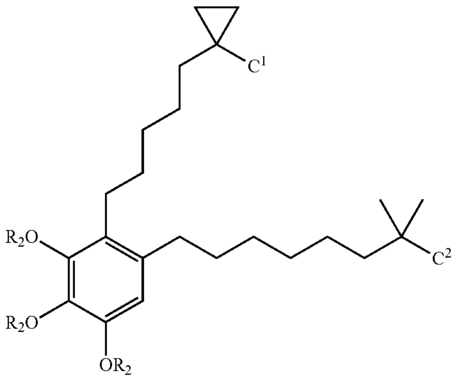 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 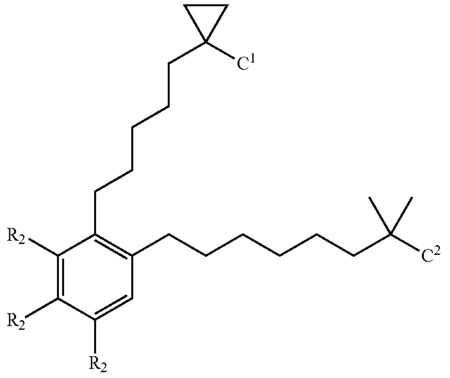 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 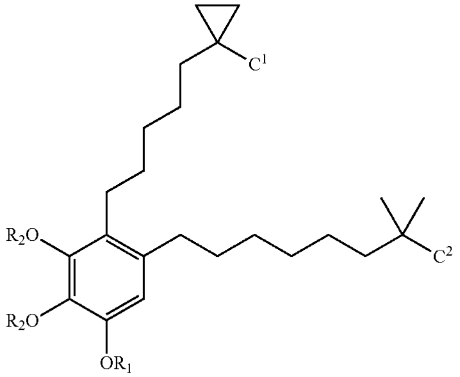 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 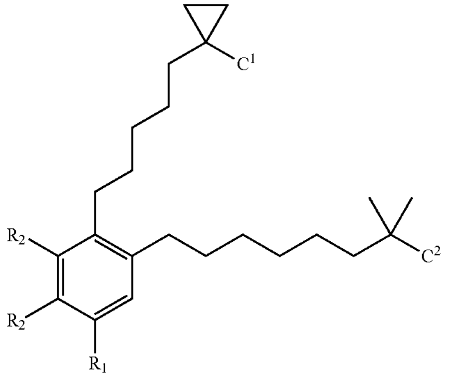 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 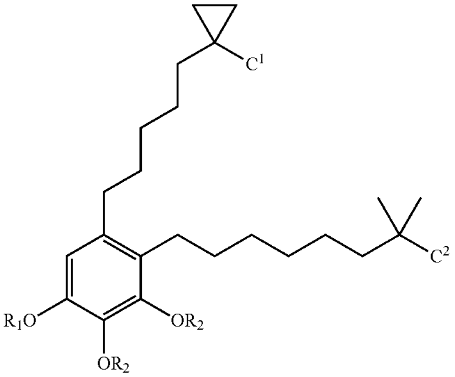 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 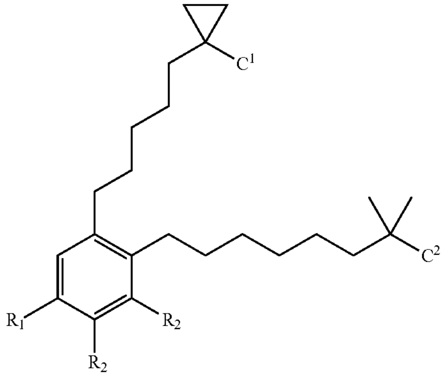 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 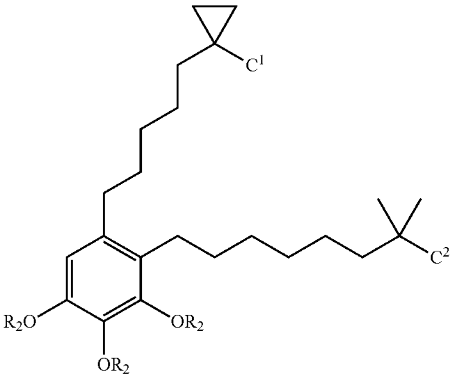 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 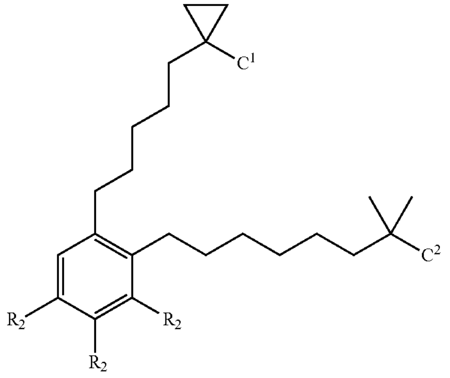 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 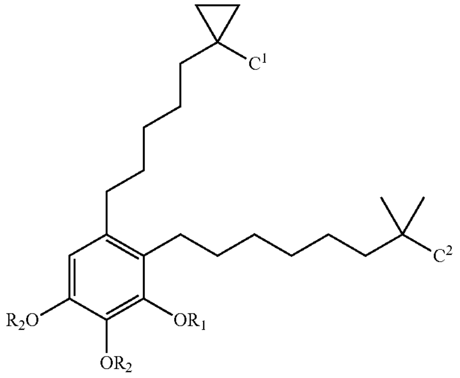 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 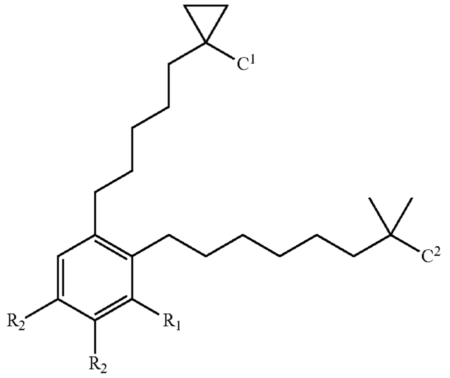 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 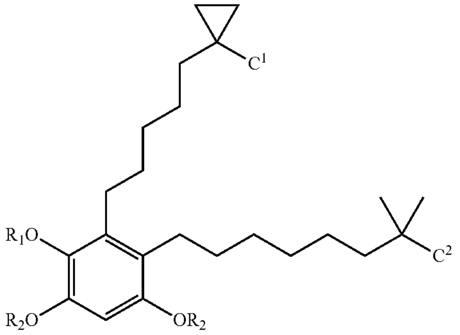 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 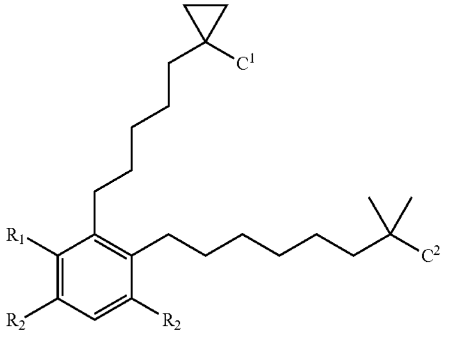 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 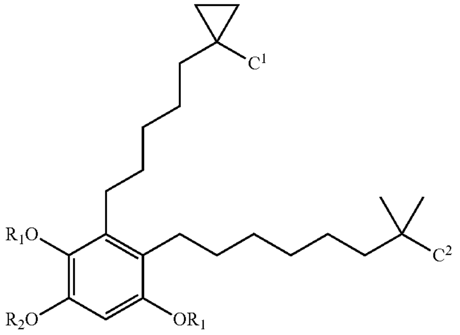 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 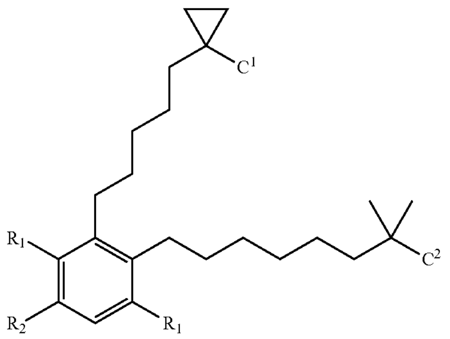 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 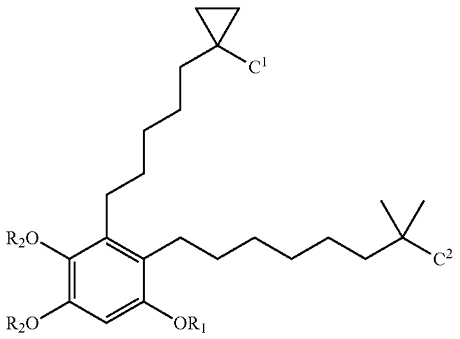 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 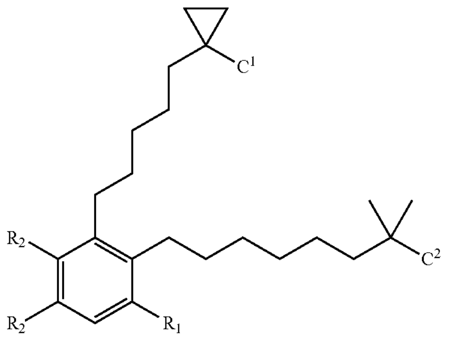 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 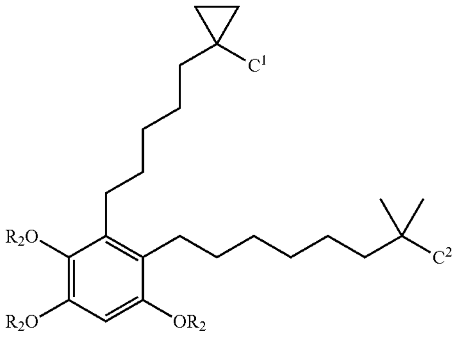 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 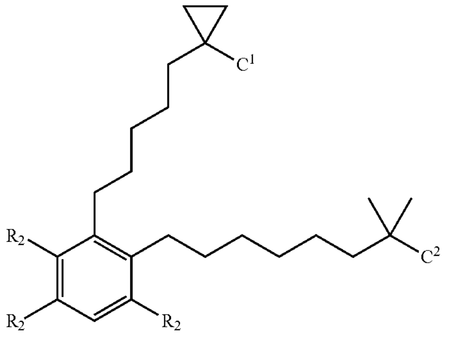 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 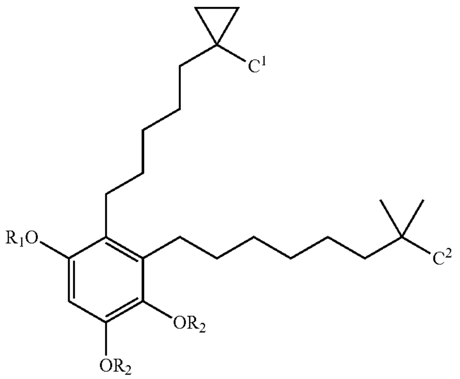 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

Structure

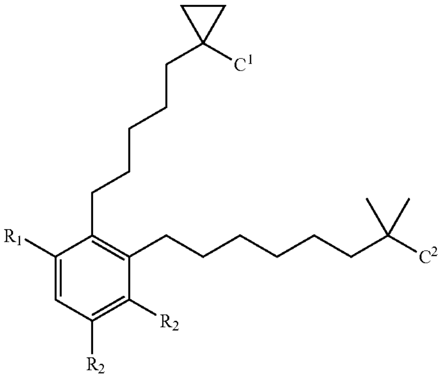

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

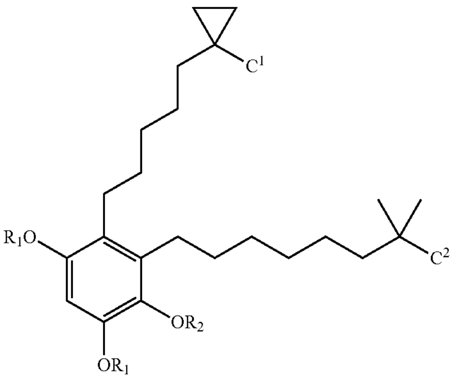

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

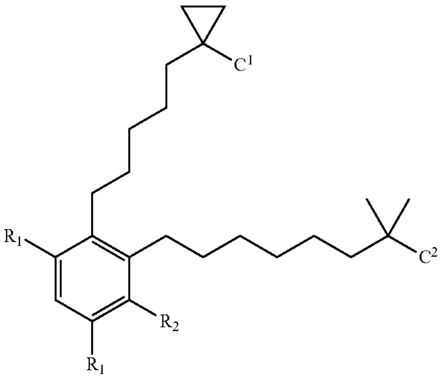

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl TABLE A-15-continued Structure

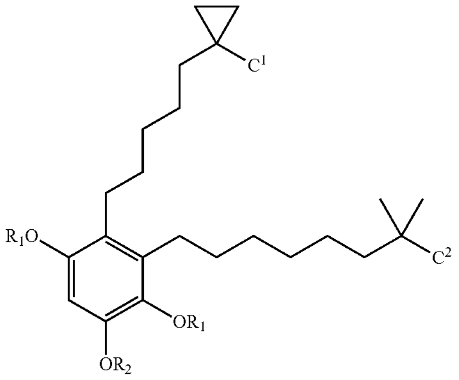

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

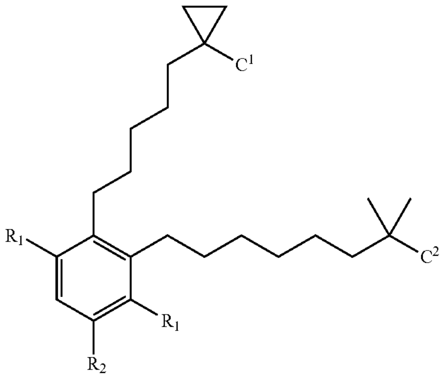

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

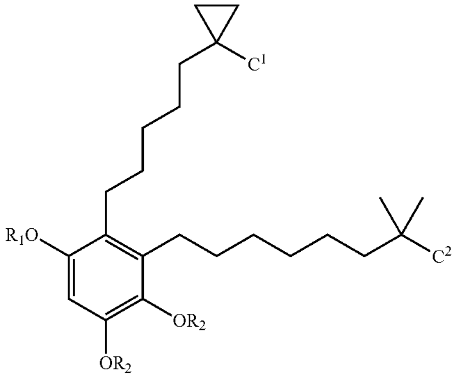

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl TABLE A-15-continued

| Structure |
|---|
| 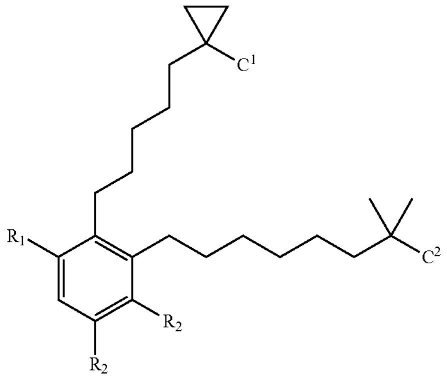 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 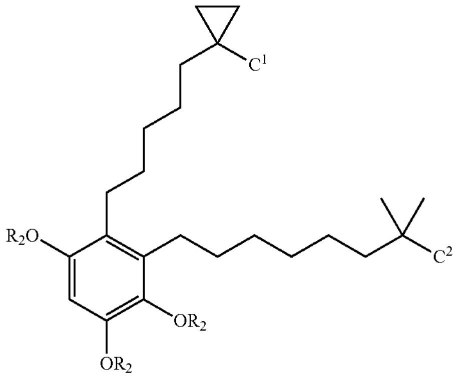 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 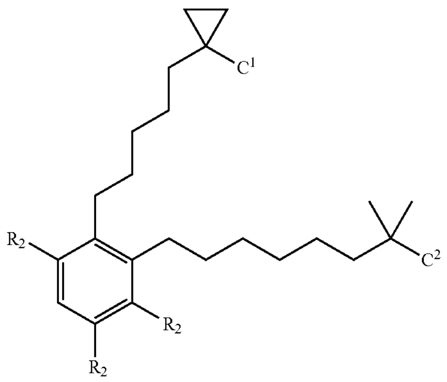 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 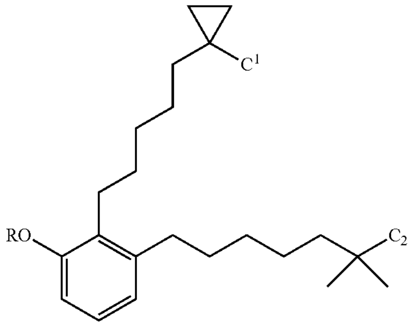 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 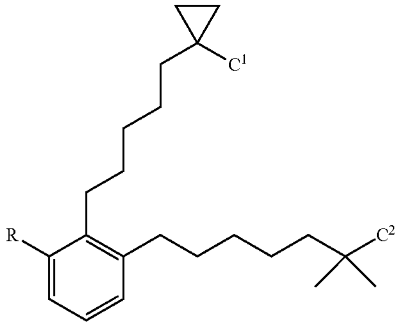 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 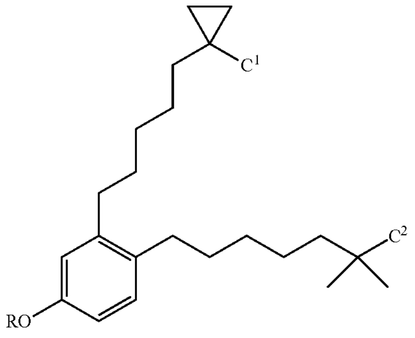 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 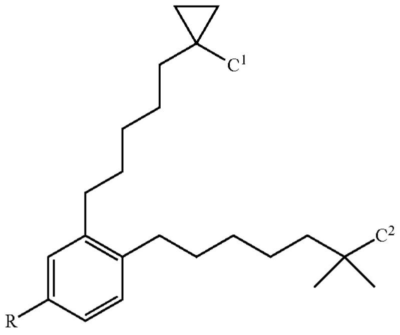<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 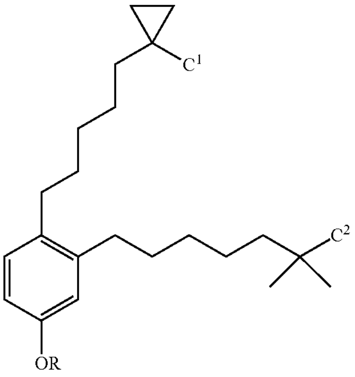<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 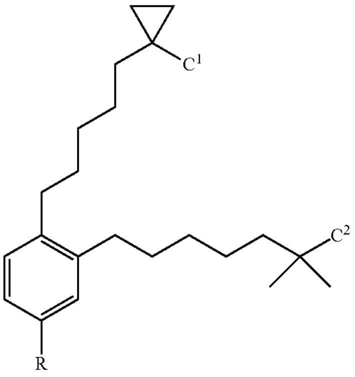<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |
| 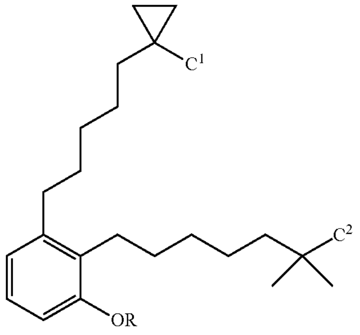<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 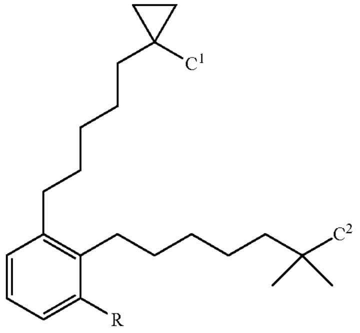<br>wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 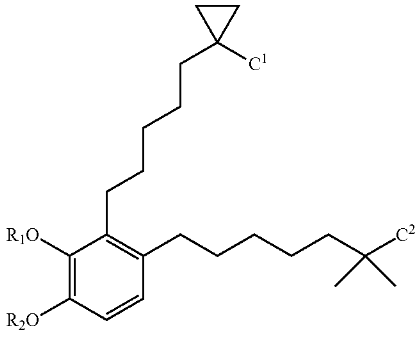<br>wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 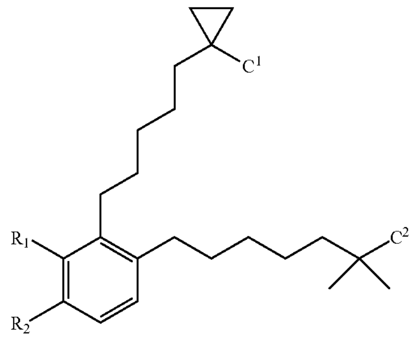 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 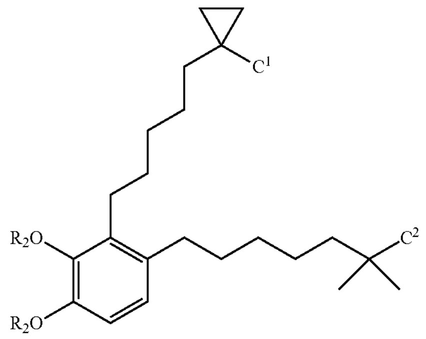 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 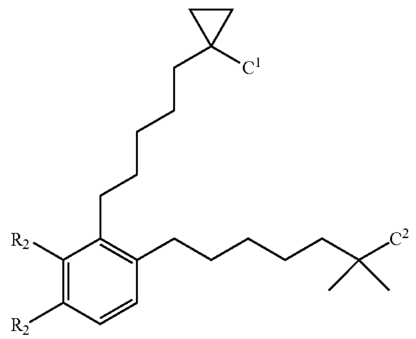 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 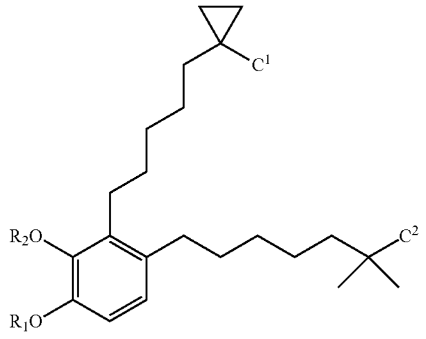 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 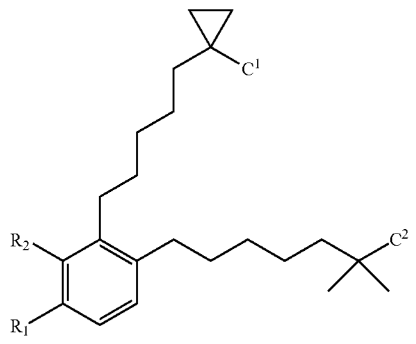 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 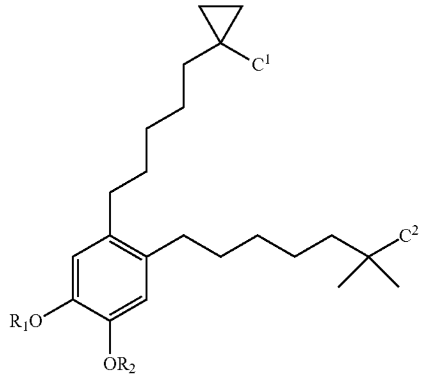 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 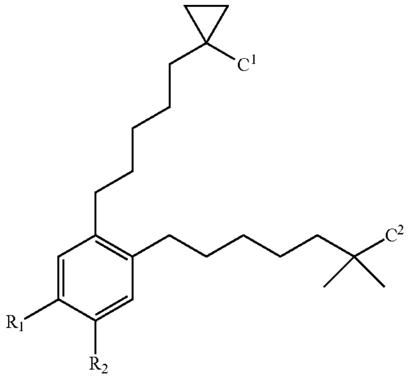 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 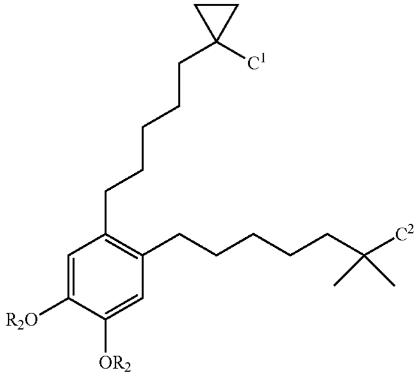 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 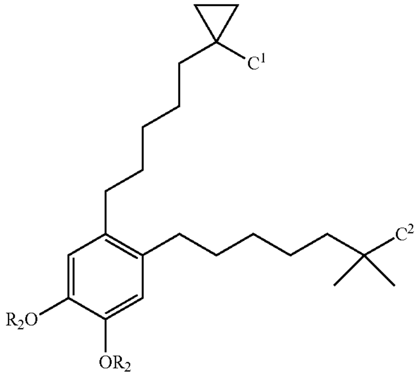 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 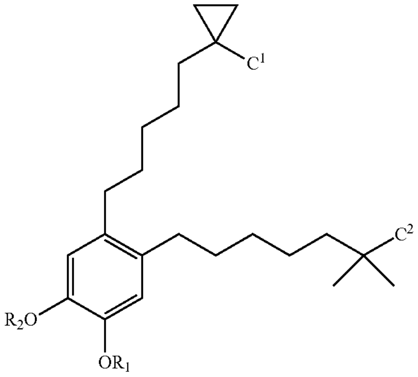 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 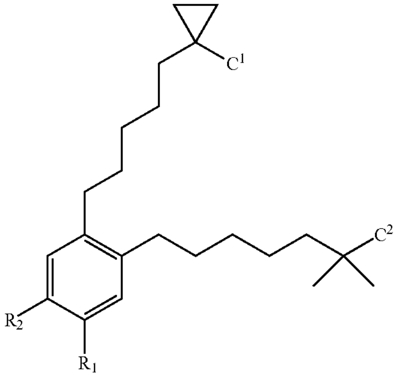 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 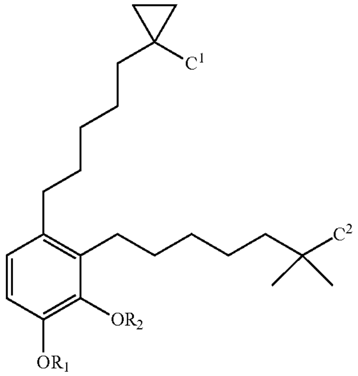 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 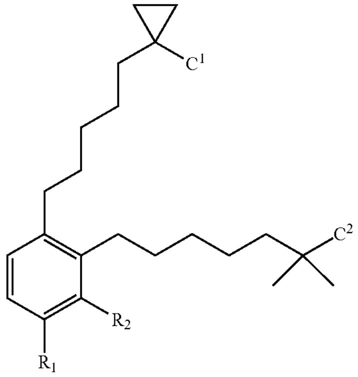 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 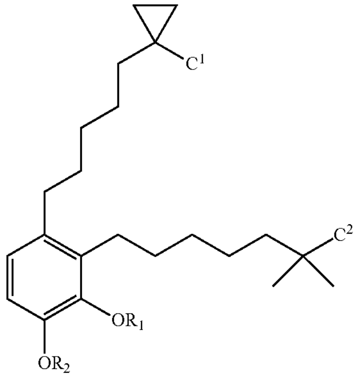 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 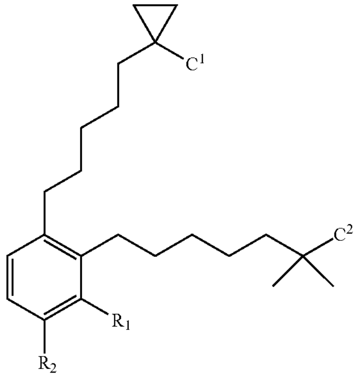 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 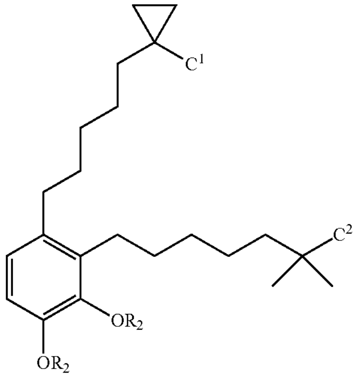 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 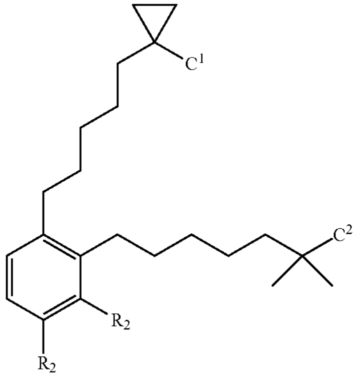 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 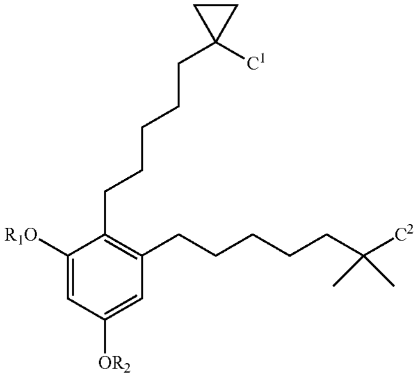 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 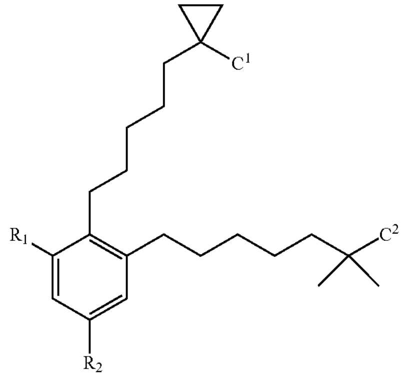 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 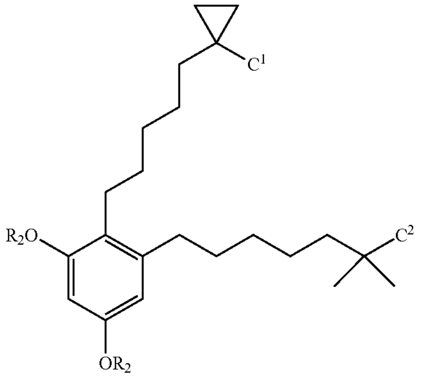 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 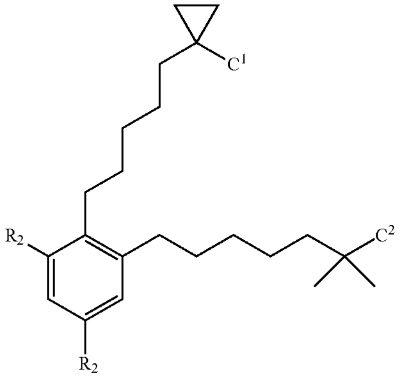 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 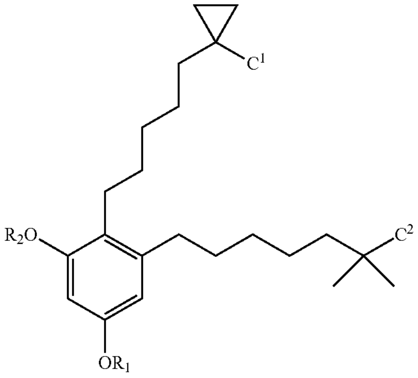 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 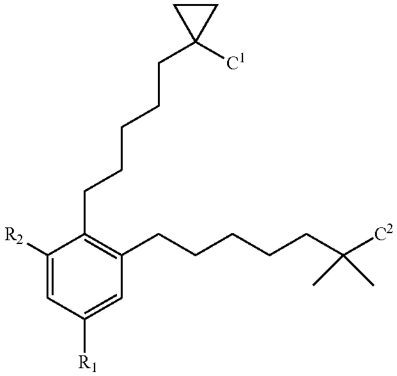 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 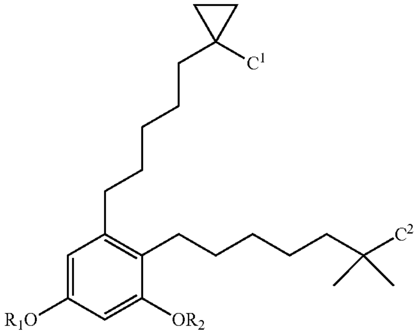 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 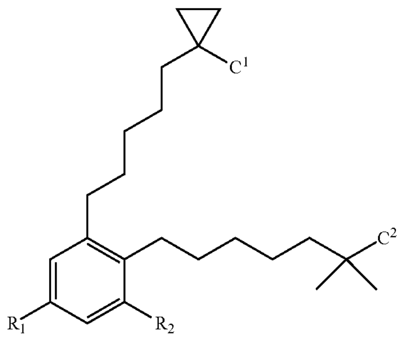 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 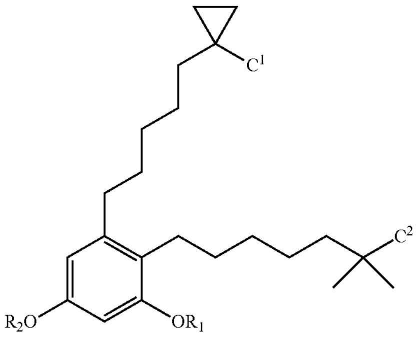 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 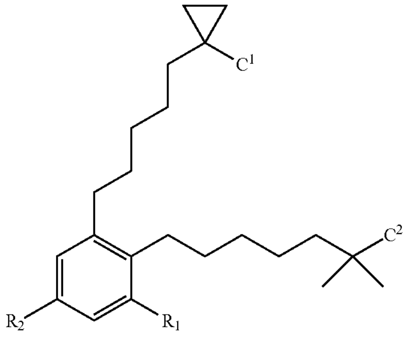 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 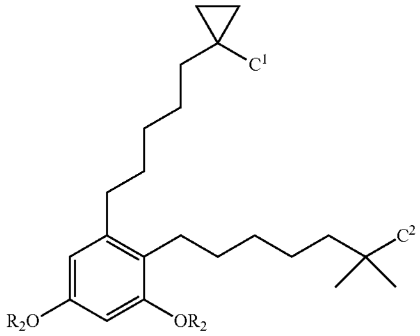 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 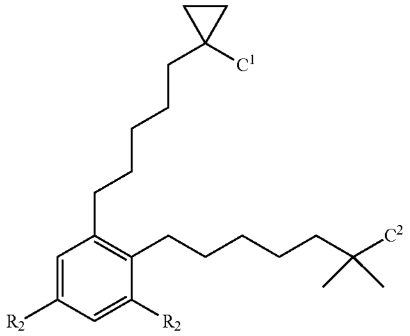 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 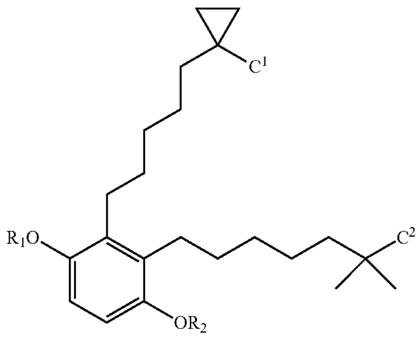 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

| Structure |
| --- |
| 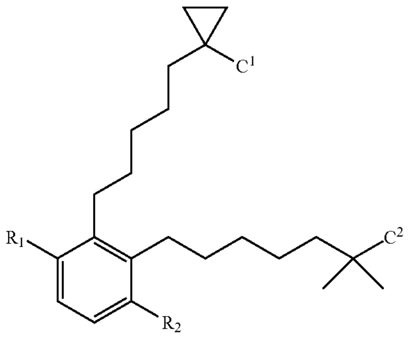 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 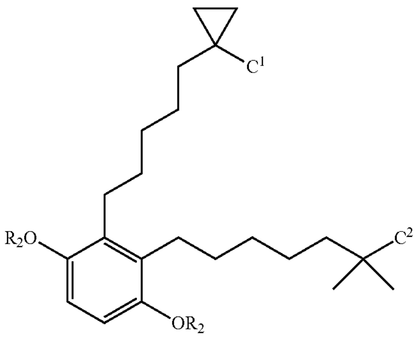 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 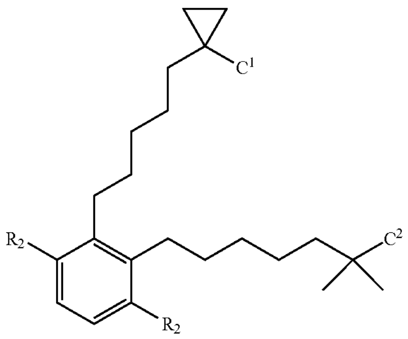 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

| Structure |
| --- |
| 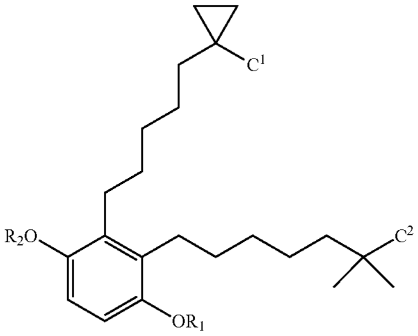 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 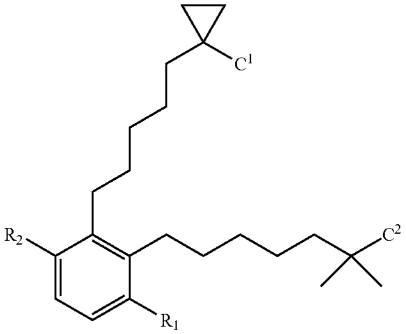 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 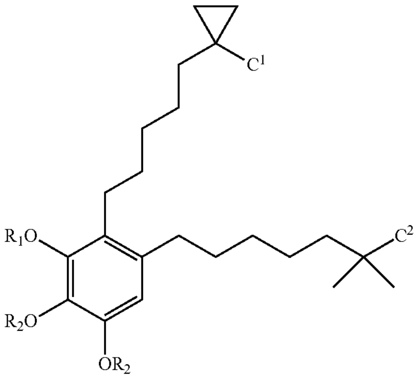 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 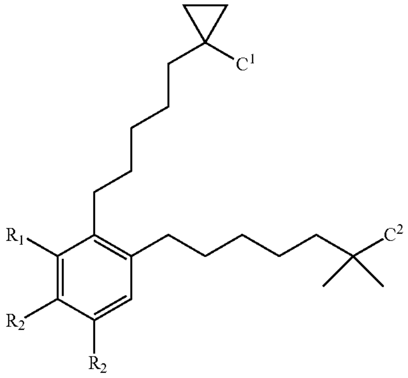 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 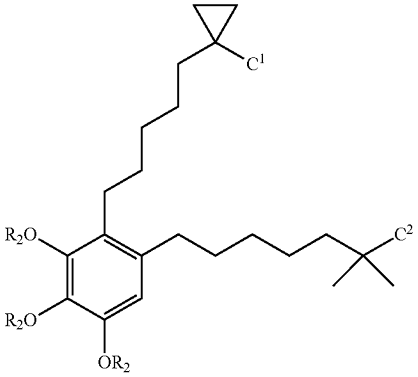 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 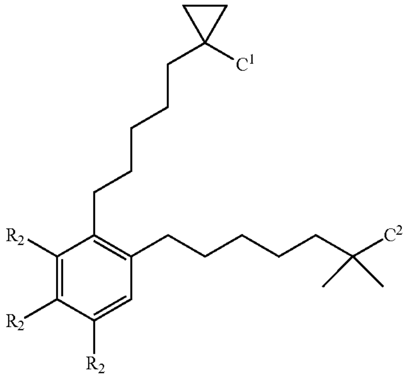 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 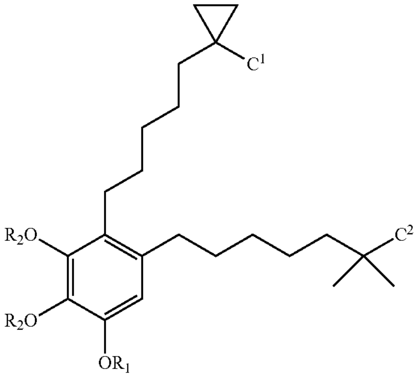 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 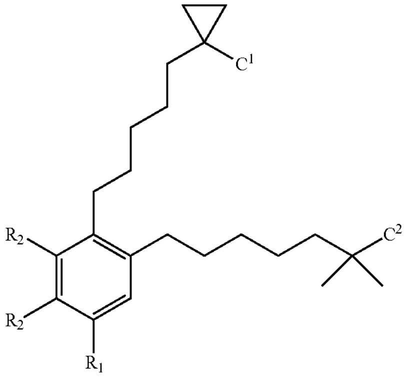 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 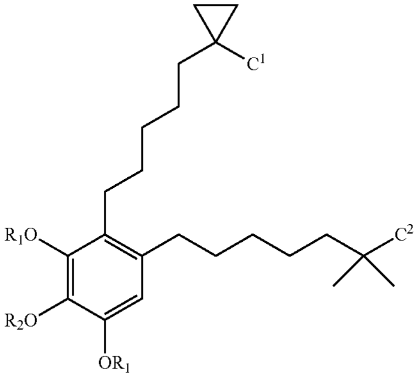 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
|---|
| 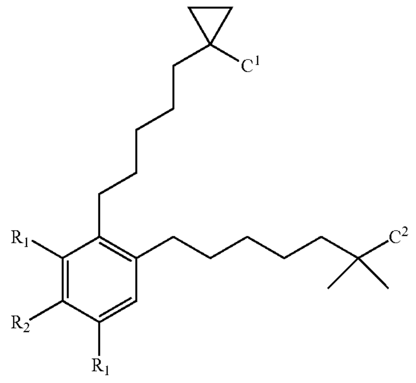 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 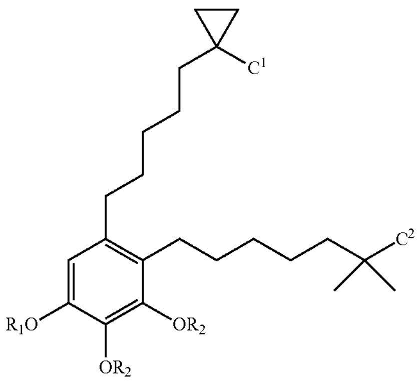 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 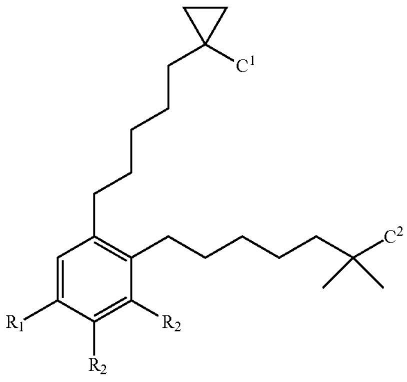 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 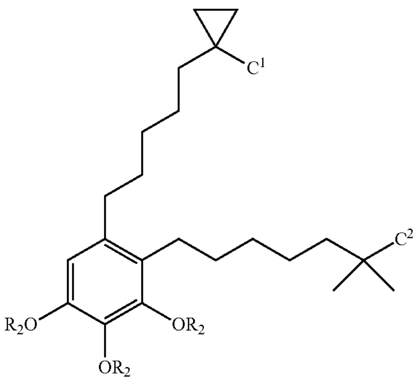 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 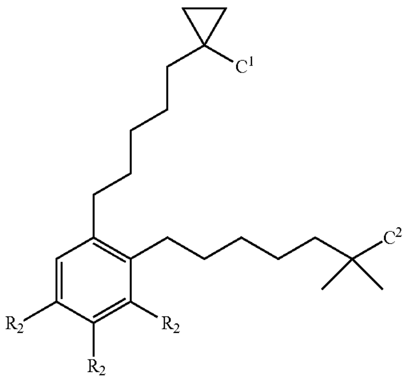 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 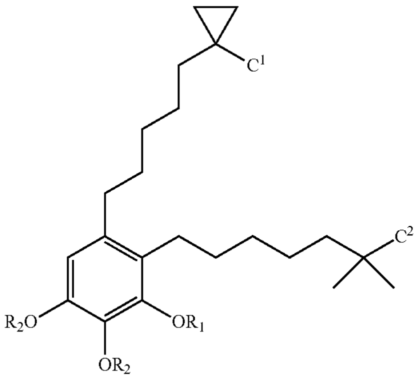 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 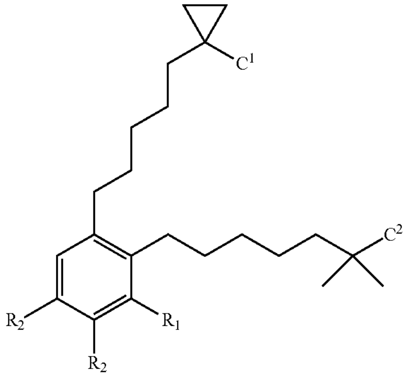 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 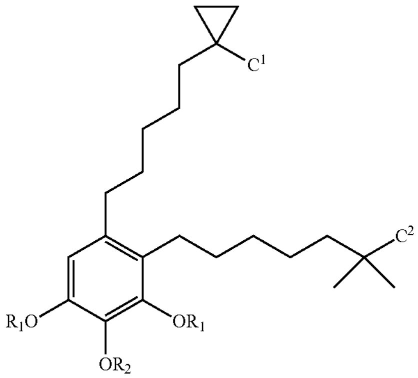 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 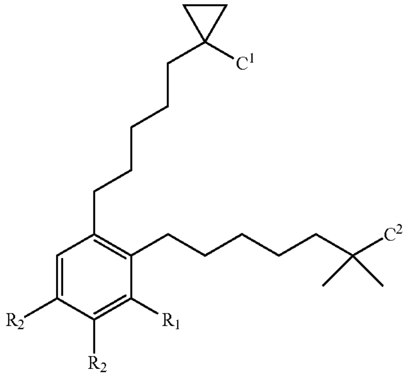 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
|---|
| 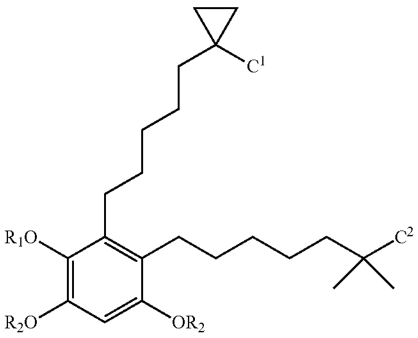 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 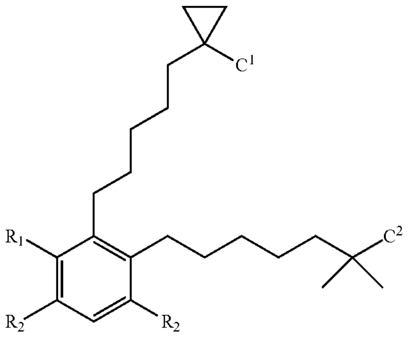 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 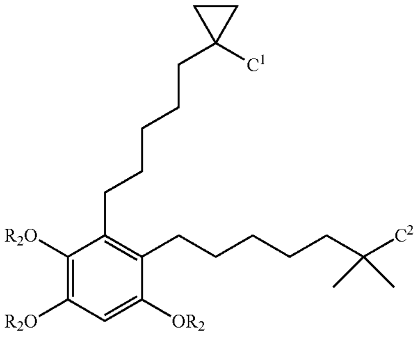 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 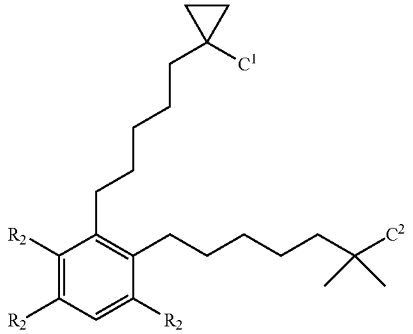 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 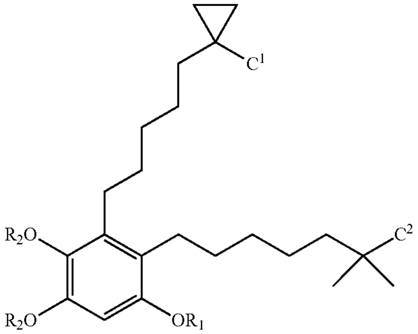 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 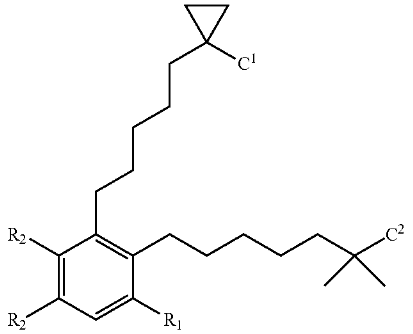 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 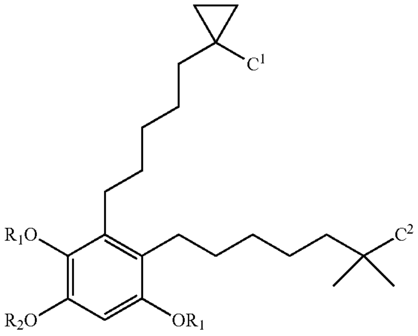 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 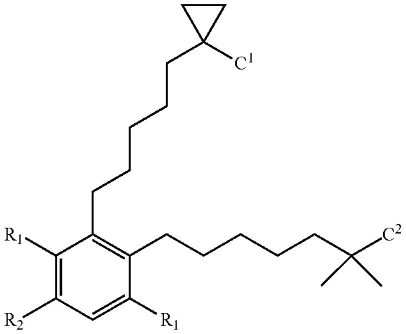 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 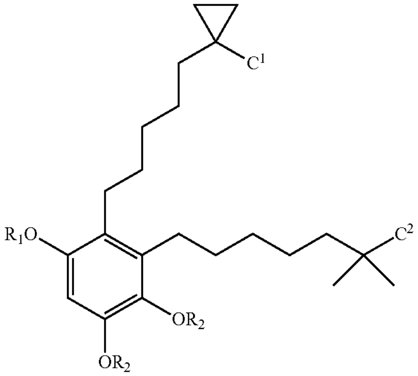 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 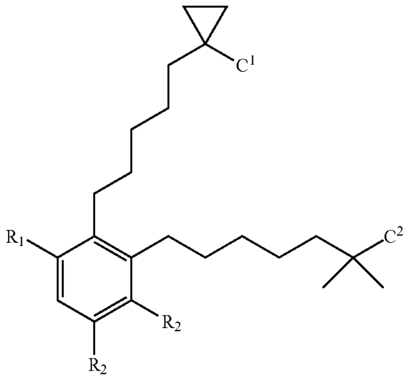 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 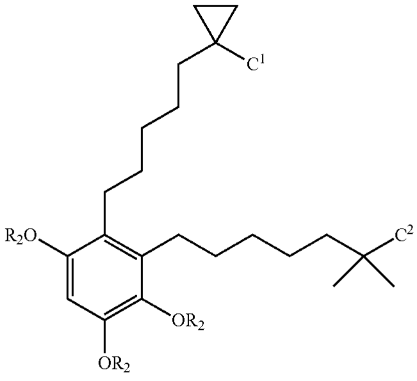 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 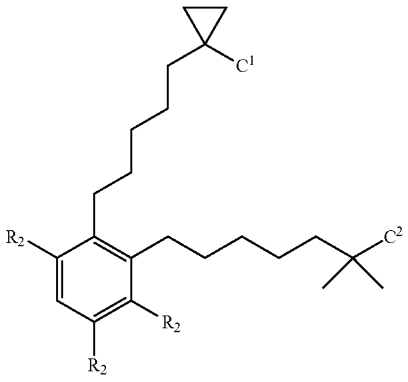 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 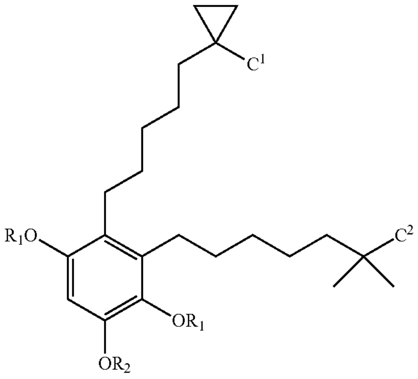 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ = H and $R_2$ is independently a (C1-C4)alkyl; or $R_2$ is H and each $R_1$ = (C1-C4)alkyl |
| 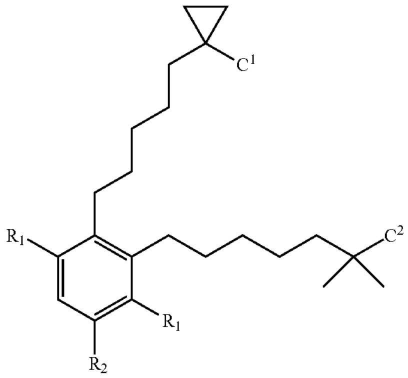 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ = F, Cl, Br, or $CF_3$ and $R_2$ is independently H or (C1-C4)alkyl; or $R_2$ is independently F, Cl, Br, or $CF_3$ and each $R_1$ = H or (C1-C4)alkyl |
| 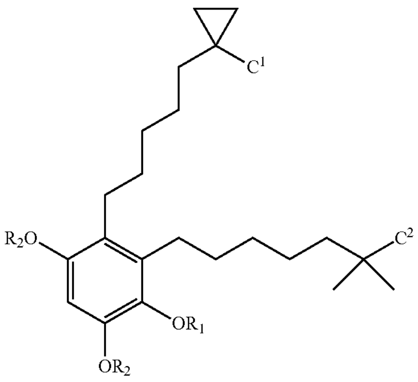 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 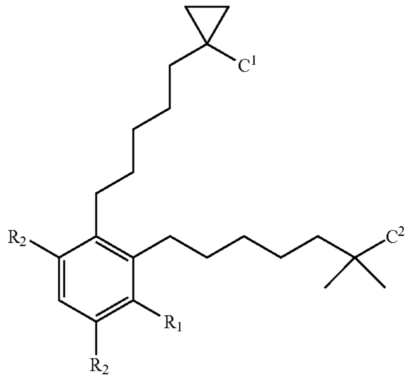 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 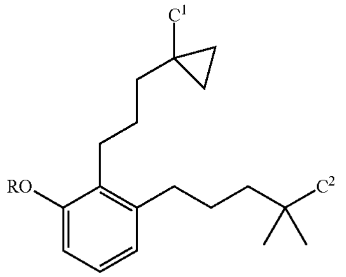 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 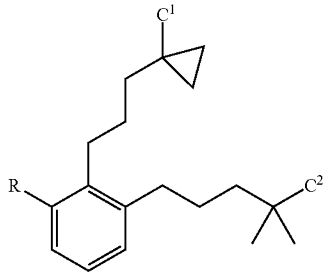 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 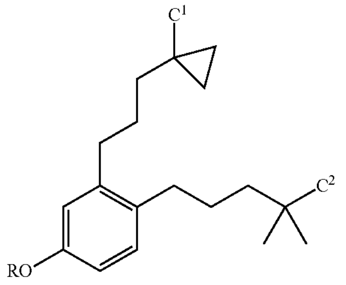 |

TABLE A-15-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 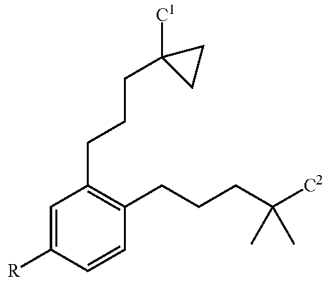 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 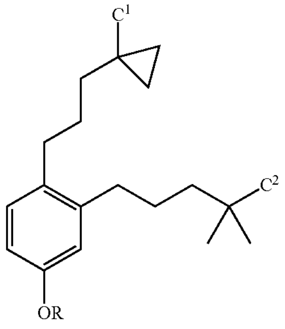 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 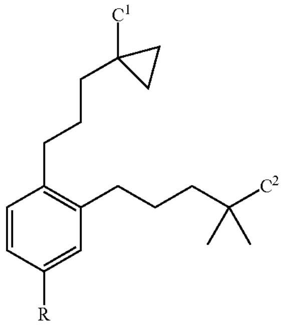 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |
| 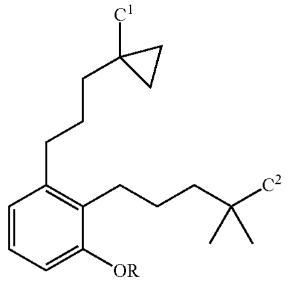 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 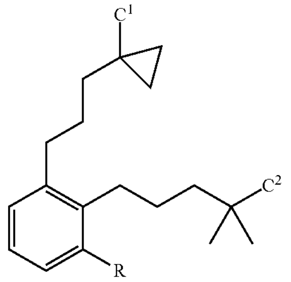 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 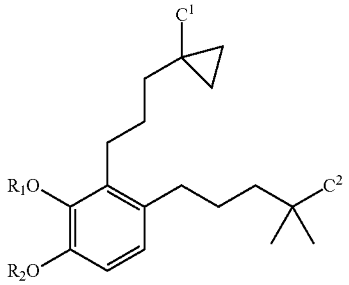 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_1$ = (C1-C4)alkyl; or $R_2$ = H and $R_1$ = (C1-C4)alkyl |
| 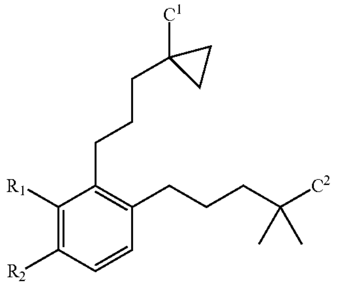 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 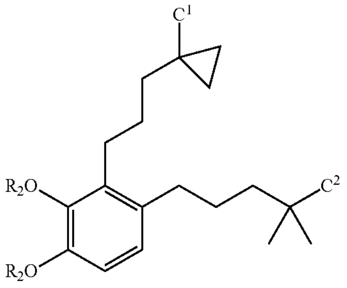 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 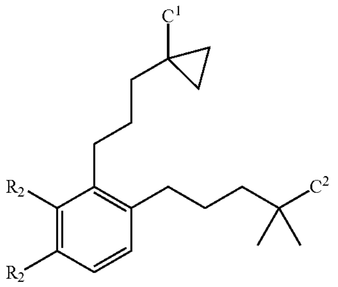 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 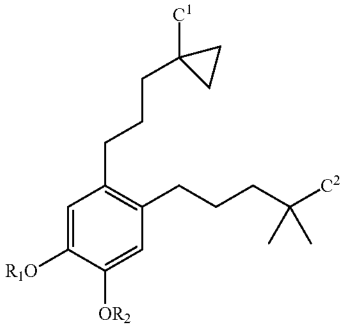 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

| Structure |
|---|
| 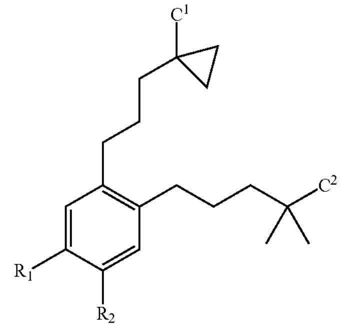 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 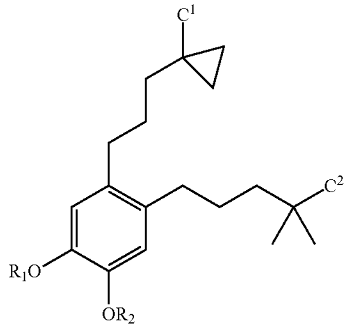 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 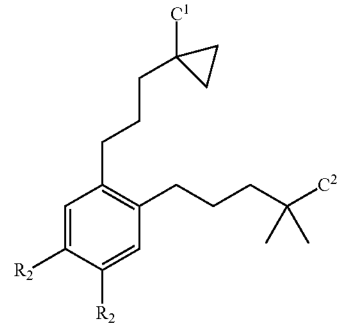 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

| Structure |
|---|
| 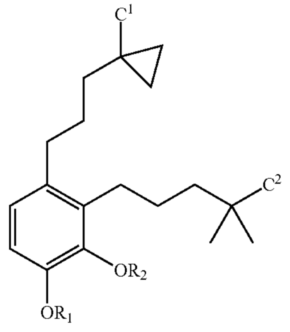 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 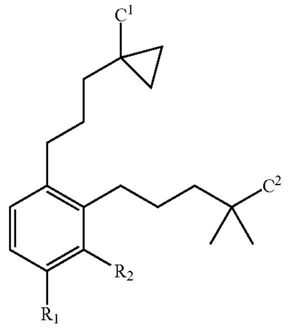 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 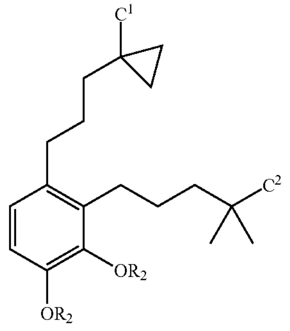 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 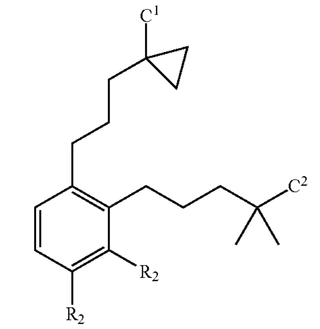 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 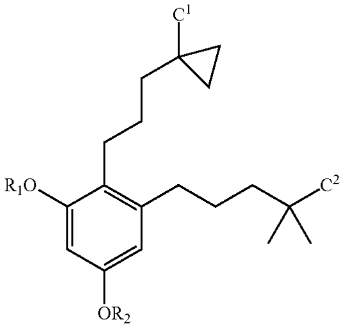 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 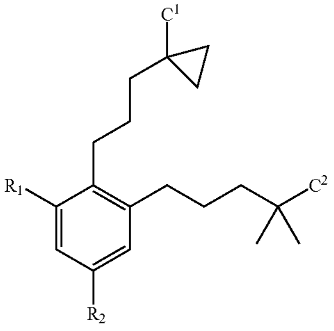 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 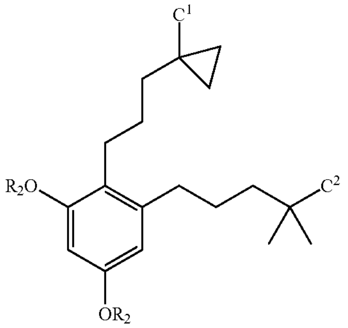 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 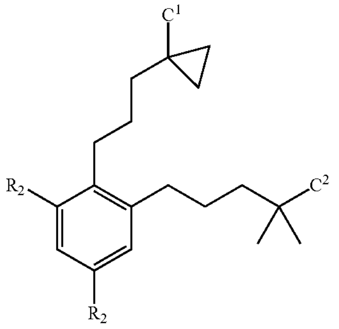 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 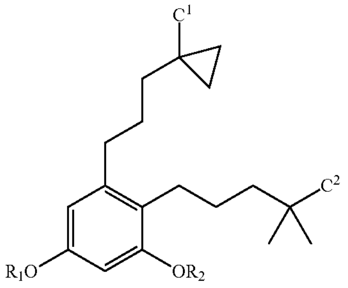 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 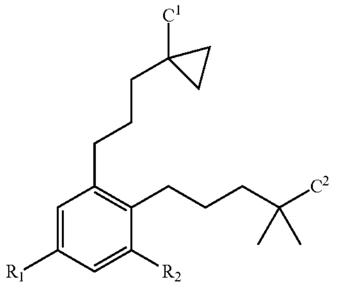 |

TABLE A-15-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 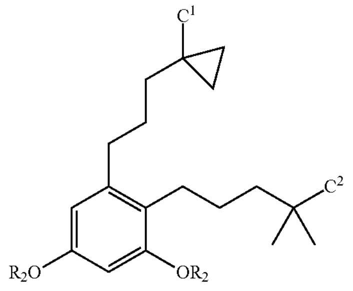 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 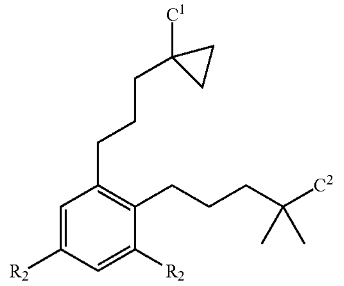 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 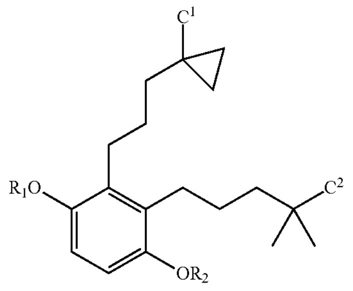 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 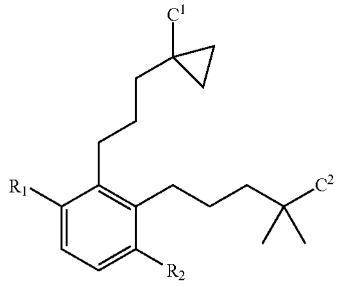 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 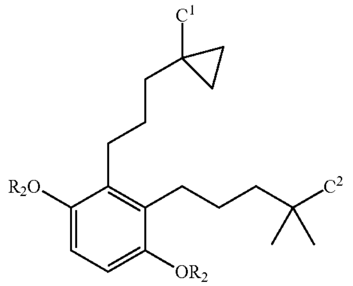 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 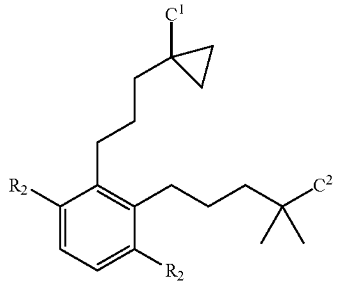 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 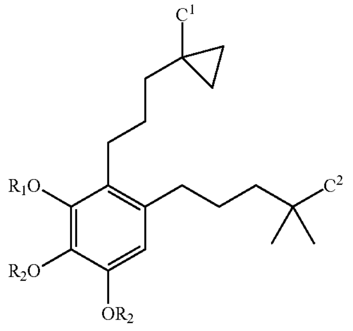 |
| wherein $C^1$ and $C^2$ = COOH; $C^1$ = COOH and $C^2$ = CO—CoA; $C^1$ = CO—CoA and $C^2$ = COOH; or |

TABLE A-15-continued

| Structure |
|---|
| $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 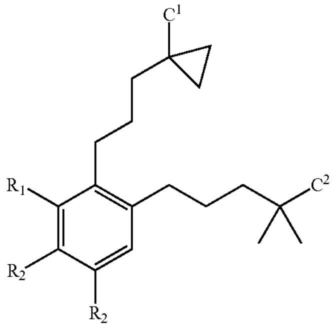 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 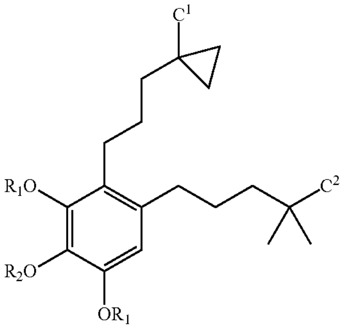 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 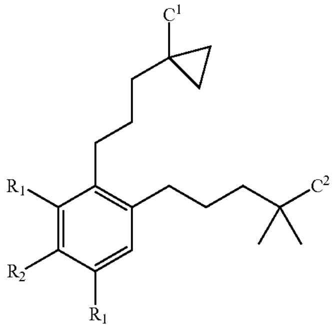 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
|---|
| 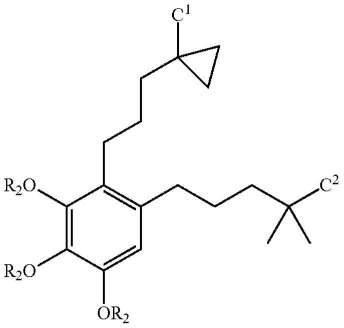 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 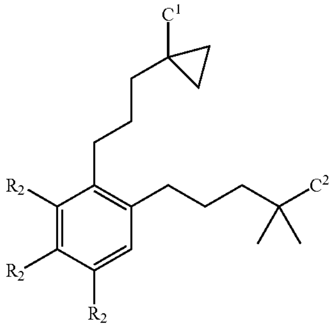 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 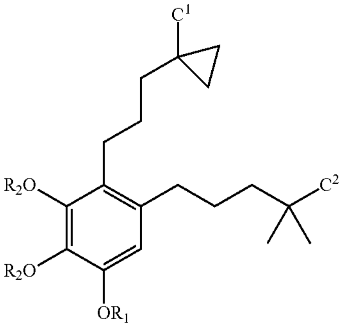 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 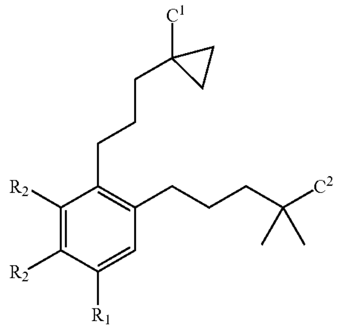 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 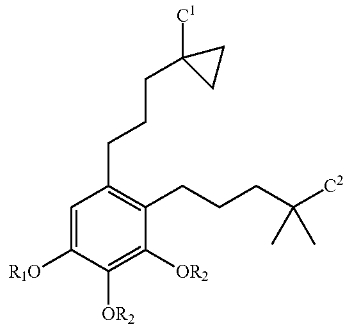 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 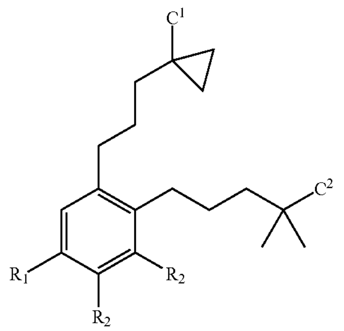 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 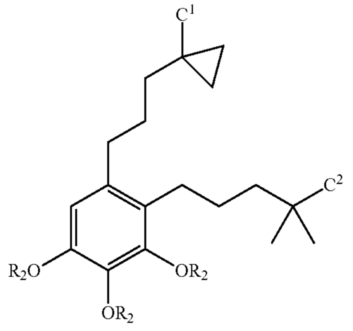 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 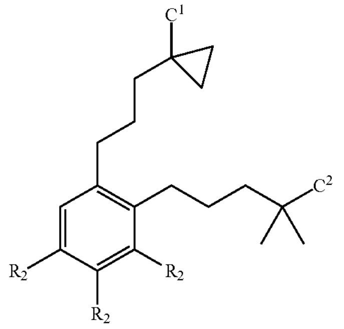 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 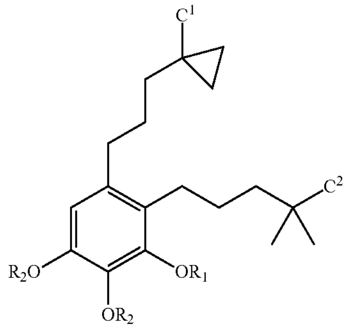 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 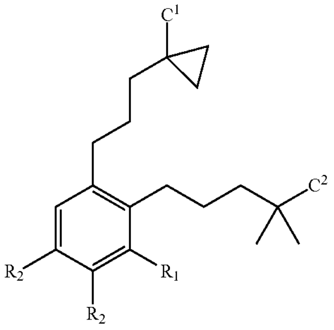 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 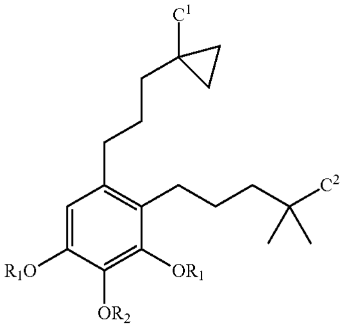 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 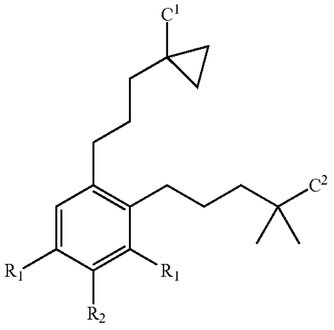 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 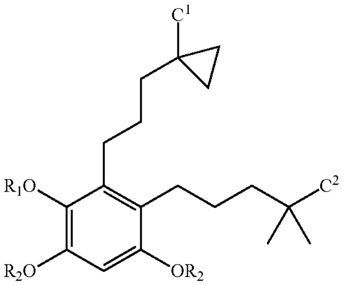 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 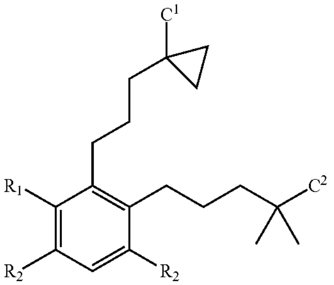 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 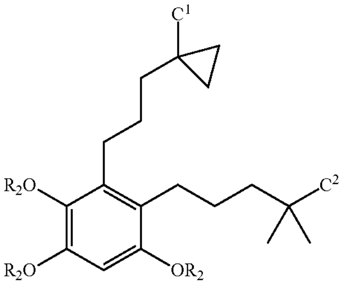 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 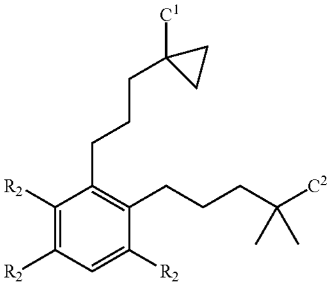 |
| wherein $C^1$ and $C^2$ = COOH; $C^1$ = COOH and $C^2$ = CO—CoA; $C^1$ = CO—CoA and $C^2$ = COOH; or |

TABLE A-15-continued

| Structure |
| --- |
| $C^1$ and $C^2$ = CO—CoA; and wherein each $R_2$ is independently F, Cl, Br, or $CF_3$ |
| 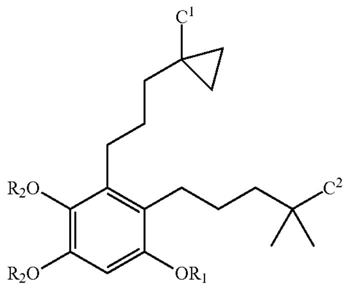 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 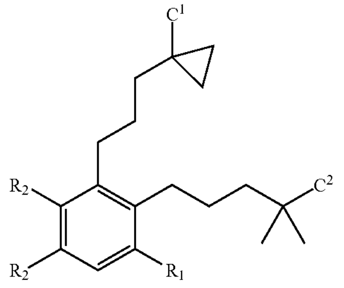 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 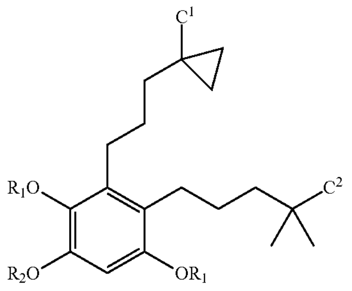 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 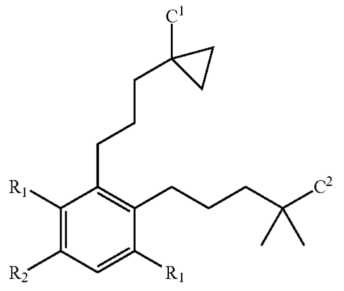 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 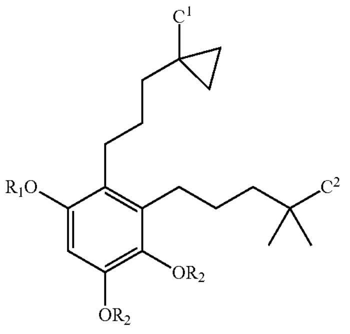 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 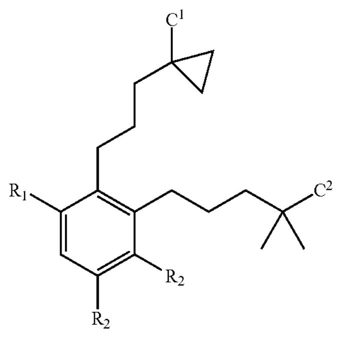 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 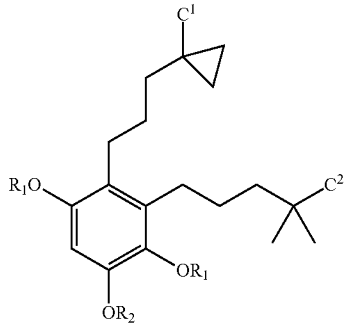 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 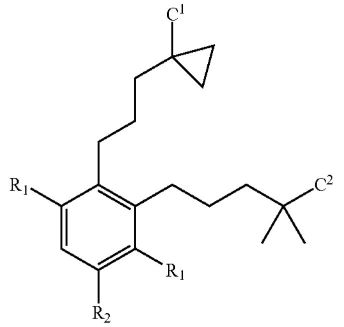 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 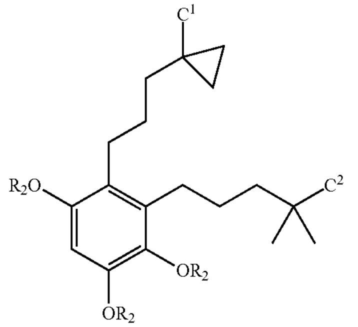 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 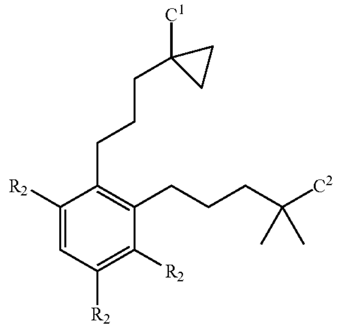 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 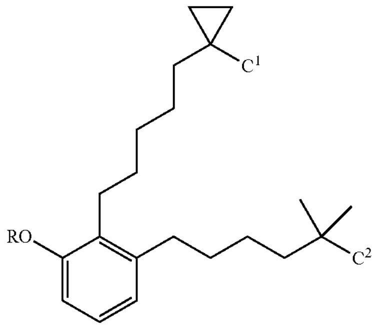 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 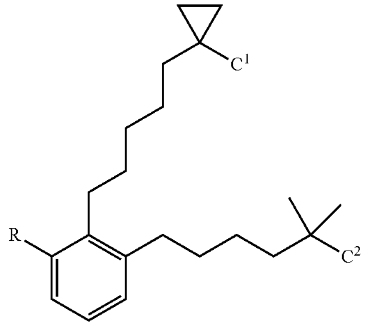 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |
| 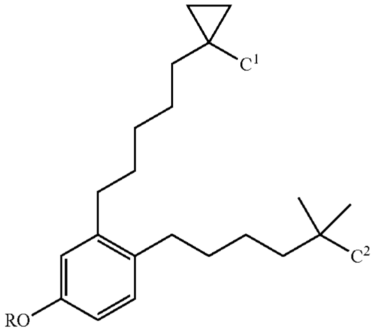 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 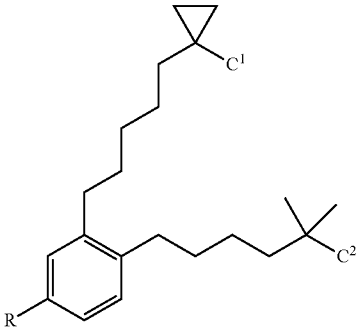 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 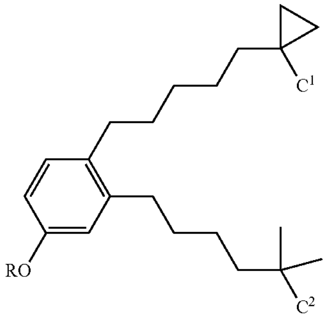 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 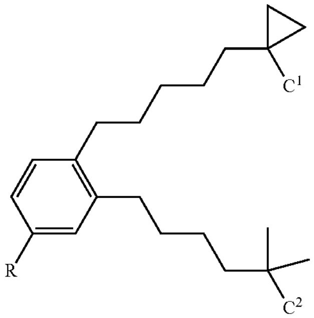 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 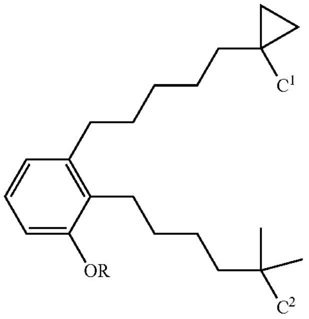 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 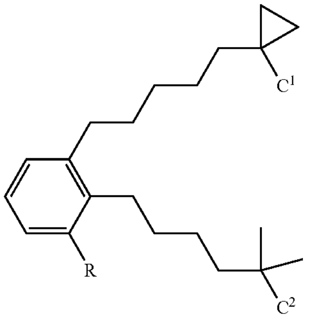 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 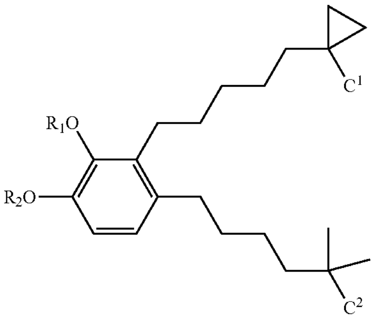 |

TABLE A-15-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 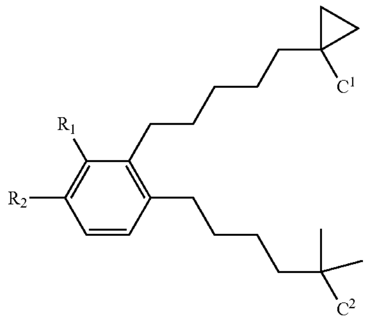 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 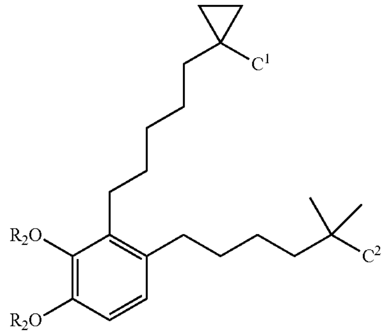 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 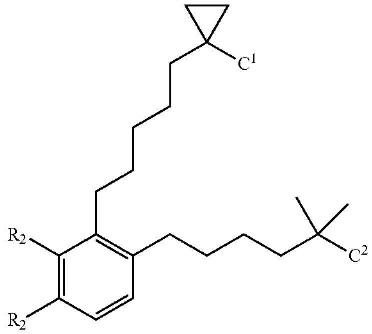 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 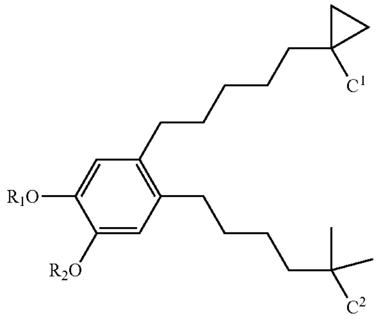 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 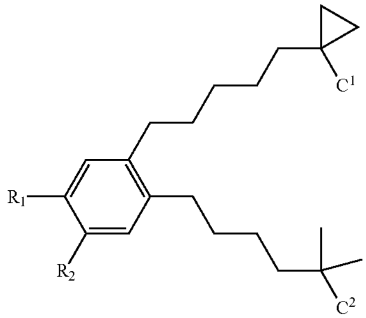 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 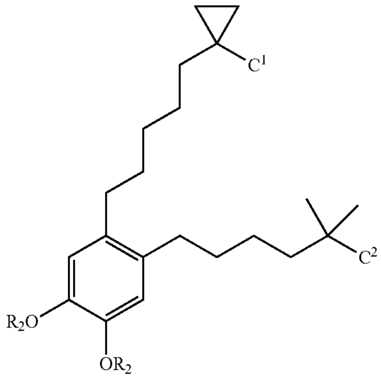 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

| Structure |
|---|
| 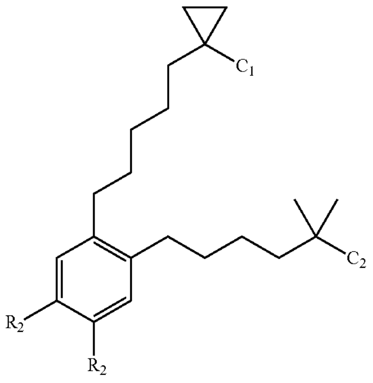 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 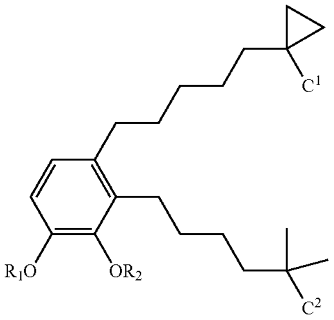 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 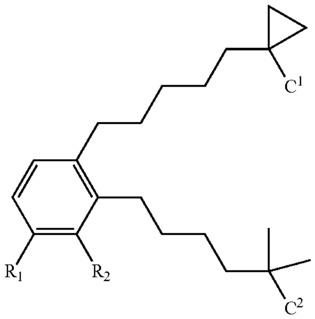 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

| Structure |
|---|
| 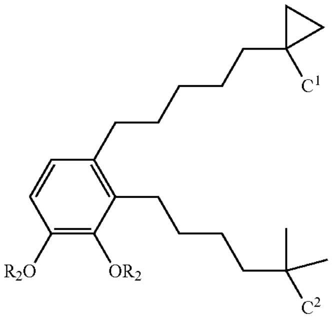 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 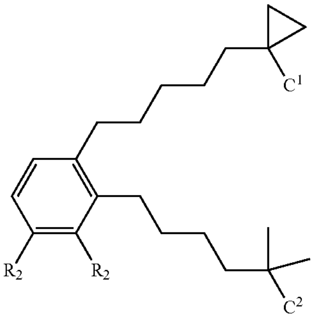 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 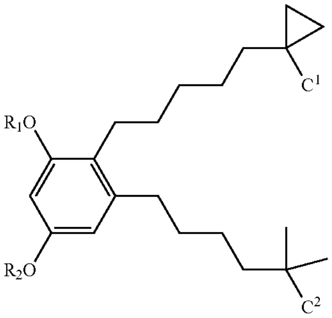 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

| Structure |
|---|
| 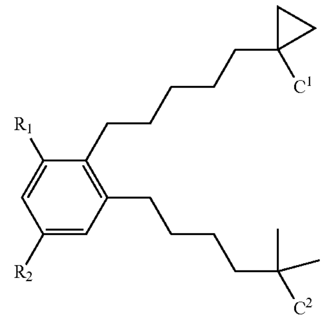 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 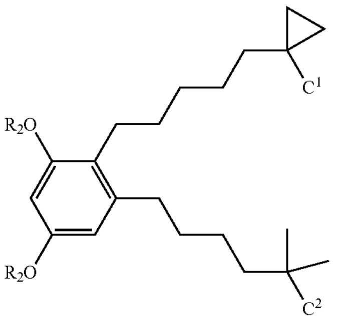 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 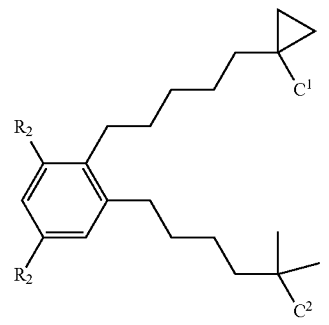 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

| Structure |
|---|
| 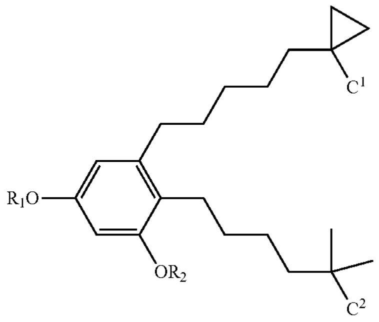 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 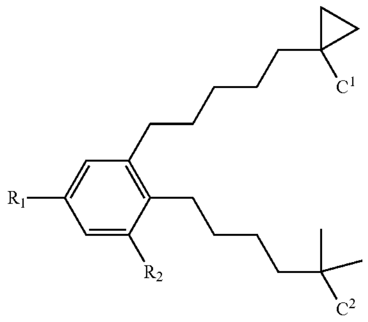 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 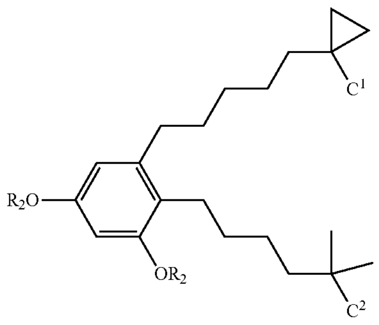 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 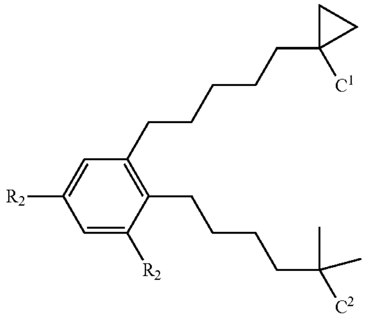 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 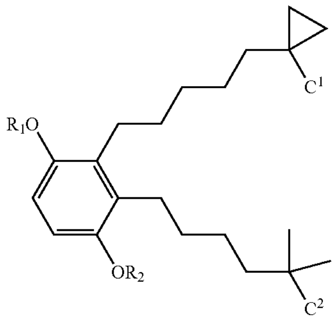 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 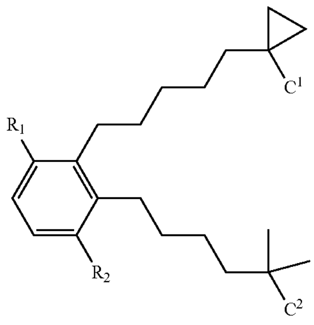 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 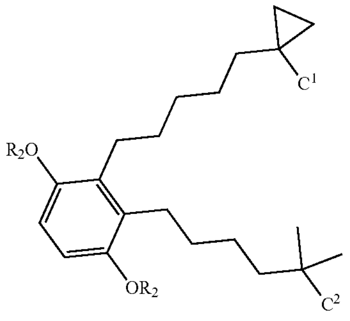 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 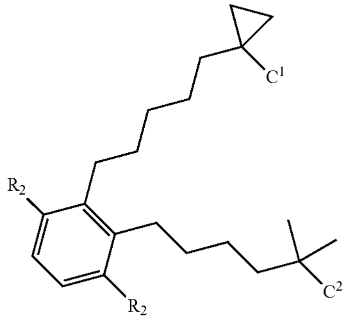 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 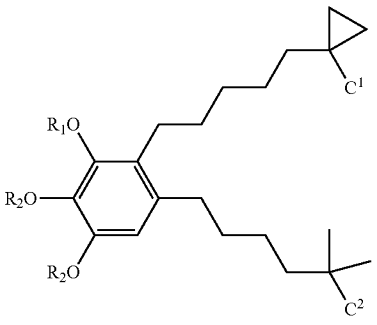 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 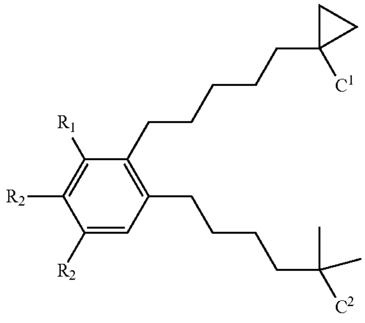 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 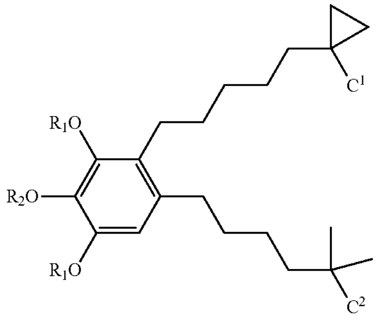 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 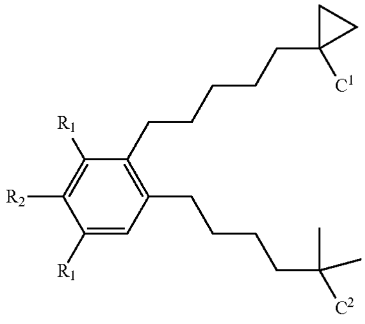 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 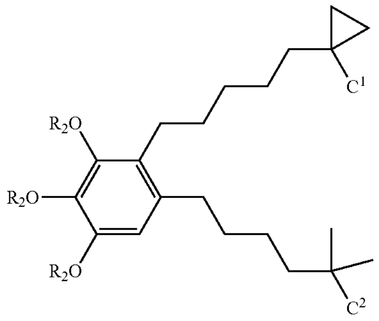 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 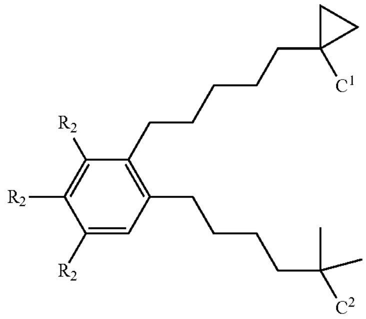 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 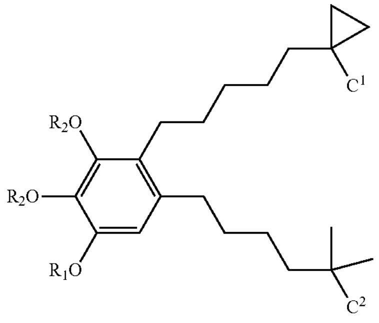 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 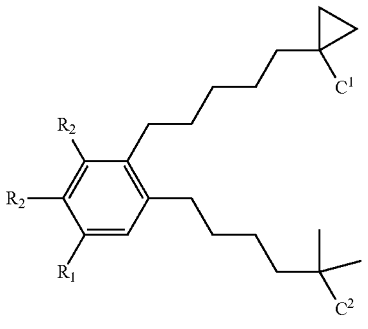 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 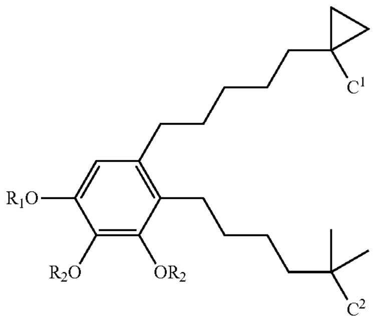 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 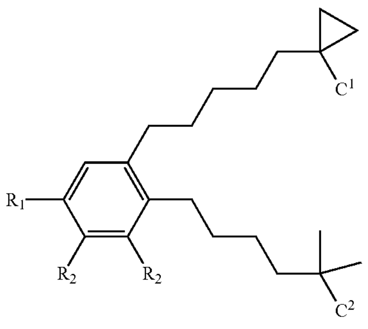 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 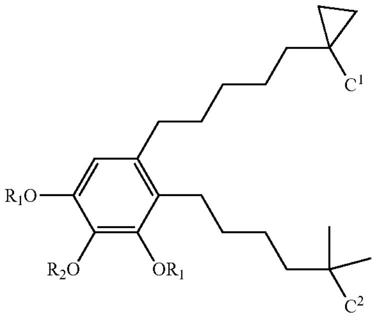 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 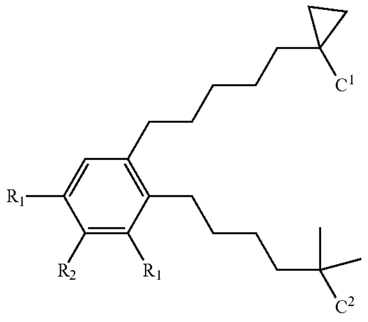 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 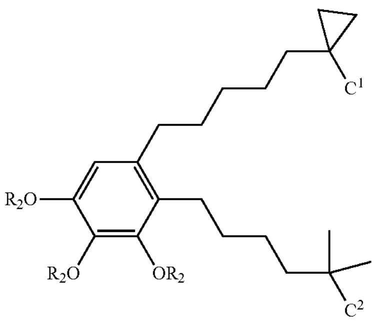 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 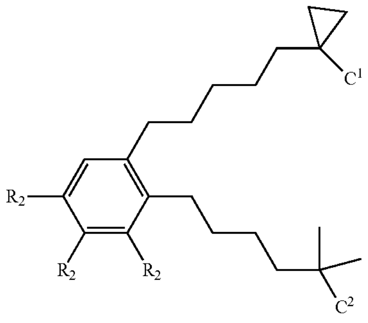 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 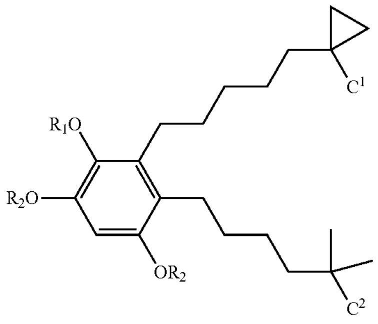 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 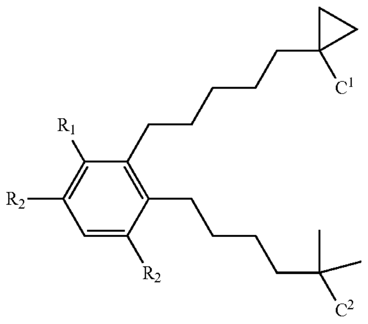 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 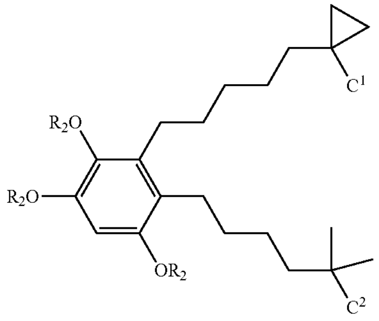 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 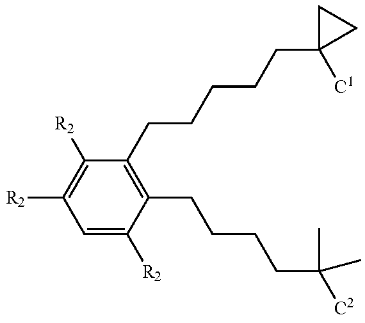 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 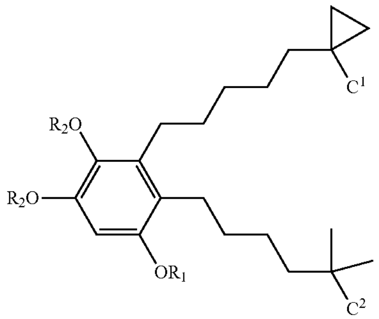 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 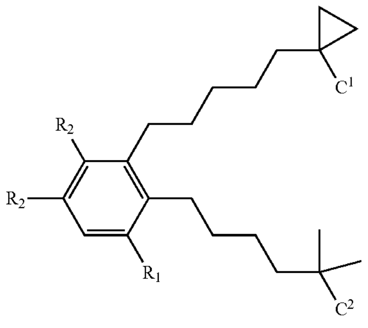 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 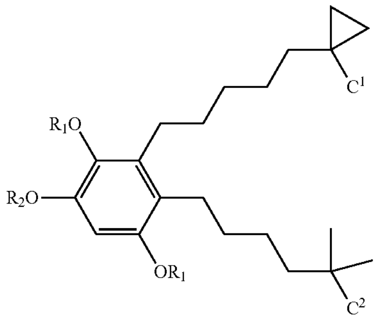 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 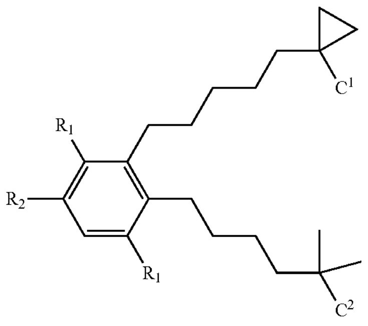 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 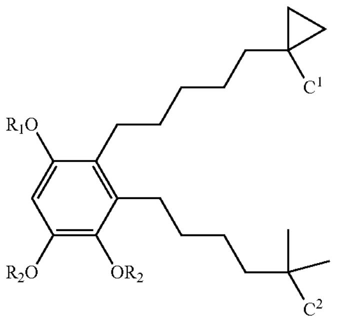 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 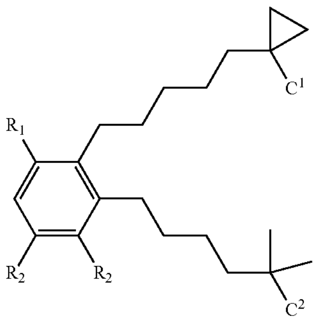 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 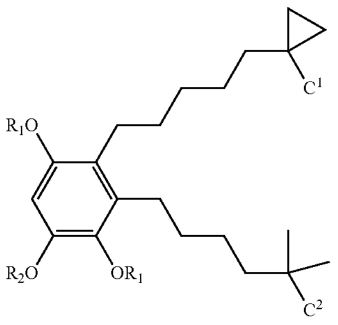 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 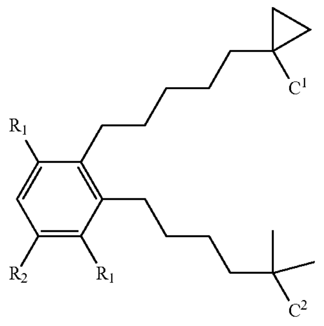 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 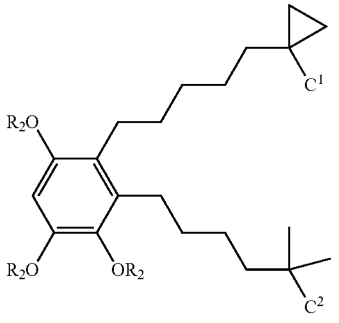 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 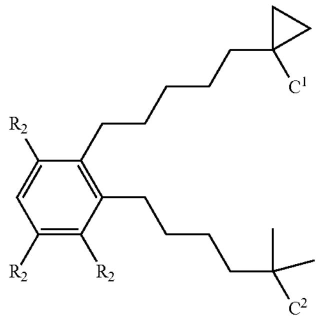 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 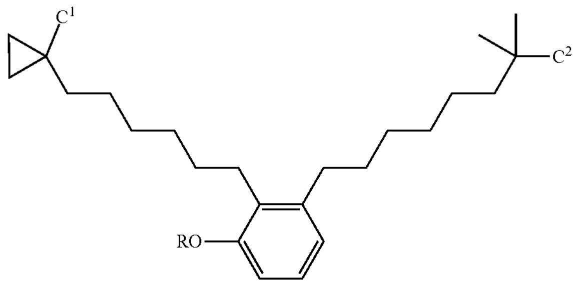 |

TABLE A-15-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 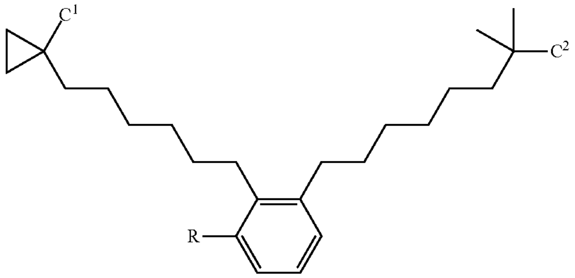 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 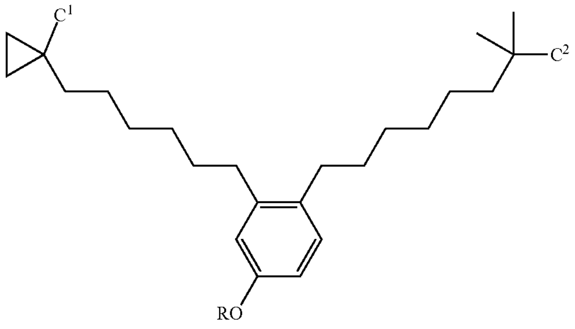 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 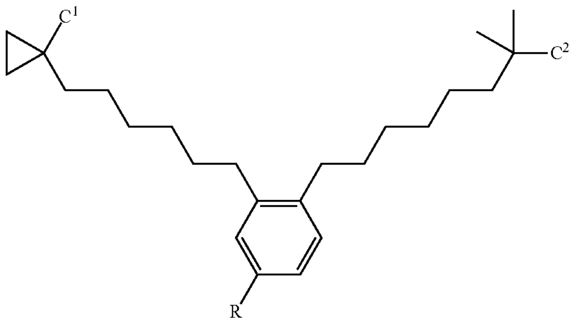 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 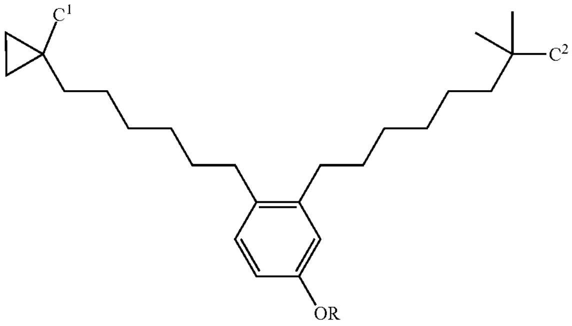 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 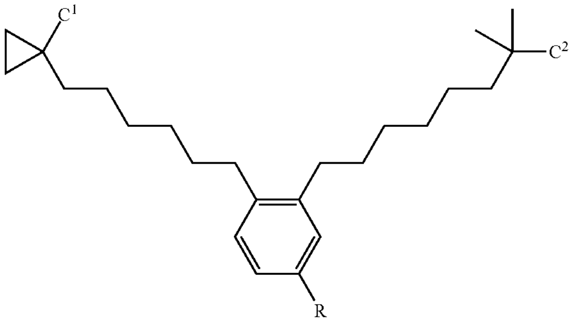 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 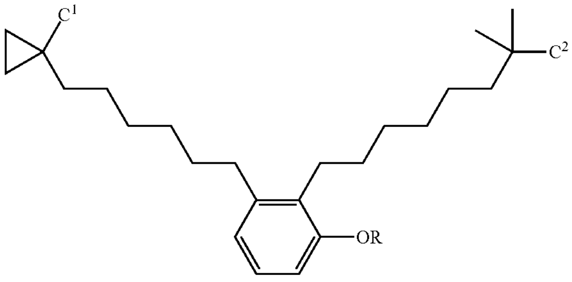 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 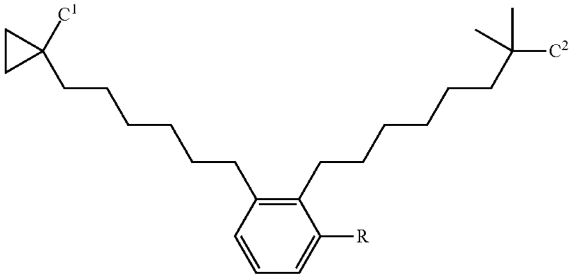 |
| wherein $C^1$ and $C^2$ = COOH; $C^1$ and $C^2$ = COOH; $C^1$ = COOH and $C^2$ = CO—CoA; $C^1$ = |

TABLE A-15-continued

| Structure |
|---|
| CO—CoA and $C^2$ = COOH; or $C^1$ and $C^2$ = CO—CoA; and wherein R = F, Cl, Br, or $CF_3$ |
| 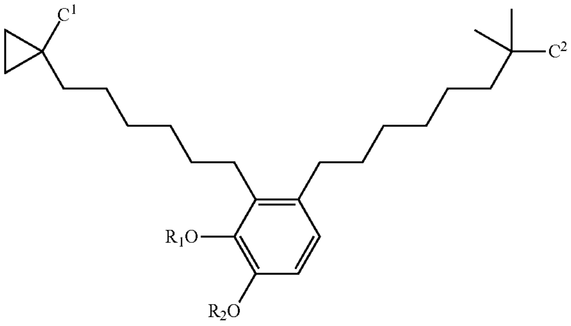 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 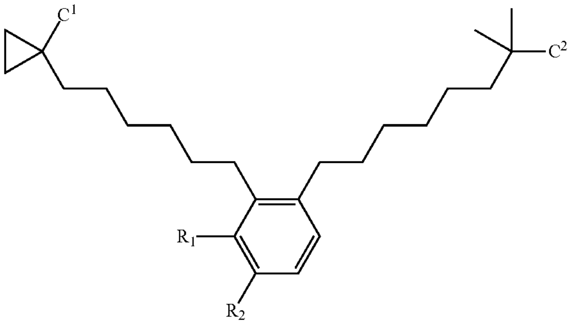 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 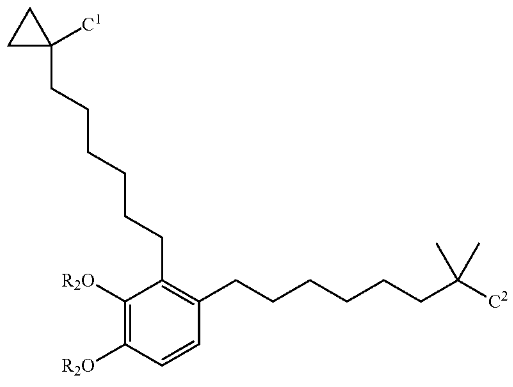 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 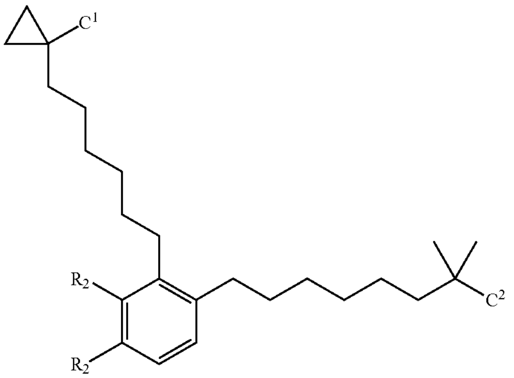 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 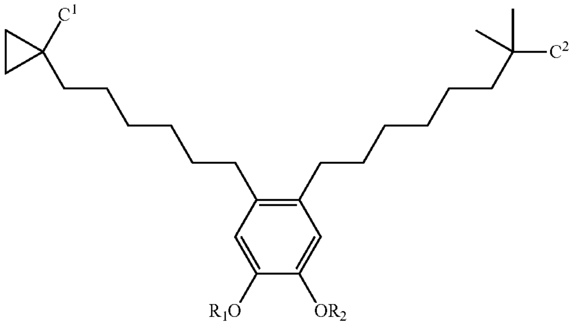 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 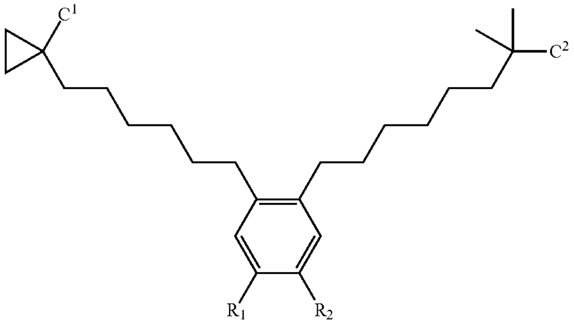 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 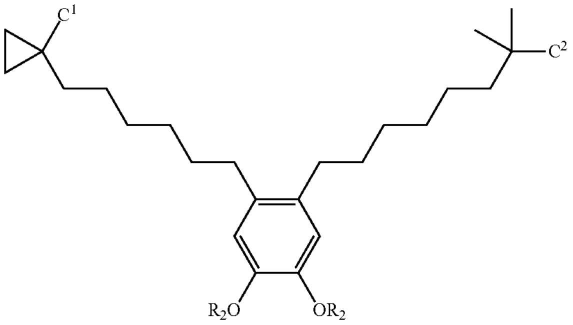 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 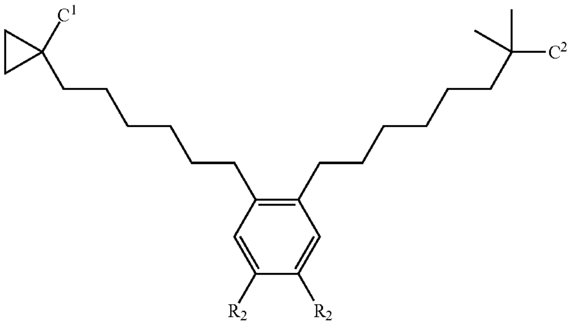 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 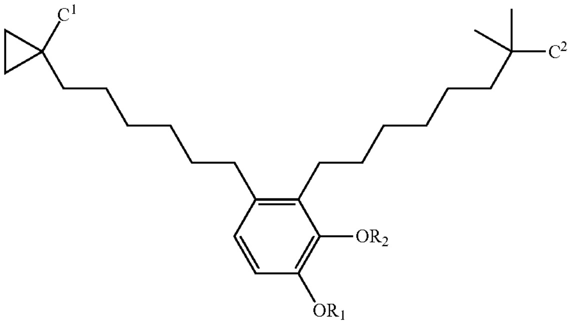 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 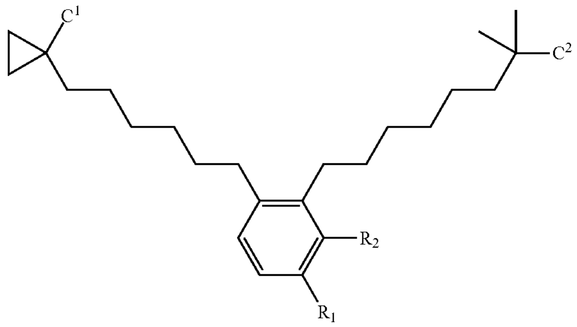 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 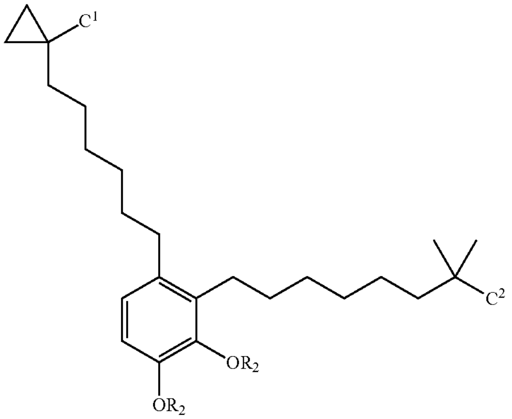 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 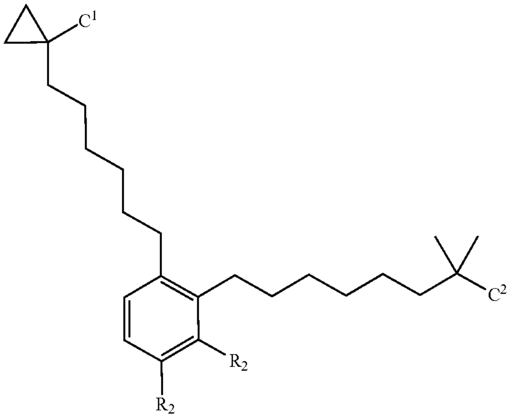 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 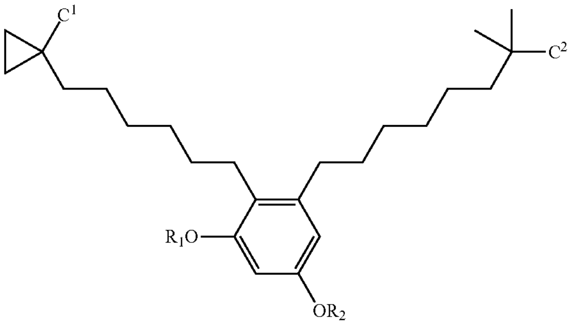 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 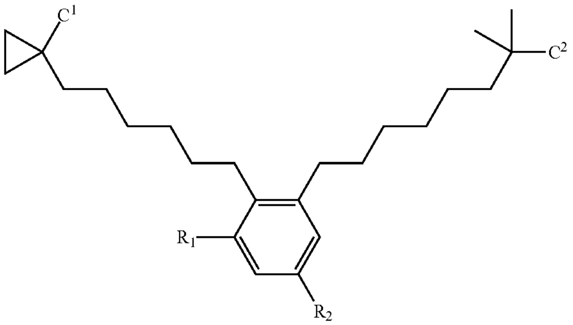 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 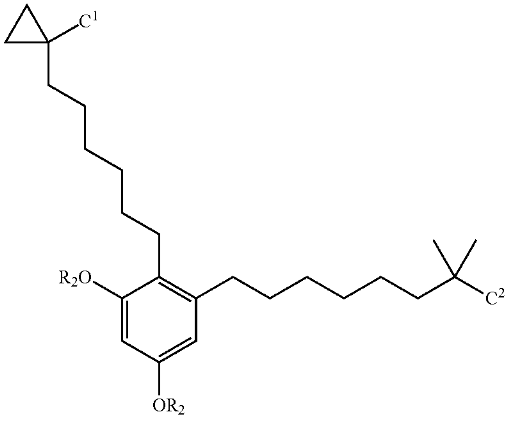 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 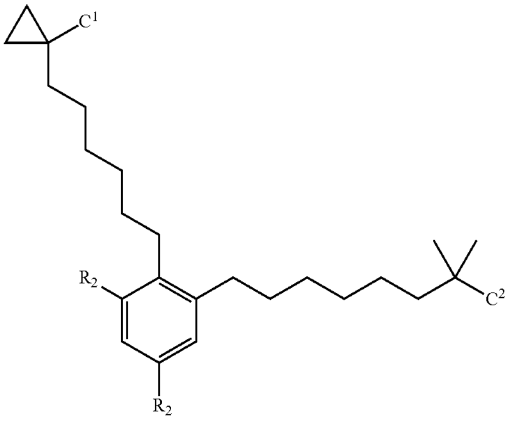 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 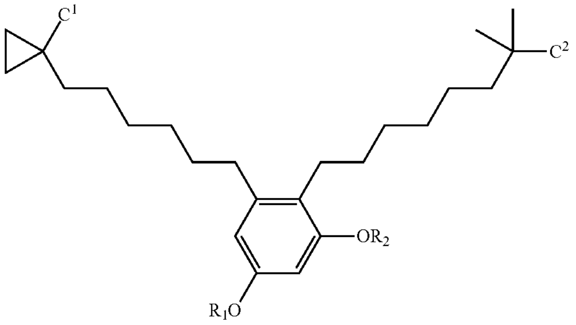 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 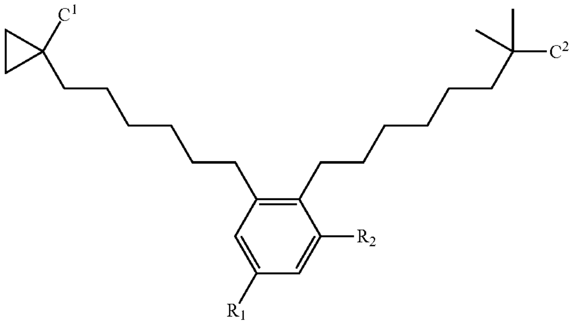 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 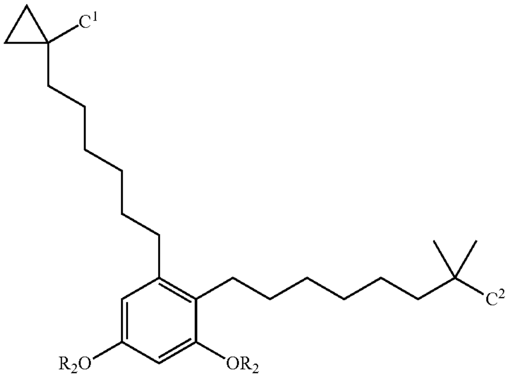 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 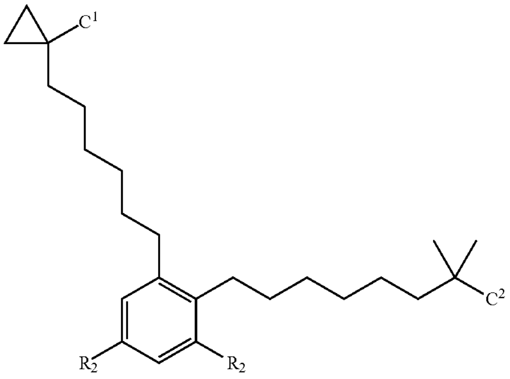 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 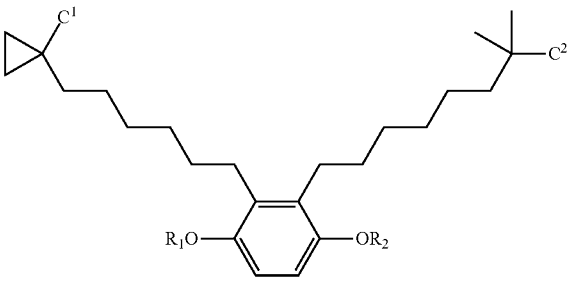 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

Structure

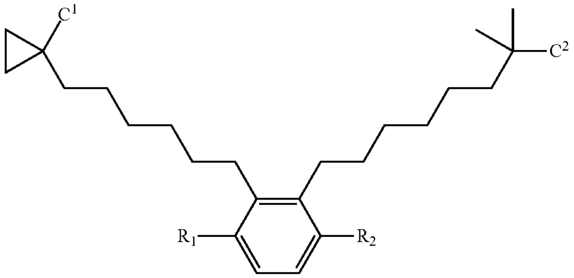

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl

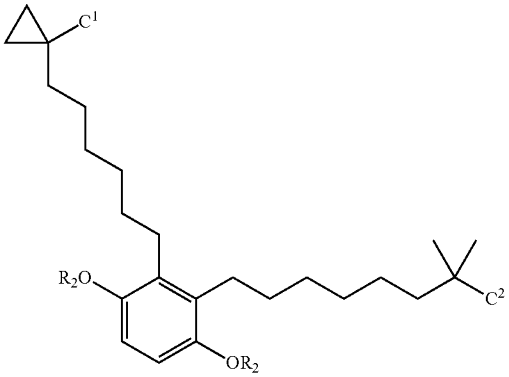

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

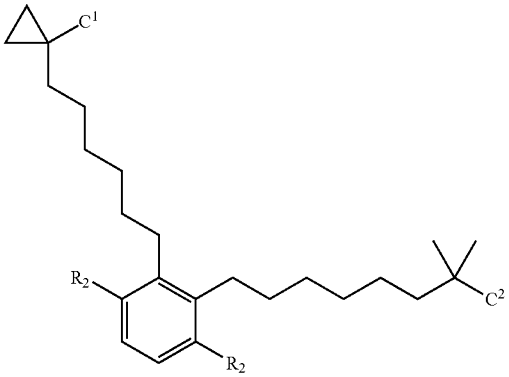

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ TABLE A-15-continued Structure

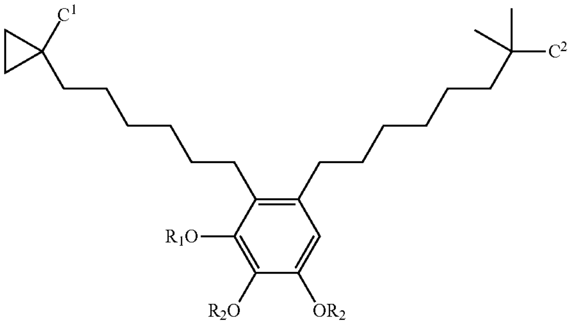

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

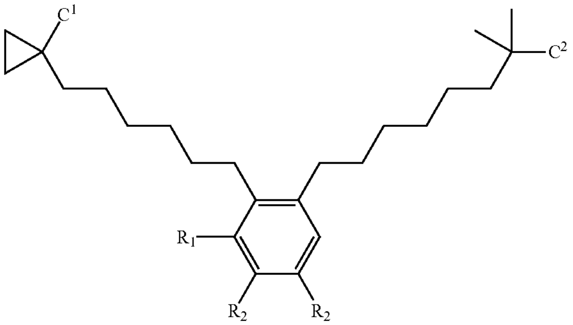

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

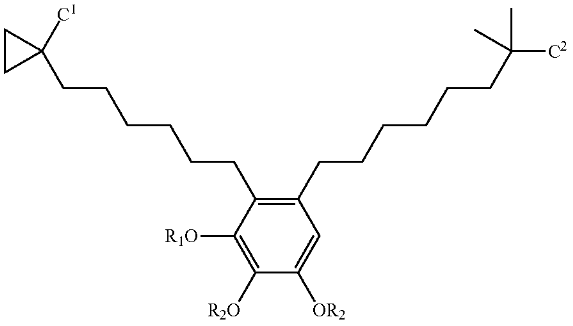

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl TABLE A-15-continued

| Structure |
|---|
| 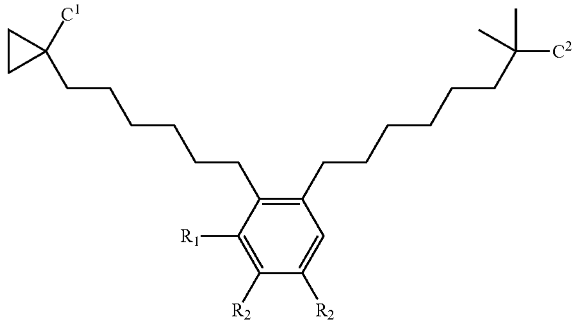 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 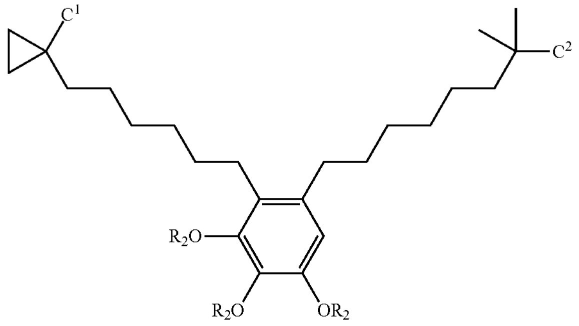 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 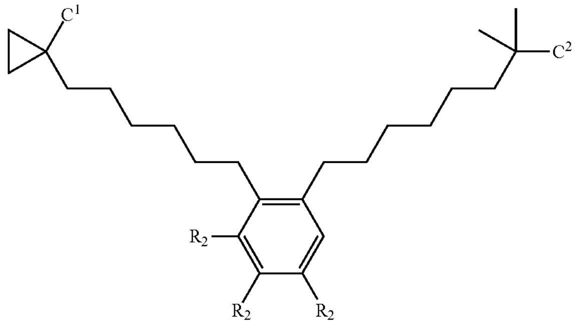 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 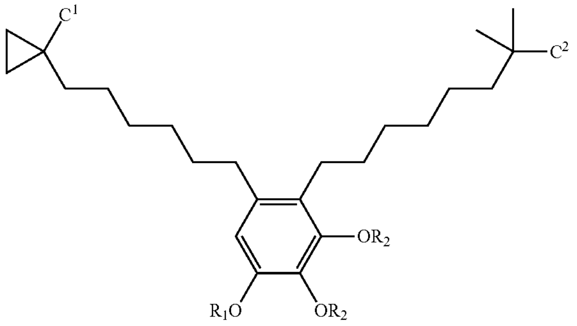 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 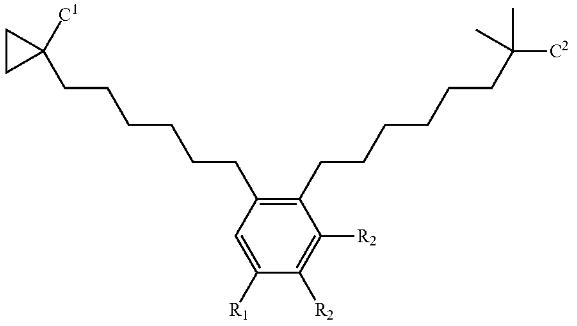 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 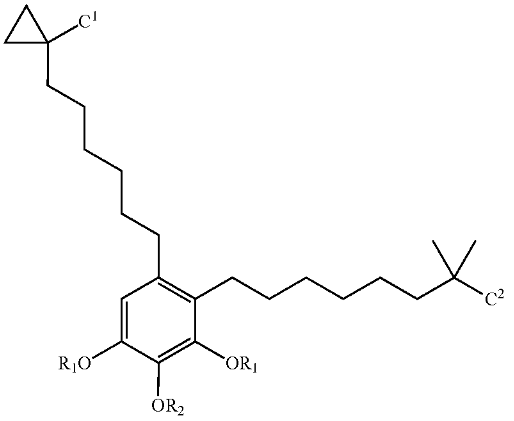 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
|---|
| 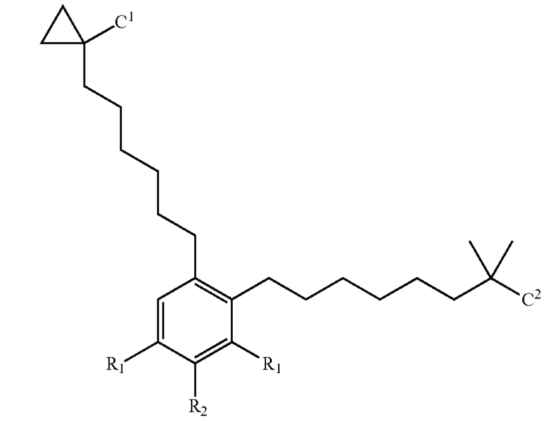 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 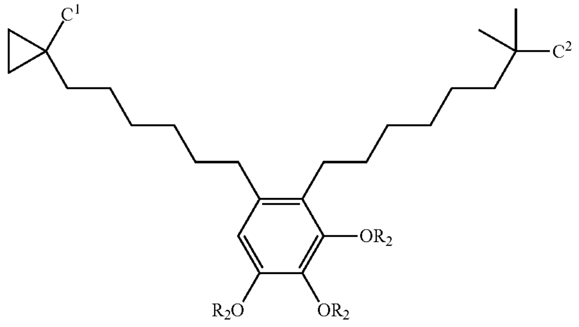 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 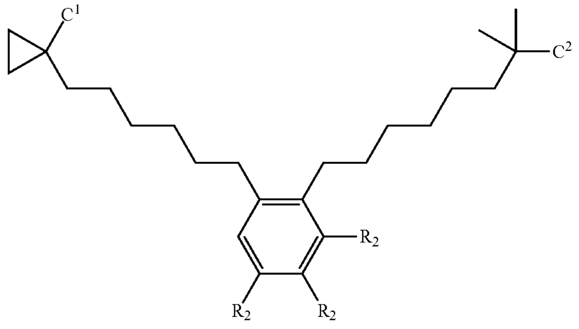 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 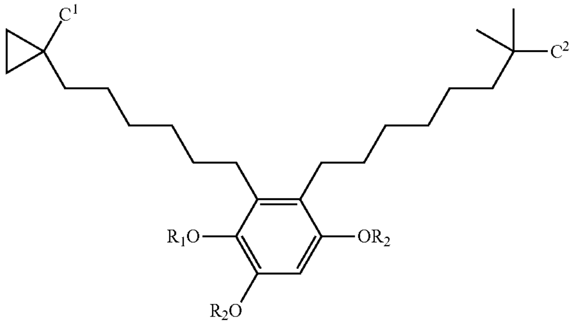 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 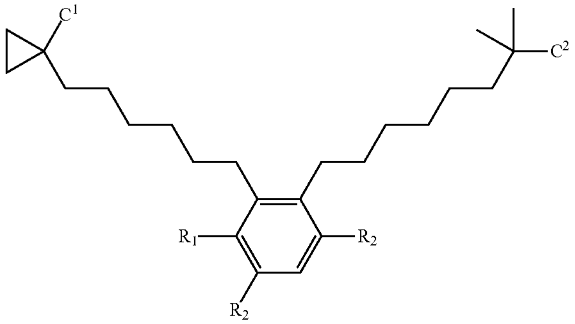 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 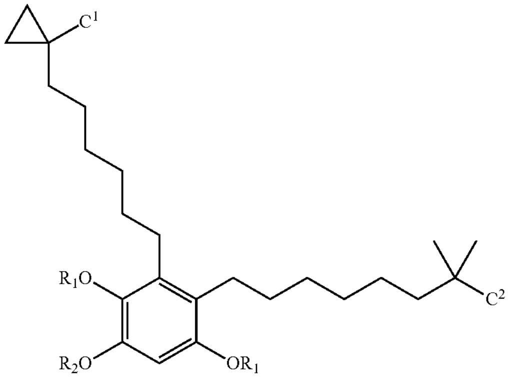 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 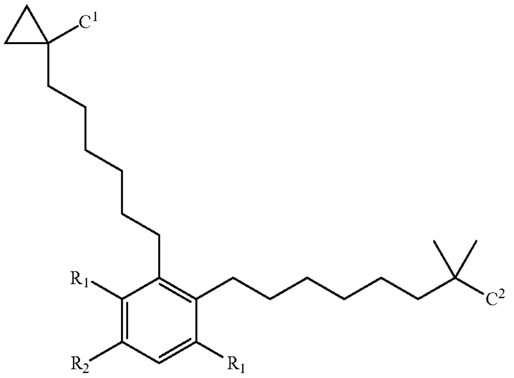 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 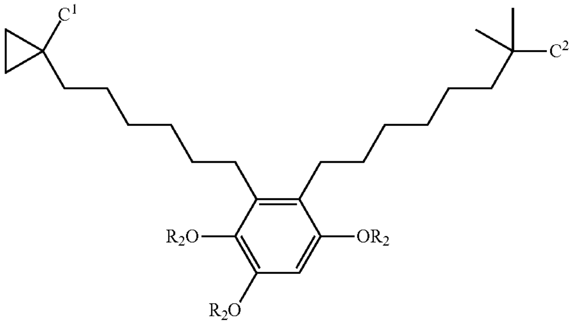 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 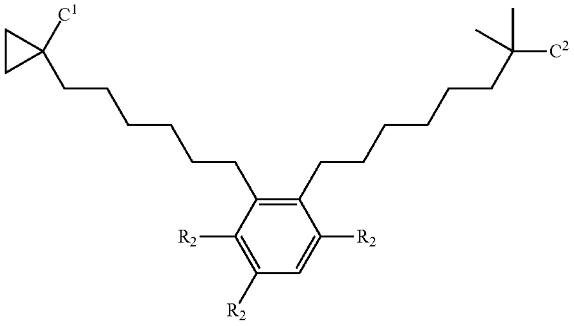 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 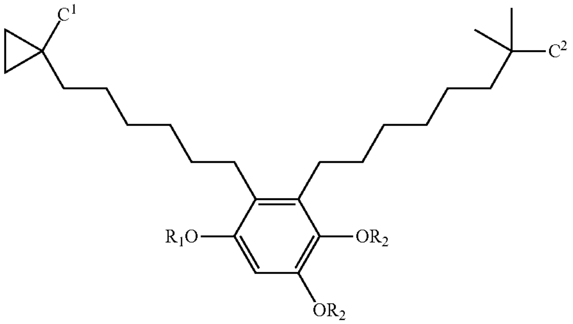 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 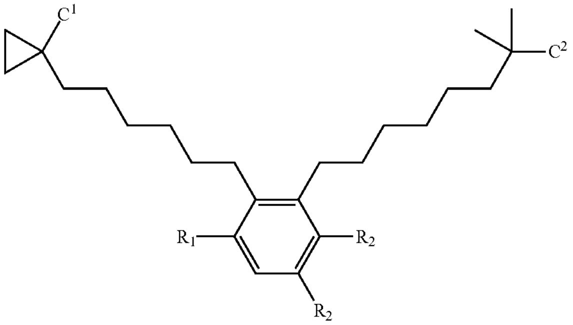 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 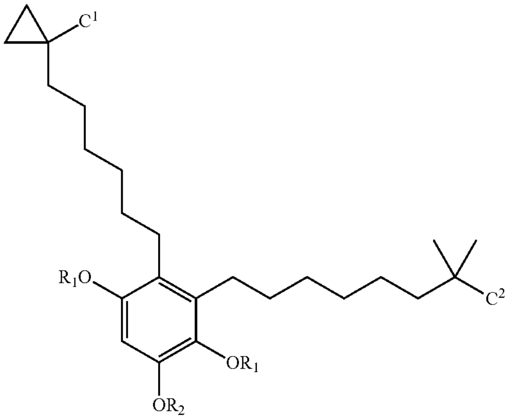 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

Structure

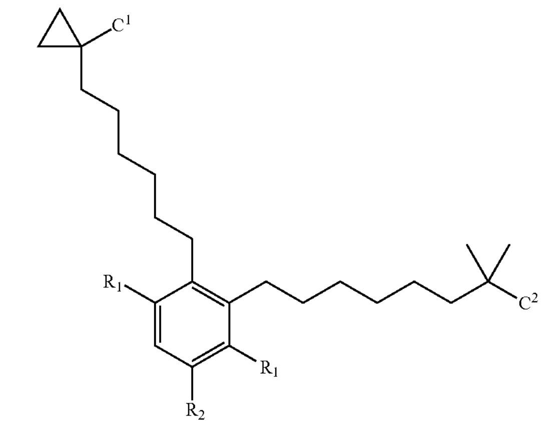

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

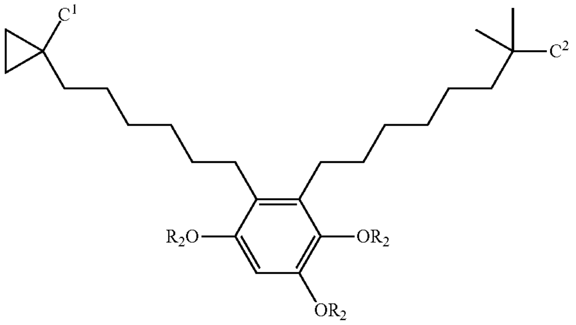

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl

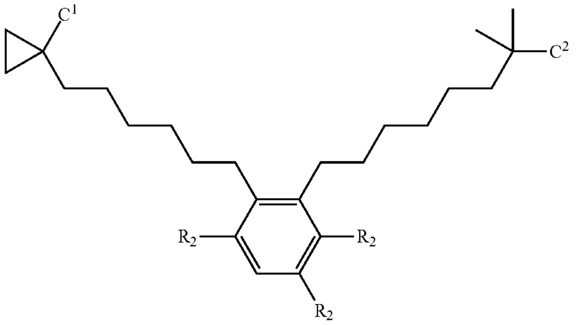

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ TABLE A-15-continued Structure

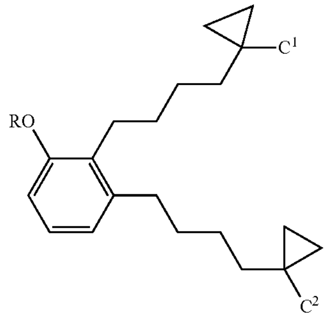

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

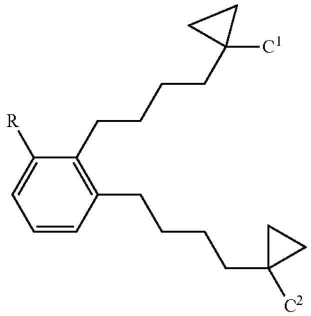

wherein $C^1$ and $C^2$ = COOH; $C^1$ and $C^2$ = COOH; $C^1$ = COOH and $C^2$ = CO—CoA; $C^1$ = CO—CoA; and $C^2$ = COOH; or $C^1$ and $C^2$ = CO—CoA; and wherein R = F, Cl, Br, or $CF_3$

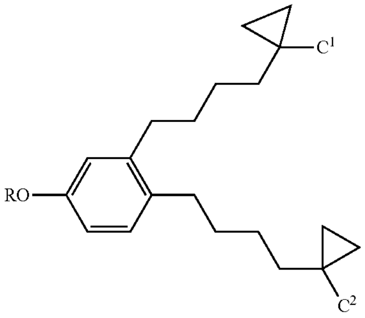

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

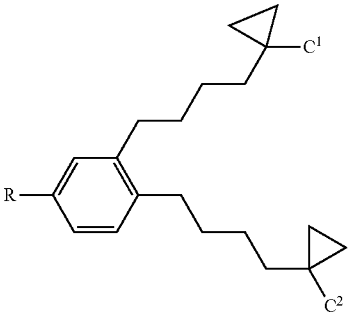

TABLE A-15-continued

| Structure |
| --- |
| wherein $C^1$ and $C^2$ = COOH; $C^1$ and $C^2$ = COOH; $C^1$ = COOH and $C^2$ = CO—CoA; $C^1$ = CO—CoA; and $C^2$ = COOH; or $C^1$ and $C^2$ = CO—CoA; and wherein R = F, Cl, Br, or $CF_3$ |
| 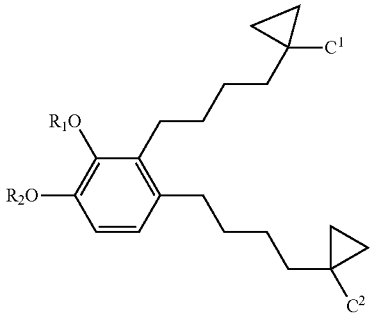 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 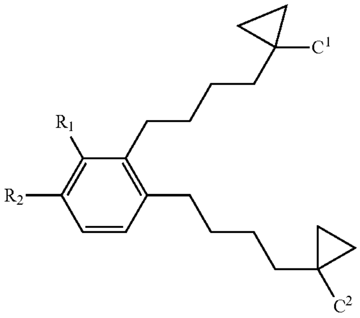 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 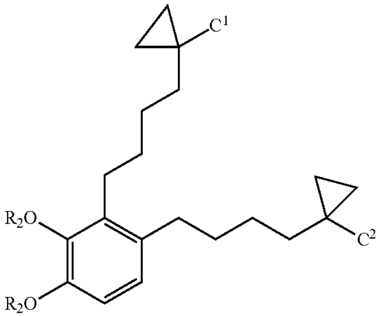 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 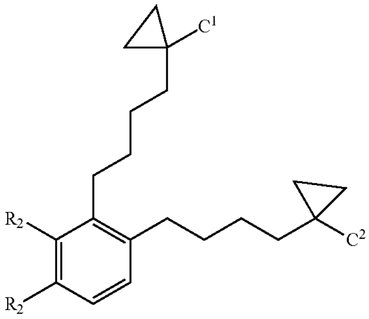 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 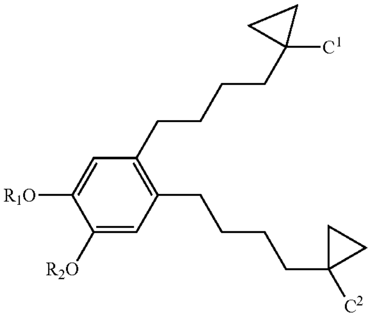 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 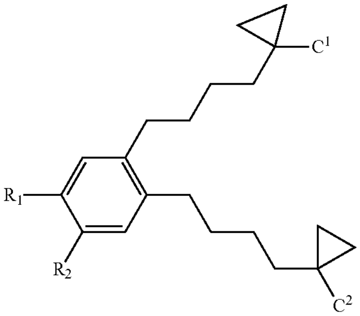 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 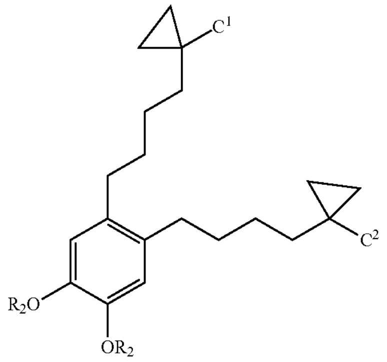 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 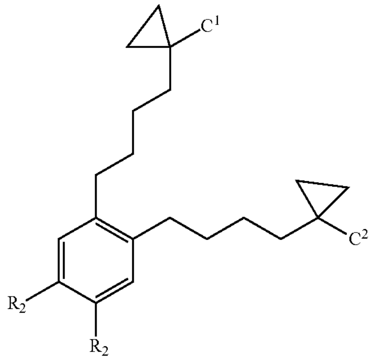 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 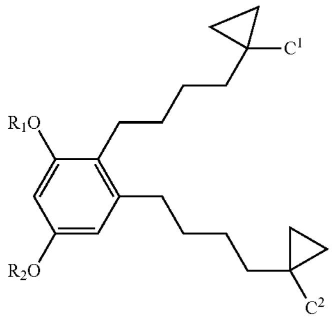 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 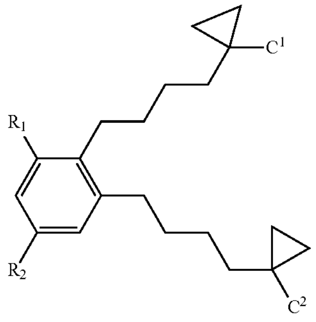 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 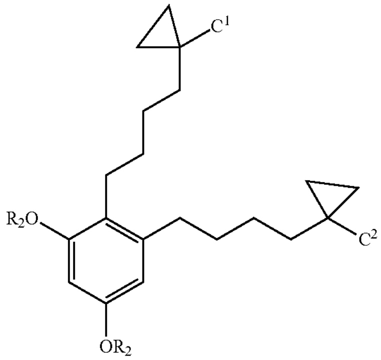 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 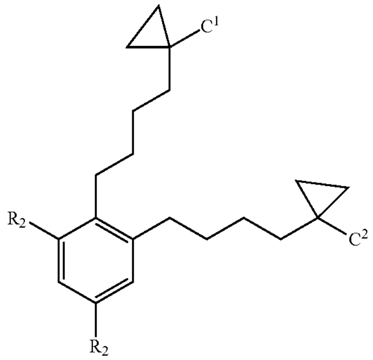 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

| Structure |
| --- |
| 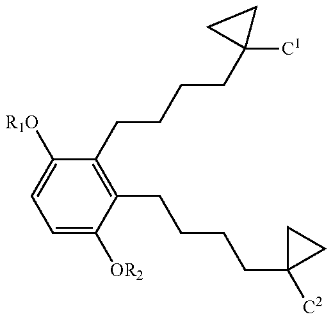 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 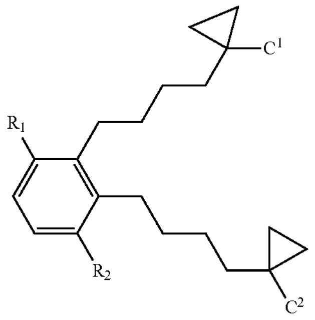 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 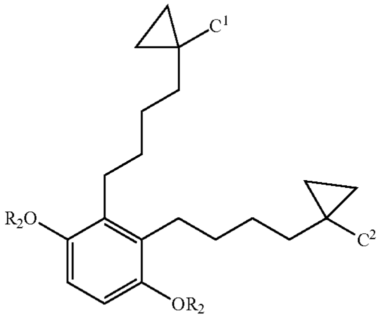 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

| Structure |
| --- |
| 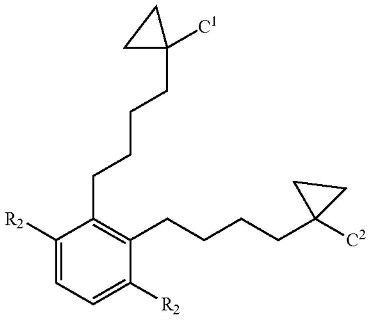 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 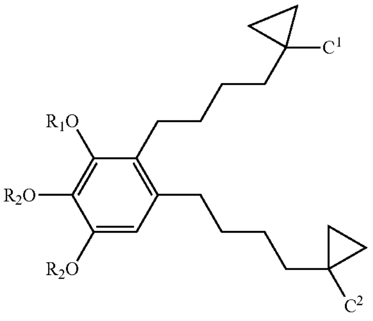 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 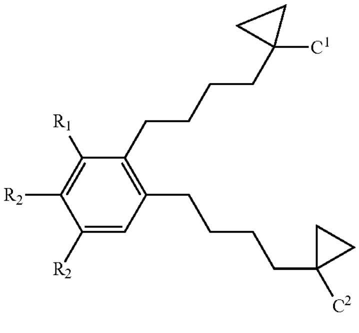 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 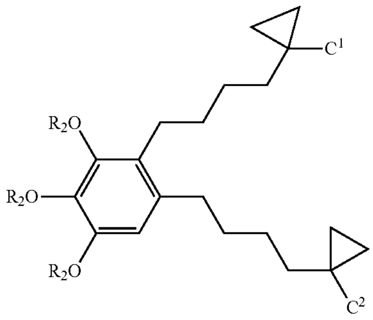 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 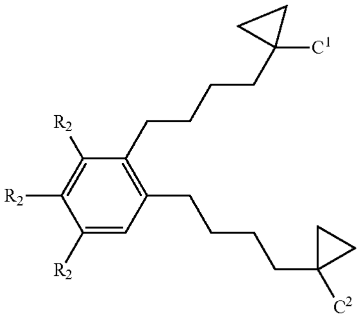 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 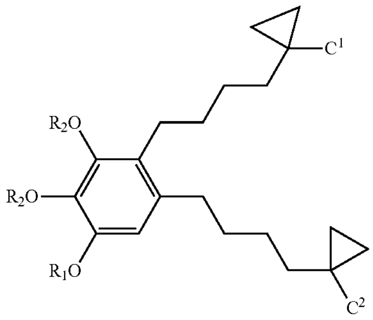 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 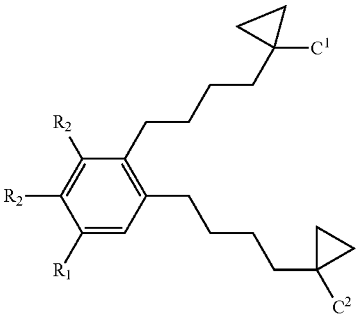 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 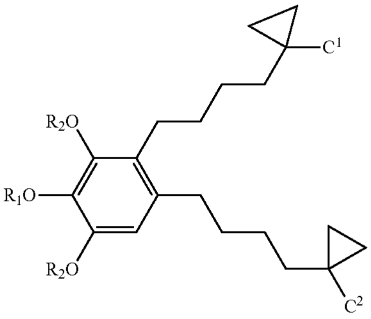 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 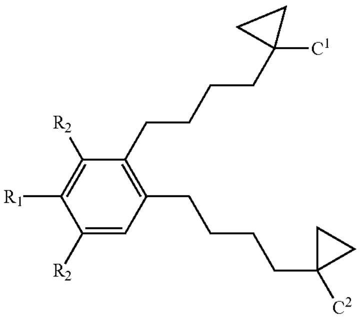 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 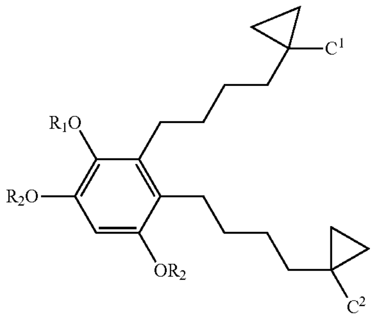 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 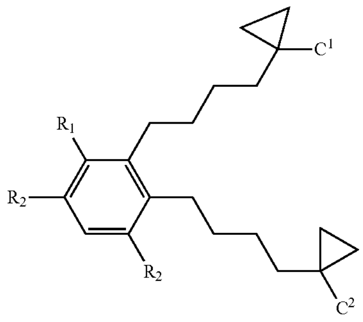 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 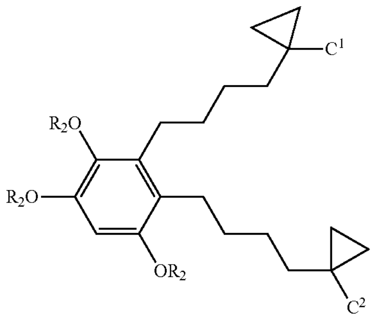 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 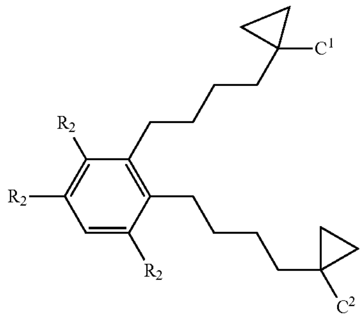 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 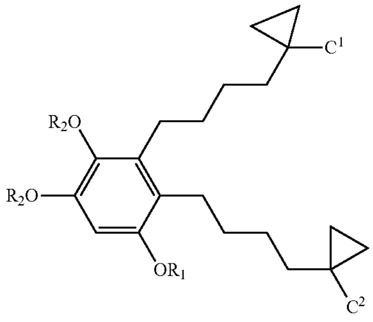 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R= H and each $R_2$ is independently a (C1-C4)alkyl; or each $R_2$ is H and $R_1$ = (C1-C4)alkyl |
| 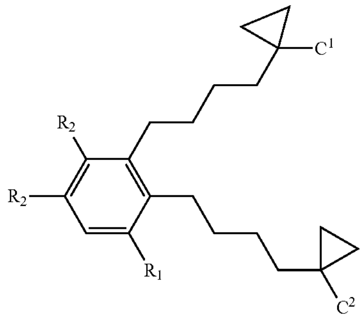 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 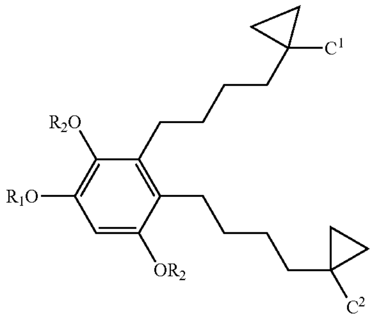 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R= H and each $R_2$ is independently a (C1-C4)alkyl; or each $R_2$ is H and $R_1$ = (C1-C4)alkyl |
| 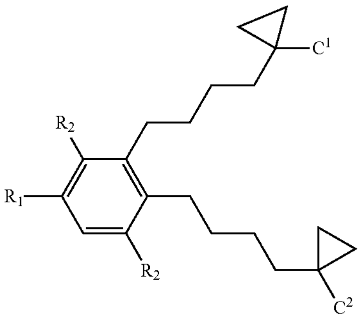 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 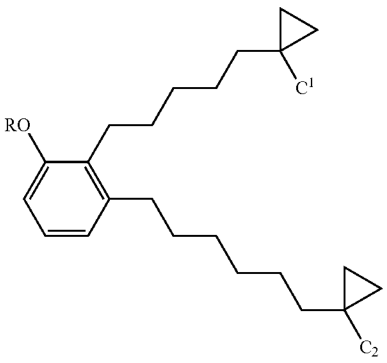 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 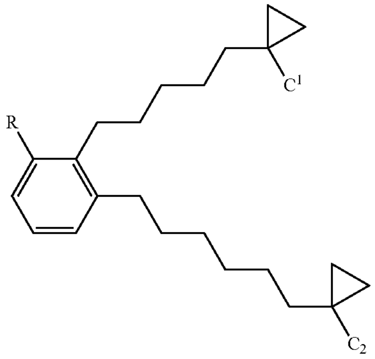 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 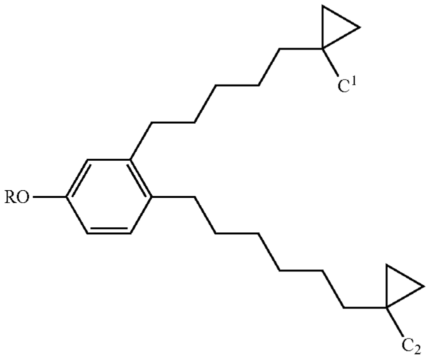 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 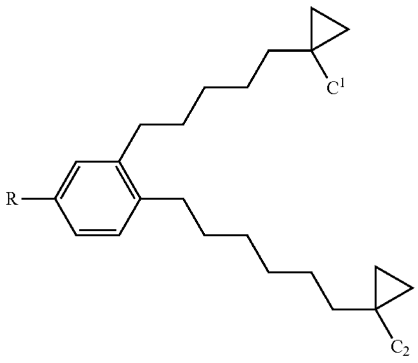 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 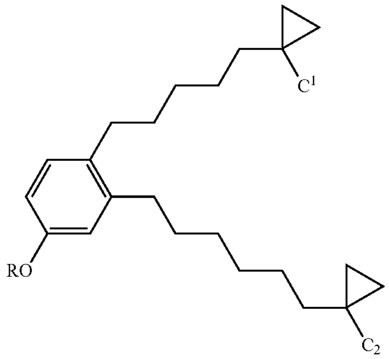 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 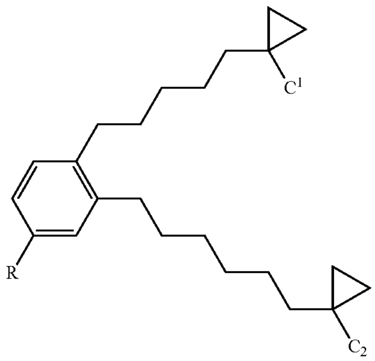 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 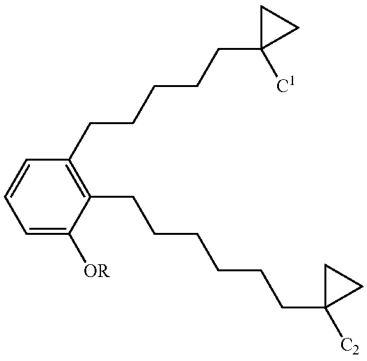 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
|---|
| 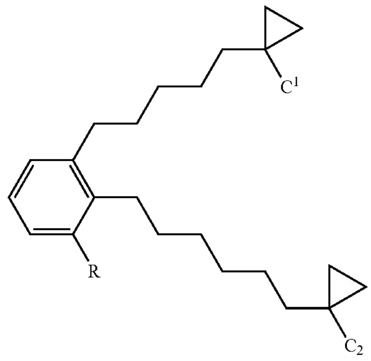 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 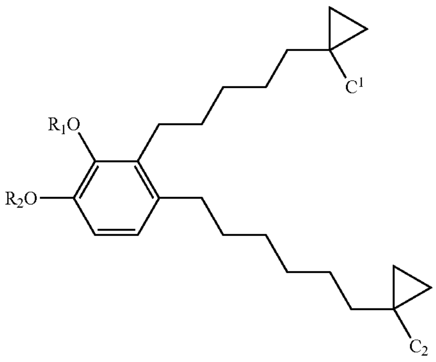 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 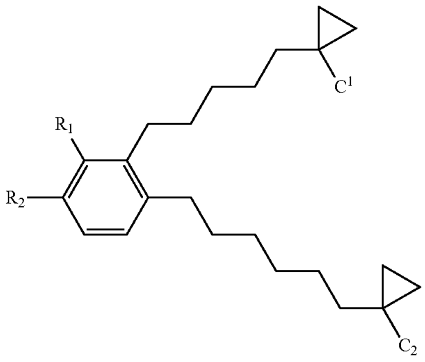 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 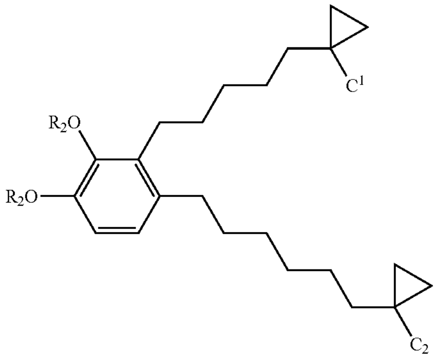 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 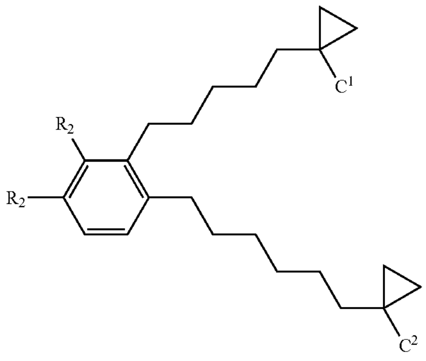 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 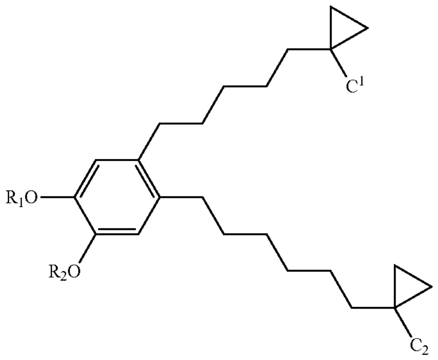 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 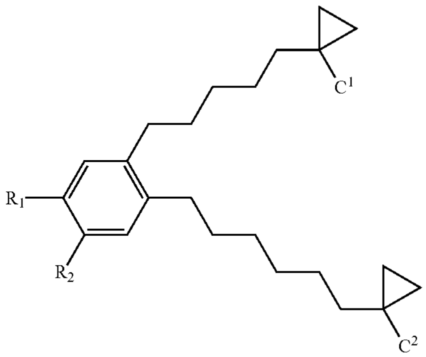 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 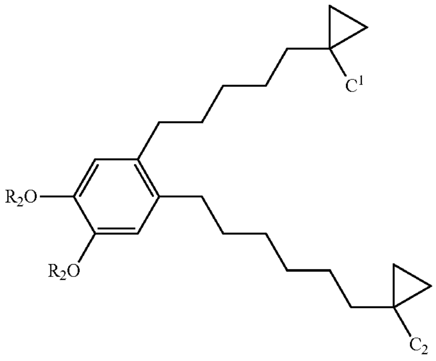 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 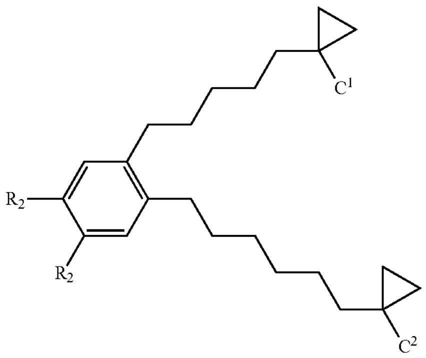 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 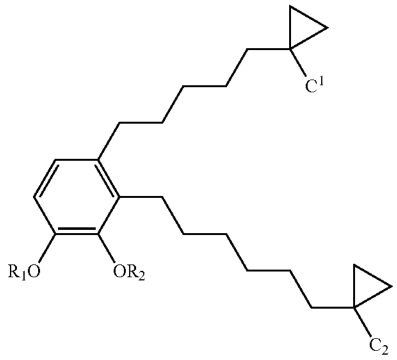 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 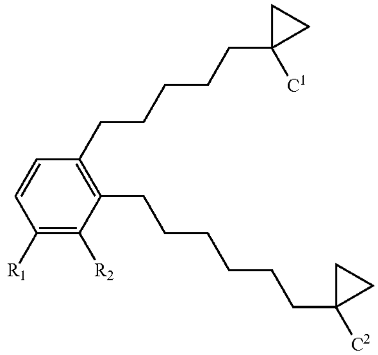 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 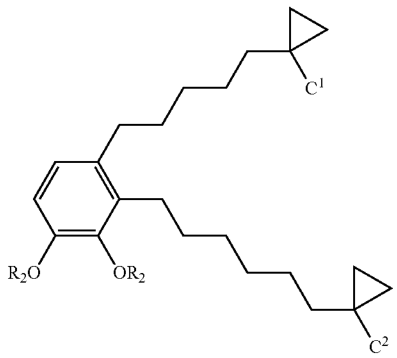 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 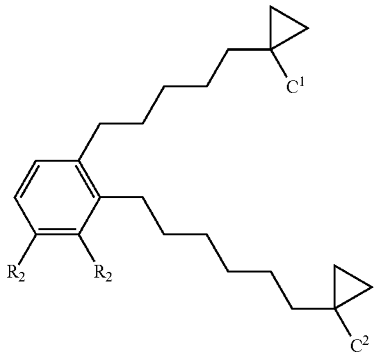 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 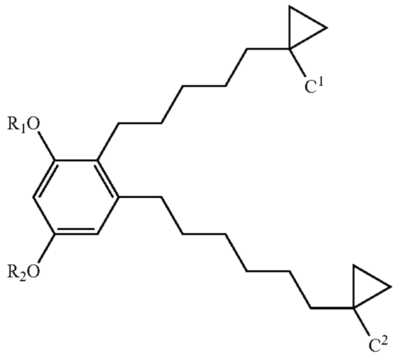 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 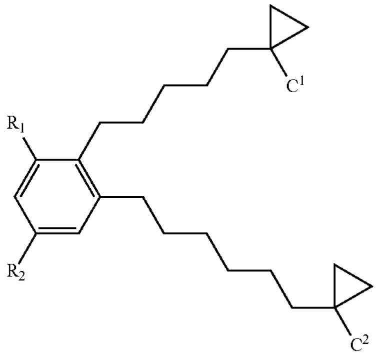 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 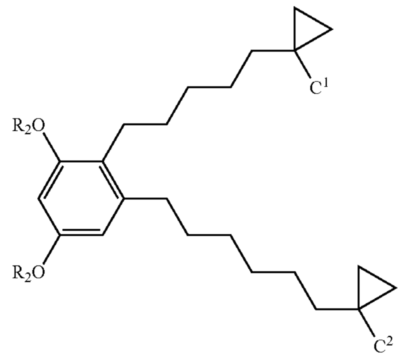 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 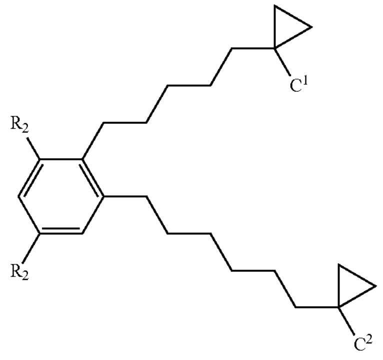 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 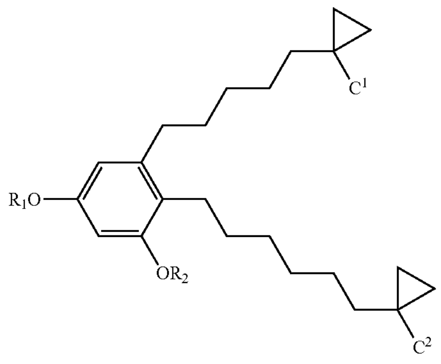 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 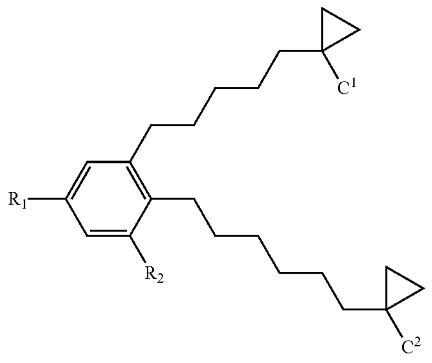 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 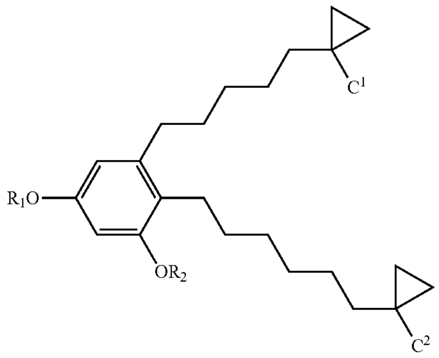 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 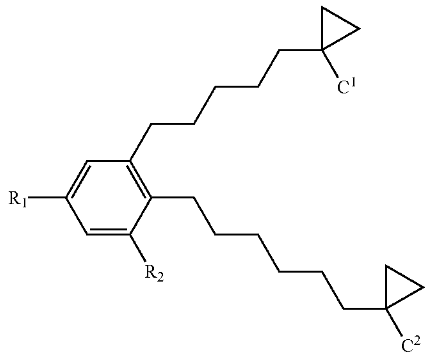 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 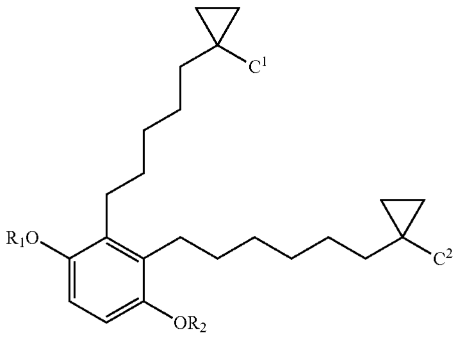 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 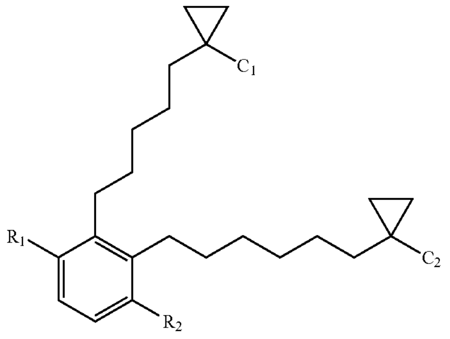 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 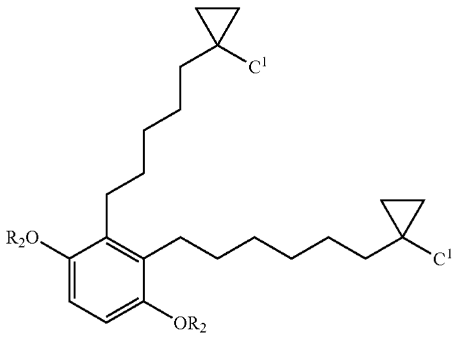 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 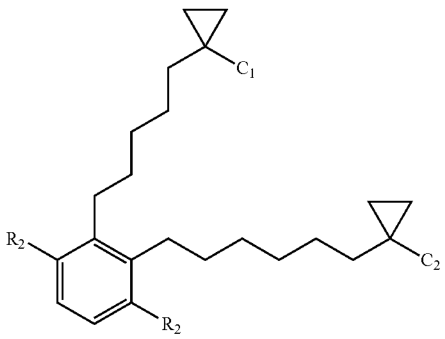 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 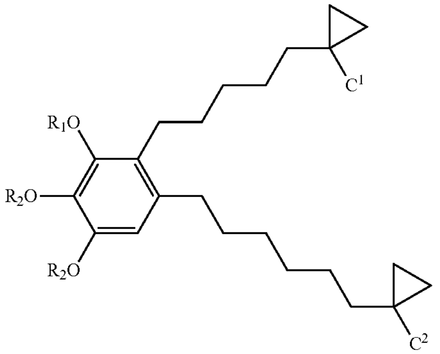 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 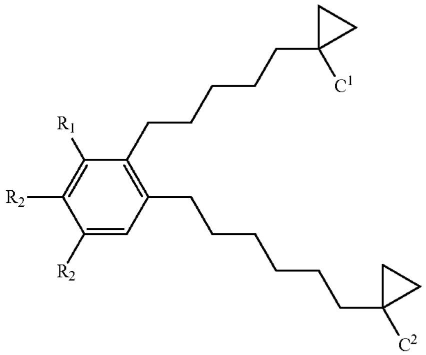 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 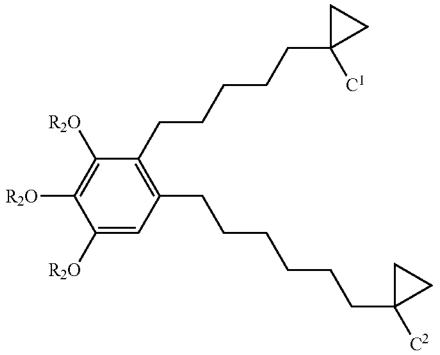 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 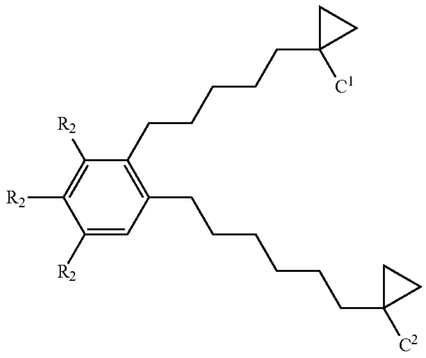 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 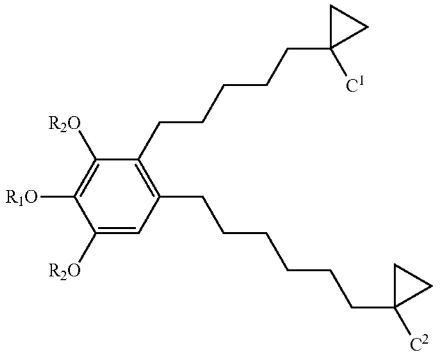 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 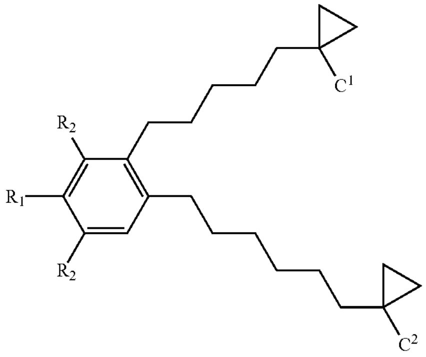 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 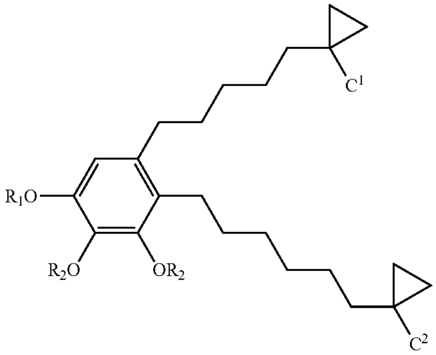 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 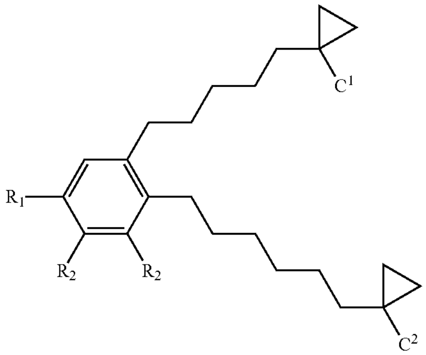 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 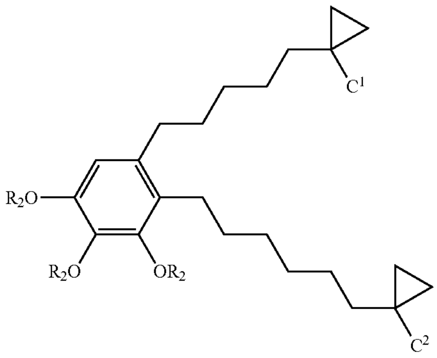 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 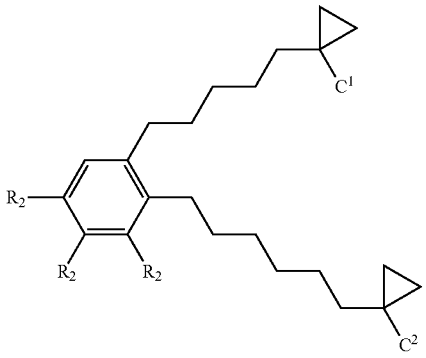 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 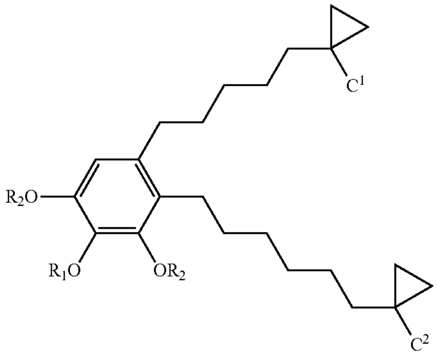 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 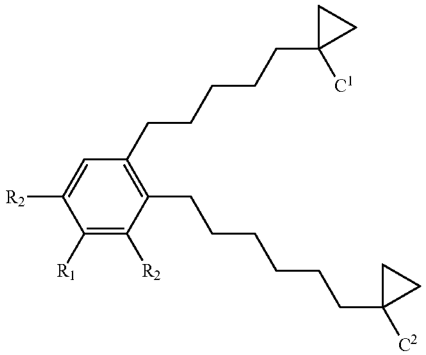 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 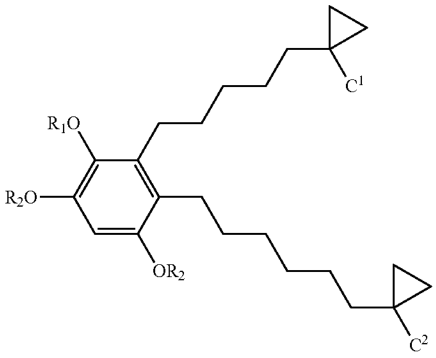 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 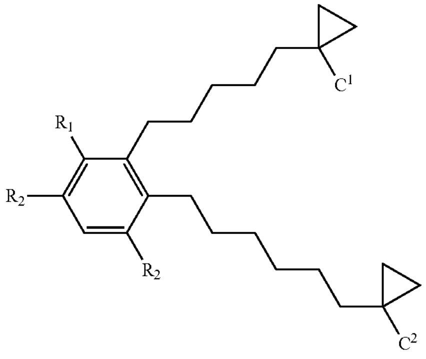 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 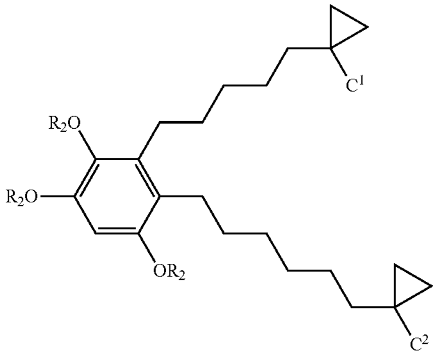 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 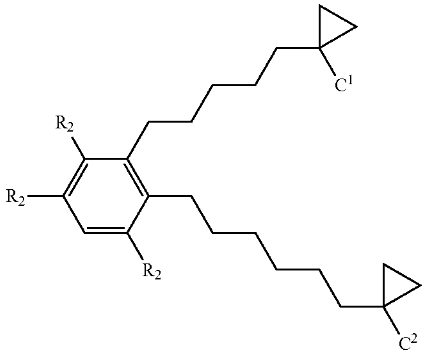 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 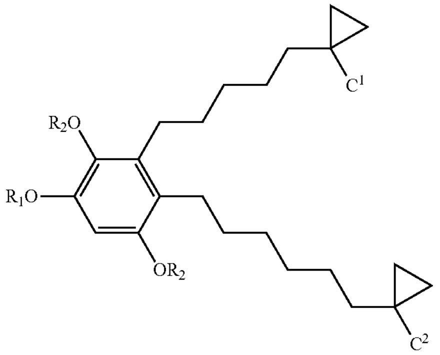 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 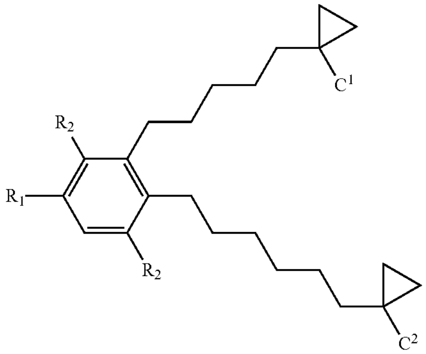 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 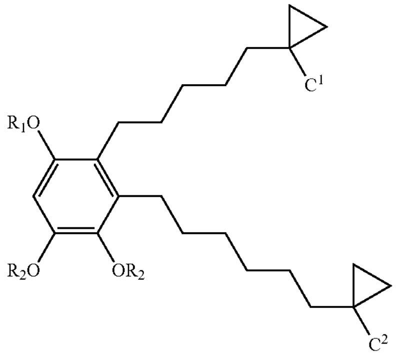 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 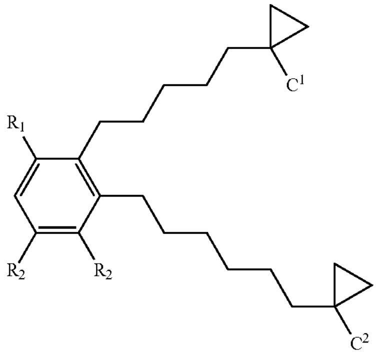 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 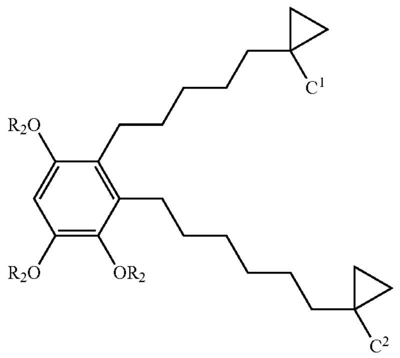 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 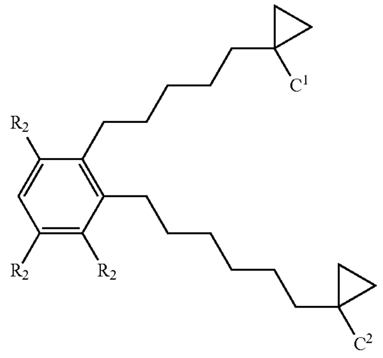 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 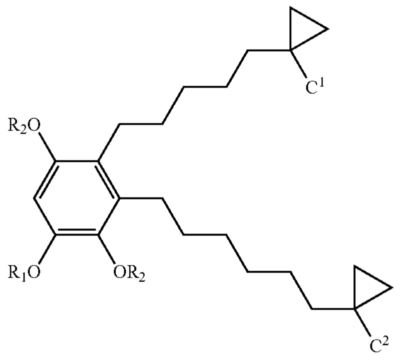 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 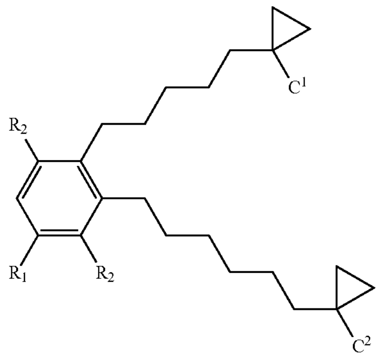 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 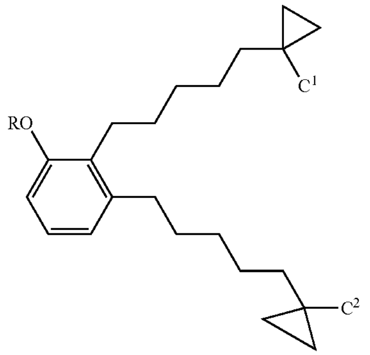 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 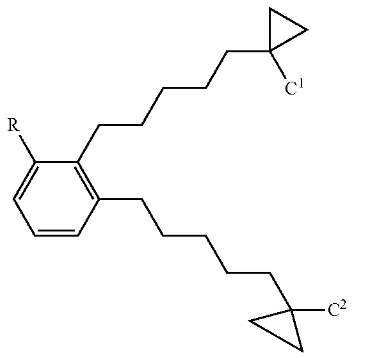 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
|---|
| 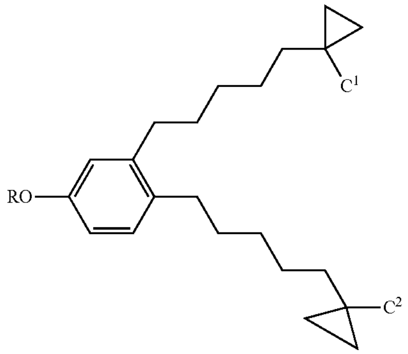 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 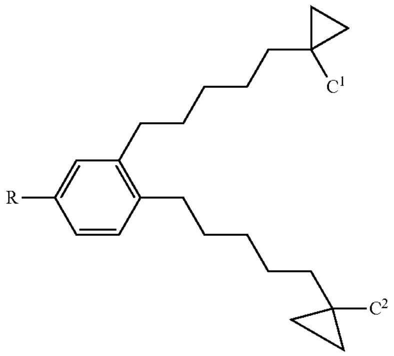 wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 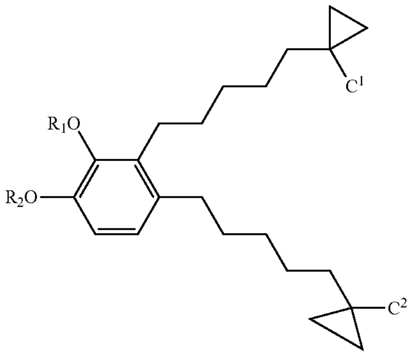 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_1$ = (C1-C4)alkyl; or $R_2$ = H and $R_1$ = (C1-C4)alkyl |

TABLE A-15-continued

| Structure |
|---|
| 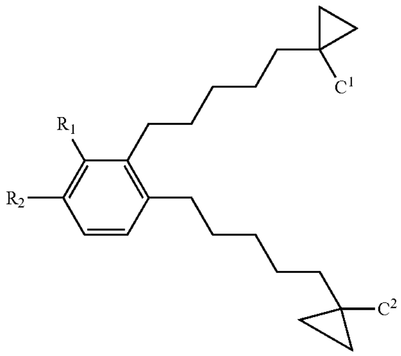 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 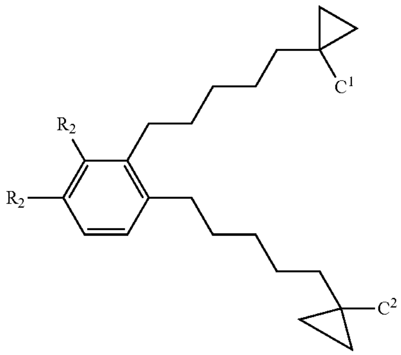 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 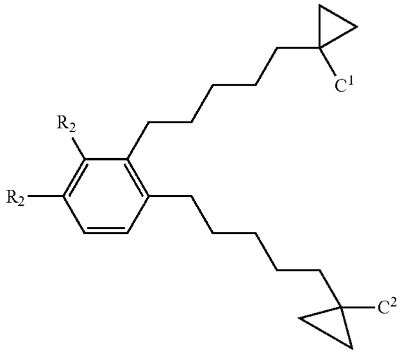 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 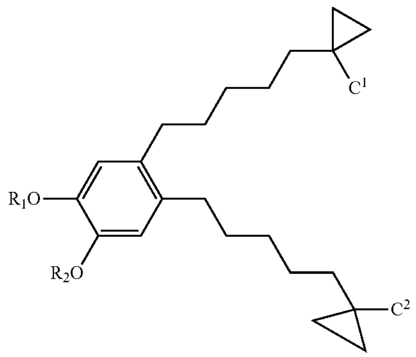 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 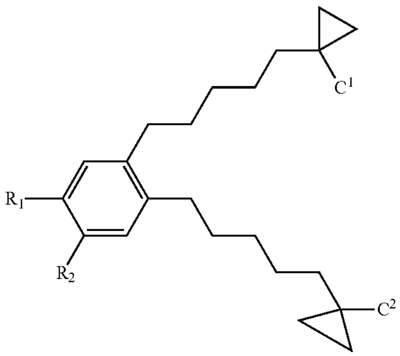 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 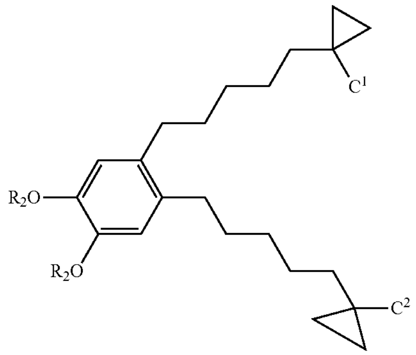 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 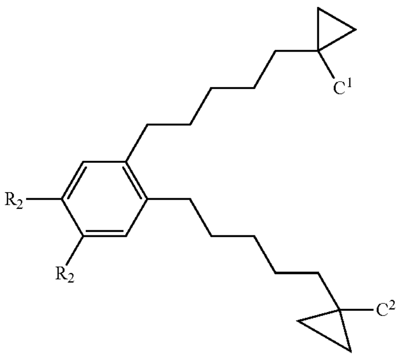 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 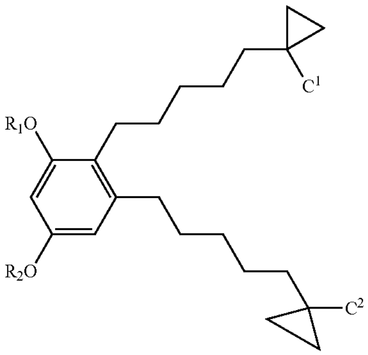 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 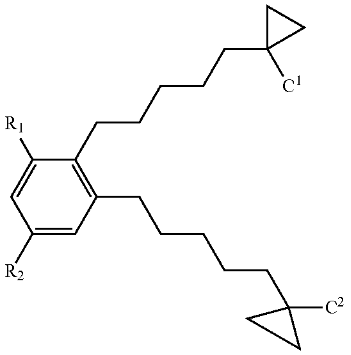 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
|---|
| 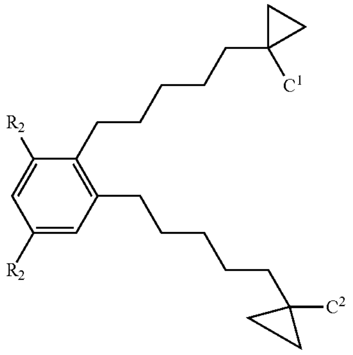 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 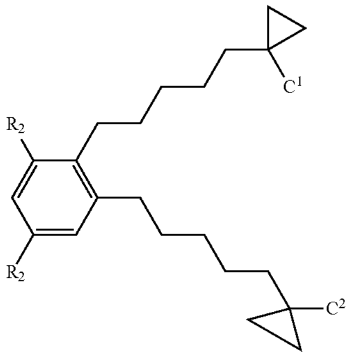 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 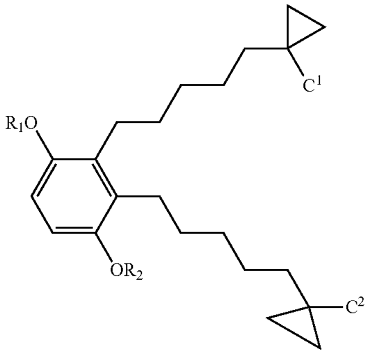 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 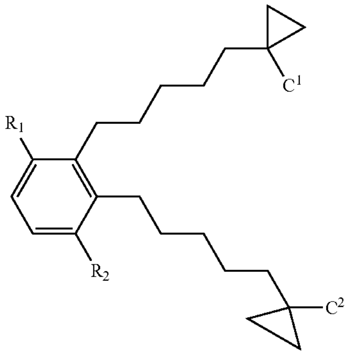 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 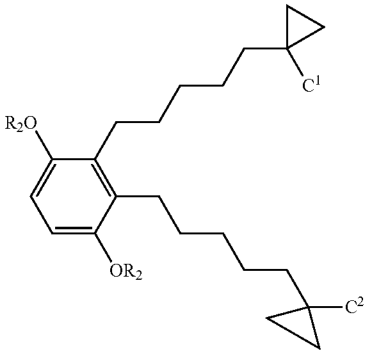 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 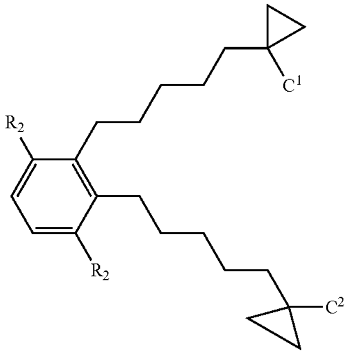 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 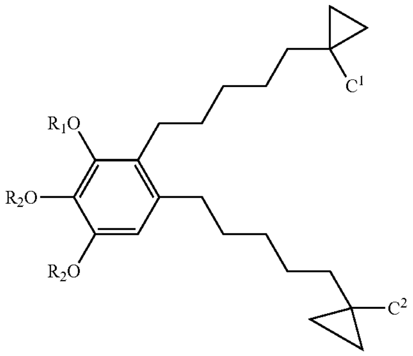 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 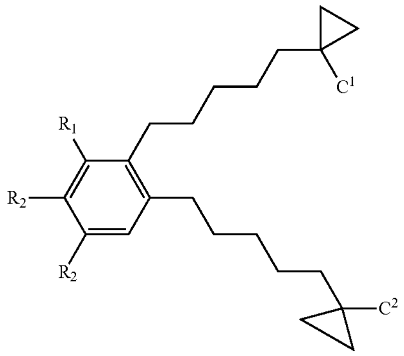 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alky |
| 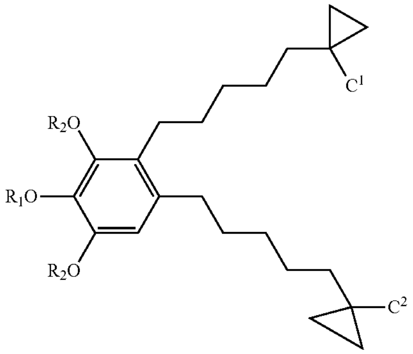 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 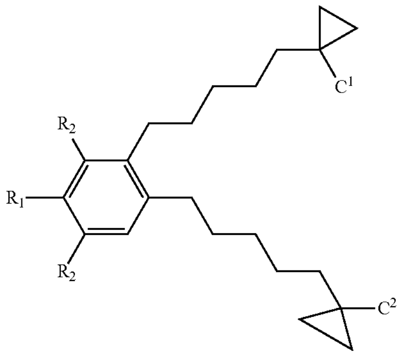 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 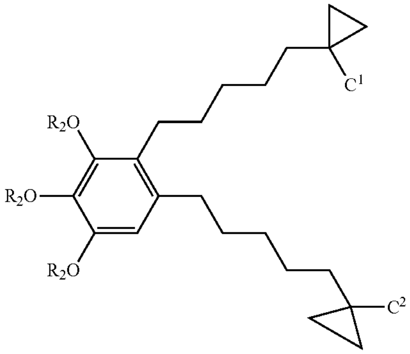 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 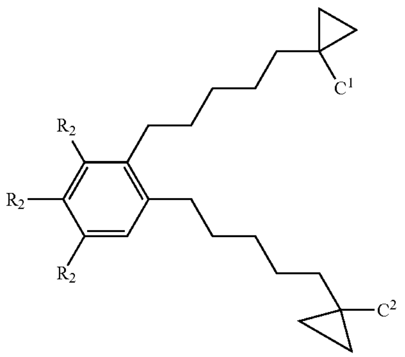 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 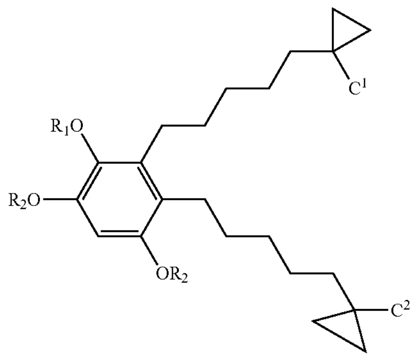 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 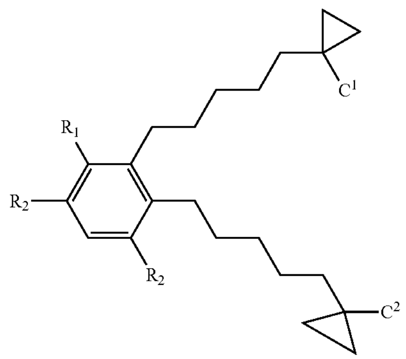 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 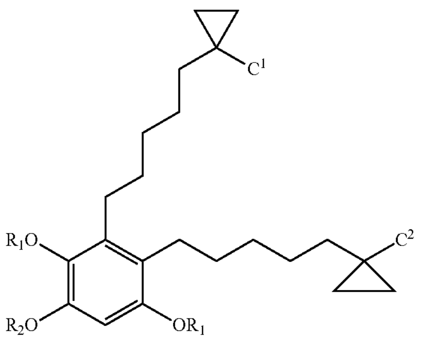 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 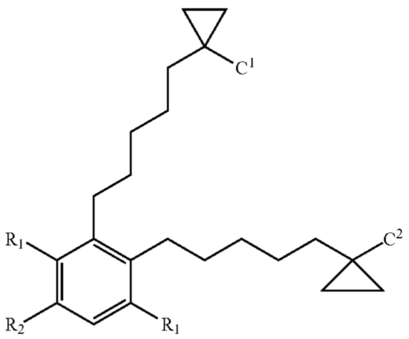 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 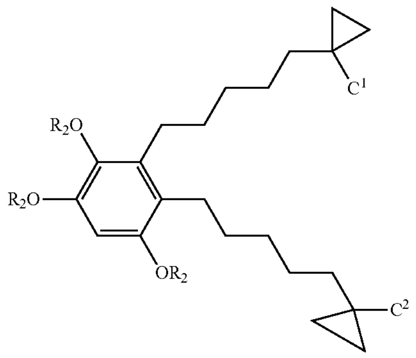 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 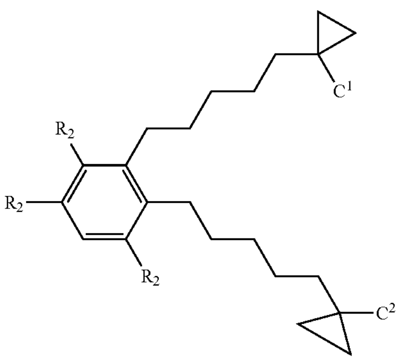 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

Structure

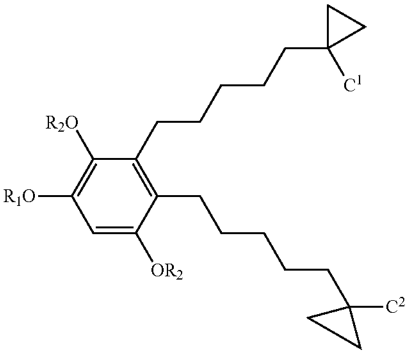

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

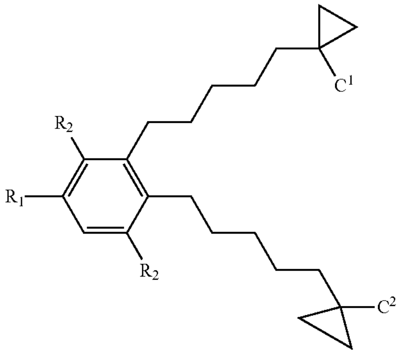

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl

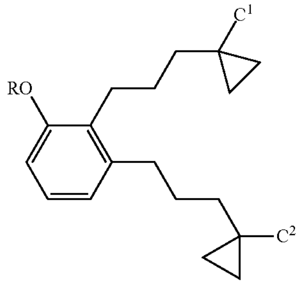

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl TABLE A-15-continued Structure

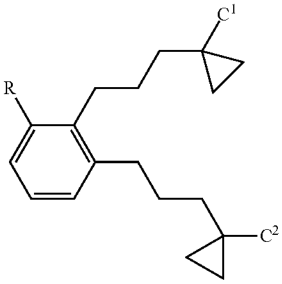

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$

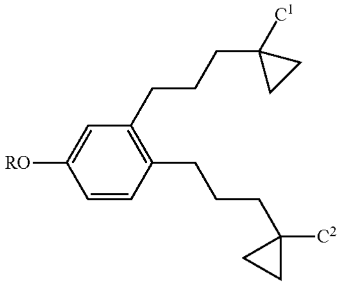

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

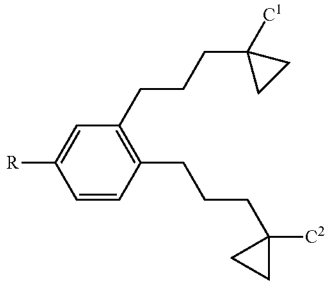

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$

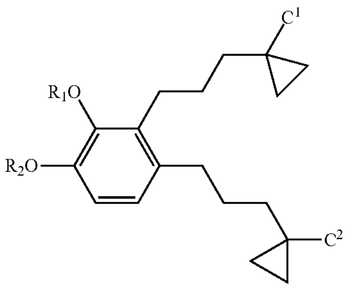

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl TABLE A-15-continued

| Structure |
| --- |
| 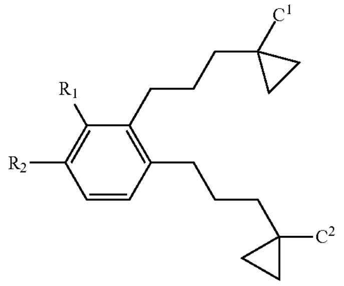 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 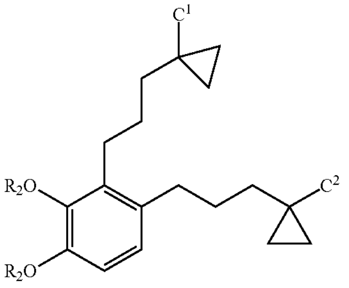 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 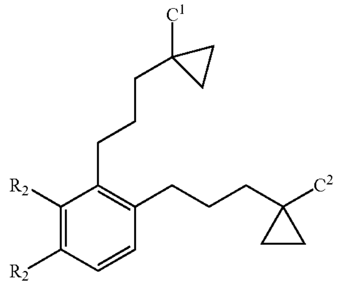 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 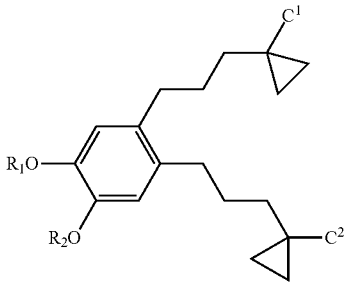 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and |

TABLE A-15-continued

| Structure |
| --- |
| $R_2$ = (C1-C4)alkyl; or $R_2$ = H and $R_1$ = (C1-C4)alkyl |
| 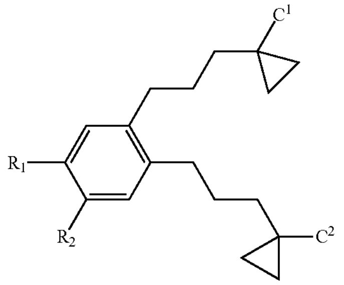 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 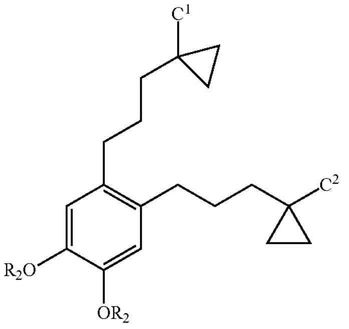 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 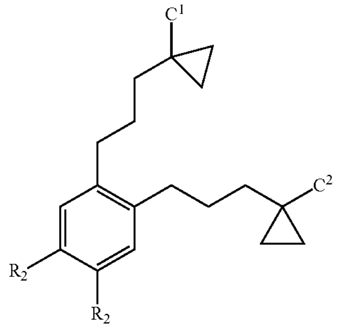 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 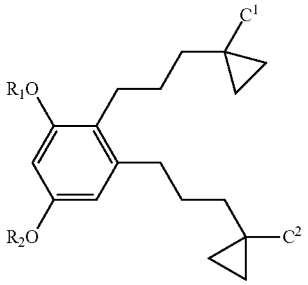 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 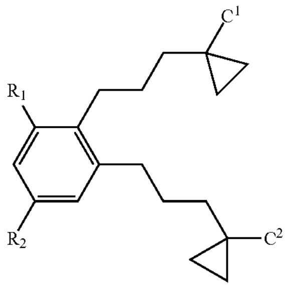 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 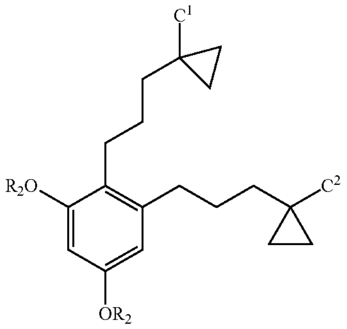 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 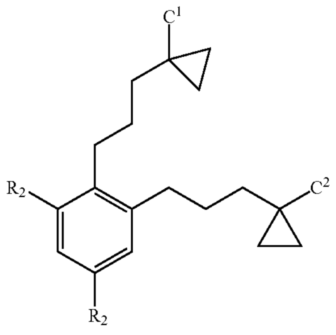 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 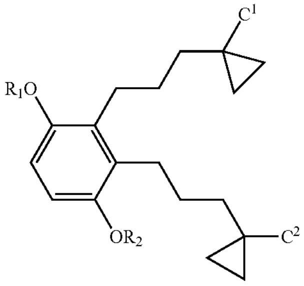 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 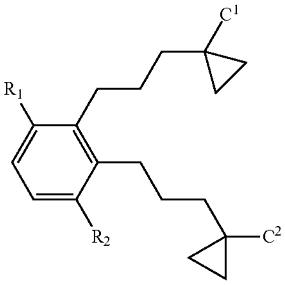 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 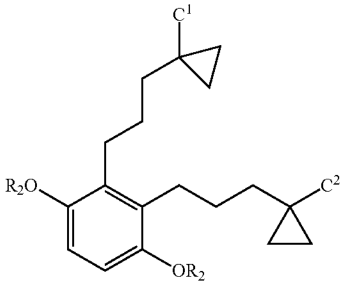 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 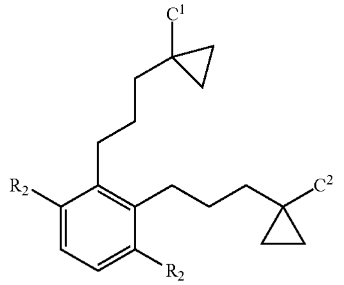 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 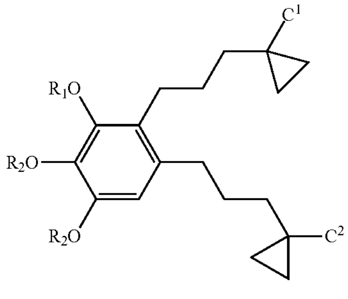 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 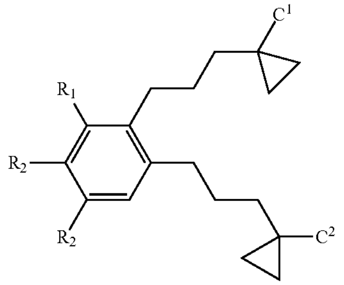 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 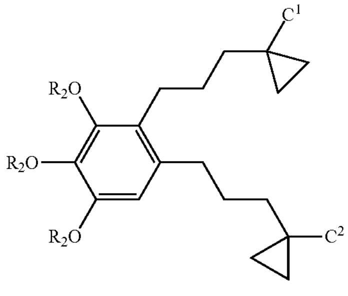 |
| wherein $C^1$ and $C^2$ = COOH; $C^1$ = COOH and $C^2$ = CO—CoA; $C^1$ = CO—CoA and $C^2$ = COOH; or |

TABLE A-15-continued

| Structure |
|---|
| $C^1$ and $C^2$ = CO—CoA; and wherein each $R_2$ is independently a (C1-C4)alkyl |
| 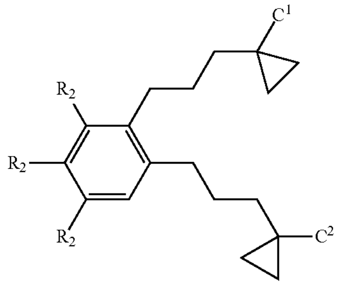 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 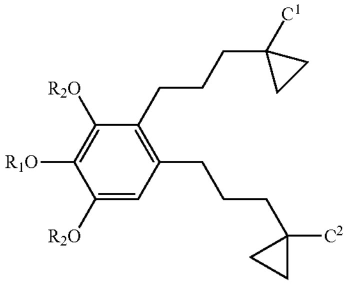 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 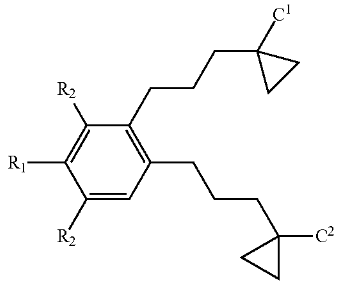 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 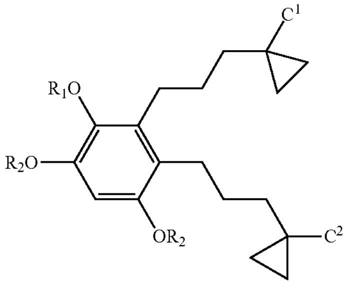 |

TABLE A-15-continued

| Structure |
|---|
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 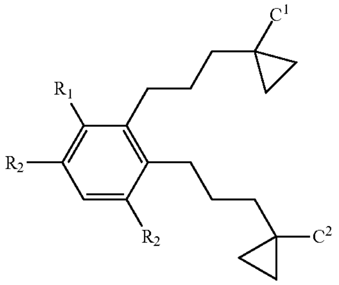 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 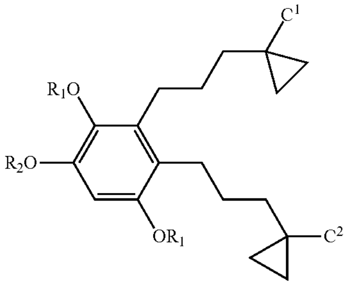 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 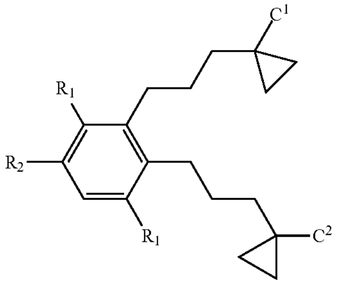 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
|---|
| 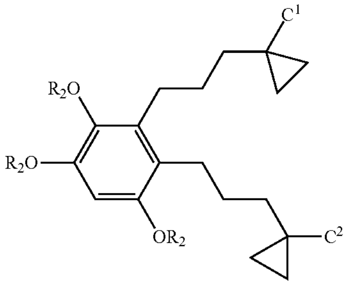 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 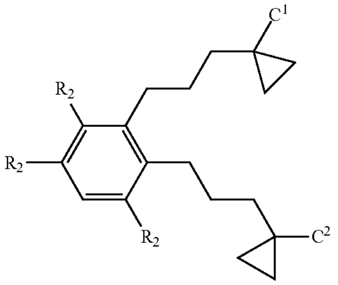 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 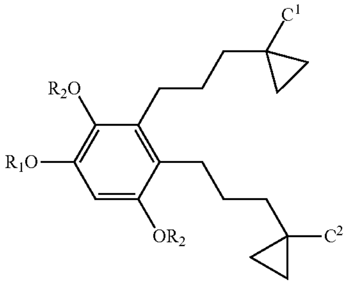 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 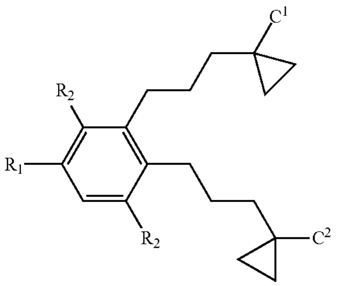 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or |

TABLE A-15-continued

| Structure |
|---|
| (C1-C4)alkyl; or each $R_2$ is independently F, Cl, Br, or $CF_3$ and $R_1$ = H or (C1-C4)alkyl |
| 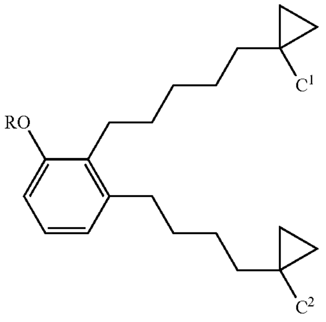 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 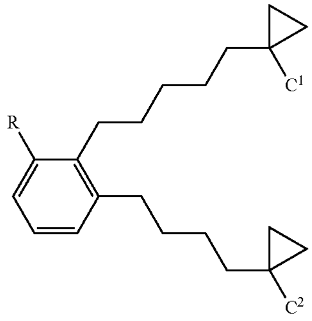 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 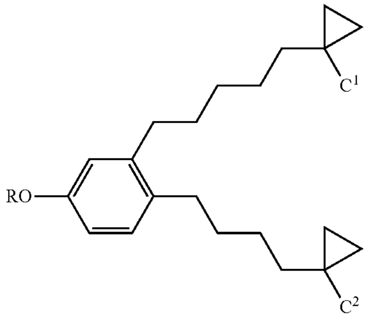 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
|---|
| 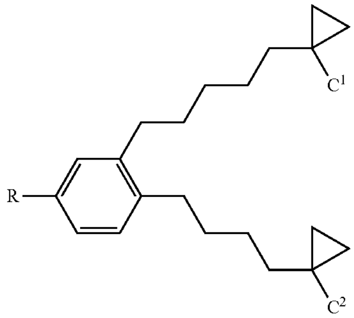 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 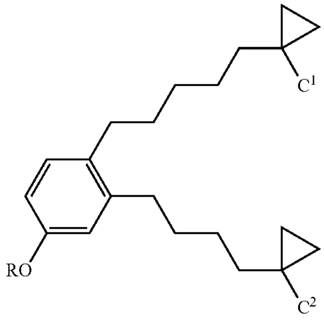 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 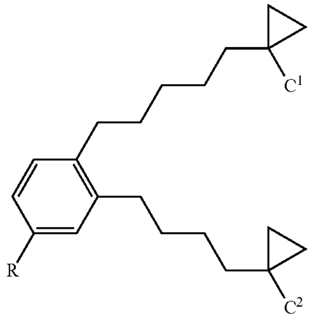 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 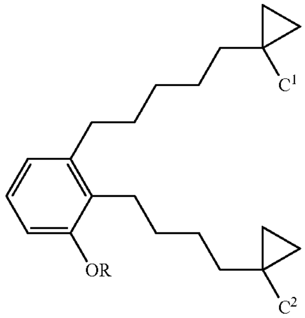 |

TABLE A-15-continued

| Structure |
| --- |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 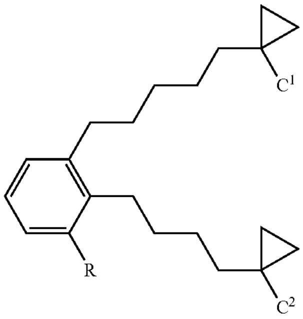 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 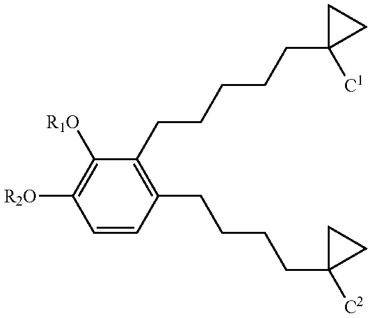 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 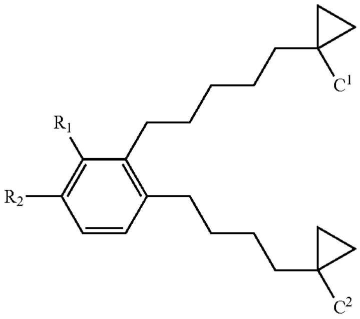 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 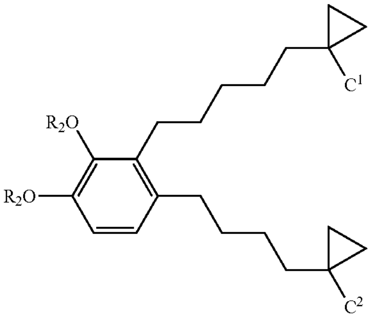 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 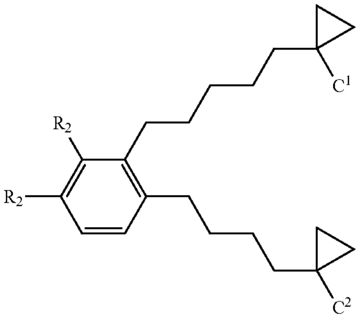 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 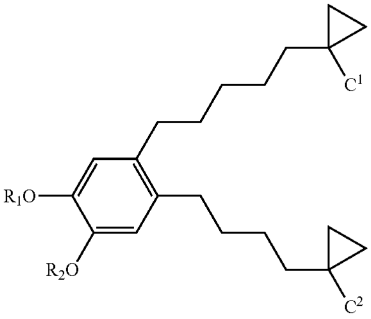 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_1$ = (C1-C4)alkyl; or $R_2$ = H and $R_1$ = (C1-C4)alkyl |

TABLE A-15-continued

| Structure |
|---|
| 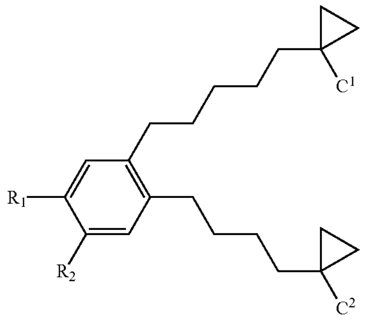 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 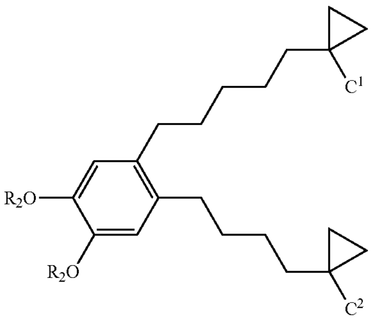 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 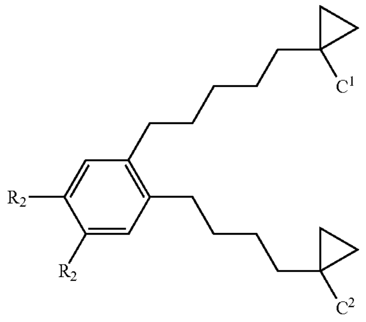 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 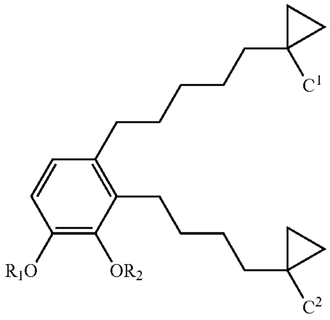 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 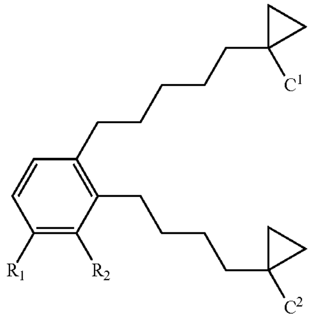 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 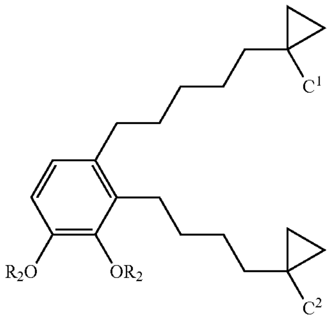 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 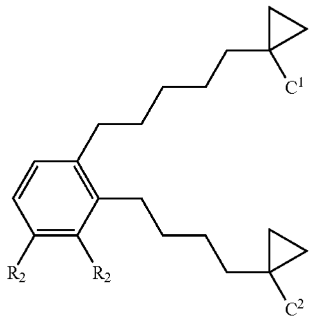 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 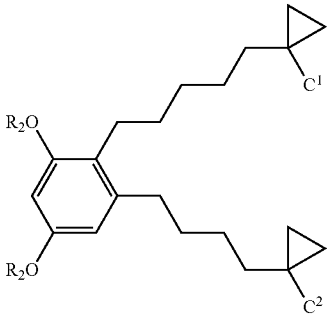 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 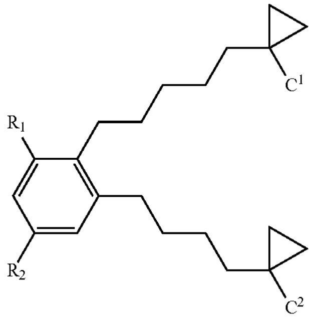 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 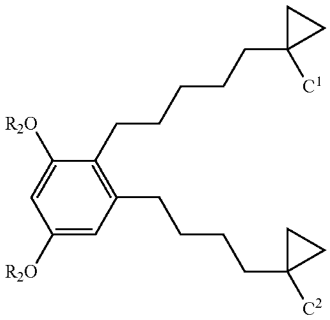 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 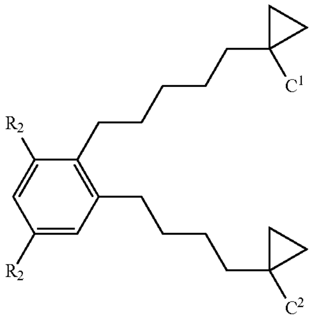 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 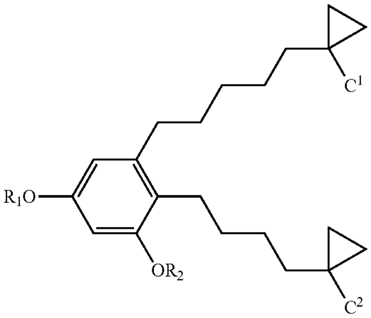 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 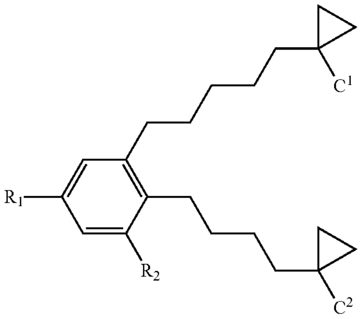 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 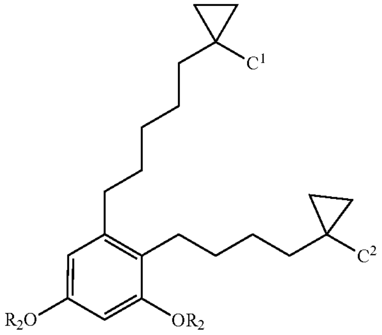 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 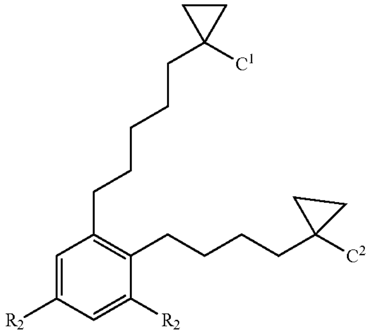 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 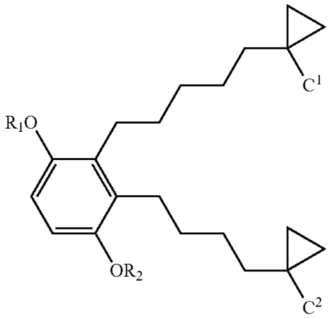 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 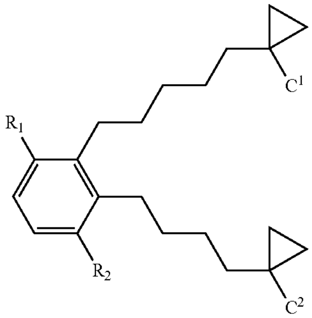 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 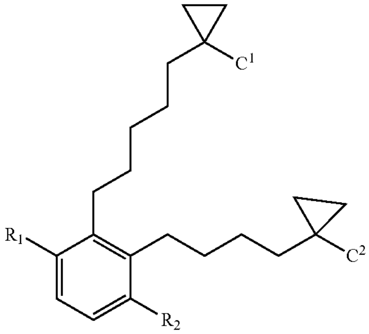 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 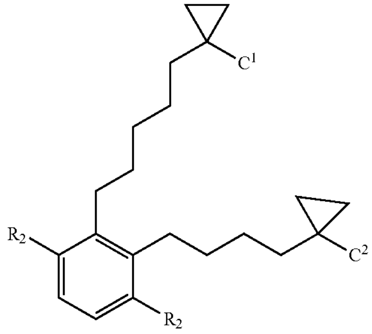 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 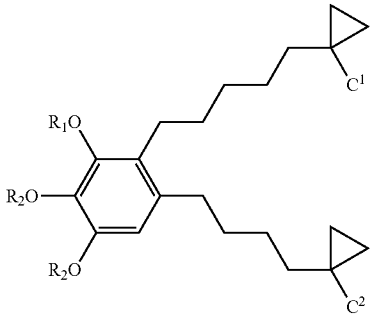 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 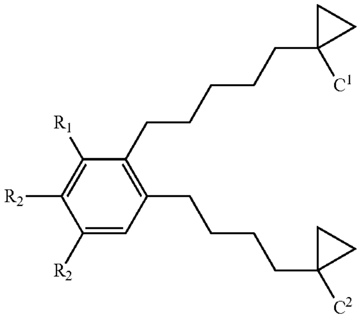 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 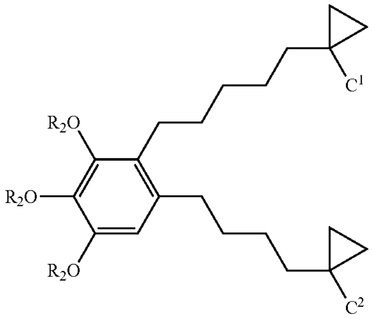 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 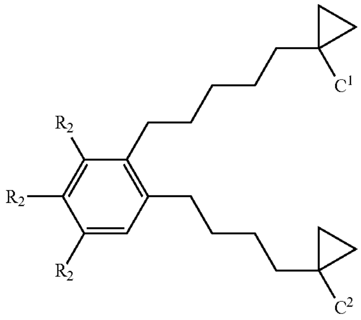 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 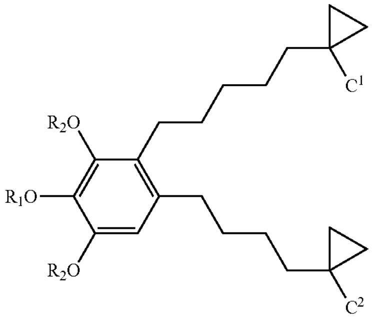 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 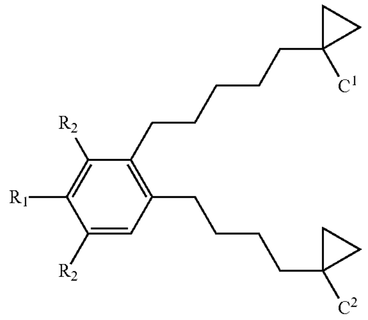 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 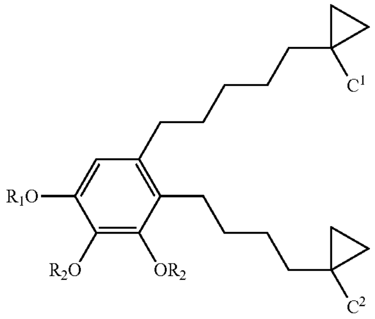 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 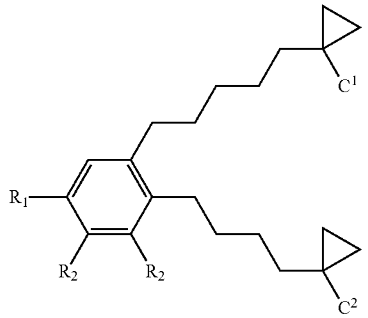 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 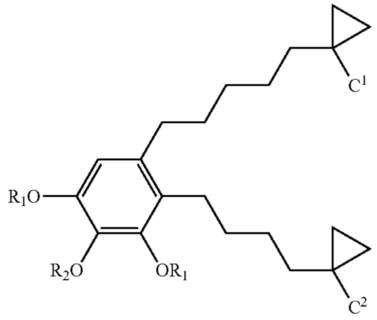 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 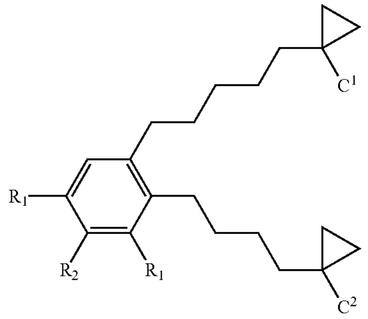 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 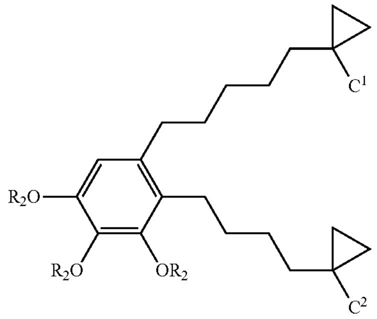 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 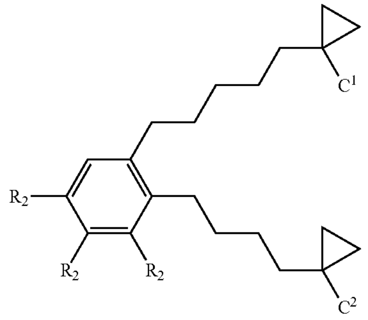 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 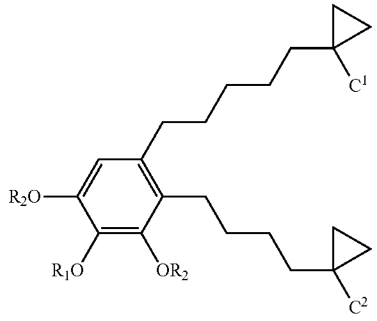 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 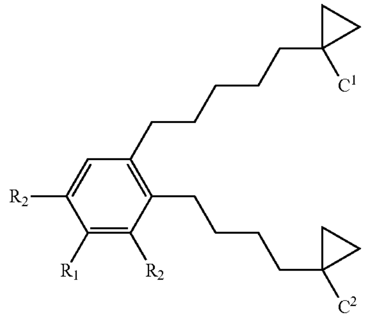 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 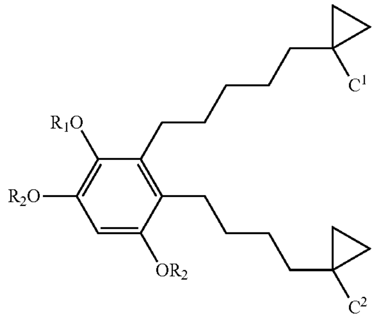 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 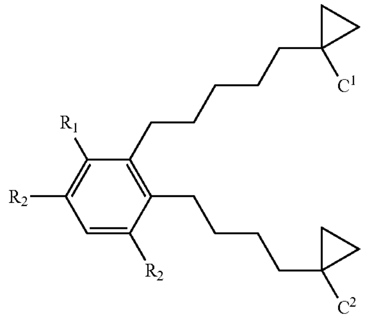 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 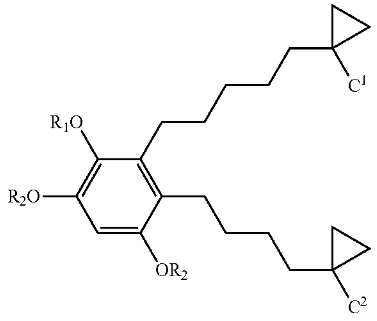 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 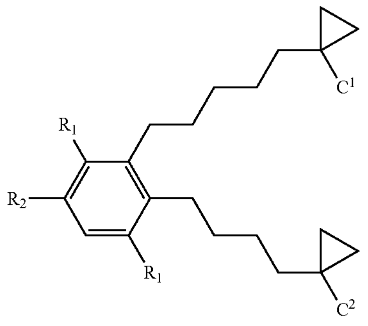 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 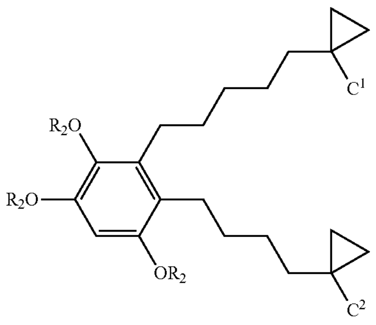 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 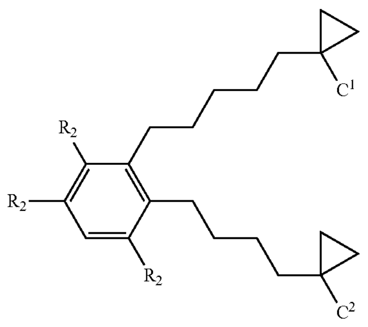 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 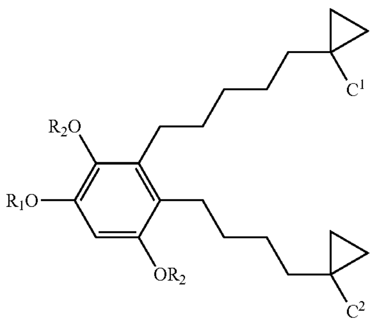 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 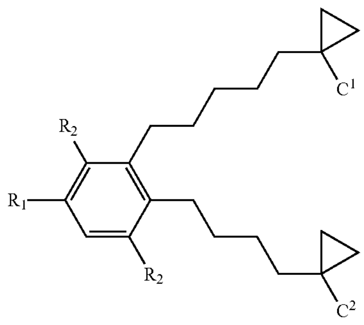 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 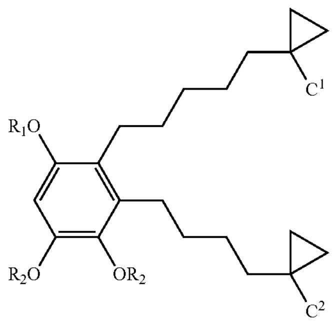 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 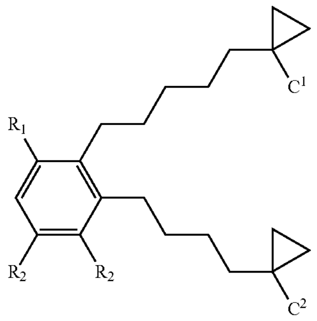 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1—C4)alkyl; or each $R_2$ is independently F, Cl, Br, or $CF_3$ and $R_1$ = H or (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 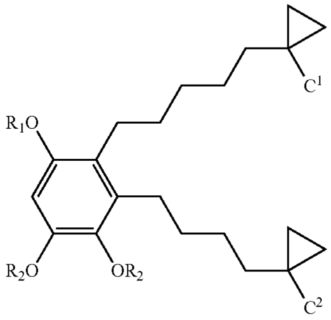 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1—C4)alkyl; or each $R_2$ is H and $R_1$ = (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
|---|
| 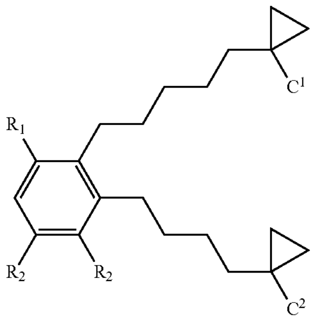 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1—C4)alkyl; or each $R_2$ is independently F, Cl, Br, or $CF_3$ and $R_1$ = H or (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 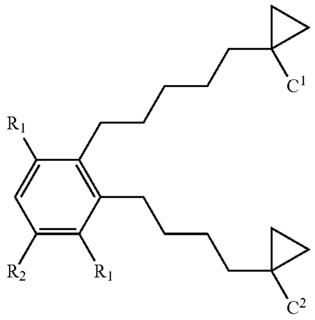 wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1—C4)alkyl; or $R_2$ = H and each $R_1$ is independently a (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

Structure

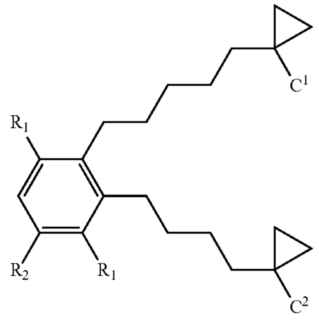

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1—C4)alkyl; or $R_2$ = F, Cl, Br, or $CF_3$ and each $R_1$ is independently H or (C1—C4)alkyl wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

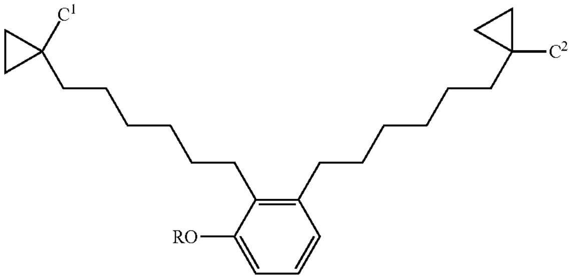

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1—C4)alkyl wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

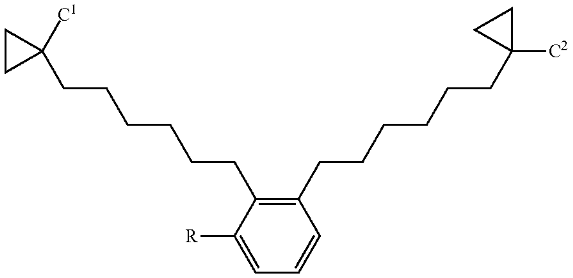

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ wherein $C^1$ and $C^2$ = COOH; $C^1$ and $C^2$ = COOH; $C^1$ = COOH and $C^2$ = CO—CoA; $C^1$ =

TABLE A-15-continued

Structure

CO—CoA and $C^2$ = COOH; or $C^1$ and $C^2$ = CO—CoA; and wherein R = F, Cl, Br, or $CF_3$

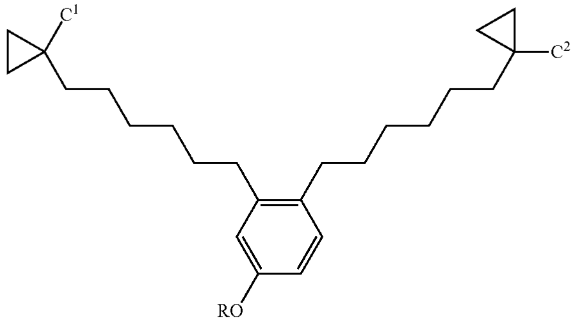

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1—C4)alkyl wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

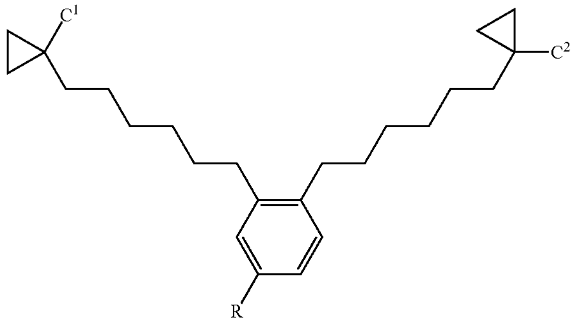

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ TABLE A-15-continued

| Structure |
| --- |
| 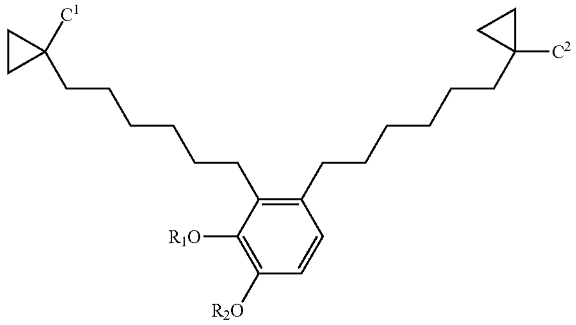 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1—C4)alkyl; or $R_2$ = H and $R_1$ = (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 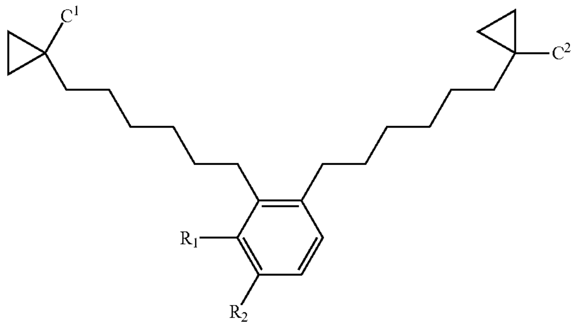 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1—C4)alkyl; or $R_2$ = F, Cl, Br, or $CF_3$ and $R_1$ = H or (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 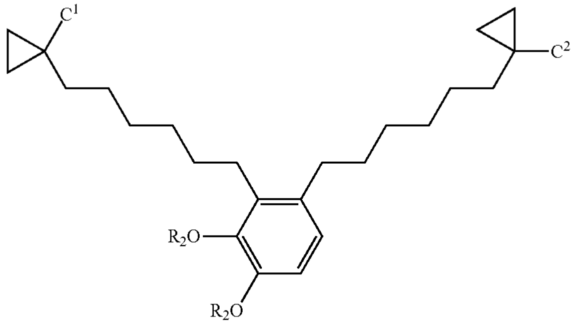 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 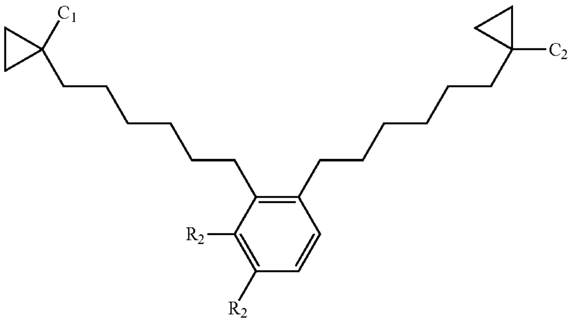 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 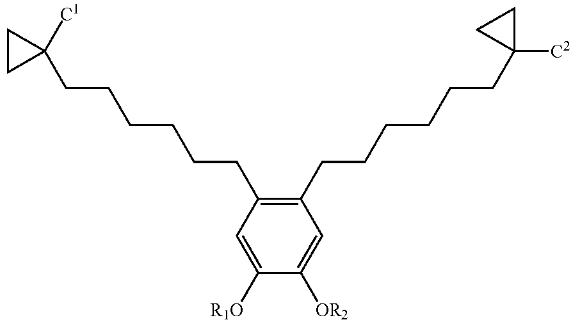 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1—C4)alkyl; or $R_2$ = H and $R_1$ = (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 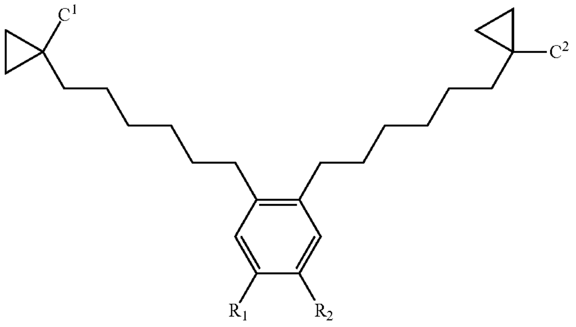 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 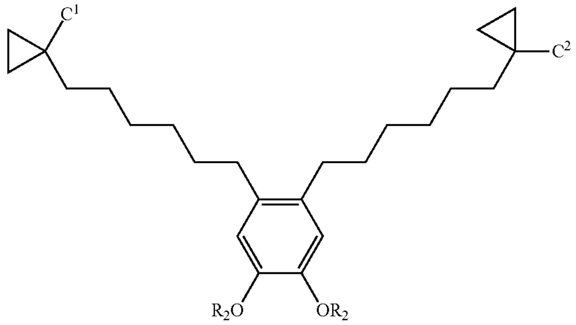 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 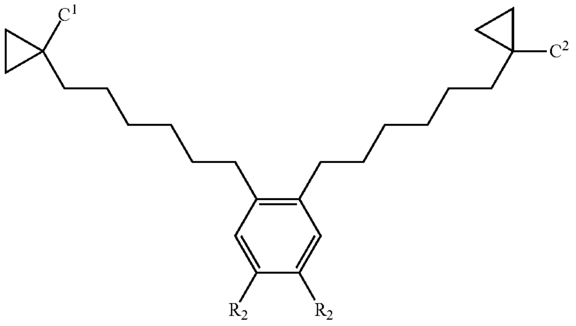 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 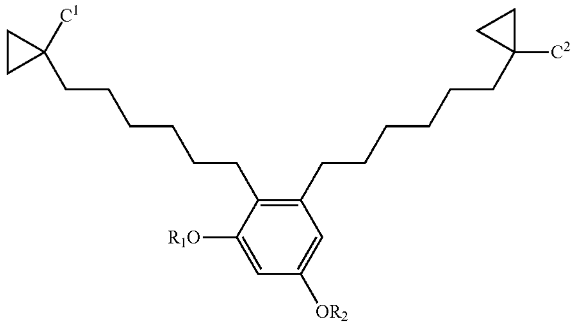 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1—C4)alkyl; or $R_2$ = H and $R_1$ = (C1—C4)alkyl |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 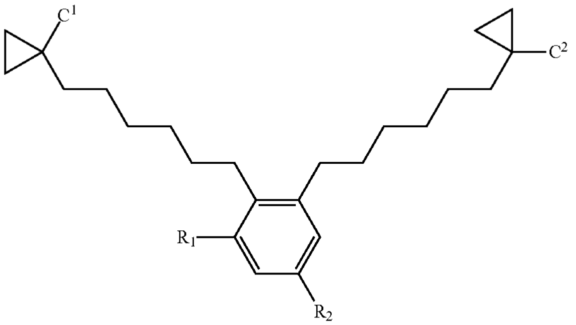 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 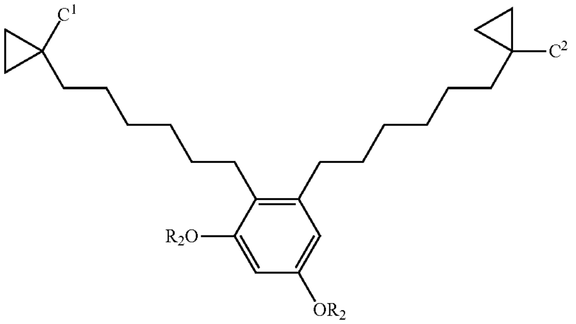 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|

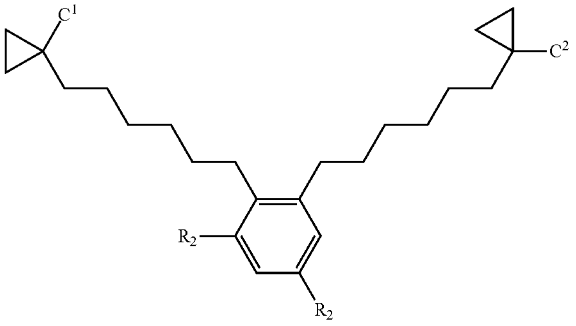

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

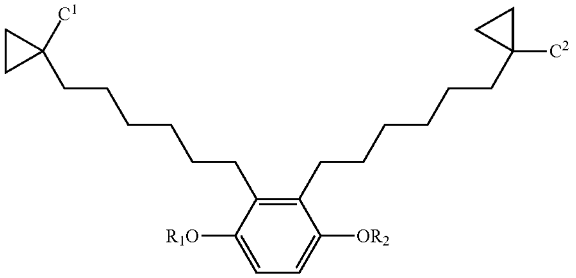

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl

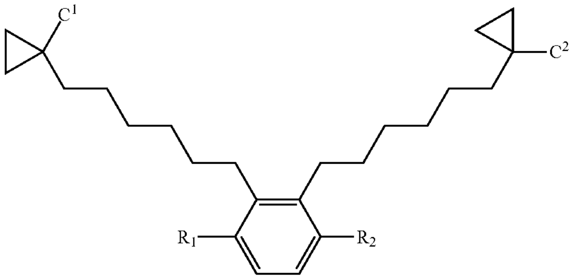

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl

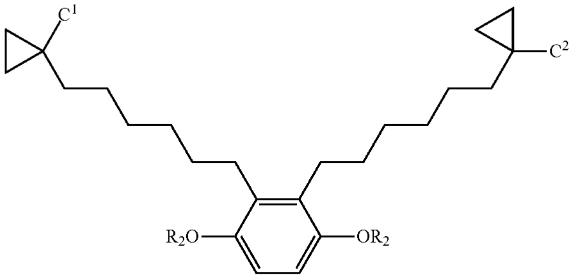

wherein $C^1$ and $C^2$ = COOH; $C^1$ = COOH and $C^2$ = CO—CoA; $C^1$ = CO—CoA and $C^2$ = COOH; or TABLE A-15-continued

| Structure |
|---|

$C^1$ and $C^2$ = CO—CoA; and wherein each $R_2$ is independently a (C1-C4)alkyl

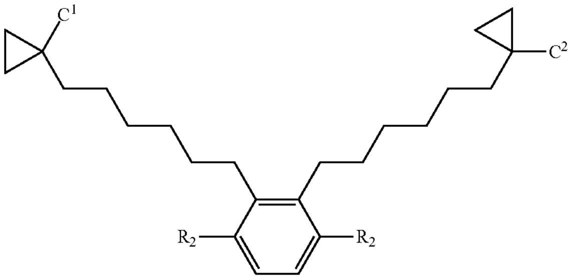

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

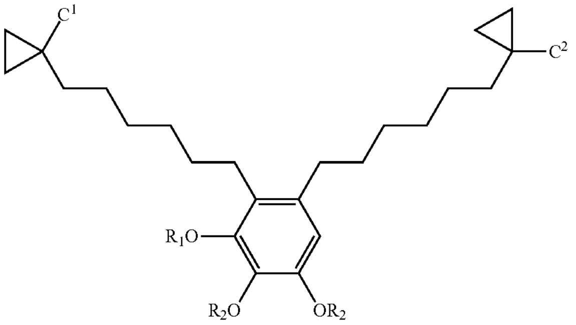

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

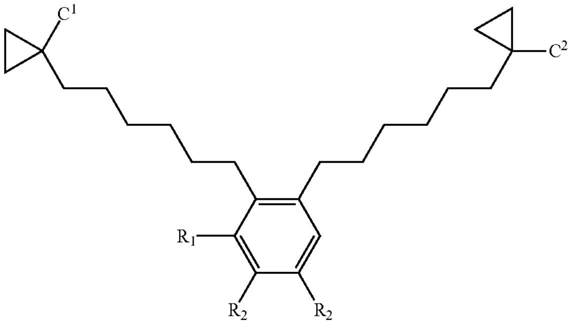

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl TABLE A-15-continued

| Structure |
|---|

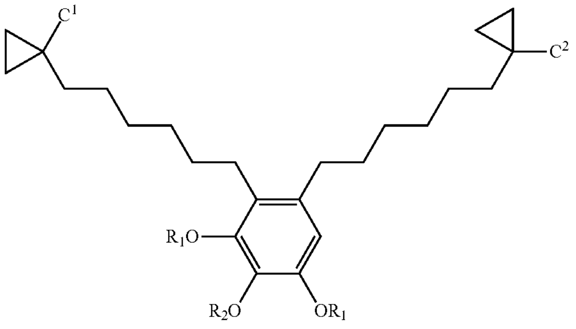

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl

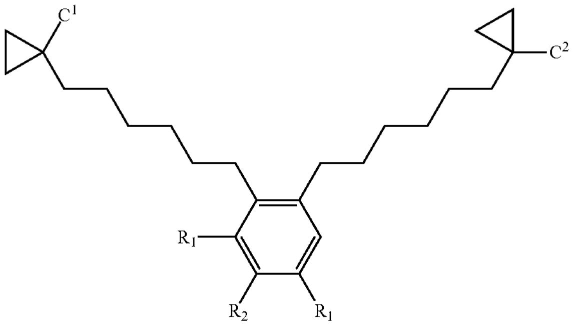

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl

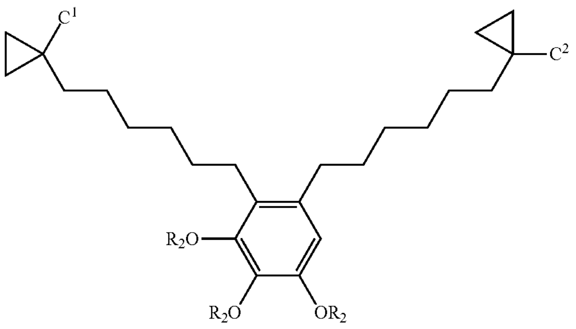

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl TABLE A-15-continued

| Structure |
|---|

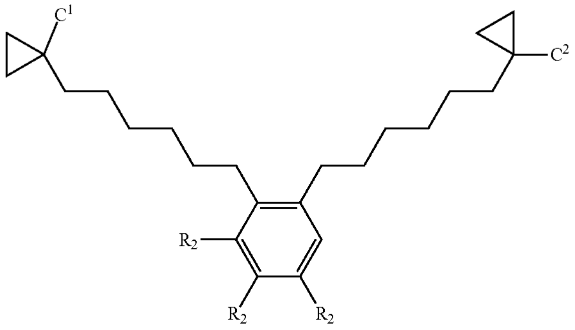

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$

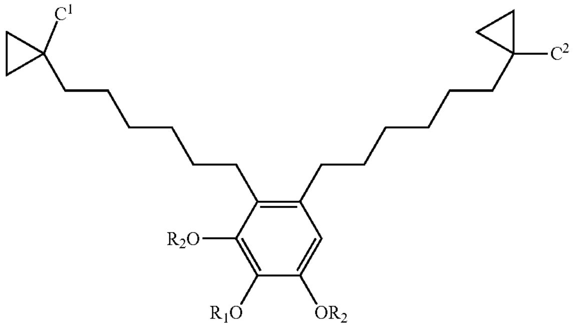

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl

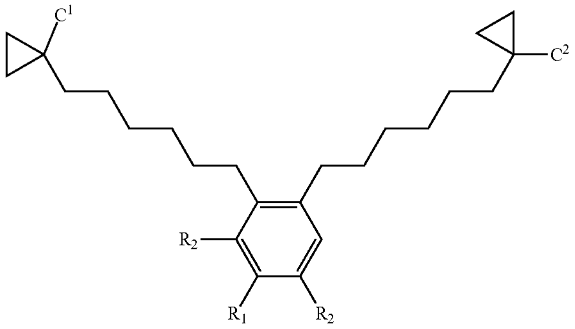

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl TABLE A-15-continued

| Structure |
| --- |
| 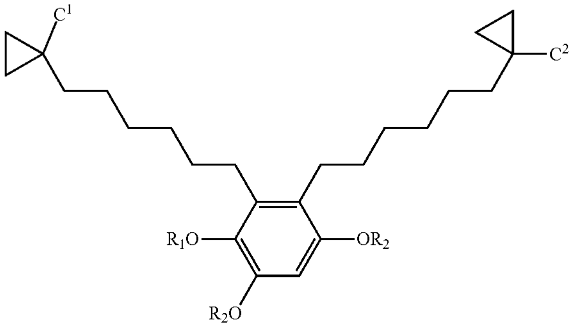 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 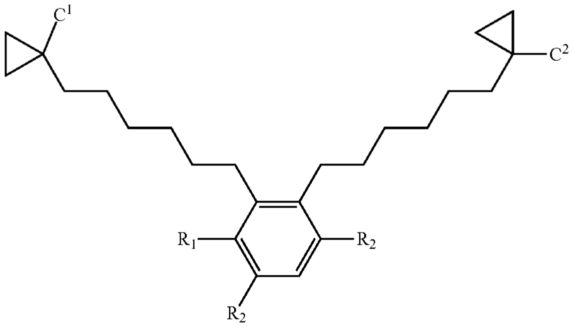 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 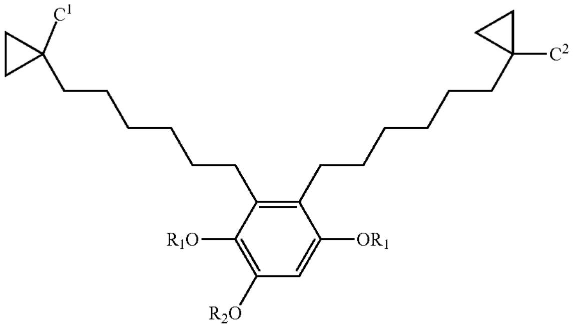 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
| --- |
| 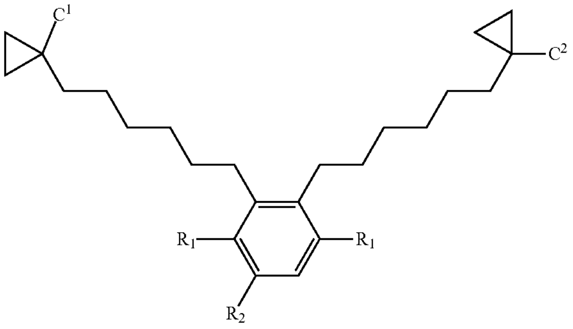 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 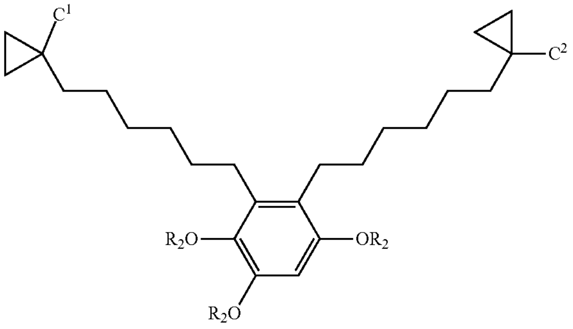 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 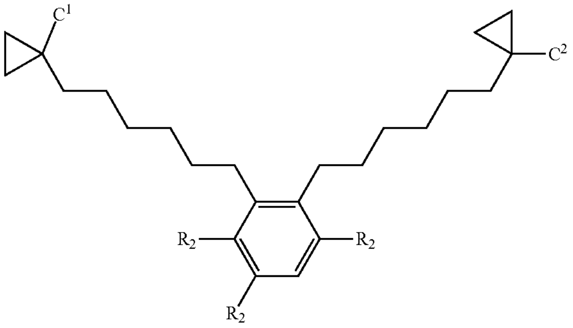 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 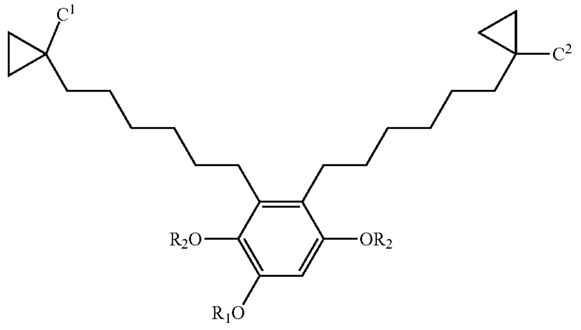 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 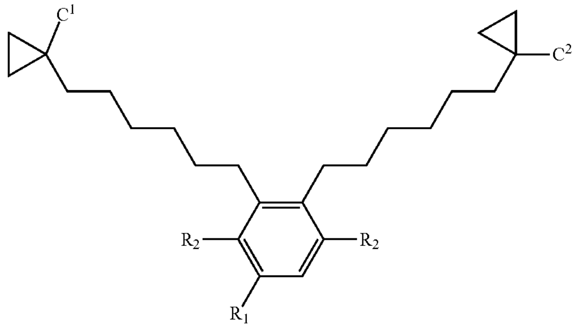 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 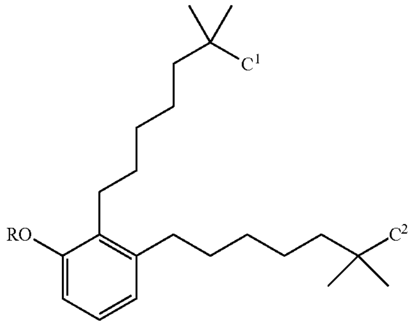 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |

TABLE A-15-continued

| Structure |
| --- |
| 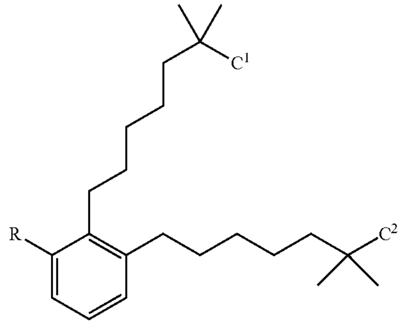 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |
| 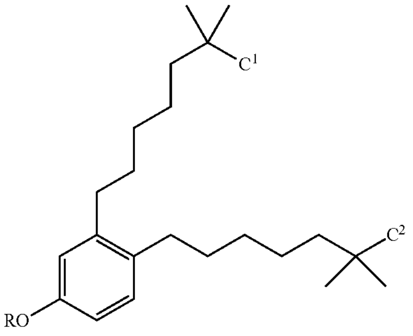 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl |
| 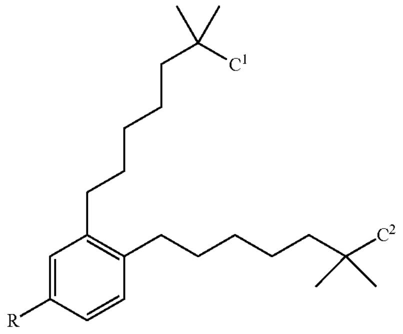 |
| wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$ |

TABLE A-15-continued

| Structure |
| --- |

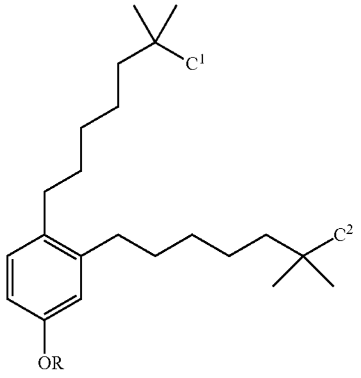

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl

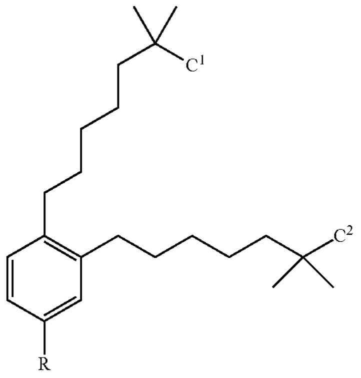

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$

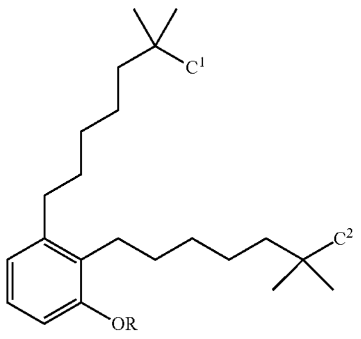

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = (C1-C4)alkyl TABLE A-15-continued

| Structure |
| --- |

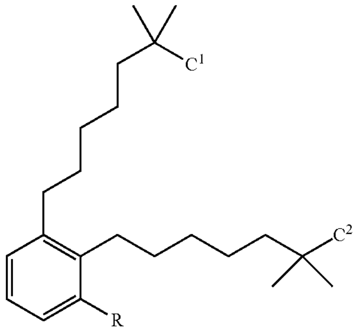

wherein $C^1$ and $C^2$ = COOH; $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein R = F, Cl, Br, or $CF_3$

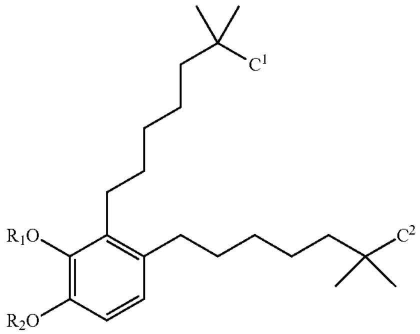

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl

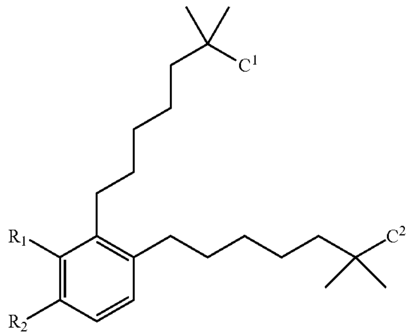

wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl TABLE A-15-continued

| Structure |
|---|
| 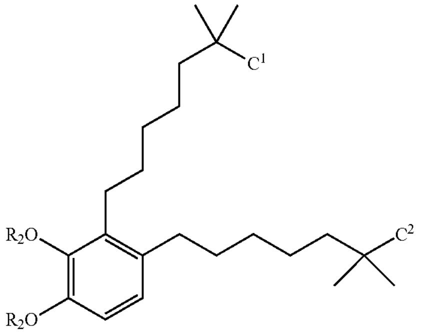 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 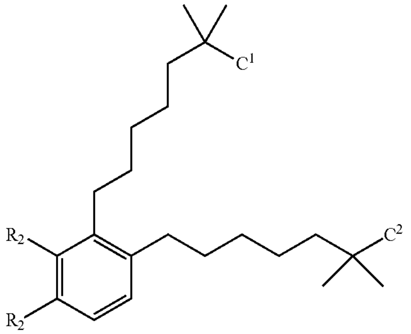 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 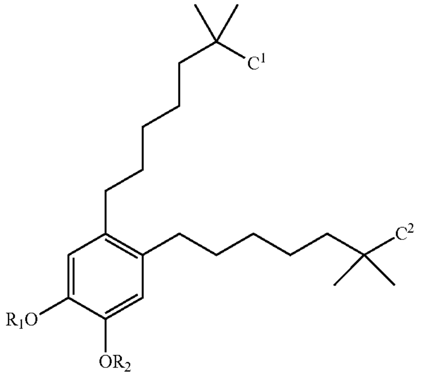 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
|---|
| 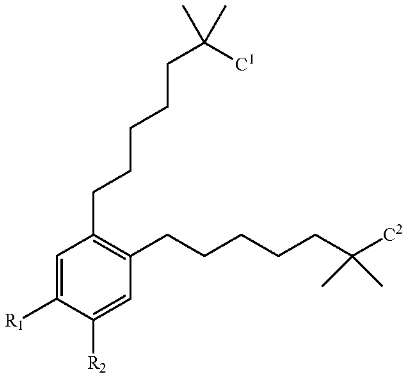 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 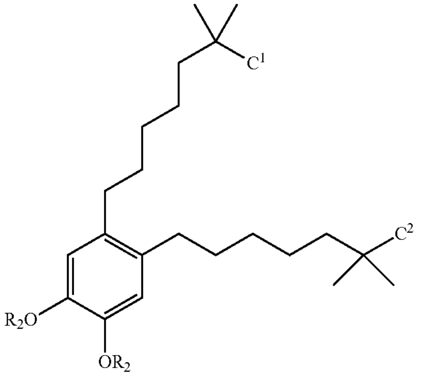 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 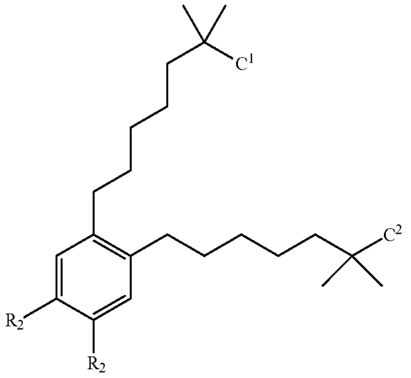 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
|---|
| 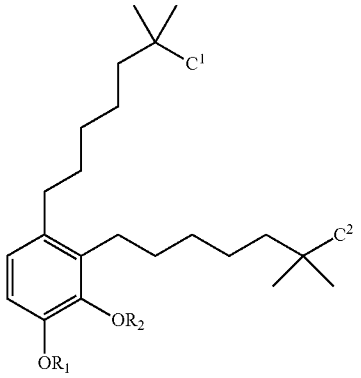 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 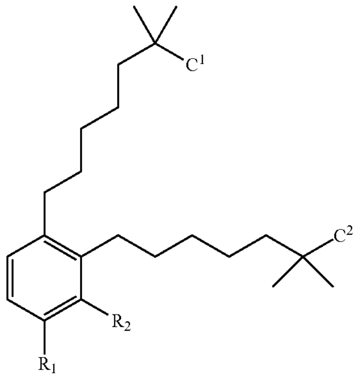 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 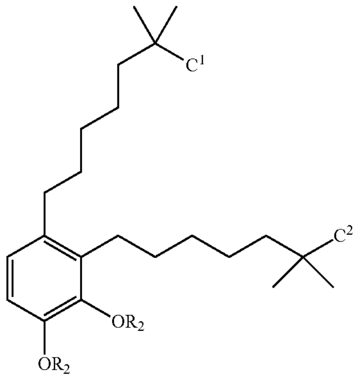 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 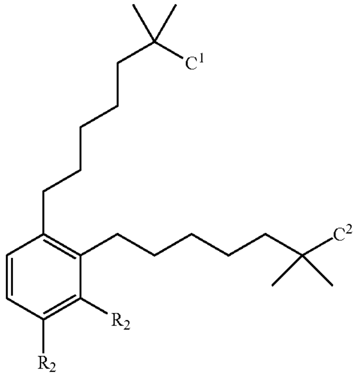 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 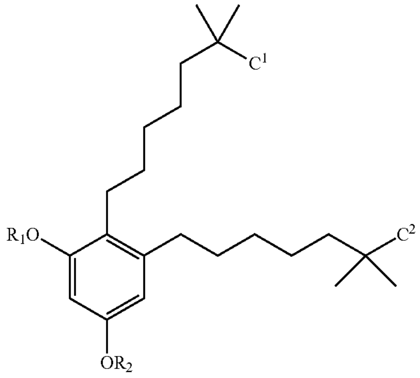 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 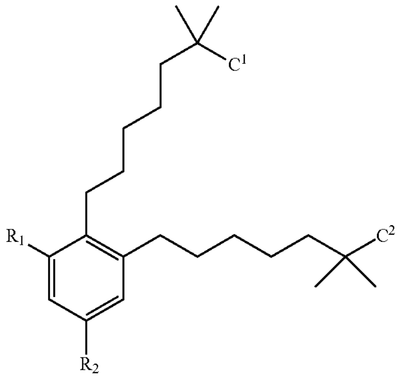 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |

TABLE A-15-continued

| Structure |
| --- |
| 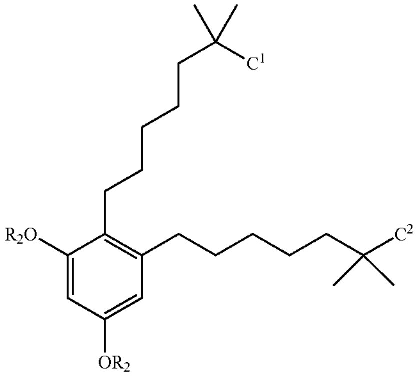 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 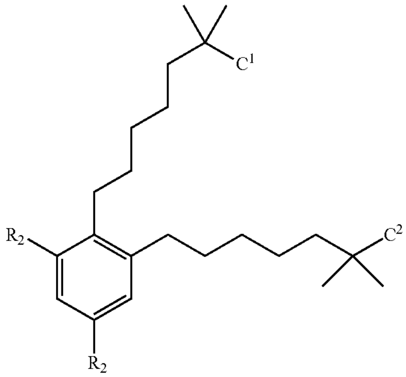 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 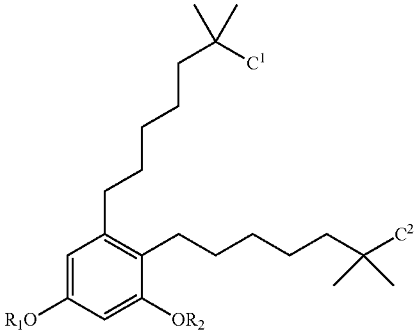 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |

TABLE A-15-continued

| Structure |
| --- |
| 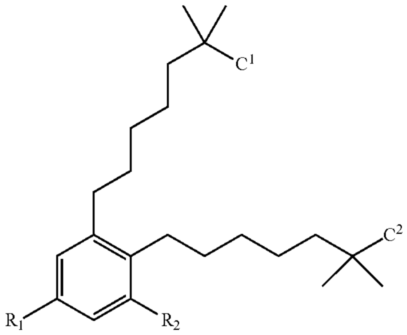 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 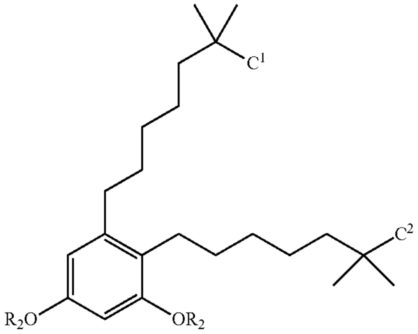 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 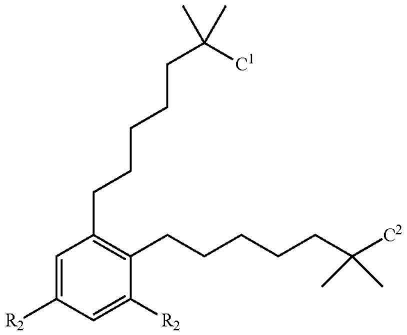 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 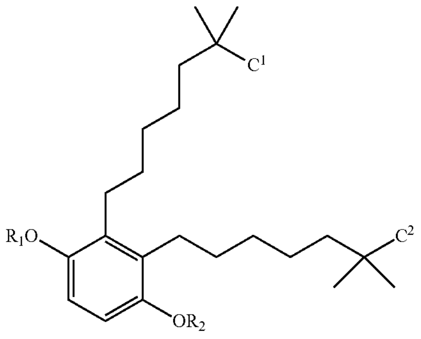 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and $R_2$ = (C1-C4)alkyl; or $R_2$ = H and $R_1$ = (C1-C4)alkyl |
| 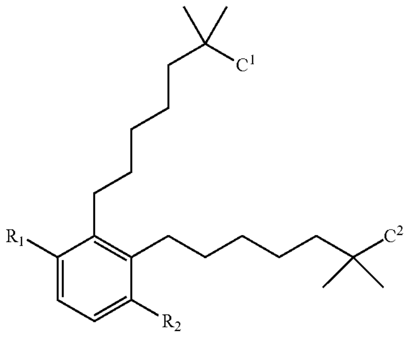 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and $R_2$ = H or (C1-C4)alkyl; or $R_2$ = F, Cl, Br, or $CF_3$ and $R_1$ = H or (C1-C4)alkyl |
| 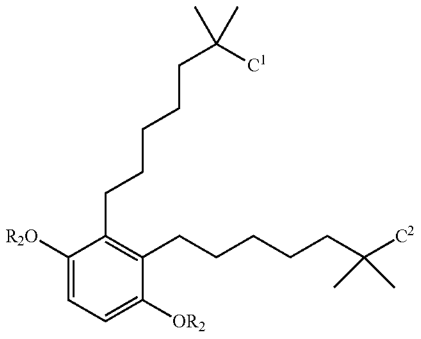 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 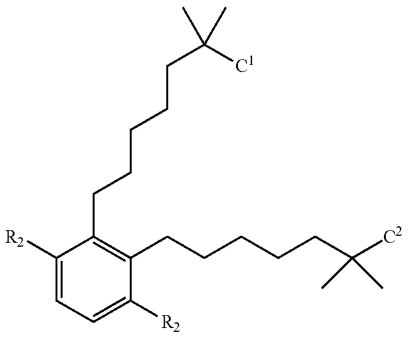 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 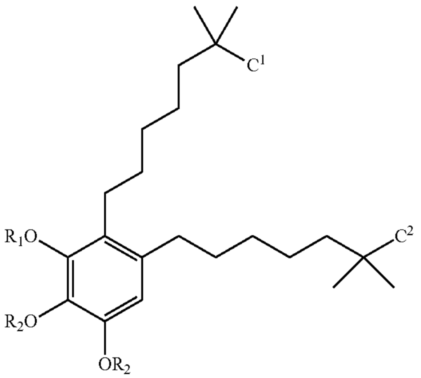 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 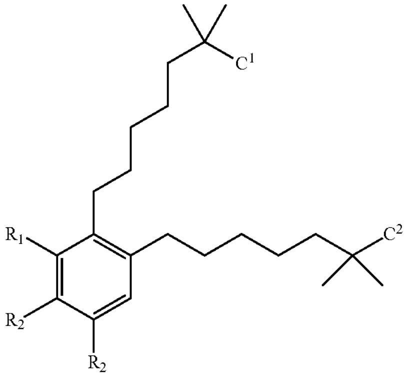 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 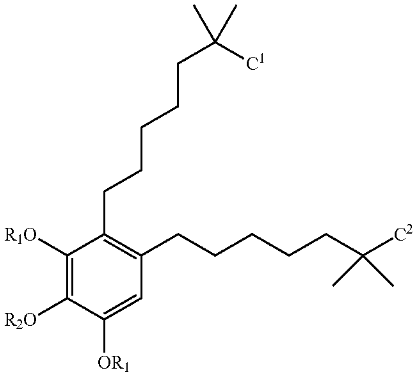 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 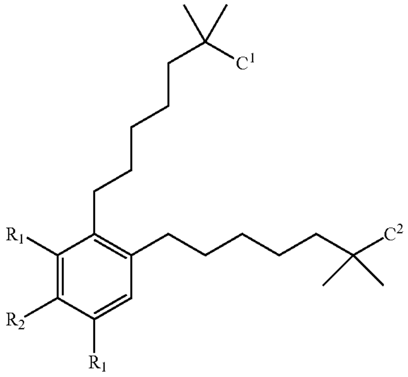 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 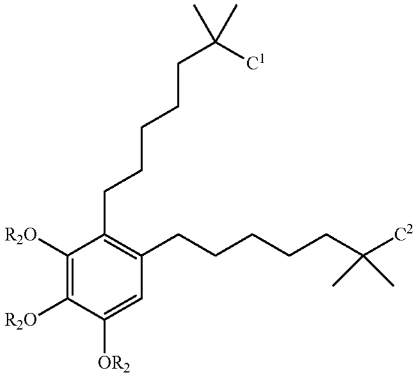 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
|---|
| 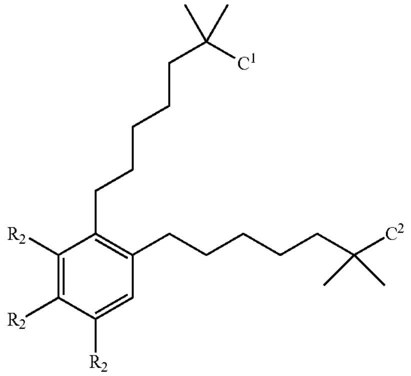 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 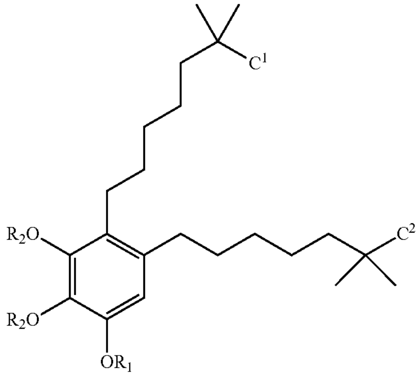 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 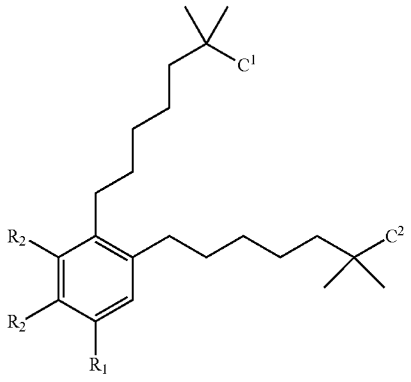 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
|---|
| 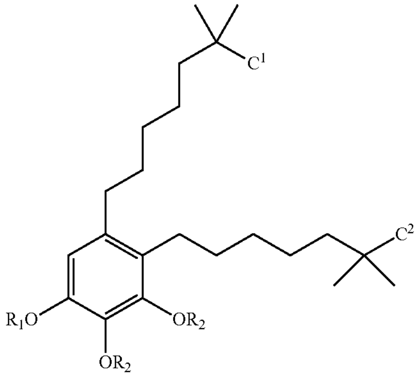 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 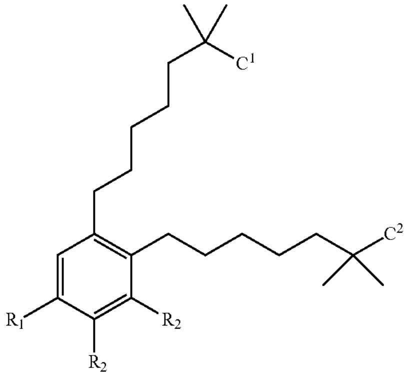 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 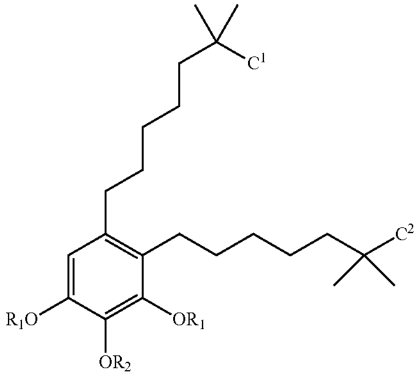 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |

TABLE A-15-continued

| Structure |
|---|
| 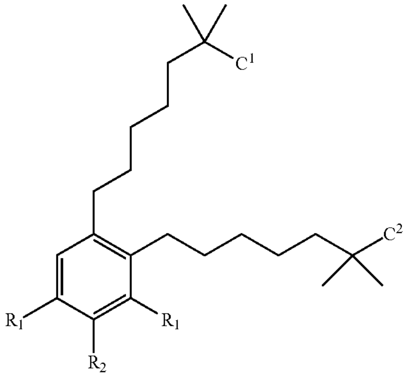 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 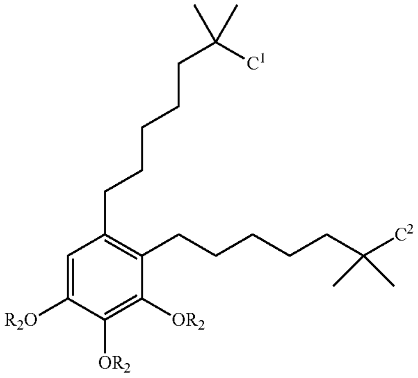 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 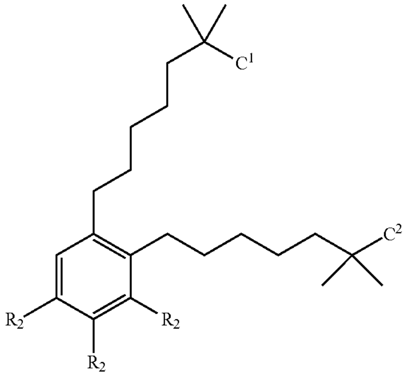 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |

TABLE A-15-continued

| Structure |
| --- |
| 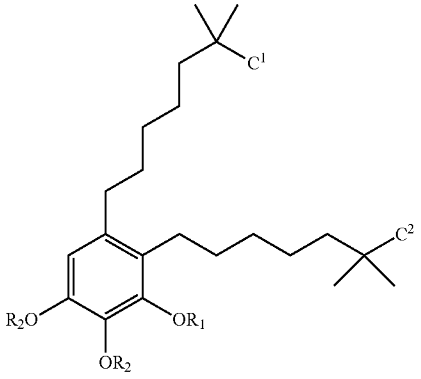 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 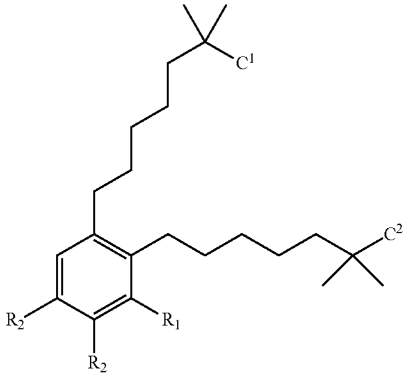 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 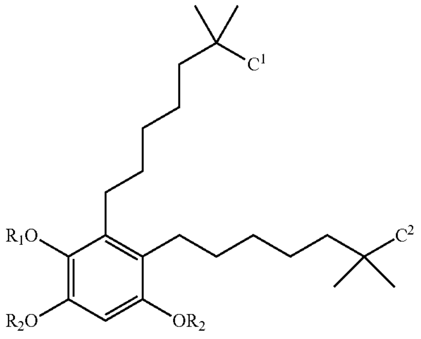 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 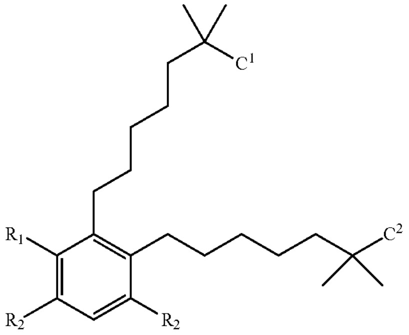 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 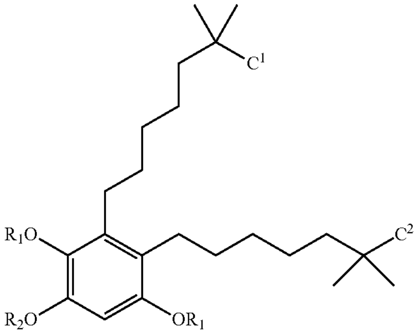 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 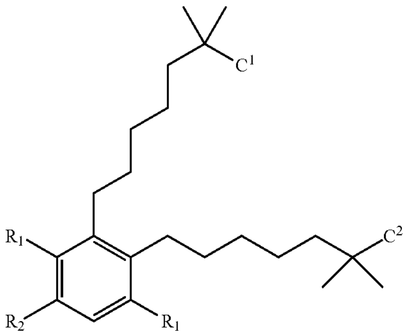 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |

TABLE A-15-continued

| Structure |
| --- |
| 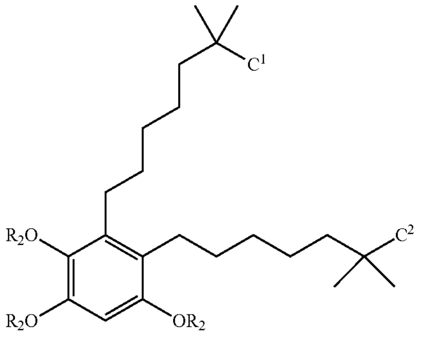 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |
| 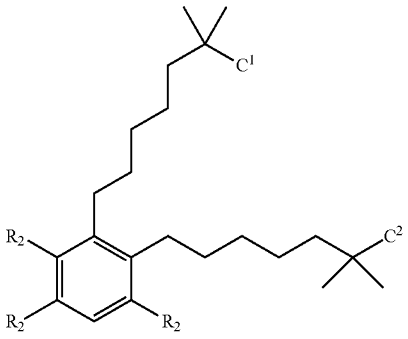 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 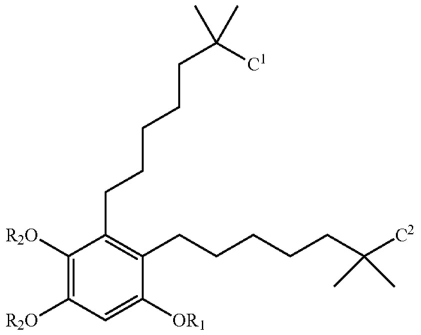 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |

TABLE A-15-continued

| Structure |
| --- |
| 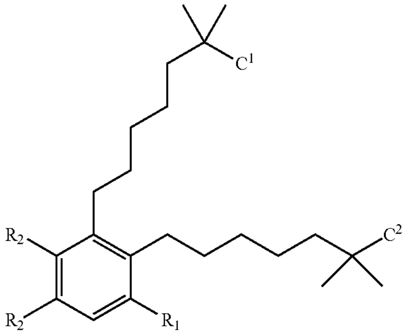 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |
| 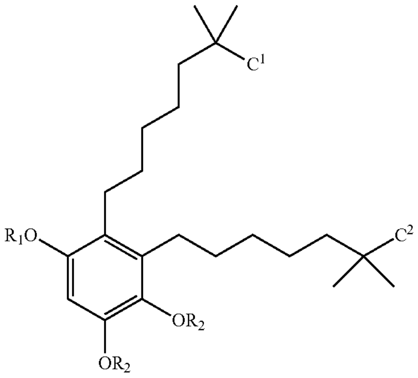 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 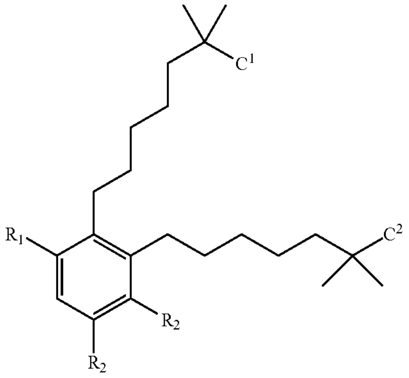 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

TABLE A-15-continued

| Structure |
| --- |
| 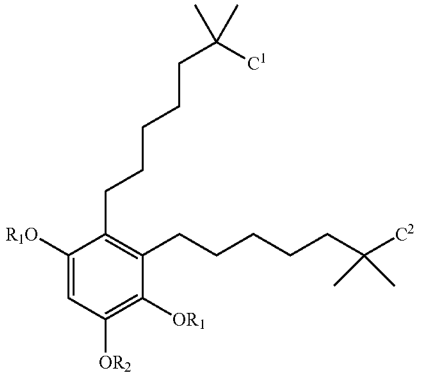 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is H and $R_2$ = (C1-C4)alkyl; or $R_2$ = H and each $R_1$ is independently a (C1-C4)alkyl |
| 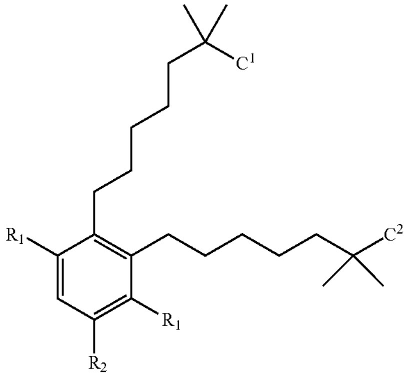 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_1$ is independently F, Cl, Br, or $CF_3$ and $R_2$ = H or (C1-C4)alkyl; or $R_2$ = F, Cl, Br, or $CF_3$ and each $R_1$ is independently H or (C1-C4)alkyl |
| 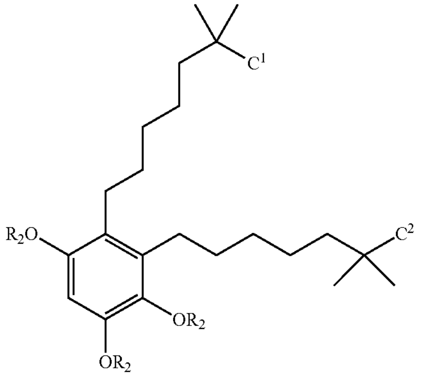 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently a (C1-C4)alkyl |

TABLE A-15-continued

| Structure |
| --- |
| 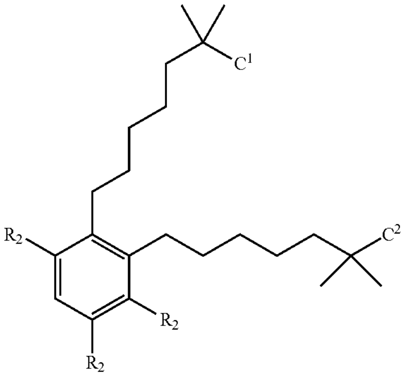 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein each $R_2$ is independently F, Cl, Br, or $CF_3$ |
| 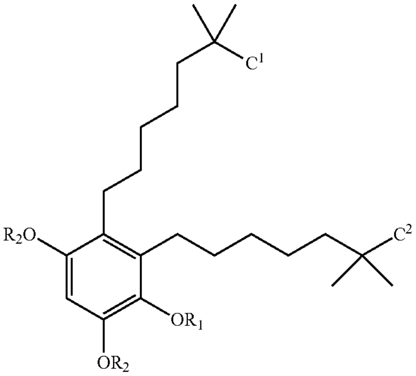 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = H and each $R_2$ is independently a (C1-C4)alkyl; or each $R_2$ is H and $R_1$ = (C1-C4)alkyl |
| 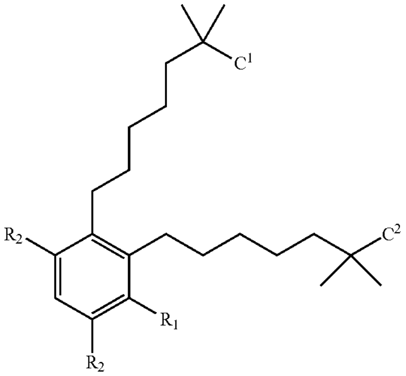 |
| wherein $C^1$ and $C^2$ = COOH; $C^1$ = COOH and $C^2$ = CO—CoA; $C^1$ = CO—CoA and $C^2$ = COOH; or $C^1$ and $C^2$ = CO—CoA; and wherein $R_1$ = F, Cl, Br, or $CF_3$ and each $R_2$ is independently H or (C1-C4)alkyl; or each $R_2$ is independently F, Cl, Br, or $CF_3$ and $R_1$ = H or (C1-C4)alkyl |

Compounds of Formula (H)

In some embodiments, the compound of the invention is a compound of Formula (IH):

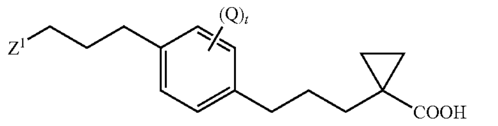

(IH)

or a pharmaceutically acceptable salt or solvate thereof, wherein:

$Z^1$ is —$C(R^1)(R^2)$—$(CH_2)_c$—X or —W—$(CH_2)_c$—$C(R^3)(R^4)$—Y;

c is 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

Q is independently —OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

t is 0, 1, 2, 3, or 4;

each X and Y is independently —OH, —COOH, —$COOR^5$, —$CONH_2$, —$CONHR^5$, —CONHMs, —CONHTs, —$SO_3H$,

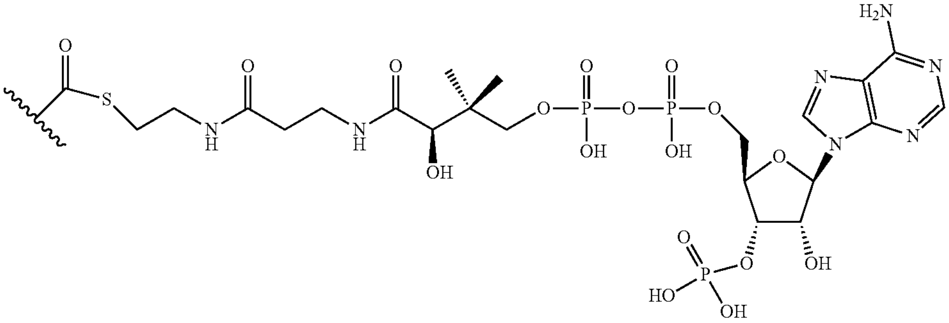

(-CO-CoA),

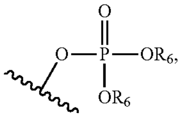
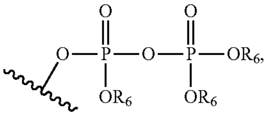
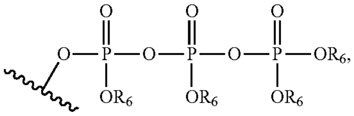
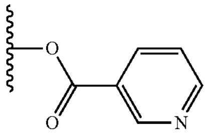
,

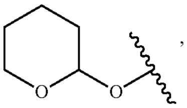
,
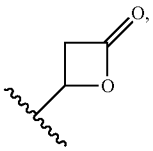
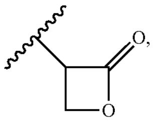
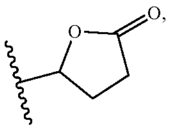
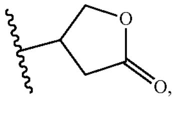
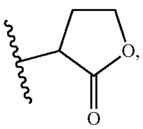

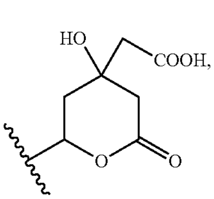
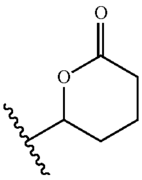
,
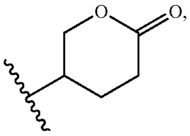
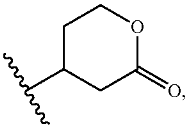
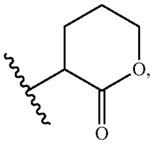

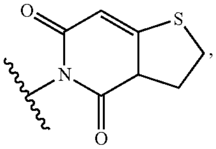
,
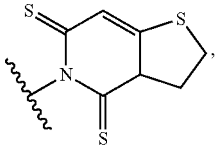
,
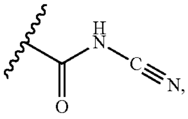
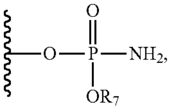
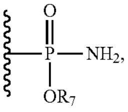

-continued

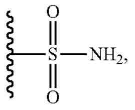,
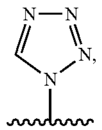,
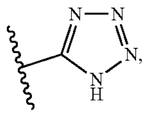,
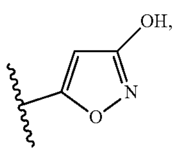,
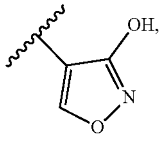,
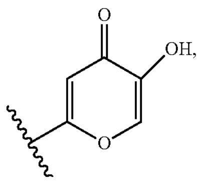,
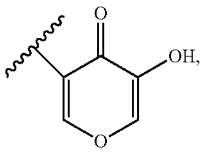,
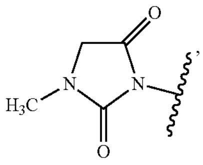,
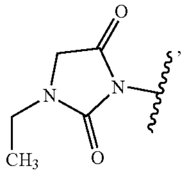,
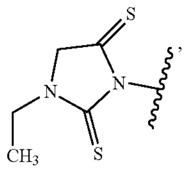,
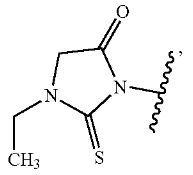, or
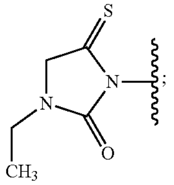;

each $R^7$ is independently H, $-C_1$-$C_6$ alkyl, $-C_2$-$C_6$ alkenyl, or $-C_2$-$C_6$ alkynyl; wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups;

each $R^7$ is independently H, $-C_1$-$C_6$ alkyl, $-C_2$-$C_6$ alkenyl, or $-C_2$-$C_6$ alkynyl;

each W is independently —O—, —NH—, —N(OH)—, —N(→O)—, —S—, —S(═O)—, $-S(O)_2-$, or —Se—;

each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups.

In some embodiments of the compound of formula (IH), $Z^1$ is $-C(R^1)(R^2)-(CH_2)_c-X$. In some embodiments, $Z^1$ is $-C(R^1)(R^2)-(CH_2)_c-X$ and X is —COOH, $-COOR^5$, or —CO—CoA. In some embodiments, $Z^1$ is $-C(R^1)(R^2)-(CH_2)_c-X$ and X is —COOH. In some embodiments, c is 0.

In some embodiments of the compound of formula (IH), each $R^1$ and $R^2$ is independently $-C_1$-$C_6$ alkyl. In some embodiments, $R^1$ and $R^2$ are methyl.

In some embodiments of the compound of formula (IH), each carbon atom together with the $R^1$ and $R^2$ attached to the carbon atom independently form a $-C_3$-$C_7$ cycloalkyl group. In some embodiments, each carbon atom together with the $R^1$ and $R^2$ attached to the carbon atom independently form a cyclopropyl ring.

In some embodiments of the compound of formula (IH), t is 0.

In some embodiments, the compound of Formula (IH) has any one of the structures shown in Table A-16, or a pharmaceutically acceptable salt or solvate thereof. In some embodiments, the pharmaceutically acceptable salt of a compound having any one of the structures shown in Table A-16 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt. In some embodiments, the pharmaceutically acceptable salt of a compound having any one of the structures shown in Table A-16 is a zinc salt.

TABLE A-16

| Compound No. | Structure and Name |
|---|---|
| I-11 | 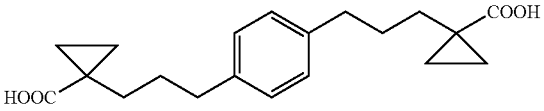 [SMILES: O=C(O)C1(CCCc2ccc(CCCC3(C(=O)O)CC3)cc2)CC1] 1,1'-(1,4-phenylenebis(propane-3,1-diyl))bis(cyclopropane-1-carboxylic acid) |
| I-12 | 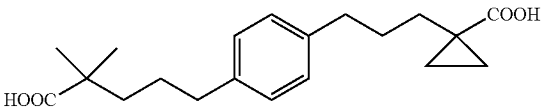 [SMILES: CC(C)(CCCc1ccc(CCCC2(C(=O)O)CC2)cc1)C(=O)O] 1-(3-(4-(4-carboxy-4-methylpentyl)phenyl)propyl)cyclopropane-1-carboxylic acid |

Compounds of Formula (IJ)

In some embodiments, the compound of the invention is a compound of Formula (IJ):

(IJ)

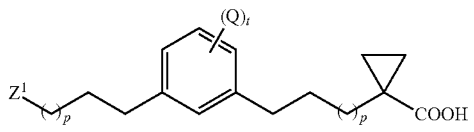

or a pharmaceutically acceptable salt or solvate thereof, wherein:

each p is independently 1 or 2;

$Z^1$ is $-C(R^1)(R^2)-(CH_2)_c-X$ or $-W-(CH_2)_c-C(R^3)(R^4)-Y$;

c is 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

Q is independently —OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

t is 0, 1, 2, 3, or 4;

each X and Y is independently —OH, —COOH, —$COOR^5$, —$CONH_2$, —$CONHR^5$, —CONHMs, —CONHTs, —$SO_3H$,

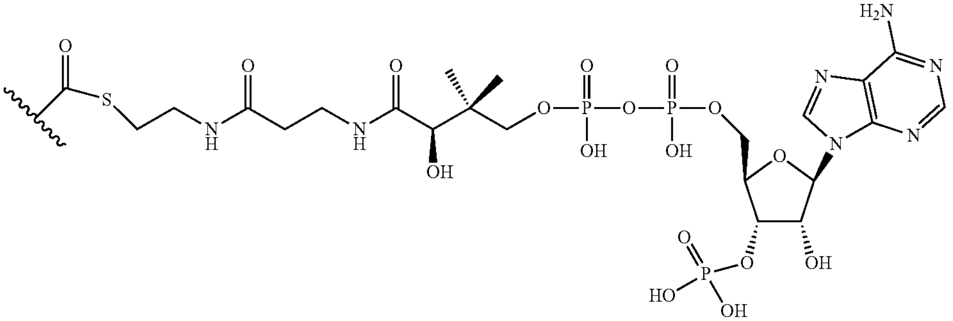
(-CO-CoA),

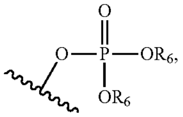
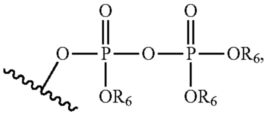
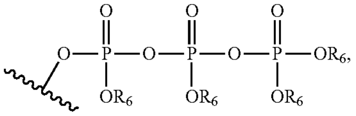
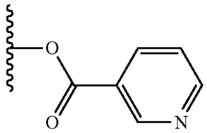
,

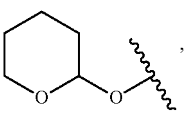
,
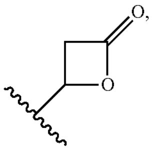
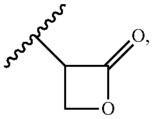
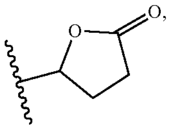
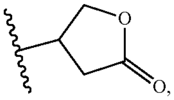
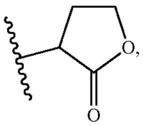

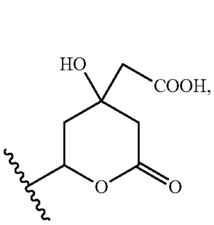
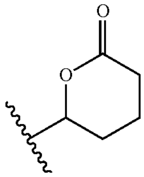
,
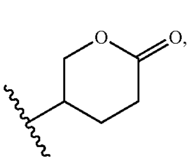
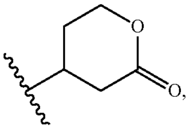
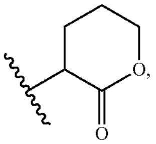

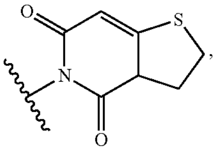
,
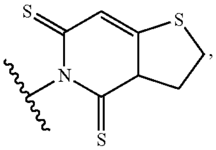
,
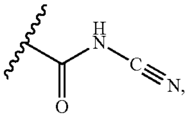
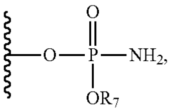
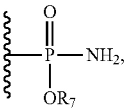

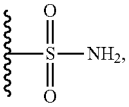
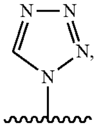
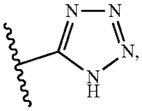
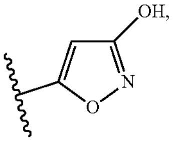
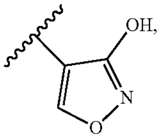
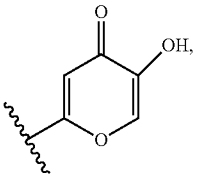

-continued

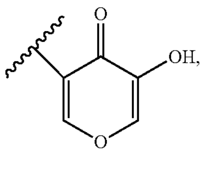
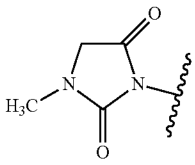
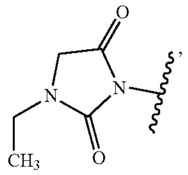
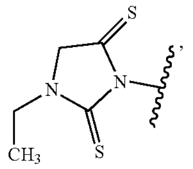
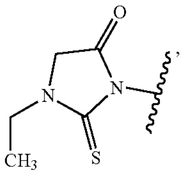
or
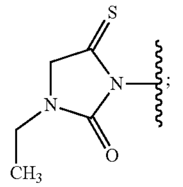

each $R^7$ is independently H, —$C_1$-$C_6$ alkyl, —$C_2$-$C_6$ alkenyl, or —$C_2$-$C_6$ alkynyl;

each W is independently —O—, —NH—, —N(OH)—, —N(→O)—, —S—, —S(→O)—, —$S(O)_2$—, or —Se—;

each $R^6$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups.

In some embodiments of the compound of formula (IJ), $Z^1$ is —$C(R^1)(R^2)$—$(CH_2)_c$—X. In some embodiments, $Z^1$ is —$C(R^1)(R^2)$—$(CH_2)_c$—X and X is —COOH, —$COOR^5$, or —CO—CoA. In some embodiments, $Z^1$ is —$C(R^1)(R^2)$—$(CH_2)_c$—X and X is —COOH. In some embodiments, c is 0.

In some embodiments of the compound of formula (IJ), each $R^1$ and $R^2$ is independently —$C_1$-$C_6$ alkyl. In some embodiments, $R^1$ and $R^2$ are methyl.

In some embodiments of the compound of formula (IJ), each carbon atom together with the $R^1$ and $R^2$ attached to the carbon atom independently form a —$C_3$-$C_7$ cycloalkyl group. In some embodiments, each carbon atom together with the $R^1$ and $R^2$ attached to the carbon atom independently form a cyclopropyl ring.

In some embodiments of the compound of formula (IJ), t is 0.

In some embodiments, the pharmaceutically acceptable salt of the compounds of Formula (IJ), is a zinc salt.

In some embodiments, the pharmaceutically acceptable salt of the compounds of Formula (IJ) is a zinc salt, wherein each X and Y is —COOH.

In some embodiments, the compound of Formula (IJ) has any one of the structures shown in Table A-17, or a pharmaceutically acceptable salt or solvate thereof. In some embodiments, the pharmaceutically acceptable salt of a compound having any one of the structures shown in Table A-17 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt. In some embodiments, the pharmaceutically acceptable salt of a compound having any one of the structures shown in Table A-17 is a zinc salt.

TABLE A-17

| Compound No. | Structure and Name |
|---|---|
| I-45 | 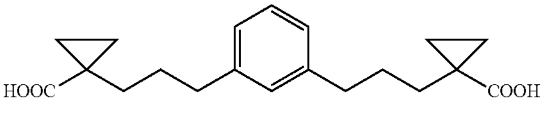 [SMILES: O=C(O)C1(CCCc2cccc(CCCC3(C(=O)O)CC3)c2)CC1] 1,1'-(1,3-phenylenebis(propane-3,1-diyl))bis(cyclopropane-1-carboxylic acid) |
| I-46 | 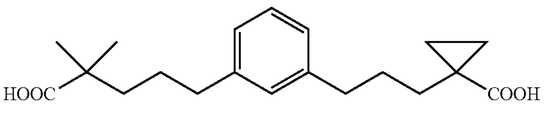 [SMILES: CC(C)(CCCc1cccc(CCCC2(C(=O)O)CC2)c1)C(=O)O] 1-(3-(3-(4-carboxy-4-methylpentyl)phenyl)propyl)cyclopropane-1-carboxylic acid |
| I-47 | 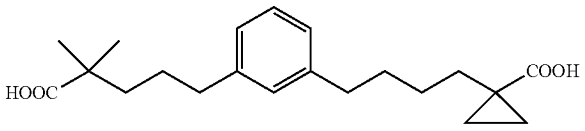 [SMILES: CC(C)(CCCc1cccc(CCCCC2(C(=O)O)CC2)c1)C(=O)O] 1-(4-(3-(4-carboxy-4-methylpentyl)phenyl)butyl)cyclopropane-1-carboxylic acid |

TABLE A-17-continued

| Compound No. | Structure and Name |
|---|---|
| I-48 | 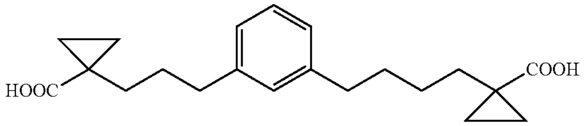 [SMILES: O=C(O)C1(CCCCc2cccc(CCCC3(C(=O)O)CC3)c2)CC1]<br>1-(3-(3-(4-(1-carboxycyclopropyl)butyl)phenyl)propyl)cyclopropane-1-carboxylic acid |
| I-49 | 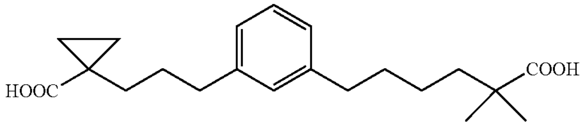 [SMILES: CC(C)(CCCCc1cccc(CCCC2(C(=O)O)CC2)c1)C(=O)O]<br>1-(3-(3-(5-carboxy-5-methylhexyl)phenyl)propyl)cyclopropane-1-carboxylic acid |
| I-50 | 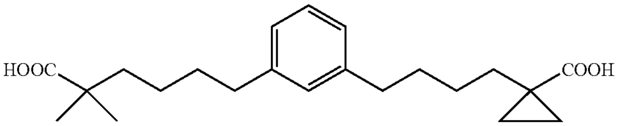 [SMILES: CC(C)(CCCCc1cccc(CCCCC2(C(=O)O)CC2)c1)C(=O)O]<br>1-(4-(3-(5-carboxy-5-methylhexyl)phenyl)butyl)cyclopropane-1-carboxylic acid |
| I-51 | 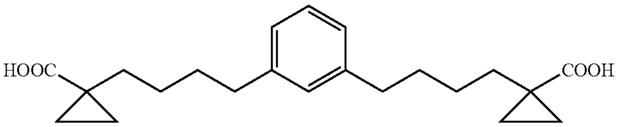 [SMILES: O=C(O)C1(CCCCc2cccc(CCCCC3(C(=O)O)CC3)c2)CC1]<br>1,1'-(1,3-phenylenebis(butane-4,1-diyl))bis(cyclopropane-1-carboxylic acid) |

Compounds of Table A-18

In some embodiments, the compound of the invention is a compound having any one of the structures shown in Table A-18, or a pharmaceutically acceptable salt or solvate thereof. In some embodiments, the pharmaceutically acceptable salt of a compound having any one of the structures shown in Table A-18 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt. In some embodiments, the pharmaceutically acceptable salt of a compound having any one of the structures shown in Table A-18 is a zinc salt.

TABLE A-18

| Compound No. | Structure and Name |
|---|---|
| I-86 | 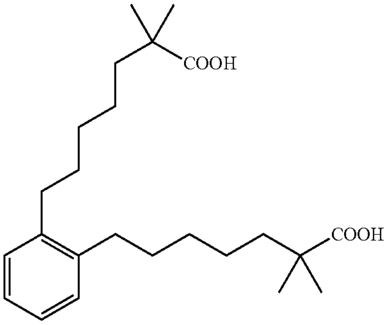 [SMILES: CC(C)(CCCCCc1ccccc1CCCCCC(C)(C)C(=O)O)C(=O)O]<br>7,7'-(1,2-phenylene)bis(2,2-dimethylheptanoic acid) |

TABLE A-18-continued
| Compound No. | Structure and Name |
| --- | --- |
| I-79 | 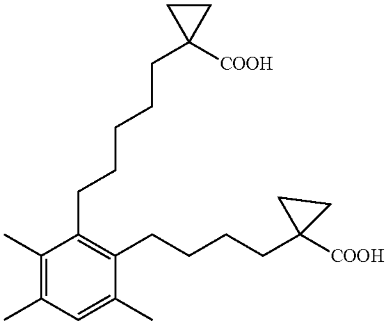 [SMILES: Cc1cc(C)c(CCCCC2(C(=O)O)CC2)c(CCCCCC2(C(=O)O)CC2)c1C] 1-(5-(2-(4-(1-carboxycyclopropyl)butyl)-3,5,6-trimethylphenyl)pentyl)cyclopropane-1-carboxylic acid |
| I-80 | 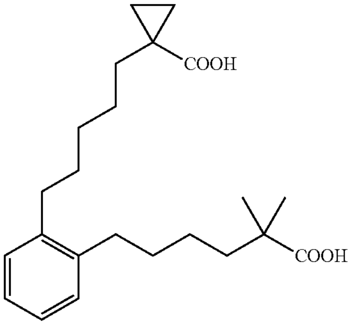 [SMILES: CC(C)(CCCCc1ccccc1CCCCCC1(C(=O)O)CC1)C(=O)O] 71-(5-(2-(5-carboxy-5-methylhexyl)phenyl)pentyl)cyclopropane-1-carboxylic acid |
| I-81 | 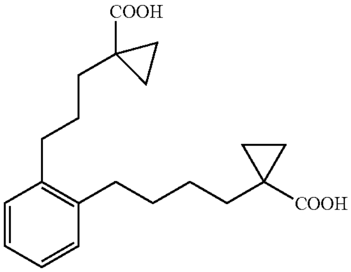 [SMILES: O=C(O)C1(CCCCc2ccccc2CCCC2(C(=O)O)CC2)CC1] 1-(3-(2-(4-(1-carboxycyclopropyl)butyl)phenyl)propyl)cyclopropane-1-carboxylic acid |
| I-82 | 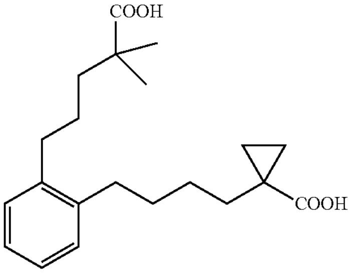 [SMILES: CC(C)(CCCc1ccccc1CCCCC1(C(=O)O)CC1)C(=O)O] 1-(4-(2-(4-carboxy-4-methylpentyl)phenyl)butyl)cyclopropane-1-carboxylic acid |

TABLE A-18-continued

| Compound No. | Structure and Name |
| --- | --- |
| I-83 | 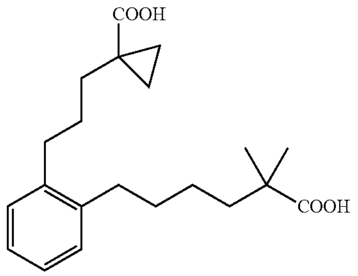 [SMILES: CC(C)(CCCCc1ccccc1CCCC1(C(=O)O)CC1)C(=O)O] 1-(3-(2-(5-carboxy-5-methylhexyl)phenyl)propyl)cyclopropane-1-carboxylic acid |
| I-87 | 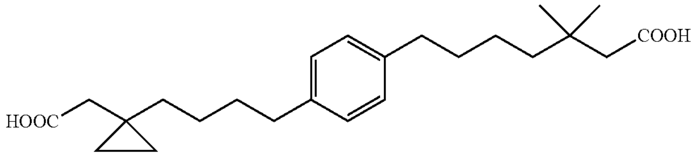 [SMILES: CC(C)(CCCCc1ccc(CCCCC2(CC(=O)O)CC2)cc1)CC(=O)O] 7-(4-(4-(1-(carboxymethyl)cyclopropyl)butyl)phenyl)-3,3-dimethylheptanoic acid |
| I-88 | 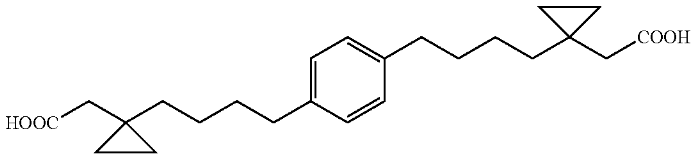 [SMILES: O=C(O)CC1(CCCCc2ccc(CCCCC3(CC(=O)O)CC3)cc2)CC1] 2,2'-((1,4-phenylenebis(butane-4,1-diyl))bis(cyclopropane-1,1-diyl))diacetic acid |
| I-89 | 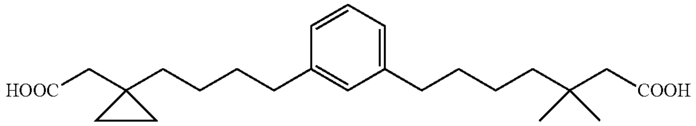 [SMILES: CC(C)(CCCCc1cccc(CCCCC2(CC(=O)O)CC2)c1)CC(=O)O] 7-(3-(4-(1-(carboxymethyl)cyclopropyl)butyl)phenyl)-3,3-dimethylheptanoic acid |
| I-90 | 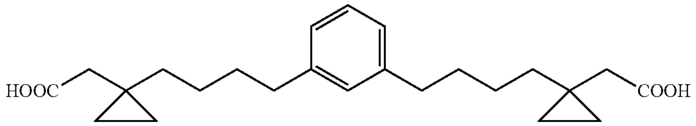 [SMILES: O=C(O)CC1(CCCCc2cccc(CCCCC3(CC(=O)O)CC3)c2)CC1] 2,2'-((1,3-phenylenebis(butane-4,1-diyl))bis(cyclopropane-1,1-diyl))diacetic acid |
| I-92 | 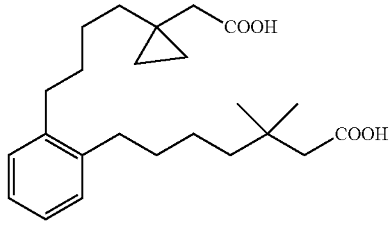 [SMILES: CC(C)(CCCCc1ccccc1CCCCC1(CC(=O)O)CC1)CC(=O)O] 7-(2-(4-(1-(carboxymethyl)cyclopropyl)butyl)phenyl)-3,3-dimethylheptanoic acid |

TABLE A-18-continued

| Compound No. | Structure and Name |
|---|---|
| I-93 | 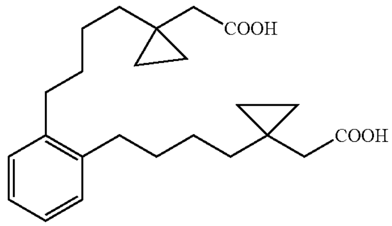 [SMILES: O=C(O)CC1(CCCCc2ccccc2CCCCC2(CC(=O)O)CC2)CC1]<br>2,2'-((1,2-phenylenebis(butane-4,1-diyl))bis(cyclopropane-1,1-diyl))diacetic acid |
| I-98 | 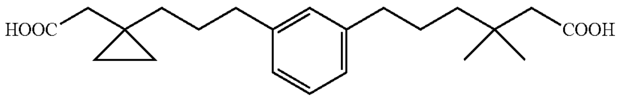 [SMILES: CC(C)(CCCc1cccc(CCCC2(CC(=O)O)CC2)c1)CC(=O)O]<br>6-(3-(3-(1-(carboxymethyl)cyclopropyl)propyl)phenyl)-3,3-dimethylhexanoic acid |
| I-99 | 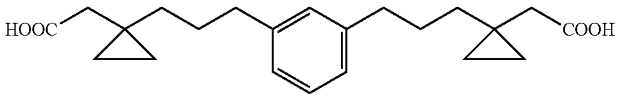 [SMILES: O=C(O)CC1(CCCc2cccc(CCCC3(CC(=O)O)CC3)c2)CC1]<br>2,2'-((1,3-phenylenebis(propane-3,1-diyl))bis(cyclopropane-1,1-diyl))diacetic acid |

Compounds of Table A-19

In some embodiments, the compound of the invention is a compound having any one of the structures shown in Table A-19, defined by $C^1$, $C^2$, and R, or a pharmaceutically acceptable salt or solvate thereof. In some embodiments, the compound of Formula (I) has any one of the structures shown in Table A-19, or a pharmaceutically acceptable salt or solvate thereof, where at least one of $C^1$ or $C^2$ is CO—CoA. In some embodiments, the compound of Formula (ID) has any one of the structures shown in Table A-19, or a pharmaceutically acceptable salt or solvate thereof, where at least one R is F, Cl, Br, —$CF_3$, or —O($C_1$-$C_4$ alkyl). In some embodiments, R of the compound is $CH_3$. In some embodiments, at least one R of the compound of Table A-19 is $CH_3$. In some embodiments, at least one R of the compound of Table A-19 is F. In some embodiments, at least one R of the compound of Table A-19 is Cl. In some embodiments, at least one R of the compound of Table A-19 is Br. In some embodiments, at least one R of the compound of Table A-19 is $CF_3$.

In some embodiments, the pharmaceutically acceptable salt of a compound having any one of the structures shown in Table A-19 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt. In some embodiments, the pharmaceutically acceptable salt of a compound having any one of the structures shown in Table A-19 is a zinc salt.

TABLE A-19

| Structure |
|---|
| 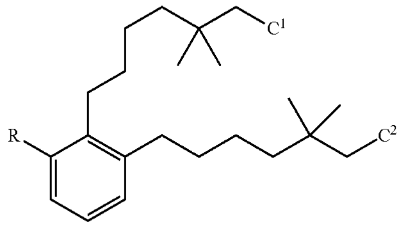<br>wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 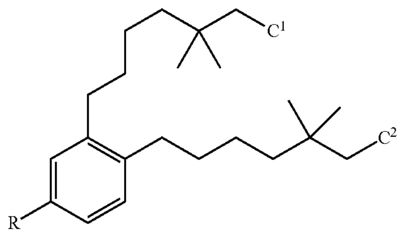<br>wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |

TABLE A-19-continued

| Structure |
|---|
| 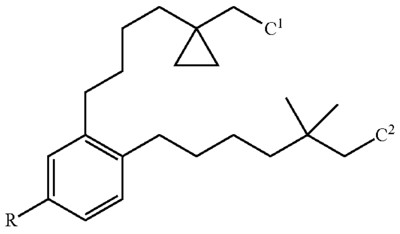 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 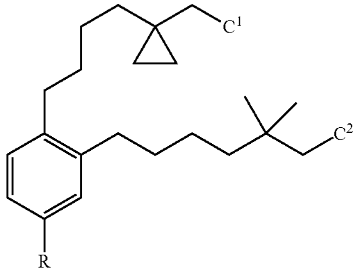 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 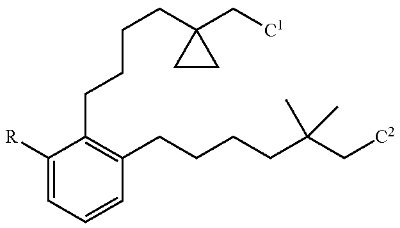 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 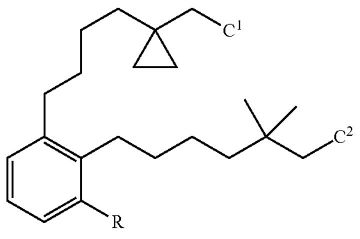 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |

TABLE A-19-continued

| Structure |
|---|
| 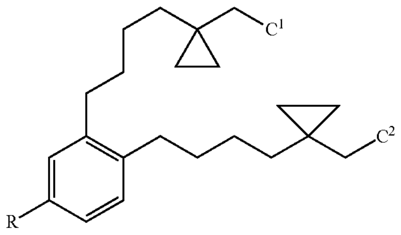 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 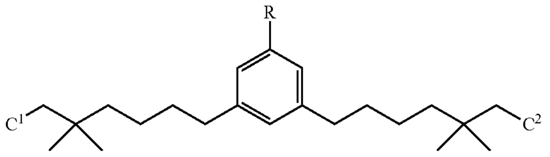 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 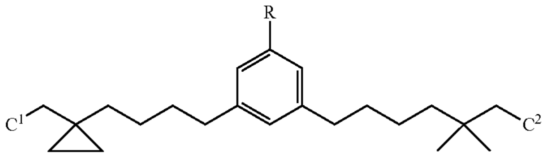 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C′-C4)alkyl, O(C1-C4)alkyl, F, Br, I, or $CF_3$ |
| 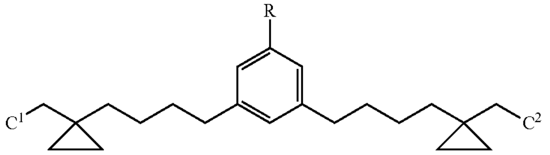 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 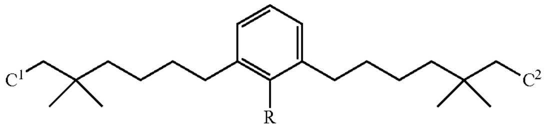 |
| wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |

TABLE A-19-continued

| Structure |
| --- |
| 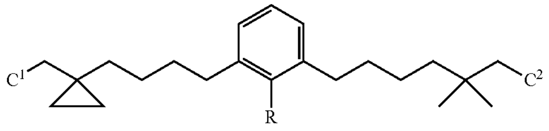 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (Cl-C4)alkyl, O(C1-C4)alkyl, F, Br, I, or $CF_3$ |
| 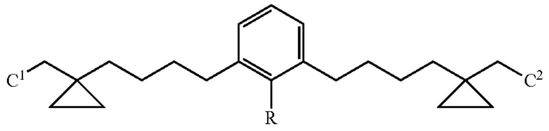 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 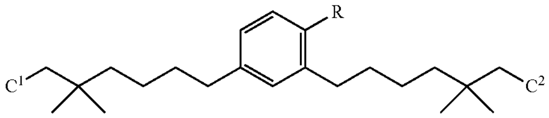 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 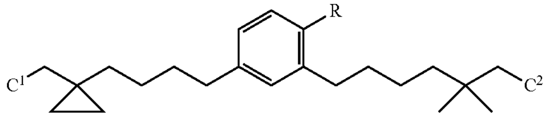 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 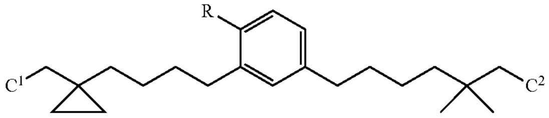 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 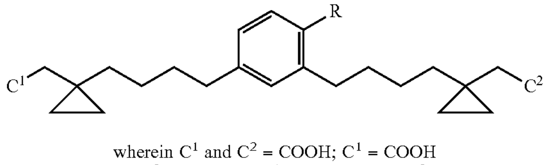 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |

TABLE A-19-continued

| Structure |
| --- |
| 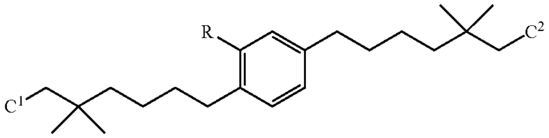 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 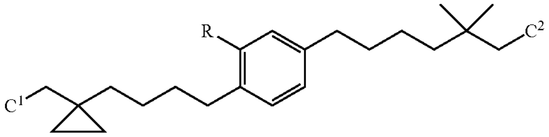 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 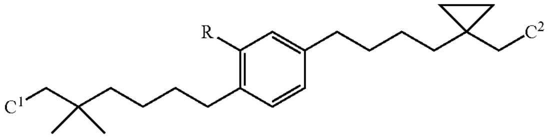 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, F, Br, I, or $CF_3$ |
| 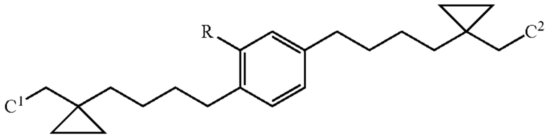 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein R = (C1-C4)alkyl, O(C1-C4)alkyl, |
| 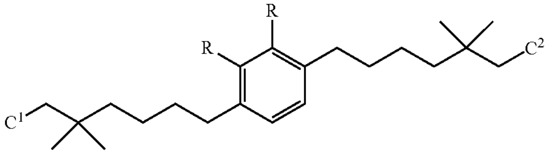 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |
| 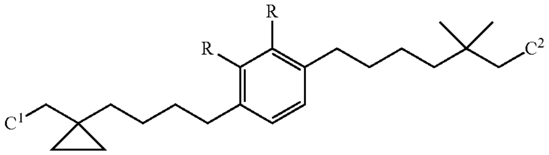 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and |

TABLE A-19-continued

| Structure |
|---|
| wherein each R is independently a (C1-C4)alkyl, O(C1-C4)alkyl, F, Br, I, or $CF_3$ |
| 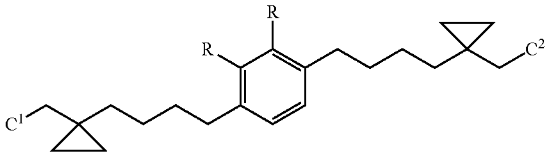 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |
| 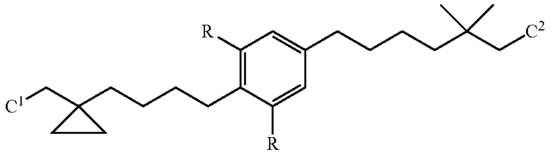 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |
| 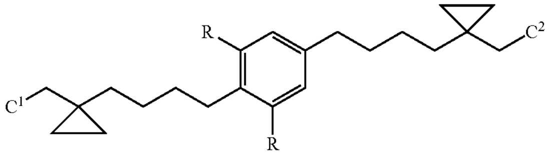 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl), F, Br, I, or $CF_3$ |
| 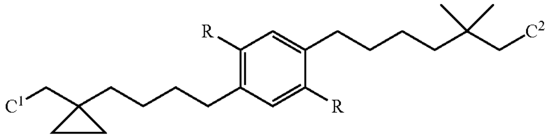 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |
| 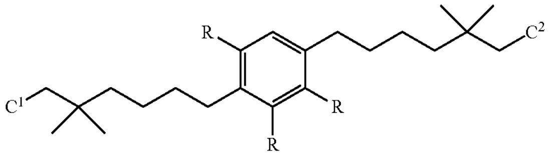 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |

TABLE A-19-continued

| Structure |
|---|
| 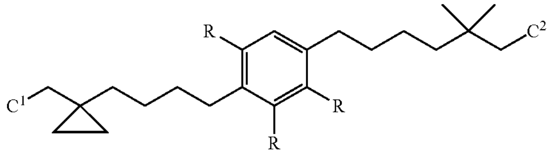 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |
| 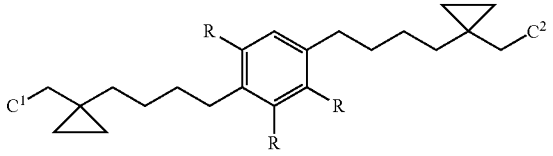 wherein $C^1$ and $C^2$ = COOH; $C^1$ = COOH and $C^2$ = CO-CoA; $C^1$ = CO-CoA and $C^2$ = COOH; or $C^1$ and $C^2$ = CO-CoA; and wherein each R is independently a (C1-C4)alkyl, O(C1-C4)alkyl, F, Br, I, or $CF_3$ |

Pharmaceutically Acceptable Salts of Compounds of Formula (I)

In some embodiments, the compound of the invention is a pharmaceutically acceptable salt of a compound of Formula (I):

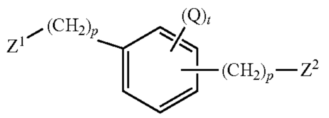

(I)

wherein:

each p is independently 1, 2, 3, 4, 5, 6, or 7;

each $Z^1$ and $Z^2$ is independently —$C(R^1)(R^2)$—$(CH_2)_c$—X or —W—$(CH_2)_c$—$C(R^3)(R^4)$—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

Q is independently —OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —$CF_3$, —$COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

t is 0, 1, 2, 3, or 4;

each X and Y is independently —OH, —COOH, —$COOR^5$, —$CONH_2$, —$CONHR^5$, —CONHMs, —CONHTs, —$SO_3H$,

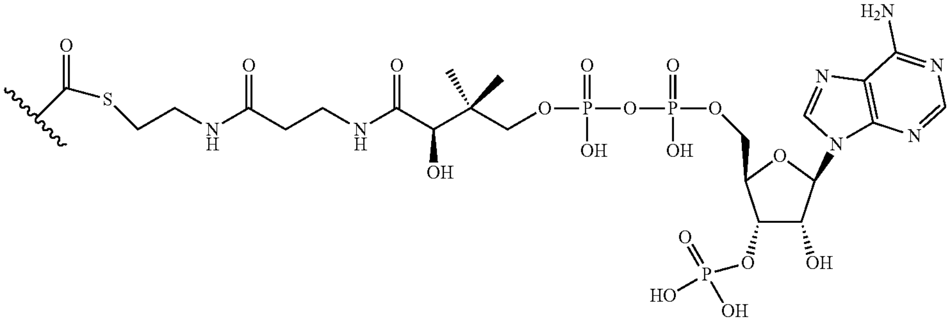
(-CO-CoA),
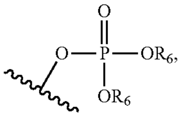, 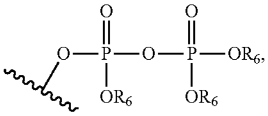, 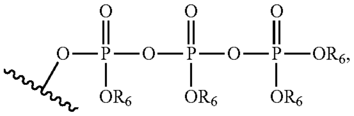, 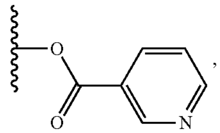,
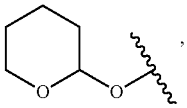, 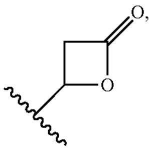, 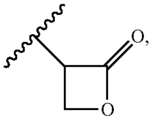, 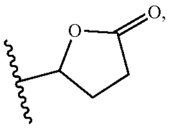, 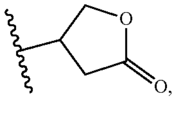, 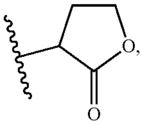,
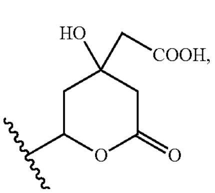, 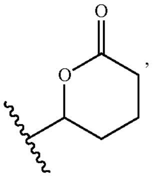, 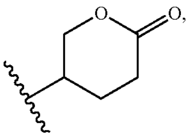, 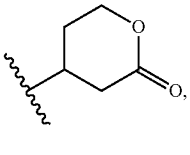, 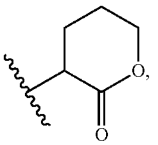,
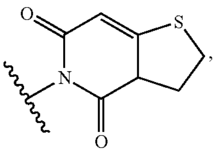, 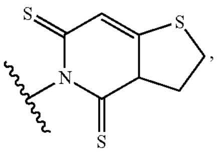, 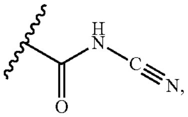, 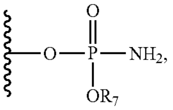, 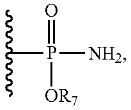,
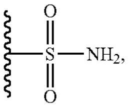, 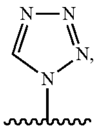, 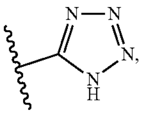, 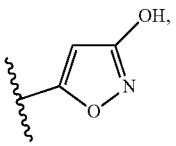, 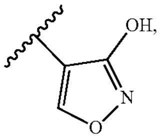, 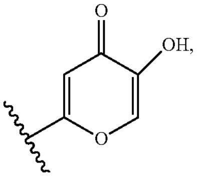,
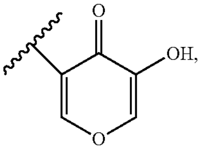, 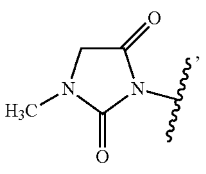, 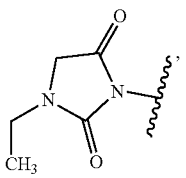, 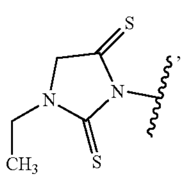, 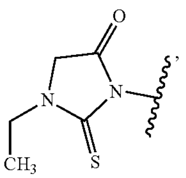, or
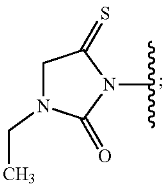;

each $R^6$ is independently H, $-C_1-C_6$ alkyl, $-C_2-C_6$ alkenyl, or $-C_2-C_6$ alkynyl, wherein the $-C_1-C_6$ alkyl, $-C_2-C_6$ alkenyl, or $-C_2-C_6$ alkynyl is unsubstituted or substituted with one or two halogen, —OH, $-O(C_1-C_6$ alkyl), or phenyl groups;

each $R^7$ is independently H, $-C_1-C_6$ alkyl, $-C_2-C_6$ alkenyl, or $-C_2-C_6$ alkynyl;

each W is independently —O—, —NH—, —N(OH)—, —N(→O)—, —S—, —S(=O)—, $-S(O)_2-$, or —Se—;

each $R^5$ is independently $-C_1-C_6$ alkyl, $-C_2-C_6$ alkenyl, $-C_2-C_6$ alkynyl, phenyl, or benzyl, each being unsubstituted or substituted with one or more halogen, —OH, $-O(C_1-C_6$ alkyl), or phenyl groups; and wherein the pharmaceutically acceptable salt is a salt of an amino acid, a meglumine salt, an eglumine salt, a D-glucamine salt, or a glucosamine salt, or a choline salt.

In some embodiments, the pharmaceutically acceptable salt of a compound of Formula (I) is a pharmaceutically acceptable salt of Formula (IA), Formula (IB), or Formula (IC):

(IA)

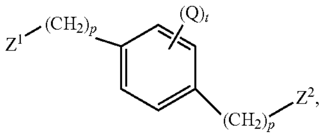

(IB)

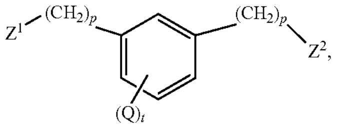

or (IC)

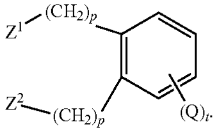

In some embodiments of the pharmaceutically acceptable salt of the compound of Formula (I), (IA), (IB), or (IC), the salt is a salt of an amino acid, and the amino acid is a D,L-amino acid, L-amino acid, or D-amino acid. In some embodiments, the amino acid is a natural amino acid or a synthetic amino acid. In some embodiments, the amino acid is a basic amino acid. In some embodiments, the amino acid is lysine, arginine histidine, or glutamine. In some embodiments, the amino acid is L-lysine, L-arginine, L-histidine, or L-glutamine. In some embodiments, the pharmaceutically acceptable salt is a meglumine salt, an eglumine salt, or a D-glucamine salt. In some embodiments, the pharmaceutically acceptable salt is a choline salt In some embodiments of the pharmaceutically acceptable salt of the compounds of Formula (I), (IA), (IB), or (IC), $Z^1$ and $Z^2$ are each independently $-C(R^1)(R^2)-(CH_2)_c-COOH$ or $-C(R^1)(R^2)-(CH_2)_c-COOR^5$.

In some embodiments of the pharmaceutically acceptable salt of the compounds of Formula (I), (IA), (IB), or (IC), each $R^1$ and $R^2$ is independently $-C_1-C_6$ alkyl, $-C_2-C_6$ alkenyl, or $-C_2-C_6$ alkynyl. In some embodiments, each $R^1$ and $R^2$ is independently $-C_1-C_3$ alkyl, $-C_2-C_3$ alkenyl, or $-C_2-C_3$ alkynyl. In some embodiments, $R^1$ and $R^2$ are methyl.

In some embodiments of the pharmaceutically acceptable salt of the compounds of Formula (I), (IA), (IB), or (IC), c is 0 or 1. In some embodiments, c is 0. In some embodiments, c is 1. In some embodiments, c is 2. In some embodiments, c is 3.

In some embodiments of the pharmaceutically acceptable salt of the compounds of Formula (I), (IA), (IB), or (IC), each carbon atom together with the $R^1$ and $R^2$ attached to the carbon atom independently form a $-C_3-C_7$ cycloalkyl group. In some embodiments, each carbon atom together with the $R^1$ and $R^2$ attached to the carbon atom independently form a cyclopropyl ring.

In some embodiments of the pharmaceutically acceptable salt of the compounds of Formula (I), (IA), (IB), or (IC), at least one $R^1$ and one $R^2$ together with the carbon atom to which they are attached form a $-C_3-C_7$ cycloalkyl group. In some embodiments, at least one $R^1$ and one $R^2$ together with the carbon atom to which they are attached form a cyclopropyl ring.

In some embodiments of the pharmaceutically acceptable salt of the compounds of Formula (I), (IA), (IB), or (IC), $R^3$ and $R^4$ is independently H, $-C_1-C_6$ alkyl, $-C_2-C_6$ alkenyl, or $-C_2-C_6$ alkynyl.

In some embodiments of the pharmaceutically acceptable salt of the compounds of Formula (I), (IA), (IB), or (IC), Y is —COOH or $-COOR^5$.

In some embodiments of the pharmaceutically acceptable salt of the compounds of Formula (I), (IA), (IB), or (IC), $R^5$ is $-C_1-C_6$ alkyl, $-C_2-C_6$ alkenyl, or $-C_2-C_6$ alkynyl. In some embodiments, $R^5$ is $-C_1-C_3$ alkyl, $-C_2-C_3$ alkenyl, or $-C_2-C_3$ alkynyl.

In some embodiments of the pharmaceutically acceptable salt of the compounds of Formula (I), (IA), (IB), or (IC), p is 3, 4, 5, 6, or 7. In some embodiments, p is 4, 5, 6, or 7.

In some embodiments of the pharmaceutically acceptable salt of the compounds of Formula (I), (IA), (IB), or (IC), $Z^1$ and $Z^2$ are each independently $-W-(CH_2)_c-C(R^3)(R^4)-Y$, and $R^3$ and $R^4$ is independently H, $-C_1-C_6$ alkyl, $-C_2-C_6$ alkenyl, or $-C_2-C_6$ alkynyl. In some embodiments, Y is —CO—CoA, —COOH or $-COOR^5$.

In some embodiments of the pharmaceutically acceptable salt of the compound of Formula (I), (IA), (IB), or (IC), Q is independently methyl, —OH, F, Cl, Br, $-CF_3$, or $-O(C_1-C_4$ alkyl). In some embodiments, Q is independently methyl, —OH, F, Cl, Br, $-CF_3$, or methoxy. In some embodiments, Q is independently methyl, methoxy, or —OH. In some embodiments, Q is methyl or —OH.

In some embodiments of the pharmaceutically acceptable salt of the compound of Formula (I), (IA), (IB), or (IC), t is 0. In some embodiments, t is 1. In some embodiments, t is 2. In some embodiments, t is 3.

In some embodiments, the pharmaceutically acceptable salt of the compound of Formula (I) or (IA) is the pharmaceutically acceptable salt of any one of the structures shown in Table A-7, Table A-8, Table A-9, Table A-10, Table A-11, or Table A-12.

Compounds of Formula (II)

In some embodiments, the compound of the invention is a compound of Formula (II):

(II)

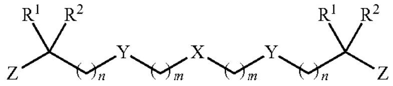

or a pharmaceutically acceptable salt or solvate thereof, wherein:

each $R^1$ and $R^2$ is independently H, —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each n is independently 0, 1, 2, or 3;

each m is independently 1, 2, 3, 4, 5, 6, 7, 8 or 9;

X is —C(═O)—, —CH$R^3$—, —CH—$CH_2(OR^3)$—, —O—, —S—, —S(═O)—, —$S(O)_2$—, —$NR_3$—, —N(OH)—, —N(→O)—, or —Se—;

$R^3$ is H, —OH, —O($C_1$-$C_6$ alkyl), —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$cycloalkynyl, phenyl, or benzyl, each —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$ cycloalkynyl, phenyl and benzyl being unsubstituted or substituted with one or more halogen, —CN, —$NO_2$, or —$CF_3$ groups;

each Y is independently —O—, —NH—, —N(OH)—, —N(→O)—, —S—, —S(═O)—, —$S(O)_2$—, or —Se—;

each Z is independently —OH, —COOH, —COO$R^5$, —CO—CoA, —$CONH_2$, —CONH$R^5$, —CONHMs, —CONHTs, —$SO_3H$, —$SO_3R^5$,

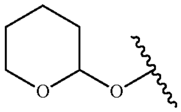 ,
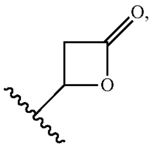
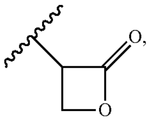
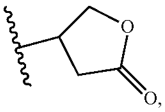
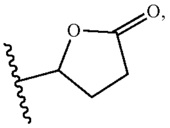
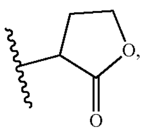
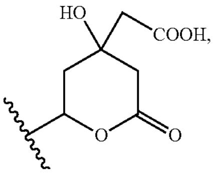
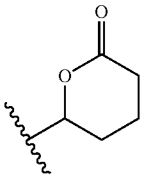 ,
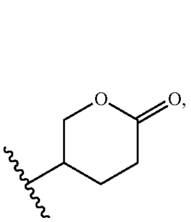
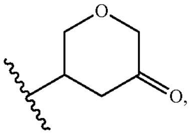
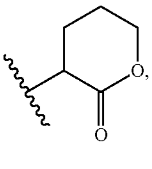
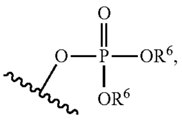

-continued

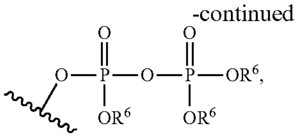
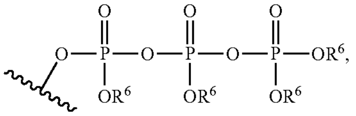
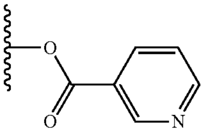 ,
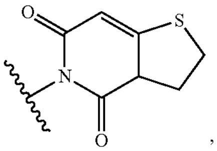 ,
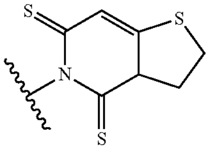 ,
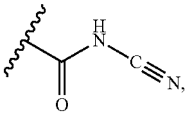
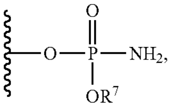
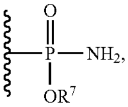
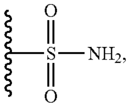
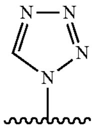 ,
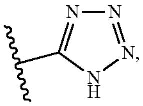
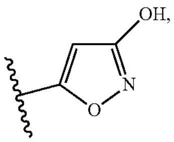
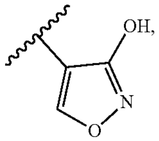
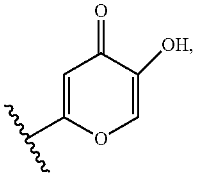
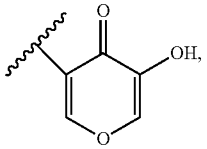
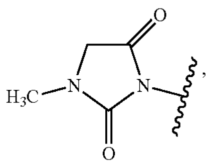
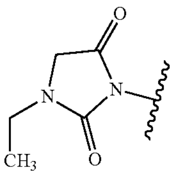 ,
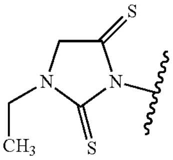 ,
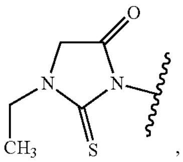 , or
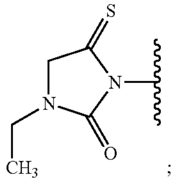 ;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein one or both Z groups is —CO—CoA.

In some embodiments of compounds of Formula (II), X is —C(═O)—, —$CHR^3$—, —O—, —S—, —S(═O)—, or Se. In some embodiments, X is —C(═O)—, —CH(OH)—, —O—, —S—, —S(═O)—, or Se.

In some embodiments of compounds of Formula (II), $R^3$ is H, —OH, —O($C_1$-$C_3$ alkyl), or —$C_1$-$C_3$ alkyl.

In some embodiments of compounds of Formula (II), each Y is independently —O— or —S—.

In some embodiments of compounds of Formula (II), each $R^1$ and $R^2$ is independently H, —$C_1$-$C_3$ alkyl, —$C_2$-$C_3$ alkenyl, or —$C_2$-$C_3$ alkynyl. In some embodiments, each $R^1$ and $R^2$ is independently H or methyl.

In some embodiments of compounds of Formula (II), each Z is independently —COOH or —$COOR^5$. In some embodiments, each Z is —COOH.

In some embodiments of compounds of Formula (II), each $R^5$ is independently —$C_1$-$C_3$ alkyl, —$C_2$-$C_3$ alkenyl, or —$C_2$-$C_3$ alkynyl.

In some embodiments of compounds of Formula (II), each n is independently 0, 1, or 2. In some embodiments, n is 1.

In some embodiments of compounds of Formula (II), each m is independently 3, 4, 5, or 6. In some embodiments, each m is independently 4 or 5.

In some embodiments, the compound of Formula (II) has any one of the structures shown in Table B1, defined by $C^1$ and $C^2$, or a pharmaceutically acceptable salt or solvate thereof.

In some embodiments, the compound of Formula (II) is a Coenzyme A mono(thioester) or di(thioester) of a compound having any one of the structures shown in Table B2, or a pharmaceutically acceptable salt or solvate thereof.

TABLE B1

| Structure and Name |
|---|
| 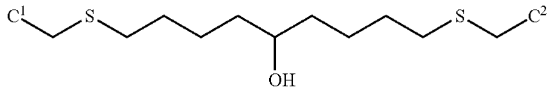 |
| wherein $C^1$ = COOH and $C^2$ = CO-CoA; $C^1$ = CO-CoA and $C^2$ = COOH; or $C^1$ and $C^2$ = CO-CoA |
| 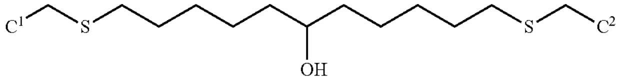 |
| wherein $C^1$ = COOH and $C^2$ = CO-CoA; $C^1$ = CO-CoA and $C^2$ = COOH; or $C^1$ and $C^2$ = CO-CoA |
| 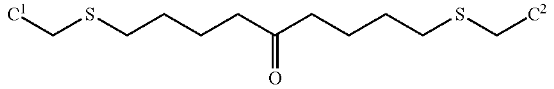 |
| wherein $C^1$ = COOH and $C^2$ = CO-CoA; $C^1$ = CO-CoA and $C^2$ = COOH; or $C^1$ and $C^2$ = CO-CoA |
| 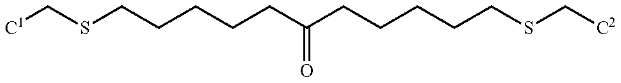 |
| wherein $C^1$ = COOH and $C^2$ = CO-CoA; $C^1$ = CO-CoA and $C^2$ = COOH; or $C^1$ and $C^2$ = CO-CoA |
| 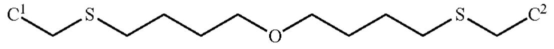 |
| wherein $C^1$ = COOH and $C^2$ = CO-CoA; $C^1$ = CO-CoA and $C^2$ = COOH; or $C^1$ and $C^2$ = CO-CoA |
| 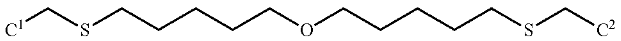 |
| wherein $C^1$ = COOH and $C^2$ = CO-CoA; $C^1$ = CO-CoA and $C^2$ = COOH; or $C^1$ and $C^2$ = CO-CoA |
| 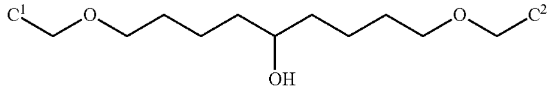 |
| wherein $C^1$ = COOH and $C^2$ = CO-CoA; $C^1$ = CO-CoA and $C^2$ = COOH; or $C^1$ and $C^2$ = CO-CoA |
| 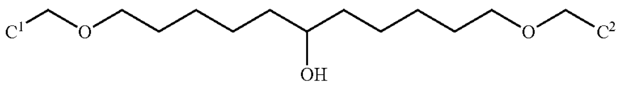 |
| wherein $C^1$ = COOH and $C^2$ = CO-CoA; $C^1$ = CO-CoA and $C^2$ = COOH; or $C^1$ and $C^2$ = CO-CoA |

TABLE B1-continued

| Structure and Name |
|---|
| 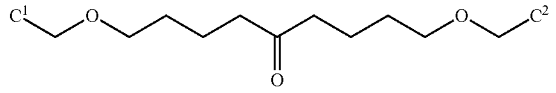 |
| wherein $C^1$ = COOH and $C^2$ = CO-CoA; $C^1$ = CO-CoA and $C^2$ = COOH; or $C^1$ and $C^2$ = CO-CoA |
| 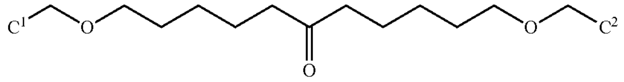 |
| wherein $C^1$ = COOH and $C^2$ = CO-CoA; $C^1$ = CO-CoA and $C^2$ = COOH; or $C^1$ and $C^2$ = CO-CoA |
| 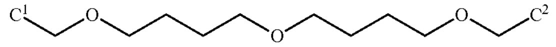 |
| wherein $C^1$ = COOH and $C^2$ = CO-CoA; $C^1$ = CO-CoA and $C^2$ = COOH; or $C^1$ and $C^2$ = CO-CoA |
| 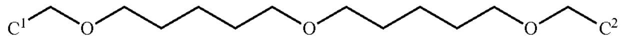 |
| wherein $C^1$ = COOH and $C^2$ = CO-CoA; $C^1$ = CO-CoA and $C^2$ = COOH; or $C^1$ and $C^2$ = CO-CoA |
| 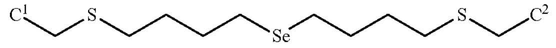 |
| wherein $C^1$ = COOH and $C^2$ = CO-CoA; $C^1$ = CO-CoA and $C^2$ = COOH; or $C^1$ and $C^2$ = CO-CoA |
| 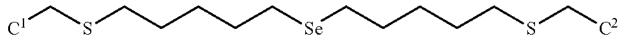 |
| wherein $C^1$ = COOH and $C^2$ = CO-CoA; $C^1$ = CO-CoA and $C^2$ = COOH; or $C^1$ and $C^2$ = CO-CoA |
| 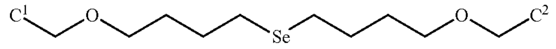 |
| wherein $C^1$ = COOH and $C^2$ = CO-CoA; $C^1$ = CO-CoA and $C^2$ = COOH; or $C^1$ and $C^2$ = CO-CoA |
| 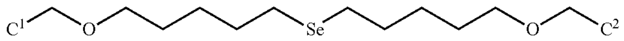 |
| wherein $C^1$ = COOH and $C^2$ = CO-CoA; $C^1$ = CO-CoA and $C^2$ = COOH; or $C^1$ and $C^2$ = CO-CoA |
| 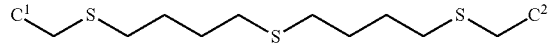 |
| wherein $C^1$ = COOH and $C^2$ = CO-CoA; $C^1$ = CO-CoA and $C^2$ = COOH; or $C^1$ and $C^2$ = CO-CoA |
| 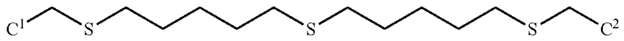 |
| wherein $C^1$ = COOH and $C^2$ = CO-CoA; $C^1$ = CO-CoA and $C^2$ = COOH; or $C^1$ and $C^2$ = CO-CoA |
| 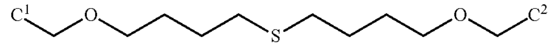 |
| wherein $C^1$ = COOH and $C^2$ = CO-CoA; $C^1$ = CO-CoA and $C^2$ = COOH; or $C^1$ and $C^2$ = CO-CoA |
| 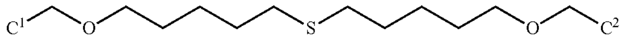 |
| wherein $C^1$ = COOH and $C^2$ = CO-CoA; $C^1$ = CO-CoA and $C^2$ = COOH; or $C^1$ and $C^2$ = CO-CoA |
| 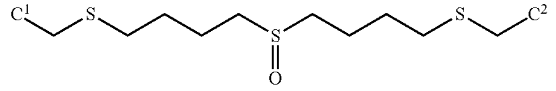 |
| wherein $C^1$ = COOH and $C^2$ = CO-CoA; $C^1$ = CO-CoA and $C^2$ = COOH; or $C^1$ and $C^2$ = CO-CoA |
| 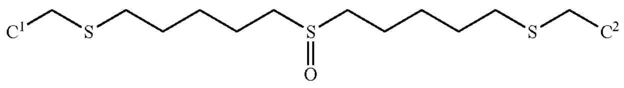 |
| wherein $C^1$ = COOH and $C^2$ = CO-CoA; $C^1$ = CO-CoA and $C^2$ = COOH; or $C^1$ and $C^2$ = CO-CoA |

TABLE B1-continued

| Structure and Name |
|---|
| 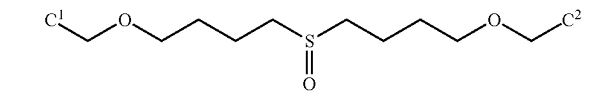 |
| wherein $C^1$ = COOH and $C^2$ = CO-CoA; $C^1$ = CO-CoA and $C^2$ = COOH; or $C^1$ and $C^2$ = CO-CoA |
| 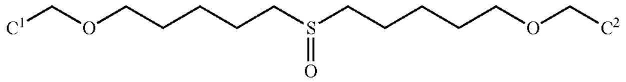 |
| wherein $C^1$ = COOH and $C^2$ = CO-CoA; $C^1$ = CO-CoA and $C^2$ = COOH; or $C^1$ and $C^2$ = CO-CoA |

TABLE B2

| Compound No. | Structure and Name |
|---|---|
| II-1 | 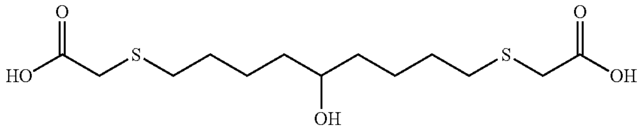 [SMILES: O=C(O)CSCCCCC(O)CCCCSCC(=O)O] (9-Carboxymethylsulfanyl-5-hydroxy-nonylsulfanyl)-acetic acid |
| II-2 | 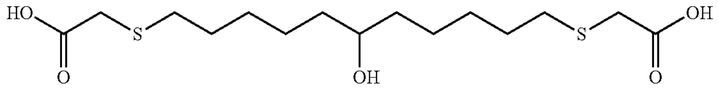 (11-Carboxymethylsulfanyl-6-hydroxy-undecylsulfanyl)-acetic acid |
| II-3 | 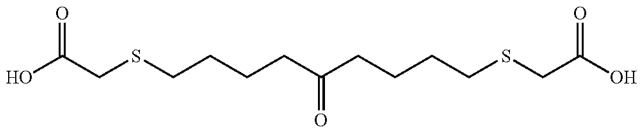 (9-Carboxymethylsulfanyl-5-oxo-nonylsulfanyl)-acetic acid |
| II-4 | 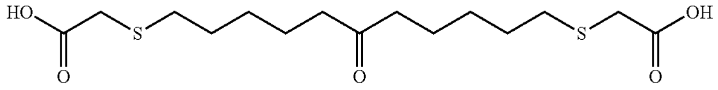 (11-Carboxymethylsulfanyl-6-oxo-undecylsulfanyl)-acetic acid |
| II-5 | 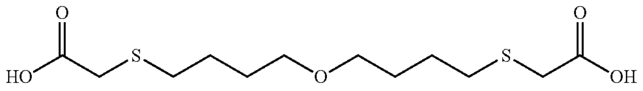 [4-(4-Carboxymethylsulfanyl-butoxy)-butylsulfanyl]-acetic acid |
| II-6 | 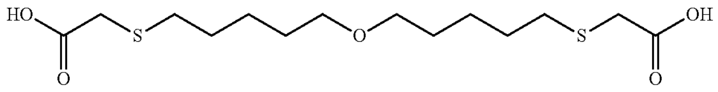 [5-(5-Carboxymethylsulfanyl-pentyloxy)-pentylsulfanyl]-acetic acid |
| II-7 | 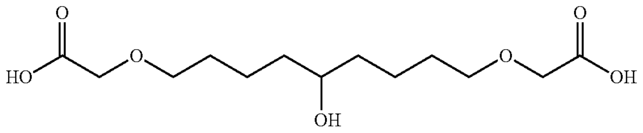 (9-Carboxymethoxy-5-hydroxy-nonyloxy)-acetic acid |

TABLE B2-continued

| Compound No. | Structure and Name |
|---|---|
| II-8 | 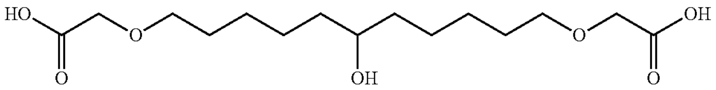 [SMILES: O=C(O)CSCCCCCC(O)CCCCCSCC(=O)O]<br>(11-Carboxymethoxy-6-hydroxy-undecyloxy)-acetic acid |
| II-9 | 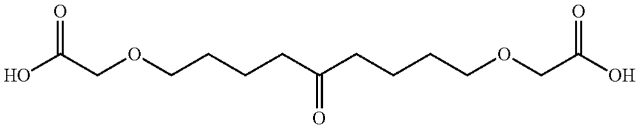 [SMILES: O=C(O)COCCCCC(=O)CCCCOCC(=O)O]<br>(9-Carboxymethoxy-5-oxo-nonyloxy)-acetic acid |
| II-10 | 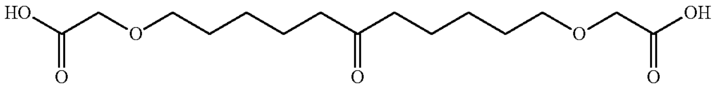<br>(11-Carboxymethoxy-6-oxo-undecyloxy)-acetic acid |
| II-11 | 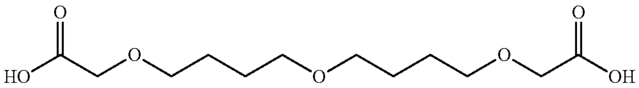<br>[4-(4-Carboxymethoxy-butoxy)-butoxy]-acetic acid |
| II-12 | 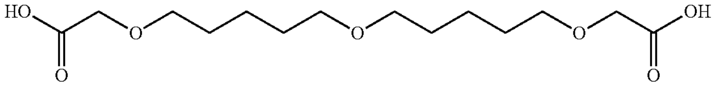 [SMILES: O=C(O)COCCCCCOCCCCCOCC(=O)O]<br>[5-(5-Carboxymethoxy-pentyloxy)-pentyloxy]-acetic acid |
| II-13 | 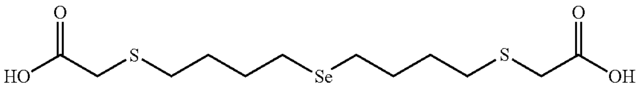<br>[4-(4-Carboxymethylsulfanyl-butylselanyl)-butylsulfanyl]-acetic acid |
| II-14 | 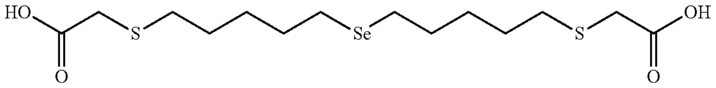<br>[5-(5-Carboxymethylsulfanyl-pentylselanyl)-pentylsulfanyl]-acetic acid |
| II-15 | 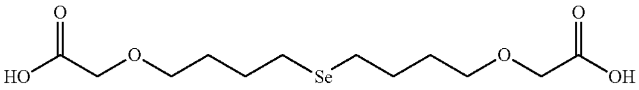 [SMILES: O=C(O)COCCCC[Se]CCCCOCC(=O)O]<br>[4-(4-Carboxymethoxy-butylselanyl)-butoxy]-acetic acid |
| II-16 | 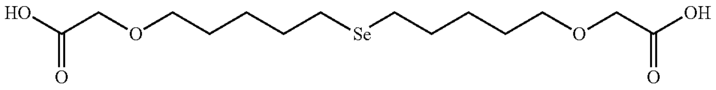 [SMILES: O=C(O)COCCCCC[Se]CCCCCOCC(=O)O]<br>[5-(5-Carboxymethoxy-pentylselanyl)-pentyloxy]-acetic acid |
| II-17 | 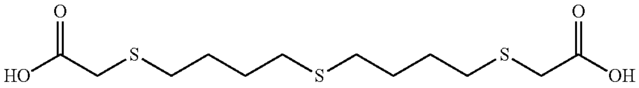<br>[4-(4-Carboxymethylsulfanyl-butylsulfanyl)-butylsulfanyl]-acetic acid |
| II-18 | 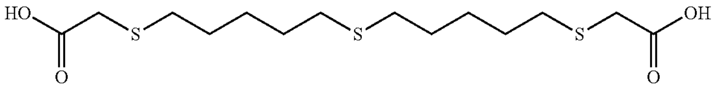<br>[5-(5-Carboxymethylsulfanyl-pentylsulfanyl)-pentylsulfanyl]-acetic acid |

TABLE B2-continued

| Compound No. | Structure and Name |
|---|---|
| II-19 | 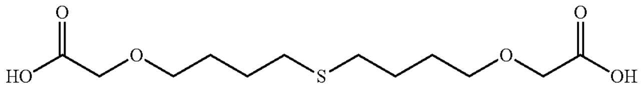 [SMILES: O=C(O)COCCCCSCCCCOCC(=O)O] [4-(4-Carboxymethoxy-butylsulfanyl)-butoxy]-acetic acid |
| II-20 | 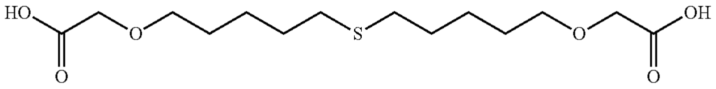 [SMILES: O=C(O)COCCCCCSCCCCCOCC(=O)O] [5-(5-Carboxymethoxy-pentylsulfanyl)-pentyloxy]-acetic acid |
| II-21 | 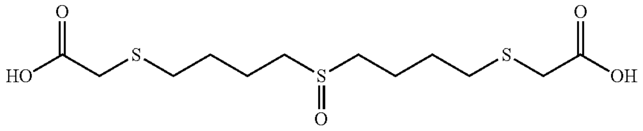 [SMILES: O=C(O)CSCCCCS(=O)CCCCSCC(=O)O] [4-(4-Carboxymethylsulfanyl-butane-1-sulfinyl)-butylsulfanyl]-acetic acid |
| II-22 | 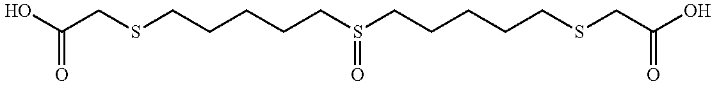 [SMILES: O=C(O)CSCCCCCS(=O)CCCCCSCC(=O)O] [5-(5-Carboxymethylsulfanyl-pentane-1-sulfinyl)-pentylsulfanyl]-acetic acid |
| II-23 | 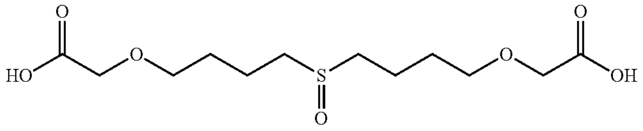 [4-(4-Carboxymethoxy-butane-1-sulfinyl)-butoxy]-acetic acid |
| II-24 | 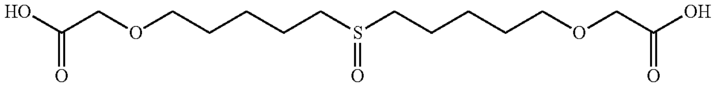 [SMILES: O=C(O)COCCCCCS(=O)CCCCCOCC(=O)O] [5-(5-Carboxymethoxy-pentane-1-sulfinyl)-pentyloxy]-acetic acid |

In some embodiments, the compound of Formula (II), or a pharmaceutically acceptable salt or solvate thereof is isolated and purified. In some embodiments, the compound of Formula (II), or a pharmaceutically acceptable salt or solvate thereof, is ex vivo.

Pharmaceutically Acceptable Salts of Compounds of Formula (II)

In some embodiments, the compound of the invention is a pharmaceutically acceptable salt of a compound of Formula (II):

(II)

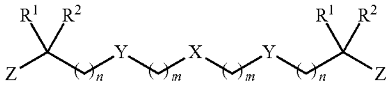

wherein:

each $R^1$ and $R^2$ is independently H, —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each n is independently 0, 1, 2, or 3;

each m is independently 1, 2, 3, 4, 5, 6, 7, 8 or 9;

X is —C(═O)—, —$CHR^3$—, —CH—$CH_2(OR^3)$—, —O—, —S—, —S(═O)—, —$S(O)_2$—, —$NR_3$—, —N(OH)—, —N(→O)—, or —Se—;

$R^3$ is H, —OH, —O($C_1$-$C_6$ alkyl), —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$cycloalkynyl, phenyl, or benzyl, each —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$ cycloalkynyl, phenyl and benzyl being unsubstituted or substituted with one or more halogen, —CN, —$NO_2$, or —$CF_3$ groups;

each Y is independently —O—, —NH—, —N(OH)—, —N(→O)—, —S—, —S(═O)—, —$S(O)_2$—, or —Se—;

each Z is independently —OH, —COOH, —$COOR^5$, —CO—CoA, —$CONH_2$, —$CONHR^5$, —CONHMs, —CONHTs, —$SO_3H$, —$SO_3R^5$,

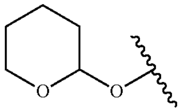,
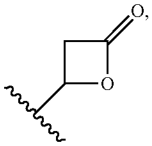
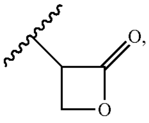
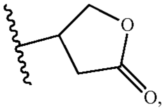
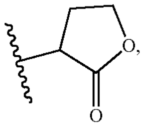
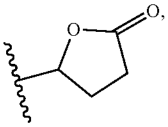
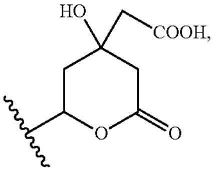
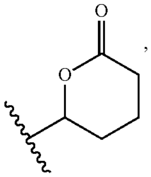,
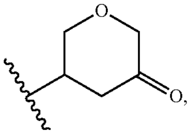
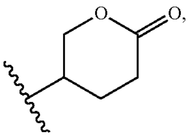
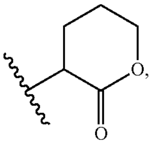
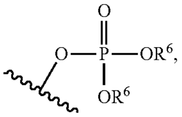
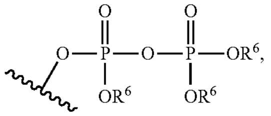
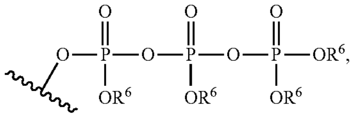
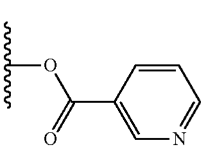,
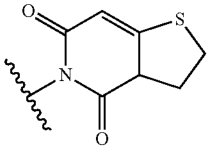,
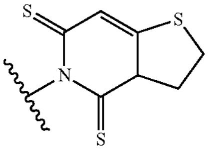,
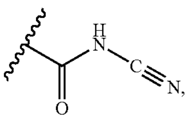
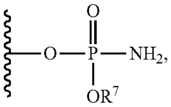
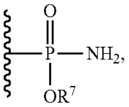
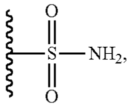

-continued

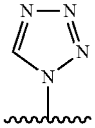,
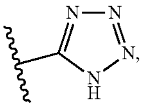
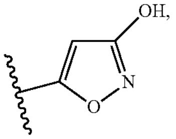
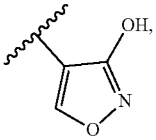
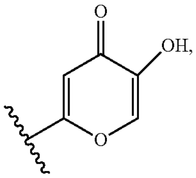
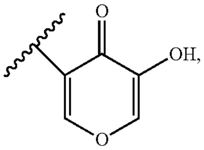
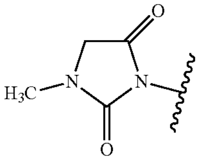
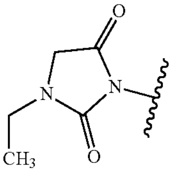,
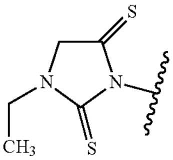,
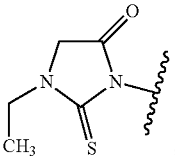, or
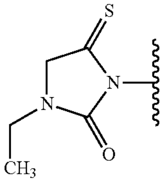;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein the pharmaceutically acceptable salt is a salt of an amino acid, a meglumine salt, an eglumine salt, D-glucamine salt, a glucosamine salt, or a choline salt.

In some embodiments of the pharmaceutically acceptable salt of the compound of Formula (II), the salt is a salt of an amino acid, and the amino acid is a D,L-amino acid, L-amino acid, or D-amino acid. In some embodiments, the amino acid is a natural amino acid or a synthetic amino acid. In some embodiments, the amino acid is a basic amino acid. In some embodiments, the amino acid is lysine, arginine, histidine, or glutamine. In some embodiments, the amino acid is L-lysine, L-arginine, L-histidine or L-glutamine. In some embodiments, the pharmaceutically acceptable salt is a meglumine salt, an eglumine salt, or a D-glucamine salt. In some embodiments, the pharmaceutically acceptable salt is a choline salt.

In some embodiments of the pharmaceutically acceptable salt of the compounds of Formula (II), X is —C(═O)—, —$CHR^3$—, —O—, —S—, —S(═O)—, or Se. In some embodiments, X is —C(═O)—, —CH(OH)—, —O—, —S—, —S(═O)—, or Se.

In some embodiments of the pharmaceutically acceptable salt of the compounds of Formula (II), $R^3$ is H, —OH, —O($C_1$-$C_3$ alkyl), or —$C_1$-$C_3$ alkyl.

In some embodiments of the pharmaceutically acceptable salt of the compounds of Formula (II), each Y is independently —O— or —S—.

In some embodiments of the pharmaceutically acceptable salt of the compounds of Formula (II), each $R^1$ and $R^2$ is independently H, —$C_1$-$C_3$ alkyl, —$C_2$-$C_3$ alkenyl, or —$C_2$-$C_3$ alkynyl. In some embodiments, each $R^1$ and $R^2$ is independently H or methyl.

In some embodiments of the pharmaceutically acceptable salt of the compounds of Formula (II), each Z is independently —COOH or —$COOR^5$. In some embodiments, each Z is —COOH.

In some embodiments of the pharmaceutically acceptable salt of the compounds of Formula (II), each $R^5$ is independently —$C_1$-$C_3$ alkyl, —$C_2$-$C_3$ alkenyl, or —$C_2$-$C_3$ alkynyl.

In some embodiments of the pharmaceutically acceptable salt of the compounds of Formula (II), each n is independently 0, 1, or 2. In some embodiments, n is 1.

In some embodiments of the pharmaceutically acceptable salt of the compounds of Formula (II), each m is independently 3, 4, 5, or 6. In some embodiments, each m is independently 4 or 5.

In some embodiments of the pharmaceutically acceptable salt of the compounds of Formula (II), the compound has any one of the structures shown in Table B1 as defined by $C^1$ and $C^2$, or Table B2. In some embodiments, the pharmaceutically acceptable salt is a meglumine salt, a lysine salt, or an arginine salt of the compound having any one of the structures shown in Table B1 as defined by $C^1$ and $C^2$, or Table B2. In some embodiments, the lysine salt is an L-lysine salt. In some embodiments, the arginine salt is an L-arginine salt.

Compounds of Formulas (III), (IIIA), (IIIB), and Table B5

In some embodiments, the compound of the invention is a compound of Formula (III):

(III)

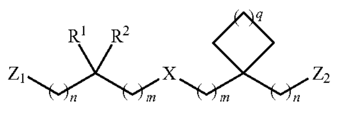

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 3, 4, 5, 6, or 7;

each n is independently 0, 1, 2, 3, 4, or 5;

each q is 0, 1, 2, 3, or 4;

X is —O—, —S—, —S(═O)—, —$S(O)_2$-, —NH—, —N(OH)—, —N(→O)—, N(alkyl)-, or —N(aryl)-;

$Z_1$ and $Z_2$ are independently —$C_1$-$C_6$ alkyl, —OH, —COOH, —$COOR^5$, —CO—CoA, —$CONH_2$, —$CONHR^5$, —CONHMs, —CONHTs, —$SO_3H$, —$SO_3R^5$,

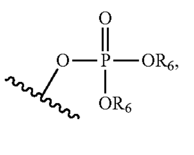
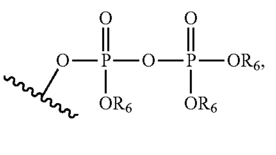

-continued

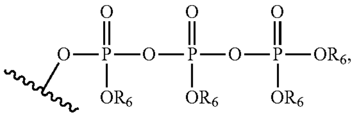
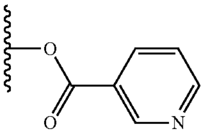
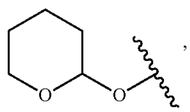
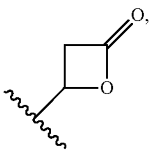
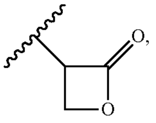
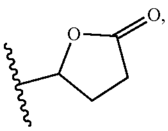
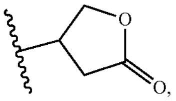
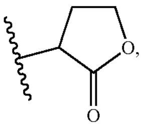
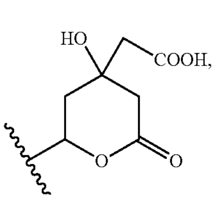
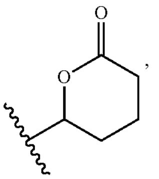
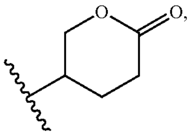
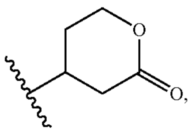
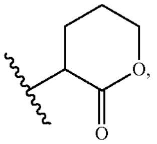
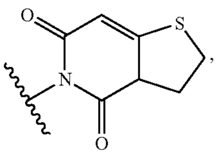
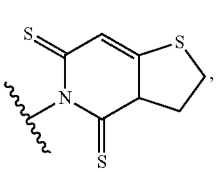
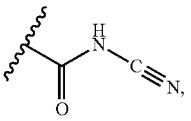
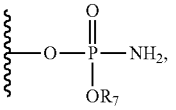
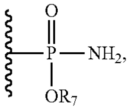
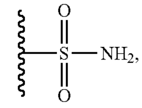
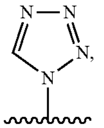
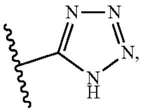
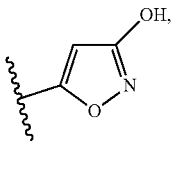

-continued

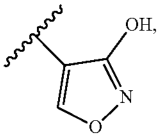

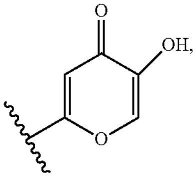

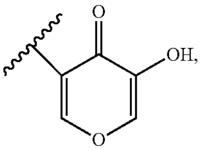

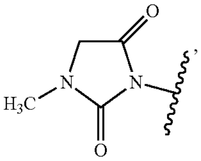

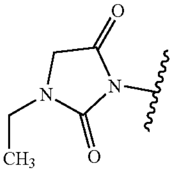

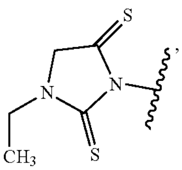

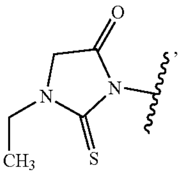

or

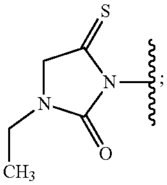

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein one or both of $Z_1$ and $Z_2$ is —CO—CoA.

In some embodiments, the compound of the invention is a compound of Formula (IIIA):

(IIIA)

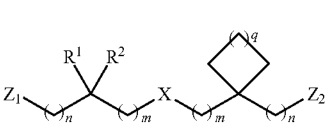

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —O—, —S—, —S(═O)—, —S(O)$_2$—, —NH—, —N(OH)—, —N(→O)—, N(alkyl)-, or —N(aryl)-;

$Z_1$ and $Z_2$ are —$C_1$-$C_6$ alkyl, —COOH, —COOR$^5$, —CO—CoA, —CONH$_2$, —CONHR$^5$, —CONHMs, —CONHTs, —SO$_3$R$^5$,

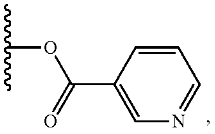

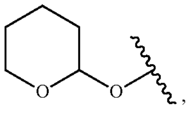

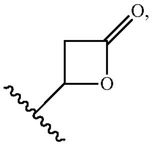

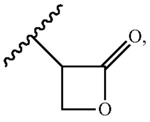

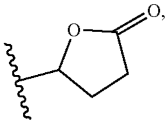

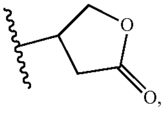

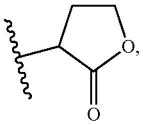

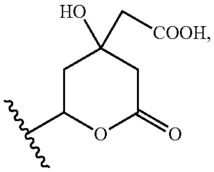

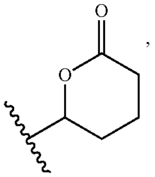

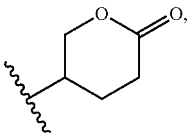

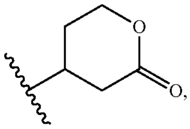

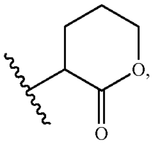

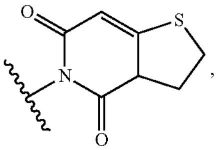

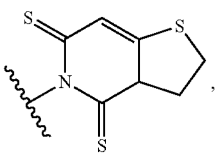

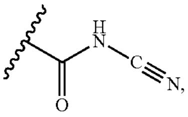

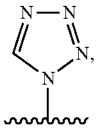

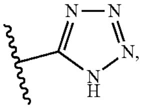

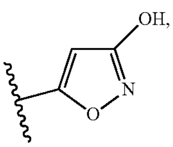

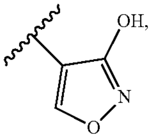

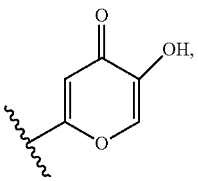

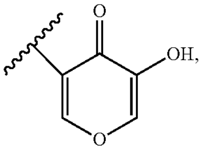

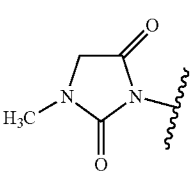

,

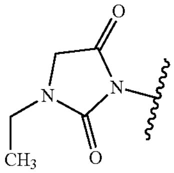

,

-continued

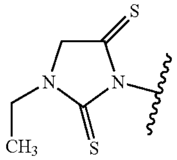 , 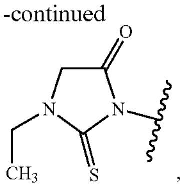 , or

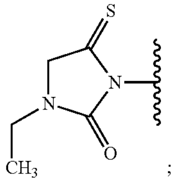 ;

wherein $Z_1$ and $Z_2$ are the same;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein one or both of $Z_1$ and $Z_2$ is —CO—CoA.

In some embodiments, the compound of the invention is a compound of Formula (IIIB):

(IIIB)

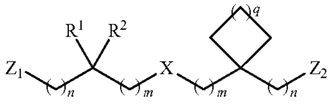

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —S—, —S(═O)—, —$S(O)_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —$COOR^5$, —CO—CoA, —$CONH_2$, —$CONHR^5$, —CONHMs, —CONHTs, —$SO_3H$, —$SO_3R$,

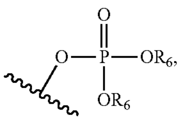 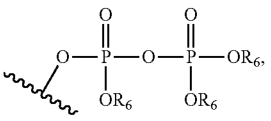

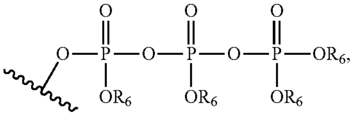

-continued

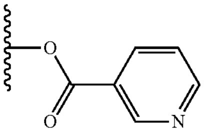 , 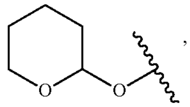 ,

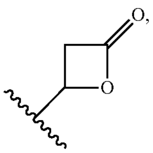 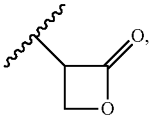 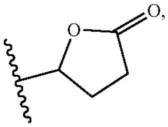

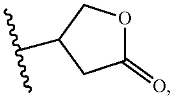 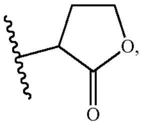

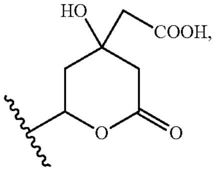 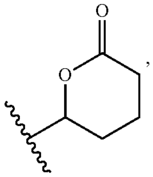 ,

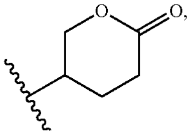 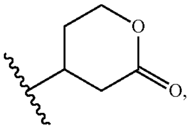

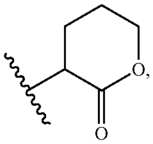 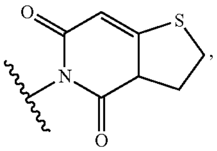 ,

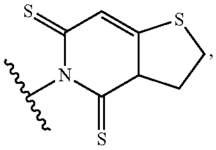 , 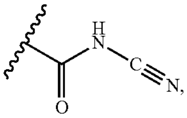

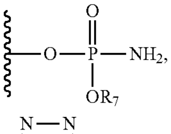 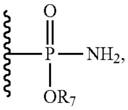 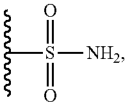

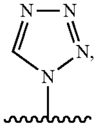 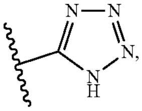 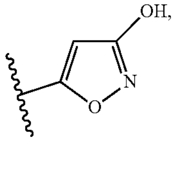

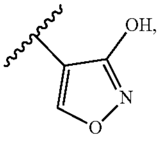 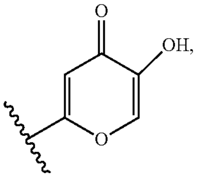

-continued

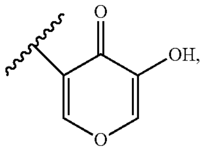

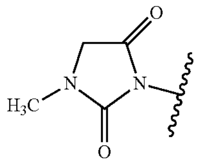

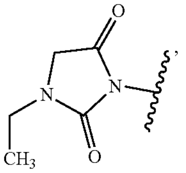

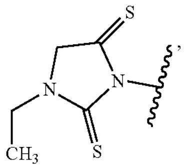

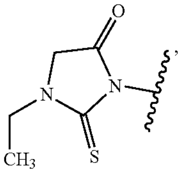

or

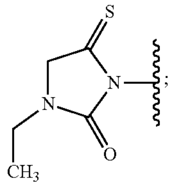

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_2$-$C_6$ alkyl, —$C_2$-$C_6$ alkenyl, or —$C_2$-$C_6$ alkynyl;

wherein one or both of $Z_1$ and $Z_2$ is —CO—CoA.

In some embodiments of compounds of Formula (III) and (IIIB), $Z^1$ is —CO—CoA and $Z^2$ is —OH, —COOH, —CO—CoA, or —COOR$^5$. In some embodiments, $Z^2$ is —CO—CoA and $Z^1$ is —OH, —COOH, —CO—CoA, or —COOR$^5$—.

In some embodiments of compounds of Formula (II), (IIIA), and (IIIB), $Z^1$ and $Z^2$ are each —CO—CoA.

In some embodiments of compounds of Formula (III), X is —S—, —S(=O)—, —S(O)$_2$—, —NH—, —N(OH)—, —N(→O)—, N(alkyl)-, or —N(aryl)-.

In some embodiments of compounds of Formula (III) and (IIIA), X is O. In some embodiments of compounds of Formula (III), when X is O, m is 2, 3, 5, 6, or 7.

In some embodiments of compounds of Formula (III), (IIIA), and (IIIB), each n is independently 0 or 1. In some embodiments, n is 0. In some embodiments, n is 1.

In some embodiments of compounds of Formula (III), (IIIA), and (IIIB), each m is independently 4, 5, or 6. In some embodiments, m is 5 or 6. In some embodiments, m is 4. In some embodiments, m is 5. In some embodiments, m is 6. In some embodiments, m is 2 or 3.

In some embodiments of compounds of Formula (III), (IIIA), and (IIIB), $R^1$ and $R^2$ together with the carbon atom to which they are attached form a —$C_3$-$C_7$ cycloalkyl group.

In some embodiments, the compound of Formula (III) or (IIIA) has any one of the structures shown in Table B3, defined by $C^1$ and $C^2$, or a pharmaceutically acceptable salt or solvate thereof.

In some embodiments, the compound of Formula (III) or (IIIA) has any one of the structures shown in Table B4, or a pharmaceutically acceptable salt or solvate thereof.

In some embodiments, the compound of Formula (III) or (IIIA) is a Coenzyme A mono(thioester) or di(thioester) of a compound having any one of the structures shown in Table B4, or a pharmaceutically acceptable salt or solvate thereof.

In some embodiments, the compound of Formula (III) or (IIIA) has any one of the structures shown in Table B5, or a pharmaceutically acceptable salt or solvate thereof.

In some embodiments, the compound of Formula (III) or (IIIA) is a Coenzyme A mono(thioester) or di(thioester) of a compound having any one of the structures shown in Table B5, or a pharmaceutically acceptable salt or solvate thereof.

TABLE B3

| Structure |
| --- |
| 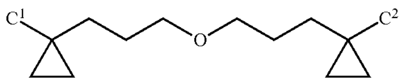 |
| wherein $C^1$ = COOH and $C^2$ = CO-CoA; $C^1$ = CO-CoA and $C^2$ = COOH; or $C^1$ and $C^2$ = CO-CoA |
| 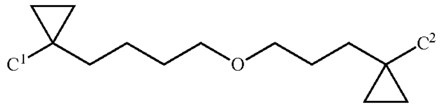 |
| wherein $C^1$ = COOH and $C^2$ = CO-CoA; $C^1$ = CO-CoA and $C^2$ = COOH; or $C^1$ and $C^2$ = CO-CoA |
| 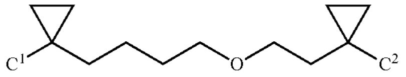 |
| wherein $C^1$ = COOH and $C^2$ = CO-CoA; $C^1$ = CO-CoA and $C^2$ = COOH; or $C^1$ and $C^2$ = CO-CoA |
| 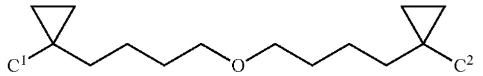 |
| wherein $C^1$ = COOH and $C^2$ = CO-CoA; $C^1$ = CO-CoA and $C^2$ = COOH; or $C^1$ and $C^2$ = CO-CoA |

TABLE B3-continued

| Structure |
| --- |
| 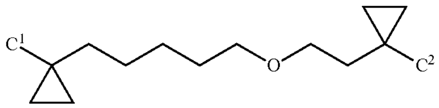 |
| wherein $C^1$ = COOH and $C^2$ = CO-CoA; $C^1$ = CO-CoA and $C^2$ = COOH; or $C^1$ and $C^2$= CO-CoA |
| 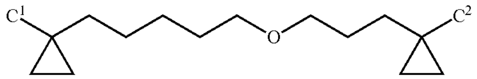 |
| wherein $C^1$ = COOH and $C^2$ = CO-CoA; $C^1$ = CO-CoA and $C^2$ = COOH; or $C^1$ and $C^2$ = CO-CoA |
| 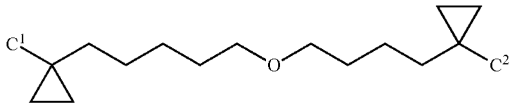 |
| wherein $C^1$ = COOH and $C^2$ = CO-CoA; $C^1$ = CO-CoA and $C^2$ = COOH; or $C^1$ and $C^2$ = CO-CoA |
| 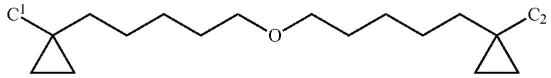 |
| wherein $C^1$ = COOH and $C^2$ = CO-CoA; $C^1$ = CO-CoA and $C^2$ = COOH; or $C^1$ and $C^2$ = CO-CoA |
| 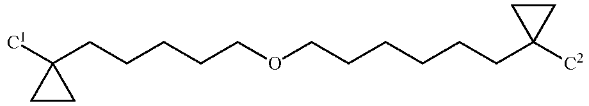 |
| wherein $C^1$ = COOH and $C^2$ = CO-CoA; $C^1$ = CO-CoA and $C^2$ = COOH; or $C^1$ and $C^2$ = CO-CoA |
| 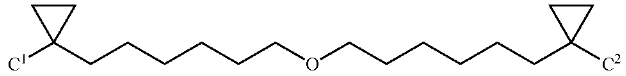 |
| wherein $C^1$ = COOH and $C^2$= CO-CoA; $C^1$ = CO-CoA and $C^2$ = COOH; or $C^1$ and $C^2$ = CO-CoA |
| 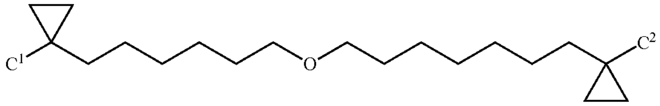 |
| wherein $C^1$ = COOH and $C^2$ = CO-CoA; $C^1$ = CO-CoA and $C^2$ = COOH; or $C^1$ and $C^2$= CO-CoA |
| 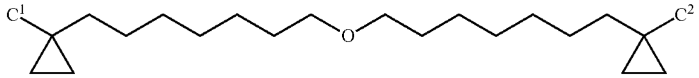 |
| wherein $C^1$ = COOH and $C^2$ = CO-CoA; $C^1$ = CO-CoA and $C^2$ = COOH; or $C^1$ and $C^2$ = CO-CoA |
| 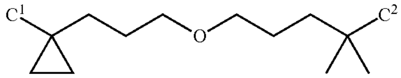 |
| wherein $C^1$ = COOH and $C^2$ = CO-CoA; $C^1$ = CO-CoA and $C^2$ = COOH; or $C^1$ and $C^2$ = CO-CoA |
| 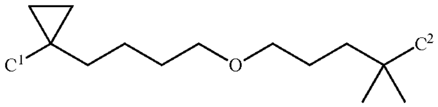 |
| wherein $C^1$ = COOH and $C^2$ = CO-CoA; $C^1$ = CO-CoA and $C^2$ = COOH; or $C^1$ and $C^2$ = CO-CoA |
| 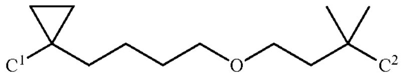 |
| wherein $C^1$ = COOH and $C^2$ = CO-CoA; $C^1$ = CO-CoA and $C^2$ = COOH; or $C^1$ and $C^2$ = CO-CoA |

TABLE B3-continued

| Structure |
|---|
| 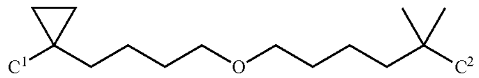 |
| wherein $C^1$ = COOH and $C^2$ = CO-CoA; $C^1$ = CO-CoA and $C^2$ = COOH; or $C^1$ and $C^2$ = CO-CoA |
| 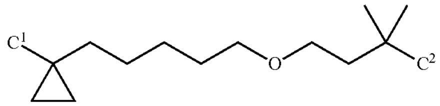 |
| wherein $C^1$ = COOH and $C^2$ = CO-CoA; $C^1$ = CO-CoA and $C^2$ = COOH; or $C^1$ and $C^2$ = CO-CoA |
| 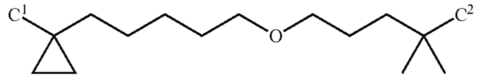 |
| wherein $C^1$ = COOH and $C^2$ = CO-CoA; $C^1$ = CO-CoA and $C^2$ = COOH; or $C^1$ and $C^2$ = CO-CoA |
| 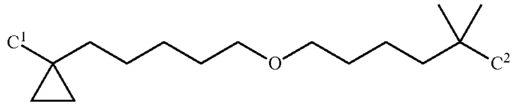 |
| wherein $C^1$ = COOH and $C^2$ = CO-CoA; $C^1$ = CO-CoA and $C^2$ = COOH; or $C^1$ and $C^2$ = CO-CoA |
| 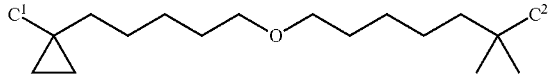 |
| wherein $C^1$ = COOH and $C^2$ = CO-CoA; $C^1$ = CO-CoA and $C^2$ = COOH; or $C^1$ and $C^2$ = CO-CoA |
| 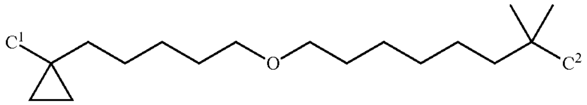 |
| wherein $C^1$ = COOH and $C^2$ = CO-CoA; $C^1$ = CO-CoA and $C^2$ = COOH; or $C^1$ and $C^2$ = CO-CoA |
| 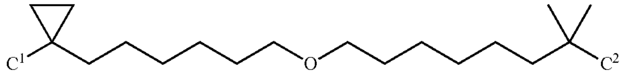 |
| wherein $C^1$ = COOH and $C^2$ = CO-CoA; $C^1$ = CO-CoA and $C^2$ = COOH; or $C^1$ and $C^2$ = CO-CoA |
| 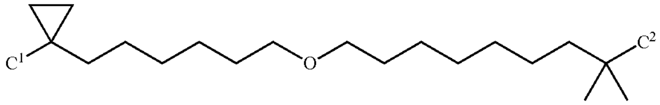 |
| wherein $C^1$ = COOH and $C^2$ = CO-CoA; $C^1$ = CO-CoA and $C^2$= COOH; or $C^1$ and $C^2$= CO-CoA |

TABLE B4

| Compound No. | Structure and Name |
|---|---|
| III-10 | 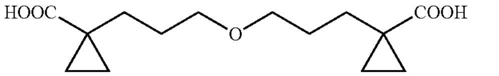 [SMILES: O=C(O)C1(CCCOCCCC2(C(=O)O)CC2)CC1] 1,1'-(oxybis(propane-3,1-diyl))bis(cyclopropane-1-carboxylic acid) |
| III-11 | 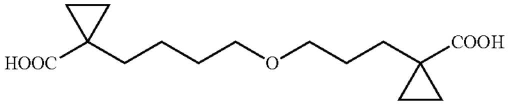 [SMILES: O=C(O)C1(CCCCOCCCC2(C(=O)O)CC2)CC1] 1-(3-(4-(1-carboxycyclopropyl)butoxy)propyl)cyclopropane-1-carboxylic acid |

TABLE B4-continued

| Compound No. | Structure and Name |
| --- | --- |
| III-12 | 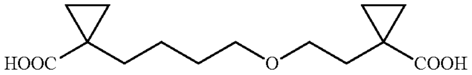 [SMILES: O=C(O)C1(CCCCOCCC2(C(=O)O)CC2)CC1] 1-(2-(4-(1-carboxycyclopropyl)butoxy)ethyl)cyclopropane-1-carboxylic acid |
| III-13 | 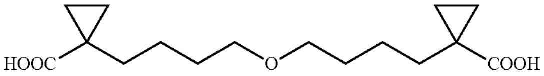 [SMILES: O=C(O)C1(CCCCOCCCCC2(C(=O)O)CC2)CC1] 1,1'-(oxybis(butane-4,1-diyl))bis(cyclopropane-1-carboxylic acid) |
| III-14 | 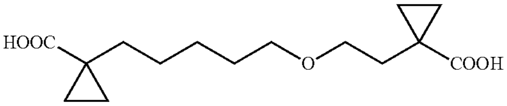 [SMILES: O=C(O)C1(CCCCCOCCC2(C(=O)O)CC2)CC1] 1-(5-(2-(1-carboxycyclopropyl)ethoxy)pentyl)cyclopropane-1-carboxylic acid |
| III-15 | 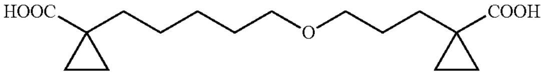 [SMILES: O=C(O)C1(CCCCCOCCCC2(C(=O)O)CC2)CC1] 1-(3-((5-(1-carboxycyclopropyl)pentyl)oxy)propyl)cyclopropane-1-carboxylic acid |
| III-16 | 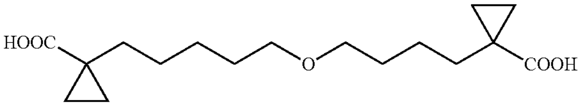 [SMILES: O=C(O)C1(CCCCCOCCCCC2(C(=O)O)CC2)CC1] 1-(5-(4-(1-carboxycyclopropyl)butoxy)pentyl)cyclopropane-1-carboxylic acid |
| III-17 | 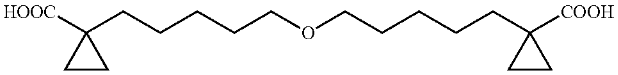 [SMILES: O=C(O)C1(CCCCCOCCCCCC2(C(=O)O)CC2)CC1] 1,1'-(oxybis(pentane-5,1-diyl))bis(cyclopropane-1-carboxylic acid) |
| III-18 | 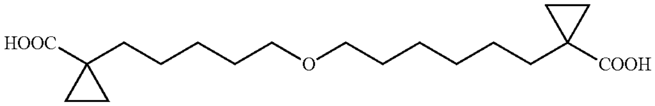 [SMILES: O=C(O)C1(CCCCCCOCCCCCC2(C(=O)O)CC2)CC1] 1-(5-((6-(1-carboxycyclopropyl)hexyl)oxy)pentyl)cyclopropane-1-carboxylic acid |
| III-19 | 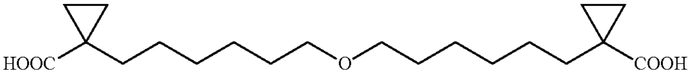 [SMILES: O=C(O)C1(CCCCCCOCCCCCCC2(C(=O)O)CC2)CC1] 1,1'-(oxybis(hexane-6,1-diyl))bis(cyclopropane-1-carboxylic acid) |
| III-20 | 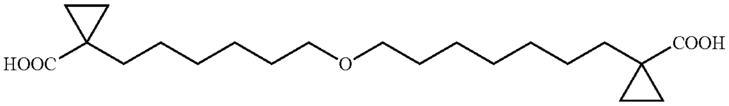 [SMILES: O=C(O)C1(CCCCCCCOCCCCCCC2(C(=O)O)CC2)CC1] 1-(6-((7-(1-carboxycyclopropyl)heptyl)oxy)hexyl)cyclopropane-1-carboxylic acid |
| III-21 | 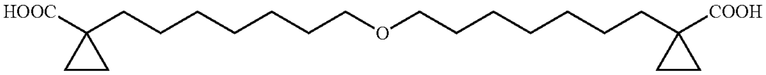 [SMILES: O=C(O)C1(CCCCCCCOCCCCCCCC2(C(=O)O)CC2)CC1] 1,1'-(oxybis(heptane-7,1-diyl))bis(cyclopropane-1-carboxylic acid) |

In some embodiments, the compound of the invention is a compound having any one of the structures shown in Table B5, or a pharmaceutically acceptable salt or solvate thereof.

TABLE B5

| Compound No. | Structure and Name |
|---|---|
| III-22 | 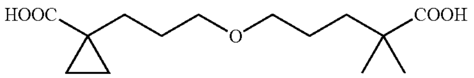 [SMILES: CC(C)(CCCOCCCC1(C(=O)O)CC1)C(=O)O] 1-(3-((4-carboxy-4-methylpentyl)oxy)propyl)cyclopropane-1-carboxylic acid |
| III-23 | 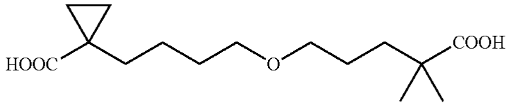 [SMILES: CC(C)(CCCOCCCCC1(C(=O)O)CC1)C(=O)O] 1-(4-((4-carboxy-4-methylpentyl)oxy)butyl)cyclopropane-1-carboxylic acid |
| III-24 | 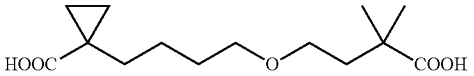 [SMILES: CC(C)(CCOCCCCC1(C(=O)O)CC1)C(=O)O] 1-(4-(3-carboxy-3-methylbutoxy)butyl)cyclopropane-1-carboxylic acid |
| III-25 | 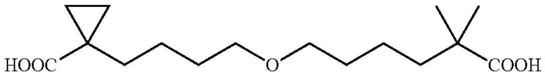 [SMILES: CC(C)(CCCCOCCCCC1(C(=O)O)CC1)C(=O)O] 1-(4-((5-carboxy-5-methylhexyl)oxy)butyl)cyclopropane-1-carboxylic acid |
| III-26 | 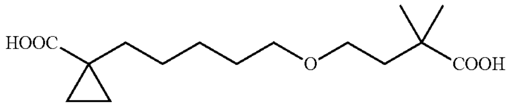 [SMILES: CC(C)(CCOCCCCCC1(C(=O)O)CC1)C(=O)O] 1-(5-(3-carboxy-3-methylbutoxy)pentyl)cyclopropane-1-carboxylic acid |
| III-27 | 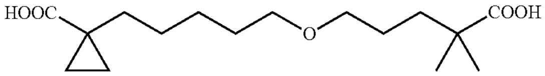 [SMILES: CC(C)(CCCOCCCCCC1(C(=O)O)CC1)C(=O)O] 1-(5-((4-carboxy-4-methylpentyl)oxy)pentyl)cyclopropane-1-carboxylic acid |
| III-28 | 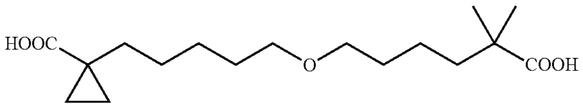 [SMILES: CC(C)(CCCCOCCCCCC1(C(=O)O)CC1)C(=O)O] 1-(5-((5-carboxy-5-methylhexyl)oxy)pentyl)cyclopropane-1-carboxylic acid |
| III-29 | 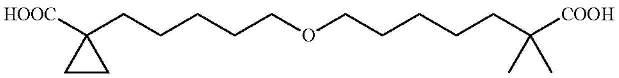 [SMILES: CC(C)(CCCCCOCCCCCC1(C(=O)O)CC1)C(=O)O] 1-(5-((6-carboxy-6-methylheptyl)oxy)pentyl)cyclopropane-1-carboxylic acid |
| III-30 | 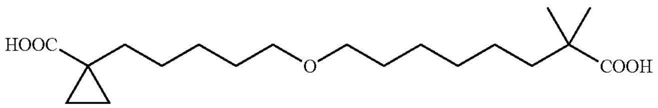 [SMILES: CC(C)(CCCCCCOCCCCCC1(C(=O)O)CC1)C(=O)O] 1-(5-((7-carboxy-7-methyloctyl)oxy)pentyl)cyclopropane-1-carboxylic acid |

TABLE B5-continued

| Compound No. | Structure and Name |
|---|---|
| III-31 | 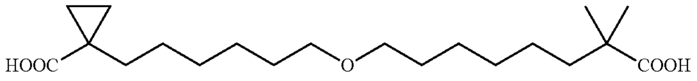 [SMILES: CC(C)(CCCCCCOCCCCCCC1(C(=O)O)CC1)C(=O)O] 1-(6-((7-carboxy-7-methyloctyl)oxy)hexyl)cyclopropane-1-carboxylic acid |
| III-32 | 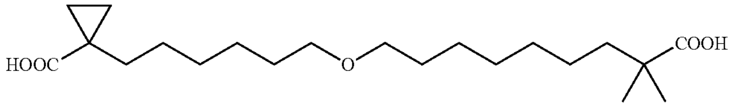 [SMILES: CC(C)(CCCCCCCOCCCCCCC1(C(=O)O)CC1)C(=O)O] 1-(6-((8-carboxy-8-methylnonyl)oxy)hexyl)cyclopropane-1-carboxylic acid |

In some embodiments, the compound of Formulae (III), (IIIA), or (IIIB), or a compound shown in Table B5, or a pharmaceutically acceptable salt or solvate thereof is isolated and purified. In some embodiments, the compound of Formulae (III), (IIIA), or (IIIB), or a compound shown in Table B5, or a pharmaceutically acceptable salt or solvate thereof, is ex vivo.

Pharmaceutically Acceptable Salts of Compounds of Formula (III), (IIIA), or (IIIB)( In some embodiments, the compound of the invention is a pharmaceutically acceptable salt of a compound of Formula (III):

(III)

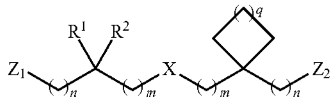

wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 3, 4, 5, 6, or 7;

each n is independently 0, 1, 2, 3, 4, or 5;

each q is 0, 1, 2, 3, or 4;

X is —O—, —S—, —S(═O)—, —S(O)$_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —COOR$^5$, —CO—CoA, —CONH$_2$, —CONHR$^5$, —CONHMs, —CONHTs, —SO$_3$R$^5$,

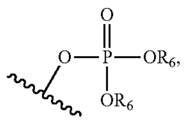

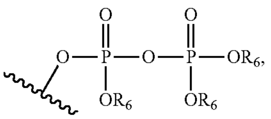

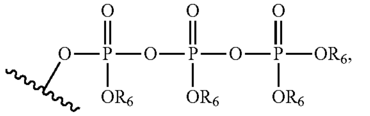

-continued

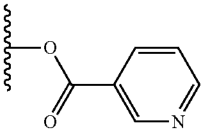 , 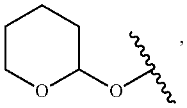 ,

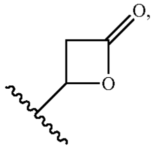 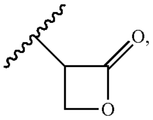 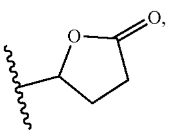

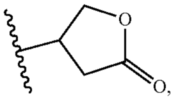 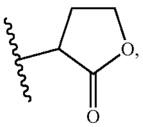

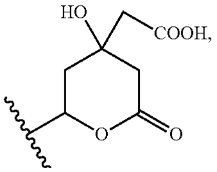 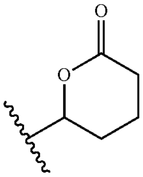 ,

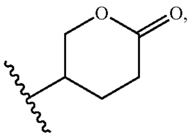 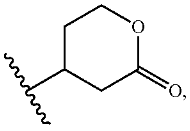

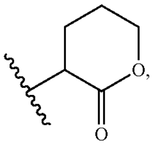 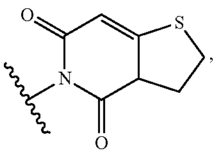

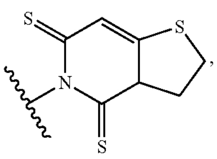 , 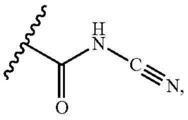

-continued

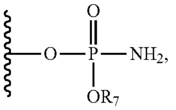 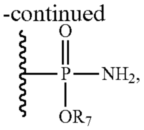 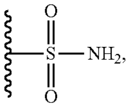

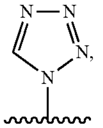 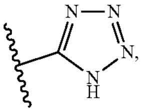 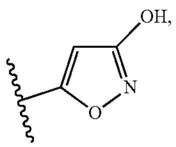

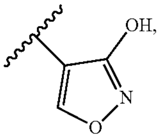 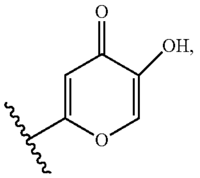

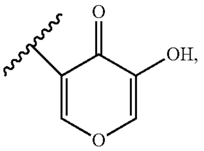 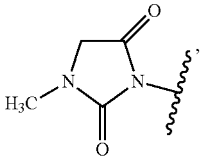

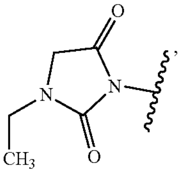 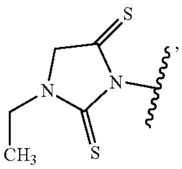

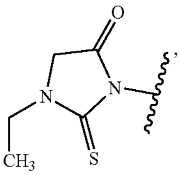 or 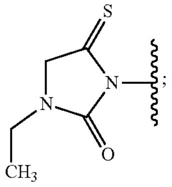

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein the pharmaceutically acceptable salt is a salt of an amino acid, a meglumine salt, an eglumine salt, a D-glucamine salt, a glucosamine salt, or a choline salt.

In some embodiments, the compound of the invention is a pharmaceutically acceptable salt of a compound of Formula (IIIA):

(IIIA)

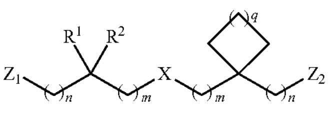

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —O—, —S—, —S(═O)—, —$S(O)_2$—, —NH—, —N(OH)—, —N(→O)—, N(alkyl)-, or —N(aryl)-;

$Z_1$ and $Z_2$ are —$C_1$-$C_6$ alkyl, —COOH, —$COOR^5$, —CO—CoA, —$CONH_2$, —$CONHR^5$, —CONHMs, —CONHTs, —$SO_3R^5$,

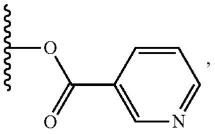 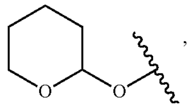

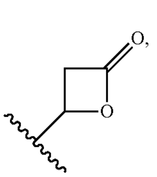 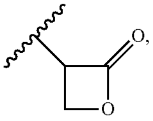 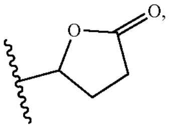

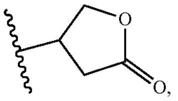 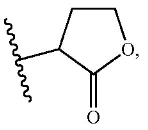

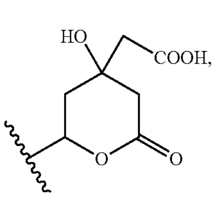 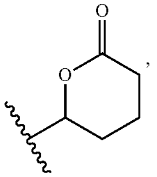

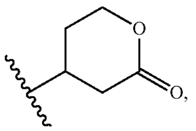

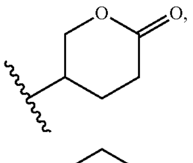

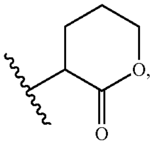 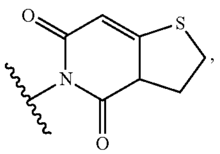

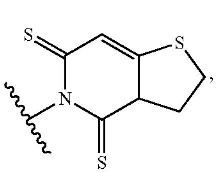 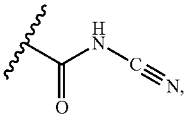

-continued

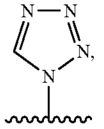 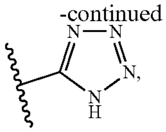 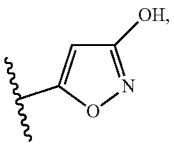

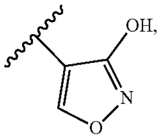 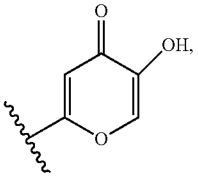

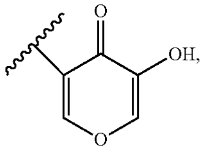 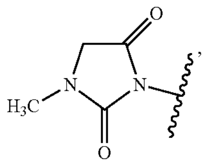

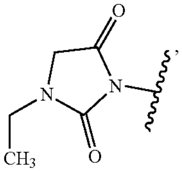 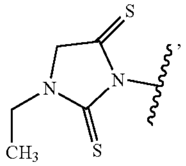

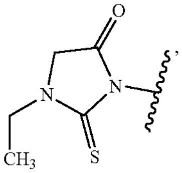 or 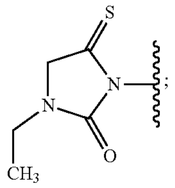

wherein $Z_1$ and $Z_2$ are the same;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein the pharmaceutically acceptable salt is a salt of an amino acid, a meglumine salt, an eglumine salt, a D-glucamine salt, a glucosamine salt, or a choline salt.

In some embodiments, the compound of the invention is a pharmaceutically acceptable salt of a compound of Formula (IHB):

(IIIB)

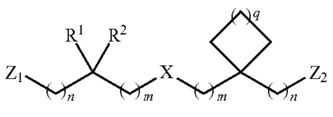

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —S—, —S(=O)—, —S(O)$_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —COOR$^5$, —CO—CoA, —CONH$_2$, —CONHR$^5$, —CONHMs, —CONHTs, —SO$_3$H, —SO$_3$R$^5$,

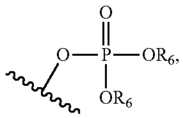 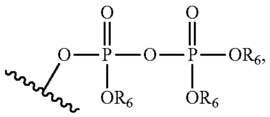

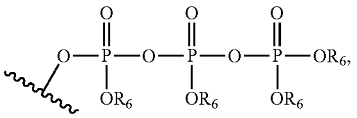

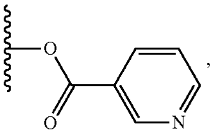 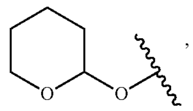

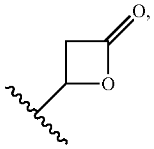 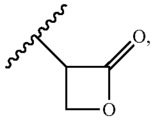 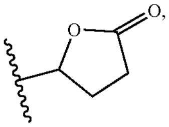

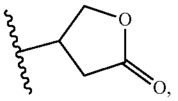 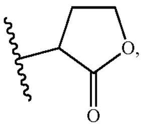

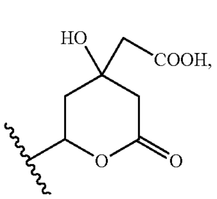 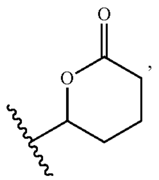

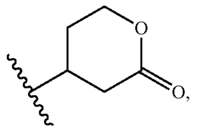 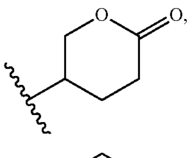

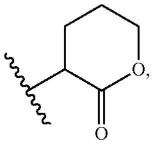 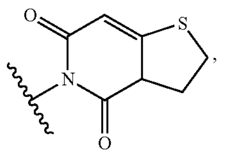

-continued

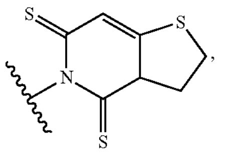

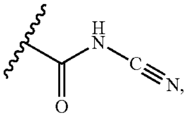

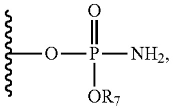

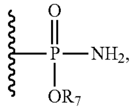

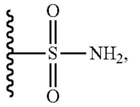

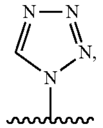

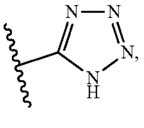

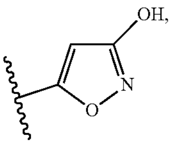

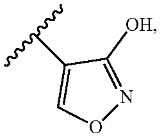

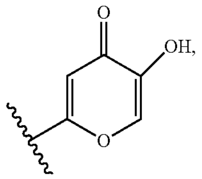

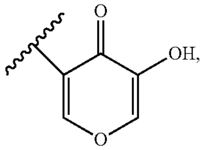

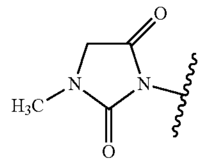

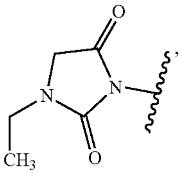

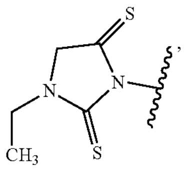

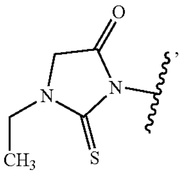

or

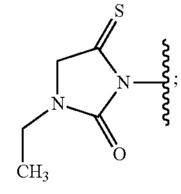

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl;

wherein the pharmaceutically acceptable salt is a salt of an amino acid, a meglumine salt, an eglumine salt, a D-glucamine salt, or a glucosamine salt, or a choline salt.

In some embodiments of the pharmaceutically acceptable salt of the compound of Formula (III), (IIIA), and (IIIB), the salt is a salt of an amino acid, and the amino acid is a D,L-amino acid, L-amino acid, or D-amino acid. In some embodiments, the amino acid is a natural amino acid or a synthetic amino acid. In some embodiments, the amino acid is a basic amino acid. In some embodiments, the amino acid is lysine, arginine, histidine, or glutamine. In some embodiments, the amino acid is L-lysine, L-arginine, L-histidine, or L-glutamine. In some embodiments, the pharmaceutically acceptable salt is a meglumine salt, an eglumine salt, or aD-glucamine salt. In some embodiments, the pharmaceutically acceptable salt is a choline salt.

In some embodiments of the pharmaceutically acceptable salt of the compounds of Formula (III) and (IIIB), $Z^1$ is —CO—CoA and $Z^2$ is —OH, —COOH, —CO—CoA, or —COOR$^5$. In some embodiments, $Z^2$ is —CO—CoA and $Z^1$ is —OH, —COOH, —CO—CoA, or —COOR$^5$.

In some embodiments of the pharmaceutically acceptable salt of the compounds of Formula (III), (IIIA), and (IIIB), $Z^1$ and $Z^2$ are each —CO—CoA.

In some embodiments of the pharmaceutically acceptable salt of the compounds of Formula (III), X is —S—, —S(=O)—, —S(O)$_2$—, —NH—, —N(OH)—, —N(→O)—, N(alkyl)-, or —N(aryl)-.

In some embodiments of the pharmaceutically acceptable salt of the compounds of Formula (III) and (IIIA), X is O. In some embodiments of the pharmaceutically acceptable salt of the compounds of Formula (III), when X is O, m is 2, 3, 5, 6, or 7.

In some embodiments of the pharmaceutically acceptable salt of the compounds of Formula (III), (IIIA), and (IIIB), each n is independently 0 or 1. In some embodiments, n is 0. In some embodiments, n is 1.

In some embodiments of the pharmaceutically acceptable salt of the compounds of Formula (III), (IIIA), and (IIIB), each m is independently 4, 5, or 6. In some embodiments, m is 5 or 6. In some embodiments, m is 4. In some embodiments, m is 5. In some embodiments, m is 6. In some embodiments, m is 2 or 3.

In some embodiments of the pharmaceutically acceptable salt of the compounds of Formula (III), (IIIA), and (IIIB), $R^1$ and $R^2$ together with the carbon atom to which they are attached form a —$C_3$-$C_7$ cycloalkyl group.

In some embodiments of the pharmaceutically acceptable salt of the compounds of Formula (III) or (IIIA) has any one of the structures shown in Table B3 as defined by $C^1$ and $C^2$, Table B4, or Table B5. In some embodiments, the pharmaceutically acceptable salt is a meglumine salt, a lysine salt, or an arginine salt of the compound having any one of the structures shown in Table B3 as defined by $C^1$ and $C^2$, Table B4, or Table B5. In some embodiments, the lysine salt is an L-lysine salt. In some embodiments, the arginine salt is an L-arginine salt.

Compostions of the Invention

In some embodiments, the composition of the invention comprises (i) an effective amount of a compound of the invention and (ii) a pharmaceutically acceptable carrier or vehicle.

In some embodiments, the composition of the invention comprises an effective amount of a compound having a structure depicted in Tables A-1, A-2, A-3, A-4, A-5, A-6, A-13, A-14, A-15, A-16, A-17, A-18, or A-19, or a pharmaceutically acceptable salt or solvate thereof. In some embodiments, the composition of the invention comprises an effective amount of a Coenzyme A ester of an acid having a structure depicted in Tables A-7, A-8, A-9, A-10, A-11, or A-12, or a pharmaceutically acceptable salt or solvate thereof. In some embodiments, the composition of the invention comprises an effective amount of a compound having a structure depicted in Table B1. In some embodiments, the composition of the invention comprises an effective amount of a mono- or di-Coenzyme A ester of an acid having a structure depicted in Table B2, or a pharmaceutically acceptable salt or solvate thereof. In some embodiments, the composition of the invention comprises an effective amount of a compound having a structure depicted in Table B3. In some embodiments, the composition of the invention comprises an effective amount of a mono- or di-Coenzyme A ester of an acid having a structure depicted in Table B4, or a pharmaceutically acceptable salt or solvate thereof. In some embodiments, the composition of the invention comprises an effective amount of a mono- or di-Coenzyme A ester of an acid having a structure depicted in Table B5, or a pharmaceutically acceptable salt or solvate thereof.

In some embodiments, the compositions of the invention comprise (i) an effective amount of a compound of formula (I), (IA), (IB), (IC), (ID), (IE), (IF), (IG), (IH), (IJ), (II), (III), (IIIA), and (IIIB), or Table A-18, Table A-19 or Table B5, or a pharmaceutically acceptable salt or solvate thereof, and (ii) a pharmaceutically acceptable carrier or vehicle.

In some embodiments, the compositions of the invention comprise an effective amount of a compound having a structure depicted in Tables A-1, A-2, A-3, A-4, A-5, A-6, A-13, A-14, A-15, A-16, A-17, A-18, or A-19, or a pharmaceutically acceptable salt or solvate thereof. In some embodiments, the compositions of the invention comprise an effective amount of a Coenzyme A ester of an acid having a structure depicted in Tables A-7, A-8, A-9, A-10, A-11, or A-12, or a pharmaceutically acceptable salt or solvate thereof. In some embodiments, the compositions of the invention comprise an effective amount of a compound having a structure depicted in Table B1. In some embodiments, the compositions of the invention comprise an effective amount of a mono- or di-Coenzyme A ester of an acid having a structure depicted in Table B2, or a pharmaceutically acceptable salt or solvate thereof. In some embodiments, the compositions of the invention comprise an effective amount of a compound having a structure depicted in Table B3. In some embodiments, the compositions of the invention comprise an effective amount of a mono- or di-Coenzyme A ester of an acid having a structure depicted in Table B4, or a pharmaceutically acceptable salt or solvate thereof. In some embodiments, the compositions of the invention comprise an effective amount of a mono- or di-Coenzyme A ester of an acid having a structure depicted in Table B5, or a pharmaceutically acceptable salt or solvate thereof.

In some embodiments, the compositions of the invention comprise (i) an effective amount of a compound of formula (I), (IA), (IB), (IC), (ID), (IE), (IF), (IG), (IH), (IJ), (II), (III), (IIIA), and (IIIB), or Table A-18, Table A-19 or Table B5, or a pharmaceutically acceptable salt or solvate thereof, and (ii) a pharmaceutically acceptable carrier or vehicle.

In some embodiments, the compositions of the invention comprise (i) a pharmaceutically acceptable amino acid, meglumine, eglumine, D-glucamine, glucosamine, or choline salt of compounds of Formulae (I), (IA), (IB), (IC), (II), (III), (IIIA), (IIIB), Table A-7, Table A-8, Table A-9, Table A-10, Table A-11, Table A-12, Table B1, Table B2, Table B3, Table B4, and Table B5, and (ii) a pharmaceutically acceptable carrier or vehicle.

In some embodiments, the composition of the invention or the compositions of the invention further comprises another pharmaceutically active agent. In some embodiments, the composition is a fixed dose composition.

In some embodiments, the compositions of the invention is further combined with another composition comprising another pharmaceutically active agent. In some embodiments, the composition of the invention and the composition comprising another pharmaceutically active agents are formulated separately. In some embodiments, the composition of the invention and the composition comprising another pharmaceutically active agents are formulated separately but administered together. In some embodiments, the composition of the invention and the composition comprising another pharmaceutically active agents are formulated and administered separately. In some embodiments, the composition of the invention and the composition comprising another pharmaceutically active agents are useful in adjuvant therapy.

In some embodiments, the other pharmaceutically active agent is a statin, a thiazolidinedione or fibrate, a bile-acid-binding-resin, a niacin, an anti-obesity drug, a hormone, a tyrophostine, a sulfonylurea-based drug, a biguanide, an α-glucosidase inhibitor, an apolipoprotein A-I agonist, apolipoprotein E agonist, a phosphodiesterase type-5 inhibitor, a cardiovascular drug, an HDL-raising drug, an HDL enhancer, an agonist of the apolipoprotein A-I gene or protein, an agonist of the apolipoprotein A-IV gene or protein, an agonist of an apolipoprotein gene, an ATP citrate lyase modulator, an ATP citrate lyase allosteric inhibitor, an acetyl-CoA carboxylase modulator, or an acetyl-CoA carboxylase allosteric inhibitor.

In some embodiments, the other pharmaceutically active agent is an antagonist or an inhibitor of a proinflammatory gene or protein or an agonist of an anti-inflammatory gene or protein. In some embodiments, the other pharmaceutically active agent inhibits or reduces a proinflammatory function or increases an anti-inflammatory function of IL-6, CRP, TNF-α, MCP-1, MIP-1β, CCR5, CCR2, NF-κB or TGF-β1.

In some embodiments, the other pharmaceutically active agent affects the expression or function of a fibrosis gene or protein or a mitogenesis gene or protein. In some embodiments, the other pharmaceutically active agent regulates the expression or function of FGF-21, MMP-2, TIMP-1, ASK1 or Collagen type 3.

In some embodiments, the other pharmaceutically active agent is a regulator of lipid metabolism- or -trafficking-related genes, a regulator of PPAR-α target genes such as, but not limited to, HD (ECHS1), PDK4 and Cyp7A1, a regulator of SGLT1, SGL2, ApoC-III, Sulf-2, ANGPTL3, ANGPTL4 and LPL genes.

In some embodiments, the other pharmaceutically active agent is a statin. In some embodiments, the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt thereof. In some embodiments, statin is lovastatin.

In some embodiments, the other pharmaceutically active agent is a fibrate. In some embodiments, the fibrate is fenofibrate, gemfibrozil, or fenofibric acid.

In some embodiments, the other pharmaceutically active agent is sorafenib. In some embodiments, the sorafenib is a pharmaceutically acceptable salt. In some embodiments, the sorafenib is sorafenib tosylate. In some embodiments, the sorafenib is a free base. In yet some other embodiments, the other pharmaceutically active agent is paclitaxel. In some embodiments, the paclitaxel is a pharmaceutically acceptable salt. In some embodiments, the paclitaxel is a free base. In yet some other embodiments, the other pharmaceutically active agent is carotuximab. In yet some other embodiments, the other pharmaceutically active agent is pembrolizumab. In yet some other embodiments, the other pharmaceutically active agent is lenvatinib. In some embodiments, the lenvatinib is a pharmaceutically acceptable salt. In some embodiments, the lenvatinib is lenvatinib mesylate. In some embodiments, the lenvatinib is a free base. In yet some other embodiments, the other pharmaceutically active agent is avelumab. In some embodiments, the other pharmaceutically active agent is durvalumab. In yet some other embodiments, the other pharmaceutically active agent is tremelimumab. In yet some other embodiments the other pharmaceutically active agent is nivolumab. In yet some other embodiments, the other pharmaceutically active agent is regorafenib. In some embodiments, the regorafenib is a pharmaceutically acceptable salt or solvate. In some embodiments, the regorafenib is a hydrate. In some embodiments, the regorafenib is a monohydrate. In some embodiments, the regorafenib is a free base. In yet some other embodiments the other pharmaceutically active agent is tazemetostat; cemiplimab; ABX196; T-cell receptor (TCR) immune cell therapy agent, such as LioCyx TBI-302; namodenoson; MM-310; a tumor-injected oncolytic virus or gene-modified oncolytic virus such as, but not limited to, telomelysin and imlygic; or an immunomodulating gene-therapy agent, such as MDA-7/IL-24, GLIPR1/RTVP-1, and REIC/Dkk-3.

In yet some other embodiments the other pharmaceutically active agent is cenicriviroc, elafibranor, eicosapentaenoic acid, galunisertib, LY2109761, LDE225, nivolumub, firsocostat, apararenone, metformin, leucine-metformin-sildenafil combination, IMM-124E, RG-125, vitamin E, cysteamine, selonsertib, losartan, RO5093151, pradigastat, sitagliptin, vildagliptin, NGM282, pegbelfermin, PF-05231023, obeticholic acid, cilofexo, tropifexor, EDP-305, INT-767, galactoarabino-rhamnogalacturonate, liraglutide, semaglutide, exenatide, ND-L02-s0201/BMS-986263, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK28(9, MGL-3196, or nalmafene. In some embodiments, the other pharmaceutically active agent is pentamidine, berberine, L-carnitine, EYP001a, silymarin, miricorilant, ursodeoxycholic acid, metadoxine, ezetimibe, cystadane, L-alanine, saroglitazar magnesium, volixibat, firsocostat, cilofexor, elafibranor, nalmefene, solithromycin, 99m technetium-mebrofenin, tropifexor, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, regorafenib, zotiraciclib citrate, sintilimab, camrelizumab, spartalizumab, toripalimab, bispecific antibody XmAb20717, mapatumumab, tremelimumab, carotuximab, tocilizumab, ipilimumab, atezolizumab, bevacizumab, ramucirumab, IBI305, ascrinvacumab, tislelizumab, sitravatinib, cytokine-based biologic agent IRX-2, bempegaldesleukin, DKN-01, PTX-9908, AK104, PT-112, SRF388, ET1402L1-CART, glypican 3-specific chimeric antigen receptor expressing T cells (CAR-T cells), CD147-targeted CAR-T cells, NKG2D-based CAR T-cells, neoantigen reactive T cells, pexastimogene devacirepvec, talimogene laherparepvec, GNOS-PV02, INO-9012, ABBV-176, NCI-4650, DNAJB1-PRKACA fusion kinase peptide vaccine, IMA970A, or an anti-SARS-CoV-2 vaccine, novantrone, prednisone, pixantrone, losoxantrone, cytidine-phosphate-guanosine (CpG) DNA, paclitaxel, oraxol, MTL-CEBPA, ribavirin, elbasvir, grazoprevir, lipotecan, ZSP1241, U3-1784, avadomide, INCAGN01949, BLU-554 (FGFR4 inhibitor) or CMP-001. In some embodiments, anti-SARS-CoV-2 vaccine is BNT162b2 (Pfizer/BioNTech), mRNA-1273 (Moderna), JNJ-78436735 (Janssen), ADZ1222 (Oxford/AstraZeneca), NVX-CoV2373 (Novavax) BBIBP-CorV (vero cells) (Sinopharm), BBV152 (Bharat Biotech), or inactivated SARS-CoV-2 virus (CZ02 strain) (Sinovac).

In some embodiments, the other pharmaceutically active agent is an anti-cancer agent. In some embodiments, the anti-cancer agent is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, zotiraciclib citrate, camrelizumab, rivoceranib, toripalimab, tislelizumab, sitravatinib, CT0180 cells, nivolumab, rHuPH20 (Halozyme Therapeutics, Inc.; recombinant human hyaluronidase PH20 enzyme), sintilimab, cabozantinib, pembrolizumab/vibostolimab coformulation (MK-7684A), envafolimab, retifanlimab, INCB106385 (Incyte Corporation), tocilizumab, ERY974 (Chugai Pharmaceutical; an anti-Gglypican3 (GPC3)/CD3 bispecific antibody), or INCA00186 (Incyte Corporation).

In yet some other embodiments the other pharmaceutically active agent is sorafenib, lenvatinib, regorafenib, camrelizumab, rivoceranib, toripalimab, tislelizumab, sitravatinib, CT0180 cells (chimeric antigen receptor T cells targeting glypican-3 cells), nivolumab, rHuPH20, sintilimab, cabozantinib, pembrolizumab/vibostolimab coformulation (MK-7684A), envafolimab, retifanlimab, INCB106385 (Incyte Corporation), tocilizumab, ERY974 (Chugai Pharmaceutical), or INCA00186 (Incyte Corporation).

In some embodiments, the compositions of the invention further comprises an anti-cancer agent. In some embodiments, the compositions of the invention further comprise an anti-NASH or an anti-cancer agent.

In some embodiments, the anti-cancer agent is sorafenib, paclitaxel, lenvatinib, tazemetostat, TBI-302, namodenoson, MM-310, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, regorafenib, or zotiraciclib citrate.

In some embodiments, the anti-NASH agent is cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, or doxorubicin.

In some embodiments, the other pharmaceutically active agent is an immunotherapeutic agent. In some embodiments, the immunotherapeutic agent is pembrolizumab, avelumab, durvalumab, nivolumab, cemiplimab, ABX196, sintilimab, camrelizumab, spartalizumab, toripalimab, bispecific antibody XmAb20717, mapatumumab, tremelimumab, carotuximab, tocilizumab, ipilimumab, atezolizumab, bevacizumab, ramucirumab, IBI305, ascrinvacumab, TCR T-cell therapy agent, tislelizumab, sitravatinib, cytokine-based biologic agent IRX-2, bempegaldesleukin, DKN-01, PTX-9908, AK104, PT-112, SRF388, ET1402L1-CART, glypican 3-specific chimeric antigen receptor expressing T Cells (CAR-T cells), CD147-targeted CAR-T cells, NKG2D-based CAR T-cells, or neoantigen reactive T cells. In some embodiments, the other pharmaceutically active agent is atezolizumab or bevacizumab, or a combination thereof. In some embodiments, the other pharmaceutically active agent is nivolumab or ipilimumab, or a combination thereof.

In some embodiments, the compositions of the invention further comprises an immunotherapeutic agent.

In some embodiments, the other pharmaceutically active agent is an oncologic virus. In some embodiments, the oncologic virus is pexastimogene devacirepvec or talimogene laherparepvec. In some embodiments, the compositions of the invention further comprises an oncologic virus.

In some embodiments, the other pharmaceutically active agent is a vaccine. In some embodiments, the vaccine is GNOS-PV02, INO-9012, ABBV-176, NCI-4650, DNAJB1-PRKACA fusion kinase peptide vaccine, IMA970A, or an anti-SARS-CoV-2 vaccine. In some embodiments, the compositions of the invention further comprises a vaccine. In some embodiments, anti-SARS-CoV-2 vaccine is BNT162b2 (Pfizer/BioNTech), mRNA-1273 (Moderna), JNJ-78436735 (Janssen), ADZ1222 (Oxford/AstraZeneca), NVX-CoV2373 (Novavax) BBIBP-CorV (vero cells) (Sinopharm), BBV152 (Bharat Biotech), or inactivated SARS-CoV-2 virus (CZ02 strain) (Sinovac).

In some embodiments, the other pharmaceutically active agent is novantrone, prednisone, pixantrone, losoxantrone, cytidine-phosphate-guanosine (CpG) DNA, paclitaxel, oraxol, MTL-CEBPA, ribavirin, elbasvir, grazoprevir, lipotecan, ZSP1241, U3-1784, avadomide, INCAGN01949, or CMP-001.

In some embodiments, the compositions of the invention further comprises two or more other pharmaceutically active agents. In some embodiments, the two or more other pharmaceutically active agents are oncolytic agents, such as, but not limited to, nanatinostat and valganciclovir.

In some embodiments, the compositions of the invention further comprises a pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF 1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the composition of the invention, the composition comprises (a) an effective amount of Compound I-1-CoA, Compound I-32-CoA, Compound I-61-CoA, or Compound III-1-CoA, or a pharmaceutically acceptable salt or solvate thereof and (b) a pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments, the compositions of the invention comprise (a) an effective amount of Compound 1-1, Compound I-1-CoA, Compound 1-32, Compound I-32-CoA, Compound I-61, Compound I-61-CoA, Compound III-1, or Compound III-1-CoA, or a pharmaceutically acceptable salt or solvate thereof and (b) a pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the composition of the invention, the composition comprises an effective amount of (a) a compound of the invention and (b) a pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus or a gene-modified oncolytic virus, or an immunomodulating gene-therapy agent.

In some embodiments, the compositions of the invention comprise an effective amount of (a) a compound of formula (I), (IA), (IB), (IC), (ID), (IE), (IF), (IG), (IH), (IJ), (II), (III), (IIIA), and (IIIB), or Table A-18, Table A-19 or Table B5, or a pharmaceutically acceptable salt or solvate thereof, and (b) a pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus or a gene-modified oncolytic virus, or an immunomodulating gene-therapy agent.

In some embodiments, the compositions of the invention comprise (a) an effective amount of Compound I-1-CoA, Compound I-32-CoA, Compound I-61-CoA, or Compound III-1-CoA, or a pharmaceutically acceptable salt or solvate thereof and (b) a pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus or gene-modified oncolytic virus, or an immunomodulating gene-therapy agent.

In some embodiments, the compositions of the invention comprise (a) an effective amount of Compound I-1, Compound I-1-CoA, Compound I-32, Compound I-32-CoA, Compound I-61, Compound I-61-CoA, Compound III-1, or Compound III-1-CoA, or a pharmaceutically acceptable salt or solvate thereof and (b) a pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent. TBI-302, namodenoson, MM-310, a tumor-injected oncolytic virus or gene-modified oncolytic virus, or an immunomodulating gene-therapy agent.

In some embodiments, the compositions of the invention comprise an effective amount of a compound of the invention and sorafenib or lenvatinib. In some embodiments, the compositions of the invention comprise (a) an effective amount of Compound I-1-CoA, Compound I-32-CoA, Compound I-61-CoA, or Compound III-1-CoA, or a pharmaceutically acceptable salt or solvate thereof and (b) sorafenib or lenvatinib. In some embodiments, the compositions of the invention comprise (a) an effective amount of Compound I-1-CoA or a pharmaceutically acceptable salt or solvate thereof and (b) sorafenib or lenvatinib. In some embodiments, the compositions of the invention comprise (a) an effective amount of Compound I-32-CoA or a pharmaceutically acceptable salt or solvate thereof and (b) sorafenib or lenvatinib. In some embodiments, the compositions of the invention comprise (a) an effective amount of Compound I-32-CoA or a pharmaceutically acceptable salt or solvate thereof and (b) sorafenib. In some embodiments, the compositions of the invention comprise (a) an effective amount of Compound I-32-CoA or a pharmaceutically acceptable salt or solvate thereof and (b) lenvatinib. In some embodiments, the compositions of the invention comprise (a) an effective amount of Compound I-61-CoA or a pharmaceutically acceptable salt or solvate thereof and (b) sorafenib or lenvatinib. In some embodiments, the compositions of the invention comprise (a) an effective amount of Compound I-61-CoA or a pharmaceutically acceptable salt or solvate thereof and (b) sorafenib. In some embodiments, the compositions of the invention comprise (a) an effective amount of Compound I-61-CoA or a pharmaceutically acceptable salt or solvate thereof and (b) lenvatinib. In some embodiments, the compositions of the invention comprise (a) an effective amount of Compound III-1-CoA or a pharmaceutically acceptable salt or solvate thereof and (b) sorafenib or lenvatinib.

In some embodiments, the compositions of the invention comprise an effective amount of a compound of Formula (I), (IA), (IB), (IC), (ID), (IE), (IF), (IG), (IH), (IJ), (II), (III), (IIIA), or (IIIB), or a pharmaceutically acceptable salt or solvate thereof, and sorafenib or lenvatinib. In some embodiments, the compositions of the invention comprise (a) an effective amount of Compound I-1, Compound I-1-CoA, Compound I-32, Compound I-32-CoA, Compound I-61, Compound I-61-CoA, Compound III-1, or Compound III-1-CoA, or a pharmaceutically acceptable salt or solvate thereof and (b) sorafenib or lenvatinib. In some embodiments, the compositions of the invention comprise (a) an effective amount of Compound I-1 or Compound I-1-CoA or a pharmaceutically acceptable salt or solvate thereof and (b)

sorafenib or lenvatinib. In some embodiments, the compositions of the invention comprise (a) an effective amount of Compound I-32 or Compound I-32-CoA or a pharmaceutically acceptable salt or solvate thereof and (b) sorafenib or lenvatinib. In some embodiments, the compositions of the invention comprise (a) an effective amount of Compound I-32 or Compound I-32-CoA or a pharmaceutically acceptable salt or solvate thereof and (b) sorafenib. In some embodiments, the compositions of the invention comprise (a) an effective amount of Compound I-32 or Compound I-32-CoA or a pharmaceutically acceptable salt or solvate thereof and (b) lenvatinib. In some embodiments, the compositions of the invention comprise (a) an effective amount of Compound I-61 or Compound I-61-CoA or a pharmaceutically acceptable salt or solvate thereof and (b) sorafenib or lenvatinib. In some embodiments, the compositions of the invention comprise (a) an effective amount of Compound I-61 or Compound I-61-CoA or a pharmaceutically acceptable salt or solvate thereof and (b) sorafenib. In some embodiments, the compositions of the invention comprise (a) an effective amount of Compound I-61 or Compound I-61-CoA or a pharmaceutically acceptable salt or solvate thereof and (b) lenvatinib. In some embodiments, the compositions of the invention comprise (a) an effective amount of Compound III-1 or Compound III-1-CoA or a pharmaceutically acceptable salt or solvate thereof and (b) sorafenib or lenvatinib.

In some embodiments, the compositions of the invention comprise an effective amount of a compound of Formula (I), (IA), (IB), (IC), (ID), (IE), (IF), (IG), (IH), (IJ), (II), (III), (IIIA), or (IIIB), or a pharmaceutically acceptable salt or solvate thereof, and regorafenib. In some embodiments, the compositions of the invention comprise (a) an effective amount of Compound I-1, Compound I-1-CoA, Compound I-32, Compound I-32-CoA, Compound I-61, Compound I-61-CoA, Compound III-1, or Compound III-1-CoA, or a pharmaceutically acceptable salt or solvate thereof and (b) regorafenib. In some embodiments, the compositions of the invention comprise (a) an effective amount of Compound I-1 or Compound I-1-CoA or a pharmaceutically acceptable salt or solvate thereof and (b) regorafenib. In some embodiments, the compositions of the invention comprise (a) an effective amount of Compound I-32 or Compound I-32-CoA or a pharmaceutically acceptable salt or solvate thereof and (b) regorafenib. In some embodiments, the compositions of the invention comprise (a) an effective amount of Compound I-61 or Compound I-61-CoA or a pharmaceutically acceptable salt or solvate thereof and (b) regorafenib. In some embodiments, the compositions of the invention comprise (a) an effective amount of Compound III-1 or Compound III-1-CoA or a pharmaceutically acceptable salt or solvate thereof and (b) regorafenib.

In some embodiments, a compound of formula (I), (IA), (IB), (IC), (ID), (IE), (IF), (IG), (IH), (IJ), (II), (III), (IIIA), and (IIIB), or Table A-18 or A-19, or a pharmaceutically acceptable salt or solvate thereof, and another pharmaceutically active agent are synergistic in the compositions or methods of the invention. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, a pharmaceutically acceptable amino acid, meglumine, eglumine, D-glucamine, glucosamine, or choline salt of a compound of formula (I), (IA), (IB), and (IC), or Table A-7, A-8, A-9, A-10, A-11, or A12, and another pharmaceutically active agent are synergistic in the compositions or methods of the invention. In some embodiments, a pharmaceutically acceptable meglumine, lysine, or arginine salt of a compound of formula (I), (IA), (IB), and (IC), or Table A-7, A-8, A-9, A-10, A-11, or A12, and another pharmaceutically active agent are synergistic in the compositions or methods of the invention. In some embodiments, the lysine salt is an L-lysine salt. In some embodiments, the arginine salt is an L-arginine salt.

Table D sets forth illustrative compositions A1-A4, B1-B4, C1-C4, D1-D4, E1-E4, F1-F4, G1-G4, H1-H4, I1-I4, J1-J4, K1-K4, L1-L4, M1-M4, N1-N4, O1-O4, P1-P4, Q1-Q4, R1-R4, S1-S4, and T1-T4. Each composition of Table D comprises (a) an effective amount of a compound of invention and (b) another pharmaceutically active agent. For example, composition A1 comprises (a) an effective amount of Compound I-1 (or a pharmaceutically acceptable salt, solvate, or a CoA mono(thioester) or di(thioester) thereof) and (b) sorafenib; composition A2 comprises (a) an effective amount of Compound I-32 (or a pharmaceutically acceptable salt, solvate, or a CoA mono(thioester) or di(thioester) thereof) and (b) sorafenib; etc.

TABLE D

Illustrative compositions of the invention

| | | 1 Compound I-1 or a pharmaceutically acceptable salt, solvate, or a CoA mono-(thioester) or di(thioester) thereof | 2 Compound I-32 or a pharmaceutically acceptable salt, solvate, or a CoA mono-(thioester) or di(thioester) thereof | 3 Compound I-61 or a pharmaceutically acceptable salt, solvate, or a CoA mono-(thioester) or di(thioester) thereof | 4 Compound III-1 or a pharmaceutically acceptable salt, solvate, or a CoA mono-(thioester) or di(thioester) thereof |
|---|---|---|---|---|---|
| A | sorafenib | A1 | A2 | A3 | A4 |
| B | lenvatinib | B1 | B2 | B3 | B4 |
| C | paclitaxel | C1 | C2 | C3 | C4 |
| D | carotuximab | D1 | D2 | D3 | D4 |
| E | pembrolizumab | E1 | E2 | E3 | E4 |
| F | avelumab | F1 | F2 | F3 | F4 |
| G | durvalumab | G1 | G2 | G3 | G4 |
| H | tremelimumab | H1 | H2 | H3 | H4 |
| I | nivolumab | I1 | I2 | I3 | I4 |
| J | tazemetostat | J1 | J2 | J3 | J4 |

TABLE D-continued

| Illustrative compositions of the invention | | 1 Compound I-1 or a pharmaceutically acceptable salt, solvate, or a CoA mono-(thioester) or di(thioester) thereof | 2 Compound I-32 or a pharmaceutically acceptable salt, solvate, or a CoA mono-(thioester) or di(thioester) thereof | 3 Compound I-61 or a pharmaceutically acceptable salt, solvate, or a CoA mono-(thioester) or di(thioester) thereof | 4 Compound III-1 or a pharmaceutically acceptable salt, solvate, or a CoA mono-(thioester) or di(thioester) thereof |
|---|---|---|---|---|---|
| K | cemiplimab | K1 | K2 | K3 | K4 |
| L | ABX196 | L1 | L2 | L3 | L4 |
| M | T-cell receptor (TCR) immune cell therapy | M1 | M2 | M3 | M4 |
| N | TBI-302 | N1 | N2 | N3 | N4 |
| O | namodenoson | O1 | O2 | O3 | O4 |
| P | MM-310 | P1 | P2 | P3 | P4 |
| Q | tumor-injected oncolytic virus | Q1 | Q2 | Q3 | Q4 |
| R | gene-modified oncolytic virus | R1 | R2 | R3 | R4 |
| S | immunomodulating gene-therapy agent | S1 | S2 | S3 | S4 |
| T | regorafenib | T1 | T2 | T3 | T4 |

In some embodiments, the pharmaceutically acceptable carrier or vehicle includes, but is not limited to, a binder, filler, diluent, disintegrant, wetting agent, lubricant, glidant, coloring agent, dye-migration inhibitor, sweetening agent or flavoring agent.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof.

Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In some embodiments, the binder is hydroxypropylcellulose.

The binder or filler can be present from about 2% to about 49% by weight of the compositions of the invention provided herein or any range within these values. In some embodiments, the binder or filler is present in the compositions of the invention from about 5% to about 15% by weight. In some embodiments, the binder or filler is present in the compositions of the invention at about 5%, 6%, 7%, 8%, 9%, 8%, 10%, 11%, 12%, 13%, 14%, or 15% by weight or any range within any of these values.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. In some embodiments, the diluent is lactose monohydrate. In some embodiments, the diluent is lactose monohydrate Fast-Flo 316 NF.

The compositions of the invention can comprise a diluent, e.g., from about 5% to about 49% of a diluent by weight of composition or any range between any of these values. In some embodiments, the diluent is present in the compositions of the invention from about 15% to about 30% by weight. In some embodiments, the diluent is present in the compositions of the invention at about 15%, 16%, 17%, 18%, 19%, 18%, 20%, 21%, 22%, 23%, 24%, 25%, 26%, 27%, 28%, 29%, or 30% by weight or any range within any of these values.

Suitable disintegrants include, but are not limited to, agar; bentonite; celluloses, such as methylcellulose and carboxymethylcellulose; wood products; natural sponge: cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the compositions of the invention can vary. In some embodiments, the disintegrant is croscarmellose sodium. In some embodiments, the disintegrant is croscarmellose sodium NF (Ac-Di-Sol).

The compositions of the invention can comprise a disintegrant, e.g., from about 0.5% to about 15% or from about 1% to about 10% by weight of a disintegrant. In some embodiments, the compositions of the invention comprise a disintegrant in an amount of about 5%, 6%, 7%, 8%, 9%, 8%, 10%, 11%, 12%, 13%, 14%, or 15% by weight of the composition or in any range within any of these values.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co, of Boston, Mass.); and mixtures thereof. In some embodiments, the lubricant is magnesium stearate.

The compositions of the invention can comprise a lubricant, e.g., about 0.1 to about 5% by weight of a lubricant. In some embodiments, the compositions of the invention comprise a lubricant in an amount of about 0.5%, 0.6%, 0.7%, 0.8%, 0.9%, 0.8%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, or 3.0%, by weight of the composition or in any range within any of these values.

Suitable glidants include colloidal silicon dioxide, CAB-O-SIL® (Cabot Co. of Boston, Mass.), and talc, including asbestos-free talc.

Coloring agents include any of the approved, certified, water soluble FD&C dyes, and water insoluble FD&C dyes suspended on alumina hydrate, and color lakes and mixtures thereof.

Flavoring agents include natural flavors extracted from plants, such as fruits, and synthetic blends of compounds that provide a pleasant taste sensation, such as peppermint and methyl salicylate.

Sweetening agents include sucrose, lactose, mannitol, syrups, glycerin, sucralose, and artificial sweeteners, such as saccharin and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth. Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether.

Solvents include glycerin, sorbitol, ethyl alcohol, and syrup.

Examples of non-aqueous liquids utilized in emulsions include mineral oil and cottonseed oil. Organic acids include citric and tartaric acid. Sources of carbon dioxide include sodium bicarbonate and sodium carbonate.

The compounds of the invention and the compositions of the invention can be formulated for administration by a variety of means including orally, parenterally, by inhalation spray, topically, or rectally in formulations containing pharmaceutically acceptable carriers, adjuvants and vehicles. The term "parenteral" as used here includes subcutaneous, intravenous, intramuscular, and intraarterial injections with a variety of infusion techniques. Intraarterial and intravenous injection as used herein includes administration through catheters.

The compounds of the invention and the compositions of the invention can be formulated in accordance with the routine procedures adapted for desired administration route. Accordingly, the compositions of the invention can take such forms as suspensions, solutions or emulsions in oily or aqueous vehicles, and can contain formulatory agents such as suspending, stabilizing and/or dispersing agents. The compounds of the invention and the compositions of the invention can be formulated as a preparation suitable for implantation or injection. Thus, for example, the compositions of the invention can be formulated with suitable polymeric or hydrophobic materials (e.g., as an emulsion in an acceptable oil) or ion exchange resins, or as sparingly soluble derivatives (e.g., as a sparingly soluble salt). The compounds of the invention and the compositions of the invention can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In some embodiments, the compositions of the invention are suitable for oral administration. These compositions can comprise solid, semisolid, gelmatrix or liquid dosage forms suitable for oral administration. As used herein, oral administration includes buccal, lingual, and sublingual administration. Suitable oral dosage forms include, without limitation, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups or any combination thereof. In some embodiments, compositions of the invention suitable for oral administration are in the form of a tablet or a capsule. In some embodiments, the compositions of the invention are in a form of a tablet. In some embodiments, the compositions of the invention are in a form of a capsule. In some embodiments, the compounds of the invention are contained in a capsule.

In some embodiments, capsules are immediate release capsules. Non-limiting example of a capsule is a Coni-snap® hard gelatin capsule.

The compositions of the invention can be in the form of compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which can be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. A film coating can impart the same general characteristics as a sugar coating. Multiple compressed tablets are compressed tablets made by more than one compression cycle, including layered tablets, and press-coated or dry-coated tablets.

In some embodiments, the coating is a film coating. In some embodiments, the film coating comprises Opadry White and simethicone emulsion 30% USP. In some other embodiments, the film coating comprises Opadry Yellow.

In some embodiments, the compounds of the invention are contained in a tablet. In some embodiments, the tablet is a compressed tablet. In some embodiments, the tablet is a film-coated compressed tablet.

In some embodiments, the compositions of the invention are prepared by fluid bed granulation of the compounds of the invention with one or more pharmaceutically acceptable carrier, vehicle, or excipients. In some embodiments, the compositions of the invention are prepared by fluid bed granulation process can provide tablet formulation with good flowability, good compressibility, fast dissolution, good stability, and/or minimal to no cracking. In some embodiments, the fluid bed granulation process allows preparation of formulations having high drug loading, such as over 70% or over 75% of a compound of the invention.

The compositions of the invention can be in the form of soft or hard capsules, which can be made from gelatin, methylcellulose, starch, or calcium alginate. The hard gelatin capsule, also known as the dry-filled capsule (DFC), can comprise of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells can contain a preservative to prevent the growth of microorganisms. Suitable preservatives are those as described herein, including methyl- and propyl-parabens, and sorbic acid. The liquid, semisolid, and solid dosage forms provided herein can be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules can also be coated as known by those of skill in the art in order to modify or sustain dissolution of the active ingredient.

The compositions of the invention can be in liquid or semisolid dosage forms, including emulsions, solutions, suspensions, elixirs, and syrups. An emulsion can be a two-phase system, in which one liquid is dispersed in the form of small globules throughout another liquid, which can be oil-in-water or water-in-oil. Emulsions can include a pharmaceutically acceptable non-aqueous liquids or solvent, emulsifying agent, and preservative. Suspensions can include a pharmaceutically acceptable suspending agent and preservative. Aqueous alcoholic solutions can include a pharmaceutically acceptable acetal, such as a di-(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs can be clear, sweetened, and hydroalcoholic solutions. Syrups can be concentrated aqueous solutions of a sugar, for example, sucrose, and can comprise a preservative. For a liquid dosage form, for example, a solution in a polyethylene glycol can be diluted with a sufficient quantity of a pharmaceutically acceptable liquid carrier, e.g., water, to be measured conveniently for administration.

The compositions of the invention for oral administration can be also provided in the forms of liposomes, micelles, microspheres, or nanosystems. Miccellar dosage forms can be prepared as described in U.S. Pat. No. 6,350,458.

The compositions of the invention can be provided as non-effervescent or effervescent, granules and powders, to be reconstituted into a liquid dosage form. Pharmaceutically acceptable carriers and excipients used in the non-effervescent granules or powders can include diluents, sweeteners, and wetting agents. Pharmaceutically acceptable carriers and excipients used in the effervescent granules or powders can include organic acids and a source of carbon dioxide.

Coloring and flavoring agents can be used in all of the above dosage forms. And, flavoring and sweetening agents are especially useful in the formation of chewable tablets and lozenges.

The compositions of the invention can be formulated as immediate or modified release dosage forms, including delayed-, extended-, pulsed-, controlled-, targeted-, and programmed-release forms.

In some embodiments, the compositions of the invention comprise a film-coating.

The compositions of the invention can comprise another active ingredient that does not impair the composition's therapeutic or prophylactic efficacy or can comprise a substance that augments or supplements the composition's efficacy.

The tablet dosage forms can comprise the compound of the invention in powdered, crystalline, or granular form, and can further comprise a carrier or vehicle described herein, including binder, disintegrant, controlled-release polymer, lubricant, diluent, or colorant.

In some embodiments, the compositions of the invention can further comprise an excipient such as a diluent, a disintegrant, a wetting agent, a binder, a glidant, a lubricant, or any combination thereof. In some embodiments, a tablet comprises a binder. And, in some embodiments, the binder comprises microcrystalline cellulose, dibasic calcium phosphate, sucrose, corn starch, polyvinylpyrridone, hydroxypropyl cellulose, hydroxymethyl cellulose, or any combination thereof. In other embodiments, the tablet comprises a disintegrant. In other embodiments, the disintegrant comprises sodium croscarmellose, sodium starch glycolate, or any combination thereof. In other embodiments, the tablet comprises a lubricant. And, in some embodiments, the lubricant comprises magnesium stearate stearic acid, hydrogenated oil, sodium stearyl fumarate, or any combination thereof.

In some embodiments, the compositions of the invention are in the form of a tablet that comprises a binder such as any of the binders described herein.

In some embodiments, the compositions of the invention are in the form of a tablet that comprises a disintegrant such as any of the disintegrants described herein.

In some embodiments, the compositions of the invention are in the form of a tablet that comprises a lubricant such as any of the lubricants described herein.

In some embodiments, the compositions of the invention can be in a modified release or a controlled release dosage form. In some embodiments, the compositions of the invention can comprise particles exhibiting a particular release profile. For example, the compositions of the invention can comprise the compounds of the invention in an immediate release form while also comprising a statin or a pharmaceutically acceptable salt thereof in a modified release form, both compressed into a single tablet. Other combination and modification of release profile can be achieved as understood by one skilled in the art. Examples of modified release dosage forms suited for compositions of the invention are described, without limitation, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830;

6,087,324; 6,113,943; 6,197,350; 6,248,363; 6,264,970; 6,267,981; 6,376,461; 6,419,961; 6,589,548; 6,613,358; and 6,699,500.

In some embodiments, the compositions of the invention are a matrix-controlled release dosage form. For example, the compositions of the invention can comprise about 300 mg to about 600 mg of a compound of the invention provided as a matrix-controlled release form. In some embodiments, a matrix-controlled release form can further comprise another pharmaceutically active agent. In some embodiments, the release profile of the compounds of the invention and of the other pharmaceutically active agent is the same or different. Suitable matrix-controlled release dosage forms are described, for example, in Takada et al in "Encyclopedia of Controlled Drug Delivery," Vol. 2, Mathiowitz ed., Wiley, 1999.

In some embodiments, the compositions of the invention comprise from about 10 mg to about 400 mg of another pharmaceutically active agent and from about 300 mg to about 600 mg of a compound of the invention. In some embodiments, the compositions of the invention comprise from about 10 mg to about 400 mg of the anti-cancer agent and from about 300 mg to about 600 mg of a compound of the invention. In some embodiments, the composition is in a matrix-controlled modified release dosage form.

In some embodiments, the compositions of the invention comprise from about 10 mg to about 40 mg of a statin and from about 300 mg to about 600 mg of a compound of the invention, wherein the composition is in a matrix-controlled modified release dosage form.

In some embodiments, the matrix-controlled release form comprises an erodible matrix comprising water-swellable, erodible, or soluble polymers, including synthetic polymers, and naturally occurring polymers and derivatives, such as polysaccharides and proteins.

In some embodiments, the erodible matrix of the matrix-controlled release form comprises chitin, chitosan, dextran, or pullulan; gum agar, gum arabic, gum karaya, locust bean gum, gum tragacanth, carrageenans, gum ghatti, guar gum, xanthan gum, or scleroglucan; starches, such as dextrin or maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), carboxymethyl ethyl cellulose (CMEC) hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), or ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; or other acrylic acid derivatives, such as homopolymers and copolymers of butylmethacrylate, methylmethacrylate, ethylmethacrylate, ethylacrylate, (2-dimethylaminoethyl)methacrylate, or (trimethylaminoethyl)methacrylate chloride; or any combination thereof.

In other embodiments, the compositions of the invention are in a matrix-controlled modified release form comprising a non-erodible matrix. In some embodiments, the statin or the compound of the invention is dissolved or dispersed in an inert matrix and is released primarily by diffusion through the inert matrix once administered. In some embodiments, the non-erodible matrix of the matrix-controlled release form comprises an insoluble polymer, such as polyethylene, polypropylene, polyisoprene, polyisobutylene, polybutadiene, polymethylmethacrylate, polybutylmethacrylate, chlorinated polyethylene, polyvinylchloride, a methyl acrylate-methyl methacrylate copolymer, an ethylene-vinylacetate copolymer, an ethylene/propylene copolymer, an ethylene/ethyl acrylate copolymer, a vinylchloride copolymer with vinyl acetate, a vinylidene chloride, an ethylene or a propylene, an ionomer polyethylene terephthalate, a butyl rubber epichlorohydrin rubber, an ethylene/vinyl alcohol copolymer, an ethylenevinyl acetate/vinyl alcohol terpolymer, an ethylene/vinyloxy ethanol copolymer, a polyvinyl chloride, a plasticized nylon, a plasticized polyethyleneterephthalate, a natural rubber, a silicone rubber, a polydimethylsiloxane, a silicone carbonate copolymer, or a hydrophilic polymer, such as an ethyl cellulose, a cellulose acetate, a crospovidone, or a cross-linked partially hydrolyzed polyvinyl acetate; a fatty compound, such as a carnauba wax, a microcrystalline wax, or a triglyceride; or any combination thereof.

The compositions of the invention that are in a modified release dosage form can be prepared by methods known to those skilled in the art, including direct compression, dry or wet granulation followed by compression, melt-granulation followed by compression.

In some embodiments, the compositions of the invention comprise a tablets-in-capsule system, which can be a multifunctional and multiple unit system comprising versatile mini-tablets in a hard gelatin capsule. The mini-tablets can be rapid-release, extended-release, pulsatile, delayed-onset extended-release minitablets, or any combination thereof. In some embodiments, combinations of mini-tablets or combinations of mini-tablets and minibeads comprising multiple active pharmaceutical agents can each have specific lag times, of release multiplied pulsatile drug delivery system (DDS), site-specific DDS, slow-quick DDS, quick/slow DDS and zero-order DDS.

In some embodiments, the compositions of the invention are in an osmotic-controlled release dosage form.

In some embodiments, the osmotic-controlled release device comprises a one-chamber system, a two-chamber system, asymmetric membrane technology (AMT), an extruding core system (ECS), or any combination thereof. In some embodiments, such devices comprise at least two components: (a) the core which contains the active pharmaceutical agent(s); and (b) a semipermeable membrane with at least one delivery port, which encapsulates the core. The semipermeable membrane controls the influx of water to the core from an aqueous environment of use so as to cause drug release by extrusion through the delivery port(s).

In some embodiments, the core of the osmotic device optionally comprises an osmotic agent, which creates a driving force for transport of water from the environment of use into the core of the device. One class of osmotic agents useful in the compositions of invention comprise water-swellable hydrophilic polymers, which are also referred to as "osmopolymers" or "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP), cross-linked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

Another class of osmotic agents useful in the compositions of the invention comprises osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea and mixtures thereof.

Osmotic agents of different dissolution rates can be employed to influence how rapidly the compounds of the invention dissolve following administration. For example, an amorphous sugar, such as Mannogeme EZ (SPI Pharma, Lewes, Del.) can be included to provide faster delivery during the first couple of hours (e.g., about 1 to about 5 hrs) to promptly produce prophylactic or therapeutic efficacy, and gradually and continually release of the remaining amount to maintain the desired level of therapeutic or prophylactic effect over an extended period of time. In some embodiments, the compounds of the invention are released from the compositions of the invention at such a rate to replace the amount of the compounds of the invention metabolized or excreted by the subject.

The core can also include a wide variety of other excipients and carriers as described herein to enhance the performance of the dosage form or to promote stability or processing.

Materials useful for forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The semipermeable membranes can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the compounds of the invention released and the release rate can substantially be modulated via the thickness and porosity of the semipermeable membrane, the composition of the core, and the number, size, and position of the delivery ports.

In some embodiments, the compositions of the invention wherein an osmotic controlled-release dosage form can further comprise additional conventional excipients as described herein to promote performance or processing of the formulation.

The osmotic controlled-release dosage forms can be prepared according to conventional methods and techniques known to those skilled in the art (see, *Remington: The Science and Practice of Pharmacy*, supra: Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In some embodiments, the compositions of the invention are formulated as asymmetric membrane technology (AMT) controlled-release dosage form that comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In some embodiments, the compositions of the invention are formulated as ESC controlled-release dosage form that comprises an osmotic membrane that coats a core comprising the compound of the invention, hydroxylethyl cellulose, and other pharmaceutically acceptable excipients.

In some embodiments, the compositions of the invention are a modified release dosage form that is fabricated as a multiparticulate-controlled release dosage form that comprises a plurality of particles, granules, or pellets, microparticulates, beads, microcapsules and microtablets, ranging from about 10 μm to about 3 mm, about 50 μm to about 2.5 mm, or from about 100 μm to 1 mm in diameter.

The multiparticulate-controlled release dosage forms can provide a prolonged release dosage form with an improved bioavailability. Suitable carriers to sustain the release rate of the compounds of the invention include, without limitation, ethyl cellulose, HPMC, HPMC-phthalate, colloidal silicondioxide and Eudragit-RSPM.

The compositions of the invention in pellet form can comprise 50-80% (w/w) of a drug and 20-50% (w/w) of microcrystalline cellulose or other polymers. Suitable polymers include, but are not limited to, microcrystalline wax, pregelatinized starch and maltose dextrin.

Beads can be prepared in capsule and tablet dosage forms. Beads in tablet dosage form can demonstrate a slower dissolution profile than microparticles in capsule form. Microparticle fillers suitable for compositions and therapeutic or prophylactic methods of the invention include, without limitation, sorbitan monooleate (Span 80), HPMC, or any combination thereof. Suitable dispersions for controlled release latex include, for example, ethyl-acrylate and methyl-acrylate.

In some embodiments, the compositions of the invention are in the form or microcapsules and/or microtablets. In some embodiments, microcapsules comprise extended release polymer microcapsules containing a statin and the compound of the invention with various solubility characteristics. Extended release polymer microcapsules can be prepared with colloidal polymer dispersion in an aqueous environment. In other embodiments, microcapsules suitable for the compositions and methods provided herein can be prepared using conventional microencapsulating techniques (Bodmeier & Wang, 1993).

Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989. Excipients for such technologies are commercially available and described in US Pharmacopeia.

Other excipients as described herein can be blended with the compositions of the invention to aid in processing and forming the multiparticulates. The resulting particles can themselves constitute the multiparticulate dosage form or can be coated by various film-forming materials, such as enteric polymers, water-swellable, or water-soluble polymers. The multiparticulates can be further processed as a capsule or a tablet.

In other embodiments, the compositions of the invention are in a dosage form that has an instant releasing component and at least one delayed releasing component, and is capable of giving a discontinuous release of the compound in the form of at least two consecutive pulses separated in time from about 0.1 hour to about 24 hours.

In some embodiments, the compositions of the invention comprise from about 1 mg to about 1000 mg of a compound of the invention or any amount ranging from and to these values. In some embodiments, the compositions of the invention comprise from about 1 mg to about 500 mg of a compound of the invention or any amount ranging from and to these values. In some embodiments, the compositions of the invention comprise from about 1 mg to about 400 mg of a compound of the invention or any amount ranging from and to these values. In some embodiments, the compositions of the invention comprise from about 200 mg to about 600 mg of a compound of the invention or any amount ranging from and to these values. In some embodiments, the compositions of the invention comprise from about 1 mg to about 200 mg of a compound of the invention or any amount ranging from and to these values.

In other embodiments, the compositions of the invention comprise a compound of the invention in an amount that is a molar equivalent to about 1 mg to about 1000 mg of the compound of the invention or any amount ranging from and to these values. In other embodiments, the compositions of the invention comprise a compound of the invention in an amount that is a molar equivalent to about 1 mg to about 500 mg of the compound of the invention or a compound useful in the methods of the invention or any amount ranging from and to these values. In other embodiments, the compositions of the invention comprise a compound of the invention in an amount that is a molar equivalent to about 1 mg to about 400 mg of the compound of the invention or any amount ranging from and to these values. In other embodiments, the compositions of the invention comprise a compound of the invention in an amount that is a molar equivalent to about 200 mg to about 600 mg of the compound of the invention or any amount ranging from and to these values. In other embodiments, the compositions of the invention comprise a compound of the invention in an amount that is a molar equivalent to about 1 mg to about 200 mg of the compound of the invention or any amount ranging from and to these values.

In some embodiments, the compositions of the invention comprise a compound of the invention in an amount of about 10 wt % to about 99 wt % of the total weight of the compositions of the invention.

Methods of the Invention

1. Methods Comprising Administration of a Compound of the Invention or a Composition of the Invention The present invention provides methods for treating or preventing a disease, comprising administering to a subject in need thereof an effective amount of the compound of the invention or the composition of the invention, wherein the disease is liver disease or an abnormal liver condition; cancer (such as hepatocellular carcinoma, cholangiocarcinoma, or cancer of the digestive tract); a malignant or benign tumor of the lung, liver, gall bladder, bile duct or digestive tract; an intra- or extra-hepatic bile duct disease; a disorder of lipoprotein; a lipid-and-metabolic disorder; cirrhosis; fibrosis, a disorder of glucose metabolism; a cardiovascular or related vascular disorder; a disease resulting from steatosis, fibrosis, or cirrhosis; a disease resulting from steatosis, fibrosis, and cirrhosis; a disease associated with increased inflammation (such as hepatic inflammation, pulmonary inflammation, inflammation of the heart, inflammation of the uterus, cystic fibrosis, inflammation of the kidney); hepatocyte ballooning; a peroxisome proliferator activated receptor-associated disorder; an ATP citrate lyase disorder; an acetyl-coenzyme A carboxylase disorder; obesity; pancreatitis; or renal disease. In some embodiments, renal disease is end-stage renal disease.

In some embodiments, disease associated with increased inflammation is hepatic inflammation, pulmonary inflammation, inflammation of the heart, inflammation of the uterus, cystic fibrosis, inflammation of the kidney, fatty liver disease, endometriosis, type-2 diabetes mellitus, type-1 diabetes mellitus, inflammatory bowel disease, asthma, rheumatoid arthritis, obesity, Alzheimer's disease. Parkinson's disease, or cancer.

The present invention provides methods for treating or preventing a disease, comprising administering to a subject in need thereof an effective amount of the compound of the invention or the composition of the invention, wherein the disease is cancer; a lipid-and-metabolic disorder; a liver disorder; cirrhosis; fibrosis; a disorder of glucose metabolism; a peroxisome proliferator activated receptor-associated disorder; a malignant or benign tumor of the lung, liver, bile and digestive tract; an ATP citrate lyase disorder; an acetyl-coenzyme A carboxylase disorder; obesity, pancreatitis;

renal disease; hepatocyte ballooning; hepatic inflammation; or pulmonary inflammation. In some embodiments, fibrosis is liver fibrosis.

In some embodiments of the methods as disclosed herein, the disease is cancer. In some embodiments, the cancer is hepatocellular carcinoma (HCC). HCC with cirrhosis, HCC without cirrhosis, HCC with fibrosis, HCC without fibrosis. In some embodiments, HCC is early HCC or advanced HCC. In some embodiments, HCC is localized, regional, advanced, metastatic, or unstaged. In some embodiments, HCC is HCC subtype S1, HCC subtype S2. HCC subtype S3-1, or HCC subtype S3-2. In some embodiments, the cancer is HCC, intrahepatic cholangiocarcinoma or hemangiosarcoma.

In some embodiments, treating cancer comprises reducing tumor burden. In some embodiments, treating HCC comprises reducing HCC tumor burden.

In some embodiments of the methods as disclosed herein, the cancer is cholangiocarcinoma, colorectal cancer, biliary tract cancer, or pulmonary cancer. In some embodiments, the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma. Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, clear cell sarcoma of kidney, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemias, Hodgkin's disease, non-Hodgkin's lymphoma, multiple myeloma, Waldenström's macroglobulinemia, heavy chain disease, gastrointestinal cancer, head-and-neck cancer, hematopoietic cancer, or polycythemia vera. In some embodiments, the cancer is renal cell carcinoma or clear cell sarcoma of kidney.

In some embodiments, gastrointestinal (digestive) cancer is gastrointestinal stromal tumor (GIST), esophageal cancer, gallbladder cancer, gastrointestinal carcinoid tumor, cholangiocarcinoma, duodenal cancer, gastroesophageal (ge) junction cancer, islet cell cancer, pancreatic cancer, stomach cancer, colon cancer, rectal cancer, colorectal cancer, anal cancer, liver cancer, biliary tract cancer, bile duct cancer, cancer of the small intestine, seudomyxoma peritonei, small bowel cancer, or cancer of unknown primary.

In some embodiments, the hematopoietic cancer is non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), or chronic myeloid leukemia (CML).

In some embodiments, the disease is hepatocellular adenoma, bile duct adenoma, or digestive system adenoma.

In some embodiments of the methods as disclosed herein, the cancer is in any stage. In some embodiments, the cancer can be in stage 0, stage I, stage II, stage III, or stage IV. In some embodiments of the methods as disclosed herein, the disease is tumor. In some embodiments, the tumor is in any grade. In some embodiments, the tumor is grade 1, grade 2, grade 3, or grade 4.

The present invention provides methods for treating or preventing a disease, comprising administering to a subject in need thereof an effective amount of the compound of the invention or the composition of the invention, wherein the disease is renal cell carcinoma, autosomal dominant polycystic kidney disease, autosomal dominant polycystic kidney disease type 1 with tuberous sclerosis, autosomal dominant tubulointerstitial kidney disease, bilateral multicystic dysplastic kidney, clear cell sarcoma of kidney, de novo thrombotic microangiopathy after kidney transplantation, HNF1B-related autosomal dominant tubulointerstitial kidney disease, IgG4-related kidney disease, MUC1-related autosomal dominant tubulointerstitial kidney disease, medullary cystic kidney disease type 1, MUC1-related medullary cystic kidney disease, medullary sponge kidney, multicystic dysplastic kidney, multilocular cyst of the kidney, multinodular goiter-cystic kidney-polydactyly syndrome, neonatal diabetes-congenital hypothyroidism-congenital glaucoma-hepatic fibrosis-polycystic kidneys syndrome, REN-related autosomal dominant tubulointerstitial kidney disease, rare disorder potentially indicated for kidney transplant, renal cell carcinoma, renal dysplasia and unilateral or bilateral renal dysplasia, renal or urinary tract malformation, sex reversion-kidneys, adrenal and lung dysgenesis syndrome (SERKAL syndrome), serpentine fibula-polycystic kidneys syndrome, uromodulin-associated kidney disease, Medullary cystic kidney disease type 2 (UMOD-related autosomal dominant tubulointerstitial kidney), unilateral multicystic dysplastic kidney, or ventriculomegaly-cystic kidney disease. In some embodiments, the disease is renal cell carcinoma or clear cell sarcoma of kidney.

In some embodiments of the methods as disclosed herein, the disease is a lipid-and-metabolic disorder. In some embodiments, the lipid-and-metabolic disorder is characterized by high C-reactive protein (CRP), high serum amyloid A (SAA), high alanine aminotransferase (ALT), high aspartate aminotransferase (AST), high alkaline phosphatase (ALP), high gamma-glutamyl transferase (GGT), high low-density lipoprotein (LDL), high very-low-density lipoprotein (VLDL), high Lp(a), low lipoprotein lipase (LPL), high apolipoprotein C-III (ApoCIII), high apolipoprotein B (ApoB) and ApoB/Lp(a) (lipoprotein(a)) ratio, high total cholesterol, low high-density lipoprotein (HDL), or high non-HDL-cholesterol in the subject's plasma or blood serum; or by high glucose and insulin resistance in a subject with diabetes. In some embodiments, the lipid-and-metabolic disorder is non-alcoholic fatty liver disease (NAFLD), non-alcoholic steatohepatitis (NASH), or alcoholic steatohepatitis (ASH).

In some embodiments of the methods as disclosed herein, the disease is a disorder of glucose metabolism. In some embodiments, the disorder of glucose metabolism is type I diabetes or type II diabetes.

In some embodiments of the methods as disclosed herein, the disease is a disease resulting from steatosis, fibrosis, and cirrhosis. In some embodiments, the disease resulting from steatosis is inflammation. In some embodiments, the disease resulting from steatosis is NAFLD, NASH, or ASH. In some embodiments, the disease resulting from fibrosis is liver cirrhosis, portal hypertension or liver failure. In some embodiments, the disease resulting from cirrhosis is, hepatocellular carcinoma, liver damage, or hepatic encephalopathy.

In some embodiments, the liver disease is Alagille Syndrome (ALGS), alpha-1-anti-trypsin deficiency (AATD), hereditary hemochromatosis (HH), Crigler Najjar Syndrome, glycogen storage disease—type 1, liposomal acid lipase deficiency, tyrosinemia, or Wilson's Disease.

The present invention provides methods for reducing in a subject's blood plasma or blood serum the subject's C-reactive protein (CRP) concentration, serum amyloid A (SAA) concentration, alanine aminotransferase (ALT) concentration, aspartate aminotransferase (AST) concentration, alkaline phosphatase (ALP) concentration, gamma-glutamyl transferase (GGT) concentration, serum creatinine concentration, 7α-hydroxy-4-cholesten-3-one (C4) concentration, protein:creatinine ratio, creatine kinase concentration, angiopoietin-like protein 3 concentration, angiopoietin-like protein 4 concentration, angiopoietin-like protein 8 concentration, fibrinogen concentration, total cholesterol concentration, low-density lipoprotein cholesterol concentration, low-density lipoprotein concentration, very low-density lipoprotein cholesterol concentration, very low-density lipoprotein concentration, non-HDL cholesterol concentration, non-HDL concentration, apolipoprotein B concentration, apolipoprotein C concentration, lipoprotein(a) concentration, or serum triglyceride concentration, comprising administering to a subject in need thereof an effective amount of the compound of the invention or the composition of the invention.

The present invention provides methods for reducing triglyceride concentration in a subject's liver, comprising administering to a subject in need thereof an effective amount of the compound of the invention or the composition of the invention.

The present invention provides methods for elevating in a subject's blood plasma or blood serum a concentration of high-density lipoprotein cholesterol, high-density lipoprotein or lipoprotein lipase, comprising administering to a subject in need thereof an effective amount of a compound of the invention or the composition of the invention.

The present invention provides methods for increasing functionalization of the high-density lipoprotein cholesterol, without increasing its concentration in a subject's blood plasma or blood serum, comprising administering to a subject in need thereof an effective amount of a compound of the invention or the composition of the invention, wherein an amount or rate of excretion of cholesterol and triglycerides increases.

The present invention provides methods for treating a disease, comprising administering to a subject in need thereof an effective amount of the compound of the invention or the composition of the invention, wherein the disease is inflammatory disease, gastrointestinal disease, irritable bowel syndrome (IBS), inflammatory bowel disease (IBD), or autoimmune disease.

In some embodiments of the methods as disclosed herein, the disease is inflammatory bowel disease. In some embodiments, the inflammatory bowel disease is Crohn's Disease or ulcerative colitis.

In some embodiments of the methods as disclosed herein, the disease is autoimmune disease. In some embodiments, the autoimmune disease is systemic lupus erythematosus.

The present invention provides methods for regressing, reducing the rate of progression or inhibiting progression of fibrosis, hepatocyte ballooning or hepatic inflammation, comprising administering to a subject in need thereof an effective amount of the compound of the invention or the composition of the invention.

The present invention provides methods for inhibiting, reducing, or delaying advancement of a subject's lipid synthesis, liver steatosis, hepatocyte ballooning or inflammation, liver fibrosis, lung fibrosis, or cirrhosis, comprising administering to a subject in need thereof an effective amount of the compound of the invention or the composition of the invention.

The present invention provides methods for reducing a subject's risk of developing or having atherosclerosis, coronary heart disease, peripheral vascular disease, stroke, or restenosis, comprising administering to a subject in need thereof an effective amount of a compound of the invention or the composition of the invention.

The present invention provides methods for elevating HDL concentration in the subject's blood serum or plasma, comprising administering to a subject in need thereof an effective amount of the compound of the invention or the composition of the invention.

The present invention further provides methods for lowering LDL concentration in a subject's blood serum or plasma, comprising administering to a subject in need thereof an effective amount of a compound of the invention.

The present invention provides methods for inhibiting NF-kB or stellate cell activation, comprising administering to a subject in need thereof an effective amount of the compound of the invention or the composition of the invention.

The present invention provides methods for activating PPAR (peroxisome proliferator-activated receptor) in a subject, comprising administering to a subject in need thereof an effective amount of the compound of the invention or the composition of the invention.

The present invention provides methods for CCR2/CCR5 gene downregulation, comprising administering to a subject in need thereof an effective amount of a compound of the invention or the composition of the invention.

The present invention provides methods for inhibiting one or more of NF-kB activation, CCR2 activation, CCR5 activation, α-SMA upregulation, and stellate cell activation, comprising administering to a subject in need thereof an effective amount of the compound of the invention or the composition of the invention.

The present invention provides methods for inhibiting an interleukin's activation or concentration, comprising administering to a subject in need thereof an effective amount of a compound of the invention or the composition of the invention. In some embodiments, the interleukin (IC) is IL-2, IL-6, IL-17 or IL-18.

The present invention provides methods for inhibiting formation of fibrin/fibrinogen, inhibiting secretion of gastrin, lactate dehydrogenase, prostatic acid phosphatase (PAP), or thyroglobulin, or inhibiting production of urine catecholamine, urine vanillylmandelic acid (VMA) or urine homovanillic acid (HVA), comprising administering to a subject in need thereof an effective amount of a compound of the invention or the composition of the invention.

The present invention provides methods for inhibiting production of beta-human chorionic gonadotropin (beta-hCG), beta-2-microglobulin (B2M), B-cell immunoglobulin, comprising administering to a subject in need thereof an effective amount of a compound of the invention or the composition of the invention.

The present invention provides methods for inhibiting production of alpha-fetoprotein (AFP), comprising administering to a subject in need thereof an effective amount of a compound of the invention or the composition of the invention.

The present invention also provides methods for inhibiting hepatic fatty acid or sterol synthesis, comprising administering to a subject in need thereof an effective amount of the compound of the invention or the composition of the invention.

The present invention also provides methods for treating or preventing a disease or disorder that is capable of being treated or prevented by increasing HDL levels, comprising administering to a subject in need thereof an effective amount of the compound of the invention or the composition of the invention.

The present invention also provides methods for treating or preventing a disease or disorder that is capable of being treated or prevented by lowering LDL levels, which comprises administering to a subject in need thereof an effective amount of the compound of the invention or the composition of the invention.

Without being limited by theory, it is believed that the compounds of the invention favorably alter lipid metabolism at least in part by enhancing oxidation of fatty acids through the ACC/malonyl-CoA/CPT-I regulatory axis. Accordingly, the invention also provides methods for treating or preventing a metabolic syndrome disorder, comprising administering to a subject in need thereof an effective amount of the compound of the invention or the composition of the invention.

The present invention further provides methods for modulating, directly inhibiting or allosterically inhibiting ATP citrate lyase (ACLY) in a subject, comprising administering to the subject an effective amount of the compound of the invention or the composition of the invention.

The present invention further provides methods for modulating, directly inhibiting or allosterically inhibiting acetyl-CoA carboxylase 1 (ACC1) or acetyl-CoA carboxylase 2 (ACC2) in a subject, comprising administering to the subject an effective amount of the compound of the invention or the composition of the invention.

The present invention further provides methods for reducing fat or cholesterol content of livestock meat or poultry eggs, comprising administering to the livestock or poultry an effective amount of the compound of the invention or the composition of the invention.

The present invention further provides methods for reducing risk of cancer, slowing the onset of cancer or slowing progression of cancer, comprising administering to a subject in need thereof an effective amount of the compound of the invention or the composition of the invention.

In some embodiments, the cancer is hepatocellular carcinoma (HCC), HCC with cirrhosis, HCC without cirrhosis, HCC with fibrosis, HCC without fibrosis, cholangiocarcinoma, colorectal cancer, biliary tract cancer, or pulmonary cancer. In some embodiments, HCC is early HCC or advanced HCC. In some embodiments, HCC is localized, regional, advanced, metastatic, or unstaged. In some embodiments, HCC is HCC subtype S1, HCC subtype S2, HCC subtype S3-1, or HCC subtype S3-2. In some embodiments, the cancer is HCC, intrahepatic cholangiocarcinoma or hemangiosarcoma. In some embodiments, the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, clear cell sarcoma of kidney, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemias, Hodgkin's disease, non-Hodgkin's lymphoma, multiple myeloma, Waldenström's macroglobulinemia, heavy chain disease, gastrointestinal cancer, head-and-neck cancer, hematopoietic cancer, or polycythemia vera. In some embodiments, cancer is brain cancer, lung cancer, prostate cancer, bladder cancer, breast cancer, liver cancer, stomach cancer, colon cancer, or renal cell carcinoma. In some embodiments, lung cancer is non-small cell lung cancer. In some embodiments, brain cancer is glioblastoma multiforme. In some embodiments, liver cancer is HCC, intrahepatic cholangiocarcinoma or hemangiosarcoma.

The present invention provides methods for reducing risk of tumor growth, slowing the onset of tumor growth or slowing progression of tumor growth, comprising administering to a subject in need thereof an effective amount of the compound of the invention or the composition of the invention.

In some embodiments, tumor is lung, prostate, bladder, breast, liver, stomach, or colon tumor.

In some other embodiments, the compounds of the invention or the compositions of the invention are used as an adjuvant therapy in patients following surgical or procedural treatments of cancer, and for improvement of the tumor environment.

The present invention further provides methods for treating or preventing a viral infection, comprising administering to the subject an effective amount of the compound of the invention or the composition of the invention. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

The present invention further provides methods for inhibiting replication of a virus, comprising contacting the virus with an effective amount of the compound of the invention or the composition of the invention. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the viral infection is an infection by a human virus, a non-human mammalian virus, an avian virus, a plant virus, a bacteria virus or an archaeal virus. In some embodiments, the virus is a human virus, a non-human mammalian virus, an avian virus, a plant virus, a bacteria virus or an archaeal virus.

In some embodiments, the non-human mammalian virus is a bat virus, bovine virus, canine virus, equine virus, feline virus or porcine virus.

In some embodiments, the viral infection is an infection by an oncovirus. In some embodiments, the virus is an oncovirus. Accordingly, the invention further provides methods for treating or preventing an oncovirus infection, comprising administering to the subject an effective amount of the compound of the invention or the composition of the invention. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

The present invention further provides methods for inhibiting replication of an oncovirus, comprising contacting the oncovirus with an effective amount of the compound of the invention or the composition of the invention. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the oncovirus is human papillomavirus, hepatitis B virus, hepatitis C virus, Epstein-Barr virus. Kaposi's sarcoma-associated herpesvirus, human T-lymphotropic virus, polyomavirus, T-lymphotropic virus, herpesvirus, or Epstein-Barr virus. In some embodiments, polyomavirus is Merkel cell polyomavirus. In some embodiments, herpesvirus is Kaposi's sarcoma-associated herpesvirus.

In some embodiments, the viral infection is an infection by a class I virus, a class II virus, a class III virus, a class IV virus, a class V virus, a class VI virus, or a class VII virus. In some embodiments, the virus is a class I virus, a class II virus, a class III virus, a class IV virus, a class V virus, a class VI virus, or a class VII virus.

In some embodiments, the class I virus is a dsDNA virus. In some embodiments, the dsDNA virus is adenovirus, herpesvirus, or poxvirus.

In some embodiments, the class II virus is an ssDNA virus. In some embodiments, the ssDNA virus is a +strand ssDNA virus. In some embodiments, the ssDNA virus is parvovirus.

In some embodiments, the class III virus is a dsRNA virus. In some embodiments, the dsRNA virus is reovirus.

In some embodiments, the class IV virus is a (+)ssRNA virus. In some embodiments, the (+)ssRNA virus is a coronavirus, picornavirus, or togavirus.

In some embodiments, the class V virus is a (−)ssRNA virus. In some embodiments, the (−)ssRNA virus is an orthomyxovirus or a rhabdovirus.

In some embodiments, the class VI virus is an ssRNA-RT virus. In some embodiments, the ssRNA-RT virus is a +strand ssRNA-RT virus. In some embodiments, the ssRNA-RT virus is a +strand ssRNA-RT virus with DNA intermediate in life-cycle. In some embodiments, the ssRNA-RT virus is hepadnavirus.

In some embodiments, the class VII virus is a dsDNA-RT virus. In some embodiments, the dsDNA-RT virus is a virus DNA with RNA intermediate in life cycle. In some embodiments, the dsDNA-RT virus is a hepadnavirus.

In some embodiments, the virus is human cytomegalovirus (HCMV), influenza A, HIV-1, classical swine fever virus, chikungunya virus, MERS-CoV, SARS-CoV, SARS-CoV-2, Ebola virus, or dengue virus.

In some embodiments, the SARS-CoV-2 is a variant. In some embodiments, the variant is B.1.1.7 or 501.V2. In some embodiments, the variant is B.1.1.7, B.1.351, P.1, B.1.617.2, C.37, B.1.1.529, B.1.621 or 501.V2.

In some embodiments of the methods as disclosed herein, the compound of the invention is administered to the subject in need thereof in the range from about 1 mg to about 1000 mg or any amount ranging from and to these values. In some embodiments, the compound of the invention is administered to the subject in need thereof in the rage from about 1 mg to about 900 mg, about 1 mg to about 800 mg, about 1 mg to about 700 mg, about 1 mg to about 600 mg, about 1 mg to about 500 mg, about 1 mg to about 400 mg, or about 1 mg to about 300 mg.

In some embodiments of the methods as disclosed herein, the compound of the invention is administered to the subject in need thereof in a daily dose ranging from about 1 mg to about 1000 mg or any amount ranging from and to these values. In some embodiments, the compound of the invention is administered to the subject in need thereof at a daily dose of about 1000 mg, about 950 mg, about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compound of the invention is administered to the subject in need thereof once a day at a dose of about 1 mg to about 1000 mg or any amount ranging from and to these values.

In some embodiments of the methods as disclosed herein, the compound of the invention is administered to the subject in need thereof twice a day, each dose comprising the compound of the invention in about 1 mg to about 500 mg or any amount ranging from and to these values. In some embodiments, the compound of the invention is administered to the subject in need thereof twice a day, each dose comprising the compound of the invention in about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compound of the invention is administered to the subject in need thereof three times a day, each dose comprising the compound of the invention in about 1 mg to about 400 mg or any amount ranging from and to these values. In some embodiments, the compound of the invention is administered to the subject in need thereof three times a day, each dose comprising the compound of the invention in about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the methods further comprise administering an effective amount of another pharmaceutically active agent. In some embodiments, the other pharmaceutically active agent is administered concurrently or sequentially with (prior or subsequent to) the administration of the compound of the invention or the composition of the invention. In some embodiments, the other pharmaceutically active agent is administered as an adjuvant therapy. In some embodiments, the other pharmaceutically active agent is a statin, a thiazolidinedione or fibrate, a bile-acid-binding-resin, a niacin, an anti-obesity drug, a hormone, a tyrophostine, a sulfonylurea-based drug, a biguanide, an α-glucosidase inhibitor, an apolipoprotein A-I agonist, apolipoprotein E agonist, a phosphodiesterase type-5 inhibitor, a cardiovascular drug, an HDL-raising drug, an HDL enhancer, a regulator of the apolipoprotein A-I gene, a regulator of the apolipoprotein A-IV gene, a regulator of the apolipoprotein gene, an ATP citrate lyase modulator, an ATP citrate lyase allosteric inhibitor, an acetyl-CoA carboxylase modulator, or an acetyl-CoA carboxylase allosteric inhibitor. In some embodiments, the other pharmaceutically active agent is lovastatin. In some embodiments, the other pharmaceutically active agent is sorafenib; paclitaxel; carotuximab; pembrolizumab; lenvatinib; avelumab; durvalumab; tremelimumab; nivolumab; tazemetostat; cemiplimab; ABX196; T-cell receptor (TCR) immune cell therapy agent; TBI-302; namodenoson; MM-310; a tumor-injected oncolytic virus or gene-modified oncolytic virus such as, but not limited to, telomelysin and imlygic; or an immunomodulating gene-therapy agent such as MDA-7/IL-24, GLIPR1/RTVP-1, and REIC/Dkk-3.

In some embodiments of the methods as disclosed herein, the methods further comprise administering two or more other pharmaceutically active agents. In some embodiments, the methods of the invention comprise administering two or more other pharmaceutically active agents, optionally in combination. In some embodiments, the two or more other pharmaceutically active agents are oncolytic agents, such as, but not limited to, nanatinostat and valganciclovir. In other embodiments, the methods of the invention comprise orally administering a compound of the invention and further comprise administering a tumor-injected oncolytic treatment. In some embodiments, the combination is administered orally.

In some embodiments, the other pharmaceutically active agent is cenicriviroc, elafibranor, eicosapentaenoic acid, galunisertib, LY2109761, LDE225, nivolumub, firsocostat, apararenone, metformin, leucine-metformin-sildenafil combination (NS-0200), IMM-124E, RG-125, vitamin E, cysteamine, selonsertib, losartan, RO5093151, pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, ND-L02-s0201/BMS-986263, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, solithromycin, 99m technetium-mebrofenin, tropifexor, S-adenosylmethionine, pentoxifylline, olesoxime, AKR-001, or seladelpar.

In some embodiments of the methods as disclosed herein, the methods of the invention comprise administering to a subject in need thereof an effective amount of Compound I-1-CoA, Compound I-32-CoA, Compound I-61-CoA, or Compound III-1-CoA, or a pharmaceutically acceptable salt or solvate thereof.

In some embodiments of the methods as disclosed herein, the methods of the invention comprise administering to a subject in need thereof an effective amount of (a) a compound of the invention and (b) another pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, Leucine-Metformin-Sildenafil Combination, Vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the methods as disclosed herein, the methods of the invention comprise administering to a subject in need thereof an effective amount of (a) Compound I-1-CoA, Compound I-32-CoA, Compound I-61-CoA, or Compound III-1-CoA, or a pharmaceutically acceptable salt or solvate thereof and (b) another pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine. L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO71199N29, guadecitabine, linrodostat, copanlisib. MIV-818, vorolanib, RO7070179, axitinib, sunitinib, zotiraciclib citrate, camrelizumab, rivoceranib, toripalimab, tislelizumab, sitravatinib, CT0180 cells, rHuPH20, sintilimab, pembrolizumab/vibostolimab coformulation (MK-7684A), envafolimab, retifanlimab, INCB106385 (Incyte Corporation), tocilizumab, ERY974 (Chugai Pharmaceutical), or INCA00186 (Incyte Corporation).

In some embodiments of the methods as disclosed herein, the methods of the invention comprise administering to a subject in need thereof an effective amount of (a) a compound of the invention and (b) another pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent. In some embodiments of the methods as disclosed herein, the methods of the invention comprise administering to a subject in need thereof an effective amount of (a) Compound I-1-CoA, Compound I-32-CoA, Compound I-61-CoA, or Compound III-1-CoA, or a pharmaceutically acceptable salt or solvate thereof and (b) another pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent.

In some embodiments, the methods of the invention comprise administering to a subject in need thereof an effective amount of a compound of the invention and another pharmaceutically active agent set forth of an embodiment of Table D. In some embodiments, the other pharmaceutically active agent is administered concurrently with, prior to or subsequent to the administration of the compound of the invention or the composition of the invention.

In some embodiments, a compound of the invention and another pharmaceutically active agent are synergistic in the compositions or methods of the invention.

In some embodiments of the methods as disclosed herein, the methods further comprise administering radiation therapy to the subject. In some embodiments, the radiation therapy is gamma ray radiation therapy or x-ray radiation therapy. In some embodiments, the radiation therapy is administered via a gamma ray or x-ray radiation apparatus.

In some embodiments, the radiation therapy is administered concurrently with, prior to or subsequent to the administration of the compound of the invention or the composition of the invention. In some embodiments, the radiation therapy is administered prior to or subsequent to the administration of the compound of the invention or the composition of the invention.

In some embodiments of the methods as disclosed herein, the methods further comprise transarterial chemoembolization (TACE).

In some embodiments of the methods as disclosed herein, the methods further comprise performing resection, transplantation, or percutaneous ablation.

In some embodiments of the methods as disclosed herein, the subject is or was obese or diabetic. In some embodiments, the subject has or had diabetes, cirrhosis, hypertension, hypertriglyceridemia, metabolic syndrome, hyperlipidemia, hypercholesterolemia, coronary heart disease (CHD), one or more risk factors of CHD, acute coronary syndrome (ACS) or a history of acute coronary syndrome, non-ST-segment elevation ACS (unstable angina (UA)/non-ST-elevation myocardial infarction (NSTEMI)), ST-elevation myocardial infarction (STEMI), dysbetalipoproteinemia, hypoalphalipoproteinemia, a risk of pancreatitis, or sitosterolemia. In some embodiments, hyperlipidemia is primary hyperlipidemia or mixed hyperlipidemia. In some embodiments, hypercholesterolemia is primary hypercholesterolemia, homozygous familial hypercholesterolemia (HoFH) or heterozygous familial hypercholesterolemia (HeFH). In some embodiments, dysbetalipoproteinemia is primary dysbetalipoproteinemia. In some embodiments, sitosterolemia is homozygous familial sitosterolemia. In some embodiments, the subject has had a previous myocardial infraction, previous stroke or established peripheral arterial disease. In some embodiments, diabetes is type-2 diabetes. In some embodiments, the subject has abnormally high LDL-C. In some embodiments, the subject has type 2 diabetes and does not have CHD. In some embodiments, the subject has or had hepatitis B, hepatitis C, non-alcoholic fatty liver disease (NAFLD), nonalcoholic steatohepatitis (NASH), or cirrhosis.

In some embodiments, the risk factors of CHD is high LDL cholesterol, low HDL cholesterol, high total cholesterol, high triglycerides, high blood pressure, family history of CHD, diabetes, smoking, age (older than 40 for men; older than 45 for women), or obesity.

In some embodiments of the methods as disclosed herein, the subject is or was exposed to aflatoxin. In some embodiments, the subject uses or used tobacco. In some embodiments, the subject is or was a tobacco smoker. In some embodiments, the subject drinks or drank alcohol (ethyl alcohol).

In some embodiments of the methods as disclosed herein, the subject has one or more risk factors for HCC, such as cirrhosis, non-alcoholic fatty liver disease (NAFLD), non-alcoholic steatohepatitis (NASH), alcoholic steatohepatitis (ASH), cirrhosis, hepatitis B, and hepatitis C, type IIb hyperlipidemia, mixed dyslipidemia, obesity, type 2 diabetes, chronic alcohol consumption, tobacco use, or exposure to aflatoxin. In some embodiments, the subject does not have one or more risk factors for HCC.

In some embodiments, the risk factors for HCC is cirrhosis of the liver; liver fibrosis; viral infections, such as hepatitis B infection and hepatitis C infection; exposures to toxins, such as alcohol and aflatoxins; metabolic condition and disorder, such as diabetes, obesity. NAFLD, and hereditary haemochromatosis; or immune-related conditions, such as primary biliary cirrhosis and autoimmune hepatitis.

2. Methods Comprising Administering a Compound of Formulae (I), (IA), (IB), (IC), (II), (III), (IIIA), and (IIIB), or a Pharmaceutically Acceptable Salt or Solvate Thereof, or a Composition Thereof In some embodiments, the methods of the invention comprise administering to a subject in need thereof an effective amount of a compound of Formulae (I), (IA), (IB), (IC), (II), (III), (IIIA), and (IIIB), or a pharmaceutically acceptable salt or solvate thereof (a "compound of the invention"), as discussed below.

In some embodiments, the methods of the invention comprise administering to a subject in need thereof an effective amount of a compound of Formula (I):

(I)

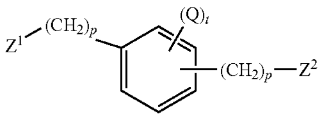

or a pharmaceutically acceptable salt or solvate thereof, wherein:

each p is independently 1, 2, 3, 4, 5, 6, or 7;

each $Z^1$ and $Z^2$ is independently —$C(R^1)(R^2)$—$(CH_2)_c$—X or —W—$(CH_2)_c$—$C(R^3)(R^4)$—Y;

each c is independently 0, 1, 2, or 3;

each $R^1$ and $R^2$ is independently —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each $R^3$ and $R^4$ is independently H, —$C_1$-$C_6$ alkyl, —$C_2$-$C_6$ alkenyl, —$C_2$-$C_6$ alkynyl, —O($C_1$-$C_6$ alkyl), phenyl, benzyl, Cl, Br, CN, $NO_2$, or $CF_3$, or each carbon atom together with the $R^3$ and $R^4$ attached to the carbon atom independently form a —$C_3$-$C_7$ cycloalkyl group;

Q is independently —OH, —$C_1$-$C_6$ alkyl, —O($C_1$-$C_6$ alkyl), phenoxy, aryloxy, benzyl, —S-aryl, —$SR^{1A}$, —$NR^{1A}R^{2A}$, F, Cl, Br, I, —CF, —$COR^{1A}$, heteroaryl, heterocyclyl, or —V—OH, or two Q with each carbon atoms which it is attached together independently form a heterocyclyl or a carbocyclyl group;

V is $(CH_2)_t$ or arylene;

each $R^{1A}$ and $R^{2A}$ is independently H, —$C_1$-$C_6$ alkyl, —$C_2$-$C_6$ alkenyl, —$C_2$-$C_6$ alkynyl, phenyl or benzyl;

t is 0, 1, 2, 3, or 4;

each X and Y is independently —OH, —COOH, —$COOR^5$, —$CONH_2$, —$CONHR^5$, —CONHMs, —CONHTs, —$SO_3H$,

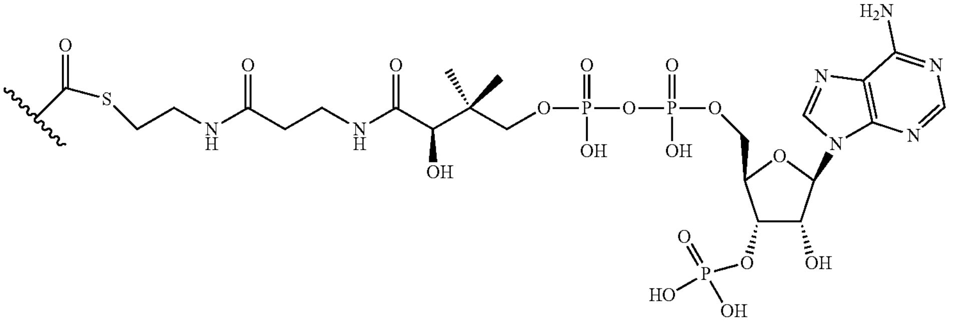

(-CO-CoA),

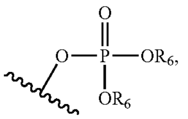
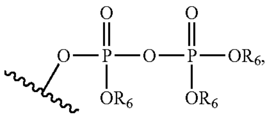
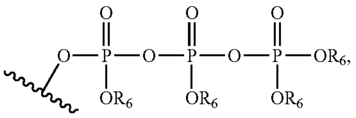
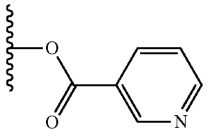
,

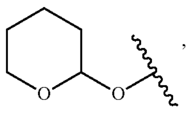
,
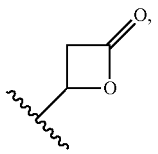
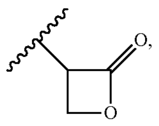
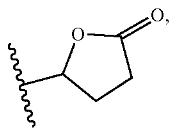
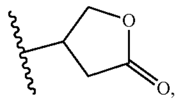
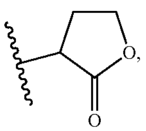

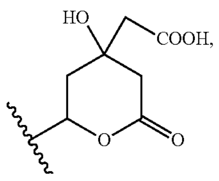
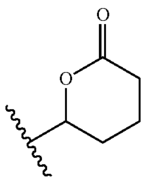
,
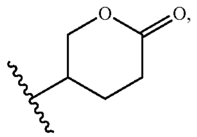
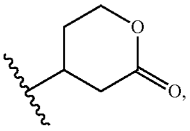
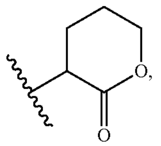

-continued

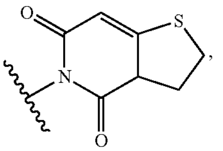,
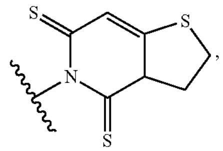,
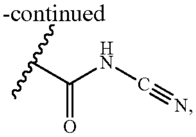,
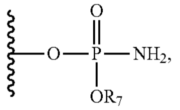,
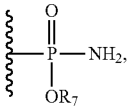,

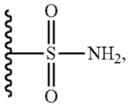,
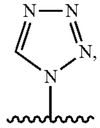,
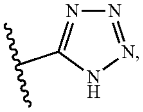,
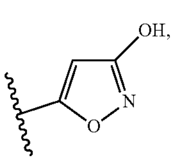,
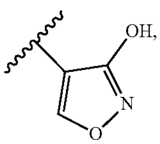,
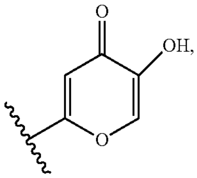,

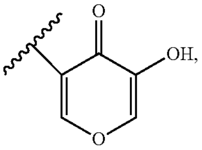,
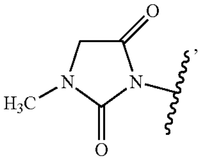,
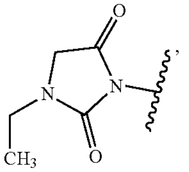,
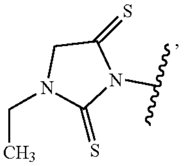,
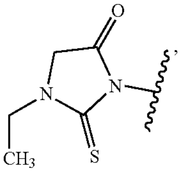, or

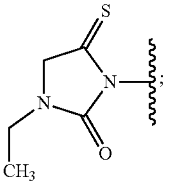;

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups;

each $R^7$ is independently H, $-C_1$-$C_6$ alkyl, $-C_2$-$C_6$ alkenyl, or $-C_2$-$C_6$ alkynyl;

each W is independently —O—, —NH—, —N(OH)—, —N(→O)—, —S—, —S(═O)—, $-S(O)_2-$, or —Se—;

each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups.

In some embodiments, the compound of formula (I) has the structure of Formula (IA), Formula (IB), or Formula (IC), or a pharmaceutically acceptable salt or solvate thereof:

(IA)

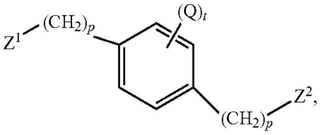, (IB)

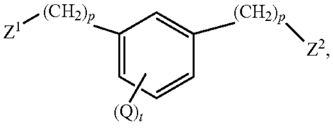, or

-continued (IC)

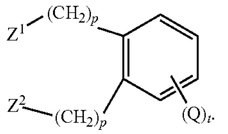.

In some embodiments of the compounds of Formula (I), (IA), (IB), or (IC), $Z^1$ and $Z^2$ are each independently $-C(R^1)(R^2)-(CH_2)_c-X$. In some embodiments, one or both of $Z^1$ and $Z^2$ is $-W-(CH_2)_c-C(R^3)(R^4)-Y$.

In some embodiments of the compounds of Formula (I), (IA), (IB), or (IC). X is —COOH, —CO—CoA, or $-COOR^5$.

In some embodiments, of the compounds of Formula (I), (IA), (IB), or (IC), $Z^1$ is $-C(R^1)(R^2)(CH_2)_c-CO-CoA$ and $Z^2$ is $-C(R^1)(R^2)-(CH_2)_c-COOH$ or $-C(R^1)(R^2)-(CH_2)_c-COOR^5$.

In some embodiments of the compounds of Formula (I), (IA), (IB), or (IC), each $R^1$ and $R^2$ is independently $-C_1$-$C_6$ alkyl, $-C_2$-$C_6$ alkenyl, or $-C_2$-$C_6$ alkynyl. In some embodiments, each $R^1$ and $R^2$ is independently $-C_1$-$C_3$ alkyl, $-C_2$-$C_3$ alkenyl, or $-C_2$-$C_3$ alkynyl. In some embodiments, $R^1$ and $R^2$ are methyl.

In some embodiments of the compounds of Formula (I), (IA), (IB), or (IC), $Z^1$ and $Z^2$ are each independently $-C(R^1)(R^2)(CH_2)_c-X$, wherein X is —CO—CoA, —COOH or $-COOR^5$, and $R^1$ and $R^2$ are methyl. In some embodiments, $Z^1$ and $Z^2$ are each independently $-C(R^1)(R^2)-(CH_2)_c-X$, wherein X is —COOH or $-COOR^5$. In some embodiments, $Z^1$ and $Z^2$ are each independently $-C(R^1)(R^2)-(CH_2)_c-X$, wherein X is —COOH.

In some embodiments of the compounds of Formula (I), (IA), (IB), or (IC), c is 0 or 1.

In some embodiments of the compounds of Formula (I), (IA), (IB), or (IC), each carbon atom together with the $R^1$ and $R^2$ attached to the carbon atom independently form a —$C_3$-$C_7$ cycloalkyl group. In some embodiments, each carbon atom together with the $R^1$ and $R^2$ attached to the carbon atom independently form a cyclopropyl ring.

In some embodiments of the compounds of Formula (I), (IA), (IB), or (IC), $Z^1$ and $Z^2$ are each —C($R^1$)($R^2$)—$(CH_2)_c$—X and at least one $R^1$ and one $R^2$ together with the carbon atom to which they are attached form a —$C_3$-$C_7$ cycloalkyl group. In some embodiments, $Z^1$ and $Z^2$ are each —C($R^1$)($R^2$)—$(CH_2)_c$—X and at least one $R^1$ and one $R^2$ together with the carbon atom to which they are attached form a cyclopropyl ring.

In some embodiments of the compounds of Formula (I), (IA), (IB), or (IC), $R^3$ and $R^4$ is independently H, —$C_1$-$C_6$ alkyl, —$C_2$-$C_6$ alkenyl, or —$C_2$-$C_6$ alkynyl.

In some embodiments of the compounds of Formula (I), (IA), (IB), or (IC), Y is —COOH or —$COOR^5$.

In some embodiments of the compounds of Formula (I), (IA), (IB), or (IC), $R^5$ is —$C_1$-$C_6$ alkyl, —$C_2$-$C_6$ alkenyl, or —$C_2$-$C_6$ alkynyl. In some embodiments, $R^5$ is —$C_1$-$C_3$ alkyl, —$C_2$-$C_3$ alkenyl, or —$C_2$-$C_3$ alkynyl.

In some embodiments of the compounds of Formula (I), (IA), (IB), or (IC), p is 3, 4, 5, 6, or 7. In some embodiments, p is 4, 5, 6, or 7.

In some embodiments of the compounds of Formula (I), (IA), (IB), or (IC), one or both of $Z^1$ and $Z^2$ is —W—$(CH_2)_c$—C($R^3$)($R^4$)—Y, and $R^3$ and $R^4$ is independently H, —$C_1$-$C_6$ alkyl, —$C_2$-$C_6$ alkenyl, or —$C_2$-$C_6$ alkynyl. In some embodiments, one or both of $Z^1$ and $Z^2$ is —W—$(CH_2)_c$—C($R^3$)($R^4$)—Y, and Y is —CO—CoA, —COOH or —$COOR^5$. In some embodiments, one or both of $Z^1$ and $Z^2$ is —W—$(CH_2)_c$—C($R^3$)($R^4$)—Y, Y is —CO—CoA, —COOH or —$COOR^5$, and $R^5$ is —$C_1$-$C_6$ alkyl, —$C_2$-$C_6$ alkenyl, or —$C_2$-$C_6$ alkynyl. In some embodiments, one or both of $Z^1$ and $Z^2$ is —W—$(CH_2)_c$—C($R^3$)($R^4$)—Y, Y is —CO—CoA, —COOH or —$COOR^5$, and $R^5$ is —$C_1$-$C_3$ alkyl, —$C_2$-$C_3$ alkenyl, or —$C_2$-$C_3$ alkynyl.

In some embodiments of the compound of Formula (I), (IA), (IB), or (IC), Q is independently methyl, methoxy, or —OH. In some embodiments, Q is methyl or —OH.

In some embodiments of the compound of Formula (I), (IA), (IB), or (IC), t is 0 or 1. In some embodiments, t is 2. In some embodiments, t is 3.

In some embodiments, the compound of Formula (I), (IA), (IB), or (IC), has any one of the structures shown in Table A-1, A-2, A-3, A-4, A-5, A-6, A-7, A-8, A-9, A-10, A-11, A-12, A-13, A-14, A-15, A-16, A-17, A-18, or A-19, or a pharmaceutically acceptable salt or solvate thereof. In some embodiments, the pharmaceutically acceptable salt of the compounds of Table A-1, A-2, A-3, A-4, A-5, A-6, A-7, A-8, A-9, A-10, A-11, A-12, A-13, A-14, A-15, A-16, A-17, A-18, or A-19 is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the methods of the invention comprise administering to a subject in need thereof an effective amount of a compound of Formula (II):

(II)

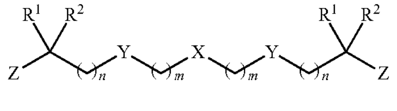

or a pharmaceutically acceptable salt or solvate thereof, wherein:

each $R^1$ and $R^2$ is independently H, —$C_1$-$C_6$ alkyl, —$C_2$-$C_6$ alkenyl, —$C_2$-$C_6$ alkynyl, phenyl or benzyl, or each carbon atom together with the $R^1$ and $R^2$ attached to the carbon atom independently form a —$C_3$-$C_7$ cycloalkyl group;

each n is independently 0, 1, 2, or 3;

each m is independently 1, 2, 3, 4, 5, 6, 7, 8 or 9;

X is —C(=O)—, —$CHR^3$—, —CH—$CH_2(OR^3)$—, —O—, —S—, —S(=O)—, —$S(O)_2$—, —$NR^3$—, —N(OH)—, —N(→O)—, or —Se—;

$R^3$ is H, —OH, —O($C_1$-$C_6$ alkyl), —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$cycloalkynyl, phenyl, or benzyl, each —$C_1$-$C_6$ alkyl, —$C_2$-$C_6$ alkenyl, —$C_2$-$C_6$ alkynyl, —$C_3$-$C_7$ cycloalkyl, $C_4$-$C_7$ cycloalkenyl, $C_5$-$C_8$cycloalkynyl, phenyl and benzyl being unsubstituted or substituted with one or more halogen, —CN, —$NO_2$, or —$CF_3$ groups;

each Y is independently —O—, —NH—, —N(OH)—, —N(→O)—, —S—, —S(=O)—, —$S(O)_2$—, or —Se—.

each Z is independently —OH, —COOH, —$COOR^5$, —CO—CoA, —$CONH_2$, —$CONHR^5$, —CONHMs, —CONHTs, —$SO_3H$, —$SO_3R^5$,

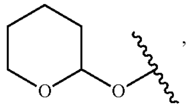, 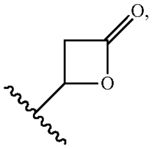

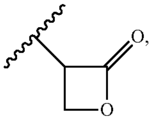 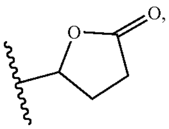 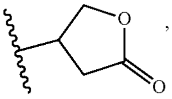,

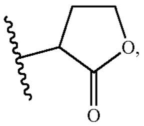 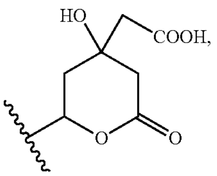

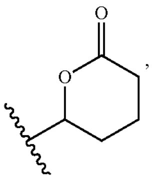, 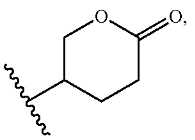

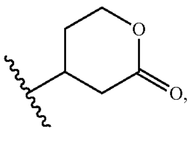 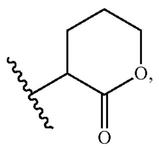

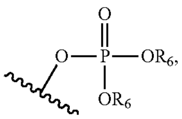 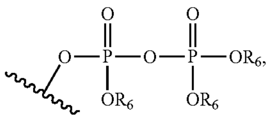

-continued

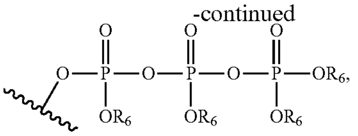

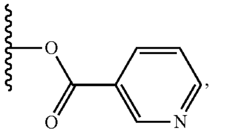

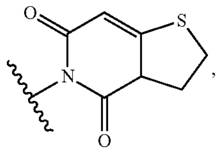

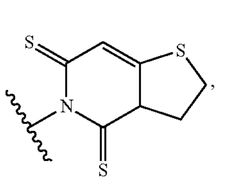

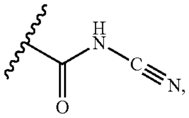

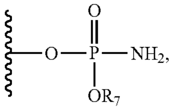

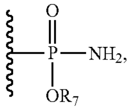

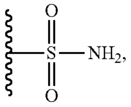

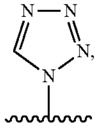

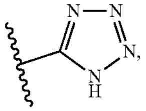

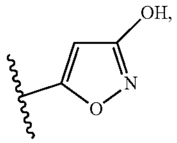

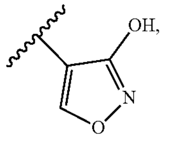

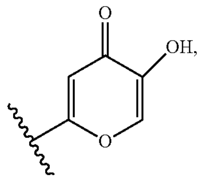

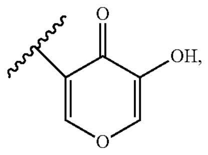

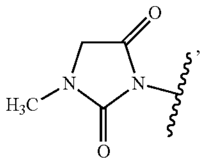

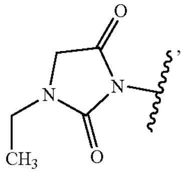

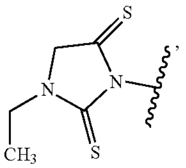

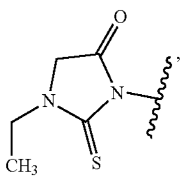

or

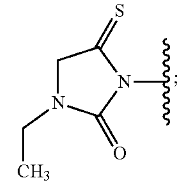

each $R^3$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl.

In some embodiments of compounds of Formula (II), X is —C(═O)—, —$CHR^3$—, —O—, —S—, —S(═O)—, or Se. In some embodiments, X is —C(═O)—, —CH(OH)—, —O—, —S—, —S(═O)—, or Se.

In some embodiments of compounds of Formula (II), R; is H, —OH, —O($C_1$-$C_3$ alkyl), or —$C_1$-$C_3$ alkyl.

In some embodiments of compounds of Formula (II), each Y is independently —O— or —S—.

In some embodiments of compounds of Formula (II), each $R^1$ and $R^2$ is independently H, —$C_1$-$C_3$ alkyl, —$C_2$-$C_3$ alkenyl, or —$C_2$-$C_3$ alkynyl. In some embodiments, each $R^1$ and $R^2$ is independently H or methyl.

In some embodiments of compounds of Formula (II), each Z is independently —COOH or —$COOR^5$. In some embodiments, each Z is —COOH.

In some embodiments of compounds of Formula (II), each $R^5$ is independently —$C_1$-$C_3$ alkyl, —$C_2$-$C_3$ alkenyl, or —$C_2$-$C_3$ alkynyl.

In some embodiments of compounds of Formula (II), each n is independently 0, 1, or 2. In some embodiments, n is 1.

In some embodiments of compounds of Formula (II), each m is independently 3, 4, 5, or 6. In some embodiments, each m is independently 4 or 5.

In some embodiments, the methods of the invention comprise administering to a subject in need thereof an effective amount of a compound of Formula (III):

(III)

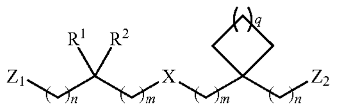

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 3, 4, 5, 6, or 7;

each n is independently 0, 1, 2, 3, 4, or 5;

each q is 0, 1, 2, 3, or 4;

X is —O—, —S—, —S(═O)—, —$S(O)_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —$COOR^5$, —CO—CoA, —$CONH_2$, —$CONHR^5$, —CONHMs, —CONHTs, —$SO_3H$, —$SO_3R^5$,

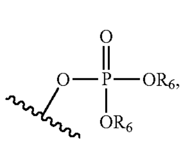

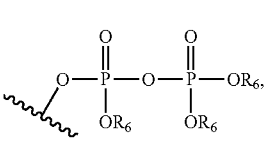

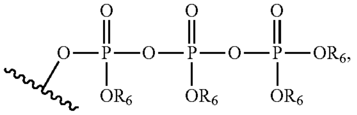

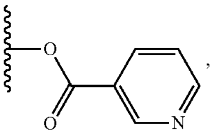

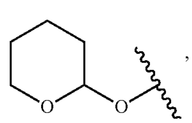
,

-continued

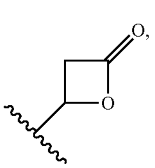
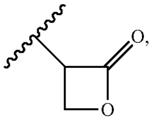
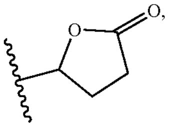
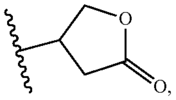
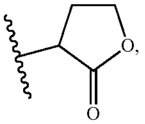
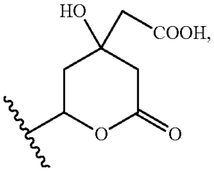
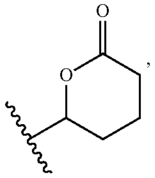
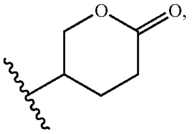
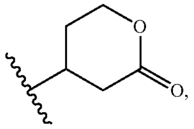
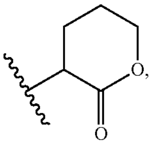
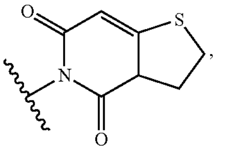
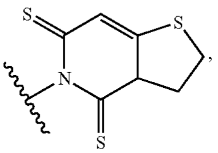
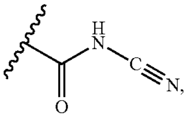
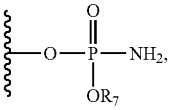
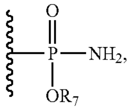
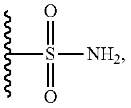
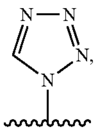
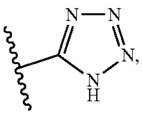
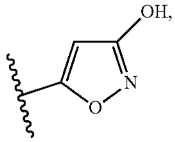
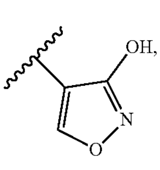
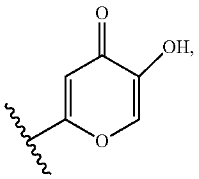

-continued

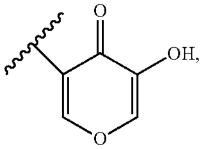
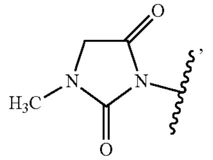
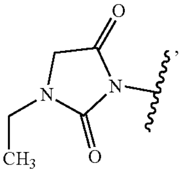
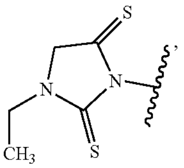
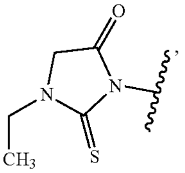
or
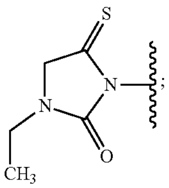

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl.

In some embodiments, the methods of the invention comprise administering to a subject in need thereof an effective amount of a compound of Formula (IIIA):

(IIIA)

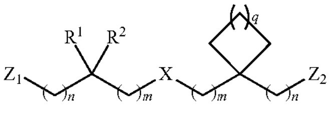

or a pharmaceutically acceptable salt or solvate thereof, wherein:

$R^1$ and $R^2$ are independently —$C_1$-$C_6$ alkyl, —$C_2$-$C_6$ alkenyl, —$C_2$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —O—, —S—, —S(═O)—, —S(O)$_2$—, —NH—, —N(OH)—, —N(→O)—, N(alkyl)-, or —N(aryl)-;

$Z_1$ and $Z_2$ are —$C_1$-$C_6$ alkyl, —COOH, —COOR$^5$, —CO—CoA, —CONH$_2$, —CONHR$^5$, —CONHMs, —CONHTs, —SO$_3$R,

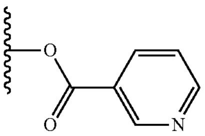
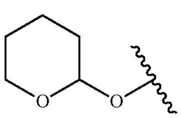

-continued

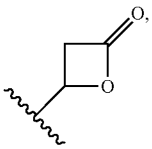 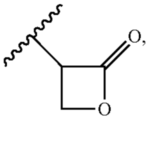 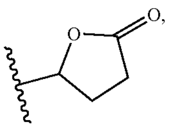

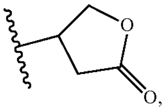 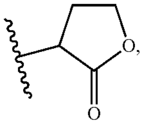

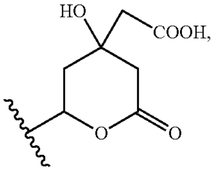 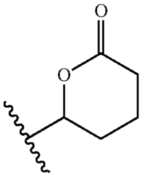 ,

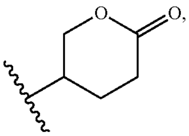 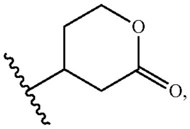

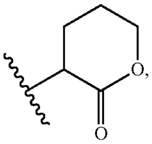 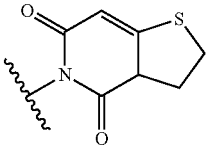 ,

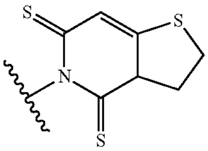 , 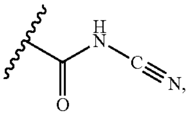 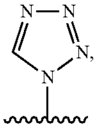

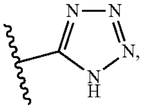 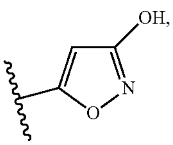 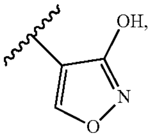

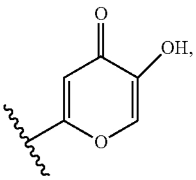 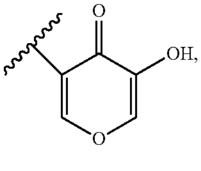

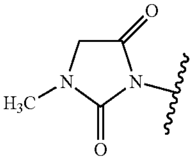 , 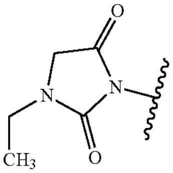 ,

-continued

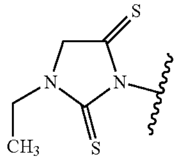 , 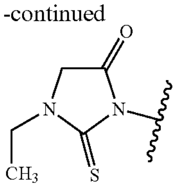 , or

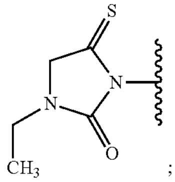 ;

wherein $Z_1$ and $Z_2$ are the same;

each $R^5$ is independently —$C_1$-$C_6$ alkyl, —$C_2$-$C_6$ alkenyl, —$C_2$-$C_6$ alkynyl, phenyl, or benzyl, each being unsubstituted or substituted with one or more halogen, —OH, —O($C_1$-$C_6$ alkyl), or phenyl groups;

each $R^6$ is independently H, —$C_1$-$C_6$ alkyl, —$C_2$-$C_6$ alkenyl, or —$C_2$-$C_6$ alkynyl, wherein the —$C_1$-$C_6$ alkyl, —$C_2$-$C_6$ alkenyl, or —$C_2$-$C_6$ alkynyl is unsubstituted or substituted with one or two halogen, —OH, —O($C_1$-$C_6$ alkyl), or phenyl groups; and each $R^7$ is independently H, —$C_1$-$C_6$ alkyl, —$C_2$-$C_6$ alkenyl, or —$C_2$-$C_6$ alkynyl.

In some embodiments, the methods of the invention comprise administering to a subject in need thereof an effective amount of a compound of Formula (IIIB):

(IIIB)

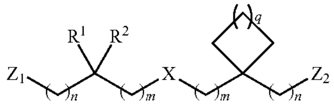

or a pharmaceutically acceptable salt or solvate thereof, wherein:

$R^1$ and $R^2$ are independently —$C_1$-$C_6$alkyl, —$C_2$-$C_6$ alkenyl, —$C_1$-$C_6$ alkynyl, phenyl or benzyl, or $R^1$ and $R^2$ together with the carbon atom to which they are attached form a —$C_3$-$C_7$ cycloalkyl group;

each m is independently 2, 3, 4, 5, 6, or 7;

each n is independently 0, 1, 2, 3, 4, or 5;

each q is 0, 1, 2, 3, or 4;

X is —S—, —S(═O)—, —S(O)$_2$—, —NH—, —N(OH)—, —N(→O)—, N(alkyl)-, or —N(aryl)-;

$Z_1$ and $Z_2$ are independently —$C_1$-$C_6$ alkyl, —OH, —COOH, —COOR$^5$, —CO—CoA, —CONH$_2$, —CONHR$^3$, —CONHMs, —CONHTs, —SO$_3$H, —SO$_3$R$^5$,

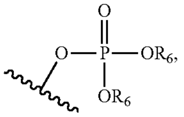 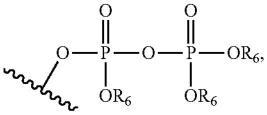

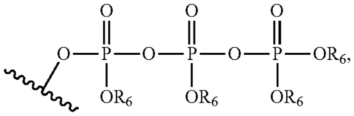

-continued

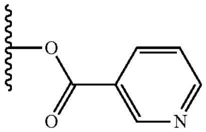
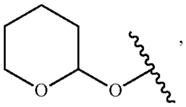
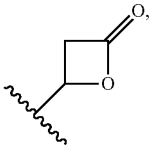
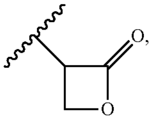
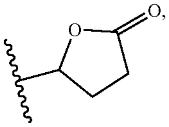
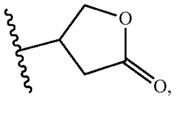
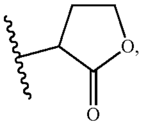
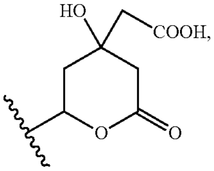
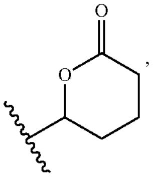
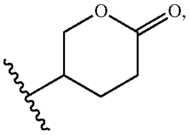
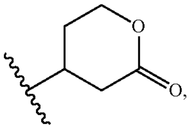
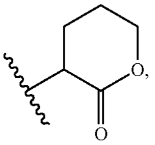
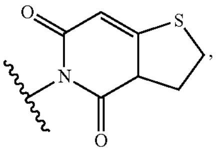
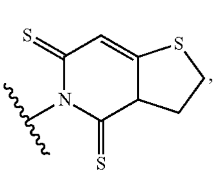
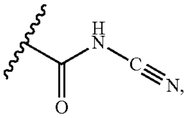
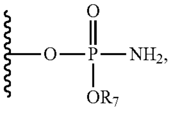
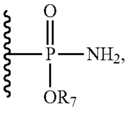
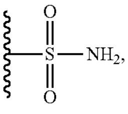
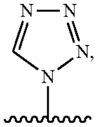
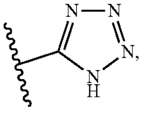
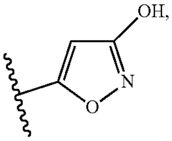
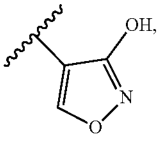
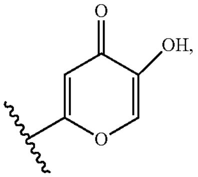

-continued

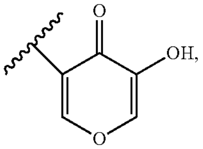
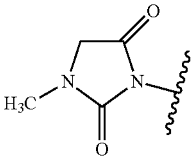
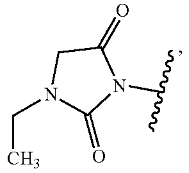
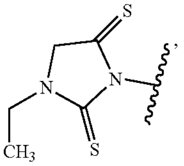
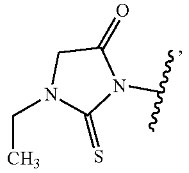

or

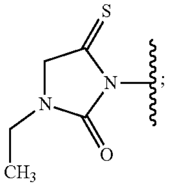

each $R^5$ is independently $-C_1$-$C_6$ alkyl, $-C_2$-$C_6$ alkenyl, $-C_2$-$C_6$ alkynyl, phenyl, or benzyl, each being unsubstituted or substituted with one or more halogen, —OH, $-O(C_1$-$C_6$ alkyl), or phenyl groups;

each $R^6$ is independently H, $-C_1$-$C_6$ alkyl, $-C_2$-$C_6$ alkenyl, or $-C_2$-$C_6$ alkynyl, wherein the $-C_1$-$C_6$ alkyl, $-C_2$-$C_6$ alkenyl, or $-C_2$-$C_6$ alkynyl is unsubstituted or substituted with one or two halogen, —OH, $-O(C_1$-$C_6$ alkyl), or phenyl groups; and each $R^7$ is independently H, $-C_1$-$C_6$ alkyl, $-C_2$-$C_6$ alkenyl, or $-C_2$-$C_6$ alkynyl.

In some embodiments of compounds of Formula (III) and (IIIB), $Z^1$ is —CO—CoA and Z is —OH, —COOH, —CO—CoA, or $-COOR^5$. In some embodiments, $Z^2$ is —CO—CoA and $Z^1$ is —OH, —COOH, —CO—CoA, or $-COOR^5$.

In some embodiments of compounds of Formula (III), (IIIA), and (IIIB), $Z^1$ and $Z^2$ are each —CO—CoA.

In some embodiments of compounds of Formula (III), X is —S—, —S(═O)—, $-S(O)_2-$. —NH—, —N(OH)—, —N(→O)—, N(alkyl)-, or —N(aryl)-.

In some embodiments of compounds of Formula (III) and (IIIA), X is O. In some embodiments of compounds of Formula (III), when X is O, m is 2, 3, 5, 6, or 7.

In some embodiments of compounds of Formula (III), (IIIA), and (IIIB), each n is independently 0 or 1. In some embodiments, n is 0. In some embodiments, n is 1.

In some embodiments of compounds of Formula (III), (IIIA), and (IIIB), each m is independently 4, 5, or 6. In some embodiments, m is 5 or 6. In some embodiments, m is 4. In some embodiments, m is 5. In some embodiments, m is 6. In some embodiments, m is 2 or 3.

In some embodiments of compounds of Formula (III), (IIIA), and (IIIB), $R^1$ and $R^2$ together with the carbon atom to which they are attached form a $-C_3$-$C_7$ cycloalkyl group.

In some embodiments, the compound of Formulae (II), (III), (IIIA), or (IIIB), has any one of the structures shown in Table B1 or Table B2, or a pharmaceutically acceptable salt or solvate thereof. In some embodiments, the compound of Formula (II), (III), (IIIA), or (IIIB), has any one of the structures shown in Table B1 or Table B2, or a pharmaceutically acceptable salt or solvate thereof, wherein one or both of the compound's —COOH group is replaced with —CO—CoA.

The present invention provides methods for reducing risk of cancer, slowing the onset of cancer or slowing progression of cancer, comprising administering to a subject in need thereof an effective amount of the compound of Formula (I), (IA), (IB), (IC), (II), (III), (IIIA), or (IIIB), or a pharmaceutically acceptable salt or solvate thereof, or a composition thereof.

In some embodiments, the cancer is hepatocellular carcinoma (HCC), HCC with cirrhosis. HCC without cirrhosis, HCC with fibrosis, HCC without fibrosis, cholangiocarcinoma, colorectal cancer, biliary tract cancer, or pulmonary cancer. In some embodiments, HCC is early HCC or advanced HCC. In some embodiments, HCC is localized, regional, advanced, metastatic, or unstaged. In some embodiments, the cancer is HCC, intrahepatic cholangiocarcinoma or hemangiosarcoma. In some embodiments, cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, clear cell sarcoma of kidney, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemias, Hodgkin's disease, non-Hodgkin's lymphoma, multiple myeloma, Waldenström's macroglobulinemia, heavy chain disease, gastrointestinal cancer, head-and-neck cancer, hematopoietic cancer, or polycythemia vera. In some embodiments, cancer is brain cancer, lung cancer, prostate cancer, bladder cancer, breast cancer, liver cancer, stomach cancer, colon cancer, or renal cell carcinoma. In some embodiments, lung cancer is non-small cell lung cancer. In some embodiments, brain cancer is glioblastoma multiforme. In some embodiments, the cancer is renal cell carcinoma or clear cell sarcoma of kidney.

The present invention provides methods for reducing risk of tumor growth, slowing the onset of tumor growth or slowing progression of tumor growth, comprising administering to a subject in need thereof an effective amount of the compound of Formula (I), (IA), (IB), (IC), (II), (III), (IIIA), or (IIIB), or a pharmaceutically acceptable salt or solvate thereof, or a composition thereof.

In some embodiments, tumor is a lung, prostate, bladder, breast, liver, stomach, or colon tumor.

The present invention further provides methods for treating or preventing a viral infection, comprising administering to the subject an effective amount of a compound of Formula (I), (IA), (IB), (IC), (II), (III), (IIIA), or (IIIB), or a pharmaceutically acceptable salt or solvate thereof, or a composition thereof. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

The present invention further provides methods for inhibiting replication of a virus, comprising contacting the virus with an effective amount of a compound of Formula (I), (IA), (IB), (IC), (II), (III), (IIIA), or (IIIB), or a pharmaceutically acceptable salt or solvate thereof, or a composition thereof. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the viral infection is an infection by a human virus, a non-human mammalian virus, an avian virus, a plant virus, a bacteria virus or an archaeal virus. In some embodiments, the virus is a human virus, a non-human mammalian virus, an avian virus, a plant virus, a bacteria virus or an archaeal virus.

In some embodiments, the non-human mammalian virus is a bat virus, bovine virus, canine virus, equine virus, feline virus or porcine virus.

In some embodiments, the viral infection is an infection by an oncovirus. In some embodiments, the virus is an oncovirus. Accordingly, the invention further provides methods for treating or preventing an oncovirus infection, comprising administering to the subject an effective amount of a compound of Formula (I), (IA), (IB), (IC), (II), (III), (IIIA), or (IIIB), or a pharmaceutically acceptable salt or solvate thereof, or a composition thereof. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

The present invention further provides methods for inhibiting replication of an oncovirus, comprising contacting the oncovirus with an effective amount of a compound of Formula (I), (IA), (IB), (IC), (II), (III), (IIIA), or (IIIB), or a pharmaceutically acceptable salt or solvate thereof, or a composition thereof. In some embodiments, the pharmaceutically acceptable salt is a zinc salt. In some embodiments, the pharmaceutically acceptable salt is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the oncovirus is human papillomavirus, hepatitis B virus, hepatitis C virus, Epstein-Barr virus, Kaposi's sarcoma-associated herpesvirus, human T-lymphotropic virus, polyomavirus, T-lymphotropic virus, herpesvirus, or Epstein-Barr virus. In some embodiments, polyomavirus is Merkel cell polyomavirus. In some embodiments, herpesvirus is Kaposi's sarcoma-associated herpesvirus.

In some embodiments, the viral infection is an infection by a class I virus, a class II virus, a class III virus, a class IV virus, a class V virus, a class VI virus, or a class VII virus. In some embodiments, the virus is a class I virus, a class II virus, a class III virus, a class IV virus, a class V virus, a class VI virus, or a class VII virus.

In some embodiments, the class I virus is a dsDNA virus. In some embodiments, the dsDNA virus is adenovirus, herpesvirus, or poxvirus.

In some embodiments, the class II virus is an ssDNA virus. In some embodiments, the ssDNA virus is a +strand ssDNA virus. In some embodiments, the ssDNA virus is parvovirus.

In some embodiments, the class III virus is a dsRNA virus. In some embodiments, the dsRNA virus is reovirus.

In some embodiments, the class IV virus is a (+)ssRNA virus. In some embodiments, the (+)ssRNA virus is a coronavirus, picornavirus, or togavirus.

In some embodiments, the class V virus is a (−)ssRNA virus. In some embodiments, the (−)ssRNA virus is an orthomyxovirus or a rhabdovirus.

In some embodiments, the class VI virus is an ssRNA-RT virus. In some embodiments, the ssRNA-RT virus is a +strand ssRNA-RT virus. In some embodiments, the ssRNA-RT virus is a +strand ssRNA-RT virus with DNA intermediate in life-cycle. In some embodiments, the ssRNA-RT virus is hepadnavirus.

In some embodiments, the class VII virus is a dsDNA-RT virus. In some embodiments, the dsDNA-RT virus is a virus DNA with RNA intermediate in life cycle. In some embodiments, the dsDNA-RT virus is a hepadnavirus.

In some embodiments, the virus is human cytomegalovirus (HCMV), influenza A, HIV-1, classical swine fever virus, chikungunya virus, MERS-CoV, SARS-CoV, SARS-CoV-2, Ebola virus, or dengue virus.

In some embodiments, the SARS-CoV-2 is a variant. In some embodiments, the variant is B.1.1.7 or 501.V2. In some embodiments, the variant is B.1.1.7, B.1.351, P.1, B.1.617.2, C.37, B.1.1.529, B.1.621 or 501.V2.

In some other embodiments, the compounds of the invention or the compositions of the invention are used as an adjuvant therapy in patients following surgical or procedural treatments of cancer, and for improvement of the tumor environment.

In some embodiments of the methods as disclosed herein, the compounds of the invention are administered to the subject in need thereof in the range from about 1 mg to about 1000 mg or any amount ranging from and to these values. In some embodiments, the compounds of the invention are administered to the subject in need thereof in the rage from about 1 mg to about 900 mg, about 1 mg to about 800 mg, about 1 mg to about 700 mg, about 1 mg to about 600 mg, about 1 mg to about 500 mg, about 1 mg to about 400 mg, or about 1 mg to about 300 mg.

In some embodiments of the methods as disclosed herein, the compounds of the invention are administered to the subject in need thereof in a daily dose ranging from about 1 mg to about 1000 mg or any amount ranging from and to these values. In some embodiments, the compounds of the invention are administered to the subject in need thereof at a daily dose of about 1000 mg, about 950 mg, about 90 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compounds of the invention are administered to the subject in need thereof once a day at a dose of about 1 mg to about 1000 mg or any amount ranging from and to these values.

In some embodiments of the methods as disclosed herein, the compounds of the invention are administered to the subject in need thereof twice a day, each dose comprising the compounds of the invention in about 1 mg to about 500 mg or any amount ranging from and to these values. In some embodiments, the compounds of the invention are administered to the subject in need thereof twice a day, each dose comprising the compounds of the invention in about 500 mg, about 450 mg, about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the compounds of the invention are administered to the subject in need thereof three times a day, each dose comprising the compounds of the invention in about 1 mg to about 400 mg or any amount ranging from and to these values. In some embodiments, the compounds of the invention is administered to the subject in need thereof three times a day, each dose comprising the compounds of the invention in about 400 mg, about 350 mg, about 300 mg, about 250 mg, about 200 mg, about 150 mg, about 100 mg, about 80 mg, about 60 mg, about 40 mg, about 20 mg, about 10 mg, about 5 mg, or about 1 mg.

In some embodiments of the methods as disclosed herein, the methods further comprise administering an effective amount of another pharmaceutically active agent. In some embodiments, the other pharmaceutically active agent is administered concurrently or sequentially with (prior or subsequent to) the administration of the compounds of the invention or the compositions of the invention.

In some embodiments of the methods as disclosed herein, the subject undergoes treatment with another pharmaceutically active agent.

In some embodiments, the other pharmaceutically active agent is a statin, a thiazolidinedione or fibrate, a bile-acid-binding-resin, a niacin, an anti-obesity drug, a hormone, a tyrophostine, a sulfonylurea-based drug, a biguanide, an α-glucosidase inhibitor, an apolipoprotein A-I agonist, apolipoprotein E agonist, a phosphodiesterase type-5 inhibitor, a cardiovascular drug, an HDL-raising drug, an HDL enhancer, a regulator of the apolipoprotein A-I gene, a regulator of the apolipoprotein A-IV gene, a regulator of the apolipoprotein gene, an ATP citrate lyase modulator, an ATP citrate lyase allosteric inhibitor, an acetyl-CoA carboxylase modulator, or an acetyl-CoA carboxylase allosteric inhibitor. In some embodiments, the other pharmaceutically active agent is lovastatin. In some embodiments, the other pharmaceutically active agent is sorafenib; paclitaxel; carotuximab; pembrolizumab: lenvatinib; avelumab; durvalumab; tremelimumab: nivolumab; tazemetostat; cemiplimab: ABX196; T-cell receptor (TCR) immune cell therapy agent: TBI-302; namodenoson; MM-310; a tumor-injected oncolytic virus or gene-modified oncolytic virus such as, but not limited to, telomelysin and imlygic; or an immunomodulating gene-therapy agent such as MDA-7/IL-24, GLIPR1/RTVP-1, and REIC/Dkk-3.

In some embodiments of the methods as disclosed herein, the methods further comprise administering two or more other pharmaceutically active agents. In some embodiments, the methods of the invention comprise administering two or more other pharmaceutically active agents, optionally in combination. In some embodiments, the two or more other pharmaceutically active agents are oncolytic agents, such as, but not limited to, nanatinostat and valganciclovir. In other embodiments, the methods of the invention comprise orally administering a compound of the invention and further comprise administering a tumor-injected oncolytic treatment. In some embodiments, the combination is administered orally.

In some embodiments, the other pharmaceutically active agent is cenicriviroc, elafibranor, eicosapentaenoic acid, galunisertib, LY2109761, LDE225, nivolumub, firsocostat, apararenone, metformin, leucine-metformin-sildenafil combination (NS-0200), IMM-124E, RG-125, vitamin E, cysteamine, selonsertib, losartan, RO5093151, pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, ND-L02-s0201/BMS-986263, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-carnitine, EYP001a, silymarin, miricorilant, ursodeoxycholic acid, metadoxine, ezetimibe, cystadane, L-alanine, saroglitazar magnesium, volixibat, solithromycin, 99m technetium-mebrofenin, tropifexor, S-adenosylmethionine, pentoxifylline, olesoxime, AKR-001, or seladelpar.

In some embodiments of the methods as disclosed herein, the methods of the invention comprise administering to a subject in need thereof an effective amount of Compound I-1-CoA, Compound I-32-CoA, Compound I-61-CoA, or Compound III-1-CoA, or a pharmaceutically acceptable salt or solvate thereof. In some embodiments, the pharmaceutically acceptable salt of Compound I-1-CoA, of Compound I-32-CoA, of Compound I-61-CoA, or of Compound III-1-CoA is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments of the methods as disclosed herein, the methods of the invention comprise administering to a subject in need thereof an effective amount of (a) a compound of Formulae (I), (IA), (IB), (IC), (II), (III), (IIIA), and (IIIB), or a pharmaceutically acceptable salt or solvate thereof, and (b) another pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, zotiraciclib citrate, camrelizumab, rivoceranib, toripalimab, tislelizumab, sitravatinib, CT0180 cells, rHuPH20, sintilimab, pembrolizumab/vibostolimab coformulation (MK-7684A), envafolimab, retifanlimab, INCB106385 (Incyte Corporation), tocilizumab. ERY974 (Chugai Pharmaceutical), or INCA00186 (Incyte Corporation).

In some embodiments of the methods as disclosed herein, the methods of the invention comprise administering to a subject in need thereof an effective amount of (a) Compound I-1, Compound I-1-CoA, Compound I-32, Compound I-32-CoA, Compound I-61, Compound I-61-CoA, Compound III-1, or Compound III-1-CoA, or a pharmaceutically acceptable salt or solvate thereof and (b) another pharmaceutically active agent that is sorafenib, paclitaxel, lenvatinib, tazemetostat, TBI-302, namodenoson, MM-310, cenicriviroc, elafibranor, eicosapentaenoic acid, galunisertib, LY2109761, LDE225, firsocostat, apararenone, metformin, leucine-metformin-sildenafil combination, vitamin E, cysteamine, selonsertib, losartan, RO5093151 pradigastat, sitagliptin, vildagliptin, NGM282, pegbelfermin, PF-05231023, obeticholic acid, cilofexor, tropifexor, EDP-305, INT-767, galactoarabino-rhamnogalacturonate, liraglutide, semaglutide, exenatide, volixibat, amlexanox, PF-06835919, leptin, metreleptin, simtuzumab, tipelukast, oltipraz, MSDC-0602K, ASP9831, roflumilast, elafibranor, pioglitazone, rosiglitazone, fenofibrate, saroglitazar, lanifibranor, aramchol, ipragliflozin, dapagliflozin, empagliflozin, BI 1467335, rosuvastatin, atorvastatin, pitavastatin, VK2809, MGL-3196, nalmafene, pentamidine, berberine, L-camitine, EYP001a, silymarin, miricorilant, ursodeoxycholic acid, metadoxine, ezetimibe, cystadane, L-alanine, saroglitazar magnesium, volixibat, elafibranor, nalmefene, solithromycin, 99m technetium-mebrofenin, S-adenosylmethionine, pentoxifylline, olesoxime, AKR-001, seladelpar, fisogatinib, doxorubicin, cabozantinib, deferoxamine, itacitinib, chiauranib, SF1126, anlotinib, P1101, varlitinib, SHR-1210, SHR6390, capmatinib, dabrafenib, trametinib, sapanisertib, meclizine, enzalutamide, H3B-6527, OBI-3424, brivanib, tepotinib, temsirolimus, epacadostat, RO7119929, guadecitabine, linrodostat, copanlisib, MIV-818, vorolanib, RO7070179, axitinib, sunitinib, or zotiraciclib citrate.

In some embodiments of the methods as disclosed herein, the methods of the invention comprise administering to a subject in need thereof an effective amount of (a) a compound of Formulae (I), (IA), (IB), (IC), (II), (III), (IIIA), and (IIIB), or a pharmaceutically acceptable salt or solvate thereof, and (b) another pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent. In some embodiments of the methods as disclosed herein, the methods of the invention comprise administering to a subject in need thereof an effective amount of (a) Compound I-1. Compound I-1-CoA, Compound I-32, Compound I-32-CoA, Compound I-61, Compound I-61-CoA, Compound III-1, or Compound III-1-CoA, or a pharmaceutically acceptable salt or solvate thereof and (b) another pharmaceutically active agent that is sorafenib, paclitaxel, carotuximab, pembrolizumab, lenvatinib, avelumab, durvalumab, tremelimumab, nivolumab, tazemetostat, cemiplimab, ABX196, T-cell receptor (TCR) immune cell therapy agent, TBI-302, namodenoson, MM-310, a tumor-injected oncolytic virus, a gene-modified oncolytic virus, or an immunomodulating gene-therapy agent. In some embodiments, the pharmaceutically acceptable salt of Compound I-1, of Compound I-1-CoA, of Compound I-32, of Compound I-32-CoA, of Compound I-61, of Compound I-61-CoA, of Compound III-1, or of Compound III-1-CoA is a sodium salt, a potassium salt, a magnesium salt, an ammonium salt, a calcium salt, a meglumine salt, a lysine salt, or an arginine salt. In some embodiments, the lysine salt is an L-lysine salt. In some embodiments, the arginine salt is an L-arginine salt.

In some embodiments, the methods of the invention comprise administering to a subject in need thereof an effective amount of a compound of the invention and another pharmaceutically active agent set forth of an embodiment of Table D. In some embodiments, the other pharmaceutically active agent is administered concurrently with, prior to or subsequent to the administration of the compounds of the invention.

In some embodiments of the methods as disclosed herein, the methods further comprise administering radiation therapy to the subject. In some embodiments, the radiation therapy is gamma ray radiation therapy or x-ray radiation therapy. In some embodiments, the radiation therapy is administered via a gamma ray or x-ray radiation apparatus.

In some embodiments, the radiation therapy is administered concurrently with, prior to or subsequent to the administration of the compounds of the invention or the compositions of the invention. In some embodiments, the radiation therapy is administered prior to or subsequent to the administration of the compounds of the invention or the compositions of the invention.

In some embodiments of the methods as disclosed herein, the methods further comprise transarterial chemoembolization (TACE).

In some embodiments of the methods as disclosed herein, the methods further comprise performing resection, transplantation, or percutaneous ablation.

In some embodiments of the methods as disclosed herein, the subject is or was obese or diabetic. In some embodiments, the subject has or had diabetes, cirrhosis, hypertension, hypertriglyceridemia, metabolic syndrome, hyperlipidemia, hypercholesterolemia, coronary heart disease (CHD), one or more risk factors of CHD, acute coronary syndrome (ACS) or a history of acute coronary syndrome, non-ST-segment elevation ACS (unstable angina (UA)/non-ST-elevation myocardial infarction (NSTEMI)), ST-elevation myocardial infarction (STEMI), dysbetalipoproteinemia, hypoalphalipoproteinemia, a risk of pancreatitis, or sitosterolemia. In some embodiments, hyperlipidemia is primary hyperlipidemia or mixed hyperlipidemia. In some embodiments, hypercholesterolemia is primary hypercholesterolemia, homozygous familial hypercholesterolemia (HoFH) or heterozygous familial hypercholesterolemia (HeFH). In some embodiments, dysbetalipoproteinemia is primary dysbetalipoproteinemia. In some embodiments, sitosterolemia is homozygous familial sitosterolemia. In some embodiments, the subject has had a previous myocardial infraction, previous stroke or established peripheral arterial disease. In some embodiments, diabetes is type-2 diabetes. In some embodiments, the subject has abnormally high LDL-C. In some embodiments, the subject has type 2 diabetes and does not have CHD. In some embodiments, the subject has or had hepatitis B, hepatitis C, non-alcoholic fatty liver disease (NAFLD), nonalcoholic steatohepatitis (NASH), or cirrhosis.

In some embodiments of the methods as disclosed herein, the subject is or was exposed to aflatoxin. In some embodiments, the subject uses or used tobacco. In some embodiments, the subject is or was a tobacco smoker. In some embodiments, the subject drinks or drank alcohol (ethyl alcohol).

In some embodiments of the methods as disclosed herein, the subject has one or more risk factors for HCC, which includes, cirrhosis, non-alcoholic fatty liver disease (NAFLD), nonalcoholic steatohepatitis (NASH), alcoholic steatohepatitis (ASH), cirrhosis, chronic alcohol consumption, tobacco use, exposure to aflatoxin, hepatitis B, and hepatitis C, type IIb hyperlipidemia, mixed dyslipidemia, obesity, and type 2 diabetes. In some embodiments, the subject does not have one or more risk factors for HCC.

Synthesis Examples

Synthesis and General Protocols

The compounds of Formulae (I), (IA), (IB), (IC), (ID), (IE), (IF), (IG), (IH), and (IJ), can be prepared via the synthetic methodologies illustrated in Schemes 1-7. The starting materials useful for preparing the compounds of the invention and intermediates thereof are commercially available or can be prepared from commercially available materials using known synthetic methods and reagents.

Scheme 1: General Synthesis of Formula (I)

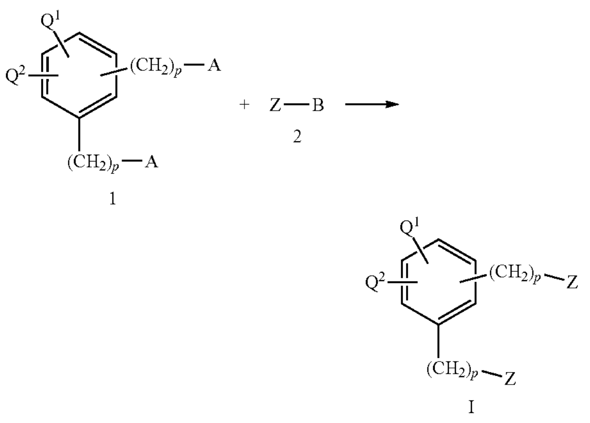

In Scheme 1, A can be halogen, such as Cl, Br, or I. In some embodiments, A is Br. In Scheme 1, B can be carbanions of esters of carboxylic or malonic esters. In Scheme 1, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 2: General Synthesis of Formula (I)

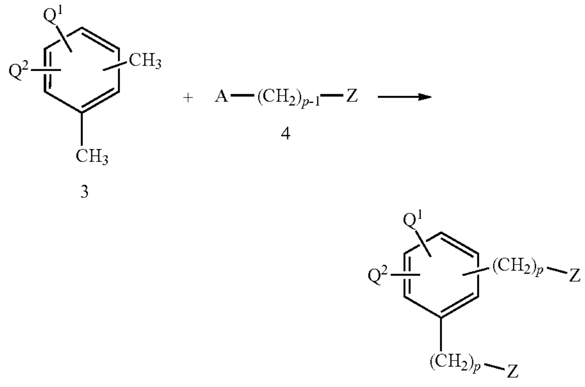

3

4

I

In Scheme 2, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I)

Scheme 3: General Synthesis of Formula (I) where Z is —$C(R^1)(R^2)$—$(CH_2)_c$—X, X is $COOR^5$, or COOH, and c is 0.

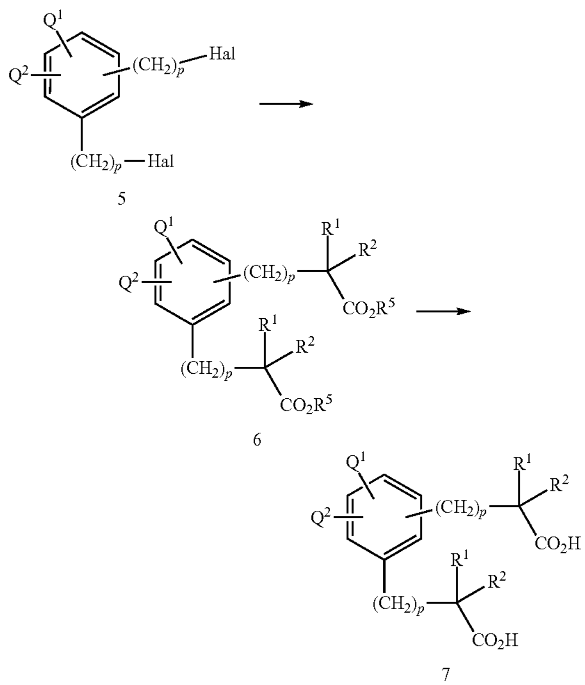

5

6

7

In Scheme 3, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 3 illustrates the transformation of ortho, meta, or para ω-haloalkyl substituted arenes of the formula 5, wherein p is an integer in the range of 2-5 and Hal is Cl, Br, or I, to dicarboxylic acids of the formula 7, wherein $R^1$ and $R^2$ are alkyl and/or aryl moieties or are connected in a three- to seven-membered cycle. This transformation can be accomplished by two different, however related pathways. According to the first method, esters of the formula $R^1R^2CHCO_2R^5$, wherein $R^1$ and $R^2$ are alkyl and/or aryl moieties or are connected in a three- to seven-membered cycle and $R^5$ is typically ethyl or methyl, are deprotonated by strong bases, preferably, but not limited to, butyl lithium or lithium diisopropylamide, and then reacted with dihalides of the formula 5 to furnish the corresponding diesters of the formula 6. Generally, the reaction is performed at temperatures from about −78° C., to about 25° C. and the reaction solvent is preferably THF or diethyl ether (see Larock, R. C. *Comprehensive Organic Transformations: A Guide to Functional Group Preparations,* $2^{nd}$ ed.; Wiley-VCH, New York, 1999, pp 1725-1726 for a discussion of the scope of this method. See, Dasseux et al., U.S. Pat. Nos. 6,646,170 and 6,410,802, Oniciu et al. U.S. Pat. No. 10,227,285 and Ackerley et al., *J. Med Chem.* 1995, 38, 1608-1628 for specific examples of this method). In the second step, a diester of the formula 6 is saponified (see Larock, R. C. *Comprehensive Organic Transformations: A Guide to Functional Group Preparations,* $2^{nd}$ ed.; Wiley-VCH, New York, 1999, pp 1959-1968 and Smith, M. B.; March, J. *March's Advanced Organic Chemistry, Reactions, Mechanisms, and Structure,* $5^{th}$ ed.; John Wiley and Sons, New York, 2001, pp 469-474 for an overview) to a diacid of the formula 7. As an alternative, this transformation of a dihalide of the formula 5 to a diacid of the formula 7 can also be achieved in one step, when a carboxylic acid of the formula $R^1R^2CHCO_2H$, wherein $R^1$ and $R^2$ are alkyl and/or aryl, is deprotonated twice under conditions similar to the alkylation of $R^1R^2CHCO_2R^5$ described above and subsequently reacted with dibromide 5 (for a discussion, see Larock, R. C. *Comprehensive Organic Transformations: A Guide to Functional Group Preparations,* $2^{nd}$ ed.; Wiley-VCH, New York, 1999, pp 1717-1718). For example, a compound of the formula 5 (ortho, p=3, Hal=Br) is reacted with lithio ethyl isobutyrate (prepared from ethyl isobutyrate with lithium diisopropylamide) in a solvent mixture of THF and DMPU at a temperature ranging from about −78° C., to room temperature, affording the corresponding diester of formula 7 (ortho, p=3). This diester is subsequently hydrolyzed under standard conditions (aqueous ethanol, potassium hydroxide, reflux temperature) to provide, after re-acidification with dilute aqueous hydrochloric acid, the dicarboxylic acid of the formula 7 with ortho substitution pattern, $R^1$=$R^2$=methyl and p=3. In another method, which is described in Gleiter et al., *J. Org. Chem.* 1992, 57, 252-258, isobutyric acid is deprotonated twice with n-butyl lithium and diisopropylamine in THF solution first at about −20° C. and then at about 50° C. After re-cooling to about −20° C., a solution of a compound of the formula 5 (ortho, $R^1$=$R^2$=methyl, p=3, Hal=Br) in THF is then added dropwise, while the temperature is kept below 10° C. The mixture is subsequently stirred first at room temperature and then at about 40° C., and worked up in a typical manner to afford the corresponding diacid 7. Halide derivatives of type 5 can be obtained by several methods, described for instance in Gleiter et al., *J. Org. Chem.* 1992, 57, 252-258.

Scheme 4: General Synthesis of Compound 5-Br (Compound 5 where Hal = Br)

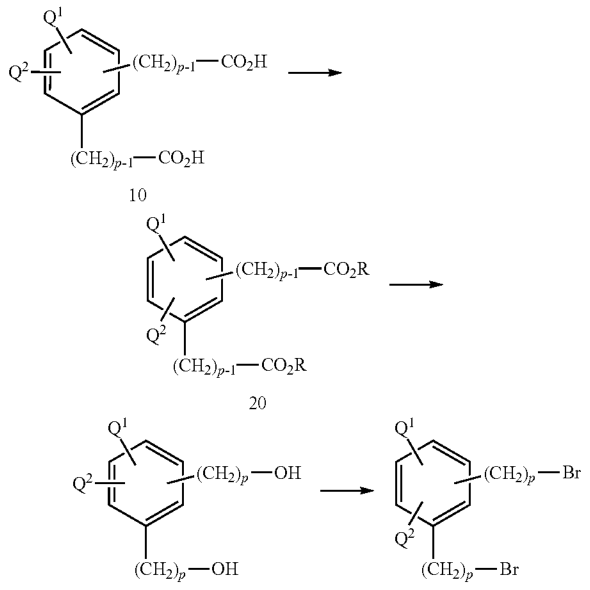

10

20

30

5-Br

In Scheme 4, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 4 illustrates the synthesis of para, meta, and ortho di-bromoalkyl substituted arene compounds 5-Br from the parent dicarboxylic acids 10 wherein (p−1) is an integer in the range from 1-2. Scheme 4 first outlines the esterification of compounds of the formula 10 to diesters of the formula 20, wherein R is an alkyl moiety such as, but not limited to, methyl, ethyl, or isopropyl using general procedures referenced in Larock, R. C. *Comprehensive Organic Transformations: A Guide to Functional Group Preparations, 2nd* ed., Wiley-VCH, New York, 1999, pp 1932-1941 and Smith, M. B.; March, J. *March's Advanced Organic Chemistry, Reactions, Mechanisms, and Structure, 5th* ed.; John Wiley and Sons, New York, 2001, pp 484-486. Diols 30 can be prepared from diesters 20 by well-known synthetic methods (for a discussion of suitable reduction methods, see for example Hudlicky, M. *Reductions in Organic Chemistry, 2nd* ed.; ACS Monograph 188, Washington, DC, 1996, pp 212-216). In the next step, transformation of the alcohol functionalities in 30 to the bromo moieties in Compound 5-Br can be accomplished by a variety of standard methods as referenced in Larock, R. C. *Comprehensive Organic Transformations: A Guide to Functional Group Preparations, 2nd* ed.; Wiley-VCH, New York, 1999, pp 693-695. For example, a compound of the formula 10 with para substitution pattern and (p−1)=1 (available from Aldrich Chemical Co., Milwaukee, Wis.) is treated with an excess of methanol and concentrated sulfuric acid at reflux temperature to give the corresponding dimethyl ester of the formula 2. A procedure that can be used for this transformation is, for example, referenced in Schimelpfenig, C. W. *J. Org. Chem.* 1975, 40, 1493-1494, incorporated by reference herein. In addition, a compound of the formula 20 (para, (p−1)=1) can be transformed to the corresponding compound of the formula 30 by reaction with a complex metal hydride, preferably, but not limited to, lithium aluminum hydride in an aprotic organic solvent, such as THF or diethyl ether, as referenced in Reynolds et al. U.S. Pat. No. 2,789,970, Appl. No. 397,037, filed Dec. 8, 1953. Further, a diol of the formula 30 (para, p=1) can be converted to a bromide of the formula 5-Br (para, p=1) by treatment with sodium bromide and concentrated sulfuric acid at elevated temperature. A useful solvent for this conversion is water, as is described in Schimelpfenig, C. W. *J. Org. Chem.* 1975, 40, 1493-1494.

Scheme 5: General Synthesis of Compound 5A-Br

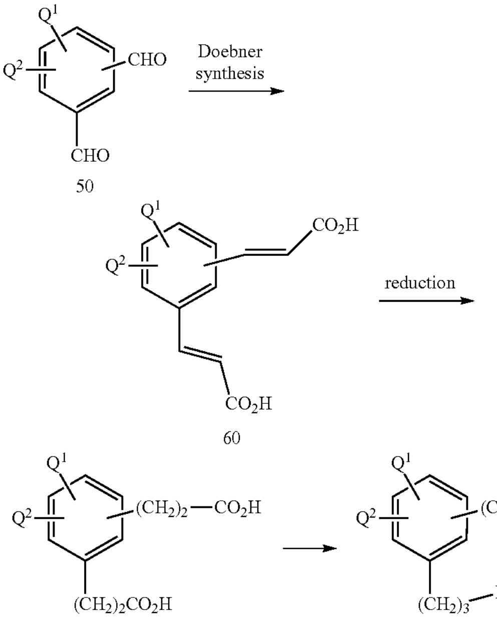

50

60

70

5A-Br

In Scheme 5, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 5 illustrates the preparation of ortho, meta, and para substituted arene compounds with two 3-bromopropyl substituents of the formula 5A-Br. Specific examples for the synthesis of compounds 5A-Br with meta and para substitution are given in Schimelpfenig, C. W. *J Org. Chem.* 1975, 40, 1493-1494 and Gleiter et al., *J. Org. Chem.* 1992, 57, 252-258, respectively. For example, a compound of the formula 50 is treated with malonic acid and piperidine in pyridine solution at about 90-110° C., to give an α,β-unsaturated carboxylic acid of the formula 60. The end point of this conversion is typically indicated by cessation of the $CO_2$ effervescence. This procedure is known as a Knoevenagel-Doebner reaction and a useful reaction protocol for this conversion is given in *Organikum, Organisch-Chemisches Grundpraktikum*, VEB Verlag Deutscher Wissenschaften. Berlin 1984, pp 572-574. Reduction of compounds of the formula 60 to compounds of the formula 70 can be accomplished by catalytic hydrogenation over colloidal palladium, Raney nickel, or copper chromite as discussed in Hudlicky, M. *Reductions in Organic Chemistry,* 2nd ed.; ACS Monograph 188, Washington, D C, 1996, pp 196-197. Conversion of a compound of the formula 60 with meta substitution to the corresponding compound 70 by treatment with hydrogen gas at pressures from ca. 20-60 psi and palladium on carbon catalyst in aqueous sodium hydroxide solution is reported in Schimelpfenig, C. W. *J. Org. Chem.* 1975, 40, 1493-1494, which is included herein as a reference in its entirety. The further transformation of compounds of the formula 70 to compounds of formula 5A-Br can then be accomplished according to the methodology described in Scheme 4.

saponified to give compounds of the formula 110, which can be heated above their melting point for decarboxylation to compounds of the formula 120. The transformation from dicarboxylic acids 120 via diesters 20 to the chain-elongated dibromides 5-Br is then conducted according to the methodologies described in Scheme 4. Alternatively, a direct decarbalkoxylation of geminal diesters 100 to compounds of the formula 20 can be achieved by treatment with water and DMSO with or without the presence of added salts. However, the addition of salts such as KCN. NaCl or LiCl to the water/DMSO solvent can enhance the decarbalkoxylation rates of theses substrates (Fakhri, S. A.; Yousefi, B. H. *Tetrahedron* 2000, 56, 8301-8308). For example, ethyl Scheme 6: General Synthesis of Compound 5-Br by Chain Elongation

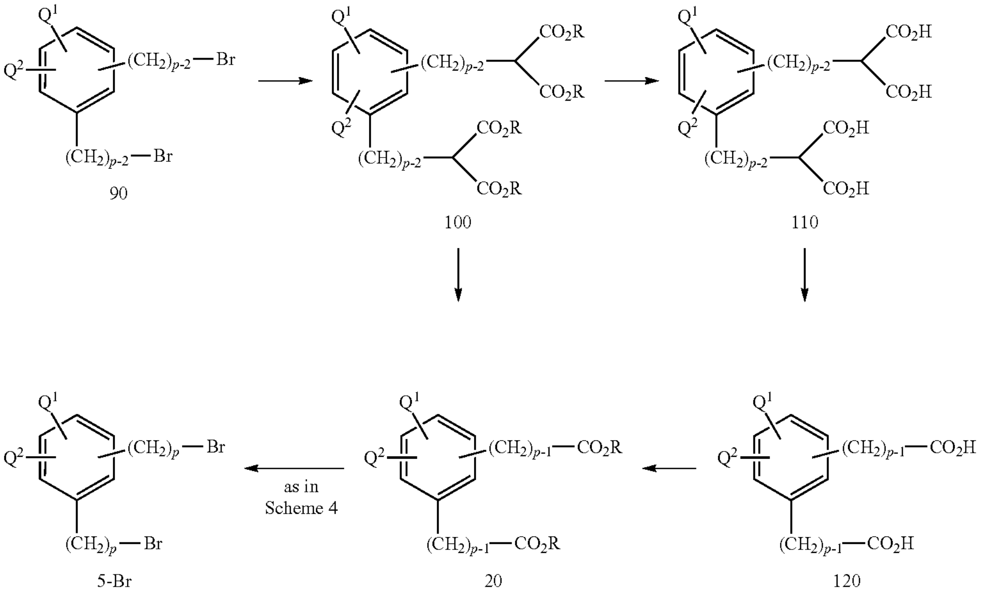

In Scheme 6, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 6 illustrates a general method for the chain elongation of bromides of the formula 90 with an alkyl chain consisting of (p−2) methylene groups to bromides of the formula 5-Br with an alkyl chain consisting of p methylene groups. The conversion sequence from alkyl halides (such as 90) to carboxylic acid (such as 120) can be accomplished using a malonic ester synthesis referenced in Smith, M. B.; March, J. *March's Advanced Organic Chemistry, Reactions, Mechanisms, and Structure,* 5th ed.; John Wiley and Sons, New York, 2001, p 549 and Larock, R. C. *Comprehensive Organic Transformations: A Guide to Functional Group Preparations,* 2nd ed.; Wiley-VCH, New York, 1999, p 1765. Generally, the monoalkylation of malonic esters (R is typically ethyl or methyl) employs the base-solvent combination of sodium ethoxide in ethanol, which inhibits the formation of dialkylated side-products (*Organic Reactions, Volume IX,* editor-in-chief: R. Adams: Robert E. Krieger Publishing Company, Malabar, Fla., 1957, p 132) to give compounds of the formula 100. Compounds of the formula 100 are then malonate is reacted with sodium metal in ethanol and a solution of a compound of the formula 90 with (p−2)=2, and ethyl malonate is added to give the corresponding compound of the formula 100. This tetraester is subsequently saponified using, for example, aqueous ethanol and potassium hydroxide, yielding the corresponding tetraacid of the formula 110. The tetraacid is then decarboxylated at a temperature of ca. 200° C., to the diacid of the formula 120. After esterification with methanol and concentrated sulfuric acid (see Scheme 4) to diester 20. Useful methods for the transformation of a tetraester of the formula 100 (ortho, (p−2)=1, R=ethyl) to a diester of the formula 20 are described in Fakhri, S. A.; Yousefi, B. H. *Tetrahedron* 2000, 56, 8301-8308, which is included herein in its entirety as a reference.

Scheme 7: General Synthesis for Compounds of Formula 7

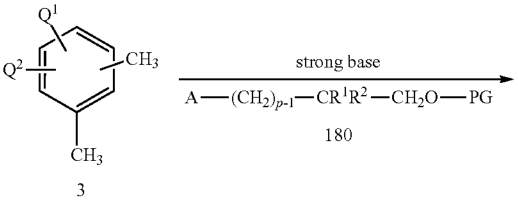

-continued

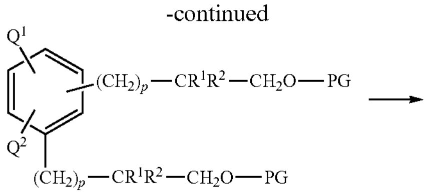

190

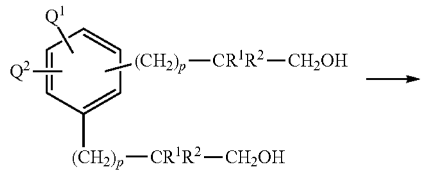

200

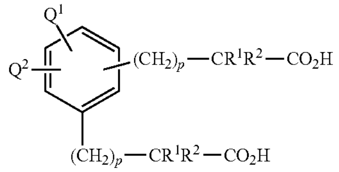

7

In Scheme 7, $Q^1$ and $Q^2$ can each independently be —O-alkyl, —S-alkyl, —S-aryl, —$NR^{1A}R^{2A}$, $NHR^{1A}$, phenoxy, aryloxy, benzyl, aryl, cycloalkyl, F, Cl, Br, I, —$CF_3$, —$COR^{1A}$, heteroaryl, or heterocyclyl, or each carbon atom together with the $Q^1$ and $Q^2$ attached to the carbon atom independently form a heterocyclyl or a carbocyclyl group. $R^{1A}$ and $R^{2A}$ are as defined herein for formula (I).

Scheme 7 illustrates the synthesis of ortho, meta, and para substituted arene compounds of the formula 7 with ω-carboxyalkyl substitution, wherein (p−1) is an integer in the range from 2-12 and $R^1$ and $R^2$ are either alkyl and/or aryl moieties or two alkyl moieties connected in a 3- to 7-membered cycle. The synthesis starts with the twofold deprotonation of ortho-, meta-, or para-xylene 3 with a strong base, such as, but not limited to, a combination of n-butyl lithium and potassium tert-butoxide in an aprotic solvent, such as, but not limited to, hexane and reaction of the formed dianion of 3 with suitable electrophiles A-$(CH_2)_{p-1}$—$CR^1R^2$—$CH_2O$-PG, wherein (p−1), $R^1$, and $R^2$ are defined as above and A is Cl, Br, or I. "PG" is a hydroxyl-protecting group. Examples of hydroxyl-protecting groups are described in Greene, T. W.; Wuts, P. G. M. *Protective groups in organic synthesis,* $3^{rd}$ ed., John Wiley and Sons, New York, 1999, pp 17-245, which is incorporated herein by reference. Methyl arenes can be alkylated via deprotonation using lithium bases followed by alkylation with suitable electrophiles according to Larock, R. C. *Comprehensive Organic Transformations: A Guide to Functional Group Preparations,* $2^{nd}$ ed.; Wiley-VCH, New York, 1999, p 88. See, Bates et al., *J. Am. Chem. Soc.* 1981, 103, 5052-5058, for an example for the preparation of xylene dianions. In the following step, the protective groups of 190 are removed to liberate the terminal hydroxylmethyl moieties in 200, which are the oxidized using a suitable oxidizing agent (Larock, R. C. *Comprehensive Organic Transformations. A Guide to Functional Group Preparations,* $2^{nd}$ ed.; Wiley-VCH, New York, 1999, pp 1646-1648 and Smith, M. B.; March, J. *March's Advanced Organic Chemistry, Reactions, Mechanisms, and Structure,* $5^{th}$ ed.; John Wiley and Sons, New York, 2001, p 1537) to give a dicarboxylic acid of the formula 7. For example, m-xylene (meta-3) is reacted with n-butyl lithium and potassium tert-butoxide in hexanes, first at room temperature and then at reflux temperature. After cooling to 0° C., a compound of the formula 180 (A=Br, (p−1)=3, $R^1$=$R^2$=methyl, PG=tetrahydropyranyl, prepared according to Dasseux et al., U.S. Pat. Nos. 6,646,170 and 6,410,802) is added and reaction is continued at reflux temperature, affording, after the usual workup and purification by column chromatography, the corresponding compound of the formula 190. Deprotection of 190 to 200 ($R^1$, $R^2$=methyl, p=3) is then accomplished by heating in methanol and concentrated, aqueous hydrochloric acid (Vogel, A. I. *Vogel's textbook of practical organic chemistry,* $5^{th}$ ed., Longman Scientific and Technical, 1989, p. 552). This compound 200 is then treated with pyridinium dichromate in N,N'-dimethylformamide according to Vedejs, E.; Dent, W. H., III; Gapinski, D. M.; McClure, C. K. *J. Am. Chem. Soc.* 1987, 109, 5437-5446 to yield the dicarboxylic acid of the formula 7 (meta, p=3; $R^1$, $R^2$=methyl).

Scheme 8 shows illustrative alternate syntheses of compounds I-1 and I-32. Commercially available benzene-dicarboxaldehydes (Sigma-Aldrich, AK Scientific, etc.) are reacted with (5-ethoxy-4,4-dimethyl-5-oxopentyl)triphenylphosphonium bromide (220) (prepared as described in Oniciu, D. C. et al., WO2012/054535 and U.S. Pat. No. 8,349,833 B2) in the presence of base (including but not limited to sodium or potassium hydroxide, potassium or sodium tert-butoxide, potassium or sodium carbonate, and sodium hydride), in the manner described in Le Bigot Y. et al., 1988, Tetrahedron 44(4), pp. 1057-1072, as a mixture of cis and trans isomers. The mixture of cis and trans isomers of formula (230) or (240) can be reduced catalytically by methods for the hydrogenation of olefins known in the art, such as the methods described by H.-U. Blaser, F. Spindler, M. Thommen, The Handbook of Homogeneous Hydrogenation, J. G. De Vries, C. J. Elsevier, Eds. (Wiley-VCH, 2008), chap. 37; Scharnagl, F. K. et al., Sci. Adv. 2018: 4: eaau1248, 21 Sep. 2018; and references cited herein. The esters thus obtained are subjected to hydrolysis after the hydrogenation reaction is deemed substantially complete by using an appropriate analytical methods. The reaction mixtures containing compounds of formula (250) or (260), respectively, are hydrolyzed in the presence of an alkaline earth metal salt or base, or oxide, or alkali metal salt or base, in refluxing alcohols for 2 to 96 hours. Typical examples include, but are not limited to, hydrolysis with $K_2CO_3$ in a refluxing mixture of DMSO and water. Other suitable procedures are referenced in Houben-Weyl. Methoden der Organische Chemie, Georg Thieme Verlag Stuttgart 1964, vol. XII/2, pp. 143-210 and 872-879, or Anderson, N. G., Practical Process Research & Development, Academic Press, London, 2000, pp. 93-94 and 181-182.

Scheme 8. Illustrative Synthesis of Compounds I-1 and I-32.

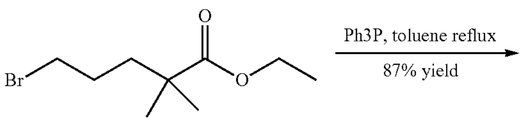

210

-continued
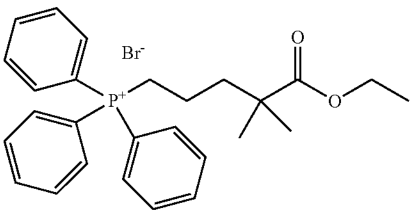
220
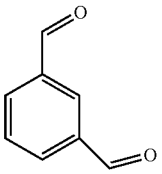
220, DCM
water, NaOH
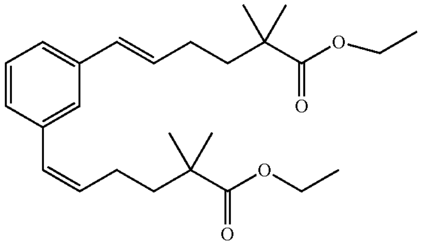
230
$H_2$, 5% Pd/C
EtOH
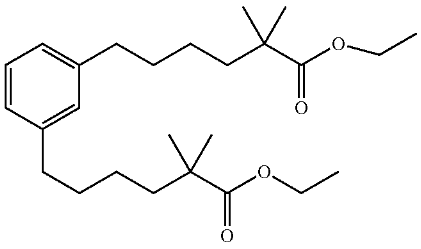
250
EtOH, water
KOH reflux
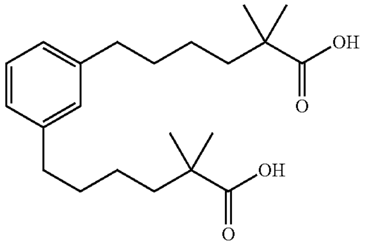
I-32
-continued
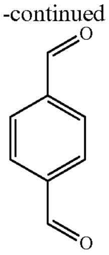
220, DCM
water, NaOH
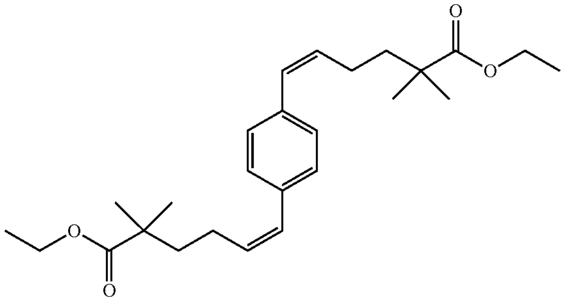
240
$H_2$, 5% Pd/C
EtOH
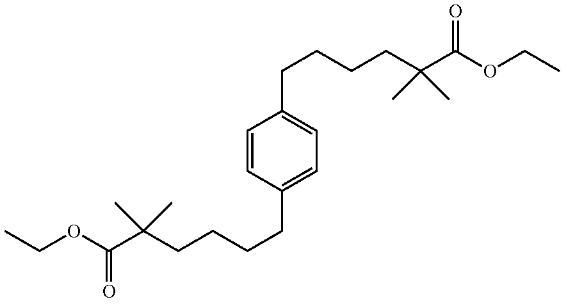
260
EtOH, water
KOH reflux
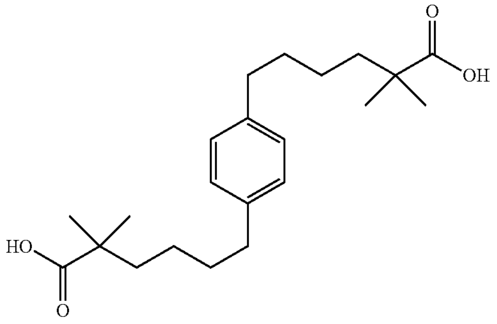
I-1

Scheme 9. General Synthesis of Compounds of Formula (III) or (IIIA) where X = O, $Z^1$, $Z^2$ = COOH, q = 0, and $R^1$ and $R^2$ together form a cyclopropyl ring

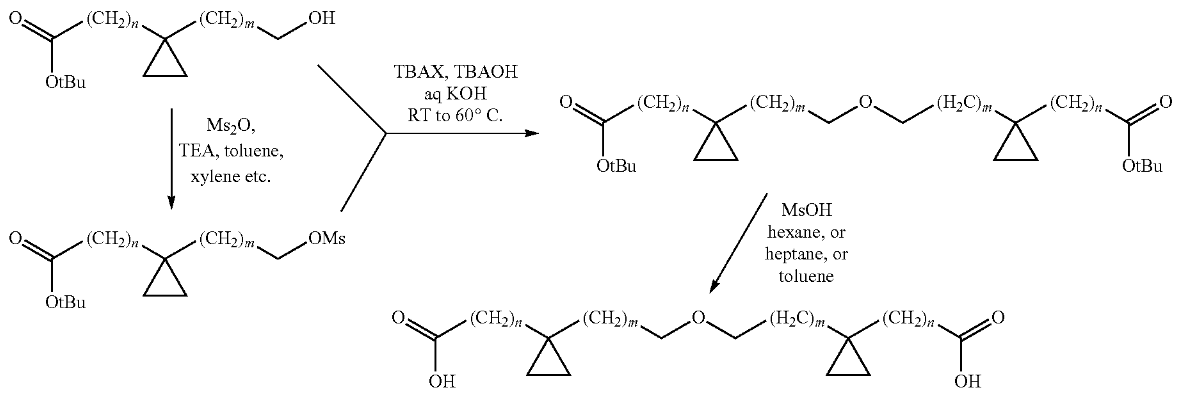

The compound of Formula (III) or (IIIA) where X=O can be prepared by a Williamson synthesis, by reacting an alcohol with a derivative comprising a leaving group such as halide, tolylsulphonate or mesylate. See Scheme 9.

Example 1A: Synthesis of 1,1'-(oxybis(pentane-5,1-diyl))bis(cyclopropane-1-carboxylic acid) (Compound III-17)

Step 1: 2-((5-bromopentyl)oxy)tetrahydro-2H-pyran (adapted from Kanth et al, Tetrahedron, 58 (6), 1069-1074 (2002))

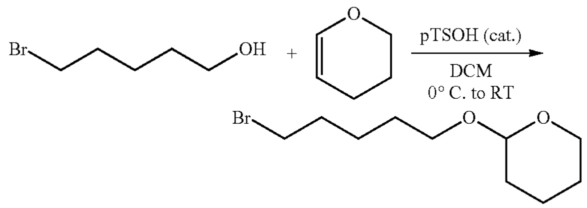

3,4-dihydro-2H-pyran (36.9 ml, 404 mmol) was added slowly to a stirred orange solution of 5-bromopentan-1-ol (32.6 ml, 269 mmol) and pTsOH (5.12 g, 26.9 mmol) in Dichloromethane (540 ml) on an ice bath. After addition, the orange mixture turned green. The reaction mixture was allowed to warm up to room temperature and was stirred for 2 h. The dark green reaction mixture was diluted with $NaHCO_3$ and extracted with dichloromethane three times. The combined organic phases were washed with brine, dried over anhydrous $Na_2SO_4$, filtered and concentrated under reduced pressure to afford 78.27 g of a brown solution. The target was purified four times by Flash Column Chromatography, 220 g silica column with gradient EtOAc (0 to 10%) in heptane. Combined fractions were concentrated to afford 56 g of a colorless liquid. The target was stripped with ether and once more concentrated under reduced pressure to dryness to afford 54.6 g of a colorless liquid with 99% purity (GCMS). $^1H$ NMR (400 MHz, $CDCl_3$/TMS): δ 4.57 (t, J=4.5 Hz, 1H), 3.86 (m, 1H), 3.75 (m, 1H), 3.51 (m, 1H), 3.42 (m, 2H), 3.40 (m, 1H), 1.87 (quin, 2H), 1.82 (m, 1H), 1.74-1.61 (m, 3H), 1.60-1.51 (m, 6H). $^{13}C$ NMR (100 MHz, $CDCl_3$/TMS): δ 98.9, 67.2, 62.4, 33.8, 32.6, 30.8, 28.9, 25.5, 25.0, 19.7. MS (HRMS): Calcd. for $C_{10}H_{19}O_2$ $[M+Na^+]^+$: 273.04606, found 273.04611.

Step2: tert-butyl 1-(5-((tetrahydro-2H-pyran-2-yl)oxy)pentyl)cyclopropane-1-carboxylate (adapted from US2013/109699)

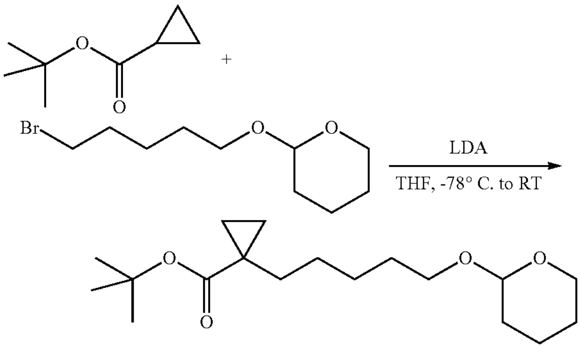

LDA (47.0 ml, 94 mmol) was cooled down to −78° C. under $N_2$ atmosphere. A solution of 2-((5-bromopentyl)oxy)tetrahydro-2H-pyran (11.80 g, 47 mmol) and tert-butyl cyclopropanecarboxylate (10.02 g, 70.5 mmol) in Tetrahydrofuran (dry, 94 ml) was slowly added to the mixture in the course of about 4 h. After addition, the mixture was allowed to warm up slowly to room temperature by removal of the dry ice from the isopropanol cold bath. Sample analysis showed 73% conversion towards the target and about 2% of remaining starting material. The reaction mixture was poured into a mixture of ice-water (20 mL and 60 mL, respectively) and saturated aqueous $NaHCO_3$ (40 mL), then the product was extracted with EtOAc (3×50 mL). The organic layers were combined and washed with a mixture of brine and saturated aqueous $NaHCO_3$, dried over anhydrous $Na_2SO_4$, filtered and concentrated under reduced pressure to afford an orange liquid (20.74 g). The product was further purified by flash chromatography on two column batches of 220 g silica using a gradient of EtOAc (0 to 10%) in heptane. Second elute was collected and concentrated to afford 12 g of product as a colorless oil with 95% purity (GC). Yield 60%. $^1H$ NMR (400 MHz, $CDCl_3$/TMS): δ 4.57 (t, 1H), 3.86 (m, 1H), 3.73 (m, 1H), 3.49 (m, 1H), 3.38 (m, 1H), 1.82 (m, 1H), 1.70 (m, 1H), 1.61-1.53 (m, 6H), 1.42 (s, 9H), 1.35 (m, 2H), 1.09 (q, J=4 Hz, 2H), 0.57 (q, J=4 Hz, 2H). MS (GCMS): Calcd. for $C_{14}H_{23}O_4$[M−tBu]: 255.16, found 255.1.

Step 3: tert-butyl 1-(5-hydroxypentyl)cyclopropane-1-carboxylate (adapted from US2013/109699)

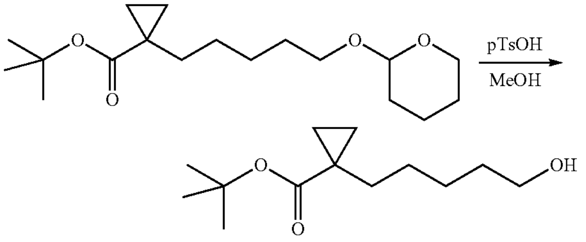

p-Toluenesulfonic acid monohydrate (1.681 g, 8.84 mmol) was added to a stirring solution of tert-butyl 1-(5-((tetrahydro-2H-pyran-2-yl)oxy)pentyl)cyclopropane-1-carboxylate (27.62 g, 88 mmol) in Methanol (325 ml) at room temperature. After 6 h sample shows ~1% of remaining starting material and the product in >80% pty. Mixture left stirring at room temperature overnight. The volatiles were removed under vacuum, water (50 mL) was added, and the product extracted with EtOAc (3×50 mL), then washed with brine, dried with sodium sulfate, filtered and concentrated to afford 25 g of a yellow oil. Product stability is compromised at room temperature for which batches were stored at 4° C. and purified by chromatography immediately before next step. Purification by flash chromatography was performed with, e.g. 2 g of material in 80 g silica with gradient of EtOAc (0 to 22%) in heptane. Main component collected to afford 1.37 g of product as a colorless oil. Molecular ion not found by LCMS or GCMS techniques; only [M-OtBu] m/z 155 found in 99% (GCMS). NMR in agreement with structure confirming 99% purity (yield 90%). $^1$H NMR (400 MHz, $CDCl_3$/TMS): δ 3.64 (t, 6.6 Hz, 2H), 1.57 (quin, 2H), 1.46-1.51 (m, 4H), 1.42 (s, 9H), 1.35 (m, 2H), 1.10 (q, 5.2 Hz, 2H), 0.59 (q, 5.2 Hz, 2H). $^{13}$C NMR (100 MHz, $CDCl_3$/TMS): δ 174.6, 79.9, 62.9, 34.1, 32.7, 28.1, 27.5, 25.9, 24.2, 15.2. GCMS: 99%, Mass: m/z $[M-OtBu]^+$ calc. 155.11, found 155.1.

Step 4: di-tert-butyl 1,1'-(oxybis(pentane-5,1-diyl)) bis(cyclopropane-1-carboxylate)

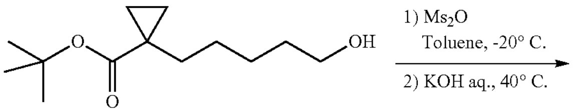

-continued

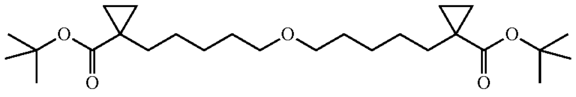

To a solution of tert-butyl 1-(5-hydroxypentyl)cyclopropane-1-carboxylate (7.36 g, 32.2 mmol) in dry toluene (150 ml), triethylamine (3.00 ml, 21.60 mmol) was added, the mixture set under $N_2$ and cooled in a dry ice/acetone bath until it reached −20° C. for 10 minutes. Methanesulfonic anhydride (3.66 ml, 19.34 mmol) was added and the reaction mixture was kept at this temperature for 30 min. The mixture was then left to reach r.t, and was subsequently heated to 30° C. The formation of the methanesulfonic intermediate of half equivalent of the starting material was controlled by GCMS. A fresh aq. solution of KOH 61% w/w was prepared by dissolving potassium hydroxide (70.4 g, 1255 mmol) in demineralized water (45 ml) under stirring and cooling using an ice bath; the resulting total volume is about 75 mL and was set aside. After an additional hour of reaction, tetrabutylammonium hydroxide 55% w/w aq. (0.627 ml, 1.289 mmol) was added, followed by the KOH (aq.) solution above under vigorous stirring. The mixture was then stirred at 40° C. overnight, and the conversion in final product is controlled by a chromatography or NMR technique. After 17 h of heating at 40° C., the conversion in the final product was over 80%; the reaction was considered complete and the heating was stopped. Water (50 mL) was added, and the reaction mixture was stirred to quench. The organic fraction was collected, and the aq. fraction washed with toluene. The two organic fractions were combined, washed with water, sulfuric acid (2N) and brine, then dried with anhydrous sodium sulfate, filtered, and concentrated to yield 7.72 g of a yellow oil, which was further purified by flash column chromatography on 120 g of silica using gradient eluent % of EtOAc (0 to 25%) in heptane. The product eluted with the 10% EtOAc in heptane fraction. The concentrated fractions afforded 5.5 g of a colorless oil. Properties of final compound proved incompatible for its detection by UV-LC and GCMS. $^1$H NMR (400 MHz, CDC/TMS): δ 3.38 (t, 4H), 1.56 (quin, 4H), 1.46 (d, 4H), 1.42 (s, 18H), 1.35-1.28 (m, 6H), 1.0) (q, 4H), 0.88 (t, 2H), 0.59 (q, 4H). $^{13}$C NMR (100 MHz, $CDCl_3$/TMS): δ 174.6, 79.8, 70.9, 34.1, 29.7, 28.1, 27.6, 26.4, 24.2, 15.2.

Step 5: 1,1'-(oxybis(pentane-5,1-diyl))bis(cyclopropane-1-carboxylic acid) (Compound III-17)

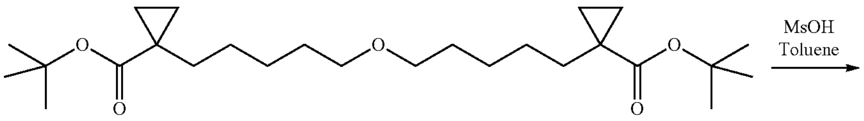

-continued

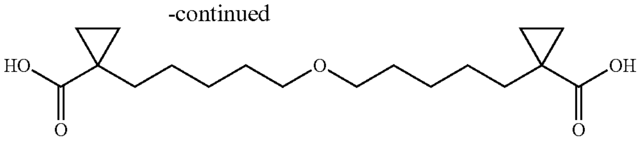

Di-tert-butyl 1,1'-(oxybis(pentane-5,1-diyl))bis(cyclopropane-1-carboxylate) (5.6 g, 12.77 mmol) was stirred in dry toluene (42.6 ml) and methanesulfonic acid (2.071 ml, 31.9 mmol) was slowly added at r.t. Stirring continued overnight. Aq. sulfuric acid 2N (10 mL) was added and stirred to quench. After 30 min, the originally orange mixture turned to almost colorless. The organic layer was collected and the aq. layer was washed with toluene. The combined organic fractions were treated with aq. NaOH 2M (50 mL) and stirred for 15 min, and the aq. fraction containing the product was collected. The organic layer was washed with additional NaOH 2M (20 mL). The combined aqueous fractions were stirred and HCl 6M (100 mL) was slowly added until the mixture became turbid white, stirring continued until pH remained stable. When the mixture started to form an emulsion, diethyl ether (100 mL) was added and stirring was continued vigorously until both aqueous and ethereal phases were translucid. The organic fraction was collected, and the aq. fraction washed with diethyl ether (2×50 mL). The combined organic fractions were dried on anhydrous sodium sulfate, filtered and concentrated to afford 3.85 g of an off-white oil. The product solidified overnight and then it was triturated with diethyl ether and subjected to rotary evaporation at r.t. for 4 h to afford a white crystalline powder (85% yield). $^1$H NMR (400 MHz, $CDCl_3$/TMS): δ 10.83 (bs, 2H), 3.39 (t, 4H), 1.56 (t, J=6.8 Hz, 4H), 1.49 (m, 4H), 1.46 (m, 4H), 1.33 (q, 4H), 1.26 (dd, J=4 Hz, J=3 Hz 4H), 0.75 (dd, J=4 Hz, J=3 Hz, 4H). $^{13}$C NMR (100 MHz, $CDCl_3$/TMS): δ 182.5, 70.8, 33.5, 29.6, 27.4, 26.3, 23.3, 16.5. MS (HRMS): Calcd. for $C_{18}H_{30}O_5$ $[M+H^+]^+$: 327.21660, found 327.21592

Example 1B: 6-[3-(5-Carboxy-5-methylhexyl)-phenyl]-2,2-dimethylhexanoic acid (I-32)

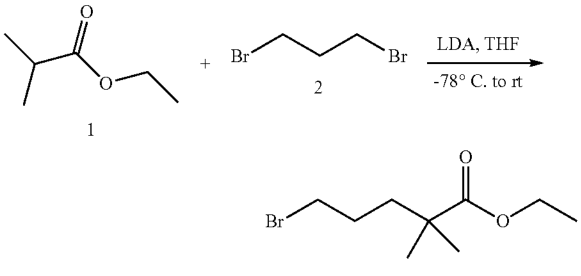

1 2 3

Step 1: ethyl 5-bromo-2,2-dimethylpentanoate

Under an argon atmosphere, ethyl isobutyrate (30 g, 258 mmol) was dissolved in anhydrous THF (250 mL). The flask was cooled in a dry ice/acetone bath and 2 M lithium diisopropylamide solution (150 mL) was added dropwise over 30-40 minutes. The mixture stirred for an additional hour at −78° C. when 1,3-dibromopropane (150 g, 743 mmol, 2.88 eq) was added dropwise (fast) over 5-10 minutes. The mixture slowly warmed to room temperature and stirred overnight. After 16 hours at room temperature, the reaction was quenched with saturated ammonium chloride (200 mL) and the product was extracted with ethyl acetate (2×500 mL). The combined ethyl acetate extracts were washed with 10% HCl (2×200 mL), brine (200 mL), dried over magnesium sulfate, filtered, and concentrated on a rotovap. The remaining tan oil (200 g) was filtered through silica gel (800 g), eluting with heptane followed by 2-5% ethyl acetate in heptane. The product containing fractions were combined and concentrated on a rotovap. The experiment generated ethyl 5-bromo-2,2-dimethylpentanoate 3 (49.3 g, 80.5% yield) as a colorless oil. $^1$H NMR (300 MHz, $CDCl_3$) δ 4.10 (q, 1H, J=7.2 Hz), 3.63 (t, 2H, J=6.3 Hz), 1.85-1.70 (m, 2H), 1.70-1.60 (m, 2H), 1.24 (t, 3H, J=7.2 Hz), 1.17 (s, 6H). $^{13}$C NMR (75 MHz, $CDCl_3$) δ 177.6, 60.5, 41.9, 39.2, 34.0, 28.7, 25.3, 14.4.

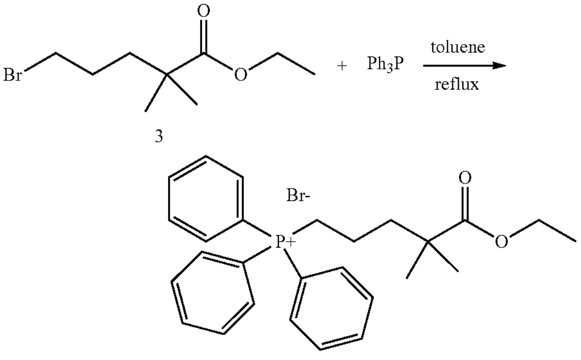

3 4

Step 2: (5-ethoxy-4,4-dimethyl-5-oxopentyl)(triphenyl)phosphanium bromide

Triphenylphosphine (77.4 g, 0.295 mol) was added to a solution of 5-bromo-2,2-dimethylpentanoic acid ethyl ester 3 (70.5 g, 0.295 mol) in toluene (600 mL). The solution was heated to reflux for 24 h. The toluene was concentrated to ~250 mL on a rotovap. The toluene was decanted and saved. The residue was stirred with heptane (200 mL) for 1 hour at room temperature under an argon atmosphere. The heptane was decanted remaining solid was dried under high vacuum. The procedure generated a first crop of intermediate 4 (68.4 g, crop 1). The toluene and heptane washes were combined and concentrated. The remaining residue (75.3 g) was mixed with toluene (200 mL) and heated to reflux under argon for 24 hours. After 24 hours, the flask was cooled to room temperature and stored in a freezer (−15° C.) for 1 hour. The toluene was decanted and the remaining residue was stirred with heptane (200 mL) for 1 hour under an argon atmosphere. The heptane was decanted and the solid was dried under high vacuum to prepare a second crop of intermediate 4 (52.5 g). After the crops were combined, the experiment generated intermediate 4 (120.9 g, 82% yield) as an off white solid. $^1$H NMR (300 MHz, $CDCl_3$) δ 7.89-7.70 (m, 15H), 3.97 (q, 2H, J=7.2 Hz), 3.82 (m, 2H), 1.92 (m, 2H), 1.60 (m, 2H), 1.11 (m, 9H). $^{13}$C NMR (75 MHz, $CDCl_3$) δ 177.2, 135.1, 133.6 (d, J=9.2 Hz), 130.4 (d, J=12.6 Hz), 118.1 (d, J=84.7 Hz), 60.3, 42.1, 40.7 (d, J=16 Hz), 25.0, 23.1 (d, J=49.3 Hz), 18.4, 14.2. $^{31}$P (292 MHz, $CDCl_3$) δ 24.0.

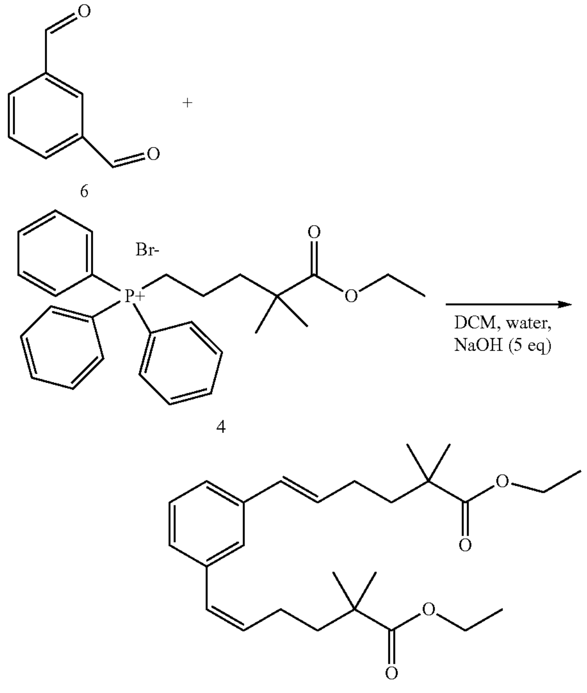

6 + 4 → 7

Step 3: ethyl (5E/Z)-6-{3-[(1E/Z)-5,5-dimethyl-6-ethoxy-6-oxohex-1-en-1-yl]phenyl}2,2-dimethyl-hex-5-enoate (5-ethoxy-4,4-dimethyl-5-oxopentyl)(triphenyl)phosphanium bromide 4 (56.4 g, 112.9 mmol) and isophthalaldehyde (8.0 g, 59.6 mmol) were dissolved in dichloromethane (170 mL) at room temperature under an argon atmosphere. The flask was cooled in a water bath at room temperature. Sodium hydroxide (32.0 g, 800 mmol) in water (32 g) was added dropwise over 10 minutes. After 30 minutes, additional intermediate 4 (14.0 g, 28.0 mmol) was added and the mixture was vigorously stirred for 2 hours at room temperature. Water (DI, 400 mL) was added and the layers were separated. The aqueous fraction was extracted with dichloromethane (200 mL). The dichloromethane extracts were combined, dried over magnesium sulfate, filtered, and concentrated. The remaining yellow solid (62.5 g) was dissolved in dichloromethane (200 mL) and filtered through a column of silica gel (400 g), eluting with dichloromethane. The product containing fractions were combined and concentrated. The remaining yellow oil (17.23 g) was purified by column chromatography on silica gel (350 g) eluting with 4% ethyl acetate in heptane. The procedure generated intermediate 7 (10.65 g, 43% yield, E/Z mixture of isomers) as a light yellow oil (that retained some heptane). A second fraction of the mono-olefination intermediate (3.28 g) was also recovered. (E/Z mixture of isomers). $^1$H NMR (300 MHz, $CDCl_3$) δ 7.28-7.13 (m, 4H), 6.40-6.32 (m, 2H), 6.22-6.12 (m, 1H), 5.65-5.56 (m, 1H), 4.15-4.04 (m, 4H), 2.30-2.12 (m, 4H), 1.73-1.65 (m, 4H), 1.30-1.17 (m, 18H). $^{13}$C NMR (75 MHz, $CDCl_3$) δ 177.6, 137.8, 137.6, 137.4, 132.3, 130.5, 129.9, 129.0, 128.2, 127.9, 127.1, 126.7, 126.4, 124.5, 124.1, 123.6, 60.3, 42.1, 41.9, 40.7, 40.2, 28.7, 25.2, 25.1, 24.3, 14.2.

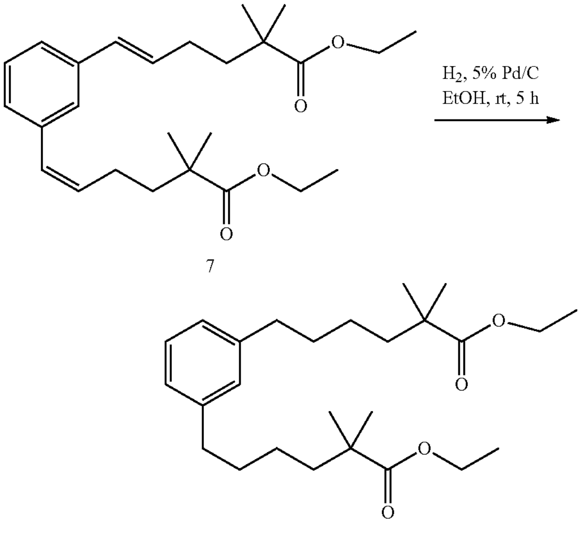

7 → 8

Step 4: 6-[3-(5-Carboxy-5-methylhexyl)-phenyl]-2,2-dimethylhexanoic acid diethyl ester Intermediate 7 (10.5 g, 25.3 mmol) was dissolved in ethanol (120 mL) and added to 5% palladium on carbon (2.5 g) under a nitrogen atmosphere at room temperature. The nitrogen atmosphere was replaced with hydrogen gas (40-45 psi) and the mixture was hydrogenated on a Parr hydrogenator for 5 hours at room temperature. After 5 hours, the hydrogen was replaced with nitrogen and the mixture was filtered through a pad of celite. The ethanol was concentrated on a rotovap and the crude material was used for the final step without purification. The procedure generated intermediate 8 (8.59 g, 81% yield, pure by NMR) as a very light yellow oil. $^1$H NMR (300 MHz. $CDCl_3$) δ 7.21 (t, 1H, J=8.4 Hz), 7.03-7.01 (m, 3H), 4.15 (q, 4H, J=6.9 Hz), 2.62 (t, 4H, J=7.5 Hz), 1.70-1.55 (m, 8H), 1.38-1.30 (m, 4H), 1.27 (t, 6H, J=6.9 Hz), 1.21 (s, 12H). $^{13}$C NMR (75 MHz, $CDCl_3$) δ 177.9, 142.5, 128.5, 128.1, 125.6, 60.1, 42.1, 40.5, 35.8, 32.0, 25.1, 24.7, 14.2.

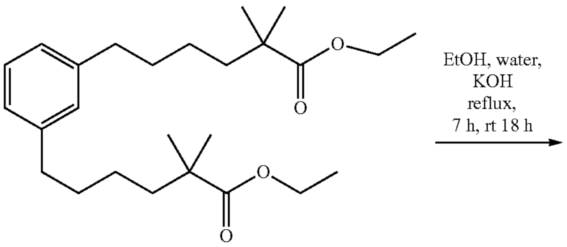

8

-continued

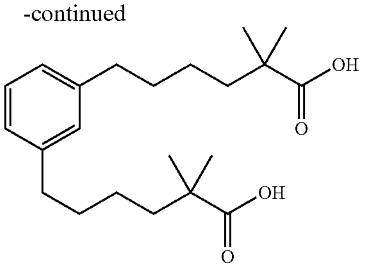

I-32

Step 5: 6-[3-(5-Carboxy-5-methylhexyl)-phenyl]-2,2-dimethylhexanoic acid (Compound I-32)

Intermediate 8 (8.50 g, 20.3 mmol) was dissolved in ethanol (65 mL). Di water (60 mL) containing potassium hydroxide (8.0 g, 143 mmol) was added and the mixture was heated to reflux under an argon atmosphere. After 7 hours, the heat was turned off and the mixture cooled to room temperature and stirred overnight. After 18 hours, the solution was concentrated on a rotovap to remove the ethanol. The remaining aqueous solution diluted with DI water (100 mL) and extracted with diethyl ether (100 mL). The aqueous portion was acidified (to pH=2) with concentrated hydrochloric acid and the solid product was extracted with ethyl acetate (2×100 mL). The combined ethyl acetate extracts were washed with brine (100 mL), dried over magnesium sulfate, filtered, and concentrated on a rotovap. The remaining white solid (7.0 g) was mixed with heptane (50 mL) and stirred overnight at room temperature under an argon atmosphere. After 20 hours, the solids were filtered and dried at 35° C. under high vacuum. The procedure generated 6-[3-(5-Carboxy-5-methylhexyl)-phenyl]-2,2-dimethylhexanoic acid I-32 (6.47 g, 88% yield, 99.4% by HPLC as a white solid (mp=99-101° C.). NMR $^1$H (300 MHz, $CDCl_3$), δ 7.18 (t, 1H, J=7.2 Hz), 7.00-6.90 (m, 3H), 2.58 (t, 4H, J=6.9 Hz), 1.66-1.54 (m, 8H), 1.32-1.22 (m, 4H), 1.18 (s, 12H). $^{13}$C (75 MHz, $CDCl_3$), δ 185.3; 142.4; 128.5; 128.2; 127.8; 42.1; 40.5; 35.7; 31.6; 25.0; 24.5.

Example 1C: 6-[4-(5-carboxy-5-methylhexyl)-phenyl]-2,2-dimethylhexanoic acid (Compound I-1)

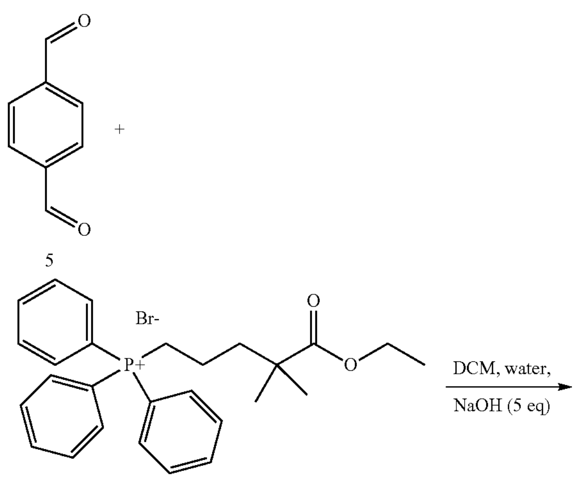

5

4

-continued

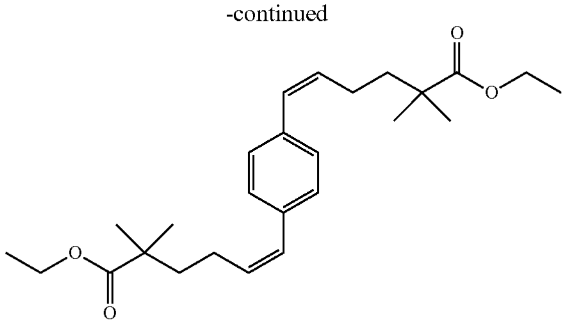

9 cis/trans mixture

Step 1: Ethyl (5E/Z)-6-{4-[(1E/Z)-5,5-dimethyl-6-ethoxy-6-oxohex-1-en-1-yl]phenyl}2,2-dimethylhex-5-enoate (5-Ethoxy-4,4-dimethyl-5-oxopentyl)(triphenyl)phosphanium bromide 4 (60.0 g, 120.1 mmol), prepared as described in Example 1B, step 2, and terephthalaldehyde 5 (8.0 g, 59.6 mmol) were dissolved in dichloromethane (180 mL) at room temperature under an argon atmosphere. The flask was cooled in a water bath at room temperature. Sodium hydroxide (32.0 g, 800 mmol) in water (38 g) was added dropwise over 10-15 minutes. After 30 minutes, additional intermediate 4 (14.47 g, 28.97 mmol) was added and the mixture was vigorously stirred for 2 hours at room temperature. Water (DI, 200 mL) was added and the layers were separated. The aqueous fraction was extracted with dichloromethane (200 mL). The dichloromethane extracts were combined, dried over magnesium sulfate, filtered, and concentrated. The remaining yellow solid (64.2 g) was dissolved in dichloromethane (100 mL) and filtered through a column of silica gel (400 g), eluting with dichloromethane. The product containing fractions were combined and concentrated. The remaining yellow oil (18.0 g) was purified by column chromatography on silica gel (360 g) eluting with 5% ethyl acetate in heptane. The procedure generated intermediate 9 (9.5 g, 38.5% yield, E/Z mixture of isomers) as a yellow oil (that retained a trace of heptane). A second fraction of the mono-olefination intermediate (3.62 g) was also recovered. (E/Z mixture of isomers): $^1$H NMR (300 MHz, $CDCl_3$) δ 7.29-7.16 (m, 4H), 6.40-6.30 (m, 2H), 6.22-6.12 (m, 1H), 5.70-5.50 (m, 1H), 4.15-4.05 (m, 4H), 2.30-2.10 (m, 4H), 1.74-1.65 (m, 4H), 1.28-1.17 (m, 18H). $^{13}$C NMR (75 MHz, $CDCl_3$) δ 177.6, 136.3, 136.1, 1375.9, 135.8, 132.2, 131.9, 130.2, 129.9, 129.6, 128.8, 128.4, 125.9, 125.6, 60.2, 42.0, 41.9, 40.6, 40.2, 25.1, 25.0, 24.4, 14.2.

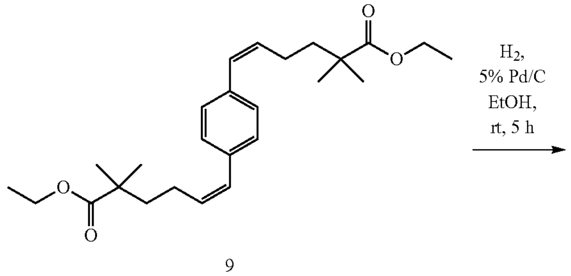

9 cis/trans mixture

-continued

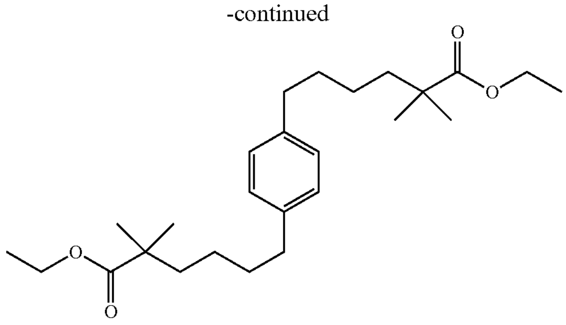

10

Step 2: 6-[4-(5-Carboxy-5-methylhexyl)-phenyl]-2,2-dimethylhexanoic acid diethyl ester Intermediate 9 (11.0 g, 26.5 mmol) was dissolved in ethanol (200 mL) and added to 5% palladium on carbon (3.0 g) under a nitrogen atmosphere at room temperature. The nitrogen atmosphere was replaced with hydrogen gas (40-45 psi) and the mixture was hydrogenated on a Parr hydrogenator for 5 hours at room temperature. After 5 hours, the hydrogen was replaced with nitrogen and the mixture was filtered through a pad of celite. The ethanol was concentrated on a rotovap and the crude material was used for the final step without purification. The procedure generated intermediate 10 (10.24 g, 92% yield, pure by NMR) as a colorless oil. $^{1}H$ NMR (300 MHz, $CDCl_3$) δ 7.06 (s, 4H), 4.09 (q, 4H, J=7.2 Hz), 2.56 (t, 4H, J=7.5 Hz), 1.62-1.50 (m, 8H), 1.32-1.22 (m, 4H), 1.22 (t, 6H, J=7.2 Hz), 1.10 (s, 12H). $^{13}C$ NMR (75 MHz, $CDCl_3$) δ 177.9, 139.8, 128.2, 60.1, 42.1, 40.5, 35.3, 31.9, 25.1, 24.6, 14.2.

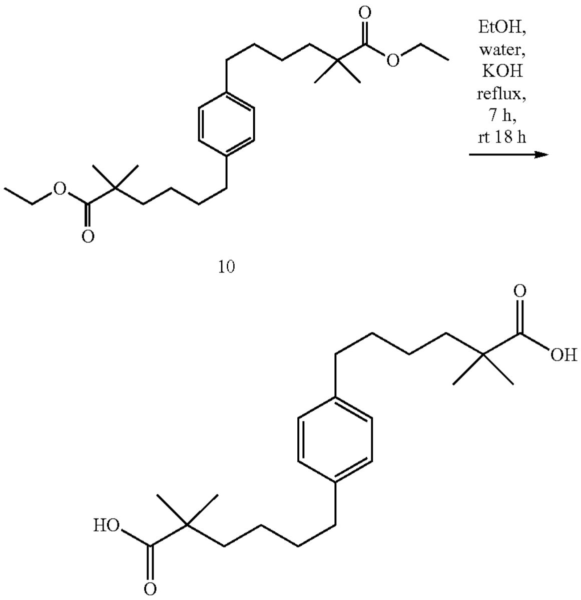

10

I-1

Step 3: 6-[4-(5-carboxy-5-methylhexyl)-phenyl]-2,2-dimethylhexanoic acid (Compound I-1)

Intermediate 10 (10.2 g, 24.4 mmol) was dissolved in ethanol (85 mL). Di water (80 mL) containing potassium hydroxide (9.57 g, 170.5 mmol) was added and the mixture was heated to reflux under an argon atmosphere. After 7 hours, the heat was turned off and the mixture cooled to room temperature and stirred overnight. After 18 hours, the solution was concentrated on a rotovap to remove the ethanol. The remaining mixture was diluted with DI water (250 mL) and acidified (to pH=2) with concentrated hydrochloric acid. After mixing for 1 hour the solid product was extracted with ethyl acetate (2×150 mL). The combined ethyl acetate extracts were washed with brine (100 mL), dried over magnesium sulfate, filtered, and concentrated on a rotovap. The remaining white solid (8.5 g) was mixed with heptane (40 mL) and stirred overnight at room temperature under an argon atmosphere. After 20 hours, the solids were filtered and dried at 45° C. under high vacuum. The procedure generated 6-[4-(5-Carboxy-5-methylhexyl)-phenyl]-2,2-dimethylhexanoic acid I-1 (7.82 g, 88.5% yield, 99.6% by HPLC as a white solid (mp=126-127° C.). NMR $^{1}H$ (300 MHz, $CDCl_3$) δ 7.03 (s, 4H), 2.62 (m, 4H), 1.67-1.54 (m, 4H), 1.53-1.44 (m, 4H), 1.15 (s, 12H), 1.07-0.96 (m, 4H). $^{13}C$ (75 MHz, $CDCl_3$): δ 185.3, 138.7, 128.5, 42.4, 41.5, 34.5; 30.6; 24.9; 23.3.

Example 1D: Synthesis of 6,6'-(1,2-phenylene)bis(2,2-dimethylhexanoic acid) (Compound I-62)

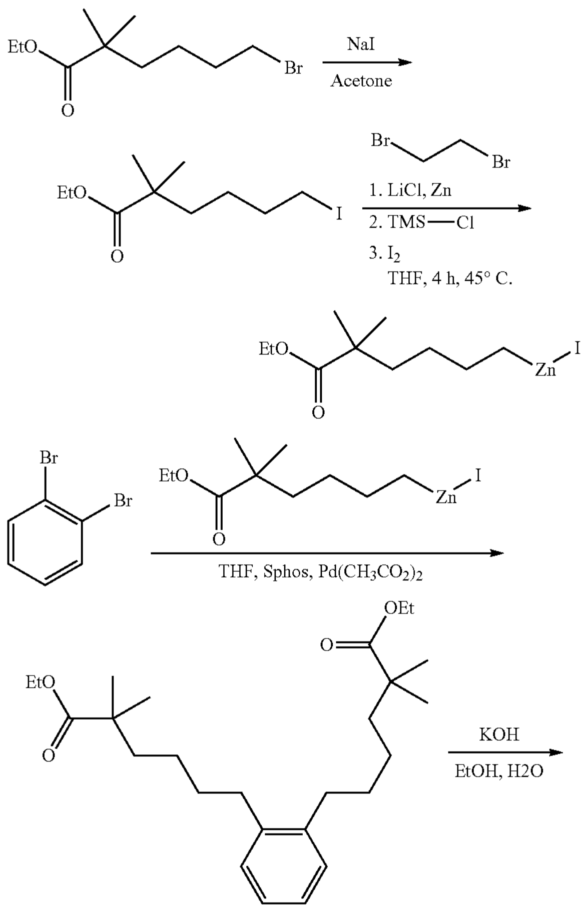

-continued

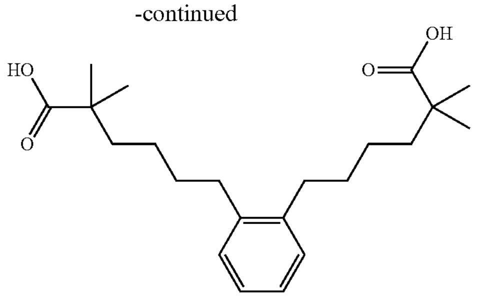

I-62

Step 1: Ethyl 6-iodo-2,2-dimethylhexanoate

Commercially available ethyl 6-bromo-2,2-dimethylhexanoate (1 g, 3.98 mmol) and acetone (6 ml) were added to a 20 mL round bottomed flask. Sodium iodide (1.194 g, 7.96 mmol) was added, and the flask was covered with aluminum-foil. The reaction mixture was stirred at room temperature over 48-72 hr. The solids were filtered off and rinsed with dichloromethane. The filtrate was concentrated in vacuo, to give a slurry of solids, dichloromethane was added and the solids were removed by filtration. The filtrate was concentrated under reduced pressure to give ethyl 6-iodo-2,2-dimethylhexanoate (1.125 g, 3.77 mmol, 95% yield). $^{1}H$ NMR (400 MHz, DMSO/TMS): δ 4.05 (q, J=7.1 Hz, 2H), 3.26 (t, J=6.8 Hz, 2H), 1.71 (p, J=7.0 Hz, 2H), 1.52-1.43 (m, 2H), 1.33-1.23 (m, 2H), 1.18 (t, J=7.1 Hz, 3H), 1.10 (s, 6H), GCMS: >95%, Mass: m/z $[M-C_2H_5O]^-$ 253.1.

Step 2: (6-Ethoxy-5,5-dimethyl-6-oxohexyl)zinc(II) iodide

An oven dried 50 ml three necked round bottomed glass flask with teflon stirrer (vacuo outlet, inlet to argon filled balloon, stopper) was charged with lithium chloride, anhydrous (239 mg, 5.63 mmol) and zinc (dust (<10 μM), 368 mg, 5.63 mmol) and heated under vacuo (standard lab vacuo pump) using a heat gun for ~5 minutes. The mixture was cooled to room temperature. The mixture was suspended in dry THF (dry) (10 ml). The zinc was activated by the addition of 1,2-dibromoethane (0.024 ml, 0.282 mmol) and warmed for a few seconds using a heat gun, stirred for 5 min at room temperature. Trimethylsilyl chloride (0.024 ml, 0.188 mmol) was added, and the mixture was heated with a heat gun for a few seconds, stirred for 5 minutes at room temp. Iodine (19.07 mg, 0.075 mmol) was added as a solid. A yellow suspension formed in ~1 minute and the mixture was stirred for 10 minutes at room temperature. A solution of ethyl 6-iodo-2,2-dimethylhexanoate (1120 mg, 3.76 mmol) in dry THF (5.00 ml) was dropwise added within 1-2 minutes at room temperature. The reaction mixture was stirred at 45° C. (oil bath) under argon for 1 h, then cooled to room temperature and left for 1 h before using it in the next step.

Step 3: Diethyl 6,6'-(1,2-phenylene)bis(2,2-dimethylhexanoate)

A 40 ml screw cap vial was placed under argon and charged with 1,2-dibromobenzene (0.112 ml, 0.933 mmol) and dry THF (10 ml) followed by the addition of the S-Phos (38.3 mg, 0.093 mmol) and palladium(II) acetate (10.47 mg, 0.047 mmol). (6-Ethoxy-5,5-dimethyl-6-oxohexyl)zinc(II) iodide (1017 mg, 2.80 mmol) in THF was filtered and added dropwise (1-2 min) at room temp. The reaction was stirred at 40° C., overnight. The reaction was stopped and EtOH (5 mL) was added. Hydromatrix was added and the solvent was evaporated. The crude product was purified by straight phase chromatography using heptane/diisopropyl ether 0=>20%. Fractions containing the product were combined and concentrated under reduced pressure to give diethyl 6,6'-(1,2-phenylene)bis(2,2-dimethylhexanoate) (210 mg). The product was used without further characterization. LCMS:72% m/z$[M+NH_4]^+$ 436.3.

Step 4: 6,6'-(1,2-phenylene)bis(2,2-dimethylhexanoic acid)

Crude diethyl 6,6'-(1,2-phenylene)bis(2,2-dimethylhexanoate) (210 mg) above was dissolved in ethanol (1 ml) and aqueous 6 M KOH (1.254 ml, 7.52 mmol) was added. A precipitate was formed; the reaction mixture was stirred at 60° C., overnight. The mixture was cooled to room temperature and acidified to a pH of about 8. The reaction mixture was concentrated under reduced pressure to give the crude product. The residue was dissolved in $H_2O$/acetonitrile/THF and subjected to the basic prep for purification. The product fractions were concentrated in the genevac, reformatted and freeze-dried to give 6,6'-(1,2-phenylene)bis(2,2-dimethylhexanoic acid) (95.4 mg, 0.263 mmol, 28% yield over two steps). $^{1}H$ NMR (400 MHz, [MeOD]/TMS): δ 7.11-7.02 (m, 4H), 2.63-2.56 (m, 4H), 1.60-1.48 (m, 8H), 1.41-1.29 (m, 4H), 1.14 (s, 12H). $^{13}C$ NMR (100 MHz, [MeOD]/TMS): δ 183.02, 141.37, 130.27, 126.84, 43.34, 42.05, 33.64, 33.30, 26.37, 25.98. LCMS: >95%, Mass: m/z$[M-H]^-$ 361.3.

Example 1E: Synthesis of 7,7'-(1,4-phenylene)bis(3,3-dimethylheptanoic acid) (Compound I-84)

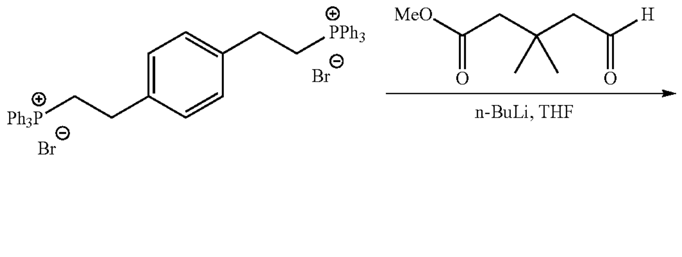

-continued

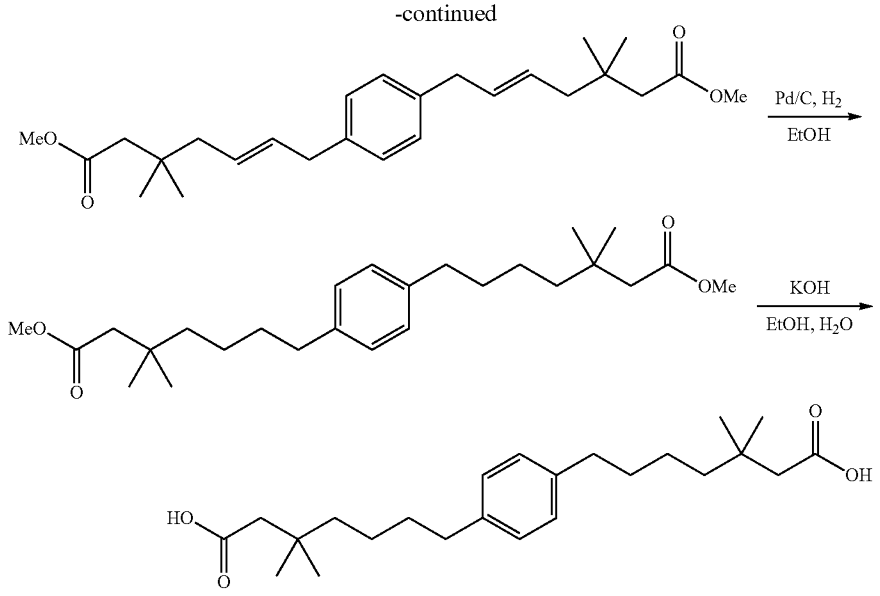

I-84

Step 1: Dimethyl 7,7'-(1,4-phenylene)(5E,5'E)-bis(3,3-dimethylhept-5-enoate)

The reaction was carried out in a 500-milliliter round-bottom flask under argon atmosphere. (1,4-Phenylenebis(ethane-2,1-diyl))bis(triphenyl-phosphonium) bromide (3.18 g, 3.58 mmol, prepared as described in to U.S. Pat. No. 4,689,344) was co-evaporated with dry tetrahydrofuran (THF, 150 mL) to remove solvent residues. To a stirred suspension of (1,4-phenylenebis(ethane-2,1-diyl))bis(triphenyl-phosphonium) bromide (3.18 g, 3.58 mmol) in dry THF (150 mL), was added n-butyllithium (13.44 mL, 21.50 mmol) at room temperature. A dark orange/brown solution was obtained. After 10 minutes, a solution of freshly prepared (same day) methyl 3,3-dimethyl-5-oxopentanoate (2.324 g, 14.69 mmol) in dry THF (25 mL) was added dropwise over a period of 2 minutes. A light amber solution was obtained. The mixture was stirred for 30 minutes at room temperature for complete conversion. The reaction mixture was quenched with saturated aqueous $NH_4Cl$ solution (100 mL) and partitioned between $Et_2O$ (250 mL) and EtOAc (250 mL). Phases were separated and the organic phase was washed with saturated aqueous NaCl (4×500 mL), followed by brine (250 mL). The aqueous phases were then back-extracted with a single portion of $Et_2O$ (500 mL). This $Et_2O$-phase was then washed with brine (250 mL). The combined organic phases were dried over $Na_2SO_4$ and left standing overnight. The $Na_2SO_4$ was filtered off and the filtrate was concentrated under reduced pressure affording 4.09 g crude product. The crude product was dissolved in dichloromethane, coated onto hydromatrix and purified by flash column chromatography (silica 80 g, gradient, heptane/EtOAc, 1:0-9:1, collection by ELSD, 50-milliliter fractions). Fraction 28-33 were combined and the solvent was removed under reduced pressure affording 466 mg of the product as a clear, colourless oil (LCMS, m/z of 415 [M+H]+. $^1$H NMR (400 MHz, $CDCl_3$/TMS): δ 7.10 (s, 4H), 5.68 (m, J=12.6, 7.3 Hz, 2H), 5.61-5.46 (m, 2H), 3.65 (s, 6H), 3.64 (s, 1H), 3.37 (d, J=7.2 Hz, 4H), 3.33 (d, J=6.1 Hz, 1H), 2.25 (s, 4H), 2.19 (d, J=7.7 Hz, 5H), 2.03 (d, J=6.7 Hz, 1H), 1.04 (s, 12H), 0.99 (s, 2H).

Step 2: Dimethyl 7,7'-(1,4-phenylene)bis(3,3-dimethylheptanoate)

Dimethyl 7,7'-(1,4-phenylene)(5E,5'E)-bis(3,3-dimethylhept-5-enoate) (466 mg, 1.124 mmol) was dissolved in ethanol (Abs) (14.410 mL) in a 20-milliliter biotage microwave vial and the solution was purged with nitrogen. Pd—C (on activated carbon, 10 w % Pd, 50 w % water-wet, unreduced (59.8 mg, 0.056 mmol) was added and the vial was capped. The reaction mixture was flushed with hydrogen and then stirred under hydrogen atmosphere (balloon) for 1 h at room temperature. The reaction mixture was filtered through 3 high-capacity nylon microfilters. The filters were each rinsed with EtOH (20 mL). The combined filtrates were concentrated under reduced pressure affording 472 mg of crude product. The product was coated onto hydromatrix using dichloromethane and purified using flash column chromatography (silica 24 g, gradient 5/20/5-min, heptane/EtOAc, 1:0-9:1, 32 mL/min, collection 220 nm/ELSD, collect all fractions, 25-milliliter fractions). Selected fractions were combined and concentrated under reduced pressure affording 441 mg (94%) of the product as a clear, colourless oil, LCMS m/z 441.4 $[M+Na]^+$. $^1$H-NMR in agreement with structure. $^1$H NMR (400 MHz, $CDCl_3$/TMS): δ 7.08 (s, 4H), 3.64 (s, 6H), 2.63-2.53 (m, 4H), 2.19 (s, 4H), 1.64-1.50 (m, 8H) (water signal), 1.32 (m, J=3.7 Hz, 8H), 0.97 (s, 12H).

Step 3: 7,7'-(1,4-Phenylene)bis(3,3-dimethylheptanoic acid)

1M aqueous potassium hydroxide (16.86 mL, 16.86 mmol) was added to a solution of dimethyl 7,7'-(1,4-phenylene)bis(3,3-dimethyl-heptanoate) (441 mg, 1.053 mmol) in ethanol (Abs) (8.042 mL). The reaction mixture was stirred at 70° C., overnight. A clear, colourless solution had formed (LCMS shows complete and clean conversion. Observed with m/z 389.2 $[M-H]^-$ and 194.2 $[M-2H]^{2-}/2$). The mixture was allowed to cool down to room temperature. The reaction mixture was diluted with demi water (75 mL) and extracted with dichloromethane (2×75 mL). Complete phase separation was not entirely possible because the deprotonated product behaves very soapy in the aqueous phase. The organic phases were discarded. The aqueous phase was acidified with 1M aqueous KHSO₄ solution (50 mL), dichloromethane (50 mL) was added, and phases were partitioned. The pH of the aqueous phase was measured at 1. Phases were separated and the aqueous phase was extracted with dichloromethane (4×50 mL). The combined organic phases were dried over Na₂SO₄, filtered and concentrated under reduced pressure affording 403.1 mg (98%) of the product as a white solid. The product was under reduced pressure affording 398 mg of the product as a white solid (LCMS m/z 389.2 [M–H]⁻. ¹H NMR (400 MHz, CDCl₃/TMS): δ 7.07 (s, 4H), 2.64-2.51 (m, 4H), 2.21 (s, 4H), 1.58 (p, J=7.3 Hz, 4H), 1.46-1.20 (m, 8H), 1.01 (s, 12H).

Example 1F: Synthesis of 7,7'-(1,3-phenylene)bis(3,3-dimethylheptanoic acid) (Compound I-85)

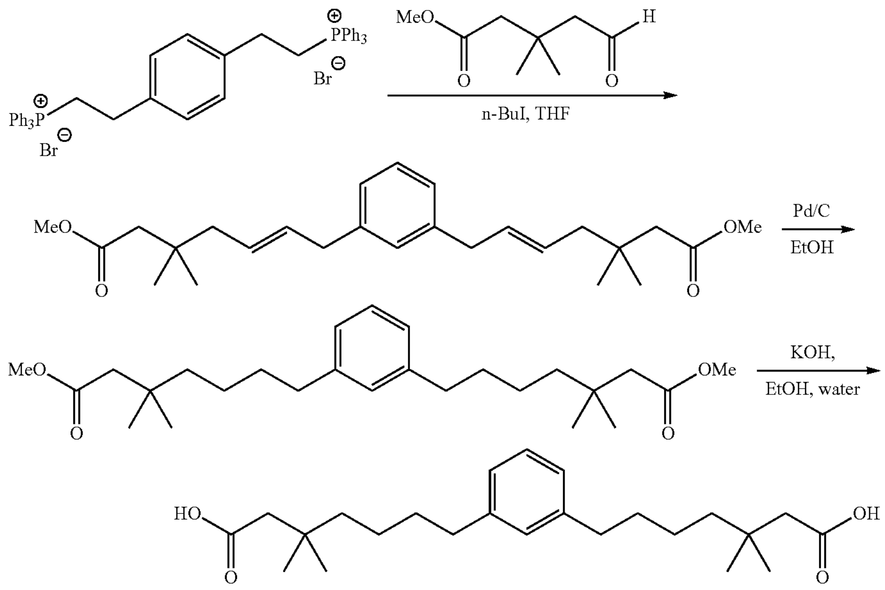

I-85

Step 1: Dimethyl 7,7'-(1,3-phenylene)(5E,5'E)-bis(3,3-dimethylhept-5-enoate)

(1,4-Phenylenebis(ethane-2,1-diyl))bis(triphenyl-phosphonium) bromide (4.1 g, 3.56 mmol, prepared as described in U.S. Pat. No. 4,689,344) was co-evaporated with dry tetrahydrofuran (THF) (150 ml) to remove residues of solvents. To a stirred suspension of 1,3-bis(2-(bromotriphenyl-15-phosphaneyl)ethyl)benzene (4.1 g, 3.56 mmol) in tetrahydrofuran (dry) (150 ml), in a 250 ml dried round bottom flask under argon, was added n-butyllithium (13.37 ml, 21.39 mmol) at room temperature. A dark orange solution was obtained, but still some small white lumps were present. After 10 minutes, methyl 3,3-dimethyl-5-oxopentanoate (2.312 g, 14.62 mmol) diluted in dry THF (25 ml) was added dropwise over a period of 2 minutes. A yellow solution was obtained. The mixture was stirred for 30 minutes. TLC (heptane/EtOAc, 9/1) was taken and showed one new main signal. The mixture was quenched with water (1 ml) and concentrated in vacuo to a small volume (40 ml).

Water (100 ml) was added, and the mixture was extracted with EtOAc (2×100 ml). The organic layers were combined and washed with brine (50 ml), dried over Na₂SO₄ and concentrated in vacuo. The residue was dissolved in dichloromethane, coated in hydromatrix and purified by flash column chromatography (80 g silicagel, heptane, EtOAc 0-10%). After a second column chromatography (40 g silicagel) to obtain 650 mg desired compound. ¹H NMR (400 MHz, CDCl₃/TMS): δ 7.23-7.16 (m, 1H), 7.00-70.2 (m, 3H), 5.71-5.51 (m, 4H), 3.64 (s, 6H), 3.42-3.35 (m, 4H), 2.25 (s, 4H), 2.22-2.16 (m, 4H), 1.12-0.94 (m, 12H).

Step 2: Dimethyl 7,7'-(1,3-phenylene)bis(3,3-dimethylheptanoate)

Dimethyl 7,7'-(1,3-phenylene)(5E,5'E)-bis(3,3-dimethylhept-5-enoate) (650 mg, 1.568 mmol) was diluted in absolute ethanol (20 ml). The solution was purged with nitrogen for 5 minutes. Pd/C (10% on activated carbon, (50% wet with water) unreduced (167 mg, 0.078 mmol) was added under nitrogen atmosphere. A hydrogen balloon was applied, and the mixture was purged with hydrogen for 5 minutes. The round bottom flask was sealed under hydrogen atmosphere and stirred for 1 hour. TLC (heptane/EtOAc, 9/1) was taken and showed spot to spot conversion. The mixture was filtered over a pad of celite. The residue was rinsed with EtOH (10 ml). The filtrate was concentrated in vacuo. The obtained colorless oil was dissolved in dichloromethane, coated in hydromatrix and purified by flash column chromatography (24 g, heptane, EtOAc 0-10%) to obtain 590 mg desired compound. ¹H NMR (400 MHz, CDCl₃/TMS): δ 7.22-7.13 (m, 1H), 6.99 (d, J=6.1 Hz, 3H), 3.64 (s, 6H), 2.58 (t, J=9.0, 6.7 Hz, 4H), 2.19 (s, 4H), 1.64-1.51 (m, 4H), 1.33-1.31 (m, 8H), 0.98 (s, 12H).

Step 3: 7,7'-(1,4-Phenylene)bis(3,3-dimethylheptanoic acid)

Dimethyl 7,7'-(1,3-phenylene)bis(3,3-dimethylheptanoate) (550 mg, 1.314 mmol) was dissolved in absolute ethanol (10 ml). KOH (1 M in water) (21.02 ml, 21.02 mmol) was added, and the mixture was stirred at 70° C. for 5 hours and at 60° C., overnight. Complete conversion of the starting material was observed according to LCMS analysis. The mixture was cooled to room temperature, 75 ml water was added. The mixture was extracted with dichloromethane (2×75 ml) and the organic layers were discarded. The water layer was acidified with 1 M HCl (30 ml) and extracted with dichloromethane (5×50 ml). The organic layers were combined and washed with brine, dried over $Na_2SO_4$, concentrated in vacuo and co-evaporated with $Et_2O$. The obtained solids were triturated with heptane (10 ml), filtered off, rinsed with pentane (2×5 ml) and air dried to obtain 385 mg of desired product. LCMS: Mass: m/z $[M+Na]^+$ 441. $^1H$ NMR (400 MHz, $CDCl_3$/TMS): δ 7.22-7.13 (m, 1H), 6.99 (d, J=6.1 Hz, 3H), 3.64 (s, 6H), 2.58 (t, J=9.0, 6.7 Hz, 4H), 2.19 (s, 4H), 1.64-1.51 (m, 4H), 1.33-1.31 (m, 8H), 0.98 (s, 12H).

Example 1G: Synthesis of 7,7'-(1,3-phenylene)bis (3,3-dimethylheptanoic acid) (Compound I-94)

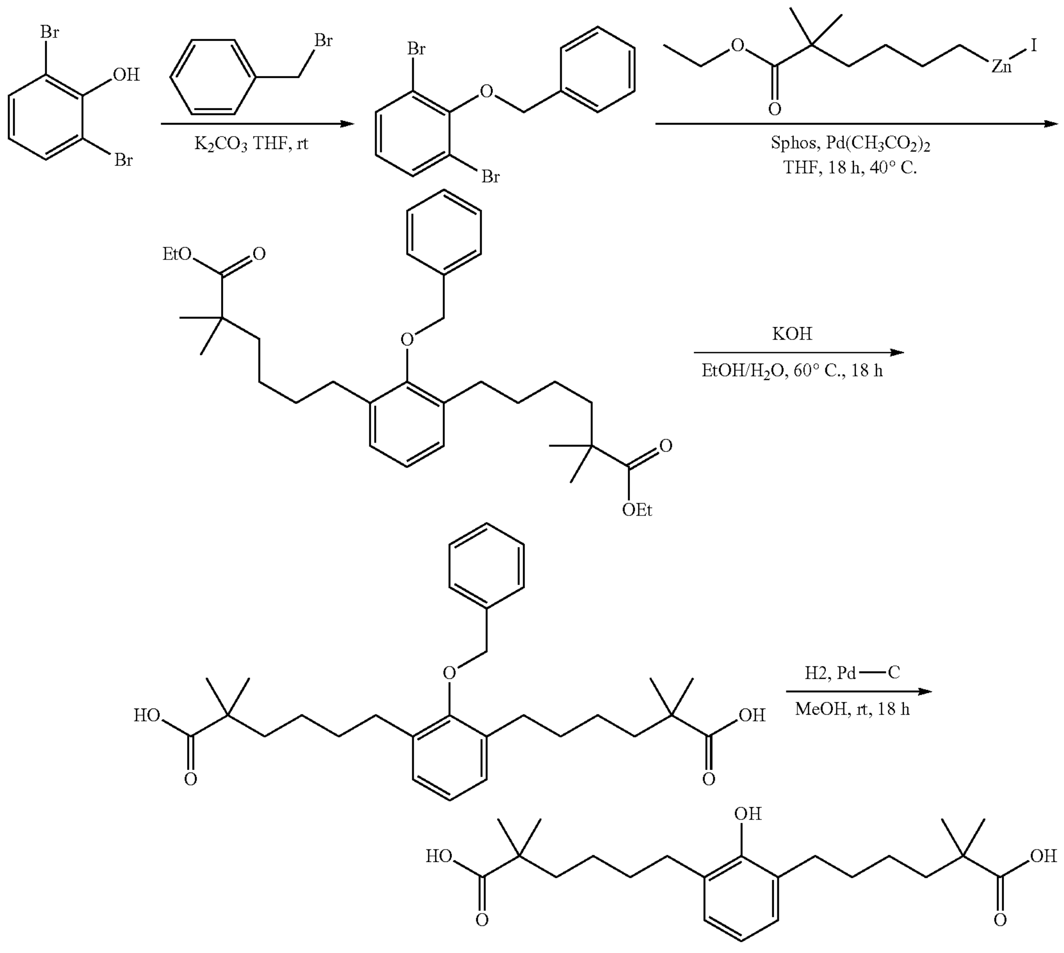

I-94

Step 1. 2-(Benzyloxy)-1,3-dibromobenzene 2,6-Dibromophenol (2.01 g, 7.98 mmol) was dissolved in tetrahydrofuran (5 ml). Benzyl bromide (1.139 ml, 9.58 mmol) and potassium carbonate (2.206 g, 15.96 mmol) were added. The reaction mixture was stirred over the weekend at rt. dichloromethane (10 mL) and saturated aqueous $NaHCO_3$ (10 mL) were added. The water layer was extracted 2 more times with dichloromethane (10 mL) the organic layers were combined, dried over $Na_2SO_4$, filtered and concentrated under reduced pressure to give the crude product. heptane/EtOAc 0=>10% was used as gradient for flash column chromatography. Product containing fractions were combined and concentrated under reduced pressure to give 2-(benzyloxy)-1,3-dibromobenzene (1.2 g, 3.51 mmol, 44.0% yield). GCMS>95% Mass; m/z [M]+342.0.

Step 2. Diethyl 6,6'-(2-(benzvloxy)-1,3-phenylene) bis(2,2-dimethylhexanoate)

A 40 ml screw cap vial was placed under argon and charged with 2-(benzyloxy)-1,3-dibromobenzene (300 mg, 0.877 mmol) and Tetrahydrofuran (dry) (10 ml) followed by S-phos (36.0 mg, 0.088 mmol) and palladium(II) acetate (9.85 mg, 0.044 mmol). A solution of (6-ethoxy-5,5-dimethyl-6-oxohexyl)-zinc(II) iodide (957 mg, 2.63 mmol, prepared as in example above) in THF was filtered and added dropwise (1-2 min) at room temp. The reaction mixture was stirred at 40° C., overnight. EtOH (5 mL) was added, followed by hydromatrix and the solvent was removed under reduced pressure. The crude product was purified by flash chromatography using heptane/DIPE 0=>20% to give diethyl 6,6'-(2-(benzyloxy)-1,3-phenylene)bis(2,2-dimethylhexanoate) (170 mg). LCMS: 87%, mass: m/z [M+NH4]+ 542.7.

Step 3: 6,6'-(2-(Benzyloxy)-1,3-phenylene)bis(2,2-dimethylhexanoic acid)

Diethyl 6,6'-(2-(benzyloxy)-1,3-phenylene)bis(2,2-dimethylhexanoate) (170 mg) was dissolved in Ethanol (1 ml). Aqueous 6 M KOH (0.81 ml, 4.86 mmol) was added and the reaction mixture was stirred at 60° C., overnight. The mixture was cooled to rt, acidified to pH 2 and extracted with dichloromethane (3×15 mL). The organic layers were combined, dried over Na2SO4, filtered and concentrated under reduced pressure to give the crude product 6,6'-(2-(benzyloxy)-1,3-phenylene)bis(2,2-dimethylhexanoic acid) (60 mg). LCMS: 90% m/z[M−H]− 467.6.

Step 4. 6,6'-(2-Hydroxy-1,3-phenylene)bis(2,2-dimethylhexanoic acid)

To an 8 mL reaction vial was added 6,6'-(2-(benzyloxy)-1,3-phenylene)bis(2,2-dimethylhexanoic acid) (60 mg) and Methanol (2 ml). The mixture was purged with N2 and then 5% Pd—C (13.63 mg, 6.40 μmol) was added. The mixture was evacuated and refilled with $H_2$ 3×. The reaction mixture was stirred overnight, filtered through celite and concentrated under reduced pressure. The residue was submitted to the basic prep for purification. The product fractions were concentrated in the genevac, reformatted and freeze-dried to give 6.6'-(2-hydroxy-1,3-phenylene)bis(2,2-dimethvl-hexanoic acid) (8.5 mg, 0.022 mmol, 2.7% yield over 3 steps). $^{1}$H NMR (400 MHz. [MeOD]/TMS): δ 6.87 (d, J=7.5 Hz, 2H), 6.67 (t, J=7.5 Hz, 1H), 2.58 (t, 4H), 1.61-1.49 (m, 8H), 1.39-1.27 (m, 4H), 1.12 (s, 12H). $^{13}$C NMR (100 MHz, [MeOD]/TMS): δ 184.18, 153.38, 130.72, 128.53, 120.85, 43.64, 42.31, 31.93, 31.44, 26.31, 26.22.

Example 2A: Synthesis of 6-[3-(5-Carboxy-5-methylhexyl)-phenyl]-2,2-dimethylhexanoic acid Coenzyme A Ester (Compound I-32-CoA)

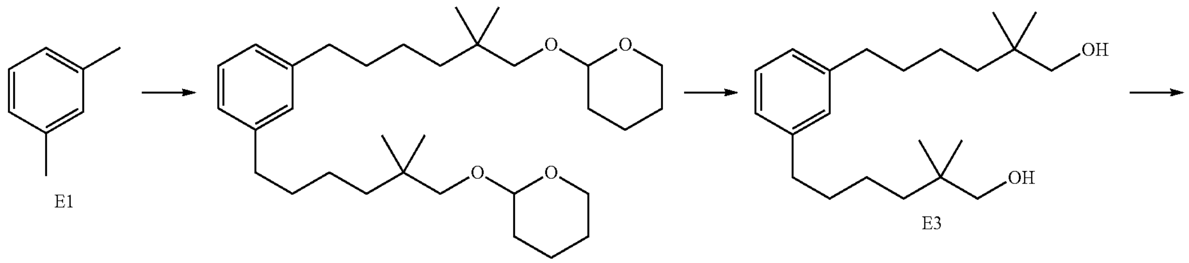

E1

E2

E3

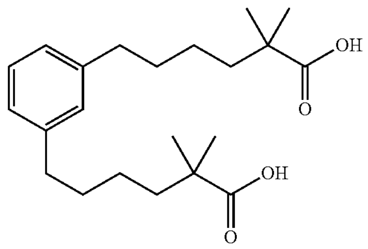

I-32

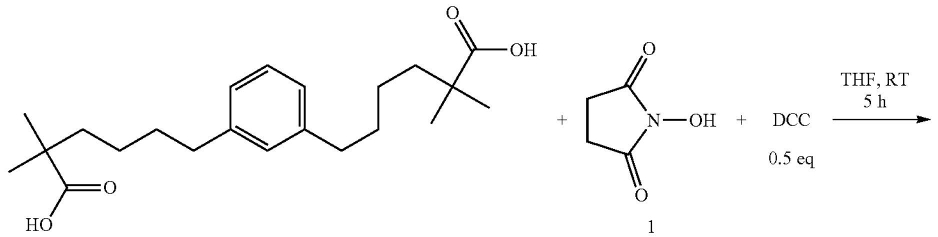

I-32

1
0.5 eq

-continued

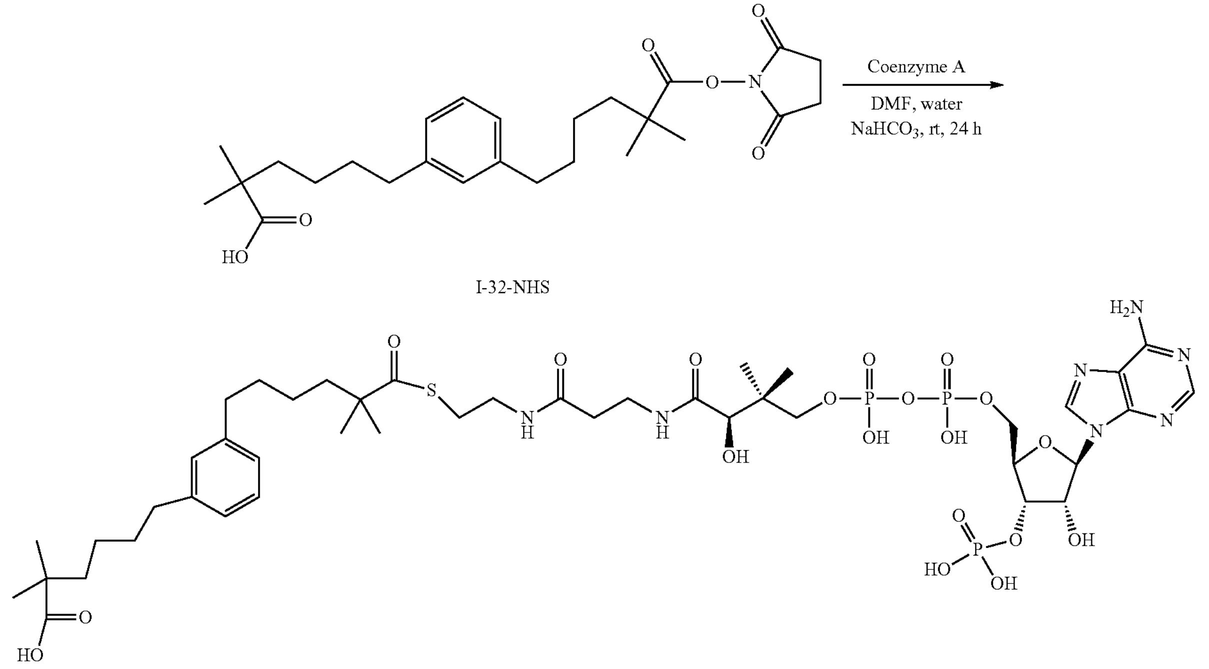

I-32-NHS

I-32-CoA

Step 1: [1,3-Bis(5,5-dimethyl-6-(tetrahydropyran-2-yloxy)-hexyl]-phenylene (E2)

A solution of n-butyl lithium (38.8 mL, 2.5 M in hexanes/THF/EtPh, 96.9 mmol) was added to a mixture of m-xylene (E1) (5.0 g, 47.1 mmol) and potassium tert-butoxide (5.4 g, 48.1 mmol) in hexanes (100 mL) at room temperature. The reaction mixture was heated to reflux for 1 h. A yellow precipitate was formed. The reaction mixture was cooled to 0° C. and 2-(5-bromo-2,2-dimethylpentyloxy)-tetrahydropyran (prepared as described in U.S. Pat. Nos. 6,646.170 and 6,410,802) (30.0 g, 107.5 mmol) was added dropwise. The reaction mixture was heated to reflux for 20 h. Water (150 mL) was added and the organic phase was separated. The aqueous solution was extracted with EtOAc (2×100 mL). The organic phases were combined, washed with brine (50 mL), and dried over $MgSO_4$. The solvent was evaporated and the residue was purified by column chromatography (silica gel, EtOAc:hexanes, 1:30) to give [1,3-bis(5,5-dimethyl-6-(tetrahydropyran-2-yloxy)-hexyl]-phenylene (14.8 g, 62%, 96.1% pure by HPLC) as an oil. $^1H$ NMR ($CDCl_3$): δ=7.17-7.14 (m, 1H), 7.00-6.98 (m, 3H), 4.54 (t, J=3.0 Hz, 2H), 3.78-3.86 (m, 2H), 3.50-3.45 (m, 2H), 3.47 (d, J=9.1 Hz, 2H) 2.98 (d, J=9.1 Hz, 2H), 2.59 (t, J=7.6 Hz, 4H), 1.90-1.28 (m, 24H), 0.89 (s, 12H). $^{13}C$ NMR ($CDCl_3$): δ=142.8, 128.5, 128.1, 125.6, 99.1, 77.5, 61.8, 39.2, 36.0, 34.2, 32.5, 30.7, 25.6, 24.6, 23.7, 19.4. HRMS calcd for $C_{32}H_{54}O_4$ ($M^+$): 501.3943, found: 501.3943.

Step 2: 6-[3-(6-Hydroxy-5,5-dimethylhexyl)-phenyl]-2,2-dimethylhexan-1-ol (E3)

Concentrated, aqueous HCl (20 mL) was added to 1,3-bis(5,5-dimethyl-6-(tetrahydropyran-2-yloxy)-hexyl]-phenylene (18.0 g, 35.7 mmol) in MeOH (200 mL). The reaction mixture was heated to reflux for 2 h and stirred overnight at room temperature. MeOH was evaporated in vacuum and the residue was dissolved in methylene chloride (200 mL). The solution was washed with water (100 mL), saturated $NaHCO_3$ solution (100 mL) and brine (100 mL), and dried over $MgSO_4$. The solvent was evaporated and the residue was purified by column chromatography (silica gel, EtOAc:hexanes, 1:1) to give 6-[3-(6-hydroxy-5,5-dimethylhexyl)-phenyl]-2,2-dimethylhexan-1-ol (10.41 g, 87%, 86.4% by HPLC) as an oil. $^1H$ NMR ($CDCl_3$): δ=7.21-7.19 (m, 1H), 7.02-6.99 (3H), 3.32 (s, 4H), 2.62 (t, J=7.8 Hz, 4H), 1.64-1.26 (m, 12H), 0.89 (s, 12H). $^{13}C$ NMR ($CDCl_3$): δ=142.6, 128.5, 128.1, 125.6, 71.9, 38.4, 35.8, 35.0, 32.4, 23.7, 23.5. HRMS calcd for $C_{22}H_{38}O_4$ ($M^+$): 335.2950, found: 335.2950.

Step 3: 6-[3-(5-Carboxy-5-methylhexyl)-phenyl]-2,2-dimethylhexanoic acid

Pyridinium dichromate (74.85 g, 199 mmol) was added to a solution of 6-[3-(6-hydroxy-5,5-dimethylhexyl)-phenyl]-2,2-dimethylhexan-1-ol (8.5 g, 25.4 mmol) in DMF (200 mL) at room temperature. The reaction mixture was stirred for 30 h, then heated to 40° C. for 10 h. Ethyl acetate (100 mL) was added, followed by the addition of water (200 mL) and coned $H_2SO_4$ (20 mL) under stirring. The organic layer was separated, and the aqueous layer was extracted with EtOAc (3×100 mL). The combined organic solutions were washed with water (100 mL), saturated $NaHCO_3$ solution (10 mL) and brine (2×100 mL) and dried over $MgSO_4$. The solvent was evaporated and the residue was purified by column chromatography (silica gel, EtOAc:hexanes, 1:1). The obtained oil was stirred in $Et_2O$:hexanes (1:10, 50 mL) for 3 h and the precipitated solid product was filtered (7.2 g, 78%, 96.1% by HPLC) (Compound I-32). Mp 99-101° C. Elemental analysis ($C_{22}H_{34}O_4$): Calcd for C, 72.89; H, 9.45; found: C, 73.02; H, 9.57. $^1H$ NMR ($CDCl_3$): δ=7.19-7.16 (m, 1H), 6.99-6.94 (m, 3H), 2.58 (t, J=7.1 Hz, 4H), 1.63-1.56 (m, 8H), 1.32-1.22 (m, 4H), 1.18 (s, 12H). $^{13}C$ NMR ($CDCl_3$): δ=185.5, 142.2, 128.6, 128.3, 126.0, 42.0, 40.8, 35.7, 31.0, 25.1, 24.4. HRMS calcd for $C_{22}H_{35}O_4$ ($MH^+$): 363.2535, found: 363.2530.

Step 4: A mixture of Compound I-32 (1.0 g, 2.75 mmol), N-hydroxysuccinimide (150 mg, 1.3 mmol), and dicyclohexylcarbodiimide (DCC, 290 mg, 1.4 mmol) were stirred for 5 hours in THF (15 mL) at room temperature under an argon atmosphere. The mixture was filtered to remove dicyclohexylurea (DCU) and concentrated on the rotary evaporator Compound I-32-NHS was combined with recovered material (0.22 g, from the previous experiment) and was purified by column chromatography on silica gel (50 g) eluting with 20%-50% ethyl acetate/heptane. The procedure generated Compound I-32-NHS (0.56 g, 68% yield) as a clear gel.

$^1H$ NMR (300 MHz, $CDCl_3$) δ. 7.20-7.15 (m, 1H), 7.00-6.92 (m, 3H), 2.82 (m, 4H), 2.59 (q, 4H, J=6.9 Hz), 1.74-1.56 (m, 8H), 1.51-1.35 (m, 4H), 1.35 (s, 6H), 1.19 (s, 6H). $^{13}C$ NMR (75 MHz, $CDCl_3$) δ 173.2, 169.5, 142.7, 128.4, 125.9, 65.9, 42.5, 40.5, 35.9, 32.2, 25.8, 25.2, 24.8, 24.7.

Step 5: Compound I-32-NHS (0.55 g, 1.19 mmol) was dissolved in DMF (4 mL) under an argon atmosphere at room temperature. Sodium bicarbonate (201 mg, 2.39 mmol) was added along with water (250 uL). Coenzyme A hydrate (MP Biologics, 100 mg, 0.12 mmol) was added and the solution stirred for 24 hours at room temperature. After 24 hours, DI water (20 mL) was added and the solution was acidified to pH=2 with 5% hydrochloric acid. The sample was freeze dried overnight. The remaining solid was stirred with diethyl ether (25 mL) at room temperature under argon for 2 hours. The ether was decanted and the washing process was repeated twice with diethyl ether (10 mL). After drying, the remaining solid (0.32 g) was purified by reverse phase column (25 g C18, 17% carbon load), eluting with 25%-100% methanol/water (0.1% TFA), followed by 100% methanol (200 mL). The product containing fraction was concentrated under reduced pressure. The remaining solids were stirred with diethyl ether (20 mL) under argon. The experiment produced a small quantity of Compound I-32-CoA (20 mg, 15% yield) as a clear to slightly tan glass. Chromatographic purity (HPLC): 82.6% (rt=2.76 min, UV detection, 220 nm, a/a). NMR $^1H$ (300 MHz, DMSO-d6): δ 8.42 (s, 1H), 8.18 (s, 1H), 7.75 (s, 1H), 7.36 (s, 1H), 7.10-6.85 (m, 4H), 5.96 (d, 1H, J=4.5 Hz), 4.89 (m, 1H), 4.75 (m, 1H), 4.41 (m, 1H), 4.13 (m, 2H), 3.88 (m, 1H), 3.74 (s, 1H), 3.50-3.40 (m, 1H), 3.15-3.10 (m, 2H), 2.82 (t, 2H, J=7.2 Hz), 2.75 (s, 2H), 2.28 (m, 2H), 1.58-1.41 (m, 8H), 1.28-1.10 (m, 4H), 1.14 (s, 6H), 1.07 (s, 6H), 0.97 (s, 3H), 0.73 (s, 3H). MS: $[M+H]^+$ calculated: 1115.4, found: 1115.4.

Example 2B: Synthesis of 6-[4-(5-carboxy-5-methylhexyl)-phenyl]-2,2-dimethylhexanoic acid Coenzyme A ester (Compound I-1-CoA)

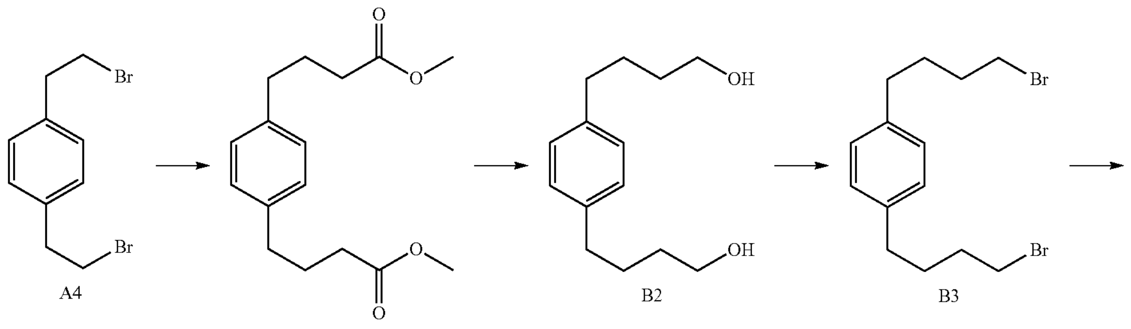

A4 B1 B2 B3

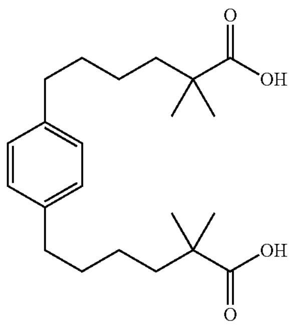

I-1

-continued

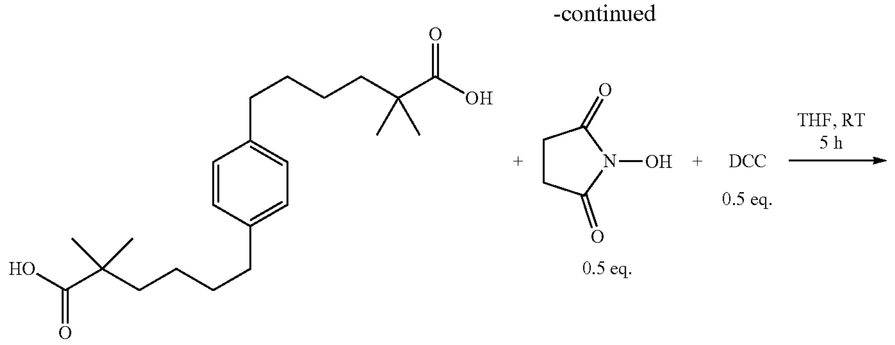

I-1

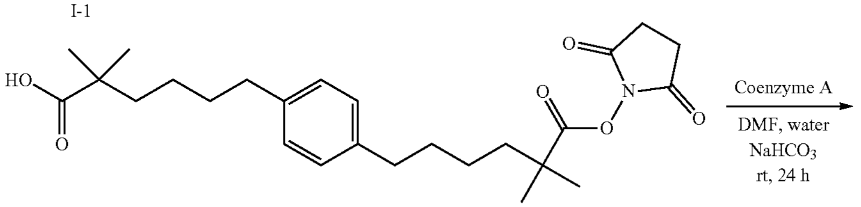

I-1-NHS

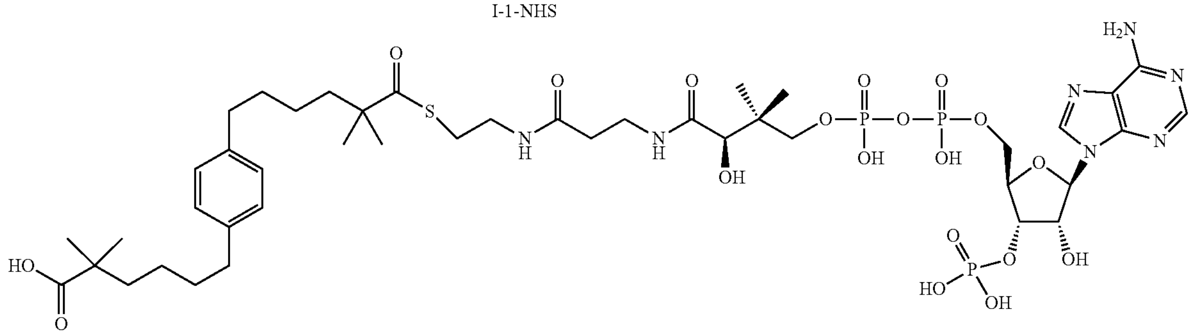

I-1-CoA

Step 1: 4-[4-(3-Methoxycarbonylpropyl)-phenyl]-butyric acid methyl ester (B1)

The compound was prepared by a modified method than reported in Cram, D. J.; Allinger, N. L.; Steinberg, H. *J. Amer. Chem. Soc.* 1954, 76, 6132.

Under $N_2$ atmosphere, sodium (3.5 g, 0.152 mol) was dissolved in EtOH (200 mL) and ethyl malonate (50.0 g, 0.31 mol) was added to the warm solution. The reaction mixture was heated to reflux for 5 min and a solution of 1,4-bis-(2-bromoethyl)-benzene (A4) (22.02 g, 75.4 mmol) in ethyl malonate (50 mL) was added dropwise at the room temperature over 5 min. The reaction mixture was heated to reflux for 0.5 h. After the addition of water (150 mL) and EtOAc (200 mL), the solvents were evaporated, and the residue was dissolved in EtOAc (200 mL). The solution was washed with water (100 mL) and brine (100 mL), dried over $MgSO_4$, and concentrated in vacuo. The residue was dried in high vacuum at 80-100° C. (oil bath). The obtained crude 2-{2-[4-(3,3-bis-ethoxycarbonylpropyl)-phenyl]-ethyl}malonic acid diethyl ester was dissolved in aqueous EtOH (80%, 200 mL) and KOH (85%, 35.0 g, 0.53 mol) was added. The reaction mixture was heated to reflux for 2 h. The solvent was partially evaporated and EtOAc (150 mL) was added. The aqueous laver was separated and extracted with EtOAc (2×100 mL). The combined organic solutions were washed with brine (100 mL), dried over $MgSO_4$, and concentrated. The crude 2-{2-[4-(3,3-bis-carboxypropyl)-phenyl]-ethyl}malonic acid (28.0 g) was heated on an oil bath at 200-210° C. for 1.5 h. The obtained, crude 4-[4-(3-carboxypropyl)-phenyl]-butyric acid (16.3 g) was dissolved in MeOH (100 mL) and concentrated sulfuric acid (40 mL) was added. The reaction mixture was refluxed for 5 h, then stirred overnight at room temperature. The MeOH was partially evaporated, the residue was dissolved in EtOAc (150 mL), washed with water (150 mL) and brine (150 mL), and dried over $MgSO_4$. The solvent was evaporated to yield crude 4-[4-(3-methoxycarbonylpropyl)-phenyl]-butyric acid methyl ester (H1) (17.9 g, 85%) as a yellow oil, which was used without purification for the next step. $^1H$ NMR ($CDCl_3$): δ=7.10 (s, 4H), 3.67 (s, 6H), 2.59 (t, J=7.4 Hz, 4H), 2.33 (t, J=7.4 Hz, 4H), 1.95-1.90 (m, 4H). $^{13}C$ NMR ($CDCl_3$): δ=174.0, 138.9, 128.4, 51.5, 34.6, 33.3, 26.5.

Step 2: 4-[4-(4-Hydroxybutyl)-phenyl]-butan-1-ol (B2)

The compound is prepared according to Cram, D. J.; Allinger, N. L.; Steinberg. H. *J. Am. Chem. Soc.* 1954, 76, 6132-6141). A solution of 4-[4-(3-methoxycarbonylpropyl)-phenyl]-butyric acid methyl ester (17.7 g, 63.6 mmol) in THF (50 mL) was added to a suspension of $LiAlH_4$ (7.2 g, 0.19 mol) in THF (300 mL) with stirring at 0° C. The reaction mixture was heated to reflux for 1 h. Water (100 mL) and aqueous HCl (10%, 200 mL) were added. The aqueous layer was separated and extracted with EtOAc (2×50 mL). The combined organic solutions were washed with brine, dried over $MgSO_4$, and concentrated. The residue was purified by column chromatography (silica gel, ETOAc:hexanes, 1:1) to yield 4-[4-(4-hydroxybutyl)-phenyl]-butan-1-ol (7.5 g, 53%, 96.2% pure by HPLC) as white crystals. Mp 60-62° C. (60.5-62.4° C., Cram, D. J.; Allinger, N. L.; Steinberg, H. *J. Am. Chem. Soc.* 1954, 76, 6132-6141). $^1$H NMR ($CDCl_3$): δ=7.10 (s, 4H), 3.63 (t, J=6.4 Hz, 4H), 2.61 (t, J=7.1 Hz, 4H), 2.12 (br s, 2H), 1.71-1.57 (n, 8H). $^{13}$C NMR ($CDCl_3$): δ=140.7, 129.4, 63.8, 36.3, 33.4, 28.67.

Step 3: 1,4-Bis-(4-bromobutyl)-benzene (B3)

Concentrated sulfuric acid (30 mL) was added dropwise to a boiling mixture of 4-[4-(4-hydroxybutyl)-phenyl]-butan-1-ol (9.4 g, 42.3 mmol), NaBr (17.4 g, 0.169 mol) and water (50 mL) over 1 h. The reaction mixture was refluxed for 1 h. Additional concentrated sulfuric acid (10 mL) was added over 20 min and refluxing was continued for 1.5 h. After the addition of water (300 mL) and methylene chloride (500 mL), the aqueous solution was separated and extracted with methylene chloride (2×50 mL). The combined organic solutions were washed with water (200 mL) and brine (150 mL), and dried over $MgSO_4$. The solvent was evaporated and residue was purified by column chromatography (silica gel, EtOAc:hexanes, 1:20) to yield 1,4-bis-(4-bromobutyl)-benzene (11.8 g, 80%, 96.1% pure by HPLC) as an oil. $^1$H NMR ($CDCl_3$): δ=7.14 (s, 4H), 3.46 (t, J=6.6 Hz, 4H), 2.65 (t, J=7.5 Hz, 4H), 1.96-1.89 (m, 4H), 1.83-1.75 (m, 4H). $^{13}$C NMR ($CDCl_3$): δ=139.5, 128.6, 34.7, 34.0, 32.5, 30.1. This procedure is modified from the one described by Cram, D. J.; Allinger, N. L.; Steinberg, H. *J. Am. Chem. Soc.* 1954, 76, 6132-6141.

Step 4: 6-[4-(5-Carboxy-5methylhexyl)-phenyl]-2,2-dimethylhexanoic acid

A solution of lithium diisopropylamide (90 mmol, 1.8 M in heptane/THF/EtPh, 50 mL) was added dropwise to a solution of ethyl isobutyrate (8.97 g, 77.2 mmol) in THF (200 mL) at −78° C. The reaction mixture was stirred for 1 h before a solution of 1,4-bis-(4-bromobutyl)-benzene (11.2 g, 32.2 mmol) in THF (50 mL) was added slowly, followed by addition of DMPU (10 mL). The reaction mixture was warmed to room temperature over 2 h and stirred for 1 h at 40-50° C. Water (200 mL) was added, the aqueous solution was separated, and extracted with EtOAc (3×80 mL). The combined organic solutions were washed with water (100 mL) and brine (100 mL). The solvent was evaporated, and the residue was dissolved in EtOH (100 mL). Water (50 mL) and KOH (85%, 15.0 g, 227 mmol) were added and the reaction mixture was heated to reflux for 3 h. After addition of water (200 mL) and cooling to room temperature, the reaction mixture was acidified with concentrated HCl to pH 1 and stirred for 1 h. The precipitate was filtered, washed with water and dissolved in methylene chloride (40 mL). The solution was dried with $MgSO_4$ and evaporated in vacuum. The residue was dissolved under heating in EtOAc: hexanes (1:30, 200 mL) and cooled in a freezer. The solution was decanted from the oil and evaporated to a volume of 60 mL. The mixture was stirred overnight, the precipitate was filtered, washed with hexanes, and dried in vacuum to yield 6-[4-(5-carboxy-5-methylhexyl)-phenyl]-2,2-dimethylhexanoic acid (8.02 g, 69%, 96.4% pure by HPLC) as a white solid (Compound I-1). Mp 129-131° C. Elemental analysis ($C_{22}H_{34}O_4$): Calcd for C, 72.89; H, 9.45. Found: C, 72.90; H, 9.49. $^1$H NMR ($CDCl_3$): δ=7.05 (s, 4H), 2.66-2.62 (m, 4H), 1.68-1.56 (m, 4H), 1.53-1.47 (m, 4H), 1.17 (s, 12H), 1.08-0.98 (m, 4H). $^{13}$C NMR (CDC): δ=185.3, 138.6, 128.5, 42.3, 41.5, 34.5, 30.6, 25.0, 23.2. HRMS calcd for $C_{22}H_{34}O_4$ ($M^+$): 362.2457, found: 362.2453.

Step 5: A mixture of Compound I-1 (2.0 g, 5.51 mmol), N-hydroxysuccinimide (300 mg, 2.6 mmol), and dicyclohexylcarbodiimide (DCC, 580 mg, 2.8 mmol) were stirred for 5 hours in THF (35 mL) at room temperature under an argon atmosphere. The mixture was filtered to remove DCU and concentrated on the rotary evaporator. Compound I-1-NHS was purified by column chromatography on silica gel (60 g) eluting with 20%-50% ethyl acetate/heptane. The procedure generated Compound I-1-NHS (0.92 g, 77% yield) as a white solid. $^1$H NMR (300 MHz, $CDCl_3$) δ. 7.08 (s, 4H), 2.82 (m, 4H), 2.58 (q, 4H, J=7.2 Hz), 1.74-1.56 (m, 8H), 1.51-1.38 (m, 4H), 1.34 (s, 6H), 1.19 (s, 6H).

Step 6: Compound I-1-NHS (0.40 g, 0.87 mmol) was dissolved in DMF (4 mL) under an argon atmosphere at room temperature. Sodium bicarbonate (146 mg, 1.74 mmol) was added along with water (250 uL). Coenzyme A hydrate (MP Biologic, 100 mg, 0.12 mmol) was added and the solution stirred for 24 hours at room temperature. After 24 hours, D1 water (25 mL) and the sample was freeze dried to remove DMF. To the remaining solid DI water (10 mL) was added and the solution was acidified to pH=2 with 5% hydrochloric acid. The sample was freeze dried overnight. The remaining solid was stirred with diethyl ether (10 mL) at room temperature under argon for 2 hours. The ether was decanted and the washing process was repeated twice with diethyl ether (10 mL). After drying, the remaining solid (0.19 g) was purified by reverse phase column (25 g C18, 17% carbon load), eluting with 25%-100% methanol/water (0.1% TFA), followed by 100% methanol (200 mL). The product containing fraction was concentrated under reduced pressure. The remaining solids were stirred with diethyl ether (10 mL) under argon. The experiment produced a small quantity of Compound I-1-CoA (40 mg, 29% yield) as a clear to slightly tan glass. Chromatographic purity (HPLC): 91.9% (rt=11.1 min, UV detection, 245 nm, a/a). NMR $^1$H (300 MHz, DMSO-d6): δ 8.54 (s, 1H), 8.29 (s, 1H), 8.09 (s, 1H), 7.73 (s, 1H), 7.04 (s, 4H), 5.95 (d, 1H, J=4.5 Hz), 4.81 (m, 1H), 4.70 (m, 1H), 4.37 (m, 1H), 4.14 (m, 2H), 3.88 (m, 1H), 3.74 (s, 1H), 3.50-3.40 (m, 1H), 3.15-3.10 (m, 2H), 2.83 (t, 2H, J=7.2 Hz), 2.71 (s, 2H), 2.24 (m, 2H), 1.58-1.41 (m, 8H), 1.21-1.10 (m, 4H), 1.11 (s, 6H), 1.04 (s, 6H), 0.93 (s, 3H), 0.72 (s, 3H), MS: $[M+H]^+$ calculated: 1115.4, found: 1115.4.

Example 3: Synthesis of Compound I-32-CoA and Compound I-1-CoA in Rat Liver Microsomes Materials: Medica-16 (Cat #M5693), palmitic acid (Cat #P9767), Adenosine 5'triphosphate sodium salt (Cat #A26209), Coenzyme A sodium salt (Cat #C3144), palmitoyl-CoA lithium salt (Cat #P9716) where obtained from Sigma Aldrich, St Louise Mo., U.S.A. 1-14 C-Palmitic acid (Cat #NEC075H250UC) was obtained from PerkinElmer Canada, Woodbridge ON, Canada.

Compound I-32, Compound I-61, Compound I-1 or Compound III-1 Preparation: Each compound was resuspended at a concentration of 100 mM stock solution in DMSO and stored at −80° C. Prior to the experiment a 1 mM working stock was created in primary hepatocyte media which was used to create the final dilution series of 0 (vehicle), 0.3, 1, 3, 10, and 30 μM. The final concentration of DMSO in all samples was <1%.

Synthesis of CoA derivatives in rat liver microsomes: Synthesis of the CoA derivatives of palmitate, Medica-16 and Compound I-32, Compound I-61, Compound I-1 and Compound III-1 were performed using rat liver microsomes as described in Pande S V et al. J Biol Chem 1968; 243:352-61 and Marra C A et al. Lipids 1999; 34:343-54. The reaction was carried out in 200 μl of buffer (0.5 M Tris-HCl (pH 8), 5 mM dithiothreitol, 0.15 M KCl, 15 mM $MgCl_2$) containing 10 mM ATP (Na2) as substrates, 1 mM CoA ($Na_2$) and 1 mM of either palmitate or Medica-16, and Compound I-32, Compound I-61, Compound I-1 or Compound III-1. For initial validation of ACS activity using palmitate, 14C-palmitate was added (0.5 μCi/ml). Each sample was equilibrated at 37° C. while shaking for 10 min before the reaction was initiated by the addition of 0.04 mg of rat microsomal preparation (ThermoFisher Scientific. Cat #RTM-CPL, Lot #RT060-A) followed by incubation for 1, 3, 10, or 30 mins. Time 0 sample with no added microsomes was used as a control. The reaction was stopped by immediately placing the reaction tube on ice followed by the rapid addition of the reaction mixture to 2.25 ml ice-cold isopropanol/heptane/2M-sulfuric acid (40:10:1, vol/vol) in a 5 ml glass vial. 1.5 ml of heptane and 1 ml of Milli-Q water were added resulting in the partitioning of the aqueous and organic phases. The mixture was then vortexed for 12 seconds, the upper phase was discarded, and the lower phase was washed 3 times with 2 ml of heptane. For studies that involved measurement of 14C Palmitoyl-CoA formation, 200 μl of the lower aqueous phase was added to the 5 ml of scintillation fluid and the number of DPMs were determined by liquid scintillation counting for 5 minutes using a LS6500 Liquid Scintillation Counter (Beckman Coulter). For studies using cold substrate, the lower aqueous phase (~1 mL final volume) was placed on ice until LCMS analysis.

LCMS Analysis: The reaction products were analyzed on an Agilent 1290 series HPLC system coupled with a Thermo Scientific Orbitrap LTQ mass spectrometer. Prior to sample introduction on the LCMS, the samples were further processed. One milliliter of reaction mixture was removed, dried under nitrogen and reconstituted in 100 μL of methanol. For each run, 5 μL of sample was injected onto an Eclipse XDB-C18 (2.1×100 mm, 3.5 μm) reverse phase C18 column at a flow rate of 0.2 mL/min, using a mobile phase consisting of 10 mM ammonium acetate, adjusted to pH 8.7 with ammonium hydroxide (A) and acetonitrile (B). Reaction products were eluted using the gradient shown below:

| Time (minutes) | Flow rate (mL/min) | Mobile Phase A (%) | Mobile Phase B (%) |
|---|---|---|---|
| 0.0 | 0.2 | 80 | 20 |
| 5.0 | 0.2 | 5 | 95 |
| 14.5 | 0.2 | 5 | 95 |
| 15.0 | 0.2 | 80 | 20 |
| 20.0 | 0.2 | 80 | 20 |

The reaction products were ionized by electrospray ion source (ESI) in positive mode. Data were acquired spanning an m/z range of 100-2000. The resulting mass spectra were analyzed using the Xcalibur 2.1 Qualitative software package. Samples were run in a sequence with a 100 ppm standard of Palmitoyl-CoA (Sigma).

Statistical Tests: Data was analyzed using one-way analyses of variance followed by a Dunnett's multiple comparisons post hoc test where appropriate. $IC_{50}$ values were determined by nonlinear regression. All statistical analysis was carried out using GraphPad Prism 8 software. A p-value of less than or equal 0.05 was considered significant.

Validation of palmitoyl-CoA formation in rat liver microsomes: Acyl-CoA synthetase activity in rat liver microsomes preparation using radiolabeled 14C-palmitate as a substrate was confirmed. The method involved the extraction of heptane soluble fatty acids from aqueous soluble acyl-CoA derivatives. In this case, radiolabeled 14C-palmitate was converted to 14-C palmitoyl-CoA in the presence of rat liver microsomes. It was found that the formation of palmitoyl-CoA was approximately linear over a 30 min period, demonstrating the presence of sufficient ACS activity in the rat microsomal preparation.

Detection of palmitoyl-CoA and Medica 16-CoA using LCMS: An LCMS method for detection for non-radiolabeled CoA derivatives was developed using palmitate and Medica-16 (a beta beta'-methyl-substituted, C16, alpha, omega-dicarboxylic acid). Either palmitate or Medica-16 at a concentration of 1 mM was added as substrate in the presence of rat liver microsomes for 0 (control, no microsomes added) and 30 minutes and the CoA-derivative were extracted as described above. Briefly, the reaction products of palmitoyl-CoA and Medica16-CoA were detected in the 30 min samples with good signal at the expected masses of [M+H]=1006.3 Da and [M+H]=1092.3 Da, respectively. Further confirmation was obtained by exposing the compound to a collision energy causing the characteristic neutral loss of 3'-phosphonucleoside diphosphate (507 Da) producing fragment ions 499.3 m/z and 585.3 m/z for palmitoyl-CoA and Medical6-CoA, respectively. There was no evidence of the CoA derivatives in either of the 0 min samples.

Formation and detection of the Co-A derivatives of Compounds I-32, I-61, I-1 or III-1 in rat liver microsomes: 1 mM of each compound (Compounds I-32, I-61, I-1 or III-1) or palmitic acid (control) were used as substrate in the rat microsomal preparation for 0 and 30 min and extracted as described above. Briefly, the control reaction using palmitate produced the expected product of palmitoyl-CoA which was detected in the 30 min sample with good signal at the expected mass of [M+H]=1006.3 Da. Further confirmation was obtained by exposing the compound to a collision energy causing the characteristic neutral loss of 3'-phosphonucleoside diphosphate (507 Da) producing the fragment ion 499.3 m/z. There was no evidence of the CoA derivative in the time 0 min sample.

The expected CoA derivative of Compounds 1-32 and I-1 were detected in the 30 min sample with good signal at the expected mass of [M+H]=1112.3 Da. Further confirmation of these reaction products was obtained by fragmentation which produced the characteristic neutral loss of 507 Dalton, resulting in the fragment ion 605.3 m/z. Again, there was no evidence of the CoA derivative in the 0 min samples.

Compound I-61-CoA and Compound III-1-CoA could not be confirmed using fragmentation analysis.

Biological Assays

Example 4: Kinase Assay for the Screening of Wild Type Kinases with Illustrative Compounds Compounds I-32, I-32-CoA, I-1, and I-1-CoA were tested against 370 kinases (Table 1) in a single dose duplicate mode at a concentration of 10 μM. Control compound Staurosporine was tested in 10-dose $IC_{50}$ mode with 4-fold serial dilution starting at 20 or 100 μM. Alternate control compounds were tested in 10-dose $IC_{50}$ mode with 3 or 4-fold serial dilution starting at 10, 20, 50, or 100 μM. Reactions were carried out at 10 μM ATP.

Table 2 shows effects of the tested compounds on selected wild type kinases. In Table 2, a percentage that is >100 indicates enzyme activation and a percentage that is <100 indicates enzyme inhibition.

TABLE 1

| List of Kinases Tested | | | |
|---|---|---|---|
| ABL1 | DDR2 | MAK | PKCzeta |
| ABL2/ARG | DMPK | MAPKAPK2 | PKD2/PRKD2 |
| ACK1 | DMPK2 | MAPKAPK3 | PKG1a |
| AKT1 | DRAK1/STK17A | MAPKAPKS/PRAK | PKG1b |
| AKT2 | DYRK1/DYRK1A | MARK1 | PKG2/PRKG2 |
| AKT3 | DYRK1B | MARK2/PAR-1Ba | PKN1/PRK1 |
| ALK | DYRK2 | MARK3 | PKN2/PRK2 |
| ALK1/ACVRL1 | DYRK3 | MARK4 | PKN3/PRK3 |
| ALK2/ACVR1 | DYRK4 | MAST3 | PLK1 |
| ALK3/BMPR1A | EGFR | MASTL | PLK2 |
| ALK4/ACVR1B | EPHA1 | MEK1 | PLK3 |
| ALK5/TGFBR1 | EPHA2 | MEK2 | PLK4/SAK |
| ALK6/BMPR1B | EPHA3 | MEK3 | PRKX |
| ARAF | EPHA4 | MEK5 | PYK2 |
| ARK5/NUAK1 | EPHA5 | MEKK1 | RAF1 |
| ASK1/MAP3K5 | EPHA6 | MEKK2 | RET |
| Aurora A | EPHA7 | MEKK3 | RIPK2 |
| Aurora B | EPHA8 | MEKK6 | RIPK4 |
| AURORA C | EPHB1 | MELK | RIPK5 |
| AXL | EPHB2 | MINK/MINK1 | ROCK1 |
| BLK | EPHB3 | MKK4 | ROCK2 |
| BMPR2 | EPHB4 | MKK6 | RON/MSTIR |
| BMX/ETK | ERBB2/HER2 | MKK7 | ROS/ROS1 |
| BRAF | ERBB4/HER4 | MLCK/MYLK | RSK1 |
| BRK | ERK1 | MLCK2/MYLK2 | RSK2 |
| BRSKI | ERK2/MAPK1 | MLK1/MAP3K9 | RSK3 |
| BRSK2 | ERK5/MAPK7 | MLK2/MAP3K10 | RSK4 |
| BTK | ERK7/MAPK15 | MLK3/MAP3K11 | SBK1 |
| c-Kit | ERN1/RE1 | MLK4 | SGK1 |
| c-MER | ERN2/IRE2 | MNK1 | SGK2 |
| c-MET | FAK/PTK2 | MNK2 | SGK3/SGKL |
| c-Src | FER | MRCKa/CDC42BPA | SIK1 |
| CAMK1a | FES/FPS | MRCKb/CDC42BPB | SIK2 |
| CAMK1b | FGFR1 | MSK1/RPSSKA5 | SIK3 |
| CAMKd | FGFR2 | MSK2/RPS6KA4 | SLK/STK2 |
| CAMK1g | FGFR3 | MSSK1/STK23 | SNARK/NUAK2 |
| CAMK2a | FGFR4 | MST1/STK4 | SNRK |
| CAMK2b | FGR | MST2/STK3 | SRMS |
| CAMK2d | FLT1/VEGFR1 | MST3/STK24 | SRPK1 |
| CAMK2g | FLT3 | MST4 | SRPK2 |
| CAMK4 | FLT4/VEGFR3 | MUSK | SSTK/TSSK6 |
| CAMKK1 | FMS | MYLK3 | STK16 |
| CAMKK2 | FRK/PTK5 | MYLK4 | STK21/CIT |
| CDC7/DBF4 | FYN | MYO3A | STK22D/TSSK1 |
| CDK1/cyclin A | GCK/MAP4K2 | MYO3b | STK25/YSK1 |
| CDK1/cyclin B | GLK/MAP4K3 | NEK1 | STK32B/YANK2 |
| CDK1/cyclin E | GRK1 | NEK11 | STK32C/YANK3 |
| CDK14/cyclin Y (PFTK1) | GRK2 | NEK2 | STK33 |
| CDK16/cyclin Y (PCTAIRE) | GRK3 | NEK3 | STK38/NDR1 |
| CDK17/cyclin Y (PCTK2) | GRK4 | NEK4 | STK38L/NDR2 |
| CDK18/cyclin Y (PCTK3) | GRK5 | NEK5 | STK39L/STLK3 |
| CDK19/cyclin C | GRK6 | NEK6 | SYK |
| CDK2/cyclin A | GRK7 | NEK7 | TAK1 |
| CDK2/cyclin A1 | GSK3a | NEK9 | TAOK1 |
| CDK2/CYCLIN E | GSK3b | NIM1 | TAOK2/TAO1 |
| CDK2/cyclin E2 | Haspin | NLK | TAOK3/JIK |
| CDK2/cyclin O | HCK | OSR1/OXSR1 | TBK1 |
| CDK3/cyclin E | HGK/MAP4K4 | P38a/MAPK14 | TEC |
| CDK3/yclin E2 | HIPK1 | P38b/MAPK11 | TESK1 |
| CDK4/cyclin D1 | HIPK2 | P38d/MAPK13 | TESK2 |
| CDK4/cyclin D3 | HIPK3 | P38g | TGFBR2 |
| CDK5/P25 | HIPK4 | p70S6K/RPSGKB1 | TIE2/TEK |
| CDK5/p35 | HPK1/MAP4K1 | p70S6Kb/RPS6KB2 | TLK1 |
| CDK6/cyclin D1 | IGF1R | PAKI | TLK2 |
| CDKB/cyclin D3 | IKKa/CHUK | PAK2 | TNIK |
| CDK7/cyclin H | IKKb/IKBKB | PAK3 | TNK1 |
| CDK8/cyclin C | IKKe/IKBKE | PAK4 | TRKA |
| CDK9/cyciin K | IR | PAKS | TRKB |
| CDK9/cyclin T1 | IRAK1 | PAK6 | TRKC |
| CDK9/cyclin T2 | IRAK4 | PASK | TSSK2 |
| CHK1 | IRR/INSRR | PBK/TOPK | TSSK3/STK22C |
| CHK2 | ITK | PDGFRa | TTBK |
| CK1a1 | JAK1 | PDGFRb | TTBK2 |
| CK1a1L | JAK2 | PDK1/PDPK1 | TXK |
| CK1d | JAK3 | PHKg1 | TYK1/LTK |
| CK1epsilon | JNK1 | PHKg2 | TYK2 |
| CK1g1 | JNK2 | PIM1 | TYRO3/SKY |

TABLE 1-continued

| List of Kinases Tested | | | |
|---|---|---|---|
| CK1g2 | JNK3 | PIM2 | ULK1 |
| CK1G3 | KDR/EGFR2 | PIM3 | ULK2 |
| CK2a | KHS/MAP4K5 | PKA | ULK3 |
| CK2a2 | KSR1 | PKAcb | VRK1 |
| CLK1 | KSR2 | PKAcg | VRK2 |
| CLK2 | LATS1 | PKCa | WEE1 |
| CLK3 | LATS2 | PKCb1 | WNK1 |
| CLK4 | LCK | PKCb2 | WNK2 |
| COT1/MAP3K8 | LCK2/ICK | PKCd | WNK3 |
| CSK | LIMK1 | PKCepsiion | YES/YES1 |
| CTK/MATK | LIMK2 | PKCeta | YSK4/MAP3K19 |
| DAPK1 | LKB1 | PKCg | ZAK/MLTK |
| DAPK2 | LOK/STK10 | PKCIOTA | ZAP70 |
| DCAMKL1 | LRRK2 | PKCmu/PRKD1 | ZIPK/DAPK3 |
| DCAMKL2 | LYN | PKCnu/PRKD3 | |
| DDR1 | LYN B | PKCtheta | |

The control compound Staurosporine has the following structure:

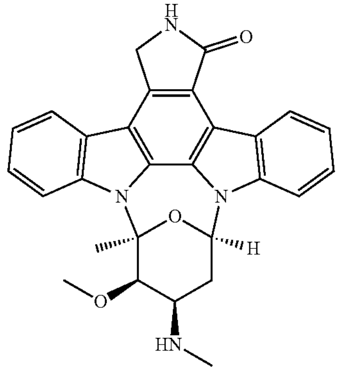 [SMILES: CN[C@@H]1C[C@H]2O[C@@](C)([C@@H]1OC)n1c3ccccc3c3c4c(c5c6ccccc6n2c5c31)C(=O)NC4]

TABLE 2

| Percent Enzyme Activity for Selected Kinases | | | | | | | | | |
|---|---|---|---|---|---|---|---|---|---|
| | % Enzyme Activity (relative to DMSO controls) | | | | | | | | |
| | Compound I-32 (10 μM) | | Compound I-32-CoA (10 μM) | | Compound I-1 (10 μM) | | Compound I-1-CoA (10 μM) | | IC50 (M) Stauro- |
| Kinases | Data 1 | Data 2 | Data 1 | Data 2 | Data 1 | Data 2 | Data 1 | Data 2 | sporine |
| Aurora A | 94.94 | 93.33 | 13.04 | 11.95 | 89.09 | 83.92 | 12.44 | 12.42 | 1.80E−09 |
| Aurora B | 71.42 | 67.29 | 33.27 | 30.67 | 69.04 | 63.21 | 36.79 | 32.68 | 6.04E−09 |
| AURORA C | 104.5 | 97.44 | 48.46 | 46.83 | 100.96 | 93.1 | 78.81 | 72.15 | 1.14E−09 |
| BMX/ETK | 53.7 | 52.97 | 49.54 | 43.87 | 54.96 | 51.72 | 49.55 | 47.76 | 6.87E−09 |
| c-Kit | 73.62 | 71.52 | 49.53 | 49.21 | 85.48 | 81.06 | 73.56 | 73.24 | 3.58E−09 |
| CAMK2g | 73.24 | 66.13 | 35.05 | 34.20 | 60.64 | 57.02 | 53.91 | 53.05 | 3.88E−10 |
| DDR2 | 91.37 | 85.83 | 29.98 | 25.40 | 79.82 | 69.84 | 88.28 | 79.94 | 4.90E−10 |
| ERK7/MAPK15 | 103.8 | 102.21 | 88.39 | 80.61 | 100.49 | 100.06 | 51.57 | 45.02 | 1.18E−08 |
| GSK3b | 78.05 | 72.67 | 23.69 | 22.51 | 83.23 | 82.73 | 63.29 | 62.44 | 4.92E−09 |
| LIMK1 | 83.79 | 71.71 | 47.31 | 45.01 | 81.03 | 71.9 | 77.88 | 76.61 | 6.60E−10 |
| MAPKAPK2 | 91.73 | 90.61 | 17.17 | 15.90 | 93.09 | 92.75 | 85.04 | 84.66 | 1.58E−07 |
| MELK | 114.06 | 110.73 | 28.56 | 27.35 | 109.96 | 106.55 | 23.02 | 21.99 | 1.11E−09 |
| MLCK/MYLK | 106.46 | 103.59 | 3.21 | 1.59 | 110.02 | 106.34 | 2.06 | −0.71 | 1.54E−08 |
| NEK2 | 87.82 | 87.7 | 35.98 | 34.99 | 90.26 | 85.17 | 0.89 | 0.63 | 2.69E−07 |
| PIM3 | 90.04 | 86.73 | 51.10 | 43.67 | 87.9 | 83 | 73.92 | 70.32 | 2.02E−10 |
| RIPK4 | 43.00 | 42.74 | 33.02 | 32.84 | 45.13 | 42.78 | 32.26 | 29.70 | 2.58E−07 |
| TNIK | 100.81 | 99.68 | 70.02 | 66.13 | 106.39 | 101.58 | 39.22 | 36.50 | 3.54E−10 |
| FLT1/VEGFR1 | 92.26 | 91.15 | 52.06 | 51.61 | 90.31 | 87.88 | 84.17 | 82.94 | 7.52E−09 |

Example 5: In Vitro Evaluation of Compound I-1, Compound I-1-CoA, Compound I-32, and Compound I-32-CoA in ACC1/ACC2 Enzymatic Assays Human ACC1 (Cat#50202 Lot #120830) and ACC2 (Cat #50201 Lot #160217) were obtained from BPS Biosciences, San Diego, Calif. 92121. Human ACC1 had C-terminal flag and His-tags with a MW of 270 KDa after purification from Baculovirus infected Sf9 cell expression system and came as a solution in 50 mM Tris-HCl, pH 8.0, 500 mM NaCl, 10% glycerol, 1 mM DTT, 100 μg/ml FLAG peptide with 70% purity. The stock concentration was 0.25 mg/ml corresponding to 0.926 μM. Human ACC2 was also purified from Baculovirus infected Sf9 expression system. It had a MW of 277 KDa with C-terminal flag and His-tags and came as a solution in 40 mM Tris pH 8.0, 110 mM NaCl, 2.2 mM KCl, 0.04% Tween-20, 20% glycerol, and 3 mM DTT with 56% purity. The stock concentration was 0.1 mg/ml corresponding to 0.36 μM. The assay buffer for measuring the activity of ACC contained: 30 mM HEPES (pH 7.4), 2 mM $MgCl_2$, 0.01% Brij35, 2 mM DTT, 1% DMSO (solvent for compound). For ACC1 and ACC2 assays, the following concentrations of substrate and cofactors were used: 12 mM $NaHCO_3$, 10 μM acetyl CoA, 10 μM ATP, and 2 mM K-citrate. The recombinant human enzyme was used at 5 nM for ACC1 and 1 nM for ACC2. In brief, enzyme alone in the above buffer without substrate was used for background. All test materials were dissolved in 100% DMSO using acoustic technology (Echo550). The prepared solution was preincubated for 15 min followed by the addition of 5 μL/well of ADP standard. ATP was then added to start the reaction. The assay contents were spun and briefly shaken followed by incubation at room temperature for 1 h. At the end of completion of assay, 5 μL of ADP-Glo was added to each well to stop the reaction. The contents were mixed, spun and incubated at room temperature for 40 min followed by the addition of 10 μL/well of ADP detection reagent. The contents were spun, mixed and covered with plastic to measure luminescence. As shown in FIG. 1, this assay is performed in two steps: i) after the ACC-mediated enzymic reaction that utilizes ATP and produces ADP, ADP-Glo™ Reagent is added to terminate the kinase reaction and deplete the remaining ATP, and ii) the Kinase Detection Reagent is added to convert ADP to ATP and allow the newly synthesized ATP to be measured using a luciferase/luciferin reaction. The light generated, measured in a luminometer, correlates to the amount of ADP generated in the ACC assay, which is indicative of ACC activity.

$K_m$ and $V_{max}$ Determination of Acetyl-CoA and ATP: Michaelis-Menten constant ($K_m$) and $V_{max}$ of acetyl-CoA and ATP were determined for both ACC1 and ACC2 using varying concentrations of ATP (2.5 to 50 μM) and acetyl-CoA (5 to 50 μM). The enzyme concentrations for ACC1 and ACC2 were 5 nM and 1 nM, respectively.

$IC_{50}$ Determination: Test and reference agents were evaluated at 10-concentrations with 3-fold serial dilution starting at 300 μM to determine an $IC_{50}$. Data represent nM or μM ADP produced, % Activity (relative to no inhibitor controls), and curve fits were performed by GraphPad Prism software. The $IC_{50}$ concentration-response curves were generated for both the ACC1 and ACC2 assays using recombinant human ACC.

Table 3 shows the summary of results for ACC1 inhibition by Compound I-1, Compound I-1-CoA, Compound I-32, and Compound I-32-CoA. Reference compound CP 640186 has the following structure:

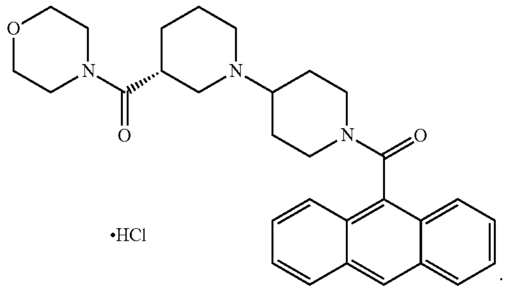 [SMILES: O=C(c1c2ccccc2cc2ccccc12)N1CCC(N2CCC[C@@H](C(=O)N3CCOCC3)C2)CC1 ; Cl]

•HCl

TABLE 3

ACC1/ACC2 Inhibition

| Comp. | Compound $IC_{50}$ (M) | | | | | |
|---|---|---|---|---|---|---|
| | ACC1 | | | ACC2 | | |
| | Run 1 | Run 2 | Run 3 | Run 1 | Run 2 | Run 3 |
| I-32 | 2.84E−04 | 2.72E−04 | 2.20E−04 | * | * | * |
| I-32-CoA | 5.07E−06 | 5.00E−06 | 6.03E−06 | 5.02E−06 | 4.22E−06 | 3.33E−06 |
| I-1 | * | * | * | * | * | * |
| I-1-CoA | 1.63E−05 | 1.33E−05 | 1.25E−05 | 9.41E−06 | 7.72E−06 | 9.06E−06 |
| CP 640186 (reference) | | 2.14E−06 | | | 7.81E−08 | |

*No detectible inhibition or compound activity

Figure 2A:
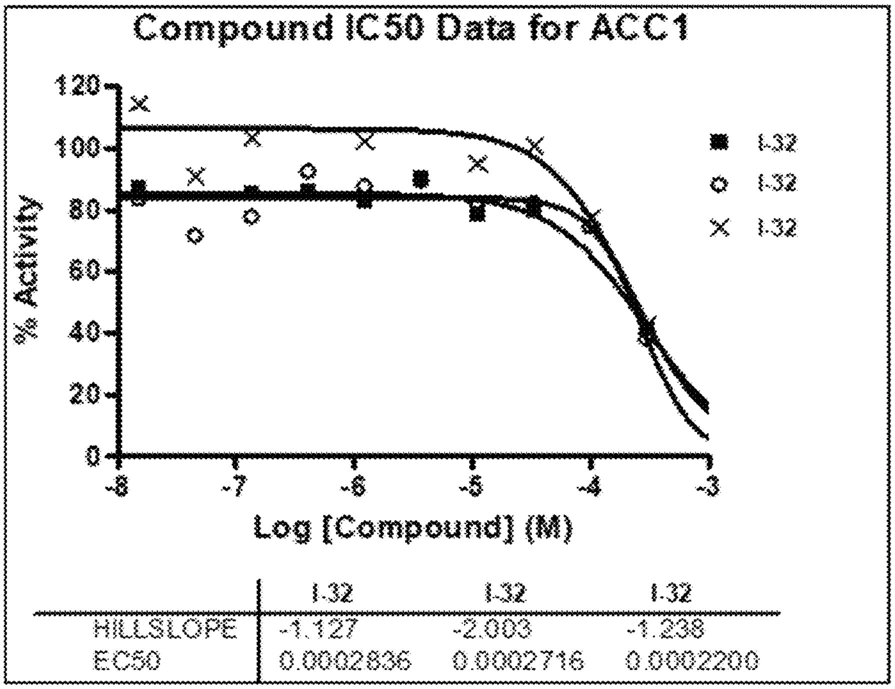
FIG. 2A shows the $IC_{50}$ data for ACC1 inhibition of Compound I-32.
Figure 2B:
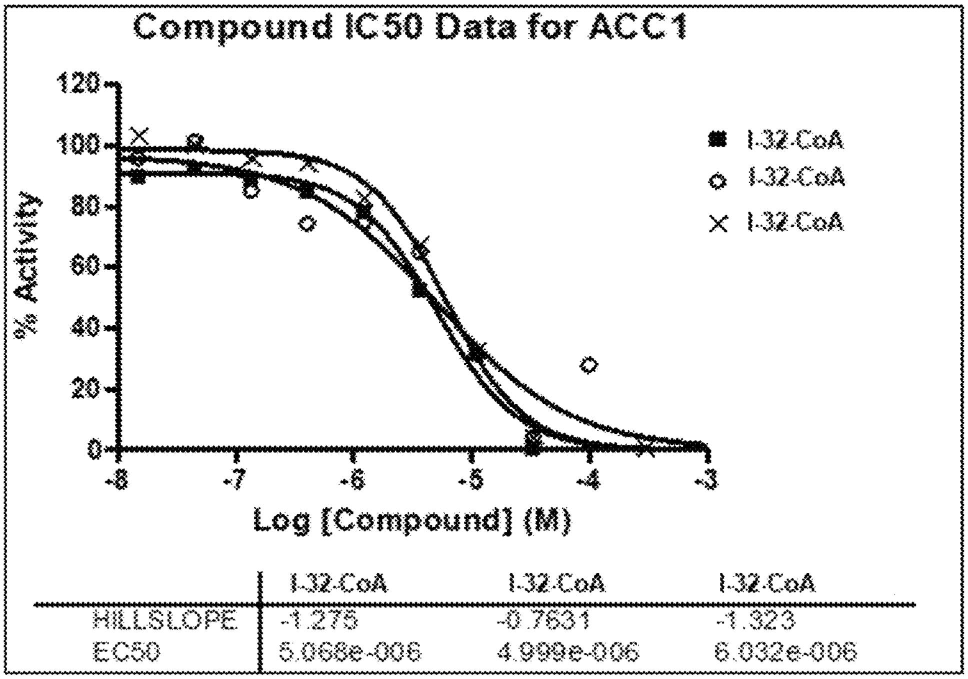
FIG. 2B shows $IC_{50}$ data for ACC1 inhibition of Compound I-32-CoA.
Figure 2C:
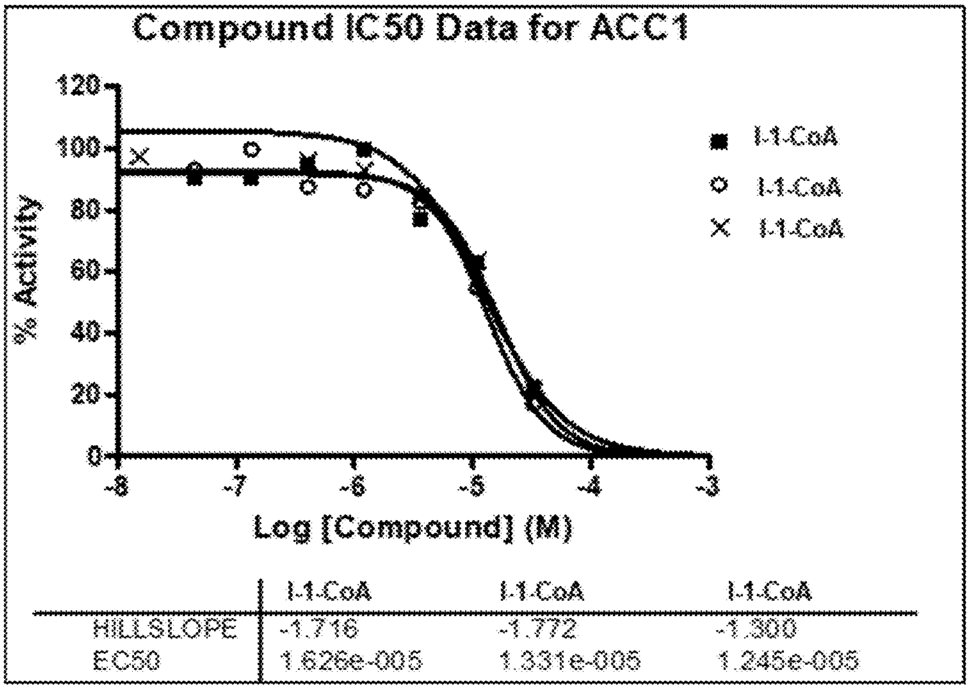
FIG. 2C shows $IC_{50}$ data for ACC1 inhibition of Compound I-1-CoA and FIG. 2D shows $IC_{50}$ data for ACC1 inhibition of the reference compound CP 640186.
Figure 2D:
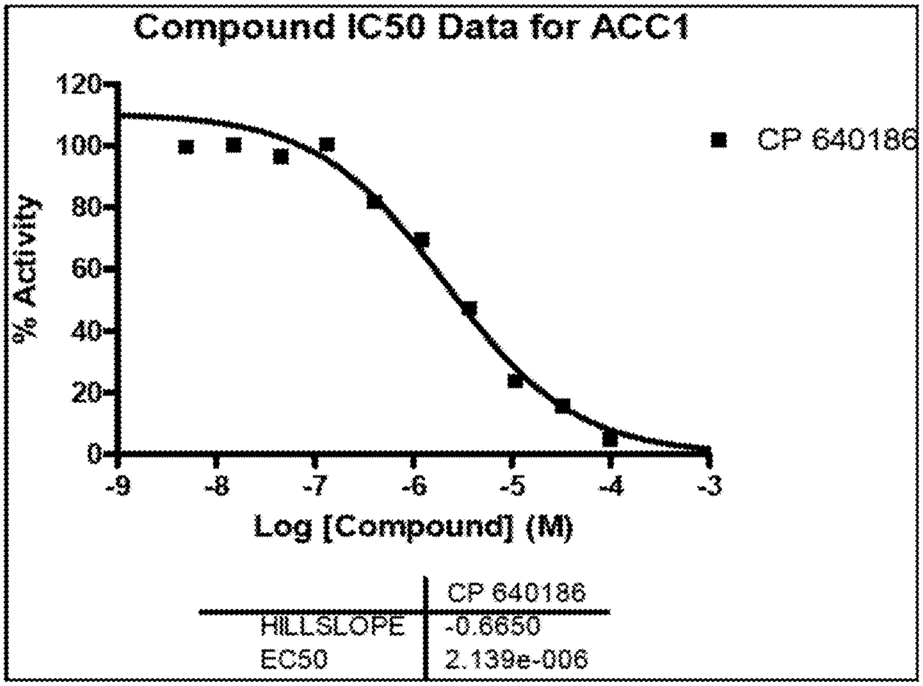

FIG. 2A presents the $IC_{50}$ data for ACC1 inhibition by Compound I-32. FIG. 2B presents $IC_{50}$ data for ACC1 inhibition by Compound I-32-CoA. FIG. 2C presents $IC_{50}$ data for ACC1 inhibition by Compound I-1-CoA and FIG. 2D presents $IC_{50}$ data for ACC1 inhibition by the reference compound CP 640186.

Figure 3A:
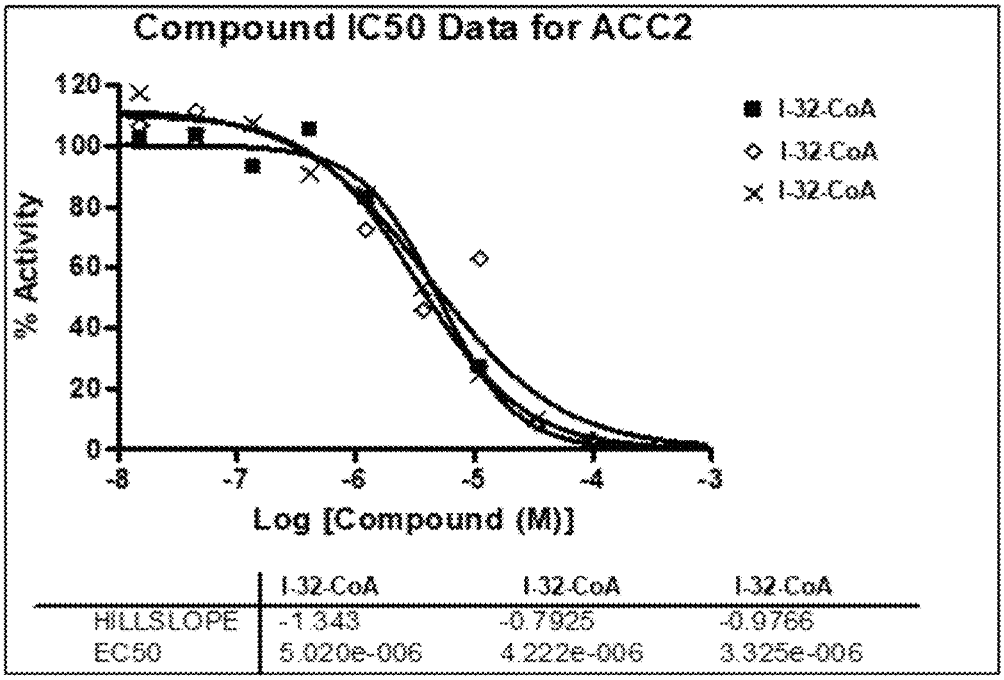
FIG. 3A shows $IC_{50}$ data for ACC2 inhibition of Compound I-32-CoA.
Figure 3B:
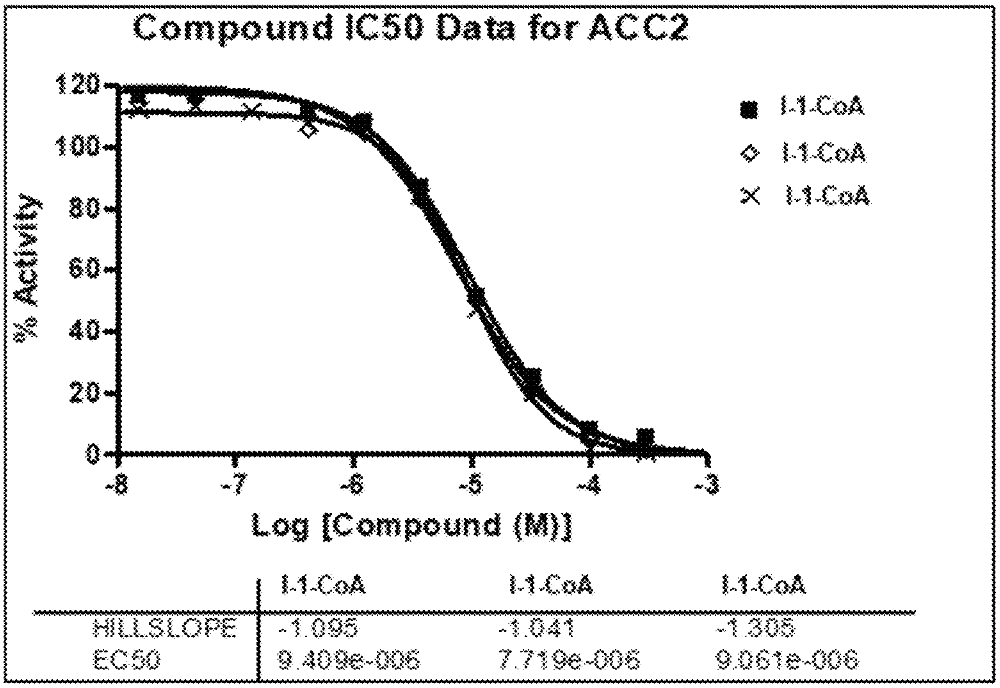
FIG. 3B shows $IC_{50}$ data for ACC2 inhibition of Compound I-1-CoA and FIG. 3C shows $IC_{50}$ data for ACC2 inhibition of the reference compound CP 640186.
Figure 3C:
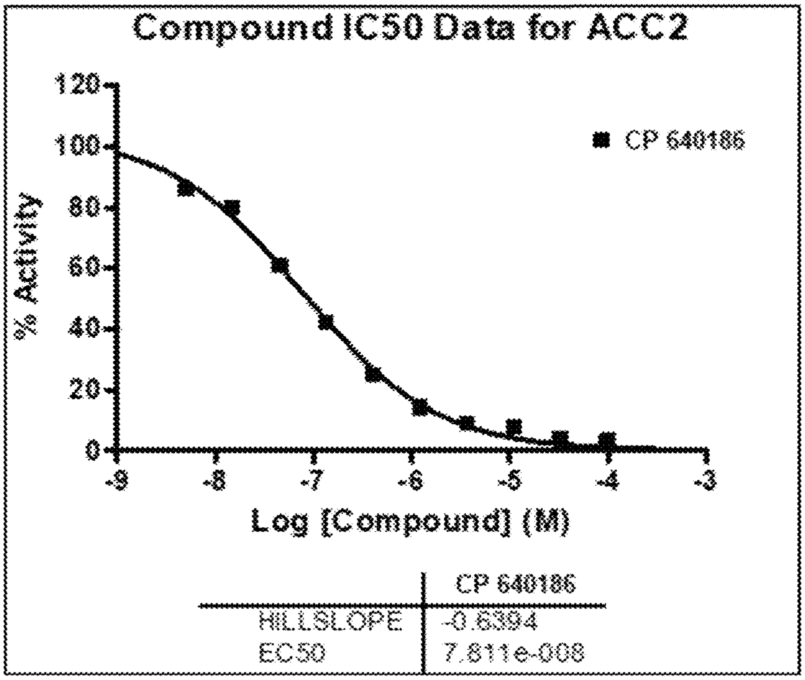

FIG. 3A presents $IC_{50}$ data for ACC2 inhibition by Compound I-32-CoA. FIG. 3B presents $IC_{50}$ data for ACC2 inhibition of Compound I-1-CoA and FIG. 3C presents $IC_{50}$ data for ACC2 inhibition of the reference compound CP 640186.

Example 6: In Vitro Evaluation of Compound I-1, Compound I-1-CoA, Compound I-32, and Compound I-32-CoA in ATP-Citrate Lyase (ACLY) Enzymatic Assay ATP citrate lyase was obtained from Sino Biological Inc. Cat #11769-H07B, Lot #LC08DE1701. It was prepared from a DNA sequence encoding the human ACLY (P533%) (Met 1-Met 1101) expressed in Baculovirus-Insect Cells, with a polyhistidine tag at the N-terminus. The recombinant human ACLY consists of 1120 amino acids and has a calculated molecular mass of 123 kDa. It migrates as an approximately 110 kDa band in SDS-PAGE under reducing conditions. The enzyme came as a lyophilized powder in sterile 20 mM Tris, 500 mM NaCl, pH 8.0, 10% glycine. Normally 5%-8% trehalose and mannitol are added as protectants before lyophilization. The recombinant human ACLY from Sino Biological was formulated in 45 mM Tris-HCl, pH 8.0, 124 mM NaCl, 2.4 mM KCl, 18 mM glutathione, 10% glycerol, and 3 mM DTT.

To detect ADP produced from ACL assay, the ADP-Glo™ assay format from Promega, Madison, Wis., was used, to detect the conversion of ATP to ADP. In the ADP-Glo™ (Promega. Cat #V9101) method, as shown in FIG. 1, the protocol provided by the manufacturer was followed. This assay is performed in two steps: i) after the ACL-mediated enzymatic reaction that utilizes ATP and produces ADP, ADP-Glo™ Reagent is added to terminate the kinase reaction and deplete the remaining ATP, and ii) the Kinase Detection Reagent is added to convert ADP to ATP and allow the newly synthesized ATP to be measured using a luciferase/luciferin reaction. The light generated, measured in a luminometer, correlates to the amount of ADP generated in the ACL assay, which is indicative of ACL activity.

Compound I-1, Compound I-1-CoA, Compound I-32, and Compound I-32-CoA and reference compound were evaluated at 10-concentrations with 3-fold serial dilution starting at 300 μM to determine an $IC_{50}$. Data represent nM or μM ADP produced, % Activity (relative to no inhibitor controls), and curve fits were performed by GraphPad Prism software. The $IC_{50}$ concentration-response curves were generated for ADPGlo™ using recombinant human ACL from Sino Biologicals Inc.

Table 4 presents the summary of results for Compound I-1, Compound I-1-CoA, Compound I-32, and Compound I-32-CoA and for the reference compound BMS-303141. BMS-303141 has the following structure:

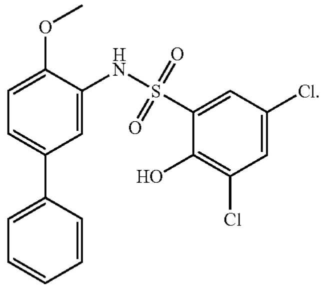 [SMILES: COc1ccc(-c2ccccc2)cc1NS(=O)(=O)c1cc(Cl)cc(Cl)c1O]

TABLE 4

$IC_{50}$ in ATP-citrate lyase (ACLY) enzymatic assay

| Compound | Compound $IC_{50}$ (M) ACLY Run 1 | Run 2 | Run 3 |
|---|---|---|---|
| I-32 | * | * | * |
| I-32-CoA | 9.88E−07 | 1.22E−06 | 1.44E−06 |
| I-1 | * | * | * |
| I-1-CoA | 3.34E−06 | 2.28E−06 | 2.50E−06 |
| BMS-303141 | | 4.45E−07 | |

* No detectable inhibition or compound activity

Figure 4A:
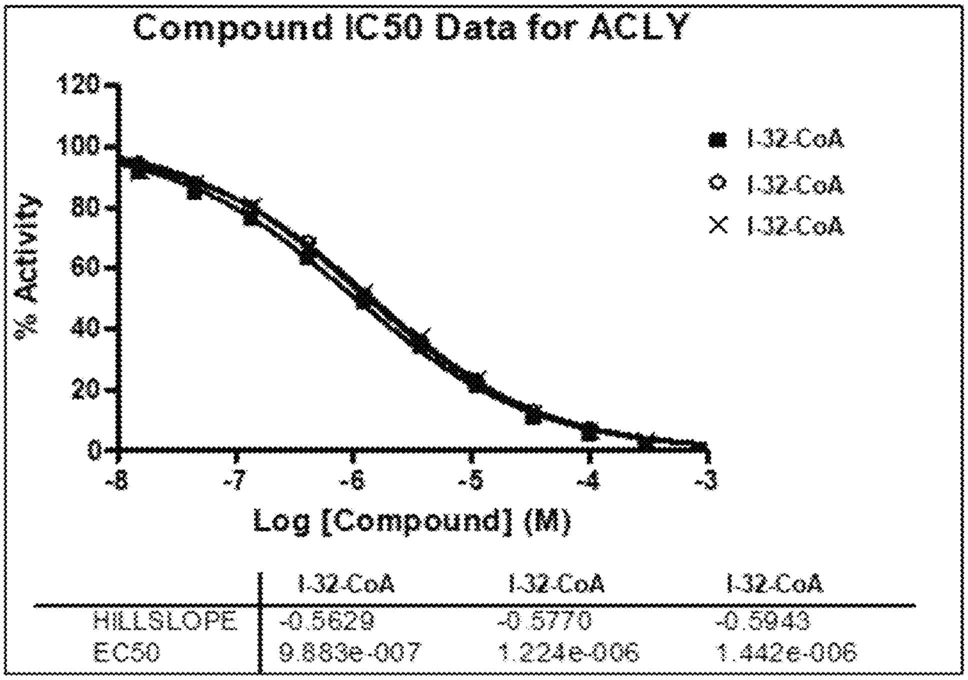
FIG. 4A shows the $IC_{50}$ data for ACLY inhibition of Compound I-32-CoA.
Figure 4B:
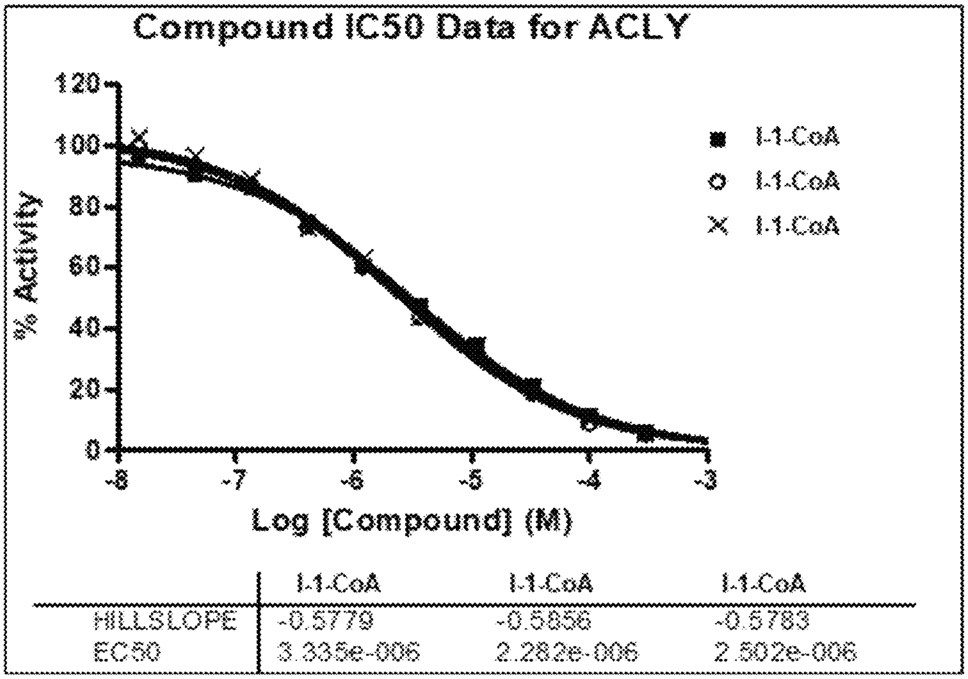
FIG. 4B shows $IC_{50}$ data for ACLY inhibition of Compound I-1-CoA and FIG. 4C shows $IC_{50}$ data for ACLY inhibition of the reference compound BMS-303141.
Figure 4C:
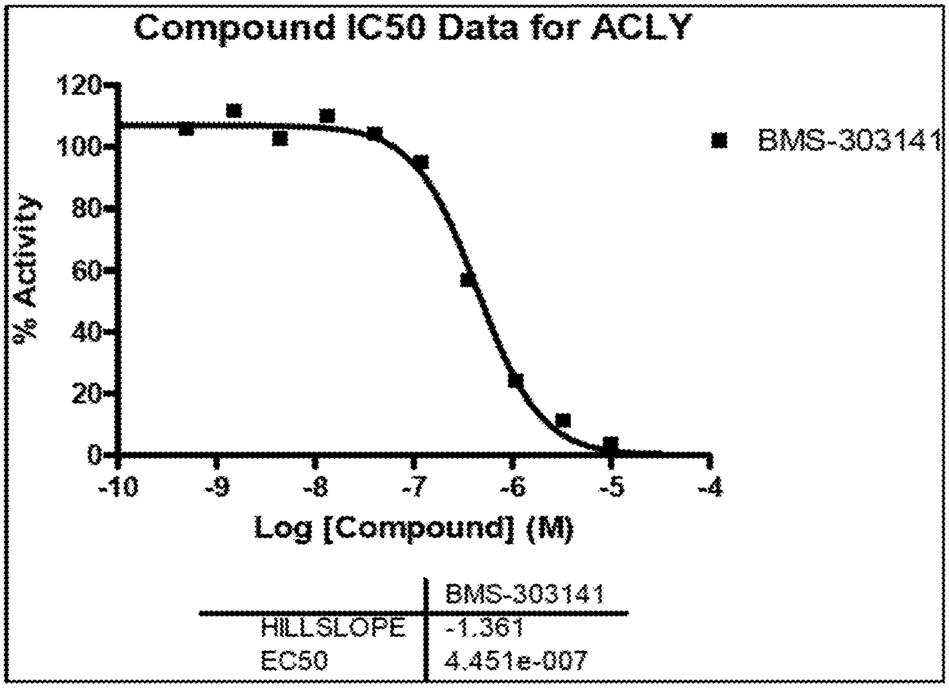
Figure 4D:
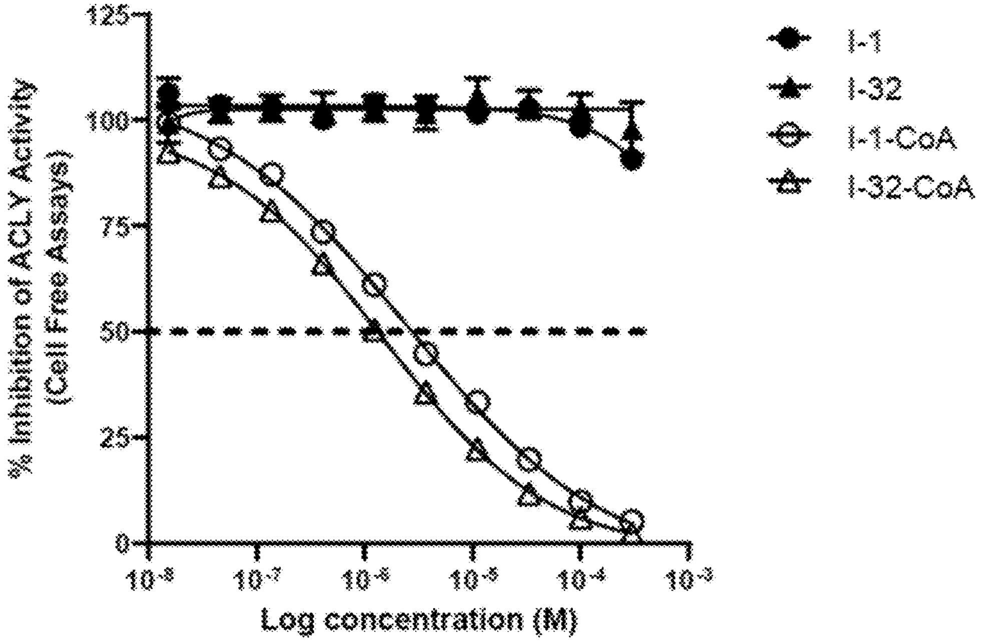
FIG. 4D shows results for Compound I-1, Compound I-1-CoA, Compound I-32, and Compound I-32-CoA in an ACLY inhibition assay.

FIG. 4A presents the $IC_{50}$ data for ACLY inhibition of Compound I-32-CoA. FIG. 4B presents $IC_{50}$ data for ACLY inhibition of Compound I-1-CoA and FIG. 4C presents $IC_{50}$ data for ACLY inhibition of the reference compound BMS-303141. FIG. 4D presents results for Compound I-1, Compound I-1-CoA, Compound I-32, and Compound I-32-CoA in the ACLY inhibition assay.

Example 7: Effect of Compound I-1 and Compound I-32 on Lipids, Liver Fibrosis, and Liver Gene Expression in an Ultrafast Metabolic Model Recapitulating Features of Obese/Diabetic/Cirrhotic Population at Risk of HCC Male mice C57BL6/J (48 animals, 8-week-old) from Janvier Labs, France, were fed a high fat/high cholesterol/high cholic acid diet with 2% 2-hydroxypropyl beta-cyclodextrin in drinking water. Under this diet, mice develop in 3 weeks NASH with fibrosis, and concomitant increase in plasma ALT/AST levels. Each of the 48 animals have been housed in housing cages GM500 (501 $CM^2$) throughout the experimental phase. Animals' cages litters have been changed at least once a week. They have been housed in groups of 5 animals on a normal 12 hours light cycle (at 08:00 μm lights off), 22±2° C. and 50±10% relative humidity. The mice were divided in four groups as displayed in Table 5 and were fed standard chow diet with normal tap water (untreated control group–vehicle group) or a 60% high fat, 1.25% cholesterol and 0.5% cholic acid (diet #D11061901 from Research Diets) with 2% 2-hydroxypropyl beta-cyclodextrin in drinking water (HFCC/CDX diet) provided ad libitum.

Mice were treated with vehicle or Compound I-32 or Compound I-1 orally QD for 2 weeks, as described in the table below.

TABLE 5

Treatment Groups

| Group# | n | Diet | Treatment | Route | Dose | Dose volume | Treatment duration |
|---|---|---|---|---|---|---|---|
| 1 | 10 | chow | vehicle | Oral QD | — | 10 mL/kg | 2 weeks |
| 2 | 10 | HFCC/CDX | vehicle | Oral QD | — | 10 mL/kg | 2 weeks |
| 3 | 10 | HFCC/CDX | Compound I-32 | Oral QD | 100 mg/kg QD | 10 mL/kg | 2 weeks |
| 4 | 10 | HFCC/CDX | Compound I-1 | Oral QD | 100 mg/kg QD | 10 mL/kg | 2 weeks |

After 1 week of diet, blood was collected (~150 μL/heparin) in non-fasting conditions at ~1:00 μm and plasma ALT and AST levels were measured. Mice were then randomized into 4 homogenous treatment groups (n=10 mice per group) according to their 1) ALT and 2) AST and 3) body weight.

2 mice on control chow diet and 6 mice on HFCC/CDX showing extreme ALT/AST/body weight values were excluded from the study. Among these excluded mice, 5 individuals on HFCC/CDX were 4 h-fasted at ~09:00 am sacrificed and exsanguinated with saline at ~1:00 μm, then liver was collected and weighted. Liver samples were dissected from the left lateral lobe for formalin-fixed paraffin-embedded samples for shipment for histology analysis (H&E and Sirius Red staining), % Sirius Red labelling and NAS scoring at baseline. The remaining liver was flash-frozen and stored at −80° C. for eventual additional analysis. Other mice included were then treated orally QD with either vehicle, Compound I-32, or Compound I-1 for 2 weeks. At the end of the treatment period, mice were weighted, and 4-hour fasted at ~9:00 am prior to blood collection (maximal volume/heparin) at ~1:00 μm. Plasma was isolated and immediately stored at −80° C. prior to assay plasma ALT and AST levels. Plasma left over was immediately stored as 2 individually identified aliquots at −80° C. for additional analysis: plasma total cholesterol. LDL-cholesterol, HDL-cholesterol, triglycerides, C-reactive protein (CRP) and Serum Amyloid A (SAA). After blood collection, mice were sacrificed by cervical dislocation under isoflurane anesthesia and exsanguinated with sterile saline. Liver was collected and weighted then liver samples were dissected from the left lateral lobe for histology analysis (H&E, Sirius Red staining, % Sirius Red labelling and NAS scoring), α-SMA (smooth muscle actin) immunohistochemistry and quantification of % labelling for hepatic stellate cells.

A NAFLD scoring system (NAS) adapted from Kleiner et al. (2005), was performed using H&E and Sirius Red staining and a total of four variables were qualitatively assessed and ranked with a score: (1) hepatocellular steatosis, (2) liver inflammation, (3) lobular fibrosis, and (4) hepatocyte ballooning.

Other liver samples were collected from the left lateral lobe for liver lipids (total cholesterol, triglycerides and fatty acids) assay after liver lipid solubilization with deoxycholate as described by and hepatic gene expression by qPCR as follows:

(i) IL-1b, MCP-1, IL-6, NF-κB, TLR4, MCP-1, TNF-α, for inflammation;

(ii) Col1alpha1 and TGF-beta for fibrosis, (iii) ACLY, ACCS2, ACC1, ACC2, FASN, SCD1, SERBP-1c for lipid synthesis, (iv) beta-catenin, hypoxia inducible factor-1-alpha (HIF-1 alpha) for fatty acids oxidation (v) VEGFR1-3, FGFR-1, p38 MAP kinase for hepatocarcinoma markers.

(vi) Sdc1, SULF2, DGAT, apoC-III, MTTP, apoB and RIPK4 to investigate the liver TG effects.

Data are shown as mean±SEM. Statistical analysis was performed on GraphPad Prism software, using either a 1-way or 2-way ANOVA followed by Dunnett's or Bonferroni post-tests, respectively, or a Kruskal-Wallis and Dunn's post-test, or an unpaired two-tailed Student t-test. A $p<0.05$ was considered significant.

Figure 5A:
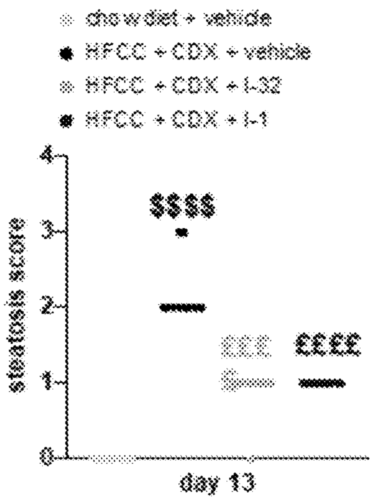
FIGS. 5A-5D shows the following measurements in mice treated with vehicle or Compound I-32 or Compound I-1: steatosis (FIG. 5A), inflammation (FIG. 5B), fibrosis (FIG. 5C), NAFLD scores (FIG. 5D).
Figure 5B:
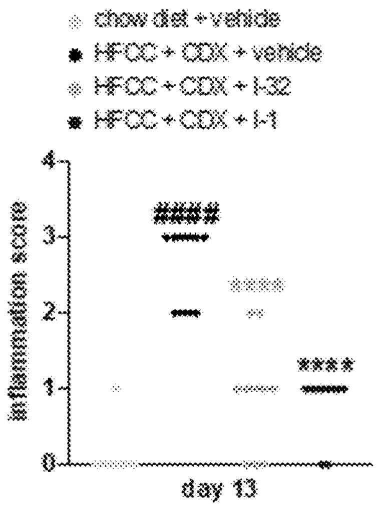
Figure 5C:
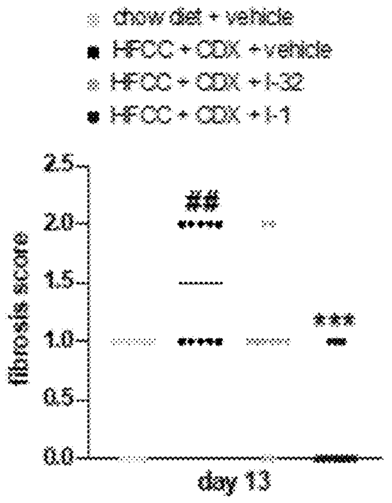
Figure 5D:
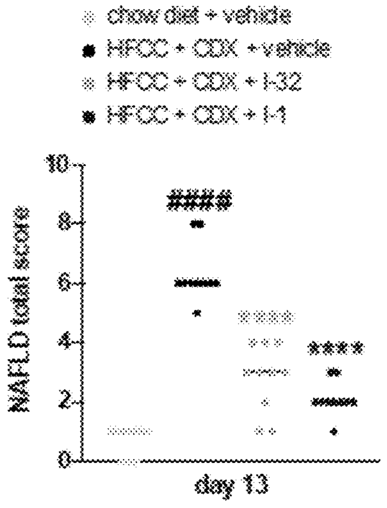

FIGS. 5A-5D displays the following measurements: steatosis (FIG. 5A), inflammation (FIG. 5B), fibrosis (FIG. 5C), NAFLD (FIG. 5D) scores. FIG. 5A: $$$$ p<0.0001 vs. chow diet+vehicle with a Mann-Whitney test; ££££ p<0.0001 vs. HFCC+CDX+vehicle with a Kruskal-Wallis plus Dunns post test. FIGS. 5B-D: ##p<0.01 and ####p<0.0001 vs. chow diet+vehicle with a t-test; * p<0.001 and ** p<0.0001 vs HFCC+CDX+vehicle with an ANOVA 2-ways plus Bonferroni's post test.

Figure 6A:
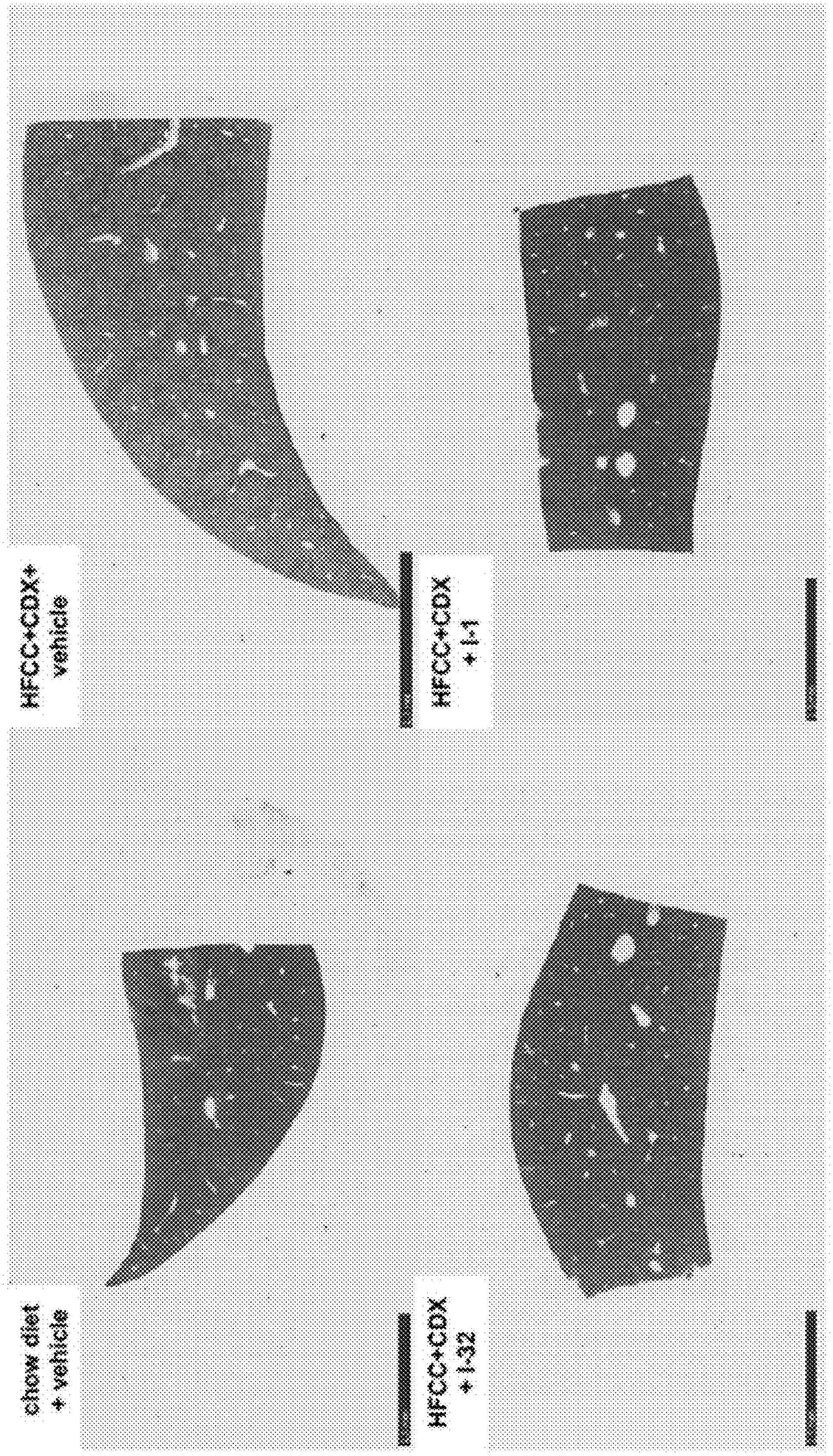
FIG. 6A shows a representative H&E staining (×1.25 magnification) and FIG. 6B displays a representative H&E staining (×10 magnification) at the end of the treatment period in mice with vehicle or Compound I-32 or Compound I-1.
Figure 6B:
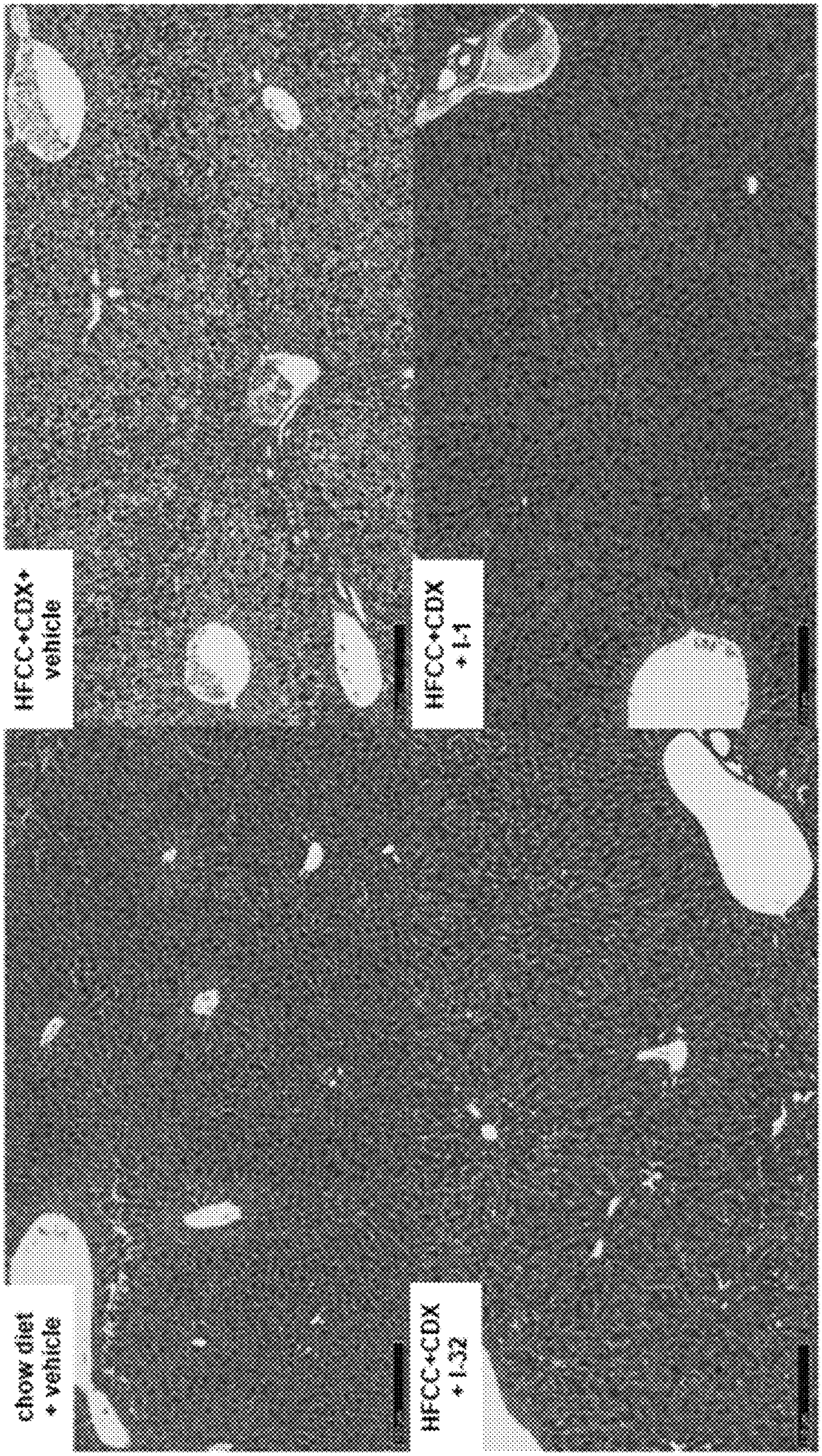

FIG. 6A displays a representative H&E staining (×1.25 magnification) and FIG. 6B displays a representative H&E staining (×10 magnification) at the end of the treatment period.

Figure 7A:
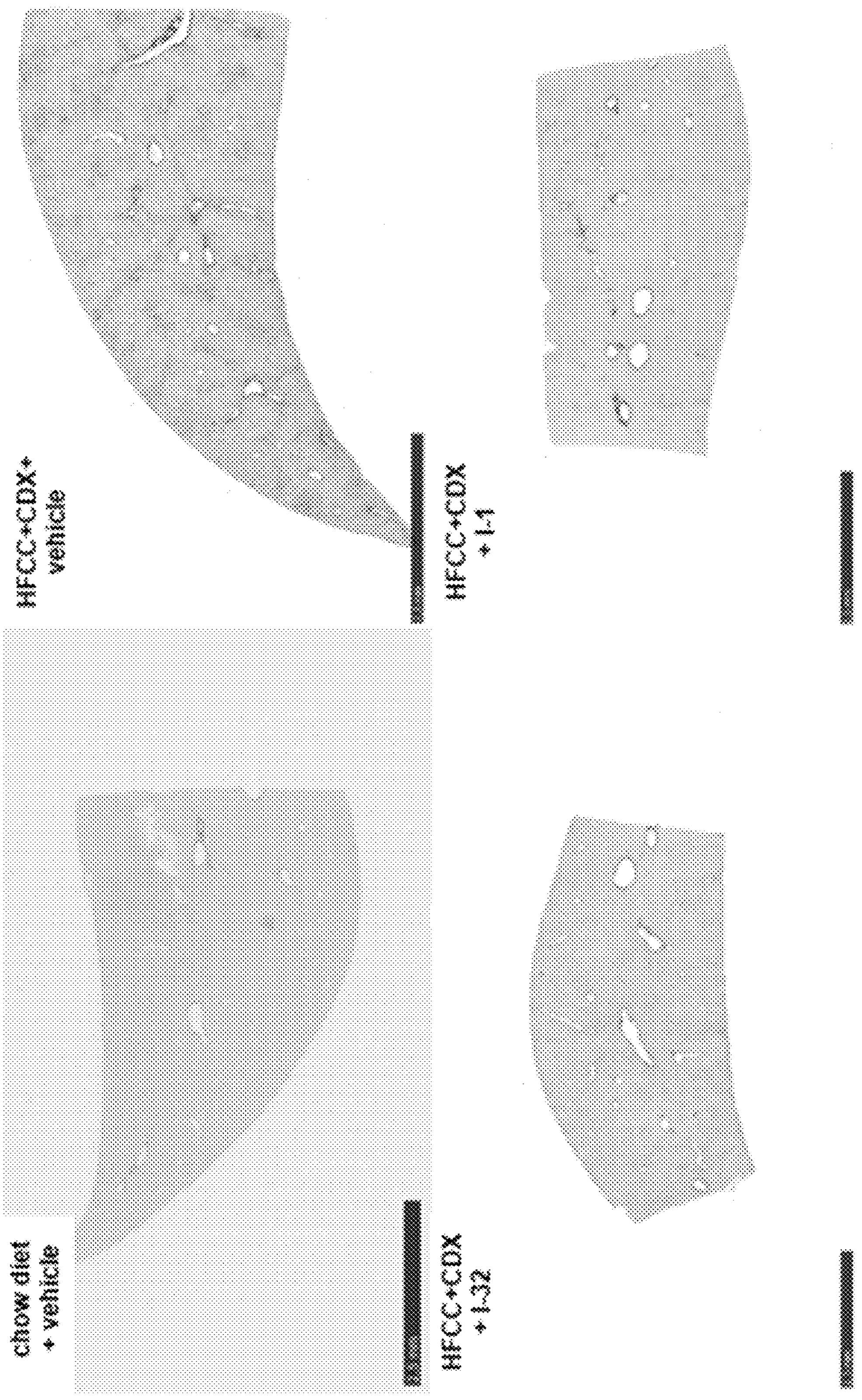
FIG. 7A displays a representative Sirius Red staining (×1.25 magnification) and FIG. 7B displays a representative Sirius Red staining (×10 magnification) at the end of the treatment period in mice with vehicle or Compound I-32 or Compound I-1. Arrows indicate perisinusoidal and portal fibrosis.
Figure 7B:
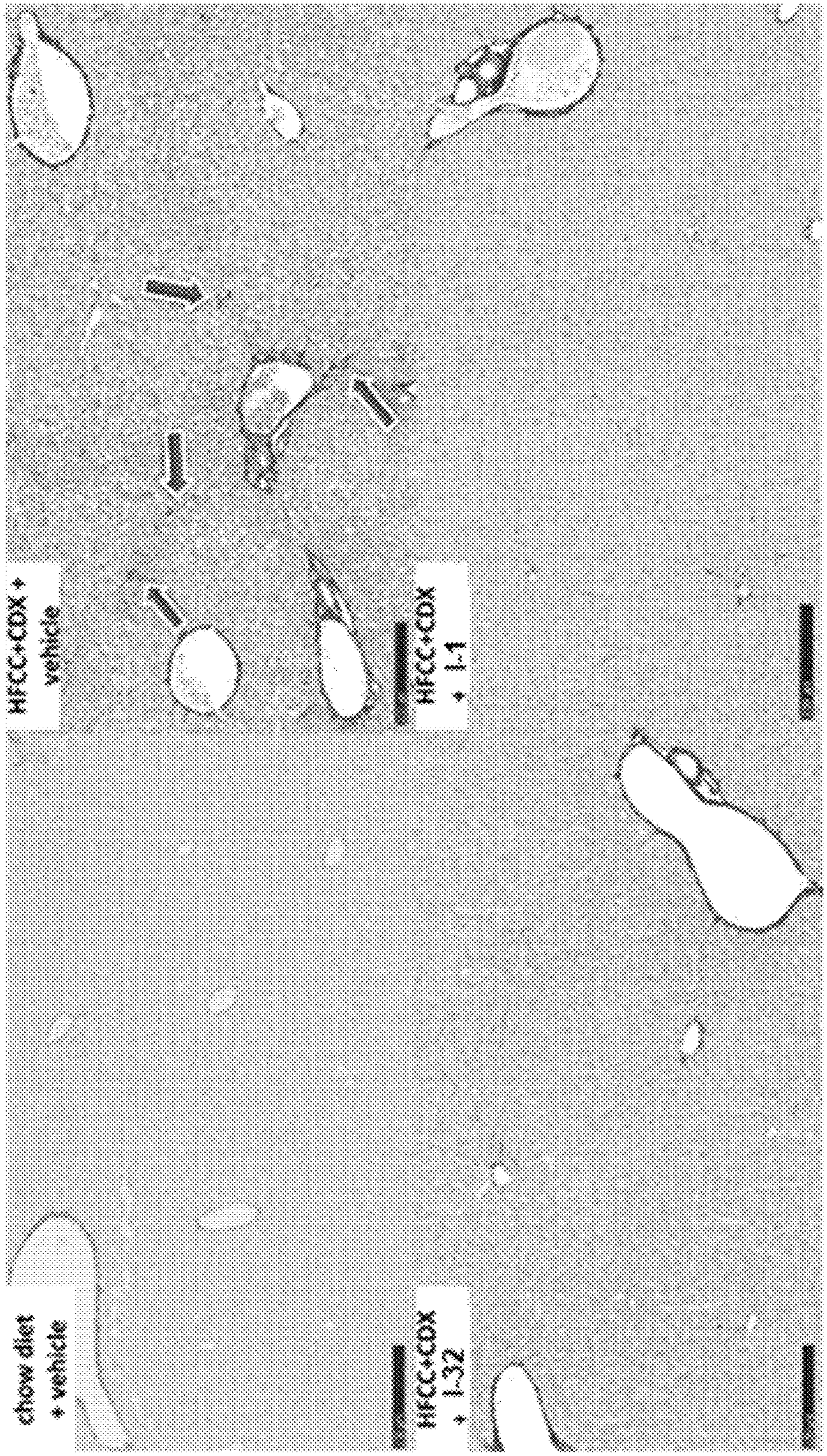

FIG. 7A displays a representative Sirius Red staining (×1.25 magnification) and FIG. 7B displays a representative Sirius Red staining (×10 magnification) at the end of the treatment period. Arrows indicate perisinusoidal and portal fibrosis.

Figure 8:
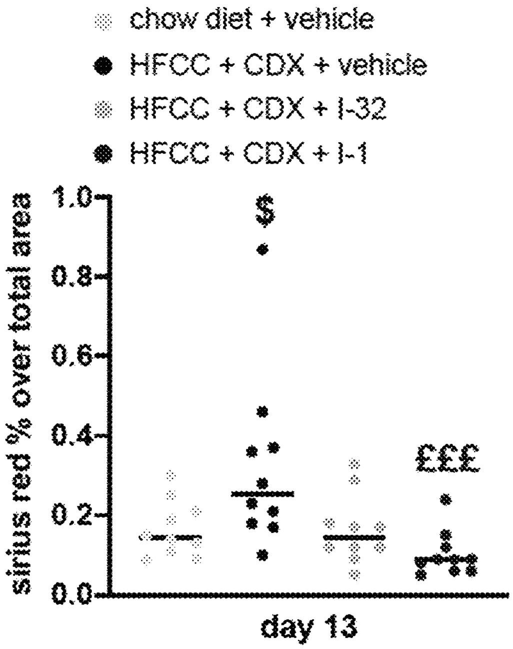
FIG. 8 presents Sirius red % over total liver area in mice treated with vehicle or Compound I-32 or Compound I-1.

FIG. 8 presents Sirius red % over total liver area: $ p<0.05 vs. chow diet+vehicle with a Mann-Whitney test. £££ p<0.001 vs. HFCC+CDX+vehicle with a Kruskal-Wallis plus Dunns post test.

Figure 9A:
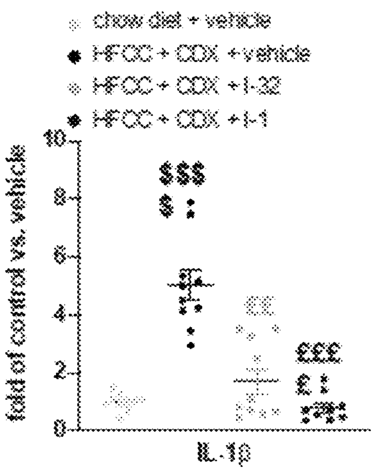
FIGS. 9A-9F display liver inflammation gene expression of the following in mice treated with vehicle or Compound I-32 or Compound I-1: IL-1β (FIG. 9A), MCP-1 (FIG. 9B), IL-6 (FIG. 9C), NF-κβ (FIG. 9D), TLR-4 (FIG. 9E) and TNF-α (FIG. 9F).
Figure 9B:
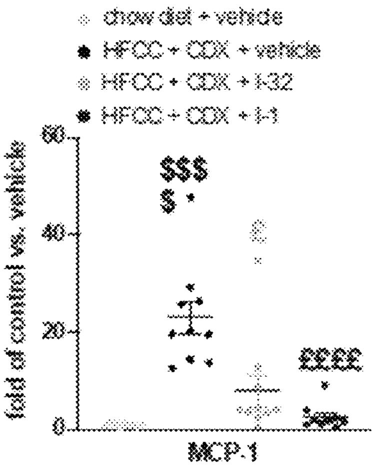
Figure 9C:
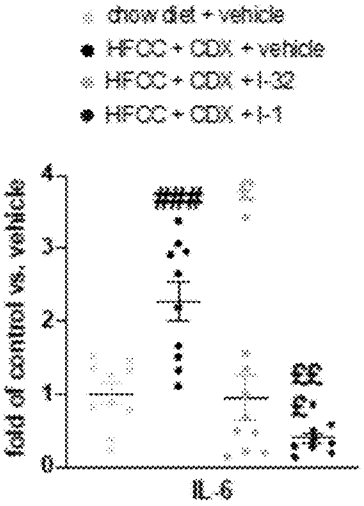
Figure 9D:
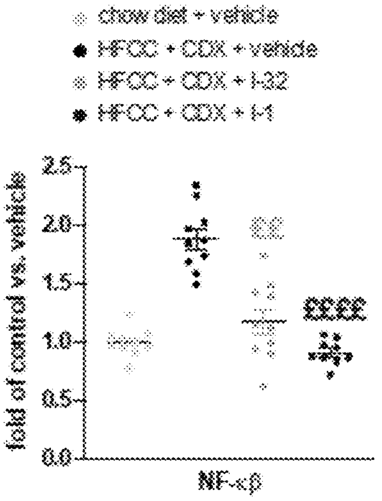
Figure 9E:
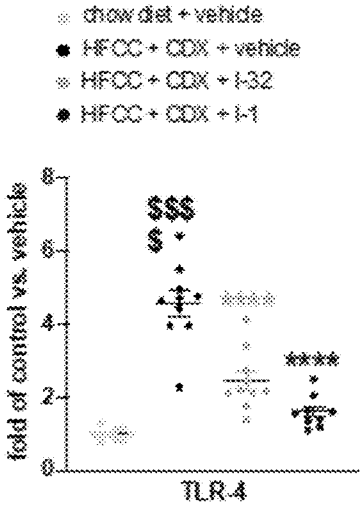
Figure 9F:
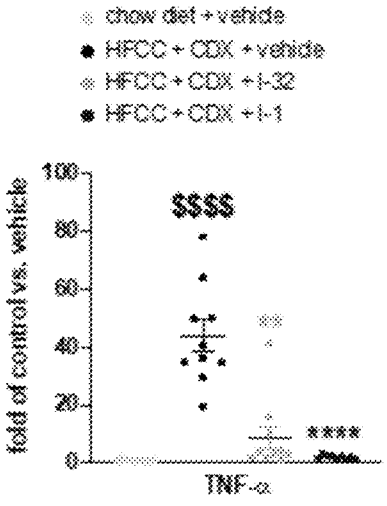

FIGS. 9A-9F display liver inflammation gene expression of IL-10 (FIG. 9A), MCP-1 (FIG. 9B), IL-6 (FIG. 9C), NF-κβ (FIG. 9D), TLR-4 (FIG. 9E) and TNF-α (FIG. 9F): (C) ### p<0.001 vs. chow diet+vehicle with a t-test. FIGS. 9A-9B and FIGS. 9D-9F: $$$$ p<0.0001 vs. chow diet+vehicle with a Mann-Whitney test. FIGS. 9E-9F:  p<0.01 and  p<0.0001 vs HFCC+CDX+vehicle with an ANOVA 2-ways plus Bonferroni's post test. FIGS. 9A-9**D: £ p<00.5, ££ p<0.01, £££ p<0.001 and ££££ p<0.0001 vs. HFCC+CDX+vehicle with a Kruskal-Wallis plus Dunns post test.

Figure 10A:
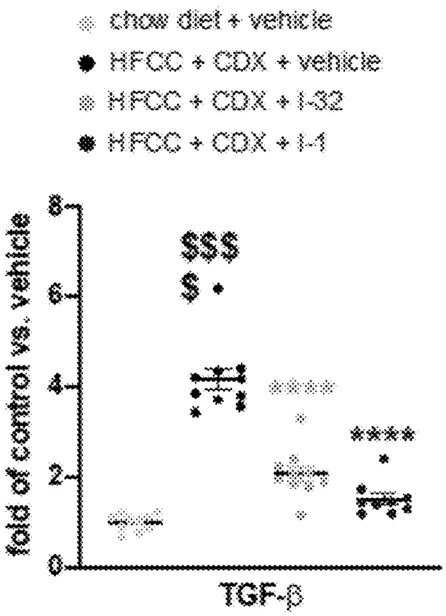
FIGS. 10A and 10B show liver fibrosis gene expression in mice treated with vehicle or Compound I-32 or Compound I-1: TGF-β (FIG. 10A) and coll1a1 (FIG. 10B).
Figure 10B:
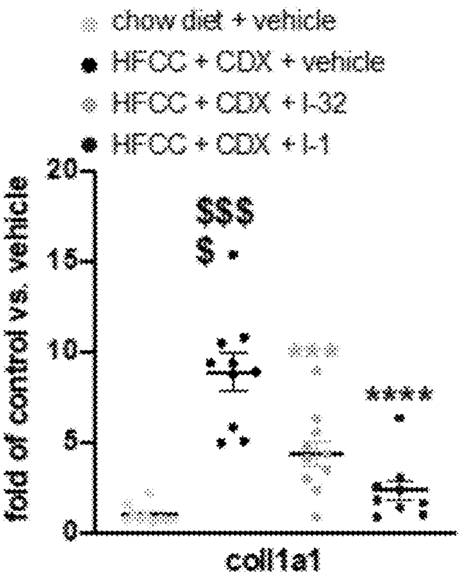

FIGS. 10A-10B present Liver fibrosis gene expression: TGF-β (FIG. 10A), coll1a1 $$$$ p<0.0001 vs. chow diet+vehicle with a Mann-Whitney test. * p<0.001 and ** p<0.0001 vs HFCC+CDX+vehicle with an ANOVA 2-ways plus Bonferroni's post test.

Figure 19A:
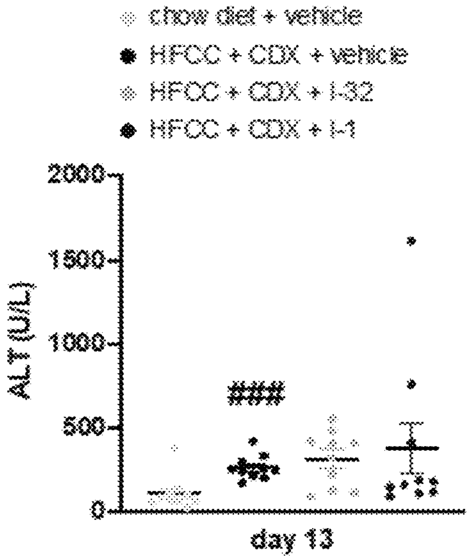
FIGS. 19A-19B display alanine aminotransferase (ALT) (FIG. 19A) and aspartate aminotransferase (AST) (FIG. 19B) plasma levels with Compound I-1 or Compound I-32.
Figure 19B:
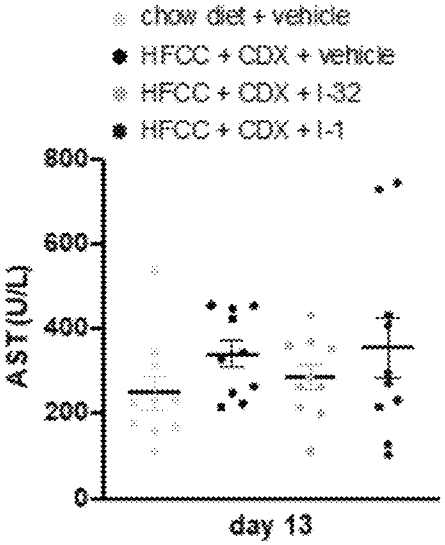

FIGS. 19A-19B display ALT (FIG. 19A) and AST (FIG. 19B) plasma levels with Compound I-1 or I-32. ###p<0.001 vs. chow diet+vehicle with a t-test.

Figure 20A:
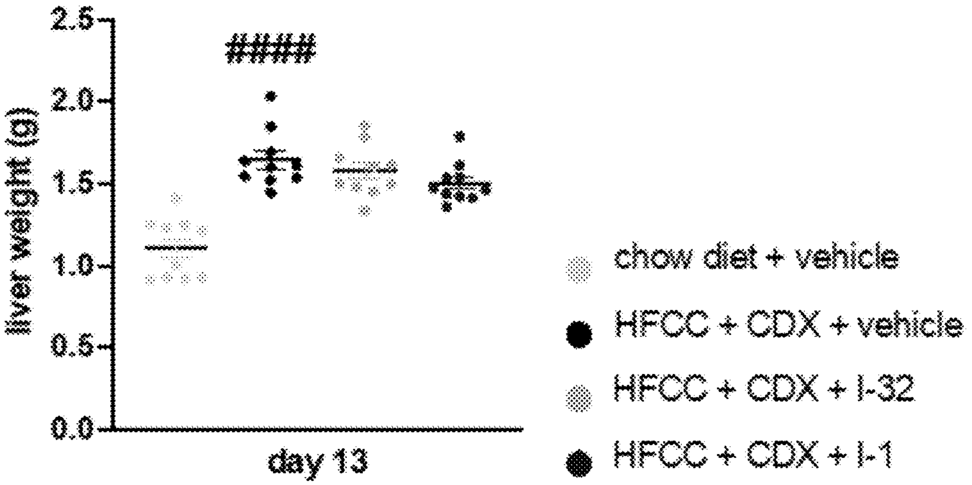
FIGS. 20A-20E shows liver weight (FIG. 20A), relative liver weight (FIG. 20B), hepatic free fatty acids (FIG. 20C), triglycerides (FIG. 20D) and cholesterol (FIG. 20E) with Compound I-1 or Compound I-32.
Figure 20B:
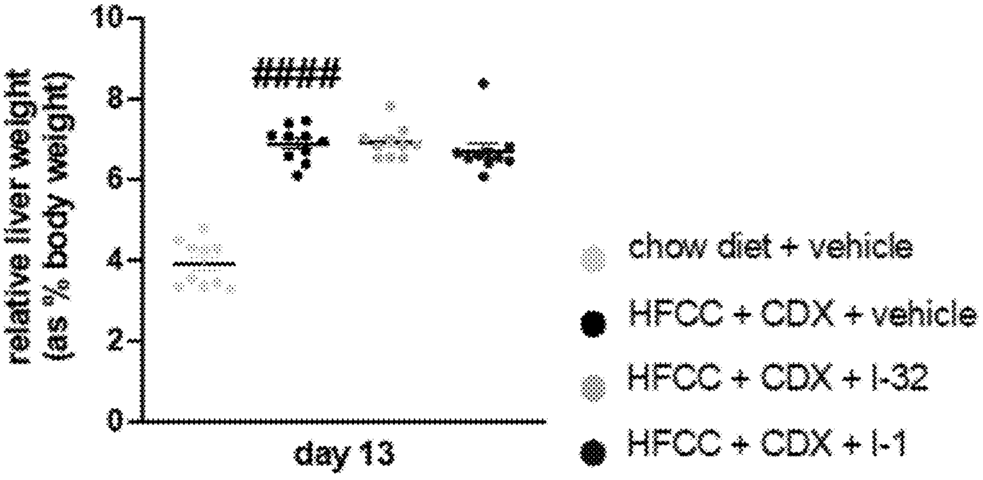
Figure 20C:
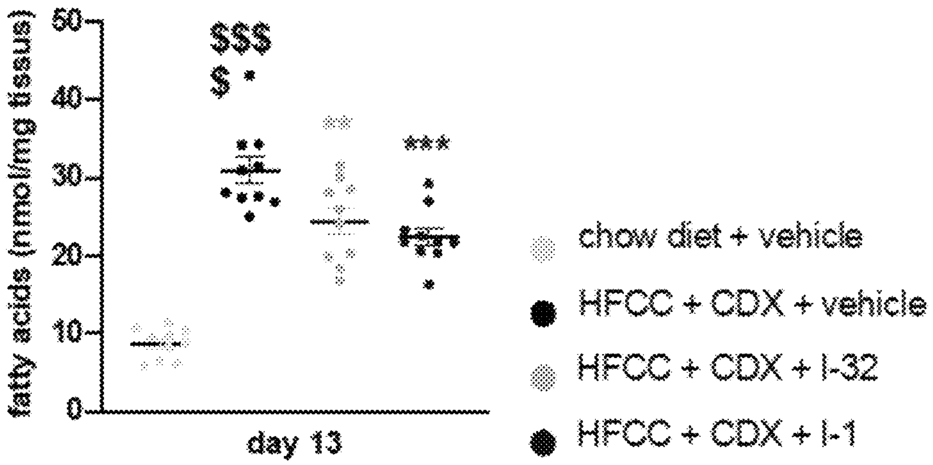
Figure 20D:
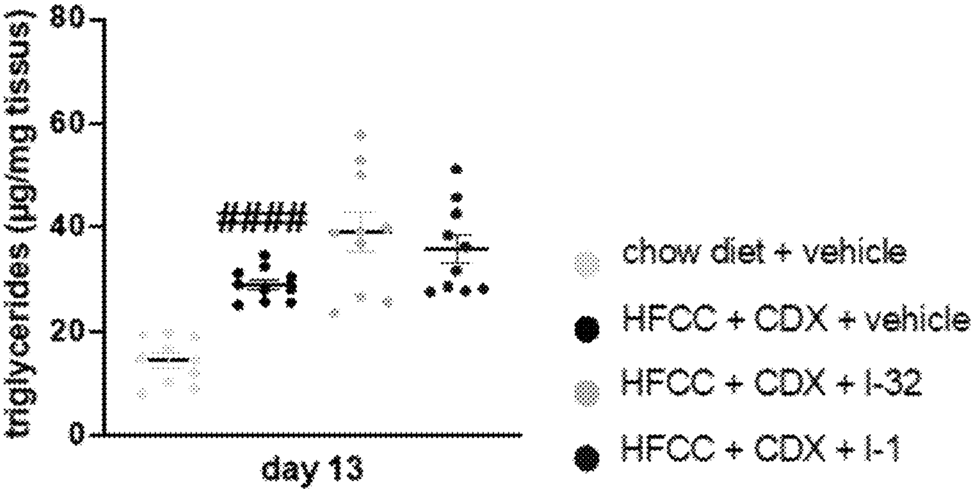
Figure 20E:
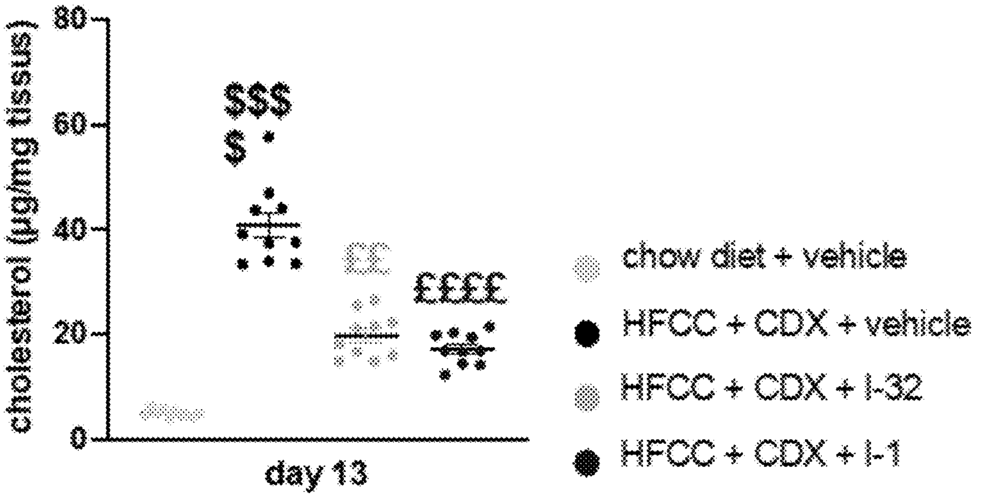

FIGS. 20A-20E shows liver weight (FIG. 20A), relative liver weight (FIG. 20B), hepatic free fatty acids (FIG. 20C), triglycerides (FIG. 20D) and cholesterol (FIG. 20E) with Compound I-1 or I-32. FIGS. 20A, 20B, and 20D: ####p<0.0001 vs. chow diet+vehicle with a t-test. FIGS. 20C and 20E: $$$$ p<0.0001 vs. chow diet+vehicle with a Mann-Whitney test. FIG. 20C:  p<0.01 and * p<0.001 vs HFCC+CDX+vehicle with an ANOVA 2-ways plus Bonferroni's post test. FIG. 20E: ££ p<0.01 and ££££ p<0.001 vs. HFCC+CDX+vehicle with a Kruskal-Wallis plus Dunns post test.

Figure 21A:
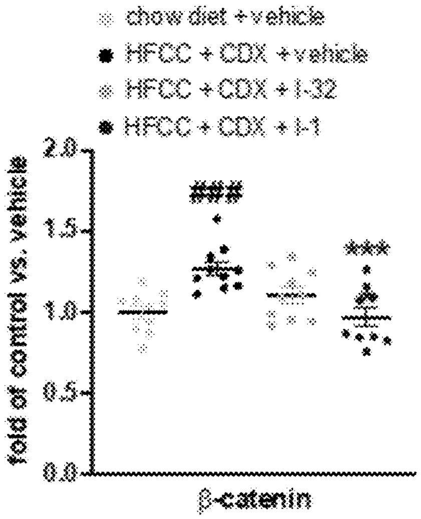
FIGS. 21A-21B display liver expression of β-catenin (FIG. 21A) and HIF-1α genes (FIG. 21B) genes.
Figure 21B:
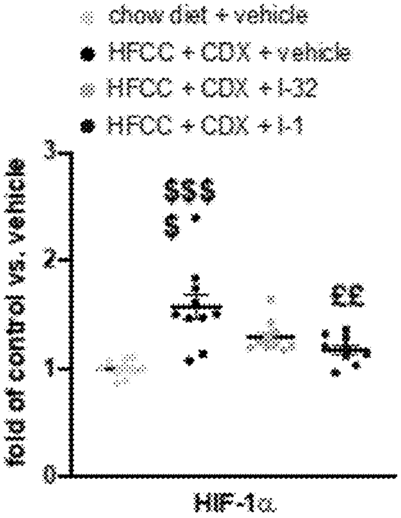

FIGS. 21A-21B display liver expression of β-catenin (FIG. 21A) and HIF-1α genes (FIG. 21B) genes. FIG. 21A: ###p<0.001 vs. chow diet+vehicle with a t-test; * p<0.001 vs HFCC+CDX+vehicle with an ANOVA 2-ways plus Bonferroni's post test. FIG. 21**B: $$$$ p<0.0001 vs. chow diet+vehicle with a Mann-Whitney test; ££ p<0.01 vs. HFCC+CDX+vehicle with a Kruskal-Wallis plus Dunns post test.

Figure 22A:
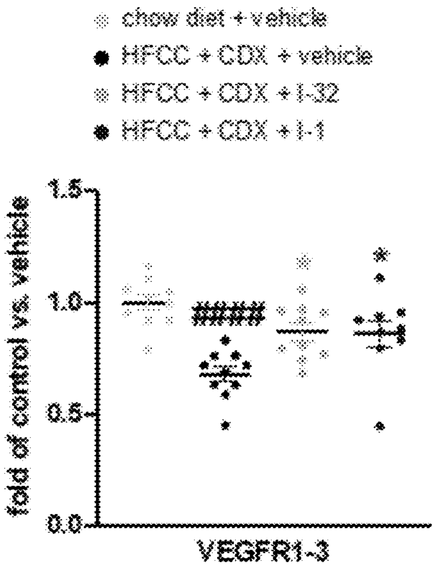
FIGS. 22A-22D show liver hepatocarcinoma gene expression of VEGFR1-3 (FIG. 22A), FGFR-1 (FIG. 22B), p38 MAP kinase (FIG. 22C), RIPK4 (FIG. 22D).
Figure 22B:
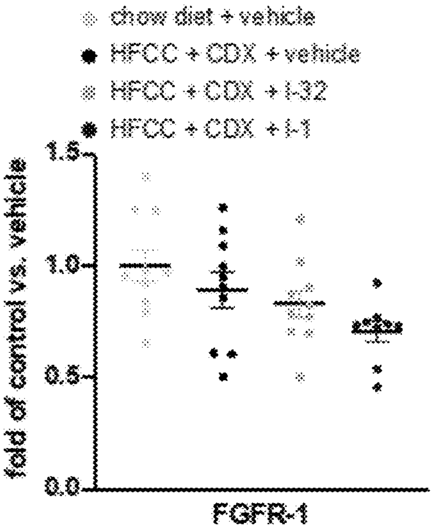
Figure 22C:
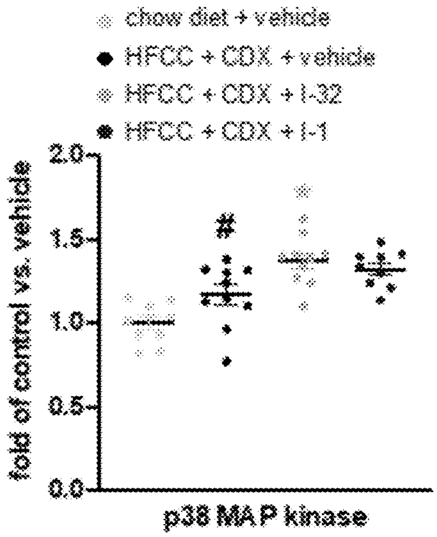
Figure 22D:
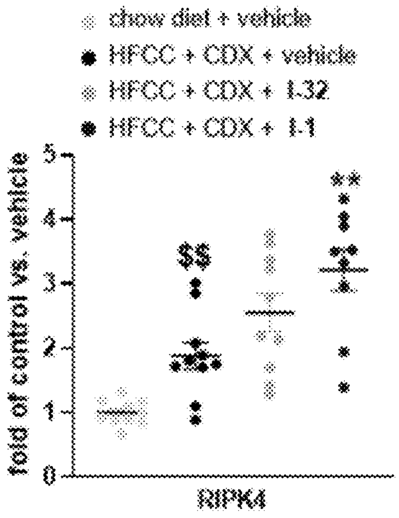

FIGS. 22A-22D show liver hepatocarcinoma gene expression of VEGFR 1-3 (FIG. 22A), FGFR-1 (FIG. 22B), p38 MAP kinase (FIG. 22C), RIPK4 (FIG. 22D). FIGS. 22A and 22C: #p<0.05 and ####p<0.0001 vs. chow diet+vehicle with a t-test. FIG. 22D: $$ p<0.01 vs. chow diet+vehicle with a Mann-Whitney test. FIGS. 22A, 22C, and 22D: * p<0.05, ** p<0.01 vs HFCC+CDX+vehicle with an ANOVA 2-ways plus Bonferroni's post test.

Figure 23A:
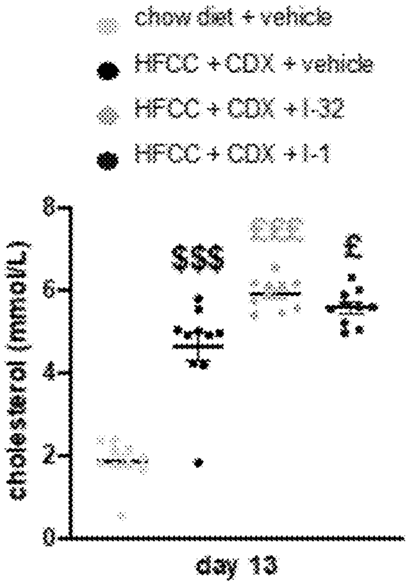
FIGS. 23A-23E display the plasma markers cholesterol (FIG. 23A), HDL (FIG. 23B), LDL (FIG. 23C), triglycerides (FIG. 23D), free fatty acids (FIG. 23E).
Figure 23B:
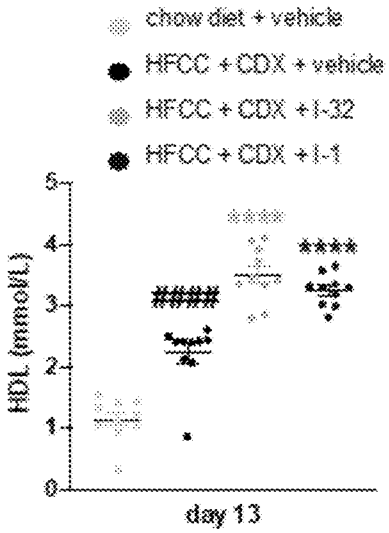
Figure 23C:
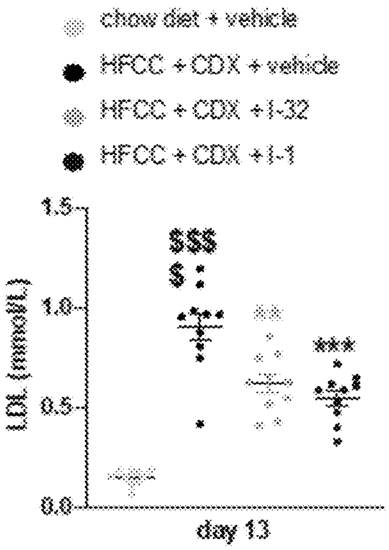
Figure 23D:
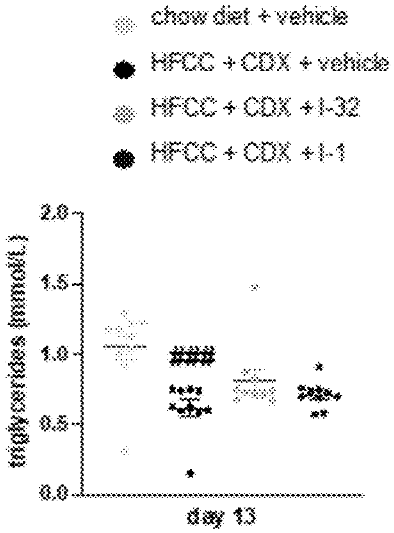
Figure 23E:
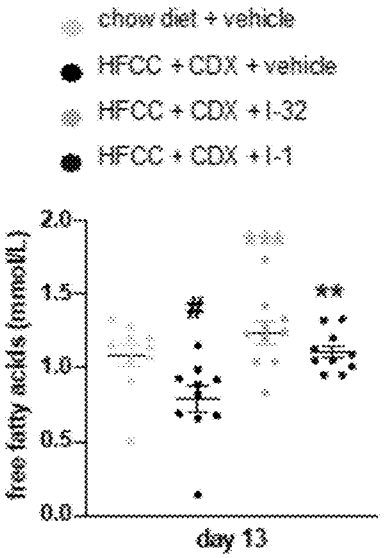

FIGS. 23A-23E display the plasma markers cholesterol (FIG. 23A), HDL (FIG. 23B), LDL (FIG. 23C), triglycerides (FIG. 23D), free fatty acids (FIG. 23E). FIGS. 23B, 23D, and 23E: #p<0.05, ###p<0.001 and ####p<0.0001 vs. chow diet+vehicle with a t-test. FIG. 23A and FIG. 23C: $$$ p<0.001 and $$$$ p<0.0001 vs. chow diet+vehicle with a Mann-Whitney test. FIGS. 23B, 23C, and 23E:  p<0.01, * p<0.001, ** p<0.0001 vs HFCC+CDX+vehicle with an ANOVA 2-ways plus Bonferroni's post test. FIG. 23**A: £ p<0.05 and £££ p<0.001 vs. HFCC+CDX+vehicle with a Kruskal-Wallis plus Dunns post test.

Figure 24A:
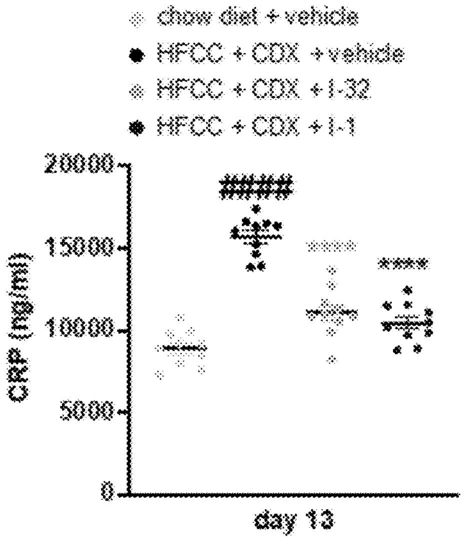
FIGS. 24A-24B display the plasma markers C-reactive protein CRP (FIG. 24A) and Serum amyloid A protein SAA (FIG. 24B).
Figure 24B:
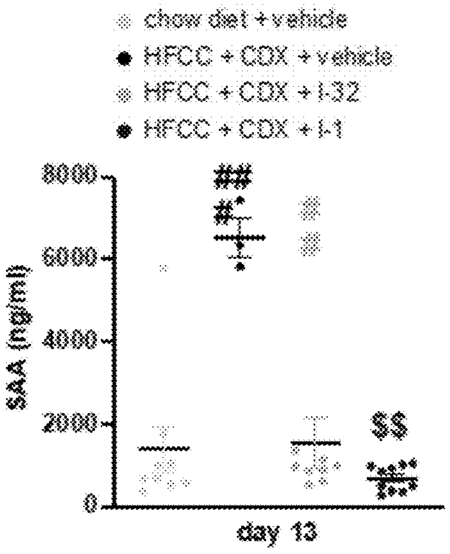
Figure 25A:
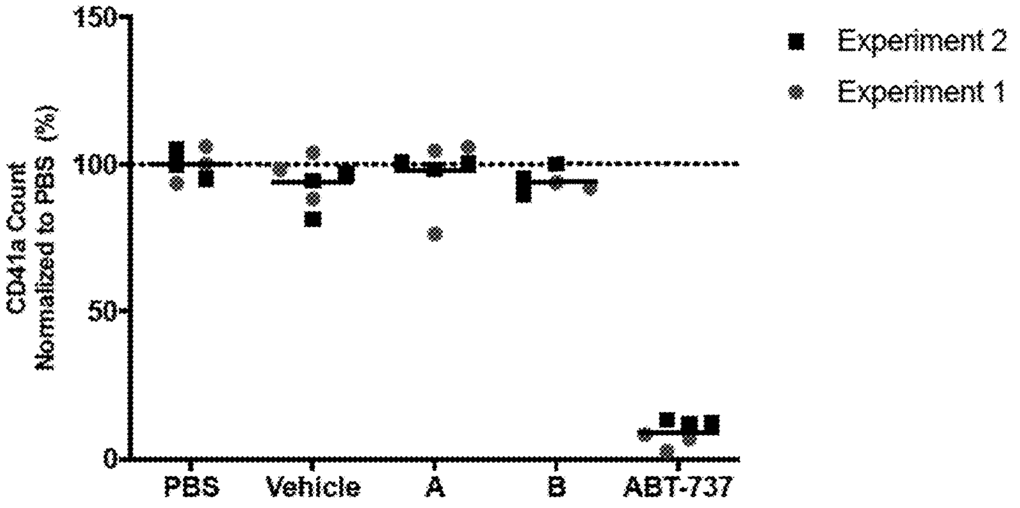
FIGS. 25A-25J shows that Compound I-32 (A) and Compound I-1 (B) do not significantly affect platelet production. Compound I-32 (A) and Compound I-1 (B) were added to expanded HSPC at day 0 (FIGS. 25A-25E) as they were cultured into megakaryocytes for 8 days or at day 6 (FIGS. 25F-25J). CD41a cell count (FIG. 25A), CD41aCd42b+ cell count (FIG. 25B), platelet levels (FIG. 25C), CD41a MFI (FIG. 25D) and CD41a FSC cell size (FIG. 25E) were analyzed at day 0. CD41a cell count (FIG. 25F), CD41aCd42b+ cell count (FIG. 25G), platelet levels (FIG. 25H), CD41a MFI (FIG. 25I) and CD41a FSC cell size (FIG. 25J) were analyzed at day 6.
Figure 25B:
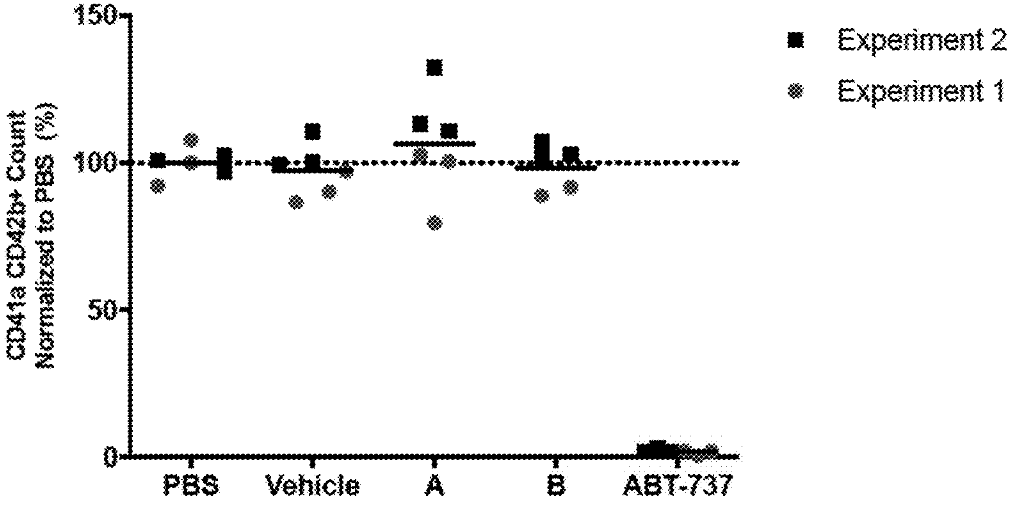
Figure 25C:
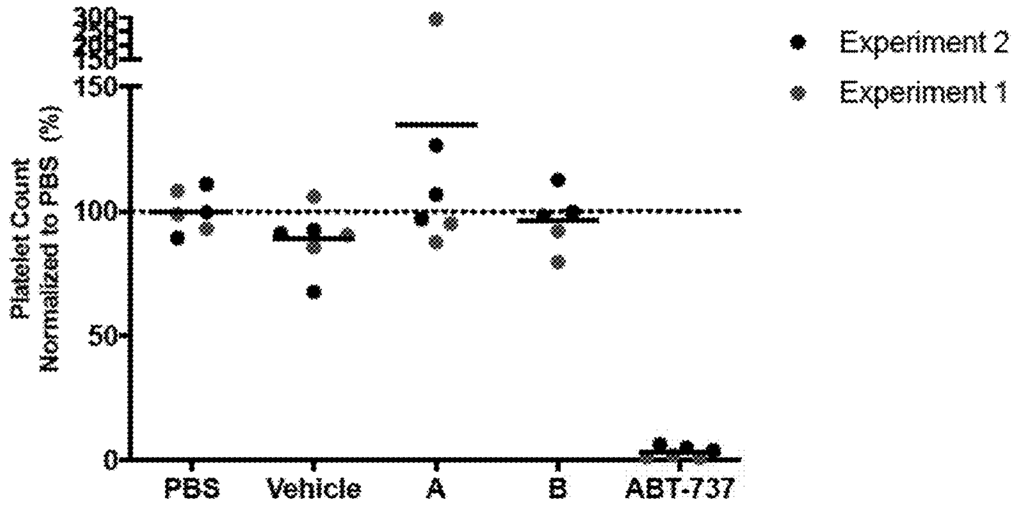
Figure 25D:
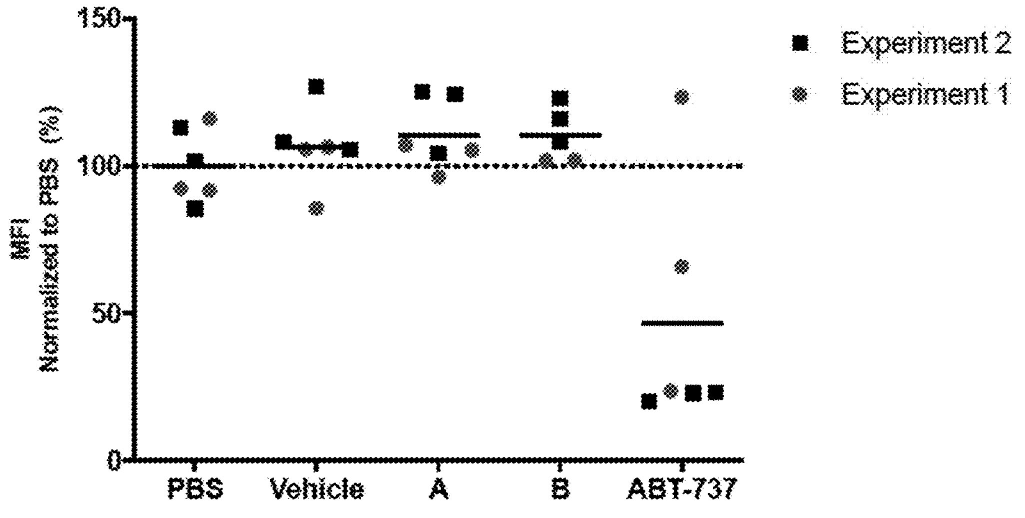
Figure 25E:
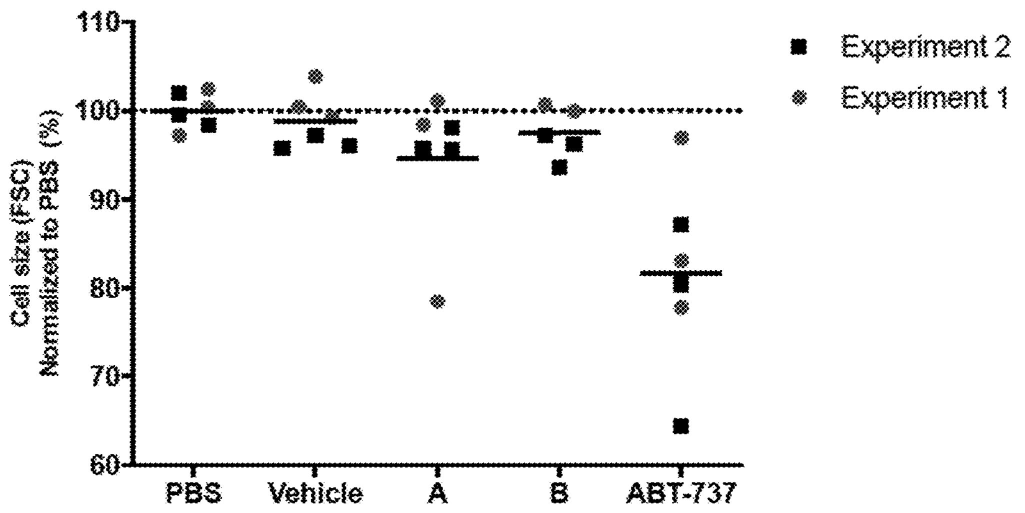
Figure 25F:
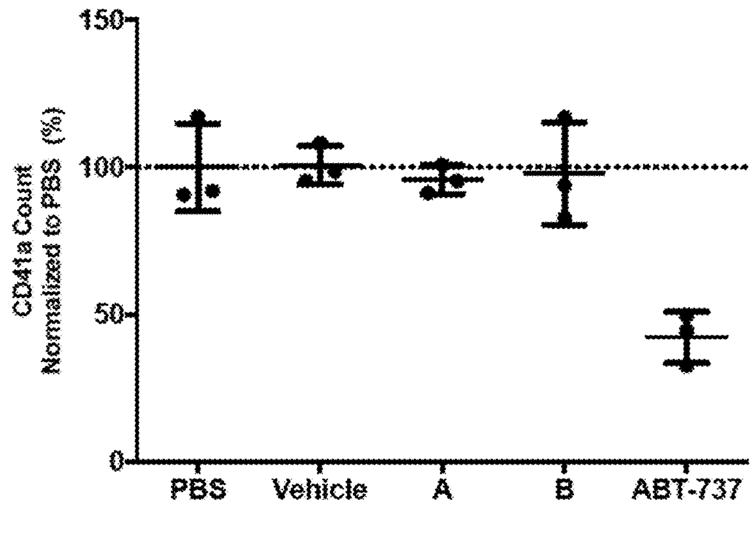
Figure 25G:
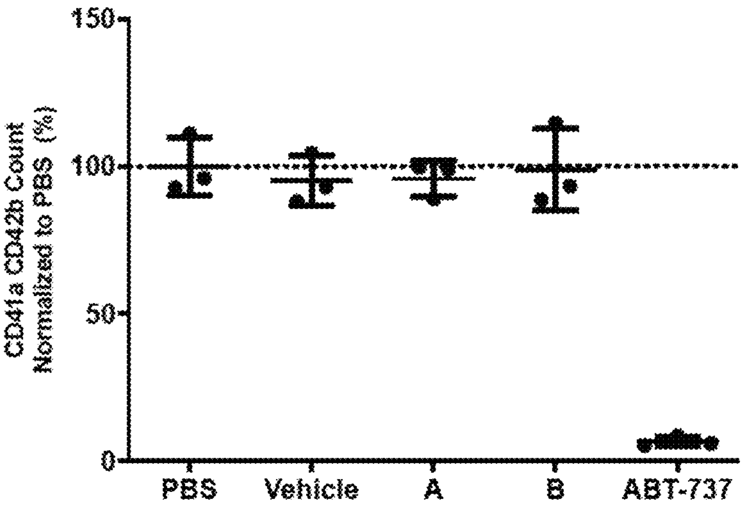
Figure 25H:
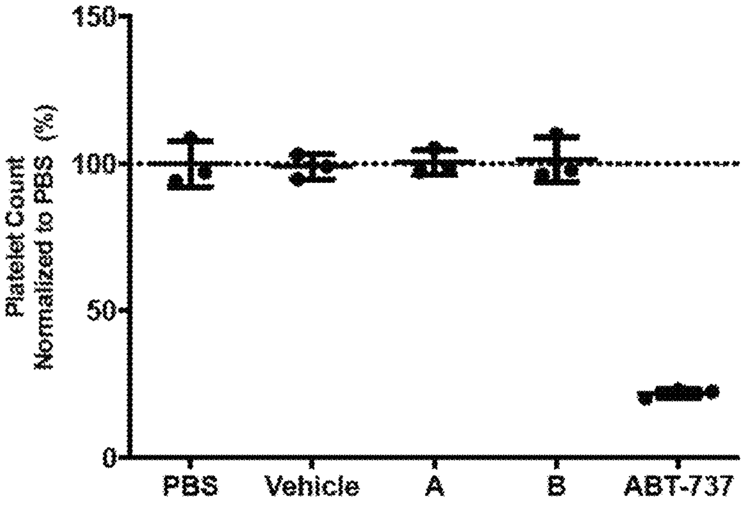
Figure 25I:
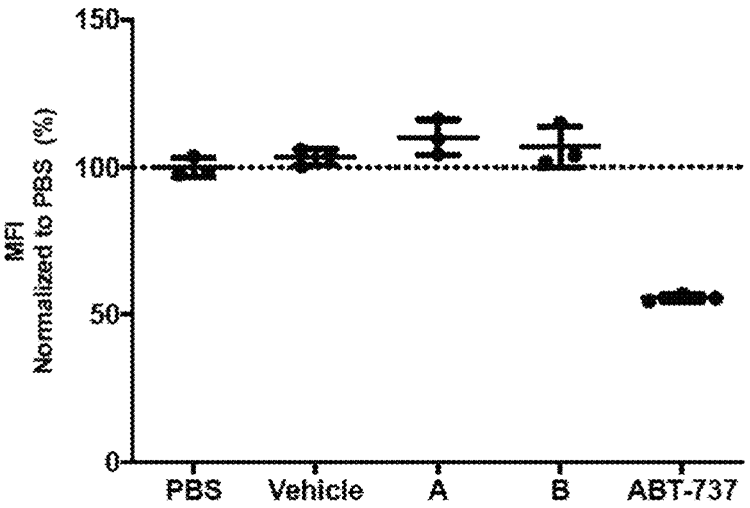
Figure 25J:
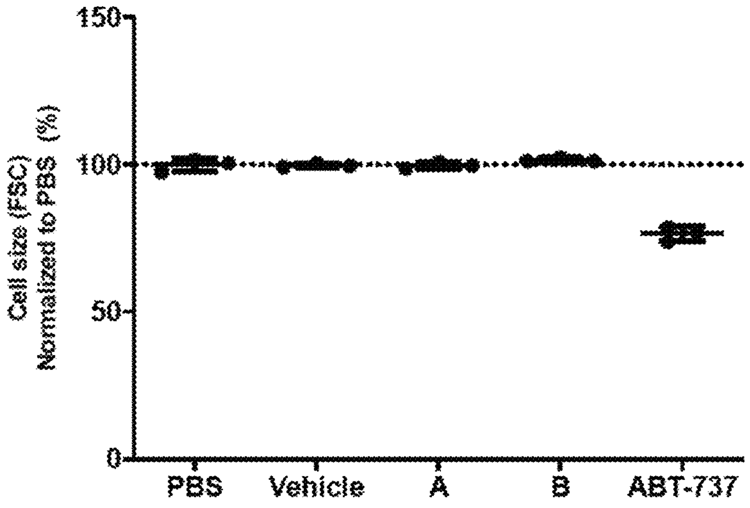

FIGS. 24A-24B display the plasma markers C-reactive protein CRP (FIG. 24A) and Serum amyloid A protein SAA (FIG. 24B). FIGS. 24A-24B: ###p<0.001 and ####p<0.0001 vs. chow diet+vehicle with a t-test. FIG. 24A: ** p<0.0001 vs HFCC+CDX+vehicle with an ANOVA 2-ways plus Bonferroni's post test. FIG. 24**B: ##p<0.01 vs. HFCC+CDX+vehicle with a t-test; $$ p<0.01 vs HFCC+CDX+vehicle with a Mann-Whitney test.

Example 8: Measurement of α-SMA (Smooth Muscle Actin) in Liver Section as a Measure of Stellate Cell Activation Detection of α-SMA by immunohistochemistry was performed on liver sections obtained from the experiment described in Example 7. Paraffin sections were deparaffinized, then incubated in antigen retrieval solution in a water bath using the "DAKO Target Retrieval Solution" solution.

Immunohistochemical staining was then performed: after blocking endogenous peroxidases (ref. S2023, Dako), and specific sites (ref. X0909, Dako, protein block). Sections were incubated with the primary antibody for 1 hour at room temperature. Slides were then rinsed and incubated with secondary antibody for 30 minutes. The signal was then revealed using a DAB solution (ref. K3468, Dako, 5 min incubation). Finally, counter-staining with hematoxylin (ref. K8008, Hematoxylin EnVision FLEX, Dako) was performed.

Negative controls were performed by substituting the primary antibody for an isotype control. Whole-section histomorphometric measurements of positive area for α-SMA were performed using computer-assisted image analysis on digitized sections. In brief, the histomorphometric measurements were generated with the software from Visiopharm (Denmark) using an automated approach. Analysis was performed on virtual whole sections at 20× magnification for morphometric evaluation. The pixel value at 20× magnification corresponded to 0.46 μm/pixel.

An algorithm was prepared for α-SMA morphometric measurement on liver-stained sections. The algorithm was generated with the Bayesian linear segmentation tool in the software package, which was further refined through training on a subset of sections from 5 animals. Major histology section artefacts, as well as, large vascular and portal structures were automatically (or manually dissected and removed from area of interest (AOI) or detected positive area.

For each section, all detected positive pixels were summed and reported in the raw data.

The following parameters were then either exported to Excel data sheets or mathematically determined in Excel:

Total area analyzed or AOI ($mm^2$),

Total α-SMA positive area ($mm^2$),

α-SMA area/total liver area analyzed (%)

Each analyzed image was individually verified for the accuracy of the morphometric evaluation.

Figure 11:
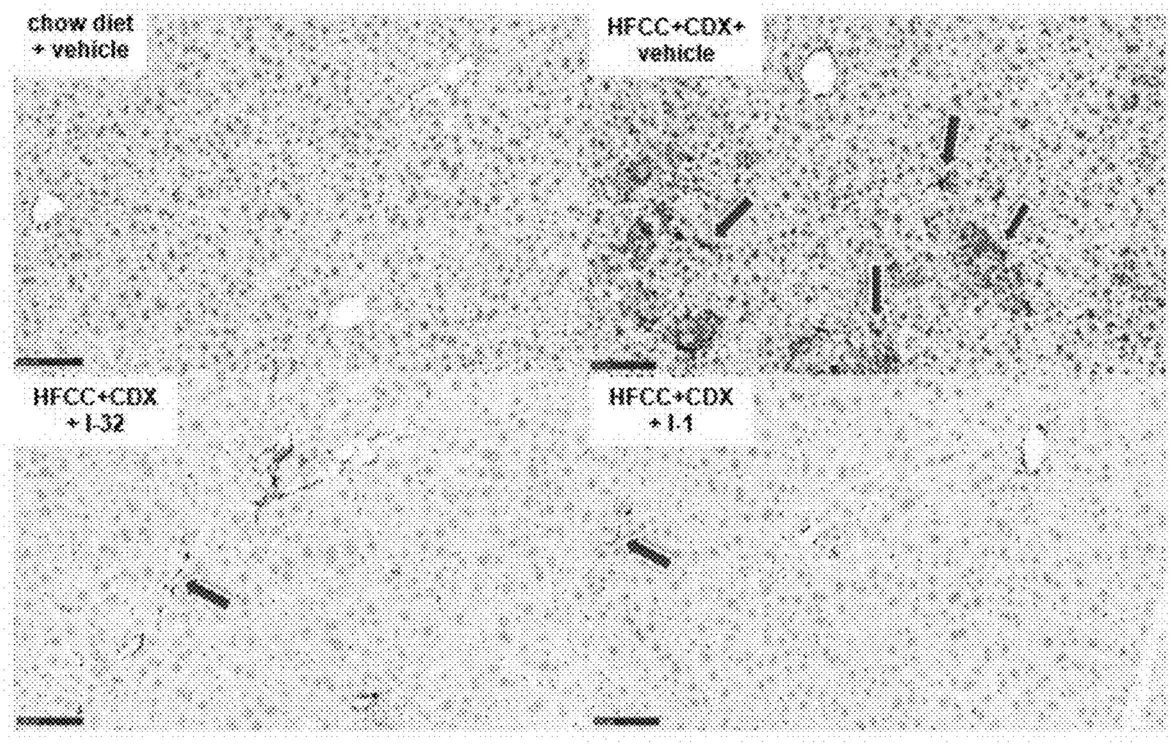
FIG. 11 shows representative α-SMA (smooth muscle actin) immunostaining (×20 magnification) at the end of the treatment in mice with vehicle or Compound I-32 or Compound I-1. Arrows indicate α-SMA immunostaining.

FIG. 11 presents representative α-SMA immunostaining (×20 magnification) at the end of the treatment period. Arrows indicate α-SMA immunostaining in brown.

Figure 12:
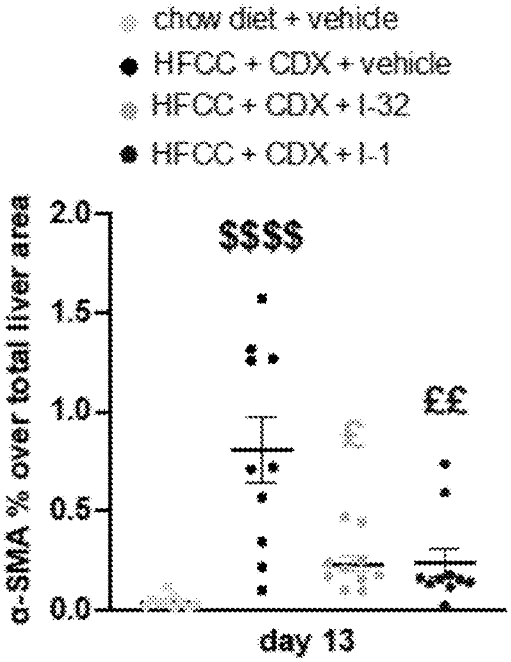
FIG. 12 shows α-SMA % over total liver area in mice treated with vehicle or Compound I-32 or Compound I-1.

FIG. 12 represents α-SMA % over total liver area. $$$$ p<0.0001 vs. chow diet+vehicle with a Mann-Whitney test. £ p<0.05 and ££ p<0.01 vs. HFCC+CDX+vehicle with a Kruskal-Wallis plus Dunns post test.

Figure 13A:
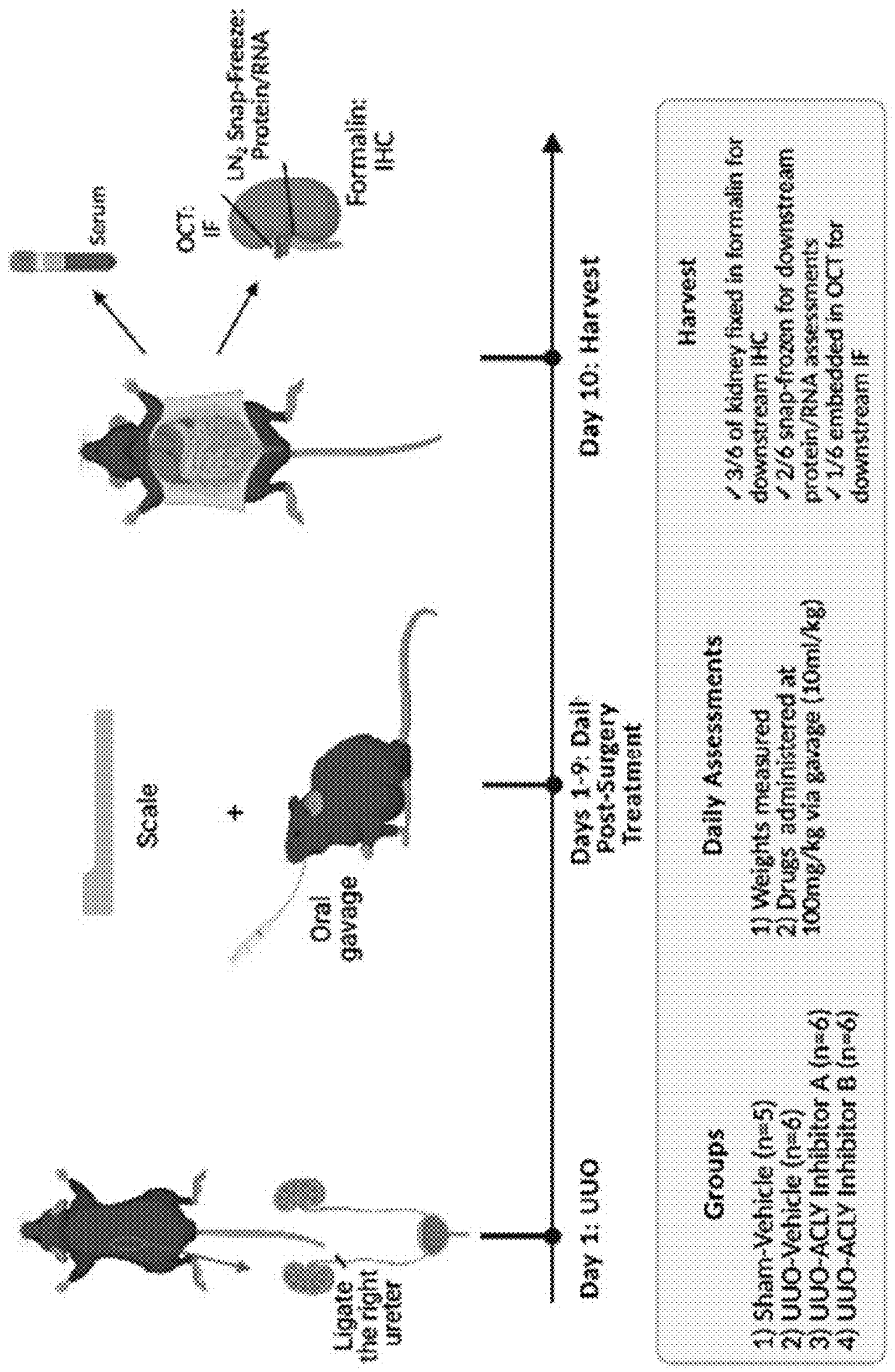
FIG. 13A shows unilateral ureter obstruction (UUO) model creation and timelines for a renal fibrosis study in mice treated daily with Compound I-1 ("UB") or Compound I-32 ("UA").
Figure 13B:
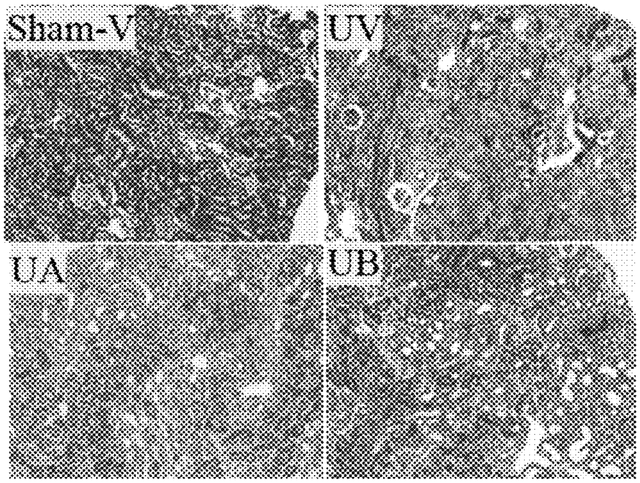
FIGS. 13B-13G show representative images and quantification of kidney fibrosis assessed using Trichrome staining (FIGS. 13B and 13C), Picosirius Red (PSR) staining (FIGS. 13D and 13E) and α-SMA staining (FIGS. 13F and 13G). (*, , *, ****p<0.05). Group Sham-V=sham surgery control group created by surgical exposure of the left ureter and lower pole of the kidney followed by closure of the incision; Group UV=vehicle; Group UA=Compound I-32; Group UB=Compound I-1.
Figure 13C:
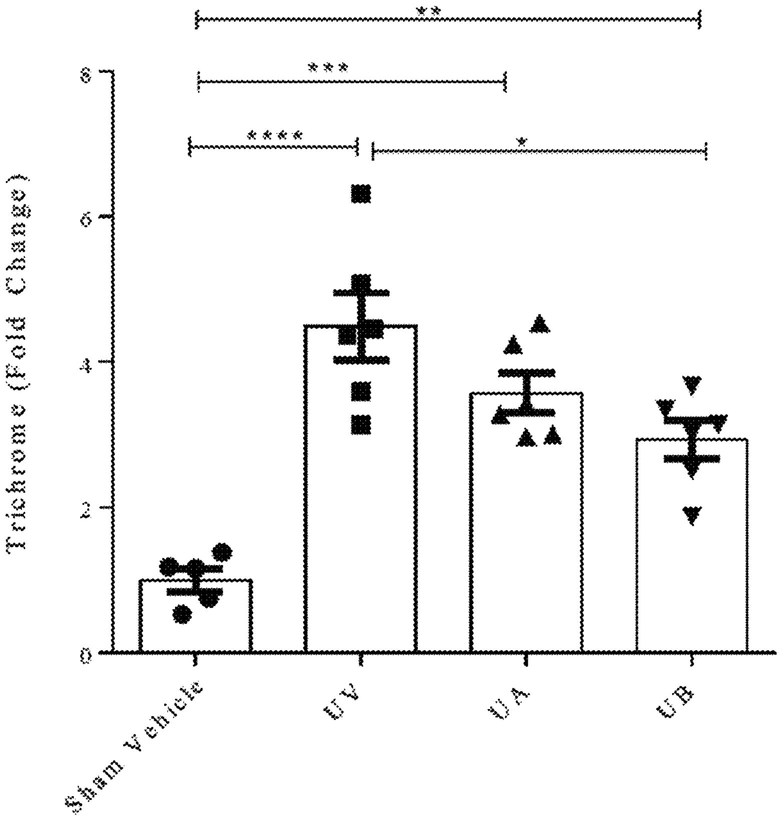

Example 9. Efficacy of Illustrative Compounds on Renal Fibrosis Using the Murine Unilateral Ureter Obstruction (UUO) Model Animal studies were carried out in accordance with the principles of laboratory animal care of the Canadian Council on Animal Care guidelines. Male C57BL/6 mice were obtained from Charles Rivers Laboratories. FIG. 13A summarizes the timeline for this experiment. UUO model was created as follows: male C57BL6J mice (8 weeks old from Charles River Laboratories) were anesthetized with 4% isofluorane and an anesthetic plane was maintained throughout surgery at 1.5-2% isofluorane with 1 L/min oxygen. A 0.5 cm incision was made longitudinally on the left flank. The left ureter and lower pole of the kidney was exposed, and the ureter was ligated with a 60 silk suture in close proximity to the renal pelvis. A sham operation control group was created by surgical exposure of the left ureter and lower pole of the kidney followed by closure of the incision. Subcutaneous fluids were given (1.5 ml 0.9% NaCl) and the incision was closed with 4'0 silk sutures followed by staples for the skin. Starting the day of model creation, the animals were given a daily dose of either vehicle alone (sham surgery and UUO control, 1.5% CMC and 0.2% Tween-20) or vehicle containing Compound I-32 or Compound I-1 (at 100 mg/kg) by oral gavage for 9 days following surgery. At the end of the treatment period mice were anesthetized prior to euthanasia by bilateral thoraco-abdominal incision. Blood was collected by cardiac puncture, followed by kidney perfusion with cold saline through left ventricular cannulation. The left kidney was removed, a sample taken and fixed in formalin for histological analysis. Trichrome staining was done on formalin-fixed sections (4 μm) following deparaffinization according to manufacturers instructions (Sigma HT15-1KT). Images were quantified by measuring the percentage of positive area using Image J on micrographs captured at ×200 magnification using the BX41 Olympus microscope. Statistical analysis was performed using GraphPad Prism 8. A one-way ANOVA was used to determine significance. A p-value of less than or equal to 0.05 was used as the criterion of significance. This route was selected because it simulates oral administration to mammalian, including human, subjects and ensures that the correct dose of compound is ingested by each animal.

Immunohistochemistry. Formalin-fixed kidneys were embedded in paraffin, then sectioned at 4 μm. After deparaffinization, they were stained with Masson's trichrome to assess collagen content (Sigma Aldrich, catalogue no. HT15-1T), picrosirius red (PSR) to more specifically assess pathogenic collagens I and III (Polysciences, Inc., catalogue no. 24901-500), αSMA as a marker of activated, profibrotic fibroblasts (PIERCE, catalogue no. MA1-06110; 30 min steaming for antigen retrieval, antibody used at 1:5000 for 2 h at room temperature), CD3 to identify T-lymphocytes (Dako, catalogue no. A0452; 30 min steaming for antigen retrieval, antibody used at 1:500 overnight at 4° C.) and F4/80 to identify, macrophages (done by the McMaster Histology Facility). Slides were counterstained with hematoxylin, dehydrated twice with 90% ethanol, cleared twice with xylene, coverslipped with mounting media, and then left to dry overnight before imaging. Masson's trichrome, αSMA, CD3 and F4/80 were imaged under transmitted light and quantified using ImageJ. The Olympus IX81 fluorescence microscope driven by Metamorph was used to image and quantify PSR staining. Images were quantified by measuring the percentage of positive area. All micrographs were captured at ×20 magnification.

Figure 13D:
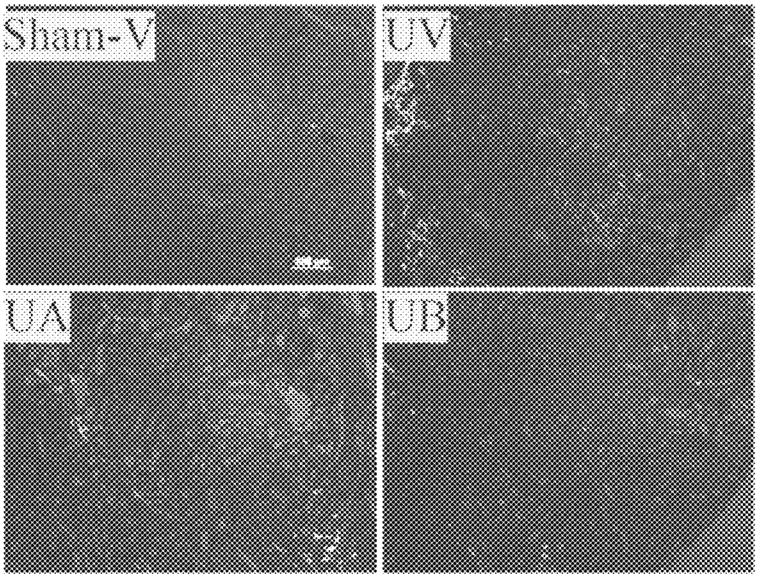
Figure 13E:
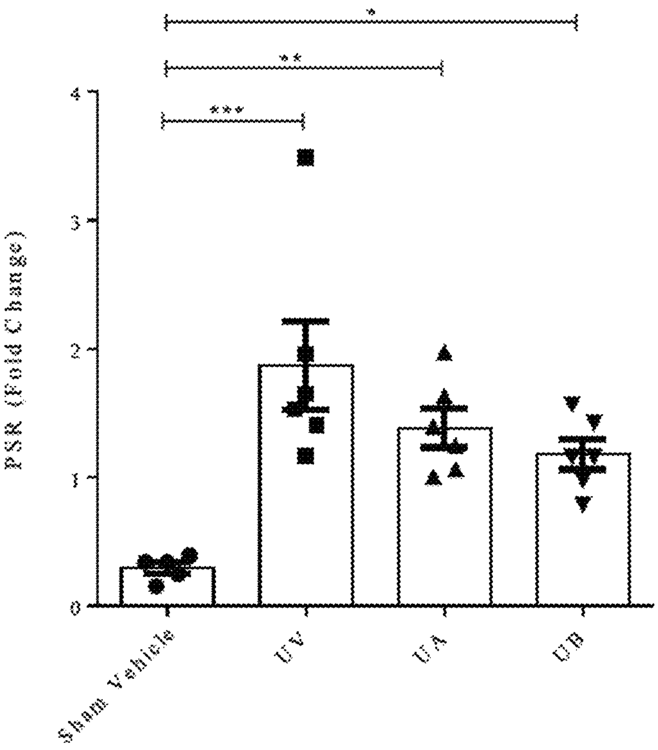
Figure 13F:
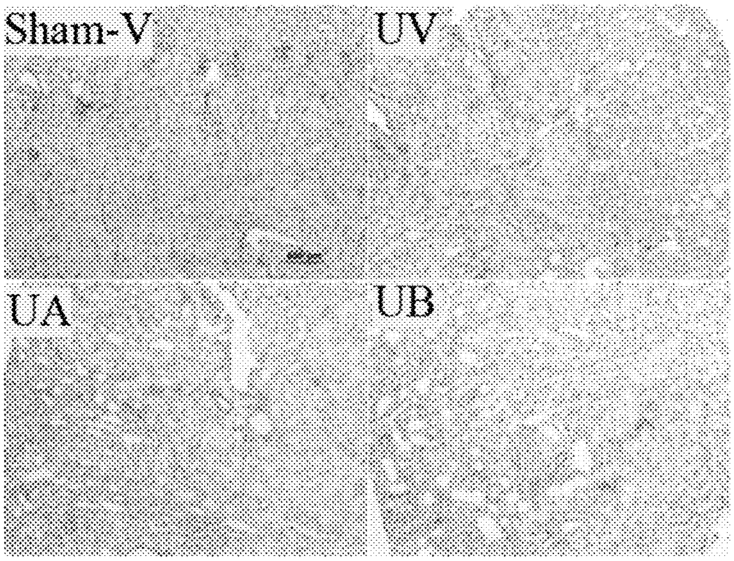
Figure 13G:
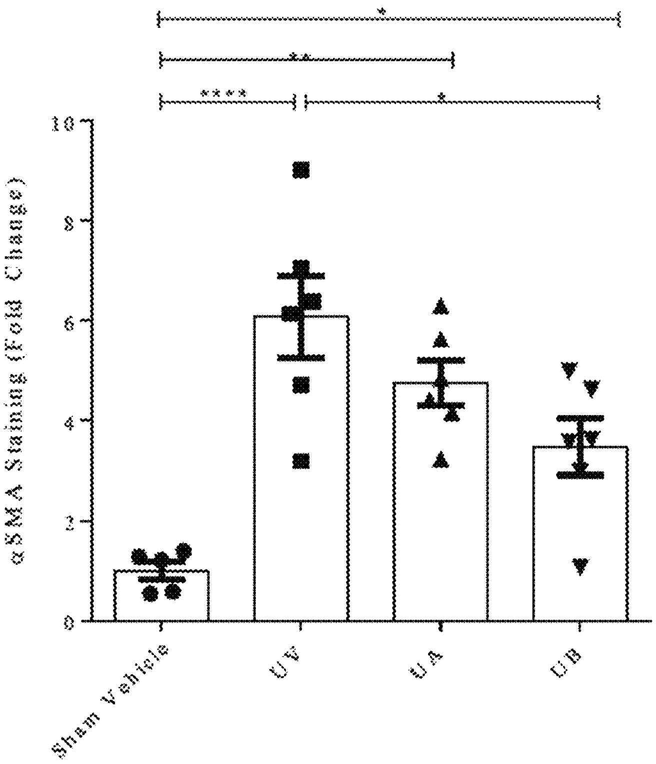
Figure 13H:
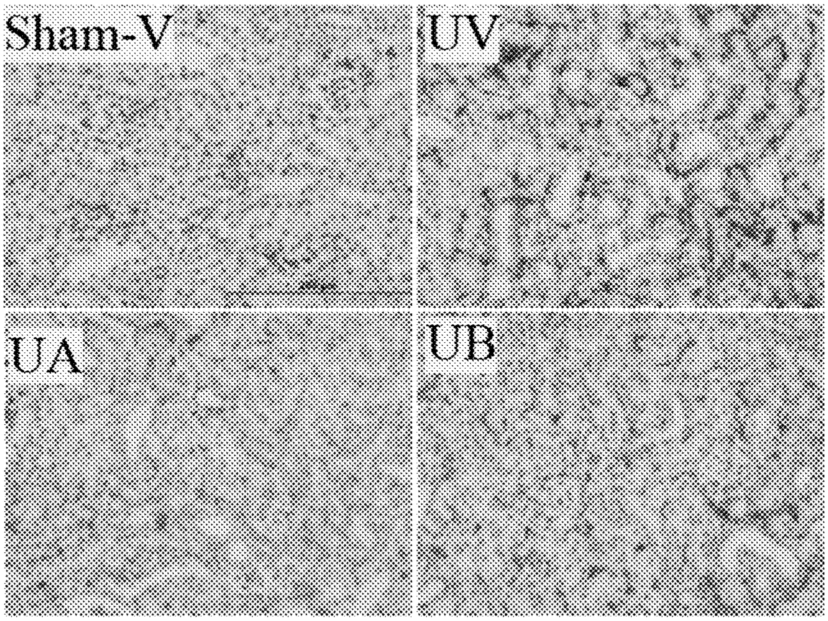
FIGS. 13H and 13I show representative images and quantification of macrophage infiltration in UUO kidneys using F4/80 staining. Group UV=vehicle; Group UA=Compound I-32; Group UB=Compound I-1.
Figure 13I:
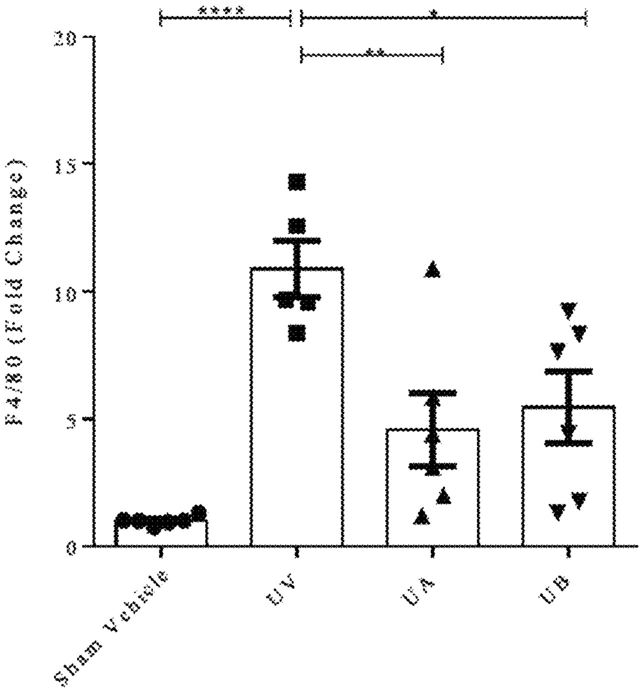
Figure 13J:
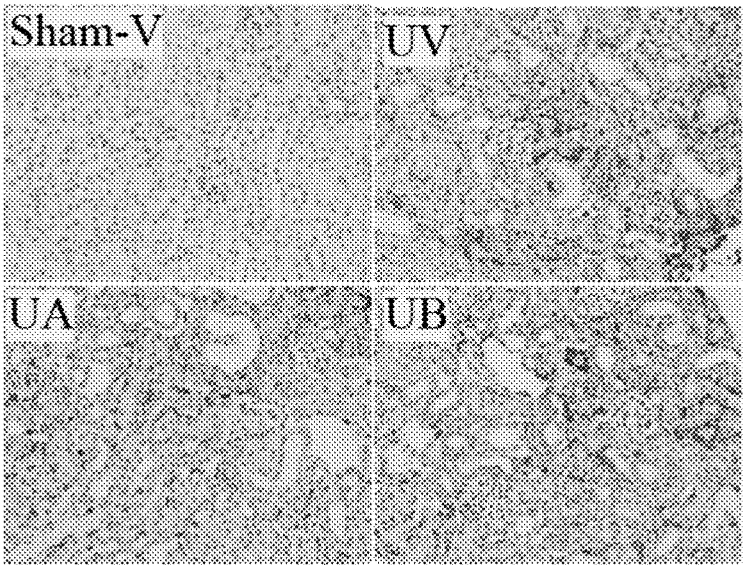
FIGS. 13J and 13K show representative images and quantification of T-lymphocyte infiltration in UUO kidney using CD3 staining. Group UV=vehicle; Group UA=Compound I-32; Group UB=Compound I-1.
Figure 13K:
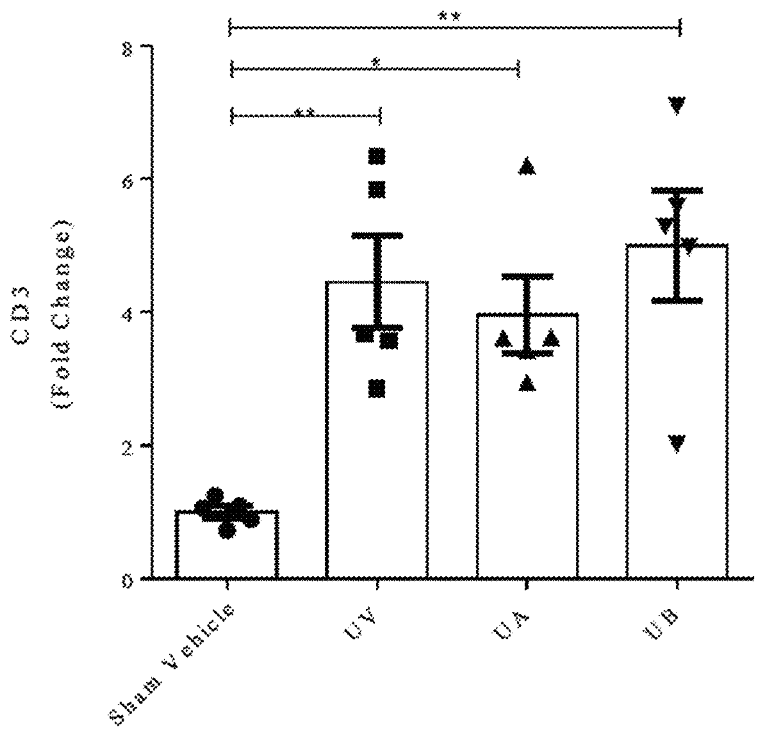

Compounds of the invention ameliorate UUO-induced renal fibrosis. FIGS. 13B-13G show that UUO in mice successfully induced renal fibrosis, with increases in Trichrome, PSR and αSMA (*, , *, **p<0.05). Increases in Trichrome and αSMA were decreased in Group UB (I-1) and showed a trend to reduction in Group UA (I-32). FIGS. 13B-13E show renal fibrosis in mice treated daily with Compound I-1 or Compound I-32 after 9 day of unilateral ureter obstruction (UUO). Percent area stained positively with immunohistochemical staining of F4/80 (FIGS. 13B-13C) or trichrome (FIGS. 13D-13E) in kidney photomicrographs taken at 200× magnification expressed as fold change relative to the sham-surgery control. In FIGS. 13D and 13**E, each bar represents the mean±the SEM, n=5-6, a p-value of <0.05 was considered to be statistically significant. * indicates statistically different from sham surgery group,  indicates statistically different for vehicle UUO group. Compounds of the invention reduce UUO-induced renal macrophage infiltration. Inflammation is a well-recognized feature of the UUO and other CKD models. The effect of Compound I-32 and Compound I-1 on both macrophage and T-lymphocyte infiltration were thus assessed. FIGS. 13H-13M show the significant increase in both macrophages (FIGS. 13H-13I, F4/80 stain) and T-lymphocytes (FIGS. 13J-13**K, CD3 stain) induced by UUO. In this experiment, both Compound I-32 (Group UA) and Compound I-1 (Group UB) significantly reduced macrophage infiltration, with no effect on T-lymphocytes.

Figure 13L:
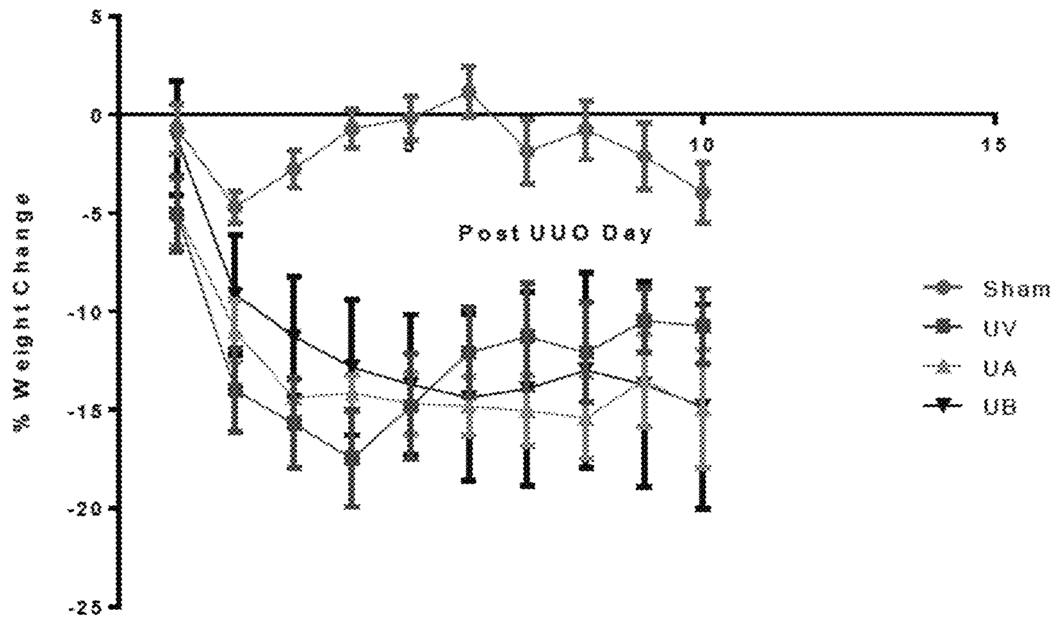
FIG. 13L shows that body weight of mice in UUO mice. Group UV=vehicle; Group UA=Compound I-32; Group UB=Compound I-1.
Figure 13M:
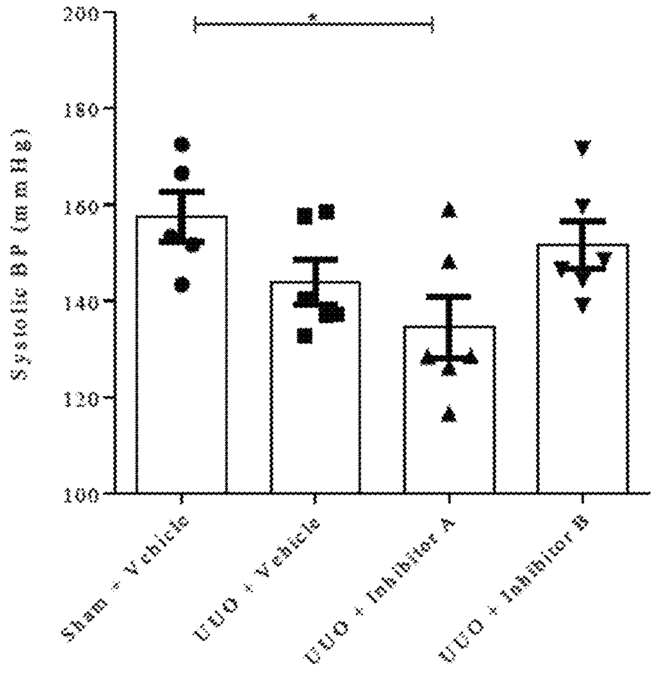
FIG. 13M shows systolic blood pressure in UUO mice. Inhibitor A=Compound I-32; Inhibitor B=Compound I-1.

Effects of treatment on weight and blood pressure. Weight was measured daily throughout the study, and is shown in FIG. 13L. All mice initially lost some weight perioperatively, with rapid recovery in sham operated mice. All mice with UUO, regardless of treatment, had weight loss to day 4-5, which subsequently stabilized. This is a greater degree of weight loss than usually observed with this model, and is likely related to the treatment with gavage and/or the viscous nature of the solution which was being gavaged. Systolic blood pressure significantly decreases in UUO mice treated with the compounds of the invention (FIG. 13M).

In conclusion, both Compound I-1 and Compound I-32 attenuated markers of fibrosis in the UUO model. Compound I-1 and Compound I-32 were similarly effective in decreasing macrophage infiltration, while T-lymphocyte infiltration was unaffected.

Example 10: Treatment of Bone Marrow Derived Macrophages Mϕ (BMDMs) with Compound I-1 Suppresses Lipopolysaccharide (LPS)-Induced Glycolysis and Inflammation Macrophage were isolated as follows: femurs and tibia were collected from mice, cleaned of any soft tissues and the ends were cut off from each bone. The tibia and femur were then transferred into 1.5 mL Eppendorf tubes and the marrow was extracted via centrifugation (1900 g×5 min), resuspended in DMEM and strained through a 40 μm strainer into a 50 ml falcon tube. The strainer was rinsed with an additional 40 mL of DMEM, the cell suspension was transferred to a T175 flask, an additional 60 mL of DMEM was added and the cells were cultured at 37° C. for 4 hours. Differentiation was initiated by adding 20 mL of L929 fibroblast conditioned media and 12 mL was plated on 100 mm dishes. The cells were then left for 7 days to differentiate into macrophages. The media was then aspirated, cells were scraped in 3 mL of DMEM, then pooled and diluted at a ratio of 1:2 with DMEM. The cell suspension was plated in 12-well plates and cells were allowed to adhere overnight. After adhesion, BMDMs were serum-starved for 2 hours then treated with lipopolysaccharide (LPS) (10 ng/mL) with or without Compound I-1 at a concentration of 50 μM for 4 hours. The media was removed, cells were washed in ice cold PBS, and mRNA extracted with Trizol reagent (ThermoFisher Scientific). cDNA was synthesized (Superscript III, ThermoFisher), and gene expression was assessed using the following Taqman probes (Thermofisher): IIIb (cat #Mm00434228_m1), 116 (cat #Mm00446190_m1) and Ppia (cat #Mm02342430_g1, used as an internal standard). Changes in gene expression were calculated using 2-delta cT method. Macrophage glycolytic rates were assessed using a Seahorse Bioanalyzer (XFe96, Agilent Scientific Instruments). Cells were differentiated for 7 days (as described above) then plated at a density of 70,000 cells/well on a 96-well Seahorse plate and allowed to adhere overnight. The following day cells were serum-starved for 2 hours then treated with LPS (100 ng/mL) and Compound I-1 (50 μM) and glycolytic rate was analyzed (Agilent Seahorse XFp Cell Energy Phenotype Test Kit, Cat #103275-100).

Figure 14:
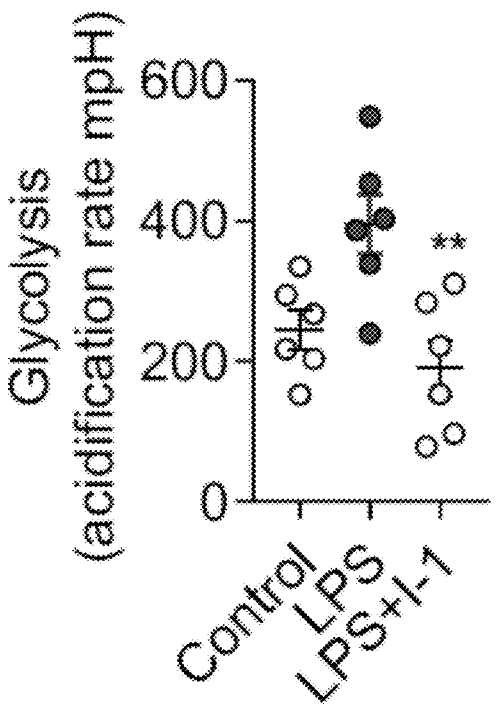
FIG. 14 shows suppression of LPS-induced glycolysis by treatment of bone marrow derived macrophages (BMDMs) with Compound I-1. Differentiated bone marrow derived macrophages were serum-starved for 2 hours then treated with vehicle (Control), LPS (10 ng/mL) or LPS+ACLYi (I-1) for 4 hours. Glycolytic rate was assessed using Seahorse bioanalyzer.
Figure 15:
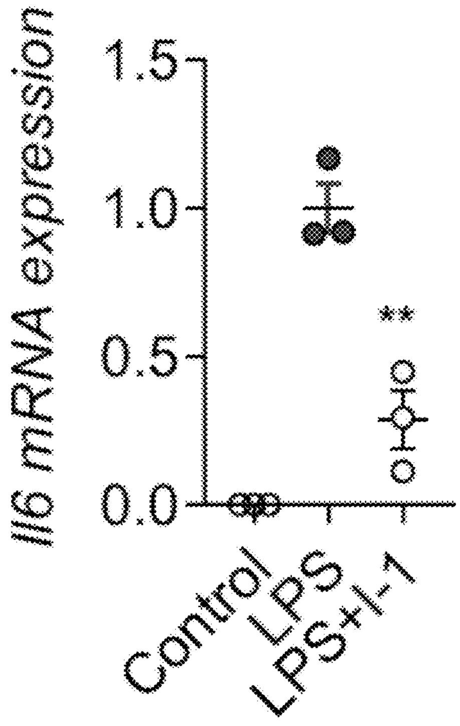
FIG. 15 shows suppression of the marker of inflammation, Il-6 mRNA, by Compound I-1 assessed by RT-qPCR.
Figure 16:
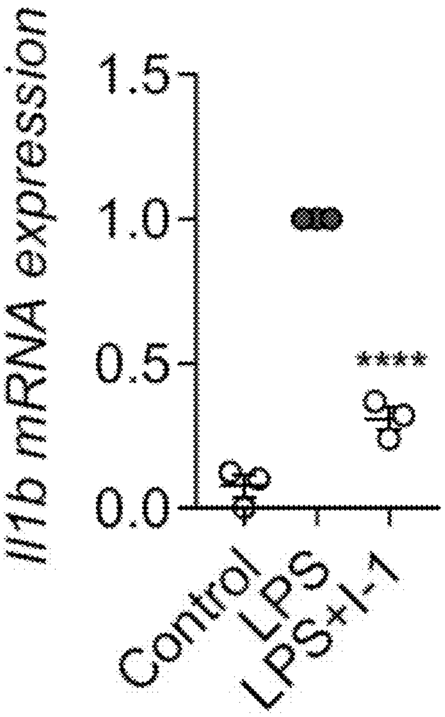
FIG. 16 shows suppression of the marker of inflammation, Il-1b mRNA, by Compound I-1 assessed by RT-qPCR.

FIGS. 14-16 show suppression of LPS-induced glycolysis and inflammation by treatment of BMDMs with Compound I-1. Differentiated bone marrow derived macrophages were serum-starved for 2 hours then treated with vehicle (Control), LPS (10 ng/mL) or LPS+ACLYi (1-1) for 4 hours. Glycolytic rate was assessed using Seahorse bioanalyzer (FIG. 14) and Il-6 (FIG. 15) and Il-1b mRNA (FIG. 16) were assessed by RT-qPCR.  p<0.001 and **p<0.0001 relative LPS.

Figure 17A:
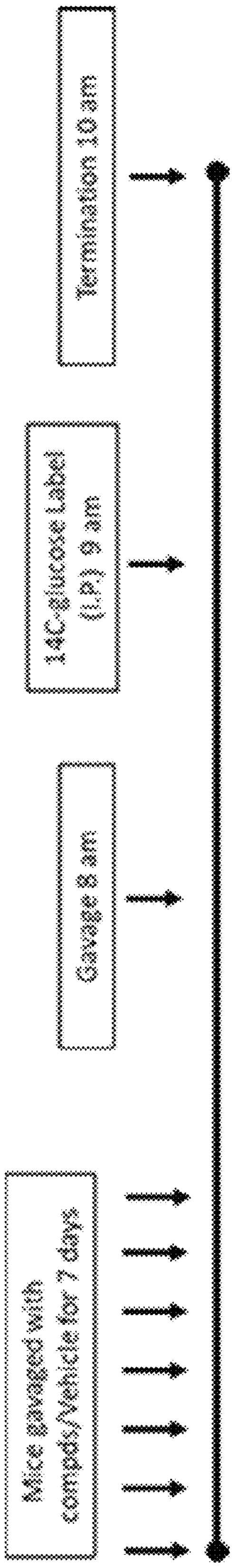
FIG. 17A shows an experimental protocol for assessing effects of compounds of the invention on liver de novo lipogenesis.

Example 11. Efficacy of Compound I-1 and Compound I-32 on Hepatic De Novo Lipogenesis (DNL) in a Murine Model of NASH Experimental Protocol. FIG. 17A describes the study protocol. Mice were dosed daily for 7 days with a single dose of either Compound I-32 or Compound I-1 at a dose of 10 mg/kg, 30 mg/kg or 60 mg/kg. On the $8^{th}$ day of the experiment mice receive final dose of Compound I-32 or Compound I-1, followed one hour later by an I.P. bolus of 14-C Glucose.

C57BL6J (8 weeks of age) were obtained for the Jackson Laboratory and fed a normal chow diet upon arrival. At ~10 weeks of age, mice were given a diet containing high fat and high fructose (Rodent Diet with 40 kcal % Fat (Mostly Palm Oil), 20 kcal % fructose, and 0.02% cholesterol, obtained from Research Diets, Product Code: D19101102) and housed at thermoneutral conditions (26-29° C.). After 7-8 months the mice were divided into 7 groups and received a single daily dose via gavage of either vehicle (1.5% CMC and 0.2% Tween-20) or vehicle containing Compound I-32 or Compound I-1 at a concentration of 10 mg/kg, 30 mg/kg, or 60 mg/kg for 7 days. On the morning of day 8, animals received a final dose and after 1 hour $^{4}$C-glucose (PerkinElmer) was administered at a concentration of 12 μCi per mouse in a volume of 0.1 ml in 0.9% saline I.P. One hour after $^{14}$C-glucose was given, animals were anesthetized by I.P. injection of Ketamine/Xylazine (150 mg/12.4 mg/kg, respectively). Blood was drawn through cardiac puncture; the liver was removed, and a sample was from the left lobe and frozen in liquid nitrogen. Liver tissue was chipped on dry-ice and the weight of the chip weight recorded (30-50 mg of tissue). Liver tissue was homogenized in 1 ml of 2:1 chloroform:methanol using a bead homogenizer at 5000 rpm for 2×12 seconds. Samples were incubated with gentle shaking at 4° C. for 2 hours, vortexed for 2×12 seconds, and then centrifuge at 7000 rpm for 10 minutes at 4° C. The supernatant was transferred to a 1.5 ml Eppendorf and 200 μl of 0.9% saline was added. Samples were vortexed for 2×12 seconds and centrifuged at 3000 rpm for 10 minutes at 4° C. 200 μl of the lower organic phase was removed and added to 5 ml of scintillation fluid. The amount radioactivity in the sample was measured by scintillation counting. The number of disintegrations per minute (DPM) were determined over a 5-minute period and normalized to the amount of liver tissue. 5-10 μl of plasma obtained at termination was also counted and lipid/gram tissue counts were normalized to plasma counts. Statistical comparisons were carried out using a one-way ANOVA followed by Dunnett's post hoc test using GraphPad Prism 8 software. A p-value of less than or equal to 0.05 was used as the criterion of significance.

Figure 17B:
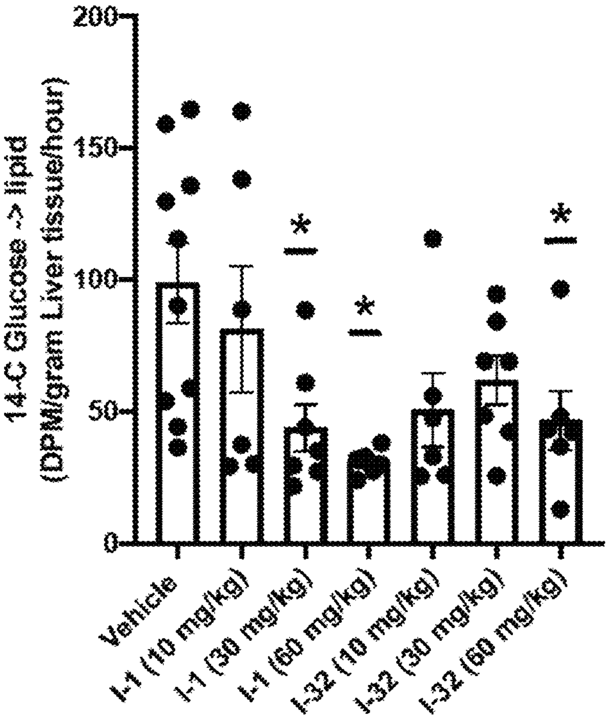
FIG. 17B displays hepatic de novo lipogenesis in mice treated with Compound I-1 or Compound I-32 for 7 days. $^{14}C$-Labeled lipids from glucose in the liver tissue after treatment with 10, 30, or 60 mg/kg of either Compound I-1 or Compound I-32 for seven days. Each bar represents the mean±the SEM, n=6-10. * indicates statistically different for vehicle group with a p-value <0.05.

Results. Total lipid synthesis was measured in C57BL/6J mice by incorporation of $^{14}$C-Glucose in the lipid fraction extracted with organic solvents. Compound I-1 did not significantly inhibit liver lipogenesis when mice were administered at 10 mg/kg. However, when mice were administered at 30 mg/kg and 100 mg/kg. Compound I-1 significantly inhibited lipogenesis by 56% (p=0.022) and 69% (p=0.005), respectively (FIG. 17B and Table 6). Compound I-32 inhibited lipogenesis at 10 mg/kg, 30 mg/kg and 100 mg/kg by ~50% at all three doses tested, however, this was only significant at 100 mg/kg (p=0.044). In FIG. 17B, each bar represents the mean±the SEM, n=6-10, and * indicates statistically different from vehicle group with a p-value <0.05.

TABLE 6

Descriptive statistics for hepatic de novo lipogenesis in mice treated with Compound I-1 or Compound I-32 for 7 days

| | Vehicle | I-1 (10 mg/kg) | I-1 (30 mg/kg) | I-1 (60 mg/kg) | I-32 (10 mg/kg) | I-32 (30 mg/kg) | I-32 (60 mg/kg) |
|---|---|---|---|---|---|---|---|
| Mean (DPM/gram liver tissue/hour) | 98.83 | 81.25 | 43.83 | 30.68 | 50.61 | 61.85 | 46.55 |
| Std. Error of Mean | 15.33 | 24.06 | 8.88 | 1.96 | 13.92 | 9.18 | 11.17 |
| % change from vehicle control | | 17.79 | 55.65 | 68.96 | 48.79 | 37.42 | 52.90 |
| p-value | | 0.887 | 0.022 | 0.005 | 0.073 | 0.210 | 0.044 |
| Number of values | 10 | 6 | 7 | 6 | 6 | 7 | 6 |

Compound I-1 inhibits liver lipogenesis in C57Bl6J mice by 56% and 69% when administered to mice at 30 mg/kg and 60 mg/kg. Compound I-32, lowered lipogenesis at 10 mg/kg, 30 mg/kg and 60 mg/kg by 49%, 37% and 53%, respectively. In conclusion, eight days of daily oral gavage of mice with 60 mg/kg of Compound I-32 or Compound I-1 in mice fed a high-fat and high-fructose diet suppresses liver lipogenesis.

Example 12: Effects of Compound I-32, Compound I-1, and Compound III-1 on In Vitro Lipid Synthesis in Isolated Hepatocytes Mouse primary hepatocytes were obtained by perfusing the mouse liver with collagenase solution through catheterization of the inferior vena cava (as described in Ford, et al. *Biochem J* 468, 125-132 (2015) and Fullerton, M. D., et al. *Nat Med* 19, 1649-1654 (2013)). After perfusion, collagen digested liver cells were re-suspended in William's E media (11 mM glucose) (Gibco) supplemented with 10% fetal bovine serum (FBS) (Gibco), 2 mM L-glutamine (Gibco) and 1% Antibiotic-Antimycotic (Gibco) mixture and seeded in white opaque 96-well plates. On the following day, the cells were serum-starved for 2 hours, then treated with 0 μM, 0.1 μM, 0.3 μM, 0.5 μM, 1 μM, 3 μM, 10 μM, and 100 μM of Compound I-32, Compound I-1, or Compound III-1 or Reference Compound (e.g., Compounds A-E and bempedoic acid) in the presence of $^{14}$C-Acetate (1 μCi/ml, PerkinElmer). Each of Compound I-32, Compound I-1, Compound III-1, and Reference Compound was solubilized in 100% DMSO to a final concentration of 100 mM stock solution. In the experimental condition, the stock solution was diluted in serum free media (William's E media (11 mM glucose) (Gibco), 2 mM L-glutamine (Gibco) and 1% Anti biotic-Antimycotic) to yield the desired concentration of each compound. DMSO was added where necessary such that all treatment conditions including control had a final concentration of DMSO of 0.03% v/v. After 4 hours of treatment, the plates were washed two times with PBS (×1) and 100 μL microscint fluid (Microscint O, part #601361) was added in each well. Plates were wrapped with aluminum foil and were shaken at 250 rpm for 2 h. After 2 h of shaking, $^{14}$C incorporation into lipid was determined by liquid scintillation counting using a TopCount NXT Microplate Scintillation and Luminescence Counter (Perkin Elmer).

The effects of Compound I-32. Compound I-1, and Compound III-1 on mouse primary hepatocyte lipogenesis are represented in Table 1. Each Compound was assayed at a concentration of 0 μM (vehicle control), 0.1 μM, 0.3 μM, 0.5 μM, 1 μM, 3 μM, 10 μM, and 100 μM, unless otherwise noted. Statistically significant inhibition was determined by one-way ANOVA and Dennett's post hoc test where appropriate. Table 7 shows the percent change and p-value determined at 100 μM compared to the vehicle control. $IC_{50}$ values were determined by nonlinear regression. All statistical analyses were carried out using GraphPad Prism 8 software. A p-value of less than or equal 0.05 was considered significant.

TABLE 7

Activity of Illustrative Compounds of the Invention and of Reference Compounds for Inhibition of Incorporation of 14C-Acetate in Primary Mouse Hepatocyte Total Lipids over a 4-Hour Period

| Compd | Structure | % change from control at 100 μM ± SEM(n) | Statistical difference vs control | p-value | $IC_{50}$ in μM |
|---|---|---|---|---|---|
| A | 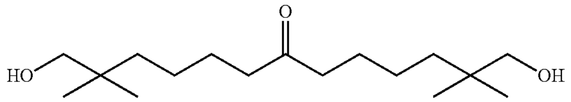 [SMILES: CC(C)(CO)CCCCC(=O)CCCCC(C)(C)CO] | −41 ± 4.8 (n = 2) | Yes | 0.0229 | 73.23 |
| B | 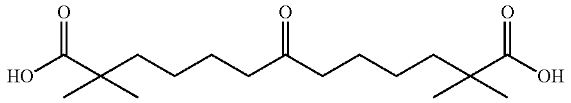 [SMILES: CC(C)(CCCCC(=O)CCCCC(C)(C)C(=O)O)C(=O)O] | −69 ± 2.3 (n = 4) | Yes | <0.0001 | 25.58 |

TABLE 7-continued

Activity of Illustrative Compounds of the Invention and of Reference Compounds for Inhibition of Incorporation of 14C-Acetate in Primary Mouse Hepatocyte Total Lipids over a 4-Hour Period

| Compd | Structure | % change from control at 100 μM ± SEM(n) | Statistical difference vs control | p-value | $IC_{50}$ in μM |
|---|---|---|---|---|---|
| C | 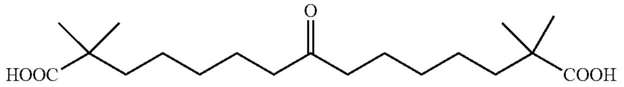 [SMILES: CC(C)(CCCCCC(=O)CCCCCC(C)(C)C(=O)O)C(=O)O] | −76 ± 4.7 (n = 4) | Yes | 0.0014 | 0.46 |
| D | 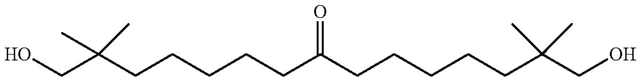 [SMILES: CC(C)(CO)CCCCCC(=O)CCCCCC(C)(C)CO] | −90 ± 1.5 (n = 4) | Yes | <0.0001 | 5.39 |
| E | 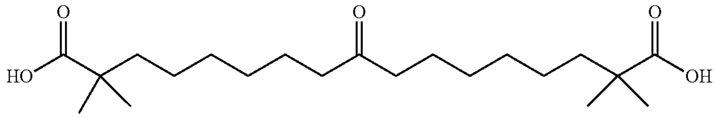 [SMILES: CC(C)(CCCCCCC(=O)CCCCCCC(C)(C)C(=O)O)C(=O)O] | −62 ± 4.5 (n = 4) | Yes | <0.0001 | 0.35 |
| F | 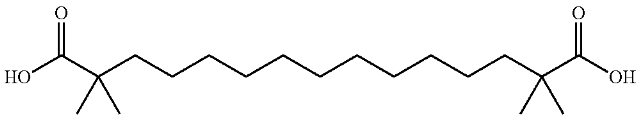 [SMILES: CC(C)(CCCCCCCCCCCC(C)(C)C(=O)O)C(=O)O] | −91 ± 3.6 (n = 4) | Yes | <0.0001 | <0.3 |
| I-32 | 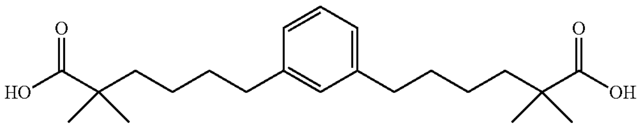 [SMILES: CC(C)(CCCCc1cccc(CCCCC(C)(C)C(=O)O)c1)C(=O)O] | −82 ± 2.8 (n = 6) | Yes | <0.0001 | 0.34 |
| I-61 | 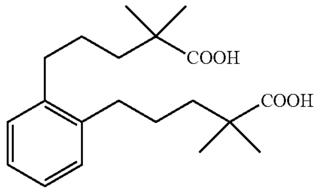 [SMILES: CC(C)(CCCc1ccccc1CCCC(C)(C)C(=O)O)C(=O)O] | +44 ± 8.1 (n = 4) | Yes | <0.0001 | ND |
| I-1 | 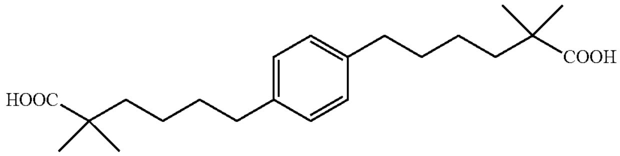 [SMILES: CC(C)(CCCCc1ccc(CCCCC(C)(C)C(=O)O)cc1)C(=O)O] | −84 ± 1.0 (n = 6) | Yes | <0.0001 | 0.46 |
| III-1 | 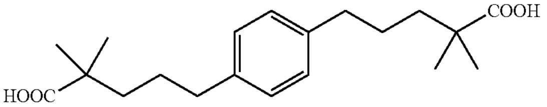 [SMILES: CC(C)(CCCc1ccc(CCCC(C)(C)C(=O)O)cc1)C(=O)O] | −70 ± 2.2 (n = 4) | Yes | <0.0001 | 27.66 |
| BA* | 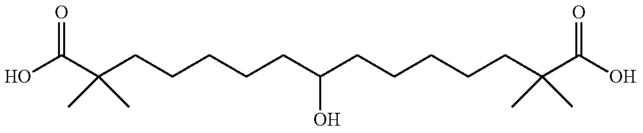 [SMILES: CC(C)(CCCCCC(O)CCCCCC(C)(C)C(=O)O)C(=O)O] | −79 ± 1.5 (n = 4) | Yes | <0.0001 | 0.68 |

*BA = Bempedoic acid

Example 13. Effects of Compound I-1 and Compound I-32 on Cell Death Pathways

Compound I-1 and Compound I-32 were tested for their ability to alter hepatic cell death pathways (i.e., pyroptosis, necroptosis, and apoptosis) using liver samples from Example 7. Detection was performed on liver sections obtained from the experiment described in Example 7. Paraffin sections were deparaffinized. Western blot analysis was performed by the We-Met platform. Toulouse. France, France. Commercial primary antibodies for Gasdermin D (reference ab209845; Abcam, Cambridge, UK), cleaved caspase 3 (reference 9664, Cell Signaling Technology. Danvers, Mass.), cleaved receptor interacting protein 3 (RIP3; reference ab56164; Abcam) and actin (reference 4970; Cell Signaling Technology) for control, were used on the WES automated western blot system (Proteinsimple, San Jose, Calif.). Data are presented as mean±SEM, with n=6-10 mice per experimental group, as indicated in the legends. Two-way analysis of variance with Bonferroni post-test. Mann-Whitney U-test, or unpaired two-tailed Student's t-test were used for statistical analysis using GraphPad Prism software (GraphPad Software, La Jolla, Calif.). A $P<0.05$ was considered significant. Compound I-1 and Compound I-32 significantly repressed pyroptosis and apoptosis cell death pathways with a trend towards necroptosis.

Figure 18A:
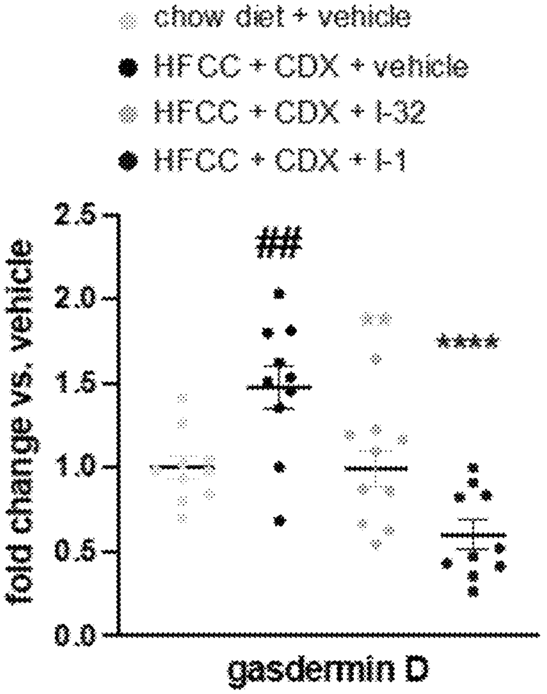
FIGS. 18A-18C show effects of Compound I-1 or Compound I-32 on gasdermin D (FIG. 18A), cleaved caspase 3 (FIG. 18B), and cleaved RIP 3 (FIG. 18C) measured by Western blot.
Figure 18B:
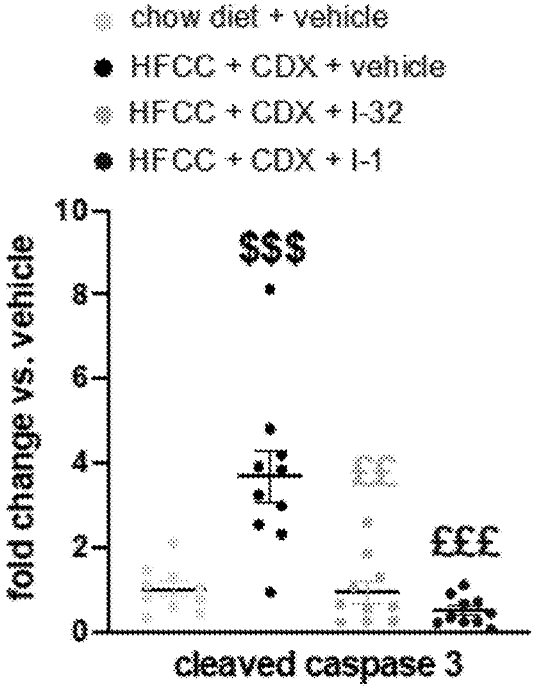
Figure 18C:
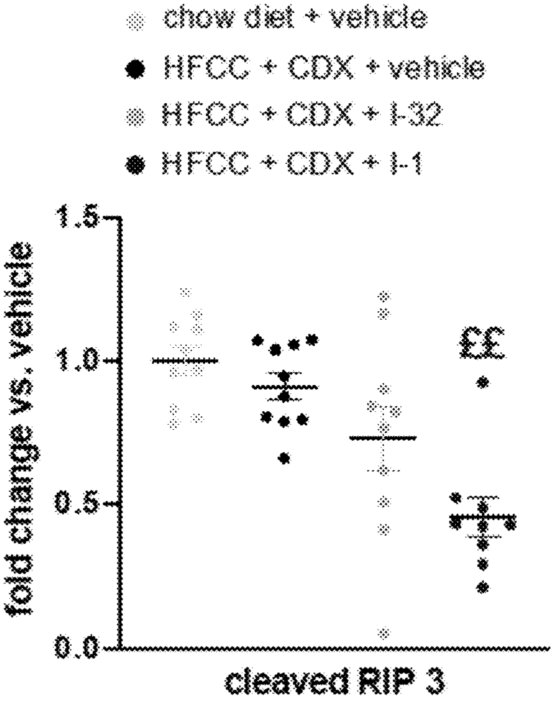

FIGS. 18A-18C show effects of Compound I-1 or Compound I-32 on gasdermin D (FIG. 18A), cleaved caspase 3 (FIG. 18B), and cleaved RIP 3 (FIG. 18C) measured by Western blot. ##$p<0.01$ vs. chow diet+vehicle with a t-test. $$$ $p<0.001$ vs. chow diet+vehicle with a Mann-Whitney test.  $p<0.01$ and ** $p<0.001$ vs HFCC+CDX+vehicle with an ANOVA 2-ways plus Bonferroni's post test. ££ $p<0.01$ and £££ $p<0.001$ vs. HFCC+CDX+vehicle with a Kruskal-Wallis plus Dunns post test.

Example 14: Effects of Compound I-32 and Compound I-1 on Megakaryopoiesis and Platelet Production in Cultured Human Hematopoietic Stem and Progenitor Cells Materials and Methods. Hematopoietic stem and progenitor cells, identified as viable CD45+CD34+ cells, were isolated from peripheral blood of healthy donors by a method known in the art (see Ivetic N. Nazi I, Karim N et al. Producing megakaryocytes from a human peripheral blood source. Transfusion 2016; 56:1066-74). These isolated cells were then analyzed for purity before being expanded for four days using a commercial supplement to increase their cell population. After expansion, the cells were analyzed for purity, washed, and stimulated with a saturating concentration of thrombopoietin (20 ng/mL) and stem cell factor (50 ng/mL) to begin megakaryopoiesis. Compound I-32 and Compound I-1 were added at this timepoint at a concentration of 30 μM. The cells were then cultured for 8 days to develop into megakaryocytes and analyzed via flow cytometry to assess their number, maturity, and platelet count as defined by CD41a, CD42b and Calcein-AM expression. In addition, Compound I-32 and Compound I-1 were added to cells during the later stages of development (day 6) to assess their impact on maturation. ABT-737 (6 μmol) was used as a positive control and a DMSO vehicle control (<0.15% v/v) was the negative control. All counts are normalized to a media control (PBS) as a reference for basic cell growth.

Statistical analysis. Statistical analyses were carried out by comparing effects on measured parameters in comparison to vehicle control. A value of $p<0.05\%$ (One-way ANOVA multiple comparisons) was considered as significant.

Two isolations were performed from two healthy donors (2 males, ages 30 and 63) and used to assess the impacts of Compound I-32 and Compound I-1. For one of the isolations, enough expanded hematopoietic stem and progenitor cells (HSPC) (Experiment 1) were obtained so that the addition of the compounds on day 6 was also performed along with the initial experiment. For the other experiment (Experiment 2) only an 8-day incubation was performed.

Results. Neither Compound I-32 nor Compound I-1 inhibited megakaryopoiesis as defined by the number of megakaryocytes cultured (CD41a+), mature megakaryocytes generated (CD41a CD42b+). Also, they did not inhibit platelet levels detected (CD41a+Calcein-AM+) as shown in FIGS. 25A-25E (no inhibition detected after addition on day 0 for CD41a+, CD41a CD42b+, platelet, CD41a MFI, CD41a+ cell size). When comparing the normalized number of CD41a+ cells present, Compound I-32 had 98±3%, Compound I-1 94±2%, and the vehicle was 94±4% of the yield generated from the reference media control (average±SD from both experiments). Only the positive control ABT-737 showed inhibition reducing CD41a+ cells count to 9±5% of the reference media. For CD41a CD42b+ counts the same observation were present with Compound I-32 at 106±17%, Compound I-1 97±9%, and the vehicle was 97±9% of the yield generated from the reference media control (average±SD from both experiments). The positive control ABT-737 control was at 2±1%. For platelet counts the same trends remained with Compound I-32 at 134±34%, Compound I-1 94±12%, and the vehicle was 97±6% of the yield generated in reference to the media control (average±SD). The positive control ABT-737 was 3±3%. Similar findings were found for also CD41a+ mean fluorescence intensity (MFI) and for normalized cell size. Compound I-32 (MFI 110±11%, Size 94±3%), compound I-1 (MFI 109±10%, Size 98±3%), vehicle (MFI 106±10%, Size 99±3%) and ABT-737 was (MFI 46±34%, Size 81±6%). Neither Compound I-32 nor Compound I-1 had inhibitory effects on any of the parameters measured in comparison to vehicle control ($p>0.05\%$ One-way ANOVA multiple comparisons). ABT-737 was significant in all parameters other than cell size. The addition of Compound I-32 or Compound I-1 on day 6 of culture yielded identical findings with those cultured for 8 days with no inhibition detected for Compound I-32 and Compound I-1 and only the positive control demonstrating an inhibitory effect (FIGS. 25F-25J; no inhibition detected after addition on day 6 for CD41a+, CD41a CD42b+, platelet, CD41a MFI, CD41a+ cell size). These results demonstrate that Compound I-32 and Compound I-1 do not inhibit megakaryopoiesis or platelet production from cultured human hematopoietic stem and progenitor cells.

All results were normalized to a reference media (PBS) and Compound I-32 and Compound I-1 were compared to a vehicle control. Reference compound ABT-737 is a known BCL-2 inhibitor and was used a positive control. Results in FIGS. 25A-25J are the summary of a single experiments conducted in triplicates. No statistical inhibition was detected for Compound I-32 or Compound I-1 ($p>0.05$ one-way ANOVA). ABT-737 has the following structure:

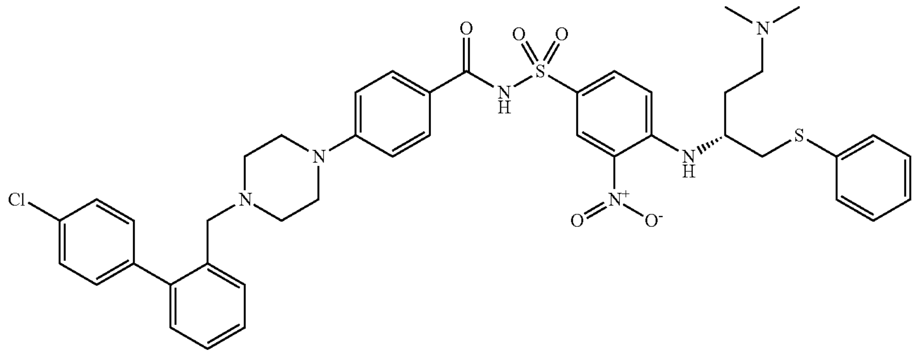 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

Example 15: Single and Repeat Dose Plasma and Tissue Pharmacokinetic Profile of Compounds Compound I-32 and Compound I-1 in Male C57BL/6 Mice Materials and methods. The study involved two arms; a single dose pharmacokinetic study and a 4-day repeated-dose pharmacokinetic study. For each arm, 56 inbred male C57BL/6 mice, aged at 6-7 week, were included. All animals were purchased from Charles River Lab (CRL, MA). Upon their arrival, they were kept in special-pathogen-free environment all the time. Briefly, they were housed in group on corncob bedding (ScottPharma, MA) in Innovive® caging system (Innovive, Calif.) on a 12-hour light-dark cycle (0700-1900) at 68-74° F., and 30-70% humidity. They were allowed continually to access water and regular rodent Purina 5001 diet (ScottPharma, MA) ad libitum and to acclimate in the facility for 5 days. Animal handling and procedures were conducted under the protocols and/or guidelines approved by the Institutional Animal Care and Use Committee (IACUC) of Cephrim Biosciences, Inc.

Stock dosing solutions for Compound I-32 and Compound I-1 were prepared as 20 mg/mL disodium salts (pH=8.2-8.6) in 1.5% Carboxymethyl cellulose+0.2% Tween 20, were aliquoted into 1 mL tubes and subsequently stored −80° C. freezer. Also, 2× drug vehicle (3% CMC+0.4% Tween-20) was prepared and stored at 4° C. for a week. On the day of injection, 1 ml frozen 2× aqueous stock solution (20 mg/ml drug solution) aliquot is thawed and mix with another 1 ml 2× drug vehicle (3% Carboxymethyl cellulose+0.4% Tween 20) to prepare 10 mg/ml drug solution. A 25 g mouse would receive 250 µl of 10 mg/ml solution for a dose of 100 mg/kg. Lower concentrations can be achieved by further diluting the 10 mg/ml in 1× vehicle solution with 1× vehicle prepared with milliQ water. On each dosing day, both compound stocks and 2× vehicle were warmed to room temperature and was mixed at 1:1 ratio, given to a concentration of 10 mg/mL. Then 1: 5-fold dilutions were obtained with 1× vehicle to 2 mg/mL. Dosing volume at 10 mL/kg (final dosage: 20 mg/kg) in the morning. Route of administration is oral gavage (volume of 10 ml/kg body weight).

Figure 26:
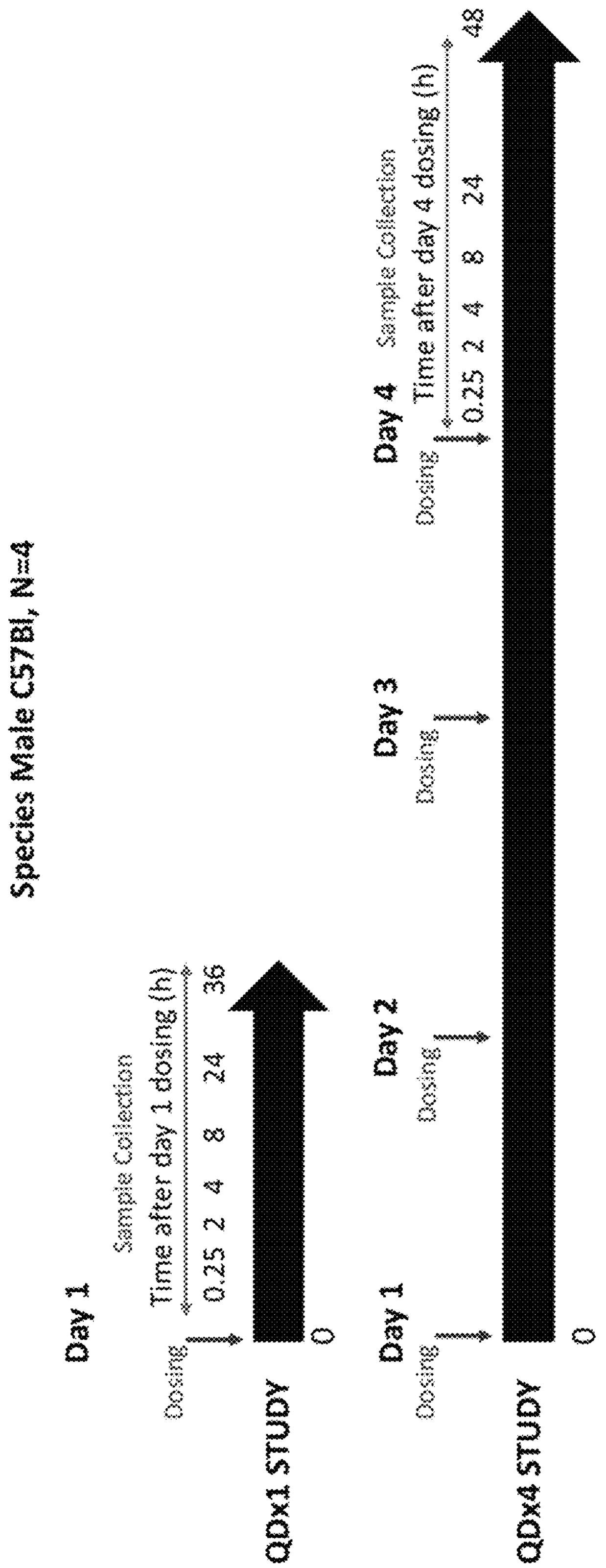
FIG. 26 shows the study design for pharmacokinetic experiment (Example 15).

Study Design. In each group 4 male 6-7-week-old C57BL/6 mice were used. Doses were administered once daily via oral gavage for either a day (single dose arm, QD×1) or 4 consecutive days (repeated dose arm, QD×4) (FIG. 26).

TABLE 8

Study groups and dose

| Comp. | Group[1] | Route | n | Dose Level (mg/kg) | Dose Conc (mg/mL) | Dosing Vol (mL/kg) | Time points (h)*# |
|---|---|---|---|---|---|---|---|
| I-32 | 7 QD × 1* | PO | 4 | 20 | 2 | 10 | 0.5, 2, 6, 8, 24, 36 |
| | 7 QD × 4[#] | PO | 4 | 20 | 2 | 10 | 0.5, 2, 6, 8, 24, 48 |
| I-1 | 7 QD × 1* | PO | 4 | 20 | 2 | 10 | 0.5, 2, 6, 8, 24, 36 |
| | QD × 4[#] | PO | 4 | 20 | 2 | 10 | 0.5, 2, 6, 8, 24, 48 |

*Single dose;
[#]Repeat dose for 4 days;
[1]7 groups for 7 timepoints, Each timepoint has 4 mice, so groups QD × 1 and QD × 4 both had 28 mice each Blood, half of brain hemisphere, and one lobe of liver samples were collected from all animals of Day 1 (QD×1 arm) at pre-dose and 0.25, 2, 4, 8, 24 and 36 hours post dose, or Day 4 (QD×4 arm) at pre-dose and 0.25, 2, 4, 8, 24 and 48 hours post dose. Blood samples were collected by cardiac puncture. The blood samples were maintained in wet ice first and centrifuged to obtain plasma (2000×g, 4° C., 5 min). All three samples from each mouse were analyzed for either Compound I-1 or Compound I-32 contents by Integrated Analytical Solutions (Berkeley, Calif.) and the results were used for the generation of the pharmacokinetic graphs.

Sample collection, storage, bioanalysis and statistical analysis. All plasma and tissue samples were analyzed by discovery grade bioanalytical method developed for estimation of each test compound in plasma and tissue samples using LC-MS/MS systems. Plasma samples were prepared as follows. Three volumes of acetonitrile containing internal standard was added to one volume of plasma to precipitate proteins. Samples were centrifuged (3000×g for 10 min) and supernatant removed for analysis by LC-MS/MS. Calibration standards and quality controls were made by preparation of a 1 mg/mL stock solution in MeOH and subsequently a series of working solutions in MeOH:water (1/1, v/v) which were spiked into blank plasma to yield a series of calibration standard samples in the range of 1.0 ng/mL to 10

μg/mL. All incurred PK/PD plasma samples were treated identically to the calibration standards and quality control samples. LC-MS/MS analysis was performed utilizing multiple reaction monitoring for detection of characteristic ions for each drug candidate, additional related analytes and internal standard.

Tissue samples were prepared as follows, three volumes of PBS buffer (pH 7.4) were added to one volume of each tissue sample which was then homogenized to obtain each tissue homogenate sample. Subsequently, three volumes of acetonitrile containing internal standard was added to one volume of each tissue homogenate, and the mixture was vortexed, centrifuged (3000 g for 10 min) and supernatant removed for analysis by LC-MS/MS (Shimadzu HPLC; AB/MDS Sciex MS/MS System). The column used was Phenomenex Kinetex C18, 2.6 μm (4.6×50 mm) and the mobile phases A and B were 0.1% Formic Acid in Water and 0.1% Formic Acid in Acetonitrile, respectively. Calibration standards were made by preparation of a 1 mg/mL stock solution and subsequently a series of working solutions in methanol:water (1/1, v/v) which were spiked into blank tissue homogenate to yield a series of calibration standard samples in the range of 1 ng/mL to 10 μg/mL. All incurred PK/PD tissue samples were treated identically to the calibration standards. LC-MS/MS analysis was performed utilizing multiple reaction monitoring for detection of characteristic ions for each drug candidate, additional related analytes, and internal standard. Compounds I-32 and I-1 were evaluated for PK parameters by Microsoft Excel and GraphPad Prism software.

Results. Compound I-32 and Compound I-1 concentrations in plasma, liver, and brain.

Compound I-32 and Compound I-1 were evaluated for their pharmacokinetics profile in C57B1 mice. Brain exposure was also measured to understand the transport of Compound I-32 and Compound I-1 through the blood-brain barrier. Preparation of plasma and sample preparation for measurement of test compound concentration by LC-MS/MS were performed by standard methods and parameters were evaluated both in the single-dose as well as repeat-dose administered mice.

Figure 27:
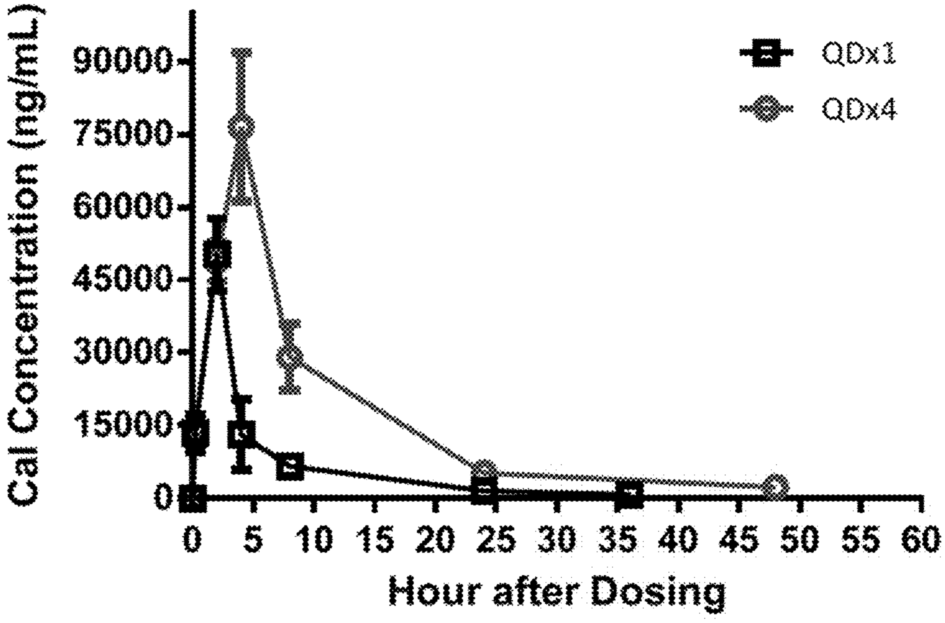
FIG. 27 displays mean (+SEM) concentrations (ng/mL) of Compound I-32 in male mouse plasma following a single or repeated oral gavage administration. QD×1=once daily, single dose; QD×4=once daily for 4 consecutive days.
Figure 28:
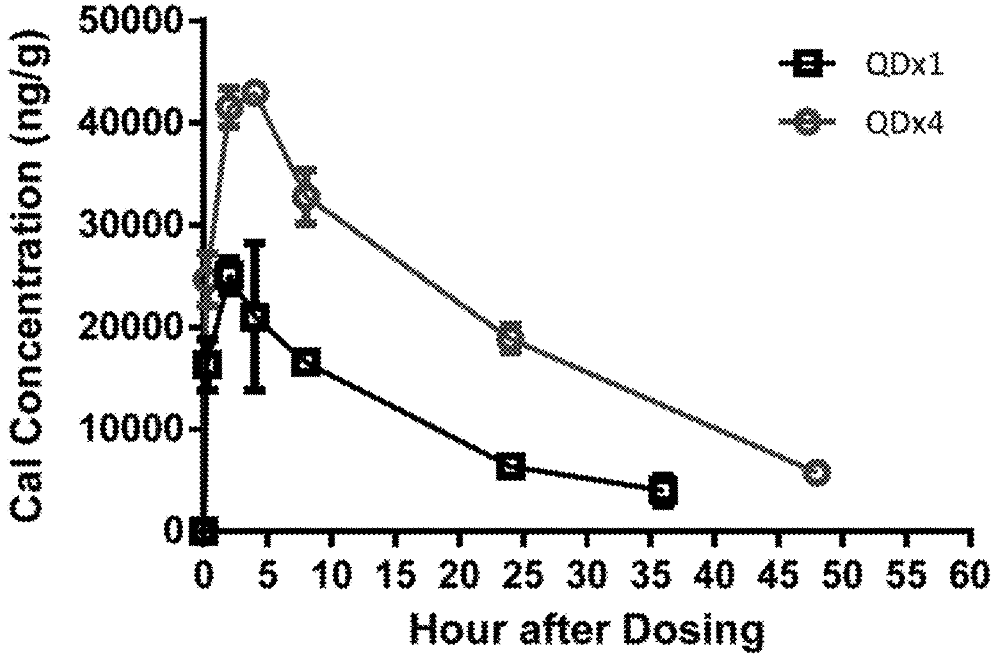
FIG. 28 displays mean (+SEM) concentrations (ng/g) of Compound I-32 in male mouse liver following a single or repeated oral gavage administration. QD×1=once daily, single dose; QD×4=once daily for 4 consecutive days.
Figure 29:
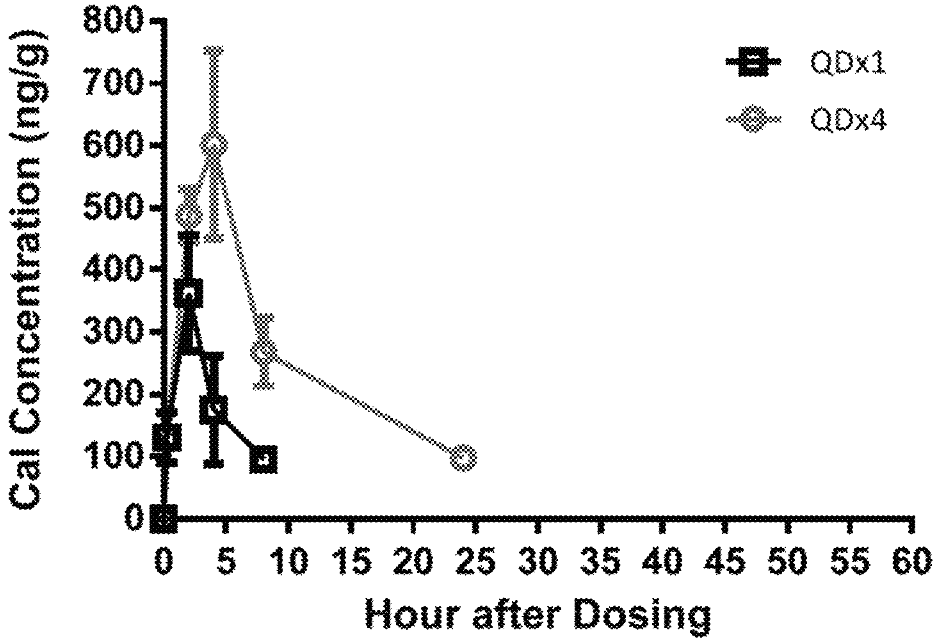
FIG. 29 displays mean (+SEM) concentrations (ng/g) of Compound I-32 in male mouse brain following a single or repeated oral gavage administration. QD×1=once daily, single dose; QD×4=once daily for 4 consecutive days.
Figure 30:
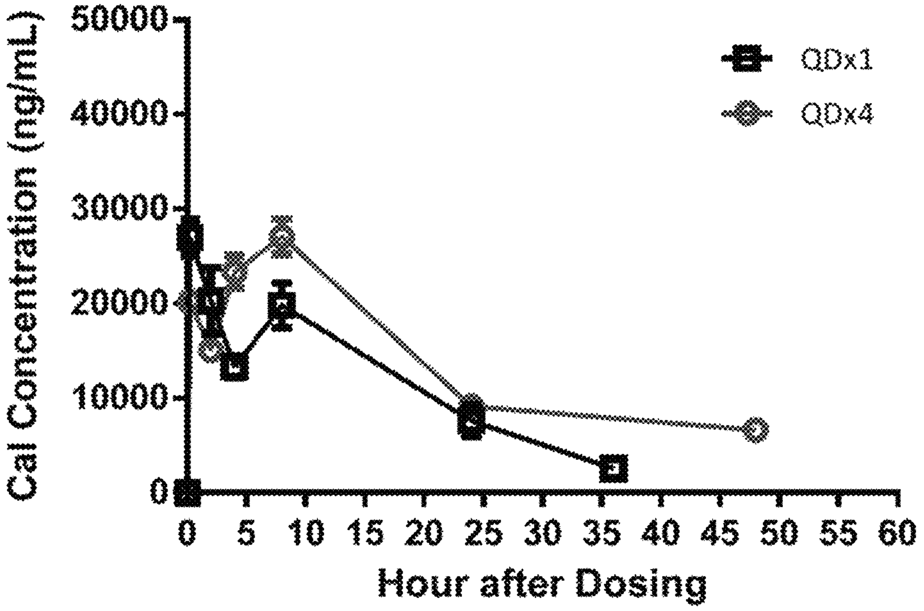
FIG. 30 shows mean (+SEM) concentrations (ng/mL) of Compound I-1 in male mouse plasma following a single or repeated oral gavage administration. QD×1=once daily, single dose; QD×4=once daily for 4 consecutive days.
Figure 31:
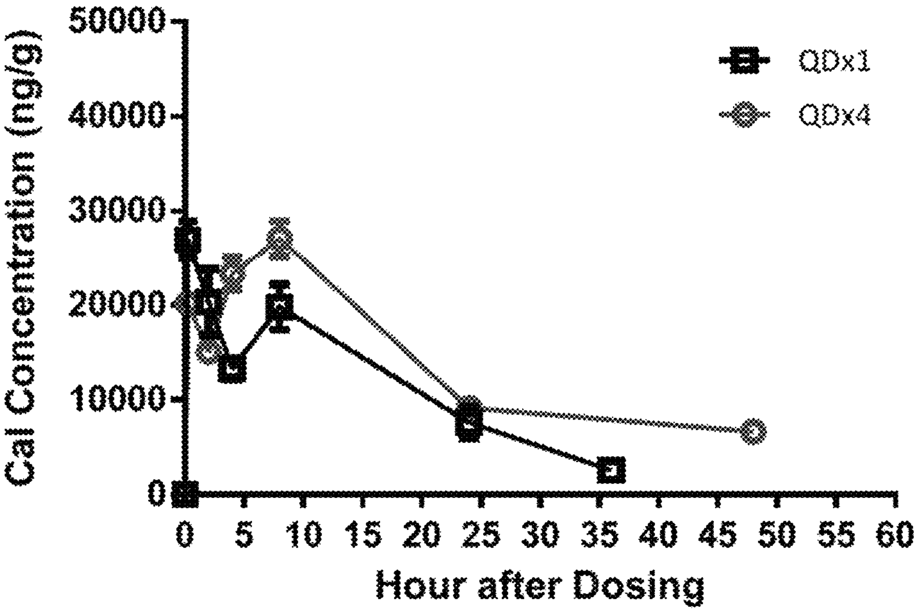
FIG. 31 shows mean (+SEM) concentrations (ng/g) of Compound I-1 in male mouse liver following a single or repeated oral gavage administration. QD×1=once daily, single dose; QD×4=once daily for 4 consecutive days.
Figure 32:
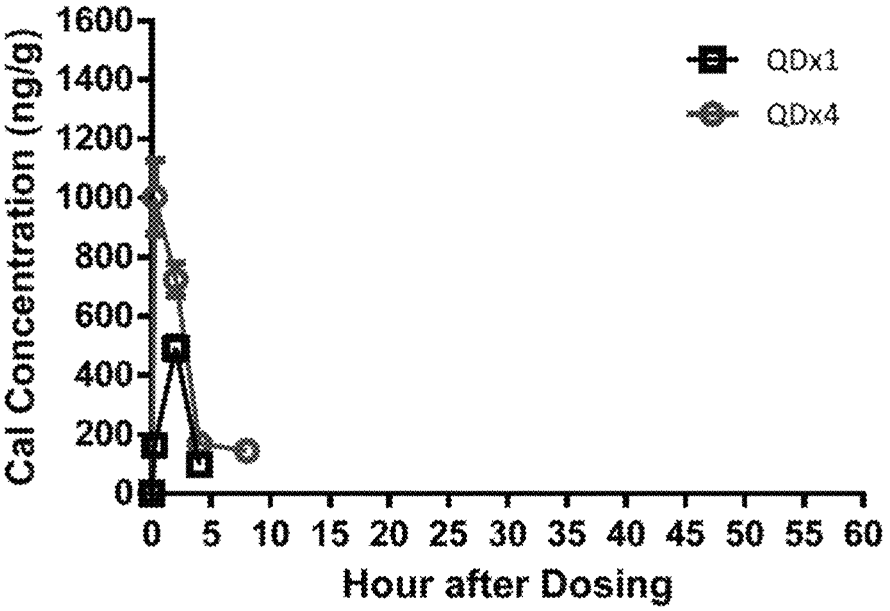
FIG. 32 shows mean (+SEM) Concentrations (ng/g) of Compound I-1 in male mouse brain following a single or repeated oral gavage administration. QD×1=once daily, single dose; QD×4=once daily for 4 consecutive days.

Compounds 1-32 and I-1 PK parameters in plasma and tissues. The pharmacokinetics parameters, $C_{max}$, $t_{1/2}$, $T_{max}$, and $AUC_{0-t}$ were calculated from the concentration curves of Compound I-32 over 0→36 h for QD×1 groups and 0→48 h for QD×4 groups in plasma, liver, and brain. The concentration curves for Compound I-32 are shown in FIGS. 27, 28, and 29, respectively, and for Compound I-1, the concentration curves are shown in FIGS. 30-32. The difference between the single dose (QD×1) PK profile and the repeat dose (QD×4) profile is more pronounced in Compound I-32 administered mouse plasma and liver (FIGS. 27 and 28) compared to I-1 administered mice (FIGS. 30 and 31). Tables 9-11 summarize the mean pharmacokinetic parameters for Compound I-1 and Compound I-32.

TABLE 9

Summary of the Mean Pharmacokinetic Parameters in Mouse Plasma for Compounds I-1 and I-32

| Comp. | Dose Level (mg/kg/day) | Total Dose (mg) | $C_{max}$ (ng/mL) | $t_{1/2}$ | $T_{max}$ (h) | $AUC_{0-t}$ (h*ng/mL) |
|---|---|---|---|---|---|---|
| I-32 | 20 | 20 × 1 [QD × 1] | 50,225 | 9.0 | 2 | 239,532 |
| I-1 | 20 | 20 × 1 [QD × 1] | 102,300 | 15.3 | 0.25 | 1,375,865 |
| | | | (90,000)* | | (0.25)* | (1,673,493)* |
| I-32 | 20 | 20 × 4 [QD × 4] | 76,550 | 9.2 | 4 | 758,046 |
| I-1 | 20 | 20 × 4 [QD × 4] | 102,225 | 22.0 | 0.25 | 1,167,819 |
| | | | (76,075)* | | (0.25)* | (1,089,207)* |

*Values represent Compound I-1 timepoint 0.25 h samples after reanalysis

TABLE 10

Summary of the Mean Pharmacokinetic Parameters in Mouse Liver for Compounds I-1 and I-32

| Comp. | Dose Level (mg/kg/day) | Total Dose (mg) | $C_{max}$ (ng/g) | $t_{1/2}$ | $T_{max}$ (h) | $AUC_{0-t}$ (h*ng/g) |
|---|---|---|---|---|---|---|
| I-32 | 20 | 20 × 1 [QD × 1] | 25,088 | 13 | 2 | 405,934 |
| I-1 | 20 | 20 × 1 [QD × 1] | 26,985 | 9.6 | 0.25 | 425,184 |
| | | | (21,518)* | | (0.25)* | (469,726)* |
| I-32 | 20 | 20 × 4 [QD × 4] | 42,975 | 16 | 4 | 100,6991 |
| I-1 | 20 | 20 × 4 [QD × 4] | 30,862 | 20.4 | 0.25 | 687,414 |
| | | | (46,575)* | | (0.25)* | (718,455)* |

*Values represent Compound I-1 timepoint 0.25 h samples after reanalysis

TABLE 11

Summary of the Mean Pharmacokinetic Parameters in Mouse Brain for Compounds I-1 and I-32

| Comp. | Dose Level (mg/kg/day) | Total Dose (mg) | $C_{max}$ (ng/g) | $t_{1/2}$ | $T_{max}$ (h) | $AUC_{0-t}$ (h*ng/g) |
|---|---|---|---|---|---|---|
| I-32 | 20 | 20 × 1 [QD × 1] | 362 | 3 | 2 | 1,527 |
| I-1 | 20 | 20 × 1 [QD × 1] | 492 (1,025)* | ND# | (0.25)* | 1,183 (2,091)* |
| I-32 | 20 | 20 × 4 [QD × 4] | 604 | 8 | 4 | 6,304 |
| I-1 | 20 | 20 × 4 [QD × 4] | 169 (1,390)* | ND# | 4 (0.25)* | 1,220 (3,995)* |

In conclusion, in this PK study, both Compound I-32 and Compound I-1 show adequate exposure in the plasma and liver and minimal exposure in the brain for the study duration. Both Compound I-32 and Compound I-1 show adequate bioavailability in the liver when administered orally. The brain showed 300-400-fold lower bioavailability compared to liver. Both Compound I-32 and Compound I-1 show adequate clearance from the plasma and organs during the PK study duration.

Example 16: 4-Day Oral Gavage Toxicity and Toxicokinetic Study in Female Rats The purpose of this study was to evaluate the toxicity and determine the toxicokinetics of Compounds I-1 or I-32 when administered once daily via oral gavage to female rats for at least 4 days.

Materials and Methods. All procedures in the Protocol were in compliance with applicable animal welfare acts and were approved by the local Institutional Animal Care and Use Committee (IACUC). Thirty female Wistar Han (RccHan®:WIST) rats were received from Envigo RMS, Inc., Indianapolis, Ind. Animals were acclimated to the test facility for 7 days prior to initiation. At initiation of dosing, animals were 7 to 8 weeks old, and body weights ranged from 130 to 176 g. Animals not used on study were placed in the training colony.

Animals were group-housed (three animals/cage) in polycarbonate cages with hardwood chip bedding. Animals were individually housed in stainless steel or polycarbonate cages for study-related procedures. Water was provided ad libitum. Animals were offered Certified Rodent Diet #2014C (Envigo RMS, Inc.) ad libitum, unless fasted for study procedures. Animals were given various cage-enrichment devices and dietary enrichment (which did not require analyses). Any variations to these conditions are maintained in the raw data and had no effect on the study outcome. Animals were identified using tail markings, implantable microchip identification device, and/or cage card. Animals were assigned sequentially to study groups based on pretest numbers, unless they were eliminated from consideration for study selection based on data collected during acclimation (predose phase). Prior to initiation of the study, a statistical comparison of body weights across groups/subgroups were done to establish whether homogeneity of variance was achieved at the 5.0% probability level, as indicated by Levene's test for heterogeneity of variance. Additionally, the mean body weight for each subgroup was not statistically different at the 5.0% probability level, as indicated by analysis of variance (ANOVA) F probability.

Environmental controls were set to maintain a temperature range of 20 to 26° C., a relative humidity range of 30 to 70%, eight or greater air changes/hour, and a 12-hour light/12-hour dark cycle.

Toxicokinetic animals were sacrificed with carbon dioxide and discarded without necropsy after the final blood collection.

Dosing Solutions. The dosing solutions of Compound I-1 and Compound I-32 were prepared as follows: a 60-mg/mL stock solution was prepared for Compound I-1 or Compound I-32 by dissolving Compound I-1 or Compound I-32 in DI water. Two molar equivalents of NaOH was added for every 1 mole of Compound I-1 or Compound I-32 (1.1 μL of 5 N NaOH was added for every mg of Compound I-32 or Compound I-1). The pH of the stock solution for Compound I-1 or Compound I-32 was adjusted to achieve a final pH of 8.2 to 8.6. The resultant stock formulations were further diluted with vehicle to achieve the 30 mg/mL concentration. The 30-mg/mL formulations were diluted with control article to achieve the 10-mg/mL concentration. All dilution calculations were based on the nominal concentration of the stock solution. Formulations of Compound I-1 or Compound I-32 were prepared on the day of dosing were stored at room temperature (15 to 30° C.) and used within 8 hours of preparation completion. The control was 1.5% (w/v) carboxymethyl cellulose+0.2% (v/v) Tween 20 in DI water for as Group 1 formulations. The vehicle used for Compound I-1 and Compound I-32 formulations was 3% (w/v) carboxymethyl cellulose+0.4% (v/v) Tween 20 in DI water.

Bioanalytical and Toxicokinetic Analyses. Blood samples (approximately 0.3 mL) were collected from nonfasted toxicokinetic animals via a jugular vein on Day 1 of the dosing phase, as indicated in the following table. Samples were collected predose and approximately 1, 2, 4, and 24 hours postdose.

Blood was collected into tubes containing potassium (K2) EDTA as the anticoagulant. Samples were maintained on chilled cryoracks and were centrifuged within 1 hour of collection. Plasma was harvested into two approximately equal aliquots and stored on dry ice until placed in a freezer, set to maintain −60 to −80° C., until analyzed. Plasma samples were analyzed for Compound I-1 and Compound I-32 content using a generic Tier 1 qualified liquid chromatography-tandem mass spectrometry (LC-MS/MS) method. The toxicokinetic analysis was performed by Covance and included parameters listed below.

$C_{max}$: Maximum observed concentration

DN $C_{max}$: Dose-normalized maximum concentration, calculated as Cmax/dose $T_{max}$: Time of maximum observed concentration $AUC_{0-t}$: Area under the curve from time 0 to the time of the last measurable concentration, calculated using the linear trapezoidal rule $AUC_{0-24}$: Area under the curve from 0 to 24 hours postdose, calculated using the linear trapezoidal rule DN $AUC_{0-24}$: Dose normalized AUC0-24, calculated as AUC0-24/dose $AUC_{0-inf}$: Area under the curve from time 0 to infinity, calculated as $AUC_{0-inf}=AUC_{0-t}+Ct/\lambda z$, where Ct is the last observed quantifiable concentration and λz is the elimination rate constant $t_{1/2}$: Elimination half-life, calculated as ln(2)/λz In-Life Phase. Female rats were assigned to five groups, and doses were administered as indicated in the Table 12. Animals were dosed once daily for up to 4 days via oral gavage at a volume of 10 mL/kg. Animals in Group 2 and 3 were administered Compound I-1. Animals in Group 4 and 5 were administered Compound I-32. The control article for Group 1 was 1.5% (w/v) carboxymethyl cellulose+0.2% (v/v) Tween 20 in deionized (DI) water. The vehicle used to prepare Compound I-1 and Compound I-32 formulations was 3% (w/v) carboxymethyl cellulose+0.4% (v/v) Tween 20 in DI water.

TABLE 12

| Study Design | | | | |
|---|---|---|---|---|
| Group[a] | Subgroup[c] | Dose Level[b] (mg/kg/day) | Dose Concentration[b] (mg/mL) | Number of Females |
| 1 (Control) | 1 (Toxicity) | 0 | 0 | 3 |
| 2 (Comp. I-1 Low) | 1 (Toxicity) | 100 | 10 | 3 |
| | 2 (Toxicokinetic) | 100 | 10 | 3 |
| 3 (Comp, I-1 High) | 1 (Toxicity) | 300 | 30 | 3 |
| | 2 (Toxicokinetic) | 300 | 30 | 3 |
| 4 (Comp. I-32 Low) | 1 (Toxicity) | 100 | 10 | 3 |
| | 2 (Toxicokinetic) | 100 | 10 | 3 |
| 5 (Comp. I-32 High) | 1 (Toxicity) | 300 | 30 | 3 |
| | 2 (Toxicokinetic) | 300 | 30 | 3 |

[a]Group 1 were administered vehicle control only.
[b]Animals were dosed at a volume of 10 mL/kg
[c]Toxicokinetic animals were sacrificed and discarded after the final blood collection Dose formulations were administered once daily by oral gavage for up to 4 days at a dose volume of 10 mL/kg. Doses were administered within 8 hours of preparation and based on the most recently recorded scheduled body weight. Dosing continued through the day prior to the terminal sacrifice or the designated dosing phase (toxicokinetic animals). Dose formulations were maintained at room temperature and were stirred using a magnetic stir plate and stir bar for at least 30 minutes prior to and throughout dosing.

Animals were checked twice daily (a.m. and p.m.) for mortality, abnormalities, and signs of pain or distress. Cageside observations were conducted for each animal once daily on Days 2, 3, 4, and 5 of the dosing phase. Detailed observations were conducted for each animal once during the predose phase and for each toxicity animal prior to dosing on Days 1 to 5 of the dosing phase. An indication of normal was recorded. Unscheduled observations were recorded. On each day of dosing, cageside observations were conducted for each toxicity animal at approximately 1 and 6 hours postdose. Postdose observation start times for each toxicity group were based on the dosing completion time for each group. An indication of normal was recorded. Body weights were recorded for toxicokinetic animals once during the predose phase and before dosing on Day 1 of the dosing phase. Body weights were recorded for toxicity animals once during the predose phase, before dosing on Days 1 and 4 of the dosing phase. The amount of food consumed by each cage of toxicity animals was recorded from Days 1 to 4 of the dosing phase. Consumption was calculated as g/animal/day.

Assessment of toxicity was based on mortality, clinical observations, body weights, food consumption, and clinical and anatomic pathology. Blood samples were collected for toxicokinetic evaluation.

Clinical Pathology. Blood samples for hematology, coagulation, and clinical chemistry were collected from fasted toxicity animals via a jugular vein (clinical chemistry only) or the vena cava (hematology and coagulation only) on the day of scheduled sacrifice. Animals were anesthetized with isoflurane prior to collection of samples from the vena cava The anticoagulants were sodium citrate for coagulation tests and potassium EDTA for hematology tests. Samples for clinical chemistry were collected without anticoagulant.

| Hematology Tests | |
|---|---|
| red blood cell (erythrocyte) count gated | platelet count |
| hemoglobin | white blood cell (leukocyte) count |

-continued

| | |
|---|---|
| hematocrit gated | absolute neutrophil count |
| mean corpuscular volume gated | absolute lymphocyte count |
| mean corpuscular hemoglobin gated | absolute monocyte count |
| mean corpuscular hemoglobin concentration gated | absolute eosinophil count |
| red cell distribution width gated | absolute basophil count |
| absolute reticulocyte count gated | absolute large unstained cell count blood smear |
| **Coagulation Tests** | |
| prothrombin time | |
| fibrinogen | |
| activated partial thromboplastin time | |
| **Clinical Chemistry Tests** | |
| glucose | aspartate aminotransferase |
| urea nitrogen | alanine aminotransferase |
| creatinine | alkaline phosphatase |
| total protein | gamma glutamyltransferase |
| albumin | creatine kinase |
| globulin | calcium |
| albumin: globulin ratio | inorganic phosphorus |
| total cholesterol | sodium |
| triglycerides | potassium |
| total bilirubin | chloride |

Necropsy and Macroscopic Observations. On Day 5 of the dosing phase, all surviving toxicity animals, having been fasted overnight, were anesthetized with isoflurane inhalation, exsanguinated, and necropsied. Terminal body weights were recorded for sacrificed toxicity animals. A macroscopic examination of the external features of the carcass; external body orifices; abdominal, thoracic, and cranial cavities; organs; and tissues was performed. A Pathologist was available for consultation during necropsies. Bone marrow smears (two slides) were prepared from the femur of each animal at scheduled sacrifices. The following tissues (when present) from each animal were preserved in 10% neutral-buffered formalin, unless otherwise indicated.

| Organ/Tissue | |
|---|---|
| animal identification | |
| bone, sternum with bone marrow | P, E |
| brain | P, E |
| gross lesions | P, E |
| heart | P, E |
| kidney (2) | P, E |
| liver | P, E |
| lungs with large bronchi | P, E |

E = Examined microscopically; P = Processed

Data Evaluation and Statistical Analysis. Various models of calculators, computers, and computer programs were used to analyze data in this study. Values in some tables (e.g., means, standard deviations, or individual values) may differ slightly from those in other tables, from individually calculated data, or from statistical analysis data, because different models round off or truncate numbers differently. Neither the integrity nor the interpretation of the data was affected by these differences.

Data for each sex were analyzed separately; only data collected on or after the first day of dosing were analyzed statistically. Only data from toxicity animals (Subgroup 1) were evaluated. Analysis of variance (ANOVA) and pairwise comparisons were used to analyze the following.

Absolute body weight

Body weight change

Quantitative food consumption

Continuous clinical pathology values

The pairwise comparisons of interest were:

Group 1 versus Groups 2, 3, 4, and 5

Group 2 versus Group 4

Group 3 versus Group 5

Prior to performing the ANOVA. Levene's test was performed to test for equality of variances between groups:

Where Levene's test was significant ($P \leq 0.05$), a rank transformation (to stabilize the variances) was applied before the ANOVA was conducted (note: Levene's test was not applied to the rank-transformed data).

Where Levene's test was not significant ($P > 0.05$), ANOVA was conducted.

For comparisons to a single control or combined identical controls:

If the group effect of the ANOVA was significant ($P \leq 0.05$), Dunnett's test was used for pairwise comparisons between each treated and control group.

If the ANOVA was not significant ($P > 0.05$), the Dunnett's test results were not applicable to the evaluation and were not reported or used to interpret study data.

For other comparisons (i.e., not against a single control or combined identical controls):

If the group effect of the ANOVA is significant ($P \leq 0.05$), t-tests were used for pairwise comparisons.

If the ANOVA was not significant ($P > 0.05$), the t-test results were not applicable to the evaluation and were not reported or used to interpret study data.

Where only two groups were available for analysis, a two-sample t-test was performed. Data containing values above/below the limit of quantitation were not analyzed, and the tables were footnoted accordingly. Where insufficient data were available for meaningful analysis, no analysis was performed, and the tables were footnoted accordingly. All statistical tests were evaluated at the 5.0% probability level. Due to system limitations, additional statistical analyses may have been run but were not reported or used to interpret study data. A sex/group may have been omitted from hypothesis testing when the number of data points for a given interval and data type from that sex/group fell below three.

Toxicokinetics. The summary of the mean toxicokinetic parameters and dose normalized $C_{max}$ and $AUC_{0-24}$ relationships of Compounds I-32 and I-1 in female rat plasma are presented are presented in Table 13.

TABLE 13

Summary of the Mean Toxicokinetic Parameters in Female Rat Plasma for Compound I-32 and Compound I-1

| Comp. | Dose Group | Dose Level (mg/kg/dav) | $C_{max}$ (ng/mL) | $T_{max}$ (h) | $AUC_{0-24}$ (h*ng/mL) |
|---|---|---|---|---|---|
| I-1 | 2 | 100 | 41,5000 | 2.00 | 5,460,000 |
| | 3 | 300 | 78,7000 | 1.00 | 7,520,000 |
| I-32 | 4 | 100 | 142,000 | 2.00 | 2,030,000 |
| | 5 | 300 | 406,000 | 4.00 | 7,880,000 |

Exposure, as assessed by Compound I-1 mean $C_{max}$ and $AUC_{0-24}$ values, increased with the increase in dose level from 100 to 300 mg/kg/day. The increases in mean $C_{max}$ and $AUC_{0-24}$ values were less than dose proportional. Exposure, as assessed by Compound I-32 mean $C_{max}$ and $AUC_{0-24}$ values, increased with the increase in dose level from 100 to 300 mg/kg/day. The increases in mean $C_{max}$ and $AUC_{0-24}$ were approximately dose proportional.

Toxicokinetic Profile of Compound I-32. After a single oral gavage administration, Compound I-32 appeared in plasma, with median $T_{max}$ values of 2.00 and 4.00 hours at 100 and 300 mg/kg/day, respectively. Due to the lack of a distinct elimination phase, estimation of elimination phase tin was not attempted for any profile. Mean concentration values for Compound I-32 were measurable through 24 hours postdose. The mean concentration-time profiles for females show that mean concentrations of Compound I-32 increased with the increase in dose level from 100 to 300 mg/kg/day.

Toxicokinetic Profile of Compound I-1. After a single oral gavage administration, Compound I-1 was absorbed, with median $T_{max}$ values of 2.00 and 1.00 hour at 100 and 300 mg/kg/day, respectively. Due to the lack of a distinct elimination phase, estimation of elimination phase half-life ($t_{1/2}$) was not attempted for any profile. Mean concentration values for Compound I-1 were measurable through 24 hours postdose. The mean concentration-time profiles for females show that mean concentrations of Compound I-1 generally increased with the increase in dose level from 100 to 300 mg/kg/day.

Dose Proportionality of Compound I-32. Exposure, as assessed by Compound I-32 mean $C_{max}$ and $AUC_{0-24}$ values, increased with the increase in dose level from 100 to 300 mg/kg/day. The increases in Compound I-32 mean $C_{max}$ and $AUC_{0-24}$ values were approximately dose proportional.

Dose Proportionality of Compound I-1. Exposure, as assessed by Compound I-1 mean $C_{max}$ and $AUC_{0-24}$ values, increased with the increase in dose level from 100 to 300 mg/kg/day. The increases in Compound I-1 mean $C_{max}$ and $AUC_{0-24}$ values were less than dose proportional.

Clinical observations. No Compound I-1- or Compound I-32-related clinical observations were noted. No Compound I-1- or Compound I-32-related mortality, clinical observations, body weight effects, or changes in food consumption were noted. The other clinical observation was audible and fast respiration in one toxicokinetic female (Animal RO405) administered 300 mg/kg/day Compound I-32. This appeared rather infrequently, was transient, or was noted with comparable incidences as controls; therefore, it was considered not Compound I-1- or Compound I-32-related.

Hematology and Coagulation. No Compound I-1- or Compound I-32-related effects in hematology or coagulation test results were identified. No differences in hematology or coagulation test results were identified between animals administered Compound I-1 and animals administered Compound I-32.

All differences in hematology and coagulation test results, statistically significant or not, between control and Compound I-1- or Compound I-32-treated animals were consistent with normal variation and considered incidental. Most or all of the following characterized these differences: small magnitude, lack of dose relationship, and/or the absence of correlative findings Clinical chemistry. Minor test-article related effects in clinical chemistry results consisted of minimally lower globulin concentration and minimally higher albumin: globulin ratio in animals administered 100 mg/kg/day Compound I-1 or 300 mg/kg/day Compound I-1 or Compound I-32. These differences were of a similar magnitude of change. Minimally lower serum urea nitrogen concentration in animals administered 300 mg/kg/day Compound I-32 was considered potentially Compound I-32-related; however, the difference was small and lacked correlative findings, and, therefore, a clear relation was not established. All other differences in clinical chemistry test results, statistically significant or not, between control and Compound I-1- or Compound I-32-treated animals were consistent with normal variation and considered incidental. Most or all of the following characterized these differences: small magnitude, lack of dose relationship, and/or the absence of correlative findings.

Summary Female Wistar Han (RccHan®:WIST) rats were administered control article or 100 or 300 mg/kg/day Compound I-1 or Compound I-32 via oral gavage once daily for at least 4 days. No Compound I-1- or Compound I-32-related mortality, clinical observations, body weight effects, or changes in food consumption were noted. No Compound I-1- or Compound I-32-related effects in hematology and coagulation parameters or macroscopic observations were noted, nor were any differences in these parameters identified between animals administered either Compound I-1 or Compound I-32. Minor Compound I-1- or Compound I-32-related effects in clinical pathology results consisted of minimally lower globulin concentration and minimally higher albumin:globulin ratio in animals administered 100 mg/kg/day Compound I-1 or 300 mg/kg/day Compound I-1 or Compound I-32; these differences were of a similar magnitude of change in all groups affected. Compound I-1- or Compound I-32-related microscopic findings were noted in the liver and/or kidney.

Microscopically, Compound I-1- or Compound I-32-related findings were noted in the liver and/or kidney. In the liver, findings included an increase in mitoses in hepatocytes in females administered ≥100 mg/kg/day Compound I-1 or 300 mg/kg/day Compound I-32 and periportal hepatocyte vacuolation in females administered 300 mg/kg/day Compound I-32. In the kidney, tubular degeneration/necrosis, tubular regeneration, and increased mitoses were noted in females administered 300 mg/kg/day Compound I-1. In general, more severe changes were noted in animals administered Compound I-1.

In general, more severe changes were noted in animals administered Compound I-1. The changes in kidney were considered adverse. Due to the mild severity of findings and the lack of impact on the health and wellbeing of animals administered 300 mg/kg/day Compound I-32 or 100 mg/kg/day Compound I-1, effects for this dose were considered nonadverse and considered suitable for future longer-term toxicity studies in the rat. This dose level corresponded to mean maximum observed concentration ($C_{max}$) values of 406,000 μg/mL or 415,000 μg/mL and area under the concentration-time curve (AUC) 7,880,000 h*ng/mL or 5,460,000 h*ng/mL, respectively, for animals administered 300 mg/kg/day Compound I-32 or 100 mg/kg/day Compound I-1 on Day 1 of the dosing phase.

Example 17. Study of Compound I-32 and Compound I-1 in a NASH-HCC Model Generated by Chemical Induction of HCC with Diethylnitrosamine (DEN)

Materials and Methods. All experiments were carried out using the guidelines approved by the Animal Research Ethics Board at McMaster University, Canada. Male mice obtained from Steinberg Lab Breeding Colony housed within the McMaster University Central Animal Facility were used for these experiments. The test agents were prepared by solubilizing them in a solution of sodium bicarbonate. Compound I-32 and Compound I-1 were administered at a dose of 30 or 100 mg/kg with a dosing volume of 10 ml/kg by daily oral gavage for 4 weeks. This route was selected because it simulates the oral administration route intended for use in human clinical studies and ensures the correct dose of compound is ingested by each animal. Data are expressed as means±the standard error of the mean. Statistical comparisons were carried out using a one-way analysis of variance followed by Dunnett's post hoc test using GraphPad Prism 8 software. A p-value of less than or equal to 0.05 will be used as the criterion of significance.

Figure 33:
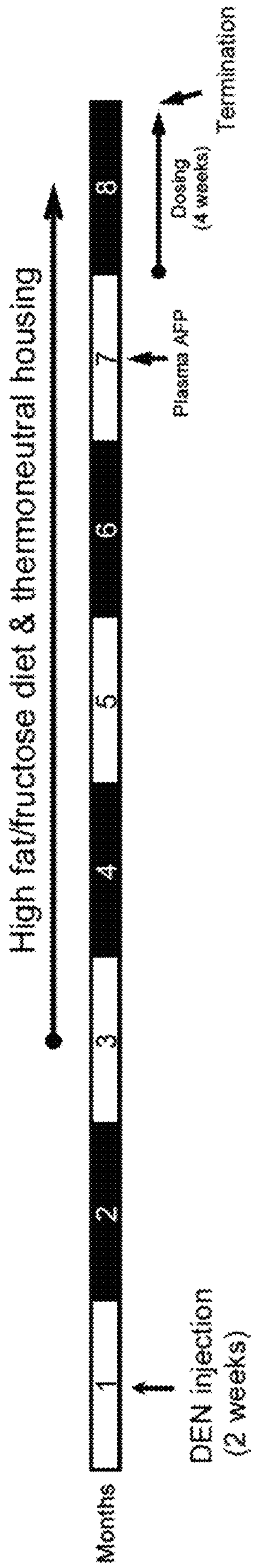
FIG. 33 shows an experimental protocol for NASH-HCC model study (Example 17).

Experimental Protocol. The experimental protocol is summarized in FIG. 33. At 2 weeks of age mice were injected with diethylnitrosamine (DEN) at 25 mg/kg body weight. After weaning mice were housed with littermates and fed a normal chow diet (Teklad 8640 22/5). At 10 weeks of age, mice were switched to a diet containing high fat and high fructose (HFFD-Research Diets, Inc. D19101102) and housed under thermoneutral conditions (29° C.) as this been shown to promote the development of NASH (Morrow and Steinberg, Keystone NASH Conference February 2020, Morrow et al. in review). After 7.5 months, mice were bled from the tail vein and plasma alpha-fetoprotein (AFP) levels were determined. AFP is a serum biomarker of HCC progression in humans and mice treated with DEN. At 8 months, mice were divided into 5 groups, based on mean AFP levels and then received a single daily dose of either vehicle (1.5% CMC and 0.2% Tween-20) or 30 mg/kg or 100 mg/kg of Compound I-32 or Compound I-1 via gavage. Throughout the experiments mice were housed in ventilated cage racks with ad libitum access to the food and water. An automatic timing device was used to maintain an alternating 12-hour cycle of light and dark.

After 4 weeks of daily treatments mice were anesthetized by I.P. injection of Ketamine/Xylazine (150 mg/12.4 mg/kg, respectively) in saline. When anesthetic plane has been achieved, 0.5 ml of blood was drawn by cardiac puncture, and plasma was isolated and frozen in liquid nitrogen. The liver was excised intact and rinsed briefly in PBS on ice. The liver was weighed, a photo was taken and the number of visible lesions on the surface of the liver was counted and recorded. A portion of tumor-free liver (~200 mg, caudate lobe) and up to three individual tumors were removed, flash frozen in liquid nitrogen and stored for molecular analysis. The remainder of the liver was placed in 10% formalin, fixed for 48 hours, and stored in 70% ethanol until it was embedded in paraffin, sectioned, and mounted on slides for histological analysis.

Analytical Methods

AFP assay. Before starting the treatment, mice were bled from the tail vein and plasma alpha-fetoprotein (AFP) levels were determined using mouse alpha-Feto protein/AFP Duoset ELISA kit (R&D Systems, Inc., MN, USA) as recommended by the manufacturer. 100 μl sample (1:1000 in reagent diluent) was added on each well of 96-well plate coated with mouse AFP capture antibody. Next, the plates were washed with wash buffer and 100 μl detection antibody was added to each well, followed by the Streptavidin HRP and substrate solution. The reaction was stopped by stop solution and the optical density of each well was measured in a microplate reader set to 450 nm. After measuring AFP levels, mice were divided into five groups (>800 ng/ml) and treatment was initiated.

ALT/AST assay. Plasma Alanine Transaminase (ALT) and Aspartate Transaminase (AST) levels were determined using ALT (CAK1002, Cohesion Biosciences) and AST (CAK 1004, Cohesion Biosciences) activity kits following the manufacturer instructions. 10 μl of plasma sample was added with 50 μl of substrate in 96-well plate. The reaction was carried out for 30 minutes at 37° C., detected by dye reagent I and II and absorbance was measured at 520 nm. The plasma ALT and AST levels was calculated as:

$$\text{ALT (U/ml)}=(C_{Standard}-V_{Standard})\times(OD_{Sample}-OD_{Control})/(OD\text{Standard}-OD_{Blank})/V_{Sample}/T=40\times(OD_{Sample}-OD_{Control})/(OD_{Standard}-OD_{Blank})$$

$$\text{AST (U/ml)}=(C_{Standard}\times V_{Standard})\times(OD_{Sample}-OD_{Control})/(OD\text{Standard}-OD_{Blank})/V_{Sample}/T=40\times(OD_{Sample}-OD_{Control})/(OD_{Standard}-OD_{Blank})$$

where C=concentration; V=volume; T=time; OD=optical density; U/ml=unit/milliliter Liver Histology. Following fixation with 10% neutral buffered formalin for 46 hours, the medial lobe of the liver was dissected and switched to 70% ethanol. Livers were then processed, paraffin embedded, serially sectioned, and stained with haematoxylin and eosin (H&E), Masson's Trichrome (MTC), and Picrosirius Red (PSR) by the McMaster Immunology Research Centre histology Core Facility. Images were taken using Nikon 90i Eclipse (Nikon Inc., NY, USA) upright microscope at indicated magnifications. Blinded liver histology scores were assigned to liver sections by a pathologist. Steatosis, lobular inflammation, and hepatocellular ballooning scores were assigned from H&E stained liver sections as described by Kleiner and colleagues (Kleiner et al., 2005). NAFLD Activity Scores (NAS) were obtained from the sum of these three scores. Fibrosis scores were assigned from analysis of both MTC and PSR stained liver sections as described by Kleiner (Kleiner et al., 2005).

Kidney Histology. Following fixation with 10% neutral buffered formalin for 46 hours, kidneys were cleaved longitudinally through hilium and immersed in 70% ethanol. Kidneys were then processed, paraffin embedded, serially sectioned and stained with haematoxylin and eosin (H&E) and Masson's Trichrome (MTC) by the McMaster Immunology Research Centre histology Core Facility. Blinded kidney histological scores for tubular injury, tubular mitoses, tubular vacuoles, interstitial inflammation, interstitial fibrosis, glomerular were assigned by pathologists.

Nanostring Analysis. RNA was extracted from paired liver and tumor tissue from vehicle, Compound I-1 (100 mg/kg) and Compound I-32 (100 mg/kg) treated mice using an RNeasy kit (Qiagen, Calif., USA) as per manufacturer's protocol. All RNA samples passed the BioAnalyzer quality control test. The expression of target genes in liver and tumor were analyzed using the nCounter Fibrosis and Cancer Panel (NanoString Technologies, Inc., WA, USA), respectively according to manufacturer's protocol at the McMaster Genomics Facility. Technical and biological normalization against global geometric mean was performed in nSolver 4.0 software (NanoString Technologies). Technical normalization was performed in the nSolver software (version 4.0.70) by normalizing sample target raw counts to the geometric mean of positive control spike-ins. Biological normalization was performed by normalizing sample target raw counts to the geometric mean of selected housekeeping genes (Ppia, Nubp1, Nol7, Armh3, Rplp0, Cnot10, Pgk1, and Acad9). Pathway scores were calculated as the first principal component of the normalized expression values for all genes in each pathway and samples were compiled according to experimental groups to determine average pathway scores. Statistical significance was calculated between experimental groups using multiple t-tests and p-values were corrected for multiple comparisons using Benjamin-Hochberg false discovery rate.

Figure 34A:
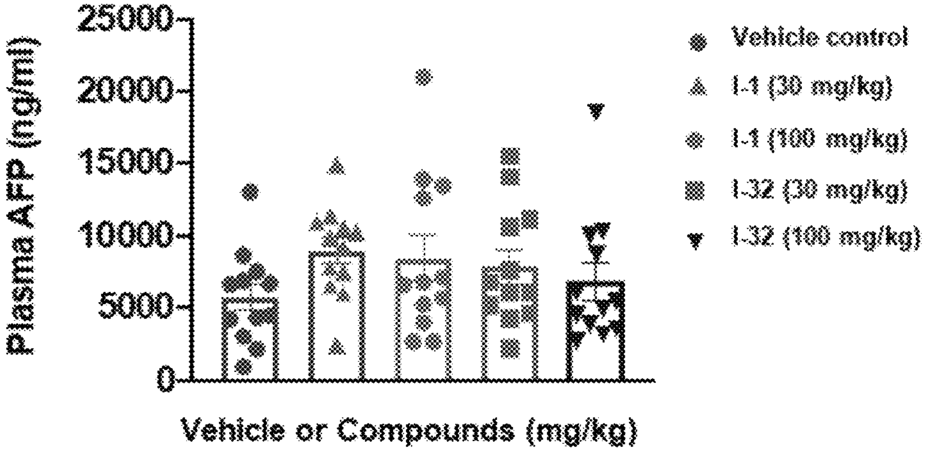
FIG. 34A shows plasma AFP values in mouse plasma before initiating treatments (n=11-12 per group).

Results. AFP is a serum biomarker of HCC and was utilized in this study to standardize tumor burden between the different treatment groups before initiating treatments. Mice with AFP levels >800 ng/ml were randomized across the 5 different groups so that mean starting AFP levels were not different between treatment groups (FIG. 34A). Table 14 shows specific Group # and animal # assignment to each treatment group.

TABLE 14

| Dosing Regimens | | | | |
|---|---|---|---|---|
| Group | N | Animal Nos. | Compound | Doses, mg/kg |
| 1 | 12 | 451, 474, 487, 508, 38, 42, 62.1, 62.2, 493, 497, 503, 465 | None-vehicle (CMC/Tween) | 0 |
| 3 | 12 | 472, 475, 490, 495, 485, 505, 45, 71, 515, 518, 39, 44 | I-32 | 30 |
| 4 | 12[a] | 454, 471, 504, 464, 466, 48, 59, 501, 494, 484, 31, 49 | I-32 | 100 |
| 6 | 12 | 450, 467, 499, 512, 513, 43, 58, 66 506, 73, 502, 511 | I-1 | 30 |
| 7 | 12 | 470, 483, 516, 517, 463, 27, 37, 41, 468, 462, 50, 32 | I-1 | 100 |

[a]One animal developed a severe neck lesion, could no longer be dosed due to ethical concerns and was excluded from the study.

Figure 34B:
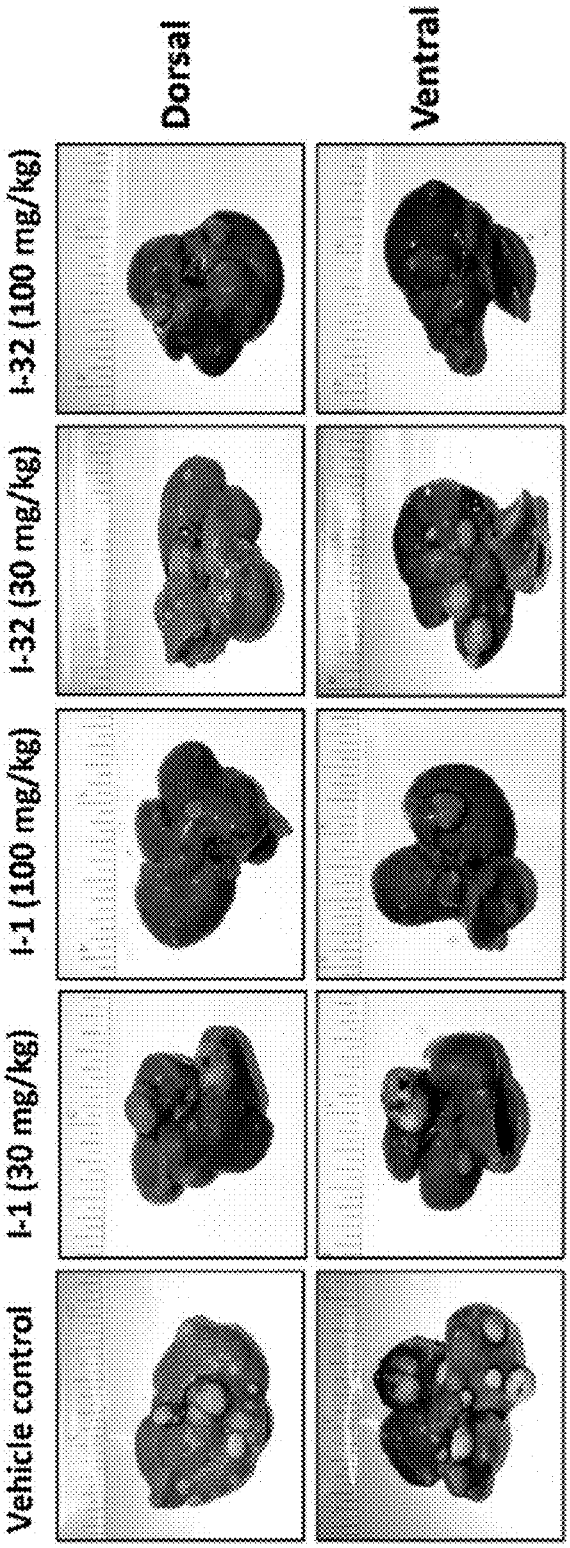
FIGS. 34B-34C shows tumor burden in diethylnitrosamine (DEN)-induced NASH-HCC murine model treated daily with Compound I-1 or Compound I-32 for 4 weeks. Representative images (FIG. 34B) and number of visible surface tumors (FIG. 34C) on livers of DEN-treated mice maintained on a high-fat and fructose diet and housed at thermoneutrality for 9 months (n=11-12 mice per group). Each bar represents the mean±the SEM, n=11-12. *$p<0.05$, $p<0.01$, *$p<0.001$, ****$p<0.0001$ vs. vehicle control, one-way ANOVA followed by Dunnett's post hoc test.
Figure 34C:
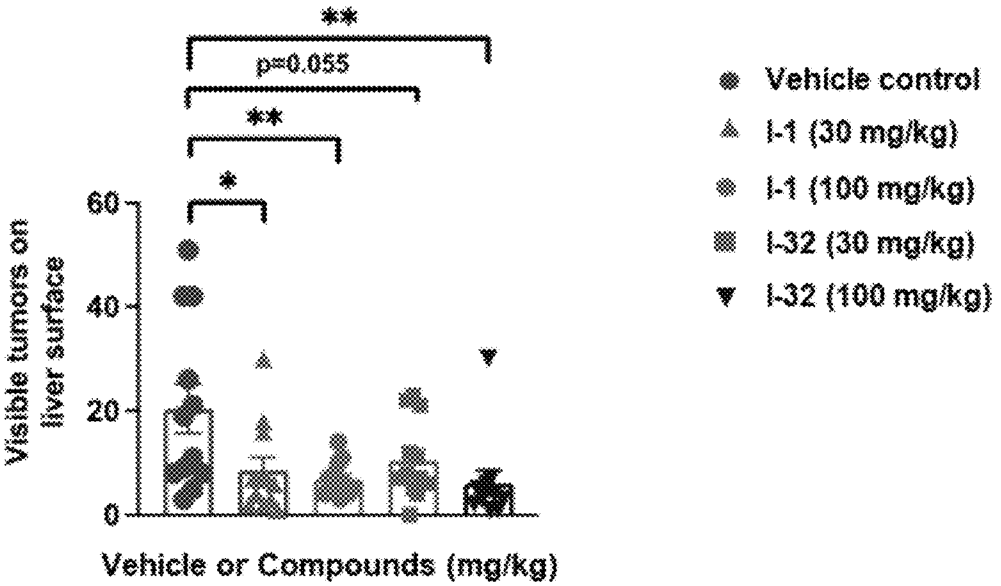

Liver Surface Tumors. After 4 weeks of daily treatment livers were collected from mice and visible surface tumors counted. Visual inspection of livers showed that livers from Compound I-32 and Compound I-1 mice were less pale in appearance compared to vehicle treated mice suggestive of reduced lipid accumulation (FIG. 34B). Treatment of mice with both 30 mg/kg and 100 mg/kg Compound I-1 reduced the number of surface tumors by over 70%. Similar observations were made with Compound I-32 however the 30 mg/kg dose did not reach statistical significance. These data indicate the daily oral dosing of Compound I-32 and Compound I-1 dramatically reduces the number of surface tumors (FIG. 34C).

Figure 34D:
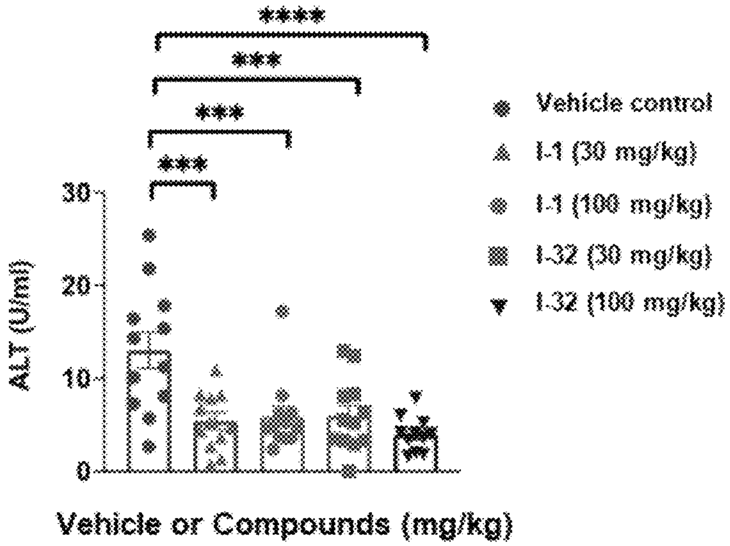
FIGS. 34D-34E display alanine aminotransferase (ALT) (FIG. 34D) and aspartate aminotransferase (AST) (FIG. 34E) levels in the plasma diethylnitrosamine (DEN)-induced NASH-HCC mice after being treated with 30 mg/kg or 100 mg/kg of Compound I-1 or Compound I-32 for 4 weeks. Each bar represents the mean±the SEM, n=11-12. *$p<0.05$, $p<0.01$, *$p<0.001$, ****$p<0.0001$ vs. vehicle control, One-way Anova followed by Dunnett's multiple.
Figure 34E:
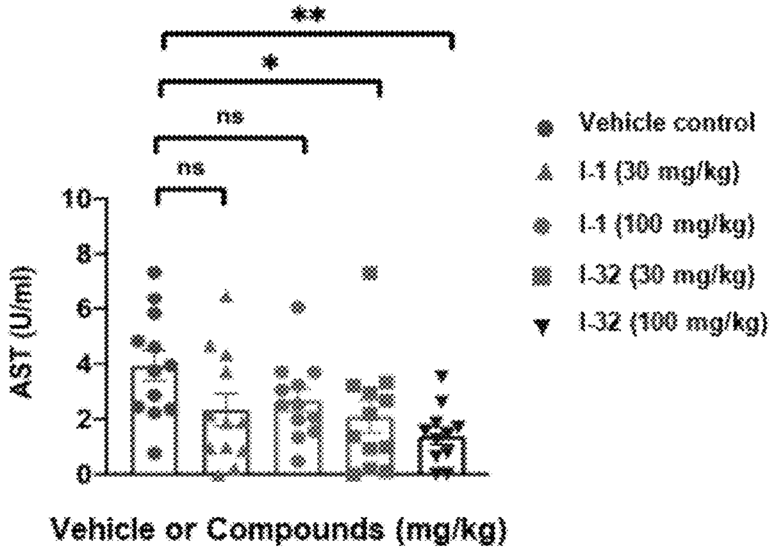

Plasma ALT/AST levels. Plasma ALT and AST levels are widely used as a marker for hepatocellular damage. To investigate whether illustrative compounds of the invention are able to reduce the hepatic damage, ALT and AST levels were examined in plasma. Plasma ALT and AST levels were significantly decreased by both Compound I-32 and Compound I-1 in a dose-dependent manner indicating that the compounds may protect liver damage (FIGS. 34D-34E).

Figure 35A:
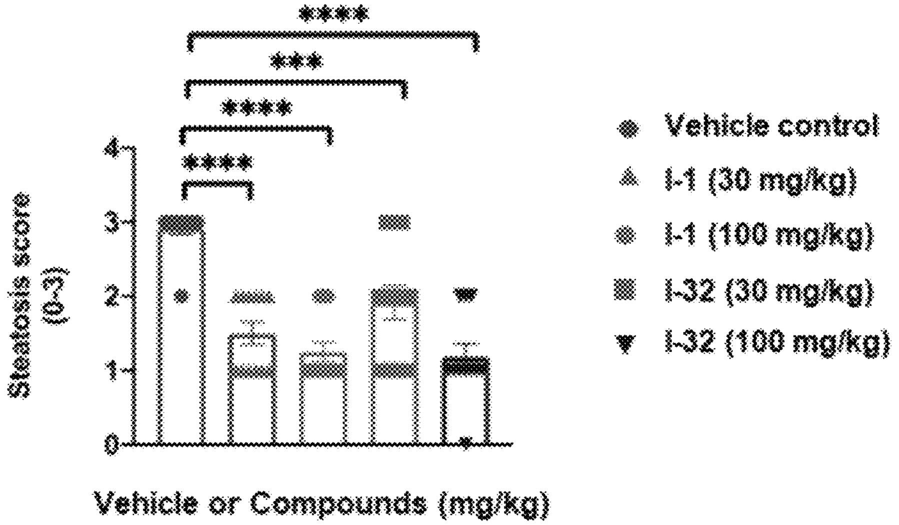
FIGS. 35A-35E show histological analysis of livers treated daily with Compound I-1 or Compound I-32 for 4 weeks. Histological scores for steatosis (FIG. 35A), ballooning degeneration (FIG. 35B), inflammation (FIG. 35C), NAS (FIG. 35D), and fibrosis (FIG. 35E) in liver sections from 9 months old DEN injected NASH-HCC mice treated with 30 mg/kg or 100 mg/kg of Compound I-1 or Compound I-32. Each bar represents the mean±the SEM, n=11-12. *$p<0.05$, $p<0.01$, *$p<0.001$, ****$p<0.0001$ vs. vehicle control, one-way Anova followed by Dunnett's multiple.
Figure 35B:
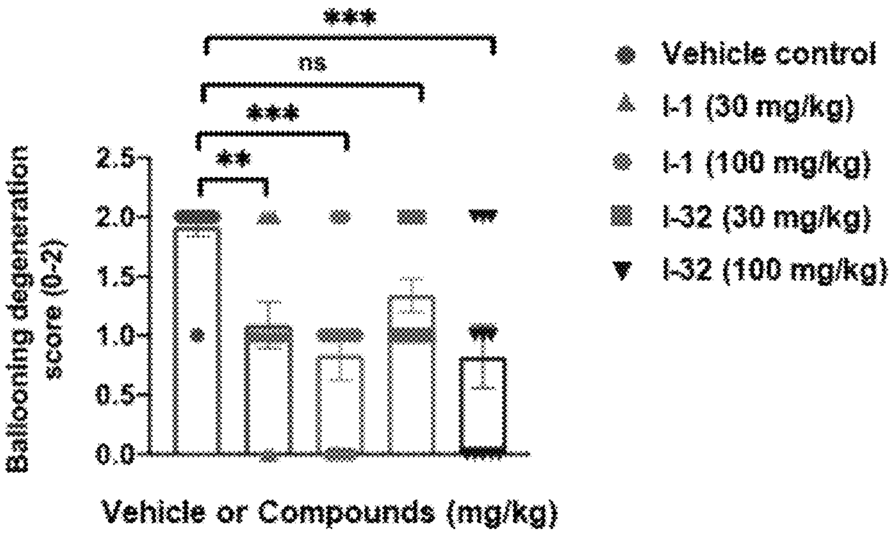
Figure 35C:
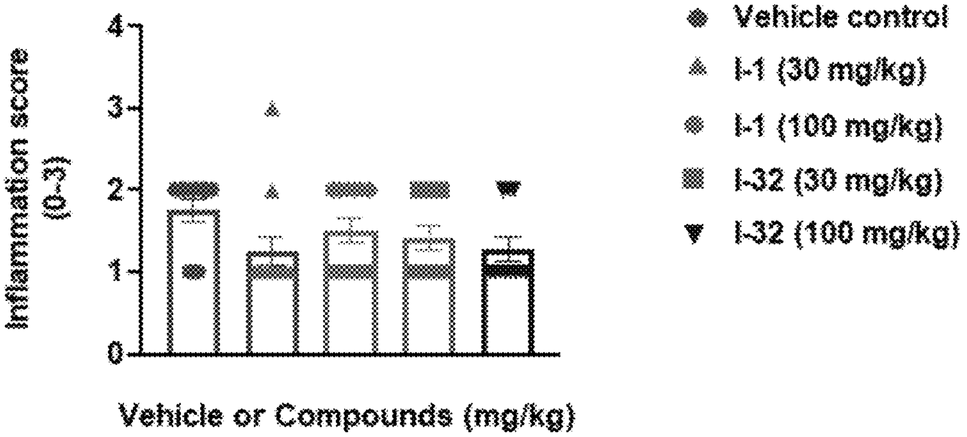
Figure 35D:
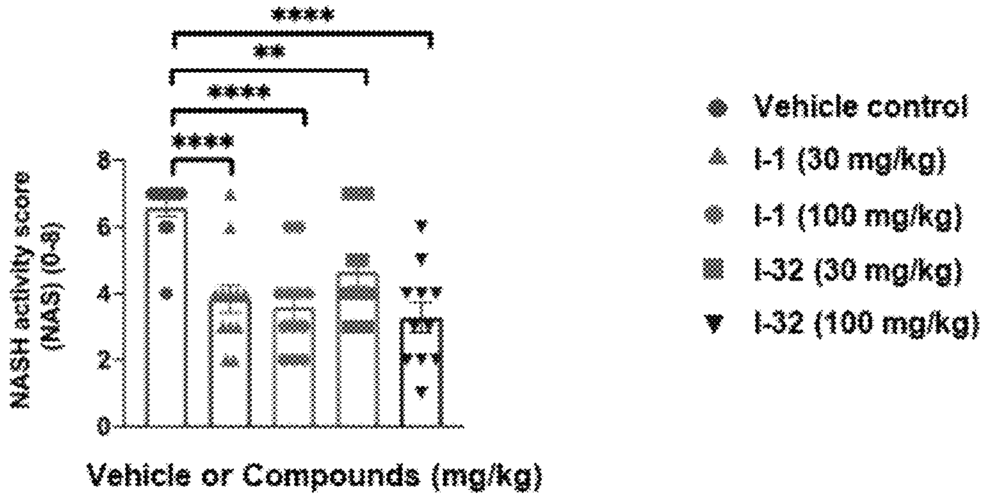
Figure 35E:
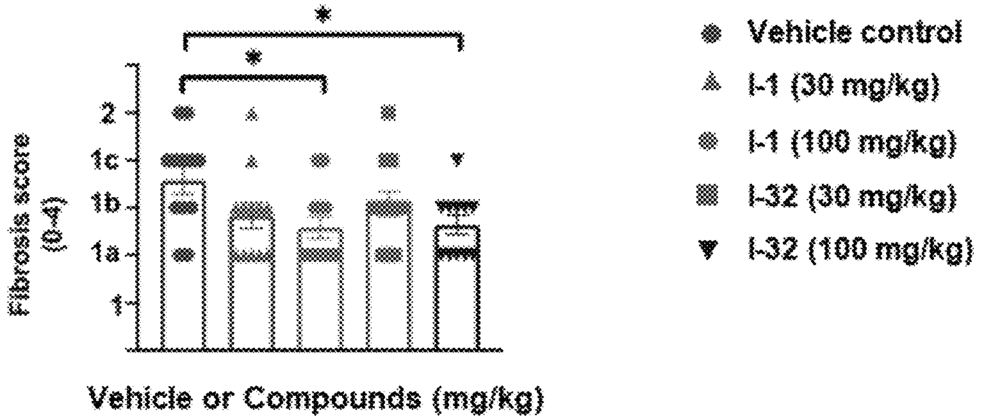

Liver Histology. After formalin embedding and staining, liver sections were analyzed in a blinded manner by a pathologist. Compound I-32 and Compound I-1 dramatically reduced steatosis (FIG. 35A) and ballooning (FIG. 35B) scores at both doses tested without altering inflammation scores (FIG. 35C). The summation of these scores indicated that both Compound I-32 and Compound I-1 reduced NAFLD activity scores (NAS) at both 30 and 100 mg/kg (FIG. 35D). Analysis of trichrome stained livers revealed that fibrosis was significantly reduced in mice treated with 100 mg/kg of Compound I-32 and Compound I-1 (FIG. 35E). These data indicate that Compound I-32 and Compound I-1 reduce liver steatosis and ballooning at 30 and 100 mg/kg and liver fibrosis at 100 mg/kg.

Kidney Histology. Preliminary short-term studies have indicated that Compound I-32 and Compound I-1 may have activity in the kidney of rodents. To investigate whether any pathological effects were observed in mice treated daily for one-month kidneys were collected from mice after 4 weeks of treatment. The data presented in Table 15 below indicates there were no pathological differences between Vehicle and Compound I-32 or Compound I-1 treated mice. In Table 15, pathologist's scoring is as follows: 0—not present; 1—minimal, inconspicuous change; 2—slight, noticeable but not a prominent feature; 3—moderate, prominent feature; 4—marked, dominant but not overwhelming feature; 5—severe, overwhelming change.

TABLE 15

Pathological effects on kidney from mice treated with vehicle, Compound I-32 or Compound I-1 for 4 weeks

| Mouse no. | Tubular injury | Tubular mitoses | Tubular vacuoles | Interstitial inflammation | Interstitial fibrosis | Glomerular |
|---|---|---|---|---|---|---|
| Control (Vehicle) | | | | | | |
| 451 | 0.5 | 0 | 2 | 0 | 0 | 0 |
| 474 | 0.5 | 0 | 2.5 | 0 | 1.5 | 0.5 |
| 487 | 0.5 | 0.5 | 1 | 0 | 2 | 1.5 |
| 508 | 1 | 0.5 | 2 | 0.5 | 1.5 | 0.5 |
| 38 | 0.5 | 0.5 | 0.5 | 0 | 1 | 0.5 |
| 42 | 0.5 | 0.5 | 1 | 0 | 0.5 | 1 |
| 62.1 | 0.5 | 0.5 | 0.5 | 0 | 0.5 | 1 |
| 62.2 | 1 | 0.5 | 2.5 | 0 | 0.5 | 0.5 |
| Average | 0.63 | 0.38 | 1.5 | 0.06 | 0.94 | 0.69 |
| Compound I-1 | | | | | | |
| 470 | 1.5 | 1 | 3.5 | 0 | 1 | 0 |
| 483 | 1 | 0 | 1.5 | 0 | 0.5 | 0 |
| 516 | 0.5 | 0 | 3 | 0 | 1 | 1 |
| 517 | 0.5 | 0.5 | 1.5 | 0 | 1 | 1 |
| 463 | 0.5 | 0.5 | 1.5 | 0.5 | 0 | 0.5 |
| 27 | 0 | 0.5 | 0.5 | 0.5 | 1.5 | 0.5 |
| 37 | 0 | 0 | 1 | 0.5 | 1 | 0.5 |
| 41 | 0.5 | 0.5 | 0.5 | 0 | 0.5 | 0 |
| Average | 0.56 | 0.38 | 1.63 | 0.19 | 1.0 | 0.44 |
| Compound I-32 | | | | | | |
| 454 | 0 | 0 | 0.5 | 0 | 0.5 | 0 |
| 471 | 1.5 | 0 | 3.5 | 0 | 1 | 0.5 |
| 501 | 1.5 | 1 | 1.5 | 2.5 | 2 | 1 |
| 504 | 1.5 | 0.5 | 3 | 1 | 1 | 0.5 |
| 464 | 1.5 | 0.5 | 2 | 1.5 | 1.5 | 0.5 |
| 466 | 0 | 0 | 1 | 0 | 1 | 1 |
| 48 | 0 | 0 | 1 | 0.5 | 0.5 | 0.5 |
| 59 | 1 | 1 | 1 | 0.5 | 1.5 | 0.5 |
| Average | 0.88 | 0.38 | 1.69 | 0.75 | 1.13 | 0.56 |

Molecular analysis. To identify the pathways modulated in the liver and tumor tissue, nanostring analysis of fibrosis and cancer, pathways, respectively were completed in an n=8 mice treated with vehicle or Compound I-32 or Compound I-1 at 100 mg/kg.

Table 16 indicates the mouse numbers that were studied, the number of surface tumors detected in the mouse and NAFLD activity and fibrosis scores assigned to that animal and indicate the animals selected are representative of the entire group.

TABLE 16

| Histological characteristics of the liver and tumor samples analyzed by Nanostring analysis | | | | | | | | | | | |
|---|---|---|---|---|---|---|---|---|---|---|---|
| Vehicle | | | | I-1 | | | | I-32 | | | |
| Mouse # | No. of Surface Tumors | NAFLD Activity Score | Fibrosis Score | Mouse # | No. of Surface Tumors | NAFLD Activity Score | Fibrosis Score | Mouse # | No. of Surface Tumors | NAFLD Activity Score | Fibrosis Score |
| 451 | 11 | 7 | 2 | 470 | 7 | 3 | 1a | 454 | 2 | 3 | 1a |
| 474 | 19 | 7 | 1b | 483 | 3 | 2 | 1a | 471 | 3 | 1 | 1a |
| 487 | 26 | 7 | 1c | 516 | 8 | 4 | 1a | 501 | 7 | 2 | 1b |
| 508 | 8 | 6 | 1a | 517 | 6 | 4 | 1b | 504 | 6 | 5 | 1c |
| 38 | 42 | 7 | 1c | 463 | 11 | 4 | 1b | 464 | 3 | 4 | 1a |
| 42 | 51 | 7 | 2 | 27 | 10 | 6 | 1c | 466 | 1 | 4 | 1b |
| 62.1 | 42 | 7 | 1c | 37 | 14 | 4 | 1c | 48 | 30 | 4 | 1b |
| 62.2 | 21 | 7 | 1c | 41 | 6 | 6 | 1b | 59 | 4 | 6 | 1b |
| Avg | 27.5 | 6.9 | NA | Avg | 8.1 | 4.1 | NA | Avg | 7 | 3.625 | NA |

1a: Mild (delicate) zone 3 perisinusoidal fibrosis, requires Masson's trichome stain to identify
1b: Moderate(dense) zone 3 perisinusoidal fibrosis
1c: Portal fibrosis only The liver fibrosis panel measured 770 genes and of these genes measured it was found that Compound I-1 altered the expression of 256 genes (86 upregulated, 170 downregulated) relative to vehicle controls (Table 17). Similar observations were also made with Compound I-32 which affected the expression of 231 genes (71 upregulated and 159 downregulated) (Table 18).

TABLE 17

| Significantly affected expression of genes in Compound I-1 vs vehicle control-treated livers | | | | | |
|---|---|---|---|---|---|
| Genes | Log2FC | Gene ID | Genes | Log2FC | Gene ID |
| Apoa4 | −4.07 | NM_007468 | Lyn | −0.32 | NM_010747 |
| Saa1/2 | −3.03 | NM_009117 | Irf1 | −0.32 | NM_008390 |
| Pek1 | −1.88 | NM_011044 | Smad3 | −0.317 | NM_016769 |
| C9 | −1.55 | NM_013485 | Kdm2a | −0.312 | NM_001001984 |
| Mmp12 | −1.53 | NM_008605 | Vim | −0.309 | NM_011701 |
| Cfh | −1.41 | NM_009888 | Kng2 | −0.305 | NM_001102410 |
| Hsd11b1 | −1.33 | NM_008288 | Cpt1a | −0.302 | NM_013495 |
| S100a4 | −1.28 | NM_011311 | Anapc10 | −0.291 | NM_026904 |
| Apoc2 | −1.26 | NM_001277944 | Apob | −0.289 | NM_009693 |
| C8a | −1.21 | NM_146148 | Txndc5 | −0.284 | NM_145367 |
| Col1a1 | −1.21 | NM_007742 | H2-K1 | −0.284 | NM_001001892 |
| Ccr2 | −1.18 | NM_009915 | Itch | −0.277 | NM_008395 |
| Slc37a4 | −1.17 | NM_008063 | Depdc5 | −0.27 | NM_001025426 |
| Egfr | −1.12 | NM_207655 | H2-D1 | −0.266 | NM_010380 |
| Loxl1 | −1.1 | NM_010729 | Cyfip1 | −0.264 | NM_001164661 |
| Tlr1 | −1.09 | NM_030682 | Rapgef2 | −0.262 | NM_001099624 |
| Psmb8 | −1.07 | NM_010724 | Ep300 | −0.258 | NM_177821 |
| Cyp7a1 | −1.07 | NM_007824 | Aldh7a1 | −0.252 | NM_001127338 |
| Col6a3 | −1.06 | XM_897036 | Traf2 | −0.247 | NM_009422 |
| Apoal | −1.03 | NM_009692 | Nfkb1 | −0.241 | NM_008689 |
| Il1r1 | −0.998 | NM_001123382 | Masp1 | −0.24 | NM_008555 |
| Aqp8 | −0.993 | NM_001109045 | Ube2d2a | −0.237 | NM_019912 |
| Pkhd1 | −0.99 | NM_153179 | Tin1 | −0.237 | NM_011602 |
| C6 | −0.969 | NM_016704 | Mmm1 | −0.231 | NM_001163507 |
| P3h3 | −0.96 | NM_013534 | Akt1 | −0.226 | NM_001165894 |
| H2-DMB1 | −0.938 | NM_010387 | Apoh | −0.225 | NM_013475 |
| Crp | −0.931 | NM_007768 | Pros1 | −0.22 | NM_011173 |
| Cxcr4 | −0.931 | NM_009911 | Erp29 | −0.217 | NM_026129 |
| Col1a2 | −0.924 | NM_007743 | Cflar | −0.214 | NM_207653 |
| C1s1 | −0.902 | NM_144938 | Jak1 | −0.203 | NM_146145 |
| Spp1 | −0.879 | NM_009263 | Serpinf1 | −0.18 | NM_011340 |
| Fbp1 | −0.878 | NM_019395 | Ssr2 | −0.177 | NM_025448 |
| P4hb | −0.842 | NM_011032 | Ctnnb1 | −0.17 | NM_007614 |
| Thbs2 | −0.831 | NM_011581 | Phykpl | −0.165 | NM_028398 |
| Tnfsf10 | −0.823 | NM_009425 | Cdh2 | −0.164 | NM_007664 |
| Il1rap | −0.815 | NM_134103 | Prkacb | −0.158 | NM_011100 |
| Adh4 | −0.808 | NM_011996 | Irf3 | −0.154 | NM_016849 |
| H2-Aa | −0.78 | NM_010378 | Ube2n | −0.15 | NM_080560 |
| Cd180 | −0.776 | NM_008533 | Map2k1 | −0.145 | NM_008927 |

TABLE 17-continued

Significantly affected expression of genes in Compound I-1 vs vehicle control-treated livers

| Genes | Log2FC | Gene ID | Genes | Log2FC | Gene ID |
|---|---|---|---|---|---|
| H2-Eb1 | −0.772 | NM_010382 | Ilk | −0.143 | NM_010562 |
| Col3a1 | −0.764 | NM_009930 | Psenen | −0.126 | NM_025498 |
| Ncf4 | −0.746 | NM_008677 | Rac1 | −0.093 | NM_009007 |
| Xaf1 | −0.742 | NM_001037713 | Itgb1 | 0.106 | NM_010578 |
| Il10ra | −0.737 | NM_008348 | Csnk2b | 0.114 | NM_009975 |
| Nid1 | −0.733 | NM_010917 | Nedd8 | 0.139 | NM_008683 |
| Isg15 | −0.727 | NM_015783 | Psmc3 | 0.145 | NM_008948 |
| H2-Ab1 | −0.716 | NM_207105 | Ppm1a | 0.148 | NM_008910 |
| Smurf1 | −0.697 | NM_001038627 | Atox1 | 0.157 | NM_009720 |
| H2-M3 | −0.69 | NM_013819 | Apoa2 | 0.172 | NM_013474 |
| Loxl2 | −0.689 | NM_033325 | Sugt1 | 0.185 | NM_026474 |
| Fn1 | −0.666 | NM_010233 | Mapk9 | 0.185 | NM_207692 |
| Aldob | −0.665 | NM_144903 | Spop | 0.186 | NM_025287 |
| Apoc3 | −0.657 | NM_023114 | Lamtor2 | 0.195 | NM_031248 |
| Stat3 | −0.646 | NM_213659 | Casp8 | 0.195 | NM_009812 |
| Casp12 | −0.633 | NM_009808 | Chuk | 0.202 | NM_001162410 |
| Serping1 | −0.631 | NM_009776 | Psmb7 | 0.204 | NM_011187 |
| Cfhr2 | −0.626 | NM_001025575 | Tjp2 | 0.204 | NM_011597 |
| Prir | −0.619 | NM_011169 | Got2 | 0.224 | NM_010325 |
| C3ar1 | −0.618 | NM_009779 | Ndufa1 | 0.226 | NM_019443 |
| Pparg | −0.615 | NM_011146 | Skp1a | 0.227 | NM_011543 |
| Cd68 | −0.613 | NM_001291058 | Hikeshi | 0.233 | NM_026304 |
| Timp2 | −0.609 | NM_011594 | Ap1s1 | 0.242 | NM_007457 |
| Gas1 | −0.608 | NM_008086 | Ndufb6 | 0.243 | NM_001033305 |
| Srebf1 | −0.608 | NM_011480 | Smad2 | 0.246 | NM_010754 |
| Tlr4 | −0.608 | NM_021297 | Uqcrfs1 | 0.255 | NM_025710 |
| Cxcl12 | −0.597 | NM_021704 | Ndufs3 | 0.26 | NM_026688 |
| Cyp27a1 | −0.594 | NM_024264 | Cdk4 | 0.26 | NM_009870 |
| Cpb2 | −0.58 | NM_019775 | Myd88 | 0.261 | NM_010851 |
| Pcx | −0.57 | NM_008797 | Casp6 | 0.266 | NM_009811 |
| Prkdc | −0.568 | NM_011159 | Hadh | 0.28 | NM_008212 |
| Fga | −0.563 | NM_010196 | Txn1 | 0.281 | NM_011660 |
| Cfi | −0.56 | NM_007686 | Hmgcs2 | 0.291 | NM_008256 |
| Irf8 | −0.55 | NM_008320 | Ctsd | 0.297 | NM_009983 |
| Slc2a2 | −0.543 | NM_031197 | Ywhag | 0.305 | NM_018871 |
| Fcgr4 | −0.541 | NM_144559 | Mbtps2 | 0.309 | NM_172307 |
| Em1 | −0.533 | NM_023913 | Uqcrh | 0.311 | NM_025641 |
| Casp7 | −0.522 | NM_00761-1 | Banf1 | 0.319 | NM_001038231 |
| Mmp14 | −0.522 | NM_008608 | Ptpn6 | 0.326 | NM_013545 |
| Cybb | −0.522 | NM_007807 | Ndufb8 | 0.327 | NM_026061 |
| Ptafr | −0.518 | NM_001081211 | Sod1 | 0.352 | NM_011434 |
| Fgg | −0.517 | NM_133862 | Hif1a | 0.358 | NM_010431 |
| Col5a1 | −0.513 | NM_015734 | Pgm2 | 0.361 | NM_028132 |
| Lgmn | −0.499 | NM_011175 | Cpn1 | 0.371 | NM_030703 |
| Igf1 | −0.496 | NM_001111274 | Ptpa | 0.372 | NM_138748 |
| Axl | −0.493 | NM_009465 | Sem1 | 0.385 | NM_009169 |
| Ptprc | −0.49 | NM_011210 | Hsp90ab1 | 0.407 | NM_008302 |
| Serpinh1 | −0.486 | NM_009825 | Ndufs5 | 0.414 | NM_001030274 |
| Isg20 | −0.48 | NM_020583 | Ndufb5 | 0.415 | NM_025316 |
| Nckap1l | −0.473 | NM_153505 | Eef2k | 0.422 | NM_007908 |
| Gpc4 | −0.469 | NM_008150 | Cox6a1 | 0.432 | NM_007748 |
| Ppard | −0.466 | NM_011145 | Brpf3 | 0.434 | NM_001081315 |
| Ifi35 | −0.465 | NM_027320 | Ndufc1 | 0.438 | NM_025523 |
| Mylk | −0.458 | NM_139300 | Mlxipl | 0.439 | NM_021455 |
| Rein | −0.45 | NM_011261 | Acaa2 | 0.464 | NM_177470 |
| Gpr65 | −0.447 | NM_008152 | Uqcrb | 0.476 | NM_026219 |
| Tgfbr1 | −0.445 | NM_009370 | Scd1 | 0.478 | NM_009127 |
| Abcb11 | −0.442 | NM_021022 | Uba52 | 0.484 | NM_019883 |
| Cd84 | −0.439 | NM_001252472 | Cox7c | 0.501 | NM_007749 |
| Lrrc32 | −0.438 | NM_001113379 | Slc25a10 | 0.508 | NM_013770 |
| Atg101 | −0.436 | NM_026566 | Fas | 0.528 | NM_007987 |
| Pik3cb | −0.421 | NM_029094 | Cox6b1 | 0.532 | NM_025628 |
| Fcer1g | −0.406 | NM_010185 | Aldh9a1 | 0.545 | NM_019993 |
| H2-T23 | −0.403 | NM_010398 | Nceh1 | 0.592 | NM_178772 |
| Xbp1 | −0.397 | NM_013842 | Bst2 | 0.596 | NM_198095 |
| Kng1 | −0.396 | NM_023125 | Adh1 | 0.603 | NM_007409 |
| Ikbkb | −0.395 | NM_010546 | Vegfb | 0.603 | NM_011697 |
| Itga1 | −0.394 | NM_001033228 | Acacb | 0.612 | NM_133904 |
| Plg | −0.393 | NM_008877 | Hsd17b4 | 0.637 | NM_008292 |
| H2-Dma | −0.391 | NM_010386 | Acsl4 | 0.645 | NM_207625 |
| Jmjd4 | −0.385 | NM_178659 | Acaca | 0.655 | NM_133360 |
| Creb3 | −0.38 | NM_013497 | Nrp2 | 0.665 | NM_001077403 |
| Anapc1 | −0.378 | NM_008569 | Hsp90aa1 | 0.693 | NM_010480 |
| Mfap3 | −0.377 | NM_180599 | Angpti4 | 0.707 | NM_020581 |
| Cxcl16 | −0.374 | NM_023158 | Ephx2 | 0.794 | NM_007940 |

TABLE 17-continued

Significantly affected expression of genes in Compound I-1 vs vehicle control-treated livers

| Genes | Log2FC | Gene ID | Genes | Log2FC | Gene ID |
|---|---|---|---|---|---|
| Icam1 | −0.371 | NM_010493 | Map1lc3a | 0.807 | NM_025735 |
| F5 | −0.363 | NM_007976 | Elovl6 | 0.819 | NM_130450 |
| Cebpa | −0.363 | NM_007678 | Fasn | 0.831 | NM_007988 |
| Sec61b | −0.355 | NM_024171 | Fabp4 | 1.01 | NM_024406 |
| Casp3 | −0.346 | NM_009810 | Aldh3a2 | 1.1 | NM_007437 |
| Bcl2l1 | −0.344 | NM_009743 | Fabp5 | 1.1 | NM_010634 |
| Lrp1 | −0.339 | NM_008512 | Hadha | 1.12 | NM_178878 |
| Fgb | −0.336 | NM_181849 | Cd36 | 1.32 | NM_007643 |
| Calm1 | −0.334 | NM_009790 | Pltp | 1.39 | NM_011125 |
| Derl2 | −0.334 | NM_033562 | Cyp4a12a | 1.65 | NM_177406 |
| Hc | −0.325 | NM_010406 | Hcar2 | 1.71 | NM_030701 |
| Stat5b | −0.322 | NM_001113563 | Lpl | 1.98 | NM_008509 |
| Ssr4 | −0.321 | NM_009279 | Chil1 | 2.06 | NM_007695 |
| Plcb3 | −0.321 | NM_008874 | Cyp4a10/31/32 | 3.15 | NM_010011 |

TABLE 18

Significantly affected expression of genes in Compound I-32 vs vehicle control-treated livers

| Gene | Log2FC | Gene ID | Gene | Log2FC | Gene ID |
|---|---|---|---|---|---|
| Apoa4 | −3.4 | NM_007468 | Il6st | −0.296 | NM_010560 |
| Mmp12 | −2.05 | NM_008605 | Itch | −0.295 | NM_008395 |
| Pck1 | −1.99 | NM_011044 | Lyn | −0.295 | NM_010747 |
| Saa1/2 | −1.96 | NM_009117 | F5 | −0.29 | NM_007976 |
| Marco | −1.54 | NM_010766 | Xbp1 | −0.29 | NM_013842 |
| Cfh | −1.41 | NM_009888 | Atf7ip | −0.289 | NM_019426 |
| Cyp7a1 | −1.38 | NM_007824 | Phykpl | −0.288 | NM_028398 |
| C8a | −1.37 | NM_146148 | Htra2 | −0.286 | NM_019752 |
| C9 | −1.25 | NM_013485 | Cfhr1 | −0.283 | NM_015780 |
| Hsd11b1 | −1.23 | NM_008288 | hfl | −0.282 | NM_008390 |
| Il1r1 | −1.16 | NM_001123382 | Erp29 | −0.277 | NM_026129 |
| Pkhdi | −1.12 | NM_153179 | Diaph1 | −0.265 | NM_007858 |
| C6 | −1.04 | NM_016704 | Masp1 | −0.26 | NM_008555 |
| Thbs2 | −1.01 | NM_011581 | Kdm2a | −0.255 | NM_001001984 |
| Fbp1 | −0.981 | NM_019395 | Cflar | −0.25 | NM_207653 |
| Smurf | −0.969 | NM_001038627 | Bcl2l1 | −0.248 | NM_009743 |
| P3h3 | −0.96 | NM_013534 | Casp3 | −0.237 | NM_009810 |
| Prir | −0.948 | NM_011169 | Ube2d2a | −0.231 | NM_019912 |
| Apoc2 | −0.94 | NM_001277944 | Cyfip1 | −0.229 | NM_001164661 |
| Egfr | −0.93 | NM_207655 | Ssr4 | −0.228 | NM_009279 |
| Il1rap | −0.868 | NM_134103 | Apob | −0.227 | NM_009693 |
| Crp | −0.857 | NM_007768 | H2-T23 | −0.224 | NM_010398 |
| Adh4 | −0.855 | NM_011996 | Kikb1 | −0.217 | NM_008455 |
| Slc37a4 | −0.843 | NM_008063 | Ctsb | −0.216 | NM_007798 |
| C3ar1 | −0.825 | NM_009779 | Itga9 | −0.212 | NM_001113514 |
| Psmb8 | −0.801 | NM_010724 | Serpinf1 | −0.208 | NM_011340 |
| S100a4 | −0.79 | NM_011311 | Ssr2 | −0.208 | NM_025448 |
| Syk | −0.772 | NM_001198977 | Pros1 | −0.208 | NM_011173 |
| P4hb | −0.765 | NM_011032 | Irf3 | −0.206 | NM_016849 |
| C1s1 | −0.755 | NM_144938 | Ube2n | −0.194 | NM_080560 |
| Cd68 | −0.732 | NM_001291058 | Actr1a | −0.192 | NM_016860 |
| Cyp27a1 | −0.71 | NM_024264 | Ap1g1 | −0.189 | NM_009677 |
| Xaf1 | −0.701 | NM_001037713 | Ldlrap1 | −0.189 | NM_145554 |
| Gas1 | −0.696 | NM_008086 | Slc25a13 | −0.179 | NM_001177572 |
| Tnfsf10 | −0.692 | NM_009425 | Map2k1 | −0.177 | NM_008927 |
| Rnf152 | −0.687 | NM_001160368 | H2-D1 | −0.175 | NM_010380 |
| Stat3 | −0.686 | NM_213659 | H2-K1 | −0.168 | NM_001001892 |
| Col6a3 | −0.679 | XM_897036 | Jak1 | −0.166 | NM_146145 |
| Col3a1 | −0.679 | NM_009930 | Cdh2 | −0.165 | NM_007664 |
| Isg15 | −0.673 | NM_015783 | Hsbp1 | −0.155 | NM_024219 |
| Hck | −0.667 | NM_010407 | Psenen | −0.154 | NM_025498 |
| Serping1 | −0.66 | NM_009776 | Bcap31 | −0.145 | NM_012060 |
| Nckap1l | −0.653 | NM_153505 | Ppp2ca | −0.123 | NM_019411 |
| Cyp2c29 | −0.646 | NM_007815 | Ilk | −0.109 | NM_010562 |
| Cybb | −0.644 | NM_007807 | Nedd8 | 0.0875 | NM_008683 |
| Fegr4 | −0.638 | NM_144559 | Csnk2b | 0.0913 | NM_009975 |
| Ncf1 | −0.635 | NM_001286037 | Ppm1a | 0.136 | NM_008910 |
| Srebf1 | −0.634 | NM_011480 | Itgb1 | 0.143 | NM_010578 |
| H2-M3 | −0.633 | NM_013819 | Ndufs3 | 0.148 | NM_026688 |
| Aqp8 | −0.632 | NM_001109045 | Sugt1 | 0.15 | NM_026474 |

TABLE 18-continued

Significantly affected expression of genes in Compound I-32 vs vehicle control-treated livers

| Gene | Log2FC | Gene ID | Gene | Log2FC | Gene ID |
|---|---|---|---|---|---|
| Cd180 | −0.606 | NM_008533 | Atp6v1e1 | 0.153 | NM_007510 |
| Lgmn | −0.601 | NM_011175 | Ndufa1 | 0.156 | NM_019443 |
| Col5a1 | −0.601 | NM_015734 | Got2 | 0.156 | NM_010325 |
| Aldob | −0.6 | NM_144903 | Cdk4 | 0.181 | NM_009870 |
| Cd84 | −0.6 | NM_001252472 | Uqcrfs1 | 0.188 | NM_025710 |
| Cfhr2 | −0.596 | NM_001025575 | Lamtor2 | 0.189 | NM_031248 |
| Prdx6 | −0.595 | NM_007453 | Tjp2 | 0.199 | NM_011597 |
| Pparg | −0.592 | NM_011146 | Seh1l | 0.216 | NM_001039088 |
| Igf1 | −0.588 | NM_001111274 | Ptpa | 0.222 | NM_138748 |
| Col1a2 | −0.588 | NM_007743 | Fas | 0.226 | NM_007987 |
| Fn1 | −0.584 | NM_010233 | Hadh | 0.258 | NM_008212 |
| Il10ra | −0.578 | NM_008348 | Rora | 0.258 | NM_013646 |
| Cxcl12 | −0.535 | NM_021704 | Ywhag | 0.265 | NM_018871 |
| Mylk | −0.532 | NM_139300 | Ero1l | 0.269 | NM_015774 |
| Serpinh1 | −0.531 | NM_009825 | Ndufb8 | 0.279 | NM_026061 |
| Ikbkb | −0.526 | NM_010546 | Uqcrh | 0.28 | NM_025641 |
| Prkdc | −0.525 | NM_011159 | Hif1a | 0.283 | NM_010431 |
| Pcx | −0.521 | NM_008797 | Sod1 | 0.284 | NM_011434 |
| Jmjd4 | −0.516 | NM_178659 | Sem1 | 0.298 | NM_009169 |
| Abcb11 | −0.503 | NM_021022 | Brpf3 | 0.3 | NM_001081315 |
| Isg20 | −0.491 | NM_020583 | Mbtps2 | 0.306 | NM_172307 |
| Hmox1 | −0.484 | NM_010442 | Acaa2 | 0.314 | NM_177470 |
| Atg101 | −0.483 | NM_026566 | Slc25a10 | 0.324 | NM_013770 |
| Apoa1 | −0.481 | NM_009692 | Ctsd | 0.331 | NM_009983 |
| Dock2 | −0.474 | NM_033374 | Cox6a1 | 0.336 | NM_007748 |
| Slc2a2 | −0.47 | NM_031197 | Banf1 | 0.339 | NM_001038231 |
| Ptprc | −0.47 | NM_011210 | Pgm2 | 0.339 | NM_028132 |
| Cpb2 | −0.467 | NM_019775 | Cpn1 | 0.351 | NM_030703 |
| Mmp14 | −0.465 | NM_008608 | Ndufb5 | 0.36 | NM_025316 |
| Ern1 | −0.451 | NM_023913 | Hsp90aa1 | 0.361 | NM_010480 |
| Timp2 | −0.451 | NM_011594 | Ndufc1 | 0.363 | NM_025523 |
| Ifi35 | −0.447 | NM_027320 | Uqcrb | 0.377 | NM_026219 |
| Cxcl16 | −0.445 | NM_023158 | Ndufs5 | 0.381 | NM_001030274 |
| Fcer1g | −0.427 | NM_010185 | Cox6b1 | 0.405 | NM_025628 |
| Axl | −0.418 | NM_009465 | Angptl4 | 0.413 | NM_020581 |
| Cebpa | −0.413 | NM_007678 | Uba52 | 0.433 | NM_019883 |
| Pik3cb | −0.412 | NM_029094 | Nceh1 | 0.444 | NM_178772 |
| Creb3 | −0.409 | NM_013497 | Hsd17b4 | 0.446 | NM_008292 |
| Ptafr | −0.408 | NM_001081211 | Cox7c | 0.459 | NM_007749 |
| Itga5 | −0.402 | NM_001314041 | Aldh9a1 | 0.467 | NM_019993 |
| H2-Aa | −0.4 | NM_010378 | Bst2 | 0.494 | NM_198095 |
| Rps6kb2 | −0.398 | NM_021485 | Vegfb | 0.521 | NM_011697 |
| Cfi | −0.395 | NM_007686 | Adh1 | 0.536 | NM_007409 |
| Apoc3 | −0.391 | NM_023114 | Ephx2 | 0.562 | NM_007940 |
| Fgg | −0.387 | NM_133862 | Scd1 | 0.602 | NM_009127 |
| Icam1 | −0.382 | NM_010493 | Lepr | 0.604 | NM_010704 |
| Gpc4 | −0.381 | NM_008150 | Nrp2 | 0.619 | NM_001077403 |
| Lrp1 | −0.376 | NM_008512 | Acacb | 0.681 | NM_133904 |
| Sec61b | −0.37 | NM_024171 | Acsl4 | 0.737 | NM_207625 |
| Cpt1a | −0.363 | NM_013495 | Map1lc3a | 0.744 | NM_025735 |
| Mfap3 | −0.362 | NM_180599 | Aldh3a2 | 0.869 | NM_007437 |
| Irf8 | −0.357 | NM_008320 | Fabp4 | 0.887 | NM_024406 |
| Tln1 | −0.355 | NM_011602 | Acaca | 0.893 | NM_133360 |
| Dock1 | −0.347 | NM_001033420 | Hadha | 0.903 | NM_178878 |
| Traf2 | −0.346 | NM_009422 | Scd2 | 0.949 | NM_009128 |
| Aldh7a1 | −0.344 | NM_001127338 | Cd36 | 1.02 | NM_007643 |
| Calm1 | −0.327 | NM_009790 | Fasn | 1.09 | NM_007988 |
| Txndc5 | −0.321 | NM_145367 | Elovl6 | 1.22 | NM_130450 |
| Anapc1 | −0.316 | NM_008569 | Pitp | 1.37 | NM_011125 |
| Itga1 | −0.312 | NM_001033228 | Hcar2 | 1.41 | NM_030701 |
| Casp7 | −0.31 | NM_007611 | Cyp4a12a | 1.42 | NM_177406 |
| Tgfbr1 | −0.309 | NM_009370 | Fabp5 | 1.44 | NM_010634 |
| Sorbs1 | −0.302 | NM_009166 | Lpl | 1.8 | NM_008509 |
| Plcb3 | −0.297 | NM_008874 | Chil1 | 2.58 | NM_007695 |
| Plg | −0.296 | NM_008877 | Cyp4a10/31/32 | 2.88 | NM_010011 |

A Nanostring analysis of fibrosis pathways in livers from DEN-injected mice treated with or without Compound I-1 (100 mg/kg) or with or without Compound I-32 (100 mg/kg) was performed (n=8 each for Compound I-1, Compound I-32, and vehicle). The primary pathways regulated by Compound I-32 and Compound I-1 were similar and involved down regulation of cytokine, chemokine, angiogenesis, TLR and interferon signaling pathways. There were only three pathways upregulated and these were fatty acid metabolism, de novo lipogenesis and PPAR signaling. These data indicate that consistent with similar effects on liver histology, Compound I-32 and Compound I-1 also exert similar effects on gene expression profiles in the liver; inhibiting pathways related to cytokine and chemokine signaling and upregulating pathways associated with fatty acid metabolism. The study has established that in a mouse model of NASH and HCC, Compound I-1 and Compound I-32 (100 mg/kg) reduced tumor burden by ~7(0% when delivered orally to mice for 4 weeks. In addition to reducing tumor burden, Compound I-1 and Compound I-32 also lowered steatosis, hepatocellular ballooning, and liver fibrosis. The analysis of over 750 genes in the liver related to fibrosis revealed that both Compound I-1 and Compound I-32 exerted similar effects on over 200 genes. In contrast in the tumor, Compound I-1 but not Compound I-32 exerted pronounced effects on gene expression pathways related to cancer progression and survival including cytokine and chemokine signaling, immune cell adhesion and migration and matrix remodeling and metastasis. In summary these data indicate dramatic effects of both Compound I-1 and Compound I-32 on reducing both NASH and HCC in a mouse model with an intact immune system. The data in the current study indicate that both Compound I-1 and Compound I-32 potently reduce liver steatosis and ballooning when delivered at doses as low as 30 mg/kg. Both compounds also reduce fibrosis when delivered at 100 mg/kg. Consistent with these reductions in steatosis, ballooning and fibrosis, transcriptional profiling found that both Compound I-1 and Compound I-32 exert marked effects on fibrosis related gene signatures as shown by reductions in chemokine and cytokines and angiogenesis while upregulating pathways related to fatty acid metabolism. Both compounds increased genes related to de novo lipogenesis, downregulating signaling pathways related to chemokine and cytokines and angiogenesis while upregulating pathways related to fatty acid metabolism.

Example 18. Effect of Illustrative Compounds on Cell Proliferation and Clonogenic Survival in Hep3B Human and Hepa1-6 Murine Hepatocellular Carcinoma Cell Lines Materials and Methods. Hep3B (catalog #HB-8064) human hepatocarcinoma and Hepa1-6 (catalog #CRL-1830) murine hepatoma cell lines were purchased from ATCC, Manassas, Va., USA and grown in Eagle's Minimum Essential Medium (catalog #10-009-CV. Mediatech Inc. A Corning Subsidiary, Manassas, Va., USA), and Dulbecco's Modified Eagle's Medium (catalog #319-005-CL, Wisent Bioproducts, St. Bruno, QC, Canada) respectively supplemented with 10% FBS (catalog #098150, Wisent Bioproducts) and 1% penicillin/streptomycin (catalog #15140122, Gibco. ThermoFisher Scientific, Waltham, Mass., USA) in a humidified incubator at 5% CO2/95% air as described.

Cell cultures. Hep3B (ATCC) and Hepa1-6 (ATCC) cells were seeded in 96-well plates at a density of 3000 cells/well with complete media. On day 2, media in each well was aspirated and replaced with 100 µl of fresh complete media and cells were treated with or without Compound I-1, Compound I-32, Compound I1-84, and Compound I-85, in a concentration dependent manner. Then, cells were incubated in an incubator for 72 h. On day 5, 10 µl of presto blue (Invitrogen, cat #A13261) cell viability reagent was added in each 96-well plate and incubated at 37° C. for 1-2 h. After incubation, fluorescence was measured with an excitation/emission wavelength of 560/590 nm.

Colony formation assay. Hep3B and Hepa1-6 cells were seeded in 12-well plates at a cell density of 1000 and 500 cells/well, respectively. On day 2, media in each well was aspirated and replaced with 1000 µl of fresh complete media and cells were treated with or without the respective drugs in an increasing concentration followed by the incubation of the cells for 7 days in an incubator.

On day 9, the media in each well was aspirated and cells were fixed with 10% formalin (500 µl) for 10 minutes at room temperature. Formalin was aspirated and the plates were washed with 1×PBS and stained with crystal violet for another 10 minutes. After 10 minutes of staining, crystal violet was poured over the cells, rinsed with tap water for three times and the plates were dried overnight. Next day, colonies (>50 cells) were counted and analyzed.

Statistical tests. Results were indicated as mean±standard deviation (SD). All line graphs were prepared using Graph Pad Prism 8 software. Proliferation and clonogenics IC50 values were calculated using a non-linear regression model in Graph pad Prism 8.

Figure 36:
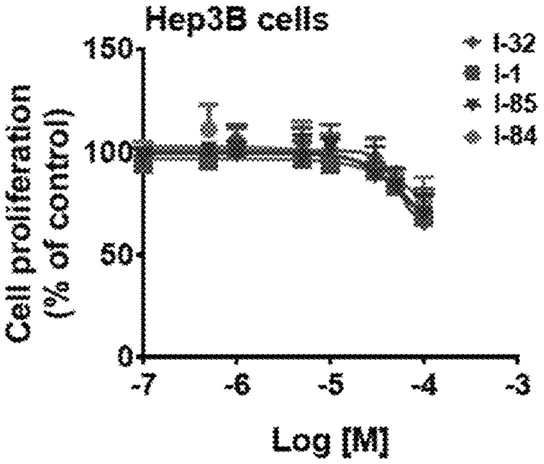
FIG. 36 show anti-proliferative effect of illustrative compounds of the invention in Hep3B cells.
Figure 37:
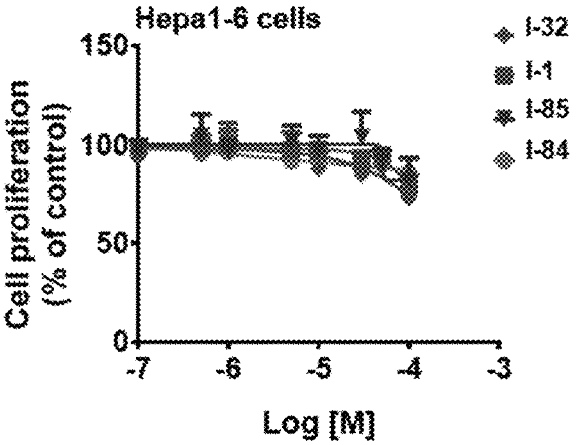
FIG. 37 show anti-proliferative effect of illustrative compounds of the invention in Hepa1-6 cells.

Results. Increased supply of lipids through lipogenesis fuels cell membrane biogenesis and enables cancer cells to grow and proliferate (Yahagi N, Shimano H. Hasegawa K et al. Co-ordinate activation of lipogenic enzymes in hepatocellular carcinoma. European journal of cancer 2005; 41:1316-22). When Hep3B cells or Hepa1-6 cells were treated with Compound I-1, Compound I-32, Compound I-84, or Compound I-85 for 72 h, each showed mild anti-proliferation activity with $IC_{50}$>100 µM (Table 19: FIGS. 36-37).

TABLE 19

Summary of Anti-Proliferation Activity in Hep3B and Hepa1-6 Cells

| Compound | Hep3B ($IC_{50}$) | Hepa1-6 ($IC_{50}$) |
|---|---|---|
| I-32 | >100 µM | >100 µM |
| I-1 | >100 µM | >100 µM |
| I-85 | >100 µM | >100 µM |
| 1-84 | >100 µM | >100 µM |

Figure 38A:
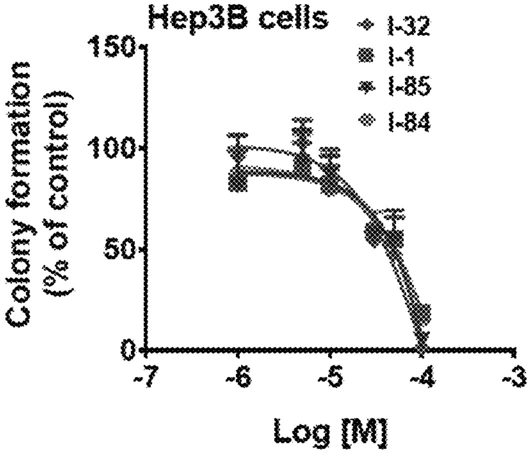
FIGS. 38A-38B show anti-clonogenic effect of illustrative compounds of the invention in Hep3B cells (FIG. 38A) and Hepa1-6 cells (FIG. 38B).
Figure 38B:
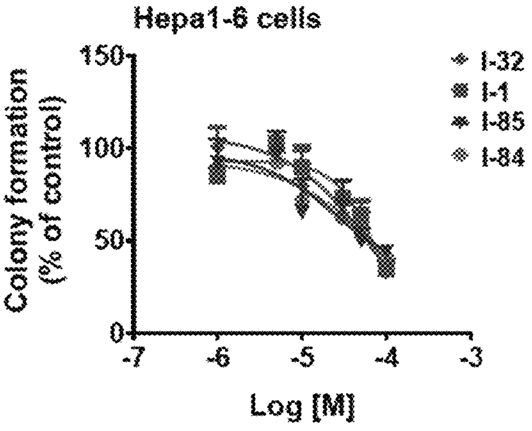

When the cells were treated with Compound I-1. Compound I-32, Compound I-84, or Compound I-85 for 7 days, all Compounds had strong anti-clonogenic effects in both Hep3B and Hepa1-6 cells (FIG. 38A-38B). In Hep3B cells, Compound I-32 showed highest anti-clonogenic effect with $IC_{50}$ of 40.80 µM followed by Compound I-85 ($IC_{50}$: 49.12 µM), Compound I-84 ($IC_{50}$: 50.11 µM) and I-1 ($IC_{50}$: 50.66 µM) (FIG. 38A; Table 20). Similarly, in Hepa1-6 cells, 1-32 showed highest anti-clonogenic activity with $IC_{50}$ of 58.88 µM followed by 1-85 ($IC_{50}$: 60.98 µM), 1-84 ($IC_{50}$: 64.87 µM) and 1-1 ($IC_{50}$: 67.60 µM) (FIG. 38B; Table 20).

TABLE 20

Summary of Anti-Clonogenic Activity in Hep3B and Hepa1-6 Cells

| Compound | Hep3B ($IC_{50}$) | Hepa1-6 ($IC_{50}$) |
|---|---|---|
| I-32 | 40.80 µM | 58.88 µM |
| I-1 | 50.66 µM | 67.60 µM |
| I-85 | 49.12 µM | 60.98 µM |
| 1-84 | 50.11 µM | 64.87 µM |

Example 19. Synergistic Anti-Proliferative Effect of Illustrative Compounds of the Invention with Regorafenib in Hep3B Human and Hepa1-6 Murine Hepatocellular Carcinoma Cell Lines Cell cultures. Hep3B (catalog #HB-8064) human hepatocarcinoma and Hepa1-6 (catalog #CRL-1830) murine hepatoma cell lines were purchased from ATCC, Manassas, Va., USA and grown in Eagle's Minimum Essential Medium (catalog #10-009-CV, Mediatech Inc. A Corning Subsidiary, Manassas, Va., USA), and Dulbecco's Modified Eagle's Medium (catalog #319-005-CL, Wisent Bioproducts, St. Bruno, QC, Canada) respectively supplemented with 10% FBS (catalog #098150, Wisent Bioproducts) and 1% penicillin/streptomycin (catalog #15140122, Gibco, ThermoFisher Scientific, Waltham, Mass., USA) in a humidified incubator at 5% CO2/95% air.

Reagents. Regorafenib (Free base, #R-8024) was obtained from LC laboratories, MA, USA.

Proliferation assay. Hep3B (ATCC) and Hepa1-6 (ATCC) cells were seeded in 96-well plates at a density of 3000 cells/well with complete media. On day 2, media in each well was aspirated and replaced with 100 μl of fresh complete media and cells were treated with/without testing compounds in a concentration dependent manner. Then, cells were incubated in an incubator for 72 h. On day 5, 10 μl of presto blue (Invitrogen, cat #A13261) cell viability reagent was added in each 96-well plate and incubated at 37° C. for 1-2 h. After incubation, fluorescence was measured with an excitation/emission wavelength of 560/590 nm. Anti-proliferative combination effects of Compound I-1 or Compound I-32 and regorafenib were determined in Hep3B and Hepa1-6 cells. Drug combination interaction was determined by the Chou-Talalay method (23), which is based on well-known equations for different reaction sequences and mechanisms, and different types of inhibition. These equations provide the theoretical basis for the combination index (CI)-isobologram equation that allows quantitative determination of drug interactions, where CI<1, =1, and >1 indicate synergism, additive effect, and antagonism, respectively. CI is calculated based on in vitro measurements implemented in the Compusyn software (www.combosyn.com), a platform for drug combinations pharmacodynamics with automated simulations. The software calculates CI based on the Fractional Inhibition (Fa), which is the potency expressed by the average effect values for each drug concentrations as determined by in vitro experiments. The dose-effect data entries are utilized for automated computerized analysis by the Compusyn software.

Data entered was obtained by in vitro experiments performed as follows: Hep3B or Hepa 1-6 cells were plated in a 96-well format and cell proliferation rates were determined as described above. Cells were treated with 5 doses of each test agent alone at the following concentrations: compounds of the invention dosed at 1, 5, 10, 50, or 100 μM for both Hep3B and Hepa1-6 cells, regorafenib dosed at 0.015, 0.075, 0.15, 0.75, and 1.5 μM for Hep3B cells or 0.05, 0.25, 0.5, 2.5, 5 μM for Hepa 1-6 cells. Effects of the compounds of the invention in combinations with regorafenib were determined by combining each of the 5 doses such that a constant ratio was maintained between compounds and regorafenib, as follows:

Hep3B cells: 66.67:1 compound/regorafenib

Hepa 1-6 cells: 20:1 compound/regorafenib

Combination Index (CI) was calculated using Compusyn software (wvww.combosyn.com) where a CI value of <1 indicates of synergy between two test agents. Data are shown as Fa-CI plots where CI is the combination index and Fa is fractional inhibition. Results were indicated as mean±standard deviation (SD). All bar diagrams and line graphs were prepared using Graph Pad Prism 8 software. Drug synergy was calculated using the CompuSyn software.

Figure 39A:
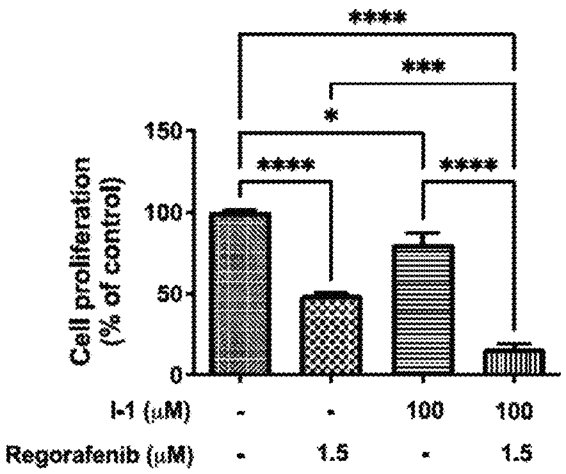
FIGS. 39A-39B display anti-proliferation effect of Compound I-1 (FIG. 39A) and Compound I-32 (FIG. 39B) with or without regorafenib (1.5 μM) in Hep3B cells. Each bar represents the mean±the SEM, n=5. *$p<0.03$, $p<0.002$, *$p<0.0002$, ****$p<0.0001$, One-way ANOVA followed by Tukey's multiple comparison.
Figure 39B:
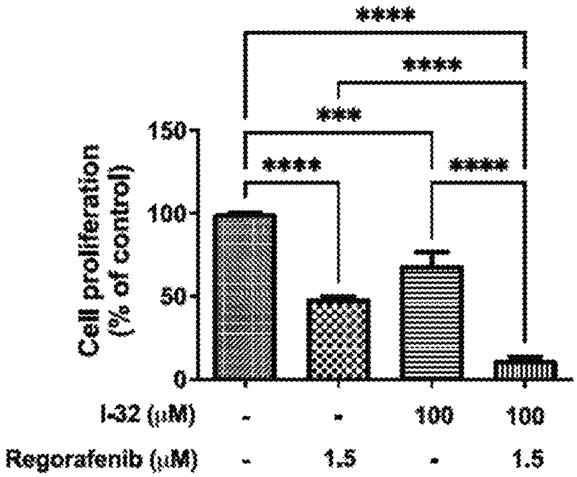

Synergistic effect of Compounds of the invention with regorafenib. Synergistic or additive anti-proliferation effects of Compound I-1 and Compound I-32 compounds were examined in Hep3B and Hepa1-6 cells with approximate proliferation $IC_{50}$ of regorafenib. It was observed that combined treatment with Compound I-32 (100 μM) or Compound I-1 (100 μM) in combination with regorafenib (1.5 μM) for 72 h in Hep3B cells showed greater inhibition of cell proliferation compared to their individual effects, as evidenced by the decrease in $IC_{50}$ (FIGS. 39A-39B).

Figure 40A:
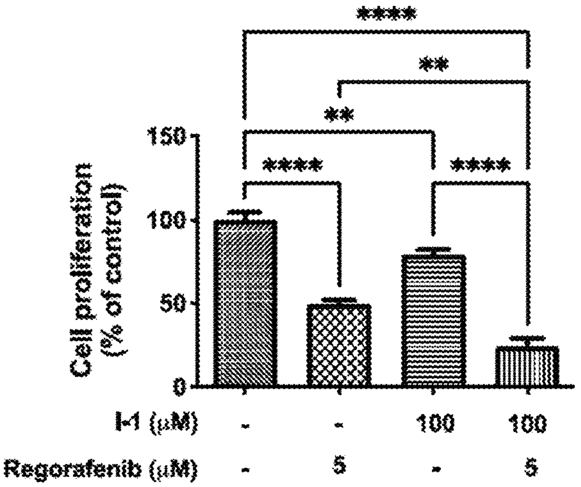
FIGS. 40A-40B display anti-proliferation effect of Compound I-1 (FIG. 40A) and Compound I-32 (FIG. 40B) with or without regorafenib (5 μM) in Hepa1-6 cells. *$p<0.03$, $p<0.002$, *$p<0.0002$, ****$p<0.0001$, One-way ANOVA followed by Tukey's multiple comparison.
Figure 40B:
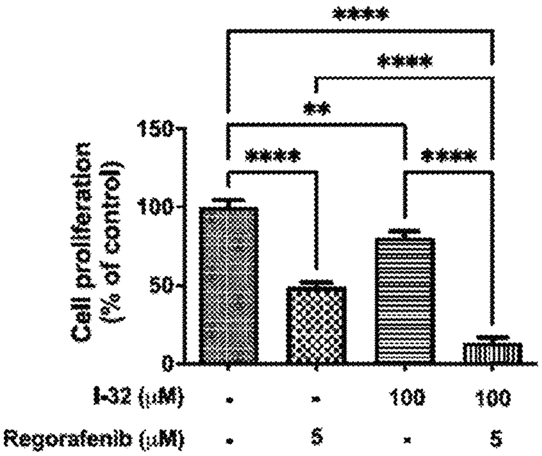

To study whether this type of synergy is common in Hepa 1-6 murine hepatoma cell line, similar to Hep3B cells, Hepa 1-6 cells when treated with Compound I-32 or Compound I-1 (100 μM) in combination with regorafenib (5 μM) for 72 h showed greater inhibition of cell proliferation compared to their individual effects, as evidenced by the decrease in $IC_{50}$ (FIGS. 40A-40B).

Figure 41A:
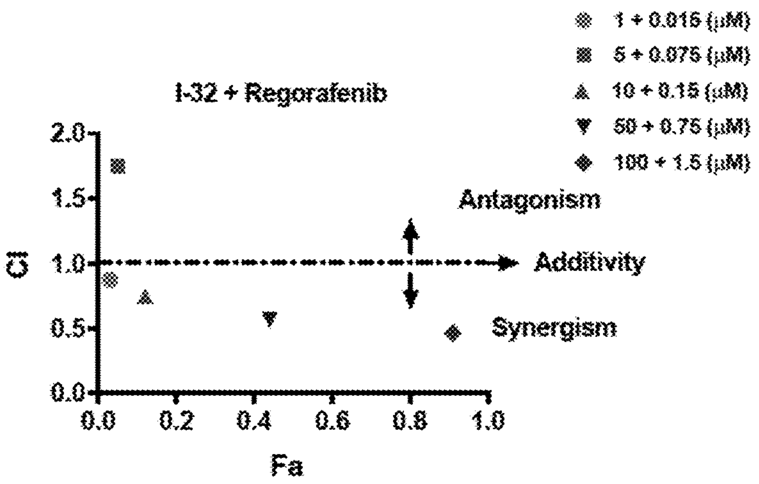
FIGS. 41A-41B show drug interaction effect of Compound I-32 (FIG. 41A) and Compound I-1 (FIG. 41B) in combination with regorafenib in Hep3B cell proliferation.
Figure 41B:
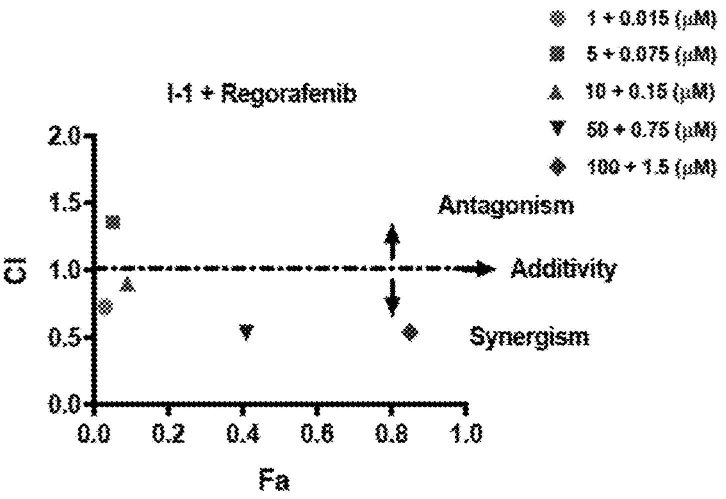
Figure 42A:
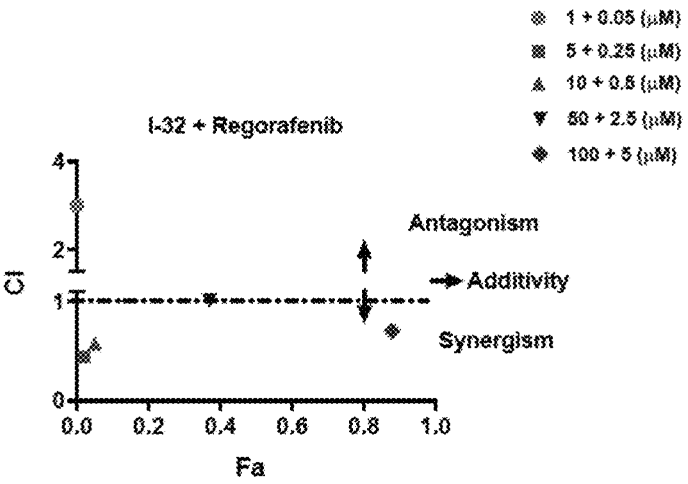
FIGS. 42A-42B show drug interaction effect of Compound I-32 (FIG. 42A) and Compound I-1 (FIG. 42B) in combination with regorafenib in Hepa1-6 cell proliferation.
Figure 42B:
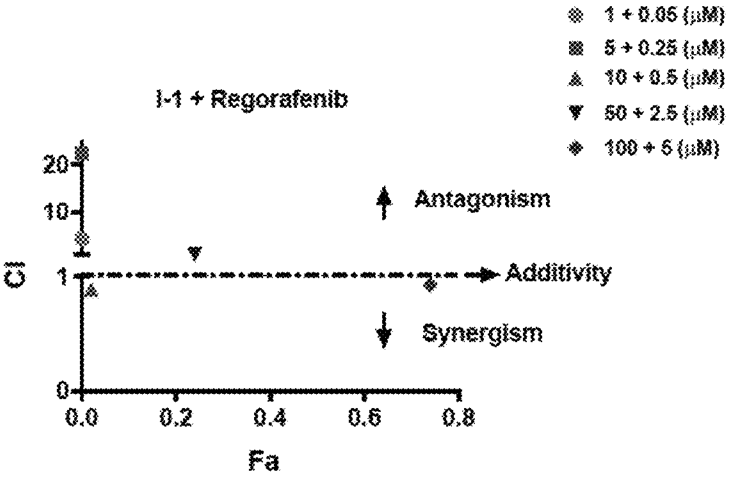

As additional inhibition of cell proliferation was observed in the combination studies, the results were analyzed using CompuSyn software to examine if there was a synergistic or additive effect on the antiproliferative activity in Hep3B and Hepa1-6 cells. As shown in FIGS. 41A-41B (Hep3B cells) and FIGS. 42A-42B (Hepa 1-6 cells), Compound I-32 (100 μM) and Compound I-1 (100 μM) showed synergistic inhibition in combination with regorafenib (Combination Index (CI)=1 additivity, CI<1 synergism and CI>1, antagonism). Generally, synergism between Compounds of the invention and regorafenib became more apparent as the fractional inhibition (Fa), a measure of potency, increased with the highest dose combination.

Hep3B Cells:

Compound I-32: CI<1 for all dose combinations with regorafenib except one dose combination (Compound I-32: regorafenib (5:0.075). Lowest CIs are observed at the highest doses: Compound I-32: regorafenib 100 μM: 1.5 μM and at higher potency (Fa).

Compound I-1: CI<1 for all dose combinations with regorafenib except one dose combination (Compound I-1: regorafenib (5:0.075). Highest potency (Fa) is observed at the highest doses: Compound I-1: regorafenib 100 μM: 1.5 μM.

Hepa1-6 Cells:

Compound I-32: CI<1 for dose combinations with regorafenib, Compound I-32: regorafenib 100 μM: 5 μM Compound I-1: CI<1 for dose combinations with regorafenib, Compound I-32: regorafenib 100 μM: 5 μM

Example 20. Synergistic Anti-Proliferative Effect of Illustrative Compounds of the Invention with Sorafenib or Lenvatinib in Hep3B Human and Hepa1-6 Murine Hepatocellular Carcinoma Cell Lines Materials: Sorafenib (p-Toluenesulfonate Salt, catalog #S8502) and levantinib (free base, catalog #L5400) were obtained from LC laboratories, MA, USA.

Methods: Hep3B cells (supplied by ATCC) and Hepa1-6 cells (supplied by ATCC) were seeded in 96-well plates at a density of 3000 cells/well with complete media. On day 2, the media in each well was aspirated and replaced with 100 μL of fresh complete media, and the cells were treated in a concentration dependent manner with either Compound I-1, Compound I-32, Compound I-84, Compound I-85, sorafenib, lenvatinib, Compound I-1 in combination with sorafenib. Compound I-1 in combination with lenvatinib, Compound I-32 in combination with sorafenib, or Compound I-32 in combination with lenvatinib. The cells were then incubated in an incubator at 37° C. for 72 h. On day 5, 10 μL of presto blue (Invitrogen, cat #A13261) cell viability reagent was added to each 96-well plate and incubated at 37° C. for 1-2 h. After incubation, fluorescence was measured with an excitation/emission wavelength of 560/590 nm.

The cells were treated as follows:

Compound I-1. A stock solution of 100 mM Compound I-1 in DMSO was prepared and was aliquoted into 20 μL stock solutions. The aliquots were stored in a freezer at −20° C. On the day of treatment, a stock solution was defrosted and further diluted with media and 1 μL of dimethyl sulfoxide ("DMSO") to provide Compound I-1 working solutions (1 mL each) having working concentrations of 1 μM, 5 μM, 10 μM, 50 μM and 100 μM. For Hep3B cells, the media was Eagle's Minimum Essential Medium, 10% Fetal Bovine Serum (FBS), 1% Antibiotic/Antimycotic (A/A) (Gibco, cat #15240-062) (the "Hep3B cell media"). For Hepa1-6 cells, the media was Dulbecco's Modified Eagle's Medium, 10% FBS, 1% A/A (the "Hepa1-6 cell media"). The Hep3B cell media was diluted with DMSO to a concentration of 0.1% DMSO and was used as a control for all Hep3B cell experiments. The Hepa1-6 cell media was diluted with DMSO to a concentration of 0.1% DMSO and was used as control for Hepa1-6 cell experiments. Hep3B and Hepa1-6 cells at a seeding density of 3000 cells/well were treated with each Compound I-1 working concentration.

Compound I-32. A stock solution of 100 mM Compound I-32 in DMSO was prepared and was aliquoted into 20 μL stock solutions. The aliquots were stored in a freezer at −20° C. On the day of treatment, a stock solution was defrosted and further diluted with media and 1 μL of DMSO to provide Compound I-32 working solutions (1 mL each) having working concentrations of 1 μM, 5 μM, 10 μM, 50 μM and 100 μM. For Hep3B cells, the media was the Hep3B cell media described above. For Hepa1-6 cells, the media was the Hepa1-6 cell media described above. The Hep3B cell media was diluted with DMSO to a concentration of 0.1% DMSO and was used as a control for all Hep3B cell experiments. The Hepa1-6 cell media was diluted with DMSO to a concentration of 0.1% DMSO and was used as control for Hepa1-6 cell experiments. Hep3B and Hepa1-6 cells at a seeding density of 3000 cells/well were treated with each Compound I-32 working concentration.

Compound I1-84. A stock solution of 100 mM Compound I-84 in DMSO was prepared and was aliquoted into 20 μL stock solutions. The aliquots were stored in a freezer at −20° C. On the day of treatment, a stock solution was defrosted and further diluted with media and 1 μL of DMSO to provide Compound I-84 working solutions (1 mL each) having working concentrations of 0.1 μM, 0.5 μM, 1 μM, 5 μM, 10 μM, 30 μM, 50 μM and 100 μM. The Hep3B cell media was diluted with DMSO to a concentration of 0.2% DMSO and was used as a control for all Hep3B cell experiments. The Hepa1-6 cell media was diluted with DMSO to a concentration of 0.2% DMSO and was used as control for Hepa1-6 cell experiments. Hep3B and Hepa1-6 cells at a seeding density of 3000 cells/well were treated with each Compound I-84 working concentration.

Compound I-85. A stock solution of 100 mM Compound I-85 in DMSO was prepared and was aliquoted into 20 μL stock solutions. The aliquots were stored in a freezer at −20° C. On the day of treatment, a stock solution was defrosted and further diluted with media and 1 μL of DMSO to provide Compound I-85 working solutions (1 mL each) having working concentrations of 0.1 μM, 0.5 μM, 1 μM, 5 μM, 10 μM, 30 μM, 50 μM and 100 μM. The Hep3B cell media was diluted with DMSO to a concentration of 0.2% DMSO and was used as a control for all Hep3B cell experiments. The Hepa1-6 cell media was diluted with DMSO to a concentration of 0.2% DMSO and was used as control for Hepa1-6 cell experiments. Hep3B and Hepa1-6 cells at a seeding density of 3000 cells/well were treated with each Compound I-85 working concentration.

Sorafenib. The stock solution and aliquots were prepared as described above for Compound I-1, except that the sorafenib working concentrations were: for Hep3B cells, 0.03 μM, 0.15 μM, 0.3 μM, 1.5 μM and 3 μM; and for Hepa1-6 cells, 0.05 μM, 0.25 μM, 0.5 μM, 2.5 μM and 5 μM. Hep3B and Hepa1-6 cells at a seeding density of 3000 cells/well were treated with each sorafenib working concentration.

Lenvatinib. The stock solution and aliquots were prepared as described above for Compound I-1, except that the lenvatinib working concentrations were: for Hep3B cells, 0.005 μM, 0.025 μM, 0.05 μM, 0.25 μM and 0.5 μM; for Hepa1-6 cells, 0.3 μM, 1. μM, 3 μM, 15 μM, and 30 μM. Hep3B and Hepa1-6 cells at a seeding density of 3000 cells/well were treated with each lenvatinib working concentration.

Compound I-1 in combination with sorafenib. The stock solution and aliquots were prepared as described above for each of Compound I-1 and sorafenib, except that the Compound I-1-and-sorafenib working concentrations were prepared without additional 1 μL DMSO (total DMSO concentration was 0.2%) and as follows: for Hep3B cells, combining 1 μM, 5 μM, 10 μM, 50 μM and 100 μM Compound I-1 working concentration with 0.03 μM, 0.15 μM, 0.3 μM, 1.5 μM and 3 μM sorafenib working concentration, respectively; and for Hepa1-6 cells, combining 1 μM, 5 μM, 10 μM, 50 μM and 100 μM Compound I-1 working concentration with 0.05 μM, 0.25 μM, 0.5 μM, 2.5 μM and 5 μM sorafenib working concentration, respectively. Each Compound I-1-and-sorafenib working concentration contained, for Hep3B cells, a 33.33:1 molar ratio of Compound I-1 to sorafenib, and for Hepa1-6 cells, a 20:1 molar ratio of Compound I-1 to sorafenib. Hep3B and Hepa1-6 cells at a seeding density of 3000 cells/well were treated with each Compound I-1-and-sorafenib working concentration.

Compound I-1 in combination with lenvatinib. The stock solution and aliquots were prepared as described above for each of Compound I-1 and lenvatinib, except that the Compound I-1-and-lenvatinib working concentrations were prepared without additional 1 μL DMSO (total DMSO concentration was 0.2%) and as follows: for Hep3B cells, combining 1 μM, 5 μM, 10 μM, 50 μM and 100 μM Compound I-1 working concentration with 0.005 μM, 0.025 μM, 0.05 μM, 0.25 μM and 0.5 μM lenvatinib working concentration, respectively; and for Hepa1-6 cells, combining 1 μM, 5 μM, 10 μM, 50 μM and 100 μM Compound I-1 working concentration with 0.3 μM, 1.5 μM, 3 μM, 15 μM, and 30 μM lenvatinib working concentration, respectively. Each Compound I-1-and-lenvatinib working concentration contained, for Hep3B cells, a 200:1 molar ratio of Compound I-1 to lenvatinib, and for Hepa1-6 cells, a 3.33:1 molar ratio of Compound I-1 to lenvatinib. Hep3B and Hepa1-6 cells at a seeding density of 3000 cells/well were treated with each Compound I-1-and-lenvatinib working concentration.

Compound I-32 in combination with sorafenib. The stock solution and aliquots were prepared as described above for each of Compound I-32 and sorafenib, except that the Compound I-32-and-sorafenib working concentrations were prepared without additional 1 μL DMSO (total DMSO concentration was 0.2%) and as follows: for Hep3B cells, combining 1 μM, 5 μM, 10 μM, 50 μM and 100 μM Compound I-32 working concentration with 0.03 μM, 0.15 μM, 0.3 μM, 1.5 μM and 3 μM sorafenib working concentration, respectively; and for Hepa1-6 cells, combining 1 μM, 5 μM, 10 μM, 50 μM and 100 μM Compound I-32 working concentration with 0.05 μM, 0.25 μM, 0.5 μM, 2.5 μM and 5 μM sorafenib working concentration, respectively. Each Compound I-32-and-sorafenib working concentration contained, for Hep3B cells, a 33.33:1 molar ratio of Compound I-32 to sorafenib, and for Hepa1-6 cells, a 20:1 molar ratio of Compound I-32 to sorafenib. Hep3B and Hepa1-6 cells at a seeding density of 3000 cells/well were treated with each Compound I-32-and-sorafenib working concentration.

Compound I-32 in combination with lenvatinib. The stock solution and aliquots were prepared as described above for each of Compound I-32 and lenvatinib, except that the Compound I-32-and-lenvatinib working concentrations were prepared without additional 1 μL DMSO (total DMSO concentration was 0.2%) and as follows: for Hep3B cells, combining 1 μM, 5 μM, 10 μM, 50 μM and 100 μM Compound I-32 working concentration with 0.005 μM, 0.025 μM, 0.05 μM, 0.25 μM and 0.5 μM lenvatinib working concentration, respectively; and for Hepa1-6 cells, combining 1 μM, 5 μM, 10 μM, 50 μM and 100 μM Compound I-32 working concentration with 0.3 μM, 1.5 μM, 3 μM, 15 μM, and 30 μM lenvatinib working concentration, respectively. Each Compound I-32-and-lenvatinib working concentration contained, for Hep3B cells, a 200:1 molar ratio of Compound I-32 to lenvatinib, and for Hepa1-6 cells, a 3.33:1 molar ratio of Compound I-32 to lenvatinib. Hep3B and Hepa1-6 cells at a seeding density of 3000 cells/well were treated with each Compound I-32-and-lenvatinib working concentration.

Figure 43A:
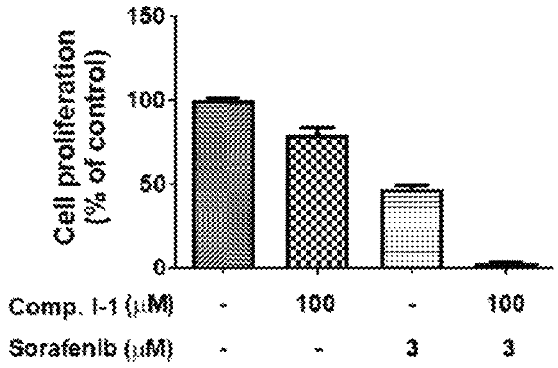
FIG. 43A shows Hep3B cell proliferation (as a percent of control) for control (Hep3B cell media containing 0.2% DMSO), Compound I-1 (100 μM), sorafenib (3 μM), and Compound I-1 (100 μM) in combination with sorafenib (3 μM).

FIG. 43A shows Hep3B cell proliferation (as a percent of control) for control (Hep3B cell media containing 0.2% DMSO), Compound I-1 (100 μM), sorafenib (3 μM), and Compound I-1 (100 μM) in combination with sorafenib (3 μM). Surprisingly and unexpectedly, Compound I-1 in the absence of sorafenib significantly (p=0.0002, determined by one-way ANOVA, followed by Tukey's multiple comparison) inhibited Hep3B cell proliferation compared to control, after incubation for 72 h; moreover, Compound I-1 in combination with sorafenib showed significantly greater inhibition of Hep3B cell proliferation compared to Compound I-1 in the absence of sorafenib and to sorafenib in the absence of Compound I-1, after incubation for 72 h.

Figure 44A:
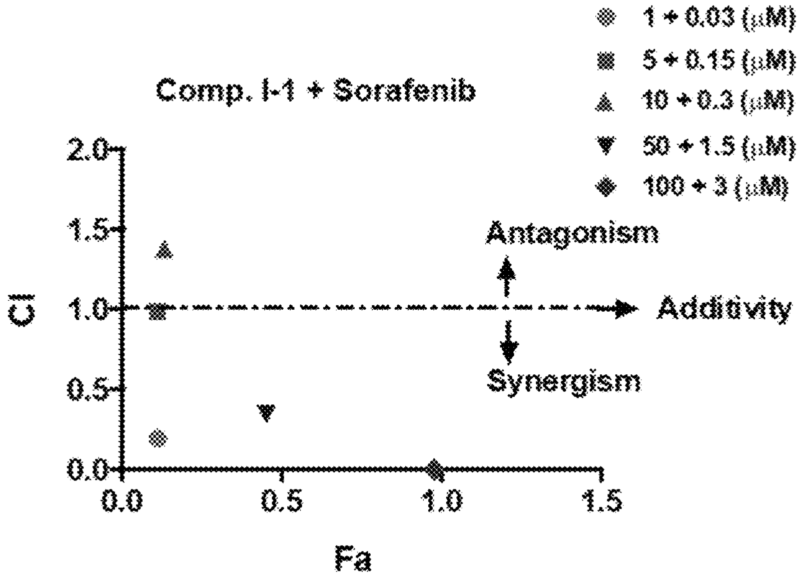
FIGS. 44A-44D show drug interaction effects of Compound 1-32 and Compound I-1 in combination with sorafenib and lenvatinib, as follows.

FIG. 44A shows synergism of Compound I-1 in combination with sorafenib at various concentrations in Hep3B cells. CompuSyn software (https://www.combosyn.com/) analysis demonstrated that Compound I-1 in combination with sorafenib showed significant synergism at the following concentrations of Compound I-1 and sorafenib, respectively: 1 μM and 0.03 μM; 50 μM and 1.5 μM; and 100 μM and 3 μM. Modest synergism was determined for Compound I-1 (5 μM) and sorafenib (0.15 μM). Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 43B:
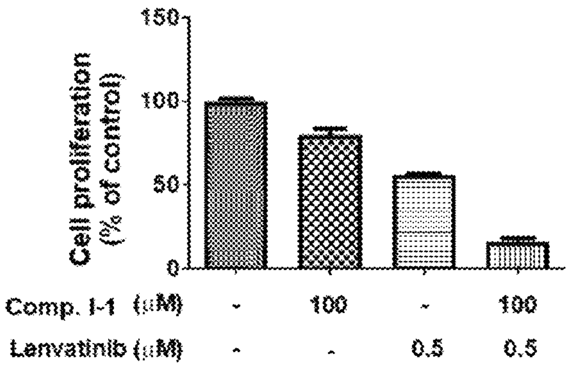
FIG. 43B shows Hep3B cell proliferation (as a percent of control) for control (Hep3B cell media containing 0.2% DMSO), Compound I-1 (100 μM), lenvatinib (3 μM), and Compound I-1 (100 μM) in combination with lenvatinib (3 μM).

FIG. 43B shows Hep3B cell proliferation (as a percent of control) for control (Hep3B cell media containing 0.2% DMSO), Compound I-1 (100 μM), lenvatinib (0.5 μM), and Compound I-1 (100 μM) in combination with lenvatinib (0.5 μM). Surprisingly and unexpectedly, Compound I-1 in the absence of lenvatinib significantly (p=0.0002, determined by one-way ANOVA, followed by Tukey's multiple comparison) inhibited Hep3B cell proliferation compared to control, after incubation for 72 h; moreover, Compound I-1 in combination with lenvatinib showed significantly greater inhibition of Hep3B cell proliferation compared to Compound I-1 in the absence of lenvatinib and to lenvatinib in the absence of Compound I-1, after incubation for 72 h.

Figure 44B:
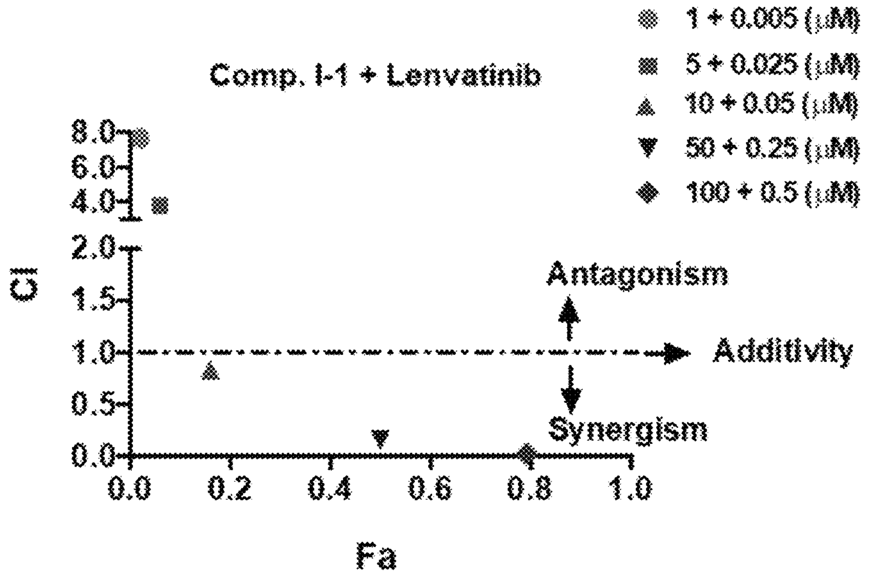

FIG. 44B shows synergism of Compound I-1 in combination with lenvatinib at various concentrations in Hep3B cells. CompuSyn software analysis demonstrated that Compound I-1 in combination with lenvatinib showed significant synergism at the following concentrations of Compound I-1 and lenvatinib, respectively: 50 μM and 0.25 μM; and 100 μM and 0.5 μM. Moderate synergism was determined for Compound I-1 (10 μM) and lenvatinib (0.05 μM). Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 43C:
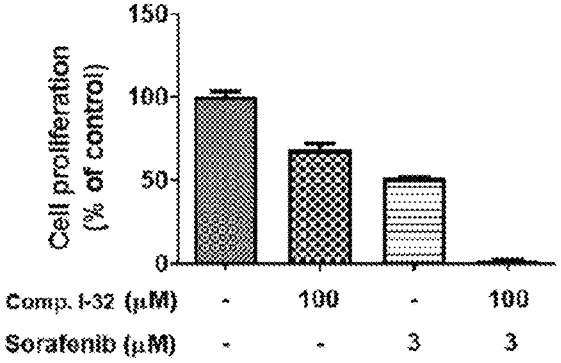
FIG. 43C shows Hep3B cell proliferation (as a percent of control) for control (Hep3B cell media containing 0.2% DMSO), Compound I-32 (100 μM), sorafenib (3 μM), and Compound I-32 (100 μM) in combination with sorafenib (3 μM).

FIG. 43C shows Hep3B cell proliferation (as a percent of control) for control (Hep3B cell media containing 0.2% DMSO), Compound I-32 (100 μM), sorafenib (3 μM), and Compound I-32 (100 μM) in combination with sorafenib (3 μM). Surprisingly and unexpectedly, Compound I-32 in the absence of sorafenib significantly (p<0.0001, determined by one-way ANOVA, followed by Tukey's multiple comparison) inhibited Hep3B cell proliferation compared to control, after incubation for 72 h; moreover, Compound I-32 in combination with sorafenib showed significantly greater inhibition of Hep3B cell proliferation compared to Compound I-32 in the absence of sorafenib and to sorafenib in the absence of Compound I-32, after incubation for 72 h.

Figure 44C:
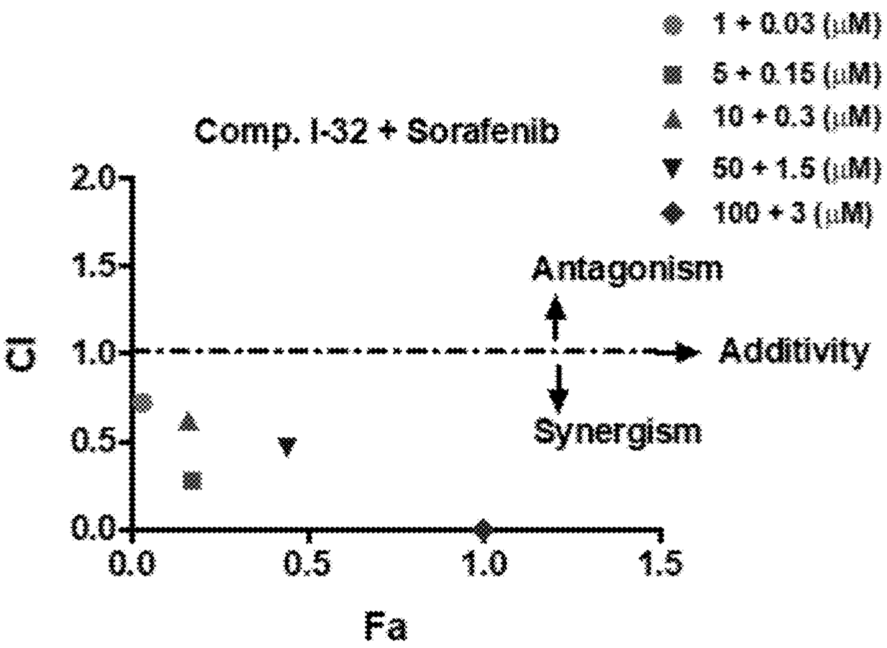

FIG. 44C shows synergism of Compound I-32 in combination with sorafenib at all tested concentrations of Compound I-32 and sorafenib, respectively, in Hep3B cells: 1 μM and 0.05 μM; 5 μM and 0.15 μM: 10 μM and 0.3 μM; 50 μM and 1.5 μM; and 100 μM and 3 μM. Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 43D:
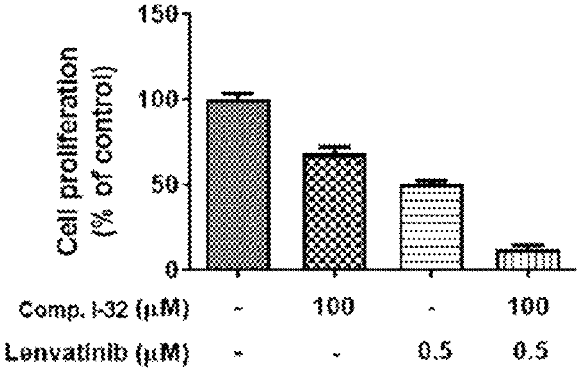
FIG. 43D shows Hep3B cell proliferation (as a percent of control) for control (Hep3B cell media containing 0.2% DMSO), Compound I-32 (100 μM), lenvatinib (3 μM), and Compound I-32 (100 μM) in combination with lenvatinib (3 μM).

FIG. 43D shows Hep3B cell proliferation (as a percent of control) for control (Hep3B cell media containing 0.2% DMSO), Compound I-32 (100 μM), lenvatinib (0.5 μM), and Compound I-32 (100 μM) in combination with lenvatinib (0.5 μM). Surprisingly and unexpectedly, Compound I-32 in the absence of lenvatinib significantly (p<0.0001, determined by one-way ANOVA, followed by Tukey's multiple comparison) inhibited Hep3B cell proliferation compared to control, after incubation for 72 h; moreover, Compound I-32 in combination with lenvatinib showed significantly greater inhibition of Hep3B cell proliferation compared to Compound I-32 in the absence of lenvatinib and to lenvatinib in the absence of Compound I-32, after incubation for 72 h.

Figure 44D:
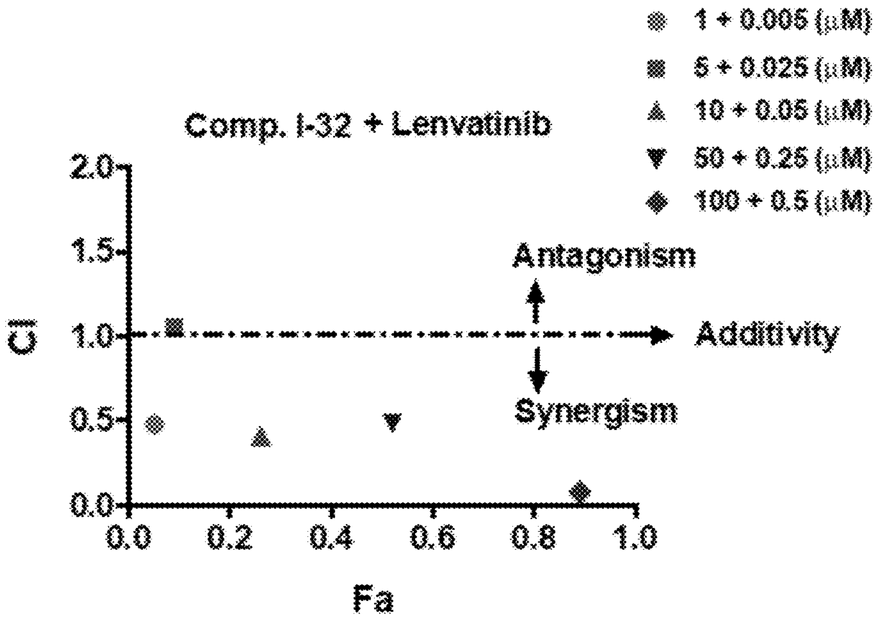

FIG. 44D shows synergism of Compound I-32 in combination with lenvatinib at various concentrations in Hep3B cells. CompuSyn software analysis demonstrated that Compound I-32 in combination with lenvatinib showed significant synergism at the following concentrations of Compound I-32 and lenvatinib, respectively: 1 μM and 0.005 μM: 10 μM and 0.05 μM; 50 μM and 0.25 μM; and 100 μM and 0.5 μM. Modest synergism was determined for Compound I-32 (5 μM) and lenvatinib (0.025 μM). Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 43E:
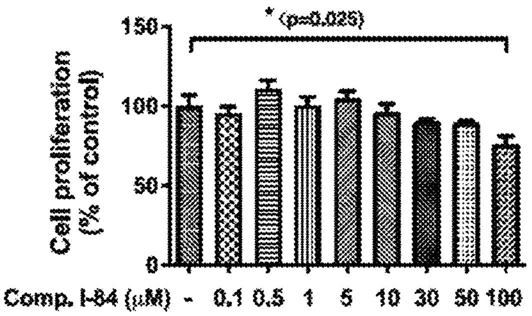
FIG. 43E shows Hep3B cell proliferation (as a percent of control) for Compound I-84 (0.1 μM, 0.5 μM, 1 μM, 5 μM, 10 μM, 30 μM, 50 μM and 100 μM) after incubation for 72 h.
Figure 43F:
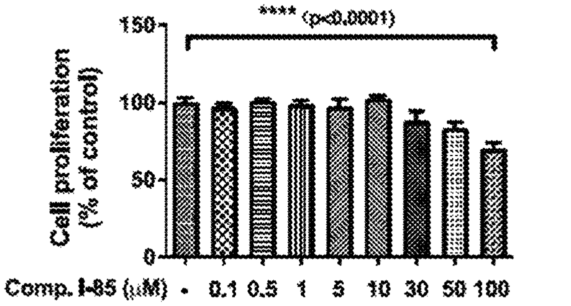
FIG. 43F shows Hep3B cell proliferation (as a percent of control) for Compound I-85 (0.1 μM, 0.5 μM, 1 μM, 5 μM, 10 μM, 30 μM, 50 μM and 100 μM) after incubation for 72 h.

FIG. 43E shows Hep3B cell proliferation (as a percent of control) for Compound I-84 (0.1 μM, 0.5 μM, 1 μM, 5 μM, 10 μM, 30 μM, 50 μM and 100 μM) after incubation for 72 h. FIG. 43F shows Hep3B cell proliferation (as a percent of control) for Compound I-85 (0.1 μM, 0.5 μM, 1 μM, 5 μM, 10 μM, 30 μM, 50 μM and 100 μM) after incubation for 72 h.

Figure 45A:
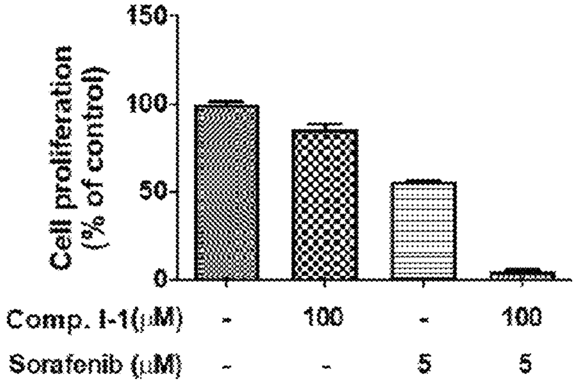
FIG. 45A shows Hepa1-6 cell proliferation (as a percent of control) for control (Hepa1-6 cell media containing 0.2% DMSO), Compound I-1 (100 μM), sorafenib (5 μM), and Compound I-1 (100 μM) in combination with sorafenib (5 μM).

FIG. 45A shows Hepa1-6 cell proliferation (as a percent of control) for control (Hepa1-6 cell media containing 0.2% DMSO), Compound I-1 (100 μM), sorafenib (5 μM), and Compound I-1 (100 μM) in combination with sorafenib (5 μM). Surprisingly and unexpectedly, Compound I-1 in the absence of sorafenib significantly (p=0.0001, determined by one-way ANOVA, followed by Tukey's multiple comparison) inhibited Hepa1-6 cell proliferation compared to control, after incubation for 72 h; moreover, Compound I-1 in combination with sorafenib showed significantly greater inhibition of Hepa1-6 cell proliferation compared to Compound I-1 in the absence of sorafenib and to sorafenib in the absence of Compound I-1, after incubation for 72 h.

Figure 46A:
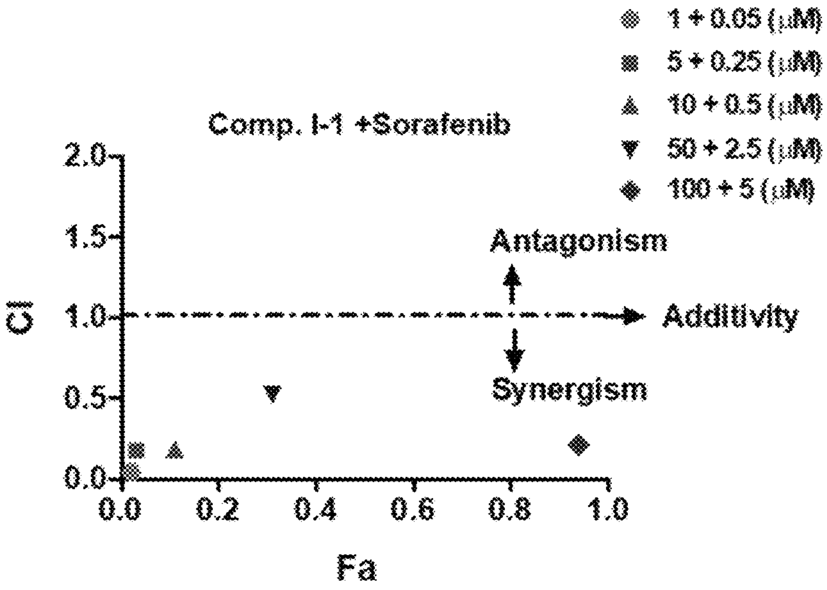
FIG. 46A shows synergism of Compound I-1 in combination with sorafenib at all tested concentrations of Compound I-1 and sorafenib in Hepa1-6 cells.

FIG. 46A shows synergism of Compound I-1 in combination with sorafenib at all tested concentrations of Compound I-1 and sorafenib, respectively, in Hepa1-6 cells: 1 μM and 0.05 μM: 5 μM and 0.25 μM: 10 μM and 0.5 μM: 50 μM and 2.5 μM; and 100 μM and 5 μM. Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 45B:
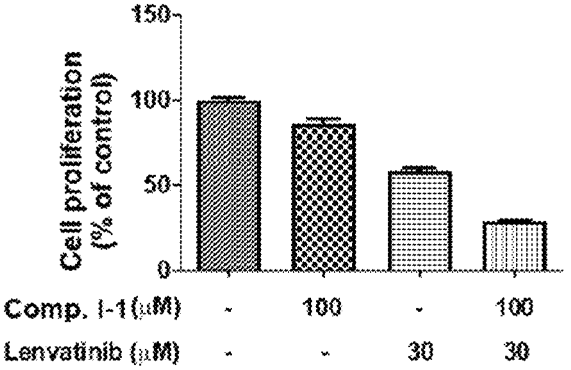
FIG. 45B shows Hepa1-6 cell proliferation (as a percent of control) for control (Hepa1-6 cell media containing 0.2% DMSO), Compound I-1 (100 μM), lenvatinib (30 μM), and Compound I-1 (100 μM) in combination with lenvatinib (30 μM).

FIG. 45B shows Hepa1-6 cell proliferation (as a percent of control) for control (Hepa1-6 cell media containing 0.2% DMSO), Compound I-1 (100 μM), lenvatinib (30 μM), and Compound I-1 (100 μM) in combination with lenvatinib (30 μM). Surprisingly and unexpectedly, Compound I-1 in the absence of lenvatinib significantly (p=0.0004, determined by one-way ANOVA, followed by Tukey's multiple comparison) inhibited Hepa1-6 cell proliferation compared to control, after incubation for 72 h; moreover, Compound I-1 in combination with lenvatinib showed significantly greater inhibition of Hepa1-6 cell proliferation compared to Compound I-1 in the absence of lenvatinib and to lenvatinib in the absence of Compound I-1, after incubation for 72 h.

Figure 46B:
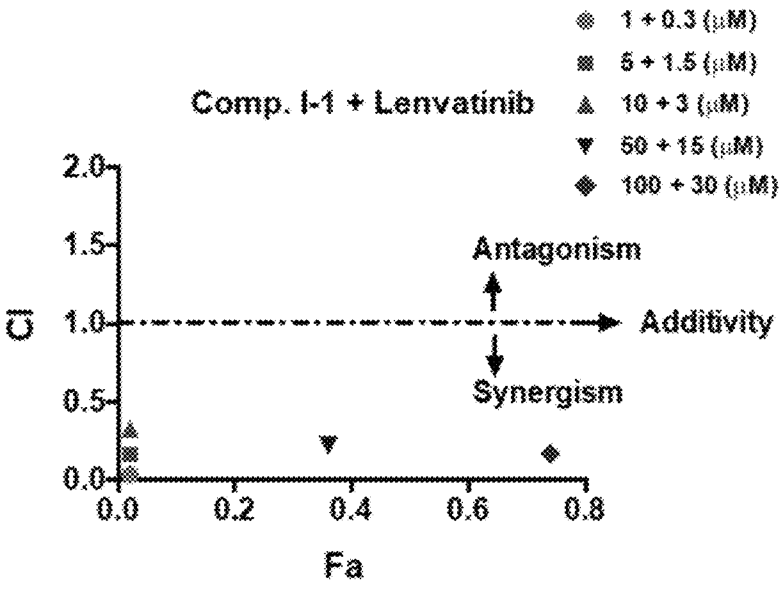
FIG. 46B shows synergism of Compound I-1 in combination with lenvatinib at all tested concentrations of Compound I-1 and lenvatinib in Hepa1-6 cells.

FIG. 46B shows synergism of Compound I-1 in combination with lenvatinib at all tested concentrations of Compound I-1 and lenvatinib, respectively, in Hepa1-6 cells: 1 μM and 0.3 μM; 5 μM and 1.5 μM; 10 μM and 3 μM; 50 μM and 15 μM; and 100 μM and 30 μM. Combination Index (CI)=1 shows additivity: CI<1 shows synergism; and CI>1 shows antagonism. Fractional Inhibition (Fa) is the potency expressed by the anti-proliferative effect relative to control, where an Fa value of 1=100% inhibition for each working concentration.

Figure 45C:
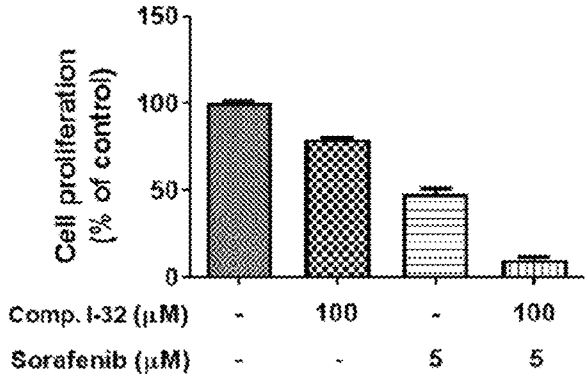
FIG. 45C shows Hepa1-6 cell proliferation (as a percent of control) for control (Hepa1-6 cell media containing 0.2% DMSO), Compound I-32 (100 μM), sorafenib (5 μM), and Compound I-32 (100 μM) in combination with sorafenib (5 μM).

FIG. 45C shows Hepa1-6 cell proliferation (as a percent of control) for control (Hepa1-6 cell media containing 0.2% DMSO), Compound I-32 (100 μM), sorafenib (5 μM), and Compound I-32 (100 μM) in combination with sorafenib (5 μM). Surprisingly and unexpectedly, Compound I-32 in the absence of sorafenib significantly (p<0.0001, determined by one-way ANOVA, followed by Tukey's multiple comparison) inhibited Hepa1-6 cell proliferation compared to control, after incubation for 72 h; moreover, Compound I-32 in combination with sorafenib showed significantly greater inhibition of Hepa1-6 cell proliferation compared to Compound I-32 in the absence of sorafenib and to sorafenib in the absence of Compound I-32, after incubation for 72 h.

Figure 46C:
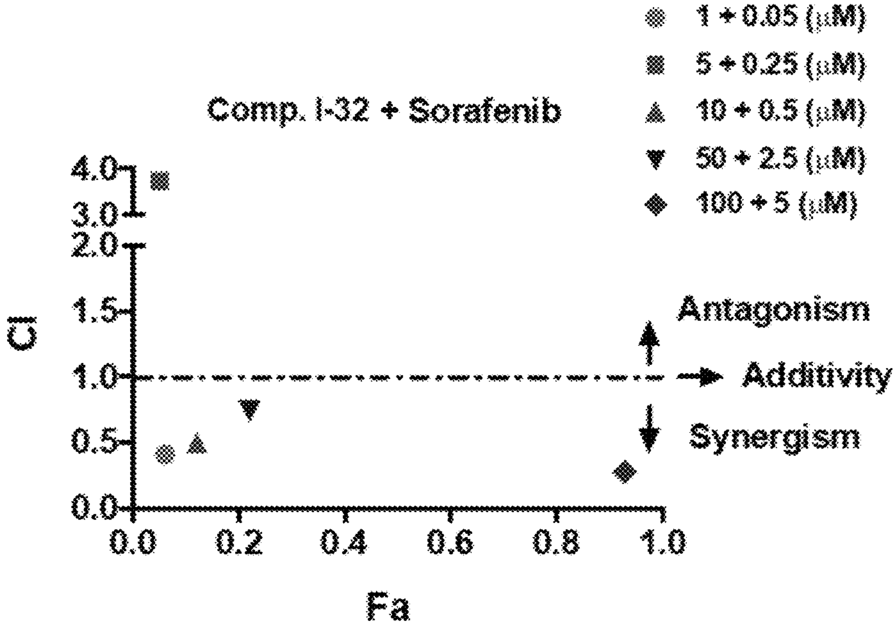
FIG. 46C shows synergism of Compound I-32 in combination with sorafenib at various concentrations in Hepa1-6 cells.

FIG. 46C shows synergism of Compound I-32 in combination with sorafenib showed significant synergism at the following concentrations of Compound I-32 and sorafenib, respectively: 1 μM and 0.05 μM; 10 μM and 0.25 μM: 50 μM and 2.5 μM; and 100 μM and 5 μM. Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 45D:
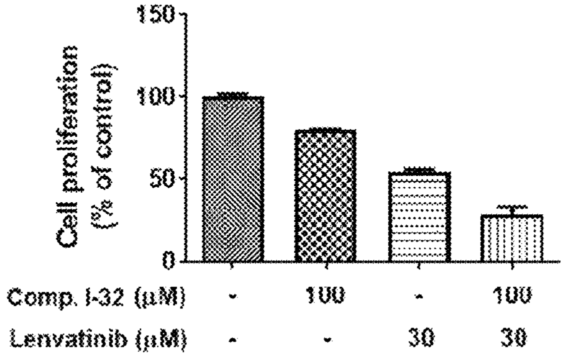
FIG. 45D shows Hepa1-6 cell proliferation (as a percent of control) for control (Hepa1-6 cell media containing 0.2% DMSO), Compound I-32 (100 μM), lenvatinib (30 μM), and Compound I-32 (100 μM) in combination with lenvatinib (30 μM).

FIG. 45D shows Hepa1-6 cell proliferation (as a percent of control) for control (Hepa1-6 cell media containing 0.2% DMSO), Compound I-32 (100 μM), lenvatinib (30 μM), and Compound I-32 (100 μM) in combination with lenvatinib (30 μM). Surprisingly and unexpectedly. Compound I-32 in the absence of lenvatinib significantly (p<0.0001, determined by one-way ANOVA, followed by Tukey's multiple comparison) inhibited Hepa1-6 cell proliferation compared to control, after incubation for 72 h: moreover, Compound I-32 in combination with lenvatinib showed significantly greater inhibition of Hepa1-6 cell proliferation compared to Compound I-32 in the absence of lenvatinib and to lenvatinib in the absence of Compound I-32, after incubation for 72 h.

Figure 46D:
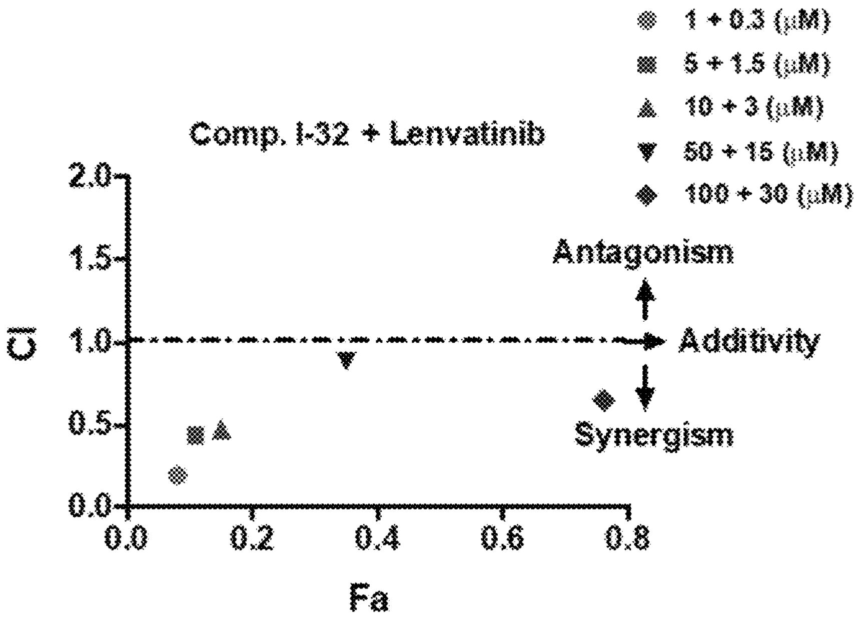
FIG. 46D shows synergism of Compound I-32 in combination with lenvatinib at all tested concentrations of Compound I-32 and lenvatinib in Hepa1-6 cells.

FIG. 46D shows synergism of Compound I-32 in combination with lenvatinib at all tested concentrations of Compound I-32 and lenvatinib, respectively, in Hepa1-6 cells: 1 μM and 0.3 μM; 5 μM and 1.5 μM; 10 μM and 3 μM; 50 μM and 15 μM; and 100 μM and 30 μM. Combination Index (CI)=1 shows additivity; CI<1 shows synergism; and CI>1 shows antagonism. Fractional Inhibition (Fa) is the potency expressed by the anti-proliferative effect relative to control, where an Fa value of 1=100% inhibition for each working concentration.

Figure 45E:
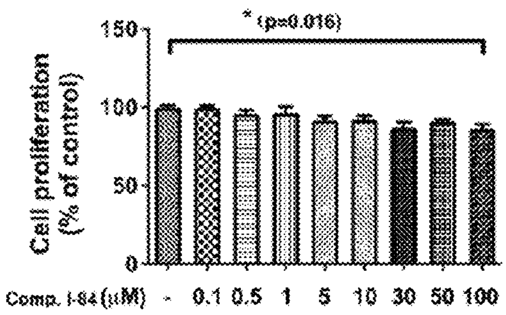
FIG. 45E shows Hepa1-6 cell proliferation (as a percent of control) for Compound I-84 (0.1 μM, 0.5 μM, 1 μM, 5 μM, 10 μM, 30 μM, 50 μM and 100 μM) after incubation for 72 h.
Figure 45F:
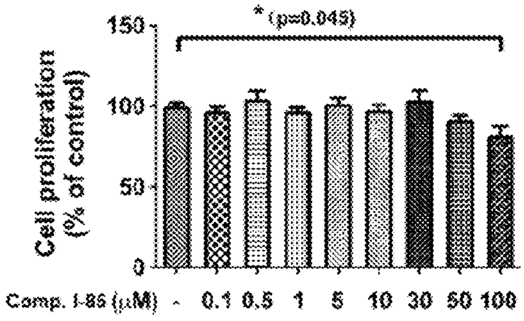
FIG. 45F shows Hepa1-6 cell proliferation (as a percent of control) for Compound I-85 (0.1 μM, 0.5 μM, 1 μM, 5 μM, 10 μM, 30 μM, 50 μM and 100 μM) after incubation for 72 h.

FIG. 45E shows Hepa1-6 cell proliferation (as a percent of control) for Compound I-84 (0.1 μM, 0.5 μM, 1 μM, 5 μM, 10 μM, 30 μM, 50 μM and 100 μM) after incubation for 72 h. FIG. 45F shows Hepa1-6 cell proliferation (as a percent of control) for Compound I-85 (0.1 μM, 0.5 μM, 1 μM, 5 μM, 10 μM, 30 μM, 50 μM and 100 μM) after incubation for 72 h.

The results described in FIGS. 43A-43D, 44A-44D, 45A-45D and 46A-46D are significant, surprising and unexpected, and clearly show anti-proliferation activity of Compound I-1 in Hep3B and Hepa1-6 cells, anti-proliferation activity of Compound I-32 in Hep3B and Hepa1-6 cells, synergistic anti-proliferation activity of Compound I-1 in combination with sorafenib or lenvatinib in Hep3B and Hepa1-6 cells and synergistic anti-proliferation activity of Compound I-32 in combination with sorafenib or lenvatinib in Hep3B and Hepa1-6 cells.

Example 21. Effect of Illustrative Compounds of the Invention on De Novo Lipid Synthesis Suppression in C57BL6 Mice Using Indirect Calorimetry Materials and Methods. All experiments were carried out using the methods approved by the Animal Research Ethics Board at McMaster University, Canada (Steinberg Laboratory Animal Utilization Protocol #16-12-42). 8-Week-old male C57BL6/J mice were ordered from Jackson Laboratory, Bar Harbor, Me. and housed at the McMaster University Central Animal Facility. Animals were housed in the ventilated cages racks system and provided with ad libitum access to normal chow diet (Teklad 8640 22/5 rodent diet, procured from Envigo, Mississauga ON) and water supplemented with fructose (30% weight/volume, made fresh weekly) for at least 2-weeks before testing commenced. A 12-hour light/dark cycle and a temperature of 23±2° C. were maintained throughout the animal housing. Data were analyzed using one-way analyses of variance followed by a Tukey's multiple comparisons post hoc test where appropriate. All statistical analysis was carried out using GraphPad Prism 8 software. A p-value of less than or equal 0.05 was considered significant.

Experimental and Results. Respiratory Exchange Ratio (RER) and related metabolic parameters were measured using the Comprehensive Lab Animal Monitoring System (CLAMS, Columbus Instruments, Columbus, Ohio). Animals were placed in CLAMS and allowed ad libitum access to normal chow diet and water supplemented with fructose (30% weight/volume) for at least 24 hours before the experiment began. At 5:30 p.m. chow diet was removed and water containing 30% fructose was replaced with normal tap water. Animals were fasted overnight until food and 30% fructose water were made accessible the next day at 7:30 am. (14 hours total). Animals were allowed to feed ad libitum for ~2 hours. RER was monitored and those animals with RER values >1 were administered either vehicle (1.5% Carboxymethyl cellulose and 0.2% Tween 20) alone or vehicle containing Compound I-1 or Compound I-32 at a dose of 100 mg/kg via oral gavage. Animals remained in the metabolic cages and RER, activity level, locomotor activity, and food intake were monitored for 24 hours. Metabolic parameters were calculated using Oxymax software included with Comprehensive Lab Animal Monitoring System (CLAMS). RER was calculated as the ratio of oxygen consumed ($VO_2$) versus the amount of $CO_2$ produced ($VCO_2$) given by the following equation:

$$RER=VCO_2/VO_2$$

Locomotor activity was calculated as the total number of beam breaks in each cage over a 24-hour period. The heat (calorific value, CV) was calculated by the following equation:

$$\text{Heat}=CV\times VO2$$

$$CV=3.815+1.232\times RER$$

Figure 47A:
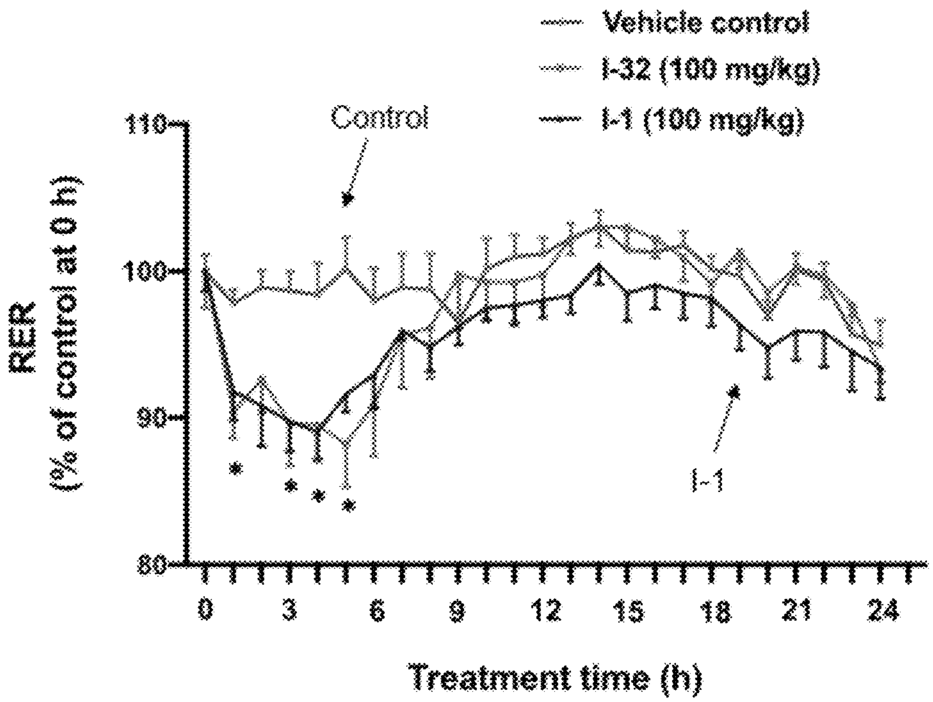
FIGS. 47A-47B show the effects of Compound I-1 and Compound I-32 on respiratory exchange ratio (RER) in C57Bl/6 mice fed a high fructose diet.
Figure 47B:
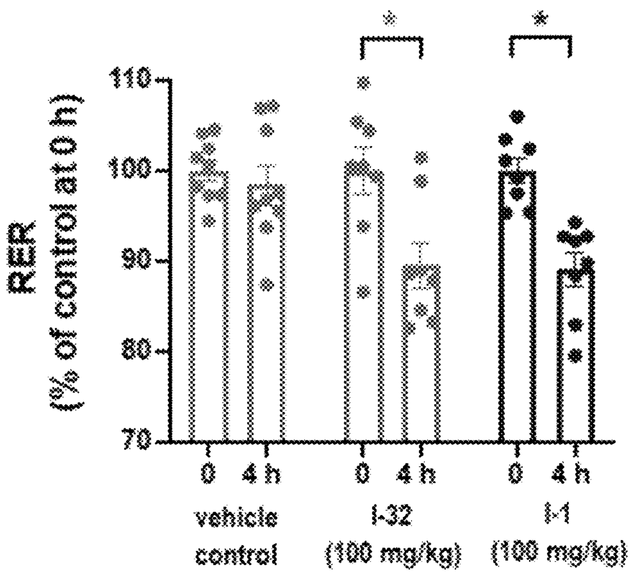

In vehicle treated mice RER was not different at any time point (FIG. 47A). However, when mice were treated with Compound I-32 or Compound I-1, there was a significant reduction in the RER compared to the vehicle treated group. (FIGS. 47A-47B). Specifically, reductions in the RER were detected within 1 hr of treatment with Compound I-32 or Compound I-1 and this effect was maintained for 6 hr.

Figure 48A:
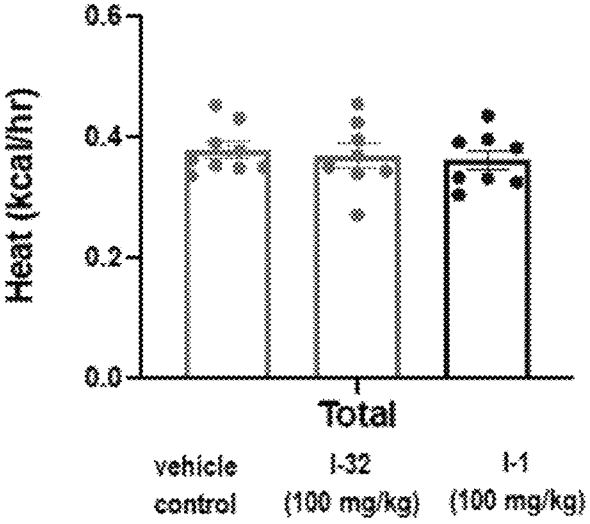
FIGS. 48A-48B show the effects of Compound I-1 and Compound I-32 on heat production in high fructose-fed C57BL/6 mice up to 24 hr following treatment with Compound I-1 or Compound I-32.
Figure 48B:
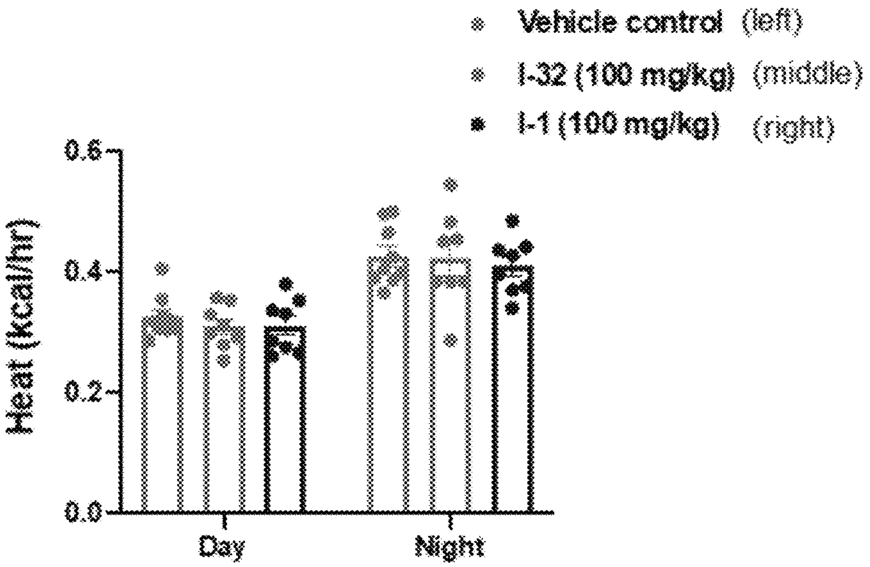

Heat production is a measure of total energy expenditure and is elevated by increases in physical activity (locomotion) or agents that induce mitochondrial uncoupling such as salsalate. There was no difference in heat between the untreated and the treated groups, (FIGS. 48A-48B). As anticipated, given the increased mobility of mice during the dark cycle, heat was higher during the dark cycle (Night) compared to the heat produced during the light cycle (Day) for all groups (FIG. 48B).

Figure 49A:
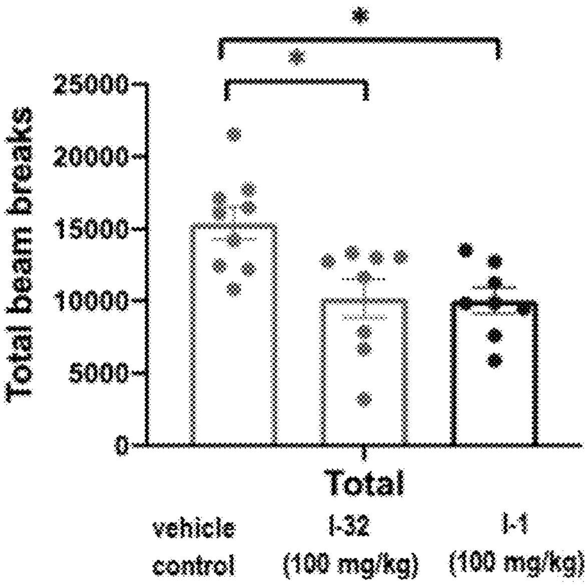
FIGS. 49A-49B show the effects of Compound I-1 and Compound I-32 on locomotor activity, calculated as the total number of beam breaks in each cage over 24-hour period, in fructose-fed C57BL/6 mice.
Figure 49B:
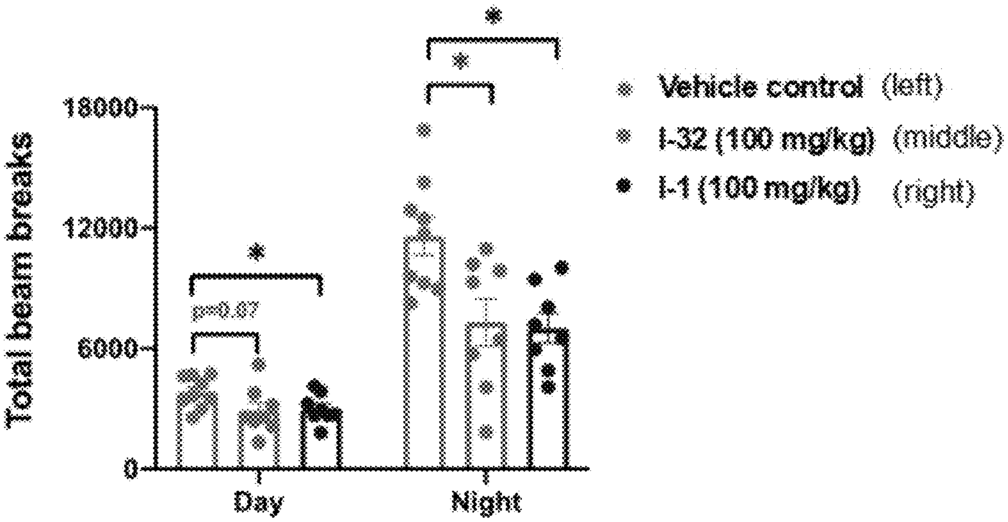

As the RER can be influenced by food intake and physical activity (locomotor activity) these parameters were also assessed. Total locomotor activity was significantly lower in mice treated with Compound I-32 and Compound I-1 compared to vehicle treated mice (FIG. 49A). As anticipated the locomotor activity in all groups was lower during the light cycle (Day) compared to the dark cycle (Night) (FIG. 49B).

Figure 50A:
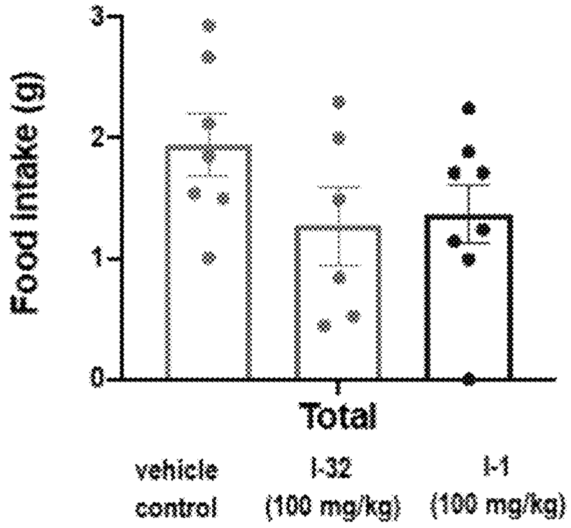
FIGS. 50A-50B show the effects of Compound I-1 and Compound I-32 on food intake.
Figure 50B:
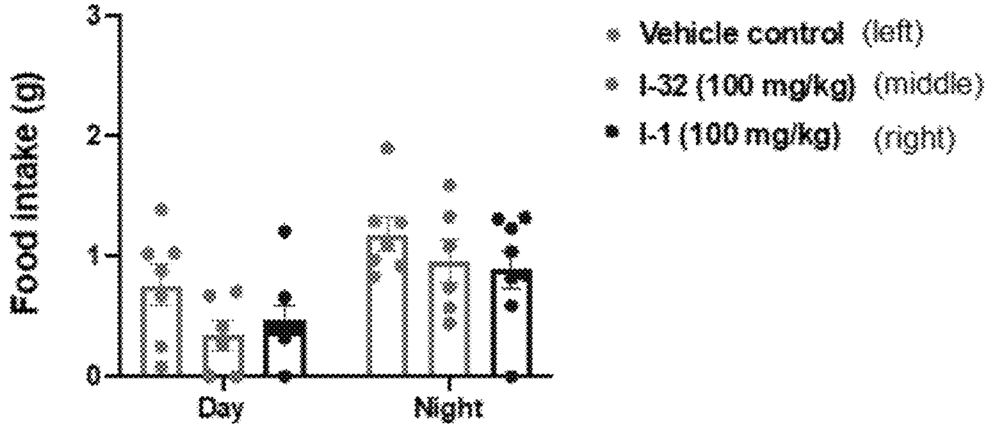

Consistent with reductions in locomotor activity Compound I-32 and Compound I-1 tended to suppress food intake compared to vehicle controls, however, this was not significant (FIG. 50A). As expected, food intake was greater during the dark cycle (Night) for all mice (FIG. 50B).

Example 22. Salts of 6-[3-(5-carboxy-5-methyl-hexyl)-phenyl]-2,2-dimethylhexanoic acid (Compound I-32)

The following salts of Compound I-32 were obtained by admixing Compound I-32 (1.0 equiv) and a base (1.1 equiv) in the presence of a solvent, e.g., water, methanol, ethanol, 2-propanol, tetrahydrofuran, 2-methyltetrahydrofuran, acetonitrile, methyl t-butyl ether, methyl ethyl ketone, ethyl acetate, acetone, or n-heptane, or a mixture thereof.

Illustrative salts of Compound I-32 include:

Compound I-32 L-arginine salt, which precipitated from an admixture of Compound I-32, L-arginine and a solvent. The resultant slurry was directly air-dried in a fume hood then dried in a vacuum oven to obtain Compound I-32 L-arginine salt as a white solid.

Compound I-32 meglumine salt, which precipitated from an admixture of Compound I-32, N-methylglucamine and a solvent. The resultant slurry was directly air-dried in a fume hood then dried in a vacuum oven to obtain Compound I-32 meglumine salt as a white solid.

Compound I-32 lysine salt, which precipitated from an admixture of Compound I-32, L-lysine monohydrate and a solvent. The resultant slurry was centrifuged, air-dried in a fume hood then dried in a vacuum oven to obtain Compound I-32 lysine salt as a white solid.

Compound I-32 potassium salt, which precipitated from an admixture of Compound I-32, potassium hydroxide and a solvent. The resultant slurry was centrifuged, air-dried in a fume hood then dried in a vacuum oven to obtain Compound I-32 potassium salt as a white solid.

Compound I-32 sodium salt, which precipitated from an admixture of Compound I-32, sodium hydroxide and a solvent. The resultant slurry was centrifuged, air-dried in a fume hood then dried in a vacuum oven to obtain Compound I-32 sodium salt as a white solid.

Compound I-32 calcium salt, which precipitated from an admixture of Compound I-32, calcium hydroxide and a solvent. The resultant slurry was centrifuged, air-dried in a fume hood then dried in a vacuum oven to obtain Compound I-32 calcium salt as a white solid.

Compound I-32 ammonium salt, which precipitated from an admixture of Compound I-32, ammonia and a solvent. The resultant slurry was directly air-dried in a fume hood then dried in a vacuum oven to obtain Compound I-32 ammonium salt as a white solid.

Compound I-32 magnesium salt, which precipitated from an admixture of Compound I-32, magnesium hydroxide and a solvent. The resultant slurry was directly air-dried in a fume hood then dried in a vacuum oven to obtain Compound I-32 magnesium salt as a white solid.

Example 23. Salts of 6-[4-(5-carboxy-5-methyl-hexyl)-phenyl]-2,2-dimethylhexanoic acid (Compound I-1)

The following salts of Compound I-1 were obtained by admixing Compound I-1 (1.0 equiv) and a base (1.1 equiv) in the presence of a solvent, e.g., water, methanol, ethanol, 2-propanol, tetrahydrofuran, 2-methyltetrahydrofuran, acetonitrile, methyl t-butyl ether, methyl ethyl ketone, ethyl acetate, acetone, or n-heptane, or a mixture thereof.

Illustrative salts of Compound I-1 include:

Compound I-1 arginine salt, which precipitated from an admixture of Compound I-1, L-arginine and a solvent. The resultant slurry was centrifuged, air-dried in a fume hood then dried in a vacuum oven to obtain Compound I-1 arginine salt as a white solid.

Compound I-1 meglumine salt, which precipitated from an admixture of Compound I-1, N-methyl-D-glucamine and a solvent. The resultant slurry was centrifuged, air-dried in a fume hood then dried in a vacuum oven to obtain Compound I-1 meglumine salt as a white solid.

Compound I-1 lysine salt, which was prepared from an admixture of Compound I-1, L-lysine monohydrate and a solvent. The resultant solution was centrifuged, air-dried in a fume hood then dried in a vacuum oven to obtain Compound I-1 lysine salt as a yellow solid.

Compound I-1 potassium salt, which precipitated from an admixture of Compound I-1, potassium hydroxide and a solvent. The resultant slurry was centrifuged, air-dried in a fume hood then dried in a vacuum oven to obtain Compound I-1 potassium salt as a white solid.

Compound I-1 sodium salt, which precipitated from an admixture of Compound I-1, sodium hydroxide and a solvent. The resultant slurry was centrifuged, air-dried in a fume hood then dried in a vacuum oven to obtain Compound I-1 sodium salt as a white solid.

Compound I-1 calcium salt, which precipitated from an admixture of Compound I-1, calcium hydroxide and a solvent. The resultant slurry was directly air-dried in a fume hood then dried in a vacuum oven to obtain Compound I-1 calcium salt as a white solid.

Compound I-1 ammonium salt, which precipitated from an admixture of Compound I-1, ammonia and a solvent. The resultant slurry was centrifuged, air-dried in a fume hood then dried in a vacuum oven to obtain Compound I-1 ammonium salt as a white solid.

Compound I-1 magnesium salt, which precipitated from an admixture of Compound I-1, magnesium hydroxide and a solvent. The resultant slurry was directly air-dried in a fume hood then dried in a vacuum oven to obtain Compound I-1 magnesium salt as a white solid.

What is claimed is:

1. A compound having the structure

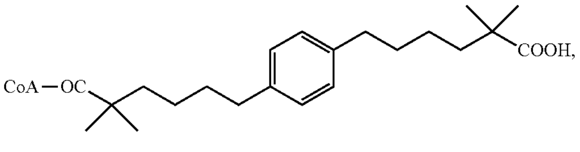

-continued

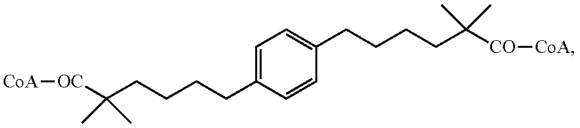

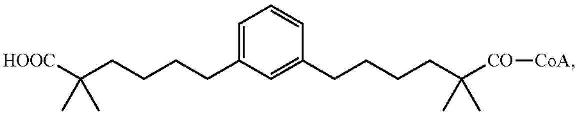

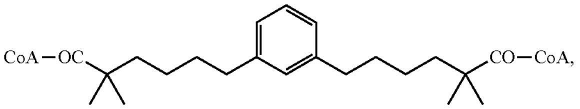

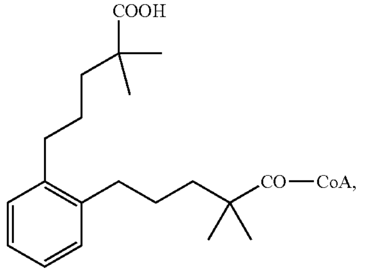

or

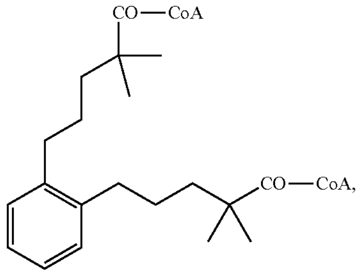

or a pharmaceutically acceptable salt or solvate thereof;

wherein —CO—CoA and CoA-OC— have the structure:

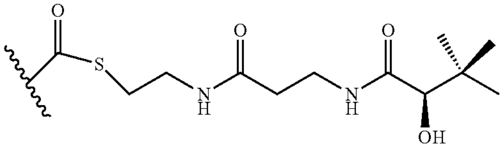

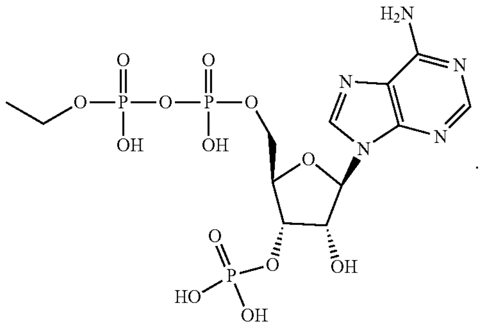

.

2. The compound of claim 1, wherein the compound has the structure

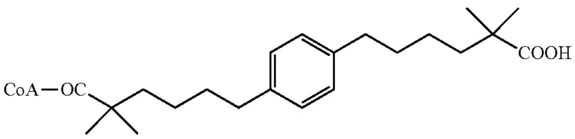

or a pharmaceutically acceptable salt or solvate thereof.

3. The compound of claim 1, wherein the compound has the structure

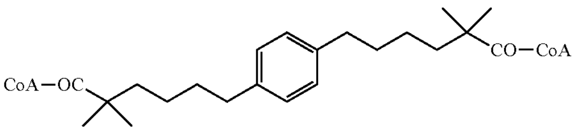

or a pharmaceutically acceptable salt or solvate thereof.

4. The compound of claim 1, wherein the compound has the structure

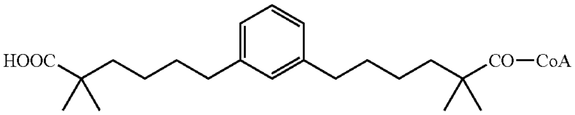

or a pharmaceutically acceptable salt or solvate thereof.

5. The compound of claim 1, wherein the compound has the structure

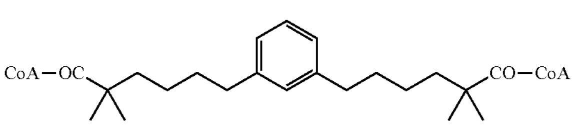

or a pharmaceutically acceptable salt or solvate thereof.

6. The compound of claim 1, wherein the compound has the structure

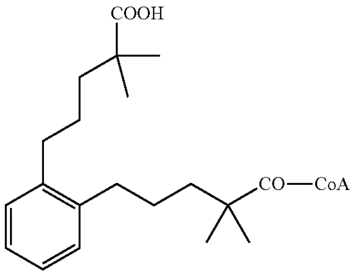

or a pharmaceutically acceptable salt or solvate thereof.

7. The compound of claim 6, wherein the compound has the structure

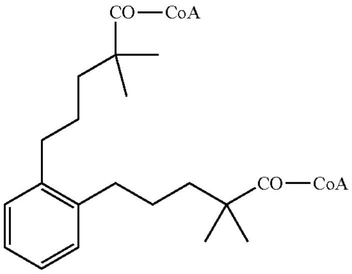

or a pharmaceutically acceptable salt or solvate thereof.

8. The compound or pharmaceutically acceptable salt or solvate of the compound of claim 1, wherein the compound or pharmaceutically acceptable salt or solvate of the compound is isolated and purified.

9. The compound or pharmaceutically acceptable salt or solvate of the compound of claim 2, wherein the compound or pharmaceutically acceptable salt or solvate of the compound is isolated and purified.

10. The compound or pharmaceutically acceptable salt or solvate of the compound of claim 3, wherein the compound or pharmaceutically acceptable salt or solvate of the compound is isolated and purified.

11. The compound or pharmaceutically acceptable salt or solvate of the compound of claim 4, wherein the compound or pharmaceutically acceptable salt or solvate of the compound is isolated and purified.

12. The compound or pharmaceutically acceptable salt or solvate of the compound of claim 5, wherein the compound or pharmaceutically acceptable salt or solvate of the compound is isolated and purified.

13. The compound or pharmaceutically acceptable salt or solvate of the compound of claim 6, wherein the compound or pharmaceutically acceptable salt or solvate of the compound is isolated and purified.

14. The compound or pharmaceutically acceptable salt or solvate of the compound of claim 7, wherein the compound or pharmaceutically acceptable salt or solvate of the compound is isolated and purified.

15. A composition comprising:

(i) a compound or pharmaceutically acceptable salt or solvate of the compound of claim 1; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

16. A composition comprising:

(i) a compound or pharmaceutically acceptable salt or solvate of the compound of claim 2; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

17. A composition comprising:

(i) a compound or pharmaceutically acceptable salt or solvate of the compound of claim 3; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

18. A composition comprising:

(i) a compound or pharmaceutically acceptable salt or solvate of the compound of claim 4; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

19. A composition comprising:

(i) a compound or pharmaceutically acceptable salt or solvate of the compound of claim 5; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

20. A composition comprising:

(i) a compound or pharmaceutically acceptable salt or solvate of the compound of claim 6; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

21. A composition comprising:

(i) a compound or pharmaceutically acceptable salt or solvate of the compound of claim 7; and (ii) a pharmaceutically acceptable carrier or vehicle;

wherein the compound or pharmaceutically acceptable salt or solvate of the compound is present in an amount of 10 (plus or minus up to 1%) wt % to 99 (plus or minus up to 1%) wt % of the total weight of the composition.

* * * * *